(12) United States Patent
Wang et al.

(10) Patent No.: US 12,398,154 B2
(45) Date of Patent: Aug. 26, 2025

(54) AZAQUINAZOLINE PAN-KRas INHIBITORS

(71) Applicant: Mirati Therapeutics, Inc., San Diego, CA (US)

(72) Inventors: Xiaolun Wang, San Diego, CA (US); Svitlana Kulyk, San Diego, CA (US); John David Lawson, Carlsbad, CA (US); Matthew Arnold Marx, San Diego, CA (US); Christopher Ronald Smith, San Diego, CA (US)

(73) Assignee: Mirati Therapeutics, Inc., San Diego, CA (US)

( * ) Notice: Subject to any disclaimer, the term of this patent is extended or adjusted under 35 U.S.C. 154(b) by 489 days.

(21) Appl. No.: 17/300,930

(22) Filed: Dec. 15, 2021

(65) Prior Publication Data

US 2023/0072276 A1 Mar. 9, 2023

Related U.S. Application Data

(60) Provisional application No. 63/164,338, filed on Mar. 22, 2021, provisional application No. 63/159,868, filed on Mar. 11, 2021, provisional application No. 63/125,776, filed on Dec. 15, 2020.

(51) Int. Cl.
  *C07D 519/00* (2006.01)
  *C07D 471/04* (2006.01)

(52) U.S. Cl.
  CPC ......... *C07D 519/00* (2013.01); *C07D 471/04* (2013.01)

(58) Field of Classification Search
  CPC .............................. C07D 519/00; C07D 471/04
  See application file for complete search history.

(56) References Cited

U.S. PATENT DOCUMENTS

| | | |
|---|---|---|
| 6,924,284 B2 | 8/2005 | Beaton et al. |
| 8,163,763 B2 | 4/2012 | Bergeron et al. |
| 8,426,401 B2 | 4/2013 | Bian et al. |
| 9,562,019 B2 * | 2/2017 | Djaballah ............ C07D 307/68 |
| 9,840,516 B2 | 12/2017 | Li et al. |
| 10,125,134 B2 | 11/2018 | Blake et al. |
| 2003/0191143 A1 | 10/2003 | Pitts et al. |
| 2006/0229307 A1 | 10/2006 | Blurton et al. |
| 2007/0021445 A1 | 1/2007 | Berthel et al. |
| 2009/0312342 A1 | 12/2009 | Wilson et al. |
| 2010/0081654 A1 | 4/2010 | Stockwell et al. |
| 2011/0269244 A1 | 11/2011 | Petter et al. |
| 2013/0029978 A1 | 1/2013 | Kamino et al. |
| 2014/0288045 A1 | 9/2014 | Ren et al. |
| 2015/0175558 A1 | 6/2015 | Stockwell et al. |
| 2015/0239900 A1 | 8/2015 | Li et al. |
| 2016/0031898 A1 | 2/2016 | Ren et al. |
| 2016/0108019 A1 | 4/2016 | Li et al. |
| 2016/0166571 A1 | 6/2016 | Janes et al. |
| 2016/0229836 A1 | 8/2016 | Stockwell et al. |
| 2016/0264627 A1 | 9/2016 | Henning et al. |
| 2016/0297774 A1 | 10/2016 | Li et al. |
| 2017/0022184 A1 | 1/2017 | Li et al. |
| 2017/0115303 A1 | 4/2017 | Cravatt et al. |
| 2017/0190672 A1 | 7/2017 | Mani et al. |
| 2017/0197945 A1 | 7/2017 | Li et al. |
| 2017/0275289 A1 | 9/2017 | Albrecht et al. |
| 2018/0015087 A1 | 1/2018 | Liu et al. |
| 2018/0072723 A1 | 3/2018 | Blake et al. |
| 2018/0118757 A1 | 5/2018 | Li et al. |
| 2018/0118761 A1 | 5/2018 | Sebti et al. |
| 2018/0127396 A1 | 5/2018 | Li et al. |
| 2018/0141927 A1 | 5/2018 | Li et al. |
| 2018/0155348 A1 | 6/2018 | Li et al. |
| 2018/0162812 A1 | 6/2018 | Ren et al. |
| 2018/0177767 A1 | 6/2018 | Lanman et al. |
| 2018/0194748 A1 | 7/2018 | Li et al. |
| 2018/0201610 A1 | 7/2018 | Tao et al. |
| 2018/0273515 A1 | 9/2018 | Li et al. |
| 2018/0273523 A1 | 9/2018 | Li et al. |
| 2018/0273577 A1 | 9/2018 | Revenko et al. |
| 2018/0282307 A1 | 10/2018 | Li et al. |
| 2018/0282308 A1 | 10/2018 | Li et al. |
| 2018/0289683 A1 | 10/2018 | McCormick et al. |
| 2019/0144444 A1 | 5/2019 | Blake et al. |
| 2019/0374542 A1 | 12/2019 | Allen et al. |
| 2020/0069657 A1 | 3/2020 | Lanman et al. |
| 2020/0262837 A1 | 8/2020 | Marx et al. |
| 2020/0331911 A1 | 10/2020 | Marx et al. |
| 2020/0399297 A1 | 12/2020 | Campbell et al. |

(Continued)

FOREIGN PATENT DOCUMENTS

| | | |
|---|---|---|
| CN | 113999226 A | 2/2022 |
| WO | 02/053558 A1 | 7/2002 |
| WO | 02/087513 A2 | 11/2002 |
| WO | 2007/146122 A2 | 12/2007 |
| WO | 2008/009078 A2 | 1/2008 |
| WO | 2009/047255 A1 | 4/2009 |
| WO | 2010/014939 A1 | 2/2010 |
| WO | 2010/120996 A1 | 10/2010 |
| WO | 2013/155223 A1 | 10/2013 |
| WO | 2014/143659 A1 | 9/2014 |
| WO | 2014/152588 A1 | 9/2014 |
| WO | 2016/049568 A1 | 3/2015 |
| WO | 2015/054572 A1 | 4/2015 |
| WO | 2016/025650 A1 | 2/2016 |

(Continued)

OTHER PUBLICATIONS

Patani, G. A., et al., Chem. Rev. 1996, 96, 3147-3176 (Year: 1996).*

(Continued)

*Primary Examiner* — Joseph K McKane
*Assistant Examiner* — Quincy McKoy
(74) *Attorney, Agent, or Firm* — Sterne, Kessler, Goldstein & Fox P.L.L.C.

(57) ABSTRACT

The present invention relates to compounds that inhibit at least one of KRas G12A, KRas G12C, KRas G12D, KRas G12R, KRas G12S, KRas G12V, KRas G13D and KRas Q61H, pharmaceutical compositions comprising the compounds and methods of use therefor.

49 Claims, No Drawings

(56) References Cited

U.S. PATENT DOCUMENTS

| | | | |
|---|---|---|---|
| 2021/0024501 A1 | 1/2021 | Liansheng et al. | |
| 2021/0139517 A1 | 5/2021 | Gill et al. | |
| 2023/0077225 A1* | 3/2023 | Wang | C07D 519/00 |
| 2023/0339976 A1* | 10/2023 | Wang | A61P 35/00 |

FOREIGN PATENT DOCUMENTS

| | | |
|---|---|---|
| WO | 2016/044772 A1 | 3/2016 |
| WO | 2016/049565 A1 | 3/2016 |
| WO | 2016130460 A2 | 8/2016 |
| WO | 2016/164675 A1 | 10/2016 |
| WO | 2016/168540 A1 | 10/2016 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/079864 A1 | 5/2017 |
| WO | 2017/080980 A1 | 5/2017 |
| WO | 2017/087528 A1 | 5/2017 |
| WO | 2017/100546 A1 | 6/2017 |
| WO | WO-2017/172979 A1 | 10/2017 |
| WO | 2018/064510 A1 | 4/2018 |
| WO | 2018/068017 A1 | 4/2018 |
| WO | 2018/102452 A2 | 6/2018 |
| WO | 2018/102453 A1 | 6/2018 |
| WO | 2018/112420 A1 | 6/2018 |
| WO | 2018/115380 A1 | 6/2018 |
| WO | 2018/119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/143315 A1 | 8/2018 |
| WO | 2018/195439 A2 | 10/2018 |
| WO | 2018218070 A2 | 11/2018 |
| WO | 2019/051291 A1 | 3/2019 |
| WO | 2019099524 A1 | 5/2019 |
| WO | 202063594 | 4/2020 |
| WO | 202098488 | 5/2020 |
| WO | 2020097537 A2 | 5/2020 |
| WO | 2020118066 A1 | 6/2020 |
| WO | 2020123395 A1 | 6/2020 |
| WO | 2020146613 A1 | 7/2020 |
| WO | 202027202 | 8/2020 |
| WO | 2020163598 | 8/2020 |
| WO | 2020165670 | 8/2020 |
| WO | 2020169838 | 8/2020 |
| WO | 2020171499 | 8/2020 |
| WO | 2020172332 | 8/2020 |
| WO | 2020176693 | 9/2020 |
| WO | 2020176963 | 9/2020 |
| WO | 2020177629 | 9/2020 |
| WO | 2020178282 | 9/2020 |
| WO | 2020181142 | 9/2020 |
| WO | 2020198125 | 10/2020 |
| WO | 2020204359 | 10/2020 |
| WO | 2020205473 | 10/2020 |
| WO | 2020205486 | 10/2020 |
| WO | 2020212895 | 10/2020 |
| WO | 2020214537 | 10/2020 |
| WO | 2020221239 | 11/2020 |
| WO | 2020230028 | 11/2020 |
| WO | 2020230091 | 11/2020 |
| WO | 2020231806 | 11/2020 |
| WO | 2020231808 | 11/2020 |
| WO | 2020232130 | 11/2020 |
| WO | 2020233592 | 11/2020 |
| WO | 2020234103 | 11/2020 |
| WO | 2020236940 | 11/2020 |
| WO | 2020236947 | 11/2020 |
| WO | 2020236948 | 11/2020 |
| WO | 2020247914 | 12/2020 |
| WO | 2020252336 | 12/2020 |
| WO | 2020252353 | 12/2020 |
| WO | 2021000885 | 1/2021 |
| WO | 2021023154 | 2/2021 |
| WO | 2021023247 | 2/2021 |
| WO | 2021027911 | 2/2021 |
| WO | 2021027943 | 2/2021 |
| WO | 2021031952 | 2/2021 |
| WO | 2021034992 | 2/2021 |
| WO | 2021037018 | 3/2021 |
| WO | 2021041671 | 3/2021 |
| WO | 2021043322 | 3/2021 |
| WO | 2021045279 | 3/2021 |
| WO | 2021050732 | 3/2021 |
| WO | 2021051034 | 3/2021 |
| WO | 2021052499 | 3/2021 |
| WO | 2021055728 | 3/2021 |
| WO | 2021057832 | 4/2021 |
| WO | 2021058018 | 4/2021 |
| WO | 2021061515 | 4/2021 |
| WO | 2021061749 | 4/2021 |
| WO | 2021063346 | 4/2021 |
| WO | 2021068898 | 4/2021 |
| WO | 2021075147 | 4/2021 |
| WO | 2021076655 | 4/2021 |
| WO | 2021078285 | 4/2021 |
| WO | 2021078312 | 4/2021 |
| WO | 2021080359 | 4/2021 |
| WO | 2021081212 | 4/2021 |
| WO | 2021083167 | 5/2021 |
| WO | 2021084765 | 5/2021 |
| WO | 2021085653 | 5/2021 |
| WO | 2021086833 | 5/2021 |
| WO | 2021088458 | 5/2021 |
| WO | 2021088938 | 5/2021 |
| WO | 2021091956 | 5/2021 |
| WO | 2021091967 | 5/2021 |
| WO | 2021091982 | 5/2021 |
| WO | 2021093758 A1 | 5/2021 |
| WO | 2021104431 A1 | 6/2021 |
| WO | 2021106230 A1 | 6/2021 |
| WO | 2021106231 A1 | 6/2021 |
| WO | 2021107160 A1 | 6/2021 |
| WO | 2021108683 A1 | 6/2021 |
| WO | 2021109737 A1 | 6/2021 |
| WO | 2021113595 A1 | 6/2021 |
| WO | 2021120045 A1 | 6/2021 |
| WO | 2021121330 A1 | 6/2021 |
| WO | 2021121367 A1 | 6/2021 |
| WO | 2021121371 A1 | 6/2021 |
| WO | 2021121397 A1 | 6/2021 |
| WO | 2021126120 A1 | 6/2021 |
| WO | 2021126799 A1 | 6/2021 |
| WO | 2021127404 A1 | 6/2021 |
| WO | 2021129820 A1 | 7/2021 |
| WO | 2021129824 A1 | 7/2021 |
| WO | 2021139678 A1 | 7/2021 |
| WO | 2021139748 A1 | 7/2021 |
| WO | 2021141628 A1 | 7/2021 |
| WO | 2021142252 A1 | 7/2021 |
| WO | 2021143693 A1 | 7/2021 |
| WO | 2021145520 A1 | 7/2021 |
| WO | 2021145521 A1 | 7/2021 |
| WO | 2021147965 A1 | 7/2021 |
| WO | 2021147967 A1 | 7/2021 |
| WO | 2021150613 A1 | 7/2021 |
| WO | 2021152149 A1 | 8/2021 |
| WO | 2021168193 A1 | 8/2021 |
| WO | 2021169963 A1 | 9/2021 |
| WO | 2021169990 A1 | 9/2021 |
| WO | 2021173923 A1 | 9/2021 |
| WO | 2021175199 A1 | 9/2021 |
| WO | 2021177721 A1 | 9/2021 |
| WO | 2021178740 A2 | 9/2021 |
| WO | 2021178741 A1 | 9/2021 |
| WO | 2021180181 A1 | 9/2021 |

(56) References Cited

FOREIGN PATENT DOCUMENTS

| | | |
|---|---|---|
| WO | 2021185233 A1 | 9/2021 |
| WO | 2021190467 A2 | 9/2021 |
| WO | 2021197499 A1 | 10/2021 |
| WO | 2021203768 A1 | 10/2021 |
| WO | 2021207172 A1 | 10/2021 |
| WO | 2021211864 A1 | 10/2021 |
| WO | 2021215544 A1 | 10/2021 |
| WO | 2021216770 A1 | 10/2021 |
| WO | 2021217019 A1 | 10/2021 |
| WO | 2021090855 A1 | 11/2021 |
| WO | 2021218110 A1 | 11/2021 |
| WO | 2021219072 A1 | 11/2021 |
| WO | 2021219090 A2 | 11/2021 |
| WO | 2021219091 A1 | 11/2021 |
| WO | 2021228161 A1 | 11/2021 |
| WO | 2021231526 A1 | 11/2021 |
| WO | 2021236475 A1 | 11/2021 |
| WO | 2021239058 A1 | 12/2021 |
| WO | 2021243280 A1 | 12/2021 |
| WO | 2021244603 A1 | 12/2021 |
| WO | 2021245051 A1 | 12/2021 |
| WO | 2021245055 A1 | 12/2021 |
| WO | 2021245499 A1 | 12/2021 |
| WO | 2021248079 A1 | 12/2021 |
| WO | 2021248082 A1 | 12/2021 |
| WO | 2021248083 A1 | 12/2021 |
| WO | 2021248090 A1 | 12/2021 |
| WO | 2021248095 A1 | 12/2021 |
| WO | 2021249563 A1 | 12/2021 |
| WO | 2021252339 A1 | 12/2021 |
| WO | 2021257828 A1 | 12/2021 |
| WO | 2021259331 A1 | 12/2021 |
| WO | 2022002102 A1 | 1/2022 |
| WO | 2022015375 A1 | 1/2022 |
| WO | 2022017339 A1 | 1/2022 |
| WO | 2022028346 A1 | 2/2022 |
| WO | 2022028492 A1 | 2/2022 |
| WO | 2022031678 A1 | 2/2022 |
| WO | 2022036176 A1 | 2/2022 |
| WO | WO-2022236578 A1 * | 11/2022 |
| WO | 2022258974 A1 | 12/2022 |
| WO | 2023039240 A1 | 3/2023 |

OTHER PUBLICATIONS

Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.
Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right col., Para 2.
Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.
Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.
Broutin, S. et al., "Insights into significance of combined inhibition of MEK and m-TOR signalling output in KRAS mutant non-small-cell lung cancer", British Journal of Cancer (2016), 1-4 | doi: 10.1038/bjc.2016.220.
Burgess, M. et al., "KRAS Allelic Imbalance Enhances Fitness and Modulates MAP Kinase Dependence in Cancer", Cell 168, 817-829, Feb. 23, 2017, Elsevier Inc.
Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.

Costa-Cabral, S. et al., "CDK1 Is a Synthetic Lethal Target for KRAS Mutant Tumours", PLoS One | DOI: 10.137/journal.pone. 0149099 Feb. 16, 2016.
Cully, "Closing the door on KRAS-mutant lung cancer", Nature Reviews Drug Discovery | Published online Nov. 3, 2016; doi:10. 1038/nrd.2016.216, MacMillan Publishers.
Dharmaiah, S. et al., "Structural basis of recognition of farnesylated and methylated KRAS4b by PDEδ", E6766-E6775, PNAS, Published online Oct. 17, 2016.
Fiala, O. et al., "The dominant role of G12C over other KRAS mutation types in the negative prediction of efficacy of epidermal growth factor receptor tyrosine kinase inhibitors in nonesmall cell lung cancer", Cancer Genetics 206 (2013) 26-31.
Ford, B. et al., "Structure of the G60A Mutant of Ras Implications for the Dominant Negative Effect", J. Biol. Chem., vol. 280, No. 27, Issue of Jul. 8, pp. 25697-25705, 2005.
Hall, B. et al., "The structural basis for the transition from Ras-GTP to Ras-GDP", PNAS, vol. 99, No. 19, pp. 12138-12142, Sep. 17, 2002.
Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.
Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.
Jarvis, L., "Have drug hunters finally cracked KRas?", c&en, vol. 94, Issue 23, pp. 28-33, Jun. 6, 2016.
Kamerkar, S. et al., "Exosomes facilitate therapeutic targeting of oncogenic KRAS in pancreatic cancer", Nature 546, 498-503 (Jun. 22, 2017) doi:10.1038/nature22341.
Kaufman, J. et al., "Treatment of KRAS-Mutant Non-Small Cell Lung Cancer The End of the Beginning for Targeted Therapies", JAMA May 9, 2017 vol. 317, No. 18.
Kerr, E. et al., "Mutant Kras copy number defines metabolic reprogramming and therapeutic susceptibilities", Nature 531, 110-113, (Mar. 3, 2016) doi:10.1038/nature16967.
Kim, J. et al., "CPS1 maintains pyrimidine pools and DNA synthesis in KRAS/LKB1-mutant lung cancer cells", Nature 546, 168-172, (Jun. 1, 2017) doi:10.1038/nature22359.
Kim, J. et al., "XPO1-dependent nuclear export is a druggable vulnerability in KRAS-mutant lung cancer", Nature 538, 114-117 (Oct. 6, 2016) doi:10.1038/nature19771.
Kitai, H. et al., "Key roles of EMT for adaptive resistance to MEK inhibitor in KRAS mutant lung cancer", SSN: 2154-1248 (Print) 2154-1256 (Online) Journal homepage: http://www.tandfonline.com/loi/ksgt20.
Kosloff, M. et al., "GTPase Catalysis by Ras and Other G-proteins: Insights from Substrate Directed SuperImposition", J. Mol. Biol. (2003) 331, 1157-1170, doi:10.1016/S0022-2836(03)00847-7.
Ledford, H., "Thirty years of pursuit have failed to yield a drug to take on one of the deadliest families of cancer- causing proteins. Now some researchers are taking another shot." The RAS Renaissance, Nature, vol. 520, 278-280, Apr. 16, 2015.
Lim, S. et all., "Therapeutic Targeting of Oncogenic K-Ras by a Covalent Catalytic Site Inhibitor", Angew. Chem. Int. Ed. 2014, 53, 199-204.
Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.
Manchado, E. et al., "A combinatorial strategy for treating KRAS-mutant lung cancer", Nature 534, 647-651 (Jun. 30, 2016) doi:10. 1038/nature18600.
Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.
Muller, M. et al., "Nucleotide based covalent inhibitors of KRas can only be efficient in vivo if they bind reversibly with GTP-like affinity", Scientific Reports, 7: 3687 | DOI:10.1038/s41598-017-03973-6.
Nadal, E. et al., "Abstract C141: KRAS G12C mutation is prognostic of poor outcome in resected lung adenocarcinomas and

(56) References Cited

OTHER PUBLICATIONS predictive of poor response to MEK inhibition in vitro", Mol Cancer Ther Nov. 12, 2013; C141, doi: 10.1158/1535-7163.TARG-13-C141.

Nussinov, R. et al., "Independent and core pathways in oncogenic KRAS signaling", Journal: Expert Review of Proteomics, DOI: 10.1080/14789450.2016.1209417, Published by Taylor & Francis.

Ostrem, J. et al., "Direct small-molecule inhibitors of KRAS: from structural insights to mechanism-based design", Nature Reviews Drug Discovery 15, 771-785 (2016) doi:10.1038/nrd.2016.139.

Ostrem, J. et al., "K-Ras(G12C) inhibitors allosterically control GTP affinity and effector interactions", Nature, vol. 503: 548, Nov. 28, 2013.

Papke, B. et al., "Drugging RAS: Know the enemy", Science 355, 1158-1163 (2017) Mar. 17, 2017.

Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.

Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15-1105.

Perara, D. et al., "Oncogenic KRAS triggers MAPK-dependent errors in mitosis and MYC-dependent sensitivity to anti-mitotic agents", Scientific Reports, 6:29741, DOI: 10.1038/srep29741.

Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.

Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15-1141, American Association for Cancer Research.

Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.

Rudoni, S. et al., "Role of guanine nucleotides in the regulation of the Ras/cAMP pathway in *Saccharomyces cerevisiae*", Biochimica et Biophysica Acta 1538 (2001) 181189.

Samatar, A. et al., "Targeting RAS-ERK signalling in cancer: promises and challenges", Nature Reviews Drug Discovery, vol. 13, pp. 928-942, Dec. 2014.

Sautier, B. et al., "Latest advances towards RAS inhibition—A medicinal chemistry perspective", Angewandte Chemie International Edition, 10.1002/anie.201608270.

Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.

Shima, F. et al., "Structural Basis for Conformational Dynamics of GTP-bound Ras Protein", The Journal of Biological Chemistry, vol. 285, No. 29, pp. 22696-22705, Jul. 16, 2010.

Shipman, L., "Putting the brakes on KRAS-G12C nucleotide cycling", Nature Reviews Cancer, Published online Feb. 19, 2016; doi:10.1038/nrc.2016.13.

Spoerner, M. et al., "Dynamic properties of the Ras switch I region and its importance for binding to effectors", PNAS, vol. 98, No. 9, pp. 4944-4949, Apr. 24, 2001.

Sun, Q. et al., "Discovery of Small Molecules that Bind to K-Ras and Inhibit Sos-Mediated Activation**", Angew. Chem. Int. Ed. 2012, 51, 1-5, 2012 Wiley-VCH Verlag Gmbh & Co. KGaA, Weinheim.

Sun, Q., et al., "A method for the second-site screening of K-Ras in the presence of a covalently attached first-site ligand", J Biomol NMR (2014) 60:11-14 DOI 10.1007/s10858-014-9849-8.

Sung, Y. et al., "Mutagenesis of the H-ras p21 at Glycine-60 Residue Disrupts GTP-Induced Conformational Change", Biochemistry 1995, 34, 3470-3477, American Chemical Society.

Tape, C. et al., "Oncogenic KRAS Regulates Tumor Cell Signaling via Stromal Reciprocation", Cell 165, 1-11May 5, 2016.

Thierry, A. et al., "Clinical validation of the detection of KRAS and BRAF mutations from circulating tumor DNA", Nature Medicine, vol. 20, No. 4, pp. 430-436 , Apr. 2014.

Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.

Wang, Y. et al., "Targeting Mutant KRAS for Anticancer Therapeutics: A Review of Novel Small Molecule Modulators", J. Med. Chem. 2013, 56, 5219-5230, dx.doi.org/10.1021/jm3017706; 2013 American Chemical Society, ACS Publications.

Wang, Y. et al., "Ezh2 Acts as a Tumor Suppressor in Kras-driven Lung Adenocarcinoma", International Journal of Biological Sciences 2017; 13(5): 652-659. doi: 10.7150/ijbs.19108.

Welsch, M. et al., "Multivalent Small-Molecule Pan-RAS Inhibitors", Welsch et al., 2017, Cell 168, 878-889 Feb. 23, 2017; 2017 Elsevier Inc. http://dx.doi.org/10.1016/j.cell.2017.02.006.

Winter, J. et al., "Small Molecule Binding Sites on the Ras:SOS Complex Can Be Exploited for Inhibition of Ras Activation", J. Med. Chem. 2015, 58, 2265-2274; DOI: 10.1021/jm501660t; 2015 American Chemical Society, ACS Publications.

Wood, K. et al., "Reply" Comments & Response, Letters JAMA Oncology Published online Jul. 21, 2016, American Medical Association.

Xiong, Y. et al., "Development of covalent guanosine mimetic inhibitors of G12C KRAS", ACS Med. Chem. Lett., Just Accepted Manuscript • DOI: 10.1021/acsmedchemlett.6b00373 • Publication Date (Web): Nov. 30, 2016 Downloaded from http://pubs.acs.org on Dec. 1, 2016.

Xiong, Y. et al., "Covalent Guanosine Mimetic Inhibitors of G12C KRAS" ACS Med. Chem. Lett. 2017, 8, 61-66, DOI: 10.1021/acsmedchemlett.6b00373; 2016 American Chemical Society, ACS Publications.

Janes et al., "Targeting KRAS Mutant Cancers with a Covalent G12C-Specific Inhibitor", Cell 172, 578-589, Jan. 25, 2018.

Singh et al., "A Gene Expression Signature Associated with K-Ras Addiction" Reveals Regulators of EMT and Tumor Cell Survival, Cancer Cell 15, p. 489-500, Jun. 2, 2009.

Stephen et al., "Dragging Ras Back in the Ring", Cancer Cell 25, p. 272, Mar. 17, 2014.

Zhu et al., "Inhibition of KRAS-driven tumorigenicity by interruption of an autocrine cytokine circuit", doi:10.1158/2159-8290.CD-13-0646; Cancer Discovery Published OnlineFirst Jan. 20, 2014.

Simanshu et al., "RAS Proteins and Their Regulators in Human Disease", Cell 170, p. 17, Jun. 29, 2017.

Pacold et al., "Crystal Structure and Functional Analysis of Ras Binding to Its Effector Phosphoinositide 3-Kinase gamma", Cell, vol. 103, p. 931-943, Dec. 8, 2000.

Lech-Gustav et al., "The Renaissance of Ras", ACS Chem. Biol., 2014, 9, 2447-2458.

Karachaliou et al., "KRAS Mutations in Lung Cancer", Clinical Lung Cancer, vol. 14, No. 3, p. 2015-14, 2013.

Schwartz et al., "Covalent EGFR inhibitor analysis reveals importance of reversible interactions to potency and mechanisms of drug resistance", PNAS, vol. 111, No. 1, p. 173-178, Jan. 7, 2014.

Sun et al., "A method for the second-site screening of K-Ras in the presence of a covalently attached first-site ligand", J. Biomol. NMR (2014) vol. 60 p. 11-14.

Kyriakis, J., "Thinking Outside the Box about Ras", J. Biol. Chem. 2009, 284:10993-10994, published online Dec. 17, 2008.

Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.

Serafimova et al., "Reversible targeting of noncatalytic cysteines with chemically tuned electrophiles", Nat Chem Biol.; 8(5):471-476. doi: 10.1038/nchembio.925.

Walker et al., "Structural insights into phosphoinositide 3-kinase catalysis and signalling", Nature vol. 402, p. 18 Nov. 1999; www.nature.com.

Barbie et al., "Systematic RNA interference reveals that oncogenic KRAS-driven cancers require TBK1", Nature, vol. 462, p. 108, Nov. 5, 2009; doi:10.1038/nature08460.

(56) References Cited

OTHER PUBLICATIONS

Zimmermann et al., "Small molecule inhibition of the KRAS-PDEdelta interaction impairs oncogenic KRAS signalling", Nature, vol. 497, p. 638, May 30, 2013.
Karnoub et al., "Ras oncogenes: split personalities", Nature Reviews, molecular Cell Biology, vol. 9, Jul. 2008 p. 517.
Nassar et al., "Ras/Rap effector specificity determined by charge reversal", Nature Structural Biology, vol. 3, No. 8, Aug. 1996.
De Rooij et al., "Minimal Ras-binding domain of Raf1 can be used as an activation-specific probe for Ras", Oncogene (1997) 14, 623-625, 1997 Stockton Press.
Cox et al., "The dark side of RAs: regulation of apoptosis", Oncogene (2003) 22, 8999-9006, 2003 Nature Publishing Group.
Tanaka et al., "Interfering with RAS-effector protein interactions prevent RAS-dependent tumour initiation and causes stop-start control of cancer growth", Oncogene (2010) 29, 6064-6070, 2010 Macmillan Publishers Limited.
Grant et al., "Novel Allosteric Sites on Ras for Lead Generation", PLoS One, vol. 6, Issue 10, Oct. 2011.
Maegley et al., "Ras-catalyzed hydrolysis of GTP: A new perspective from model studies", Proc. Natl. Acad. Sci. USA, vol. 93, pp. 8160-8166, Aug. 1996.
Ahmadian et al., "Guanosine triphosphatase stimulation of oncogenic Ras mutants", Proc. Natl. Acad. Sci. USA, vol. 96, pp. 7065-7070, Jun. 1999.
Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.
Kotting et al., "The GAP arginine finger movement into the catalytic site of Ras increases the activation entropy", PNAS, vol. 105, No. 17, p. 6260-6265, Apr. 29, 2008.
Shaw et al., "Selective killing of K-ras mutant cancer cells by small molecule inducers of oxidative stress", PNAS, vol. 108, No. 21, p. 8773-8778, May 24, 2011.
Ischenko et al., "Direct reprogramming by oncogenic Ras and Myc", PNAS early edition 1, 2013.
Smith et al., "NMR-based functional profiling of RASopathies and oncogenic RAS mutations", PNAS, vol. 110, No. 12, p. 4574-4579, Mar. 19, 2013.
Shima, et al., "In silico discovery of small-molecule Ras inhibitors that display antitumor activity by blocking the Ras-effector interaction", PNAS, vol. 110, No. 20, p. 8182-8187, May 14, 2013.
Burns et al., "Approach for targeting Ras with small molecules that activate SOS-mediated nucleotide exchange", PNAS, vol. 111, No. 9, p. 3401-3406, Mar. 4, 2014.
Zeng et al., "Design of inhibitors of Ras-Raf interaction using a computational combinatorial algorithm", Protein Engineering, vol. 14, No. 1, p. 39-45, 2001.
Scheffzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36 (2): 65-77. doi: 10.1016/j.tibs.2010.09.006.
Fell et al. 'Discovery of Tetrahydropyridopyrimidines as Irreversible Covalent Inhibitors of Kras-G12C with In Vivo Activity', ACS Medicinal Chemistry Letters, Nov. 7, 2018 (Jul. 11, 2018), vol. 9, pp. 1230-1234.
International Search Report and Written Opinion for corresponding PCT application No. PCT/US18/61060 mailed Feb. 7, 2019.
Martin, James S. et al., "Characterising covalent warhead reactivity", Bioorganic & Medicinal Chemistry, 27 (2019) 2066-2074.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.
Figueras, A. et al., "The impact of KRAS mutations on VEGF-A production and tumour vascular network", BMC Cancer 2013, 13:125.
Janes, M. et al., "Targeting KRAS Mutant Cancers with a Covalent G12C-Specific Inhibitor", 2018, Cell 172, 578-589, Jan. 25, 2018, Elsevier Inc.
Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.
McCormick, F., "Targeting KRAS Directly", Annual Review of Cancer Biology, 2018, 2:81, 81-90.
Misale, S. et al., Kras G12C NSCLC models are sensitive to direct targeting of KRAS in combination with PI3K inhibition, Downloaded from clincancerres.aacrjournals.org on Oct. 22, 2018. © 2018 American Association for Cancer Research.
Nabet, B. et al., "It Takes Two To Target: A Study in KRAS Dimerization", pubs.acs.org/biochemistry, DOI: 10.1021.
O'Bryan, J., "Pharmacological Targeting of RAS: Recent Success with Direct Inhibitors", Pharmacological Research (2018), https://doi.org/10.1016/j.phrs.2018.10.021.
Ruess, D. et al., "Mutant KRAS-driven cancers depend on PTPN11/SHP2 phosphatase", Nature Medicine, Letters, https://doi.org/10.1038/s41591-018-0024-8.
Simanshu, D. et al., "RAS Proteins and Their Regulators in Human Disease", Cell 170, 17-33, Jun. 29, 2017.
Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432.CCR-18-1640, Downloaded from clincancerres.aacrjournals.org on Oct. 29, 2018. © 2018 American Association for Cancer Research.
Wijeratne, A. et al., "Chemical Proteomic Characterization of a covalent KRASG12C inhibitor", ACS Med. Chem. Ltter., DOI: 10.1021/acsmedchemlett.8b00110, May 21, 2018.
Wood, K. et al., "Prognostic and Predictive Value in KRAS in Non-Small-Cell Lung Cancer A Review", JAMA Oncol. 2016:2(6), 805-812, Apr. 21, 2016.
Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.
Ziemke, E. et al., "Sensitivity of KRAS-Mutant Colorectal Cancers to Combination Therapy That Cotargets MEK and CDK4/6", Clin Cancer Res; 22(2) Jan. 15, 2016.
Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.
Hansen, R. et al., "An Internally Controlled Quantitative Target Occupancy Assay for Covalent Inhibitors", Scientific Reports, 8:14312 (2018), DOI: 10.1038/s41598-018-32683-w.
Pantsar, T. et al., "Assessment of mutation probabilities of Kras G12 missense mutants and their long-timescale dynamics by atomistic molecular simulations and Markov state modeling", PLOS Computational Biology, Sep. 10, 2018.
Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.
Yuan, T. et al., "Differential Effector Engagement by Oncogenic KRAS", Cell Reports 22, 1889-1902, Feb. 13, 2018, Cell Press.
PubChem-SID-132593111, Modify Date: May 31, 2019 (May 31, 2019), p. 2, figure, this is a purchasable chemical.
JP 2015-124211 A (Dainippon Sumitomo Pharma Co L TD) Jul. 6, 2015 (Jun. 6, 2015), especially: original document, p. 58, Table, formula 93.
Bakalova et al. "Electronic absorption and emission spectra and computational studies of some 2-aryl, 2-styryl, and 2-(40-aryl)butadienyl quinazolin-4-ones", Journal of Molecular Structure (Theochem). 2004. 710, 229-234, especially: p. 230, Scheme 2.
Orlov et al. "Rapid Improvement of the Performance Status and Reduction of the Tumor Size in KRAS-Mutated Colorectal Cancer Patient Receiving Binimetinib, Hydroxychloroquine, and Bevacizumab", Case Rep Oncol. 2020. 13: pp. 985-989, para 3; p. 988, para 4.

(56) References Cited

OTHER PUBLICATIONS

Canon et al. "The clinical KRAS(G12C) inhibitor AMG 510 drives anti-tumour immunity", Nature. 2019. vol 575, pp. 217-223, especially: abstract; p. 218, Fig. 1a, formula AMG 510; p. 220, col. 2, para 2.

Lanman et al. "Discovery of a Covalent Inhibitor of KRASG12C (Amg 510) for the Treatment of Solid Tumors" Journal of Medicinal Chemistry. Dec. 10, 2019 (Dec. 10, 2019) vol. 63, p. 52-65; p. 52, abstract.

Abe, H et al. Discovery of a Highly Potent and Selective MEK Inhibitor: GSK1120212 (JTP-74057 DMSO Solvate). ACS Medicinal Chemistry Letters, vol. 2, No. 4, Feb. 28, 2011, doi: 10.1021/ml200004g, pp. 320-324; p. 321, figure 1.

Ciapetti, P. et al. "Molecular Variations Based on Isosteric Replacements" *The Practice of Medicinal Chemistry*, Jan. 1, 2008, Elsevier, Amsterdam, NL, pp. 181-241.

Supplementary Partial European Search Report for EP Application No. 21907336, Munich, Germany, mailed on Oct. 23, 2024, 12 pages.

\* cited by examiner

AZAQUINAZOLINE PAN-KRas INHIBITORS

FIELD OF THE INVENTION

The present invention relates to compounds that inhibit multiple mutated forms of KRas, i.e., pan-KRas inhibitors. In particular, the present invention relates to pan-KRas compounds, pharmaceutical compositions comprising the compounds and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors to regulate a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas. KRas mutations at codons 12, 13, 61 and other positions of the KRas primary amino acid sequence are present in 88% of all pancreatic adenocarcinoma patients, 50% of all colon/rectal adenocarcinoma patients, and 32% lung adenocarcinoma patients (e.g., see Prior et all., (2020) Cancer Res 80:2969-74). A recent publication also suggested wild type Kras inhibition could be a viable therapeutic strategy to treat $KRas^{WT}$ dependent cancers (e.g., see Bery et al., (2020) Nat. Commun. 11: 3233).

The well-known role of KRas in malignancy and the discovery of these frequent mutations in KRas in various tumor types made KRas a highly attractive target of the pharmaceutical industry for cancer therapy. Notwithstanding thirty years of large-scale discovery efforts to develop inhibitors of KRas for treating cancer, no KRas inhibitor has yet demonstrated sufficient safety and/or efficacy to obtain regulatory approval (e.g., see McCormick (2015) Clin Cancer Res. 21 (8):1797-1801).

Compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well recent advances in the covalent targeting of an allosteric pocket of KRas G12C (e.g., see Ostrem et al., (2013) Nature 503:548-551 and Fell et al., (2018) ACS Med. Chem. Lett. 9:1230-1234). Clearly there remains a continued interest and effort to develop inhibitors of KRas, particularly inhibitors of activating KRas mutants-.

Thus, there is a need to develop new pan-KRas inhibitors that demonstrate sufficient efficacy for treating KRas-mediated cancers.

SUMMARY OF THE INVENTION

In one aspect of the invention, compounds are provided that inhibit KRas activity. In certain embodiments, the compounds are represented by Formula (I):

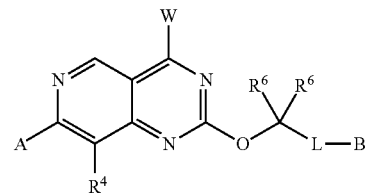

Formual (I)

or a pharmaceutically acceptable salt thereof, wherein:

W is:

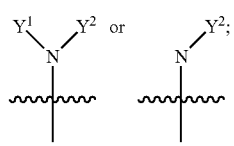

A is aryl or heteroaryl, wherein the aryl or the heteroaryl is optionally substituted with 1-4 $R^1$;

B is selected from:

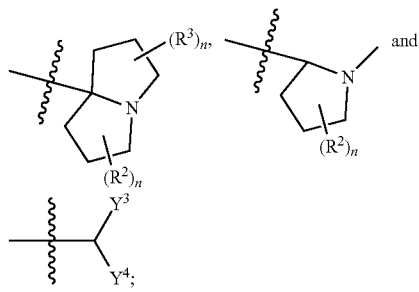

$Y^1$ is hydrogen, L-hydroxy optionally substituted with 1-4 $R^8$, L-alkoxy optionally substituted with 1-4 $R^8$, halogen, L-C3-C6 cycloalkyl optionally substituted with 1-4 $R^9$, L-heteroaryl optionally substituted with 1-4 $R^8$, L-aryl optionally substituted with 1-4 $R^8$, L-C(O)—$NH_2$, and L-heterocycle substituted with 1-2 oxo (=O) or oxo-containing substituent, and optionally further substituted with 1-2 $R^8$;

$Y^2$ is hydrogen or C1-C4 alkyl;

or $Y^1$ and $Y^2$ join to form:

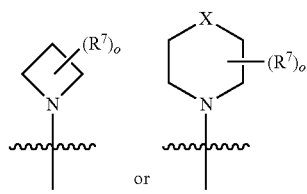

where X is selected from: a bond, —S—, —O—, —N< bound to a fused ring, —$CH_2$—, —$CH_2$—N—, —$CH_2$—N—$CH_2$—, —$CH_2$—$CH_2$—$CH_2$—, —$CH_2$—$CH_2$—, —O—$CH_2$— and —S—$CH_2$—;

$Y^3$ is hydrogen or C1-C4 alkyl;

$Y^4$ is hydrogen or C1-C4 alkyl;

or Y³ and Y⁴ join to form:

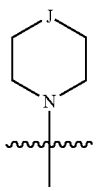

where J is selected from: a bond, —O—, —NH—, —CH₂—, —C(C1-C3 alkyl)₂-, —CH(C1-C3alkyl)- and —N(C1-C3 alkyl)-;

each $R^1$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxyC1-C3 alkyl, —CH₂C(=O)N(R⁵)₂, —C3-C4 alkynyl(NR⁵)₂, —N(R⁵)₂, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl;

each $R^2$ is independently hydrogen, hydroxy, halogen, cyano, C1-C3 alkyl, C1-C3 cyanoalkyl, C1-C3 hydroxyalkyl, HC(=O)—, -L-OC(O)N(R⁵)₂, —CO₂R⁵, or —CO₂N(R⁵)₂;

each $R^3$ is independently hydrogen, hydroxy, halogen, cyano, C1-C3 alkyl, C1-C3 cyanoalkyl, C1-C3 hydroxyalkyl, HC(=O)—, -L-OC(O)N(R⁵)₂, —CO₂R, or —CO₂N(R⁵)₂;

each $R^4$ is independently hydrogen, halogen or C1-C3 alkyl;

each $R^5$ is independently hydrogen or C1-C3 alkyl, or two $R^5$ join to form cycloalkyl or heterocycle;

each $R^6$ is independently hydrogen, hydroxy, C1-C4 hydroxyalkyl or heteroaryl, or two $R^6$ join to form C3-C6 cycloalkyl or heterocycle;

each $R^7$ is independently hydrogen, C1-C3 alkyl, hydroxy, halogen, C1-C3 haloalkyl, -L-NH₂, —NH(C1-C3 alkyl), —N(C1-C3 alkyl)₂, oxo (=O), —O—(C1-C3 alkyl), —(C1-C3 alkyl)—OH, —C(O)OH, —C(O)O(C1-C3 alkyl), —C(O)N(R¹⁰)₂, —NHC(O)H, —CN, aryl, —(CH₂)₁₋₂S(O)₂N(R¹⁰)₂, —NH—S(O)₂N(R¹⁰)₂, —O—S(O)₂N(R¹⁰)₂, S(O)₂R¹⁰, or heteroaryl or heterocycle optionally independently substituted with 1-2 substituents independently selected from C1-C3 alkyl, —CN and C(O)NH₂, two $R^7$ on the same atom optionally join to form a spirocyclic ring selected from C3-C6 cycloalkyl and heterocycle, where said spirocyclic ring is optionally substituted with 1-4 substituents independently selected from oxo (=O), halogen, hydroxy, C1-C3 alkyl and —O—(C1-C3 alkyl), two $R^7$ on adjacent atoms optionally join to form a bond or a fused ring selected from C3-C6 cycloalkyl optionally substituted with 1-4 $R^8$, heteroaryl optionally substituted with 1-4 $R^8$, aryl optionally substituted with 1-4 $R^8$, and heterocycle optionally substituted with 1-4 $R^8$, and two $R^7$ on non-adjacent atoms optionally join to form a 1-2 carbon bridge;

each $R^8$ is independently C1-C3 alkyl, hydroxy, halogen, —N(R10)₂, —N(R10)C(O)R10, oxo (=O), —O—(C1-C3 alkyl), —(C1-C3 alkyl)—OH, —C(O)OH, —C(O)O(C1-C3 alkyl), —C(O)N(R¹⁰)₂, heteroaryl or —CN;

each $R^9$ is independently C1-C3 alkyl, hydroxy, halogen, oxo (=O), —O—(C1-C3 alkyl), —(C1-C3 alkyl)—OH, —C(O)OH, —C(O)O(C1-C3 alkyl), —C(O)NH₂, —C(O)NH(C1-C3 alkyl), —C(O)N(C1-C3 alkyl)₂ or —CN;

each $R^{10}$ is independently hydrogen, halogen, C1-C3 alkyl, or two $R^{10}$ join to form cycloalkyl or heterocycle optionally substituted with 1-2 C1-C3 alkyl;

each L is independently a bond, —C1-C4 alkyl-, —C1-C4 alkyl-NH—, —NH—, —N(C1-C3 alkyl)- or cyclopropyl-CH₂—;

each n is 0-3;
o is 1-6; and
p is 1-8.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods for inhibiting the activity of cells containing wild type KRas or one or more KRas mutations, for instance the KRas mutations G12A, G12C, G12D, G12R, G12S, G12V, G13D and/or Q61H, in a in a cell, comprising contacting the cell with a compound of Formula (I), or a pharmaceutically acceptable salt thereof, or a pharmaceutical composition thereof as defined herein. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula (I), or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method of treating a KRas wild type, KRas G12A, G12C, G12D, G12R, G12S, G12V, G13D and/or Q61H-associated disease or disorder in a patient in need of such treatment, the method comprising administering to the patient a therapeutically effective amount of a compound of Formula (1), or a pharmaceutically acceptable salt thereof, or a pharmaceutical composition thereof as defined herein.

Also provided herein is a compound of Formula (I), or a pharmaceutically acceptable salt thereof, or a pharmaceutical composition thereof as defined herein for use in therapy.

Also provided herein is a compound of Formula (I), or a pharmaceutically acceptable salt thereof or a pharmaceutical composition thereof as defined herein for use in the treatment of cancer.

Also provided herein is a compound of Formula (I), or a pharmaceutically acceptable salt thereof for use in the inhibition of KRas wild type or multiple types of KRas mutations, for instance KRas G12A, G12C, G12D, G12R, G12S, G12V, G13D and/or Q61H mutations.

Also provided herein is a compound of Formula (I), or a pharmaceutically acceptable salt thereof or a pharmaceutical composition thereof as defined herein, for use in the treatment of a KRas wild type associated disease or disorder or a KRas mutation G12A, G12C, G12D, G12R, G12S, G12V, G13D and/oi Q61H-associated disease or disorder.

Also provided herein is the use of a compound of Formula (I), or a pharmaceutically acceptable salt thereof, as defined herein in the manufacture of a medicament for the treatment of cancer.

Also provided herein is a use of a compound of Formula (I), or a pharmaceutically acceptable salt thereof, as defined herein in the manufacture of a medicament for the inhibition of activity of the wild type form of KRas or mutated forms of KRas, including the mutations: G12A, G12C, G12D, G12R, G12S, G12V, G13D and/or Q61H.

Also provided herein is the use of a compound of Formula (I), or a pharmaceutically acceptable salt thereof, as defined herein, in the manufacture of a medicament for the treatment of a KRas wild type associated disease or disorder or a KRas G12A, G12C, G12D, G12R, G12S, G12V, G13D and/or Q61H-associated disease or disorder.

Also provided herein is a method for treating cancer in a patient in need thereof, the method comprising (a) determining that the cancer is associated with KRas wild type or a KRas G12A, G12C, G12D, G12R, G12S, G12V, G13D and/or Q61H mutation (i.e., a KRas G12A, G12C, G12D, G12R, G12S, G12V, G13D and/or Q61H-associated cancer); and (b) administering to the patient a therapeutically effective amount of a compound of Formula (I), or a pharmaceutically acceptable salt thereof, or a pharmaceutical composition thereof.

One potential utility of the herein-described pan-KRas inhibitors, including pan-KRas inhibitors such as (R)-1-(7-(8-ethyl-7-fluoro-3-hydroxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)-3-methylpiperidin-3-ol (Example 5 herein), is for the treatment of cancers that develop resistance following long-term treatment with KRas G12C inhibitors. Thus, embodiments of the invention include those wherein a patient suffering from cancer is treated with a herein-described pan-KRas inhibitor such as Example 5 after treatment with a G12C inhibitor becomes ineffective or less effective due to the emergence of resistance-imparting mutations.

Treatment of KRas G12C mutant cancers with covalent KRas G12C inhibitors such as adagrasib (MRTX849) or sotorasib (AMG510) may result in the incorporation of additional mutations that confer resistance to adagrasib. These mutations could confer resistance through numerous mechanisms.

Mutations that change the mutant cysteine at codon 12 to another amino acid would render the current covalent KRas G12C inhibitors ineffective since current inhibitors make a covalent bond with the mutant cysteine amino acid side chain. Likewise, in patients that have one wild type KRas allele in addition to the KRas G12C-mutant allele, mutations in the wild type codon 12 glycine to another codon would allow bypass signaling in these tumors through the novel mutant protein. The repertoire of codon 12 mutations that can occur with a single nucleotide substitution in the wild type gene (glycine codon) includes mutations commonly observed in cancer such as G12S, G12V, G12R, G12C. The repertoire of codon 12 mutations that can occur with single nucleotide base substitutions of the cysteine codon 12 include mutations not frequently observed in cancer, G12Y, G12F and G12W, in addition to G12S and G12R.

Second-site mutations may also occur in another location in the KRas G12C mutant gene that confers resistance to KRas G12C inhibitor treatment. These mutations may confer resistance through different mechanisms. RAS proteins are small GTPases that normally cycle between an active, GTP-bound state and an inactive, GDP-bound state. RAS proteins are loaded with GTP through guanine nucleotide exchange factors (GEFs; e.g., SOS1) which are activated by upstream receptor tyrosine kinases, triggering subsequent interaction with effector proteins that activate RAS-dependent signaling. RAS proteins hydrolyze GTP to GDP through their intrinsic GTPase activity which is dramatically enhanced by GTPase-activating proteins (GAPs). Mutations at codons 12 and 13 in RAS proteins impair GAP-stimulated GTP hydrolysis leaving RAS predominantly in the GTP-bound, active state. Covalent KRas G12C inhibitors in current clinical development only bind GDP-bound KRas G12C. Mutations such as Q61 codon mutations, which may or may not occur on the same allele as the G12C mutation, reduce the intrinsic GTPase activity of KRas and may represent a mechanism of resistance to KRas G12C inhibitor treatment by shifting KRas into the GTP-loaded state where it is not susceptible to covalent inhibition. Co-mutations such as R68, H95 and Y96 may be present along with the KRas G12C mutation and may diminish the binding affinity of KRas G12C inhibitors to the Switch II binding pocket.

The herein-described pan-KRas inhibitors may demonstrate activity against common as well as uncommon codon 12 mutations or mutations that occur in the KRas protein that diminish binding of KRas G12C inhibitors to the KRas protein.

Also provided herein is a process for preparing a compound of Formula (I), or a pharmaceutically acceptable salt thereof.

Also provided herein is a compound of Formula (I), or a pharmaceutically acceptable salt thereof obtained by a process of preparing the compound as defined herein.

DETAILED DESCRIPTION OF THE INVENTION

The present invention relates to inhibitors of KRas wild type and/or multiple mutated forms of KRas, for instance KRas G12A, G12C, G12D, G12R, G12S, G12V, G13D and/or Q61H mutations. In particular, the present invention relates to compounds that inhibit the activity of KRas wild type and/or KRas mutations such as G12A, G12C, G12D, G12R, G12S, G12V, G13D and/or Q61H, pharmaceutical compositions comprising a therapeutically effective amount of the compounds and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "wild type KRas" refers to a non-mutant form of a mammalian KRas protein. The assignment of amino acid codon and residue positions for human KRas is based on the amino acid sequence identified by UniProtKB/Swiss-Prot P01116: Variantp.Gly12Asp. As used herein, a "wild type KRas inhibitor" refers to compounds of the present invention that are represented by Formula (I), as described herein. These compounds are capable of negatively modulating or inhibiting all or a portion of the enzymatic activity of wild type KRas G12A. A "wild type KRas-associated disease or disorder" as used herein refers to diseases or disorders associated with or mediated by or having wild type KRas. A non-limiting example of a wild type KRas-associated disease or disorder is a wild type KRas-associated cancer.

As used herein, "KRas G12A" refers to a mutant form of a mammalian KRas protein that contains an amino acid substitution of an alanine for a glycine at amino acid position 12. The assignment of amino acid codon and residue positions for human KRas is based on the amino acid sequence identified by UniProtKB/Swiss-Prot P01116:

Variantp.Gly12Asp. As used herein, a "KRas G12A inhibitor" refers to compounds of the present invention that are represented by Formula (I), as described herein. These compounds are capable of negatively modulating or inhibiting all or a portion of the enzymatic activity of KRas G12A. A "KRas G12A-associated disease or disorder" as used herein refers to diseases or disorders associated with or mediated by or having a KRas G12A mutation. A non-limiting example of a KRas G12A-associated disease or disorder is a KRas G12A-associated cancer.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variantp.Gly12Asp. As used herein, a "KRas G12C inhibitor" refers to compounds of the present invention that are represented by Formula (I), as described herein. These compounds are capable of negatively modulating or inhibiting all or a portion of the enzymatic activity of KRas G12C. A "KRas G12C-associated disease or disorder" as used herein refers to diseases or disorders associated with or mediated by or having a KRas G12C mutation. A non-limiting example of a KRas G12C-associated disease or disorder is a KRas G12CD-associated cancer.

As used herein, "KRas G12D" refers to a mutant form of a mammalian KRas protein that contains an amino acid substitution of an aspartic acid for a glycine at amino acid position 12. The assignment of amino acid codon and residue positions for human KRas is based on the amino acid sequence identified by UniProtKB/Swiss-Prot P01116: Variantp.Gly12Asp. As used herein, a "KRas G12D inhibitor" refers to compounds of the present invention that are represented by Formula (I), as described herein. These compounds are capable of negatively modulating or inhibiting all or a portion of the enzymatic activity of KRas G12D. A "KRas G12D-associated disease or disorder" as used herein refers to diseases or disorders associated with or mediated by or having a KRas G12D mutation. A non-limiting example of a KRas G12D-associated disease or disorder is a KRas G12D-associated cancer.

As used herein, "KRas G12R" refers to a mutant form of a mammalian KRas protein that contains an amino acid substitution of an arginine for a glycine at amino acid position 12. The assignment of amino acid codon and residue positions for human KRas is based on the amino acid sequence identified by UniProtKB/Swiss-Prot P01116: Variantp.Gly12Asp. As used herein, a "KRas G12R inhibitor" refers to compounds of the present invention that are represented by Formula (1), as described herein. These compounds are capable of negatively modulating or inhibiting all or a portion of the enzymatic activity of KRas G12R. A "KRas G12R-associated disease or disorder" as used herein refers to diseases or disorders associated with or mediated by or having a KRas G12R mutation. A non-limiting example of a KRas G12R-associated disease or disorder is a KRas G12R-associated cancer.

As used herein, "KRas G12S" refers to a mutant form of a mammalian KRas protein that contains an amino acid substitution of a serine for a glycine at amino acid position 12. The assignment of amino acid codon and residue positions for human KRas is based on the amino acid sequence identified by UniProtKB/Swiss-Prot P01116: Variantp.Gly12Asp. As used herein, a "KRas G12S inhibitor" refers to compounds of the present invention that are represented by Formula (1), as described herein. These compounds are capable of negatively modulating or inhibiting all or a portion of the enzymatic activity of KRas G12S. A "KRas G12S-associated disease or disorder" as used herein refers to diseases or disorders associated with or mediated by or having a KRas G12S mutation. A non-limiting example of a KRas G12S-associated disease or disorder is a KRas G12S-associated cancer.

As used herein, "KRas G12V" refers to a mutant form of a mammalian KRas protein that contains an amino acid substitution of a valine for a glycine at amino acid position 12. The assignment of amino acid codon and residue positions for human KRas is based on the amino acid sequence identified by UniProtKB/Swiss-Prot P01116: Variantp.Gly12Asp. As used herein, a "KRas G12V inhibitor" refers to compounds of the present invention that are represented by Formula (I), as described herein. These compounds are capable of negatively modulating or inhibiting all or a portion of the enzymatic activity of KRas G12V. A "KRas G12V-associated disease or disorder" as used herein refers to diseases or disorders associated with or mediated by or having a KRas G12V mutation. A non-limiting example of a KRas G12V-associated disease or disorder is a KRas G12V-associated cancer.

As used herein, "KRas G13D" refers to a mutant form of a mammalian KRas protein that contains an amino acid substitution of an aspartic acid for a glycine at amino acid position 13. The assignment of amino acid codon and residue positions for human KRas is based on the amino acid sequence identified by UniProtKB/Swiss-Prot P01116: Variantp.Gly12Asp. As used herein, a "KRas G13D inhibitor" refers to compounds of the present invention that are represented by Formula (I), as described herein. These compounds are capable of negatively modulating or inhibiting all or a portion of the enzymatic activity of KRas G13D. A "KRas G13D-associated disease or disorder" as used herein refers to diseases or disorders associated with or mediated by or having a KRas G13D mutation. A non-limiting example of a KRas G13D-associated disease or disorder is a KRas G13D-associated cancer.

As used herein, "KRas Q61H" refers to a mutant form of a mammalian KRas protein that contains an amino acid substitution of a histidine for a glutamine at amino acid position 61. The assignment of amino acid codon and residue positions for human KRas is based on the amino acid sequence identified by UniProtKB/Swiss-Prot P01116: Variantp.Gly12Asp. As used herein, a "KRas Q61H inhibitor" refers to compounds of the present invention that are represented by Formula (I), as described herein. These compounds are capable of negatively modulating or inhibiting all or a portion of the enzymatic activity of KRas Q61H. A "KRas Q61H-associated disease or disorder" as used herein refers to diseases or disorders associated with or mediated by or having a KRas Q61H mutation. A non-limiting example of a KRas Q61H-associated disease or disorder is a KRas Q61H-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having wild type KRas or a KRas G12A, G12C, G12D, G12R, G12S, G12V, G13D and/or Q61H mutation (e.g., as determined using a regulatory agency-approved, e.g., FDA-approved, assay or kit). In some embodiments, the subject has a tumor that is positive for wild type KRas or a KRas G12A, G12C, G12D, G12R, G12S, G12V, G13D and/or Q61H mutation (e.g., as determined using a regulatory agency-approved assay or kit). The subject can be a subject with a tumor(s) that is positive for wild type KRas or a KRas G12A, G12C, G12D, G12R, G12S, G12V, G13D and/or Q61H mutation (e.g., identified as positive using a regulatory agency-approved, e.g., FDA-approved, assay or kit). The subject can be a subject whose tumors have wild type KRas or a KRas G12A, G12C, G12D, G12R, G12S, G12V, G13D and/or Q61H mutation (e.g., where the tumor is identified as such using a regulatory agency-approved, e.g., FDA-approved, kit or assay). In some embodiments, the subject is suspected of having wild type KRas or a KRas G12A, KRas G12C, KRas G12D, KRas G12R, KRas G12S, KRas G12V, KRas G13D or KRas Q61H gene-associated cancer. In some embodiments, the subject has a clinical record indicating that the subject has a tumor that has wild type KRas or a KRas G12A, G12C, G12D, G12R, G12S, G12V, G13D and/or Q61H mutation (and optionally the clinical record indicates that the subject should be treated with any of the compositions provided herein).

In some embodiments of any of the methods or uses described herein, an assay is used to determine whether the patient has wild type KRas or a KRas G12A, G12C, G12D, G12R, G12S, G12V, G13D and/or Q61H mutation using a sample (e.g., a biological sample or a biopsy sample (e.g., a paraffin-embedded biopsy sample) from a patient (e.g., a patient suspected of having wild type KRas-associated or a KRas G12A, G12C, G12D, G12R, G12S, G12V, G13D and/or Q61H-associated cancer, a patient having one or more symptoms of wild type KRas-associated or a KRas G12A, G12C, G12D, G12R, G12S, G12V, G13D and/or Q61H-associated cancer, and/or a patient that has an increased risk of developing wild type KRas-associated or a KRas G12A, G12C, G12D, G12R, G12S, G12V, G13D and/or Q61H-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "acyl" refers to —C(O)CH$_3$.

The terms "C1-C6 alkyl", "C1-C4 alkyl" and "C1-C3 alkyl" as employed herein refers to straight and branched chain aliphatic groups having from 1-6 carbon atoms, or 1-4 carbon atoms, or 1-3 carbon atoms, respectively. Examples of alkyl groups include, without limitation, methyl, ethyl, propyl, isopropyl, butyl, isobutyl, sec-butyl, tert-butyl, pentyl, and hexyl.

The terms "C1-C3 haloalkyl" and "C1-C4 haloalkyl" refer to a C1-C3 alkyl chain or C1-C4 alkyl chain, respectively, as defined herein in which one or more hydrogen has been replaced by a halogen. Examples include trifluoromethyl, difluoromethyl and fluoromethyl.

An "C1-C4 alkylene," group is a C1-C4 alkyl group, as defined hereinabove, that is positioned between and serves to connect two other chemical groups. Exemplary alkylene groups include, without limitation, methylene, ethylene, propylene, and butylene.

The terms "C1-C3 alkoxy" and "C1-C4 alkoxy" refer to —OC1-C3 alkyl and —OC1-C4 alkyl, respectively, wherein the alkyl portion is as defined herein above.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted with one or more R$^8$ or R$^9$ groups as defined herein. Examples of cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkyl" also includes bridged cycloalkyls, such as bicyclo[1.1.1]pentanyl.

As used herein, the terms "C1-C3 hydroxyalkyl" and "C1-C4 hydroxyalkyl" refer to —C1-C3 alkylene-OH and —C1-C4 alkylene-OH, respectively.

As used herein, the term "C2-C4 hydroxyalkynyl" refers to —C2-C4 alkynylene-OH.

An "aryl" group is a C$_6$-C$_{14}$ aromatic moiety comprising one to three aromatic rings, which is optionally substituted with one or more R$^8$ or R$^9$ groups as defined herein. As one embodiment, the aryl group is a C$_6$-C$_{10}$ aryl group. Examples of aryl groups include, without limitation, phenyl, naphthyl, anthracenyl, fluorenyl, and dihydrobenzofuranyl. "Aryl" also refers to bicyclic or tricyclic ring systems in which one or two rings, respectively, of said aryl ring system may be saturated or partially saturated, and wherein if said ring system includes two saturated rings, said saturated rings may be fused or spirocyclic. An example of an aryl ring system comprising two saturated rings wherein the rings are spirocyclic includes the following ring system:

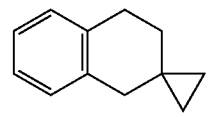

An "araC1-C6 alkyl" or "arylalkyl" group comprises an aryl group covalently linked to an alkyl group, either of which may independently be optionally substituted or unsubstituted. An example of an aralkyl group is (C$_6$-C$_{10}$)aryl(C$_1$-C$_6$)alkyl-, including, without limitation, benzyl, phenethyl, and naphthylmethyl. An example of a substituted araC1-C6 alkyl is wherein the alkyl group is substituted with hydroxyalkyl.

A "heterocyclyl" or "heterocyclic" group is a ring structure having from 3 to 12 atoms, for example 4 to 8 atoms, wherein one or more atoms are selected from the group consisting of N, O, and S wherein the ring N atom may be oxidized to N—O, and the ring S atom may be oxidized to SO or SO$_2$, the remainder of the ring atoms being carbon. The heterocyclyl may be a monocyclic, a bicyclic, a spirocyclic or a bridged ring system. The heterocyclic group is optionally substituted with one or more R$^8$ or R$^9$ groups on ring carbon or ring nitrogen at one or more positions, wherein R$^6$ is as defined for Formula I. The heterocyclic group is also independently optionally substituted on a ring nitrogen atom with alkyl, aralkyl, alkylcarbonyl, or on sulfur with lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, imidazopyridinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, thiomorpholinyl 1,1 dioxide, morpholinyl, azepanyl, oxazepanyl, azabicyclohexanyls, azabicycloheptanyl, azabicyclooctanyls, azabicyclononanyls (e.g., octahydroindolizinyl), azaspiroheptanyls, dihydro-1H, 3H, 5H-oxazolo[3,4-c]oxazolyl, tetrahydro-1'H, 3'H-spiro[cyclopropane-1,2'-pyrrolizine], hexahydro-1H-pyrrolizinyl, hexahydro-1H-pyrrolo[2,1-c][1,4]oxazinyl, octahydroindolizinyl, oxaazaspirononanyls, oxaazaspirooctanyls, diazaspirononanyls, oxaazabiocycloheptanyls, hexahydropyrrolizinyl 4 (1H)-oxide, tetrahydro-2H-thiopyranyl 1-oxide and tetrahydro-2H-thiopyranyl 1,1-dioxide. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14π electrons shared in a cyclic array; and having, in addition to carbon atoms, from one to three heteroatoms per ring, or from one to three heteroatoms in at least one ring, selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 6,7-dihydro-5H-pyrrolo[1,2-a]imidazole, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4 triazolyl, and xanthenyl. "Heteroaryl" also refers to bicyclic ring systems having, in addition to carbon atoms, from one to three heteroatoms per ring selected from the group consisting of N, O, and S in which one ring system may be saturated or partially saturated.

As used herein, "an effective amount" of a compound is an amount that is sufficient to negatively modulate or inhibit the activity of one or more of wild type KRas, KRas G12A, KRas G12C, KRas G12D, KRas G12R, KRas G12S, KRas G12V, KRas G13D or KRas Q61H. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of one or more of wild type KRas, KRas G12A, KRas G12C, KRas G12D, KRas G12R, KRas G12S, KRas G12V, KRas G13D or KRas Q61H. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

Compounds

In certain embodiments of the invention there are provided compounds of Formula (I):

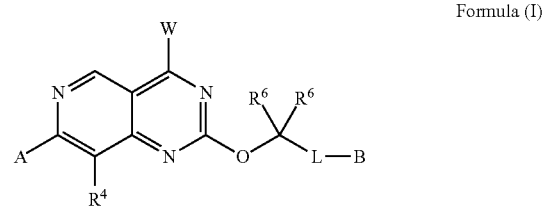

Formula (I)

or a pharmaceutically acceptable salt thereof, wherein:

W is:

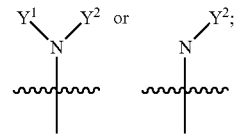

A is aryl or heteroaryl, wherein the aryl or the heteroaryl is optionally substituted with 1-4 $R^1$;

B is selected from:

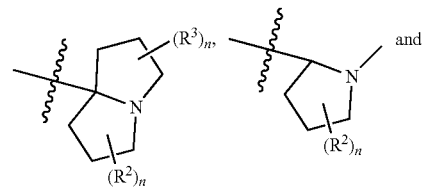

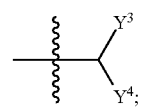

$Y^1$ is hydrogen, L-hydroxy optionally substituted with 1-4 $R^8$, L-alkoxy optionally substituted with 1-4 $R^8$, halogen, L-C3-C6 cycloalkyl optionally substituted with 1-4 $R^9$, L-heteroaryl optionally substituted with 1-4 $R^8$, L-aryl optionally substituted with 1-4 $R^8$, L-C(O)—NH$_2$, and L-heterocycle substituted with 1-2 oxo (=O) or oxo-containing substituent, and optionally further substituted with 1-2 $R^8$;

$Y^2$ is hydrogen or C1-C4 alkyl;

or $Y^1$ and $Y^2$ join to form:

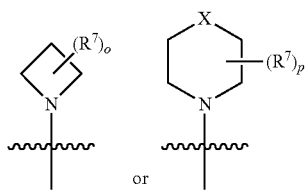

or where X is selected from: a bond, —S—, —O—, —N< bound to a fused ring, —CH$_2$—, —CH$_2$—N—, —CH$_2$—N—CH$_2$—, —CH$_2$—CH$_2$—CH$_2$—, —CH$_2$—CH$_2$—, —O—CH$_2$— and —S—CH$_2$—;

$Y^3$ is hydrogen or C1-C4 alkyl;

$Y^4$ is hydrogen or C1-C4 alkyl;

or $Y^3$ and $Y^4$ join to form:

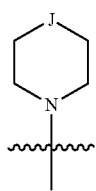

where J is selected from: a bond, —O—, —NH—, —CH$_2$—, —C(C1-C3 alkyl)$_2$-, —CH(C1-C3alkyl)- and —N(C1-C3 alkyl)-;

each $R^1$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxyC1-C3 alkyl, —CH$_2$C(=O)N(RV)$_2$, —C3-C4 alkynyl(NR$^5$)$_2$, —N(R)$_2$, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl;

each $R^2$ is independently hydrogen, hydroxy, halogen, cyano, C1-C3 alkyl, C1-C3 cyanoalkyl, C1-C3 hydroxyalkyl, HC(=O)—, -L-OC(O)N(R$^5$)$_2$, —CO$_2$R$^5$, or —CO$_2$N(R$^5$)$_2$;

each $R^3$ is independently hydrogen, hydroxy, halogen, cyano, C1-C3 alkyl, C1-C3 cyanoalkyl, C1-C3 hydroxyalkyl, HC(=O)—, -L-OC(O)N(R$^5$)$_2$, —CO$_2$R$^5$, or —CO$_2$N(R$^5$)$_2$;

each $R^4$ is independently hydrogen, halogen or C1-C3 alkyl;

each $R^5$ is independently hydrogen or C1-C3 alkyl, or two $R^5$ join to form cycloalkyl or heterocycle;

each $R^6$ is independently hydrogen, hydroxy, C1-C4 hydroxyalkyl or heteroaryl, or two $R^6$ join to form C3-C6 cycloalkyl or heterocycle;

each $R^7$ is independently hydrogen, C1-C3 alkyl, hydroxy, halogen, C1-C3 haloalkyl, -L-NH$_2$, —NH(C1-C3 alkyl), —N(C1-C3 alkyl)$_2$, oxo (=O), —O—(C1-C3 alkyl), —(C1-C3 alkyl)—OH, —C(O)OH, —C(O)O(C1-C3 alkyl), —C(O)N(R$^{10}$)$_2$, —NHC(O)H, —CN, aryl, —(CH$_2$)$_{1-2}$S(O)$_2$N(R$^{10}$)$_2$, —NH—S(O)$_2$N(R$^{10}$)$_2$, —O—S(O)$_2$N(R$^{10}$)$_2$, S(O)$_2$R$^{10}$, or heteroaryl or heterocycle optionally independently substituted with 1-2 substituents independently selected from C1-C3 alkyl, —CN and C(O)NH$_2$, two $R^7$ on the same atom optionally join to form a spirocyclic ring selected from C3-C6 cycloalkyl and heterocycle, where said spirocyclic ring is optionally substituted with 1-4 substituents independently selected from oxo (=O), halogen, hydroxy, C1-C3 alkyl and —O—(C1-C3 alkyl), two $R^7$ on adjacent atoms optionally join to form a bond or a fused ring selected from C3-C6 cycloalkyl optionally substituted with 1-4 $R^8$, heteroaryl optionally substituted with 1-4 $R^8$, aryl optionally substituted with 1-4 $R^8$, and heterocycle optionally substituted with 1-4 $R^8$, and two $R^7$ on non-adjacent atoms optionally join to form a 1-2 carbon bridge;

each $R^8$ is independently C1-C3 alkyl, hydroxy, halogen, —N(R$^{10}$)$_2$, —N(R$^{10}$)C(O)R$^{10}$, oxo (=O), —O—(C1-C3 alkyl), —(C1-C3 alkyl)—OH, —C(O)OH, —C(O)O(C1-C3 alkyl), —C(O)N(R$^{10}$)$_2$, heteroaryl or —CN;

each $R^9$ is independently C1-C3 alkyl, hydroxy, halogen, oxo (=O), —O—(C1-C3 alkyl), —(C1-C3 alkyl)—OH, —C(O)OH, —C(O)O(C1-C3 alkyl), —C(O)NH$_2$, —C(O)NH(C1-C3 alkyl), —C(O)N(C1-C3 alkyl)$_2$ or —CN;

each $R^{10}$ is independently hydrogen, halogen, C1-C3 alkyl, or two $R^{10}$ join to form cycloalkyl or heterocycle optionally substituted with 1-2 C1-C3 alkyl;

each L is independently a bond, —C1-C4 alkyl-, —C1-C4 alkyl-NH—, —NH—, —N(C1-C3 alkyl)- or cyclopropyl-CH$_2$—;

each n is 0-3;

o is 1-6; and p is 1-8.

Embodiments of the invention also include compounds of Formula (I):

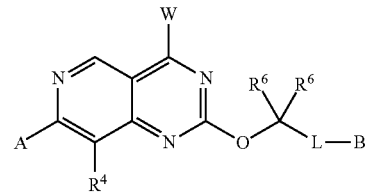

Formula (I)

or a pharmaceutically acceptable salt thereof, wherein:

W is:

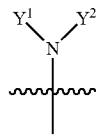

A is naphthyl optionally substituted with 1-4 $R^1$;

B is:

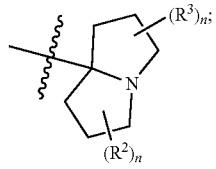

$Y^1$ and $Y^2$ join to form:

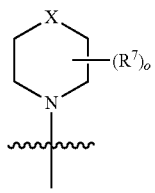

where X is selected from: —CH$_2$—, —CH$_2$—CH$_2$— and —O—CH$_2$—;

each $R^1$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxyC1-C3 alkyl, —CH$_2$C(═O)N(R$^5$)$_2$, —C3-C4 alkynyl(NR$^5$)$_2$, —N(R$^5$)$_2$, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl;

each $R^2$ is independently hydrogen, hydroxy, halogen, cyano, C1-C3 alkyl, C1-C3 cyanoalkyl, C1-C3 hydroxyalkyl, HC(═O)—, -L-OC(O)N(R$^5$)$_2$, —CO$_2$R, or —CO$_2$N(R$^5$)$_2$;

each $R^3$ is independently hydrogen, hydroxy, halogen, cyano, C1-C3 alkyl, C1-C3 cyanoalkyl, C1-C3 hydroxyalkyl, HC(═O)—, -L-OC(O)N(R$^5$)$_2$, —CO$_2$R$^3$, or —CO$_2$N(R$^5$)$_2$;

each $R^4$ is independently hydrogen, halogen or C1-C3 alkyl;

each $R^5$ is independently hydrogen or C1-C3 alkyl, or two $R^5$ join to form cycloalkyl or heterocycle;

each $R^6$ is independently hydrogen, hydroxy, C1-C4 hydroxyalkyl or heteroaryl,
or two $R^6$ join to form C3-C6 cycloalkyl or heterocycle;

each $R^7$ is independently hydrogen, C1-C3 alkyl, hydroxy, halogen, C1-C3 haloalkyl, -L-NH$_2$, —NH(C1-C3 alkyl), —N(C1-C3 alkyl)$_2$, oxo (═O), —O—(C1-C3 alkyl), —(C1-C3 alkyl)—OH, —C(O)OH, —C(O)O(C1-C3 alkyl), —C(O)N(R$^{10}$)$_2$, —NHC(O)H, —CN, aryl, —(CH$_2$)$_{1-2}$S(O)$_2$N(R$^{10}$)$_2$, —NH—S(O)$_2$N(R$^{10}$)$_2$, —O—S(O)$_2$N(R$^{10}$)$_2$, S(O)$_2$R$^{10}$, or heteroaryl or heterocycle optionally independently substituted with 1-2 substituents independently selected from C1-C3 alkyl, —CN and C(O)NH$_2$, two $R^7$ on the same atom optionally join to form a spirocyclic ring selected from C3-C6 cycloalkyl and heterocycle, where said spirocyclic ring is optionally substituted with 1-4 substituents independently selected from oxo (═O), halogen, hydroxy, C1-C3 alkyl and —O—(C1-C3 alkyl), two $R^7$ on adjacent atoms optionally join to form a bond or a fused ring selected from C3-C6 cycloalkyl optionally substituted with 1-4 $R^8$, heteroaryl optionally substituted with 1-4 $R^8$, aryl optionally substituted with 1-4 $R^8$, and heterocycle optionally substituted with 1-4 $R^8$, and two $R^7$ on non-adjacent atoms optionally join to form a 1-2 carbon bridge;

each $R^8$ is independently C1-C3 alkyl, hydroxy, halogen, —N(R$^{10}$)$_2$, —N(R$^{10}$)C(O)R$^{10}$, oxo (═O), —O—(C1-C3 alkyl), —(C1-C3 alkyl)—OH, —C(O)OH, —C(O)O(C1-C3 alkyl), —C(O)N(R$^{10}$)$_2$, heteroaryl or —CN;

each $R^9$ is independently C1-C3 alkyl, hydroxy, halogen, oxo (═O), —O—(C1-C3 alkyl), —(C1-C3 alkyl)—OH, —C(O)OH, —C(O)O(C1-C3 alkyl), —C(O)NH$_2$, —C(O)NH(C1-C3 alkyl), —C(O)N(C1-C3 alkyl)$_2$ or —CN;

each $R^{10}$ is independently hydrogen, halogen, C1-C3 alkyl, or two $R^{10}$ join to form cycloalkyl or heterocycle optionally substituted with 1-2 C1-C3 alkyl;

each L is independently a bond, —C1-C4 alkyl-, —C1-C4 alkyl-NH—, —NH—, —N(C1-C3 alkyl)- or cyclopropyl-CH$_2$—;

each n is 0-3;

o is 1-6; and p is 1-8.

Embodiments also include such compounds or salts wherein each $R^1$ is independently selected from halogen, hydroxy, C1-C3 alkoxy and C1-C4 alkyl.

Embodiments also include such compounds or salts wherein each $R^2$, if present, is selected from hydrogen and halogen, and wherein each $R^3$, if present, is selected from hydrogen and halogen.

Embodiments also include such compounds or salts wherein each $R^7$ is independently selected from hydrogen, C1-C4 alkyl, hydroxy, C1-C3 alkoxy, and wherein two $R^7$ on non-adjacent atoms optionally join to form a 1-2 carbon bridge.

Embodiments also include such compounds or salts wherein each $R^6$ is independently hydrogen or hydroxy.

Embodiments also include such compounds or salts wherein B is:

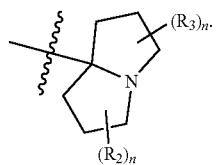

Embodiments also include such compounds or salts wherein B is:

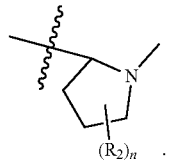

Embodiments also include such compounds or salts wherein B is:

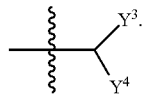

Embodiments also include such compounds or salts wherein $Y^1$ and $Y^2$ join to form:

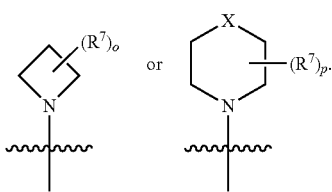

Embodiments also include such compounds or salts wherein $Y^1$ and $Y^2$ join to form:

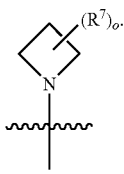

Embodiments also include such compounds or salts wherein $Y^1$ and $Y^2$ join to form:

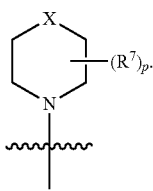

Embodiments also include such compounds or salts wherein A is naphthyl.

Embodiments also include such compounds or salts wherein A is indazolyl.

Embodiments also include such compounds or salts wherein A is phenyl.

Embodiments also include such compounds or salts wherein A is pyridyl.

In certain embodiments of the invention at least one $R^1$ is C1-C4 alkyl.

In certain embodiments of the invention at least one $R^1$ is halogen, preferably fluorine or chlorine.

In certain embodiments of the invention at least one $R^1$ is hydroxy

In certain embodiments of the invention at least one $R^2$ is C1-C4 alkyl.

In certain embodiments of the invention at least one $R^2$ is halogen, preferably fluorine or chlorine.

In certain embodiments of the invention at least one $R^2$ is hydroxy.

In certain embodiments of the invention at least one $R^3$ is C1-C4 alkyl.

In certain embodiments of the invention at least one $R^3$ is halogen, preferably fluorine or chlorine.

In certain embodiments of the invention at least one $R^3$ is hydroxy.

In certain embodiments of the invention $R^4$ is halogen, preferably fluorine.

In certain embodiments of the invention at least one $R^5$ is C1-C4 alkyl.

In certain embodiments of the invention at least one $R^5$ is hydrogen.

In certain embodiments of the invention at least one $R^6$ is C1-C4 alkyl.

In certain embodiments of the invention, two $R^6$ join to form C3-C6 cycloalkyl or heterocycle.

In certain embodiments of the invention at least one $R^6$ is hydrogen.

In certain embodiments of the invention both $R^6$ are C1-C4 alkyl.

In certain embodiments of the invention both $R^6$ are hydrogen.

In certain embodiments $Y^1$ is L-C3-C6 cycloalkyl, L-heteroaryl, L-aryl, or L-heterocycle. In certain of these embodiments, L is a bond. In certain of these embodiments L is C1-C4 alkyl. In certain of these embodiments L is NH or N(C1-C3) alkyl.

In certain embodiments $Y^1$ is L-heteroaryl where the heteroaryl is thietane dioxide, iso-thiazolidine dioxide, imidazopyrazine, pyridine or pyrimidine.

In certain embodiments $Y^1$ is L-C3-C6 cycloalkyl where the cycloalkyl is preferably cyclobutane, cyclopentane, cyclohexane or cycloheptane.

In certain embodiments $Y^1$ is L-heterocycle where the heterocycle is preferably pyrrolidinone.

In certain embodiments of the invention $Y^2$ is hydrogen.

In certain embodiments of the invention $Y^2$ is C1-C4 alkyl;

In certain embodiments of the invention at least one $R^8$ is C1-C4 alkyl, preferably methyl.

In certain embodiments of the invention at least one $R^8$ is hydroxy or C1-C3 alkyl-hydroxy.

In certain embodiments of the invention one or two $R^8$ is oxo (=O).

In certain embodiments of the invention at least one $R^8$ is aryl or heteroaryl.

In certain embodiments of the invention at least one $R^8$ is C(O)OH.

In certain embodiments of the invention at least one $R^8$ is —C(O)NH$_2$, —C(O)NH(C1-C3 alkyl) or —C(O)N(C1-C3 alkyl)$_2$.

In certain embodiments of the invention $R^8$ is —NH$_2$, —NH(C1-C3 alkyl); —N(C1-C3 alkyl)$_2$.

In certain embodiments of the invention at least one $R^9$ is C1-C4 alkyl, preferably methyl.

In certain embodiments of the invention at least one $R^9$ is hydroxy or C1-C3 alkyl-hydroxy.

In certain embodiments of the invention one or two $R^9$ is oxo (=O).

In certain embodiments of the invention at least one $R^9$ is aryl or heteroaryl.

In certain embodiments of the invention at least one $R^9$ is C(O)OH.

In certain embodiments of the invention at least one $R^9$ is —C(O)NH$_2$, —C(O)NH(C1-C3 alkyl) or —C(O)N(C1-C3 alkyl)$_2$.

In certain embodiments of the invention $Y^1$ and $Y^2$ join to form a piperidine, azepane, azocane, thiazepine, diazepane, oxazepane, azetidine, pyrrolidine, piperazine bound to a fused ring via nitrogen or thiomorpholine.

In certain embodiments of the invention, two $R^7$ on the same atom join to form a spirocyclic ring selected from C3-C6 cycloalkyl and heterocycle, where said spirocyclic ring is optionally substituted with oxo (=O), halogen, hydroxy, C1-C3 alkyl and —O—(C1-C3 alkyl).

In certain embodiments of the invention, two $R^7$ on adjacent atoms optionally join to form a bond or a fused ring selected from C3-C6 cycloalkyl optionally substituted with 1-4 R$^8$; heteroaryl optionally substituted with 1-4 R$^8$; aryl optionally substituted with 1-4 R$^8$, and heterocycle optionally substituted with 1-4 R$^8$.

In certain embodiments of the invention, two R$^7$ on non-adjacent atoms optionally join to form a 1-2 carbon bridge.

Non-limiting examples of compounds of Formula (I) are selected from the group consisting of the compounds described in the below Examples, and pharmaceutically acceptable salts thereof.

In one embodiment, the compounds of Formula (1) include bis-hydrochloride, tris-hydrochloride, trifluoroacetic acid, bis-trifluoroacetic acid, and tris-trifluoroacetic acid salts of the above compounds. The compounds of Formula (I) or pharmaceutically acceptable salt thereof may be formulated into pharmaceutical compositions.

Pharmaceutical Compositions

In another aspect, the invention provides pharmaceutical compositions comprising a wild type KRas, KRas G12A, KRas G12C, KRas G12D, KRas G12R, KRas G12S, KRas G12V, KRas G13D and/or KRas Q61H inhibitor according to the invention and a pharmaceutically acceptable carrier, excipient, or diluent. Compounds of the invention may be formulated by any method well known in the art and may be prepared for administration by any route, including, without limitation, parenteral, intraperitoneal, intradermal, intracardiac, intraventricular, intracranial, intracerobrospinal, intrasynovial, intrathecal administration, intramuscular injection, intravitreous injection, intravenous injection, intra-arterial injection, oral, buccal, sublingual, transdermal, topical, intranasal, intratracheal, intrarectal, subcutaneous, and topical administration. In certain embodiments, compounds of the invention are administered intravenously in a hospital setting. In one embodiment, administration may be by the oral route. In some embodiments, the provided pharmaceutical compositions may be administered to a subject in need of treatment by injection systemically, such as by intravenous injection; or by injection or application to the relevant site, such as by direct injection via syringe, or direct application to the site when the site is exposed in surgery; or by topical administration.

Parenteral administration can be by bolus injection or continuous infusion. Pharmaceutical compositions for injection may be presented in unit dosage form, e.g., in ampoules or in multi-dose containers, with an added preservative.

The provided pharmaceutical compositions can also be formulated as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or a medical device, including but not limited to a dispenser device which may contain one or more unit dosage forms containing the active ingredient. In one embodiment the dispenser device can comprise a syringe having a single dose of the liquid formulation ready for injection. The syringe can be accompanied by instructions for administration.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods of use described herein.

Methods of Use

In yet another aspect, the invention provides for methods for inhibiting wild type KRas, KRas G12A, KRas G12C, KRas G12D, KRas G12R, KRas G12S, KRas G12V and/or KRas Q61H activity in a cell, comprising contacting the cell in which inhibition of wild type KRas, KRas G12A, KRas G12C, KRas G12D, KRas G12R, KRas G12S, KRas G12V and/or Q61H activity is desired with an effective amount of a compound of Formula (I), pharmaceutically acceptable salts thereof, or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" wild type KRas, KRas G12A, KRas G12C, KRas G12D, KRas G12R, KRas G12S, KRas G12V, KRas G13D and/or KRas Q61H with a compound provided herein includes the administration of a compound provided herein to an individual or patient, such as a human, having wild type KRas or a KRas G12A, KRas G12C, KRas G12R, KRas G12S, KRas G12V, KRas G13D and/or KRas Q61H mutation, as well as, for example, introducing a compound provided herein into a sample containing a cellular or purified preparation containing wild type KRas or a KRas G12A, KRas G12C, KRas G12D, KRas G12R, KRas G12S, KRas G12V, KRas G13D or KRas Q61H mutation.

In one embodiment, a cell in which inhibition of wild type KRas or KRas G12A, KRas G12C, KRas G12D, KRas G12R, KRas G12S, KRas G12V, KRas G13D and/or KRas Q61H activity is desired is contacted with an effective amount of a compound of Formula (I) or pharmaceutically acceptable salt thereof to negatively modulate the activity of one or more of wild type KRas or KRas G12A, KRas G12C, KRas G12D, KRas G12R, KRas G12S, KRas G12V, KRas G13D and KRas Q61H.

By negatively modulating the activity of one or more of wild type KRas or KRas G12A, KRas G12C, KRas G12D, KRas G12R, KRas G12S, KRas G12V, KRas G13D and KRas Q61H, the methods described herein are designed to inhibit undesired cellular proliferation resulting from enhanced wild type KRas or KRas G12A, KRas G12C, KRas G12D, KRas G12R, KRas G12S, KRas G12V, KRas G13D and/or KRas Q61H activity within the cell. The cells may be contacted in a single dose or multiple doses in accordance with a particular treatment regimen to affect the desired negative modulation of wild type KRas or KRas G12A, KRas G12C, KRas G12D, KRas G12R, KRas G12S, KRas G12V, KRas G13D and/or KRas Q61H. The ability of compounds to bind one or more of wild type KRas or KRas G12A, KRas G12C, KRas G12D, KRas G12R, KRas G12S, KRas G12V, KRas G13D and KRas Q61H may be monitored in vitro using well known methods, including those described in Examples A and B below. In addition, the inhibitory activity of exemplary compounds in cells may be monitored, for example, by measuring the inhibition of one or more of wild type KRas or KRas G12A, KRas G12C, KRas G12D, KRas G12R, KRas G12S, KRas G12V, KRas G13D and/or KRas Q61H activity of the amount of phosphorylated ERK, for example using the method described in Example C below.

In another aspect, methods of treating cancer in a patient in need thereof, comprising administering to said patient a therapeutically effective amount of a compound of Formula (I) or a pharmaceutically acceptable salt thereof, or a pharmaceutical composition comprising the compound or pharmaceutically acceptable salt thereof are provided.

The compositions and methods provided herein may be used for the treatment of a wild type KRas-associated or KRas G12A, KRas G12C, KRas G12D, KRas G12R, KRas G12S, KRas G12V, KRas G13D and/or KRas Q61H-associated cancer in a patient in need thereof, comprising administering to said patient a therapeutically effective amount of a compound of Formula (I), a pharmaceutically acceptable salt thereof, or a pharmaceutical composition comprising the compound or pharmaceutically acceptable salt thereof are provided. In one embodiment, the wild type KRas-associated or KRas G12A, KRas G12C, KRas G12D, KRas G12R, KRas G12S, KRas G12V, KRas G13D and/or KRas Q61H-associated cancer is lung cancer.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer, small cell lung cancer, colorectal cancer, rectal cancer or pancreatic cancer. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other antineoplastic compounds, e.g., chemotherapy, or used in combination with other treatments, such as radiation or surgical intervention, either as an adjuvant prior to surgery or post-operatively.

Also provided herein is a compound of Formula (I) or a pharmaceutically acceptable salt thereof, or a pharmaceutical composition thereof as defined herein for use in therapy.

Also provided herein is a compound of Formula (I) or a pharmaceutically acceptable salt thereof, or a pharmaceutical composition thereof as defined herein for use in the treatment of cancer.

Also provided herein is a compound of Formula (I) or a pharmaceutically acceptable salt thereof, or a pharmaceutical composition thereof for use in the inhibition of wild type KRas or KRas G12A, KRas G12C, KRas G12D, KRas G12R, KRas G12S, KRas G12V, KRas G13D and/or KRas Q61H.

Also provided herein is a compound of Formula (I) or a pharmaceutically acceptable salt thereof, or a pharmaceutical composition thereof as defined herein, for use in the treatment of wild type KRas-associated or a KRas G12A, KRas G12C, KRas G12D, KRas G12R, KRas G12S, KRas G12V, KRas G13D and/or KRas Q61H-associated disease or disorder.

Also provided herein is the use of a compound of Formula (I) or a pharmaceutically acceptable salt thereof, as defined herein in the manufacture of a medicament for the treatment of cancer.

Also provided herein is a use of a compound of Formula (I) or a pharmaceutically acceptable salt thereof, as defined herein in the manufacture of a medicament for the inhibition of activity of wild type KRas or KRas G12A, KRas G12C, KRas G12D, KRas G12R, KRas G12S, KRas G12V, KRas G13D and/or KRas Q61H.

Also provided herein is the use of a compound of Formula (I) or a pharmaceutically acceptable salt thereof, as defined herein, in the manufacture of a medicament for the treatment of wild type KRas-associated or a KRas G12A, KRas G12C, KRas G12D, KRas G12R, KRas G12S, KRas G12V, KRas G13D and/or KRas Q61H-associated disease or disorder.

Also provided herein is a method for treating cancer in a patient in need thereof, the method comprising (a) determining that cancer is associated with wild type KRas or a KRas G12A, KRas G12C, KRas G12D, KRas G12R, KRas G12S, KRas G12V, KRas G13D and/or KRas Q61H mutation (e.g., as determined using a regulatory agency-approved, e.g., FDA-approved, assay or kit); and (b) administering to the patient a therapeutically effective amount of a compound of Formula (1), or a pharmaceutically acceptable salt thereof, or a pharmaceutical composition thereof.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

Reaction Schemes and Examples

The compounds of the present invention may be prepared from commercially available reagents using the synthetic methods and reaction schemes described herein, or using other reagents and conventional methods well known to those skilled in the art. For instance, compounds of the present invention may be prepared according to the reaction schemes and examples outlines below.

The compounds of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

The compounds of the present invention may be in anhydrous, solvated or hydrated forms, and all such forms are included within the scope of the invention.

The following Intermediates are intended to illustrate further certain embodiments of the invention and are not intended to limit the scope of the invention.

Intermediate 1

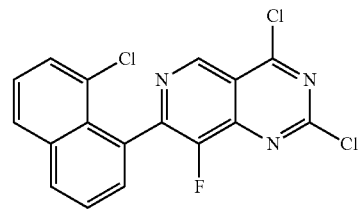 [SMILES: Fc1c(-c2cccc3cccc(Cl)c23)ncc2c(Cl)nc(Cl)nc12]

2,4-dichloro-7-(8-chloro-1-naphthyl)-8-fluoro-pyrido[4,3-d]pyrimidine

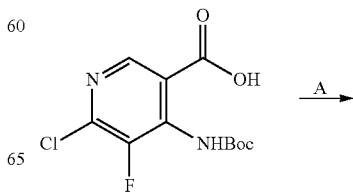

-continued

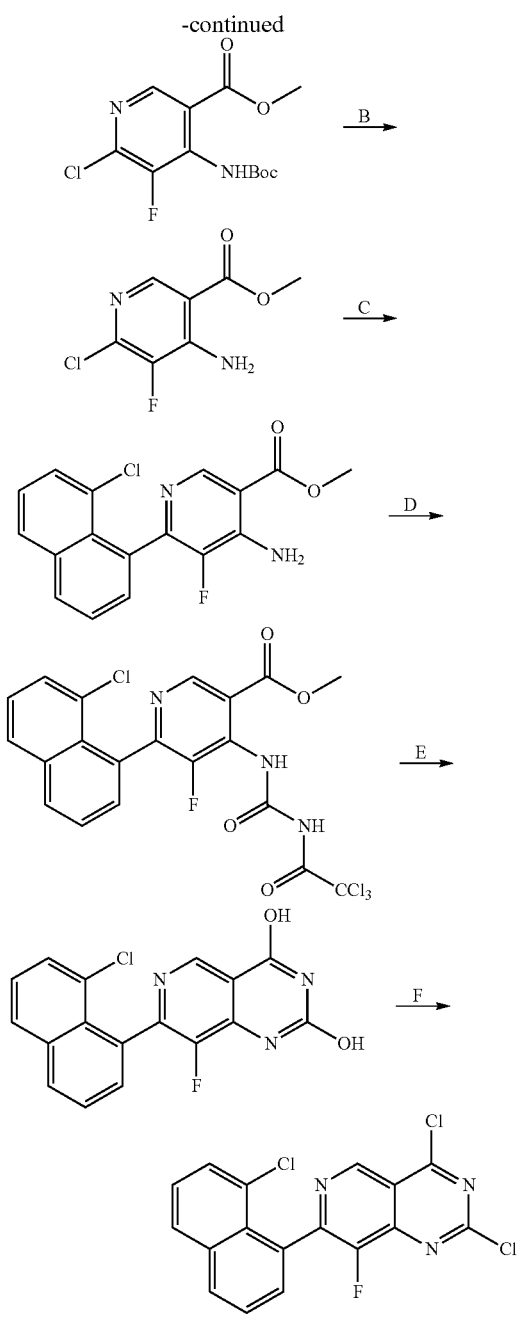

Step A. methyl 4-(tert-butoxycarbonylamino)-6-chloro-5-fluoro-pyridine-3-carboxylate. To a solution of 4-((tert-butoxycarbonyl)amino)-6-chloro-5-fluoronicotinic acid (14.3 g, 49.2 mmol, 1 equiv.) in MeOH (70 mL) and toluene (210 mL) was added TMSCHN$_2$ (2 M in hexane, 44.3 mL, 1.8 equiv.) slowly. After stirring at 15° C. for 2 hours, the mixture was quenched with 2N HCl (100 mL) and layers were separated. The organic phase was washed with saturated aqueous NaHCO$_3$ (150 mL), followed by brine (150 mL). The organic layer was dried over Na$_2$SO$_4$, filtered and concentrated in vacuum. The residue was purified by silica gel chromatography (petroleum ether/ethyl acetate 10:1 to 1:1) to give methyl 4-(tert-butoxycarbonylamino)-6-chloro-5-fluoro-pyridine-3-carboxylate (15 g, 91%). Colorless oil; Rf=0.50 (3:1 petroleum ether/ethyl acetate); $^1$H NMR (400 MHz, CDCl$_3$): δ 8.85 (br s, 1H), 8.68 (s, 1H), 3.98 (s, 3H), 1.57-1.49 (m, 9H); LCMS [ESI, M+1]: 305.

Step B. methyl 4-amino-6-chloro-5-fluoro-pyridine-3-carboxylate. To a solution of methyl 4-(tert-butoxycarbonylamino)-6-chloro-5-fluoro-pyridine-3-carboxylate (15 g, 49.2 mmol, 1.0 equiv.) in MeCN (150 mL) was added HCl.dioxane (4 M, 290 mL, 23.6 equiv.) at 0° C. The mixture was stirred at 15° C. for 0.5 hour, and the solvent was removed under reduced pressure. The residue was diluted with saturated Na$_2$CO$_3$ solution (100 mL) and extracted with ethyl acetate (3×200 mL). The organic layers were dried over Na$_2$SO$_4$ and concentrated in vacuum to give methyl 4-amino-6-chloro-5-fluoro-pyridine-3-carboxylate (9.07 g, 89%) which was used directly in the next step without further purification. Orange solid; LCMS [ESI, M+1]: 205.

Step C. methyl 4-amino-6-(8-chloro-1-naphthyl)-5-fluoro-pyridine-3-carboxylate. A mixture of methyl 4-amino-6-chloro-5-fluoro-pyridine-3-carboxylate (6 g, 29.3 mmol, 1.0 equiv.), (8-chloronaphthalen-1-yl)trimethylstannane (21.0 g, 64.5 mmol, 2.2 equiv.), CuI (1.68 g, 8.80 mmol, 0.3 equiv.), Pd(dppf)Cl$_2$ (2.15 g, 2.93 mmol, 0.1 equiv.), and BINAP (3.65 g, 5.87 mmol, 0.2 equiv.) in toluene (120 mL) was degassed and then heated to 100° C. for 11 hours under N$_2$. The mixture was filtered and the filtrate was concentrated in vacuum. The residue was diluted with water (50 mL) and extracted with ethyl acetate (2×60 mL). The organic layers were dried over Na$_2$SO$_4$ and concentrated in vacuum. The residue was purified by chromatography (Al$_2$O$_3$, petroleum ether/ethyl acetate 30/1 to 1/1). The product was triturated with a mixed solution (DMAc/methanol 1/2, 30 mL) at 15° C. for 10 minutes to give methyl 4-amino-6-(8-chloro-1-naphthyl)-5-fluoro-pyridine-3-carboxylate (5.33 g, 54%). Yellow solid; Rf=0.20 (3:1 petroleum ether/ethyl acetate); LCMS [ESI, M+1]: 331.

Step D. methyl 6-(8-chloro-1-naphthyl)-5-fluoro-4-[(2,2,2-trichloroacetyl)carbamoylamino]pyridine-3-carboxylate. To a solution of methyl 4-amino-6-(8-chloro-1-naphthyl)-5-fluoro-pyridine-3-carboxylate (5.5 g, 16.6 mmol, 1.0 equiv.) in THF (82 mL) was added 2,2,2-trichloroacetyl isocyanate (3.45 g, 18.3 mmol, 2.17 mL, 1.1 equiv.) dropwise. The mixture was stirred at 15° C. for 10 minutes, and the mixture was concentrated in vacuum. The residue was triturated with MTBE (20 mL) at 15° C. for 15 minutes to give methyl 6-(8-chloro-1-naphthyl)-5-fluoro-4-[(2,2,2-trichloroacetyl)carbamoylamino] pyridine-3-carboxylate (8 g, crude). Yellow solid; LCMS [ESI, M+1]: 520.

Step E. 7-(8-chloro-1-naphthyl)-8-fluoro-pyrido[4,3-d]pyrimidine-2,4-diol. A suspension of methyl 6-(8-chloro-1-naphthyl)-5-fluoro-4-[(2,2,2-trichloroacetyl)carbamoylamino] pyridine-3-carboxylate (8 g, 15.4 mmol, 1.0 equiv.) in NH$_3$-MeOH (20 mL, 20% purity) was stirred at 15° C. for 0.5 hour, the mixture was concentrated in vacuum. The residue was triturated with MTBE (30 mL) at 15° C. for 15 minutes to give 7-(8-chloro-1-naphthyl)-8-fluoro-pyrido[4,3-d]pyrimidine-2,4-diol (5.3 g, two steps 93%). Yellow solid; $^1$H NMR (400 MHz, DMSO): δ 9.59-8.27 (m, 1H), 8.24-8.13 (m, 1H), 8.11-8.03 (m, 1H), 7.74-7.61 (m, 2H), 7.60-7.52 (m, 2H), 3.59-3.31 (m, 2H); LCMS [ESI, M+1]: 342.

Step F. 2,4-dichloro-7-(8-chloro-1-naphthyl)-8-fluoro-pyrido[4,3-d]pyrimidine. A solution of POCl$_3$ (1.62 g, 10.6 mmol, 985 μL, 36.2 equiv.) and N-ethyl-N-isopropylpropan-2-amine (189 mg, 1.46 mmol, 255 μL, 5.0 equiv.) was stirred at 0° C., followed by the addition of 7-(8-chloro-1-naphthyl)-8-fluoro-pyrido[4,3-d]pyrimidine-2,4-diol (0.1 g, 293 μmol, 1.0 equiv.). The suspension was stirred at 110° C. for 1 hour, the mixture was concentrated in vacuum to give 2,4-dichloro-7-(8-chloro-1-naphthyl)-8-fluoro-pyrido[4,3- d]pyrimidine (0.11 g, crude) which was used directly in the next step without further purification. Black oil.

Intermediate 2

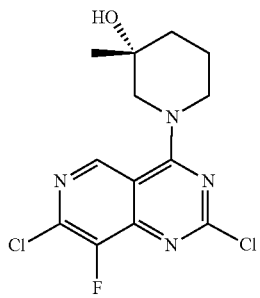 [SMILES: C[C@@]1(O)CCCN(c2nc(Cl)nc3c(F)c(Cl)ncc23)C1]

(R)-1-(2,7-dichloro-8-fluoropyrido[4,3-d]pyrimidin-4-yl)-3-methylpiperidin-3-ol

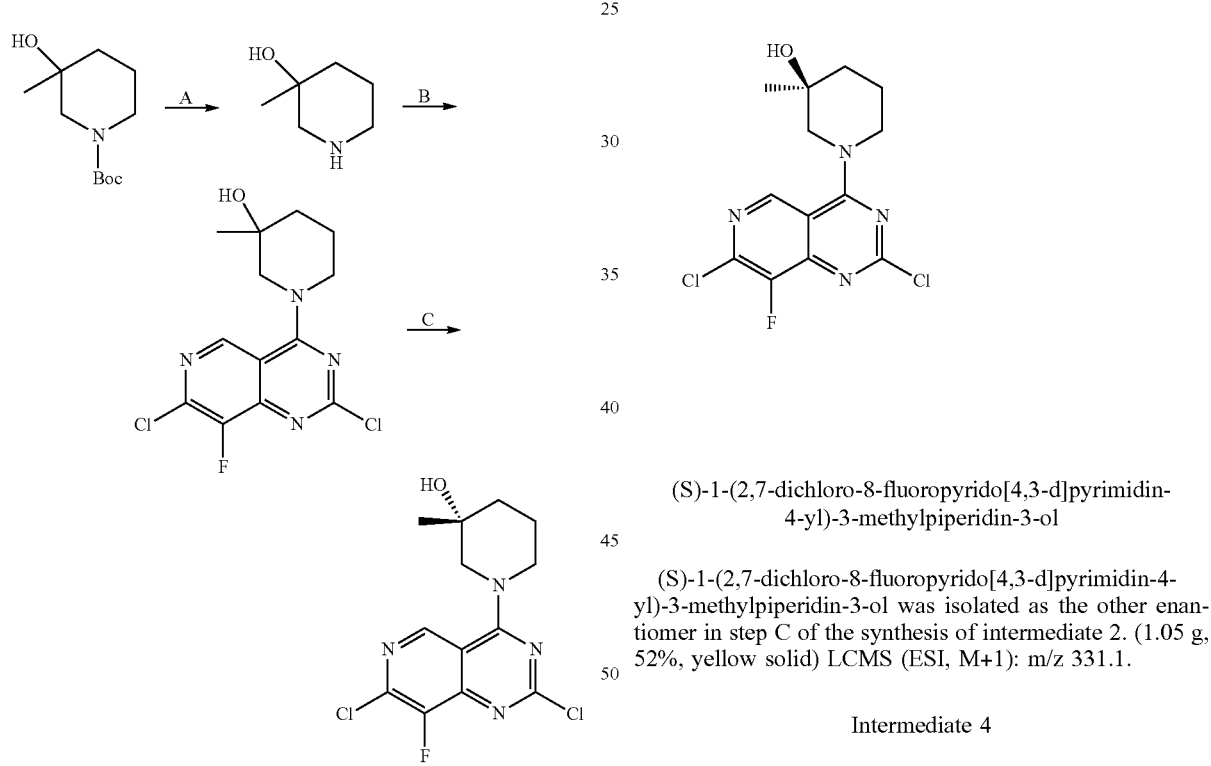

Step A. 3-methylpiperidin-3-ol: To the solution of tert-butyl 3-hydroxy-3-methyl-piperidine-1-carboxylate (2.45 g, 11.4 mmol) in acetonitrile (9 mL) was added HCl.dioxane (4 M, 18 mL) at 0° C., and the mixture was stirred at 0° C. for 0.5 h. After completion, the reaction mixture was concentrated to give 3-methylpiperidin-3-ol (1.75 g, crude) as a yellow oil which was used in the next step without further purification.

Step B. 1-(2,7-dichloro-8-fluoropyrido[4,3-d]pyrimidin-4-yl)-3-methylpiperidin-3-ol: To the mixture of 2,4,7-trichloro-8-fluoro-pyrido[4,3-d]pyrimidine (3.65 g, 14.5 mmol), DIEA (7.47 g, 57.8 mmol) in dichloromethane (40 mL) was added 3-methylpiperidin-3-ol (1.75 g, crude) at −40° C., and the mixture was stirred at −40° C. for 0.5 hour. After completion, the reaction mixture was diluted with water (50 mL) and extracted with dichloromethane (100 mL). The combined organic phase was dried over anhydrous Na$_2$SO$_4$ and concentrated to give a residue. The residue was purified by column chromatography (5% to 50% EA/PE) to give 1-(2,7-dichloro-8-fluoropyrido[4,3-d]pyrimidin-4-yl)-3-methylpiperidin-3-ol (2.05 g, 43% yield). Yellow Solid. LCMS (ESI, M+1): m/z 331.0.

Step C. (R)-1-(2,7-dichloro-8-fluoropyrido[4,3-d]pyrimidin-4-yl)-3-methylpiperidin-3-ol: 1-(2,7-dichloro-8-fluoropyrido[4,3-d]pyrimidin-4-yl)-3-methylpiperidin-3-ol (2.05 g) was separated by SFC (column: DAICEL CHIRALCEL OJ (250 mm×30 mm, 10 um); mobile phase: [0.1% NH$_3$WATER MeOH]; B %: 20%-20%, 3.7; 1035 min) to give (R)-1-(2,7-dichloro-8-fluoropyrido[4,3-d]pyrimidin-4-yl)-3-methylpiperidin-3-ol (1.00 g, 48%). Yellow Solid; LCMS (ESI, M+1): m/z 331.1.

Intermediate 3

(S)-1-(2,7-dichloro-8-fluoropyrido[4,3-d]pyrimidin-4-yl)-3-methylpiperidin-3-ol (S)-1-(2,7-dichloro-8-fluoropyrido[4,3-d]pyrimidin-4-yl)-3-methylpiperidin-3-ol was isolated as the other enantiomer in step C of the synthesis of intermediate 2. (1.05 g, 52%, yellow solid) LCMS (ESI, M+1): m/z 331.1.

Intermediate 4

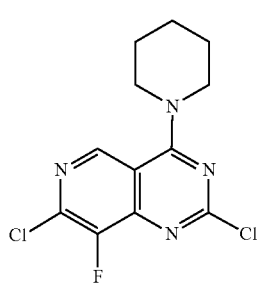 [SMILES: Fc1c(Cl)ncc2c(N3CCCCC3)nc(Cl)nc12]

29

2,7-dichloro-8-fluoro-4-(piperidin-1-yl)pyrido[4,3-d]imidine

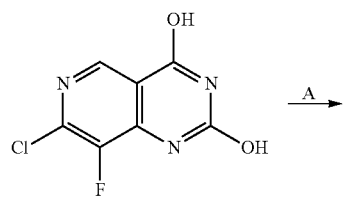

A →

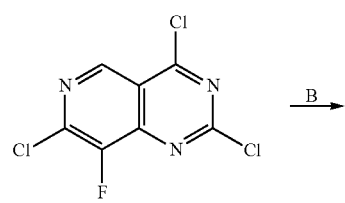

B →

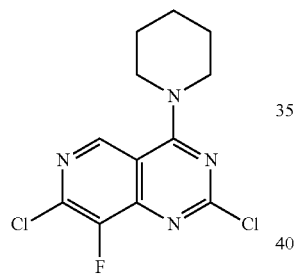

Step A. 2,4,7-trichloro-8-fluoropyrido[4,3-d]pyrimidine: To a mixture of 7-chloro-8-fluoropyrido[4,3-d]pyrimidine-2,4-diol (2.8 g, 13.0 mmol) in POCl₃ (20 mL) was added DIEA (5.04 g, 39.0 mmol, 6.79 mL) in one portion at 25° C. under N₂. The mixture was heated to 110° C. and stirred for 2 h. The mixture was concentrated in reduced pressure to give a residue. The residue was purified by silica gel chromatography (Silica gel, Petroleum ether/Ethyl acetate=20/1, 3/1) to afford 2,4,7-trichloro-8-fluoropyrido[4,3-d]pyrimidine (3.1 g, 89% yield) as a yellow solid; LCMS (ESI, M+1): m/z 251.9.

Step B. 2,7-dichloro-8-fluoro-4-(piperidin-1-yl)pyrido[4,3-d]pyrimidine: To a mixture of 2,4,7-trichloro-8-fluoropyrido[4,3-d]pyrimidine (100 mg, 396 µmol) and DIPEA (76.8 mg, 594 µmol, 103 µL) in DCM (1 mL) was added piperidine (40.5 mg, 475 µmol, 46.9 µL) in portions at −40° C. under N₂. The mixture was stirred at −40° C. for 1 hour. The reaction mixture was filtered and concentrated in vacuum. The residue was purified by silica gel chromatography (Silica gel, Petroleum ether/Ethyl acetate=1/0 to 0/1) affording 1-(2,7-dichloro-8-fluoropyrido[4,3-d]pyrimidin-4-yl)-3-methylpiperidin-3-ol (105 mg, 88% yield) as a yellow solid. LCMS (ESI, M+1): m/z 301.0.

30

Intermediate 5

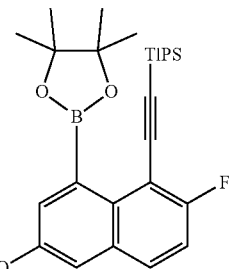

((2-fluoro-6-(methoxymethoxy)-8-(4,4,5,5-tetramethyl-1,3,2-dioxaborolan-2-yl)naphthalen-1-yl)ethynyl)triisopropylsilane

A →

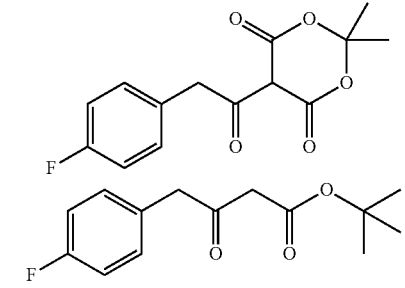

B →

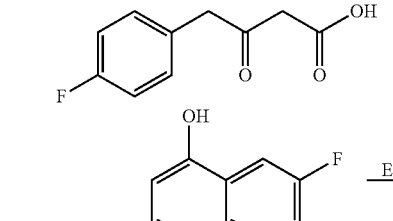

C →

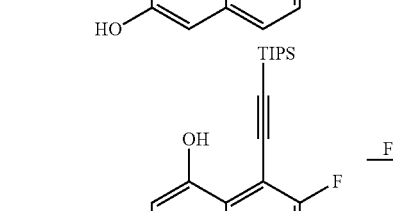

D →

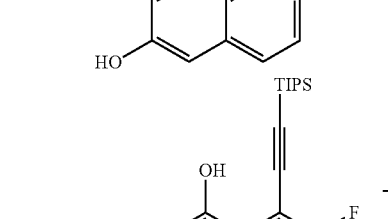

E →

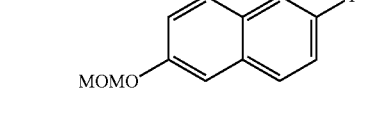

F →

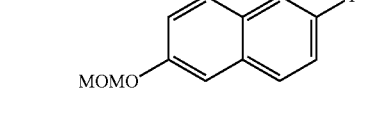

G →

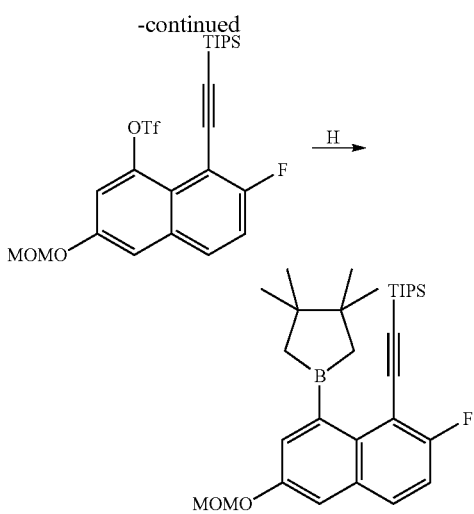

Step A. 5-(2-(4-fluorophenyl)acetyl)-2,2-dimethyl-1,3-dioxane-4,6-dione. To a solution of 2-(4-fluorophenyl)acetic acid (500 g, 3.24 mol, 1 equiv.), Meldrum's acid (514 g, 3.57 mol, 1.1 equiv.), DMAP (33.7 g, 275 mmol, 0.085 equiv.) in $CH_3CN$ (1500 mL) was added DIPEA (901 g, 6.97 mol, 1.21 L, 2.15 equiv.) while maintaining the temperature below 45° C., and then pivaloyl chloride (430 g, 3.57 mol, 439 mL, 1.1 equiv.) was slowly added over 3 hours while maintaining the temperature below 45° C. The resulted solution was stirred at 45° C. for 3 hours. The mixture solution was cooled to 0° C., then 1N HCl (5 L) was slowly added, and the resulted solution was stirred at 0° C. for 2 hours. Lot of solid was generated, and the mixture was filtered to give the crude yellow solid. The crude was washed with $CH_3CN$/WATER (3 L/12 L) to give 5-(2-(4-fluorophenyl)acetyl)-2,2-dimethyl-1,3-dioxane-4,6-dione (800 g, 88% yield). White Solid; $^1H$ NMR (400 MHz, DMSO-$d_6$) δ=15.35 (s, 1H), 7.40-7.38 (m, 2H), 7.05-7.01 (m, 2H), 4.40 (s, 2H), 1.72 (s, 6H).

Step B. tert-butyl 4-(4-fluorophenyl)-3-oxobutanoate. A solution of 5-(2-(4-fluorophenyl)acetyl)-2,2-dimethyl-1,3-dioxane-4,6-dione (1 kg) in t-BuOH (3 L) was stirred at 90° C. for 2 hours, then the mixture solution was concentrated to give the crude solid, and the crude solid was washed with petroleum ether (350 mL) to give tert-butyl 4-(4-fluorophenyl)-3-oxobutanoate (850 g, 94% yield). Light-yellow Solid; $^1H$ NMR (400 MHz, DMSO-$d_6$) δ=7.27-7.18 (m, 2H), 7.18-7.08 (m, 2H), 3.86 (s, 2H), 3.55 (s, 2H), 1.40 (s, 9H).

Step C. 4-(4-fluorophenyl)-3-oxobutanoic acid. A solution of tert-butyl 4-(4-fluorophenyl)-3-oxobutanoate (800 g, 3.17 mol, 1 equiv.) and TFA (2.46 kg, 21.6 mol, 1.6 L, 6.81 equiv.) in DCM (1.6 L) was stirred at 20° C. for 1 hour. The mixture was concentrated to dryness. The residue was washed with petroleum ether (500 mL) to give 4-(4-fluorophenyl)-3-oxobutanoic acid (516 g, 83% yield). White Solid; $^1H$ NMR (400 MHz, $CDCl_3$-d) δ=10.01 (s, 1H), 7.20-7.17 (m, 2H), 7.07-7.03 (m, 2H), 3.84 (s, 2H), 3.54-3.52 (m, 2H).

Step D. 7-fluoronaphthalene-1,3-diol. A solution of 4-(4-fluorophenyl)-3-oxobutanoic acid (450 g, 2.29 mol, 1 equiv.) in $CF_3SO_3H$ (8.5 kg, 56 mol, 5 L, 25 equiv.) was stirred at 25° C. for 24 hours, the reaction was cooled to 0° C., and slowly added to ice-water (15 L). Precipitates were formed, and the mixture was filtered to give the crude product. Then the crude was slurred with petroleum ether (1 L), and filtered to give the 7-fluoronaphthalene-1,3-diol (325 g, 79% yield). Light-yellow Solid.

Step E. 7-fluoro-8-((triisopropylsilyl)ethynyl)naphthalene-1,3-diol. To the mixture of 7-fluoronaphthalene-1,3-diol (120 g, 673 mmol, 1 equiv.), 2-bromoethynyl(triisopropyl)silane (184 g, 707 mmol, 1.05 equiv.), AcOK (132 g, 1.34 mol, 2 equiv.) in dioxane (800 mL) was added dichlororuthenium; 1-isopropyl-4-methyl-benzene dimer (41.3 g, 67.4 mmol, 0.1 equiv.) under $N_2$. The mixture was stirred at 110° C. for 2 hours. The mixture was filtered and concentrated to give a residue. Then the residue was purified by column chromatography (Silica gel, Petroleum ether/Ethyl acetate=1/0 to 5/1) to give 7-fluoro-8-((triisopropylsilyl)ethynyl)naphthalene-1,3-diol (213 g, 88% yield) was obtained. Black Oil; LCMS [ESI, M+1]: 359.2

Step F. 7-fluoro-3-(methoxymethoxy)-8-((triisopropylsilyl)ethynyl)naphthalen-1-91. To the mixture of 7-fluoro-8-((triisopropylsilyl)ethynyl)naphthalene-1,3-diol (170 g, 474 mmol, 1 equiv.), DIEA (184 g, 1.42 mol, 3 equiv.) and DCM (1700 mL) was added MOMCl (49.8 g, 618 mmol, 1.3 equiv.) at 0° C. The mixture was warmed to 15° C. and stirred for 0.5 hour. The reaction mixture was diluted with ice-water (1000 mL) and extracted with ethyl acetate (500 mL×2). The combined organic phase was washed with brine (1000 mL), dried over anhydrous sodium sulfate, filtered and concentrated to give a residue. The residue was purified by column chromatography (Silica gel, Petroleum ether/Ethyl acetate=1/0 to 50/1) to give 7-fluoro-3-(methoxymethoxy)-8-((triisopropylsilyl)ethynyl)naphthalen-1-ol (96 g, 50% yield). Yellow Solid; $^1H$ NMR (400 MHz, $CDCl_3$-d) δ=9.13 (s, 1H), 7.68-7.64 (m, 1H), 7.21-7.16 (m, 1H), 6.97-6.96 (m, 1H), 6.81-6.80 (m, 1H), 5.26 (s, 2H), 3.51 (s, 3H), 1.24-1.17 (m, 21H). LCMS [ESI, M+1]: 403.2.

Step G: 7-fluoro-3-(methoxymethoxy)-8-((triisopropylsilyl)ethynyl)naphthalen-1-yl trifluoromethanesulfonate. To the solution of 7-fluoro-3-(methoxymethoxy)-8-((triisopropylsilyl)ethynyl)naphthalen-1-ol (80 g, 198 mmol, 1 equiv.), DIEA (77.0 g, 596 mmol, 104 mL, 3 equiv.) in DCM (1200 mL) was added $Tf_2O$ (84.1 g, 298 mmol, 49.2 mL, 1.5 equiv.) at −40° C., and the mixture was stirred at −40° C. for 0.5 hour. The reaction mixture was diluted with ice-water (500 mL), and then extracted with DCM (300 mL). The combined organic phase was dried over $Na_2SO_4$ and concentrated to dryness. The residue was purified by column chromatography (Silica gel, Petroleum ether/Ethyl acetate=1/0 to 60/1) to afford 7-fluoro-3-(methoxymethoxy)-8-((triisopropylsilyl)ethynyl)naphthalen-1-yl trifluoromethanesulfonate (100 g, 94% yield). Yellow oil;

Step H. ((2-fluoro-6-(methoxymethoxy)-8-(4,4,5,5-tetramethyl-1,3,2-dioxaborolan-2-yl)naphthalen-1-yl)ethynyl)triisopropylsilane. To the mixture of 7-fluoro-3-(methoxymethoxy)-8-((triisopropylsilyl)ethynyl)naphthalen-1-yl trifluoromethanesulfonate (105 g, 196 mmol, 1 equiv.), 4,4,5,5-tetramethyl-2-(4,4,5,5-tetramethyl-1,3,2-dioxaborolan-2-yl)-1,3,2-dioxaborolane (100 g, 393 mmol, 2 equiv.), AcOK (57.8 g, 589 mmol, 3 equiv.) in toluene (1100 mL) was added Pd(dppf)$Cl_2$ (14.4 g, 20 mmol, 0.1 equiv.). The mixture was degassed and stirred at 130° C. for 3 hours. The reaction mixture was filtered and concentrated to give a residue. To the residue was added EtOAc (1000 mL) and water (800 mL). The organic phase was washed with brine (500 mL), dried over anhydrous sodium sulfate, filtered and concentrated to give a residue. The residue was purified by column chromatography (Silica gel, Petroleum ether/Ethyl acetate=100/1 to 3/1) and triturated with MeCN (40 mL) to give ((2-fluoro-6-(methoxymethoxy)-8-(4,4,5,5-tetramethyl-1,3,2-dioxaborolan-2-yl)naphthalen-1-yl)ethynyl)triisopropylsilane (41 g, 43% yield). Yellow Solid; ¹H NMR (400 MHz, CDCl₃-d) δ=7.69-7.65 (m, 1H), 7.51 (d, J=2.4 Hz, 1H), 7.38 (d, J=2.4 Hz, 1H), 7.25 (t, J=8.8 Hz, 1H), 5.28 (s, 2H), 3.50 (s, 3H), 1.44 (s, 12H), 1.18-1.16 (m, 21H); LCMS [ESI, M+1]: 513.4.

Intermediate 6

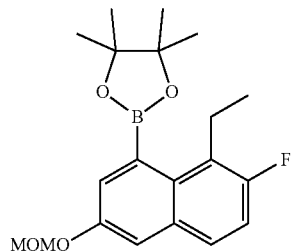

2-(8-ethyl-7-fluoro-3-(methoxymethoxy)naphthalen-1-yl)-4,4,5,5-tetramethyl-1,3,2-dioxaborolane

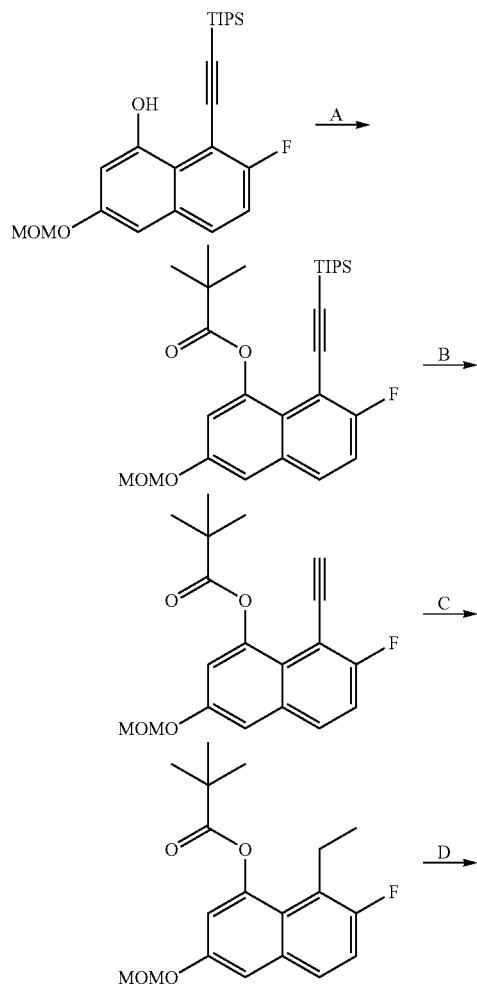

Step A. 7-fluoro-3-(methoxymethoxy)-8-((triisopropylsilyl)ethynyl)naphthalen-1-yl pivalate. To the solution of 7-fluoro-3-(methoxymethoxy)-8-((triisopropylsilyl)ethynyl)naphthalen-1-ol (2.00 g, 4.97 mmol, 1.0 equiv.), DMAP (122 mg, 999 μmol, 0.2 equiv.), TEA (1.51 g, 14.9 mmol, 3.0 equiv.) in DCM (20 mL) was added 2,2-dimethylpropanoyl chloride (1.80 g, 14.9 mmol, 3.0 equiv.) dropwise at 0° C., and then the mixture was stirred at 20° C. for 1 hour. After completion, the reaction mixture was diluted with DCM (15 mL) and water (15 mL), and then the aqueous layer was extracted with DCM (10 mL), The combined organic phase was dried over Na₂SO₄ and concentrated. The residue was purified by column chromatography (Silica gel, Petroleum ether/Ethyl acetate=I/O to 15/1) to give the title compound (3.00 g, crude). Yellow oil. LCMS [ESI, M+1]:487.2.

Step B. 8-ethynyl-7-fluoro-3-(methoxymethoxy)naphthalen-1-yl pivalate. To the solution of 7-fluoro-3-(methoxymethoxy)-8-((triisopropylsilyl)ethynyl)naphthalen-1-yl pivalate (3.00 g, 6.16 mmol, 1.0 equiv.) in DMF (50 mL) was added CsF (9.36 g, 61.6 mmol, 10 equiv.), and the mixture was stirred at 20° C. for 0.25 hour. After completion, to the reaction mixture was added water (250 mL), and then the mixture was extracted with ethyl acetate (2×120 mL). The combined organic phase was washed with brine 100 mL, dried over Na₂SO₄ and concentrated to give the title compound (2.20 g, crude). Yellow oil. LCMS [ESI, M+1]: 331.1.

Step C. 8-ethyl-7-fluoro-3-(methoxymethoxy)naphthalen-1-yl pivalate. To the solution of 8-ethynyl-7-fluoro-3-(methoxymethoxy)naphthalen-1-yl pivalate (2.00 g, 6.05 mmol, 1.0 equiv.) in MeOH (20 mL) was added Pd/C (200 mg, 10% purity) under N₂. The suspension was degassed in vacuum and purged with H₂ several times. The mixture was stirred under H₂ (15 psi) at 20° C. for 20 minutes. After completion, the mixture was filtered and concentrated to give the title compound (1.06 g, crude). LCMS [ESI, M+1]: 335.1.

Step D. 8-ethyl-7-fluoro-3-(methoxymethoxy)naphthalen-1-ol. To the solution of 8-ethyl-7-fluoro-3-(methoxymethoxy)naphthalen-1-yl pivalate (1.00 g, 2.99 mmol, 1.0 equiv.) in MeOH (15 mL) was added KOH (504 mg, 8.98 mmol, 3.0 equiv.), and the mixture was stirred at 20° C. for 0.5 hour. After completion, the reaction solution was adjusted to pH=4 with 0.5 M HCl at 0° C. and extracted with ethyl acetate (80 mL×2), the combined organic phase was washed with brine 50 mL, dried over anhydrous sodium sulfate, filtered and concentrated. The residue was purified by column chromatography (Silica gel, Petroleum ether/Ethyl acetate=50/1 to 10/1) to give the title compound (570 mg, four steps 51% yield). Yellow solid. $^1$H NMR (400 MHz, CDCl$_3$) δ=7.55-7.43 (m, 1H), 7.18 (t, J=9.2 Hz, 1H), 6.98 (d, J=2.4 Hz, 1H), 6.57 (d, J=2.0 Hz, 1H), 5.32 (s, 1H), 5.25 (s, 2H), 3.52 (s, 3H), 3.40-3.25 (m, 2H), 1.30 (t, J=7.6 Hz, 3H).

Step E. 8-ethyl-7-fluoro-3-(methoxymethoxy)naphthalen-1-yl trifluoromethane sulfonate. To the solution of 8-ethyl-7-fluoro-3-(methoxymethoxy)naphthalen-1-ol (520 mg, 2.08 mmol, 1.0 equiv.), DIEA (806 mg, 6.24 mmol, 3.0 equiv.) in DCM (10 mL), trifluoromethylsulfonyl trifluoromethanesulfonate (879 mg, 3.12 mmol, 1.5 equiv.) was added dropwise at −40° C., and then the mixture was stirred at −40° C. for 0.5 hr. After completion, the reaction mixture was quenched with ice-water (15 mL), and then extracted with DCM (2×15 mL). The combined organic phase was dried over Na$_2$SO$_4$ and concentrated. The residue was purified by column chromatography (Silica gel, Petroleum ether/Ethyl acetate=100/1 to 30/1) to give the title compound (620 mg, 78% yield). Yellow oil. $^1$H NMR (400 MHz, CDCl$_3$) δ=7.67-7.59 (m, 1H), 7.43 (d, J=2.4 Hz, 1H), 7.37 (d, J=2.4 Hz, 1H), 7.33-7.27 (m, 1H), 5.29 (s, 2H), 3.53 (s, 3H), 3.33-3.14 (m, 2H), 1.25 (t, J=7.6 Hz, 3H).

Step F. 2-(8-ethyl-7-fluoro-3-(methoxymethoxy)naphthalen-1-yl)-4,4,5,5-tetramethyl-1,3,2-dioxaborolane. To the mixture of 8-ethyl-7-fluoro-3-(methoxymethoxy)naphthalen-1-yl trifluoromethane sulfonate (500 mg, 1.31 mmol, 1.0 equiv.), 4,4,5,5-tetramethyl-2-(4,4,5,5-tetramethyl-1,3,2-dioxaborolan-2-yl)-1,3,2-dioxaborolane (665 mg, 2.62 mmol, 2.0 equiv.), AcOK (385 mg, 3.92 mmol, 3.0 equiv.) in dioxane (6 mL) was added Pd(dppf)Cl$_2$ (96.0 mg, 131 µmol, 0.1 equiv.) under N$_2$. The mixture was degassed and stirred at 100° C. for 1 hour. After completion, the mixture was diluted with ethyl acetate (20 mL) and water (10 mL), and extracted with ethyl acetate (10 mL). The combined organic phases were washed with brine (10 mL), dried over anhydrous sodium sulfate, filtered and concentrated. The residue was purified by column chromatography (Silica gel, Petroleum ether/Ethyl acetate=100/1 to 25/1) to give the title compound (143 mg, 30% yield). Yellow oil. $^1$H NMR (400 MHz, CDCl$_3$) δ=7.62-7.53 (m, 1H), 7.44-7.34 (m, 2H), 7.21 (t, J=9.2 Hz, 1H), 5.28 (s, 2H), 3.51 (s, 3H), 3.20-3.06 (m, 2H), 1.45 (s, 12H), 1.30-1.25 (m, 3H).

Intermediate 7

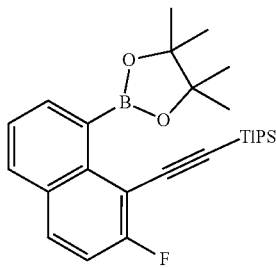

((2-fluoro-8-(4,4,5,5-tetramethyl-1,3,2-dioxaborolan-2-yl)naphthalen-1-yl)ethynyl)triisopropylsilane

Step A. 7-fluoronaphthalen-1-ol. To a solution of 7-fluoro-3,4-dihydronaphthalen-1 (2H)-one (75.0 g, 457 mmol, 1.00 equiv.) in acetic acid (1.50 L) and hydrogen bromide in AcOH (33%, 7.50 mL) was added bromine (80.3 g, 503 mmol, 25.9 mL, 1.1 equiv.) in acetic acid (50 mL) at 0° C., and the mixture was stirred at 25° C. for 3 hours. The mixture was diluted with DCM (1.5 L), washed with water (3×500 mL). The organic layer was dried over anhydrous sodium sulfate, filtered and concentrated to afford a brown oil, which was dissolved in DMF (750 mL).

Lithium bromide (67.4 g, 777 mmol, 19.5 mL, 1.70 equiv.), lithium carbonate (57.4 g, 777 mmol, 1.70 equiv.) were added. The reaction mixture was stirred at 160° C. for 3.5 hours. The reaction was diluted with ethyl acetate (1.00 L), washed with brine (2×500 mL), dried with anhydrous sodium sulfate, filtered and concentrated in vacuum to give a residue. The residue was purified by silica gel chromatography (petroleum ether/ethyl acetate=I/O to 5/1) affording the title compound (61.0 g, 82% yield). Brown solid; $^1$H NMR (400 MHz, CDCl$_3$) δ=7.84-7.77 (m, 2H), 7.44 (d, J=8.0 Hz, 1H), 7.31-7.24 (m, 2H), 6.84 (d, J=7.6 Hz, 1H), 5.39 (s, 1H).

Step B. 7-fluoro-8-(2-triisopropylsilylethynyl)naphthalen-1-ol. To a solution of (bromoethynyl)triisopropylsilane (72.0 g, 275 mmol, 1.20 equiv.) and 7-fluoronaphthalen-1-ol (37.2 g, 230 mmol, 1.0 equiv.) in DCE (500 mL) were added dichlororuthenium; 1-isopropyl-4-methyl-benzene (21.1 g, 34.4 mmol, 0.15 equiv.), K$_2$CO$_3$ (31.7 g, 230 mmol, 1.0 equiv.) and NaOAc (3.77 g, 45.9 mmol, 0.20 equiv.). The mixture was stirred at 40° C. for 12 hours. The reaction mixture was filtered and concentrated under reduced pressure to give a residue. The residue was purified by column chromatography (Silica gel, petroleum ether/ethyl acetate=I/O to 50/1) affording the title compound (73.0 g, 93% yield). Yellow oil; $^1$H NMR (400 MHz, CDCl$_3$) δ 9.10 (s, 1H), 7.79 (dd, J=5.6, 8.8 Hz, 1H), 7.41-7.33 (m, 2H), 7.23 (t, J=8.8 Hz, 1H), 7.08-7.00 (m, 1H), 1.24-1.14 (m, 21H); LCMS [ESI, M+1, 2 M+1]: 343.1, 685.3.

Step C. [7-fluoro-8-(2-triisopropylsilylethynyl)-naphthyl]trifluoromethanesulfonate. To a solution of 7-fluoro-8-(2-triisopropylsilylethynyl)naphthalen-1-ol (73.0 g, 213 mmol, 1.00 equiv.) in DCM (600 mL) were added DIEA (55.1 g, 426 mmol, 74.2 mL, 2.00 equiv.) and Tf₂O (90.2 g, 320 mmol, 52.7 mL, 1.50 equiv.) at −40° C. The mixture was stirred at −40° C. for 0.5 hour. The combined reaction mixture was filtered and concentrated under reduced pressure to give a residue. The mixture was purified by column chromatography (Silica gel, petroleum ether/ethyl acetate=I/O to 50/1) affording the title compound (78.0 g, 77% yield).

Yellow solid; ¹H NMR (400 MHz, CDCl₃) δ 7.88-7.79 (m, 2H), 7.59-7.52 (m, 1H), 7.46 (t, J=8.0 Hz, 1H), 7.37 (t, J=8.8 Hz, 1H), 1.32-1.16 (m, 21H).

Step D. ((2-fluoro-8-(4,4,5,5-tetramethyl-1,3,2-dioxaborolan-2-yl)naphthalen-1-yl)ethynyl)triisopropylsilane. To a solution of [7-fluoro-8-(2-triisopropylsilylethynyl)-1-naphthyl]trifluoromethanesulfonate (20.0 g, 42.1 mmol, 1.00 equiv.) and bis(pinacolato)diboron (16.0 g, 63.2 mmol, 1.50 equiv.) in dioxane (6.00 mL) were added KOAc (8.27 g, 84.3 mmol, 2.0 equiv.) and Pd(dppf)Cl₂ (3.08 g, 4.21 mmol, 0.10 equiv.). The mixture was stirred at 110° C. for 12 hours. The mixture was filtered and concentrated under reduced pressure to give a residue. The residue was purified by column chromatography (Silica gel, petroleum ether/ethyl acetate-I/O to 10/1) affording the title compound (9.0 g, 47% yield). Yellow solid; ¹H NMR (400 MHz, CDCl₃) δ 7.85-7.75 (m, 3H), 7.43 (dd, J=7.2, 8.0 Hz, 1H), 7.30-7.24 (m, 1H), 1.45 (s, 12H), 1.21-1.14 (m, 21H); LCMS [ESI, M+1]: 453.2.

Intermediate 8

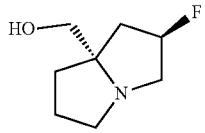 [SMILES: OC[C@@]12CCCN1C[C@H](F)C2]

((2R,7aS)-2-fluorohexahydro-1H-pyrrolizin-7a-yl)methanol

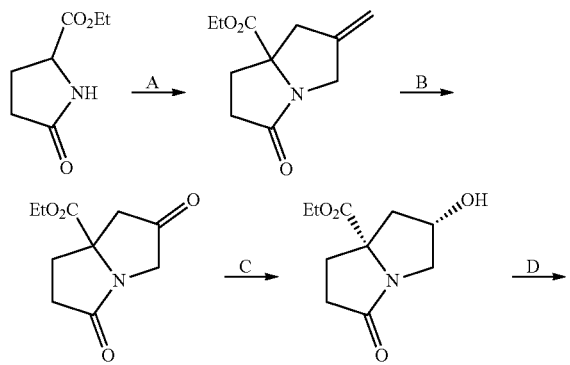

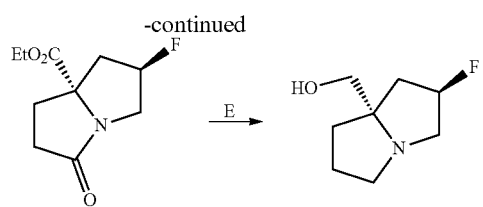

Step A. Ethyl 2-methylene-5-oxotetrahydro-1H-pyrrolizine-7a(5H)-carboxylate. To a mixture of ethyl 5-oxopyrrolidine-2-carboxylate (1.50 kg, 9.54 mol, 1.00 equiv.) and 3-chloro-2-(chloromethyl)prop-1-ene (1.91 kg, 15.3 mol, 1.77 L, 1.60 equiv.) in THF (7.50 L) was added LiHMDS (1 M, 19.1 L, 2.00 equiv.) drop-wise at −40° C. under N₂. The mixture was stirred at 25° C. for 20 hrs. The reaction mixture was poured into HCl (1 M, 2.50 L) and pH was adjusted to 7 with HCl (2 M) at 0° C. The mixture was extracted with EtOAc (4.50 L×3). The combined organic layers were washed with brine (4.50 L), dried over Na₂SO₄, filtered and concentrated under reduced pressure to give a residue. The residue was purified by column chromatography (Silica gel, Petroleum ether/Ethyl acetate=10/1 to 1/1, Rf=0.40) to afford the title compound (898 g, 3.88 mol, 40.6% yield, 82% purity) as a yellow oil. LCMS: Rt=0.716 min, m/z=210.1 (M+H). ¹H NMR: 400 MHz CDCl₃δ: 5.02-5.07 (m, 211), 4.28 (m, 1H), 4.16-4.22 (m, 2H), 3.71 (dd, J=15.6, 1.6 Hz, 1H), 3.04 (m, 1H), 2.73-2.80 (m, 1H), 2.57-2.64 (m, 1H), 2.41-2.49 (m, 2H), 2.03-2.17 (m, 2H), 1.24-1.30 (m, 3H).

Step B. ethyl 2,5-dioxotetrahydro-1H-pyrrolizine-7a(5H-carboxylate. To a mixture of ethyl 2-methylene-5-oxotetrahydro-1H-pyrrolizine-7a(5H)-carboxylate (165 g, 646 mmol, 1.00 equiv.) in DCM (1650 mL) and MeOH (165 mL) was added 03 (15 psi) at −70° C. under N₂. The solution became pale blue, and then the mixture was purged by N₂ for 30 min. Me₂S (80.4 g, 1.29 mol, 95.0 mL, 2.00 equiv.) was added to the mixture at −70° C. The mixture was stirred at 25° C. for 16 hours. The reaction mixture was concentrated under reduced pressure to give a residue. The residue was purified by column chromatography (Silica gel, Petroleum ether/Ethyl acetate=10/1 to 1/1, Rf=0.50) to afford the title compound (821 g, 3.62 mol, 93.3% yield, 93.1% purity) as a yellow oil. LCMS: Rt=0.543 min, m/z=212.1 (M+H). ¹H NMR: 400 MHz CDCl₃δ: 4.23 (m, 2H), 4.12 (m, 1H), 3.56 (m, 1H), 2.96-3.01 (m, 2H), 2.77-2.86 (m, 1H), 2.43-2.50 (m, 2H), 2.14-2.22 (m, 1H), 1.28 (m, 1H).

Step C. ethyl 2-hydroxy-5-oxotetrahydro-1H-pyrrolizine-7a(5H)-carboxylate. To a solution of ethyl 2,5-dioxotetrahydro-1H-pyrrolizine-7a(5H)-carboxylate (257 g, 1.22 mol, 1.00 equiv.) in EtOH (1300 mL) was slowly added NaBH₄ (13.8 g, 365 mmol, 0.30 equiv.) at 0° C. under N₂. The mixture was stirred at 0° C. for 10 min. The reaction was quenched with saturated NH₄Cl (65.0 mL) at 5° C. and stirred at 5° C. for 0.5 hr, then the mixture was concentrated under reduced pressure to give a residue. The residue was purified by column chromatography (Silica gel, Petroleum ether/Ethyl acetate=10/1 to 1/1) to afford the title compound (56.8% yield) as a yellow oil. ¹H NMR: 400 MHz CDCl₃δ: 4.65 (s, 1H), 4.14 (q, J=7.2 Hz, 2H), 3.95 (dd, J=12.8, 6.0 Hz, 1H), 3.10 (d, J=12.8 Hz, 1H), 2.75-2.84 (m, 2H), 2.49-2.49 (m, 2H), 2.39-2.45 (m, 1H), 2.02-2.10 (m, 1H), 1.84 (dd, J=13.6, 6.0 Hz, 1H), 1.30 (t, J=7.2 Hz, 1H).

Step D. ethyl (2S,7aR)-2-fluoro-5-oxotetrahydro-1H-pyrrolizine-7a(5H)-carboxylate. To a solution of ethyl 2-hydroxy-5-oxotetrahydro-1H-pyrrolizine-7a(5H)-carboxylate (150 g, 642 mmol, 1.00 equiv.) in DCM (750 mL) was added a solution of DAST (131 g, 813 mmol, 107 mL, 1.50 equiv.) drop-wise at −70° C. under $N_2$. The reaction mixture was warmed to 25° C. stirred at 25° C. for 16 hours. The reaction mixture was quenched with MeOH (40.0 mL) at 10° C., then diluted with water (750 mL) and extracted with DCM (750 mL×3). The combined organic layers were washed with brine (750 mL), dried over $Na_2SO_4$, filtered and concentrated under reduced pressure to give a residue. The residue was purified by column chromatography (Silica gel, Petroleum ether/Ethyl acetate=I/O to 0/1, Rf=0.30) to afford ethyl 2-fluoro-5-oxotetrahydro-1H-pyrrolizine-7a(5H)-carboxylate (50.6% yield, 74.7% purity) as a yellow oil. This compound (61 g, 283.43 mmol, 1.00 equiv.) was further purified by HPLC (column: Welch ultimate XB-NH₂ 250*50*10 um; mobile phase: [Heptane-EtOH (0.1% $NH_3$WATER)]; B %: 10%-10%, 10 min) to give a yellow oil (49.0 g, 226.08 mmol, 99.3% purity). $^1$H NMR: 400 MHz CDCl$_3$δ: 5.30 (m, 1H), 4.10-4.23 (m, 3H), 3.11-3.14 (m, 1H), 2.67-2.76 (m, 3H), 2.41-2.45 (m, 1H), 2.03-2.12 (m, 2H), 1.23-1.29 (m, 3H). SFC separation (column: DAICEL CHIRALPAK IC (250 mm*50 mm, 10 um); mobile phase: [0.1% $NH_3H_2O$-IPA]; B %: 40%-40%, 4.7 min; 200 min-min, desired product: Peak 2, Rt=1.959 min) of the racemic material (280 g, 1.22 mol, 1 equiv.) gave the title compound (114 g, 96.0% purity).

Step E. ((2R,7aS)-2-fluorohexahydro-1H-pyrrolizin-7a-yl)methanol. To a suspension of LiAlH$_4$ (33.1 g, 871 mmol, 1.50 equiv.) in THF (625 mL) was added a solution of ethyl (2S,7aR)-2-fluoro-5-oxotetrahydro-1H-pyrrolizine-7a(5H)-carboxylate (125 g, 581 mmol, 1.00 equiv.) in THF (375 mL) drop-wise at 0° C. under N$_2$. The reaction mixture was warmed to 70° C. and stirred at 70° C. for 3 hours. The mixture was cooled to 0° C. Then to the mixture was added water (33.0 mL), NaOH (15%, 99.0 mL) and water (99 mL) dropwise in sequence 0° C. After addition, the mixture was stirred at 0° C. stirred for 5 min. The mixture was filtered, and the filtered cake was washed with EtOAc (1000 mL×2). The filtrate was dried with MgSO$_4$, filtered, and concentrated under reduced pressure to give a residue. The residue was purified by column chromatography (Silica gel, DCM: MeOH=100/1 to 10/1) to afford the title compound (180 g, 1.10 mol, 94.7% yield, 97.3% purity) as a yellow oil. $^1$H NMR: 400 MHz CDCl$_3$δ: 5.12-5.27 (m, 1H), 3.25 (s, 2H), 3.14-3.18 (m, 2H), 3.12-3.13 (m, 1H), 3.02-3.09 (m, 1H), 2.01-2.11 (m, 2H), 1.75-1.86 (m, 4H).

Intermediate 9

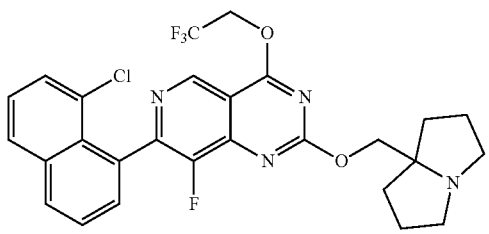 [SMILES: Fc1c(-c2cccc3cccc(Cl)c23)ncc2c(OCC(F)(F)F)nc(OCC34CCCN3CCC4)nc12]

7-(8-chloronaphthalen-1-yl)-8-fluoro-2-((tetrahydro-1H-pyrrolizin-7a(5H)-yl)methoxy)-4-(2,2,2-trifluoroethoxy)pyrido[4,3-d]pyrimidine

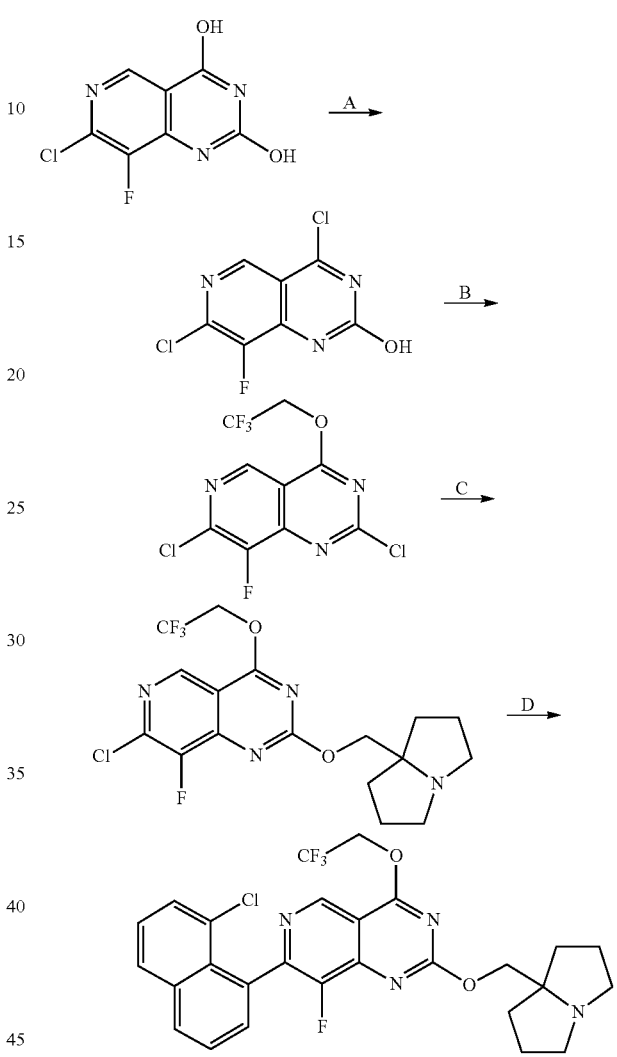

Step A. 2,4,7-trichloro-8-fluoro-pyrido[4,3-d]pyrimidine. To a mixture of -chloro-8-fluoro-pyrido[4,3-d]pyrimidine-2,4-diol (20 g, 92.8 mmol, 1.00 equiv.) in toluene (100 mL) was added POCl$_3$ (42.7 g, 278 mmol, 25.9 mL, 3.00 equiv.) and N-ethyl-N-isopropylpropan-2-amine (36.0 g, 278 mmol, 48.5 mL, 3.00 equiv.) at 0° C. The mixture was stirred at 110° C. for 3 hours. After completion, the mixture was concentrate under reduced pressure at 40° C. to dryness affording 2,4,7-trichloro-8-fluoro-pyrido[4,3-d]pyrimidine (23.4 g, crude) as a black oil.

Step B. 2,7-dichloro-8-fluoro-4-(2,2,2-trifluoroethoxy) pyrido[4,3-d]pyrimidine. To a solution of 2,2,2-trifluoroethanol (11.1 g, 111 mmol, 8.01 mL, 1.20 equiv.) in toluene (200 mL) was added t-BuONa (26.7 g, 278 mmol, 3.00 equiv.) at 0° C. The mixture was first stirred at 10° C. for 0.5 hour. Then the above mixture was added to 2,4,7-trichloro-8-fluoro-pyrido[4,3-d]pyrimidine (23.4 g, 92.7 mmol, 1.00 equiv.) in toluene (200 mL) at −10° C. After addition, the mixture was stirred at −10° C.~25° C. for 16 hours. After monitored, a mixture of t-BuONa (1.78 g, 18.5 mmol, 0.2 equiv.) and 2,2,2-trifluoroethanol (1.85 g, 18.5 mmol, 1.33 mL, 0.20 equiv.) in toluene (20.0 mL) was added thereto at 0° C. The mixture was continued to stir at 25° C. for 30 hours. After completion, the mixture was poured onto Silica gel column, purified by column chromatography (Silica gel, petroleum ether/ethyl acetate=30/1 to 10/1), and then further purified by reversed-phase flash chromatography (water (0.1% formic acid)-ACN) affording 2,7-dichloro-8-fluoro-4-(2,2,2-trifluoroethoxy)pyrido[4,3-d]pyrimidine (16.3 g, 55.6% yield); Yellow solid; LCMS [ESI, M+1]: 316.

Step C. 7-chloro-8-fluoro-2-((tetrahydro-1H-pyrrolizin-7a(5H)-yl)methoxy)-4-(2,2,2-trifluoroethoxy)pyrido[4,3-d]pyrimidine. To a mixture of (tetrahydro-1H-pyrrolizin-7a(5H)-yl)methanol (17.9 g, 126 mmol, 2.00 equiv.), 4 Å MS (15.0 g) and N-ethyl-N-isopropylpropan-2-amine (16.4 g, 126 mmol, 22.0 mL, 2.00 equiv.) in 2-methyltetrahydrofuran (200 mL) was added 2,7-dichloro-8-fluoro-4-(2,2,2-trifluoroethoxy)pyrido[4,3-d]pyrimidine (20.0 g, 63.3 mmol, 1.00 equiv.) in 2-methyltetrahydrofuran (200 mL) at 0-5° C. The mixture was stirred at 0-25° C. for 2 hours. After completion, the mixture was filtered and washed with ethyl acetate (100 mL). The filtrate was quenched by saturated NH₄Cl aqueous solution (300 mL), and the organic layer was separated and dried over anhydrous Na₂SO₄. The mixture was filtered, and the filtrate was concentrated under reduced pressure at 40° C. to dryness. The crude product was triturated with CH₃CN (20 mL) at 25° C. for 15 minutes and filtered, the filter cake was dried in vacuum at 40° C. affording the title compound (18.2 g, 64.6% yield). Light yellow solid. ¹H NMR (400 MHz, CDCl₃) δ 8.99 (s, 1H), 5.03 (q, J=8.4 Hz, 2H), 4.32 (s, 2H), 3.23-3.05 (m, 2H), 2.67 (td, J=6.8, 10.4 Hz, 2H), 2.11-1.96 (m, 21H), 1.96-1.85 (m, 4H), 1.74-1.69 (m, 2H); LCMS [ESI, M+1]: 421.

Step D. 7-(8-chloronaphthalen-1-yl)-8-fluoro-2-((tetrahydro-1H-pyrrolizin-7a(5H)-yl)methoxy)-4-(2,2,2-trifluoroethoxy)pyrido[4,3-d]pyrimidine. To a mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (5.00 g, 11.9 mmol, 1.00 equiv.), (8-chloronaphthalen-1-yl)trimethylstannane (7.73 g, 23.8 mmol, 2.00 equiv.) in toluene (150 mL) was added 4 Å MS (5.00 g) at 25° C. The mixture was stirred at 25° C. for 1 hour. Then CuI (792 mg, 4.16 mmol, 0.35 equiv.), Pd(dppf)Cl₂ (1.30 g, 1.78 mmol, 0.15 equiv.) and BINAP (1.85 g, 2.97 mmol, 0.25 equiv.) were added thereto at 25° C. The mixture was degassed in vacuum and purged with N₂ several times over 30 minutes. Then the mixture was heated to 90° C. and stirred for 2 hours. The mixture was cooled to 25° C., and then (8-chloronaphthalen-1-yl)trimethylstannane (1.93 g, 5.94 mmol, 0.50 equiv.) was added thereto at 25° C. The mixture was heated to 90° C. and stirred for 1 hour. After completion, the mixture was filtered, and the filtrate was concentrated under reduced pressure at 40° C. to dryness. The crude product was purified by reversed-phase flash chromatography (water (0.1% formic acid)-ACN) affording the title compound (2.3 g, 33.9% yield); Yellow solid. ¹H NMR (400 MHz, CDCl₃) δ 9.25 (s, 1H), 8.02 (dd, J=1.2, 8.0 Hz, 1H), 7.89 (dd, J=0.8, 8.0 Hz, 1H), 7.65-7.60 (m, 1H), 7.59-7.53 (m, 2H), 7.46-7.41 (m, 1H), 5.08 (q, J=8.0 Hz, 2H), 4.46 (s, 2H), 3.32 (br d, J=3.8 Hz, 2H), 2.83-2.70 (m, 2H), 2.20-2.09 (m, 2H), 2.03-1.90 (m, 4H), 1.82-1.72 (m, 2H); LCMS [ESI, M+1]: 547.

Intermediate 10

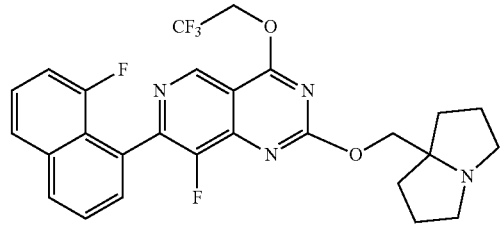 [SMILES: Fc1c(-c2cccc3cccc(F)c23)ncc2c(OCC(F)(F)F)nc(OCC34CCCN3CCC4)nc12]

8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine

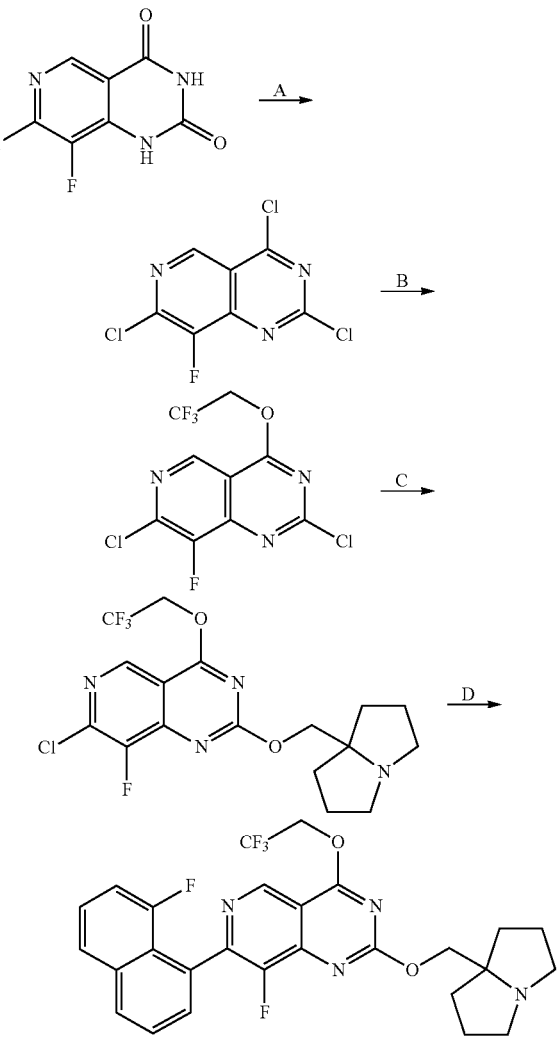

Step A. 2,4,7-trichloro-8-fluoropyrido[4,3-d]pyrimidine. To a solution of 7-chloro-8-fluoropyrido[4,3-d]pyrimidine-2,4(1H,3H)-dione (100 g, 463 mmol, 1.00 equiv.) in toluene (500 mL) were added POCl₃ (213 g, 1.39 mol, 129 mL, 3.00 equiv.) and DIEA (179 g, 1.39 mol, 242 mL, 3.00 equiv.) at 0° C. The mixture was stirred at 110° C. for 5 h. The reaction was distilled in vacuum (80° C., water pump) to give 2,4,7-trichloro-8-fluoropyrido[4,3-d]pyrimidine (100 g, 396.10 mmol, 85.39% yield) as brown oil.

Step B. 2,7-dichloro-8-fluoro-4-(2,2,2-trifluoroethoxy) pyrido[4,3-d]pyrimidine. To a solution of 2,4,7-trichloro-8-fluoropyrido[4,3-d]pyrimidine (100 g, 396 mmol, 1.00 equiv.) and 2,2,2-trifluoroethanol (59.4 g, 594 mmol, 42.7 mL, 1.50 equiv.) in toluene (2 L) was added t-BuONa (152 g, 1.58 mol, 4.00 equiv.) at 25° C. The mixture was stirred at 25° C. for 2 hr. The reaction mixture was filtered through a pad of Celite, washed with brine (3 L×2) and concentrated under reduced pressure to give a residue, which was purified by reversed-phase HPLC (water (0.1% formic acid)-ACN) to give 2,7-dichloro-8-fluoro-4-(2,2,2-trifluoroethoxy) pyrido[4,3-d]pyrimidine (45.0 g, 140 mmol, 35.5% yield, 99.0% purity) as a brown solid. LCMS: M+1, 316.

Step C. 7-chloro-8-fluoro-2-((tetrahydro-1H-pyrrolizin-7a(5H)-yl)methoxy)-4-(2,2,2-trifluoroethoxy)pyrido[4,3-d] pyrimidine. A mixture of (tetrahydro-1H-pyrrolizin-7a(5H)-yl)methanol (35.7 g, 253 mmol, 2.00 equiv.), DIEA (32.7 g, 253 mmol, 44.0 mL, 2.00 equiv.) and 4 Å molecular sieves (40.0 g) in 2-methyltetrahydrofuran (400 mL) was stirred at 25° C. for 1 hr. Then a solution of 2,7-dichloro-8-fluoro-4-(2,2,2-trifluoroethoxy)pyrido[4,3-d]pyrimidine (40.0 g, 126 mmol, 1.00 equiv.) in 2-methyltetrahydrofuran (400 mL) was added and the resulting mixture was stirred at 25° C. for 2 hrs. The reaction mixture was filtered. The filtrate was washed with sat. aq. NH$_4$Cl solution (1 L×2), dried over Na$_2$SO$_4$, filtered and concentrated under reduced pressure to give a residue. The residue was triturated with acetonitrile (300 mL) at 25° C. for 30 min to give 7-chloro-8-fluoro-2-((tetrahydro-1H-pyrrolizin-7a(5H)-yl)methoxy)-4-(2,2,2-trifluoroethoxy)pyrido[4,3-d]pyrimidine (26.0 g, 61.1 mmol, 48.3% yield, 99.0% purity) as a light yellow solid. LCMS: M+1, 421.

Step D. 8-fluoro-7-(8-fluoronaphthalen-1-yl)-2-((hexahydro-1H-pyrrolizin-7a-yl methoxy)-4-(2,2,2-trifluoroethoxy)pyrido[4,3-d]pyrimidine. A mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (17.0 g, 40.4 mmol, 1.00 equiv.), 2-(8-fluoronaphthalen-1-yl)-4,4,5,5-tetramethyl-1,3,2-dioxaborolane (16.4 g, 60.6 mmol, 1.50 equiv.), BrettPhos Pd G3 (4.25 g, 4.69 mmol, 1.16e-1 equiv.), K$_3$PO$_4$ (1.5 M, 80.8 mL, 3.00 equiv.) in toluene (170 mL) was degassed and purged with N$_2$ for 3 times, and then the mixture was stirred at 65° C. for 4 hrs under N$_2$ atmosphere. The reaction mixture was filtered. The filtrate was extracted with toluene (170 mL×3). The combined organic layers were dried over Na$_2$SO$_4$, filtered and concentrated under reduced pressure to give a residue. The residue was purified by reversed-phase HPLC (water (0.1% formic acid)-ACN) to give 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (10.85 g, 16.6 mmol, 41.2% yield, 95.8% purity) as a yellow solid. NMR: δ 9.28 (s, 1H), 8.23 (d, J=8.1 Hz, 1H), 7.97 (d, J=8.1 Hz, 1H), 7.81-7.76 (m, 1H), 7.68 (dd, J=0.9, 7.2 Hz, 1H), 7.61 (dt, J=5.1, 7.9 Hz, 1H), 7.34 (dd, J=7.1, 13.3 Hz, 1H), 5.47-5.37 (m, 2H), 4.77-4.67 (m, 2H), 3.56-3.49 (m, 2H), 3.22 (td, J=6.0, 11.7 Hz, 2H), 2.27-2.00 (m, 8H); LCMS: M+1, 531.

Intermediate 11

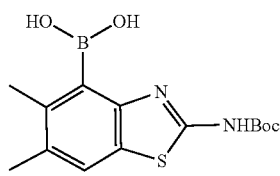 [SMILES: Cc1cc2sc(NC(=O)OC(C)(C)C)nc2c(B(O)O)c1C]

(2-((tert-butoxycarbonyl)amino)-5,6-dimethylbenzo[d]thiazol-4-yl)boronic Acid

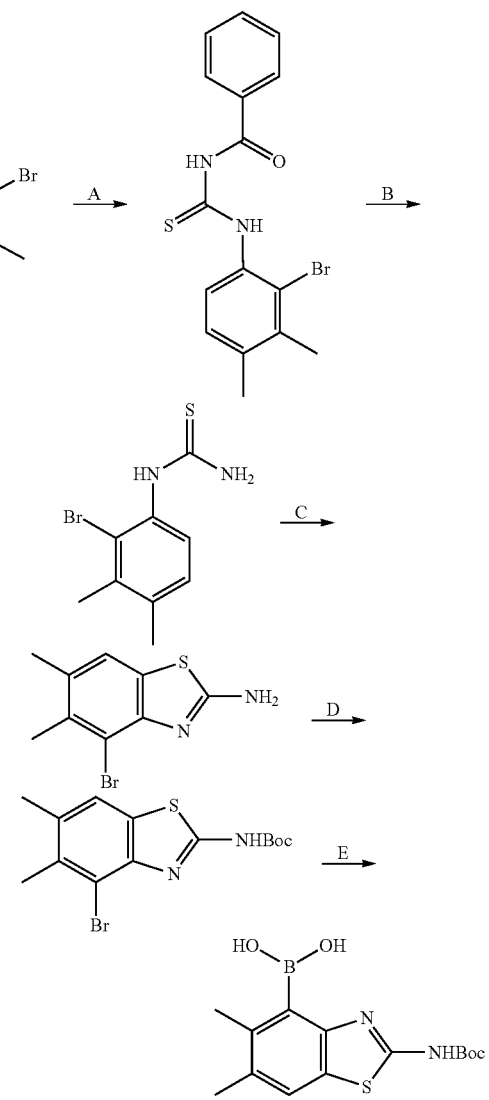

Step A. N-((2-bromo-3,4-dimethylphenyl)carbamothiol) benzamide: To a solution of 2-bromo-3,4-dimethylaniline (2.17 g, 10.9 mmol) in acetone (30 mL) was added benzoyl isothiocyanate (1.9 g, 11.6 mmol) in acetone (10 mL) at 25° C. The mixture was stirred at 25° C. for 5 minutes. The reaction mixture was concentrated under reduced pressure to give a residue. The residue was dispersed in petroleum ether/ethyl acetate=20/1 (40 mL) and stirred for 0.5 hour. The mixture was filtered and the solid was dried under reduced pressure to give N-((2-bromo-3,4-dimethylphenyl) carbamothioyl)benzamide (3.56 g, 90% yield) as a light yellow solid; $^1$H NMR (400 MHz, CDCl$_3$) δ=12.45 (br s, 1H), 9.21 (br s, 1H), 7.95-7.92 (m, 2H), 7.79 (d, J=8.0 Hz, 1H), 7.67-7.59 (m, 1H), 7.58-7.56 (m, 2H), 7.19 (d, J=8.0 Hz, 1H), 2.44 (s, 3H), 2.37 (s, 3H).

Step B. 1-(2-bromo-3,4-dimethylphenyl)thiourea: A mixture of N-((2-bromo-3,4-dimethylphenyl)carbamothioyl) benzamide (3.30 g, 9.08 mmol) and NaOH (50 mL, 10% aqueous) was stirred at 80° C. for 3 hours. A white precipitate appeared. After completion, the reaction mixture was cooled to 10° C. The mixture was filtered and filter cake was washed with water until the pH of the filtrate was 8-9. The filter cake was washed with petroleum ether (10 mL) and dried under reduced pressure to give 1-(2-bromo-3,4-dimethylphenyl)thiourea (2.2 g, 90% yield) as a white solid; LCMS (ESI, M+1): m/z 259.0, 261.0.

Step C. 4-bromo-5,6-dimethylbenzo[d]thiazol-2-amine: To a solution of 1-(2-bromo-3,4-dimethylphenyl)thiourea (2.20 g, 8.49 mmol) in CHCl$_3$ (30 mL) was added drop-wise Br$_2$ (1.36 g, 8.49 mmol) in CHCl$_3$ (2 mL) at 0° C. The mixture was stirred at 70° C. for 1 hour. The reaction mixture was concentrated under reduced pressure to give a residue. The residue was diluted with ethyl acetate (200 mL), saturated Na$_2$SO$_2$O$_3$ aqueous (50 mL) and saturated NaHCO$_3$ aqueous solution (50 mL). The mixture was extracted with ethyl acetate (50 mL×3). The combined organic layers were dried over anhydrous Na$_2$SO$_4$, filtered and concentrated under reduced pressure to give 4-bromo-5,6-dimethylbenzo[d]thiazol-2-amine (2 g, 88% yield) as a white solid; $^1$H NMR (400 MHz, DMSO-d$_6$) δ=7.66 (s, 2H), 7.43 (s, 1H), 2.34 (s, 3H), 2.29 (s, 3H). LCMS (ESI, M+1): m/z 257.0, 259.0.

Step D. tert-butyl (4-bromo-5,6-dimethylbenzo[d]thiazol-2-yl)carbamate: A mixture of 4-bromo-5,6-dimethylbenzo [d]thiazol-2-amine (2 g, 7.78 mmol), (Boc)$_2$O (2.1 g, 9.62 mmol), DIPEA (3.04 g, 23.5 mmol) and DMAP (96 mg, 786 μmol) in THF (40 mL) was stirred at 25° C. for 16 hour. Then DIPEA (1.04 g, 8.04 mmol) and (Boc)$_2$O (570 mg, 2.61 mmol) was added. The mixture was stirred at 25° C. for 4 hours. After completion, the reaction mixture was diluted with water (50 mL) and ethyl acetate (200 mL). The mixture was extracted with ethyl acetate (50 mL×3). The combined organic layers were washed with brine (20 mL) and dried over anhydrous Na$_2$SO$_4$. The mixture was filtered and concentrated under reduced pressure to give a residue. The residue was purified by reversed phase flash chromatography [water (0.1% formic acid)/acetonitrile=1/19] to give tert-butyl (4-bromo-5,6-dimethylbenzo[d]thiazol-2-yl)carbamate (2.6 g, 91% yield) as a light yellow solid; LCMS (ESI, M−55): m/z 300.9, 302.9.

Step E. (2-((tert-butoxycarbonyl)amino)-5,6-dimethylbenzo[d]thiazol-4-yl)boronic acid: A mixture of tert-butyl (4-bromo-5,6-dimethylbenzo[d]thiazol-2-yl)carbamate (1 g, 2.80 mmol), 2-(5,5-dimethyl-1,3,2-dioxaborinan-2-yl)-5,5-dimethyl-1,3,2-dioxaborinane (1.58 g, 7.00 mmol) and AcOK (1.00 g, 10.2 mmol) in dioxane (15 mL) was degassed and purged with N$_2$ for 3 times. Then [2-(2-aminophenyl)phenyl]-chloro-palladium; tricyclohexylphosphane (100 mg, 169 μmol, 0.06 equiv.) was added. The mixture was stirred at 80° C. for 40 hours under N$_2$ atmosphere. After completion, the reaction mixture was diluted with water (1 mL) and brine (1 mL), and extracted with ethyl acetate (2 mL×4). The combined organic layers were dried over anhydrous Na$_2$SO$_4$ and filtered. The mixture was concentrated under reduced pressure to give a residue. The residue was purified by reversed phase flash chromatography [water (0.1% formic acid)/acetonitrile=1/9] to give (2-((tert-butoxycarbonyl)amino)-5,6-dimethylbenzo[d]thiazol-4-yl)boronic acid (0.73 g, 65% yield) as a light yellow solid; LCMS (ESI, M+1): m/z 323.1.

Intermediate 12

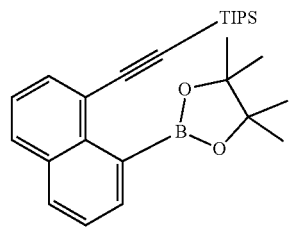

triisopropyl((8-(4,4,5,5-tetramethyl-1,3,2-dioxaborolan-2-yl)naphthalen-1-yl)ethynyl)silane

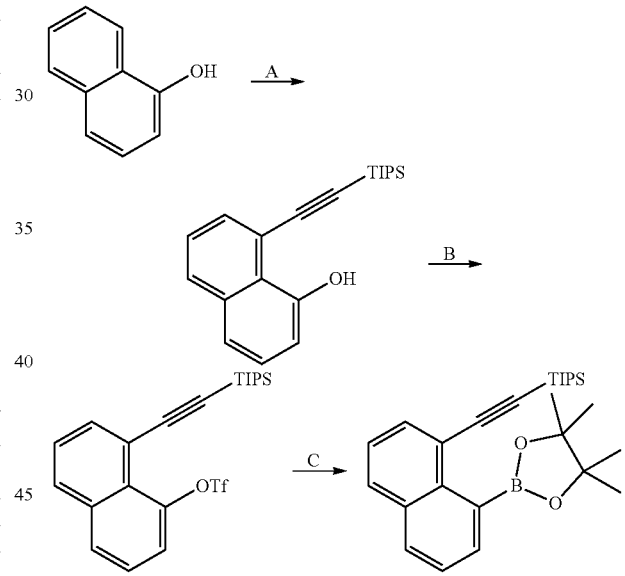

Step A. 8-((triisopropylsilyl)ethynyl)naphthalen-1-ol: To a solution of naphthalen-1-ol (500 mg, 3.47 mmol, 1.25 mL), potassium carbonate (479 mg, 3.47 mmol), dichlororuthenium; 1-isopropyl-4-methyl-benzene (531 mg, 867 μmol) and sodium acetate (56.9 mg, 694 μmol) in DCE (20.0 mL) was added 2-bromoethynyl(triisopropyl)silane (1.09 g, 4.16 mmol). The reaction was stirred at 40° C. for 12 hours. The reaction mixture was cooled to 25° C. and filtered. The filtrate was concentrated in vacuo to give a residue. The residue was purified by silica gel chromatography (Petroleum ether/ethyl acetate=I/O to 10/1) to give 8-((triisopropylsilyl)ethynyl)naphthalen-1-ol (760 mg, 67% yield) as a brown solid; $^1$H NMR (400 MHz, CDCl$_3$) δ=9.22 (s, 1H), 7.81 (dd, J=1.2, 8.4 Hz, 1H), 7.64 (dd, J=1.2, 6.8 Hz, 1H), 7.42-7.34 (m, 3H), 7.01 (dd, J=4.0, 5.6 Hz, 1H), 1.25-1.13 (m, 21H).

Step B. 8-((triisopropylsilyl)ethynyl)naphthalen-1-yl trifluoromethanesulfonate: To a solution of 8-((triisopropylsilyl)ethynyl)naphthalen-1-ol (760 mg, 2.34 mmol) and DIEA (605 mg, 4.68 mmol, 816 µL) in DCM (8.00 mL) was added Tf$_2$O (991 mg, 3.51 mmol, 580 µL) at −40° C. The reaction was stirred at 25° C. for 0.5 hour. The reaction was quenched with water (10.0 mL). The aqueous phase was extracted with DCM (2×20.0 mL). The combined organic phase was washed with brine (2×20 mL) and dried over anhydrous sodium sulfate. The mixture was filtered and concentrated in vacuum to give a residue. The residue was purified by silica gel chromatography (petroleum ether/ethyl acetate=1/0 to 10/1) to give 8-((triisopropylsilyl)ethynyl)naphthalen-1-yl trifluoromethanesulfonate (1.00 g, 93% yield) as a brown oil; $^1$H NMR (400 MHz, CDCl$_3$) δ=7.92-7.84 (m, 3H), 7.56-7.47 (m, 3H), 1.26-1.12 (m, 21H).

Step C. triisopropyl((8-(4,4,5,5-tetramethyl-1,3,2-dioxaborolan-2-yl)naphthalen-1-yl)ethynyl)silane: To a solution of 8-((triisopropylsilyl)ethynyl)naphthalen-1-yl trifluoromethanesulfonate (950 mg, 2.08 mmol) in dioxane (15.0 mL) were added 4,4,4',4',5,5,5',5'-octamethyl-2,2'-bi(1,3,2-dioxaborolane) (687 mg, 2.70 mmol), Pd(dppf)Cl$_2$ (152 mg, 208 µmol) and KOAc (408 mg, 4.16 mmol). The reaction was stirred at 110° C. for 5 hours under nitrogen. The reaction was filtered and concentrated in vacuum to give a residue. The residue was purified by silica gel chromatography (petroleum ether/ethyl acetate=I/O to 20/1) to give triisopropyl((8-(4,4,5,5-tetramethyl-1,3,2-dioxaborolan-2-yl)naphthalen-1-yl)ethynyl)silane (340 mg, 38% yield) as a red oil; $^1$H NMR (400 MHz, CDCl$_3$) δ=7.78-7.66 (m, 3H), 7.39-7.26 (m, 3H), 1.36 (s, 12H), 1.12-1.05 (m, 21H).

Intermediate 13

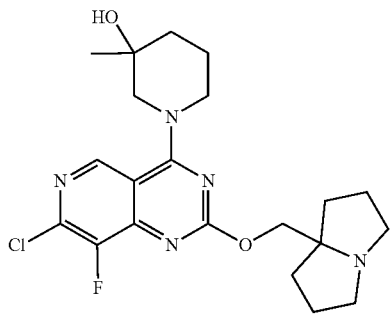 [SMILES: CC1(O)CCCN(c2nc(OCC34CCCN3CCC4)nc3c(F)c(Cl)ncc23)C1]

1-(7-chloro-8-fluoro-2-((hexahydro-1H-pyrrolizin-7a-yl)methoxy)pyrido[4,3-d]pyrimidin-4-yl)-3-methylpiperidin-3-ol

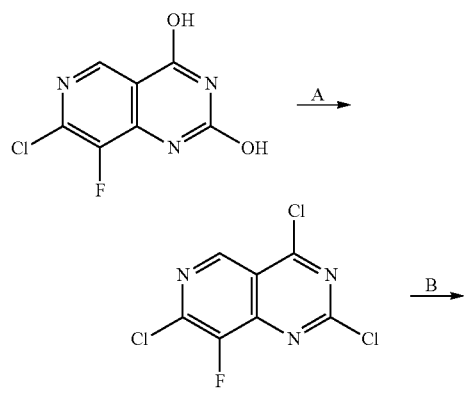

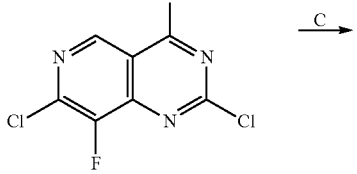

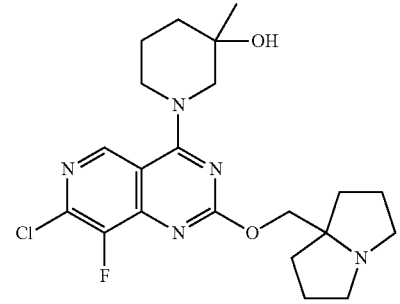

Step A. 2,4,7-trichloro-8-fluoropyrido[4,3-d]pyrimidine: To a mixture of 7-chloro-8-fluoropyrido[4,3-d]pyrimidine-2,4-diol (2.8 g, 13.0 mmol) in POCl$_3$ (20 mL) was added DIEA (5.04 g, 39.0 mmol, 6.79 mL) in one portion at 25° C. under N$_2$. The mixture was heated to 110° C. and stirred for 2 hours. After completion, the mixture was concentrated under reduced pressure at 45° C. The residue was purified by silica gel chromatography (Silica gel, Petroleum ether/Ethyl acetate=20/1, 3/1) to afford 2,4,7-trichloro-8-fluoropyrido[4,3-d]pyrimidine (3.1 g, 89% yield) as a yellow solid; LCMS (ESI, M+1): m/z 251.9.

Step B. 1-(2,7-dichloro-8-fluoropyrido[4,3-d]pyrimidin-4-yl)-3-methylpiperidin-_-ol: To a mixture of 2,4,7-trichloro-8-fluoropyrido[4,3-d]pyrimidine (3 g, 11.9 mmol) and DIEA (6.14 g, 47.5 mmol, 8.28 mL) in DCM (10 mL) was added 3-methylpiperidin-3-ol hydrochloride (1.52 g, 13.2 mmol) in portions at −40° C. under N$_2$. The mixture was stirred at −40° C. for 1 hour. After completion, the mixture was filtered and concentrated in vacuum. The residue was purified by silica gel chromatography (Silica gel, Petroleum ether/Ethyl acetate=1/0, 0/1) affording 1-(2,7-dichloro-8-fluoropyrido[4,3-d] pyrimidin-4-yl)-3-methylpiperidin-3-ol (2.81 g, 71% yield) as a yellow solid; $^1$H NMR (400 MHz, DMSO-d) δ 9.18 (s, 1H), 4.73 (s, 1H), 4.46 (d, J=12.4 Hz, 1H), 4.12 (d, J=13.2 Hz, 1H), 3.57 (d, J=13.2 Hz, 1H), 3.31-3.21 (m, 1H), 2.03-1.89 (m, 1H), 1.73-1.60 (m, 3H), 1.16 (s, 3H); LCMS (ESI, M+1): m/z 331.0.

Step C. 1-(7-chloro-8-fluoro-2-((hexahydro-1H-pyrrolizin-7a-yl)methoxy)pyrido[4,3-d]pyrimidin-4-yl)-3-methylpiperidin-3-ol: To a mixture of (hexahydro-1H-pyrrolizin-7a-yl)methanol (1.43 g, 10.1 mmol) and 1-(2,7-dichloro-8-fluoropyrido[4,3-d]pyrimidin-4-yl)-3-methylpiperidin-3-ol (2.8 g, 8.45 mmol) in dioxane (18 mL) were added DIEA (3.28 g, 25.4 mmol, 4.42 mL) and 4 Å molecular sieves (1.5 g, 8.45 mmol) in one portion at 25° C. under N$_2$. The mixture was heated to 90° C. and stirred for 20 hours. After completion, the mixture was filtered and concentrated in vacuum. The crude product was purified by reversed phase flash chromatography (water (0.1% formic acid)-ACN) affording 1-(7-chloro-8-fluoro-2-((hexahydro-1H-pyrrolizin-7a-yl)methoxy)pyrido[4,3-d]pyrimidin-4-yl)-3-methylpiperidin-3-ol (1.6 g, 41% yield) as a yellow solid;

¹H NMR (400 MHz, CDCl₃): δ 8.89 (s, 1H), 4.46-4.37 (m, 1H), 4.36-4.29 (m, 1H), 4.26-4.18 (m, 2H), 3.42-3.33 (m, 1H), 3.31-3.24 (m, 1H), 3.14-3.06 (m, 2H), 2.74-2.60 (m, 3H), 2.05-1.97 (m, 3H), 1.92-1.82 (m, 5H), 1.70-1.61 (m, 4H), 1.33 (s, 3H); LCMS (ESI, M+1): m/z 436.2.

Intermediate 14

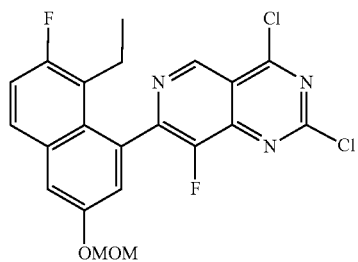

2,4-dichloro-7-(8-ethyl-7-fluoro-3-(methoxymethoxy)naphthalen-1-yl)-8-fluoropyrido[4,3-d]pyrimidine

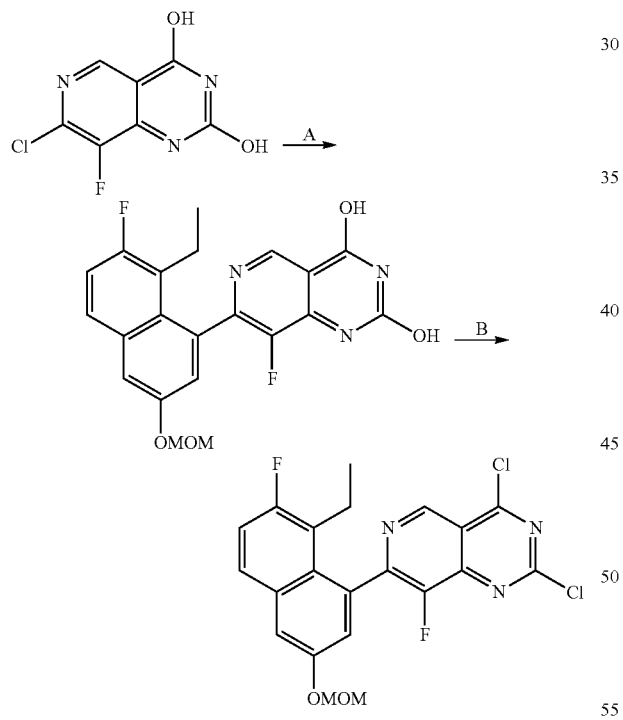

Step A. 7-[8-ethyl-7-fluoro-3-(methoxymethoxy)-1-naphthyl]-8-fluoro-pyrido[4,3-d]pyrimidine-2,4-diol: To a mixture of 7-chloro-8-fluoro-pyrido[4,3-d]pyrimidine-2,4-diol, 2-(8-ethyl-7-fluoro-3-(methoxymethoxy)naphthalen-1-yl)-4,4,5,5-tetramethyl-1,3,2-dioxaborolane (14.0 g, 39.0 mmol) and K₃PO₄ (1.5 M, 46.4 mL) in EtOH (140 mL) was added cataCXium-A-Pd-G3 cataCXium-A-Pd-G3 (1.39 g, 1.90 mmol) under N₂. The mixture was de-gassed and heated to 78° C. for 9.5 hours under N₂. The reaction mixture was concentrated in vacuum. Then the mixture was diluted with ethyl acetate (500 mL) and filtered. The filtrate was diluted with water (100 mL). The organic phase was separated. The aqueous phase was extracted with ethyl acetate (80 mL). The combined organic layers were washed with brine (120 mL) and dried over with anhydrous Na₂SO₄. The mixture was filtered and concentrated in vacuum to give a residue. The residue was purified by reversed phase flash chromatography [water (0.1% formic acid)/acetonitrile] to give 7-[8-ethyl-7-fluoro-3-(methoxymethoxy)-1-naphthyl]-8-fluoro-pyrido[4,3-d]pyrimidine-2,4-diol (2.34 g, 24% yield) as a yellow solid. LCMS [ESI, M+H]: m/z 414.1.

Step B. 2,4-dichloro-7-[8-ethyl-7-fluoro-3-(methoxymethoxy)-1-naphthyl]-8-fluoro-pyrido[4,3-d]pyrimidine: A mixture of POCl₃ (278 mg, 1.81 mmol, 169 μL) in toluene (3 mL) were added DIEA (141 mg, 1.09 mmol, 190 μL) and 7-[8-ethyl-7-fluoro-3-(methoxymethoxy)-1-naphthyl]-8-fluoro-pyrido[4,3-d]pyrimidine-2,4-diol (150 mg, 363 μmol). The reaction mixture was stirred at 110° C. for 25 minutes. After completion, the mixture was concentrated in vacuum and the pH value was adjusted to 8 with ice cold saturated NaHCO₃ solution. Then the mixture was extracted with ethyl acetate (8 mL×2). The combined organic layer was washed with brine (10 mL) and dried over Na₂SO₄. The mixture was filtered and concentrated in vacuum to give 2,4-dichloro-7-[8-ethyl-7-fluoro-3-(methoxymethoxy)-1-naphthyl]-8-fluoro-pyrido[4,3-d]pyrimidine (164 mg, crude) as a brown oil, which was used in the next step without further purification.

Intermediate 15

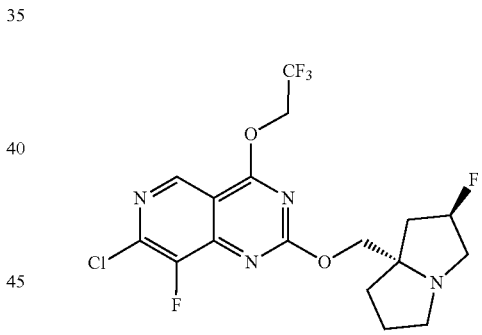

7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine

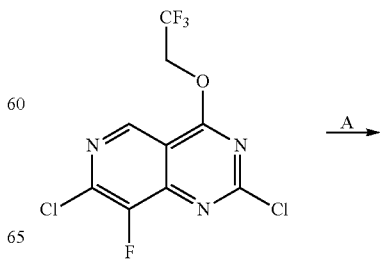

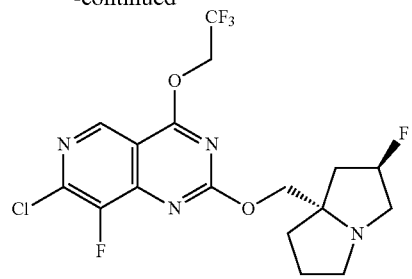

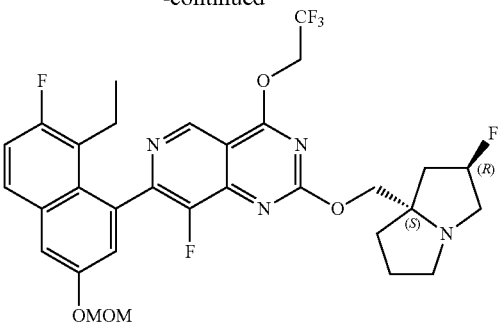

Step A. 7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine: To a mixture of 2,7-dichloro-8-fluoro-4-(2,2,2-trifluoroethoxy)pyrido[4,3-d]pyrimidine (33.3 g, 1.0 equiv.), DIEA (54.5 g, 4.0 equiv.) and 4 Å molecular sieves (4.0 g) in THF (340 mL) was added ((2R,7aS)-2-fluorohexahydro-1H-pyrrolizin-7a-yl)methanol (20.1 g, 1.2 equiv.). The reaction was stirred at 40° C. for 14 hours. The reaction mixture was diluted with water (20 mL) and was extracted with EtOAc (3×20 mL), the combined organic layers were dried over Na$_2$SO$_4$, filtered and concentrated under vacuum. The residue was purified by reversed phase flash chromatography [water (0.1% formic acid)/acetonitrile] to afford the title compound (28.8 g, 62% yield) as a yellow solid; $^1$H NMR (400 MHz, chloroform-d) δ 8.98 (s, 1H), 5.40-5.19 (m, 1H), 5.02 (q, J=8.0 Hz, 2H), 4.40-4.27 (m, 2H), 3.34-3.12 (m, 3H), 3.05-2.94 (m, 1H), 2.32-2.06 (m, 3H), 2.03-1.84 (m, 3H); LCMS [ESI, M+1]: 439.1.

Intermediate 16

Step A. 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine: To a mixture of 7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (1.0 g, 1.0 equiv.), 2-(8-ethyl-7-fluoro-3-(methoxymethoxy)naphthalen-1-yl)-4,4,5,5-tetramethyl-1,3,2-dioxaborolane (1.64 g, 2.0 equiv.) and Cs$_2$CO$_3$ (1.5 M, 3.0 equiv.) in methoxycyclopentane (15.0 mL) was added CataCXium A Pd G3 (332 mg, 0.20 equiv.). The reaction was stirred at 100° C. for 2 hours. The mixture was filtered. To the filtrate water (20 mL) was added and the aqueous layer was extracted with ethyl acetate (2×20 mL). The combined organic layers were dried over anhydrous sodium sulfate, concentrated, and purified by reversed phase flash chromatography [C18, mobile phase: [water (0.1% formic acid)/acetonitrile]] to afford the title compound (820 mg, 56% yield) as a yellow solid; LCMS (ESI, M+1): m/z=637.3.

Intermediate 17

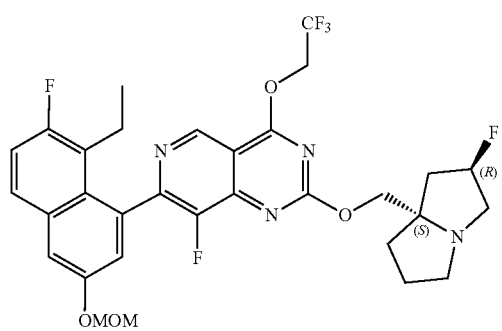

7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine

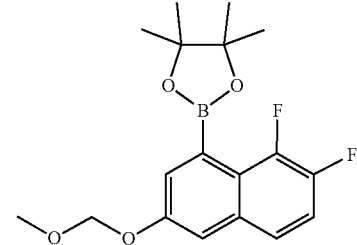 [SMILES: COCOc1cc(B2OC(C)(C)C(C)(C)O2)c2c(F)c(F)ccc2c1]

2-[7,8-difluoro-3-(methoxymethoxy)-1-naphthyl]-4,4,5,5-tetramethyl-1,3,2-dioxaborolane

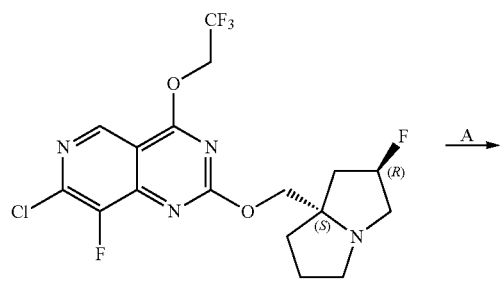

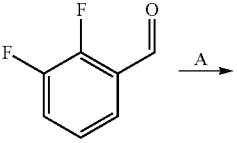

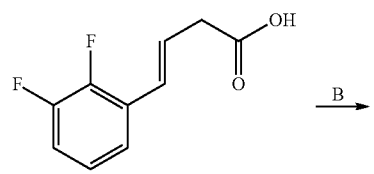

-continued

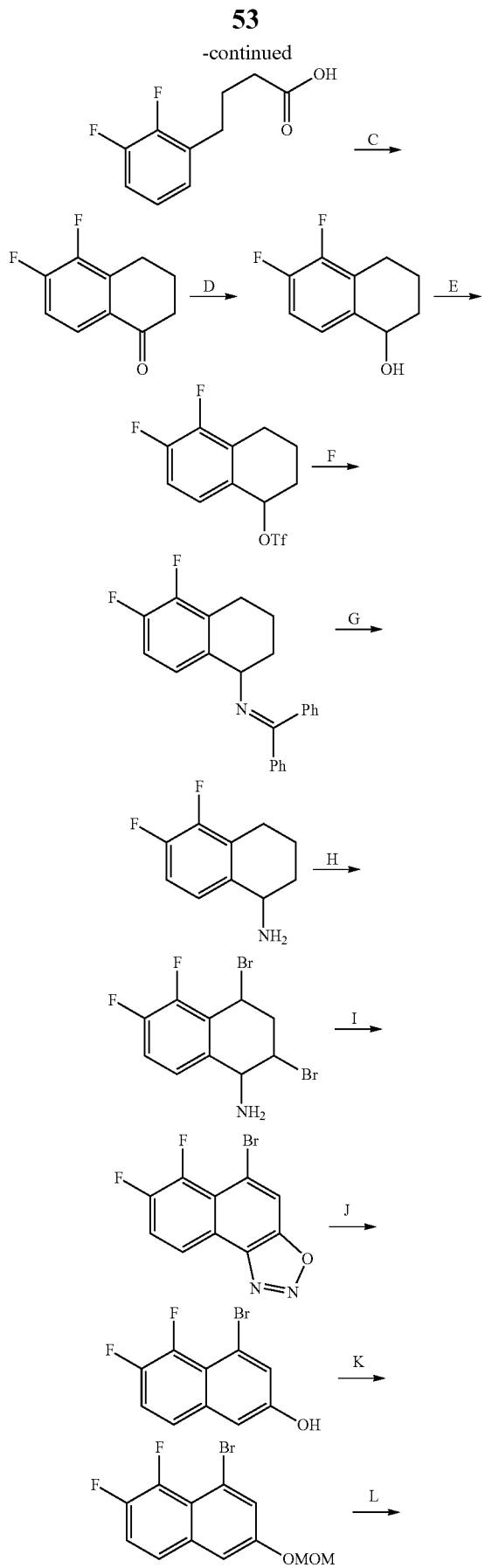

-continued

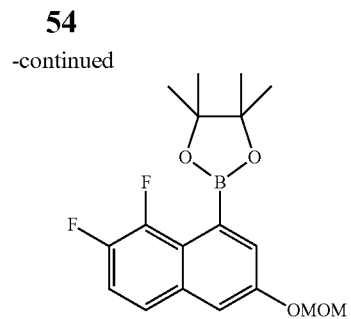

Step A. (E)-4-(2,3-difluorophenyl)but-3-enoic acid: To a solution of 2,3-difluorobenzaldehyde (100 g, 1.0 equiv.) and 2-carboxyethyl(triphenyl)phosphonium bromide (321 g, 1.1 equiv.) in THF (1 L) was added t-BuOK (1 M in THF, 1.41 L, 2.0 equiv.) at −70° C. The mixture was stirred at −70° C. for 1 hour. Then the mixture was warmed up to 20° C. and stirred for 1 hour. The reaction mixture was diluted with water (1 L) and concentrated under reduced pressure to remove the THF. Then the mixture was filtered and the filtrate was adjusted to pH~2 with HCl (1 M). The mixture was extracted with ethyl acetate (3×1000 mL). The combined organic layers were washed with brine (1000 mL), dried over Na$_2$SO$_4$, filtered and concentrated under reduced pressure to give the residue. The residue was purified by column chromatography (SiO$_2$, petroleum ether/ethyl acetate 10:1 to 2:1) to afford the title compound (75 g, 50% yield) as a pink solid; $^1$H NMR (400 MHz, chloroform-d) 5–11.50 (br s, 1H), 7.25-7.17 (m, 1H), 7.12-6.96 (m, 2H), 6.67 (d, J=16.0 Hz, 1H), 6.42 (td, J=7.2, 16.0 Hz, 1H), 3.36 (dd, J=1.2, 7.2 Hz, 2H).

Step B. 4-(2,3-difluorophenyl)butanoic acid: To a solution of (E)-4-(2,3-difluorophenyl)but-3-enoic acid (14 g, 1.0 equiv.) in EtOAc (500 mL) was added dry Pd/C (3 g, 10% purity) under N$_2$. The suspension was degassed and purged with H$_2$ several times. The mixture was stirred under H$_2$ (15 psi) at 20° C. for 1 hour. The reaction mixture was filtered and the filtrate was concentrated to afford the title compound (13.5 g, 95% yield) as a yellow solid and used to next step without purification.

Step C. 5,6-difluoro-3,4-dihydronaphthalen-1 (2H)-one: To a solution of 4-(2,3-difluorophenyl)butanoic acid (13.5 g, 1.0 equiv.) in DCM (300 mL) was added DMF (246 mg, 0.05 equiv.) and oxalyl chloride (17.1 g, 2.0 equiv.). The mixture was stirred at 20° C. for 0.5 hour. The mixture was concentrated under vacuum and then the residue was dissolved in DCM (300 mL). Then, to the mixture was added AlCl$_3$ (12.3 g, 1.5 equiv.). The reaction mixture was stirred at 40° C. for 1 hour before being quenched with water (200 mL) and extracted with T)CM (3×300 mL). The combined organic layers were washed with brine (200 mL), dried over Na$_2$SO$_4$, filtered and concentrated under reduced pressure to give a residue. The residue was purified by column chromatography (SiO$_2$, petroleum ether/ethyl acetate 100:1 to 5:1) to afford the title compound (11 g, 98% yield) as a yellow solid; LCMS (ESI, M+1): m/z=183.2.

Step D. 5,6-difluoronaphthalen-1-ol: To a solution of 5,6-difluoro-3,4-dihydronaphthalen-1 (2H)-one (11 g, 1.0 equiv.) and HBr (1.48 g, 0.1 equiv.) in AcOH (240 mL) was added a solution of Br$_2$ (9.65 g, 1.0 equiv.) in AcOH (40 mL) at 0° C. The mixture was stirred at 25° C. for 1 hour. Then the mixture was diluted with DCM (100 mL) and washed with water (3×100 mL). The organic layer was dried over anhydrous sodium sulfate, filtered and concentrated to afford a brown oil which was dissolved in DMF (260 mL). LiBr (8.91 g, 102 mmol, 2.58 mL, 1.7 equiv.), Li$_2$CO$_3$ (7.59 g, 102 mmol, 1.7 equiv.) was added. The reaction mixture was stirred at 160° C. for 1 hour. The reaction mixture was diluted with ethyl acetate (400 mL) and washed with water (3×300 mL). The organic layer was washed with brine (200 mL), dried over $Na_2SO_4$, filtered and concentrated under reduced pressure to give a residue. The residue was purified by column chromatography ($SiO_2$, petroleum ether/ethyl acetate 50:1 to 10:1) to afford the title compound (10 g, 90% yield) as a yellow solid; $^1$H NMR (400 MHz, chloroform-d) δ=8.06-7.88 (m, 1H), 7.66 (d, J=8.4 Hz, 1H), 7.40 (t, J=8.0 Hz, 1H), 7.32 (dt, J=7.6, 9.6 Hz, 1H), 6.83 (d, J=7.6 Hz, 1H), 5.44 (s, 1H).

Step E. 5,6-difluoronaphthalen-1-yl trifluoromethanesulfonate: To a solution of 5,6-difluoronaphthalen-1-ol (21 g, 1.0 equiv.) in DCM (200 mL) was added DIEA (37.6 g, 2.5 equiv.) and $Tf_2O$ (42.7 g, 1.3 equiv.) at 0° C. The mixture was stirred at 20° C. for 1 hour. The reaction mixture was diluted with water (200 mL) and extracted with DCM (3×200 mL). The combined organic layers were washed with brine (200 mL), dried over $Na_2SO_4$, filtered and concentrated under reduced pressure to give a residue. The residue was purified by column chromatography ($SiO_2$, petroleum ether/ethyl acetate 20:1 to 5:1) to afford the title compound (30 g, 82% yield) as a colorless oil; $^1$H NMR (400 MHz, chloroform-d) δ=8.14 (d, J=8.4 Hz, 1H), 7.91-7.82 (m, 1H), 7.61 (d, J=8.0 Hz, 1H), 7.57-7.46 (m, 2H).

Step F. N-(diphenylmethylene)-5,6-difluoronaphthalen-1-amine: A mixture of 5,6-difluoronaphthalen-1-yl trifluoromethanesulfonate (30 g, 1.0 equiv.), diphenylmethanimine (52.2 g, 3.0 equiv.), $Pd_2(dba)_3$ (8.80 g, 0.1 equiv.), Xantphos (11.1 g, 0.2 equiv.) and $Cs_2CO_3$ (93.9 g, 3 equiv.) in toluene (500 mL) was degassed and stirred at 90° C. for 12 hours under $N_2$ atmosphere. The reaction mixture was diluted with water (300 mL) and extracted with ethyl acetate (3×400 mL). The combined organic layers were washed with brine (300 mL), dried over $Na_2SO_4$, filtered and concentrated under reduced pressure to give a residue. The residue was purified by column chromatography ($SiO_2$, petroleum ether/ethyl acetate 100:1 to 5:1) to afford title compound (40 g, 92% yield) as a yellow solid; LCMS (ESI, M+1): m/z=344.0.

Step G. 5,6-difluoronaphthalen-1-amine: A solution of N-(5,6-difluoronaphthalen-1-yl)-1,1-diphenylmethanimine (40 g, 116 mmol, 1.0 equiv.) in HCl-MeOH (4 M, 300 mL, 10.3 equiv.) was stirred at 10° C. for 0.5 hour. The mixture was concentrated under vacuum. The pH of the residue was adjusted to ~8 with saturated aqueous $NaHCO_3$ solution and extracted with ethyl acetate (3×300 mL). The combined organic layers were washed with brine (200 mL), dried over $Na_2SO_4$, filtered and concentrated under reduced pressure to give a residue. The residue was purified by column chromatography ($SiO_2$, petroleum ether/ethyl acetate 20:1 to 3:1) to afford the title compound (14 g, 66% yield) as a yellow solid; $^1$H NMR (400 MHz, chloroform-d) δ=7.61-7.51 (m, 2H), 7.38 (t, J=8.0 Hz, 1H), 7.33-7.27 (m, 1H), 6.79 (d, J=7.2 Hz, 1H), 4.31-4.13 (S, 2H); LCMS (ESI, M+1): m/z=180.2.

Step H. 2,4-dibromo-5,6-difluoronaphthalen-1-amine: To a solution of 5,6-difluoronaphthalen-1-amine (10 g, 1.0 equiv.) in AcOH (200 mL) was added a solution of $Br_2$ (19.4 g, 2.18 equiv.) in AcOH (100 mL) at 0° C. The mixture was stirred at 70° C. for 1 hour. The reaction mixture was filtered and the filter cake was washed with AcOH (200 mL). Then the residue was diluted with 15% aqueous of NaOH (100 mL). The mixture was stirred for 20 minutes and filtered. The solid was washed with water (200 mL) and dried under vacuum to afford the title compound (16 g, 85% yield) as a yellow solid. LCMS (ESI, M+1): m/z=337.9.

Step I. 5-bromo-6,7-difluoronaphtho[1,2-d][1,2,3]oxadiazole: 2,4-dibromo-5,6-difluoronaphthalen-1-amine (16 g, 47.5 mmol, 1.0 equiv.) was dissolved in AcOH (280 g, 98.2 equiv.) and propionic acid (26.5 g, 7.53 equiv.) and cooled to 0° C. Then $NaNO_2$ (4.91 g, 1.5 equiv.) was added and the mixture was stirred at 20° C. for 1 hour. The reaction mixture was filtered and the filter cake was washed with water (300 mL) to afford the title compound (11.3 g, 83% yield) as a yellow solid and used to next step without purification; $^1$H NMR (400 MHz, chloroform-d) δ-7.51-7.40 (m, 1H), 7.24 (s, 1H), 7.08-6.99 (m, 1H).

Step J. 4-bromo-5,6-difluoronaphthalen-2-ol: To a suspension of 5-bromo-6,7-difluoronaphtho[1,2-d][1,2,3]oxadiazole (11.3 g, 1.0 equiv.) in EtOH (150 mL) and THF (50 mL) at 0° C. was added $NaBH_4$ (3.49 g, 2.33 equiv.). Bubbles evolved immediately. The mixture was stirred at 0° C. for 0.5 hour. The mixture was quenched with water (50 ml) and concentrated under vacuum to remove EtOH. The mixture was extracted with ethyl acetate (3×100 mL). The combined organic layers were washed with brine (100 mL), dried over $Na_2SO_4$, filtered and concentrated under reduced pressure to give a residue. The residue was purified by column chromatography ($SiO_2$, petroleum ether/ethyl acetate 20:1 to 3:1) to afford the title compound (6.3 g, 59% yield) as a black solid; LCMS (EST, M−1): m/z=257.1.

Step K. 8-bromo-1,2-difluoro-6-(methoxymethoxy)naphthalene: To a solution of 4-bromo-5,6-difluoronaphthalen-2-ol (6.3 g, 1.0 equiv.) in DCM (120 mL) was added DIEA (7.86 g, 2.5 equiv.) and MOMCl (3.44 g, 1.76 equiv.). The mixture was stirred at 0° C. for 0.5 hour. The reaction mixture was diluted with water (50 mL) and extracted with DCM (3×100 mL). The combined organic layers were washed with brine (100 mL), dried over $Na_2SO_4$, filtered and concentrated under reduced pressure to give a residue. The residue was purified by column chromatography ($SiO_2$, petroleum ether/ethyl acetate 20:1 to 5:1) to afford the title compound (5.5 g, 75% yield) as a yellow solid; $^1$H NMR (400 MHz, chloroform-d) δ=7.61 (d, J=2.4 Hz, 1H), 7.52-7.46 (m, 1H), 7.39-7.30 (m, 2H), 5.27 (s, 2H), 3.52 (s, 3H).

Step L. 2-(7,8-difluoro-3-(methoxymethoxy)naphthalen-1-yl)-4,4,5,5-tetramethyl-1,3,2-dioxaborolane: A mixture of 8-bromo-1,2-difluoro-6-(methoxymethoxy)naphthalene (3 g, 1.0 equiv.), $Pin_2B_2$ (6.28 g, 2.5 equiv.), KOAc (2.91 g, 3.0 equiv.), Pd(dppf)$Cl_2$ (724 mg, 0.1 equiv.) in dioxane (60 mL) was degassed and stirred at 110° C. for 1 hour under $N_2$ atmosphere. The reaction mixture was diluted with water (50 mL) and extracted with ethyl acetate (3×50 mL). The combined organic layers were washed with brine (50 mL), dried over $Na_2SO_4$, filtered and concentrated under reduced pressure to give a residue. The residue was purified by column chromatography ($SiO_2$, petroleum ether/ethyl acetate 50:1 to 5:1) to afford the title compound (2 g, 58% yield) as a white solid; $^1$H NMR (400 MHz, chloroform-d) δ=7.49-7.44 (m, 1H), 7.42 (d, J=2.4 Hz, 1H), 7.41-7.39 (m, 1H), 7.33-7.27 (m, 1H), 5.29 (s, 2H), 3.51 (s, 3H), 1.45 (s, 12H).

Intermediate 18

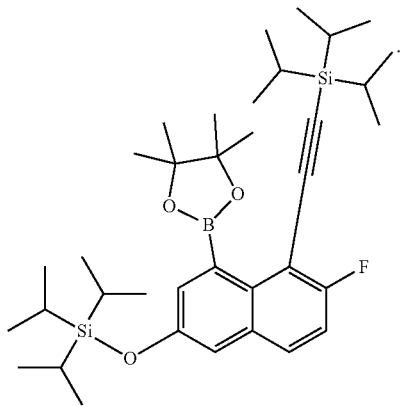 [SMILES: CC(C)[Si](C#Cc1c(F)ccc2cc(O[Si](C(C)C)(C(C)C)C(C)C)cc(B3OC(C)(C)C(C)(C)O3)c12)(C(C)C)C(C)C]

((6-fluoro-4-(4,4,5,5-tetramethyl-1,3,2-dioxaboro-lan-2-yl)-5-(((triisopropylsilyl)ethynyl)naphthalen-2-yl)oxy)triisopropylsilane

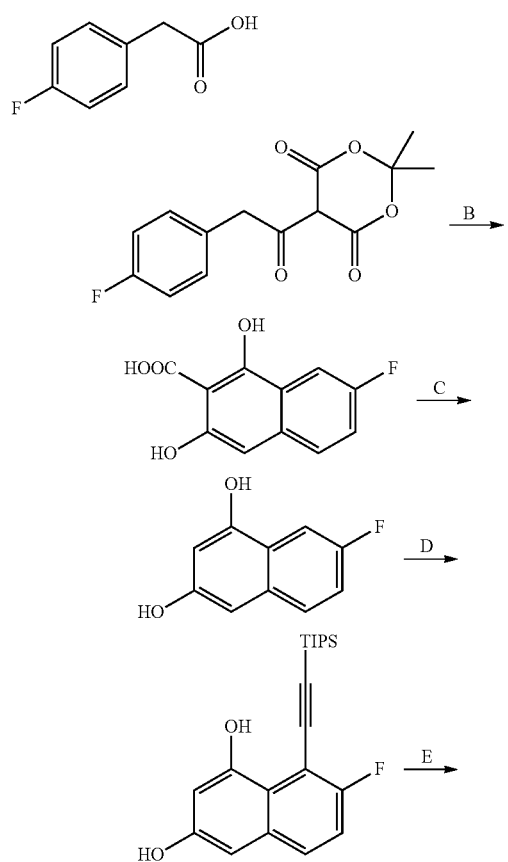

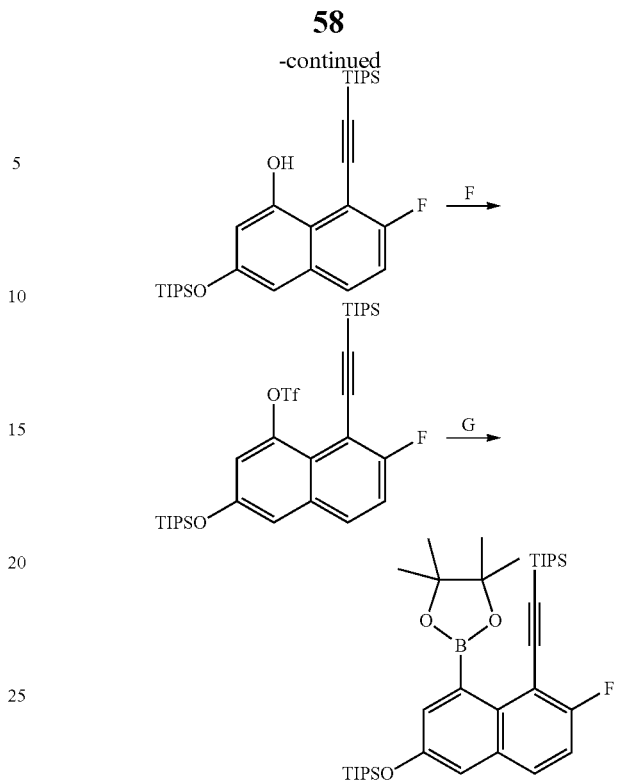

Step A. 5-(2-(4-fluorophenyl)acetyl)-2,2-dimethyl-1,3-dioxane-4,6-dione: To a mixture of 2-(4-fluorophenyl)acetic acid (250 g, 1 equiv.) and 2,2-dimethyl-1,3-dioxane-4,6-dione (257 g, 1.1 equiv.) in ACN (1.25 L) was added DMAP (16.9 g, 0.09 equiv.) at 15° C. DIPEA (451 g, 2.1 equiv.) was added dropwise below 30° C. for 1 hour. Pivaloyl chloride (215 g, 1.1 equiv.) was added dropwise below 40° C. for 1 hour. The mixture was stirred at 45° C. for 3 hours. The mixture was cooled to 0° C. 4 N aqueous HCl (5.0 L) was added dropwise to adjust pH to 5 while maintaining the temperature between below 15° C. The mixture was stirred at 0° C. for 1 hour. The mixture was diluted with $H_2O$ (15 L) and the pH of the mixture was adjusted to 2 with 4N HCl. The mixture was filtered. The filter cake was washed with $H_2O$ until the pH of filter cake was 5-6. The solid was dried under reduced pressure to afford the tittle compound (500 g, crude) as a white solid; $^1$H NMR (400 MHz, chloroform-d) 5-7.36 (dd, J=5.6, 8.4 Hz, 2H), 7.01 (t, J=8.4 Hz, 2H), 4.38 (s, 2H), 1.72 (s, 6H).

Step B. 7-fluoro-1,3-dihydroxy-2-naphthoic acid: 5-(2-(4-fluorophenyl)acetyl)-2,2-dimethyl-1,3-dioxane-4,6-dione (490 g, 1 equiv., crude) was added into $CF_3SO_3H$ (2.04 kg, 7.8 equiv.) portion wise maintaining the temperature below 30° C. The mixture was stirred at 20° C. for 2 hour. The mixture was poured into ice water (30 L) slowly. The mixture was filtered. The filter cake was washed with water until the pH of the filtrate was 3-4 to afford the tittle compound (500 g, crude, wet) as a brown solid.

Step C. 7-fluoronaphthalene-1,3-diol: A mixture of 7-fluoro-1,3-dihydroxy-2-naphthoic acid (375 g, crude, wet) in $H_2O$ (1.8 L) and ACN (1.8 L) was stirred at 78° C. for 13 hours. The mixture was concentrated to remove ACN. The mixture was diluted with $H_2O$ (1 L) and saturated $NaHCO_3$ aqueous (0.3 L), and then extracted with ethyl acetate (4×0.5 L). The combined organic layers were washed with saturated aqueous $NaHCO_3$ (0.5 L), water (0.5 L) and brine (0.5 L), dried over anhydrous $Na_2SO_4$ and concentrated. The residue was treated with n-heptanes (0.8 L) for 1 hour. The mixture filtered and the solid was dried under reduced pressure to afford the tittle compound (145 g, 60% yield over three steps) as light a red solid; $^1$H NMR (400 MHz, DMSO-d$_6$) δ=10.18 (s, 1H), 9.48 (s, 1H), 7.65-7.56 (m, 2H), 7.23 (dt, J=2.8, 8.8 Hz, 1H), 6.64 (d, J=1.6 Hz, 1H), 6.56 (d, J=1.6 Hz, 1H).

Step D. 7-fluoro-8-((triisopropylsilyl)ethynyl)naphthalene-1,3-diol: A mixture of 7-fluoronaphthalene-1,3-diol (173 g, 1 equiv.), (bromoethynyl)triisopropylsilane (266 g, 1.05 equiv.), AcOK (191 g, 2 equiv.) and dichloro(p-cymene)ruthenium(II) dimer (17.8 g, 0.03 equiv.) in dioxane (1.5 L) was degassed and stirred at 100° C. for 3.5 hours. The reaction mixture was filtered through a pad of Celite. The filter cake was washed with ethyl acetate (4×500 mL). The filtrate was concentrated under reduced pressure to give a residue. The residue was dissolved in ethyl acetate (3 L). The solution was washed with saturated NaHCO$_3$ aqueous (0.5 L) and brine (0.2 L), dried over anhydrous Na$_2$SO$_4$, and concentrated to give a residue. The residue was purified by column chromatography [SiO$_2$, petroleum ether/ethyl acetate 15:1 to 10:1] to afford a crude product. The crude product was dispersed in n-heptanes (0.5 L) and stirred for 1 hour. The mixture was filtered and the filter cake was washed with n-heptanes (0.5 L). The solid was dried under reduced pressure to afford the tittle compound (204 g, 56% yield) as a light yellow solid; $^1$H NMR (400 MHz, DMSO-d$_6$) δ=10.04 (s, 1H), 9.58 (s, 1H), 7.63 (dd, J=5.6, 9.2 Hz, 1H), 7.25 (t, J=9.2 Hz, 1H), 6.63 (d, J=2.4 Hz, 1H), 6.58 (d, J=2.0 Hz, 1H), 1.13 (s, 21H).

Step E. 7-fluoro-8-((triisopropylsilyl)ethynyl)-3-((triisopropylsilyloxy)naphthalen-1-ol: To a solution of 7-fluoro-8-((triisopropylsilyl)ethynyl)naphthalene-1,3-diol (197 g, I equiv.) and DIPEA (142 g, 2.0 equiv.) in DCM (1 L) was added TIPSCl (122 g, 1.2 equiv.) dropwise between 0 and 10° C. for 1 hour. The mixture was stirred 25° C. for 1 hour. The mixture was poured H$_2$O (2 L). The DCM phase was separated and washed with brine (3×1 L). The DCM phase was dried over anhydrous Na$_2$SO$_4$ and filtered to afford the tittle compound (282 g, in DCM) as a red liquid, which was used in next step directly.

Step F. 7-fluoro-8-((triisopropylsilyl)ethynyl)-3-((triisopropylsilyl)oxy)naphthalen-1-yltrifluoromethanesulfonate: To a solution of 7-fluoro-8-((triisopropylsilyl)ethynyl)-3-((triisopropylsilyl)oxy)naphthalen-1-ol (282 g, 1 equiv.) and DIPEA (248 g, 3.5 equiv.) in DCM (1.7 L) was added Tf$_2$O (263 g, 1.7 equiv.) dropwise at −40° C. for 3 hours. The mixture was stirred at −40° C. for 0.5 hour. The mixture was poured into water (1 L). The DCM layer was separated and washed with water (3×3 L), 0.001N HCl (3×2 L), H$_2$O (1.5 L), brine (2×1 L), dried over anhydrous Na$_2$SO$_4$ and concentrated to give a residue. The residue was purified by column chromatography [SiO$_2$, petroleum ether] to afford the tittle compound (321 g, crude) as a light red oil; $^1$H NMR (400 MHz, chloroform-d) δ=7.67 (dd, J=5.6, 9.2 Hz, 1H), 7.34-7.25 (m, 3H), 1.34-1.14 (m, 42H); $^{19}$F NMR (376 MHz, chloroform-d) 5=−79, −105.

Step G. ((6-fluoro-4-(4,4,5,5-tetramethyl-1,3,2-dioxaborolan-2-yl)-5-((triisopropylsilyl)ethynyl)naphthalen-2-yl)oxy)triisopropylsilane: A mixture of 7-fluoro-8-((triisopropylsilyl)ethynyl)-3-((triisopropylsilyl)oxy)naphthalen-1-yltrifluoromethanesulfonate (229 g, 1 equiv.), TEA (144 g, 4.0 equiv.), 4,4,5,5-tetramethyl-1,3,2-dioxaborolane (182 g, 4.0 equiv.) and Pd(dppf)Cl$_2$ (16 g, 0.06 equiv.) in MeCN (1.5 L) was degassed stirred at 78° C. for 4 hours under N$_2$ atmosphere. The mixture was slowly quenched with of MeOH (0.5 L) maintaining the temperature below 25° C. producing a precipitate. The mixture was filtered and the filter cake was washed with MeOH (1 L). The solid was dispersed in MeOH (0.5 L) and stirred for 0.5 hour. The mixture was filtered. The solid was dried under reduced pressure to afford the tittle compound (170 g, 69% yield over three steps, crude) as a white solid; $^1$H NMR (400 MHz, CHLOROFORM-d) δ=7.60 (dd, J=5.6, 9.2 Hz, 1H), 7.43 (d, J=2.4 Hz, 1H), 7.22-7.17 (m, 2H), 1.43 (s, 12H), 1.32-1.12 (m, 42H); LCMS (ESI, M+1): m/z=625.6.

Intermediate 19

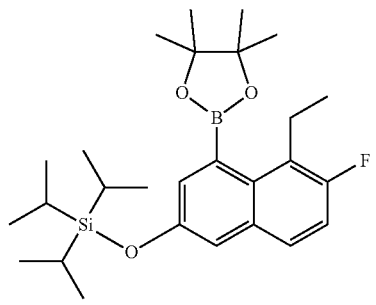 [SMILES: CCc1c(F)ccc2cc(O[Si](C(C)C)(C(C)C)C(C)C)cc(B3OC(C)(C)C(C)(C)O3)c12]

((5-ethyl-6-fluoro-4-(4,4,5,5-tetramethyl-1,3,2-dioxaborolan-2-yl)naphthalen-2-yl)oxy)triisopropylsilane

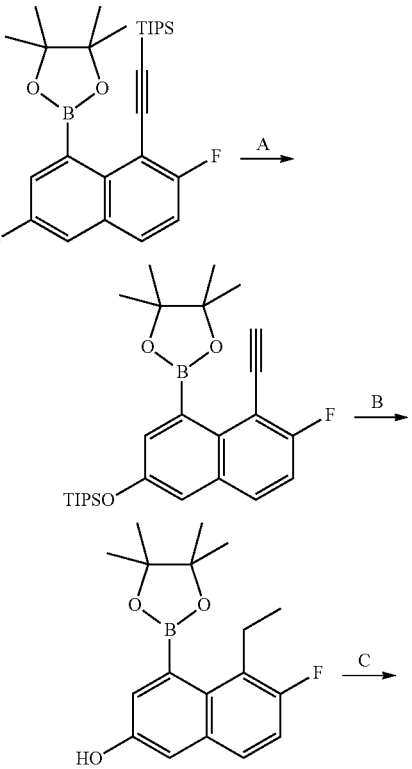

61
-continued

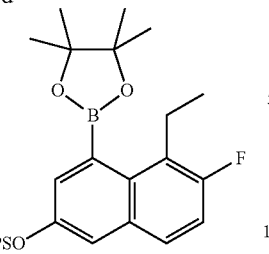

Step A. 5-ethynyl-6-fluoro-4-(4,4,5,5-tetramethyl-1,3,2-dioxaborolan-2-yl)naphthalen-2-ol: To a solution of ((6-fluoro-4-(4,4,5,5-tetramethyl-1,3,2-dioxaborolan-2-yl)-5-((triisopropylsilyl)ethynyl)naphthalen-2-yl)oxy)triisopropylsilane (1.50 kg, 1.0 equiv.) in DMSO (15.0 L) was added CsF (2.19 kg, 6.0 equiv.) in one portion at 25° C. under $N_2$. The reaction mixture was stirred at 25° C. for 12 hrs. The mixture was diluted with EtOAc (5.00 L) and water (20.0 L) and the layers were separated. The aqueous phase was extracted with EtOAc (5.00 L×3). The combined organic phase was washed with brine (5.00 L×5), dried with anhydrous $Na_2SO_4$, filtered and concentrated in vacuum. The crude product was triturated with n-heptanes (4.5 L) at 50° C. for 6 hrs. The mixture was cooled to room temperature and filtered to afford the title compound (600 g, 1.86 mol, 80.1% yield) as a yellow solid. $^1$H NMR (400 MHz, $CDCl_3$) δ 7.48-7.46 (m, 1H), 7.30-7.29 (d, J=2.4, 1H), 7.12-7.08 (m, 1H), 7.00-6.98 (m, 1H), 5.56 (s, 1H), 3.61 (s, 1H), 1.37 (s, 12H).

Step B. 5-ethyl-6-fluoro-4-(4,4,5,5-tetramethyl-1,3,2-dioxaborolan-2-yl)naphthalen-2-ol: To a solution of 5-ethynyl-6-fluoro-4-(4,4,5,5-tetramethyl-1,3,2-dioxaborolan-2-yl)naphthalen-2-ol (40.0 g, 1.00 equiv.) in THF (400 mL) was added Pd/C (4.00 g, 10.0% purity). The mixture was purged with $H_2$ three times and stirred at 25° C. under $H_2$ (15 Psi) for 5 hrs. The mixture was filtered through a diatomite powder pad and washed with THF (200 mL×2), the filtrate was concentrated in vacuum. The residue was purified by silica gel chromatography (petroleum ether/EtOAc 50:1 to 3:1) to afford the title compound (74.0 g, 88.5% yield) as a yellow solid. $^1$H NMR (400 MHz, $CDCl_3$) δ 7.57-7.55 (m, 1H), 7.41-7.37 (m, 1H), 7.23-7.18 (m, 2H), 5.28 (s, 1H), 3.15-3.12 (m, 2H), 1.45 (s, 12H), 1.29-1.26 (m, 3H).

Step C. ((5-ethyl-6-fluoro-4-(4,4,5,5-tetramethyl-1,3,2-dioxaborolan-2-yl)naphthalen-2-yl)oxy)triisopropylsilane: To a solution of 5-ethyl-6-fluoro-4-(4,4,5,5-tetramethyl-1,3,2-dioxaborolan-2-yl)naphthalen-2-ol (73.0 g, 1.0 equiv.) in DMF (750 mL) was added imidazole (47.2 g, 3.0 equiv.) and TIPSCl (89.0 g, 2.0 equiv.). The mixture was stirred at 25° C. for 12 hours. The mixture was diluted with $H_2O$ (500 mL) and extracted with MTBE (3×300 mL). The combined organic phase was washed with brine (3×300 mL), dried over anhydrous $Na_2SO_4$, concentrated and purified by silica gel chromatography [petroleum ether/ethyl acetate 100:1 to 20:1] to afford the title compound (102 g, 94% yield) as a yellow solid; $^1$H NMR (400 MHz, CHLOROFORM-d) δ=7.43-7.40 (m, 1H), 7.22-7.21 (m, 1H), 7.13-7.09 (m, 2H), 3.07-3.01 (m, 2H), 1.36 (s, 12H), 1.23-1.18 (m, 6H), 1.06-0.97 (m, 18H).

62
Intermediate 20

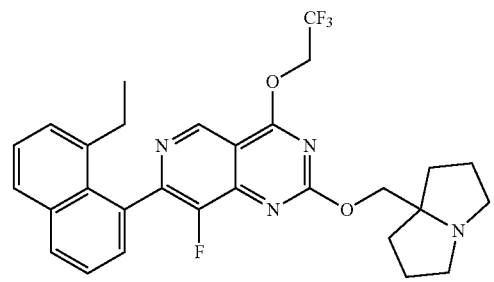 [SMILES: CCc1cccc2cccc(-c3ncc4c(OCC(F)(F)F)nc(OCC56CCCN5CCC6)nc4c3F)c12]

7-(8-ethylnaphthalen-1-yl)-8-fluoro-2-((hexahydro-1H-pyrrolizin-7a-yl)methoxy)-4-(2,2,2-trifluoroethoxy)pyrido[4,3-d]pyrimidine

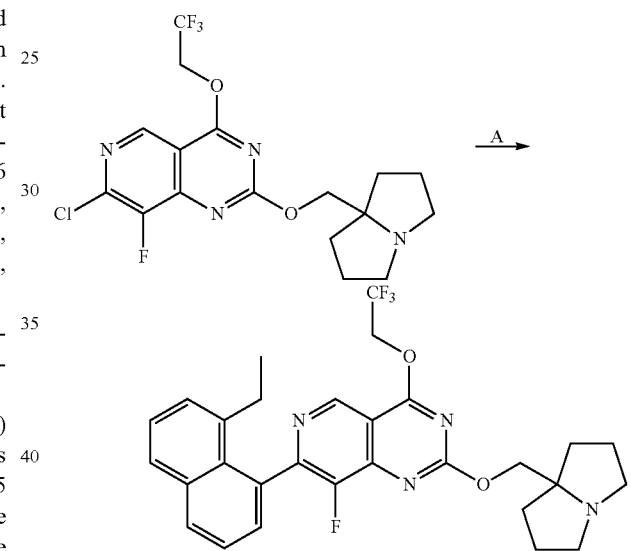

Step A. 7-(8-ethylnaphthalen-1-yl)-8-fluoro-2-((hexahydro-1H-pyrrolizin-7a-yl)methoxy)-4-(2,2,2-trifluoroethoxy)pyrido[4,3-d]pyrimidine: A mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (200 mg, 1.00 equiv.), 2-(8-ethyl-1-naphthyl)-4,4,5,5-tetramethyl-1,3,2-dioxaborolane (201 mg, 1.50 equiv.), CataCXium A Pd G3 (34.6 mg, 0.10 equiv.), $K_3PO_4$ (1.5 M, 3.0 equiv.) in THF (2 mL) was degassed and stirred at 60° C. for 12 hours under $N_2$ atmosphere. The reaction mixture was diluted with water (5 mL) and extracted with EtOAc (15 mL×3). The combined organic layers were washed with brine (5 mL×2), dried over $Na_2SO_4$, concentrated and purified by reversed-phase HPLC [column: Phenomenex Luna C18 150×25 mm×10 um; mobile phase: [water (0.225% formic acid)-ACN]; B %: 25% Y-55%, 10 min] to afford the title compound (20.0 mg, 7.8% yield) as an off-white solid; LCMS (ESI, M+1): m/z=541.3.

Intermediate 21

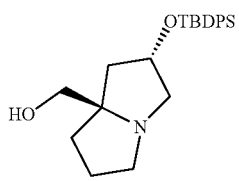

((2S,7aR)-2-((tert-butyldiphenylsilyl)oxy)tetrahydro-1H-pyrrolizin-7a(5H)-yl)methanol

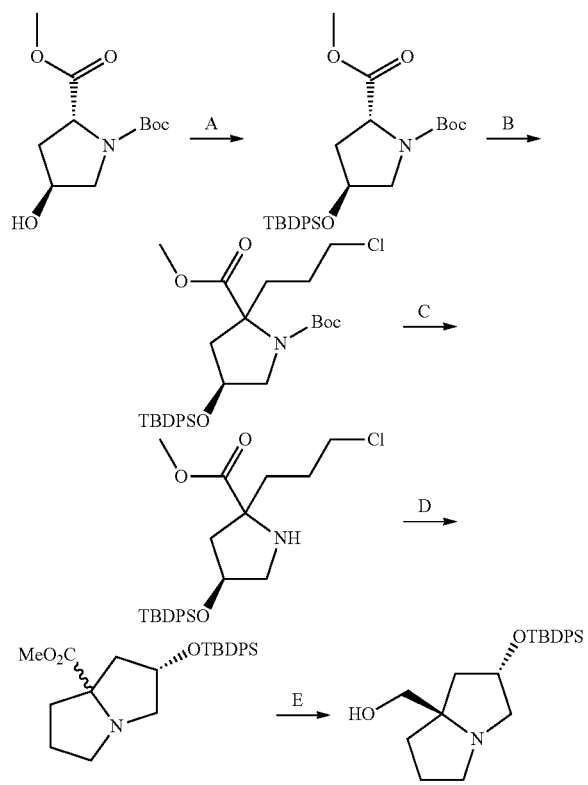

Step A: (2R,4S)-1-tert-butyl 2-methyl 4-((tert-butyldiphenylsilyl)oxy)pyrrolidine-1,2-dicarboxylate: To a solution of (2R,4S)-1-tert-butyl 2-methyl 4-hydroxypyrrolidine-1,2-dicarboxylate (20.0 g, 1.0 equiv.) and imidazole (11.1 g, 2.0 equiv.) in DCM (200 mL) was added TBDPSCl (33.6 g, 31.4 mL, 1.50 equiv.). The mixture was stirred at 25° C. for 1 hour. After reaction completion, the reaction mixture was added water (150 mL), separated, the aqueous layer was extracted with EtOAc (2×100 mL), the combined organic layer was dried over Na$_2$SO$_4$, filtered and concentrated. The crude product was purified by column chromatography (SiO$_2$, petroleum ether/ethyl acetate 100:1-30:1) to afford the title compound (39 g, 93% yield) as a white solid; LCMS (ESI, M–100): m/z=384.3.

Step B. (4S)-1-tert-butyl 2-methyl 4-((tert-butyldiphenylsilyl)oxyl-2-(3-chloropropyl)pyrrolidine-1,2-dicarboxylate: To a solution of (2R,4S)-1-tert-butyl 2-methyl 4-((tert-butyldiphenylsilyl)oxy)pyrrolidine-1,2-dicarboxylate (37.0 g, 1.0 equiv.) in THF (400 mL) was added LDA (2 M, 49.7 mL, 1.30 equiv.) at −70° C. slowly. The mixture was stirred at −70° C. for 1 hour. To the mixture was added 1-bromo-3-chloro-propane (60.2 g, 37.6 mL, 5.0 equiv.) at −70° C. The mixture was stirred at −70-20° C. for 12 hours. Upon completion, the reaction mixture was diluted with water (300 mL), separated, the aqueous layer was extracted with EtOAc (2×100 mL), the combined organic layers were dried over Na$_2$SO$_4$, filtered and concentrated. The residue was purified by reversed phase flash chromatography (C18, 0.1% formic acid condition) and column chromatography (SiO$_2$, petroleum ether/ethyl acetate 100:1-20:1) to afford the title compound (8.70 g, 20% yield) as a colorless oil; LCMS (ESI, M–55, M–100): 504.3, 461.2.

Step C. (4S)-methyl 4-((tert-butyldiphenylsilyl)oxy)-2-(3-chloropropyl)pyrrolidine-2-carboxylate: To a solution of (4S)-1-tert-butyl 2-methyl 4-((tert-butyldiphenylsilyl)oxy)-2-(3-chloropropyl)pyrrolidine-1,2-dicarboxylate (8.60 g, 1.0 equiv.) in MeCN (40 mL) was added HCl.dioxane (4 M, 40 mL, 10.4 equiv.). The mixture was stirred at 20° C. for 0.5 hour. Upon completion, the reaction mixture was concentrated to afford the title compound (7.8 g, crude, HCl salt) as a yellow solid.

Step D. (2S)-methyl 2-((tert-butyldiphenylsilyl)oxy)hexahydro-1H-pyrrolizine-7a-carboxylate (90122-E): To a solution of (4S)-methyl 4-((tert-butyldiphenylsilyl)oxy)-2-(3-chloropropyl)pyrrolidine-2-carboxylate (7.80 g, 1.0 equiv., HCl) in ACN (80 mL) was added NaHCO$_3$ (7.12 g, 3.30 mL) and KI (281 mg). The mixture was stirred at 50° C. for 12 hours. Upon completion, the reaction mixture was diluted with water (100 mL) and extracted with ethyl acetate (2×50 mL). The organic layer was dried over Na$_2$SO$_4$, filtered and concentrated. The residue was purified by prep-HPLC (column: Phenomenex luna C18 250*80 mm*10 um; mobile phase: [water (10 mM NH$_4$HCO$_3$)-ACN]; B %: 75%-100%, 20 min) to afford the title compound (1.3 g, two steps 18% yield) as a colorless oil.

Step E. ((2S,7aR)-2-((tert-butyldiphenylsilyl)oxy)tetrahydro-1H-pyrrolizin-7a(5H)-yl)methanol: To a solution of (2S)-methyl 2-((tert-butyldiphenylsilyl)oxy)hexahydro-1H-pyrrolizine-7a-carboxylate (1.30 g, 1.0 equiv.) in THF (15 mL) was added LiAlH$_4$ (349 mg, 3.0 equiv.) at −40° C. The mixture was stirred at −40° C. for 1 hour. Upon completion, the reaction mixture was quenched with saturated aqueous Na$_2$SO$_4$ solution (1 mL), filtered and concentrated to afford the title compound (1.1 g, 91% yield) as a yellow oil; $^1$H NMR (400 MHz, CDCl$_3$) δ 7.70-7.60 (m, 4H), 7.48-7.35 (m, 6H), 4.49-4.30 (m, 1H), 3.12 (d, J=2.4 Hz, 2H), 3.06-2.98 (m, 2H), 2.95 (dd, J=4.8, 11.2 Hz, 1H), 2.73 (dd, J=4.4, 11.2 Hz, 1H), 2.07-1.89 (m, 3H), 1.81-1.65 (m, 3H), 1.06 (s, 9H); LCMS (ESI, M+1): m/z=396.7.

Intermediate 22

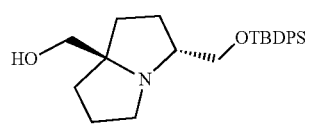

65

((3R,7aR)-3-(((tert-butyldiphenylsilyl)oxy)methyl)
hexahydro-1H-pyrrolizin-7a-yl)methanol Intermediate 23

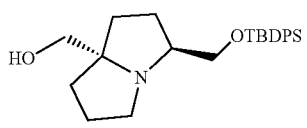

((3S,7aS)-3-(((tert-butyldiphenylsilyl)oxy)methyl)
hexahydro-1H-pyrrolizin-7a-yl)methanol Intermediate 24

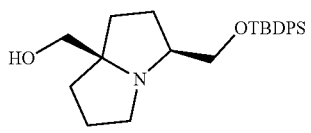

((3S,7aR)-3-(((tert-butyldiphenylsilyl)oxy)methyl)
hexahydro-1H-pyrrolizin-7a-yl)methanol Intermediate 25

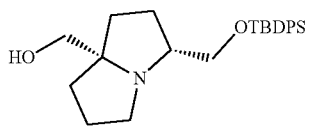

((3R,7aS)-3-(((tert-butyldiphenylsilyl)oxy)methyl)
hexahydro-1H-pyrrolizin-7a-yl)methanol

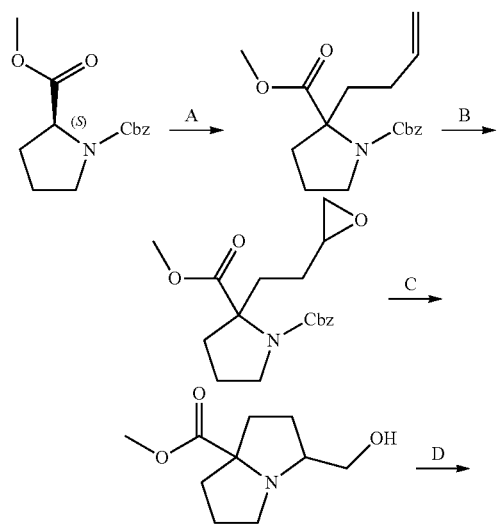

66

-continued

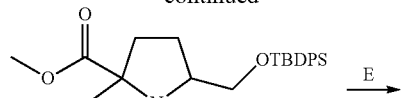
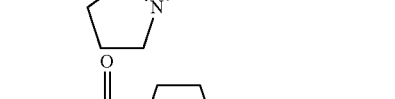
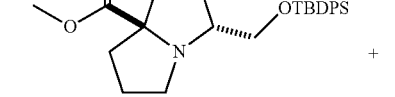
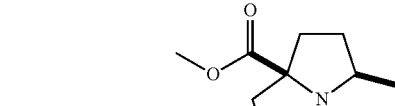

Intermediate 22

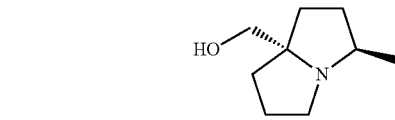

Intermediate 23

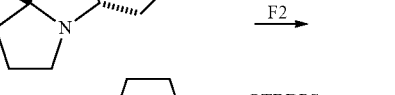
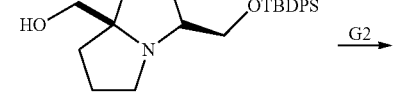
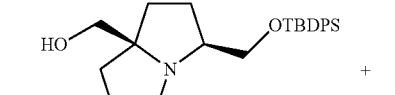

Intermediate 24

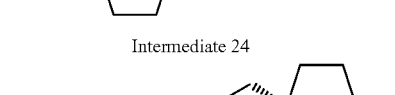

Intermediate 25

Step A. benzyl 2-methyl 2-(but-3-en-1-yl)pyrrolidine-1,
2-dicarboxylate: To a solution of 1-benzyl 2-methyl (S)-
pyrrolidine-1,2-dicarboxylate (220 g, 1 equiv.) in THF (2.2
L) was added LiHMDS (1 M, 1.00 L, 1.2 equiv.) at −65° C.
The mixture was stirred at −65° C. for 1 hour. Then 4-bromobut-1-ene (225.61 g, 2 equiv.) was added to the mixture at −65° C. The mixture was stirred at 25° C. for 12 hours. The mixture was quenched with saturated aqueous NH₄Cl (500 mL) and extracted with ethyl acetate (3×500 mL). The combined organic layer was dried over anhydrous sodium sulfate. The mixture was filtered and the filtrate was concentrated under reduced pressure to dryness. The residue was purified by column chromatography [SiO₂, petroleum ether/ethyl acetate 10:1 to 5:1] to afford the title compound (220 g, 74.6% yield) as a yellow oil; $^1$H NMR (400 MHz, chloroform-d) δ=7.25 (s, 5H), 5.88-5.63 (m, 1H), 5.17-5.05 (m, 2H), 5.04-4.88 (m, 2H), 3.83-3.62 (m, 3H), 3.54-3.42 (m, 2H), 2.48-2.17 (m, 1H), 2.15-2.03 (m, 3H), 2.02-1.77 (m, 4H); LCMS[ESI, M+1]: m/z=318.2.

Step B. benzyl 2-methyl 2-(2-(oxiran-2-yl)ethyl)pyrrolidine-1,2-dicarboxylate: To a solution of benzyl 2-methyl 2-(but-3-en-1-yl)pyrrolidine-1,2-dicarboxylate (242 g, 1 equiv.) in DCM (2.40 L) was added m-CPBA (309 g, 85% purity, 2 equiv.) in portions at 0° C. The mixture was stirred at 25° C. for 5 hours. The mixture was quenched by addition of saturated aqueous Na₂SO₃ solution (500 mL), extracted with dichloromethane (3×500 mL). The combined organic layers were washed with saturated brine (2×200 mL) and dried over anhydrous sodium sulfate. The mixture was filtered and the filtrate was concentrated under reduced pressure to give a residue. The residue was purified by column chromatography [SiO₂, petroleum ether/ethyl acetate 10:1 to 5:1) to afford the title compound (200 g, 62.9% h yield) as a yellow oil. $^1$H NMR (400 MHz, chloroform-d) δ=7.43-7.10 (m, 5H), 5.20-4.93 (m, 2H), 3.78-3.56 (m, 3H), 3.48-3.34 (m, 2H), 2.89-2.53 (m, 2H), 2.46-2.10 (m, 2H), 2.06-1.97 (m, 3H), 1.91-1.71 (m, 2H), 1.59-1.31 (m, 2H); LCMS[ESI, M+1]: m/z=334.1.

Step C. methyl 3-(hydroxymethyl)hexahydro-1H-pyrrolizine-7a-carboxylate: To a suspension of Pd/C (16.0 g, 10% purity) in MeOH (1.0 L) was added benzyl 2-methyl 2-(2-(oxiran-2-yl)ethyl)pyrrolidine-1,2-dicarboxylate (130 g, 1 equiv.) under N₂ atmosphere. The suspension was degassed under vacuum and purged with H₂ (50 psi) several times. The mixture was stirred at 25° C. under H₂ (50 psi) for 1 hour. The mixture was filtered and the filtrate was concentrated to afford the title compound (75 g, 96.5% yield) as a yellow oil; $^1$H NMR (400 MHz, chloroform-d) δ (ppm)=3.88-3.73 (m, 1H), 3.73-3.66 (m, 1H), 3.61-3.54 (m, 1H), 3.42-3.35 (m, 1H), 3.09-3.03 (m, 1H), 2.99-2.88 (m, 1H), 2.74-2.65 (m, 1H), 2.55-2.48 (m, 1H), 2.31 (td, J=4.7, 12.4 Hz, 1H), 2.14 (br d, J=1.6 Hz, 1H), 1.89-1.74 (m, 5H), 1.73-1.45 (m, 2H).

Steps D and E. methyl 3-(((tert-butyldiphenylsilyl)oxy)methyl)hexahydro-1H-pyrrolizine-7a-carboxylate: To a solution of methyl 3-(hydroxymethyl)-1,2,3,5,6,7-hexahydropyrrolizine-8-carboxylate (165 g, 1 equiv.) and imidazole (169 g, 3 equiv.), DMAP (10.1 g, 0.1 equiv.) in DCM (1.4 L) was added TBDPSCl (296 g, 1.3 equiv.) drop-wise at 0° C. The mixture was stirred at 25° C. for 2 hours. The reaction mixture was washed with H₂O (2×500 mL), the combined organic layers were dried over anhydrous Na₂SO₄, filtered and concentrated under reduce pressure to give a residue. The residue was purified by column chromatography (SiO₂, 0.1% NH₃H₂O, Petroleum ether/Ethyl acetate 20:1 to 1:1) to afford peak 1 (330 g, crude), lower polarity, as a yellow oil and peak 2 (166 g, 44.9% yield), higher polarity as a yellow oil; Peak 1: LCMS[ESI, M+1]: m/z=438.3; Peak 2 LCMS [ESI, M+1]: m/z=438.3.

Step F1: rac-((3R,7aR)-3-(((tert-butyldiphenylsilyl)oxy)methyl)hexahydro-1H-pyrrolizin-7a-yl)methanol: To a mixture of rac-(3R,7aR)-methyl 3-(((tert-butyldiphenylsilyl)oxy)methyl)hexahydro-1H-pyrrolizine-7a-carboxylate (160 g, 70% purity, 1 equiv.) in THF (2 L) was added LiAlH₄ (12.63 g, 1.3 equiv.) portion wise at −40° C. The mixture was stirred at −40° C. for 3 hours. The reaction mixture was quenched with H₂O (13 mL), 15% aqueous NaOH (13 mL), H₂O (39 mL), dried over anhydrous Na₂SO₄ at 0° C., filtered and concentrated. The residue was purified by reversed phase flash chromatography (C18, water (0.1% formic acid)-ACN) to afford the title compound (85 g, 64.87% yield) as a yellow oil. LCMS [ESI, M+1]: m/z=410.2.

Step G1. ((3R,7aR)-3-(((tert-butyldiphenylsilyl)oxy)methyl)hexahydro-1H-pyrrolizin-7a-yl)methanol and ((3S,7aS)-3-(((tert-butyldiphenylsilyl)oxy)methyl)hexahydro-1H-pyrrolizin-7a-yl)methanol: The stereoisomers of rac-((3R,7aR)-3-(((tert-butyldiphenylsilyl)oxy)methyl)hexahydro-1H-pyrrolizin-7a-yl)methanol (175 g) were separated by SFC (column: Phenomenex-Cellulose-2 (250 mm×50 mm, 10 um); mobile phase: [0.1% NH₃—H₂O IPA]; B %: 40%-40%, 4.9 min) to afford title compounds ((3R,7aR)-3-(((tert-butyldiphenylsilyl)oxy)methyl)hexahydro-1H-pyrrolizin-7a-yl)methanol (54 g, 40% yield) as a yellow oil $^1$H NMR (400 MHz, CHLOROFORM-d) δ=7.71 (br t, J=7.4 Hz, 4H), 7.47-7.34 (m, 6H), 3.77-3.57 (m, 2H), 3.35-3.21 (m, 2H), 3.01-2.78 (m, 3H), 1.98-1.84 (m, 2H), 1.83-1.64 (m, 4H), 1.64-1.51 (m, 3H), 1.13-1.01 (m, 10H), −0.89-−0.90 (m, 1H); LCMS (ESI, M+1): m/z=410.3; SFC: 100% ee.

and ((3S,7aS)-3-(((tert-butyldiphenylsilyl)oxy)methyl)hexahydro-1H-pyrrolizin-7a-yl)methanol (62 g, 48% yield) as a yellow oil. $^1$H NMR (400 MHz, CHLOROFORM-d) δ=7.77-7.64 (m, 4H), 7.48-7.35 (m, 6H), 3.96-3.62 (m, 1H), 3.57-3.30 (m, 2H), 3.18-2.85 (m, 3H), 2.01-1.90 (m, 2H), 1.89-1.70 (m, 4H), 1.69-1.56 (m, 2H), 1.11-1.03 (m, 10H); LCMS (ESI, M+1): m/z=410.3; SFC: 99.3% ee.

Step F2: rac-((3S,7aR)-3-(((tert-butyldiphenylsilyl)oxy)methyl)hexahydro-1H-pyrrolizin-7a-yl)methanol: To a solution of methyl 3-[[tert-butyl(diphenyl)silyl]oxymethyl]-1,2,3,5,6,7-hexahydropyrrolizine-8-carboxylate (83.0 g, 1 equiv.) in THF (830 mL) was added LAH (8.05 g, 1.3 equiv.) portion wise at −40° C. The mixture was stirred at −40° C. for 2 hours. The reaction mixture was quenched with H₂O (8.00 mL), NaOH (15%, 8.00 mL) and H₂O (24.0 mL), dried over anhydrous Na₂SO₄, filtered and concentrated to afford the title compound (72.0 g, crude) as yellow oil. LCMS [ESI, M+1]: m/z=410.2.

Step G2: ((3S,7aR)-3-(((tert-butyldiphenylsilyl)oxy)methyl)hexahydro-1H-pyrrolizin-7a-yl)methanol and ((3R,7aS)-3-(((tert-butyldiphenylsilyl)oxy)methyl)tetrahydro-1H-pyrrolizin-7a(5H)-yl)methanol: The stereoisomers of rac-((3S,7aR)-3-(((tert-butyldiphenylsilyl)oxy)methyl)hexahydro-1H-pyrrolizin-7a-yl)methanol (110 g) were separated by SFC (column: REGIS (s,s) WHELK-O1 (250 mm×50 mm, 10 um); mobile phase: [0.1% NH₃—H₂O ETOH]; B %: 40%-40%, 3.7 min) to afford title compounds ((3S,7aR)-3-(((tert-butyldiphenylsilyl)oxy)methyl)tetrahydro-1H-pyrrolizin-7a (5H)-yl)methanol (45 g, 40% yield) as yellow oil $^1$H NMR (400 MHz, chloroform-d) δ=7.77-7.63 (m, 4H), 7.52-7.31 (m, 6H), 3.96-3.86 (m, 1H), 3.82-3.68 (m, 1H), 3.33-3.22 (m, 2H), 3.22-3.13 (m, 1H), 2.86-2.79 (m, 1H), 2.76-2.64 (m, 1H), 2.00-1.92 (m, 1H), 1.82-1.48 (m, 7H), 1.31-1.21 (m, 1H), 1.07 (s, 9H) LCMS[ESI, M+1]: m/z=410.3.

and ((3R,7aS)-3-(((tert-butyldiphenylsilyl)oxy)methyl)tetrahydro-1H-pyrrolizin-7a(5H)-yl)methanol (90466-H2B) (45 g, 40% yield) as a yellow oil. $^1$H NMR (400 MHz, chloroform-d) δ=7.75-7.64 (m, 4ll), 7.35 (br s, 6H), 3.96-3.88 (m, 1H), 3.78-3.72 (m, 1H), 3.35-3.23 (m, 2H), 3.22-

3.13 (m, 1H), 2.87-2.79 (m, 1H), 2.74-2.65 (m, 1H), 2.00-1.92 (m, 1H), 1.83-1.63 (m, 4H), 1.63-1.43 (m, 3H), 1.28-1.23 (m, 1H), 1.10-1.04 (m, 9H); LCMS[ESI, M+1]: m/z=410.3.

Intermediate 26

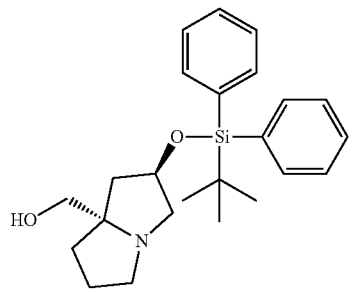 [SMILES: CC(C)(C)[Si](O[C@H]1CN2CCC[C@@]2(CO)C1)(c1ccccc1)c1ccccc1]

((2R,7aS)-2-((tert-butyldiphenylsilyl)oxy)hexa-hydro-1H-pyrrolizin-7a-yl)methanol

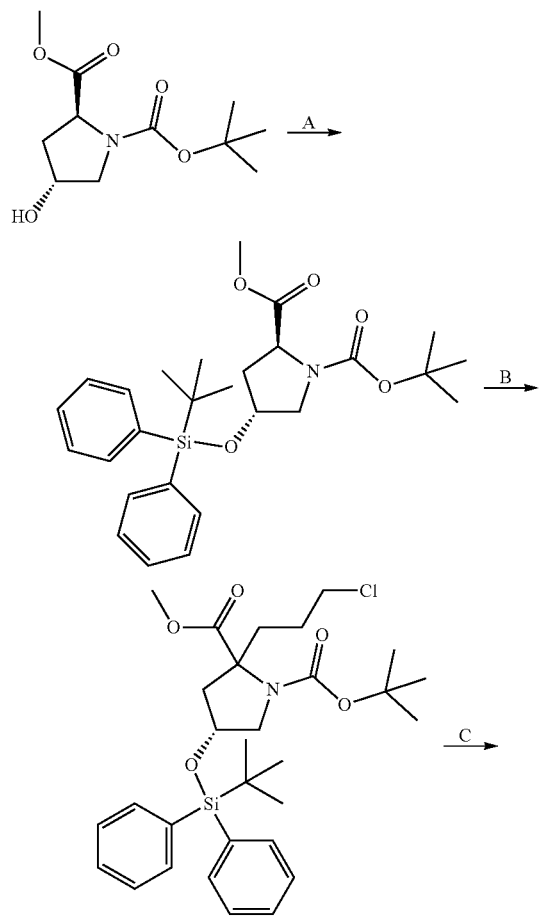

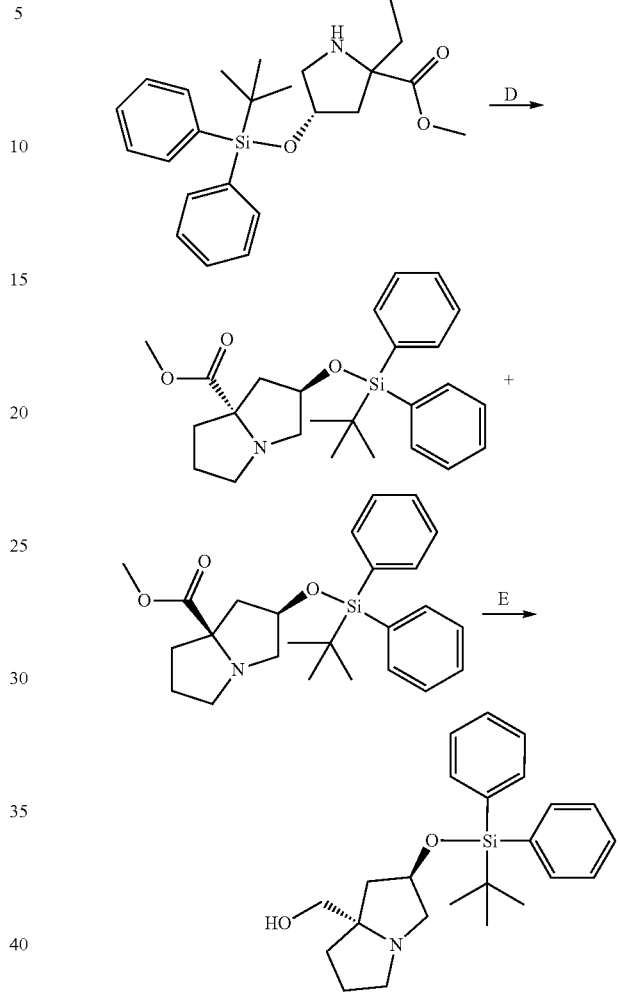

Step A. (2S,4R)-1-tert-butyl 2-methyl 4-((tert-butyldiphe-nylsilyl)oxy)pyrrolidine-1,2-dicarboxylate: To a solution of (2S,4R)-1-tert-butyl 2-methyl 4-hydroxypyrrolidine-1,2-dicarboxylate (20.0 g, 1.0 equiv.) in DCM (250 mL) was added imidazole (11.1 g, 2.0 equiv.) and TBDPSCl (26.9 g, 1.20 equiv.) at 0° C. The mixture was stirred at 25° C. for 1 hour. The reaction mixture was diluted with H₂O (100 mL) and the organic phase was separated. The aqueous phase was extracted with ethyl acetate (2×100 mL). The combined organic layers were dried over anhydrous sodium sulfate, concentrated and purified by column chromatography [SiO₂, Petroleum ether/Ethyl acetate 1:0 to 10:1] to afford the title compound (38.8 g, 98% yield) as an off-white solid; $^{1}$H NMR (400 MHz, CDCl₃) δ=7.68-7.57 (m, 4H), 7.49-7.36 (m, 6H), 4.58-4.36 (m, 2H), 3.74-3.63 (m, 3H), 3.59-3.35 (m, 2H), 2.31-2.15 (m, 1H), 1.95-1.80 (m, 1H), 1.50-1.39 (m, 9H), 1.06 (s, 9H).

Step B. (4I)-1-tert-butyl 2-methyl 4-((tert-butyldiphenyl-silyloxy)-2-(3-chloropropyl) pyrrolidine-1,2-dicarboxylate: To a solution of (2S,4R)-1-tert-butyl 2-methyl 4-((tert-butyl-diphenylsilyl)oxy)pyrrolidine-1,2-dicarboxylate (36.0 g, 1.0 equiv.) in THF (200 mL) was added LDA (2.0 M in THF, 48.4 mL, 1.30 equiv.). The mixture was stirred at −70° C. for 1 hour. To the reaction mixture was added 1-bromo-3- chloro-propane (58.6 g, 5.0 equiv.) at −70° C. The mixture was stirred at 20° C. for 12 hours. The reaction mixture was diluted with H₂O (200 mL) and extracted with ethyl acetate (3×200 mL). The combined organic layers were dried over anhydrous sodium sulfate, concentrated and purified by reversed phase flash chromatography [C18, water (0.1% formic acid)-ACN] to afford the title compound (36.0 g, 86% yield) as a yellow oil; ¹H NMR (400 MHz, CDCl₃) δ=7.68-7.59 (m, 4H), 7.49-7.34 (m, 6H), 4.46-4.19 (m, 1H), 3.88-3.66 (m, 2H), 3.62-3.55 (m, 3H), 3.53-3.22 (m, 2H), 2.38-1.71 (m, 6H), 1.46-1.36 (m, 9H), 1.10-1.01 (m, 9H).

Step C. (4R)-methyl 4-((tert-butyldiphenylsilyl)oxy)₂-(3-chloropropyl)pyrrolidine-2-carboxylate: To a solution of (4R)-1-tert-butyl 2-methyl 4-((tert-butyldiphenylsilyl)oxy)-2-(3-chloropropyl)pyrrolidine-1,2-dicarboxylate (36.0 g, 1.0 equiv.) in ACN (200 mL) was added HCl-dioxane (4.0 M, 200 mL) at 0° C. The mixture was stirred at 0° C. for 1 hour. The mixture was concentrated under reduced pressure to afford the title compound (34.0 g, crude, HCl) as a yellow solid.

Step D. (2R,7aS)-methyl 2-((tert-butyldiphenylsilyl)oxy) hexahydro-1H-pyrrolizine-7a-carboxylate (peak A) and (2R, 7aR)-methyl2-((tert-butyldiphenylsilyl)oxy)hexahydro-1H-pyrrolizine-7a-carboxylate (peak B): To a solution of (4R)-methyl 4-((tert-butyldiphenylsilyl)oxy)-2-(3-chloropropyl) pyrrolidine-2-carboxylate (34.0 g, 1.0 equiv, HCl) in ACN (300 mL) was added NaHCO₃ (28.8 g, 5.0 equiv.) and KI (1.14 g, 0.1 equiv.). The mixture was stirred at 50° C. for 12 hours. The reaction mixture was diluted with H₂O (150 mL) and extracted with ethyl acetate (3×100 mL). The combined organic phase was dried over anhydrous sodium sulfate, concentrated and purified by prep-HPLC [column: Waters Xbridge C18 150×50 mm×10 μm; mobile phase: water (10 mM NH₄HCO₃)-ACN; B %: 73%-93%, 11.5 min] and another prep-HPLC [column: Phenomenex luna C18 250 mm×100 mm×10 pm; mobile phase: water (10 mM NH₄HCO₃)-ACN; B %: 55%-85% over 30 min] to afford the peak A (10.0 g, two steps 34% yield) and the peak B (6.0 g, two steps 21% yield) as yellow oil. LCMS (ESI, M+1): m/z=424.1.

Step E. ((2R,7aS)-2-((tert-butyldiphenylsilyl)oxy)hexahydro-1H-pyrrolizin-7a-yl)methanol: To a solution of (2R, 7aS)-methyl 2-((tert-butyldiphenylsilyl)oxy)hexahydro-1H-pyrrolizine-7a-carboxylate (4.50 g, 1.0 equiv.) in THF (100 mL) was added LiAlH₄ (1.21 g, 3.0 equiv.) at −40° C. The mixture was stirred at −40° C. for 1 hour. The reaction mixture was quenched by addition of H₂O (4.0 mL) at 0° C. The mixture was dried over anhydrous sodium sulfate, filtered and concentrated to afford the title compound (4.20 g, 94% yield) as a yellow oil; ¹H NMR (400 MHz, CDCl₃) δ=7.68-7.62 (m, 4H), 7.46-7.36 (m, 6H), 4.43-4.35 (m, 1H), 3.11 (s, 2H), 3.03-2.94 (m, 3H), 2.76-2.69 (m, 1H), 2.02-1.89 (m, 3H), 1.80-1.69 (m, 3H), 1.06 (s, 9H); LCMS (ESI, M+1): m/z=396.1.

Intermediate 27

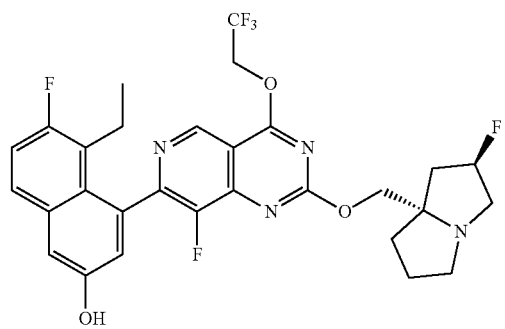 [SMILES: CCc1c(F)ccc2cc(O)cc(-c3ncc4c(OCC(F)(F)F)nc(OC[C@@]56CCCN5C[C@H](F)C6)nc4c3F)c12]

5-ethyl-6-fluoro-4-(8-fluoro-2-(((2R,7aS)-2-fluoro-tetrahydro-1H-pyrrolizin-7a(5H)-yl)methoxy)-4-(2, 2,2-trifluoroethoxy)pyrido[4,3-d]pyrimidin-7-yl) naphthalen-2-ol

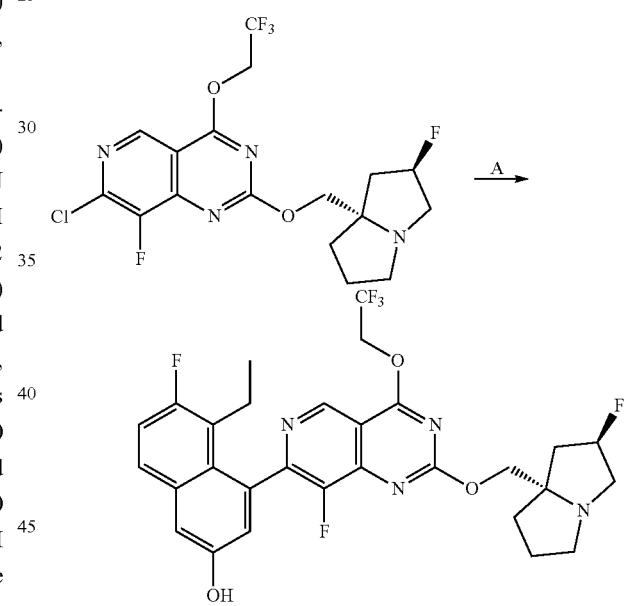

Step A. 5-ethyl-6-fluoro-4-(8-fluoro-2-(((2R,7aS)-2-fluorohexahydro-1H-pyrrolizin-7a-yl)methoxy)-4-(2,2,2-trifluoroethoxy)pyrido[4,3-d]pyrimidin-7-yl)naphthalen-2-ol: To a solution of 7-chloro-8-fluoro-2-(((2R,7aS)-2-fluoro-hexahydro-1H-pyrrolizin-7a-yl)methoxy)-4-(2,2,2-trifluoroethoxy)pyrido[4,3-d]pyrimidine (28.4 g, 1.0 equiv.), 5-ethyl-6-fluoro-4-(4,4,5,5-tetramethyl-1,3,2-dioxaborolan-2-yl)naphthalen-2-ol (25.6 g, 1.25 equiv.) and Cs₂CO₃ (1.5 M in H₂O, 129 mL, 3.0 equiv.) in methoxycyclopentane (300 mL) was added Ad₂nBuP-Pd-G3 (7.07 g, 0.15 equiv.). The reaction was stirred at 100° C. for 3 hours under N₂. The mixture was diluted with water (300 mL) and extracted with ethyl acetate (3×200 mL). The combined organic layers were dried over anhydrous sodium sulfate, concentrated. The residue was purified by reversed phase flash chromatography [water (0.1% formic acid)/acetonitrile] to afford the title compound (16.8 g, 40% yield) as a yellow solid; ¹H NMR (400 MHz, chloroform-d) δ=9.19 (d, J=10.4 Hz, 1H), 7.54 (dd, J=5.6, 8.8 Hz, 1H), 7.26-7.21 (m, 1H), 7.16-7.11 (m, 1H), 6.96-6.84 (m, 1H), 5.46-5.22 (m, 1H), 5.05-4.71 (m, 2H), 4.56-4.32 (m, 2H), 3.48-3.21 (m, 3H), 3.13-3.01 (m, 1H), 2.47-2.32 (m, 4H), 2.32-2.08 (m, 4H), 0.78 (t, J=7.2 Hz, 3H); LCMS (ESI, M+1): m/z=593.2.

Intermediate 28

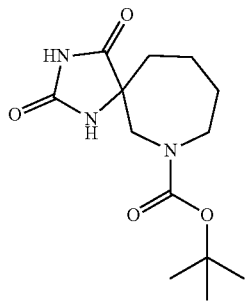 [SMILES: CC(C)(C)OC(=O)N1CCCCC2(C1)NC(=O)NC2=O]

tert-butyl 2,4-dioxo-1,3,7-triazaspiro[4.6]undecane-7-carboxylate

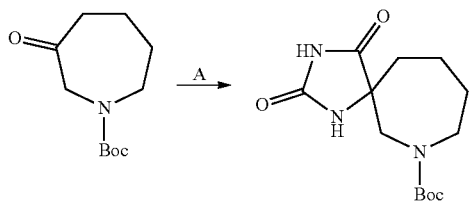

Step A. tert-butyl 2,4-dioxo-1,3,7-triazaspiro[4.6]undecane-7-carboxylate: To a solution of tert-butyl 3-oxoazepane-1-carboxylate (2.00 g, 1.0 equiv.) and $(NH_4)_2CO_3$ (2.70 g, 3.0 equiv.) in EtOH (10 mL) and $H_2O$ (10 mL) was added KCN (1.12 g, 1.83 equiv.). The reaction was stirred at 85° C. for 16 hours. The mixture was cooled to 25° C., then diluted with water (20 mL) and extracted with ethyl acetate (3×20 mL). The combined organic layers were dried over anhydrous sodium sulfate, concentrated to afford the title compound (2.20 g, 83% yield) as a white solid; $^1$H NMR (400 MHz, DMSO-$d_4$) δ=11.39-9.68 (m, 1H), 7.97-7.52 (m, 1H), 3.45 (s, 2H), 3.29-3.12 (m, 2H), 1.82-1.65 (m, 3H), 1.64-1.47 (m, 3H), 1.45-1.31 (m, 9H); LCMS (ESI, M−55): m/z=228.0.

Intermediate 29

5,6,7,8-tetrahydro-4H-pyrazolo[1,5-a][1,4]diazepin-2-ylmethanol

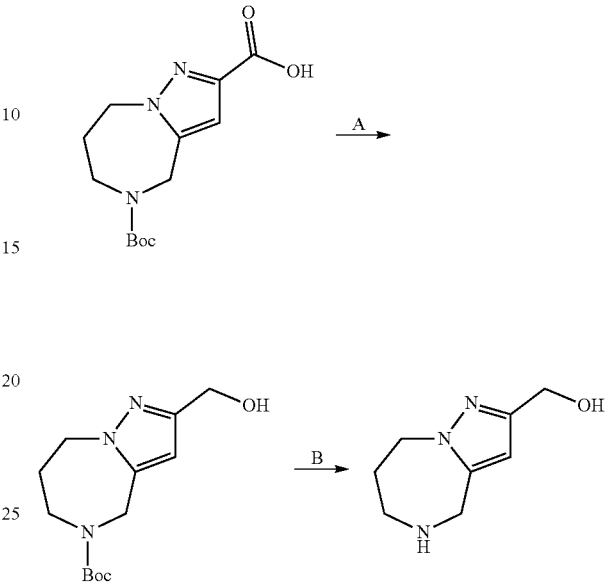

Step A. tert-butyl 2-(hydroxymethyl)-7,8-dihydro-4H-pyrazolo[1,5-a][1,4]diazepine-5 (6H)-carboxylate: To a solution of 5-(tert-butoxycarbonyl)-5,6,7,8-tetrahydro-4H-pyrazolo[1,5-a][1,4]diazepine-2-carboxylic acid (500 mg, 1.0 equiv.) in THF (10 mL) was added LiAlH$_4$ (135 mg, 2.0 equiv.) at 0° C. The mixture was stirred at 0° C. for 1.5 hours and at 20° C. for 3 hours. The mixture was quenched with ice water (20 mL) and extracted with ethyl acetate (50 mL). The organic phase concentrated to give the title compound (260 mg, 33% yield) as a yellow oil; LCMS (ESI, M+1): m/z=268.2.

Step B. 5,6,7,8-tetrahydro-4H-pyrazolo[1,5-a][1,4]diazepin-2-yl)methanol: To the solution of tert-butyl 2-(hydroxymethyl)-7,8-dihydro-4H-pyrazolo[1,5-a][1,4]diazepine-5 (6H)-carboxylate (260 mg, 1.0 equiv.) in ACN (4 mL) was added HCl.dioxane (4 M, 2.43 mL, 10 equiv.) at 0° C. The reaction was stirred at 0° C. for 0.5 hour. The reaction mixture was concentrated to give a residue. The residue was dissolved in methanol (2 mL) and the pH was adjusted to 8 with saturated aqueous NaHCO$_3$. The mixture was filtered and concentrated to give a residue. The residue was dissolved with dichloromethane (5 mL), filtered and concentrated to afford the title compound (250 mg, crude) as a yellow oil; LCMS (ESI, M+1): m/z=167.9.

Intermediate 30

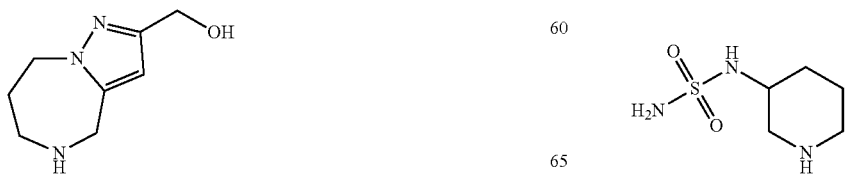

3-(sulfamoylamino)piperidine

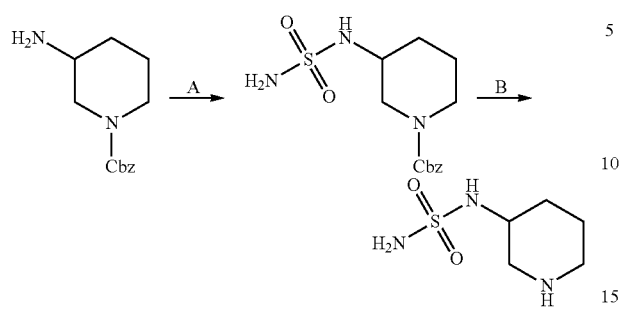

Step A. benzyl 3-(sulfamoylamino)piperidine-1-carboxylate: To a solution of benzyl 3-aminopiperidine-1-carboxylate (500 mg, 1.0 equiv.) in dioxane (10 mL) was added sulfamide (410 mg, 254 µL, 2.0 equiv.). After stirring at 80° C. for 12 hours, another portion of sulfamide (615 mg, 382 µL, 3.0 equiv.) was added. The mixture was stirred at 80° C. for 5 hours. The reaction mixture was concentrated and purified by reversed phase flash chromatography [C18, water (0.1% formic acid)/ACN] to afford the title compound (423 mg, 56% yield) as a colorless oil; LCMS (ESI, M+1): m/z=314.0.

Step B. 3-(sulfamoylamino)piperidine: To a solution of benzyl 3-(sulfamoylamino)piperidine-1-carboxylate (420 mg, 1.0 equiv.) in methanol (10 mL) was added Pd/C (0.1 g, 10% purity) under $N_2$ atmosphere. The suspension was degassed and purged with $H_2$ 3 times. The mixture was stirred under $H_2$ (15 Psi) at 20° C. for 12 hours. The reaction mixture was filtered under $N_2$ and the filtrate was concentrated to afford the title compound (240 mg, 99% yield) as a colorless oil; $^1$H NMR (400 MHz, DMSO-d) δ=7.65-7.01 (m, 5H), 6.70 (br d, J=7.2 Hz, 1H), 6.56 (s, 2H), 5.17-4.99 (m, 2H), 4.19-4.07 (m, 1H), 3.81 (br d, J=12.4 Hz, 1H), 3.11 (br s, 1H), 2.86-2.63 (m, 2H), 1.99-1.88 (m, 1H), 1.75-1.60 (m, 1H), 1.47-1.29 (m, 2H).

Intermediate 31

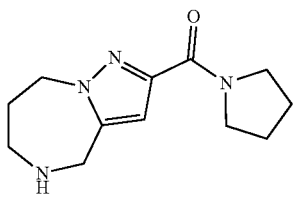 [SMILES: O=C(c1cc2n(n1)CCCNC2)N1CCCC1]

pyrrolidin-1-yl(5,6,7,8-tetrahydro-4H-pyrazolo[1,5-a][1,4]diazepin-2-yl)methanone

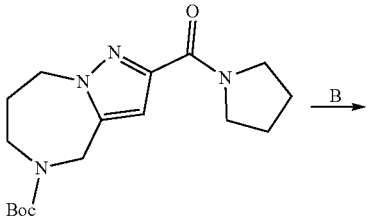

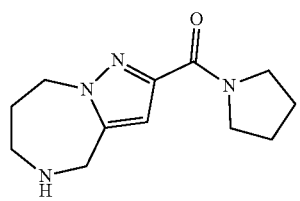

Step A. tert-butyl-2-(pyrrolidine-1-carbonyl)-7,8-dihydro-4H-pyrazolo[1,5-a][1,4]diazepine-5(6H)-carboxylate: To a solution of 5-tert-butoxycarbonyl-4,6,7,8-tetrahydropyrazolo[1,5-a][1,4]diazepine-2-carboxylic acid (160 mg, 1.0 equiv.), pyrrolidine (121 mg, 3.0 equiv.) and triethylamine (74.8 mg, 103 µL, 1.3 equiv.) in DMF (1.5 mL) was added HATU (281 mg, 1.3 equiv.) at 0° C. The mixture was stirred at 25° C. for 0.5 hour. Upon reaction completion, the mixture was filtered and the filtrate was partitioned between ethyl acetate (10 mL) and water (10 ml). The organic phase was separated, washed with brine (2×5 mL), dried over sodium sulfate, filtered and concentrated under reduced pressure to give a residue. The residue was purified by column chromatography (Silica gel, petroleum ether/ethyl acetate 1:1 to 0:1) to afford the title compound (110 mg, 58% yield) as a white solid; LCMS [ESI, M+1]: m/z=335.2.

Step B. pyrrolidin-1-yl(5,6,7,8-tetrahydro-4H-pyrazolo[1,5-a][1,4]diazepin-2-yl)methanone: To a solution of tert-butyl 2-(pyrrolidine-1-carbonyl)-4,6,7,8-tetrahydropyrazolo[1,5-a][1,4]diazepine-5-carboxylate (110 mg, 1.0 equiv.) in DCM (1.5 mL) was added trifluoroacetic acid (565 mg, 367 µL, 15.1 equiv.) at 0° C. The mixture was stirred at 25° C. for 0.5 hour. The reaction mixture was concentrated under reduced pressure to afford the title compound (65.0 mg, 84% yield) as a yellow liquid; LCMS [ESI, M+1]: m/z=235.2.

Intermediates 32, 33, 34 and 51 were synthesized according to the procedure described for Intermediate 31.

Intermediate 32

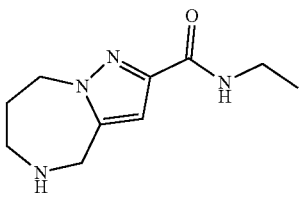

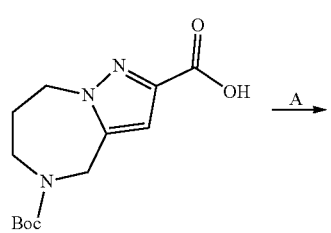

77

N-ethyl-5,6,7,8-tetrahydro-4H-pyrazolo[1,5-a][1,4]diazepine-2-carboxamide Intermediate 33

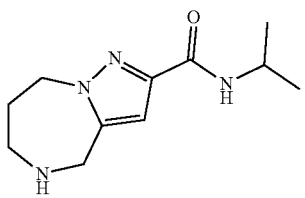 [SMILES: CC(C)NC(=O)c1cc2n(n1)CCCNC2]

N-isopropyl-5,6,7,8-tetrahydro-4H-pyrazolo[1,5-a][1,4]diazepine-2-carboxamide Intermediate 34

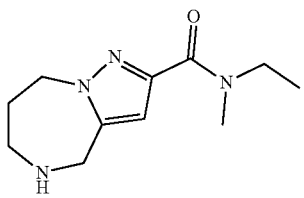

N-ethyl-N-methyl-5,6,7,8-tetrahydro-4H-pyrazolo[1,5-a][1,4]diazepine-2-carboxamide Intermediate 51

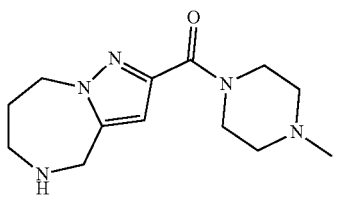 [SMILES: CN1CCN(C(=O)c2cc3n(n2)CCCNC3)CC1]

(4-methylpiperazin-1-yl)(5,6,7,8-tetrahydro-4H-pyrazolo[1,5-a][1,4]diazepin-2-yl)methanone Intermediate 35

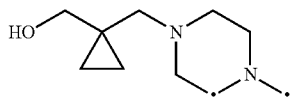

(1-((4-methylpiperazin-1-yl)methyl)cyclopropyl)methanol

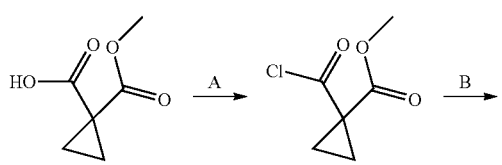

78

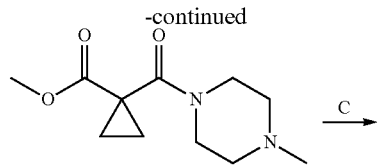

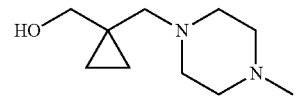

Step A. methyl 1-(chlorocarbonyl)cyclopropanecarboxylate: To a mixture of 1-(methoxycarbonyl)cyclopropanecarboxylic acid (2.0 g, 1.0 equiv.), DMF (101 mg, 0.1 equiv.) in DCM (15 mL) was added (COCl)$_2$ (2.64 g, 1.82 mL, 1.5 equiv.). The mixture was stirred at 0-20° C. for 1 hour. The mixture was concentrated and purified by column chromatography (Silica gel, Petroleum ether/Ethyl acetate 5:1 to 1:1) to afford the title compound (2.2 g, 97% yield) as a yellow oil.

Step B. methyl 1-(4-methylpiperazine-1-carbonyl)cyclopropanecarboxylate: To a mixture of methyl 1-chlorocarbonylcyclopropanecarboxylate (2.2 g, 1.0 equiv.), TEA (4.11 g, 3.0 equiv.) in DCM (15 mL) was added 1-methylpiperazine (1.63 g, 1.2 equiv.). The mixture was stirred at 0-20° C. for 1 hour. The mixture was concentrated and the residue was purified by column chromatography (Silica gel, Petroleum ether/Ethyl acetate 3:1 to 1:1) to afford the title compound (2.18 g, 71% yield) as a white solid; $^1$HNMR (400 MHz, chloroform-d) δ=3.77-3.31 (m, 7H), 2.39-2.10 (m, 7H), 1.45-1.32 (m, 2H), 1.29-1.17 (m, 2H).

Step C. (1-((4-methylpiperazin-1-yl)methyl)cyclopropyl)methanol: To a solution of methyl 1-(4-methylpiperazine-1-carbonyl)cyclopropanecarboxylate (1.5 g, 1.0 equiv.) in THF (40 mL) was added LiAlH$_4$ (503 mg, 2.0 equiv.) portion wise under N$_2$. The suspension was degassed and purged with N$_2$ for 3 times. The mixture was stirred at 0-15° C. for 2 hours. The mixture was quenched with water (500 μL), 15% NaOH aqueous (500 μL), water (1.5 mL), and filtered. The filter cake was washed with EtOAc (3×15 mL), and the filtrate was dried over anhydrous sodium sulfate, concentrated and purified by column chromatography (Silica gel, Petroleum ether/Ethyl acetate 3:1 to 0:1) to afford the title compound (716 mg, 59% yield) as a colorless oil.

Intermediate 36

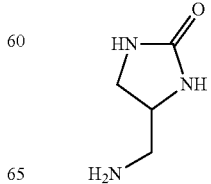

4-(aminomethyl)imidazolidin-2-one

4-(2-aminoethyl)imidazolidin-2-one

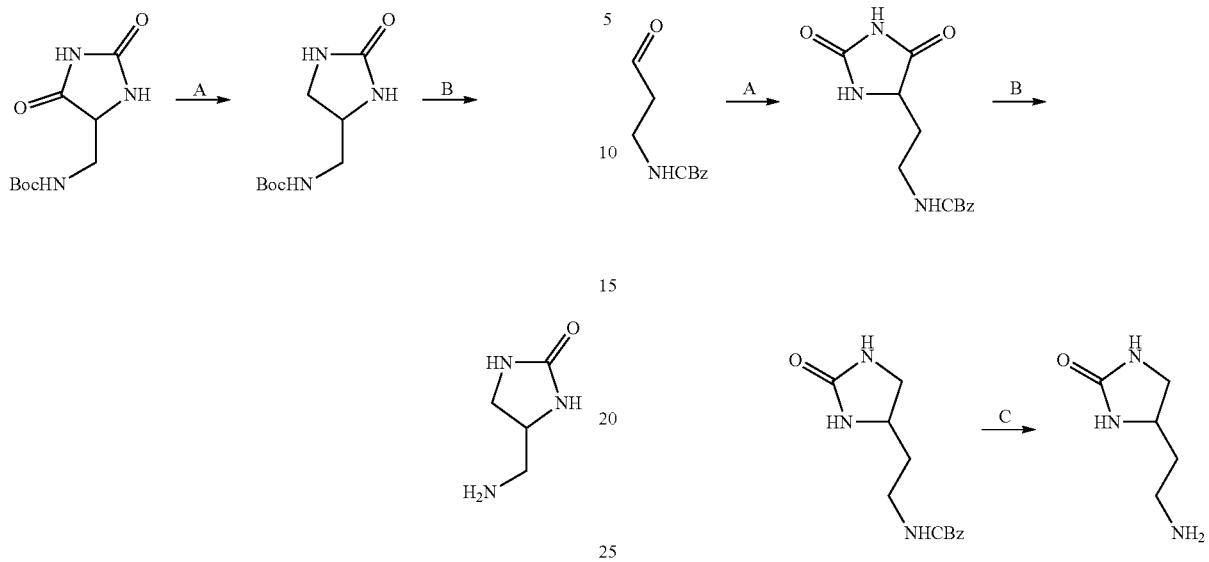

Step A. tert-butyl ((2-oxoimidazolidin-4-yl)methyl)carbamate: A mixture of tert-butyl N-[(2,5-dioxoimidazolidin-4-yl)methyl]carbamate (100 mg, 1.0 equiv.) and $BH_3 \cdot Me_2S$ (10.0 M, 2.0 equiv.) in THF (3 mL) at 0° C. was degassed and stirred at 60° C. for 1 hour under $N_2$ atmosphere. The reaction mixture was quenched by addition of MeOH (10 mL) at 0° C. Then it was extracted with ethyl acetate (3×20 mL). The combined organic layers were washed with brine (20 mL) and dried over $Na_2SO_4$, filtered and concentrated under reduced pressure to afford the title compound (60.0 mg, 64% yield) as a white solid; 1H NMR (400 MHz, DMSO-$d_6$) δ=7.77 (br s, 1H), 6.97-6.78 (m, 1H), 6.37-5.98 (m, 1H), 4.02 (br dd, J=4.4, 6.4 Hz, 1H), 3.14-2.96 (m, 2H), 2.84-2.58 (m, 1H), 1.37 (s, 9H).

Step B. 4-(aminomethyl)imidazolidin-2-one: To a solution of tert-butyl N-[(2-oxoimidazolidin-4-yl)methyl]carbamate (60.0 mg, 1.0 equiv.) in MeOH (2 mL) was added HCl (1 M, 5.0 equiv.). The mixture was stirred at 25° C. for 2 hours. The reaction mixture was concentrated under reduced pressure to afford the title compound (50.0 mg, crude) as a white solid. The crude product was used for the next step directly.

Intermediate 37

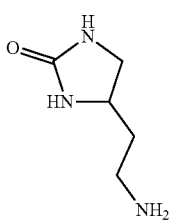

Step A. benzyl (2-(2,5-dioxoimidazolidin-4-yl)ethyl)carbamate: Ammonium carbonate (25.5 g, 11.0 equiv.) was added to benzyl N-(3-oxopropyl)carbamate (5.00 g, 1.00 equiv.) in methanol (40.0 mL) and water (36.0 mL) under a flow nitrogen gas. To the reaction mixture was added potassium cyanide (1.97 g, 1.25 equiv.) and the resulting was stirred at 20° C. for 12 hours. The suspension was filtered and the filter cake was dried under reduced to afford the title compound (3.10 g, 37.8% yield) as a white solid; 1H NMR (400 MHz, DMSO-$d_6$) δ=7.88 (s, 1H), 7.38-7.30 (m, 5H), 5.02 (s, 2H), 3.99 (dd, J=4.8, 8.0 Hz, 1H), 3.11 (d, J=6.0 Hz, 2H), 1.92-1.79 (m, 1H), 1.69-1.55 (m, 1H).

Step B. benzyl (2-(2-oxoimidazolidin-4-yl) ethyl)carbamate: To a solution of benzyl N-[2-(2,5-dioxoimidazolidin-4-yl)ethyl]carbamate (1.00 g, 1.0 equiv.) in tetrahydrofuran (15.0 mL) was added borane dimethyl sulfide complex (10 M, 1.80 mL, 5.0 equiv.) at 0° C. The mixture was stirred at 50° C. for 1.5 hours. The mixture was quenched with methanol (10.0 mL). The mixture was concentrated in vacuum to produce a residue. The residue was purified by prep-HPLC (column: Welch Ultimate XB-CN 250×50×10 um; mobile phase: [Hexane-EtOH]; B %: 10%-35%, 12 min). The desired fraction was collected and lyophilized to give a residue. The residue was further re-purified by column chromatography on silica gel (ethyl acetate) to afford the title compound (150 mg, 13.9% yield) as a white solid. 1H NMR (400 MHz, DMSO-$d_6$) δ=7.41-7.30 (m, 5H), 6.31 (s, 1H), 6.09 (s, 1H), 5.01 (s, 2H), 3.58 (q, J=6.8 Hz, 1H), 3.02 (s, 2H), 2.89 (s, 1H), 1.58-1.55 (m, 2H).

Step C. 4-(2-aminoethyl)imidazolidin-2-one: To a solution of benzyl N-[2-(2-oxoimidazolidin-4-yl)ethyl]carbamate (80.0 mg, 1.00 equiv.) in tetrahydrofuran (5.00 mL) was added palladium/carbon (20 mg, 10% purity) under nitrogen atmosphere. The suspension was degassed and purged with hydrogen for 3 times. The mixture was stirred under hydrogen (15 psi) at 20° C. for 2 hours. The mixture was filtered and the filter cake was washed with methanol (10.0 mL). The filtrate was concentrated to afford the title compound (40 mg, crude) as a white solid.

Intermediate 38

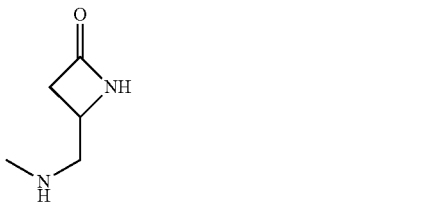

4-((methylamino)methyl)azetidin-2-one

Intermediate 39

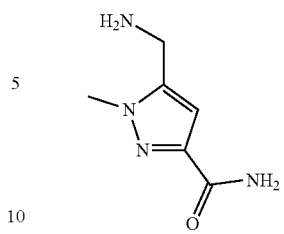

5-(aminomethyl)-1-methyl-1H-pyrazole-3-carboxamide

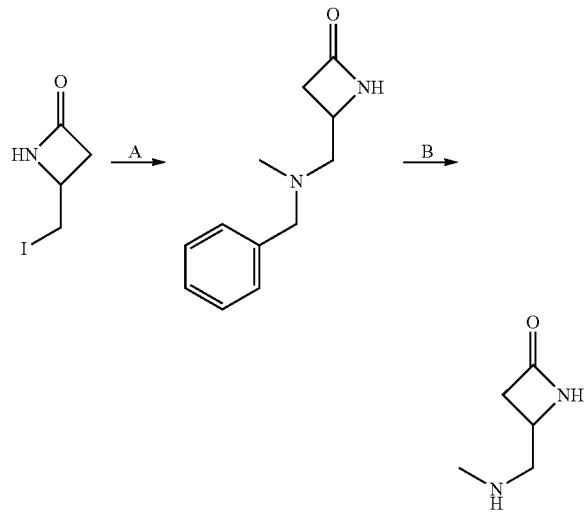

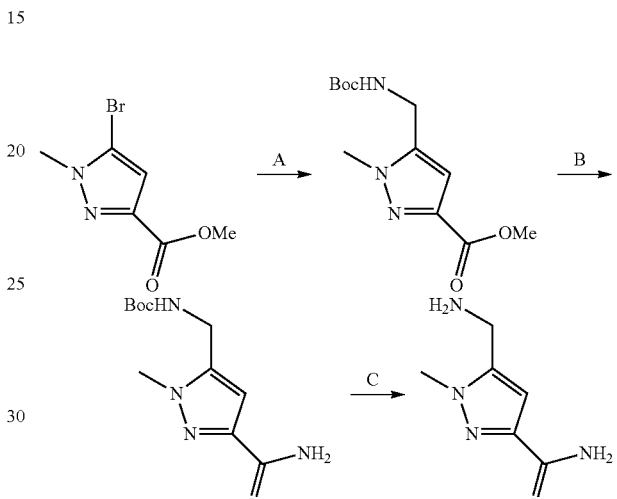

Step A. 4-(benzyl(methyl)amino)methyl)azetidin-2-one: To a solution of 4-(iodomethyl)azetidin-2-one (100 mg, 1.0 equiv.) and N-methyl-1-phenyl-methanamine (86.2 mg, 1.5 equiv.) in acetonitrile (1.5 mL) was added potassium carbonate (196 mg, 3.0 equiv.). The mixture was stirred at 60° C. for 2 hours. After completion, the reaction mixture was cooled to 25° C. and filtered. Then the filtrate was partitioned between ethyl acetate (10 mL) and water (10 ml). The organic phase was separated, and then it was washed with saturated salt solution (2×5 mL), dried over sodium sulfate, filtered and concentrated under reduced pressure to give a residue. The residue was purified by column chromatography (Silica gel, petroleum ether/ethyl acetate-1/1 to 0/1) to afford the title compound (42.0 mg, 43% yield) as a yellow liquid; LCMS [ESI, M+1]: m/z=205.0.

Step B. 4-((methylamino)methyl)azetidin-2-one: A mixture of 4-[[benzyl(methyl)amino]methyl]azetidin-2-one (60.0 mg, 1.0 equiv.) and Pd/C (20.0 mg, 10% purity) in methyl alcohol (0.5 mL) was degassed and purged with hydrogen for 3 times, and then the mixture was stirred at 25° C. for 2 hours under hydrogen atmosphere (15 psi). The reaction mixture was concentrated under reduced pressure to afford the title compound (13.0 mg, 39% yield) as yellow liquid; The crude product was used for the next step directly.

Step A. methyl 5-(((tert-butoxycarbonyl)amino)methyl)-1-methyl-1H-pyrazole-3-carboxylate: A mixture of methyl 5-bromo-1-methyl-1H-pyrazole-3-carboxylate (900 mg, 1 equiv.), Potassium [[(tert-Butoxycarbonyl)amino]methyl] trifluoroborate (1.46 g, 1.5 equiv.), Pd(OAc)$_2$ (73.8 mg, 0.08 equiv.) and XPhos (313 mg, 0.16 equiv.) and Cs$_2$CO$_3$ (4.02 g, 3 equiv.) in THF (50 mL) and water (5 mL) was degassed and stirred at 100° C. for 2 hours under N$_2$ atmosphere. The reaction mixture was diluted with water 20 mL and extracted with ethyl acetate (20 mL×3). The combined organic layers were washed with brine (20 mL×1), dried over anhydrous sodium sulfate, filtered and concentrated to give a residue, which was purified by column chromatography (Silica gel, Petroleum ether/Ethyl acetate 5:1 to 3:1) to give the title compound (420 mg, 1.56 mmol, 37.96% yield) as a white solid; $^1$H NMR (400 MHz, DMSO-d$_6$) δ=6.64 (s, 1H), 4.76 (s, 1H), 4.29 (d, J=8.0 Hz, 2H), 3.84 (d, J=8.0 Hz, 6H), 1.39 (s, 9H).

Step B. tert-butyl ((3-carbamoyl-1-methyl-1H-pyrazol-5-yl)methyl)carbamate: A mixture of methyl 5-(((tert-butoxycarbonyl)amino)methyl)-1-methyl-1H-pyrazole-3-carboxylate (400 mg, 1 equiv.) in NH$_3$·H$_2$O (3.64 g, 4 mL, 25% NH$_3$, 17.48 equiv.) was stirred at 20° C. for 2 hours under N$_2$ atmosphere. The reaction mixture was diluted with water (20 mL) and extracted with ethyl acetate (20 mL×3). The combined organic layers were washed with brine (10 mL×1), dried over anhydrous sodium sulfate, filtered and concentrated to give the title compound (220 mg, 58% yield) as a white solid.

Step C. 5-(aminomethyl)-1-methyl-1H-pyrazole-3-carboxamide: To a mixture of tert-butyl ((3-carbamoyl-1-methyl-1H-pyrazol-5-yl)methyl)carbamate (100 mg, 1 equiv.) in CH₂Cl2 (0.5 mL) was added TFA (770 mg, 0.5 mL, 17.2 equiv.) at 0° C., the mixture was stirred at 25° C. for 12 hours. The reaction mixture was concentrated under reduced pressure to give the title compound (170 mg, crude, TFA) as a yellow oil. $^1$H NMR (400 MHz, DMSO-$d_6$) δ=8.37 (s, 3H), 7.46 (s, 1H), 7.18 (m, 1H), 6.74 (s, 1H), 4.18 (d, J=5.2 Hz, 2H), 3.88 (s, 3H).

added CsF (2.53 g, 10 equiv.). The mixture was stirred at 20° C. for 2 hrs. The reaction mixture was concentrated under reduced pressure and purified by reversed phase HPLC (water (0.1% formic acid)-ACN) to afford the title compound (0.6 g, 57% yield) as a yellow solid; LCMS (ESI, M+1): m/z=589.3

Intermediate 40

Intermediate 41

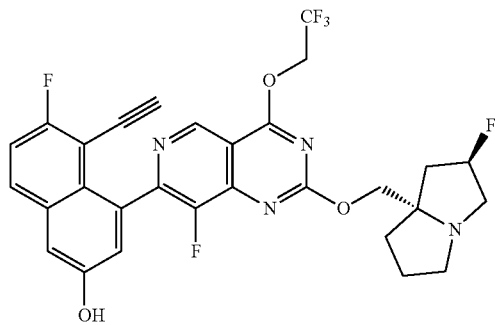 [SMILES: C#Cc1c(F)ccc2cc(O)cc(-c3ncc4c(OCC(F)(F)F)nc(OC[C@@]56CCCN5C[C@H](F)C6)nc4c3F)c12]

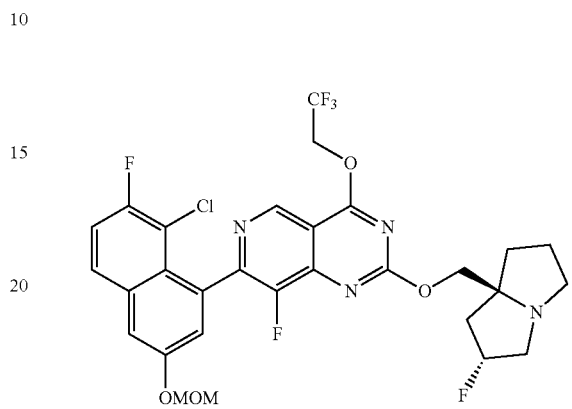

5-ethynyl-6-fluoro-4-(8-fluoro-2-(((2R,7aS)-2-fluorohexahydro-1H-pyrrolizin-7a-yl)methoxy)-4-(2,2,2-trifluoroethoxy)pyrido[4,3-d]pyrimidin-7-yl)naphthalen-2-ol 7-(8-chloro-7-fluoro-3-(methoxymethoxy)naphthalen-1-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine

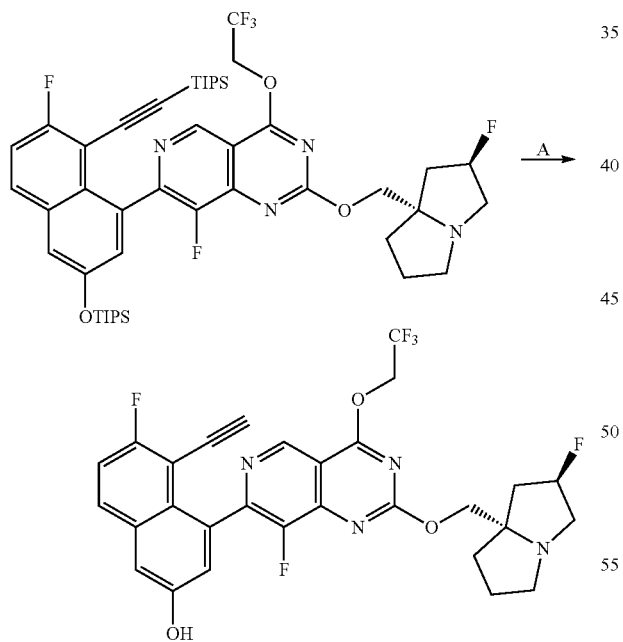

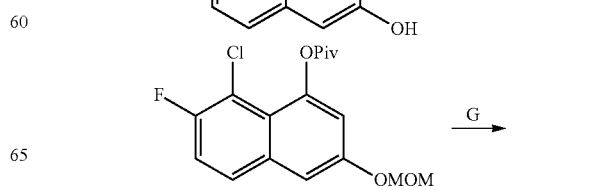

Step A. 5-ethynyl-6-fluoro-4-(8-fluoro-2-(((2R,7aS)-2-fluorohexahydro-1H-pyrrolizin-7a-yl)methoxy)-4-(2,2,2-trifluoroethoxy)pyrido[4,3-d]pyrimidin-7-yl)naphthalen-2-ol: To a solution of 8-fluoro-7-(7-fluoro-8-((triisopropylsilyl)ethynyl)-3-((triisopropylsilyl)oxy)naphthalen-1-yl)-2-(((2R,7aS)-2-fluorohexahydro-1H-pyrrolizin-7a-yl)methoxy)-4-(2,2,2-trifluoroethoxy)pyrido[4,3-d]pyrimidine (1.50 g, 1 equiv.) in DMF (20 mL) was

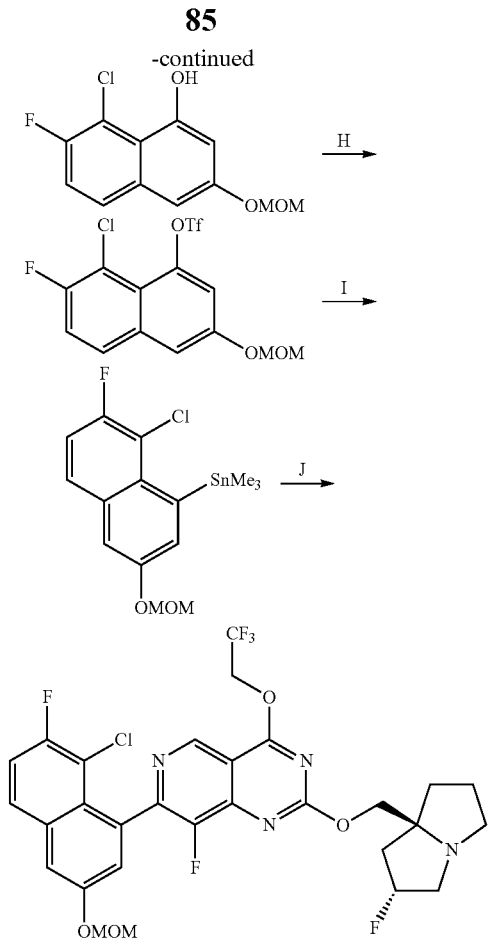

Step A. 5-chloro-6-fluoro-1,4-dihydro-1,4-epoxy)naphthalene: To a solution 1-bromo-3-chloro-2,4-difluorobenzene (250 g, 1 equiv.) and furan (150 g, 2 equiv.) in toluene (2.5 L) was added n-BuLi (2.5 M, 1.2 equiv.) dropwise over 0.5 hour at −15° C. The reaction mixture was stirred at 20° C. for 12 hours. After reaction completion, the mixture was quenched with water (2 L) and filtered. The filtrate was separated. The aqueous layer was extracted with ethyl acetate (2×2 L). The combined organic layers were dried over $Na_2SO_4$, filtered and concentrated in vacuum. The residue was purified by reversed phase flash [C18, water (0.1% formic acid)-ACN, 0-80% MeCN] to afford the title compound (81 g, 37% yield) as a yellow oil; $^1$H NMR (400 MHz, chloroform-d) δ 7.11-7.06 (m, 2H), 7.06-7.01 (m, 1H), 6.73 (dd, J=7.6, 9.6 Hz, 1H), 5.88 (s, 1H), 5.74 (s, 1H).

Step B. 8-chloro-7-fluoronaphthalen-1-yl pivalate: A reaction mixture of 5-chloro-6-fluoro-1,4-dihydro-1,4-epoxy) naphthalene (162 g, 1 equiv.) in concentrated HCl (1.02 kg, 12.2 equiv.) and EtOH (1.2 L) was heated to 80° C. for 6 hours. The reaction mixture was concentrated in vacuum. The pH of the residue was adjusted to 7 with saturated aqueous $NaHCO_3$ and extracted with ethyl acetate (2×2 L). The combined organic layers were dried over $Na_2SO_4$, filtered and concentrated. The residue was triturated with petroleum ether (100 mL), filtered and the solid was dried under vacuum to afford the title compound (124 g, 76% yield) as a white solid; $^1$H NMR (400 MHz, $CDCl_3$) δ 7.92 (s, 1H), 7.75 (dd, J=5.2, 8.8 Hz, 1H), 7.44-7.36 (m, 2H), 7.33-7.26 (m, 1H), 7.12-7.06 (m, 1H).

Step C. 8-chloro-7-fluoronaphthalen-1-yl pivalate: A mixture of 8-chloro-7-fluoronaphthalen-1-ol (124 g, 1 equiv.) and DIEA (489 g, 6 equiv.), 4 Å molecular sieves (120 g) in dichloromethane (1.5 L) was stirred for 10 minutes at 20° C. Then PivCl (231 g, 1.3 equiv.) was added to the mixture dropwise at −40° C. The reaction mixture was stirred at −40° C. for 20 minutes. The reaction mixture was quenched with water (1 L) and the layers were separated. The aqueous layer was extracted with ethyl acetate (2×1 L). The combined organic layers were dried over $Na_2SO_4$ and concentrated under vacuum. The residue was purified by silica gel chromatography (petroleum ether/ethyl acetate 1:0 to 20:1) to afford the title compound (196 g, 92% yield) as a yellow solid; $^1$H NMR (400 MHz, chloroform-d) δ 7.86 (d, J=8.0 Hz, 1H), 7.83-7.76 (m, 1H), 7.57 (d, J=8.0 Hz, 1H), 7.53-7.44 (m, 1H), 7.43-7.35 (m, 1H).

Step D. 8-chloro-7-fluoro-3-(4,4,5,5-tetramethyl-1,3,2-dioxaborolan-2-yl)naphthalen-1-yl pivalate: A mixture of 8-chloro-7-fluoronaphthalen-1-yl pivalate (8.00 g, 1.0 equiv.), 4,4,4',4',5,5,5',5'-octamethyl-2,2'-bi(1,3,2-dioxaborolane) (7.24 g, 1.0 equiv.), (1,5-Cyclooctadiene) (methoxy)iridium(I) dimer (944 mg, 0.05 equiv.) and 4-tert-butyl-2-(4-tert-butyl-2-pyridyl)pyridine (918 mg, 0.12 equiv.) in n-hexane (220 mL) was degassed and stirred at 65° C. for 1 hour under $N_2$ atmosphere. The mixture was filtered, concentrated and purified by column chromatography [$SiO_2$, Petroleum ether/Ethyl acetate 10:1 to 3:1] to afford the title compound (18.8 g, crude) as a yellow solid.

Step E. 8-chloro-7-fluoro-3-hydroxy)naphthalen-1-yl pivalate: To a solution of 8-chloro-7-fluoro-3-(4,4,5,5-tetramethyl-1,3,2-dioxaborolan-2-yl)naphthalen-1-yl pivalate (50.0 g, 1.0 equiv.) and $H_2O_2$ (116 g, 98.3 mL, 30% purity, 8.3 equiv.) in THF (300 mL) was added AcOH (502 g, 478 mL, 68 equiv.) at 0° C. The solution was stirred at 20° C. for 2 hours. The reaction mixture was quenched by saturated sodium sulfite (500 mL), extracted with ethyl acetate (3×100 mL), washed with brine (200 mL), dried over $Na_2SO_4$, concentrated and purified by reversed phase flash chromatography (C 18, water (0.1% $NH_3·H_2O$)-ACN) to afford the title compound (5.4 g, 15% yield) as a gray solid; $^1$H NMR (400 MHz, DMSO-$d_6$) δ=10.25 (s, 1H), 7.86 (dd, J=5.6, 9.2 Hz, 1H), 7.51 (t, J=9.2 Hz, 1H), 7.22 (d, J=2.4 Hz, 1H), 6.87 (d, J=2.1 Hz, 1H), 1.36 (s, 9H).

Step F. 8-chloro-7-fluoro-3-(methoxymethoxy)naphthalen-1-yl pivalate: To a solution of 8-chloro-7-fluoro-3-hydroxy)naphthalen-1-yl pivalate (5.4 g, 1.0 equiv.) in DCM (55 mL) were added DIPEA (7.06 g, 9.51 mL, 3 equiv.) and chloro(methoxy)methane (2.72 g, 2.57 mL, 1.8 equiv.) dropwise at 0° C. The mixture was stirred at 0° C. for 1.5 hours. The solution was diluted with water (50 mL), extracted with ethyl acetate (2×50 mL), dried over $Na_2SO_4$, concentrated and purified by column chromatography [$SiO_2$, Petroleum ether/Ethyl acetate 20:1 to 5:1] to afford the title compound (6 g, 97% yield) as a yellow solid.

Step G. 8-chloro-7-fluoro-3-(methoxymethoxy)naphthalen-1-ol: To a solution of 8-chloro-7-fluoro-3-(methoxymethoxy)naphthalen-1-yl pivalate (8.00 g, 1.0 equiv.) in MeOH (120 mL) was added KOH (5.38 g, 4.0 equiv.) at 0° C. The mixture was stirred at 20° C. for 1 hour. The solution was diluted with water (40 mL), extracted with ethyl acetate (3×40 mL), washed with brine (100 mL), dried over $Na_2SO_4$, concentrated and purified by column chromatography [$SiO_2$, Petroleum ether/Ethyl acetate 10:1 to 5:1] to afford the title compound (5.6 g, 93% yield) as a yellow solid.

Step H. 8-chloro-7-fluoro-3-(methoxymethoxy)naphthalen-1-yl trifluoromethanesulfonate: To a solution of 8-chloro-7-fluoro-3-(methoxymethoxy)naphthalen-1-ol (5.00 g, 1.0 equiv.) in DCM (60 mL) were added DIEA (2.52 g, 3.39 mL, 1.0 equiv.) and trifluoromethanesulfonic anhydride (8.24 g, 4.82 mL, 1.5 equiv.) dropwise at −40° C. The mixture was stirred at −40° C. for 1.5 hours. The solution was diluted with water (40 mL), extracted with ethyl acetate (3×40 mL), washed with brine (100 mL), dried over Na$_2$SO$_4$, concentrated and purified by column chromatography [SiO$_2$, Petroleum ether/Ethyl acetate 50:1 to 10:1] to afford the title compound (6.9 g, 91% yield) as a yellow solid; $^1$H NMR (400 MHz, CHLOROFORM-d) δ=7.69 (dd, J=5.2, 9.2 Hz, 1H), 7.46 (d, J=2.0 Hz, 1H), 7.42-7.34 (m, 2H), 5.30 (s, 2H), 3.53 (s, 3H).

Step I. (8-chloro-7-fluoro-3-(methoxymethoxy)naphthalen-1-yl)trimethylstannane: To the mixture of [8-chloro-7-fluoro-3-(methoxymethoxy)-1-naphthyl]trifluoromethanesulfonate (2 g, I equiv.), trimethyl(trimethylstannyl)stannane (5.40 g, 3.2 equiv.), LiCl (654.37 mg, 3.0 equiv.) in toluene (80 mL) was added Pd(PPh$_3$)$_4$ (595 mg, 0.1 equiv.) under N$_2$. The mixture was stirred at 110° C. for 16 hours. The mixture was quenched with water (200 mL), extracted with ethyl acetate (100 mL×3), the combined organic phase was washed with brine (100 mL), dried over anhydrous sodium sulfate, filtered and concentrated to give a residue. The residue was purified by column chromatography (SiO$_2$, Petroleum ether/Ethyl acetate 1:0 to 10:1) to afford the title compound (2 g, 96.35% yield) as a colorless oil; $^1$H NMR (400 MHz, CDCl$_3$) δ=7.58-7.56 (m, 1H), 7.49-7.48 (m, 1H), 7.28-7.27 (d, J=2.4 Hz, 1H), 7.22-7.20 (m, 1H), 5.19 (s, 2H), 5.43 (s, 3H); 0.40-0.27 (m, 9H).

Step J. 7-(8-chloro-7-fluoro-3-(methoxymethoxy)naphthalen-1-yl)-8-fluoro-2-(((2R,7aS)-2-fluorotetrahydro-1H-pyrrolizin-7a(5H)-yl)methoxy)-4-(2,2,2-trifluoroethoxy) pyrido[4,3-d]pyrimidine: To a to a solution of 7-chloro-8-fluoro-2-(((2R,7aS)-2-fluorohexahydro-1H-pyrrolizin-7a-yl)methoxy)-4-(2,2,2-trifluoroethoxy)pyrido[4,3-d] pyrimidine (625 mg, 1 equiv.) and [8-chloro-7-fluoro-3-(methoxymethoxy)-1-naphthyl]-trimethyl-stannane (1.72 g, 3 equiv.) in toluene (25 mL) was added Pd(dppf)Cl$_2$ (104, 0.1 equiv.), BINAP (177 mg, 285 μmol, 0.2 equiv.) and CuI (81.4 mg, 0.3 equiv.), the mixture was de-gassed and heated to 90° C. for 4 hours under N$_2$. The resulting suspension was cooled to 20° C., filtered, the filtrate was concentrated under reduced pressure. The crude product was purified by reversed-phase HPLC (water (0.1% formic acid) to afford the title compound (776 mg, 1.21 mmol, 84.73% yield) as a yellow solid; $^1$H NMR (400 MHz, CDCl$_3$) δ=9.25 (s, 1H), 7.79-7.75 (dd, J=5.6 Hz, 9.2 Hz, 1H), 7.57-7.56 (d, J=1.6 Hz, 1H), 7.38-7.27 (m, 2H), 5.34-5.29 (m, 3H), 5.09-5.05 (m, 2H), 4.38-4.12 (m, 2H); 3.53 (s, 3H); 3.29-3.28 (m, 2H); 3.19-3.18 (m, 1H); 3.05-3.01 (m, 1H); 2.23-2.22 (m, 31H); 2.00-1.95 (m, 3H); LCMS (ESI, M−55): m/z=642.8.

Intermediate 42

7-(8-bromo-7-fluoro-3-((triisopropylsilyl)oxy)naphthalen-1-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine

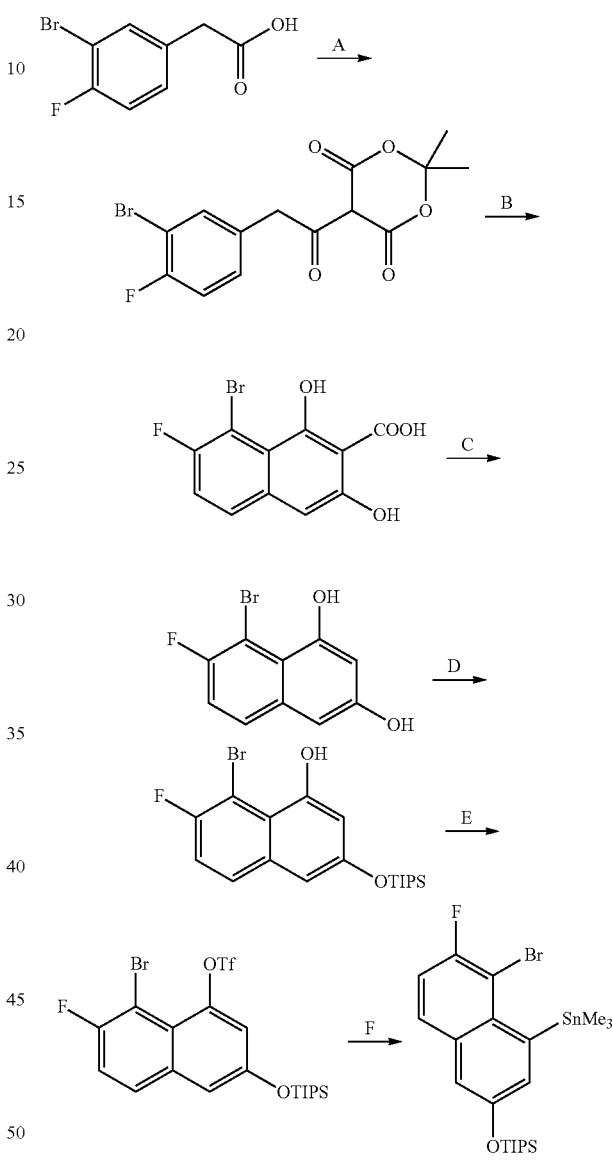

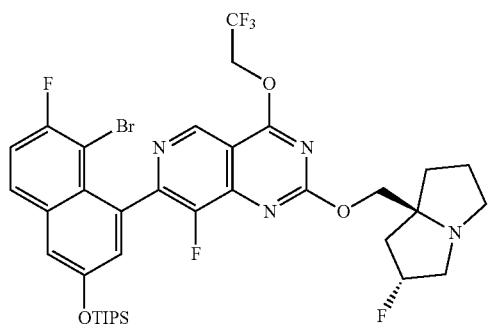

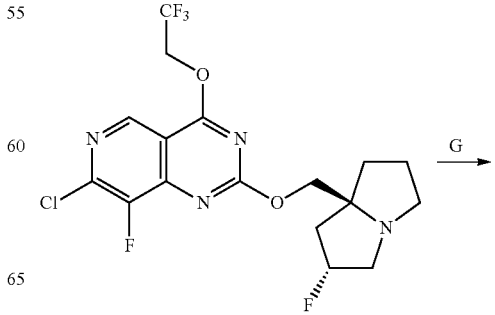

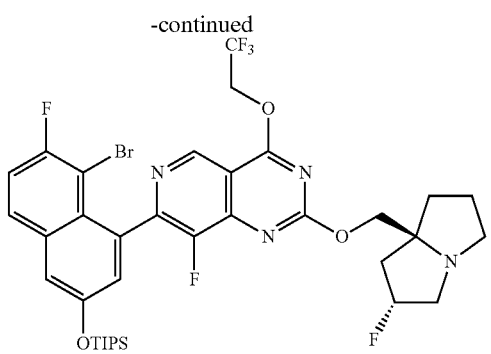

Step A. 5-(2-(3-brome-4-fluorophenyl)acetyl)-2,2-dimethyl-1,3-dioxane-4,6-ding To a mixture of 2-(3-bromo-4-fluoro-phenyl)acetic acid (330 g, 210 mL, 1.0 equiv.) and 2,2-dimethyl-1,3-dioxane-4,6-dione (225 g, 1.1 equiv.) in MeCN (1.65 L) was added DMAP (14.7 g, 0.085 equiv.) in one portion at 15° C. under $N_2$ atm. Then DIPEA (394 g, 530 mL, 2.15 equiv.) was carefully added to the reaction in four portions over a period of 1 hour while maintaining the temperature at 15~30° C. under to give a pale yellow suspension. Then pivaloyl chloride (188 g, 192 mL, 1.10 equiv.) was added slowly to the reaction mixture in five portions over a period of 1 hour maintaining 25° C.~40° C. After the addition was complete, a yellow suspension was obtained. The reaction mixture was heated at 45° C. for 3 hours under $N_2$ atm. The mixture was cooled to 0° C. and slowly diluted with 4 N HCl (2.0 L) to adjust pH to 6-7 while maintaining the temperature between 0-15° C. The mixture was stirred at 0° C. for 1 hour and then filtered. The filter cake was concentrated in vacuum to afford the title compound (450 g, 88% yield) as a white solid; LCMS (ESI, M−57, M−55): m/z=300.8.

Step B. 8-bromo-7-fluoro-1,3-dihydroxy-2-naphthoic acid: 5-[2-(3-bromo-4-fluoro-phenyl)acetyl]-2,2-dimethyl-1,3-dioxane-4,6-dione (600 g, 1.0 equiv.) was slowly added to $CF_3SO_3H$ (1.30 L) in four portions maintaining the temperature at 25° C.~50° C. for 1 hour with ice-water cooled bath. Then the mixture was stirred at 20° C. for 2 hours and water (10 L) was added slowly to the reaction mixture. The mixture was filtered. The filter cake was collected and concentrated to afford the title compound (1200 g, crude) as a yellow solid.

Step C. 8-bromo-7-fluoronaphthalene-1,3-diol: A solution of 8-bromo-7-fluoro-1,3-dihydroxy-naphthalene-2-carboxylic acid (1.3 kg, 1.0 equiv.) in water (700 mL) and ACN (700 mL) was stirred at 85° C. for 12 hours. The mixture was concentrated and the residue was diluted with water (1 L), extracted with ethyl acetate (2 L×2). The organic layer was dried over $Na_2SO_4$, concentrated in vacuum and the residue was purified by column chromatography (Silica gel, petroleum ether/ethyl acetate 3:1) and prep-HPLC (column: Phenomenex Luna C18 200×40 mm×10 um; mobile phase: [water (0.1% formic acid)-ACN]; B %: 27%-57%, 10 min). The desired fraction was collected and extracted with ethyl acetate (20 mL). The organic layer was dried over $Na_2SO_4$ and concentrated in vacuum to afford the title compound (55.0 g, 13% yield two steps) as a yellow solid.

Step D. 8-bromo-7-fluoro-3-((triisopropylsilyl)oxy)naphthalen-1-ol: To a solution of 8-bromo-7-fluoro-naphthalene-1,3-diol (10.0 g, 1.0 equiv.) and DIEA (15.1 g, 20.3 mL, 3 equiv.) in DCM (200 mL) was added TIPSCl (6.75 g, 7.49 mL, 0.90 equiv.) portion wise at 0° C. The mixture was stirred at 0° C. for 0.5 hr. The mixture was concentrated to give a residue and the residue was purified by column chromatography (Silica gel, ethyl acetate/petroleum ether 0:1 to 1:50) to afford the title compound (14.7 g, 91% yield) as a yellow oil.

Step E. 8-bromo-7-fluoro-3-((triisopropylsilyl)oxy)naphthalen-1-yl trifluoromethanesulfonate: To a solution of 8-bromo-7-fluoro-3-triisopropylsilyloxy-naphthalen-1-ol (14.7 g, 1.0 equiv.) and DIEA (13.8 g, 18.6 mL, 3.0 equiv.) in DCM (200 mL) was added $Tf_2O$ (12.0 g, 7.04 mL, 1.2 equiv.) at −40° C. The mixture was stirred at −40° C. for 0.5 hr. The mixture was quenched with water (200 mL) and the layers were separated. The organic layer was dried over $Na_2SO_4$ and concentrated. The residue was purified by column chromatography (Silica gel, petroleum ether/ethyl acetate 100:1 to 30:1) to afford the title compound (15 g, 77% yield) as a yellow oil; LCMS (ESI, M+1): m/z=547.0.

Step F. ((5-bromo-6-fluoro-4-(trimethylstannyl)naphthalen-2-yl)oxy)triisopropylsilane: To a mixture of (8-bromo-7-fluoro-3-triisopropylsilyloxy-1-naphthyl) trifluoromethanesulfonate (5 g, 9.17 mmol, 1 equiv.), trimethyl(trimethylstannyl)stannane (9.41 g, 5.96 mL, 3.13 equiv.) and $Pd(PPh_3)_2Cl_2$ (643 mg, 0.1 equiv.) in toluene (50 mL) was added LiCl (1.17 g, 563 µL, 3.0 equiv.) under $N_2$. The mixture was stirred at 100° C. for 12 hours under $N_2$. The mixture was quenched with water (100 mL) and extracted with ethyl acetate (100 mL×3), the combined organic phase was washed with brine 100 mL, dried over anhydrous sodium sulfate, filtered and concentrated to give a residue. The residue was purified by column chromatography (Silica gel, petroleum ether) to afford the title compound (3 g, 58% yield) as a yellow oil; $^1$H NMR (400 MHz, $CDCl_3$) δ 7.65 (dd, J=6.0, 9.2 Hz, 1H), 7.54 (d, J=2.4 Hz, 1H), 7.28-7.23 (m, 1H), 7.20 (d, J=2.4 Hz, 1H), 1.36-1.29 (m, 3H), 1.15 (d, J=7.2 Hz, 18H), 0.56-0.39 (m, 9H).

Step G. 7-(8-bromo-7-fluoro-3-((triisopropylsilyl)oxy)naphthalen-1-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine: To a solution of 7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (650 mg, 1.0 equiv.) and ((5-bromo-6-fluoro-4-(trimethylstannyl)naphthalen-2-yl)oxy)triisopropylsilane (1.24 g, 1.5 equiv.) in toluene (10 mL) was added BINAP (184 mg, 0.2 equiv.) and CuI (84.6 mg, 0.3 equiv.) at 25° C. The suspension was thoroughly degassed and $Pd(dppf)Cl_2$ (108 mg, 0.1 equiv.) was added. The suspension was degassed and stirred at 100° C. and for 6 hours. The mixture was filtered and the residue was washed by ethyl acetate (50 mL×3). The filtrate was concentrated in vacuum and the residue was purified by prep-HPLC (column: Welch Xtimate C18 250*50 mm*10 um; mobile phase: [water (0.1% formic acid)-ACN]; B %: 27%-57%, 20 min) to afford the title compound (1.4 g, 36% yield) as a yellow solid; LCMS (ESI, M+1, M+3): m/z=799.2, 801.2.

Intermediate 43

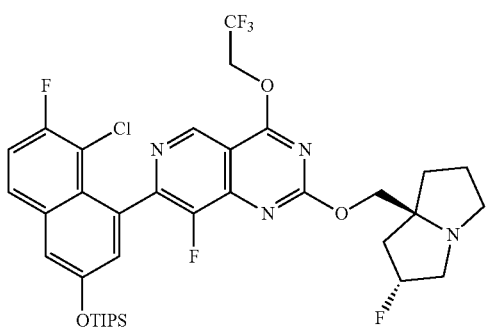

7-(8-chloro-7-fluoro-3-((triisopropylsilyl)oxy)naphthalen-1-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine The title compounds was synthesized from 2-(3-chloro-4-fluoro-phenyl)acetic acid according to the procedure described for Intermediate 42. LCMS [ESI, M+1]: m/z=755.1.

Intermediate 44

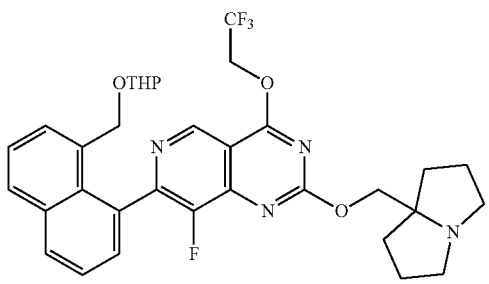

8-fluoro-2-((hexahydro-1H-pyrrolizin-7a-yl)methoxy)-7-(8-((((tetrahydro-2H-pyran-2-yl)oxy)methyl)naphthalen-1-yl)-4-(2,2,2-trifluoroethoxy)pyrido[4,3-d]pyrimidine

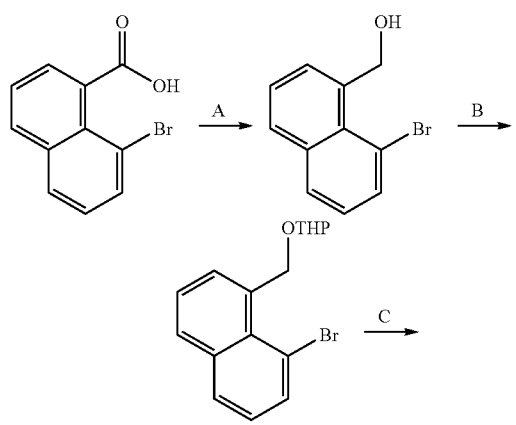

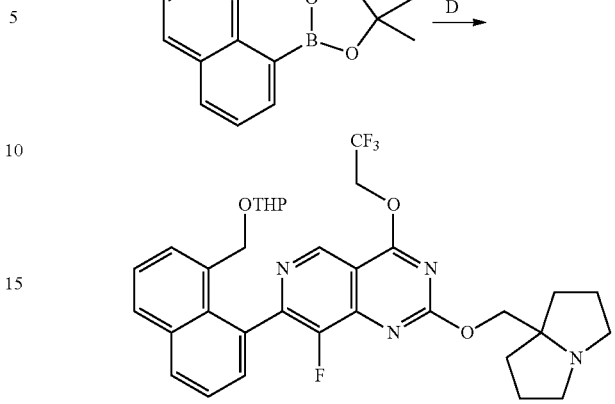

Step A. (8-bromonaphthalen-1-yl)methanol: To a solution of 8-bromonaphthalene-1-carboxylic acid (5 g, 1.0 equiv.) in 2-MeTHF (70 mL) was slowly added $BH_3 \cdot Me_2S$ (10 M, 3.0 equiv.) at 0° C. under $N_2$. The reaction was stirred at 70° C. for 12 hours. The mixture was quenched with methanol (20 mL) at 0° C. and washed with 1 M HCl (30 mL). The mixture was diluted with water (50 ml) and extracted with ethyl acetate (2×50 mL). The combined organic layers were washed with brine (60 mL), dried over anhydrous sodium sulfate, concentrated to give a residue. The residue was purified by column chromatography (Silica gel, Petroleum ether/Ethyl acetate 1:0 to 0:1 to methanol) to afford the title compound (5.4 g, 70% yield) as a white solid; $^1$H NMR (400 MHz, DMSO-$d_6$) δ 7.98 (dd, J=0.8, 8.0 Hz, 1H) 7.84-7.95 (m, 3H) 7.56 (t, J=7.6 Hz, 1H) 7.35 (t, J=7.6 Hz, 1H) 5.39-5.48 (m, 2H) 5.32-5.39 (m, 1H).

Step B. 2-((8-bromonaphthalen-1-yl)methoxy)tetrahydro-2H-pyran: To a solution of 3,4-dihydropyran (1.22 g, 1.0 equiv.), 8-bromonaphthalen-1-yl)methanol (3.44 g, 1.0 equiv.) and 4-methylbenzenesulfonic acid (514 mg, 0.1 equiv.) in DCM (40 mL) was stirred at 25° C. for 5 hours. The reaction mixture was concentrated on vacuum. The residue was purified by column chromatography (Silica gel, Petroleum ether/Ethyl acetate 1:0 to 50:1) to afford the title compound (4.8 g, 43% yield) as a light yellow oil. $^1$H NMR (400 MHz, chloroform-d) δ=7.76-7.94 (m, 4H) 7.48 (t, J=7.70 Hz, 1H) 7.27 (s, 1H) 5.58 (s, 2H) 4.88 (t, J=3.36 Hz, 1H) 3.93-4.02 (m, 1H) 3.56-3.64 (m, 1H) 1.73-1.98 (m, 3H) 1.64-1.69 (m, 1H) 1.61-1.56 (m, 2H)

Step C. 4,4,5,5-tetramethyl-2-(8-(((tetrahydro-2H-pyran-2-yl)oxy)methyl)naphthalen-yl)-1,3,2-dioxaborolane: A mixture of 2-((8-bromonaphthalen-1-yl)methoxy)tetrahydro-2H-pyran (300 mg, 1.0 equiv., 4,4,5,5-tetramethyl-2-(4,4,5,5-tetramethyl-1,3,2-dioxaborolan-2-yl)-1,3,2-dioxaborolane (356 mg, 1.5 equiv.), KOAc (27.5 mg, 0.3 equiv.) and Pd(dppf)Cl$_2$ (68.3 mg, 0.1 equiv.) in dioxane (1.5 mL) was degassed and stirred at 80° C. for 2 hrs under $N_2$ atmosphere. The combined reaction mixture was diluted with ethyl acetate (10 mL) and water (20 mL), the aqueous layer was extracted with ethyl acetate (10 mL), the combined organic phase was washed with brine (15 mL), dried over anhydrous sodium sulfate, filtered and concentrated in vacuum. The residue was purified by column chromatography (Silica gel, Petroleum ether/Ethyl acetate 100:1 to 15:1) to afford the title compound (290 mg, 85% yield) as a white solid; $^1$H NMR (400 MHz, CDCl3) δ (ppm)=7.93-7.88 (m, 1H), 7.82-7.74 (m, 2H), 7.56 (d, J=7.2 Hz, 1H), 7.48-7.39 (m, 2H), 5.74 (d, J=13.2 Hz, 1H), 5.04-4.94 (m, 1H), 4.41-4.35 (m, 1H), 3.91-3.80 (m, 1H), 3.49-3.41 (m, 1H), 1.68-1.40 (m, 18H).

Step D. 8-fluoro-2-((hexahydro-1H-pyrrolizin-7a-yl)methoxy)-7-(8-(((tetrahydro-2H-pyran-2-yl)oxy)methyl)naphthalen-1-yl)-4-(2,2,2-trifluoroethoxy)pyrido[4,3-d]pyrimidine: A mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (350 mg, 1.0 equiv.), 4,4,5,5-tetramethyl-2-(8-(((tetrahydro-2H-pyran-2-yl)oxy)methyl)naphthalen-1-yl)-1,3,2-dioxaborolane (368 mg, 1.2 equiv.), CataCXium A Pd G3 (60.6 mg, 0.1 equiv.) and Cs₂CO₃ (1.5 M in water, 3.0 equiv.) in methoxycyclopentane (8 mL) was degassed and stirred at 100° C. for 2 hours under N₂ atmosphere. The reaction mixture was diluted with ethyl acetate (50 mL) and water (60 mL), extracted with ethyl acetate (30 mL), the combined organic phase was washed with brine (40 mL), dried over anhydrous sodium sulfate, filtered and concentrated in vacuum. The residue was purified by reversed phase flash chromatography [C18, water (0.1% formic acid)-ACN] to afford the title compound (234 g, 16% yield) as a yellow solid; ¹H NMR (400 MHz, chloroform-d) δ ppm=9.22 (s, 1H) 8.02 (d, J=7.95 Hz, 1H) 7.93 (d, J=7.95 Hz, 1H) 7.45-7.62 (m, 4H) 5.00-5.18 (m, 2H) 4.24-4.61 (m, 4H) 4.09-4.20 (m, 2H) 3.13-3.41 (m, 3H) 2.62-2.85 (m, 2H) 2.07-2.21 (m, 2H) 1.85-2.02 (m, 5H) 1.67-1.82 (m, 4H) 1.19-1.33 (m, 3H); LCMS (ESI, M+1): m/z=627.2.

Intermediate 45

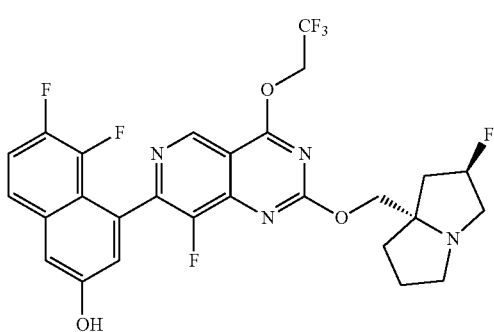

5,6-difluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol

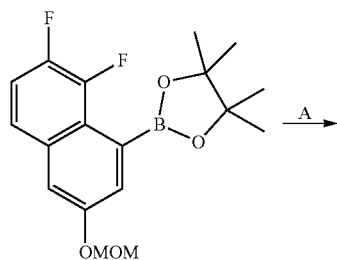

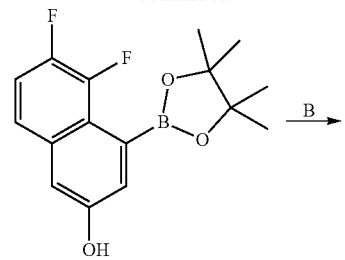

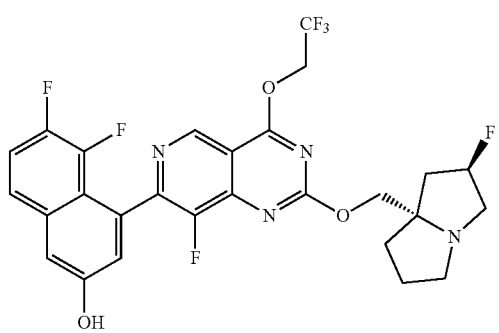 [SMILES: Oc1cc(-c2ncc3c(OCC(F)(F)F)nc(OC[C@@]45CCCN4C[C@H](F)C5)nc3c2F)c2c(F)c(F)ccc2c1]

Step A. 5,6-difluoro-4-(4,4,5,5-tetramethyl-1,3,2-dioxaborolan-2-yl)naphthalen-2-ol: To a solution of 2-[7,8-difluoro-3-(methoxymethoxy)-1-naphthyl]-4,4,5,5-tetramethyl-1,3,2-dioxaborolane (500 mg, 1.0 equiv.) in ACN (15 mL) was added HCl.dioxane (4 M, 7.50 mL, 21.0 equiv.) at 0° C. The mixture was stirred at 0° C. for 0.5 hour. The mixture was diluted with saturated aqueous NaHCO₃ (15 mL) and extracted with ethyl acetate (3×10 mL). The combined organic layers were dried over anhydrous Na₂SO₄, concentrated and purified by reversed phase flash chromatography [C18, water (0.1% formic acid)/ACN] to afford the title compound (340 mg, 74% yield) as a red solid; LCMS (ESI, M+1): m/z=307.4.

Step B. 5,6-difluoro-4-(8-fluoro-2-(((2R,7aS)-2-fluorohexahydro-1H-pyrrolizin-7a-yl)methoxy)-4-(2,2,2-trifluoroethoxy)pyrido[4,3-d]pyrimidin-7-yl)naphthalen-2-ol: To a mixture of 7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (306 mg, 1.0 equiv.) and 5,6-difluoro-4-(4,4,5,5-tetramethyl-1,3,2-dioxaborolan-2-yl)naphthalen-2-ol (320 mg, 1.50 equiv.) in water (1.4 mL) and methoxycyclopentane (4.0 mL) were added cataCXium A Pd G3 (50.7 mg, 0.1 equiv.) and Cs₂CO₃ (1.5 M, 1.39 mL, 3.0 equiv.) under N₂. The mixture was stirred at 60° C. for 1 hour. The reaction mixture was diluted with water (5.0 mL), the aqueous phase was extracted with ethyl acetate (3×10 mL). The combined organic phase was washed with brine (15 mL), dried with anhydrous Na₂SO₄, concentrated and purified by reversed phase flash chromatography (C18, water (0.1% formic acid)-ACN) to afford the title compound (270 mg, 60% yield) as a yellow solid; LCMS (ESI, M+1): m/z=583.2

Intermediate 46

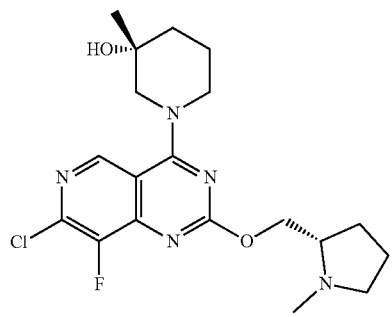 [SMILES: CN1CCC[C@H]1COc1nc(N2CCC[C@@](C)(O)C2)c2cnc(Cl)c(F)c2n1]

(R)-1-(7-chloro-8-fluoro-2-(((S)-1-methylpyrrolidin-2-yl)methoxy)pyrido[4,3-d]pyrimidin-4-yl)-3-methylpiperidin-3-ol

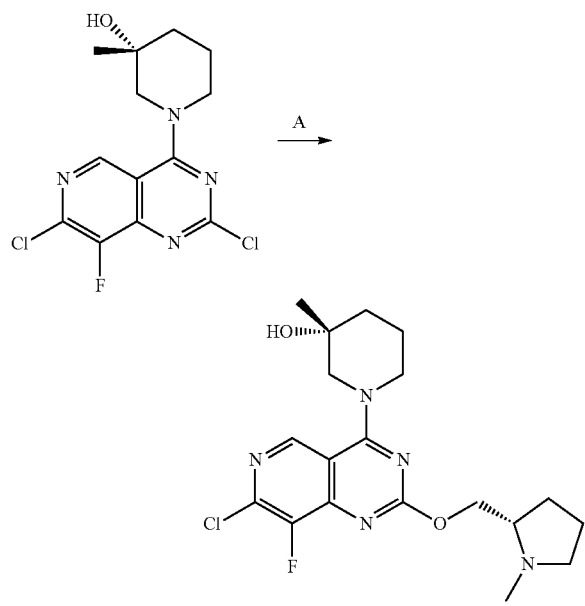

Step A. (R)-1-(7-chloro-8-fluoro-2-(((S)-1-methylpyrrolidin-2-yl)methoxy)pyrido[4,3-d]pyrimidin-4-yl)-3-methylpiperidin-3-ol: To a mixture of (R)-1-(2,7-dichloro-8-fluoropyrido[4,3-d]pyrimidin-4-yl)-3-methylpiperidin-3-ol (2.20 g, 1.0 equiv.) and 4 Å molecular sieves (500 mg) in dioxane (15 mL) was added DIEA (2.58 g, 3.0 equiv.) and [(2S)-1-methylpyrrolidin-2-yl]methanol (1.53 g, 2.0 equiv.). The mixture was stirred at 95° C. for 20 hours. The reaction mixture was filtered and concentrated under reduced pressure to remove dioxane. The residue was diluted with H$_2$O (20 mL) and extracted with EtOAc (3×20 mL). The combined organic layers were dried over anhydrous sodium sulfate, concentrated and purified by reversed phase flash chromatography [C18, water (0.1% formic acid)-ACN] to afford the title compound (1.80 g, 66% yield) as a yellow solid; LCMS (ESI, M+1): m/z=410.2.

Intermediate 47

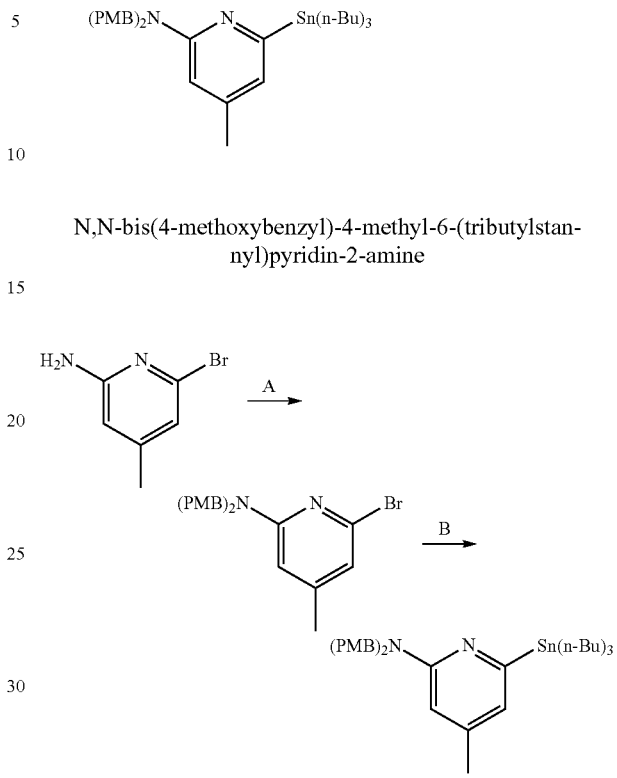

N,N-bis(4-methoxybenzyl)-4-methyl-6-(tributylstannyl)pyridin-2-amine

Step A. 6-bromo-N,N-bis(4-methoxybenzyl)-4-methylpyridin-2-amine: To a solution of 6-bromo-4-methyl-pyridin-2-amine (180 g, 1.0 equiv.) in DMAC (1.8 L) was added NaH (115 g, 60% purity, 3.0 equiv.) at 0° C. under nitrogen atmosphere. The mixture was stirred at 25° C. for 1 hour under nitrogen atmosphere. Then 1-(chloromethyl)-4-methoxy-benzene (331 g, 2.2 equiv.) was added to the reaction mixture at 25° C. The mixture was stirred at 25° C. for 2 hours. After reaction completion, the mixture was quenched with ammonium chloride solution (3 L) at 0° C. and diluted with ethyl acetate (4 L). The layers were separated. The organic layer was washed with brine (3×2 L), dried with Na$_2$SO$_4$ then concentrated in vacuum. The residue was triturated with petroleum ether (1 L) at 25° C. for 30 mins to afford the title compound (320 g, 77% yield) as a white solid; $^1$H NMR (400 MHz, CDCl$_3$-d) δ=7.16 (d, J=8.8 Hz, 4H), 6.85 (d, J=8.8 Hz, 4H), 6.60 (s, 1H), 6.17 (s, 1H), 4.64 (s, 4H), 3.80 (s, 6H), 2.13 (s, 3H); LCMS (ESI, M+1, M+3): m/z=427.1, 429.1.

Step B. N,N-bis(4-methoxybenzyl)-4-methyl-6-(tributylstannyl)pyridin-2-amine: A mixture of 6-bromo-N,N-bis[(4-methoxyphenyl)methyl]-4-methyl-pyridin-2-amine (200 g, 1.0 equiv.), tributyl(tributylstannyl)stannane (651 g, 2.4 equiv.), Pd$_2$(dba)$_3$ (42.9 g, 0.1 equiv.), PCy$_3$ (26.2 g, 0.2 equiv.) and LiCl (99.2 g, 5.0 equiv.) in dioxane (1.8 L) was degassed and stirred at 110° C. for 5 hours under N$_2$ atmosphere. After reaction completion, the mixture was concentrated in vacuum. The residue was purified by column chromatography (SiO$_2$, petroleum ether/ethyl acetate 1:0 to 10:1) followed by reversed phase flash chromatography (neutral condition) to afford the title compound (190 g, 62% yield) as a yellow oil. $^1$H NMR (400 MHz, CDCl$_3$-d) δ=7.19

(d, J=8.8 Hz, 4H), 6.87-6.82 (m, 4H), 6.62-6.55 (m, 1H), 6.15 (s, 1H), 4.70 (s, 4H), 3.80 (s, 6H), 2.15 (s, 3H), 1.63-1.51 (m, 6H), 1.32 (qd, J=7.2, 14.7 Hz, 7H), 1.09-1.01 (m, 5H), 0.90-0.84 (m, 9H). LCMS (ESI, M+1): m/z=639.3.

Intermediate 48

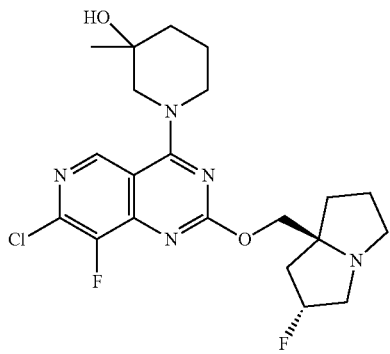 [SMILES: CC1(O)CCCN(c2nc(OC[C@@]34CCCN3C[C@H](F)C4)nc3c(F)c(Cl)ncc23)C1]

1-(7-chloro-8-fluoro-2-(((2R,7aS)-2-fluorohexa-hydro-1H-pyrrolizin-7a-yl)methoxy)pyrido[4,3-d]pyrimidin-4-yl)-3-methylpiperidin-3-ol

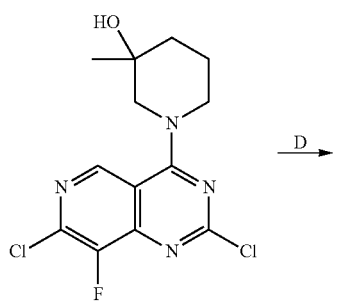

Step D. 1-(7-chloro-8-fluoro-2-(((2R,7aS)-2-fluorohexa-hydro-1H-pyrrolizin-7a-yl)methoxy)pyrido[4,3-d]pyrimidin-4-yl)-3-methylpiperidin-3-ol: A mixture of 1-(2,7-di-chloro-8-fluoropyrido[4,3-d]pyrimidin-4-yl)-3-methylpiperidin-3-ol (2.22 g, 1.0 equiv.), ((2R,7aS)-2-fluorohexahydro-1H-pyrrolizin-7a-yl)methanol (1.60 g, 1.5 equiv.), 4 Å molecular sieves (1.00 g) and DIEA (2.60 g, 3.0 equiv.) in dioxane (30.0 mL) was stirred at 90° C. for 15 hours. The mixture was diluted with water (20 mL) and extracted with ethyl acetate (2×20 mL). The combined organic layers were washed with brine (30 mL), dried over anhydrous sodium sulfate, filtered and concentrated in vacuum. The crude product was purified by reversed phase flash chromatography (water (0.1% formic acid)-ACN) to afford the tittle compound (1.90 g, 62% yield) as a yellow solid; LCMS (ESI, M+1): m/z=454.1.

Intermediate 49

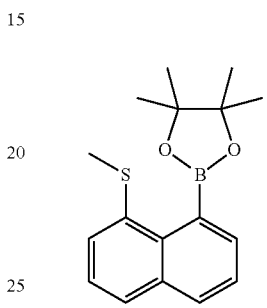

4,4,5,5-tetramethyl-2-(8-(methylthio)naphthalen-1-yl)-1,3,2-dioxaborolane

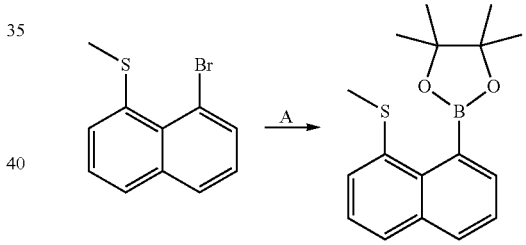

Step A. 4,4,5,5-tetramethyl-2-(8-(methylthio)naphthalen-1-yl)-1,3,2-dioxaborolane: To a solution of 1-bromo-8-methylsulfanyl-naphthalene (1.00 g, 1.0 equiv.) and 4,4,5,5-tetramethyl-1,3,2-dioxaborolane (2.53 g, 5.0 equiv.) in ACN (20 mL) were added TEA (1.20 g, 3.0 equiv.) and Pd(dppf)Cl$_2$ (433 mg, 0.15 equiv.). The mixture was stirred at 80° C. for 5 hours under N$_2$ atmosphere. The mixture was filtered, the filtrate was diluted with water (10 mL) and extracted with ethyl acetate (3×10 mL). The combined organic layers were dried over anhydrous Na$_2$SO$_4$, concentrated and purified by column chromatography [Silica gel, Petroleum ether/Ethyl acetate 1:0 to 30:1] to afford the tittle compound (1.00 g, 84% yield, 99% purity) as a yellow oil; $^1$H NMR (400 MHz, CHLOROFORM-d) δ=7.85 (dd, J=1.2, 8.4 Hz, 1H), 7.81 (d, J=7.6 Hz, 2H), 7.64 (dd, J=1.2, 6.8 Hz, 1H), 7.52-7.48 (m, 1H), 7.45-7.41 (t, J=8.0 Hz, 1H), 2.42 (s, 3H), 1.46 (s, 12H)

Intermediate 50

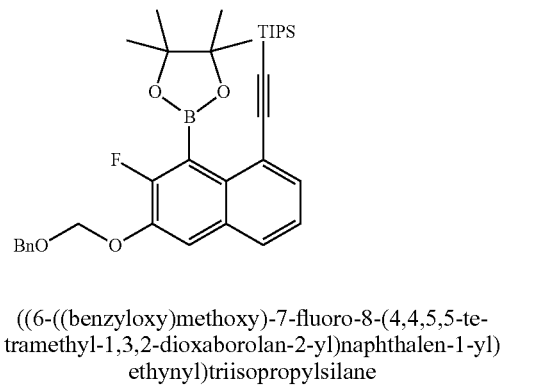

((6-((benzyloxy)methoxy)-7-fluoro-8-(4,4,5,5-tetramethyl-1,3,2-dioxaborolan-2-yl)naphthalen-1-yl)ethynyl)triisopropylsilane

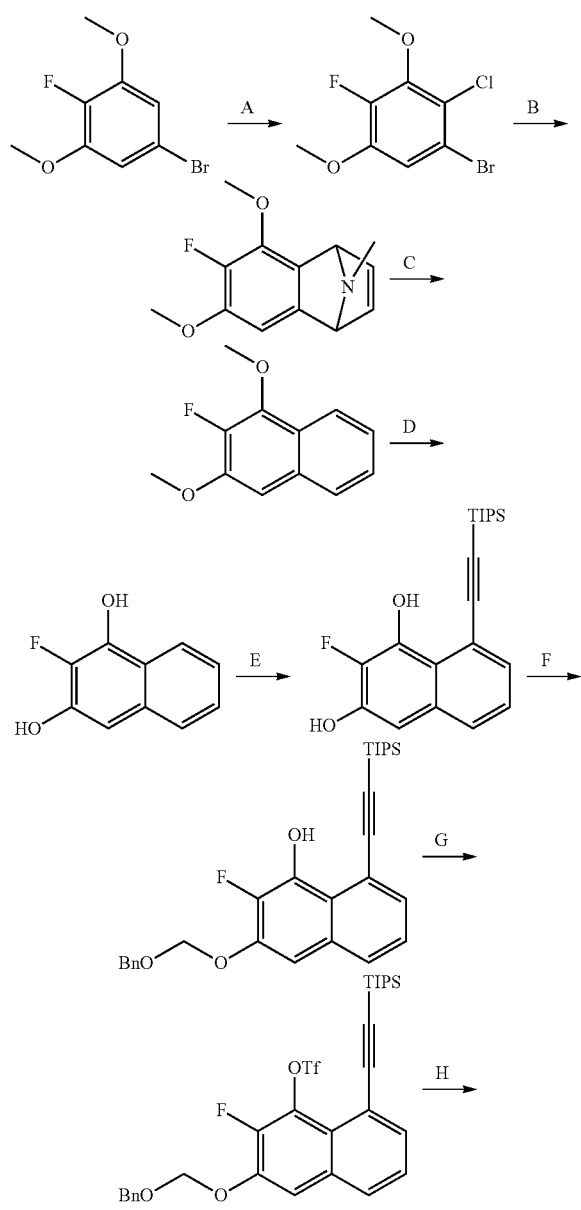

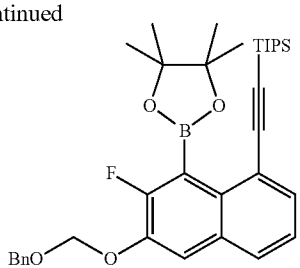

Step A. 1-bromo-2-chloro-4-fluoro-3,5-dimethoxybenzene: To a solution of 5-bromo-2-fluoro-1,3-dimethoxybenzene (50.0 g, 1.0 equiv.) and TMSCl (2.31 g, 0.1 equiv.) in MeCN (500 mL) was added NCS (34.1 g, 1.2 equiv.) at 10° C. The reaction mixture was stirred at 10° C. for 2 hours. The mixture was quenched with saturated brine (500 mL) at 0° C. and extracted with ethyl acetate (3×100 mL). The combined organic layers were dried over anhydrous sodium sulfate and filtered. The filtrate was concentrated under reduced pressure. The crude product was purified by reversed-phase flash chromatography (water (0.1% formic acid)-ACN) to afford the tittle compound (85 g, 74% yield) as a yellow solid; $^1$H NMR (400 MHz, CDCl$_3$) δ 7.05-6.95 (m, 1H), 3.98 (d, J=1.2 Hz, 3H), 3.89 (s, 3H).

Step B. 6-fluoro-5,7-dimethoxy-9-methyl-1,4-dihydro-1,4-epiminonaphthalene: To a mixture of 1-bromo-2-chloro-4-fluoro-3,5-dimethoxybenzene (20.0 g, 1.0 equiv.) and 1-methylpyrrole (12.0 g, 2.0 equiv.) in THF (240 mL) was added n-BuLi (2.5 M, 32.65 mL, 1.1 equiv.) at −65° C. The reaction was stirred at −65° C. for 1 hour and then at 25° C. for 16 hours. The mixture was quenched with saturated aqueous NH$_4$Cl solution (200 mL) and extracted with EtOAc (2×80 mL). The combined organic layers were concentrated under reduced pressure. The crude product was purified by reversed-phase flash chromatography (water (0.1% formic acid)-ACN) to afford the tittle compound (7.8 g, 44% yield) as a yellow oil. LCMS (ESI, M+1): m/z=236.

Step C. 2-fluoro-1,3-dimethoxy)naphthalene: To a solution of 6-fluoro-5,7-dimethoxy-9-methyl-1,4-dihydro-1,4-epiminonaphthalene (5.00 g, 1.0 equiv.) in DCM (60.0 mL) was added m-CPBA (5.18 g, 85% purity, 1.2 equiv.) at 0-5° C. The mixture was stirred at 15° C. for 1 hr. The mixture was quenched with saturated aqueous Na$_2$SO$_3$ solution (100 mL). The organic layer was separated and concentrated under reduced pressure. The residue was purified by column chromatography (SiO$_2$, petroleum ether/ethyl acetate 1:0 to 20:1) to afford the tittle compound (2.4 g, 54% yield) as a light yellow oil.

Step D. 2-fluoronaphthalene-1,3-diol: To a solution of 2-fluoro-1,3-dimethoxy)naphthalene (15.4 g, 1.0 equiv.) in DCM (250 mL) was added BBr$_3$ (39.3 g, 2.1 equiv.) at −30° C. The mixture was stirred at −30° C. for 30 minutes. The mixture was quenched with MeOH (2.0 mL) and concentrated under reduced pressure. The residue was purified by column chromatography (SiO$_2$, petroleum ether/ethyl acetate 50:1 to 10:1) to afford the tittle compound (7.6 g, 57% yield) as a yellow solid. $^1$H NMR (400 MHz, CDCl$_3$) δ 8.09 (d, J=8.4 Hz, 1H), 7.65 (d, J=8.0 Hz, 1H), 7.47-7.35 (m, 2H), 6.96 (d, J=8.4 Hz, 1H), 5.50 (br s, 1H), 5.21 (br s, 1H); LCMS (ESI, M+1): m/z=179.

Step E. 2-fluoro-8-((triisopropylsilyl)ethynyl)naphthalene-1,3-diol: To a solution of 2-fluoronaphthalene-1,3-diol (7.6 g, 1.0 equiv.) and 2-bromoethynyl(triisopropyl)silane (13.4 g, 1.2 equiv.) in 1,4-dioxane (150 mL) were added dichloro(p-cymene)ruthenium(II) dimer (2.61 g, 0.1 equiv.)

and AcOK (8.37 g, 2.0 equiv.). The reaction was stirred at 110° C. for 3 hours under N₂ atmosphere. The mixture was poured into H₂O (200 mL) and extracted with EtOAc (3×60 mL). The combined organic layers were concentrated under reduced pressure. The crude product was purified by reversed-phase flash chromatography (water (0.1% formic acid)-ACN) to afford the tittle compound (3.5 g, 22% yield) as a gray solid; ¹H NMR (400 MHz, CDCl₃) δ 7.65 (dd, J=0.8, 8.4 Hz, 1H), 7.52 (d, J=7.2 Hz, 1H), 7.27 (s, 2H), 6.94 (d, J=8.0 Hz, 1H), 1.24-1.17 (m, 21H); LCMS (ESI, M+1): m/z=359.

Step F. 3-((benzyloxymethoxy)-2-fluoro-8-((triisopropylsilyl)ethynyl)naphthalen-1-ol: To a solution of 2-fluoro-8-((triisopropylsilyl)ethynyl)naphthalene-1,3-diol (2.8 g, 1.0 equiv.) and DIEA (1.51 g, 1.5 equiv.) in DCM (24.0 mL) was added ((chloromethoxy)methyl)benzene (1.22 g, 1.0 equiv.) at −40° C. The reaction was stirred at 0-10° C. for 5 hours. The mixture was concentrated under reduced pressure. The residue was purified by column chromatography (SiO₂, petroleum ether/ethyl acetate 100:1 to 20:1) to afford the tittle compound (3.2 g, 77% yield) as a yellow solid; ¹H NMR (400 MHz, CDCl₃) 9.19 (s, 1H), 7.68 (dd, J=0.8, 8.4 Hz, 1H), 7.55 (d, J=7.2 Hz, 1H), 7.38-7.30 (m, 6H), 7.17 (d, J=7.6 Hz, 1H), 5.47 (s, 2H), 4.80 (s, 2H), 1.24-1.12 (m, 21H); LCMS (ESI, M+1): m/z=479.

Step G. 3-((benzyloxy)methoxy)-2-fluoro-8-((triisopropylsilyl)ethynyl)naphthalen-1-yl trifluoromethanesulfonate: To a solution of 3-((benzyloxy)methoxy)-2-fluoro-8-((triisopropylsilyl)ethynyl)naphthalen-1-ol (550 mg, 1.0 equiv.) and DIEA (297 mg, 2.0 equiv.) in DCM (3.0 mL) was added Tf₂O (486 mg, 1.5 equiv.) at −40° C. The reaction was stirred at −40° C. for 0.5 hour. The mixture was quenched with water (10 mL). The organic layer was separated and dried over anhydrous Na₂SO₄, and then filtered and concentrated under reduced pressure. The residue was purified by column chromatography (SiO₂, petroleum ether/ethyl acetate 100:1 to 20:1) to afford the tittle compound (650 mg, 92% yield) as a yellow solid; ¹H NMR (400 MHz, CDCl₃) δ 7.71 (d, J=7.2 Hz, 1H), 7.62 (d, J=8.0 Hz, 1H), 7.54 (d, J=7.6 Hz, 1H), 7.37-7.33 (m, 1H), 7.30-7.23 (m, 5H), 5.44-5.38 (m, 2H), 4.76-4.68 (m, 2H), 1.19-1.13 (m, 3H), 1.12-1.03 (m, 18H).

Step H. ((6-((benzyloxy)methoxy)-7-fluoro-8-(4,4,5,5-tetramethyl-1,3,2-dioxaborolan-2-yl)naphthalen-1-yl)ethynyl)triisopropylsilane: To a solution of 3-((benzyloxy)methoxy)-2-fluoro-8-((triisopropylsilyl)ethynyl)naphthalen-1-yl trifluoromethanesulfonate (50.0 mg, 1.0 equiv.) and TEA (24.8 mg, 3.0 equiv.) in 1,4-dioxane (1.0 mL) were added Pd(dppf)Cl₂ (5.99 mg, 0.1 equiv.) and 4,4,5,5-tetramethyl-1,3,2-dioxaborolane (31.4 mg, 3.0 equiv.). The reaction mixture was stirred under N₂ at 100° C. for 2 hours. The mixture poured into water (10 mL) and extracted with EtOAc (3×5 mL). The combined organic layers were concentrated under reduced pressure. The residue was purified by column chromatography (SiO₂, petroleum ether/ethyl acetate 100:1 to 50:1) to afford the tittle compound (32 mg, 66% yield) as a yellow oil; ¹H NMR (400 MHz, CHLOROFORM-d) δ=7.66 (d, J=7.1 Hz, 1H), 7.63-7.55 (m, 2H), 7.51-7.47 (m, 1H), 7.29-7.27 (m, 5H), 5.40-5.37 (m, 2H), 4.73-4.69 (m, 2H), 1.42 (s, 12H), 1.11-1.06 (m, 21H).

Intermediate 52

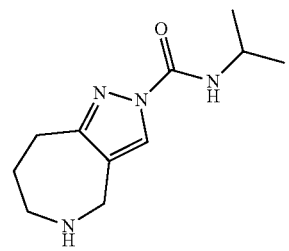 [SMILES: CC(C)NC(=O)n1cc2c(n1)CCCNC2]

N-isopropyl-5,6,7,8-tetrahydropyrazolo[4,3-c]azepine-2 (4H)-carboxamide

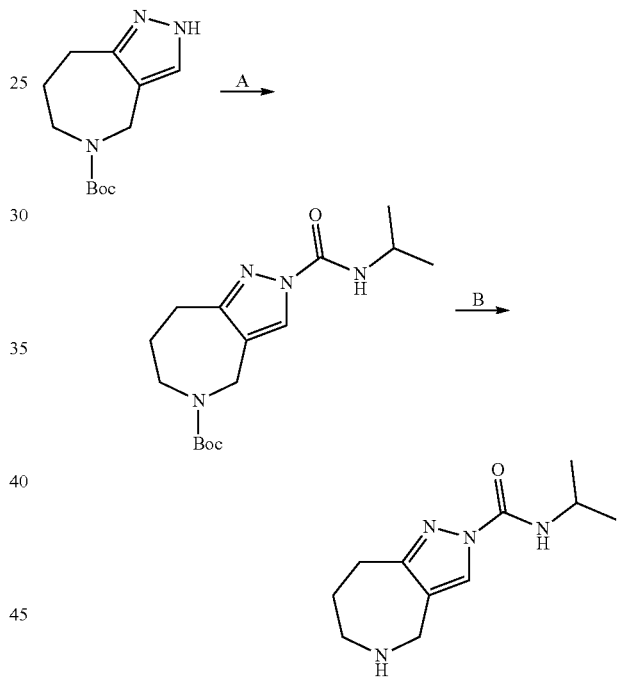

Step A. tert-butyl 2-(isopropylcarbamoyl)-4,6,7,8-tetrahydropyrazolo[4,3-c]azepine-5-carboxylate: To a solution of tert-butyl 4,6,7,8-tetrahydro-2H-pyrazolo[4,3-c]azepine-5-carboxylate (4.0 g, 1.0 equiv.) in THF (20 mL) was added portion wise CDI (2.73 g, 1 equiv.) and isopropylamine (1.1 g, 1.1 equiv.) at 25° C. The reaction was stirred at 25° C. for 1 hour. The mixture was concentrated and purified by column chromatography (SiO₂, petroleum ether/ethyl acetate 3:1 to 0:1) to afford the title compound (4.5 g, 82% yield) as a white solid; LCMS (ESI, M+1): m/z=323.2.

Step B. N-isopropyl-5,6,7,8-tetrahydro-4H-pyrazolo[4,3-c]azepine-2-carboxamide: A solution of tert-butyl 2-(isopropylcarbamoyl)-4,6,7,8-tetrahydropyrazolo[4,3-c]azepine-5-carboxylate (6.0 g, 1 equiv.) in HCl-MeOH (30 mL) was stirred at 25° C. for 0.5 hour. The mixture was concentrated to afford the title compound (3.2 g, 77% yield) as a white solid; LCMS (ESI, M+1): m/z=223.2.

Intermediate 53

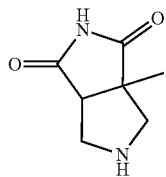

3a-methyltetrahydropyrrolo[3,4-c]pyrrole-1,3(2H,3aH)-dione

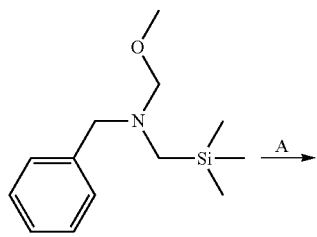

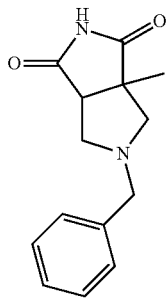

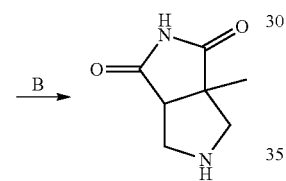

Step A. 5-benzyl-3a-methyltetrahydropyrrolo[3,4-c]pyrrole-1,3(2H, 3aH)-dione: To a mixture of 3-methylpyrrole-2,5-dione (608 mg, 1.0 equiv.) and N-(methoxymethyl)-1-phenyl-N-(trimethylsilylmethyl)methanamine (1.3 g, 1.0 equiv.) in CH$_2$Cl$_2$ (10 mL) was added a solution of TFA (62.4 mg, 40.5 uL, 0.1 equiv.) in CH$_2$Cl$_2$ (1.0 mL). The mixture was stirred at 25° C. for 1 hour. The reaction mixture was diluted with sat. aq. NaHCO$_3$ (40 mL) and extracted with CH$_2$Cl$_2$ (3×50 mL). The combined organic layers were dried, filtered and concentrated to give a residue. The residue was purified by flash silica gel chromatography (Ethyl acetate/Petroleum ether 2:1) to afford the title compound (0.8 g, 60% yield) as a colorless oil; $^1$H NMR (400 MHz, DMSO-d$_6$) δ=11.19 (s, 1H), 7.33-7.27 (m, 2H), 7.26-7.20 (m, 3H), 3.54-3.49 (m, 2H), 3.12-3.00 (m, 2H), 2.82 (d, J=7.2 Hz, 1H), 2.40 (dd, J=8.0, 9.6 Hz, 1H), 1.96-1.91 (m, 1H), 1.24 (s, 3H); LCMS (ESI, M+1): m/z=245.2.

Step B. tert-butyl N-[(5-carbamoyl-2-methyl-pyrazol-3-yl)methyl]carbamate: To a mixture of 5-benzyl-3a-methyl-tetrahydropyrrolo[3,4-c]pyrrole-1,3 (2H, 3aH)-dione (0.8 g, 1.0 equiv.) in THF (30 mL) was added Pd/C (300 mg, 10% purity), the mixture was degassed and purged with H$_2$ and stirred at 40° C. for 12 hours under H$_2$ atmosphere (15 psi). The reaction mixture was filtered and the filtrate was concentrated under the reduced pressure to afford the title compound (400 mg, 79% yield) as a colorless oil; LCMS (ESI, M+1]: m/z=155.2.

Intermediate 54

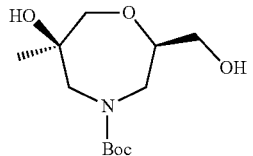 [SMILES: CC(C)(C)OC(=O)N1C[C@H](CO)OC[C@](C)(O)C1]

(2R,6R)-2-(hydroxymethyl)-6-methyl-1,4-oxazepan-6-ol

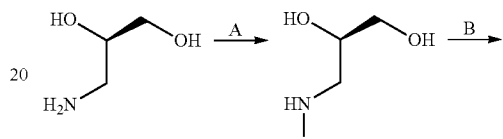

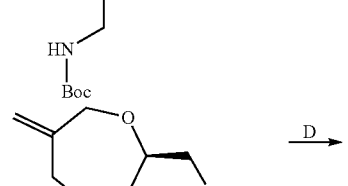

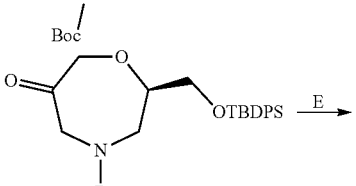

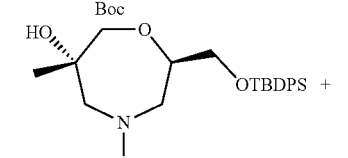

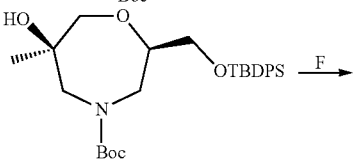

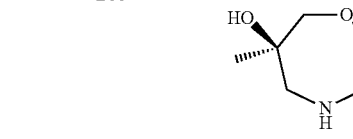

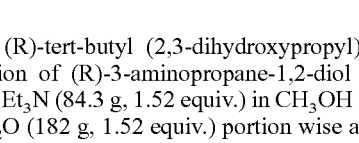

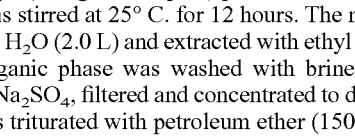

Step A. (R)-tert-butyl (2,3-dihydroxypropyl)carbamate: To a solution of (R)-3-aminopropane-1,2-diol (50.0 g, 1 equiv.) and Et$_3$N (84.3 g, 1.52 equiv.) in CH$_3$OH (1.5 L) was added Boc$_2$O (182 g, 1.52 equiv.) portion wise at 0° C. The reaction was stirred at 25° C. for 12 hours. The mixture was poured into H$_2$O (2.0 L) and extracted with ethyl acetate (1.0 L). The organic phase was washed with brine (500 mL), dried over Na$_2$SO$_4$, filtered and concentrated to dryness. The residue was triturated with petroleum ether (150 mL) at 25°

C. for 1 hour and filtered. The filter cake was washed with petroleum ether (3×50 mL) and dried to afford the tittle compound (48.0 g, 45% yield) as a colorless oil; $^1$H NMR (400 MHz, DMSO-$d_6$) δ=6.57 (t, J=4.8 Hz, 1H), 4.62 (d, J=4.8 Hz, 1H), 4.47 (t, J=6.0 Hz, 1H), 3.46-3.40 (m, 1H$_1$), 3.31-3.25 (m, 2H), 3.06-2.99 (m, 1H), 2.87-2.80 (m, 2H), 1.37 (s, 9H).

Step B. (R)-tert-butyl (3-((tert-butyldiphenylsilyl)oxy)-2-hydroxypropylcarbamate: To a solution of (R)-tert-butyl (2,3-dihydroxypropyl)carbamate (43.0 g, 1 equiv.) in CH$_2$Cl$_2$ (900 mL) were added imidazole (18.37 g, 1.2 equiv.) and TBDPSCl (67.9 g, 1.1 equiv.). The reaction mixture was stirred at 25° C. for 12 hours. The mixture was partitioned between CH$_2$Cl$_2$ (500 mL) and H$_2$O (1.0 L). The organic phase was separated and washed with brine 1.0 L (2×500 mL). The organic layer was dried over Na$_2$SO$_4$ and concentrated. The residue was purified by flash silica gel chromatography (ethyl acetate in petroleum ether 0-20%) to afford the tittle compound (42.3 g, 37.9% yield) as a colorless oil; $^1$H NMR (400 MHz, DMSO-$d_6$) δ=7.67-7.63 (m, 4H), 7.46-7.40 (m, 6H), 6.60 (t, J=5.2 Hz, 1H), 4.81 (s, 1H), 3.63 (s, 1H), 3.57-3.50 (m, 2H), 3.20-3.13 (m, 1H), 2.97-2.91 (m, 1H), 1.36 (s, 9H), 0.99 (s, 9H); LCMS (ESI, M+1): m/z=430.2.

Step C. (R-tert-butyl 2-(((tert-butyldiphenylsilyl)oxy) methyl)-6-methylene-1,4-oxazepane-4-carboxylate: To a solution of tert-butyl N-[(2R)-3-[tert-butyl(diphenyl)silyl]oxy-2-hydroxy-propyl]carbamate (20 g, 1 equiv.) in THF (400 mL) was added NaH (4.10 g, 60% purity, 2.2 equiv.) at 0° C. under N$_2$ atmosphere followed by 3-chloro-2-(chloromethyl)prop-1-ene (5.82 g, 1 equiv.). The reaction was stirred at 0° C. for 2 hours under N$_2$ atmosphere. The mixture was quenched by addition of H$_2$O (600 mL) at 0° C. and extracted with ethyl acetate (2×300 mL), the combined organic layers were washed with brine (20 mL) and dried over Na$_2$SO$_4$. The mixture was filtered and concentrated. The residue was purified by reversed-phase HPLC (Column: I.D.100 mm*H350 mm Welch Ultimate XB_C18 20-40 pm; mobile phase: water (0.1% formic acid)-ACN; B % 30-100% 50 min) to afford the tittle compound (1.8 g, 7.64% yield) as a colorless oil; $^1$H NMR (400 MHz, CDCl$_3$) δ=7.68-7.66 (m, 4H), 7.42-7.36 (m, 6H), 5.03-4.90 (m, 2H), 4.66-4.22 (m, 3H), 4.04-3.98 (m, 1H), 3.78-3.49 (m, 4H), 2.85-2.77 (m, 1H), 1.47 (s, 9H), 1.07 (s, 9H); LCMS (ESI, M+1): m/z=482.2.

Step D. (R)-tert-butyl 2-(((tert-butyldiphenylsilyl)oxy) methyl-6-oxo-1,4-oxazepane-4-carboxylate: To a solution of tert-butyl (2R)-2-[[tert-butyl(diphenyl)silyl]oxymethyl]-6-methylene-1,4-oxazepane-4-carboxylate (1.8 g, 1 equiv.) in THF (9 mL) and H$_2$O (9 mL) were added NaIO$_4$ (1.84 g, 2.3 equiv.) and K$_2$O$_s$O$_4$·2H$_2$O (68.8 mg, 0.05 equiv.). The reaction mixture was stirred at 25° C. for 1 hour. The mixture was quenched by addition of aqueous Na$_2$SO$_3$ (20 mL) at 0° C. and H$_2$O (10 mL) and then extracted with ethyl acetate (20 mL×2). The combined organic layers were washed with brine (30 mL) and concentrated. The residue was purified by column chromatography (SiO$_2$, Petroleum ether/Ethyl acetate 1:0 to 100:1) to afford the tittle compound (1.1 g, 57% yield) as a colorless oil; $^1$H NMR (400 MHz, CDCl$_3$) δ=7.67 (d, J=6.8 Hz, 4H), 7.45-7.38 (m, 6H), 4.50-4.21 (m, 3H), 4.03-3.97 (m, 1H), 3.83-3.60 (m, 4H), 3.01-2.96 (m, 1H), 1.47 (d, J=10.0 Hz, 9H), 1.07 (m, 9H); LCMS (ESI, M+23): m/z=506.2.

Step E. (2R,6S)tert-butyl 2-(((tert-butyldiphenylsilyl) oxy)methyl)-6-hydroxy-6-methyl-1,4-oxazepane-4-carboxylate and (2R,6R)-tert-butyl 2-(((tert-butyldiphenylsilyl) oxy)methyl)-6-hydroxy-6-methyl-1,4-oxazepane-4-carboxylate: To a solution of tert-butyl (2R)-2-[[tert-butyl (diphenyl)silyl]oxymethyl]-6-oxo-1,4-oxazepane-4-carboxylate (900 mg, 1 equiv.) in THF (13 mL) was added MeMgBr (3 M, 4.04 equiv.) under N$_2$ atm. at 0° C. The reaction mixture was stirred at 25° C. for 2 hours under N$_2$ atmosphere. The mixture was quenched by addition of sat.aq.NH$_4$Cl (30 mL) at 0° C. and H$_2$O (15 mL), and then was extracted with ethyl acetate (20 mL×2). The combined organic layers were washed with brine (20 mL) and concentrated. The residue was purified by flash silica gel chromatography (Ethyl acetate/Petroleum ether 0-15%) to afford two isomers: R,S (350 mg, 33% yield) as a colorless oil; $^1$H NMR (400 MHz, CDCl$_3$) δ=7.59-7.57 (m, 4H), 7.38-7.29 (m, 6H), 4.15-4.11 (m, 1H), 3.95-3.65 (m, 3H), 3.61-3.45 (m, 2H), 3.21 (d, J=12.4 Hz, 1H), 2.82 (d, J=15.2 Hz, 1H), 2.70-2.64 (m, 1H), 1.42 (s, 9H), 1.11 (s, 3H), 0.99 (s, 9H); LCMS (ESI, M−99): m/z=400.2. and R,R (190 mg, 18% yield) as a colorless oil; LCMS (ESI, M−99): m/z=400.2.

Step F. (2R,6R)-2-(hydroxymethyl)-6-methyl-1,4-oxazepan-6-ol: To a solution of (2R,6R-tert-butyl 2-(((tert-butyldiphenylsilyl)oxy)methyl)-6-hydroxy-6-methyl-1,4-oxazepane-4-carboxylate (520 mg, 1 equiv.) in CH$_2$Cl$_2$ (2 mL) was added HCl-dioxane (4 M, 10 mL). The mixture was stirred at 25° C. for 12 hours. The mixture was concentrated, the residue was diluted with H$_2$O (4 mL) and the pH of the mixture was adjusted to 7 with saturated NaHCO$_3$ aqueous. The mixture was extracted with ethyl acetate (2×5 mL). The combined organic phase was dried over anhydrous Na$_2$SO$_4$ and concentrated to afford the title compound (70 mg, crude) as a light-yellow oil.

Intermediate 55

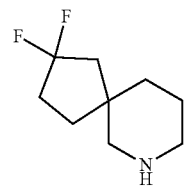 [SMILES: FC1(F)CCC2(CCCNC2)C1]

3,3-difluoro-7-azaspiro[4.5]decane

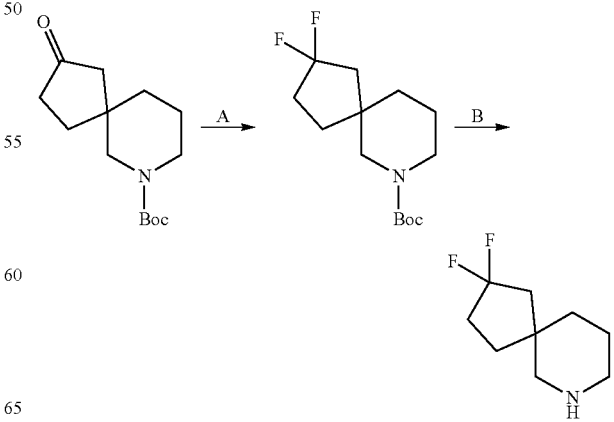

Step A. tert-butyl 3,3-difluoro-7-azaspiro[4.5]decane-7-carboxylate: To a solution of tert-butyl-3-oxo-7-azaspiro[4.5]decane-7-carboxylate (500 mg, 1.0 equiv.) in CH₂Cl2 (8 mL) was added DAST (541 mg, 443 µL, 1.7 equiv.). The mixture was stirred at 25° C. for 15 hours. The reaction mixture was diluted with water (20 mL) and extracted with ethyl acetate (2×20 mL). The combined organic layers were dried over anhydrous Na₂SO₄, concentrated and purified by column chromatography (SiO₂, petroleum ether/ethyl acetate 50:1 to 30:1) to afford the title compound (150 mg, 28% yield) as a yellow oil. $^1$H NMR (400 MHz, CHLOROFORM-d) δ=3.52-3.10 (m, 4H), 2.25-2.10 (m, 2H), 2.05-1.95 (m, 1H), 1.94-1.83 (m, 1H), 1.78-1.68 (m, 1H), 1.61-1.49 (m, 5H), 1.46 (s, 9H); $^{19}$F NMR (377 MHz, CHLOROFORM-d) δ=−87.62-90.03 (m, 1H).

Step B. 3,3-difluoro-7-azaspiro[4.5]decane: To a solution of tert-butyl 3,3-difluoro-7-azaspiro[4.5]decane-7-carboxylate (100 mg, 1.0 equiv.) in dioxane (4 mL) was added HCl.dioxane (4 M, 4 mL, 44.1 equiv.). The mixture was stirred at 0° C. for 2 hours. The reaction mixture was concentrated under reduced pressure to remove solvent. The residue was diluted with MeOH (4 mL), the pH was adjusted 9 with NaHCO₃, the mixture was stirred for 0.3 hours. The reaction mixture was concentrated to afford the title compound (70.0 mg, 91.1% yield, HCl salt, crude) as a colorless oil.

Intermediate 56

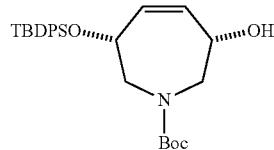

tert-butyl (3R,6S)-3-((tert-butyldiphenylsilyl)oxy)-6-hydroxy-2,3,6,7-tetrahydro-1H-azepine-1-carboxylate

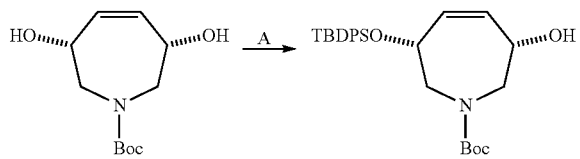

Step A. tert-butyl (3R,6S)-3-((tert-butyldiphenylsilyl)oxy)-6-hydroxy-2,3,6,7-tetrahydro-1H-azepine-1-carboxylate: To a solution of tert-butyl 3,6-dihydroxy-2,3,6,7-tetrahydroazepine-1-carboxylate (3.00 g, 1 equiv.) in DMF (20 mL) was added imidazole (2.67 g, 3 equiv.) and TBDPSCl (4.32 g, 1.2 equiv.). The mixture was stirred at 40° C. for 12 hours. The reaction mixture was concentrated under reduced pressure. The residue was diluted with water (20 mL) and extracted with ethyl acetate (20 mL×3). Combined organic phase was washed with brine (20.0 mL), dried over anhydrous sodium sulfate, filtered and concentrated to give a residue. The residue was purified by column chromatography (SiO₂, Petroleum ether/Ethyl acetate 10:1 to 5:1) to afford the title compound (1.8 g, 29.4% yield) as a white solid; $^1$H NMR (400 MHz, CDCl₃) δ=7.67-7.55 (m, 4H), 7.40-7.27 (m, 6H), 5.64-5.45 (m, 2H), 4.33-4.25 (m, 1H), 4.22-4.07 (m, 1H), 3.82-3.46 (m, 2H), 3.40-2.91 (m, 2H), 2.54-2.14 (m, 1H), 1.38 (br s, 3H), 1.24 (s, 6H), 1.00 (s, 9H).

Intermediate 57

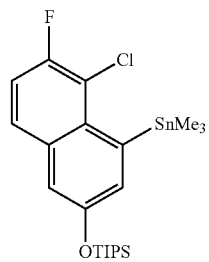

((5-chloro-6-fluoro-4-(trimethylstannyl)naphthalen-2-yl)oxy)triisopropylsilane

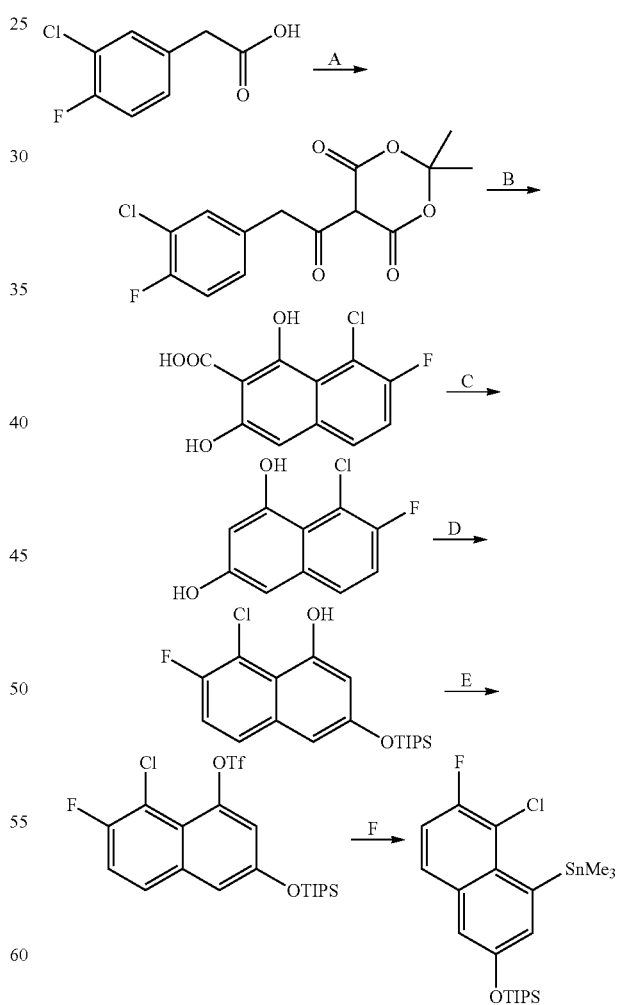

Step A. 5-(2-(3-chloro-4-fluorophenylacetyl)-2,2-dimethyl-1,3-dioxane-4,6-dione: To a mixture of 2-(3-chloro-4-fluoro-phenyl)acetic acid (330 g, 1 equiv.) and 2,2-dimethyl-1,3-dioxane-4,6-dione (277 g, 1.1 equiv.) in MeCN (1500 mL) was added DMAP (18.2 g, 0.09 equiv.) at 20° C. Then DIEA (486 g, 2.15 equiv.) was added into the mixture slowly over the course of 1 hour under 15-30° C. Following that 2,2-dimethylpropanoyl chloride (232.10 g, 1.1 equiv.) was added into the mixture over the course of 1 hour 1 hour while maintaining the temperature at 25-40° C. After the additions were complete the mixture was stirred at 45° C. for 3 hours. The mixture was cooled to 0° C., then the pH was adjusted to 3 with HCl (4N, 5 L) and mixture was stirred at 0° C. for 1 hour. The filter cake was triturated with MeCN (3 L) to afford the title compound (933 g, 84% yield) as a yellow solid that was used in next step without further purification. $^1$HNMR (400 MHz, CDCl$_3$) δ=15.36 (br s, 1H), 7.46 (dd, J=2.0, 6.8 Hz, 1H), 7.30-7.25 (m, 1H), 7.10 (t, J=8.8 Hz, 1H), 4.39-4.34 (m, 1H), 1.74 (s, 6H).

Step B. 8-chloro-7-fluoro-1,3-dihydroxy-2-naphthoic acid: A mixture of 5-(2-(3-chloro-4-fluorophenyl)acetyl)-2,2-dimethyl-1,3-dioxane-4,6-dione (650 g, 1.0 equiv.) in CF$_3$SO$_3$H (1300 mL) was stirred at 5-20° C. Then the mixture was stirred at 10° C. for 2 hours. After reaction completion, the mixture was poured into ice water (2 L) and filtered. The filter cake was washed with water (5 L) and dried to afford the title compound (2000 g, crude) as yellow solid and used in next step without further purification.

Step C. 8-chloro-7-fluoronaphthalene-1,3-diol: A mixture of 8-chloro-7-fluoro-1,3-dihydroxy-2-naphthoic acid (1.2 kg, 1.0 equiv.) in MeCN (700 mL) and H$_2$O (700 mL) was stirred at 85° C. for 12 hours under N$_2$. The mixture was concentrated under vacuum to remove acetonitrile. The residue was extracted with ethyl acetate (2 L×2), dried over Na$_2$SO$_4$ and concentrated in vacuum. The residue was purified by column chromatography (SiO$_2$, petroleum ether/ethyl acetate 3:1) and prep-HPLC (column: Phenomenex Luna C18 200*40 mm*10 um; mobile phase: water (0.1% formic acid)-ACN; B %: 27%-57%, 10 min). The desired fraction was collected and extracted with ethyl acetate (2 L), dried over Na$_2$SO$_4$ and concentrated under vacuum to afford the title compound (17 g, 16% yield two steps) as a yellow solid. $^1$H NMR (400 MHz, DMSO-d$_6$) δ 10.17 (s, 1H), 9.71 (s, 1H), 7.58 (dd, J=5.6, 8.8 Hz, 1H), 7.32 (t, J=8.8 Hz, 1H), 6.67 (d, J=2.0 Hz, 1H), 6.63 (d, J=2.0 Hz, 1H).

Step D. 8-chloro-7-fluoro-3-((triisopropylsilyl)oxy)naphthalen-1-ol: To a solution of 8-chloro-7-fluoronaphthalene-1,3-diol (10 g, 1 equiv.) and DIEA (12.2 g, 2.0 equiv.) in DCM (150 mL) was added TIPSCl (8.16 g, 0.9 equiv.) at 0° C. The mixture was stirred at 0° C. for 0.5 hour. The mixture was concentrated in vacuum and the residue was purified by column chromatography (SiO$_2$, petroleum ether/ethyl acetate 10:1) to afford the title compound (15 g, 86% yield) as a yellow oil.

Step E. 8-chloro-7-fluoro-3-((triisopropylsilyl)oxy)naphthalen-1-yl trifluoromethanesulfonate: To a mixture of 8-chloro-7-fluoro-3-((triisopropylsilyl)oxy)naphthalen-1-ol (15 g, 1.0 equiv.) and DIEA (15.8 g, 3.0 equiv.) in DCM (150 mL) was added Tf$_2$O (17.2 g, 1.5 equiv.) at 40° C. The mixture was stirred at −40° C. for 0.5 hour. The mixture was concentrated in vacuum and the residue was purified by column chromatography (SiO$_2$, petroleum ether/ethyl acetate 10:1) to afford the title compound (19 g, 90% yield) as a yellow oil.

Example F. ((5-chloro-6-fluoro-4-(trimethylstannyl)naphthalen-2-yl)oxy)triisopropylsilane: To a mixture of 8-chloro-7-fluoro-3-((triisopropylsilyl)oxy)naphthalen-1-yl trifluoromethanesulfonate (5 g, 1.0 equiv.), trimethyl(trimethylstannyl)stannane (12.7 g, 3.88 equiv.) and LiCl (1.27 g, 3.0 equiv.) in toluene (50 mL) was added Pd(PPh$_3$)$_4$ (1.15 g, 0.1 equiv.) under N$_2$. The mixture was stirred at 100° C. for 12 hours under N$_2$. The mixture was quenched with water (20 mL) and extracted with ethyl acetate (100 mL×3), the combined organic phase was washed with brine (100 mL), dried over anhydrous sodium sulfate, filtered and concentrated to give a residue and the residue was purified by column chromatography (SiO$_2$, petroleum ether) and reversed phase flash [water (0.1%, FORMIC ACID)/acetonitrile] to afford the title compound (3 g, 55% yield) as yellow oil. $^1$HNMR (400 MHz, CDCl$_3$) δ=7.60 (dd, J=5.6, 9.2 Hz, 1H), 7.52 (d, J=2.4 Hz, 1H), 7.31-7.26 (m, 1H), 7.20 (d, J=2.4 Hz, 1H), 1.35-1.30 (m, 3H), 1.15 (d, J=7.2 Hz, 18H), 0.51-0.35 (m, 9H)

Intermediate 58

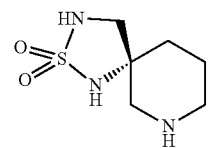 [SMILES: O=S1(=O)NC[C@]2(CCCNC2)N1]

(R)-2-thia-1,3,7-triazaspiro[4.5]decane 2,2-dioxide

Intermediate 59

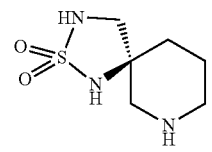 [SMILES: O=S1(=O)NC[C@@]2(CCCNC2)N1]

(S)-2-thia-1,3,7-triazaspiro[4.5]decane 2,2-dioxide

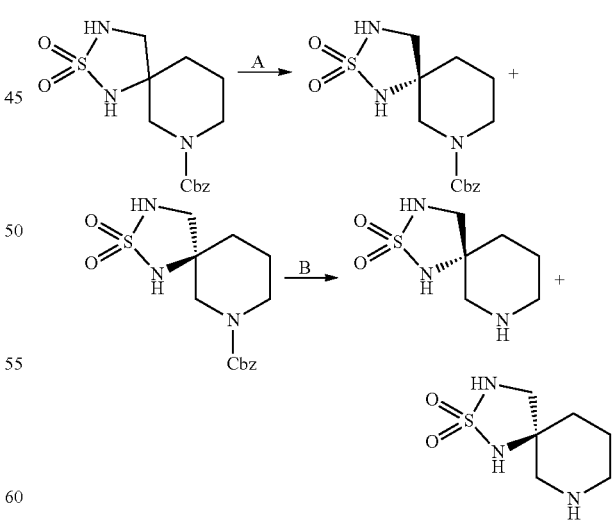

Step A. benzyl (R)-2-thia-1,3,7-triazaspiro[4.5]decane-7-carboxylate 2,2-dioxide and benzyl (S')-2-thia-1,3,7-triazaspiro[4.5]decane-7-carboxylate 2,2-dioxide: Racemic benzyl 2-thia-1,3,7-triazaspiro[4.5]decane-7-carboxylate 2,2-dioxide (46.5 g) was separated by chiral SFC (column:

DAICEL CHIRALPAK IC (250 mm*50 mm, 10 um); mobile phase: [0.1% NH₃H₂O-IPA]; B %: 55%-55%, 7 min) to afford the two title compound isomers: R-isomer (22 g, 41% yield, 99.9% ee) as a yellow solid and S-isomer (22 g, 42% yield, 99.9% ee) as a yellow solid. LCMS (ESI, M+1): m/z=326.1.

Step B. (R)-2-thia-1,3,7-triazaspiro[4.5]decane 2,2-dioxide: To a solution of (R)-2-thia-1,3,7-triazaspiro[4.5]decane-7-carboxylate 2,2-dioxide (20.0 g, 1.00 equiv.) in methanol (160 mL) was added Pd/C (10%, 3.00 g) under nitrogen atmosphere. The suspension was degassed and stirred under hydrogen (15 Psi) at 25° C. for 2 hours. The reaction mixture was filtered and concentrated under reduced pressure to afford the title compound (11 g, 93% yield) as a yellow solid. $^1$H NMR (400 MHz, MeOD-d₄) δ=3.37-3.32 (m, 1H), 3.13 (d, J=11.7 Hz, 1H), 2.93-2.84 (m, 1H), 2.82-2.72 (m, 2H), 2.72-2.62 (m, 1H), 1.82 (br dd, J=4.8, 6.7 Hz, 1H), 1.79-1.70 (m, 1H), 1.65 (td, J=4.2, 8.3 Hz, 1H), 1.60-1.49 (m, 1H)

(S)-2-thia-1,3,7-triazaspiro[4.5]decane 2,2-dioxide: To a solution of benzyl benzyl (S)-2-thia-1,3,7-triazaspiro[4.5]decane-7-carboxylate 2,2-dioxide. (22.0 g, 1.00 equiv.) in methanol (160 mL) was added Pd/C (10%, 3.00 g) under nitrogen atmosphere. The suspension was degassed and stirred under hydrogen (15 Psi) at 25° C. for 2 hours. The reaction mixture was filtered and concentrated under reduced pressure to afford the title compound (11.8 g, 91% yield) as a yellow solid. $^1$H NMR (400 MHz, MeOD-d₄) δ=3.37-3.32 (m, 1H), 3.15 (s, 1H), 3.19-3.07 (m, 1H), 2.92-2.83 (m, 1H), 2.82-2.72 (m, 2H), 2.72-2.62 (m, 1H), 1.82 (br dd, J=4.8, 6.7 Hz, 1H), 1.79-1.71 (m, 1H), 1.70-1.60 (m, 1H), 1.59-1.48 (m, 1H)

Intermediates 60

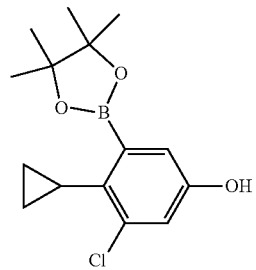 [SMILES: CC1(C)OB(c2cc(O)cc(Cl)c2C2CC2)OC1(C)C]

3-chloro-4-cyclopropyl-5-(4,4,5,5-tetramethyl-1,3,2-dioxaborolan-2-yl)phenol

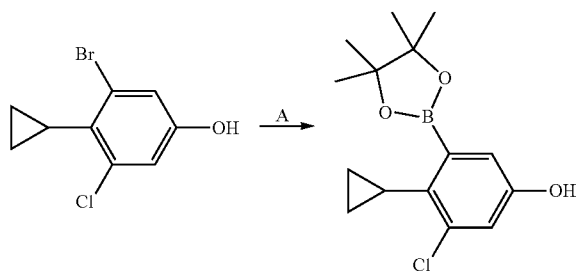

Step A. 3-chloro-4-cyclopropyl-5-(4,4,5,5-tetramethyl-1,3,2-dioxaborolan-2-yl)phenol: To a solution of 3-bromo-5-chloro-4-cyclopropyl-phenol (2.00 g, 1.0 equiv.) in dioxane (50 mL) was added KOAc (2.38 g, 3.0 equiv.), Pin₂B₂ (4.00 g, 2.0 equiv.) and Pd(dppf)Cl₂ (591 mg, 0.1 equiv.). The mixture was stirred at 100° C. for 4 hours under nitrogen atmosphere. The reaction mixture was poured into saturated aqueous NH₄Cl solution (5 mL) and extracted with EtOAc (3×2 mL). The combined organic layers were washed with brine (5 mL), dried over anhydrous sodium sulfate, filtered and concentrated. The residue was purified by flash silica gel chromatography [ethyl acetate in petroleum ether 0-35%] to afford the title compound (1.10 g, 46% yield) as a white solid; $^1$H NMR (400 MHz, CHLOROFORM-d) δ=6.92 (d, J=2.6 Hz, 1H), 6.87 (d, J=2.6 Hz, 1H), 5.33 (br s, 1H), 1.99-1.90 (m, 1H), 1.39 (s, 12H), 1.00-0.94 (m, 2H), 0.53-0.47 (m, 2H).

Intermediate 61

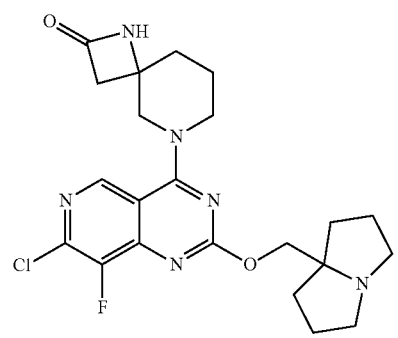 [SMILES: O=C1CC2(CCCN(c3nc(OCC45CCCN4CCC5)nc4c(F)c(Cl)ncc34)C2)N1]

6-(7-chloro-8-fluoro-2-((hexahydro-1H-pyrrolizin-7a-yl)methoxy)pyrido[4,3-d]pyrimidin-4-yl)-1,6-diazaspiro[3.5]nonan-2-one

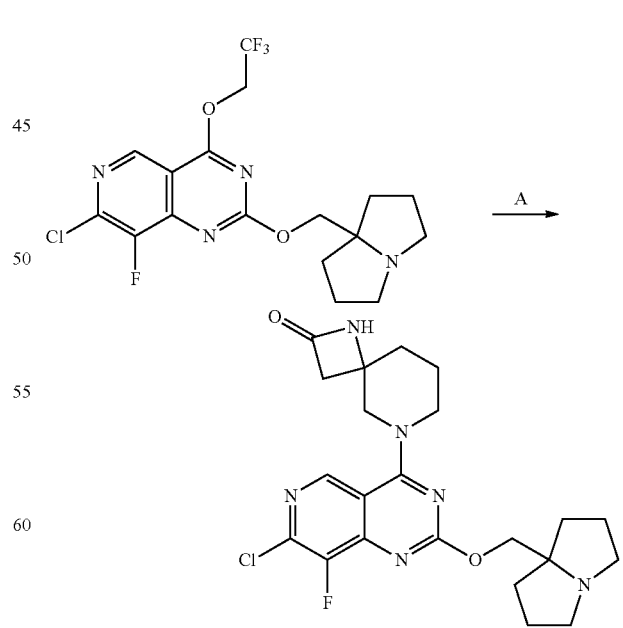

Step A. 6-(7-chloro-8-fluoro-2-((hexahydro-1H-pyrrolizin-7a-yl)methoxy)pyrido[4,3-d]pyrimidin-4-yl)-1,6-diazaspiro[3,5]nonan-2-one: To a mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (200 mg, 475 µmol, 1.0 equiv.), 1,6-diazaspiro[3.5]nonan-2-one (60.0 mg, 428 µmol, 0.9 equiv.), 4 Å molecular sieves (10.0 mg) in DMF (2 mL) was added DIEA (184 mg, 1.43 mmol, 248 µL, 3.0 equiv.). The mixture was stirred at 40° C. for 4 hours. After reaction completion, the mixture was filtered to give a filtrate. The crude product was purified by reversed-phase flash chromatography (water (0.1% formic acid)-ACN) to give the title compound (60.0 mg, 130 µmol, 27% yield) as a yellow solid; LCMS (ESI, M+1): m/z=461.3.

Intermediate 62

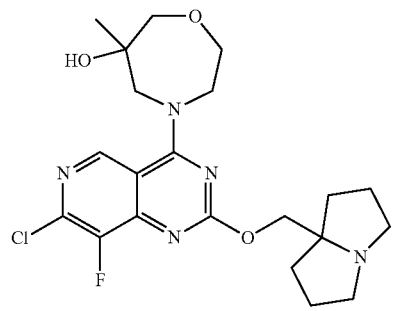 [SMILES: CC1(O)COCCN(c2nc(OCC34CCCN3CCC4)nc3c(F)c(Cl)ncc23)C1]

4-(7-chloro-8-fluoro-2-((hexahydro-1H-pyrrolizin-7a-yl)methoxy)pyrido[4,3-d]pyrimidin-4-yl)-6-methyl-1,4-oxazepan-6-ol

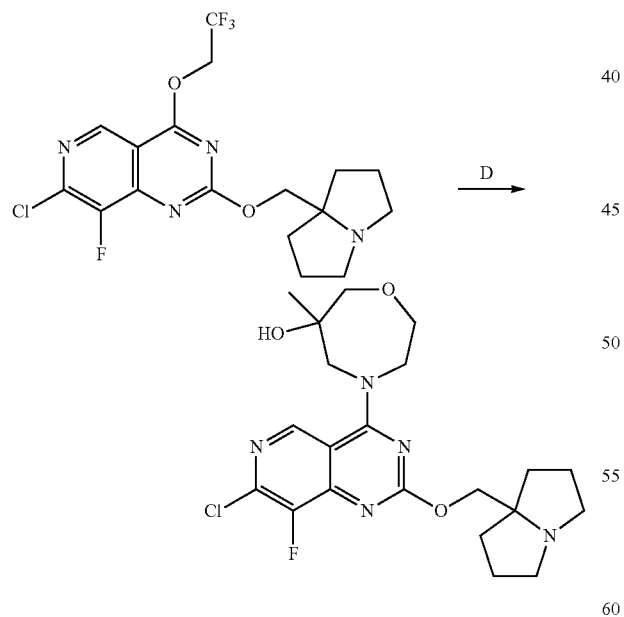

Step A. 4-(7-chloro-8-fluoro-2-((tetrahydro-1H-pyrrolizin-7a(5H)-yl)methoxy)pyrido[4,3-d]pyrimidin-4-yl)-6-methyl-1,4-oxazepan-6-ol: A mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (0.45 g, 1 equiv.), 6-methyl-1,4-oxazepan-6-ol (210 mg, 1.5 equiv.), DIPEA (276 mg, 2 equiv.) and 4 Å molecular sieves (50 mg) in DMF (4 mL) was stirred at 40° C. for 14 hours under N₂ atmosphere. The reaction mixture was filtered and the filtrate was concentrated to give a residue. The residue was purified by reversed phase flash chromatography (water (0.1% formic acid)-ACN) to afford the title compound (205 mg, 40.3% yield) as a light-yellow solid; LCMS (ESI, M+1): m/z=452.0.

Example 1

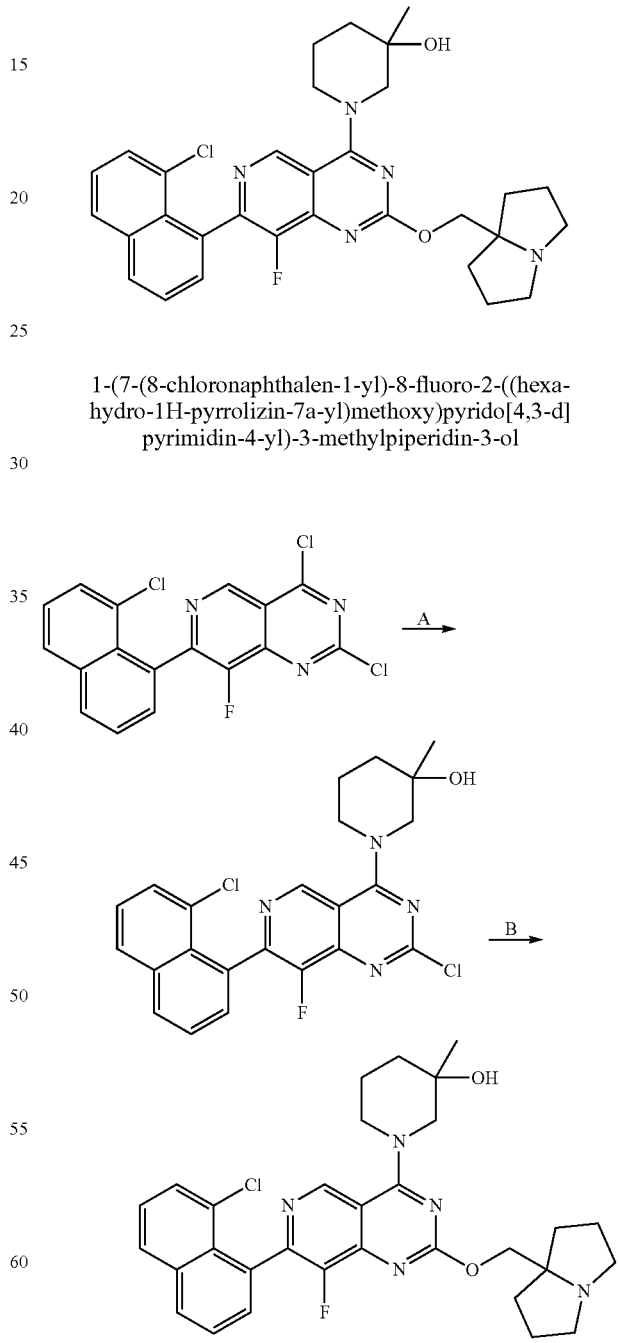

1-(7-(8-chloronaphthalen-1-yl)-8-fluoro-2-((hexahydro-1H-pyrrolizin-7a-yl)methoxy)pyrido[4,3-d]pyrimidin-4-yl)-3-methylpiperidin-3-ol Step A. 1-[2-chloro-7-(8-chloro-1-naphthyl)-8-fluoro-pyrido[4,3-d]pyrimidin-4-yl]-3-methyl-piperidin-3-ol: To a mixture of 2,4-dichloro-7-(8-chloro-1-naphthyl)-8-fluoropyrido[4,3-d]pyrimidine (1.48 g, 3.90 mmol) in dichloromethane (15 mL) was added DIEA (5.05 g, 39.0 mmol, 6.80 mL) and 3-methylpiperidin-3-ol (270 mg, 2.34 mmol) at −40° C. under N$_2$. The mixture was stirred at −40° C. for 0.5 h. After completion, the mixture was quenched by water (10 mL). The aqueous phase was extracted with dichloromethane (2×8 mL), the combined organic layer was washed with brine (10 mL) and dried over with Na$_2$SO$_4$. The mixture was filtered and concentrated in vacuum. The residue was purified by reversed phase flash chromatography [water (0.1% formic acid)/acetonitrile] to give 1-[2-chloro-7-(8-chloro-1-naphthyl)-8-fluoro-pyrido[4,3-d]pyrimidin-4-yl]-3-methyl-piperidin-3-ol (128 mg, 35% yield) as yellow solid; $^1$H NMR (400 MHz, DMSO-d$_6$): δ 9.37 (s, 1H), 8.22 (d, J=8.0 Hz, 1H), 8.11 (d, J=8.0 Hz, 1H), 7.77-7.71 (m, 1H), 7.66 (t, J=7.6 Hz, 2H), 7.61-7.55 (m, 1H), 4.84 (d, J=16.4 Hz, 1H), 4.54-4.41 (m, 1H), 4.18 (br dd, J=6.0, 12.8 Hz, 1H), 3.68-3.54 (m, 1H), 2.08-2.00 (m, 1H), 1.75-1.66 (m, 3H), 1.20-1.17 (m, 3H); LCMS (ESI, M+1): m/z 457.1.

Step B. 1-(7-(8-chloronaphthalen-1-yl)-8-fluoro-2-((hexahydro-1H-pyrrolizin-7a-yl)methoxy)pyrido[4,3-d]pyrimidin-4-yl)-3-methylpiperidin-3-ol: To a mixture of 1-[2-chloro-7-(8-chloro-1-naphthyl)-8-fluoro-pyrido[4,3-d]pyrimidin-4-yl]-3-methyl-piperidin-3-ol (112 mg, 245 µmol) and (tetrahydro-1H-pyrrolizin-7a(5H)-yl)methanol (69.2 mg, 490 µmol) in dioxane (2.0 mL) was added DIEA (95.0 mg, 735 µmol, 128 µL). The mixture was stirred at 90° C. for 15 h. After completion, the mixture was diluted with ethyl acetate (8 mL) and water (8 mL). The aqueous phase was extracted with ethyl acetate (2×5 mL) and dichloromethane:methanol=10:1 (1×5 mL). The organic layers were concentrated in vacuum. The residue was purified by prep-HPLC (Water s Xbridge 150*25 mm*5 um; mobile phase: [water (10 mM NH$_4$HCO$_3$)-ACN]; B %: 22%-52%, 10 min) to afford the title compound (23.7 mg, 16% yield) as off-white solid. 1H NMR (400 MHz, CDCl$_3$-d): δ 9.13 (d, J=2.4 Hz, 1H), 8.04-7.97 (m, 1H), 7.88 (d, J=7.6 Hz, 1H), 7.64-7.52 (m, 3H), 7.45-7.38 (m, 1H), 4.50-4.25 (m, 4H), 3.57-3.45 (m, 1H), 3.35 (br dd, J=6.8, 13.2 Hz, 1H), 3.26-2.98 (m, 3H), 2.75-2.61 (m, 2H), 2.18-2.03 (m, 3H), 1.96-1.84 (m, 5H), 1.78-1.71 (m, 4H), 1.36 (d, J=2.4 Hz, 3H); LCMS (ESI, M+1): m/z 562.1

Example 2

7-(7-(8-chloronaphthalen-1-yl)-8-fluoro-2-((tetrahydro-1H-pyrrolizin-7a(5H)-yl) methoxy)pyrido[4,3-d]pyrimidin-4-yl)-2,7-diazaspiro[4.5]decan-3-one

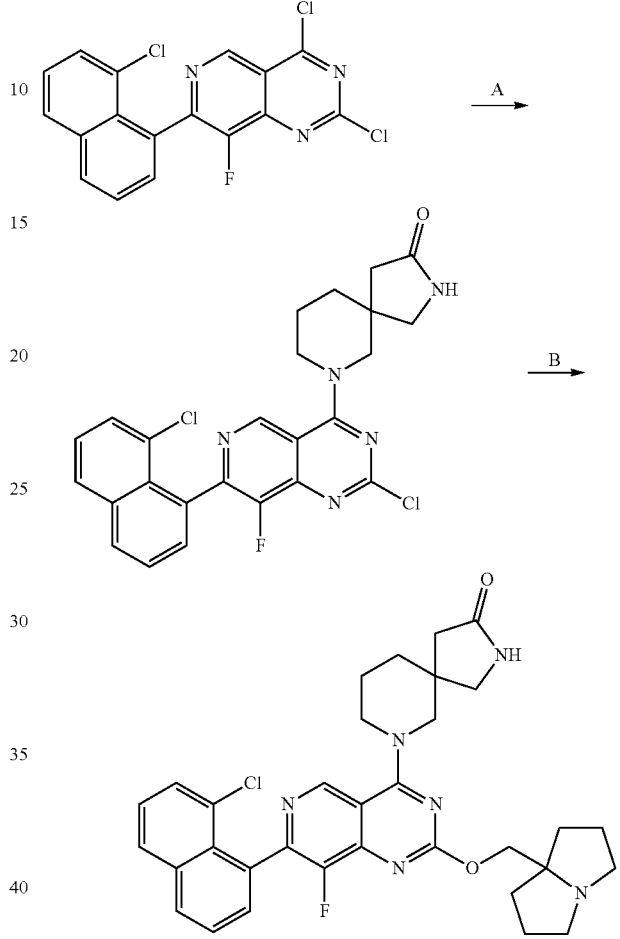

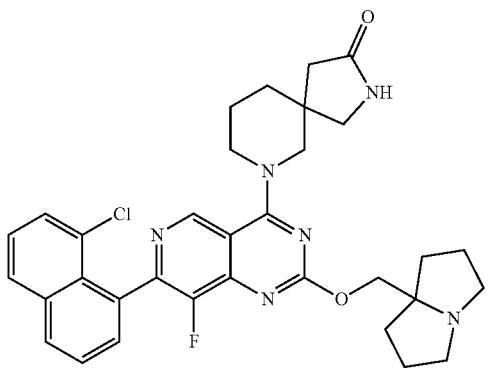 [SMILES: O=C1CC2(CCCN(c3nc(OCC45CCCN4CCC5)nc4c(F)c(-c5cccc6cccc(Cl)c56)ncc34)C2)CN1]

Step A. 7-[2-chloro-7-(8-chloro-1-naphthyl)-8-fluoro-pyrido[4,3-d]pyrimidin-4-yl]-2,7-diazaspiro[4.5]decan-3-one: To a mixture of 2,4- dichloro-7-(8-chloro-1-naphthyl)-8-fluoro-pyrido[4,3-d]pyrimidine (0.15 g, 396 µmol) in dichloromethane (5.0 mL) was added DIEA (512 mg, 3.96 mmol) at −40° C. After the mixture was stirred at −40° C. for 10 minutes, 2,9-diazaspiro[4.5]decan-3-one (73.3 mg, 475 µmol) was added into the mixture. The mixture was stirred at −40° C. for 10 minutes. After completion, the mixture was diluted with water (10 mL) and extracted with dichloromethane (2×10 mL). The combined organic layer was washed with brine (10 mL), and then dried over Na$_2$SO$_4$. The mixture was filtered and concentrated in vacuum. The residue was purified by reversed phase flash chromatography [water (0.1% formic acid)/acetonitrile] to give 7-[2-chloro-7-(8-chloro-1-naphthyl)-8-fluoro-pyrido[4,3-d]pyrimidin-4-yl]-2,7-diazaspiro[4.5]decan-3-one (120 mg, 45% yield) as a yellow Solid; LCMS [ESI, M+1]: m/z=496.0.

Step B. 7-(7-(8-chloronaphthalen-1-yl)-8-fluoro-2-((tetrahydro-1H-pyrrolizin-7a(5H-yl)methoxy)pyrido[4,3-d]pyrimidin-4-yl)-2,7-diazaspiro[4.5]decan-3-one: A mixture of 7-[2-chloro-7-(8-chloro-1-naphthyl)-8-fluoro-pyrido[4,3-d]pyrimidin-4-yl]-2,7-diazaspiro[4.5]decan-3-one (100 mg, 201 µmol), (tetrahydro-1H-pyrrolizin-7a(5H)-yl)methanol (56.9 mg, 403 µmol) and DIEA (130 mg, 1.01 mmol, 175 µL) in dioxane (1.0 mL) was stirred at 80° C. for 9 hours. After completion, the mixture was diluted with water (5.0 mL) and extracted with ethyl acetate (2×10 mL). The combined organic layer was washed with brine (10 mL), and then dried over Na$_2$SO$_4$. The mixture was filtered and concentrated in vacuum. The residue was purified by prep-HPLC (column: water s Xbridge 150*25 mm*5 um; mobile phase: [water (10 mM NH$_4$HCO$_3$)-ACN]; B %: 24%-54%, 10 min) to give the title compound (23.0 mg, 18% yield) as yellow solid; LCMS [ESI, M+1]: m/z=601. 1H NMR (400 MHz, chloroform-d) 88.98 (d, J=2.0 Hz, 1H), 8.00 (dd, J=1.6, 7.8 Hz, 1H), 7.88 (td, J=1.2, 8.4 Hz, 1H), 7.63-7.52 (m, 3H), 7.42 (t, J=7.6 Hz, 1H), 6.00 (br d, J=8.8 Hz, 1H), 4.30-4.18 (m, 2H), 4.09 (q, J=12.4 Hz, 2H), 3.84-3.71 (m, 1H), 3.64 (dd, J=13.2, 18.0 Hz, 1H), 3.48-3.38 (m, 1H), 3.21 (dd, J=4.4, 10.0 Hz, 1H), 3.16-3.06 (m, 2H), 2.64 (td, J=6.8, 10.0 Hz, 2H), 2.38-2.23 (m, 2H), 2.15-2.04 (m, 2H), 1.94-1.86 (m, 7H), 1.74-1.60 (m, 3H).

Example 3

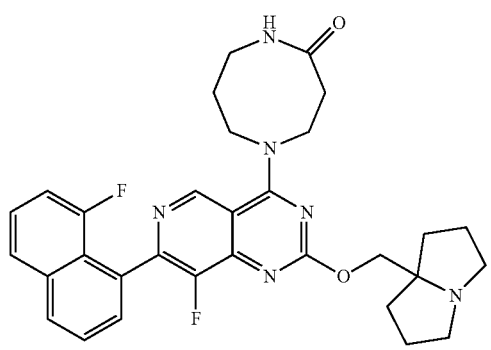 [SMILES: O=C1CCN(c2nc(OCC34CCCN3CCC4)nc3c(F)c(-c4cccc5cccc(F)c45)ncc23)CCCN1]

5-(8-fluoro-7-(8-fluoronaphthalen-1-yl)-2-((hexahydro-1H-pyrrolizin-7a-yl)methoxy)pyrido[4,3-d]pyrimidin-4-yl)-1,5-diazocan-2-one

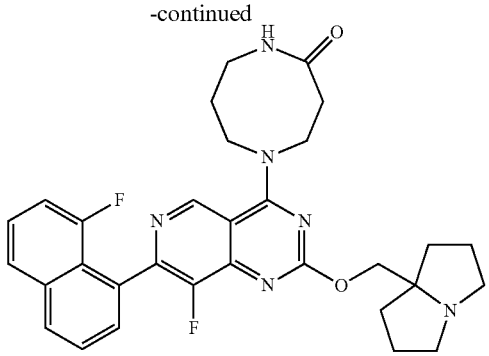

Step A. 5-(8-fluoro-7-(8-fluoronaphthalen-1-yl)-2-((hexahydro-1H-pyrrolizin-7a-yl)methoxy)pyrido[4,3-d]pyrimidin-4-yl)-1,5-diazocan-2-one: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 188 µmol), 4 Å MS (50 mg) and 1,5-diazocan-2-one (48.3 mg, 377 µmol) in DMF (2.00 mL) was added DIEA (73.1 mg, 565 µmol). The mixture was stirred at 90° C. for 2 hours. After completion, the reaction mixture was diluted with water (10 mL) and extracted with ethyl acetate (3×10 mL). The combined organic layers were washed with brine (20 mL) and dried over Na$_2$SO$_4$. The mixture was filtered and concentrated under reduced pressure to give a residue. The residue was purified by prep-HPLC (column: water s Xbridge 150*25 mm*5 um; mobile phase: [water (10 mM NH$_4$HCO$_3$)-ACN]; B %: 17%-47%, 9 min) affording 5-(8-fluoro-7-(8-fluoronaphthalen-1-yl)-2-((hexahydro-1H-pyrrolizin-7a-yl)methoxy)pyrido[4,3-d]pyrimidin-4-yl)-1,5-diazocan-2-one (18.6 mg, 17% yield) as white solid; 1H NMR (400 MHz, CDCl$_3$-d) δ 9.08 (s, 1H), 8.00 (dt, J=1.6, 8.0 Hz, 1H), 7.75 (d, J=7.6 Hz, 1H), 7.68-7.56 (m, 2H), 7.49-7.42 (m, 1H), 7.17-7.06 (m, 1H), 6.03-5.86 (m, 1H), 4.45-3.92 (m, 6H), 3.40-3.29 (m, 2H), 3.15-3.07 (m, 2H), 3.04-2.91 (m, 2H), 2.68-2.60 (m, 2H), 2.15-1.96 (m, 5H), 1.91-1.87 (m, 3H), 1.72-1.62 (m, 2H); LCMS (ESI, M+1): m/z=559.3.

Example 4

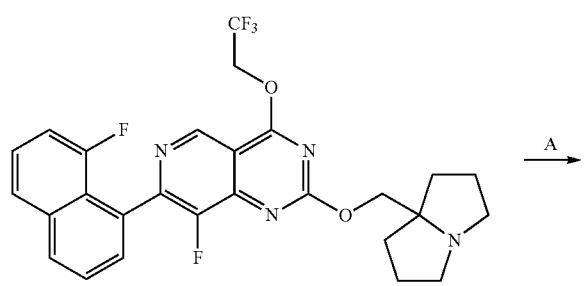

A

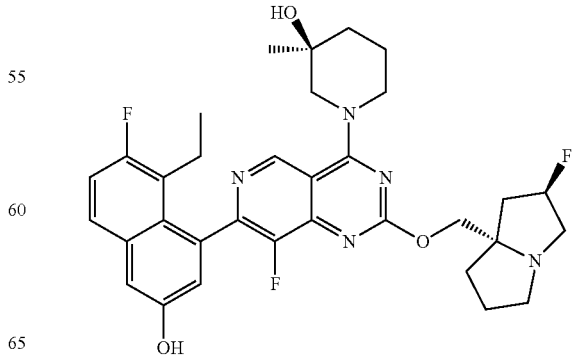

(S)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol

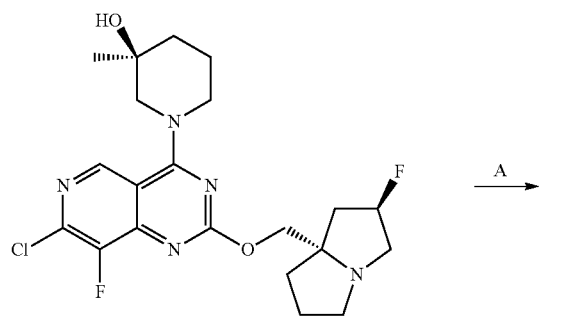

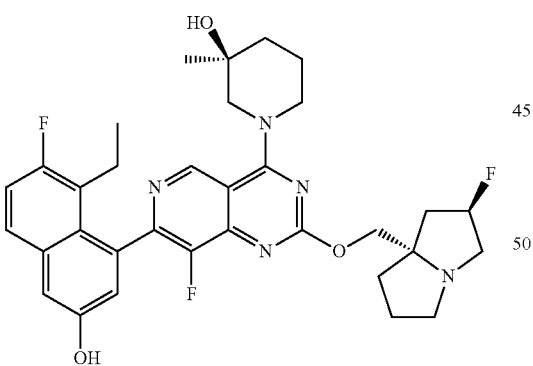

Step A. (S)-1-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a mixture of 2-(8-ethyl-7-fluoro-3-(methoxymethoxy)naphthalen-1-yl)-4,4,5,5-tetramethyl-1,3,2-dioxaborolane (103 mg, 286 μmol, 1.3 equiv.) and (4)-1-(7-chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (100 mg, 220 μmol, 10 eq, synthesized according to example 5 step A replacing (R)-1-(2,7-dichloro-8-fluoropyrido[4,3-d]pyrimidin-4-yl)-3-methylpiperidin-3-ol with (S)-1-(2,7-dichloro-8-fluoropyrido[4,3-d]pyrimidin-4-yl)-3-methylpiperidin-3-ol) in THF (1.5 mL) was added cataCXium®-A-Pd-G3 (24.07 mg, 33.05 μmol, 0.15 equiv.) in one portion at 25° C. under $N_2$. Then $K_3PO_4$ (1.5 M, 440 μL, 3.0 equiv.) was added under $N_2$. The mixture was heated to 60° C. and stirred for 4 hours. After completion, the mixture was filtered and concentrated in vacuum. The crude product was purified by reversed phase flash chromatography (water (0.1% formic acid)-ACN) to give title compound as yellow oil; 1H NMR (400 MHz, CDCl$_3$-d) δ=9.14 (d, J=8.0 Hz, 1H), 7.76 (dd, J=6.0, 8.8 Hz, 1H), 7.55-7.50 (m, 1H), 7.27-7.24 (m, 1H), 7.23-7.20 (m, 1H), 5.37-5.20 (m, 3H), 4.52-4.35 (m, 2H), 4.33-4.20 (m, 2H), 3.52 (s, 3H), 3.50-3.40 (m, 1H), 3.36-3.14 (m, 4H), 3.04-2.77 (m, 2H), 2.59-2.47 (m, 1H), 2.29-2.11 (m, 4H), 1.98-1.85 (m, 4H), 1.80-1.69 (m, 2H), 1.36 (s, 3H), 0.84 (q, J=7.6 Hz, 3H); LCMS (ESI, M+1−Boc): m/z=652.3.

Step B. (S)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a solution of 2-(8-ethyl-7-fluoro-3-(methoxymethoxy)naphthalen-1-yl)-4,4,5,5-tetramethyl-1,3,2-dioxaborolane (70 mg, 107 μmol, 1 equiv.) in MeCN (1.4 mL) was added HCl.dioxane (4 M, 1.4 mL, 52 equiv.) at 5° C. The reaction mixture was stirred at 5° C. for 0.5 hour: Upon completion, the reaction mixture was diluted with MeCN (3 mL) and basified with saturated NaHCO$_3$ solution to pH>7. The reaction mixture was extracted with ethyl acetate (3×5 mL). The combined organic layers were dried over Na$_2$SO$_4$, filtered and concentrated in vacuum. The residue was purified by prep-HPLC (column: water s Xbridge 150×25 mm×5 um; mobile phase: [water (10 mM NH$_4$HCO$_3$)-ACN]; B %: 40%-70%, 5 min) to give title compound as (32.5 mg, 50% yield) white solid; 1H NMR δ=9.21-8.99 (m, 1H), 7.51 (dd, J=6.0, 9.2 Hz, 1H), 7.17 (t, J=9.2 Hz, 1H), 7.10 (dd, J=2.4, 15.6 Hz, 1H), 6.89-6.61 (m, 1H), 5.42-5.18 (m, 1H), 4.45-4.09 (m, 4H), 3.48-3.16 (m, 4H), 3.14-2.94 (m, 2H), 2.58-2.31 (m, 2H), 2.30-2.06 (m, 4H), 2.03-1.95 (m, 2H), 1.74-1.70 (m, 1H), 1.67-1.40 (m, 3H), 1.23 (d, J=4.8 Hz, 3H), 0.81-0.75 (m, 3H); LCMS (ESI, M+1): m/z=608.2.

Example 5

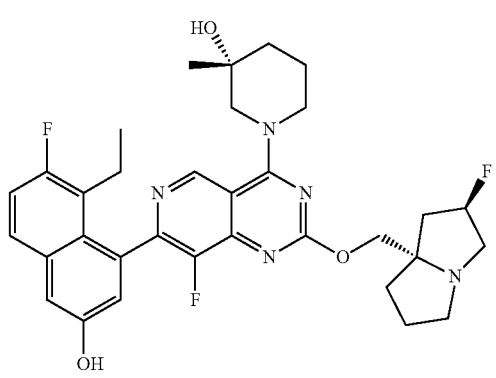 [SMILES: CCc1c(F)ccc2cc(O)cc(-c3ncc4c(N5CCC[C@@](C)(O)C5)nc(OC[C@@]56CCCN5C[C@H](F)C6)nc4c3F)c12]

(R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol

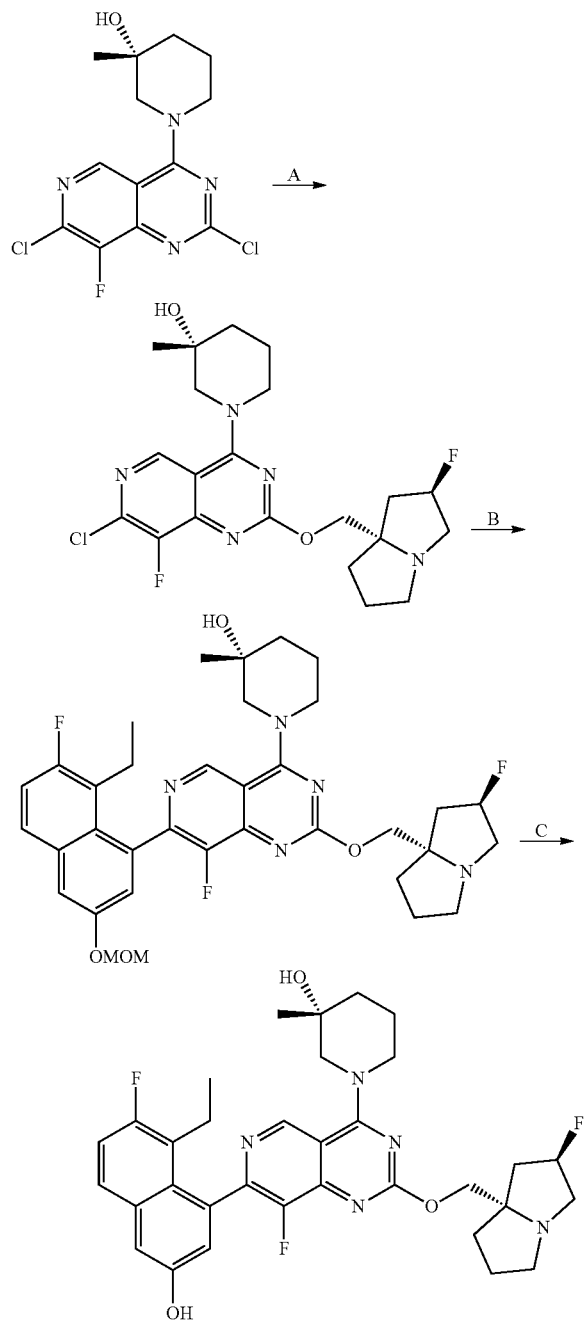

Step A. (R)-1-(7-chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To the mixture of (R)-1-(2,7-dichloro-8-fluoropyrido[4,3-d]pyrimidin-4-yl)-3-methylpiperidin-3-ol (20.0 g, 60.4 mmol), ((2R,7aS)-2-fluorohexahydro-1H-pyrrolizin-7a-yl)methanol (10.6 g, 66.4 mmol), 4 Å molecular sieves (5.00 g) in dioxane (80 mL) was added DIEA (23.4 g, 181 mmol), and the mixture was stirred at 90° C. for 10 hours. Upon completion, the reaction mixture was filtered. The mixture was diluted with ethyl acetate (300 mL) and water (200 mL), and aqueous layer was then extracted with ethyl acetate (300 mL). The combined organic phase was washed with brine (200 mL) and dried over anhydrous sodium sulfate. The mixture was filtered and concentrated to give a residue. The residue was purified by reversed phase flash chromatography [water (0.1% formic acid)/acetonitrile] to give (R)-1-(7-chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (19.5 g, 71% yield) as yellow solid; LCMS (ESI, M+1): m/z=454.2.

Step B. (R)-1-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To the solution of (R)-1-(7-chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (40.0 g, 88.1 mmol), 2-(8-ethyl-7-fluoro-3-(methoxymethoxy)naphthalen-1-yl)-4,4,5,5-tetramethyl-1,3,2-dioxaborolane (42.9 g, 119 mmol), $K_3PO_4$ (1.5 M in water, 117 mL) in THF (200 mL) was added cataCXium-A-Pd-G3cataCXium-A-Pd-G3 (6.42 g, 8.81 mmol) under $N_2$. The mixture was stirred at 65° C. for 8 hours. Upon completion, the reaction mixture was diluted with ethyl acetate (300 mL) and water (200 mL). The aqueous layer was extracted with ethyl acetate (300 mL). The combined organic phase was washed with brine (200 mL) and dried over anhydrous $Na_2SO_4$. The mixture was filtered and concentrated to give a residue. The residue was purified by reversed phase flash chromatography [water (0.1% formic acid)/acetonitrile] to give (R)-1-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (37.4 g, 65% yield) as yellow solid; LCMS (ESI, M+1): m/z=652.3.

Step C. (R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To the solution of (R)-1-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (38.0 g, 58.3 mmol) in ACN (190 mL) was added HCl.dioxane (4 M, 190 mL) at 0° C. The mixture was stirred at 0° C. for 0.5 hour. Upon completion, the mixture was concentrated to give a residue. To the residue were added ethyl acetate (300 mL) and then sat. $NaHCO_3$ (to adjust the pH to 8). The aqueous layer was extracted with ethyl acetate (300 mL). The combined organic phase was washed with brine (300 mL) and dried over with $Na_2SO_4$. The mixture was filtered and concentrated to give a residue. The residue was purified by reversed phase flash chromatography [water (0.1% formic acid)/acetonitrile]. The desired fractions were collected, and the pH value was adjusted to 8 with $NaHCO_3$ (30 g). The mixture was concentrated in vacuum to remove acetonitrile, and then was extracted with dichloromethane (2×800 mL). The combined organic layer was washed with brine (600 mL) and dried over anhydrous $Na_2SO_4$. The mixture was filtered and concentrated in vacuum. The residue was dissolved in acetonitrile (100 mL) and water (200 mL), and lyophilized to afford (R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (25.3 g, 71% yield). Yellow Solid; 1H NMR (400 MHz, $CDCl_3$) δ=9.20-8.94 (m, 1H), 7.52-7.44 (m, 1H), 7.18-7.11 (m, 1H), 7.07-7.01 (m, 1H), 6.39 (s, 1H), 5.49-5.15 (m, 1H), 4.46-3.94 (m, 5H), 3.49-2.90 (m, 7H), 2.00 (br s, 6H), 1.98-1.63 (m, 4H), 1.59-1.36 (m, 2H), 1.17 (d, J=5.6 Hz, 3H), 0.82-0.73 (m, 3H); 1H NMR (400 MHz, METHANOL-d4) δ=9.20 (d, J=0.8 Hz, 1H), 7.71-7.63 (m, 1H), 7.30 (d, J=2.8 Hz, 1H), 7.24 (t, J=9.2 Hz, 1H), 7.06 (d, J=2.4 Hz, 1H), 5.39-5.22 (m, 1H), 4.57-4.22 (m, 4H), 3.68-3.54 (m, 1H), 3.50-3.39 (m, 1H), 3.29-3.13 (m, 3H), 3.05-2.96 (m, 1H), 2.53-2.11 (m, 6H), 2.04-1.94 (m, 2H), 1.94-1.73 (m, 4H), 1.28 (d, J=9.6 Hz, 3H), 0.84-0.77 (m, 3H); LCMS (ESI, M+1): m/z=608.3.

Example 6

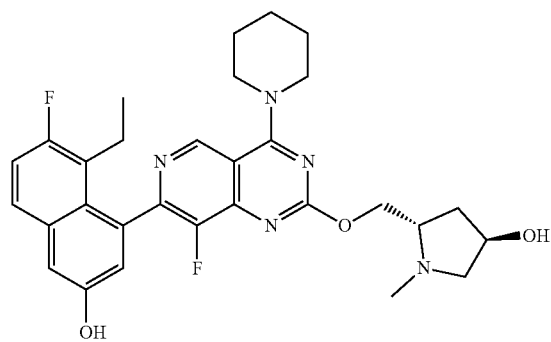 [SMILES: CCc1c(F)ccc2cc(O)cc(-c3ncc4c(N5CCCCC5)nc(OC[C@@H]5C[C@@H](O)CN5C)nc4c3F)c12]

(3R,5S)-5-(((7-(8-ethyl-7-fluoro-3-hydroxy)naphthalen-1-yl)-8-fluoro-4-(piperidin-1-yl) pyrido[4,3-d]pyrimidin-2-yl)oxy)methyl)-1-methylpyrrolidin-3-ol

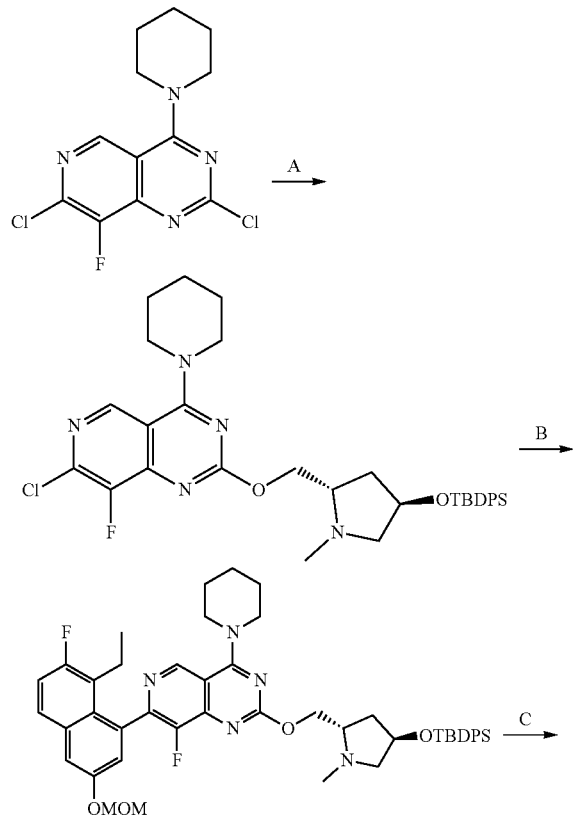

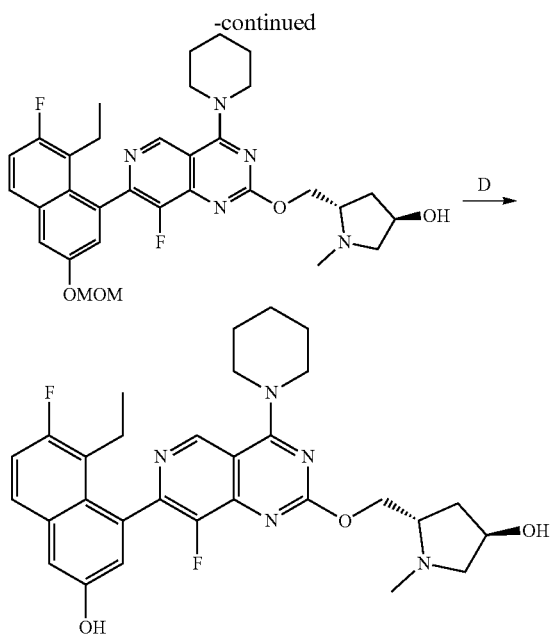

Step A. 2-(((2S,4R-4-((tert-butyldiphenylsilyl)oxy)-1-methylpyrrolidin-2-yl) methoxy-7-chloro-8-fluoro-4-(piperidin-1-yl)pyrido[4,3-d]pyrimidine: A solution of 2,7-dichloro-8-fluoro-4-(piperidin-1-yl)pyrido[4,3-d]pyrimidine (140 mg, 465 μmol) and ((2S,4R)-4-((tert-butyldiphenylsilyl)oxy)-1-methylpyrrolidin-2-yl)methanol (189 mg, 511 μmol) in toluene (3.00 mL) was added tBuONa (134 mg, 1.39 mmol). The mixture was stirred at 0° C. for 1 hr. The mixture was concentration in vacuum and was purified by prep-TLC (Silica gel, PE:EA=2:1) to give 2-(((2S,4R)-4-((tert-butyldiphenylsilyl)oxy)-1-methylpyrrolidin-2-yl)methoxy)-7-chloro-8-fluoro-4-(piperidin-1-yl)pyrido[4,3-d]pyrimidine (200 mg, 68% yield) as a yellow oil.

Step B. 2-(((2S,4R)-4-((tert-butyldiphenylsilyl)oxy)-1-methylpyrrolidin-2-yl) methoxy)-7-(8-ethyl-7-fluoro-3-(methoxymethoxy)naphthalen-1-yl)-8-fluoro-4-(piperidin-1-yl) pyrido[4,3-d]pyrimidine: A mixture of 2-(((2S,4R)-4-((tert-butyldiphenylsilyl)oxy)-1-methylpyrrolidin-2-yl) methoxy)-7-chloro-8-fluoro-4-(piperidin-1-yl)pyrido[4,3-d]pyrimidine (170 mg, 268 μmol), 2-(8-ethyl-7-fluoro-3-(methoxymethoxy)naphthalen-1-yl)-4,4,5,5-tetramethyl-1,3,2-dioxaborolane (193 mg, 536 μmol), cataCXium-A-Pd-G3cataCXium-A-Pd-G3 (19.5 mg, 26.8 μmol) and $K_3PO_4$ (1.5 M in water, 536 μL) in dioxane (5.00 mL) was degassed and purged with $N_2$ for 3 times, and then the mixture was stirred at 100° C. for 1.5 hour under $N_2$ atmosphere. The mixture was diluted with water (40.0 mL) and extracted with ethyl acetate (2×20.0 mL). The organic layers were dried over $Na_2SO_4$, concentrated in vacuum, and was purified by column (Silica gel, PE:EA=1:0 to 0:1) to give 2-(((2S,4R)-4-((tert-butyldiphenylsilyl)oxy)-1-methylpyrrolidin-2-yl) methoxy)-7-(8-ethyl-7-fluoro-3-(methoxymethoxy)naphthalen-1-yl)-8-fluoro-4-(piperidin-1-yl)pyrido[4,3-d] pyrimidine (200 mg, 54% yield, 60% purity) as a yellow oil. LCMS [ESI, M+1]: m/z=832.4.

Step C. (3R,5S)-5-(((7-(8-ethyl-7-fluoro-3-(methoxymethoxy)naphthalen-1-yl)-8-fluoro-4-(piperidin-1-yl)pyrido[4,3-d]pyrimidin-2-yl)oxy)methyl)-1-methylpyrrolidin-3-ol: To a solution of 2-(((2S,4R)-4-((tert-butyldiphenylsilyl)oxy)-1-methylpyrrolidin-2-yl)methoxy)-7-(8-ethyl-7-fluoro-3-(methoxymethoxy)naphthalen-1-yl)-

8-fluoro-4-(piperidin-1-yl)pyrido[4,3-d]pyrimidine (200 mg, 144 µmol, 60% purity) in DMF (6.0 mL) was added CsF (65.7 mg, 433 µmol, 15.9 µL). After stirred at 40° C. for 4 hours, the mixture was diluted with water (40 mL) and layers were separated. The aqueous phase was extracted with ethyl acetate (2×20 mL). Combined organic layers were dried over Na₂SO₄, filtered and concentrated in vacuum to give (3R,5S)-5-(((7-(8-ethyl-7-fluoro-3-(methoxymethoxy) naphthalen-1-yl)-8-fluoro-4-(piperidin-1-yl) pyrido[4,3-d] pyrimidin-2-yl)oxy)methyl)-1-methylpyrrolidin-3-ol (80 mg, crude) as a yellow oil. LCMS [ESI, M+1]: m/z=594.3.

Step D. (3R,5S)-5-(((7-(8-ethyl-7-fluoro-3-hydroxy) naphthalen-1-yl)-8-fluoro-4-(piperidin-1-yl)pyrido[4,3-d] pyrimidin-2-yl)oxy)methyl)-1-methylpyrrolidin-3-ol: A solution of (3R,5S)-5-(((7-(8-ethyl-7-fluoro-3-(methoxymethoxy)naphthalen-1-yl)-8-fluoro-4-(piperidin-1-yl) pyrido[4,3-d]pyrimidin-2-yl)oxy)methyl)-1-methylpyrrolidin-3-ol (80.0 mg, 135 µmol) in HCl-EtOAc (4 M, 1 mL) was stirring at 20° C. for 1 hour. The mixture was concentrated in vacuum. The pH of the mixture was adjusted to 8 with sat. NaHCO₃ (5 mL). The mixture was diluted with water (20 mL) and extracted with ethyl acetate (3×10 mL). The combined organic layers were dried over Na₂SO₄, filtered and concentrated under reduced pressure to give a residue. The residue was purified by prep-HPLC (column: water s Xbridge BEH C18 100×25 mm×5 µm; mobile phase: [water (10 mM NH₄HCO₃)-ACN]; B %: 30%-60%, 10 min) to give title compound (28.0 mg, 37% yield, 98% purity) as a white solid. 1H NMR (400 MHz, DMSO) δ 9.93 (s, 1H), 9.05 (s, 1H), 7.78-7.75 (m, 1H), 7.39-7.30 (m, 2H), 7.03 (d, J=2.6 Hz, 1H), 4.78 (d, J=4.4 Hz, 1H), 4.43-4.34 (m, 1H), 4.28-4.12 (m, 2H), 3.94 (s, 4H), 3.20-3.17 (m, 1H), 2.81 (s, 1H), 2.34 (s, 4H), 2.19-2.06 (m, 2H), 1.90-1.72 (m, 8H), 0.73 (t, J=7.3 Hz, 3H); LCMS [ESI, M+1]: m/z=550.3.

Example 7

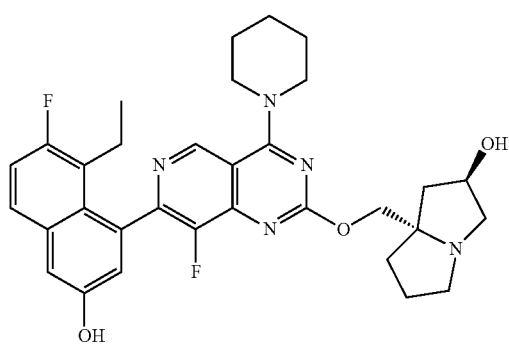 [SMILES: CCc1c(F)ccc2cc(O)cc(-c3ncc4c(N5CCCCC5)nc(OC[C@@]56CCCN5C[C@H](O)C6)nc4c3F)c12]

(2R,7aS)-7a-(((7-(8-ethyl-7-fluoro-3-hydroxy)naphthalen-1-yl)-8-fluoro-4-(piperidin-1-yl) pyrido[4,3-d]pyrimidin-2-yl)oxy)methyl)hexahydro-1H-pyrrolizin-2-ol

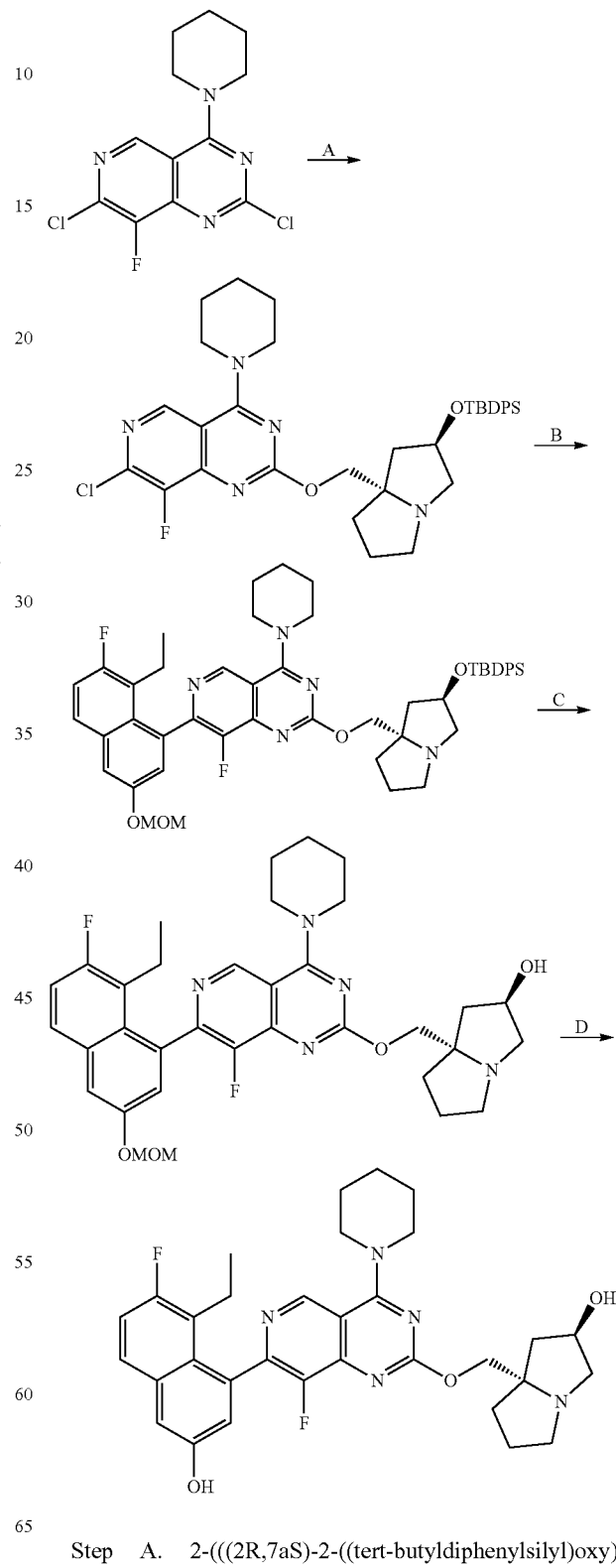

Step A. 2-(((2R,7aS)-2-((tert-butyldiphenylsilyl)oxy) hexahydro-1H-pyrrolizin-7a-yl) methoxy)-7-chloro-8- fluoro-4-(piperidin-1-yl)pyrido[4,3-d]pyrimidine: A solution of 2,7-dichloro-8-fluoro-4-(1-piperidyl)pyrido[4,3-d]pyrimidine (200 mg, 664 μmol) and ((2R,7aS)-2-((tert-butyldiphenylsilyl)oxy)tetrahydro-1H-pyrrolizin-7a(5H)-yl)methanol (315 mg, 797 μmol) in toluene (3.00 mL) was added drop-wise t-BuONa (191 mg, 1.99 mmol). The mixture was stirred at 0° C. for 1 hour under $N_2$. The reaction mixture was quenched by the addition of water (50.0 mL) at 0° C., and extracted with DCM (30.0 mL×3). The combined organic layers were washed with brine (40.0 mL), dried over $Na_2SO_4$, filtered and concentrated in vacuum. The residue was purified by prep-TLC (Silica gel, EtOAc/MeOH=50/1) to give 2-(((2R,7aS)-2-((tert-butyldiphenylsilyl)oxy)hexahydro-1H-pyrrolizin-7a-yl)methoxy)-7-chloro-8-fluoro-4-(piperidin-1-yl)pyrido[4,3-d]pyrimidine (300 mg, 68% yield) was obtained as a yellow solid. $^1$H NMR (400 MHz, CDCl$_3$) δ=8.69 (s, 1H), 7.70-7.62 (m, 4H), 7.45-7.31 (m, 6H), 4.55-4.44 (m, 1H), 4.17-4.08 (m, 1H), 4.04-3.96 (m, 1H), 3.87-3.80 (m, 4H), 3.50 (s, 2H), 3.19-2.99 (m, 3H), 2.83-2.73 (m, 1H), 2.20-1.82 (m, 7H), 1.75-1.70 (m, 2H), 1.52-1.31 (m, 1H), 1.06 (s, 9H). LCMS [ESI, M+1]: m/z=660.4.

Step B. 2-(((2R,7aS)-2-((tert-butyldiphenylsilyl)oxy)hexahydro-1H-pyrrolizin-7a-yl) methoxy)-7-(8-ethyl-7-fluoro-3-(methoxymethoxy)naphthalen-1-yl)-8-fluoro-4-(piperidin-1-yl) pyrido[4,3-d]pyrimidine: To a solution of 2-(((2R,7aS)-2-((tert-butyldiphenylsilyl)oxy)hexahydro-1H-pyrrolizin-7a-yl)methoxy)-7-chloro-8-fluoro-4-(piperidin-1-yl)pyrido[4,3-d]pyrimidine (240 mg, 363 μmol), and 2-(8-ethyl-7-fluoro-3-(methoxymethoxy)naphthalen-1-yl)-4,4,5,5-tetramethyl-1,3,2-dioxaborolane (393 mg, 1.09 mmol) in dioxane (5.00 mL) were added $K_3PO_4$ (1.50 M, 727 μL) and cataCXium-A-Pd-G3cataCXium-A-Pd-G3 (26.5 mg, 36.4 μmol) under $N_2$. The mixture was stirred at 100° C. for 1 hour under $N_2$. The reaction mixture was quenched with water (60 mL) at 0° C. and extracted with EtOAc (30:0 mL×3). The combined organic layers were washed with brine (40.0 mL), dried over $Na_2SO_4$, filtered and concentrated under reduced pressure to give a residue. The residue was purified by prep-TLC (Silica gel, EtOAc/MeOH=50/1) to give the title compound (300 mg, 77% yield) as a yellow solid; LCMS [ESI, M+1]: m/z=858.4.

Step C. (2R,7aS)-7a-(((7-(8-ethyl-7-fluoro-3-(methoxymethoxy)naphthalen-1-yl)-8-fluoro-4-(piperidin-1-yl)pyrido[4,3-d]pyrimidin-2-yl)oxy)methyl)hexahydro-1H-pyrrolizin-2-ol: To a solution of 2-(((2R,7aS)-2-((tert-butyldiphenylsilyl)oxy)hexahydro-1H-pyrrolizin-7a-yl)methoxy)-7-(8-ethyl-7-fluoro-3-(methoxymethoxy)naphthalen-1-yl)-8-fluoro-4-(piperidin-1-yl) pyrido[4,3-d]pyrimidine (250 mg, 262 μmol, 90% purity) in DMF (1.00 mL) was added CsF (398 mg, 2.62 mmol, 96.7 μL). The mixture was stirred at 40° C. for 4 hrs. The reaction mixture was quenched with water (40.0 mL) at 0° C. and extracted with EtOAc (30.0 mL×3). The combined organic layers were washed with brine (30 mL), dried over $Na_2SO_4$, filtered and concentrated under reduced pressure to give the title compound (150 mg, crude) as a yellow solid. LCMS [ESI, M+1]m/z=620.4.

Step D. (2R,7aS)-7a-(((7-(8-ethyl-7-fluoro-3-hydroxy)naphthalen-1-yl)-8-fluoro-4-(piperidin-1-yl)pyrido[4,3-d]pyrimidin-2-yl)oxy)methyl)hexahydro-1H-pyrrolizin-2-ol: To a solution of (2R,7aS)-7a-(((7-(8-ethyl-7-fluoro-3-(methoxymethoxy)naphthalen-1-yl)-8-fluoro-4-(piperidin-1-yl)pyrido[4,3-d]pyrimidin-2-yl)oxy)methyl)hexahydro-1H-pyrrolizin-2-ol (100 mg, 129 μmol, 80% purity) in EtOAc (1.00 mL) was added drop-wise HCl/EtOAc (4 M, 1.00 mL). The mixture was stirred at 20° C. for 12 hrs. The reaction mixture was quenched with sat. NaHCO$_3$ (20.0 mL) at 0° C. and then extracted with EtOAc (15.0 mL×3). The combined organic layers were washed with brine (20.0 mL) and dried over $Na_2SO_4$. The mixture was filtered and concentrated under reduced pressure to give a residue. The residue was purified by prep-HPLC (column: water s Xbridge BEH C18 100×25 mm×5 μm; mobile phase: [water (10 mM NH$_4$HCO$_3$)-ACN]; B %: 25%-65%, 10 min) to give the title compound (19.85 mg, 26% yield, 99.0% purity) as a light-yellow solid; $^1$H NMR (400 MHz, DMSO-d$_6$) δ=9.93 (s, 1H), 9.04 (s, 1H), 7.81-7.73 (m, 1H), 7.38-7.30 (m, 2H), 7.04-7.00 (m, 1H), 4.80-4.72 (m, 1H), 4.36-4.24 (m, 1H), 4.07-3.86 (m, 6H), 3.10-3.01 (m, 1H), 2.97-2.88 (m, 1H), 2.82-2.71 (m, 1H), 2.45 (br s, 1H), 2.41-2.29 (m, 1H), 2.15-2.08 (m, 2H), 1.93-1.68 (m, 10H), 1.64-1.54 (m, 1H), 0.76%-0.68 (m, 3H). LCMS [ESI, M+1]: m/z=576.1

Example 8

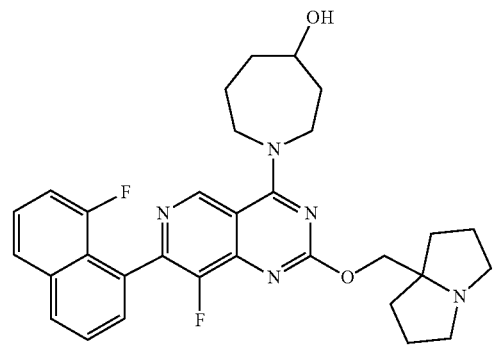 [SMILES: OC1CCCN(c2nc(OCC34CCCN3CCC4)nc3c(F)c(-c4cccc5cccc(F)c45)ncc23)CC1]

1-(8-fluoro-7-(8-fluoronaphthalen-1-yl)-2-((hexahydro-1H-pyrrolizin-7a-yl)methoxy)pyrido[4,3-d]pyrimidin-4-yl)azepan-4-ol

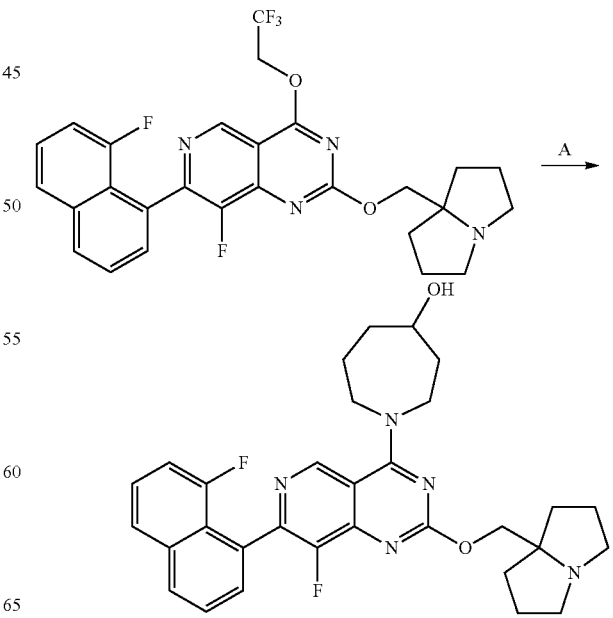

Step A. 1-(8-fluoro-7-(8-fluoronaphthalen-1-yl)-2-((hexahydro-1H-pyrrolizin-7a-yl) methoxy)pyrido[4,3-d]pyrimidin-4-yl)azepan-4-ol: To a solution of 8-fluoro-7-(8-fluoronaphthalen-1-yl)-2-((hexahydro-1H-pyrrolizin-7a-yl) methoxy)-4-(2,2,2-trifluoroethoxy)pyrido[4,3-d]pyrimidine (100 mg, 189 µmol) and azepan-4-ol hydrochloride (42.9 mg, 283 µmol, HCl) in DMF (3.00 mL) was added DIEA (73.1 mg, 566 µmol, 98.5 µL, 3 equiv.). The mixture was stirred at 60° C. for 16 hours. Upon completion, the mixture was filtered. The filtrate was purified by prep-HPLC (column: water s Xbridge BEH C18 100×25 mm×5 µm; mobile phase: [water (10 mM NH$_4$HCO$_3$)-ACN]; B %: 20%-60%, 10 min) and re-purified by prep-HPLC (column: Welch Xtimate C18 150×25 mm×5 µm; mobile phase: [water (0.04% HCl)-ACN]; B %: 10%-35%, 8 min) affording 1-(8-fluoro-7-(8-fluoronaphthalen-1-yl)-2-((hexahydro-1H-pyrrolizin-7a-yl)methoxy)pyrido[4,3-d]pyrimidin-4-yl)azepan-4-ol (23.8 mg, 37% yield, HCl salt) as a white solid; $^1$H NMR (400 MHz, DMSO-d$_6$) δ=11.04 (br s, 1H), 9.25 (s, 1H), 8.22 (d, J=8.0 Hz, 1H), 7.96 (d, J=8.0 Hz, 1H), 7.80-7.73 (m, 1H), 7.68 (d, J=6.4 Hz, 1H), 7.64-7.56 (m, 1H), 7.34 (dd, J=7.2, 13.2 Hz, 1H), 4.63 (s, 2H), 4.15-4.03 (m, 3H), 4.02-3.93 (m, 1H), 3.87-3.77 (m, 1H), 3.60-3.45 (m, 2H), 3.25-3.12 (m, 2H), 2.24-1.92 (m, 1H), 1.90-1.79 (m, 1H), 1.78-1.68 (m, 1H), 1.68-1.57 (m, 1H); $^1$H NMR (400 MHz, MeOD-d$_4$) δ=9.35 (s, 1H), 8.28-8.19 (m, 1H), 7.93 (d, J=8.0 Hz, 1H), 7.81-7.73 (m, 2H), 7.66-7.56 (m, 1H), 7.34-7.25 (m, 1H), 4.83 (s, 2H), 4.41-4.15 (m, 4H), 4.12-3.97 (m, 1H), 3.81-3.69 (m, 2H), 3.36-3.32 (m, 1H), 3.30-3.27 (m, 1H), 2.45-2.32 (m, 3H), 2.32-2.21 (m, 5H), 2.20-2.09 (m, 3H), 2.07-1.97 (m, 1H), 1.95-1.78 (m, 2H); LCMS [ESI, M+1]: m/z=546.2.

Example 9

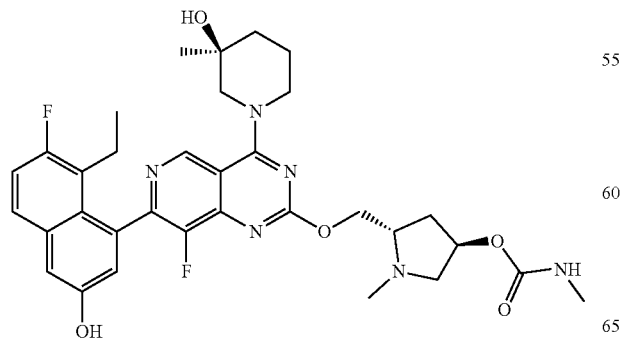

[(3R,5S)-5-[[7-(8-ethyl-7-fluoro-3-hydroxy-1-naphthyl)-8-fluoro-4-[(3S)-3-hydroxy-3-methyl-1-piperidyl]pyrido[4,3-d]pyrimidin-2-yl]oxymethyl]-1-methyl-pyrrolidin-3-yl] N-methylcarbamate

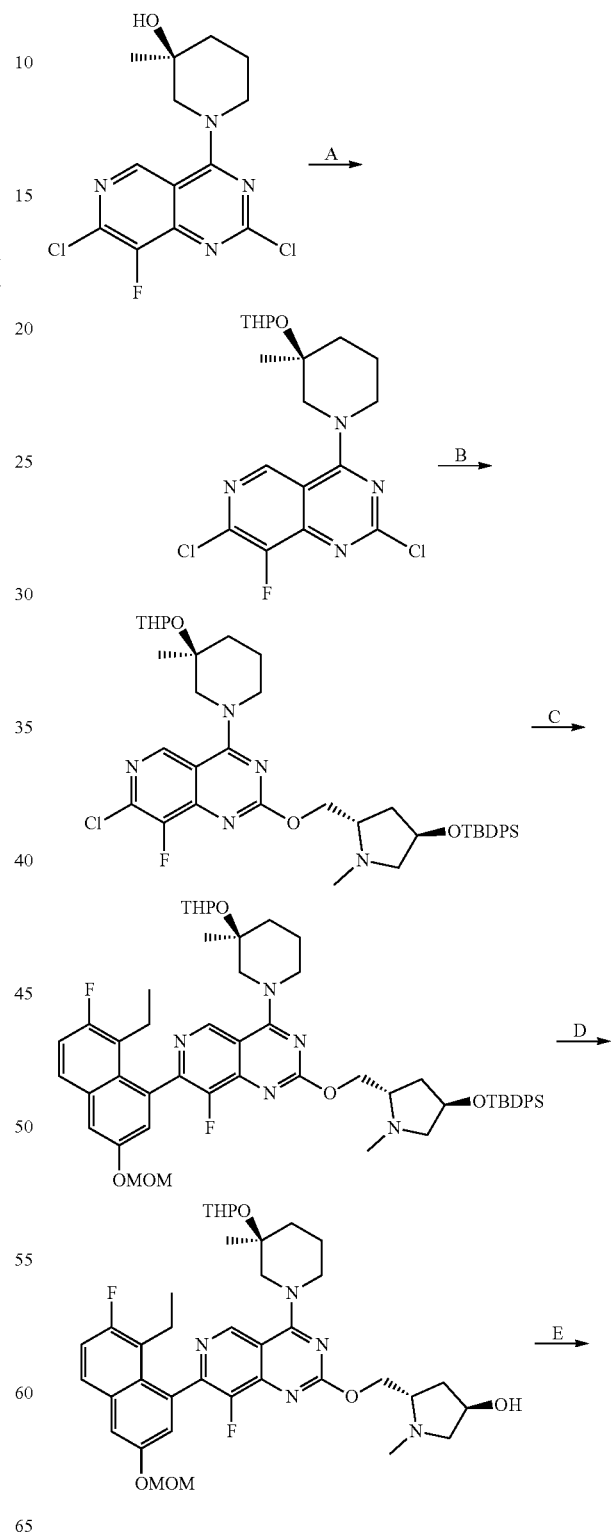

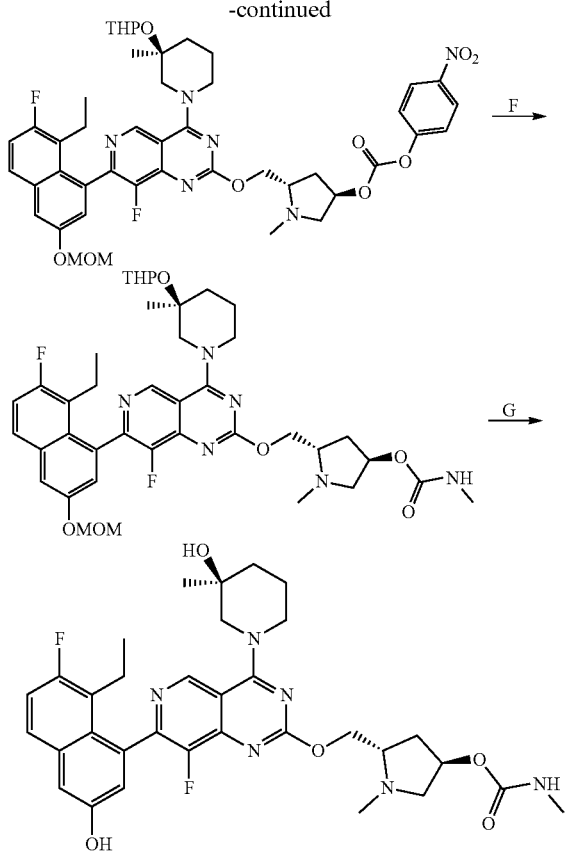

Step A. 2,7-dichloro-8-fluoro-4-((3S)-3-methyl-3-((tetrahydro-2H-pyran-2-yl) oxy)piperidin-1-yl)pyrido[4,3-d]pyrimidine: To the mixture of (S)-1-(2,7-dichloro-8-fluoropyrido[4,3-d]pyrimidin-4-yl)-3-methylpiperidin-3-ol (2.00 g, 6.04 mmol), TsOH·WATER (115 mg, 605 µmol) in dichloromethane (30 mL) was added 3,4-dihydro-2H-pyran (1.02 g, 12.1 mmol) at 0° C. The mixture was stirred at 20° C. for 1.5 h. After completion, the mixture was diluted with dichloromethane (30 mL). The mixture was washed with sat. NaHCO₃ (40 mL) wad the aqueous solution was extracted with dichloromethane (30 mL). The combined organic phase was washed with brine (50 mL) and dried over anhydrous sodium sulfate. The mixture was filtered and concentrated to give a residue. The residue was purified by column chromatography (10% to 50% EA/PE) to give the title compound (1.95 g, 65% yield) as yellow oil; LCMS (ESI, M+1): m/z=415.4

Step B. 2-(((2S,4R)-4-((tert-butyldiphenylsilyl)oxy)-1-methylpyrrolidin-2-yl) methoxy)-7-chloro-8-fluoro-4-(3S)-3-methyl-3-((tetrahydro-2H-pyran-2-yl)oxy)piperidin-1-yl)pyrido[4,3-d]pyrimidine: To the mixture of 2,7-dichloro-8-fluoro-4-((3S)-3-methyl-3-((tetrahydro-2H-pyran-2-yl)oxy)piperidin-1-yl)pyrido[4,3-d]pyrimidine (1.48 g, 3.57 mmol) and ((2S,4R)-4-((tert-butyldiphenylsilyl)oxy)-1-methylpyrrolidin-2-yl)methanol (1.45 g, 3.92 mmol) in dioxane (12 mL) was added DIEA (1.38 g, 10.7 mmol). The mixture was stirred at 90° C. for 10 h. The mixture was concentrated to give a residue. The residue was purified by reversed phase flash chromatography [water (0.1% formic acid)/acetonitrile] to give the title compound (1.00 g, 36% yield) as yellow solid; ¹H NMR (400 MHz, CDCl₃-d): δ 9.07-8.95 (m, 1H), 7.68-7.60 (m, 4H), 7.44-7.34 (m, 6H), 4.88-4.66 (m, 1H), 4.52-4.44 (m, 2H), 4.42-4.29 (m, 2H), 4.26-4.19 (m, 1H), 3.90-3.58 (m, 1H), 3.51-2.95 (m, 5H), 2.47 (d, J=1.2 Hz, 3H), 2.43-2.36 (m, 1H), 2.19-2.06 (m, 2H), 2.05-1.84 (m, 2H), 1.73-1.65 (m, 1H), 1.55-1.33 (m, 5H), 1.31-1.23 (m, 5H), 1.06 (s, 9H). LCMS (ESI, M+1): m/z=748.3.

Step C. 2-(((2S,4R)-4-((tert-butyldiphenylsilyl)oxy-1-methylpyrrolidin-2-yl) methoxy)-7-(8-ethyl-7-fluoro-3-(methoxymethoxy)naphthalen-1-yl)-8-fluoro-4-4 (3S)-3-methyl-3-((tetrahydro-2H-pyran-2-yl)oxy)piperidin-1-yl) pyrido[4,3-d]pyrimidine: To the mixture of 2-(((2S,4R)-4-((tert-butyldiphenylsilyl)oxy)-1-methylpyrrolidin-2-yl) methoxy)-7-chloro-8-fluoro-4-((3S)-3-methyl-3-((tetrahydro-2H-pyran-2-yl)oxy)piperidin-1-yl)pyrido[4,3-d]pyrimidine (400 mg, 534 µmol), 2-(8-ethyl-7-fluoro-3-(methoxymethoxy)naphthalen-1-yl)-4,4,5,5-tetramethyl-1,3,2-dioxaborolane (384 mg, 1.07 mmol), K₃PO₄ (1.50 M, 1.07 mL) in toluene (8 mL) was added [2-(2-aminophenyl)phenyl]palladium(1+); bis(1-adamantyl)-butyl-phosphane; methanesulfonate (38.9 mg, 53.4 µmol). The mixture was degassed and stirred at 90° C. for 1.5 h. The reaction mixture was diluted with ethyl acetate (30 mL) and water (15 mL), and the aqueous layer was extracted with ethyl acetate (20 mL). The combined organic phase was washed with brine (10 mL) and dried over anhydrous sodium sulfate. The mixture was filtered and concentrated to give a residue. The residue was purified by reversed phase flash chromatography [water (0.1% formic acid)/acetonitrile, MeOH] to give title compound (400 mg, 78% yield) as yellow solid; LCMS (ESI, M+1): m/z=946.3.

Step D. (3R,5S)-5-(((7-(8-ethyl-7-fluoro-3-(methoxymethoxy)naphthalen-1-yl)-8-fluoro-4-((3 S)-3-methyl-3-((tetrahydro-2H-pyran-2-l)oxy)piperidin-1-yl) pyrido[4,3-d]pyrimidin-2-yl)oxy)methyl)-1-methylpyrrolidin-3-ol: To the mixture of 2-(((2S,4R)-4-((tert-butyldiphenylsilyl)oxy)-1-methylpyrrolidin-2-yl) methoxy)-7-(8-ethyl-7-fluoro-3-(methoxymethoxy) naphthalen-1-yl)-8-fluoro-4-((3S)-3-methyl-3-((tetrahydro-2H-pyran-2-yl) oxy)piperidin-1-yl)pyrido[4,3-d]pyrimidine (950 mg, 1.00 mmol) in DMF (10 mL) was added CsF (2.28 g, 15.0 mmol). The mixture was stirred at 40° C. for 4 h. The mixture was filtered and the filtrate was purified by reversed phase flash chromatography [water (0.1% formic acid)/acetonitrile] to give the title compound (600 mg, 83% yield) as yellow solid; LCMS (ESI, M+1): m/z=708.4.

Step E. (3R,5S)-5-(((7-(8-ethyl-7-fluoro-3-(methoxymethoxy)naphthalen-1-yl)-8-fluoro-4-((3S)-3-methyl-3-((tetrahydro-2H-pyran-2-yl)oxy)piperidin-1-yl) pyrido[4,3-d]pyrimidin-2-yl)oxy)methyl)-1-methylpyrrolidin-3-yl (4-nitrophenyl) carbonate: To the mixture of (3R,5S)-5-(((7-(8-ethyl-7-fluoro-3-(methoxymethoxy)naphthalen-1-yl)-8-fluoro-4-((3S)-3-methyl-3-((tetrahydro-2H-pyran-2-yl)oxy)piperidin-1-yl) pyrido[4,3-d]pyrimidin-2-yl) oxy)methyl)-1-methylpyrrolidin-3-ol (100 mg, 141 µmol), and (4-nitrophenyl) carbonochloridate (103 mg, 509 µmol) in THF (4 mL) was added t-BuOK (1 M in THF, 424 µl) at 0° C. The mixture was stirred at 15° C. for 0.5 h. The mixture was diluted with ethyl acetate (10 mL) and water (5 mL), and the aqueous layer was extracted with ethyl acetate (10 mL). The combined organic phase was washed with brine (10 mL) and dried over anhydrous sodium sulfate. The mixture was filtered and concentrated to give a residue. The residue was purified by reversed phase flash chromatography [water (0.1% formic acid)/acetonitrile] to give the title compound (110 mg, 84% yield) as yellow oil; LCMS (ESI, M+1): m/z 873.3.

Step F. [(3R,5S)-5-[[7-[8-ethyl-7-fluoro-3-(methoxymethoxy)-1-naphthyl]-8-fluoro-4-[(3S)-3-methyl-3-tetrahydropyran-2-yloxy-1-piperidyl]pyrido[4,3-d]pyrimidin-2-yl]oxymethyl]-1-methyl-pyrrolidin-3-yl] N-methylcarbamate: A mixture of (3R,5S)-5-(((7-(8-ethyl-7-fluoro-3-(methoxymethoxy)naphthalen-1-yl)-8-fluoro-4-((3S)-3-methyl-3-((tetrahydro-2H-pyran-2-yl)oxy)piperidin-1-yl)pyrido[4,3-d]pyrimidin-2-yl)oxy)methyl)-1-methylpyrrolidin-3-yl (4-nitrophenyl) carbonate (52.0 mg, 59.6 µmol) and methanamine (2 M in THF, 745 µl) in DMF (1 mL) was stirred at 25° C. for 0.5 h. After completion, the residue was purified by reversed phase flash chromatography [water (0.1% formic acid)/acetonitrile] to give the title compound (29.0 mg, 51% yield) as yellow solid. LCMS (ESI, M+1): m/z=765.2.

Step G. [(3R,5S)₅-[[7-(8-ethyl-7-fluoro-3-hydroxy-1-naphthyl]-8-fluoro-4-[(3S)-3-hydroxy-3-methyl-1-piperidyl]pyrido[4,3-d]pyrimidin-2-yl)oxymethyl]-1-methylpyrrolidin-3-yl] N-methylcarbamate: To a mixture of [(3R,5S)-5-[[7-[8-ethyl-7-fluoro-3-(methoxymethoxy)-1-naphthyl]-8-fluoro-4-[(3S)-3-methyl-3-tetrahydropyran-2-yloxy-1-piperidyl]pyrido[4,3-d]pyrimidin-2-yl]oxymethyl]-1-methyl-pyrrolidin-3-yl] N-methylcarbamate (41.0 mg, 53.6 µmol) in MeCN (0.7 mL) was added HCl-MeOH (4 M, 1.4 mL) at 0° C. The mixture was stirred at 0° C. for 1 h. After completion, the mixture was concentrated in vacuum. Then the pH value was adjusted to 8 with saturated NaHCO₃ solution. The mixture was triturated with methanol (2×10 mL) and filtered. The filtrate was concentrated in vacuum. The residue was purified by prep-HPLC (Phenomenex Gemini-NX C18 75*30 mm*3 um; mobile phase: [water (0.05% ammonia hydroxide v/v)-ACN]; B %: 23%-53%, 11.5 min) to afford the title compound (18.6 mg, 54% yield) as white solid. ¹H NMR (400 MHz, METHANOL-d4): δ 9.21 (d, J=2.4 Hz, 1H), 7.67 (dd, J=5.6, 8.8 Hz, 1H), 7.29 (d, J=2.8 Hz, 1H), 7.24 (t, J=9.2 Hz, 1H), 7.06 (t, J=2.0 Hz, 1H), 5.10-5.04 (m, 1H), 4.57-4.47 (m, 3H), 4.29 (br t, J=12.2 Hz, 1H), 3.68-3.57 (m, 1H), 3.53-3.42 (m, 2H), 3.09-3.00 (m, 1H), 2.69 (s, 3H), 2.52 (s, 3H), 2.50-2.41 (m, 2H), 2.22-2.08 (m, 4H), 1.92-1.75 (m, 3H), 1.28 (d, J=10.0 Hz, 3H), 0.81 (q, J=7.6 Hz, 3H). ¹⁹F NMR (400 MHz, METHANOL-d4) δ=−121.268, −139.169. HPLC:>99% ee, Chiralcel OD-3 50×4.6 mm I.D., 3 µm A: 60% MeOH+40% ACN (w/0.05% DEA), B: CO₂, 3 mL/min, 220 nm, t_R: 0.597 min; LCMS (ESI, M+1): m/z=637.0.

Example 10

(S)-1-(7-(8-ethynyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol

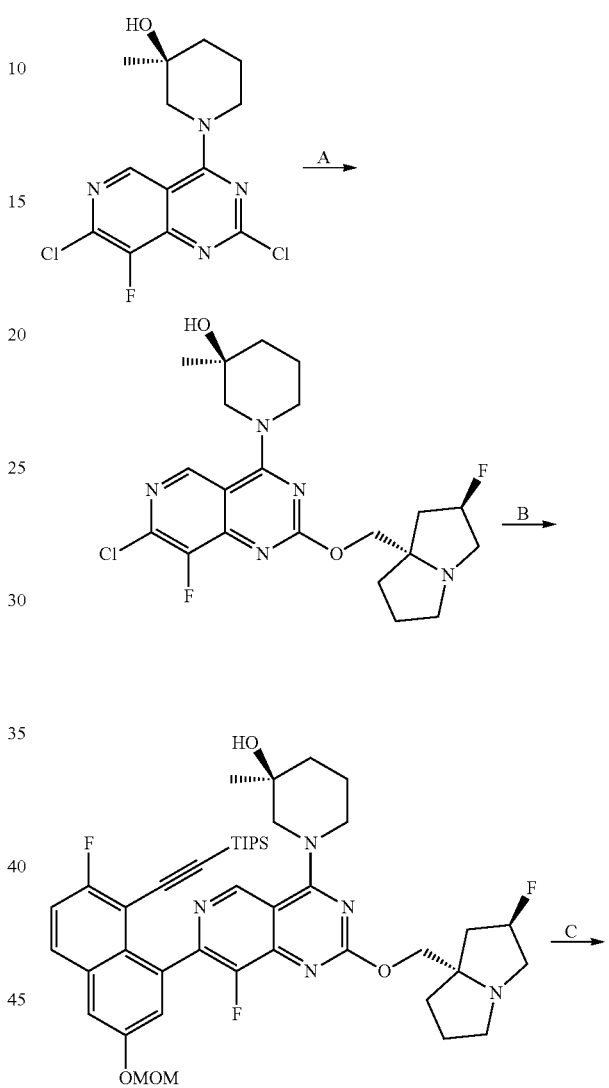

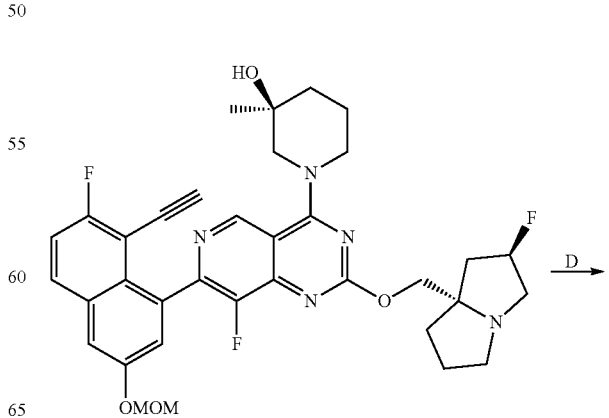

-continued

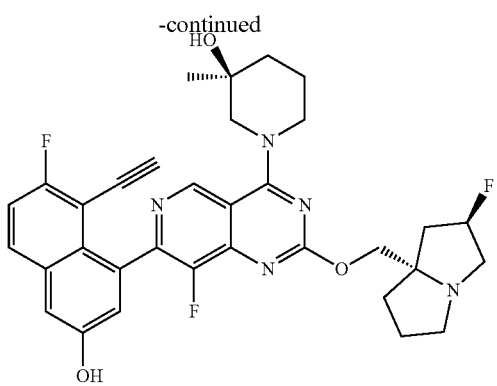

Step A. (S)-1-(7-chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: A mixture of (S)-1-(2,7-dichloro-8-fluoropyrido[4,3-d]pyrimidin-4-yl)-3-methylpiperidin-3-ol (300 mg, 906 μmol), ((2R,7aS)-2-fluorohexahydro-1H-pyrrolizin-7a-yl)methanol (150 mg, 942 μmol), DIPEA (311 mg, 2.41 mmol) and 4 Å molecular sieves (150 mg) in dioxane (1.8 mL) was stirred at 90° C. for 24 hours under $N_2$ atmosphere. The reaction mixture was filtered, and the filter cake was washed with dichloromethane (20 mL). The filtrate was concentrated under reduced pressure and the residue was purified by reversed phase flash chromatography [water (0.1% formic acid)/acetonitrile=4/1] to give the title compound as light yellow foam (247 mg, 57% yield). LCMS (EST, M+1): m/z=454.2.

Step B. (S)-1-(8-fluoro-7-(7-fluoro-3-(methoxymethoxy)-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)-3-methylpiperidin-3-ol: A mixture of (S)-1-(7-chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (290 mg, 639 μmol), $K_3PO_4$ (1.5 M in water, 1.3 mL) in THF (5.2 mL) was degassed and purged with $N_2$ for 3 times. cataCXium-A-Pd-G3 (47 mg, 64.5 μmol) and ((2-fluoro-6-(methoxymethoxy)-8-(4,4,5,5-tetramethyl-1,3,2-dioxaborolan-2-yl)naphthalen-1-yl) ethynyl)triisopropylsilane (460 mg, 898 μmol) were added. The reaction mixture was stirred at 65° C. for 6 hours. The reaction mixture was diluted with water (1 mL) and brine (1 mL), and then extracted with ethyl acetate (2 mL×4). The combined organic layers were concentrated under reduced pressure and purified by reversed phase flash chromatography [water (0.1% formic acid)/acetonitrile-9/11] to give title compound as light yellow foam (410 mg, 77% yield). LCMS (ESI, M+1): m/z=804.1.

Step C. (S)-1-(7-(8-ethynyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a solution of (S)-1-(8-fluoro-7-(7-fluoro-3-(methoxymethoxy)-8-((triisopropylsilyl)ethynyl)naphthalen-1-yl)-2-(((2R,7aS)-2-fluorohexahydro-1H-pyrrolizin-7a-yl) methoxy)pyrido[4,3-d]pyrimidin-4-yl)-3-methylpiperidin-3-ol (400 mg, 497 μmol) in DMF (3 mL) was added CsF (760 mg, 5.00 mmol). The mixture was stirred at 15° C. for 1 hour. The reaction mixture was filtered. The filtrate was purified by reversed phase flash chromatography [water (0.1% formic acid)/acetonitrile=3/2] to give the title compound as light yellow solid (310 mg, 95% yield). LCMS (ESI, M+1): m/z=648.2.

Step D. (S)-1-(7-(8-ethynyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a solution of (S)-1-(7-(8-ethynyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (100 mg, 154 μmol) in MeCN (1.5 mL) was dropwise added HCl/dioxane (4 M, 1.5 mL) at 0° C. The mixture was stirred at 0° C. for 0.5 hour. The reaction mixture was concentrated under reduced pressure to give a residue. The residue was dissolved in ethyl acetate (5 mL) and treated with saturated $NaHCO_3$ aqueous (5 mL). The mixture was extracted with ethyl acetate (5 mL×3). The combined organic layers were dried over anhydrous $Na_2SO_4$ and concentrated to give a residue. The residue was purified by prep-HPLC (column: Phenomenex Gemini-NX C18 75×30 mm×3 um; mobile phase: [water (0.225% formic acid)-ACN]; B %: 15%-45%, 9 min) to give the title compound as yellow solid (59.5 mg, 61% yield, 0.5 FORMIC ACID). $^1$H NMR (400 MHz, methanol-d4) δ=9.16 (d, J=51.2, 1H); 7.88-7.84 (m, 1H), 7.36-7.29 (m, 2H), 7.23 (dd, J=2.4, 17.2 Hz, 1H), 5.43 (d, J=51.8, 1H), 4.65-4.38 (m, 4H), 3.66-3.35 (m, 6H), 3.27-3.20 (m, 1H), 2.45-1.75 (m, 10H), 1.27 (d, J=20.0, 3H). $^{19}$F NMR (377 MHz, methanol-d4) δ=−111.68, −140.68, −173.93. LCMS (ESI, M+1): m/z=604.1.

Example 11

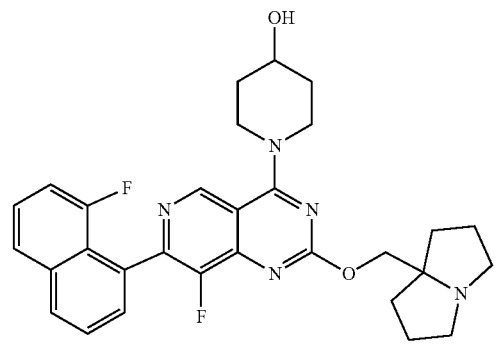 [SMILES: OC1CCN(c2nc(OCC34CCCN3CCC4)nc3c(F)c(-c4cccc5cccc(F)c45)ncc23)CC1]

1-(8-fluoro-7-(8-fluoronaphthalen-1-yl)-2-((hexahydro-1H-pyrrolizin-7a-yl)methoxy)pyrido[4,3-d]pyrimidin-4-yl)piperidin-4-ol

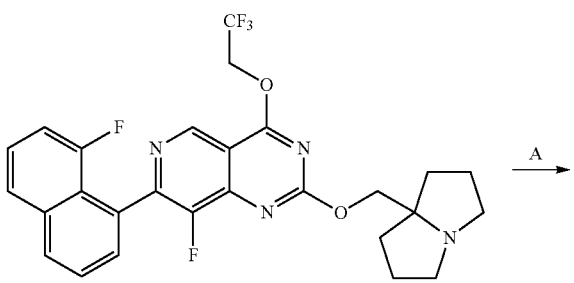

137
-continued

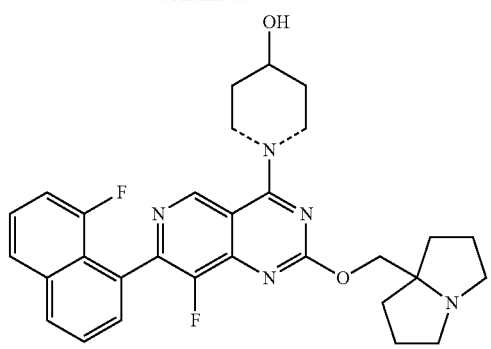

Step A: 1-(8-fluoro-7-(8-fluoronaphthalen-1-yl)-2-((hexahydro-1H-pyrrolizin-7a-yl) methoxy)pyrido[4,3-d]pyrimidin-4-ylpiperidin-4-ol: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 94.3 μmol) in DMF (2.00 mL) were added piperidin-4-ol (19.1 mg, 189 μmol) and DIEA (36.5 mg, 283 μmol, 49.3 μL). The reaction was degassed and purged with $N_2$ for 3 times and stirred at 40° C. for 2 hours. Upon completion, the reaction was filtered and purified by prep-HPLC (column: water s Xbridge BEH C18 100×25 mm×5 μm; mobile phase: [water (10 mM $NH_4HCO_3$)-ACN]; B %: 20%-60%, 10 min) affording the title compound (24.1 mg, 48% yield, 99.9% purity) as a white solid. $^1$H NMR (400 MHz, MeOD) δ=9.04 (s, 1H), 8.11 (d, J=8.4 Hz, 1H), 7.85 (d, J=8.4 Hz, 1H), 7.74-7.66 (m, 1H), 7.63-7.57 (m, 1H), 7.57-7.48 (m, 1H), 7.19 (dd, J=7.6, 12.8 Hz, 1H), 4.49-4.35 (m, 2H), 4.28 (s, 2H), 4.11-3.97 (m, 1H), 3.87-3.71 (m, 2H), 3.15-3.01 (m, 2H), 2.78-2.63 (m, 2H), 2.15-2.02 (m, 4H), 1.97-1.82 (m, 4H), 1.80-1.69 (m, 4H); LCMS (ESI, M+1): m/z 532.1.

Example 12

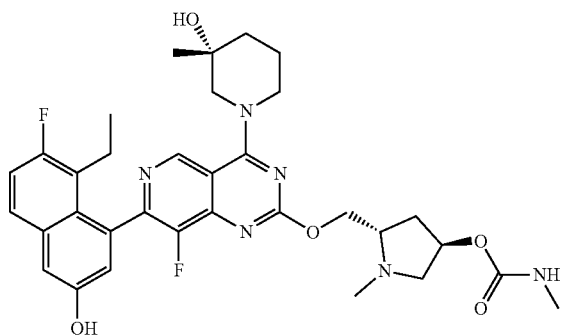 [SMILES: CCc1c(F)ccc2cc(O)cc(-c3ncc4c(N5CCC[C@@](C)(O)C5)nc(OC[C@@H]5C[C@@H](OC(=O)NC)CN5C)nc4c3F)c12]

138

(3R,5S)-5-(((7-(8-ethyl-7-fluoro-3-hydroxy)naphthalen-1-yl)-8-fluoro-4-((R)-3-hydroxy-3-methylpiperidin-1-yl)pyrido[4,3-d]pyrimidin-2-yl)oxy)methyl)-1-methylpyrrolidin-3-yl methylcarbamate

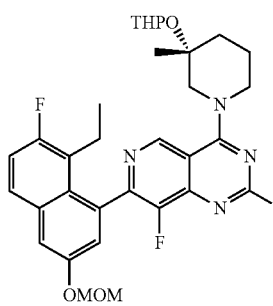

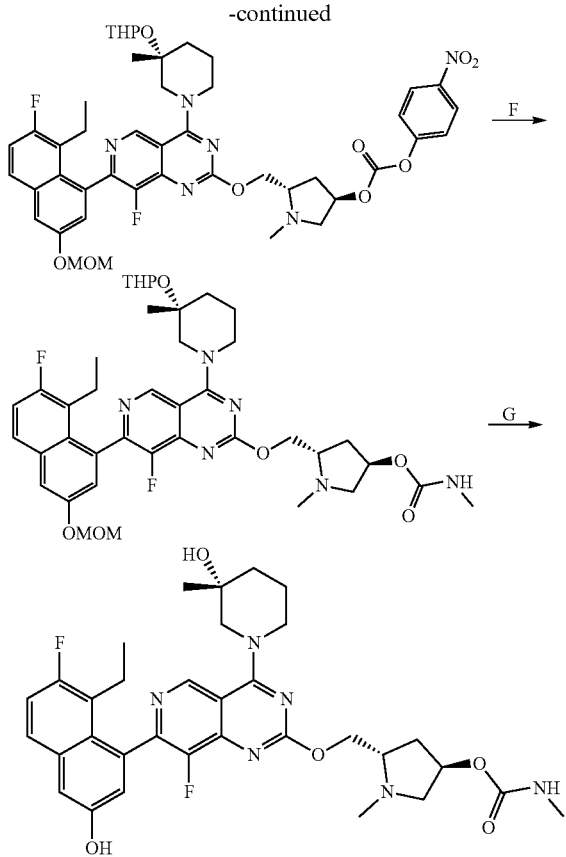

Step A. 2,7-dichloro-8-fluoro-4-((3R)-3-methyl-3-((tetrahydro-2H-pyran-2-yl) oxy)piperidin-1-yl)pyrido[4,3-d]: A mixture of (R)-1-(2,7-dichloro-8-fluoropyrido[4,3-d]pyrimidin-4-yl)-3-methylpiperidin-3-ol (2.00 g, 6.04 mmol), TsOH·H₂O (115 mg, 604 μmol) and DHP (1.02 g, 12.1 mmol, 1.10 mL) in dichloromethane (20 mL) was stirred at 15° C. for 1 h. After completion, the mixture was concentrated in vacuum. The residue was purified by reversed phase flash chromatography [water (0.1% formic acid)/acetonitrile] to give the title compound (2.3 g, 77% yield). Yellow oil. LCMS (ESI, M+1): m/z 415.0

Step B. tert-butyl-[(3R,5S)-5-[[7-chloro-8-fluoro-4-[(3R)-3-methyl-3-tetrahydropyran-2-yloxy-1-piperidyl]pyrido[4,3-d]pyrimidin-2-yl]oxymethyl]-1-methyl-pyrrolidin-3-yl)oxy-diphenyl-silane: A mixture of 2,7-dichloro-8-fluoro-4-[(3R)-3-methyl-3-tetrahydropyran-2-yloxy-1-piperidyl]pyrido[4,3-d]pyrimidine (2 g, 4.82 mmol), [(2S,4R)-4-[tert-butyl (diphenyl)silyl]oxy-1-methyl-pyrrolidin-2-yl]methanol (3.56 g, 9.63 mmol) and DIEA (1.87 g, 14.5 mmol, 2.52 mL) in dioxane (20 mL) was stirred at 90° C. for 12 h. After completion, the mixture was diluted with water (30 mL) and extracted with ethyl acetate (50 mL). The organic layer was washed with brine (50 mL), dried over anhydrous Na₂SO₄, filtered and concentrated in vacuum. The residue was purified by reversed phase flash chromatography (water (0.1% formic acid)/acetonitrile] to give the title compound (1.7 g, 38% yield). Yellow oil. LCMS (ESI, M+1): m/z 748.2.

Step C. 2-(((2S,4R)-4-((tert-butyldiphenylsilyl)oxy)-1-methylpyrrolidin-2-yl) methoxy)-7-(8-ethyl-7-fluoro-3-(methoxymethoxy)naphthalen-1-yl)-8-fluoro-4-((3R)-3-methyl-3-((tetrahydro-2H-pyran-2-yl)oxy)piperidin-1-yl) pyrido[4,3-d]pyrimidine: To a mixture of tert-butyl-[(3R, 5S)-5-[[7-chloro-8-fluoro-4-[(3R)-3-methyl-3-tetrahydropyran-2-yloxy-1-piperidyl]pyrido[4,3-d]pyrimidin-2-yl]oxymethyl]-1-methyl-pyrrolidin-3-yl]oxy-diphenyl-silane (1.20 g, 1.60 mmol), 2-(8-ethyl-7-fluoro-3-(methoxymethoxy)naphthalen-1-yl)-4,4,5,5-tetramethyl-1,3,2-dioxaborolane (869 mg, 2.41 mmol), K₃PO₄ (1.5 M, 3.21 mL) in toluene (10 mL) was added [cataCXium-A-Pd-G3 (117 mg, 160 μmol) under N₂. The mixture was stirred at 90° C. for 1.5 h. After completion, the reaction mixture was diluted with ethyl acetate (10 mL) and water (5 mL). The aqueous layer was extracted with ethyl acetate (10 mL). The combined organic phase was washed with brine (10 mL), dried over anhydrous sodium sulfate, filtered and concentrated to give a residue. The residue was purified by reversed phase flash chromatography (water (0.1% formic acid)/acetonitrile] to give 2-(((2S,4R)-4-((tert-butyldiphenylsilyl)oxy)-1-methylpyrrolidin-2-yl)methoxy)-7-(8-ethyl-7-fluoro-3-(methoxymethoxy)naphthalen-1-yl)-8-fluoro-4-((3R)-3-methyl-3-((tetrahydro-2H-pyran-2-yl)oxy) piperidin-1-yl)pyrido[4,3-d]pyrimidine (768 mg, 50% yield). Black oil; LCMS (ESI, M+1): m/z 946.5.

Step D. (3R,5S)-5-(((7-(8-ethyl-7-fluoro-3-(methoxymethoxy)naphthalen-1-yl)-8-fluoro-44 (3R)-3-methyl-3-((tetrahydro-2H-pyran-2-yl)oxy)piperidin-1-yl) pyrido[4,3-d]pyrimidin-2-yl)oxy)methyl)-1-methylpyrrolidin-3-ol: To a mixture of 2-(((2S,4R)-4-((tert-butyl diphenylsilyl)oxy)-1-methylpyrrolidin-2-yl)methoxy)-7-(8-ethyl-7-fluoro-3-(methoxymethoxy)naphthalen-1-yl)-8-fluoro-4-((3R)-3-methyl-3-((tetrahydro-2H-pyran-2-yl) oxy)piperidin-1-yl)pyrido[4,3-d]pyrimidine (650 mg, 687 μmol) and DMF (7 mL) was added CsF (1.56 g, 10.3 mmol), and the mixture was stirred at 40° C. for 16 h. The mixture was filtered and purified by reversed phase flash chromatography [water (0.1% formic acid)/acetonitrile] to give (3R,5S)-5-(((7-(8-ethyl-7-fluoro-3-(methoxymethoxy)naphthalen-1-yl)-8-fluoro-4-((3R)-3-methyl-3-((tetrahydro-2H-pyran-2-yl)oxy)piperidin-1-yl) pyrido[4,3-d]pyrimidin-2-yl) oxy)methyl)-1-methylpyrrolidin-3-ol (230 mg, 47% yield). Yellow Solid; LCMS [ESI, M+1]: m/z 708.5.

Step E. [(3R,5S)-5-[[7-[8-ethyl-7-fluoro-3-(methoxymethoxy-naphthyl]-8-fluoro-4-[(3R)-3-methyl-3-tetrahydropyran-2-yloxy-1-piperidyl]pyrido[4,3-d]pyrimidin-2-yl]oxymethyl]-1-methyl-pyrrolidin-3-yl] (4-nitrophenyl) carbonate: To a mixture of (3R,5S)-5-(((7-(8-ethyl-7-fluoro-3-(methoxymethoxy)naphthalen-1-yl)-8-fluoro-4-((3R)-3-methyl-3-((tetrahydro-2H-pyran-2-yl)oxy)piperidin-1-yl)pyrido[4,3-d]pyrimidin-2-yl)oxy)methyl)-1-methylpyrrolidin-3-ol (40.0 mg, 56.5 μmol) and (4-nitrophenyl) carbonochloridate (41.0 mg, 203 μmol) in THF (1 mL) was added t-BuOK (1 M in THF, 170 μL) at 0° C. The mixture was stirred at 25° C. for 1 h. After completion, the mixture was diluted with ethyl acetate (4 mL) and water (3 mL), and then separated. The aqueous phase was extracted with ethyl acetate (3 mL). The combined organic layer was washed with brine (4 mL), dried over anhydrous Na₂SO₄, filtered and concentrated in vacuum. The residue was purified by reversed phase flash chromatography [water (0.1% formic acid)/acetonitrile] to give [(3R,5S)-5-[[7-[8-ethyl-7-fluoro-3-(methoxymethoxy)-1-naphthyl]-8-fluoro-4-[(3R)-3-methyl-3-tetrahydropyran-2-yloxy-1-piperidyl]pyrido[4,3-d]pyrimidin-2-yl]oxymethyl]-1-methyl-pyrrolidin-3-yl] (4-nitrophenyl) carbonate (49.0 mg, 73% yield). Yellow solid. LCMS (ESI, M+1): m/z 873.4.

Step F. [(3R,5S)-5-[7-[8-ethyl-7-fluoro-3-(methoxymethoxy-1-naphthyl]-8-fluoro-4-[(3R)-3-methyl-3-tetrahydropyran-2-yloxy-1-piperidyl]pyrido[4,3-d]pyrimidin-2-yl) oxymethyl]-1-methyl-pyrrolidin-3-yl] N-methylcarbamate: A mixture of [(3R,5S)-5-[[7-[8-ethyl-7-fluoro-3-(methoxymethoxy)-1-naphthyl]-8-fluoro-4-[(3R)-3-methyl-3-tetrahydropyran-2-yloxy-1-piperidyl]pyrido[4,3-d]pyrimidin-2-yl]oxymethyl]-1-methyl-pyrrolidin-3-yl] (4-nitrophenyl) carbonate (49.0 mg, 56.1 μmol) and methanamine (2 M in THF, 702 μL) in DMF (1 mL) was stirred at 25° C. for 0.5 h. After completion, the residue was purified directly by reversed phase flash chromatography [water (0.1% formic acid)/acetonitrile] to give [(3R,5S)-5-[[7-[8-ethyl-7-fluoro-3-(methoxymethoxy)-1-naphthyl]-8-fluoro-4-[(3R)-3-methyl-3-tetrahydropyran-2-yloxy-1-piperidyl]pyrido[4,3-d]pyrimidin-2-yl]oxymethyl]-1-methyl-pyrrolidin-3-yl] N-methylcarbamate (33.0 mg, 59% yield). Yellow oil. LCMS (ESI, M+1): m/z 765.4.

Step G. [(3R,5S)-5-[[7-(8-ethyl-7-fluoro-3-hydroxy-1-naphthyl-8-fluoro-4-[(3R)-3-hydroxy-3-methyl-1-piperidyl]pyrido[4,3-d]pyrimidin-2-yl)oxymethyl]-1-methyl-pyrrolidin-3-yl] N-methylcarbamate: To a mixture of [(3R,5S)-5-[[7-[8-ethyl-7-fluoro-3-(methoxymethoxy)-1-naphthyl]-8-fluoro-4-[(3R)-3-methyl-3-tetrahydropyran-2-yloxy-1-piperidyl]pyrido[4,3-d]pyrimidin-2-yl]oxymethyl]-1-methyl-pyrrolidin-3-yl] N-methylcarbamate (34.0 mg, 44.4 μmol) and MeCN (0.5 mL) was added HCl-MeOH (4 M, I mL) at 0° C. and the mixture was stirred at a 0° C. for 0.5 h. After completion, the mixture was concentrated in vacuum. Then the pH value was adjusted to 9 with saturated NaHCO₃ solution and the mixture was triturated with methanol (2×8 mL) The filtrate was concentrated in vacuum. The residue was purified by prep-HPLC (column: Shim-pack C18 150*25*10 μm; mobile phase: [water (0.225% formic acid)-ACN]; B %: 20%-40%, 10 min) to afford [(3R,5S)-5-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]-1-methyl-pyrrolidin-3-yl] N-methylcarbamate (8.34 mg, 28% yield, 0.6 formic acid salt). ¹H NMR (400 MHz, METHANOL-d4): δ 9.22 (br d, J=3.2 Hz, 1H), 7.68 (br dd, J=5.6, 8.4 Hz, 1H), 7.30 (br d, J=2.0 Hz, 1H), 7.25 (br t, J=9.2 Hz, 1H), 7.06 (br s, 1H), 5.13 (br s, 1H), 4.62-4.53 (m, 3H), 4.31 (br t, J=12.0 Hz, 1H), 3.67-3.56 (m, 2H), 3.49-3.43 (m, 1H), 2.67 (br d, J=15.2 Hz, 8H), 2.53-2.42 (m, 1H), 2.25-2.13 (m, 4H), 1.89-1.75 (m, 3H), 1.29 (br d, J=9.6 Hz, 3H), 0.81 (q, J=7.2 Hz, 3H). ¹⁹F NMR (400 MHz, METHANOL-d4) δ=−121.123, −139.247. LCMS (ESI, M+1): m/z 637.3.

Example 13

(R)-1-(7-(8-ethynyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol

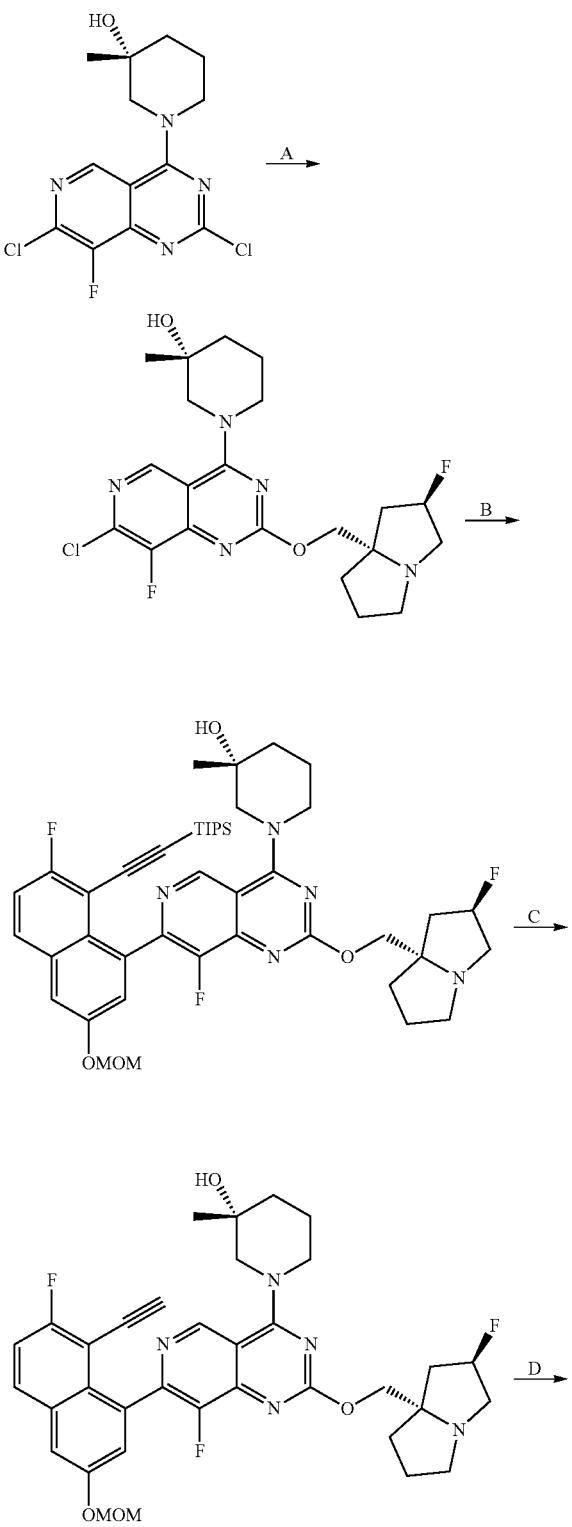

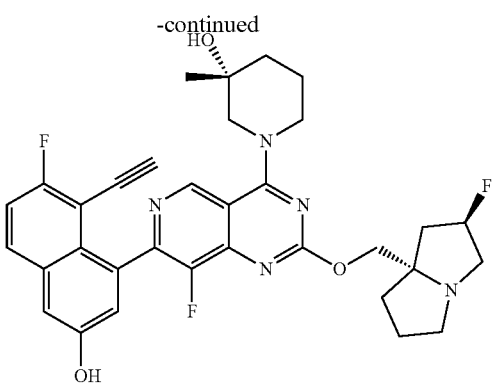

Step A. (R)-1-(7-chloro-8-fluoro-2-(((2R,7aS)-2-fluoro-hexahydro-1H-pyrrolizin-7a-yl)methoxy)pyrido[4,3-d]pyrimidin-4-yl)-3-methylpiperidin-3-ol: A mixture of (R)-1-(2,7-dichloro-8-fluoropyrido[4,3-d]pyrimidin-4-yl)-3-methylpiperidin-3-ol ((300 mg, 906 μmol), ((2R,7aS)-2-fluorohexahydro-1H-pyrrolizin-7a-yl)methanol (150 mg, 942 μmol), DIPEA (334 mg, 2.58 mmol) and 4 Å molecular sieves (150 mg) in dioxane (1.8 mL) was stirred at 90° C. for 15 hours under $N_2$ atmosphere. The reaction mixture was filtered. The filter cake was washed with dichloromethane (20 mL). The filtrate was concentrated under reduced pressure, and purified by reversed phase flash chromatography [water (0.1% formic acid)/acetonitrile=1 1/9] to give the product as light yellow gum (260 mg, 61% yield). LCMS (ESI, M+1): m/z 454.1.

Step B. (R)-1-(8-fluoro-7-(7-fluoro-3-(methoxymethoxy)-8-((triisopropylsilyl)ethynyl)naphthalen-1-yl)-2-(((2R,7aS)-2-fluorohexahydro-1H-pyrrolizin-7a-yl) methoxy)pyrido[4,3-d]pyrimidin-4-yl)-3-methylpiperidin-3-ol: A mixture of (R)-1-(7-chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (150 mg, 330 μmol), and $K_3PO_4$ (1.5 M in water, 0.7 mL) in THF (3.5 mL) was degassed and purged with $N_2$ for 3 times. cataCXium-A-Pd-G3 (25 mg, 34.3 μmol) was added, followed by ((2-fluoro-6-(methoxymethoxy)-8-(4,4,5,5-tetramethyl-1,3,2-dioxaborolan-2-yl)naphthalen-1-yl)ethynyl)triisopropylsilane (228 mg, 445 μmol). The mixture was stirred at 65° C. for 3 hours. The reaction mixture was diluted with water (5 mL), and extracted with ethyl acetate (5 mL×4). The combined organic layers were concentrated under reduced pressure, and purified by reversed phase flash chromatography [water (0.1% formic acid)/acetonitrile=7/13] to give the product as yellow foam (219 mg, 79% yield). LCMS (ESI, M+1): m/z 804.4.

Step C. (R)-1-(7-(8-ethynyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a solution of (R)-1-(8-fluoro-7-(7-fluoro-3-(methoxymethoxy)-8-((triisopropylsilyl)ethynyl)naphthalen-1-yl)-2-(((2R,7aS)-2-fluorohexahydro-1H-pyrrolizin-7a-yl) methoxy)pyrido[4,3-d]pyrimidin-4-yl)-3-methylpiperidin-3-ol (375 mg, 466 μmol) in DMF (3.5 mL) was added CsF (709 mg, 4.67 mmol). The mixture was stirred at 20° C. for 0.5 hour. The reaction mixture was filtered. The filtrate was purified by reversed phase flash chromatography [water (0.1% formic acid)/acetonitrile=11/9] to give the product as yellow solid (270 mg, 87% yield). LCMS (ESI, M+1): m/z 648.4.

Step D. (R)$_1$-(7-(8-ethynyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a mixture of (R)-1-(7-(8-ethynyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)-3-methylpiperidin-3-ol (100 mg, 154 μmol) in MeCN (3 mL) was added HCl/dioxane (4 M, 2 mL) dropwise at 0° C. The mixture was stirred at 0° C. for 0.5 hour. The reaction mixture was concentrated under reduced pressure to give a residue at room temperature (without heating). The residue was dissolved in ethyl acetate (5 mL) and saturated $NaHCO_3$ aqueous (5 mL). The mixture was extracted with ethyl acetate (5 mL×3). The combined organic layers were dried over anhydrous $Na_2SO_4$, concentrated under reduced pressure, and purified by reversed phase flash chromatography [water (0.1% formic acid)/acetonitrile=3/2] to give the product as yellow solid (63.2 mg, 63% yield, 0.4 FORMIC ACID). $^1$H NMR (400 MHz, methanol-d4) δ=9.15 (d, J=51.6, 1H), 7.88-7.84 (m, 1H), 7.36-7.32 (m, 2H), 7.23 (dd, J=2.8, 18.4 Hz, 1H), 5.40 (d, J=53.2, 1H), 4.68-4.37 (m, 4H), 3.66-3.35 (m, 6H), 3.21-3.15 (m, 1H), 2.34-1.75 (m, 10H), 1.27 (d, J=20.0, 3H). $^{19}$F NMR (377 MHz, methanol-d4) δ=−111.66,−140.59, −173.84. LCMS (ESI, M+1): m/z 604.3.

Example 14

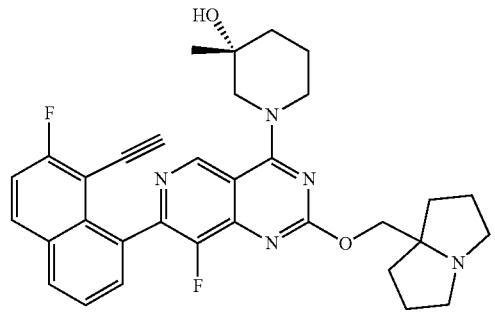 [SMILES: C#Cc1c(F)ccc2cccc(-c3ncc4c(N5CCC[C@@](C)(O)C5)nc(OCC56CCCN5CCC6)nc4c3F)c12]

(R)-1-(7-(8-ethynyl-7-fluoronaphthalen-1-yl)-8-fluoro-2-((hexahydro-1H-pyrrolizin-7a-yl)methoxy)pyrido[4,3-d]pyrimidin-4-yl)-3-methylpiperidin-3-ol

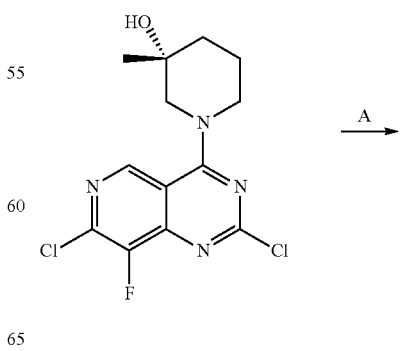

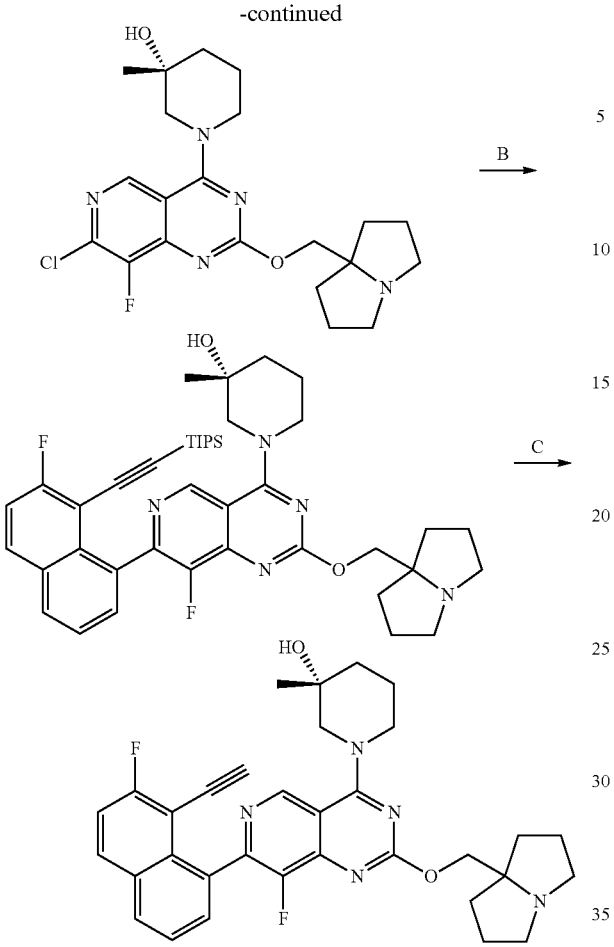

Step A. (R)-1-(7-chloro-8-fluoro-2-((hexahydro-1H-pyrrolizin-7a-yl) methoxy)pyrido[4,3-d]pyrimidin-4-yl)-3-methylpiperidin-3-ol: To a mixture of (R)-1-(2,7-dichloro-8-fluoropyrido[4,3-d]pyrimidin-4-yl)-3-methylpiperidin-3-ol (400 mg, 1.21 mmol), (hexahydro-1H-pyrrolizin-7a-yl)methanol (239 mg, 1.69 mmol), 4 Å molecular sieves (40.0 mg) in dioxane (8 mL) was added DIEA (468 mg, 3.62 mmol), the mixture was stirred at 90° C. for 3 hours. Upon completion, the reaction solution was filtered and concentrated to give a residue. The residue was purified by reversed phase flash chromatography [water (0.1% formic acid)/acetonitrile] to give (R)-1-(7-chloro-8-fluoro-2-((hexahydro-1H-pyrrolizin-7a-yl) methoxy)pyrido[4,3-d]pyrimidin-4-yl)-3-methylpiperidin-3-ol (244 mg, 44% yield). Yellow Solid; LCMS (ESI, M+1): m/z 436.3.

Step B. (R)-1-(8-fluoro-7-(7-fluoro-8-((triisopropylsilyl)ethynyl)naphthalen-1-yl)-2-((hexahydro-1H-pyrrolizin-7a-yl methoxy)pyrido[4,3-d]pyrimidin-4-yl)-3-methylpiperidin-3-ol: To the solution of (R)-1-(7-chloro-8-fluoro-2-((hexahydro-1H-pyrrolizin-7a-yl) methoxy)pyrido[4,3-d]pyrimidin-4-yl)-3-methylpiperidin-3-ol (200 mg, 459 μmol), ((2-fluoro-8-(4,4,5,5-tetramethyl-1,3,2-dioxaborolan-2-yl)naphthalen-1-yl)ethynyl)triisopropylsilane (291 mg, 642 μmol), K$_3$PO$_4$ (1.5 M, 918 μL) in THF (3 mL) was added cataCXium-A-Pd-G3cataCXium-A-Pd-G3 (33.4 mg, 45.9 μmol) under N$_2$. The mixture was stirred at 60° C. for 1 hours. Upon completion, the reaction solution was diluted with ethyl acetate (15 mL) and water (5 mL), and the aqueous layer was extracted with ethyl acetate (10 mL). The combined organic phase was washed with brine (10 mL), dried over anhydrous sodium sulfate, filtered and concentrated to give a residue. The residue was purified by reversed phase flash chromatography [water (0.1% formic acid)/acetonitrile] to give (R)-1-(8-fluoro-7-(7-fluoro-8-((triisopropylsilyl)ethynyl)naphthalen-1-yl)-2-((hexahydro-1H-pyrrolizin-7a-yl) methoxy)pyrido[4,3-d]pyrimidin-4-yl)-3-methylpiperidin-3-ol (291 mg, 87% yield). Off-white Solid; LCMS (ESI, M+1): m/z 726.5.

Step C. (R)-1-(7-(8-ethynyl-7-fluoronaphthalen-1-yl)-8-fluoro-2-((hexahydro-1H-pyrrolizin-7a-yl)methoxy)pyrido[4,3-d]pyrimidin-4-yl)-3-methylpiperidin-3-ol: To the solution of (R)-1-(8-fluoro-7-(7-fluoro-8-((triisopropylsilyl)ethynyl)naphthalen-1-yl)-2-((hexahydro-1H-pyrrolizin-7a-yl)methoxy)pyrido[4,3-d]pyrimidin-4-yl)-3-methylpiperidin-3-ol (100 mg, 138 μmol) in DMF (1.5 mL) was added CsF (209 mg, 1.38 mmol, 10 equiv.). The mixture was stirred at 20° C. for 1 hour. Upon completion, the mixture was filtered and purified by reversed phase flash chromatography [water (0.1% formic acid)/acetonitrile]. The desired fractions were lyophilized to afford R)-1-(7-(8-ethynyl-7-fluoronaphthalen-1-yl)-8-fluoro-2-((hexahydro-1H-pyrrolizin-7a-yl) methoxy)pyrido[4,3-d]pyrimidin-4-yl)-3-methylpiperidin-3-ol (51.72 mg, 60% yield, 0.77 FORMIC ACID). Yellow Solid; $^1$H NMR (400 MHz, METHANOL-d4) δ=9.31-9.07 (m, 1H), 8.18-8.05 (m, 2H), 7.73-7.61 (m, 2H), 7.50-7.39 (m, 1H), 4.74-4.24 (m, 4H), 3.72-3.38 (m, 5H), 3.18-3.01 (m, 2H), 2.34-2.21 (m, 2H), 2.19-1.92 (m, 7H), 1.86-1.66 (m, 3H), 1.36-1.17 (m, 3H); LCMS (ESI, M+1): m/z 570.4.

Example 15

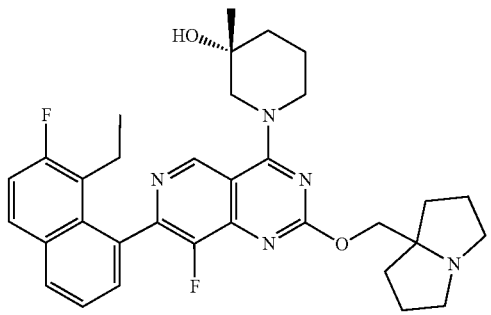 [SMILES: CCc1c(F)ccc2cccc(-c3ncc4c(N5CCC[C@@](C)(O)C5)nc(OCC56CCCN5CCC6)nc4c3F)c12]

(R)-1-(6-(8-ethyl-7-fluoronaphthalen-1-yl)-5-fluoro-3-((hexahydro-1H-pyrrolizin-7a-yl) methoxy)pyrido[4,3-d]pyrimidin-1-yl)-3-methylpiperidin-3-ol

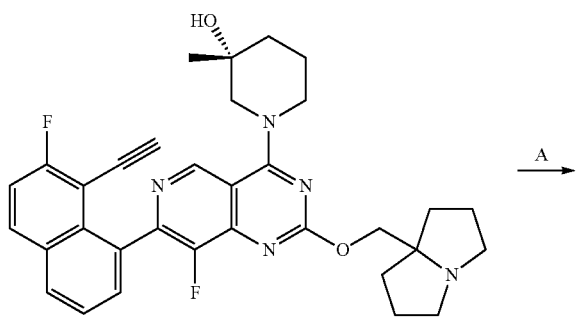

A →

147
-continued

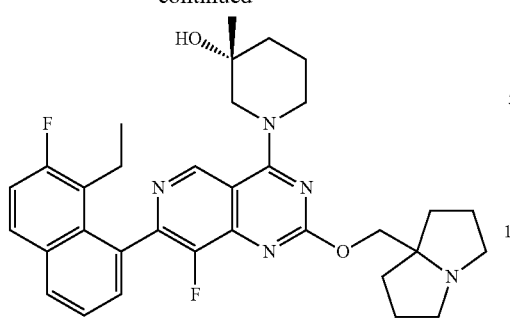

Step A. (R)-1-(6-(8-ethyl-7-fluoronaphthalen-1-yl)-5-fluoro-3-((hexahydro-1H-pyrrolizin-7a-yl)methoxy)pyrido[4,3-d]pyrimidin-1-yl)-3-methylpiperidin-3-ol: To a solution of (R)-1-(7-(8-ethynyl-7-fluoronaphthalen-1-yl)-8-fluoro-2-((hexahydro-1H-pyrrolizin-7a-yl) methoxy)pyrido[4,3-d]pyrimidin-4-yl)-3-methylpiperidin-3-ol (50.0 mg, 87.8 μmol) in MeOH (2 mL) was added Pd/C (20 mg, 10% h purity) under N₂. The suspension was degassed in vacuum and purged with H₂ several times. The mixture was stirred under H₂ (15 psi) at 20° C. for 1 hour. Upon completion, the mixture was filtered and concentrated to give a residue. The residue was purified by prep-HPLC (column: water s Xbridge 150×25 mm×5 μm; mobile phase: [water (10 mM NH₄HCO₃)-ACN]; B %: 50%-80/a, 10 min) to give (R)-1-(6-(8-ethyl-7-fluoronaphthalen-1-yl)-5-fluoro-3-((hexahydro-1H-pyrrolizin-7a-yl)methoxy)pyrido[4,3-d]pyrimidin-1-yl)-3-methylpiperidin-3-ol (16.83 mg, 33% yield). White Solid; ¹H NMR (400 MHz, CHLOROFORM-d) δ=9.14 (d, J=7.2 Hz, 1H), 7.97-7.92 (m, 1H), 7.83-7.75 (m, 1H), 7.52-7.42 (m, 2H), 7.33-7.27 (m, 1H), 4.50-4.37 (m, 2H), 4.32-4.20 (m, 2H), 3.52-3.41 (m, 1H), 3.38-3.27 (m, 1H), 3.17-3.08 (m, 2H), 3.04-2.88 (m, 1H), 2.70-2.52 (m, 3H), 2.32-2.21 (m, 1H), 2.13-2.02 (m, 3H), 1.93-1.83 (m, 5H), 1.79-1.68 (m, 4H), 1.35 (s, 3H), 0.90-0.83 (m, 3H); LCMS (ESI, M+1): m/z 574.4.

Example 16

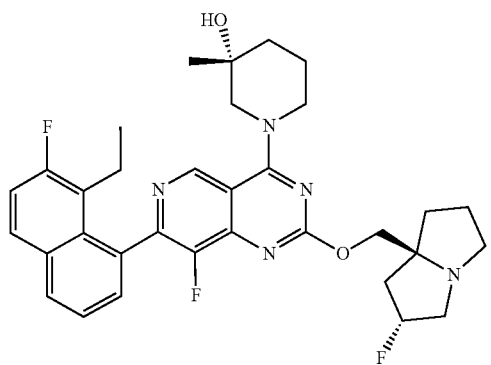 [SMILES: CCc1c(F)ccc2cccc(-c3ncc4c(N5CCC[C@@](C)(O)C5)nc(OC[C@@]56CCCN5C[C@H](F)C6)nc4c3F)c12]

148

(R)-1-(7-(8-ethyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol

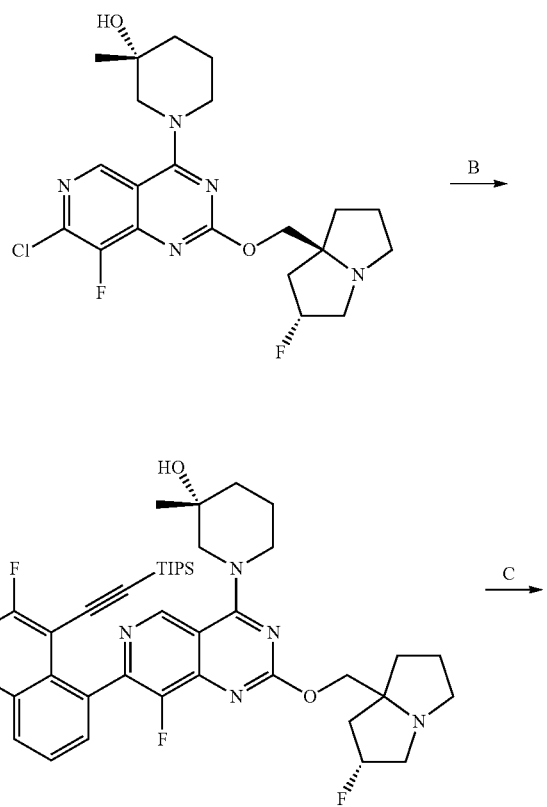

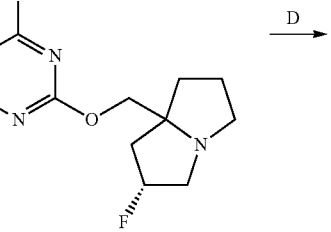

-continued

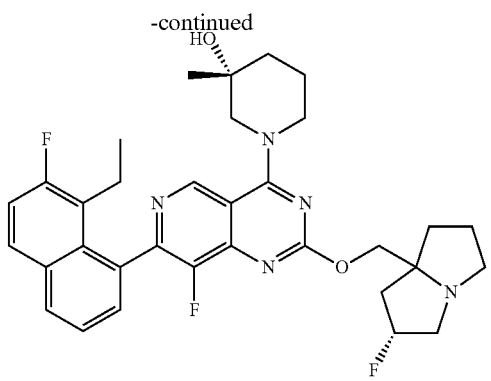

Step A. (R)-1-(7-chloro-8-fluoro-2-(((2R,7aS)-2-fluoro-hexahydro-1H-pyrrolizin-7a-yl)methoxy)pyrido[4,3-d]pyrimidin-4-yl)-3-methylpiperidin-3-ol: To a mixture of (R)-1-(2,7-dichloro-8-fluoropyrido[4,3-d]pyrimidin-4-yl)-3-methylpiperidin-3-ol (200 mg, 604 μmol), ((2R,7aS)-2-fluorohexahydro-1H-pyrrolizin-7a-yl)methanol (145 mg, 911 μmol), and 4 Å molecular sieves (20 mg) in dioxane (3 mL) was added DIEA (234 mg, 1.81 mmol). The mixture was stirred at 90° C. for 14 hours. Upon completion, the reaction solution was diluted with ethyl acetate (10 mL) and water (5 mL), and the aqueous layer was extracted with ethyl acetate (10 mL). The combined organic phase was washed with brine (10 mL), dried over anhydrous sodium sulfate, filtered and concentrated to give a residue. The residue was purified by reversed phase flash chromatography [water (0.1% formic acid)/acetonitrile] to give (R)-1-(7-chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (168 mg, 56% yield). Yellow Solid; LCMS (ESI, M+1): m/z 454.3.

Step B. (R)-1-(8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)-3-methylpiperidin-3-ol: To a solution of (R)-1-(7-chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (180 mg, 397 μmol), ((2-fluoro-8-(4,4,5,5-tetramethyl-1,3,2-dioxaborolan-2-yl)naphthalen-1-yl)ethynyl)triisopropylsilane (234 mg, 517 μmol), and $K_3PO_4$ (1.5 M, 793 μL) in THF (3 mL) was added cataCXium-A-Pd-G3cataCXium-A-Pd-G3 (28.9 mg, 39.7 μmol)under $N_2$. The mixture was stirred at 60° C. for 2 hours. Upon completion, the reaction mixture was diluted with ethyl acetate (15 mL) and water (10 mL). The mixture was extracted with ethyl acetate (15 mL). The combined organic phase was washed with brine (20 mL), dried over anhydrous sodium sulfate, filtered and concentrated to give a residue. The residue was purified by reversed phase flash chromatography [water (0.1% formic acid)/acetonitrile] to give (R)-1-(8-fluoro-7-(7-fluoro-8-((triisopropylsilyl)ethynyl)naphthalen-1-yl)-2-(((2R,7aS)-2-fluorohexahydro-1H-pyrrolizin-7a-yl) methoxy)pyrido[4,3-d]pyrimidin-4-yl)-3-methylpiperidin-3-ol (260 mg, 86% yield). Yellow Solid; LCMS (ESI, M+1)): m/z 744.5.

Step C. (R)-1-(7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To the solution of (R)-1-(8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)-3-methylpiperidin-3-ol (260 mg, 349 μmol) in DMF (2 mL) was added CsF (531 mg, 3.49 mmol). The mixture was stirred at 20° C. for 0.5 hour. Upon completion, the mixture was filtered and purified by reversed phase flash chromatography [water (0.1% formic acid)/acetonitrile] to give (R)-1-(7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (190 mg, 89% yield). Yellow Solid; LCMS (ESI, M+1)): m/z 588.4.

Step D. (R)-1-(7-(8-ethyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a solution of (R)-1-(7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (50.0 mg, 85.1 μmol) in MeOH (2.0 mL) was added Pd/C (20 mg, 10% purity) under $N_2$. The suspension was degassed in vacuum and purged with $H_2$ several times. The mixture was stirred under $H_2$ (15 psi) at 20° C. for 1 hour. Upon completion, the mixture was filtered and concentrated to give a residue. The residue was purified by prep-HPLC (column: water s Xbridge 150×25 mm×5 μm; mobile phase: [water (10 mM $NH_4HCO_3$)-ACN]; B %: 53%-83%, 10 min) to give (R)-1-(7-(8-ethyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (18.2 mg, 36% yield). White Solid; $^1$H NMR (400 MHz, CHLOROFORM-d) δ=9.15 (d, J=6.8 Hz, 1H), 8.01-7.89 (m, 1H), 7.85-7.75 (m, 1H), 7.55-7.40 (m, 2H), 7.30 (t, J=7.2 Hz, 1H), 5.40-5.16 (m, 1H), 4.50-4.37 (m, 2H), 4.35-4.29 (m, 1H), 4.26-4.18 (m, 1H), 3.54-3.41 (m, 1H), 3.38-3.09 (m, 4H), 3.06-2.85 (m, 2H), 2.64-2.47 (m, 1H), 2.31-2.05 (m, 5H), 2.01-1.86 (m, 4H), 1.80-1.67 (m, 2H), 1.35 (s, 3H), 0.94-0.79 (m, 3H); LCMS (ESI, M+1)): m/z 592.4.

Example 17

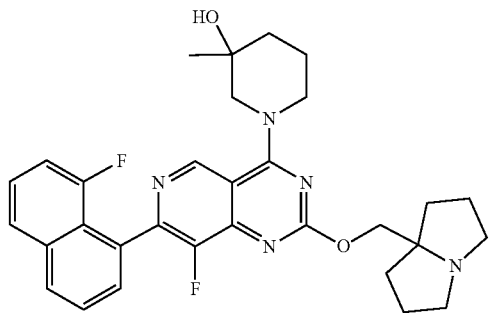 [SMILES: CC1(O)CCCN(c2nc(OCC34CCCN3CCC4)nc3c(F)c(-c4cccc5cccc(F)c45)ncc23)C1]

1-(8-fluoro-7-(8-fluoronaphthalen-1-yl)-2-((hexahydro-1H-pyrrolizin-7a-yl)methoxy)pyrido[4,3-d]pyrimidin-4-yl)-3-methylpiperidin-3-ol

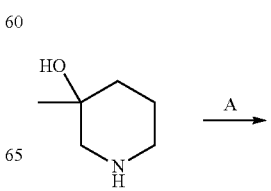

151

-continued

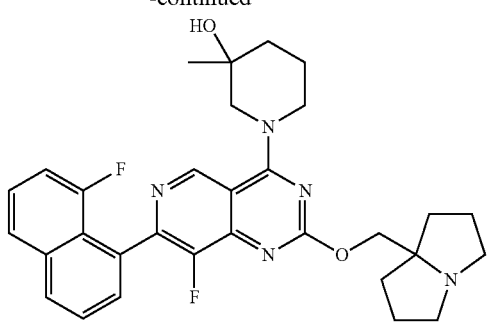

Example 18

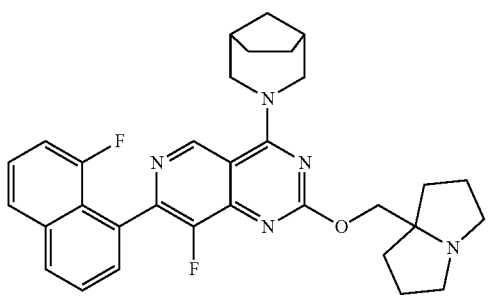 [SMILES: Fc1c(-c2cccc3cccc(F)c23)ncc2c(N3CC4CCC(C4)C3)nc(OCC34CCCN3CCC4)nc12]

152

4-((1R,5S)-3-azabicyclo[3.2.1]octan-3-yl)-8-fluoro-7-(8-fluoronaphthalen-1-yl)-2-((hexahydro-1H-pyrrolizin-7a-yl)methoxy)pyrido[4,3-d]pyrimidine

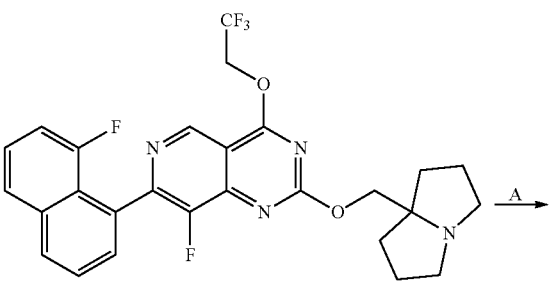

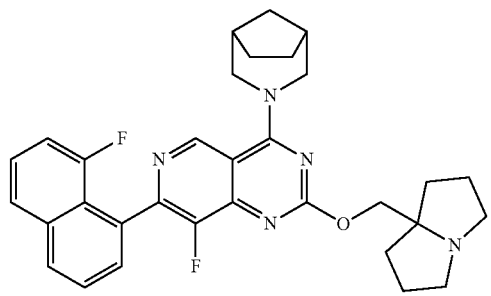

Step A. 1-(8-fluoro-7-(8-fluoronaphthalen-1-yl)-2-((hexahydro-1H-pyrrolizin-7a-yl) methoxy)pyrido[4,3-d]pyrimidin-4-yl)-3-methylpiperidin-3-ol: To a mixture of 3-methylpiperidin-3-ol and DIEA (51.1 mg, 396 μmol) and 4 Å molecular sieves (50 mg) in DMF (2 mL) was added 8-fluoro-7-(8-fluoronaphthalen-1-yl)-2-((hexahydro-1H-pyrrolizin-7a-yl) methoxy)-4-(2,2,2-trifluoroethoxy)pyrido[4,3-d]pyrimidine (69.9 mg, 132 μmol) in one portion at 20° C. under $N_2$. The mixture was heated to 40° C. and stirred for 12 hours. Upon completion, the mixture was filtered and concentrated in vacuum. The residue was purified by prep-HPLC (column: water s X-bridge 150*25 mm*5 μm; mobile phase: [water (10 mM $NH_4HCO_3$)-ACN]; B %: 31%-61%, 10 min) to afford 1-(8-fluoro-7-(8-fluoronaphthalen-1-yl)-2-((hexahydro-1H-pyrrolizin-7a-yl)methoxy)pyrido[4,3-d]pyrimidin-4-yl)-3-methylpiperidin-3-ol (24.34 mg, 33.5% yield); White solid. $^1$H NMR (400 MHz, methanol-d4) δ 9.20 (d, J=6.0 Hz, 1H) 8.10 (d, J=8.0 Hz, 1H), 7.84 (d, J=8.0 Hz, 1H), 7.70 (t, J=7.2 Hz, 1H), 7.58 (t, J=8.0 Hz, 1H), 7.53 (td, J=5.2 Hz, 8.0 Hz, 1H), 7.19 (dd, J=5.2 Hz, 8.0 Hz, 1H), 4.54 (d, J=8.4 Hz, 1H), 4.33-4.25 (m, 3H), 3.63 (dd, J=2.8 Hz, 13.2 Hz, 1H), 3.50-3.40 (m, 1H), 3.14-3.06 (m, 2H), 2.76-2.68 (m, 2H), 2.23-2.03 (m, 3H), 1.97-1.73 (m, 9H), 1.29 (d, J=5.2 Hz, 3H); LCMS (ESI, M+1): m/z 546.2.

Step A. 4-((1R,5S)-3-azabicyclo[3.2.1]octan-3-yl)-8-fluoro-7-(8-fluoronaphthalen-1-yl)-2-((hexahydro-1H-pyrrolizin-7a-yl)methoxy)pyrido[4,3-d]pyrimidine: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 94.3 μmol) in DMF (1.0 mL) were added DIEA (36.5 mg, 283 μmol, 49.3 μL) and (1R,5S)-3-azabicyclo[3.2.1]octane (31.4 mg, 283 μmol). The mixture was stirred at 40° C. for 1 hour. Upon completion, the residue was purified by prep-HPLC (column: 3_Phenomenex Luna C18 75×30 mm×3 μm; mobile phase: [water (0.2% formic acid salt)-MeOH]; B %: 25%-60%, 9 min.) affording 4-((1R,5S)-3-azabicyclo[3.2.1]octan-3-yl)-8-fluoro-7-(8-fluoronaphthalen-1-yl)-2-((hexahydro-1H-pyrrolizin-7a-yl) methoxy)pyrido[4,3-d]pyrimidine (22.7 mg, 42% yield) as a white solid. $^1$H NMR (400 MHz, CDCl$_3$) δ 9.06 (s, 1H), 7.99 (br d, J=7.6 Hz, 1H), 7.74 (d, J=8.2 Hz, 1H), 7.66-7.54 (m, 2H), 7.48-7.40 (m, 1H), 7.15-7.08 (m, 1H), 4.70 (br d, J=12.0 Hz, 1H), 4.61 (br d, J=12.0 Hz, 1H), 4.46 (s, 2H), 3.59-3.43 (m, 4H), 2.82-2.72 (m, 2H), 2.43 (br s, 2H), 2.31-2.22 (m, 2H), 2.13-1.92 (m, 4H), 1.90-1.77 (m, 3H), 1.76-1.55 (m, 5H); LCMS [ESI, M+1]: m/z 542.1.

Example 19

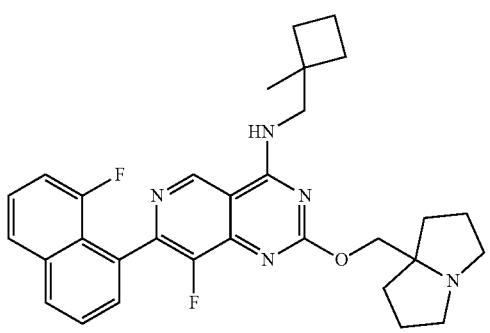 [SMILES: CC1(CNc2nc(OCC34CCCN3CCC4)nc3c(F)c(-c4cccc5cccc(F)c45)ncc23)CCC1]

8-fluoro-7-(8-fluoronaphthalen-1-yl)-2-((hexahydro-1H-pyrrolizin-7a-yl)methoxy)-N-((1-methylcyclobutyl)methyl)pyrido[4,3-d]pyrimidin-4-amine

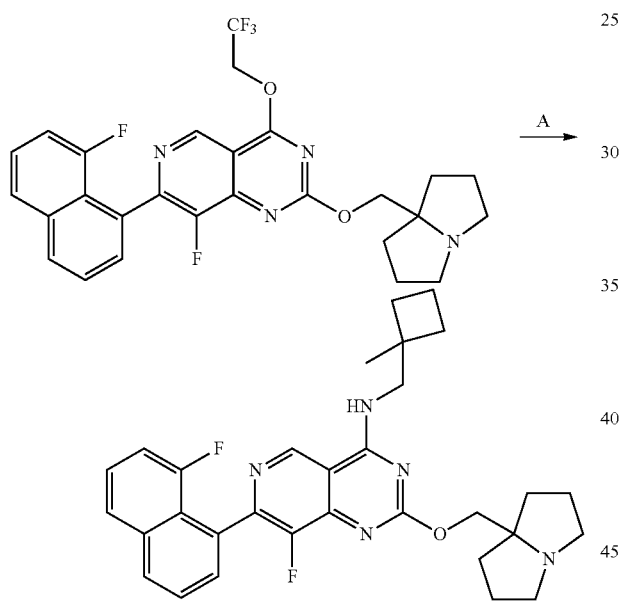

Step A. 8-fluoro-7-(8-fluoronaphthalen-yl)-2-((hexahydro-1H-pyrrolizin-7a-yl) methoxy)-N-((1-methylcyclobutyl)methyl)pyrido[4,3-d]pyrimidin-4-amine: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 94.3 μmol) in DMF (1.0 mL) were added DIEA (60.9 mg, 471 μmol, 82.1 μL) and (1-methylcyclobutyl)methanamine (38.4 mg, 283 μmol, HCl). The mixture was stirred at 40° C. for 1 hour. Upon completion, the residue was purified by prep-HPLC (column: Phenomenex Luna C18 200×40 mm×0 μm; mobile phase: [water (0.2% FORMIC ACID)-ACN]; B %: 20%-50%, 8 min.) affording 8-fluoro-7-(8-fluoronaphthalen-1-yl)-2-((hexahydro-1H-pyrrolizin-7a-yl)methoxy)-N-((1-methylcyclobutyl)methyl)pyrido[4,3-d]pyrimidin-4-amine (10.4 mg, 19% yield) as a white solid. ¹H NMR (400 MHz, CDCl₃) δ 8.94 (s, 1H), 7.99 (d, J=8.2 Hz, 1H), 7.74 (d, J=8.0 Hz, 1H), 7.65-7.59 (m, 1H), 7.59-7.55 (m, 1H), 7.48-7.40 (m, 1H), 7.14-7.06 (m, 1H), 6.39 (br s, 1H), 4.42 (s, 2H), 3.81-3.66 (m, 2H), 3.49-3.38 (m, 2H), 2.80-2.70 (m, 2H), 2.28-2.14 (m, 2H), 2.07-1.89 (m, 8H), 1.87-1.71 (m, 4H), 1.32-1.20 (m, 3H); LCMS [ESI, M+1]: m/z 530.1.

Example 20

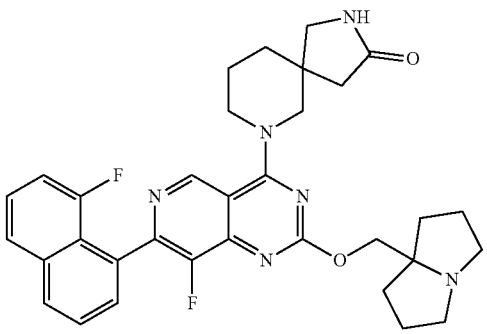 [SMILES: O=C1CC2(CCCN(c3nc(OCC45CCCN4CCC5)nc4c(F)c(-c5cccc6cccc(F)c56)ncc34)C2)CN1]

7-(8-fluoro-7-(8-fluoronaphthalen-1-yl)-2-((hexahydro-1H-pyrrolizin-7a-yl)methoxy)pyrido[4,3-d]pyrimidin-4-yl)-2,7-diazaspiro[4.5]decan-3-one

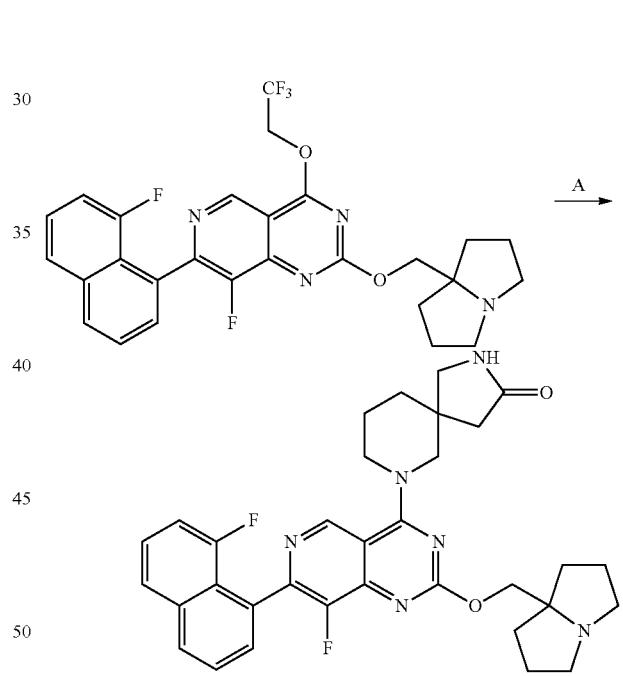

Step A. 7-(8-fluoro-7-(8-fluoronaphthalen-1-yl)-2-((hexahydro-1H-pyrrolizin-7a-yl) methoxy)pyrido[4,3-d]pyrimidin-4-yl)-2,7-diazaspiro[4.5]decan-3-one: To a mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 94.3 μmol), DIEA (60.9 mg, 471 μmol, 82.1 μL) and 4 Å molecular sieves (5.0 mg) in DMF (2.0 mL) was added 2,7-diazaspiro[4.5]decan-3-one (44.9 mg, 236 μmol, HCl). The mixture was stirred at 40° C. for 12 h. After completion, the mixture was filtered and concentrated. The residue was purified by prep-HPLC [Waters Xbridge 150×25 mm×5 μm; A: water (10 mM NH₄HCO₃), B: ACN; B %: 17%-50% over 9 min] and the desired fractions were lyophilized to afford 7-(8-fluoro-7-

(8-fluoronaphthalen-1-yl)-2-((hexahydro-1H-pyrrolizin-7a-yl) methoxy)pyrido[4,3-d]pyrimidin-4-yl)-2,7-diazaspiro[4.5]decan-3-one (10.6 mg, 19% yield). Off-white solid; ¹H NMR (400 MHz, CDCl₃) δ=8.99 (s, 1H), 8.00 (br d, J=8.0 Hz, 1H), 7.74 (d, J=8.4 Hz, 1H), 7.66-7.54 (m, 2H), 7.49-7.40 (m, 1H), 7.17-7.06 (m, 1H), 6.03-5.87 (m, 1H), 4.31-4.16 (m, 2H), 4.15-4.02 (m, 2H), 3.80-3.68 (m, 1H), 3.61 (br dd, J=8.0, 12.8 Hz, 1H), 3.43 (dd, J=10.0, 12.8 Hz, 1H), 3.22 (d, J=10.0 Hz, 1H), 3.16-3.06 (m, 2H), 2.70-2.56 (m, 2H), 2.38-2.22 (m, 2H), 2.14-2.03 (m, 2H), 1.94-1.84 (m, 8H), 1.70-1.61 (m, 2H); LCMS (ESI, M+1): m/z 585.3.

Example 21

Upon completion, the residue was purified by prep-HPLC (column: water s Xbridge BEH C18 100×25 mm×5 μm; mobile phase: [water (10 mM NH₄HCO₃)-ACN]; B %: 35%-70%, 10 mins.) affording 8-fluoro-7-(8-fluoronaphthalen-1-yl)-2-((hexahydro-1H-pyrrolizin-7a-yl)methoxy)-4-(piperidin-1-yl)pyrido[4,3-d]pyrimidine (12.5 mg, 26% yield) as a white solid. ¹H NMR (400 MHz, CDCl₃) δ 9.01 (s, 1H), 8.02-7.96 (m, 1H), 7.74 (d, J=8.4 Hz, 1H), 7.66-7.56 (m, 2H), 7.48-7.41 m, 1H), 7.16-7.07 (m, 1H), 4.25-4.17 (m, 2H), 3.96 (br s, 4H), 3.16-3.07 (m, 2H), 2.68-2.60 (m, 2H), 2.16-2.06 (m, 2H), 1.91-1.84 (m, 4H), 1.82 (br s, 6H), 1.69-1.62 (m, 2H); LCMS [ESI, M+1]: m/z 516.1.

Example 22

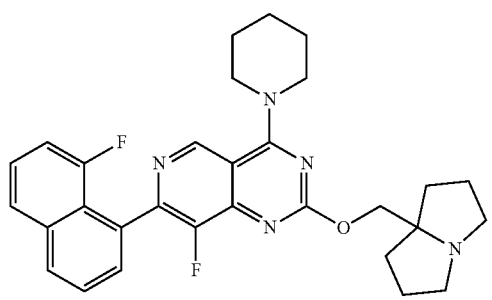

8-fluoro-7-(8-fluoronaphthalen-1-yl)-2-((hexahydro-1H-pyrrolizin-7a-yl)methoxy)-4-(piperidin-1-yl)pyrido[4,3-d]pyrimidine

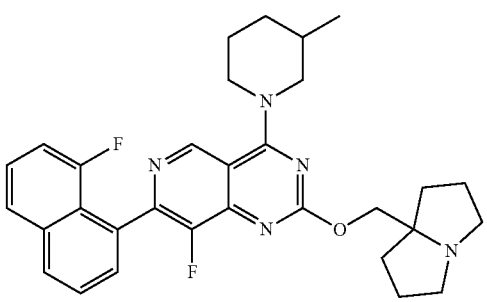 [SMILES: CC1CCCN(c2nc(OCC34CCCN3CCC4)nc3c(F)c(-c4cccc5cccc(F)c45)ncc23)C1]

8-fluoro-7-(8-fluoronaphthalen-1-yl)-2-((hexahydro-1H-pyrrolizin-7a-yl)methoxy)-4-(3-methylpiperidin-1-yl)pyrido[4,3-d]pyrimidine

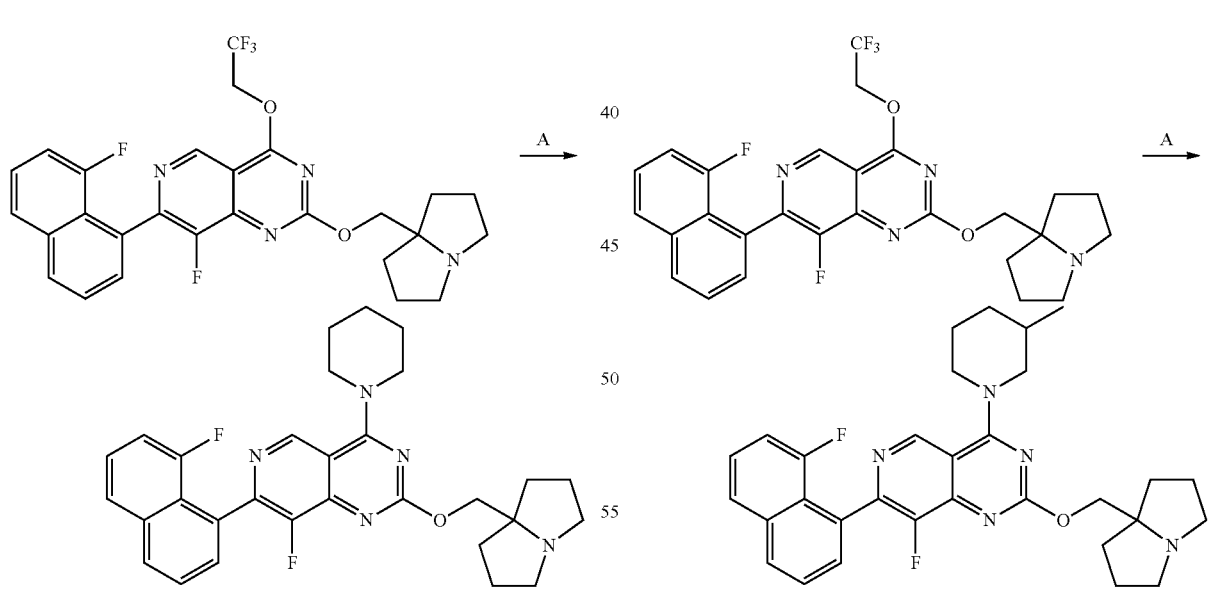

Step A. 8-fluoro-7-(8-fluoronaphthalen-1-yl)-2-((hexahydro-1H-pyrrolizin-7a-yl) methoxy)-4-(piperidin-1-yl)pyrido[4,3-d]pyrimidine: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 94.3 μmol) in DMF (1.0 mL) were added DIEA (36.5 mg, 283 μmol, 49.3 μL) and piperidine (12.0 mg, 141 μmol, 14.0 μL). The mixture was stirred at 40° C. for 1 hour.

Step A. 8-fluoro-7-(8-fluoronaphthalen-1-yl)-2-((hexahydro-1H-pyrrolizin-7a-yl) methoxy)-4-(3-methylpiperidin-1-yl)pyrido[4,3-d]pyrimidine: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d] pyrimidine (50.0 mg, 94.3 μmol) in DMF (1.0 mL) were added DIEA (36.5 mg, 283 μmol, 49.3 μL) and 3-methylpiperidine (28.0 mg, 283 μmol, 33.2 μL). The mixture was stirred at 40° C. for 1 hour. Upon completion, the residue was purified by prep-HPLC (column: water s Xbridge BEH C18 100×25 mm×5 µm; mobile phase: [water (10 mM NH₄HCO₃)-ACN]; B %: 40%-80%, 10 mins.) affording 8-fluoro-7-(8-fluoronaphthalen-1-yl)-2-((hexahydro-1H-pyrrolizin-7a-yl)methoxy)-4-(3-methylpiperidin-1-yl)pyrido[4,3-d]pyrimidine (7.87 mg, 16% yield) as a white solid. ¹H NMR (400 MHz, CDCl₃) 9.00 (s, 1H), 7.99 (br d, J=7.6 Hz, 1H), 7.74 (d, J=8.2 Hz, 1H), 7.67-7.57 (m, 2H), 7.48-7.41 (m, 1H), 7.15-7.08 (m, 1H), 4.61 (br d, J=13.2 Hz, 1H), 4.49 (br d, J=12 Hz, 1H), 4.29-4.16 (m, 2H), 3.26-3.17 (m, 1H), 3.15-3.07 (m, 2H), 3.01-2.88 (m, 1H), 2.68-2.60 (m, 2H), 2.15-2.06 (m, 2H), 2.04-1.74 (m, 8H), 1.69-1.59 (m, 2H), 1.39-1.25 (m, 1H), 1.02 (d, J=6.6 Hz, 3H); LCMS [ESI, M+1]: m/z 530.1.

Example 23

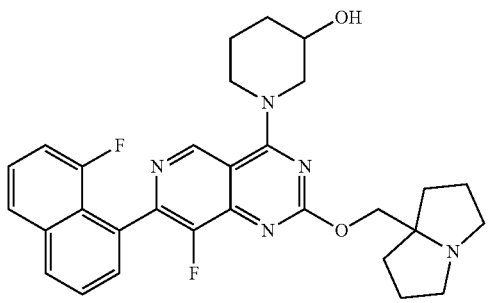 [SMILES: OC1CCCN(c2nc(OCC34CCCN3CCC4)nc3c(F)c(-c4cccc5cccc(F)c45)ncc23)C1]

1-(8-fluoro-7-(8-fluoronaphthalen-1-yl)-2-((hexahydro-1H-pyrrolizin-7a-yl)methoxy)pyrido[4,3-d]pyrimidin-4-yl)piperidin-3-ol

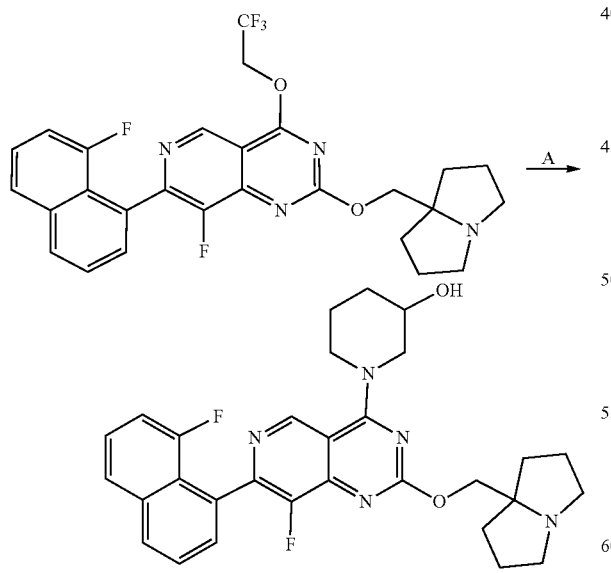

Step A. 1-(8-fluoro-7-(8-fluoronaphthalen-1-yl)-2-((hexahydro-1H-pyrrolizin-7a-yl methoxy)pyrido[4,3-d]pyrimidin-4-yl)piperidin-3-ol: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 94.3 µmol) in DMF (1.0 mL) were added DIEA (36.5 mg, 283 µmol, 49.3 µL) and piperidin-3-ol (28.6 mg, 283 µmol, 33.2 µL). The mixture was stirred at 40° C. for 1 hour. Upon completion, the residue was purified by prep-HPLC (column: water s Xbridge BEH C18 100×25 mm×5 µm; mobile phase: [water (10 mM NH₄HCO₃)-ACN]; B %: 20%-60%, 10 mins.) affording 1-(8-fluoro-7-(8-fluoronaphthalen-1-yl)-2-((hexahydro-1H-pyrrolizin-7a-yl)methoxy)pyrido[4,3-d]pyrimidin-4-yl)piperidin-3-ol (17.7 mg, 35% yield) as a white solid. ¹H NMR (400 MHz, CDCl₃) δ 9.10 (d, J=2.2 Hz, 1H), 7.99 (br d, J=8.0 Hz, 1H), 7.74 (d, J=8.2 Hz, 1H), 7.65-7.56 (m, 2H), 7.48-7.41 (m, 1H), 7.15-7.08 (m, 1H), 4.29-4.19 (m, 2H), 4.10 (br s, 1H), 4.06-3.88 (m, 4H), 3.24 (br s, 1H), 3.15-3.05 (m, 2H), 2.72-2.58 (m, 2H), 2.14-1.93 (m, 5H), 1.93-1.76 (m, 5H), 1.67-1.60 (m, 2H); LCMS [ESI, M+1]: m/z 532.1.

Example 24

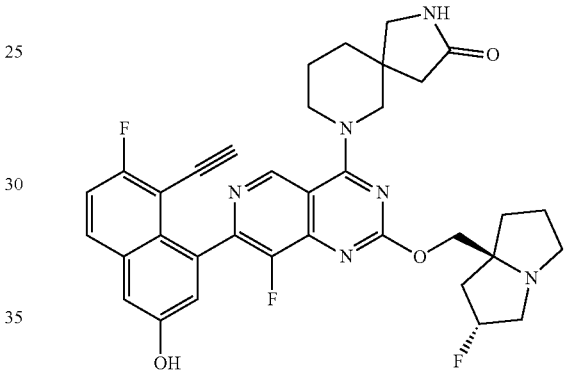

7-(7-(8-ethynyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one

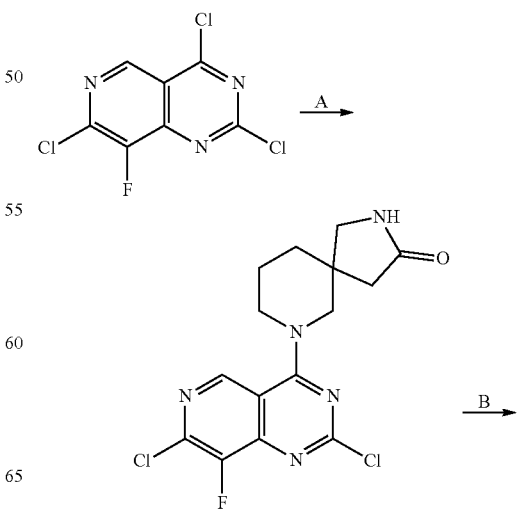

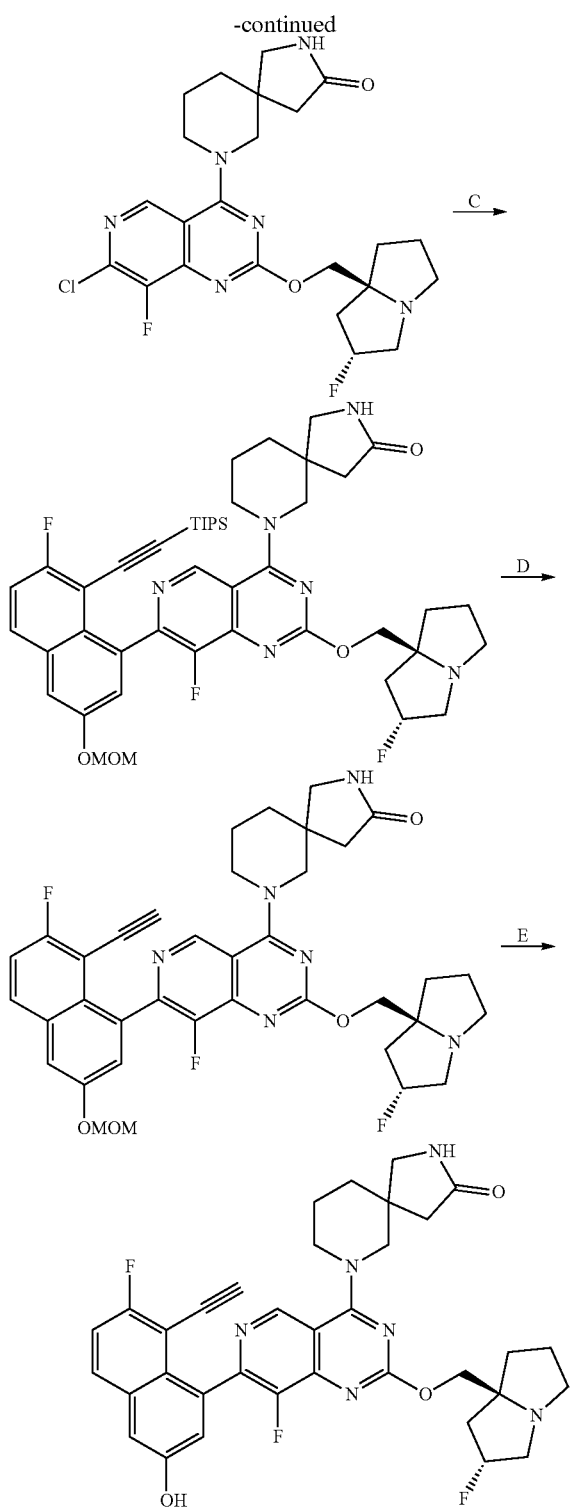

Step A. 7-(2,7-dichloro-8-fluoropyrido[4,3-d]pyrimidin-4-yl)-2,7-diazaspiro[4.5]decan-3-one: To a solution of 2,4,7-trichloro-8-fluoropyrido[4,3-d]pyrimidine (2.0 g, 6.85 mmol, 86% purity) in dichloromethane (20 mL) were added DIEA (3.54 g, 27.4 mmol, 4.77 mL) and 2,7-diazaspiro[4.5]decan-3-one (1.44 g, 7.53 mmol, HCl) at −40° C. The mixture was stirred at −40° C. for 1 h. After completion, the mixture was added water (20 mL) and extracted with EtOAc (2×20 mL). The combined organic layer was dried over anhydrous $Na_2SO_4$ and filtered. The mixture was concentrated in vacuum. The residue was purified by reversed phase flash chromatography (C18, water (0.1% formic acid)/ACN) affording 7-(2,7-dichloro-8-fluoropyrido[4,3-d]pyrimidin-4-yl)-2,7-diazaspiro[4.5]decan-3-one (1.60 g, 63% yield). Yellow solid; LCMS (ESI, M+1): m/z 370.0.

Step B. 7-(7-chloro-8-fluoro-2-(((2R,7aS)-2-fluorotetrahydro-1H-pyrrolizin-7a(5H)-yl)methoxy)pyrido[4,3-d]pyrimidin-4-yl)-2,7-diazaspiro[4.5]decan-3-one: To a mixture of 7-(2,7-dichloro-8-fluoropyrido[4,3-d]pyrimidin-4-yl)-2,7-diazaspiro[4.5]decan-3-one (300 mg, 810 μmol), DIEA (314 mg, 2.43 mmol, 423 μL) and 4 Å molecular sieves (10 mg) in dioxane (2.0 mL) was added ((2R,7aS)-2-fluorohexahydro-1H-pyrrolizin-7a-yl)methanol (142 mg, 891 μmol). The mixture was stirred at 95'° C. for 16 h. After completion, water (5.0 mL) was added and the mixture was extracted with EtOAc (2×5.0 mL). The combined organic layer was dried over anhydrous $Na_2SO_4$, filtered, and concentrated in vacuum. The residue was purified by reversed phase flash chromatography (C18, water (0.1% formic acid)/ACN) affording the title compound (120 mg, 19% yield). Yellow solid; LCMS (EST, M+1): m/z 493.2.

Step C. 7-(8-fluoro-7-(7-fluoro-3-(methoxymethoxy)-8-((triisopropylsilyl) ethynyl)naphthalen-1-yl)-2-(((2R,7aS)-2-fluorohexahydro-1H-pyrrolizin-7a-yl) methoxy)pyrido[4,3-d]pyrimidin-4-yl)-2,7-diazaspiro[4.5]decan-3-one: To a mixture of 7-(7-chloro-8-fluoro-2-(((2R,7aS)-2-fluorotetrahydro-1H-pyrrolizin-7a(5H)-yl)methoxy)pyrido[4,3-d]pyrimidin-4-yl)-2,7-diazaspiro[4.5]decan-3-one (100 mg, 203 μmol), ((2-fluoro-6-(methoxymethoxy)-8-(4,4,5,5-tetramethyl-1,3,2-dioxaborolan-2-yl)naphthalen-1-yl) ethynyl)triisopropylsilane (208 mg, 406 μmol) and $K_3PO_4$ (1.5 M, 406 μL) in THF (3.0 mL) was cataCXium-A-Pd-G3 (14.8 mg, 20.3 μmol). The mixture was stirred at 60° C. for 2 h. After completion, water (5.0 mL) was added and the mixture was extracted with EtOAc (2×5.0 mL). The combined organic layer was dried over anhydrous $Na_2SO_4$ and filtered. The mixture was concentrated in vacuum. The residue was purified by reversed phase flash chromatography (C18, water (0.1% formic acid)/ACN) affording 7-(8-fluoro-7-(7-fluoro-3-(methoxymethoxy)-8-((triisopropylsilyl) ethynyl)naphthalen-1-yl)-2-(((2R,7aS)-2-fluorohexahydro-1H-pyrrolizin-7a-yl) methoxy)pyrido[4,3-d]pyrimidin-4-yl)-2,7-diazaspiro[4.5]decan-3-one (80 mg, 45% yield). Yellow solid; LCMS (ESI, M+1): m/z 843.5.

Step D. 7-(7-(8-ethynyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one: To a solution of 7-(8-fluoro-7-(7-fluoro-3-(methoxymethoxy)-8-((triisopropylsilyl) ethynyl)naphthalen-1-yl)-2-(((2R,7aS)-2-fluorohexahydro-1H-pyrrolizin-7a-yl) methoxy)pyrido[4,3-d]pyrimidin-4-yl)-2,7-diazaspiro[4.5]decan-3-one (75.0 mg, 89.0 μmol) in DMF (1.5 mL) was added CsF (40.5 mg, 267 μmol, 9.84 μL). The mixture was stirred at 20° C. for 1 h. After completion, water (5.0 mL) was added and the mixture was extracted with EtOAc (2×5.0 mL). The combined organic layer was dried over anhydrous $Na_2SO_4$. The mixture was filtered and concentrated in vacuum. The residue was purified by reversed phase flash chromatography (C18, water (0.1% formic acid)/ACN) affording 7-(7-(8-ethynyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)-2,7-diazaspiro[4.5]decan-3-one (60 mg, 98% yield). Yellow solid; LCMS (ESI, M+1): m/z 687.3.

Step E. 7-(7-(8-ethynyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one: To a solution of 7-(7-(8-ethynyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one (55.0 mg, 80.1 µmol) in MeCN (0.5 mL) was added HCl.dioxane (4 M, 1.0 mL). The mixture was stirred at 20° C. for 0.5 h. After completion, the mixture was concentrated at 20° C. The residue was purified by prep-HPLC [Water s Xbridge 150×25 mm×5 µm; A: water (10 mM NH₄HCO₃), B: ACN; B %: 33%-63% over 10 min] and the desired fractions were lyophilized to afford 7-(7-(8-ethynyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one (6.16 mg, 12% yield). Yellow solid; ¹H NMR (400 MHz, DMSO-$d_6$) δ=10.20 (s, 1H), 9.02 (d, J=5.6 Hz, 1H), 7.98 (dd, J=6.0, 9.2 Hz, 1H), 7.74-7.59 (m, 1H), 7.47 (t, J=9.2 Hz, 1H), 7.40 (d, J=2.4 Hz, 1H), 7.20 (t, J=2.4 Hz, 1H), 5.56-5.23 (m, 1H), 4.48-4.11 (m, 2H), 4.11-3.86 (m, 3H), 3.86-3.67 (m, 2H), 3.26-2.89 (m, 4H), 2.52 (br s, 2H), 2.34-2.09 (m, 4H), 2.07-1.71 (m, 8H); LCMS (ESI, M+1): m/z 643.3.

Example 25

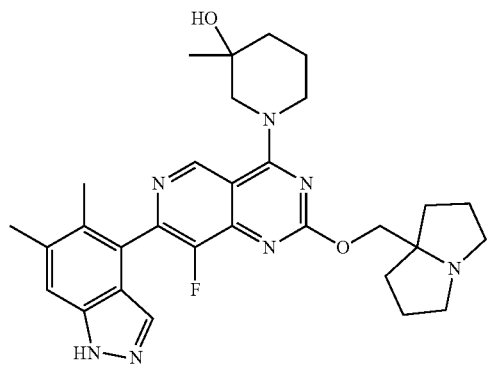 [SMILES: Cc1cc2[nH]ncc2c(-c2ncc3c(N4CCCC(C)(O)C4)nc(OCC45CCCN4CCC5)nc3c2F)c1C]

1-(7-(5,6-dimethyl-1H-indazol-4-yl)-8-fluoro-2-((hexahydro-1H-pyrrolizin-7a-yl) methoxy)pyrido[4,3-d]pyrimidin-4-yl)-3-methylpiperidin-3-ol

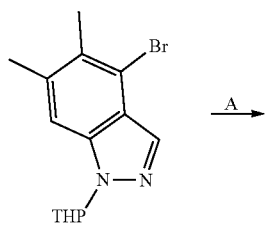

Step A. 5,6-dimethyl-1-tetrahydropyran-2-yl)-4-(4,4,5,5-tetramethyl-1,3,2-dioxaborolan-2-yl)indazole: To a solution of 4-bromo-5,6-dimethyl-1-(tetrahydro-2H-pyran-2-yl)-1H-indazole (2.00 g, 6.47 mmol), 4,4,5,5-tetramethyl-2-(4,4,5,5-tetramethyl-1,3,2-dioxaborolan-2-yl)-1,3,2-dioxaborolane (3.29 g, 12.9 mmol) and KOAc (1.90 g, 19.4 mmol) in dioxane (40 mL) was added Pd(dppf)Cl₂ (473 mg, 647 µmol). The mixture was stirred at 110° C. for 1 hour. After completion, water (30 mL) was added and the mixture was extracted with EtOAc (2×20 mL). The combined organic layer was dried over anhydrous Na₂SO₄. The mixture was filtered and concentrated under reduced pressure to give a residue. The residue was purified by column chromatography (Silica gel, petroleum ether: ethyl acetate=100:1-15:1) affording 5,6-dimethyl-1-(tetrahydro-2H-pyran-2-yl)-4-(4,4,5,5-tetramethyl-1,3,2-dioxaborolan-2-yl)-1H-indazole (1.60 g, 67% yield). Yellow oil; LCMS (ESI, M+1): m/z=357.0.

Step B. 1-(7-(5,6-dimethyl-(tetrahydro-2H-pyran-2-yl)-1H-indazol-4-yl)-8-fluoro-2-((tetrahydro-1H-pyrrolizin-7a(5H)-yl)methoxy)pyrido[4,3-d]pyrimidin-4-yl)-3-methylpiperidin-3-ol: To a mixture of 1-(7-chloro-8-fluoro-2-((hexahydro-1H-pyrrolizin-7a-yl) methoxy)pyrido[4,3-d]pyrimidin-4-yl)-3-methylpiperidin-3-ol (290 mg, 665 µmol) and 5,6-dimethyl-1-tetrahydropyran-2-yl)-4-(4,4,5,5-tetramethyl-1,3,2-dioxaborolan-2-yl)indazole (355 mg, 998

μmol) in THF (6 mL) was added K₃PO₄ (1.5 M, 1.33 mL) in one portion at 25° C. under N₂. Then cataCXium-A-Pd-G3 (96.90 mg, 133 μmol) was added. The mixture was heated to 60° C. and stirred for 2 h. The mixture was filtered and concentrated in vacuum. The crude product was purified by reversed-phase flash chromatography (water (0.1% formic acid)-ACN) to afford the title compound (300 mg, 69% h yield). LCMS (ESI, M+1): m/z 630.5.

Step C. 1-(7-(5,6-dimethyl-1H-indazol-4-yl)-8-fluoro-2-((hexahydro-1H-pyrrolizin-7a-yl)methoxy)pyrido[4,3-d]pyrimidin-4-yl)-3-methylpiperidin-3-ol: A mixture of 1-(7-(5,6-dimethyl-1-(tetrahydro-2H-pyran-2-yl)-1H-indazol-4-yl)-8-fluoro-2-((tetrahydro-1H-pyrrolizin-7a(5H)-yl)methoxy)pyrido[4,3-d]pyrimidin-4-yl)-3-methylpiperidin-3-ol (290 mg, 460 μmol) and ACN (0.2 mL) was added HCl.dioxane (4 M, 1.98 μL) in one portion at 25° C. under N₂. The mixture was stirred at 25° C. for 10 minutes. The mixture was filtered and concentrated in vacuum. The residue was purified by prep-HPLC to afford the title compound (76.4 mg, 30% yield). ¹H NMR 400 MHz, (DMSO-d₆) δ 13.0 (br s, 1H), 9.30 (d, J=9.8 Hz, 1H), 8.23 (s, 1H), 7.33-7.23 (m, 2H), 4.20-4.15 (m, 1H), 4.17-4.02 (m, 3H), 3.31-3.27 (m, 2H), 3.05-2.95 (m, 2H), 2.35-2.27 (m, 2H), 2.44 (s, 3H), 2.13 (d, J=4.4 Hz, 3H), 2.04-1.27 (m, 12H), 1.18 (s, 3H). LCMS (ESI, M+1): m/z 546.1.

Example 26

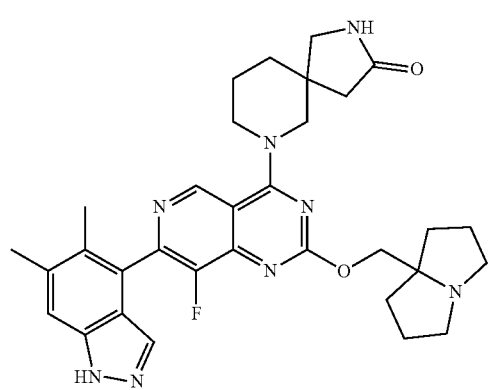 [SMILES: Cc1cc2[nH]ncc2c(-c2ncc3c(N4CCCC5(CNC(=O)C5)C4)nc(OCC45CCCN4CCC5)nc3c2F)c1C]

7-(7-(5,6-dimethyl-1H-indazol-4-yl)-8-fluoro-2-((hexahydro-1H-pyrrolizin-7a-yl) methoxy)pyrido[4,3-d]pyrimidin-4-yl)-2,7-diazaspiro[4.5]decan-3-one

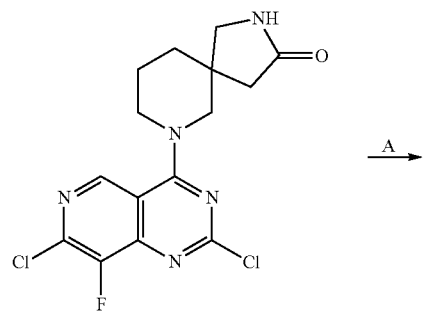

A →

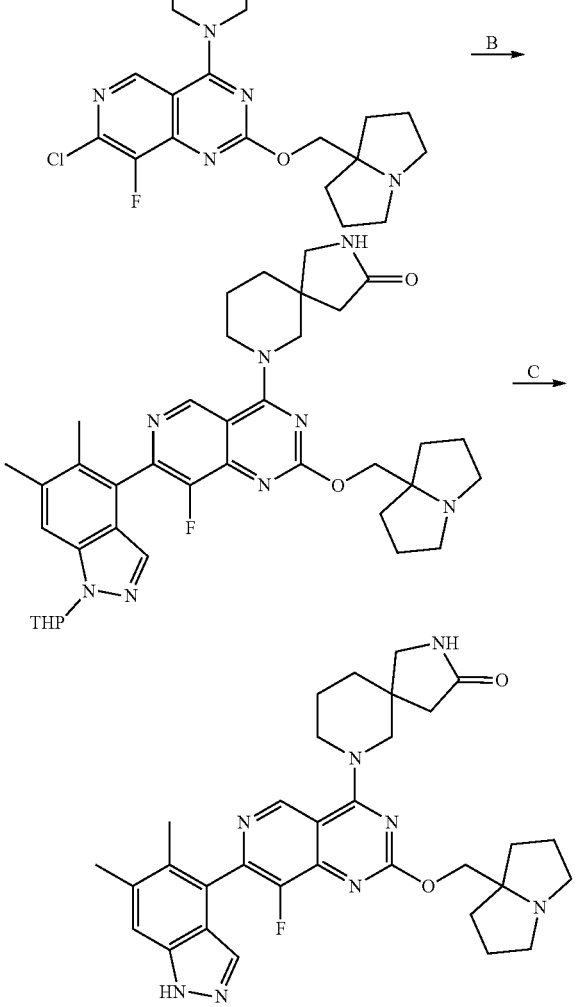

Step A. 7-(7-chloro-8-fluoro-2-((hexahydro-1H-pyrrolizin-7a-yl)methoxy)pyrido[4,3-d]pyrimidin-4-yl)-2,7-diazaspiro[4.5]decan-3-one: To a mixture of 7-(2,7-dichloro-8-fluoropyrido[4,3-d]pyrimidin-4-yl)-2,7-diazaspiro[4,5]decah-3-one (300 mg, 810 μmol), 4 Å molecular sieves (10 mg) and DIEA (314 mg, 2.43 mmol, 423 μL) in dioxane (2 mL) was added (hexahydro-1H-pyrrolizin-7a-yl)methanol (126 mg, 891 μmol). The mixture was stirred at 95° C. for 16 h. After completion, water (5.0 mL) was added and the mixture was extracted with EtOAc (2×5.0 mL). The combined organic layer was dried over anhydrous Na₂SO₄. The mixture was filtered and concentrated under reduced pressure to give a residue. The residue was purified by reversed phase flash chromatography (C18, water (0.1% formic acid)/ACN) to afford 7-(7-chloro-8-fluoro-2-((hexahydro-1H-pyrrolizin-7a-yl)methoxy)pyrido[4,3-d]pyrimidin-4-yl)-2,7-diazaspiro[4.5]decan-3-one (130 mg, 33% yield). Yellow solid; LCMS (ESI, M+1): m/z=475.3.

Step B. 7-(7-(5,6-dimethyl-1-(tetrahydro-2H-pyran-2-yl)-1H-indazol-4-yl)-8-fluoro-2-((hexahydro-1H-pyrrolizin-7a-yl)methoxy)pyrido[4,3-d]pyrimidin-4-yl)-2,7-diazaspiro[4.5]decan-3-one: To a mixture of 7-(7-chloro-8-fluoro-2-((hexahydro-1H-pyrrolizin-7a-yl)methoxy)pyrido[4,3-d]

pyrimidin-4-yl)-2,7-diazaspiro[4.5]decan-3-one (130 mg, 274 μmol), 5,6-dimethyl-1-(tetrahydro-2H-pyran-2-yl)-4-(4, 4,5,5-tetramethyl-1,3,2-dioxaborolan-2-yl)-1H-indazole (243.78 mg, 684.27 μmol) and K₃PO₄ (1.5 M, 547 μL) in THF (3 mL) was added cataCXium-A-Pd-G3 (39.9 mg, 54.7 μmol). The mixture was stirred at 60° C. for 2 hour. After completion, to the reaction mixture was added water (5.0 mL), and the mixture extracted with EtOAc (2×5.0 mL). The combined organic layer was dried over anhydrous Na₂SO₄, filtered and concentrated under reduced pressure to give a residue. The residue was purified by reversed phase flash chromatography (C18, water (0.1% formic acid)/ACN) affording 7-(7-(5,6-dimethyl-1-(tetrahydro-2H-pyran-2-yl)-1H-indazol-4-yl)-8-fluoro-2-((hexahydro-1H-pyrrolizin-7a-yl) methoxy)pyrido[4,3-d]pyrimidin-4-yl)-2,7-diazaspiro [4.5]decan-3-one (120 mg, 65% yield). Yellow solid; LCMS (ESI, M+1): m/z=669.3.

Step C. 7-(7-(5,6-dimethyl-1H-indazol-4-yl)-8-fluoro-2-((hexahydro-1H-pyrrolizin-7a-yl)methoxy)pyrido[4,3-d]pyrimidin-4-yl)-2,7-diazaspiro[4.5]decan-3-one: To a solution of 7-(7-(5,6-dimethyl-1-(tetrahydro-2H-pyran-2-yl)-1H-indazol-4-yl)-8-fluoro-2-((hexahydro-1H-pyrrolizin-7a-yl) methoxy)pyrido[4,3-d]pyrimidin-4-yl)-2,7-diazaspiro[4.5] decan-3-one (30 mg, 44.9 μmol) in MeCN (0.5 mL) was added HCl.dioxane (4 M, 1.0 mL). The mixture was stirred at 20° C. for 0.5 hour. After completion, the mixture was concentrated at 20° C. The residue was purified by prep-HPLC [Water s Xbridge 150×25 mm×5 um; A: water (10 mM NH₄HCO₃), B: ACN, B %: 16%-46% over 10 min) to afford the title compound (7.08 mg, 26% yield). White solid; ¹H NMR (400 MHz, CDCl₃) δ=10.87-10.17 (m, 1H), 8.98 (d, J=4.0 Hz, 1H), 7.56 (d, J=13.2 Hz, 1H), 7.31 (br d, J=4.8 Hz, 1H), 6.55-5.99 (m, 1H), 4.28-4.12 (m, 2H), 4.02 (br d, J=12.8 Hz, 2H), 3.66-3.52 (m, 1H), 3.42 (br d, J=12.0 Hz, 1H), 3.31 (br t, J=10.0 Hz, 1H), 3.14-3.00 (m, 3H), 2.64-2.52 (m, 2H), 2.46-2.36 (m, 3H), 2.19 (s, 2H), 2.13 (br d, J=5.2 Hz, 3H), 2.07-1.97 (m, 2H), 1.88-1.74 (m, 8H), 1.60-1.54 (m, 2H); LCMS (ESI, M+1): m/z=585.2.

Example 27

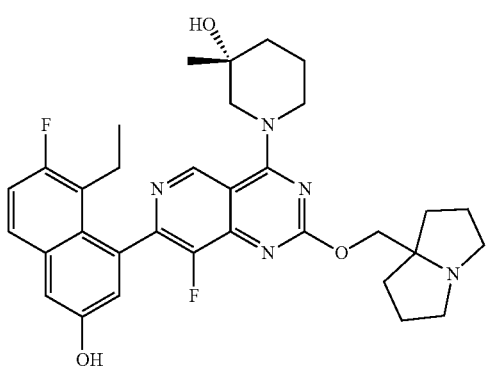 [SMILES: CCc1c(F)ccc2cc(O)cc(-c3ncc4c(N5CCC[C@@](C)(O)C5)nc(OCC56CCCN5CCC6)nc4c3F)c12]

(R)-1-(7-(8-ethyl-7-fluoro-3-hydroxy)naphthalen-1-yl)-8-fluoro-2-((hexahydro-1H-pyrrolizin-7a-yl) methoxy)pyrido[4,3-d]pyrimidin-4-yl)-3-methylpiperidin-3-ol

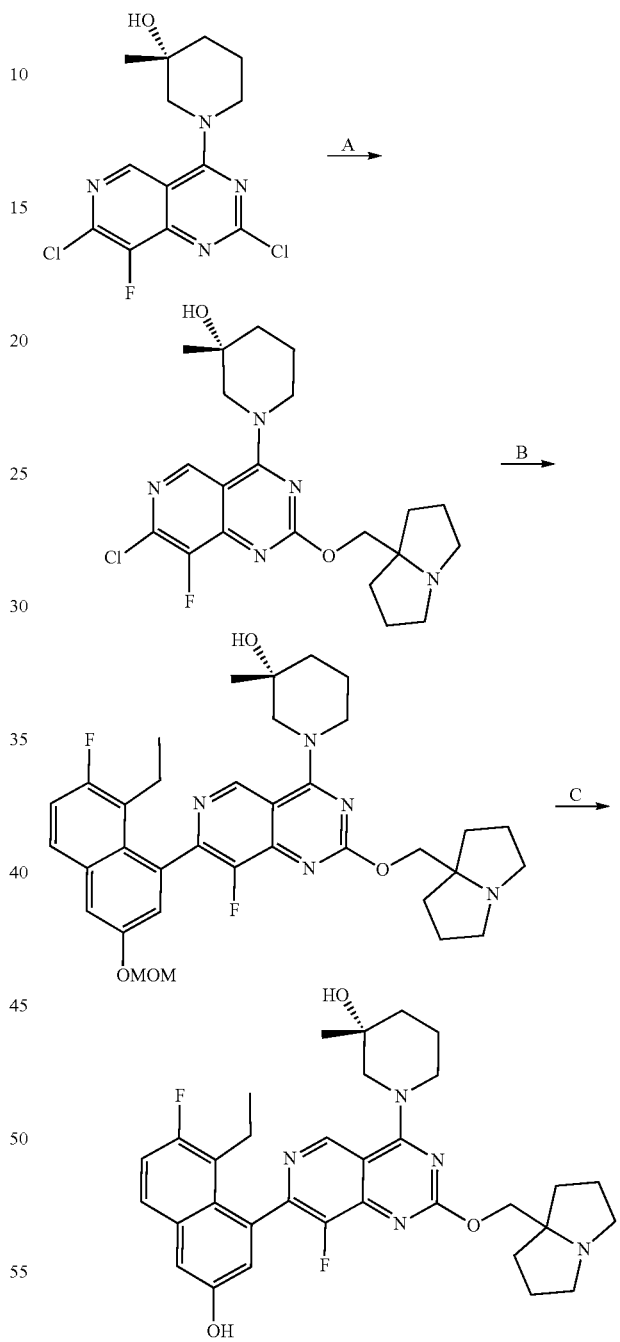

Step A. (R)-1-(7-chloro-8-fluoro-2-((hexahydro-1H-pyrrolizin-7a-yl) methoxy)pyrido[4,3-d]pyrimidin-4-yl)-3-methylpiperidin-3-ol: A mixture of (R)-1-(2,7-dichloro-8-fluoropyrido[4,3-d]pyrimidin-4-yl)-3-methylpiperidin-3-ol (125 mg, 377 μmol), (hexahydro-1H-pyrrolizin-7a-yl) methanol (56 mg, 396 μmol), DIPEA (133 mg, 1.03 mmol) and 4 Å molecular sieves (56 mg) in dioxane (0.7 mL) was stirred at 90° C. for 21 hours under N₂ atmosphere. The reaction mixture was filtered and the filter cake was washed with dichloromethane (20 mL). The filtrate was concentrated under reduced pressure and purified by reversed phase flash chromatography [water (0.1% formic acid)/acetonitrile=7/3] to give the product as white solid (40 mg, 21% yield). LCMS (ESI, M+1): m/z 436.2.

Step B. (R)-1-(7-(8-ethyl-7-fluoro-3-(methoxymethoxy) naphthalen-1-y-8-fluoro-2-((hexahydro-1H-pyrrolizin-7a-yl)methoxy)pyrido[4,3-d]pyrimidin-4-yl)-3-methylpiperidin-3-ol: A mixture of (R)-1-(7-chloro-8-fluoro-2-((hexahydro-1H-pyrrolizin-7a-yl) methoxy)pyrido[4,3-d]pyrimidin-4-yl)-3-methylpiperidin-3-ol (40 mg, 91.8 µmol), K₃PO₄ (1.5 M in water, 0.2 mL) in THF (1 mL) was degassed and purged with N₂ for 3 times. cataCXium-A-Pd-G3 (14 mg, 19.2 µmol) was added and followed by 2-(8-ethyl-7-fluoro-3-(methoxymethoxy)naphthalen-1-yl)-4,4,5,5-tetramethyl-1,3,2-dioxaborolane (50 mg, 139 µmol). The mixture was stirred at 65° C. for 4 hours. The reaction mixture was diluted with water (2 mL) and extracted with ethyl acetate (2 mL×4). The combined organic layers were concentrated under reduced pressure to give a residue. The residue was purified by reversed phase flash chromatography [water (0.1% formic acid)/acetonitrile=13/7] to give the product as brown gum (41 mg, 65% yield). LCMS (ESI, M+1): m/z 634.1.

Step C. (R)-1-(7-(8-ethyl-7-fluoro-3-hydroxy)naphthalen-1-yl)-8-fluoro-2-((hexahydro-1H-pyrrolizin-7a-yl) methoxy)pyrido[4,3-d]pyrimidin-4-yl)-3-methylpiperidin-3-ol: To a solution of (R)-1-(7-(8-ethyl-7-fluoro-3-(methoxymethoxy)naphthalen-1-yl)-8-fluoro-2-((hexahydro-1H-pyrrolizin-7a-yl)methoxy)pyrido[4,3-d] pyrimidin-4-yl)-3-methylpiperidin-3-ol (41 mg, 64.7 µmol) in MeCN (2 mL) was added HCl/dioxane (4 M, 1.5 mL) dropwise at 0° C. The mixture was stirred at 0° C. for 0.5 hour. The reaction mixture was concentrated under reduced pressure to give a residue at room temperature. The residue was dissolved in ethyl acetate (5 mL) and saturated NaHCO₃ aqueous (5 mL). The mixture was extracted with ethyl acetate (5 mL×4). The combined organic layers were dried over anhydrous Na₂SO₄. The mixture was filtered and concentrated under reduced pressure to give a residue. The residue was purified by prep-HPLC (column: Phenomenex luna C18 150×25 mm×10 um; mobile phase: [water (0.225% formic acid)-ACN]; B %: 15%-45%, 10 minutes) to give the product as yellow solid (9.02 mg, 22% yield, 0.7 FORMIC ACID). ¹H NMR (400 MHz, methanol-d4) δ=9.26 (s, 1H), 7.68 (dd, J=6.0, 9.2 Hz, 1H), 7.31 (d, J=2.8 Hz, 1H), 7.26 (t, J=9.2 Hz, 1H), 7.06 (t, J=2.4 Hz, 1H), 4.62-3.55 (m, 3H), 4.34 (t, J=11.6 Hz, 1H), 3.67-3.61 (m, 1H), 3.55-3.40 (m, 3H), 3.14-3.11 (m, 2H), 2.25-2.15 (m, 1H), 2.13-2.03 (m, 10H), 2.02-1.73 (m, 3H), 1.30 (d, J=9.2 Hz, 3H), 0.81 (q, J=7.6 Hz, 3H). ¹⁹F NMR (377 MHz, methanol-d4) δ=−121.11, −139.56. LCMS (ESI, M+1): m/z 590.4.

Example 28

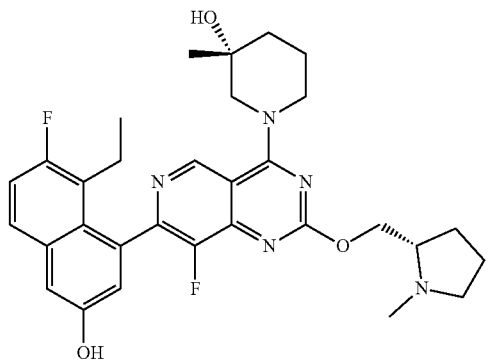 [SMILES: CCc1c(F)ccc2cc(O)cc(-c3ncc4c(N5CCC[C@@](C)(O)C5)nc(OC[C@@H]5CCCN5C)nc4c3F)c12]

(3R)-1-[7-(8-ethyl-7-fluoro-3-hydroxy-1-naphthyl)-8-fluoro-2-[[(2S)-1-methylpyrrolidin-2-yl]methoxy] pyrido[4,3-d]pyrimidin-4-yl]-3-methyl-piperidin-3-ol

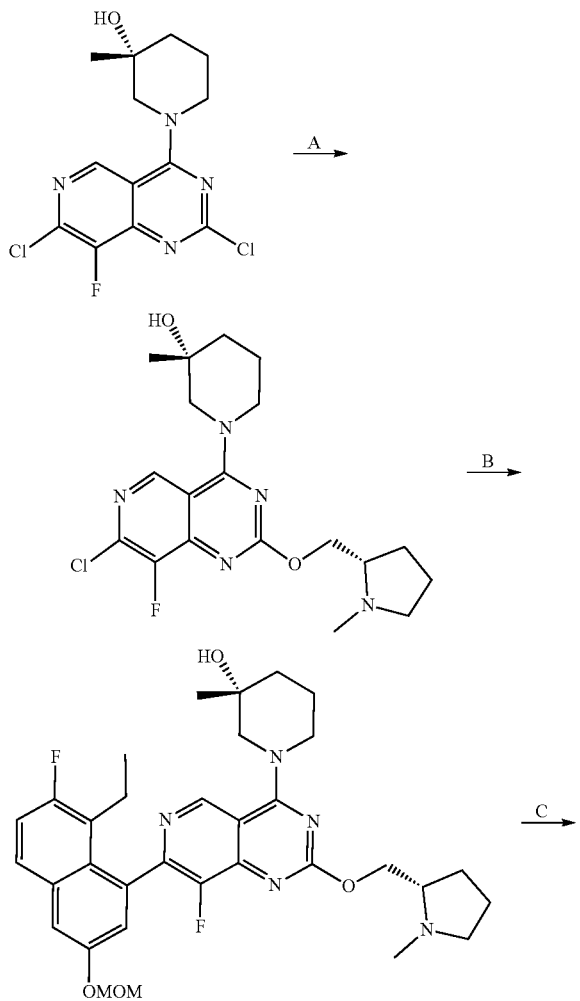

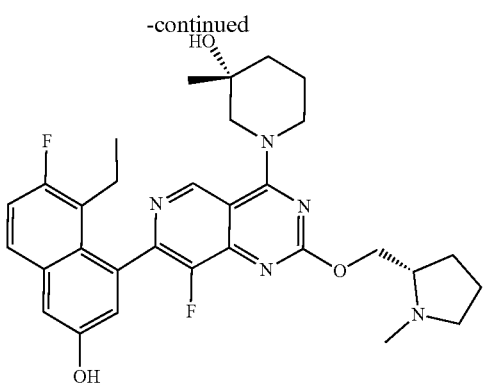

Step A. (3R)-1-[7-chloro-8-fluoro-2-f][(2S)-1-methylpyrrolidin-2-yl]methoxy]pyrido[4,3-d]pyrimidin-4-yl]-3-methyl-piperidin-3-ol: A mixture of (R)-1-(2,7-dichloro-8-fluoropyrido[4,3-d]pyrimidin-4-yl)-3-methylpiperidin-3-ol (150 mg, 453 μmol), [(2S)-1-methylpyrrolidin-2-yl]methanol (157 mg, 1.36 mmol, 161 μl), DIEA (176 mg, 1.36 mmol, 237 μl) and 4 Å molecular sieves (15.0 mg, 453 μmol) in dioxane (2 mL) was stirred at 90° C. for 15 hours. After completion, the mixture was diluted with ethyl acetate (5 mL) and water (5 mL), and then separated. The aqueous phase was extracted with ethyl acetate (5 mL). The combined organic layer was washed with brine (8 mL) and dried over anhydrous $Na_2SO_4$. The mixture was filtered and concentrated under reduced pressure to give a residue. The residue was purified by reversed phase flash chromatography [water (0.1% formic acid)/acetonitrile] to give (3R)-1-[7-chloro-8-fluoro-2-[[(2S)-1-methylpyrrolidin-2-yl]methoxy]pyrido[4,3-d]pyrimidin-4-yl]-3-methyl-piperidin-3-ol (135 mg, 70% yield). Yellow oil. LCMS (ESI, M+1): m/z 410.2.

Step B. (3R)-1-[7-[8-ethyl-7-fluoro-3-(methoxymethoxy)-1-naphthyl]-8-fluoro-2-[[2S)-1-methylpyrrolidin-2-yl]methoxy]pyrido[4,3-d]pyrimidin-4-yl]-3-methyl-piperidin-3-ol: To a mixture of (3R)-1-[7-chloro-8-fluoro-2-[[(2S)-1-methylpyrrolidin-2-yl]methoxy]pyrido[4,3-d]pyrimidin-4-yl]-3-methyl-piperidin-3-ol (135 mg, 329 μmol), 2-(8-ethyl-7-fluoro-3-(methoxymethoxy)naphthalen-1-yl)-4,4,5,5-tetramethyl-1,3,2-dioxaborolane (237 mg, 659 μmol) and $K_3PO_4$ (1.5 M, 659 μl) in THF (2.1 mL) was added [2-(2-aminophenyl)phenyl]palladium(1+); bis(1-adamantyl)-butyl-phosphane; methanesulfonate (24.0 mg, 32.9 μmol) under $N_2$. The mixture was degassed and then heated to 60° C. for 3 hours under $N_2$. After completion, the mixture was diluted with ethyl acetate (2 mL) and water (2 mL), and then separated. The aqueous phase was extracted with ethyl acetate (3 mL). The combined organic layer was washed with brine (4 mL) and dried over anhydrous $Na_2SO_4$. The mixture was filtered and concentrated under reduced pressure to give a residue. The residue was purified by reversed phase flash chromatography [water (0.1% formic acid)/acetonitrile] to give (3R)-1-[7-[8-ethyl-7-fluoro-3-(methoxymethoxy)-1-naphthyl]-8-fluoro-2-[[(2S)-1-methylpyrrolidin-2-yl]methoxy]pyrido[4,3-d]pyrimidin-4-yl]-3-methyl-piperidin-3-ol (100 mg, 50% yield). Yellow oil; LCMS (ESI, M+1): m/z 608.3.

Step C. (3R)-1-[7-(8-ethyl-7-fluoro-3-hydroxy-1-naphthyl)-8-fluoro-2-[[(2S'-1-methylpyrrolidin-2-yl]methoxy]pyrido[4,3-d]pyrimidin-4-yl]-3-methyl-piperidin-3-ol: To a mixture of (3R)-1-[7-[8-ethyl-7-fluoro-3-(methoxymethoxy)-1-naphthyl]-8-fluoro-2-[[(2S)-1-methylpyrrolidin-2-yl]methoxy]pyrido[4,3-d]pyrimidin-4-yl]-3-methyl-piperidin-3-ol (40.0 mg, 65.8 μmol) in MeCN (0.5 mL) was added HCl.dioxane (4 M, 1 mL) at 0° C. and the mixture was stirred at 0° C. for 0.5 hour. After completion, the mixture was concentrated in vacuum. Then the pH value was adjusted to 9 with saturated $NaHCO_3$ solution and the mixture was washed with methanol (2×8 mL). The mixture was filtered and concentrated in vacuum. The residue was purified by prep-HPLC (Shim-pack C18 150×25×10 um; mobile phase: [water (0.225% formic acid)-ACN]; B %: 20%-40%, 10 min) to afford (3R)-1-[7-(8-ethyl-7-fluoro-3-hydroxy-1-naphthyl)-8-fluoro-2-[[(2S)-1-methylpyrrolidin-2-yl]methoxy]pyrido[4,3-d]pyrimidin-4-yl]-3-methyl-piperidin-3-ol (14.4 mg, 36% yield, 0.6 FORMIC ACID). White solid. $^1H$ NMR (400 MHz, METHANOL-d4): δ 9.24 (d, J=3.2 Hz, 1H), 7.68 (dd, J=6.0, 8.8 Hz, 1H), 7.31 (d, J=2.4 Hz, 1H), 7.25 (t, J=9.2 Hz, 1H), 7.06 (br s, 1H), 4.78-4.71 (m, 1H), 4.66-4.56 (m, 2H), 4.33 (br t, J=11.6 Hz, 1H), 3.66-3.59 (m, 1H), 3.54-3.41 (m, 3H), 3.00-2.93 (m, 1H), 2.89 (s, 3H), 2.51-2.41 (m, 1H), 2.35-2.27 (m, 1H), 2.23-2.13 (m, 2H), 2.09-1.96 (m, 3H), 1.89-1.76 (m, 3H), 1.29 (br d, J=8.8 Hz, 3H), 0.81 (q, J=7.6 Hz, 3H). $^{19}F$ NMR (400 MHz, METHANOL-d4) δ=−121.070, −139.482. HPLC:>99% ee, Chiralcel OJ-3 50×4.6 mm I.D., 3 μm; Mobile phase: Phase A for $CO_2$, and Phase B for MeOH (0.05% DEA); Gradient elution: MeOH (0.05% DEA) in $CO_2$ from 5% to 40%; Flow rate: 3 mL/min; Detector: PDA; Column Temp: 35° C.; Back Pressure: 100 Bar". LCMS (ESI, M+1): m/z 564.3.

Example 29

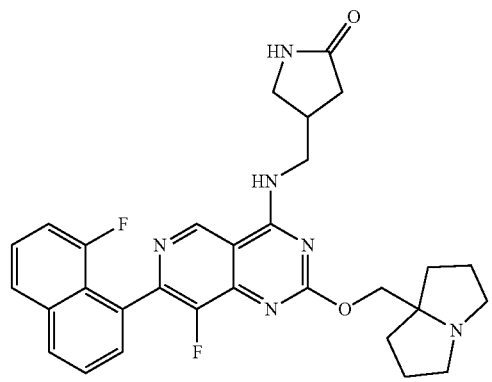 [SMILES: O=C1CC(CNc2nc(OCC34CCCN3CCC4)nc3c(F)c(-c4cccc5cccc(F)c45)ncc23)CN1]

4-(((8-fluoro-7-(8-fluoronaphthalen-1-yl)-2-((hexahydro-1H-pyrrolizin-7a-yl)methoxy)pyrido[4,3-d]pyrimidin-4-yl)amino)methyl)pyrrolidin-2-one

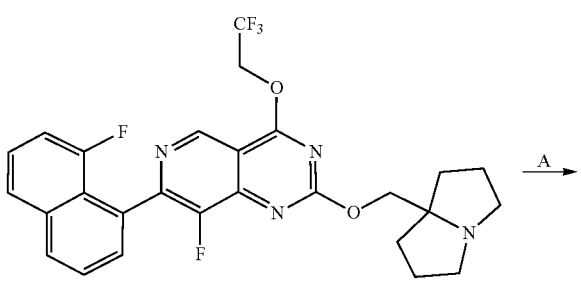

171
-continued

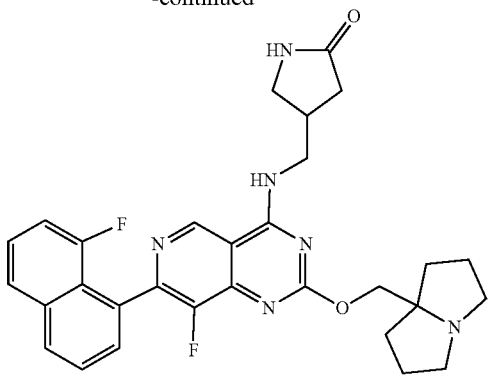

Step A. 4-(((8-fluoro-7-(8-fluoronaphthalen-1-yl)-2-((hexahydro-1H-pyrrolizin-7a-yl)methoxy)pyrido[4,3-d]pyrimidin-4-yl)amino)methyl)pyrrolidin-2-one: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 94.3 µmol) in DMF (1.0 mL) were added DIEA (36.5 mg, 283 µmol, 49.3 µL) and 4-(aminomethyl)pyrrolidin-2-one (42.6 mg, 283 µmol, HCl). The mixture was stirred at 40° C. for 1 hour. Upon completion, the residue was purified by prep-HPLC (column: Phenomenex Luna C18 200×40 mm×10 µm; mobile phase: [water (0.2% FORMIC ACID)-ACN]; B %: 20%-50%, 8 mins) to afford 4-(((8-fluoro-7-(8-fluoronaphthalen-1-yl)-2-((hexahydro-1H-pyrrolizin-7a-yl)methoxy)pyrido[4,3-d]pyrimidin-4-yl) amino)methyl)pyrrolidin-2-one (18.5 mg, 33% yield, formic acid salt) as a white solid. $^1$H NMR (400 MHz, CDCl$_3$) δ 9.45-9.15 (m, 2H), 8.01-7.89 (m, 1H), 7.74-7.70 (m, 1H), 7.65-7.50 (m, 2H), 7.48-7.35 (m, 1H), 7.17-7.05 (m, 1H), 6.34 (br d, J=72.0 Hz, 1H), 4.55-4.34 (m, 2H), 3.79-3.64 (m, 2H), 3.60-3.52 (m, 1H), 3.48-3.33 (m, 2H), 3.20-3.03 (m, 1H), 2.96-2.71 (m, 3H), 2.47-2.35 (m, 1H), 2.35-2.17 (m, 2H), 2.16-2.03 (m, 3H), 2.02-1.89 (m, 2H), 1.89-1.75 (m, 2H); $^1$H NMR (400 MHz, MeOD-d$_4$) δ 9.20 (s, 1H), 8.13 (d, J=8.4 Hz, 1H), 7.86 (d, J=8.4 Hz, 1H), 7.75-7.66 (m, 1H), 7.61-7.57 (m, 1H), 7.54 (dt, J=5.0, 8.0 Hz, 1H), 7.22-7.15 (m, 1H), 4.61-4.57 (m, 2H), 3.97-3.84 (m, 1H), 3.81-3.75 (m, 1H), 3.66-3.53 (m, 3H), 3.30-3.27 (m, 1H), 3.22-3.10 (m, 2H), 3.08-2.92 (m, 1H), 2.60-2.51 (m, 1H), 2.35-2.24 (m, 3H), 2.24-2.09 (m, 4H), 2.09-1.96 (m, 2H); LCMS (ESI, M+1): m/z 545.1.

Example 30

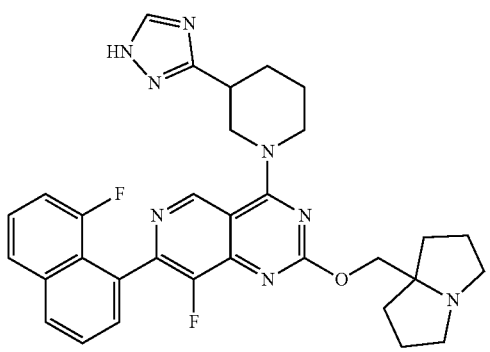 [SMILES: Fc1c(-c2cccc3cccc(F)c23)ncc2c(N3CCCC(c4nc[nH]n4)C3)nc(OCC34CCCN3CCC4)nc12]

172

4-(3-(1H-1,2,4-triazol-3-yl)piperidin-1-yl)-8-fluoro-7-(8-fluoronaphthalen-1-yl)-2-((hexahydro-1H-pyrrolizin-7a-yl)methoxy)pyrido[4,3-d]pyrimidine

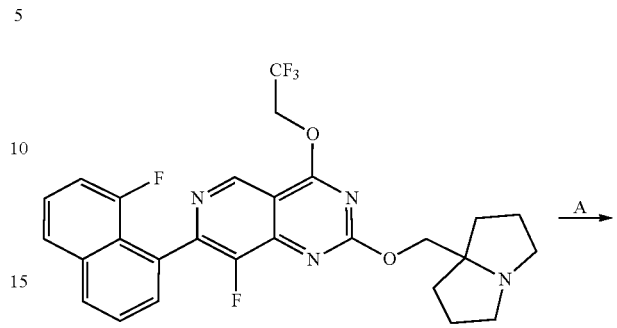

Step A. 4-(3-(1H-1,2,4-triazol-3-yl)piperidin-1-yl)-8-fluoro-7-(8-fluoronaphthalen-1-yl)-2-((hexahydro-1H-pyrrolizin-7a-yl)methoxy)pyrido[4,3-d]pyrimidine: A mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 94.3 µmol) in DMF (1.00 mL) was added DIEA (73.1 mg, 566 µmol) and 3-(1H-1,2,4-triazol-3-yl)piperidine (35.6 mg, 189 µmol, HCl). The mixture was stirred at 40° C. for 8 hours. The mixture was filtered and was purified by prep-HPLC (column: 3_Phenomenex Luna C18 75×30 mm×3 µm; mobile phase: [water (0.2% FORMIC ACID)-ACN]; B %: 15%-45%, 8 min) to afford 4-(3-(1H-1,2,4-triazol-3-yl) piperidin-1-yl)-8-fluoro-7-(8-fluoronaphthalen-1-yl)-2-((hexahydro-1H-pyrrolizin-7a-yl) methoxy)pyrido[4,3-d]pyrimidine (23.4 mg, 42% yield) as a white solid. $^1$H NMR (400 MHz, MeOD) δ 9.13 (s, 1H), 8.55 (s, 0.6H), 8.30 (s, 1H), 8.13 (d, J=7.9 Hz, 1H), 7.86 (d, J=8.1 Hz, 1H), 7.71 (t, J=7.7 Hz, 1H), 7.62 (d, J=7.1 Hz, 1H), 7.56-7.51 (m, 1H), 7.22-7.17 (m, 1H), 4.65-4.49 (m, 3H), 3.91-3.67 (m, 2H), 3.49-3.45 (m, 2H), 3.36 (d, J=5.5 Hz, 2H), 3.14-3.05 (m, 2H), 2.34 (d, J=9.2 Hz, 1H), 2.26-2.21 (m, 2H), 2.16-2.04 (m, 6H), 2.02-1.91 (m, 3H); LCMS (ESI, M+1): m/z 583.2.

Example 31

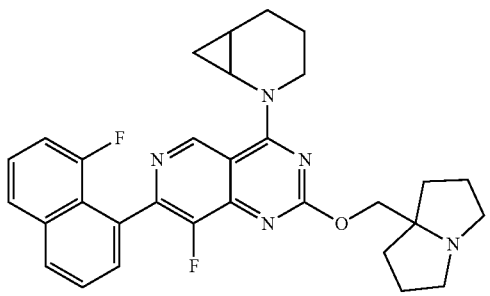 [SMILES: Fc1c(-c2cccc3cccc(F)c23)ncc2c(N3CCCC4CC43)nc(OCC34CCCN3CCC4)nc12]

4-(2-azabicyclo[4.1.0]heptan-2-yl)-8-fluoro-7-(8-fluoronaphthalen-1-yl)-2-((hexahydro-1H-pyrrolizin-7a-yl)methoxy)pyrido[4,3-d]pyrimidine

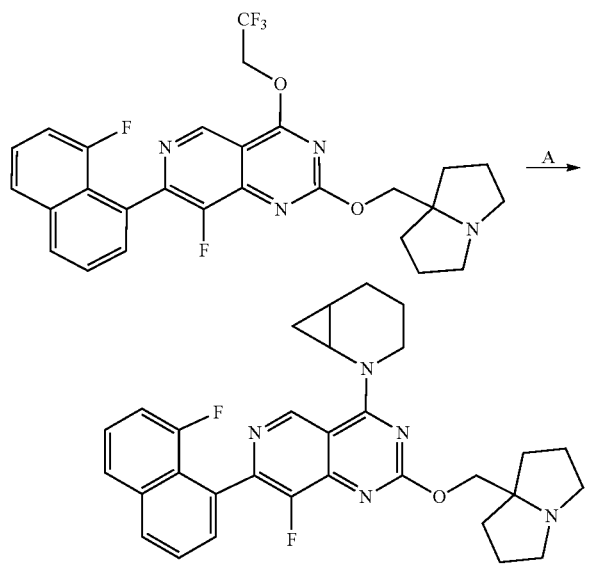

Step A. 4-(2-azabicyclo[4.1.0]heptan-2-yl)-8-fluoro-7-(8-fluoronaphthalen-1-yl)-2-((hexahydro-1H-pyrrolizin-7a-yl)methoxy)pyrido[4,3-d]pyrimidine: A mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 94.3 μmol) in DMF (1.00 mL) were added DIEA (36.5 mg, 283 μmol) and 2-azabicyclo[4.1.0]heptane (25.2 mg, 189 μmol, HCl). The mixture was stirred at 50° C. for 16 hours. The mixture was filtered and was purified by prep-HPLC (column: water s Xbridge BEH C18 100×25 mm×5 μm; mobile phase: [water (10 mM NH₄HCO₃)-ACN]; B %: 25%-65%, 12 min) to afford 4-(2-azabicyclo[4.1.0]heptan-2-yl)-8-fluoro-7-(8-fluoronaphthalen-1-yl)-2-((hexahydro-1H-pyrrolizin-7a-yl)methoxy)pyrido[4,3-d]pyrimidine (12.1 mg, 24% yield) as a white solid. $^1$H NMR (400 MHz, MeOD) δ 9.89 (s, 1H), 8.11 (d, J=8.2 Hz, 1H), 7.85 (d, J=8.1 Hz, 1H), 7.73-7.68 (m, 1H), 7.63-7.58 (m, 1H), 7.57-7.49 (m, 1H), 7.24-7.16 (m, 1H), 4.35-4.22 (m, 2H), 3.43-3.40 (m, 2H), 3.15-3.06 (m, 2H), 3.02-2.96 (t, J=12.5 Hz, 1H), 2.76-2.69 (m, 2H), 2.12-2.05 (m, 4H), 1.97-1.83 (m, 5H), 1.80-1.69 (m, 3H), 1.59-1.54 (d, J=2.8 Hz, 1H), 1.29-1.24 (td, J=5.8, 9.6 Hz, 1H), 0.88-0.80 (m, 1H); LCMS (ESI, M+1): m/z 528.2.

Example 32

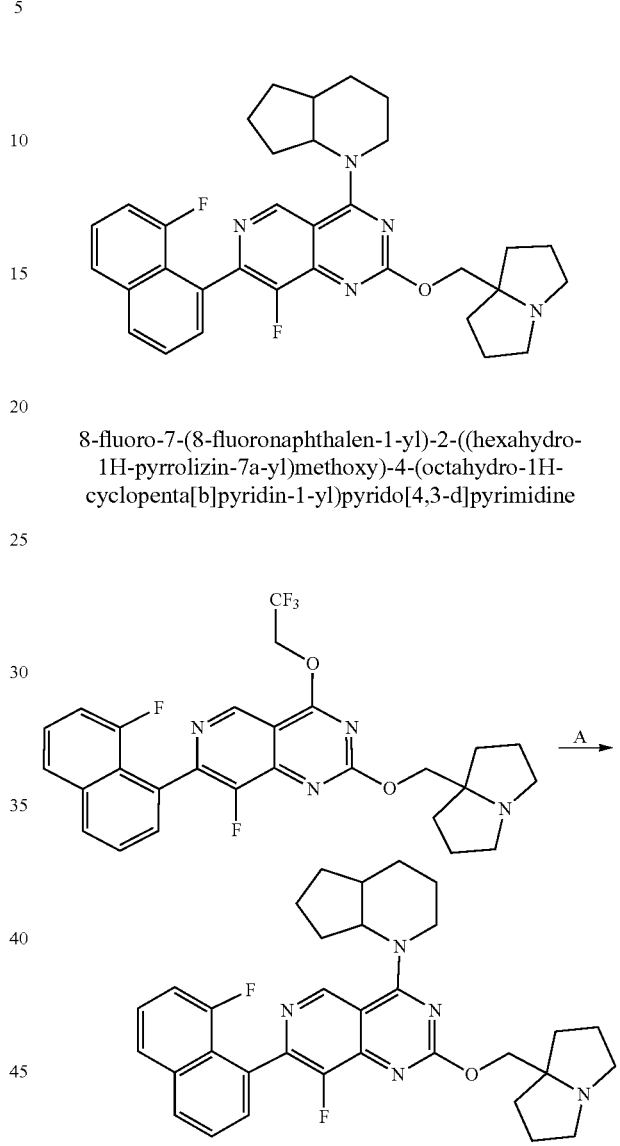

8-fluoro-7-(8-fluoronaphthalen-1-yl)-2-((hexahydro-1H-pyrrolizin-7a-yl)methoxy)-4-(octahydro-1H-cyclopenta[b]pyridin-1-yl)pyrido[4,3-d]pyrimidine Step A. 8-fluoro-7-(8-fluoronaphthalen-1-yl)-2-((hexahydro-1H-pyrrolizin-7a-yl) methoxy)-4-(octahydro-1H-cyclopenta[b]pyridin-1-yl)pyrido[4,3-d]pyrimidine: A mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 94.3 μmol) in DMF (1 mL) were added DIEA (36.5 mg, 283 μmol) and octahydro-1H-cyclopenta[b]pyridine (30.5 mg, 243 μmol). The mixture was stirred at 50° C. for 16 hours. The mixture was filtered and was purified by prep-HPLC (column: water s Xbridge BEH C18 100×25 mm×5 μm; mobile phase: [water (10 mM NH₄HCO₃)-ACN]; B %: 40%-80%, 12 min) to afford 8-fluoro-7-(8-fluoronaphthalen-1-yl)-2-((hexahydro-1H-pyrrolizin-7a-yl)methoxy)-4-(octahydro-1H-cyclopenta[b]pyridin-1-yl)pyrido[4,3-d]pyrimidine (2.07 mg, 4% yield) as a white solid. $^1$H NMR (400 MHz, MeOD) δ 9.02 (s, 1H), 8.11 (d, J=8.3 Hz, 1H), 7.85 (d, J=8.2 Hz, 1H), 7.72-7.68 (m, 1H), 7.63-7.56 (m, 1H), 7.55-7.51 (m, 1H), 7.22-7.17 (m, 1H), 5.04-4.99 (m, 1H), 4.65-4.62 (m, 1H), 4.35-4.26 (m, 2H), 3.58-3.43 (m, 1H), 3.17-3.07 (m, 2H), 2.81-2.69 (m, 2H), 2.22-2.05 (m, 5H), 2.00-1.84 (m, 7H), 1.83-1.74 (m, 5H), 1.67-1.52 (m, 2H); LCMS (ESI, M+1): m/z 556.2.

Example 33

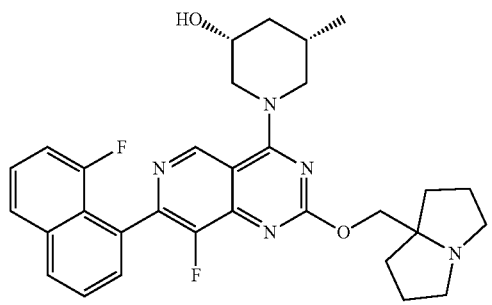 [SMILES: C[C@H]1C[C@@H](O)CN(c2nc(OCC34CCCN3CCC4)nc3c(F)c(-c4cccc5cccc(F)c45)ncc23)C1]

(3R,5S)-1-(8-fluoro-7-(8-fluoronaphthalen-1-yl)-2-((hexahydro-1H-pyrrolizin-7a-yl)methoxy)pyrido[4,3-d]pyrimidin-4-yl)-5-methylpiperidin-3-ol

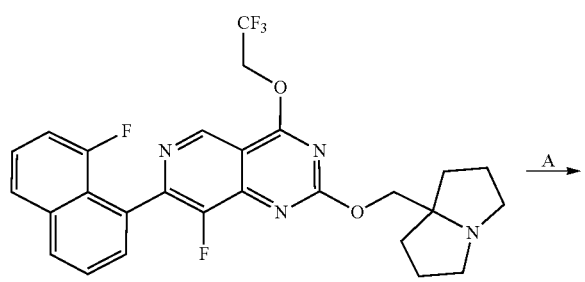

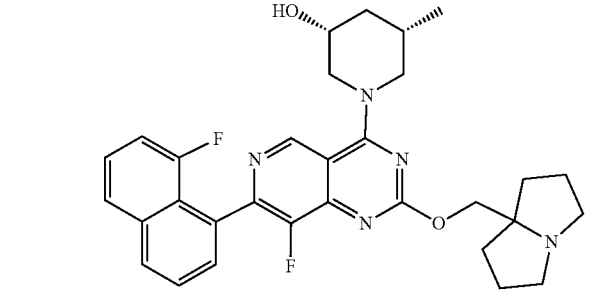

Step A. (3R,5S)-1-(8-fluoro-7-(8-fluoronaphthalen-1-yl)-2-((hexahydro-1H-pyrrolizin-7a-yl)methoxy)pyrido[4,3-d]pyrimidin-4-yl)-5-methylpiperidin-3-ol: To a solution of (3R,5S)-5-methylpiperidin-3-ol (15 mg, 98.9 µmol, HCl) and 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (52.5 mg, 98.9 µmol) in DMF (0.1 mL) was added DIEA (63.9 mg, 495 µmol). The mixture was stirred at 40° C. for 1 hour. The reaction mixture was quenched by water (10 mL) at 20° C., and extracted with EtOAc (4 mL×3). The combined organic layers were washed with brine (5 mL), dried over anhydrous Na₂SO₄. The mixture was filtered and concentrated under reduced pressure to give a residue. The residue was purified by prep-HPLC (column: water s Xbridge BEH C18 150×25 mm×5 µm; mobile phase: [water (0.05% NH3·H2O+10 mM NH₄HCO₃)-ACN]; B %: 30%-60%, 8 min) to give the title compound (8.92 mg, 16% yield) as a light yellow solid. ¹H NMR (400 MHz, DMSO-d₆): δ 9.07 (d, J=2.2 Hz, 1H), 8.18 (br d, J=8.2 Hz, 1H), 7.93 (d, J=8.2 Hz, 1H), 7.78-7.70 (m, 1H), 7.67-7.54 (m, 2H), 7.31 (dd, J=7.6, 13.2 Hz, 1H), 5.20 (d, J=4.2 Hz, 1H), 4.60 (br d, J=10.3 Hz, 1H), 4.42 (br d, J=10.9 Hz, 1H), 4.11-4.00 (m, 2H), 3.75 (td, J=4.8, 9.8 Hz, 1H), 2.96-2.88 (m, 3H), 2.88-2.80 (m, 1H), 2.58-2.51 (m, 3H), 2.07 (brd, J=12.1 Hz, 1H), 1.93-1.84 (m, 3H), 1.84-1.69 (m, 4H), 1.62-1.51 (m, 2H), 1.16 (q, J=11.7 Hz, 1H), 0.98 (d, J=6.6 Hz, 3H); LCMS (ESI, M+1): m/z 546.2.

Example 34

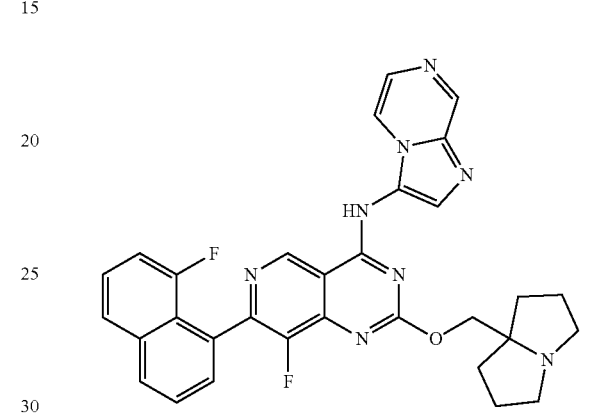

8-fluoro-7-(8-fluoronaphthalen-1-yl)-N-(imidazo[1,2-a]pyrazin-3-yl)-2-((tetrahydro-1H-pyrrolizin-7a(5H)-yl)methoxy)pyrido[4,3-d]pyrimidin-4-amine

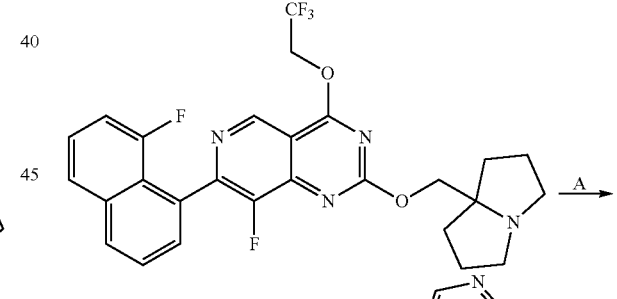

Step A: 8-fluoro-7-(8-fluoronaphthalen-1-yl)-N-(imidazo[1,2-a]pyrazin-3-yl)-2-((tetrahydro-1H-pyrrolizin-7a(5H)-yl)methoxy)pyrido[4,3-d]pyrimidin-4-amine: To a solution of imidazo[1,2-a]pyrazin-3-amine (3.0 equiv.) in DMF (1 mL) were added 4 Å molecular sieves (20 mg), t-BuONa (2.00 equiv.) and 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (0.09 mmol, 1.00 equiv.) at 0° C. The resulting mixture was stirred at 0° C. for 0.5 hour. After completion, the reaction mixture was diluted with water (10.0 mL) and extracted with ethyl acetate (3×10 mL). The combined organic layers were washed with brine (20 mL), dried over Na₂SO₄, filtered and concentrated under reduced pressure to give a residue. The residue was purified by prep-HPLC (column: water s Xbridge 150*25 mm*5 um; mobile phase: [water (10 mM NH₄HCO₃)-ACN]; B %: 27%-57%, 10 min) to afford the title compound. LCMS (ESI, M+1): m/z 565.3.

Example 35

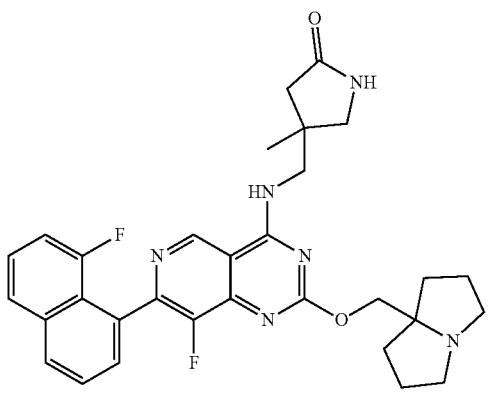 [SMILES: CC1(CNc2nc(OCC34CCCN3CCC4)nc3c(F)c(-c4cccc5cccc(F)c45)ncc23)CNC(=O)C1]

4-(((8-fluoro-7-(8-fluoronaphthalen-1-yl)-2-((hexahydro-1H-pyrrolizin-7a-yl)methoxy)pyrido[4,3-d]pyrimidin-4-yl)amino)methyl)-4-methylpyrrolidin-2-one

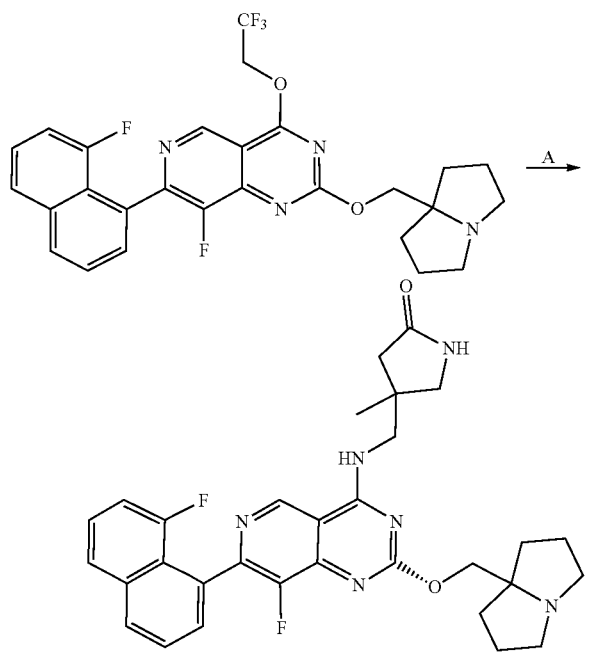

Step A. 4-(((8-fluoro-7-(8-fluoronaphthalen-1-yl)-2-((hexahydro-1H-pyrrolizin-7a-yl)methoxy)pyrido[4,3-d]pyrimidin-4-yl)amino)methyl)-4-methylpyrrolidin-2-one: To a mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (20.0 mg, 37.7 μmol) and 4-(aminomethyl)-4-methylpyrrolidin-2-one (96.6 mg, 754 μmol) in DMF (2.00 mL) was added DIEA (24.4 mg, 189 μmol) at 25° C. under N₂. The mixture was stirred at 40° C. for 2 hours. The reaction mixture was quenched with water (10.0 mL) and extracted with ethyl acetate (3×10.0 mL). The combined organic layers were washed with brine (20.0 mL), dried over sodium sulfate. The mixture was filtered and concentrated under reduced pressure to give a residue. The residue was purified by prep-HPLC (column: Phenomenex Luna C18 75×30 mm×3 μm; mobile phase: [water (0.2% FORMIC ACID)-ACN]; B %: 20%-60%, 8 min) to give 4-(((8-fluoro-7-(8-fluoronaphthalen-1-yl)-2-((hexahydro-1H-pyrrolizin-7a-yl)methoxy)pyrido[4,3-d]pyrimidin-4-yl)amino)methyl)-4-methylpyrrolidin-2-one (7.29 mg, 34% yield) as white solid. ¹H NMR (400 MHz, DMSO-d₆): δ9.39 (d, J=2.42 Hz, 1H), 8.90 (s, 1H), 8.18 (d, J=7.72 Hz, 1H), 7.93 (d, J=7.94 Hz, 1H), 7.77-7.69 (m, 1H), 7.65-7.48 (m, 3H), 7.30 (dd, J=12.58, 8.16 Hz, 1H), 4.12 (s, 2H), 3.69 (d, J=5.07 Hz, 2H), 3.00-2.96 (m, 2H), 2.61 (d, J=6.84 Hz, 2H), 2.39 (d, J=18.08 Hz, 2H), 2.00-1.52 (m, 8H), 1.64-1.60 (m, 2H), 1.19 (s, 3H); LCMS (ESI, M+1): m/z 559.1

Example 36

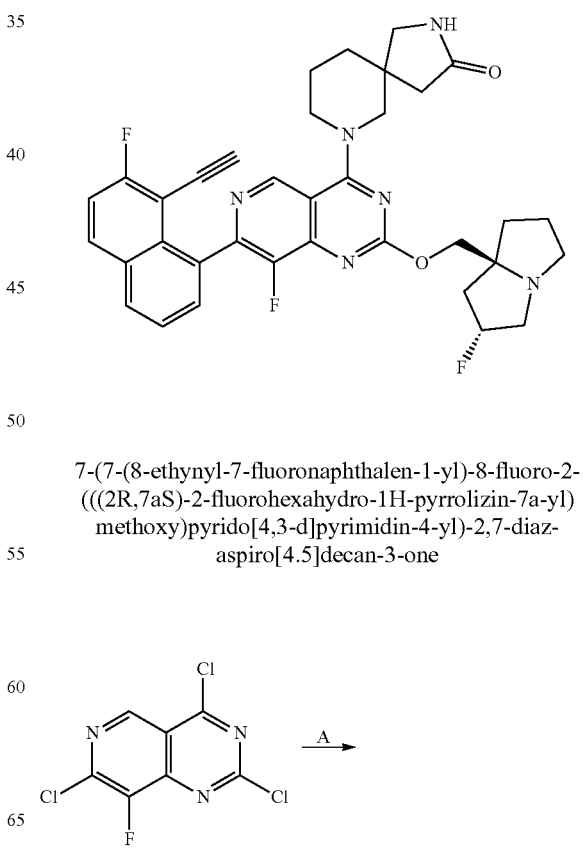

7-(7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one

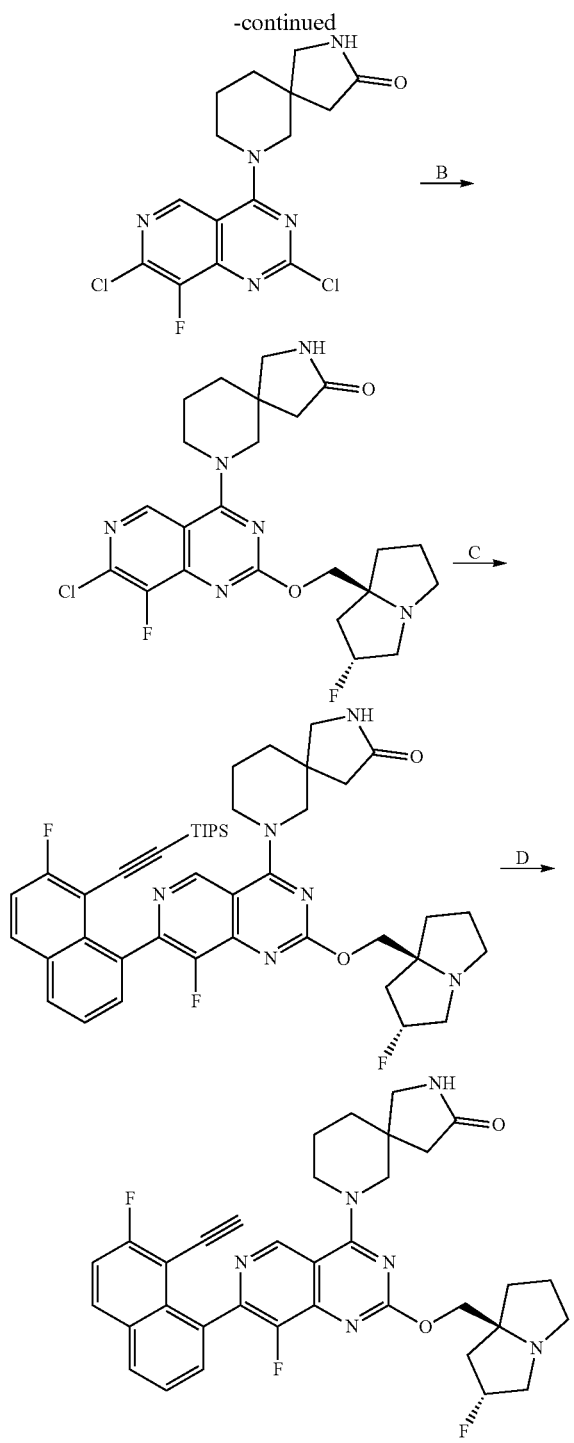

Step A. 7-(2,7-dichloro-8-fluoropyrido[4,3-d]pyrimidin-4-yl)-2,7-diazaspiro[4.5]decan-3-one: To a solution of 2,4,7-trichloro-8-fluoropyrido[4,3-d]pyrimidine (2.0 g, 6.85 mmol) in dichloromethane (20 mL) were added DIEA (3.54 g, 27.4 mmol) and 2,7-diazaspiro[4.5]decan-3-one (1.44 g, 7.53 mmol, HCl) at −40° C. The mixture was stirred at −40° C. for 1 hour. The mixture was diluted with water (20 mL), and extracted with EtOAc (2×20 mL). The combined organic layer was dried over Na$_2$SO$_4$, filtered and concentrated under reduced pressure to give a residue. The residue was purified by reversed phase flash chromatography (C18, water (0.1% formic acid)/ACN) to afford 7-(2,7-dichloro-8-fluoropyrido[4,3-d]pyrimidin-4-yl)-2,7-diazaspiro[4.5]decan-3-one (1.6 g, 63% yield) as yellow solid. LCMS (ESI, M+1): m/z 370.0

Step B. 7-(7-chloro-8-fluoro-2-(((2R,7aS)-2-fluorohexahydro-1H-pyrrolizin-7a-yl) methoxy)pyrido[4,3-d]pyrimidin-4-yl)-2,7-diazaspiro[4.5]decan-3-one: To a mixture of 7-(2,7-dichloro-8-fluoropyrido[4,3-d]pyrimidin-4-yl)-2,7-diazaspiro[4.5]decan-3-one (300 mg, 810 μmol), DIEA (314 mg, 2.43 mmol) and 4 Å molecular sieves (10 mg) in dioxane (2 mL) was added ((2R,7aS)-2-fluorohexahydro-1H-pyrrolizin-7a-yl)methanol (142 mg, 891 μmol). The mixture was stirred at 95° C. for 16 hours. The mixture was diluted with water (5 mL), and extracted with EtOAc (2×5 mL). The combined organic layer was dried over Na$_2$SO$_4$, filtered and concentrated. The residue was purified by reversed phase flash chromatography (C18, water (0.1% formic acid)/ACN) to afford 7-(7-chloro-8-fluoro-2-(((2R,7aS)-2-fluorohexahydro-1H-pyrrolizin-7a-yl) methoxy) pyrido[4,3-d]pyrimidin-4-yl)-2,7-diazaspiro[4.5]decan-3-one (120 mg, 19% yield) as yellow solid. LCMS (ESI, M+1): m/z 493.2

Step C. 7-(8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one: To a mixture of 7-(7-chloro-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one (300 mg, 608 μmol), ((2-fluoro-8-(4,4,5,5-tetramethyl-1,3,2-dioxaborolan-2-yl)naphthalen-1-yl) ethynyl)triisopropylsilane (413 mg, 913 μmol) and K$_3$PO$_4$ (1.5 M, 1.22 mL) in THF (6 mL) was added cataCXium-A-Pd-G3 (66.5 mg, 91.3 μmol). The mixture was stirred at 60° C. for 2 hours. The mixture was diluted with water (10 mL), extracted with EtOAc (3×20 mL). The combined organic layers were washed with brine (100 mL), and dried over Na$_2$SO$_4$. The mixture was filtered and concentrated under reduced pressure to give a residue. The residue was purified by reversed phase flash chromatography (C18, 0.1% formic acid in water, 0-40% ACN) to afford 7-(8-fluoro-7-(7-fluoro-8-((triisopropylsilyl)ethynyl)naphthalen-1-yl)-2-(((2R,7aS)-2-fluorohexahydro-1H-pyrrolizin-7a-yl) methoxy)pyrido[4,3-d]pyrimidin-4-yl)-2,7-diazaspiro[4.5]decan-3-one (350 mg, 70% yield) as yellow solid. LCMS (ESI, M+1): m/z 783.4

Step D. 7-(7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one: To a solution of 7-(8-fluoro-7-(7-fluoro-8-((triisopropylsilyl) ethynyl)naphthalen-1-yl)-2-(((2R,7aS)-2-fluorohexahydro-1H-pyrrolizin-7a-yl) methoxy) pyrido[4,3-d]pyrimidin-4-yl)-2,7-diazaspiro[4.5]decan-3-one (350 mg, 447 μmol) in DMF (4 mL) was added CsF (339 mg, 2.23 mmol). The mixture was stirred at 25° C. for 1 hour. The mixture was diluted with water (10 mL), extracted with EtOAc (3×20 mL). The combined organic layers were washed with brine (100 mL), and dried over Na$_2$SO$_4$. The mixture was filtered and concentrated under reduced pressure to give a residue. The residue was purified by reversed phase flash chromatography (C18, water (0.1% formic acid)/ACN) to give a crude product. The crude product was purified by prep-HPLC (column: Phenomenex luna C18 150×25 mm×10 μm; mobile phase: [water (0.225% formic acid)-ACN]; B %: 15%-45%, 10 min) to afford 7-(7-(8-ethynyl-7-fluoronaphthalen-1-yl)-8-fluoro-2-(((2R,7aS)-2-fluorohexahydro-1H-pyrrolizin-7a-yl) methoxy)pyrido[4,3-d]pyrimidin-4-yl)-2,7-diazaspiro[4.5]decan-3-one (205 mg, 0.5 FA, 70% yield) as yellow solid. $^1$H NMR (400 MHz, methanol-d4): δ 9.06 (dd, J=1.2, 2.8 Hz, 1H), 8.50 (s, 1H), 8.18-8.08 (m, 2H), 7.71-7.61 (m, 2H), 7.45 (dt, J=0.8, 9.2 Hz, 1H), 5.56-5.31 (m, 1H), 4.53-4.14 (m, 4H), 4.13-3.79 (m, 2H), 3.73-3.43 (m, 4H), 3.29-3.16 (m, 2H), 2.56-2.23 (m, 5H), 2.20-2.01 (m, 3H), 1.99-1.80 (m, 4H); LCMS (ESI, M+1): m/z 627.3

Example 37

7-(7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2,7-diazaspiro[4.5]decan-3-one

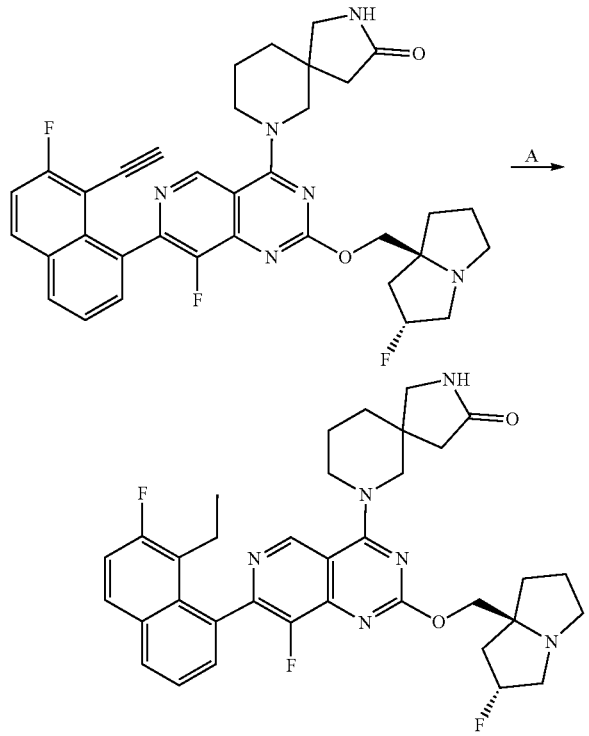

Step A. 7-(7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2,7-diazaspiro[4.5]decan-3-one: To a solution of 7-(7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2,7-diazaspiro[4.5]decan-3-one (50.0 mg, 77.0 μmol, 0.5 FORMIC ACID) in MeOH (1 mL) was added Pd/C (5.0 mg, 10% h purity). The suspension was degassed and purged with H$_2$ 3 times. The mixture was stirred at 25° C. for 1 hour under H$_2$ (15 psi). The reaction mixture was filtered and concentrated under reduced pressure to give a residue. The residue was purified by prep-HPLC (column: water s Xbridge 150×25 mm×5 μm; mobile phase: [water (10 mM NH$_4$HCO$_3$)-ACN]; B %: 33%-63%, 10 min) to afford the title compound (17.0 mg, 34% yield) as off-white solid. $^1$H NMR (400 MHz, CHLOROFORM-d) δ 8.98 (d, J=4.0 Hz, 1H), 7.95 (dd, J=1.2, 8.0 Hz, 1H), 7.80 (dd, J=6.0, 9.2 Hz, 1H), 7.53-7.40 (m, 2H), 7.30 (t, J=9.2 Hz, 1H), 5.84 (br d, J=14.8 Hz, 1H), 5.41-5.19 (m, 1H), 4.34-4.17 (m, 2H), 4.11-3.96 (m, 2H), 3.90-3.63 (m, 2H), 3.40 (dd, J=4.8, 9.6 Hz, 1H), 3.32-3.15 (m, 4H), 3.04-2.92 (m, 1H), 2.65-2.49 (m, 1H), 2.39-2.27 (m, 3H), 2.26-2.14 (m, 3H), 2.00-1.93 (m, 2H), 1.93-1.84 (m, 5H), 0.86 (t, J=7.2 Hz, 3H); LCMS (ESI, M+1): m/z 631.3

Example 38

7-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one

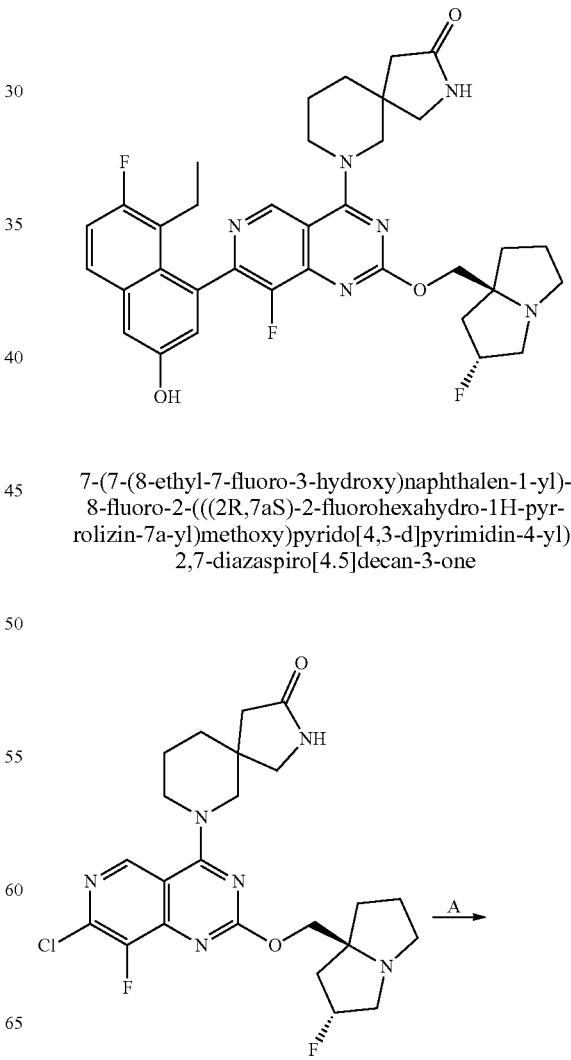

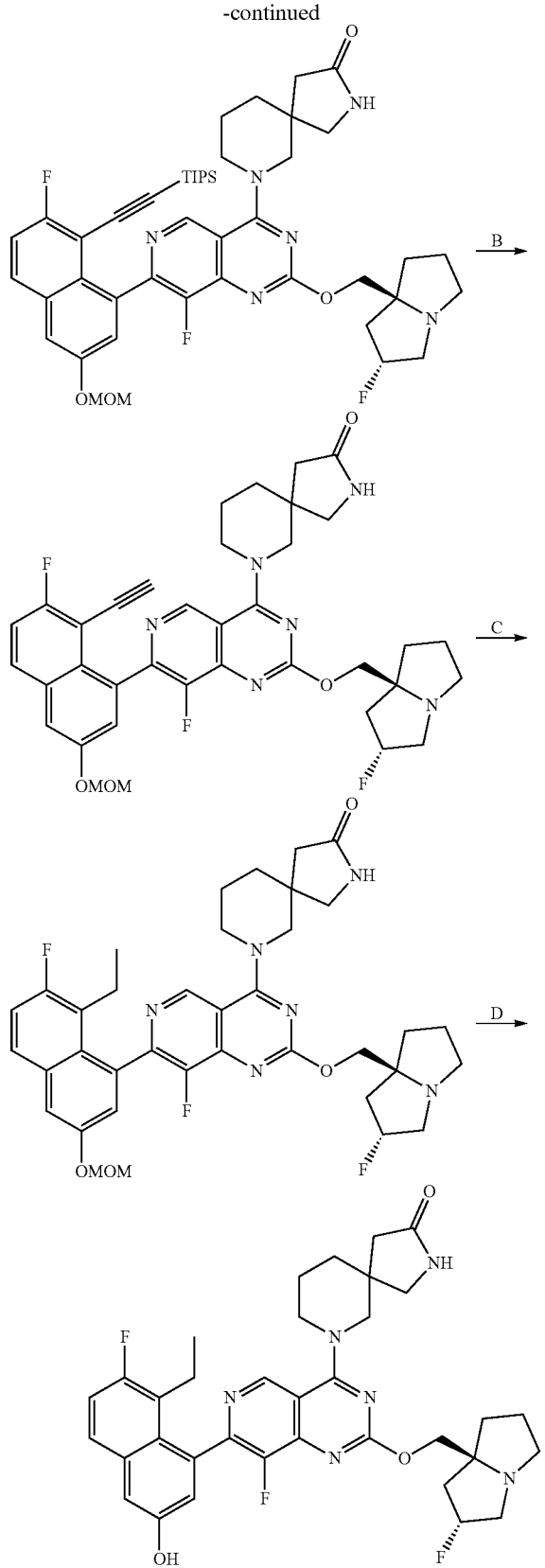

Step A. 7-(8-fluoro-7-(7-fluoro-3-(methoxymethoxy)-8-((triisopropylsilyl) ethynyl)naphthalen-1-yl)₂-(((2R,7aS)-2-fluorohexahydro-1H-pyrrolizin-7a-yl) methoxy)pyrido[4,3-d]pyrimidin-4-yl)-2,7-diazaspiro[4.5]decan-3-one: To a solution of 7-(7-chloro-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one (100 mg, 202.86 μmol) and ((2-fluoro-6-(methoxymethoxy)-8-(4,4,5,5-tetramethyl-1,3,2-dioxaborolan-2-yl)naphthalen-1-yl) ethynyl)triisopropylsilane (156 mg, 304 μmol) in THF (2 mL) were added K₃PO₄ (1.5 M, 406 μL) and cataCXium-A-Pd-G3 (22.2 mg, 30.4 μmol). The mixture was stirred at 60° C. for 2 hours. The reaction mixture was diluted with water (10 mL) and extracted with ethyl acetate (3×20 mL). The combined organic layers were washed with brine (100 mL), and dried over Na₂SO₄. The mixture was filtered and concentrated under reduced pressure to give a residue. The residue was purified by reversed phase flash chromatography (C18, 0.1% formic acid in water, 0-40% ACN) to afford the title compound (120 mg, 67% yield) as yellow solid. LCMS (ESI, M+1): m/z 843.4

Step B. 7-(7-(8-ethynyl-7-fluoro-3-(methoxymethoxy) naphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one: To a mixture of 7-(8-fluoro-7-(7-fluoro-3-(methoxymethoxy)-8-((triisopropylsilyl) ethynyl)naphthalen-1-yl)-2-(((2R,7aS)-2-fluorohexahydro-1H-pyrrolizin-7a-yl) methoxy)pyrido[4,3-d]pyrimidin-4-yl)-2,7-diazaspiro[4.5]decan-3-one (110 mg, 130 μmol) and DMF (2 mL) was added CsF (198 mg, 1.30 mmol) in one portion at 25° C. under N₂. The mixture was stirred at 25° C. for 0.5 hour. The residue was filtered. The filtrate was purified by reversed phase flash chromatography (water (0.1% formic acid)-ACN) to afford 7-(7-(8-ethynyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro [4.5]decan-3-one (75.0 mg, 80% yield) as yellow solid. LCMS (ESI, M+1): m/z 687.4

Step C. 7-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-Vi)-2,7-diazaspiro[4.5]decan-3-one: To a mixture of 7-(7-(8-ethynyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)-2,7-diazaspiro [4.5]decan-3-one (75.0 mg, 109 μmol) and MeOH (2 mL) was added Pd/C (100 mg, 10% purity) in one portion at 25° C. under N₂. The suspension was degassed and purged with H₂ 3 times. The mixture was stirred at 25° C. for 1 hour under H₂ (15 psi). The reaction mixture was filtered and concentrated under reduced pressure to afford 7-(7-(8-ethyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)-2,7-diazaspiro[4.5] decan-3-one (65.0 mg, 86% yield) as yellow solid. LCMS (ESI, M+1): m/z 691.3

Step D. 7-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one: To a mixture of 7-(7-(8-ethyl-7-fluoro-3-(methoxymethoxy) naphthalen-1-yl)-8-fluoro-2-(((2R,7aS)-2-fluorohexahydro-1H-pyrrolizin-7a-yl) methoxy)pyrido[4,3-d]pyrimidin-4-yl)-2,7-diazaspiro[4.5] decan-3-one (65.0 mg, 94.1 μmol) and ACN (1 mL) was added HCl-dioxane (4 M, 862 μL) in one portion at 25° C. under N₂. The mixture was stirred at 25° C. for 10 minutes. The mixture was concentrated under reduced pressure to give a residue. The residue was purified by prep-HPLC (column: Phenomenex Gemini-NX C18 75×30 mm×3 μm;

mobile phase: [water (0.225% formic acid)-ACN]; B %: 15%-45%, 7 min) to afford 7-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one (15.3 mg, 24% yield, 0.1 FORMIC ACID) as white solid. $^1$H NMR (400 MHz, methanol-d4): δ 9.10 (s, 1H), 7.70 (dd, J=5.6 Hz, J=8.8 Hz, 1H), 7.32 (d, J=2.4 Hz, 1H), 7.27 (t, J=9.2 Hz, 1H), 7.07 (d, J=2.4 Hz, 1H), 5.37 (d, J=5.4 Hz, 1H), 4.60 (s, 1H), 4.45-3.90 (m, 6H), 3.51-3.35 (m, 3H), 3.30-3.26 (m, 1H), 3.16-3.06 (m, 1H), 2.55-2.26 (m, 5H), 2.25-2.15 (m, 2H), 2.10-1.85 (m, 7H), 0.87-0.75 (m, 3H); LCMS (ESI, M+1): m/z 647.4

Example 39

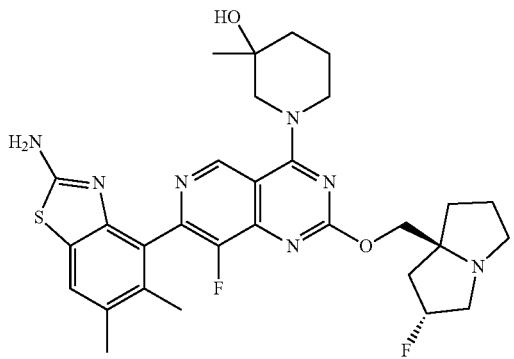 [SMILES: Cc1cc2sc(N)nc2c(-c2ncc3c(N4CCCC(C)(O)C4)nc(OC[C@@]45CCCN4C[C@H](F)C5)nc3c2F)c1C]

1-(7-(2-amino-5,6-dimethylbenzo[d]thiazol-4-yl)-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-ol

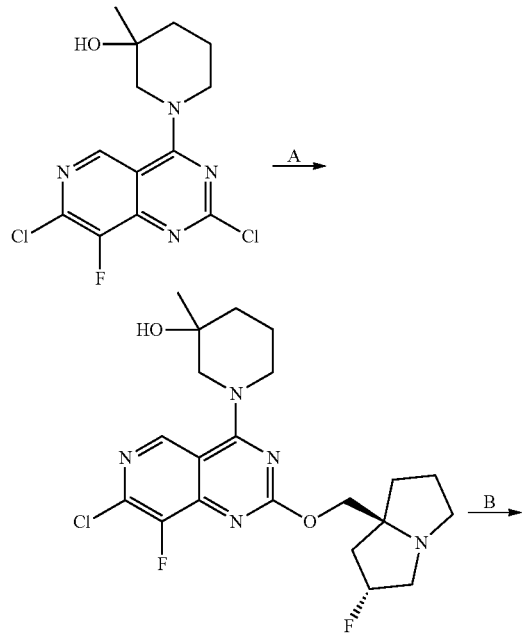

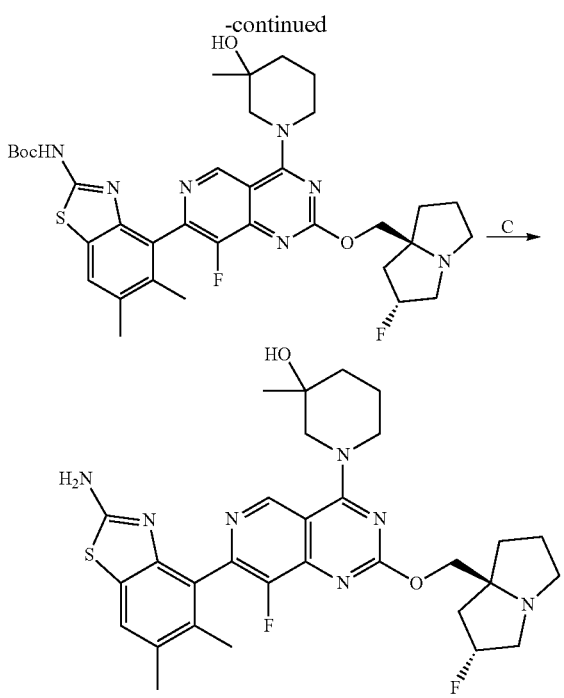

Step A. 1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-ol: A mixture of 1-(2,7-dichloro-8-fluoropyrido[4,3-d]pyrimidin-4-yl)-3-methylpiperidin-3-ol (0.200 g, 604 μmol), ((2R,7aS)-2-fluorotetrahydro-1H-pyrrolizin-7a(5H)-yl)methanol (144 mg, 906 μmol), DIEA (234 mg, 1.81 mmol, 315 μL) and 4 Å molecular sieves (20 mg) in dioxane (1.5 mL) was stirred at 90° C. for 15 h. After completion, the mixture was filtered. Then the mixture was diluted with ethyl acetate (3 mL) and water (3 mL), and then separated. The aqueous phase was extracted with ethyl acetate (5 mL). Then the aqueous phase was extracted with dichloromethane (4 mL). The combined organic layer was dried over anhydrous Na$_2$SO$_4$. The mixture was filtered and concentrated in vacuum. The residue was purified by reversed phase flash chromatography [water (0.1% formic acid)/acetonitrile] to give the title compound (184 mg, 62% yield). Yellow solid. LCMS (ESI, M+1): m/z 454.2.

Step B. tert-butyl (4-(8-fluoro-2-(((2R,7aS)-2-fluorotetrahydro-1H-pyrrolizin-7a(5H)-yl)methoxy)-4-(3-hydroxy-3-methylpiperidin-1-yl)pyrido[4,3-d]pyrimidin-7-yl)-5,6-dimethylbenzo[d]thiazol-2-yl)carbamate: To a mixture of 1-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-ol (50.0 mg, 110 μmol), [2-(tert-butoxycarbonylamino)-5,6-dimethyl-1,3-benzothiazol-4-yl]boronic acid (49.7 mg, 154 μmol) and K$_3$PO$_4$ (1.5 M in water, 220 μL) in THF (1 mL) was added [2-(2-aminophenyl)phenyl]-methylsulfonyloxy-palladium; dicyclohexyl-[3,6-dimethoxy-2-(2,4,6-triisopropylphenyl)phenyl]phosphane (9.99 mg, 11.0 μmol) under N$_2$. The mixture was de-gassed and then heated to 60° C. for 20 h under N$_2$. After completion, the mixture was diluted with ethyl acetate (2 mL) and water (2 mL), and then separated. The aqueous phase was extracted with ethyl acetate (2 mL). The combined organic layer was washed with brine (3 mL) and dried over anhydrous Na$_2$SO$_4$. The mixture was filtered and concentrated in vacuum. The residue was purified by reversed phase flash chromatography [water (0.1% formic acid)/acetonitrile] to give the title compound (40.0 mg, 52% yield). Yellow solid. LCMS (ESI, M+1): m/z 696.2.

Step C. 1-(7-(2-amino-5,6-dimethylbenzo[d]thiazol-4-yl)-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-ol: To a mixture of tert-butyl (4-(8-fluoro-2-(((2R,7aS)-2-fluorotetrahydro-1H-pyrrolizin-7a(5H)-yl)methoxy)-4-(3-hydroxy-3-methylpiperidin-1-yl)pyrido[4,3-d]pyrimidin-7-yl)-5,6-dimethylbenzo[d]thiazol-2-yl)carbamate (37.0 mg, 53.2 μmol) and dichloromethane (0.7 mL) was added TFA (2.16 g, 18.9 mmol, 1.4 mL) at 0° C. and the mixture was stirred at 0-28° C. for 1.5 h. After completion, the mixture was concentrated in vacuum and pH value was adjusted to 8 with cold saturated NaHCO₃ solution. Then the mixture was diluted with ethyl acetate (5 mL) and separated. The aqueous phase was extracted with ethyl acetate (2×4 mL). The combined organic layer was washed with brine (6 mL) and dried over anhydrous Na₂SO₄. The mixture was filtered and concentrated in vacuum. The residue was purified by prep-HPLC (Phenomenexluna C18 150*25 mm*10 um; mobile phase: [water (0.225% formic acid)-ACN]; B %: 15%-45%, 10 min) to afford the title compound (16.4 mg, 50% yield, 0.3 FORMIC ACID). White solid. ¹H NMR (400 MHz, METHANOL-d4): 89.30-9.18 (m, 1H), 7.54 (s, 1H), 5.51-5.30 (m, 1H), 4.55 (br d, J=13.2 Hz, 1H), 4.50-4.38 (m, 2H), 4.34-4.23 (m, 1H), 3.68-3.61 (m, 1H), 3.60-3.36 (m, 4H), 3.24-3.14 (m, 1H), 2.52-2.30 (m, 5H), 2.28-2.07 (m, 7H), 2.05-1.95 (m, 1H), 1.90-1.72 (m, 3H), 1.29 (s, 3H). LCMS (ESI, M+1): m/z 596.2.

Example 40

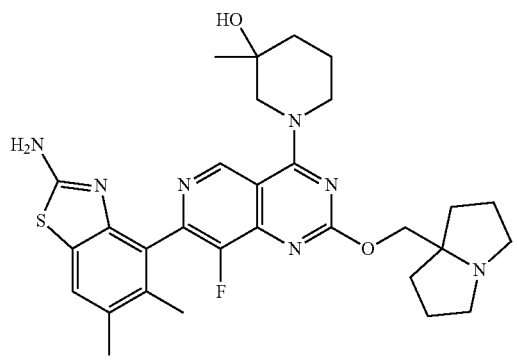 [SMILES: Cc1cc2sc(N)nc2c(-c2ncc3c(N4CCCC(C)(O)C4)nc(OCC45CCCN4CCC5)nc3c2F)c1C]

1-(7-(2-amino-5,6-dimethylbenzo[d]thiazol-4-yl)-8-fluoro-2-((hexahydro-1H-pyrrolizin-7a-yl) methoxy) pyrido[4,3-d]pyrimidin-4-yl)-3-methylpiperidin-3-ol

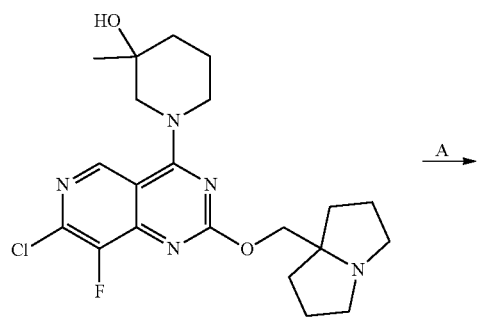

A

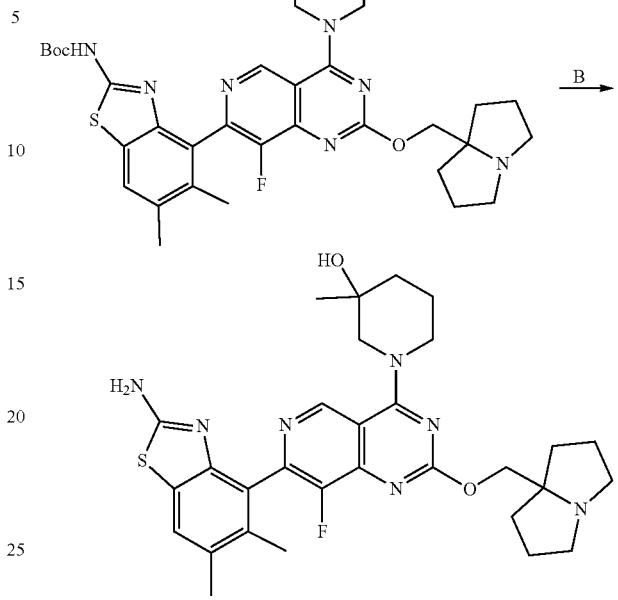

B

Step A. tert-butyl (4-(8-fluoro-2-((hexahydro-1H-pyrrolizin-7a-yl)methoxy)-4-(3-hydroxy-3-methylpiperidin-1-yl)pyrido[4,3-d]pyrimidin-7-yl)-5,6-dimethylbenzo[d]thiazol-2-yl) carbamate: To the mixture of 1-(7-chloro-8-fluoro-2-((hexahydro-1H-pyrrolizin-7a-yl) methoxy)pyrido [4,3-d]pyrimidin-4-yl)-3-methylpiperidin-3-ol (150 mg, 344 μmol), (2-((tert-butoxycarbonyl)amino)-5,6-dimethylbenzo [d]thiazol-4-yl)boronic acid (130 mg, 403 μmol), and K₃PO₄ (1.5 M, 688 μL) in THF (2 mL) was added BrettPhos Pd G3 (31.2 mg, 34.4 μmol) under N₂. The mixture was stirred at 60° C. for 4 hours. Upon completion, the mixture was partitioned between ethyl acetate (10 mL) and water (3 mL), and the aqueous layer was extracted with ethyl acetate (5 mL). The combined organic phase was washed with brine (5 mL) and dried over anhydrous sodium sulfate. The mixture was filtered and concentrated to give a residue. The residue was purified by reversed phase flash chromatography [water (0.1% formic acid)/acetonitrile] to give tert-butyl (4-(8-fluoro-2-((hexahydro-1H-pyrrolizin-7a-yl)methoxy)-4-(3-hydroxy-3-methylpiperidin-1-yl)pyrido[4,3-d]pyrimidin-7-yl)-5,6-dimethylbenzo[d]thiazol-2-yl)carbamate (132 mg, 52% yield). White Solid; LCMS (ESI, M+1): m/z 678.3.

Step B. 1-(7-(2-amino-5,6-dimethylbenzo[d]thiazol-4-yl)-8-fluoro-2-((hexahydro-1H-pyrrolizin-7a-yl)methoxy) pyrido[4,3-d]pyrimidin-4-yl)-3-methylpiperidin-3-ol: To the solution of tert-butyl (4-(8-fluoro-2-((hexahydro-1H-pyrrolizin-7a-yl)methoxy)-4-(3-hydroxy-3-methylpiperidin-1-yl)pyrido[4,3-d]pyrimidin-7-yl)-5,6-dimethylbenzo[d]thiazol-2-yl)carbamate (60.0 mg, 88.5 μmol) in dichloromethane (0.5 mL) was added TFA (770 mg, 6.75 mmol), and the mixture was stirred at 20° C. for 0.5 hour. Upon completion, to the mixture was added sat. Na₂CO₃ to adjust the pH to 7 and the mixture was extracted with dichloromethane (5 ml). The mixture was dried over anhydrous sodium sulfate, filtered and concentrated to give a residue. The residue was purified by prep-HPLC (column: Phenomenex luna C18 150×25 mm×10 μm; mobile phase: [water (0.225% formic acid formic acid)-ACN]; B %: 15%-45%, 10 min) to afford the title compound (32.46 mg, 61% yield, 0.4 formic acid salt). Off-white Solid; $^1$H NMR (400 MHz, METHANOL-d4) δ=9.33-9.18 (m, 1H), 7.55 (s, 1H), 4.58 (s, 3H), 4.32 (br d, J=13.2 Hz, 1H), 3.69-3.52 (m, 3H), 3.50-3.39 (m, 1H), 3.23-3.10 (m, 2H), 2.39 (s, 3H), 2.33-2.23 (m, 2H), 2.21-1.96 (m, 10H), 1.92-1.71 (m, 3H), 1.29 (s, 3H); LCMS (ESI, M+1): m/z 578.3.

Example 41

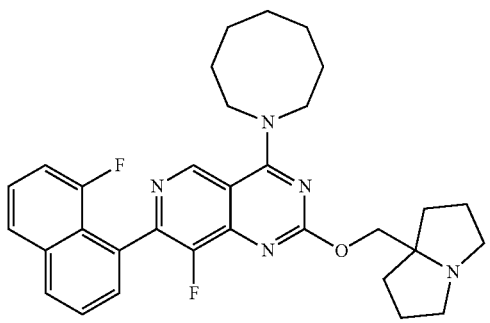 [SMILES: Fc1c(-c2cccc3cccc(F)c23)ncc2c(N3CCCCCCC3)nc(OCC34CCCN3CCC4)nc12]

4-(azocan-1-yl)-8-fluoro-7-(8-fluoronaphthalen-1-yl)-2-((hexahydro-1H-pyrrolizin-7a-yl)methoxy)pyrido[4,3-d]pyrimidine

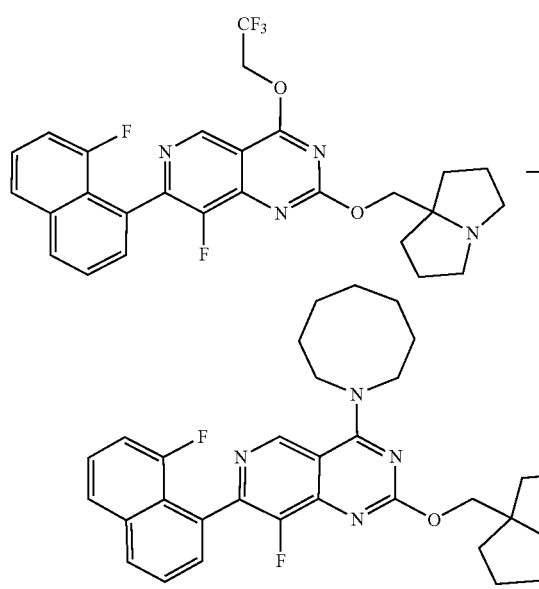

Step A 4-(azocan-1-yl)-8-fluoro-7-(8-fluoronaphthalen-1-yl)-2-((hexahydro-1H-pyrrolizin-7a-yl)methoxy)pyrido[4,3-d]pyrimidine: To a mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 94.2 μmol) and azocane (21.3 mg, 188 μmol) in DMF (I mL) were added DIEA (48.7 mg, 377 μmol) and 4 Å molecular sieves (30 mg) in one portion at 25° C. under N$_2$. The mixture was stirred at 40° C. for 12 h. After completion, the mixture was filtered. The filtrate was purification by prep-HPLC (column: Phenomenex Gemini-NX C18 75×30 mm×3 μm; mobile phase: [water (0.225% formic acid)-ACN]; B %: 20%-50%, 7 min) to afford 4-(azocan-1-yl)-8-fluoro-7-(8-fluoronaphthalen-1-yl)-2-((hexahydro-1H-pyrrolizin-7a-yl) methoxy)pyrido[4,3-d]pyrimidine (9.4 mg, 16.8 μmol, 18% yield, 99% purity, 0.24 FORMIC ACID). White solid; $^1$H NMR (400 MHz, DMSO-d$_6$): δ 9.13 (s, 1H), 8.17 (d, J=8.0 Hz, 1H), 7.93 (d, J=8.4 Hz, 1H), 7.74 (t, J=7.6 Hz, 1H), 7.65-7.55 (m, 2H), 7.30 (d d, J=7.6 Hz, 12.8 Hz, 1H), 4.11 (s, 2H), 4.06-3.99 (m, 4H), 2.93-3.02 (m, 2H), 2.64-2.56 (m, 2H), 2.00-1.70 (m, 10H), 1.68-1.49 (m, 8H); LCMS (ESI, M+1): m/z 544.3.

Example 42

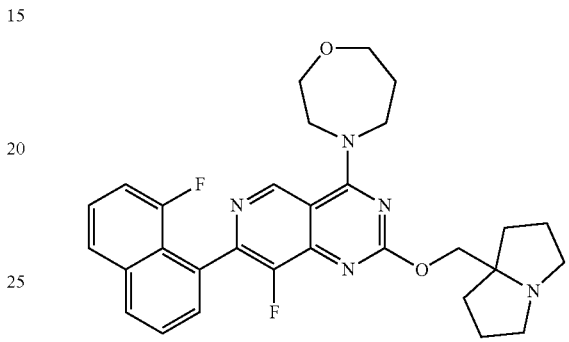

4-(8-fluoro-7-(8-fluoronaphthalen-1-yl)-2-((hexahydro-1H-pyrrolizin-7a-yl)methoxy)pyrido[4,3-d]pyrimidin-4-yl)-1,4-oxazepane

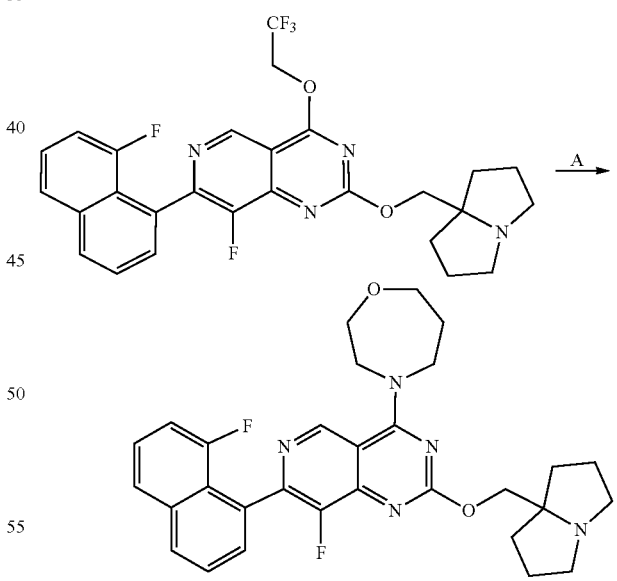

Step A. 4-(8-fluoro-7-(8-fluoronaphthalen-1-yl)-2-((hexahydro-1H-pyrrolizin-7a-yl) methoxy)pyrido[4,3-d]pyrimidin-4-yl)-1,4-oxazepane: To a mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (20.0 mg, 34.7 μmol, formic acid salt), 1,4-oxazepane (5.73 mg, 41.6 μmol, HCl), and 4 Å molecular sieves (5 mg) in DMF (0.5 mL) was added DIEA (17.9 mg, 139 μmol), and the mixture was stirred at 40° C. for 14 hours. Upon completion, the mixture was filtered and the filtrate was purified by prep-HPLC (column: Phenomenex luna C18 150×25 mm×10 μm; mobile phase: [water (0.225% formic acid formic acid)-ACN]; B %: 16%-46%, 10 min) to afford 4-(8-fluoro-7-(8-fluoronaphthalen-1-yl)-2-((hexahydro-1H-pyrrolizin-7a-yl)methoxy)pyrido[4,3-d]pyrimidin-4-yl)-1,4-oxazepane (2.05 mg, 10% yield, 0.51 formic acid salt). Off-white Gum; $^1$H NMR (400 MHz, CHLOROFORM-d) δ=9.12 (s, 1H), 8.03-7.97 (m, 1H), 7.74 (d, J=7.6 Hz, 1H), 7.67-7.58 (m, 2H), 7.48-7.42 (m, 1H), 7.16-7.08 (m, 1H), 4.51 (s, 2H), 4.26-4.18 (m, 4H), 4.08-4.01 (m, 2H), 3.91-3.85 (m, 2H), 3.61-3.50 (m, 2H), 2.85-2.76 (m, 2H), 2.31-2.23 (m, 4H), 2.04-1.96 (m, 4H), 1.90-1.83 (m, 2H); LCMS (ESI, M+1): m/z 532.4.

Example 43 filtrate was purified by prep-HPLC (column: Phenomenex Gemini-NX C18 75×30 mm×3 μm; mobile phase: [water (0.225% formic acid)-ACN]; B %: 20%-50%, 7 min) to afford 4-(8-fluoro-7-(8-fluoronaphthalen-1-yl)-2-((hexahydro-1H-pyrrolizin-7a-yl)methoxy)pyrido[4,3-d]pyrimidin-4-yl)-1,4-thiazepane (5.63 mg, 9.88 μmol, 10% yield, 99% purity, 0.37 FORMIC ACID); Yellow solid; 1H NMR (400 MHz, DMSO-d$_6$) δ 9.16 (s, 1H) 8.18 (d, J=7.6 Hz, 1H), 7.93 (d, J=7.6 Hz, 1H), 7.77-7.71 (m, 1H), 7.65-7.55 (m, 2H), 7.31 (d d, J=13.2 Hz, 7.2 Hz, 1H), 4.30-4.23 (m, 2H), 4.19-4.13 (m, 2H), 4.12-4.06 (m, 2H), 3.14-3.10 (m, 2H), 3.00-2.90 (m, 2H), 2.76-2.70 (m, 2H), 2.60-2.54 (m, 2H), 2.22-2.15 (m, 2H), 1.95-1.70 (m, 6H), 1.65-1.55 (m, 2H); LCMS (ESI, M+1): m/z 548.3.

Example 44

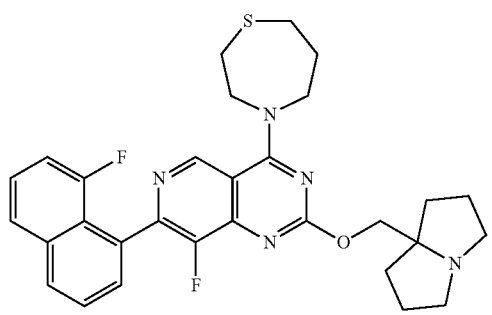 [SMILES: Fc1c(-c2cccc3cccc(F)c23)ncc2c(N3CCCSCC3)nc(OCC34CCCN3CCC4)nc12]

4-(8-fluoro-7-(8-fluoronaphthalen-1-yl)-2-((hexahydro-1H-pyrrolizin-7a-yl)methoxy)pyrido[4,3-d]pyrimidin-4-yl)-1,4-thiazepane

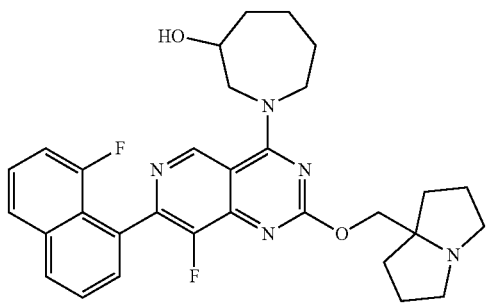 [SMILES: OC1CCCCN(c2nc(OCC34CCCN3CCC4)nc3c(F)c(-c4cccc5cccc(F)c45)ncc23)C1]

1-(8-fluoro-7-(8-fluoronaphthalen-1-yl)-2-((hexahydro-1H-pyrrolizin-7a-yl)methoxy)pyrido[4,3-d]pyrimidin-4-yl)azepan-3-ol

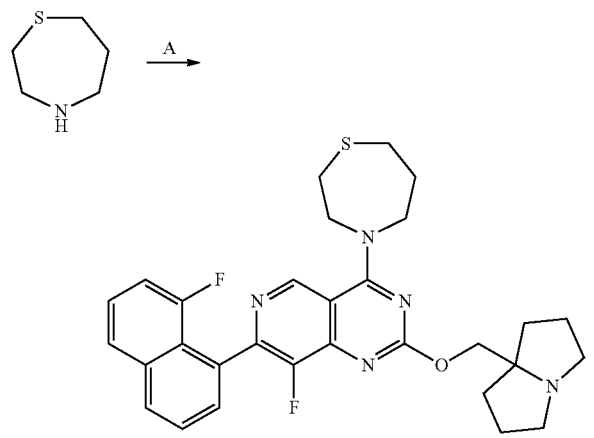

Step A. 4-(8-fluoro-7-(8-fluoronaphthalen-1-yl)-2-((hexahydro-1H-pyrrolizin-7a-yl) methoxy)pyrido[4,3-d]pyrimidin-4-yl)-1,4-thiazepane: To a mixture of 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d]pyrimidine (50 mg, 94.2 μmol) and 1,4-thiazepane (33.1 mg, 283 μmol) in DMF (1 mL) were added DIEA (48.7 mg, 377 μmol, 65.0 μL) and 4 Å molecular sieves (30 mg) in one portion at 25° C. under N$_2$. The mixture was stirred at 40° C. for 12 h. After completion, the residue was filtered. The

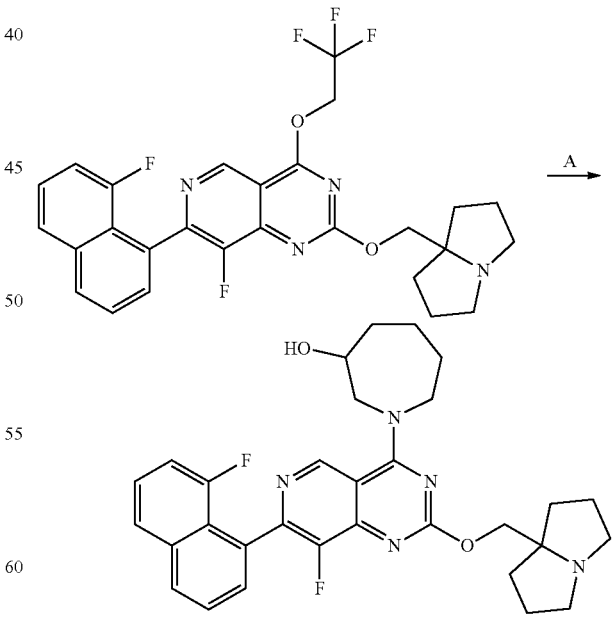

Step A. 1-(8-fluoro-7-(8-fluoronaphthalen-yl)-2-((hexahydro-1H-pyrrolizin-7a-yl) methoxy)pyrido[4,3-d]pyrimidin-4-ylazepan-3-ol: To a solution of 8-fluoro-7-(8-fluoronaphthalen-1-yl)-2-((hexahydro-1H-pyrrolizin-7a-yl)

methoxy)-4-(2,2,2-trifluoroethoxy) pyrido[4,3-d]pyrimidine (20.0 mg, 37.7 µmol) and DIEA (14.6 mg, 113 µmol, 19.7 µL) in DMF (1.0 mL) was added azepan-3-ol (8.68 mg, 75.4 µmol). The mixture was stirred at 40° C. for 24 h. After completion, the mixture was concentrated at 20° C. The residue was purified by prep-HPLC [column: Unisil 3-100 C18 Ultra 150×50 mm×3 um; A: water (0.225% formic acid formic acid), B: ACN, B %: 18%-38% over 10 min) to afford 1-(8-fluoro-7-(8-fluoronaphthalen-1-yl)-2-((hexahydro-1H-pyrrolizin-7a-yl)methoxy)pyrido[4,3-d]pyrimidin-4-yl) azepan-3-ol (6.83 mg, 11.9 µmol, 32% yield, 95.5% purity). Yellow solid; $^1$H NMR (400 MHz, METHANOL-d) δ=9.30 (d, J=4.4 Hz, 1H), 8.53 (br s, 1H), 8.13 (br d, J=8.0 Hz, 1H), 7.86 (d, J=8.0 Hz, 1H), 7.71 (t, J=8.0 Hz, 1H), 7.64-7.58 (m, 1H), 7.57-7.50 (m, 1H), 7.24-7.14 (m, 1H), 4.44 (br d, J=13.2 Hz, 1H), 4.22-4.10 (m, 3H), 3.87-3.77 (m, 1H), 3.62-3.52 (m, 2H), 3.21-3.10 (m, 2H), 2.35-2.23 (m, 2H), 2.22-2.07 (m, 6H), 2.06-1.99 (m, 5H), 1.98-1.86 (m, 1H), 1.74-1.60 (m, 1H), 1.54-1.39 (m, 1H); LCMS (ESI, M+1): m/z 546.3.

Example 45

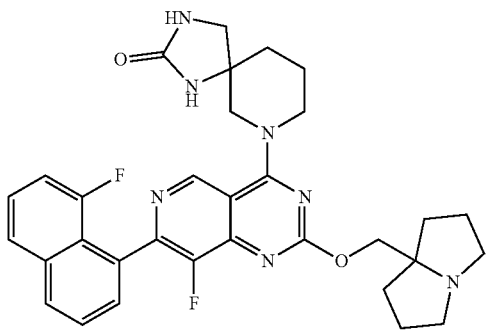 [SMILES: O=C1NCC2(CCCN(c3nc(OCC45CCCN4CCC5)nc4c(F)c(-c5cccc6cccc(F)c56)ncc34)C2)N1]

7-(8-fluoro-7-(8-fluoronaphthalen-1-yl)-2-((hexahydro-1H-pyrrolizin-7a-yl)methoxy)pyrido[4,3-d]pyrimidin-4-yl)-1,3,7-triazaspiro[4.5]decan-2-one

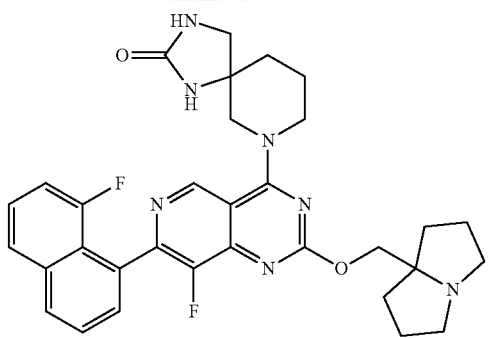

Step A. 7-(8-fluoro-7-(8-fluoronaphthalen-1-yl)-2-((hexahydro-1H-pyrrolizin-7a-yl) methoxy)pyrido[4,3-d]pyrimidin-4-yl)-1,3,7-triazaspiro[4.5]decan-2-one: To a solution of 8-fluoro-7-(8-fluoronaphthalen-1-yl)-2-((hexahydro-1 H-pyrrolizin-7a-yl)methoxy)-4-(2,2,2-trifluoroethoxy) pyrido[4,3-d]pyrimidine (20.0 mg, 37.7 µmol) and 1,3,7-triazaspiro[4.5]decan-2-one (8.78 mg, 56.6 µmol) in DMF (0.2 mL) was added DIEA (48.7 mg, 377 µmol). The mixture was stirred at 40° C. for 1 hour. The reaction mixture was quenched with water (10 mL) at 20° C. and then extracted with EtOAc (5 mL×3). The combined organic layers were washed with brine (3 mL×2), and dried over Na$_2$SO$_4$. The mixture was filtered and concentrated under reduced pressure to give a residue. The residue was purified by prep-HPLC (column: 3_Phenomenex Luna C18 75×30 mm×3 µm; mobile phase: [water (0.2% FORMIC ACID)-ACN]; B %: 20%-40%, 10 min) affording 7-(8-fluoro-7-(8-fluoronaphthalen-1-yl)-2-((hexahydro-1H-pyrrolizin-7a-yl)methoxy)pyrido[4,3-d]pyrimidin-4-yl)-1,3,7-triazaspiro[4.5]decan-2-one (2.65 mg, 12% yield). White solid; $^1$H NMR (400 MHz, MeOD) δ=9.16 (d, J=1.5 Hz, 1H), 8.54 (s, 1H), 8.13 (d, J=8.2 Hz, 1H), 7.87 (d, J=7.9 Hz, 1H), 7.74-7.69 (m, 1H), 7.65-7.59 (m, 1H), 7.54 (d, J=5.1, 7.9 Hz, 1H), 7.20 (d, J=7.7, 13.2 Hz, 1H), 4.65-4.60 (m, 1H), 4.57-4.50 (m, 1H), 4.44-4.30 (m, 1H), 4.30-4.18 (m, 1H), 4.01 (d, J=6.8, 13.9 Hz, 1H), 3.96-3.84 (m, 1H), 3.66-3.55 (m, 2H), 3.44 (d, J=5.7, 9.3 Hz, 1H), 3.32 (s, 1H), 3.24-3.14 (m, 2H), 2.33-2.24 (m, 2H), 2.15 (d, J=6.7, 13.9 Hz, 4H), 2.09-1.95 (m, 5H), 1.88 (s, 1H). LCMS (ESI, M+1): m/z 586.1.

Example 46

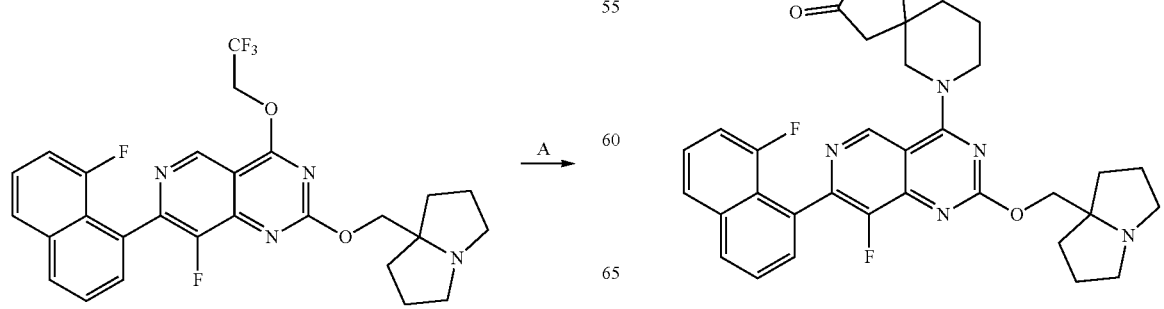

7-(8-fluoro-7-(8-fluoronaphthalen-1-yl)-2-((hexahydro-1H-pyrrolizin-7a-yl)methoxy)pyrido[4,3-d]pyrimidin-4-yl)-7-azaspiro[4.5]decan-2-one

Example 47

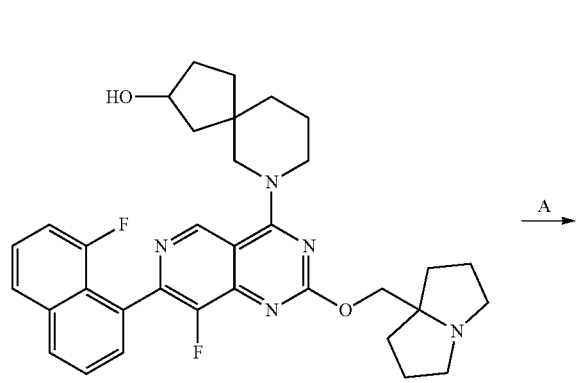

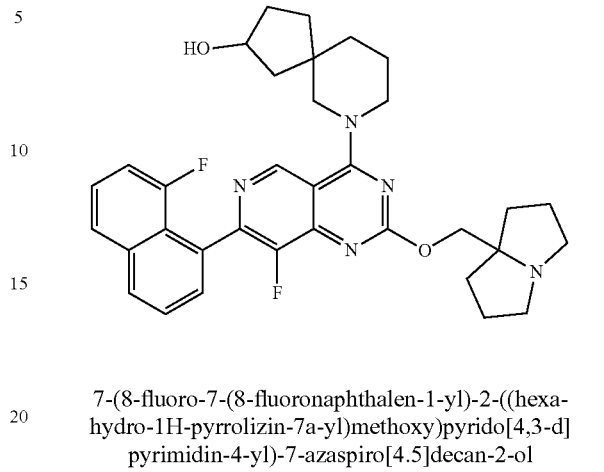

7-(8-fluoro-7-(8-fluoronaphthalen-1-yl)-2-((hexahydro-1H-pyrrolizin-7a-yl)methoxy)pyrido[4,3-d]pyrimidin-4-yl)-7-azaspiro[4.5]decan-2-ol

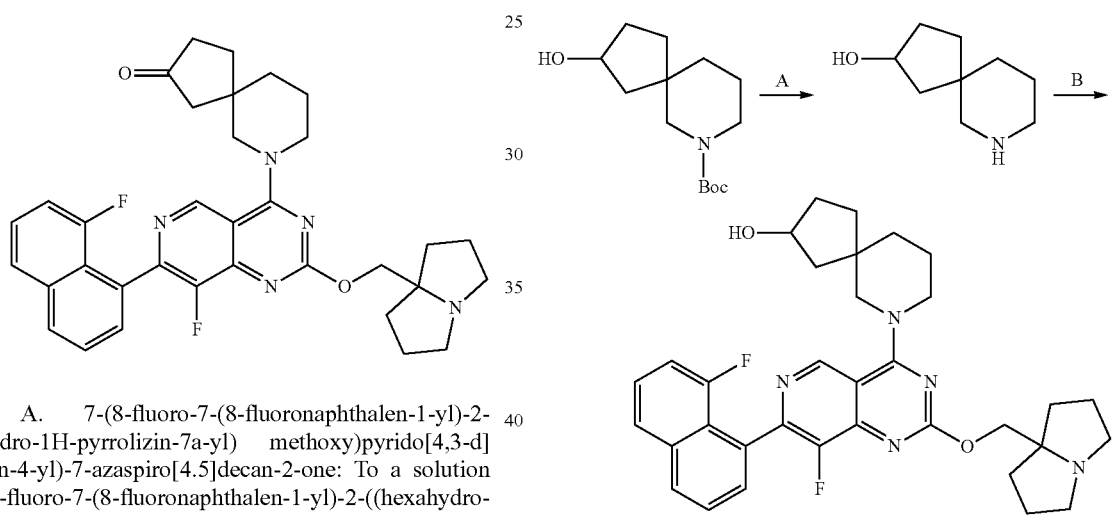

Step A. 7-(8-fluoro-7-(8-fluoronaphthalen-1-yl)-2-((hexahydro-1H-pyrrolizin-7a-yl) methoxy)pyrido[4,3-d]pyrimidin-4-yl)-7-azaspiro[4.5]decan-2-one: To a solution of 7-(8-fluoro-7-(8-fluoronaphthalen-1-yl)-2-((hexahydro-1H-pyrrolizin-7a-yl)methoxy)pyrido[4,3-d]pyrimidin-4-yl)-7-azaspiro[4.5]decan-2-ol (30.0 mg, 51.2 μmol) in dichloromethane (2.0 mL) was added Dess-Martin Reagent (43.5 mg, 102 μmol). The mixture was stirred at 20° C. for 10 hours. After completion, the reaction mixture was quenched with saturated 10 mL $Na_2SO_3$ at 20° C., and then extracted with EtOAc (5 mL×3). The combined organic layer was washed with saturated $NaHCO_3$ (3 mL×2) and brine (5 mL). The mixture was dried over anhydrous $Na_2SO_4$ and filtered. The mixture was concentrated under reduced pressure to give a residue. The residue was purified by prep-HPLC (Phenomenex Luna C18 75×30 mm×3 um; mobile phase: [water (0.2% FORMIC ACID)-ACN]; B %: 15%-45%, 8 min) affording 7-(8-fluoro-7-(8-fluoronaphthalen-1-yl)-2-((hexahydro-1H-pyrrolizin-7a-yl)methoxy)pyrido[4,3-d]pyrimidin-4-yl)-7-azaspiro[4.5]decan-2-one (6.51 mg, 22% yield). White solid; $^1$H NMR (400 MHz, DMSO-$d_6$) δ=9.10 (s, 1H), 8.18 (d, J=8.0 Hz, 1H), 7.93 (d, J=8.0 Hz, 1H), 7.78-7.71 (m, 1H), 7.63 (d, J=7.2 Hz, 1H), 7.59 (d, J=5.2, 8.0 Hz, 1H), 7.31 (d, J=7.6, 13.2 Hz, 1H), 4.09-4.02 (m, 2H), 3.96 (s, 2H), 3.89-3.81 (m, 2H), 2.99-2.90 (m, 2H), 2.56 (d, J=7.0, 9.6 Hz, 2H), 2.34-2.20 (m, 3H), 2.17-2.10 (m, 1H), 1.94-1.83 (m, 4H), 1.83-1.69 (m, 8H), 1.59-1.54 (m, 2H). LCMS (EST, M+1): m/z 584.1.

Step A. 7-azaspiro[4.5]decan-2-ol hydrochloride: To a solution of tert-butyl 2-hydroxy-7-azaspiro[4.5]decane-7-carboxylate (70 mg, 274.13 μmol) in MeOH (1 mL) was added HCl-MeOH (4 M, 1 mL). The mixture was stirred at 20° C. for 2 hours. The reaction mixture was concentrated under reduced pressure to afford 7-azaspiro[4.5]decan-2-ol hydrochloride (55 mg, HCl salt). Colorless oil; LCMS (ESI, M+1): m/z 156.2.

Step B. 7-(8-fluoro-7-(8-fluoronaphthalen-1-yl)-2-((hexahydro-1H-pyrrolizin-7a-yl) methoxy)pyrido[4,3-d]pyrimidin-4-yl)-7-azaspiro[4.5]decan-2-ol: To a solution of 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d]pyrimidine (10 mg, 18.9 μmol) and 7-azaspiro[4.5]decan-2-ol hydrochloride (8.8 mg, 56.6 μmol) in DMF (0.2 mL) was added DIEA (24.4 mg, 188 μmol, 32.8 μL). The mixture was stirred at 40° C. for 1 hr. The reaction mixture was quenched with 10 mL water at 20° C., and then extracted with EtOAc (5 mL×3). The combined organic layers were washed with brine (3 mL×2), and dried over $Na_2SO_4$. The mixture was filtered and concentrated under reduced pressure to give a residue. The residue was purified by prep-HPLC (column: water s Xbridge BEH C18 100×30 mm×10 um; mobile phase: [water (10 mM NH₄HCO₃)-ACN]; B %: 30%-55%, 10 min) to afford 7-(8-fluoro-7-(8-fluoronaphthalen-1-yl)-2-((hexahydro-1H-pyrrolizin-7a-yl)methoxy)pyrido[4,3-d]pyrimidin-4-yl)-7-azaspiro[4.5]decan-2-ol (2.43 mg, 21.0% yield). White solid; HPLC: 95.3%. $^1$H NMR (400 MHz, DMSO-$d_6$) δ=9.11 (s, 1H), 8.15 (d, J=8.4 Hz, 1H), 7.91 (d, J=8.2 Hz, 1H), 7.75-7.68 (m, 1H), 7.60 (td, J=3.3, 6.7 Hz, 1H), 7.58-7.53 (m, 1H), 7.28 (d, J=7.6, 13.1 Hz, 1H), 4.52 (s, 1H), 4.11 (s, 1H), 4.04 (s, 2H), 4.02-3.96 (m, 1H), 3.93-3.84 (m, 1H), 3.83-3.72 (m, 2H), 2.94-2.86 (m, 2H), 2.54-2.50 (m, 2H), 1.96 (s, 1H), 1.90-1.82 (m, 2H), 1.81-1.69 (m, 8H), 1.60-1.50 (m, 6H), 1.47-1.41 (m, 1H), 1.39-1.30 (m, 1H). LCMS (ESI, M+1): m/z 586.3.

Example 48

8-fluoro-4-(2-fluoro-7-azaspiro[4.5]decan-7-yl)-7-(8-fluoronaphthalen-1-yl)-2-((hexahydro-1H-pyrrolizin-7a-yl)methoxy)pyrido[4,3-d]pyrimidine

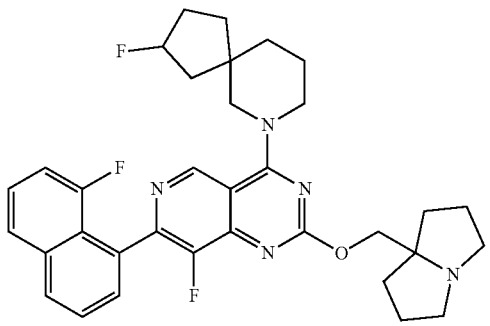 [SMILES: Fc1c(-c2cccc3cccc(F)c23)ncc2c(N3CCCC4(CCC(F)C4)C3)nc(OCC34CCCN3CCC4)nc12]

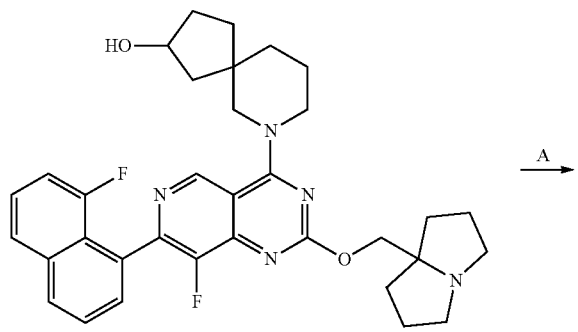

Step A. 8-fluoro-4-(2-fluoro-7-azaspiro[4.5]decan-7-yl)-7-(8-fluoronaphthalen-1-yl)-2-((hexahydro-1H-pyrrolizin-7a-yl)methoxy)pyrido[4,3-d]pyrimidine: To a solution of 7-(8-fluoro-7-(8-fluoronaphthalen-1-yl)-2-((hexahydro-1H-pyrrolizin-7a-yl)methoxy)pyrido[4,3-d]pyrimidin-4-yl)-7-azaspiro[4.5]decan-2-ol (30.0 mg, 51.2 μmol) in DCM (2 mL) was added bis(2-methoxyethyl)aminosulfur trifluoride (113 mg, 512 μmol, 112 μL) at 0° C. The mixture was stirred at 20° C. for 10 hrs. The reaction mixture was quenched with 10 mL water at 20° C., and then extracted with EtOAc (5 mL×3). The combined organic layers were washed with saturated NaHCO₃ (3 mL×2) and brine (3 mL), dried over Na₂SO₄. The mixture was filtered and concentrated under reduced pressure to give a residue. The residue was purified by prep-HPLC (column: Phenomenex Luna C18 75×30 mm×3 μm; mobile phase: [water (0.2% FORMIC ACID)-ACN]; B %: 30%-60%, 8 min) affording 8-fluoro-4-(2-fluoro-7-azaspiro[4.5]decan-7-yl)-7-(8-fluoronaphthalen-1-yl)-2-((hexahydro-1H-pyrrolizin-7a-yl)methoxy)pyrido[4,3-d]pyrimidine (5.11 mg, 16.9% yield). White solid; $^1$H NMR (400 MHz, DMSO-$d_6$) δ=9.07 (s, 1H), 8.34 (s, 1H), 8.18 (d, J=8.4 Hz, 1H), 7.93 (d, J=7.9 Hz, 1H), 7.79-7.70 (m, 1H), 7.67-7.52 (m, 2H), 7.31 (d, J=7.5, 13.3 Hz, 1H), 5.28-5.07 (m, 1H), 4.10-3.96 (m, 3H), 3.89-3.76 (m, 2H), 3.63 (d, J=13.0 Hz, 1H), 2.98-2.87 (m, 2H), 2.58-2.52 (m, 2H), 1.98-1.64 (m, 15H), 1.62-1.50 (m, 3H). $^1$H NMR (400 MHz, MeOD-$d_4$) δ=9.04 (s, 1H), 8.11 (d, J=8.4 Hz, 1H), 7.85 (d, J=7.9 Hz, 1H), 7.74-7.66 (m, 1H), 7.61 (d, J=1.0, 7.2 Hz, 1H), 7.53 (d, J=5.0, 8.0 Hz, 1H), 7.19 (d, J=7.7, 13.0 Hz, 1H), 5.27-5.05 (m, 1H), 4.28 (s, 2H), 4.22-4.07 (m, 1H), 4.02-3.87 (m, 2H), 3.78 (d, J=2.8, 12.9 Hz, 1H), 3.18-3.08 (m, 2H), 2.76 (d, J=6.6, 10.5 Hz, 2H), 2.13-1.82 (m, 14H), 1.81-1.70 (m, 4H); LCMS (ESI, M+1): m/z 588.2.

Example 49

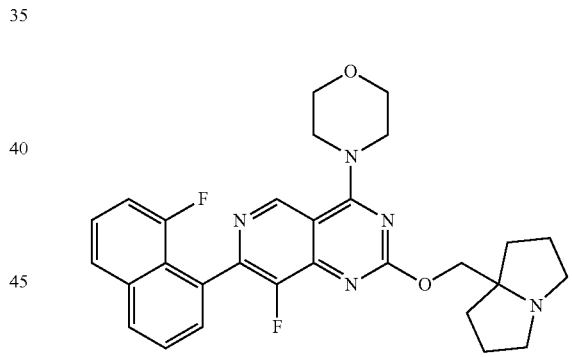

4-(8-fluoro-7-(8-fluoronaphthalen-1-yl)-2-((tetrahydro-1H-pyrrolizin-7a(5H)-yl) methoxy)pyrido[4,3-d]pyrimidin-4-yl)morpholine

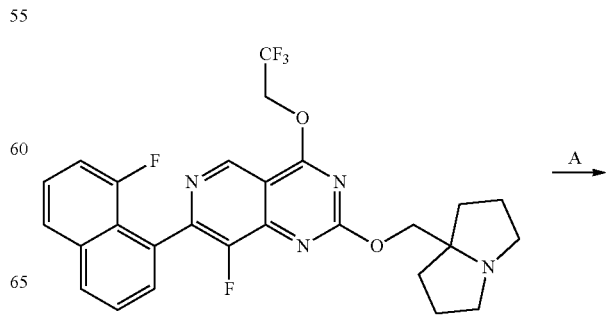

199
-continued

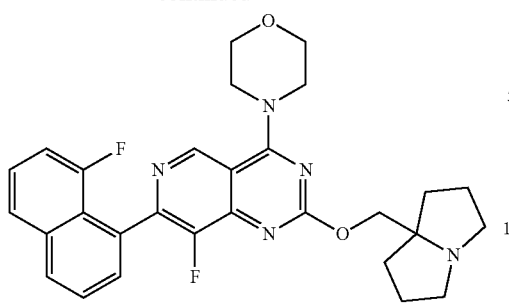

Step A. 4-(8-fluoro-7-(8-fluoronaphthalen-1-yl)-2-((tetrahydro-1H-pyrrolizin-7a(5H)-yl)methoxy)pyrido[4,3-d]pyrimidin-4-yl)morpholine: A mixture of 8-fluoro-7-(8-fluoronaphthalen-1-yl)-2-((tetrahydro-1H-pyrrolizin-7a(5H)-yl)methoxy)-4-(2,2,2-trifluoroethoxy) pyrido[4,3-d]pyrimidine (30.0 mg, 52.0 µmol, formic acid salt), morpholine (9.07 mg, 104 µmol, 9.16 µL), DIEA (26.9 mg, 208 µmol, 36.3 µL) and 4 Å molecular sieves (5 mg) in DMF (0.5 mL) was stirred at 40° C. for 1.5 h. After completion, the mixture was filtered and purified by prep-HPLC (Shim-pack C18 150*25*10 µm; mobile phase: [water (0.225% formic acid)-ACN]; B %: 15%-45%, 10 min) to afford the title compound (7.45 mg, 27% yield, 0.4 FORMIC ACID). Off-white Solid. $^1$H NMR (400 MHz, CDCl$_3$-d): δ 9.04 (s, 1H), 7.99 (td, J=1.6, 8.0 Hz, 1H), 7.74 (d, J=8.0 Hz, 1H), 7.66-7.57 (m, 2H), 7.45 (dt, J=4.8, 8.0 Hz, 1H), 7.15-7.08 (m, 1H), 4.56 (s, 2H), 4.12-4.01 (m, 4H), 3.94-3.89 (m, 4H), 3.65-3.59 (m, 2H), 2.84 (td, J=6.8, 10.8 Hz, 2H), 2.34-2.23 (m, 2H), 2.14-2.07 (m, 2H), 2.05-1.98 (m, 2H), 1.92-1.83 (m, 2H). $^{19}$F NMR (400 MHz, CDCl$_3$-d) δ=−112.256. −138.683. LCMS (ESI, M+1): m/z 518.2.

Example 50

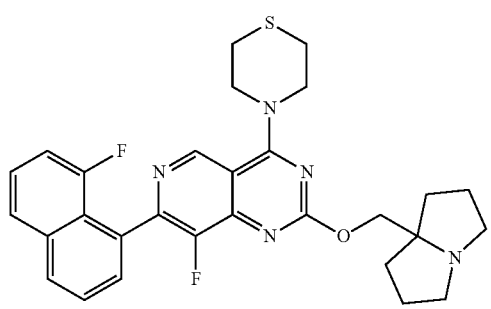 [SMILES: Fc1c(-c2cccc3cccc(F)c23)ncc2c(N3CCOCC3)nc(OCC34CCCN3CCC4)nc12]

200

4-(8-fluoro-7-(8-fluoronaphthalen-1-yl)-2-((hexahydro-1H-pyrrolizin-7a-yl)methoxy)pyrido[4,3-d]pyrimidin-4-yl)thiomorpholine

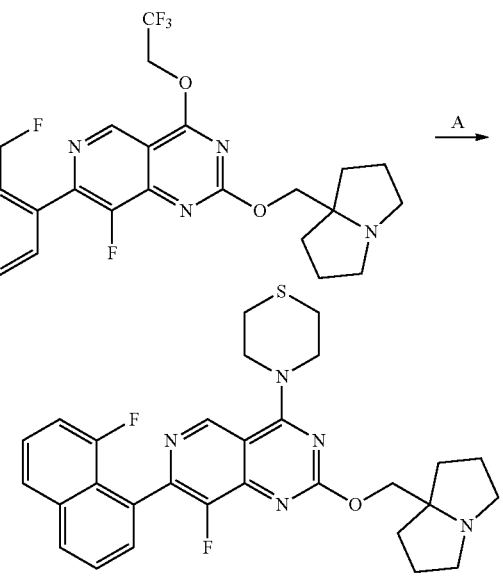

Step A. 4-(8-fluoro-7-(8-fluoronaphthalen-1-yl)-2-((hexahydro-1H-pyrrolizin-7a-yl) methoxy)pyrido[4,3-d]pyrimidin-4-ylthiomorpholine: A mixture of 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d]pyrimidine (30 mg, 56.6 µmol), thiomorpholine (18 mg, 174 µmol), DIPEA (30 µL), and 4 Å molecular sieves (10 mg) in DMF (0.5 mL) was stirred at 40° C. for 6 hours under N$_2$ atmosphere. The reaction mixture was filtered and purified by prep-HPLC (column: Shim-pack C18 150×25×10 um; mobile phase: [water (0.225% formic acid)-ACN]; B %: 19%-49%, 10 minutes) to give the product as white solid (14.5 mg, 45% yield, 0.3 FORMIC ACID). $^1$H NMR (400 MHz, DMSO-d$_6$) δ=9.05 (s, 1H), 8.18 (br d, J=8.0 Hz, 1H), 7.93 (br d, J=8.0 Hz, 1H), 7.74 (br t, J=7.6 Hz, 1H), 7.64-7.58 (m, 2H), 7.31 (br dd, J=7.6, 12.8 Hz, 1H), 4.19 (br s, 4H), 4.10 (s, 2H), 2.98-2.91 (m, 6H), 2.60-2.57 (m, 2H), 1.92-1.78 (m, 6H), 1.61-1.58 (m, 2H). LCMS (ESI, M+1): m/z 534.2.

Example 51

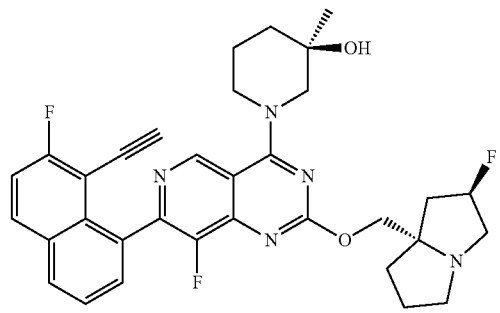 [SMILES: C#Cc1c(F)ccc2cccc(-c3ncc4c(N5CCC[C@@](C)(O)C5)nc(OC[C@@]56CCCN5C[C@H](F)C6)nc4c3F)c12]

201

(R)-1-(7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol Synthesized according to Example 16, step A to C. Yellow Solid; $^1$H NMR (400 MHz, methanol-d4) δ 9.24-9.03 (m, 1H), 8.19-8.06 (m, 2H), 7.74-7.58 (m, 2H), 7.51-7.36 (m, 1H), 5.47-5.21 (m, 1H), 4.67-4.57 (m, 2H), 4.41-4.23 (m, 3H), 3.68-3.62 (m, 1H), 3.52-3.34 (m, 2H), 3.29-3.18 (m, 2H), 3.10-2.98 (m, 1H), 2.44-2.11 (m, 4H), 2.08-1.97 (m, 2H), 1.95-1.65 (m, 4H), 1.27 (d, J=19.6 Hz, 3H); LCMS (ESI, M+1): m/z 588.3.

Example 52

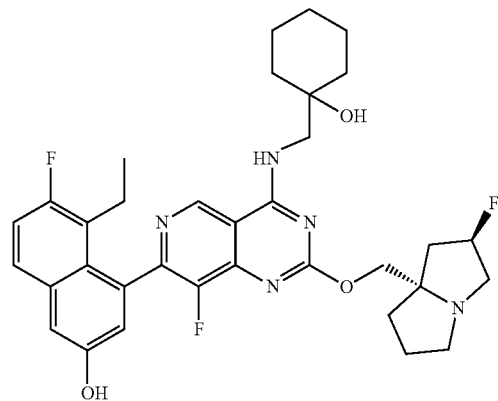 [SMILES: CCc1c(F)ccc2cc(O)cc(-c3ncc4c(NCC5(O)CCCCC5)nc(OC[C@@]56CCCN5C[C@H](F)C6)nc4c3F)c12]

5-ethyl-6-fluoro-4-(8-fluoro-2-(((2R,7aS)-2-fluorohexahydro-1H-pyrrolizin-7a-yl)methoxy)-4-(((1-hydroxycyclohexyl)methyl)amino)pyrido[4,3-d]pyrimidin-7-yl)naphthalen-2-ol

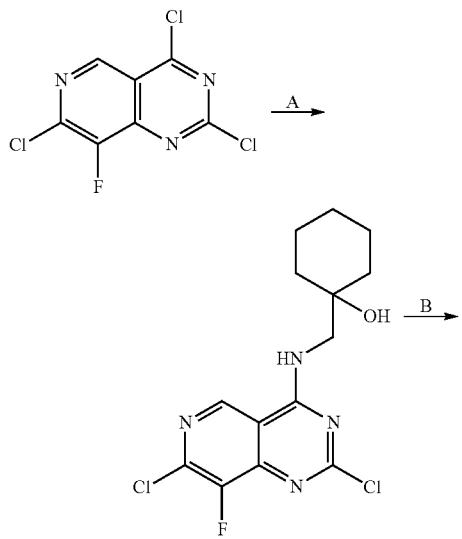

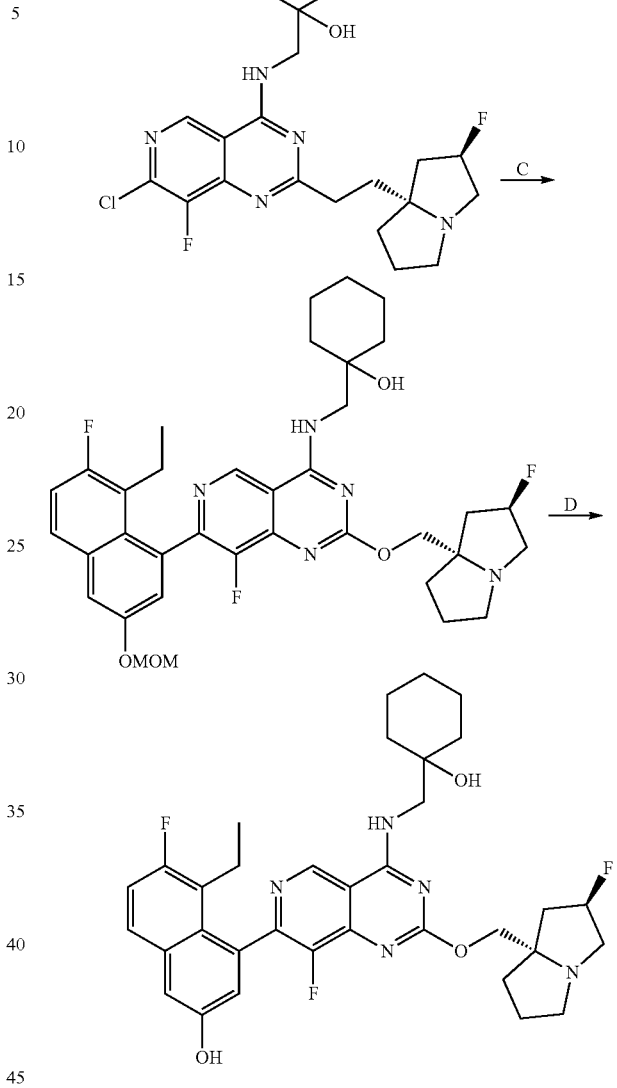

Step A 1-(((2,7-dichloro-8-fluoropyrido[4,3-d]pyrimidin-4-yl)amino)methyl) cyclohexanol: To a mixture of 1-(aminomethyl)cyclohexanol (256 mg, 1.98 mmol) and 2,4,7-trichloro-8-fluoropyrido[4,3-d]pyrimidine (500 mg, 1.98 mmol) in DMA (6 mL) was added DIEA (768 mg, 5.94 mmol) in one portion at 0° C. under N$_2$. The mixture was stirred at 0° C. for 1 h. After completion, the mixture was filtered and the filtrate was purification by reversed-phase flash chromatography (water (0.1% formic acid)-ACN) affording 1-(((2,7-dichloro-8-fluoropyrido[4,3-d]pyrimidin-4-yl)amino)methyl)cyclohexanol (530 mg, 77% yield). Yellow solid; $^1$H NMR (400 MHz, DMSO-d$_6$): δ 9.37 (br s, 1H), 9.31 (s, 1H), 4.53 (br s, 1H), 3.58 (s, 2H), 1.63-1.35 (m, 9H), 1.30-1.15 (m, 1H); LCMS (ESI, M+1): m/z 345.1.

Step B 1-(((7-chloro-8-fluoro-2-(((2R,7aS)-2-fluorohexahydro-1H-pyrrolizin-7a-yl) methoxy)pyrido[4,3-d]pyrimidin-4-yl)amino)methyl)cyclohexanol: To a mixture of ((2R,7aS)-2-fluorohexahydro-1H-pyrrolizin-7a-yl)methanol (346 mg, 2.17 mmol) and 1-(((2,7-dichloro-8-fluoropyrido[4,3-d]pyrimidin-4-yl)amino)methyl)cyclohexanol (500 mg, 1.45 mmol) in dioxane (5 mL) was added DIEA (561 mg, 4.35 mmol) in one portion at 25° C. under N₂. The mixture was heated to 95° C. and stirred for 12 h. After completion, the mixture was filtered and concentrated in vacuum. The residue was purified by reversed-phase flash chromatography (water (0.1% formic acid)-ACN) affording 1-(((7-chloro-8-fluoro-2-(((2R,7aS)-2-fluorohexahydro-1H-pyrrolizin-7a-yl) methoxy)pyrido[4,3-d]pyrimidin-4-yl)amino) methyl)cyclohexanol (630 mg, 91% yield). Off-white solid; LCMS (ESI, M+1): m/z 468.2.

Step C 1-(((7-(8-ethyl-7-fluoro-3-(methoxymethoxy) naphthalen-1-yl)-8-fluoro-2-(((2R,7aS)-2-fluorohexahydro-1H-pyrrolizin-7a-yl)methoxy)pyrido[4,3-d]pyrimidin-4-ylamino)methyl)cyclohexanol: To a mixture of 2-(8-ethyl-7-fluoro-3-(methoxymethoxy)naphthalen-1-yl)-4,4,5,5-tetramethyl-1,3,2-dioxaborolane (200 mg, 427 μmol) and 1-(((7-chloro-8-fluoro-2-(((2R,7aS)-2-fluorohexahydro-1H-pyrrolizin-7a-yl) methoxy)pyrido[4,3-d]pyrimidin-4-yl) amino)methyl)cyclohexanol (200 mg, 555 μmol) in THF (4 mL) was added K₃PO₄ (1.5 M, 855 μL) in one portion at 25° C. under N₂. Then cataCXium-A-Pd-G3 (46.7 mg, 64.1 μmol) was added. The mixture was heated to 60° C. and stirred for 2 h. After completion, the mixture was filtered and concentrated in vacuum. The residue was purified by reversed phase flash chromatography (C18, water (0.1% formic acid)-ACN) affording 1-(((7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)cyclohexanol (110 mg, 36% yield). Yellow solid; LCMS (ESI, M+1): m/z 666.2.

Step D 5-ethyl-6-fluoro-4-(8-fluoro-2-(((2R,7aS)-2-fluorohexahydro-1H-pyrrolizin-7a-yl)methoxy)-4-(((1-hydroxycyclohexyl)methyl)amino)pyrido[4,3-d]pyrimidin-7-yl)naphthalen-2-ol: A mixture of 1-(((7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)cyclohexanol (90 mg, 135 μmol) and HCl-dioxane (4 M, 4.50 mL) in ACN (0.5 mL) was stirred at 20° C. for 10 min. After completion, the residue was concentrated in vacuum. The residue was purified by prep-HPLC (column: Phenomenex Gemini-NX C18 75×30 mm×3 μm; mobile phase: [water (0.225% formic acid)-ACN]; B %: 18%-48%, 5 min) affording 5-ethyl-6-fluoro-4-(8-fluoro-2-(((2R,7aS)-2-fluorohexahydro-1H-pyrrolizin-7a-yl)methoxy)-4-(((1-hydroxycyclohexyl)methyl) amino)pyrido[4,3-d]pyrimidin-7-yl)naphthalen-2-ol (52.3 mg, 60% yield, 0.35 FORMIC ACID). White solid; ¹H NMR (400 MHz, DMSO-d₆): δ9.93 (br s, 1H), 9.40 (s, 1H), 8.75 (s, 1H), 7.76 (dd, J=6.0 Hz, 9.2 Hz, 1H), 7.38-7.30 (m, 2H), 8.99 (s, 1H), 5.28 (d, J=54.4 Hz, 1H), 4.56 (br s, 1H), 4.15 (d, J=10.4 Hz, 1H), 4.08 (d, J=10.4 Hz, 1H), 3.71-3.64 (m, 1H), 3.58-3.53 (m, 1H), 3.12-3.05 (m, 2H), 3.04-2.99 (m, 1H), 2.88-2.78 (m, 1H), 2.40-2.35 (m, 1H), 2.20-1.95 (m, 4H), 1.89-1.72 (m, 3H), 1.65-1.35 (m, 10H), 1.28-1.18 (m, 1H), 0.72 (t, J=7.6 Hz, 3H); LCMS (ESI, M+1): m/z=622.3.

Example 53

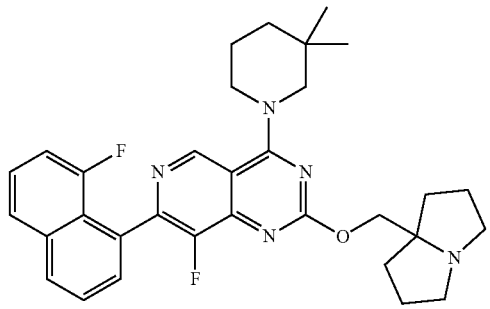 [SMILES: CC1(C)CCCN(c2nc(OCC34CCCN3CCC4)nc3c(F)c(-c4cccc5cccc(F)c45)ncc23)C1]

4-(3,3-dimethylpiperidin-1-yl)-8-fluoro-7-(8-fluoronaphthalen-1-yl)-2-((hexahydro-1H-pyrrolizin-7a-yl)methoxy)pyrido[4,3-d]pyrimidine

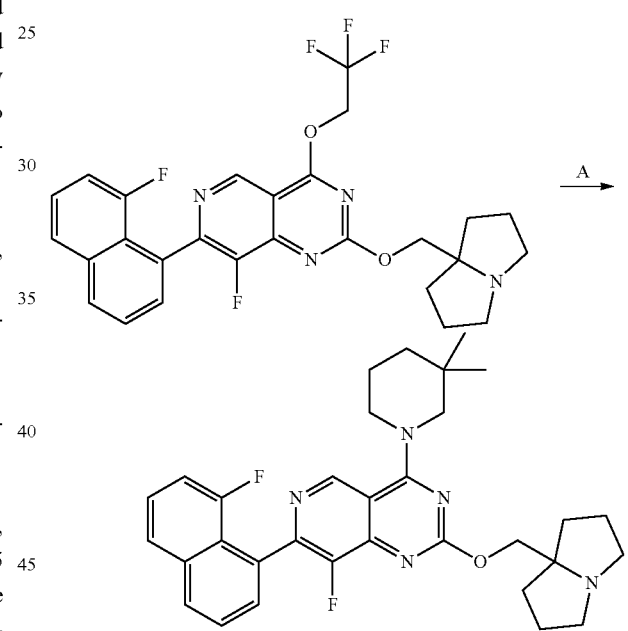

Step A. 4-(3,3-dimethylpiperidin-1-yl)-8-fluoro-7-(8-fluoronaphthalen-1-yl)-2-((hexahydro-1H-pyrrolizin-7a-yl) methoxy)pyrido[4,3-d]pyrimidine: To a solution of 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d] pyrimidine (100 mg, 188 μmol) and DIEA (73.1 mg, 565 μmol, 98.5 μL) in DMF (1.5 mL) was added 3,3-dimethylpiperidine (42.7 mg, 377 μmol). The mixture was stirred at 40° C. for 12 h. After completion, the mixture was concentrated at 20° C. The residue was purified by prep-HPLC (column: Phenomenex luna C18 150*25 mm*10 um; mobile phase: [water (0.225% formic acid)-ACN]; B %: 27%-57%, 10 min) affording 4-(3,3-dimethylpiperidin-1-yl)-8-fluoro-7-(8-fluoronaphthalen-1-yl)-2-((hexahydro-1H-pyrrolizin-7a-yl) methoxy)pyrido[4,3-d]pyrimidine (32.8 mg, 29% yield). White solid; ¹H NMR (400 MHz, METHANOL-d4) δ=9.09 (s, 1H), 8.12 (br d, J=8.0 Hz, 1H), 7.85 (br d, J=8.4 Hz, 1H), 7.74-7.66 (m, 1H), 7.65-7.59 (m, 1H), 7.57-7.49

(m, 1H), 7.19 (dd, J=7.6, 12.8 Hz, 1H), 4.47 (s, 2H), 4.08-3.94 (m, 2H), 3.83 (s, 2H), 3.44-3.36 (m, 2H), 3.06-2.95 (m, 2H), 2.26-2.15 (m, 2H), 2.13-1.98 (m, 4H), 1.98-1.86 (m, 4H), 1.69-1.59 (m, 2H), 1.03 (br d, J=4.0 Hz, 6H); LCMS (ESI, M+1): m/z=544.3.

Example 54

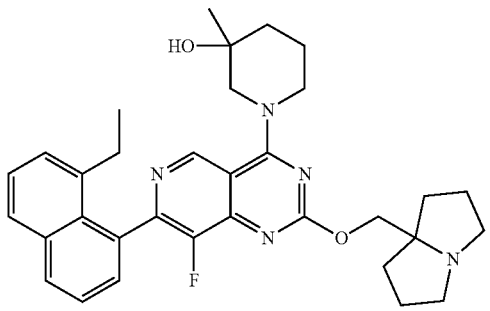 [SMILES: CCc1cccc2cccc(-c3ncc4c(N5CCCC(C)(O)C5)nc(OCC56CCCN5CCC6)nc4c3F)c12]

1-(7-(8-ethylnaphthalen-1-yl)-8-fluoro-2-((hexahydro-1H-pyrrolizin-7a-yl)methoxy)pyrido[4,3-d]pyrimidin-4-yl)-3-methylpiperidin-3-ol 22%-52%, 10 minutes) to give the product as yellow solid (13.1 mg, 18% yield, 0.9 FORMIC ACID). $^1$H NMR (400 MHz, DMSO+D$_2$O) δ=9.20 (d, J=7.2 Hz, 1H), 8.05 (d, J=8.4 Hz, 1H), 7.88 (d, J=8.0 Hz, 1H), 7.57 (t, J=7.6 Hz, 1H), 7.49 (t, J=7.6 Hz, 1H), 7.39 (dd, J=6.8, 12.8 Hz, 2H), 4.46-4.39 (m, 3H), 4.09 (br dd, J=13.6, 19.2 Hz, 1H), 3.57 (dd, J=13.2, 42.4 Hz, 1H), 3.40-3.35 (m, 3H), 3.06-3.02 (m, 2H), 2.32-2.22 (m, 2H), 2.05-1.90 (m, 12H), 1.15 (d, J=11.6 Hz, 3H), 0.83-0.78 (m, 3H). LCMS (ESI, M+1): m/z=556.3.

Example 55

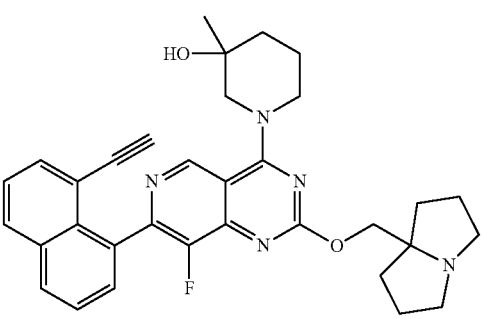 [SMILES: C#Cc1cccc2cccc(-c3ncc4c(N5CCCC(C)(O)C5)nc(OCC56CCCN5CCC6)nc4c3F)c12]

1-(7-(8-ethynyl)naphthalen-1-yl)-8-fluoro-2-((hexahydro-1H-pyrrolizin-7a-yl)methoxy)pyrido[4,3-d]pyrimidin-4-yl)-3-methylpiperidin-3-ol

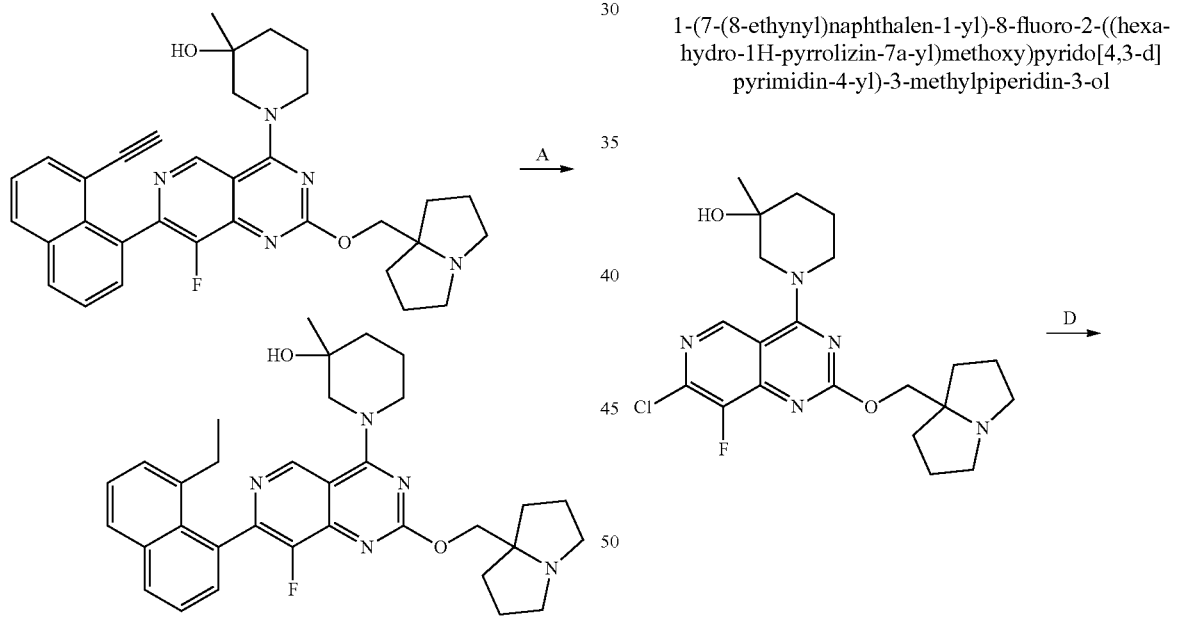

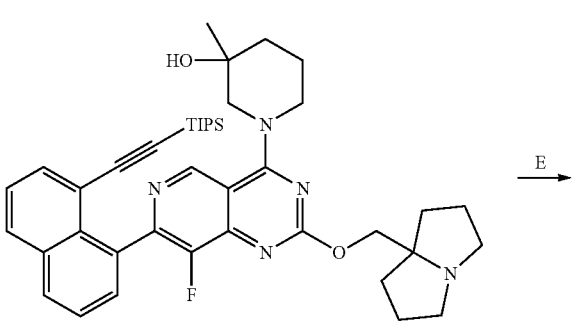

Step A. 1-(7-(8-ethylnaphthalen-1-yl)-8-fluoro-2-((hexahydro-1H-pyrrolizin-7a-yl) methoxy)pyrido[4,3-d]pyrimidin-4-yl)-3-methylpiperidin-3-ol: To a solution of 1-(7-(8-ethynyl)naphthalen-1-yl)-8-fluoro-2-((hexahydro-1H-pyrrolizin-7a-yl)methoxy)pyrido[4,3-d]pyrimidin-4-yl)-3-methylpiperidin-3-ol (65 mg, 118 μmol) in MeOH (4 ML) was added Pd/C (10 mg, 10% purity) under N$_2$ atmosphere. The mixture was degassed and purged with H$_2$ for 3 times and stirred at 25° C. for 18 hours under H$_2$ atmosphere (15 psi). The reaction mixture was filtered. The filtrate was concentrated under reduced pressure, purified by prep-HPLC (column: Phenomenex luna C18 150×25 mm×10 um; mobile phase: [water (0.225% formic acid)-ACN]; B %:

207

-continued

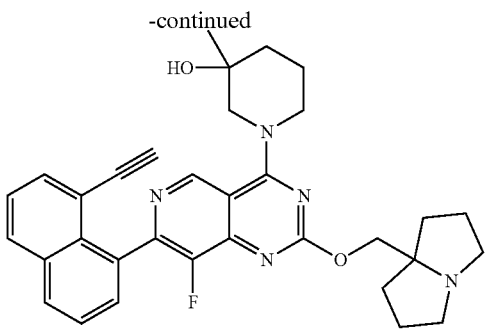

Step A. 1-(8-fluoro-2-((hexahydro-1H-pyrrolizin-7a-yl)methoxy)-7-(8-(((triisopropylsilyl) ethynyl)naphthalen-1-yl) pyrido[4,3-d]pyrimidin-4-yl)-3-methylpiperidin-3-ol: A mixture of 1-(7-chloro-8-fluoro-2-((hexahydro-1H-pyrrolizin-7a-yl)methoxy)pyrido[4,3-d]pyrimidin-4-yl)-3-methylpiperidin-3-ol (115 mg, 264 μmol) and K$_3$PO$_4$ (1.5 M in water, 550 μL) in THF (3 mL) was degassed and purged with N$_2$ for 3 times. Triisopropyl-[2-[8-(4,4,5,5-tetramethyl-1,3,2-dioxaborolan-2-yl)-1-naphthyl]ethynyl]silane (130 mg, 299 μmol) was added, followed by cataCXium-A-Pd-G3 (20 mg, 27.5 μmol). The mixture was stirred at 60° C. for 3 hours under N$_2$ atmosphere. The combined reaction mixture was diluted with water (15 ml), extracted with ethyl acetate (5 mL×4). The combined organic phase was dried with anhydrous Na$_2$SO$_4$. The mixture was filtered and concentrated under reduced pressure to give a residue. The residue was purified by reversed phase flash chromatography [water (0.1% formic acid)/acetonitrile-l/1] to give the product as a yellow gum (131 mg, 65%). LCMS (ESI, M+1): m/z=708.4.

Step B. 1-(7-(8-ethynyl)naphthalen-1-yl)-8-fluoro-2-((hexahydro-1H-pyrrolizin-7a-yl)methoxy)pyrido[4,3-d]pyrimidin-4-yl)-3-methylpiperidin-3-ol: A mixture of 1-(8-fluoro-2-((hexahydro-1H-pyrrolizin-7a-yl)methoxy)-7-(8-((triisopropylsilyl)ethynyl)naphthalen-1-yl) pyrido[4,3-d]pyrimidin-4-yl)-3-methylpiperidin-3-ol (59 mg, 83.3 μmol), and CsF (127 mg, 833 μmol) in DMF (1 mL) was stirred at 25° C. for 1 hour. The reaction mixture was filtered. The filtrate was purified by prep-HPLC (column: water s Xbridge 150×25 mm×5um; mobile phase: [water (10 mM NH$_4$HCO$_3$)-ACN]; B %: 29%-59%, 10 min) to give the product as a yellow solid (19.6 mg, 42%). $^1$H NMR (400 MHz, DMSO-d) δ=9.14 (d, J=60.4 Hz, 1H), 8.14 (t, J=8.0 Hz, 2H), 7.73-7.56 (m, 4H), 4.78-4.72 (m, 1H), 4.46-4.26 (m, 1H), 4.11-4.03 (m, 3H), 3.68 (d, J=4.4 Hz, 1H), 3.59 (t, J=13.6 Hz, 1H), 2.95-2.91 (m, 2H), 2.56-2.54 (m, 3H), 1.90-1.70 (m, 10H), 1.58-1.55 (m, 2H), 1.16 (d, J=15.2 Hz, 3H). LCMS (ESI, M+1): m/z=552.3.

Example 56

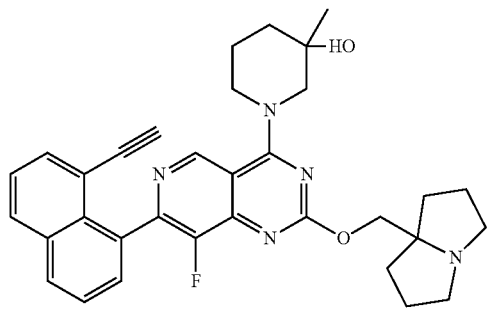 [SMILES: C#Cc1cccc2cccc(-c3ncc4c(N5CCCC(C)(O)C5)nc(OCC56CCCN5CCC6)nc4c3F)c12]

208

8-(8-fluoro-2-((hexahydro-1H-pyrrolizin-7a-yl)methoxy)-4-(3-hydroxy-3-methylpiperidin-1-yl)pyrido[4,3-d]pyrimidin-7-yl)-1-naphthonitrile

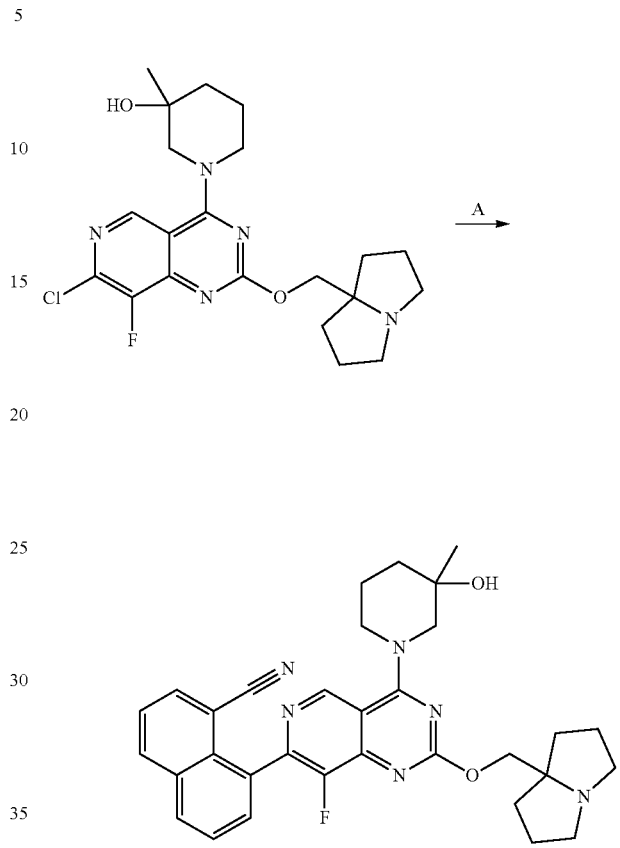

Step A. 8-(8-fluoro-2-((hexahydro-1H-pyrrolizin-7a-yl)methoxy)-4-(3-hydroxy-3-methylpiperidin-1-yl)pyrido[4,3-d]pyrimidin-7-yl)-1-naphthonitrile: To a solution of 1-(7-chloro-8-fluoro-2-((hexahydro-1H-pyrrolizin-7a-yl)methoxy)pyrido[4,3-d]pyrimidin-4-yl)-3-methylpiperidin-3-ol (50.0 mg, 115 μmol) and 8-(4,4,5,5-tetramethyl-1,3,2-dioxaborolan-2-yl)-1-naphthonitrile (48.0 mg, 172 μmol) in toluene (2.0 mL) was added K$_3$PO$_4$ (1.5 M, 229 μl) and cataCXium-A-Pd-G3 (12.53 mg, 17.20 μmol). The mixture was stirred at 90° C. for 2 hours. After completion, the reaction mixture was diluted with water (5 mL) and extracted with ethyl acetate (3×20 mL). The combined organic layers were dried over Na$_2$SO$_4$. The mixture was filtered and concentrated under reduced pressure to give a residue. The residue was purified by prep-HPLC (column: Phenomenex luna C18 150*25 mm*10 μm; mobile phase: [water (0.225% formic acid)-ACN]; B %: 18%-48%, 10 min) to give 8-(8-fluoro-2-((hexahydro-1H-pyrrolizin-7a-yl)methoxy)-4-(3-hydroxy-3-methylpiperidin-1-yl)pyrido[4,3-d]pyrimidin-7-yl)-1-naphthonitrile (22.0 mg, 33% yield, 0.6 FORMIC ACID); Yellow solid. $^1$H NMR (400 MHz, DMSO-d$_6$) δ 9.26 (s, 1H), 8.46 (d, J=8.4 Hz, 1H), 8.29 (dd, J=2.0, 7.2 Hz, 1H), 8.24 (s, 1H), 8.14 (dd, J=1.2, 7.2 Hz, 1H), 7.87-7.78 (m, 2H), 7.77-7.70 (m, 1H), 4.33-4.25 (m, 1H), 4.13 (s, 2H), 4.03 (br d, J=13.2 Hz, 2H), 3.47-3.35 (m, 2H), 3.05-2.97 (m, 2H), 2.66-2.57 (m, 2H), 2.08-1.99 m, 1H), 1.98-1.90 (m, 2H), 1.88-1.76 (m, 4H), 1.75-1.58 (m, 5H), 1.17 (br s, 3H). LCMS (ESI, M+1): m/z=553.3.

209

Example 57

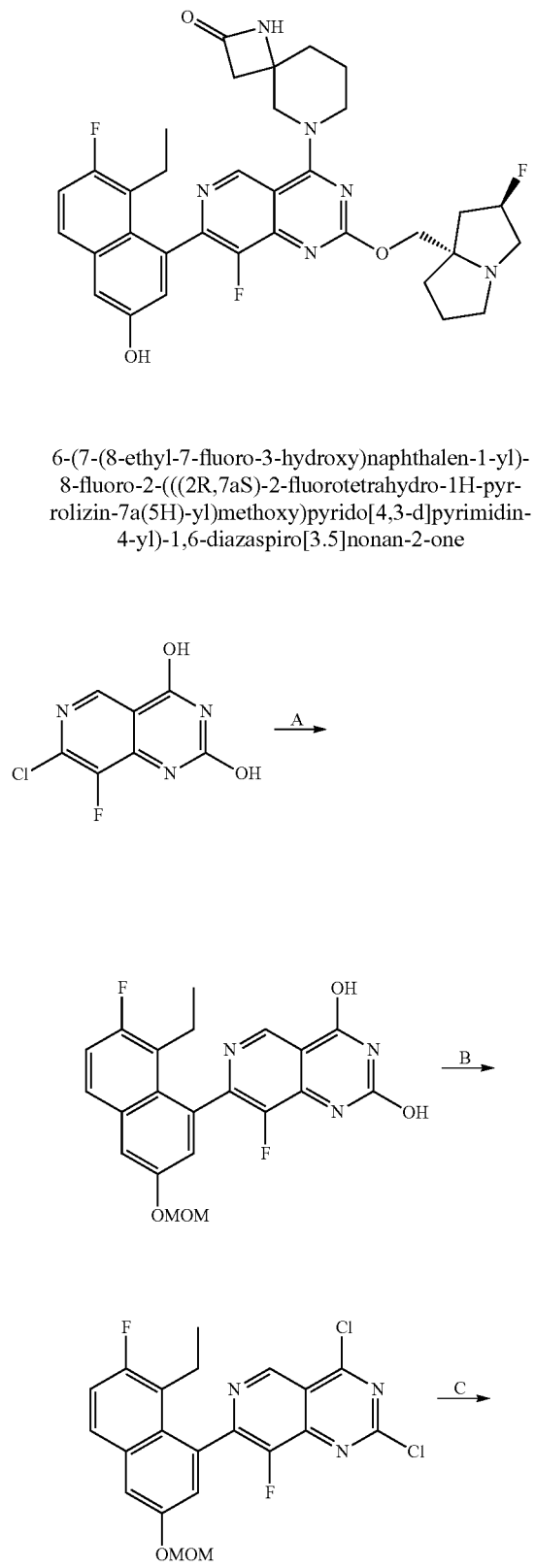

6-(7-(8-ethyl-7-fluoro-3-hydroxy)naphthalen-1-yl)-
8-fluoro-2-(((2R,7aS)-2-fluorotetrahydro-1H-pyr-
rolizin-7a(5H)-yl)methoxy)pyrido[4,3-d]pyrimidin-
4-yl)-1,6-diazaspiro[3.5]nonan-2-one

210

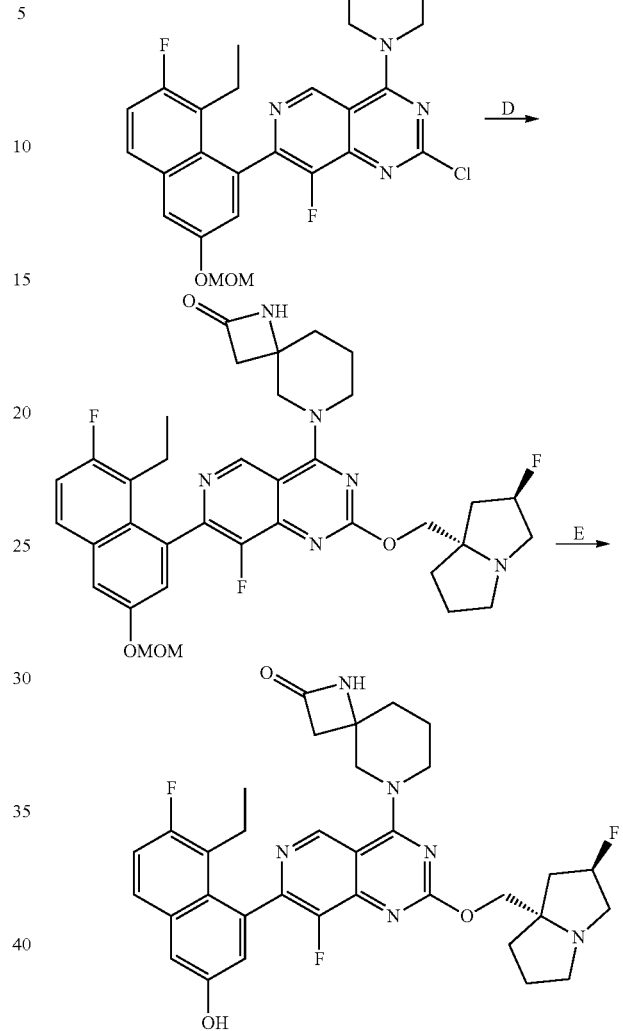

Step A. 7-[8-ethyl-7-fluoro-3-(methoxymethoxy)-1-naphthyl]-8-fluoro-pyrido[4,3-d]pyrimidine-2,4-diol: To a mixture of 7-chloro-8-fluoro-pyrido[4,3-d]pyrimidine-2,4-diol, 2-(8-ethyl-7-fluoro-3-(methoxymethoxy)naphthalen-1-yl)-4,4,5,5-tetramethyl-1,3,2-dioxaborolane (14.0 g, 39.0 mmol) and $K_3PO_4$ (1.5 M, 46.4 mL) in EtOH (140 mL) was added cataCXium-A-Pd-G3 (1.39 g, 1.90 mmol) under $N_2$. The mixture was de-gassed and then heated to 78° C. for 9.5 h under $N_2$. After completion, the mixture was concentrated in vacuum. Then the mixture was diluted with ethyl acetate (500 mL) then filtered. 100 mL water was added, and the organic layer was separated. Then the aqueous phase was extracted with ethyl acetate (80 mL). The combined organic layer was washed with brine (120 mL), dried over anhydrous $Na_2SO_4$. The mixture was filtered and concentrated in vacuum to give a residue. The residue was purified by reversed phase flash chromatography [water (0.1% formic acid)/acetonitrile] to give 7-[8-ethyl-7-fluoro-3-(methoxymethoxy)-1-naphthyl]-8-fluoro-pyrido[4,3-d]pyrimidine-2,4-diol (2.34 g, 24% yield). Yellow solid. LCMS [ESI, M+1]: m/z=414.1.

Step B. 2,4-dichloro-7-[8-ethyl-7-fluoro-3-(methoxymethoxy)-1-naphthyl]-8-fluoro-pyrido[4,3-d]pyrimidine. A mixture of POCl₃ (278 mg, 1.81 mmol, 169 µL) in toluene (3 mL) were added DIEA (141 mg, 1.09 mmol, 190 µL) and 7-[8-ethyl-7-fluoro-3-(methoxymethoxy)-1-naphthyl]-8-fluoro-pyrido[4,3-d]pyrimidine-2,4-diol (150 mg, 363 µmol) and the mixture was stirred at 110° C. for 25 mins. After completion, the mixture was concentrated in vacuum and the pH value was adjusted to 8 with cold saturated NaHCO₃ solution. Then the mixture was extracted with ethyl acetate (8 mL) twice. The combined organic layer was washed with brine (10 mL) and dried over Na₂SO₄. The mixture was filtered and concentrated in vacuum to give 2,4-dichloro-7-[8-ethyl-7-fluoro-3-(methoxymethoxy)-1-naphthyl]-8-fluoro-pyrido[4,3-d]pyrimidine (164 mg, crude) which was used to next step without further purification. Brown oil.

Step C. 8-[2-chloro-7-[8-ethyl-7-fluoro-3-(methoxymethoxy)-1-naphthyl]-8-fluoro-pyrido[4,3-d]pyrimidin-4-yl]-1,8-diazaspiro[3,5]nonan-2-one. To a mixture of 2,4-dichloro-7-[8-ethyl-7-fluoro-3-(methoxymethoxy)-1-naphthyl]-8-fluoro-pyrido[4,3-d]pyrimidine (147 mg, 326 µmol) and DIEA (127 mg, 979 µmol, 171 µL) in dichloromethane (2 mL) was added 1,8-diazaspiro[3.5]nonan-2-one (45.8 mg, 326 µmol) at −40° C. and the mixture was stirred at −40° C. for 20 mins. After completion, the mixture was quenched by water (10 mL) and filtered. Then the filtrate was extracted with dichloromethane twice. The combined organic layer was washed with brine (6 mL) and dried over anhydrous Na₂SO₄. The mixture was filtered and concentrated in vacuum to give a residue. The residue was purified by reversed phase flash chromatography [water (0.1% formic acid)/acetonitrile] to give 8-[2-chloro-7-[8-ethyl-7-fluoro-3-(methoxymethoxy)-1-naphthyl]-8-fluoro-pyrido[4,3-d]pyrimidin-4-yl]-1,8-diazaspiro[3.5]nonan-2-one (54.0 mg, 27% yield over two steps). Yellow solid. LCMS [ESI, M+1]: m/z=554.2.

Step D. 6-(7-(8-ethyl-7-fluoro-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1,6-diazaspiro[3,5]nonan-2-one. A mixture of 8-[2-chloro-7-[8-ethyl-7-fluoro-3-(methoxymethoxy)-1-naphthyl]-8-fluoro-pyrido[4,3-d]pyrimidin-4-yl]-1,8-diazaspiro[3.5]nonan-2-one (50.0 mg, 90.3 µmol), ((2R,7aS)-2-fluorotetrahydro-1H-pyrrolizin-7a(5H)-yl)methanol (43.1 mg, 271 µmol), DIEA (35.0 mg, 271 µmol, 47.2 µL) and 4 Å molecular sieves (10 mg) in dioxane (1.5 mL) was stirred at 90° C. for 22 h. After completion, the mixture was filtered and concentrated in vacuum to give a residue. The residue was purified by reversed phase flash chromatography [water (0.1% formic acid)/acetonitrile] to give the title compound (36.0 mg, 55% yield). Yellow solid. LCMS [ESI, M+1]: m/z=677.4.

Step E. 6-(7-(8-ethyl-7-fluoro-3-hydroxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1,6-diazaspiro[3,5]nonan-2-one. To a mixture of 6-(7-(8-ethyl-7-fluoro-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1,6-diazaspiro[3,5]nonan-2-one (37.0 mg, 54.7 µmol) and dichloromethane (0.5 mL) was added TFA (770 mg, 6.75 mmol, 0.5 mL) at 0° C. and the mixture was stirred at 0° C. for 1 h. After completion, the mixture was concentrated in vacuum. The pH value was adjusted to 9 with saturated NaHCO₃ solution and the mixture was extracted with ethyl acetate twice. The combined organic layer was dried over anhydrous Na₂SO₄. The mixture was filtered and concentrated in vacuum to give a residue. The residue was purified by prep-HPLC (Water s Xbridge 150*25 mm*5 µm; mobile phase: [water (10 mM NH₄HCO₃)-ACN]; B %: 35%-65%, 10 min) to afford the title compound (14.3 mg, 41% yield). Yellow solid. ¹H NMR (400 MHz, METHANOL-d4):δ 9.08 (s, 1H), 7.68 (dd, J=5.6, 8.8 Hz, 1H), 7.30 (d, J=2.4 Hz, 1H), 7.25 (t, J=9.2 Hz, 1H), 7.05 (d, J=2.0 Hz, 1H), 5.39-5.22 (m, 1H), 4.42-4.24 (m, 4H), 4.02-3.92 (m, 1H), 3.85-3.68 (m, 1H), 3.28-3.11 (m, 3H), 3.05-2.97 (m, 1H), 2.92-2.83 (m, 1H), 2.78-2.70 (m, 1H), 2.51-2.09 (m, 6H), 2.04-1.90 (m, 6H), 0.79 (td, J=2.4, 7.2 Hz, 3H). ¹⁹F NMR (400 MHz, METHANOL-d4) δ=−121.066, −138.847, −173.641; LCMS [ESI, M+1]: m/z=633.3.

Example 58

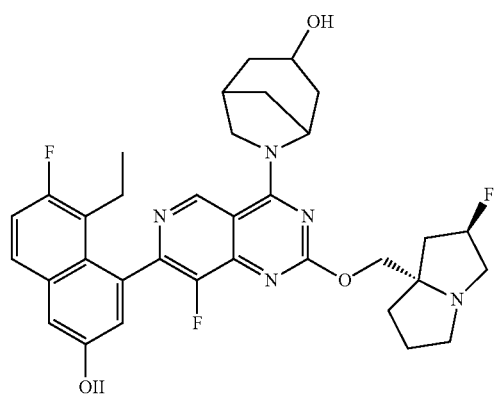

6-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azabicyclo[3.2.1]octan-3-ol

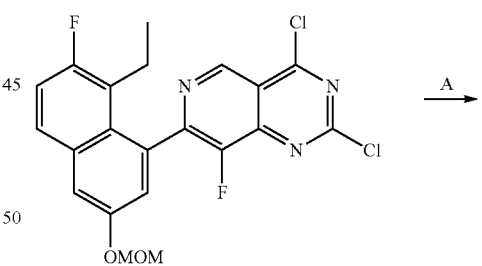

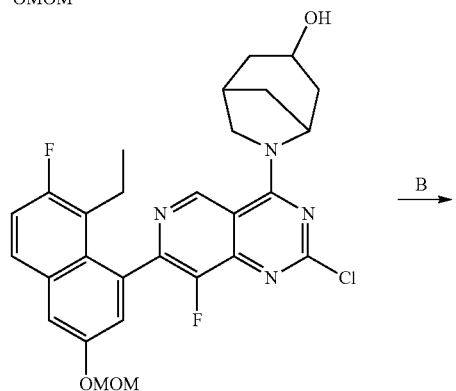

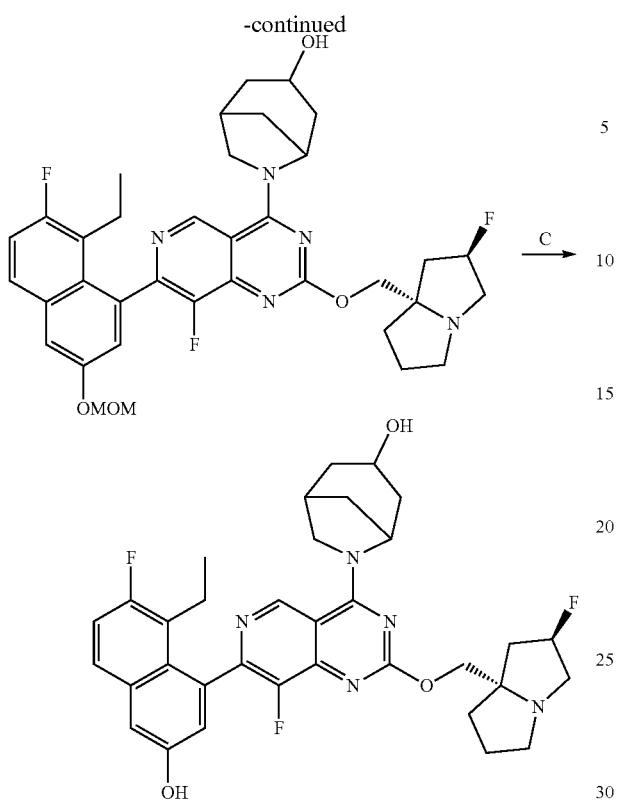

Step A. 6-(2-chloro-7-(8-ethyl-7-fluoro-3-(methoxymethoxy)naphthalen-1-yl)-8-fluoropyrido[4,3-d]pyrimidin-4-yl)-6-azabicyclo[3.2.1]octan-3-ol: To a solution of 2,4-dichloro-7-(8-ethyl-7-fluoro-3-(methoxymethoxy)naphthalen-1-yl)-8-fluoropyrido[4,3-d]pyrimidine (163 mg, 362 µmol) and DIPEA (297 mg, 2.30 mmol) in DCM (2 mL) was added 6-azabicyclo[3.2.1]octan-3-ol (33 mg, 259 µmol) in DCM (1 mL) at −40° C. slowly. The mixture was stirred at this temperature for 10 minutes. The reaction mixture was diluted with water (5 ml), and extracted with ethyl acetate (10 mL×4). The combined organic phase was dried with anhydrous Na₂SO₄. The mixture was filtered and concentrated under reduced pressure to afford a residue. The residue was purified by reversed phase flash chromatography [water (0.1% formic acid)/acetonitrile=2/3] to give the product as a red oil (88 mg, 39%). LCMS [ESI, M+1]: m/z=541.2.

Step B. 6-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azabicyclo[3.2.1]octan-3-ol: A mixture of 6-(2-chloro-7-(8-ethyl-7-fluoro-3-(methoxymethoxy)naphthalen-1-yl)-8-fluoropyrido[4,3-d]pyrimidin-4-yl)-6-azabicyclo[3.2.1]octan-3-ol (66 mg, 122 µmol), ((2R,7aS)-2-fluorohexahydro-1H-pyrrolizin-7a-yl) methanol (78 mg, 490 µmol), DIPEA (52 mg, 402 µmol), and 4 Å molecular sieves (40 mg, 40.7 µmol) in dioxane (1 mL) was degassed and purged with N₂ for 3 times, and then the mixture was stirred at 95° C. for 48 hours under N₂ atmosphere. The reaction mixture was-filtered. The residue was washed with DCM (1 mL×5). The combined DCM phase was concentrated under reduced pressure to afford a residue. The residue was purified by reversed phase flash chromatography [water (0.1% formic acid)/acetonitrile=12/13] to give the product as a yellow oil (48 mg, 59%). LCMS [ESI, M+1]: m/z=664.3.

Step C. 6-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azabicyclo[3.2.1]octan-3-ol: To a solution of 6-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azabicyclo[3.2.1]octan-3-ol (58 mg, 87.4 µmol) in DCM (2 mL) was added dropwise TFA (2.5 mL) at 0° C. The mixture was stirred between 0 and 15° C. for 1.5 hours. The reaction mixture was diluted with DCM (4 mL), and quenched with saturated NaHCO₃ aqueous (8 mL) at 0° C. The residue was washed with DCM (4 mL×4) and the combined DCM phase was concentrated under reduced pressure to afford a residue. The filtrate was purified by prep-HPLC (column: water s Xbridge 150×25 mm×5 µm; mobile phase: [water (10 mM NH₄HCO₃)-ACN]; B %: 42%-72%, 10 min) to give the product as a yellow solid. (10 mg, 18%). ¹H NMR (400 MHz, METHANOL-d4) δ=9.27-9.24 (m, 1H), 7.68-7.66 (m, 1H), 7.29-7.24 (m, 2H), 7.04 (br dd, J=2.0, 12.4 Hz, 1H), 5.31 (d, J=54.4 Hz, 1H), 4.98 (br s, 1H), 4.34-4.22 (m, 4H), 4.13 (br s, 1H), 3.22 (br d, J=14.0 Hz, 2H), 3.02-3.00 (m, 1H), 2.77-2.64 (m, 2H), 2.47-1.81 (m, 14H), 0.78 (t, J=7.2 Hz, 3H). F NMR (376 MHz, METHANOL-d4) δ=−121, −138, −173. LCMS [ESI, M+1]: m/z=620.3.

Example 59

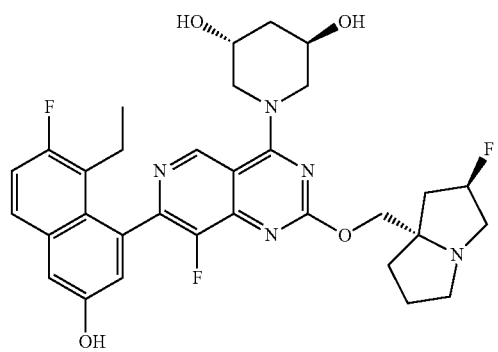 [SMILES: CCc1c(F)ccc2cc(O)cc(-c3ncc4c(N5C[C@H](O)C[C@@H](O)C5)nc(OC[C@@]56CCCN5C[C@H](F)C6)nc4c3F)c12]

(3R,5R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)piperidine-3,5-diol

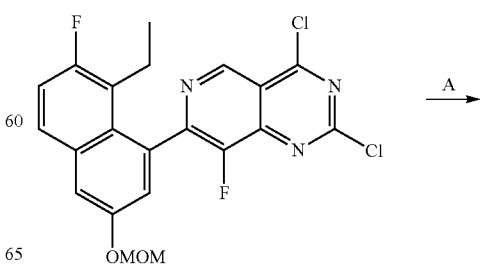

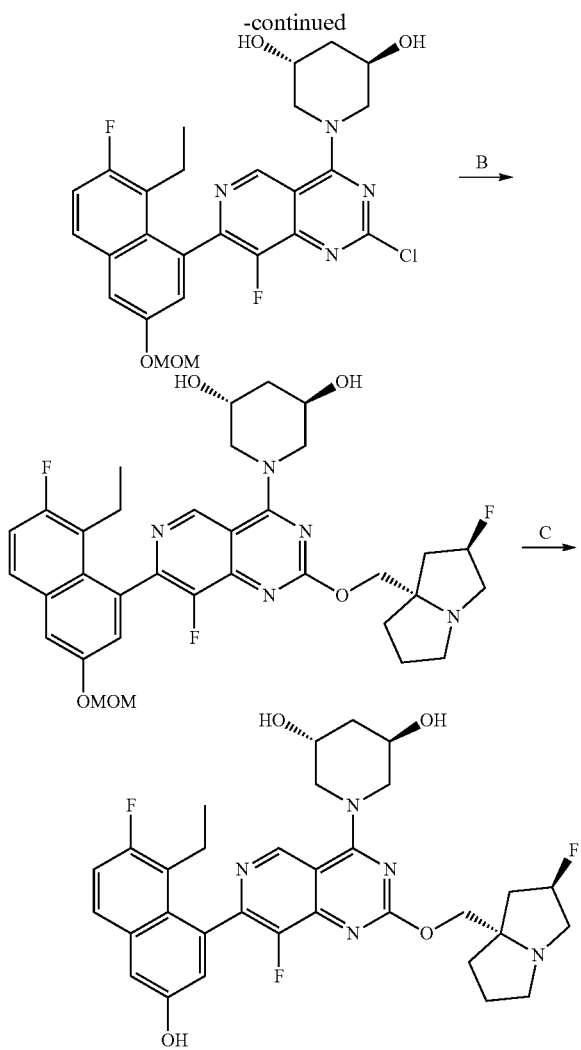

Step A. (3R,5R)-1-(2-chloro-7-(8-ethyl-7-fluoro-3-(methoxymethoxy)naphthalen-1-yl)-8-fluoropyrido[4,3-d]pyrimidin-4-yl)piperidine-3,5-diol: To a mixture of 2,4-dichloro-7-(8-ethyl-7-fluoro-3-(methoxymethoxy) naphthalen-1-yl)-8-fluoropyrido[4,3-d]pyrimidine (200 mg, 444 µmol), and DIEA (287 mg, 2.22 mmol) in dichloromethane (3 mL) was added (3R,5R)-piperidine-3,5-diol (47.8 mg, 311 µmol, HCl) at −40° C. The mixture was stirred at −40° C. for 0.5 hour. Upon completion, the reaction mixture was partitioned between dichloromethane (6 mL) and water (5 mL), and the aqueous layer was extracted with dichloromethane (5 mL) one more time. The combined organic phase was washed with brine (5 mL) and dried over anhydrous Na$_2$SO$_4$. The mixture was filtered and concentrated to give a residue. The residue was purified by reversed phase flash chromatography [water (0.1% formic acid)/acetonitrile] to give (3R,5R)-1-(2-chloro-7-(8-ethyl-7-fluoro-3-(methoxymethoxy)naphthalen-1-yl)-8-fluoropyrido[4,3-d]pyrimidin-4-yl) piperidine-3,5-diol (85.0 mg, 34% yield). Yellow Oil; LCMS [ESI, M+1]: m/z=531.2.

Step B. (3R,5R)-1-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl) piperidine-3,5-diol. To the mixture of (3R,5R)-1-(2-chloro-7-(8-ethyl-7-fluoro-3-(methoxymethoxy)naphthalen-1-yl)-8-fluoropyrido[4,3-d]pyrimidin-4-yl)piperidine-3,5-diol (75.0 mg, 141 µmol), ((2R,7aS)-2-fluorohexahydro-1H-pyrrolizin-7a-yl)methanol (45.0 mg, 282 µmol), and 4 Å molecular sieves (30.0 mg) in dioxane (1.5 mL) was added DIEA (54.8 mg, 424 µmol), and the mixture was stirred at 90° C. for 15 hours. Upon completion, the reaction mixture was partitioned between ethyl acetate (15 mL) and water (10 mL), and the aqueous layer was extracted with ethyl acetate (15 mL). The combined organic phase was washed with brine (20 mL) and dried over anhydrous sodium sulfate. The mixture was filtered and concentrated to give a residue. The residue was purified by reversed phase flash chromatography [water (0.1% formic acid)/acetonitrile] to give (3R,5R)-1-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)piperidine-3,5-diol (45.0 mg, 45% yield). Yellow Solid; LCMS [ESI, M+1]: m/z=654.1.

Step C. (3R,5R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl) piperidine-3,5-diol. To the solution of (3R,5R)-1-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)piperidine-3,5-diol (42.0 mg, 64.3 µmol) in dichloromethane (0.8 mL) was added TFA (1.47 g, 12.9 mmol), and the mixture was stirred at 0° C. for 1 hour. Upon completion, the mixture was concentrated, and the pH was adjusted to 8 with sat. NaHCO$_3$. The mixture was extracted with ethyl acetate (8 mL×2), and the combined organic phase was dried over anhydrous sodium sulfate. The mixture was filtered and concentrated to give a residue. The residue was purified by prep-HPLC (column: water s Xbridge 150×25 mm×5 µm; mobile phase: [water (10 mM NH$_4$HCO$_3$)-ACN]; B %: 29%-59%, 10 min) to afford (3R,5R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)piperidine-3,5-diol (15.71 mg, 40% yield). White Solid; $^1$H NMR (400 MHz, METHANOL-d4) δ=9.26 (d, J=7.2 Hz, 1H), 7.72-7.65 (m, 1H), 7.31 (d, J=2.4 Hz, 1H), 7.25 (t, J=9.2 Hz, 1H), 7.07-7.02 (m, 1H), 5.46-5.31 (m, 1H), 4.51-4.34 (m, 2H), 4.30-4.21 (m, 4H), 3.86-3.76 (m, 2H), 3.55-3.47 (m, 1H), 3.56-3.35 (m, 2H), 3.20-3.10 (m, 1H), 2.52-2.05 (m, 1H), 2.04-1.93 (m, 3H), 0.84-0.75 (m, 3H); LCMS [ESI, M+1]: m/z 610.2.

Example 60

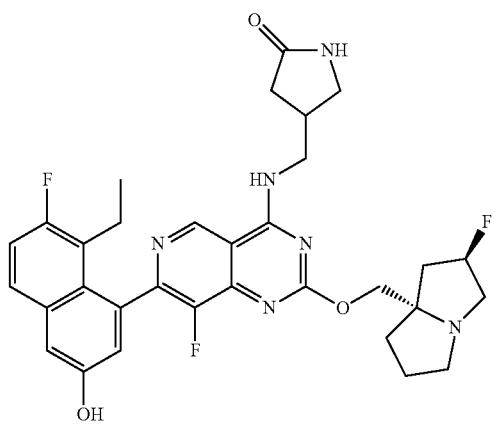 [SMILES: CCc1c(F)ccc2cc(O)cc(-c3ncc4c(NCC5CNC(=O)C5)nc(OC[C@@]56CCCN5C[C@H](F)C6)nc4c3F)c12]

4-(((7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)pyrrolidin-2-one

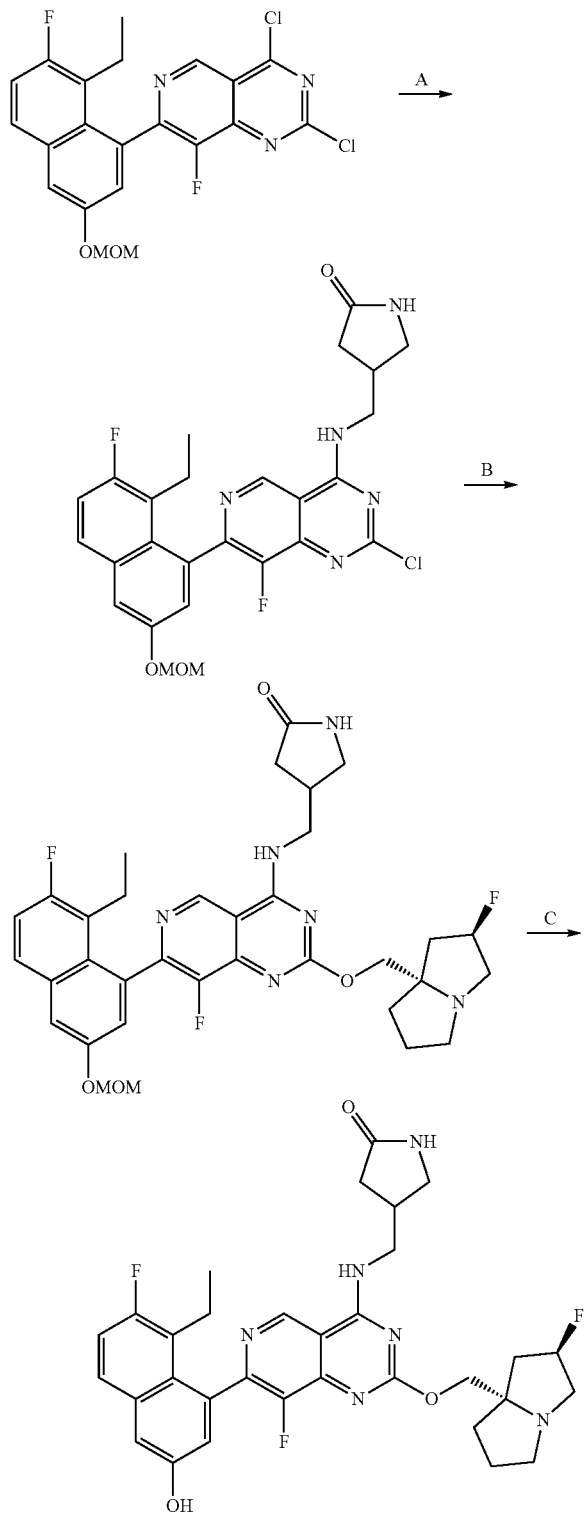

Step A. 4-(((2-chloro-7-(8-ethyl-7-fluoro-3-(methoxymethoxy)naphthalen-1-yl)-8-fluoropyrido[4,3-d] pyrimidin-4-yl)amino)methyl)pyrrolidin-2-one: To the mixture of 2,4-dichloro-7-(8-ethyl-7-fluoro-3-(methoxymethoxy)naphthalen-1-yl)-8-fluoropyrido[4,3-d]pyrimidine (170 mg, 378 μmol), and DIEA (244 mg, 1.89 mmol) in dichloromethane (3 mL) was added 4-(aminomethyl)pyrrolidin-2-one (34.5 mg, 302 μmol) at −40° C., and the mixture was stirred at −40° C. for 0.5 hour. Upon completion, the reaction mixture was quenched with water and extracted with dichloromethane twice. The combined organic phase was washed with brine (5 mL) and dried over anhydrous sodium sulfate. The mixture was filtered and concentrated to give a residue. The residue was purified by reversed phase flash chromatography [water (0.1% formic acid)/acetonitrile] to give the title compound (120 mg, 59% yield). Off-White Solid; LCMS [ESI, M+1]: m/z 528.2.

Step B. 4-(((7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)pyrrolidin-2-one: To the mixture of 4-(((2-chloro-7-(8-ethyl-7-fluoro-3-(methoxymethoxy)naphthalen-1-yl)-8-fluoropyrido[4,3-d]pyrimidin-4-yl) amino)methyl)pyrrolidin-2-one (110 mg, 208 μmol), ((2R,7aS)-2-fluorohexahydro-1H-pyrrolizin-7a-yl)methanol (66.3 mg, 417 μmol), and 4 Å molecular sieves (5.0 mg) in dioxane (1.5 mL) was added DIEA (80.8 mg, 625 μmol), and the mixture was stirred at 90° C. for 15 hours. Upon completion, the reaction mixture was quenched with water and extracted with ethyl acetate twice. The combined organic phase was washed with brine (20 mL) and dried over anhydrous sodium sulfate. The mixture was filtered and concentrated to give a residue. The residue was purified by reversed phase flash chromatography [water (0.1% formic acid)/acetonitrile] to give the title compound (83.0 mg, 59% yield). Yellow Solid; LCMS [ESI, M+1]: m/z 651.2.

Step C. 4-(((7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl) amino)methyl)pyrrolidin-2-one: To the solution of 4-(((7-(8-ethyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)amino)methyl)pyrrolidin-2-one (78.0 mg, 120 μmol) in dichloromethane (0.8 mL) was added TFA (1.54 g, 13.5 mmol), and the mixture was stirred at 0° C. for 1 hour. Upon completion, the mixture was concentrated, and the pH was adjusted with sat. NaHCO₃ to 8. The mixture was extracted with ethyl acetate (8 mL×2). The combined organic phase dried over anhydrous sodium sulfate. The mixture was filtered and concentrated to give a residue. The residue was purified by prep-HPLC (column: water s Xbridge 150×25 mm×5 μm; mobile phase: [water (10 mM NH₄HCO₃)-ACN]; B %: 29%-59%, 10 min) to afford 4-(((7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl) amino)methyl)pyrrolidin-2-one (25.04 mg, 34% yield). White Solid; $^1$H NMR (400 MHz, METHANOL-d4) δ=9.18 (s, 1H), 7.73-7.66 (m, 1H), 7.33 (d, J=2.4 Hz, 1H), 7.27 (t, J=9.6 Hz, 1H), 7.06 (d, J=2.8 Hz, 1H), 5.46-5.28 (m, 1H), 4.46-4.31 (m, 2H), 3.89-3.76 (m, 2H), 3.67-3.58 (m, 1H), 3.51-3.34 (m, 3H), 3.30 (br s, 1H), 3.17-3.00 (m, 2H), 2.62-2.15 (m, 7H), 2.11-1.94 (m, 3H), 0.81 (t, J=7.2 Hz, 3H); LCMS [ESI, M+1]: m/z 607.2.

Example 61

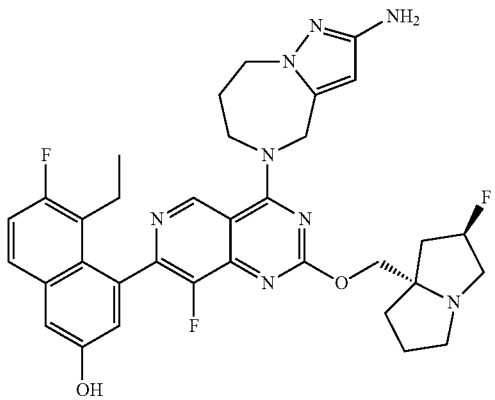 [SMILES: CCc1c(F)ccc2cc(O)cc(-c3ncc4c(N5CCCn6nc(N)cc6C5)nc(OC[C@@]56CCCN5C[C@H](F)C6)nc4c3F)c12]

4-(4-(2-amino-7,8-dihydro-4H-pyrazolo[1,5-a][1,4]diazepin-5 (6H)-yl)-8-fluoro-2-((((2R,7aS)-2-fluorohexahydro-1H-pyrrolizin-7a-yl)methoxy)pyrido[4,3-d]pyrimidin-7-yl)-5-ethyl-6-fluoronaphthalen-2-ol

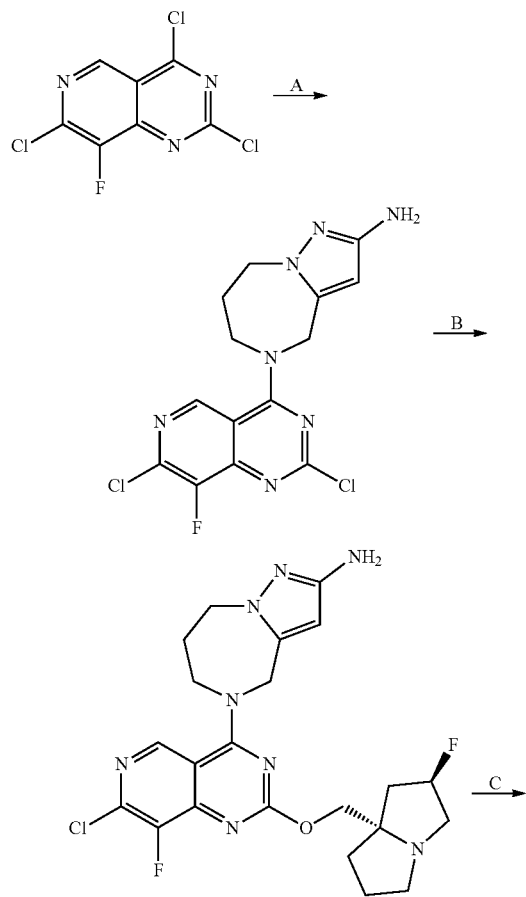

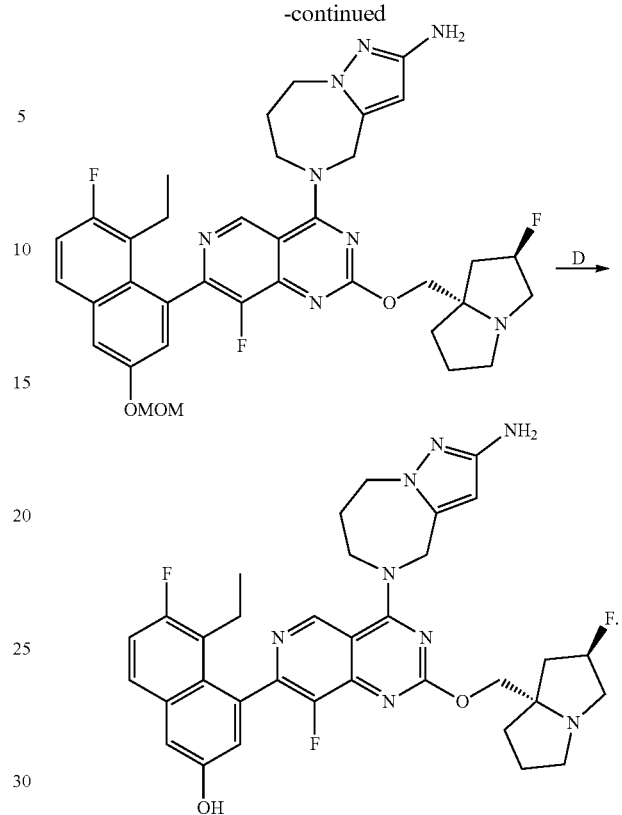

Step A. 5-(2,7-dichloro-8-fluoropyrido[4,3-d]pyrimidin-4-yl)-5,6,7,8-tetrahydro-4H-pyrazolo[1,5-a][1,4]diazepin-2-amine: To the mixture of 2,4,7-trichloro-8-fluoropyrido[4,3-d]pyrimidine (280 mg, 1.1 mmol) and DIEA (717 mg, 5.5 mmol, 966 μL) in dichloromethane (1 mL) was added 5,6,7,8-tetrahydro-4H-pyrazolo[1,5-a][1,4]diazepin-2-amine (118 mg, 776 μmol) at −40° C. and the mixture was stirred at −40° C. for 0.5 hour. After completion, the mixture was quenched by water (3 mL) and filtered. Then the mixture was extracted with dichloromethane twice. The combined organic layer was dried over anhydrous $Na_2SO_4$. The mixture was filtered and concentrated in vacuum to give 5-(2,7-dichloro-8-fluoropyrido[4,3-d]pyrimidin-4-yl)-5,6,7,8-tetrahydro-4H-pyrazolo[1,5-a][1,4]diazepin-2-amine (474 mg, crude). Brown oil; LCMS [ESI, M+1]: m/z 368.0.

Step B. 5-(7-chloro-8-fluoro-2-((((2R,7aS)-2-fluorohexahydro-1H-pyrrolizin-7a-yl) methoxy)pyrido[4,3-d]pyrimidin-4-yl)-5,6,7,8-tetrahydro-4H-pyrazolo[1,5-a][1,4]diazepin-2-amine: A mixture of 5-(2,7-dichloro-8-fluoropyrido[4,3-d]pyrimidin-4-yl)-5,6,7,8-tetrahydro-4H-pyrazolo[1,5-a][1,4]diazepin-2-amine (454 mg, 1.2 mmol), ((2R,7aS)-2-fluorohexahydro-1H-pyrrolizin-7a-yl)methanol (589 mg, 3.7 mmol), DIEA (478 mg, 3.7 mmol, 644 μL) and 4 Å molecular sieves (400 mg) in dioxane (1 mL) was stirred at 90° C. for 16 hours. After completion, the mixture was filtered and concentrated in vacuum to give a residue. The residue was purified by reversed phase flash chromatography [water (0.1% formic acid)/acetonitrile] to give 5-(7-chloro-8-fluoro-2-((((2R,7aS)-2-fluorohexahydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-amine (80 mg, 9% yield over two steps). Yellow solid; LCMS [ESI, M+1]: m/z 491.2.

Step C. 5-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-amine:
To the mixture of 5-(7-chloro-8-fluoro-2-(((2R,7aS)-2-fluorohexahydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-amine (70 mg, 143 µmol), 2-(8-ethyl-7-fluoro-3-(methoxymethoxy)naphthalen-1-yl)-4,4,5,5-tetramethyl-1,3,2-dioxaborolane (67 mg, 185 µmol), K₃PO₄ (1.5 M. 285 µL) in THF (1 mL) was added cataCXium-A-Pd-G3 (10 mg, 14 µmol) under N₂, and the mixture was stirred at 60° C. for 4 hours. After completion, the mixture was quenched by water (2 mL). Then the mixture was extracted with ethyl acetate twice. The combined organic layer was dried over anhydrous Na₂SO₄. The mixture was filtered and concentrated in vacuum to give a residue. The residue was purified by reversed phase flash chromatography [water (0.1% formic acid)/acetonitrile] to give 5-(7-(8-ethyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)-5,6,7,8-tetrahydro-4H-pyrazolo[1,5-a][1,4]diazepin-2-amine (53 mg, 43% yield). Yellow solid; LCMS [ESI, M+1]: m/z 689.4.

Step D. 4-(4-(2-amino-7,8-dihydro-4H-pyrazolo[1,5-a][1,4]diazepin-5 (6H)-yl)-8-fluoro-2-(((2R,7aS)-2-fluorohexahydro-1H-pyrrolizin-7a-yl)methoxy)pyrido[4,3-d]pyrimidin-7-l)l-5-ethyl-6-fluoronaphthalen-2-ol. 5-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-amine (14 mg, 20 µmol) was added to HCl-MeOH (4.0 mmol, 1 mL) at 0° C. and the mixture was stirred at 0° C. for 20 min. After completion, the mixture was concentrated in vacuum. The pH value was adjusted to 9.0 with saturated NaHCO₃ solution and the mixture was extracted with ethyl acetate (15 mL×2). The aqueous phase was extracted with ethyl acetate (2 mL). The combined organic layer was dried over anhydrous Na₂SO₄. The mixture was filtered and concentrated in vacuum to give a residue. The residue was purified by prep-HPLC (column: Phenomenex Gemini-NX C18 75×30 mm×3 µm; mobile phase: [water (10 mM NH₄HCO₃)-ACN]; B %: 20%-50%, 10 min) to afford 4-(4-(2-amino-7,8-dihydro-4H-pyrazolo[1,5-a][1,4]diazepin-5 (6H)-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol (4.58 mg, 34% yield). White solid; ¹H NMR (400 MHz, METHANOL-d4): δ=9.19 (s, 1H), 7.67 (dd, J=5.6, 9.2 Hz, 1H), 7.30 (d, J=2.4 Hz, 1H), 7.25 (t, J=9.2 Hz, 1H), 7.06 (d, J=2.8 Hz, 1H), 5.78 (s, 1H), 5.39-5.22 (m, 1H), 5.18-5.07 (m, 2H), 4.40-4.21 (m, 6H), 3.24-3.11 (m, 2H), 3.01 (m, 1H), 2.43-2.30 (m, 4H), 2.27-2.07 (m, 4H), 2.05-1.86 (m, 3H), 0.83-0.75 (m, 3H); LCMS [ESI, M+1]: m/z 645.3.

Example 62

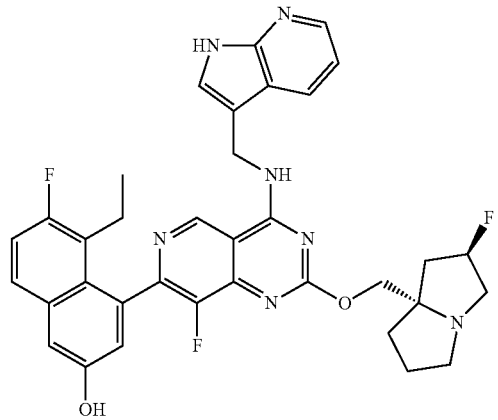 [SMILES: CCc1c(F)ccc2cc(O)cc(-c3ncc4c(NCc5c[nH]c6ncccc56)nc(OC[C@@]56CCCN5C[C@H](F)C6)nc4c3F)c12]

4-(4-(((1H-pyrrolo[2,3-b]pyridin-3-yl)methyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol

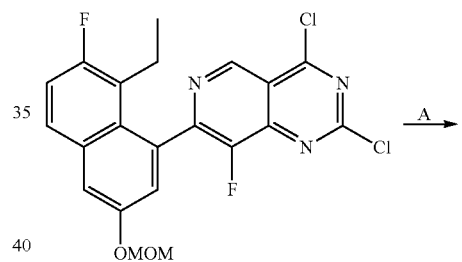

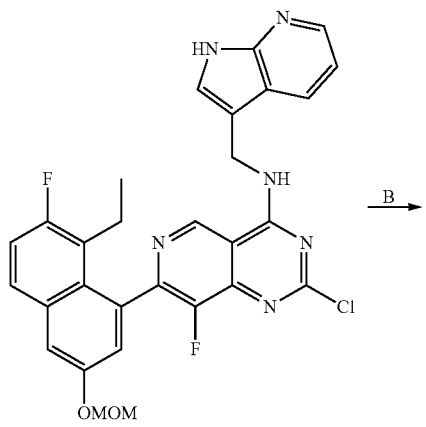

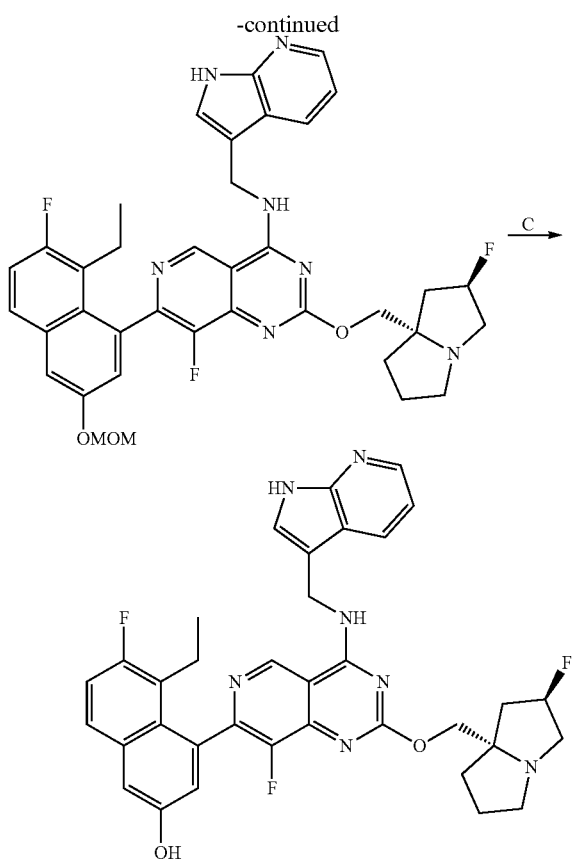

Step A. N-((1H-pyrrolo[2,3-b]pyridin-3-yl)methyl)-2-chloro-7-(8-ethyl-7-fluoro-3-(methoxymethoxy)naphthalen-1-yl)-8-fluoropyrido[4,3-d]pyrimidin-4-amine: To a solution of 2,4-dichloro-7-(8-ethyl-7-fluoro-3-(methoxymethoxy)naphthalen-1-yl)-8-fluoropyrido[4,3-d]pyrimidine (163 mg, 362 μmol) and DIPEA (148 mg, 1.15 mmol) in DCM (2 mL) were added (1H-pyrrolo[2,3-b]pyridin-3-yl)methanamine (44 mg, 200 μmol, 2HCl) and DIPEA (74.2 mg, 574 μmol) in DMF (1.5 mL) dropwise at −40° C. The mixture was stirred at −40° C. for 0.1 h. The reaction mixture was diluted with water (50 mL) and brine (10 mL), and was extracted with ethyl acetate (20 mL×4). The combined organic layers were dried over anhydrous Na$_2$SO$_4$. The mixture was filtered and concentrated under reduced pressure. The residue was purified by reversed phase flash chromatography [water (0.1% formic acid)/acetonitrile=2/3] to afford the product as light yellow solid (100 mg, 57% yield). LCMS (ESI, M+1): m/z 561.1.

Step B. N-((1H-pyrrolo[2,3-b]pyridin-3-yl)methyl)-7-(8-ethyl-7-fluoro-3-(methoxymethoxy)naphthalen-1-yl)-8-fluoro-2-(((2R,7aS)-2-fluorohexahydro-1H-pyrrolizin-7a-yl methoxy)pyrido[4,3-d]pyrimidin-4-amine: A mixture of N-((1H-pyrrolo[2,3-b]pyridin-3-yl) methyl)-2-chloro-7-(8-ethyl-7-fluoro-3-(methoxymethoxy)naphthalen-1-yl)-8-fluoropyrido[4,3-d]pyrimidin-4-amine (150 mg, 267 μmol), ((2R,7aS)-2-fluorohexahydro-1H-pyrrolizin-7a-yl)methanol (128 mg, 804 μmol), DIPEA (104 mg, 804 μmol) and 4 Å molecular sieves (60 mg) in dioxane (2.5 mL) was degassed and purged with N$_2$ for 3 times. The mixture was stirred at 95° C. for 48 hours under N$_2$ atmosphere. The reaction mixture was filtered through a pad of Celite. The filter cake was washed with DCM (10 mL). The combined organic phase was concentrated under reduced pressure, and purified by reversed phase flash chromatography [water (0.1% formic acid)/acetonitrile=1/1] to afford the product as white solid (100 mg, 54% yield). LCMS (ESI, M+1): m/z 684.3.

Step C. 4-(4-(((1H-pyrrolo[2,3-b]pyridin-3-yl)methyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol: To a solution of N-((1H-pyrrolo[2,3-b]pyridin-3-yl)methyl)-7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-amine (100 mg, 146 μmol) in DCM (2 mL) was added TFA (2.5 mL) dropwise at 0° C. The mixture was stirred between 0 and 15° C. for 1.5 hours. The reaction mixture was concentrated under reduced pressure to give a residue at room temperature. The residue was dissolved in DCM (20 mL) and water (5 mL). The pH of the mixture was adjusted to 9 with NaHCO$_3$ solid below 5° C. The mixture was extracted with DCM (10 mL×4). The combined organic layers were dried over anhydrous Na$_2$SO$_4$ and filtered. The mixture was concentrated under reduced pressure. The residue was purified by prep-HPLC (column: water s Xbridge 150×25 mm×Sum; A: [water (10 mM NH$_4$HCO$_3$)]; B: CAN, B %: 40%-70% over 10 minutes) to afford the product as white solid (53.4 mg, 55% yield). HPLC:>99% ee, Chiralcel OJ-3 50×4.6 mm I.D., 3 μm column A: CO$_2$, B: MeOH (w/0.05% DEA), 5% to 40%, 3 mL/min, 220 nm, t$_R$: 2.009 min; $^1$H NMR (400 MHz, DMSO-d$_6$): δ 11.59 (s, 1H), 9.91 (br s, 1H), 9.39-9.29 (m, 2H), 8.23-8.14 (m, 2H), 7.55-7.54 (m, 1H), 7.77-7.73 (m, 1H), 7.39-7.24 (m, 2H), 7.11-6.98 (m, 2H), 5.29 (d, J=53.6 Hz, 1H), 4.94-4.90 (m, 2H), 4.20-4.09 (m, 2H), 3.10-3.08 (m, 2H), 3.08-3.07 (m, 1H), 3.07-3.01 (m, 1H), 2.10-1.78 (m, 8H), 0.73-0.64 (m, 3H); $^{19}$F NMR (376 MHz, DMSO-d$_6$): δ−119, −139, −172; LCMS (ESI, M+1): m/z 640.3.

Example 63

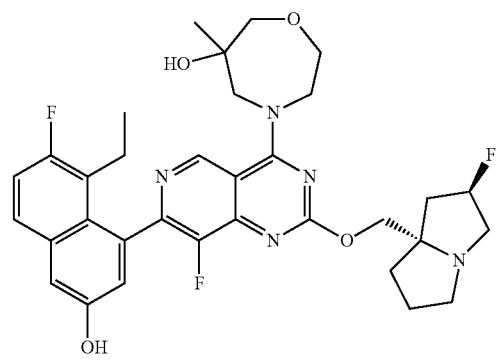 [SMILES: CCc1c(F)ccc2cc(O)cc(-c3ncc4c(N5CCOCC(C)(O)C5)nc(OC[C@@]56CCCN5C[C@H](F)C6)nc4c3F)c12]

4-(7-(8-ethyl-7-fluoro-3-hydroxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol

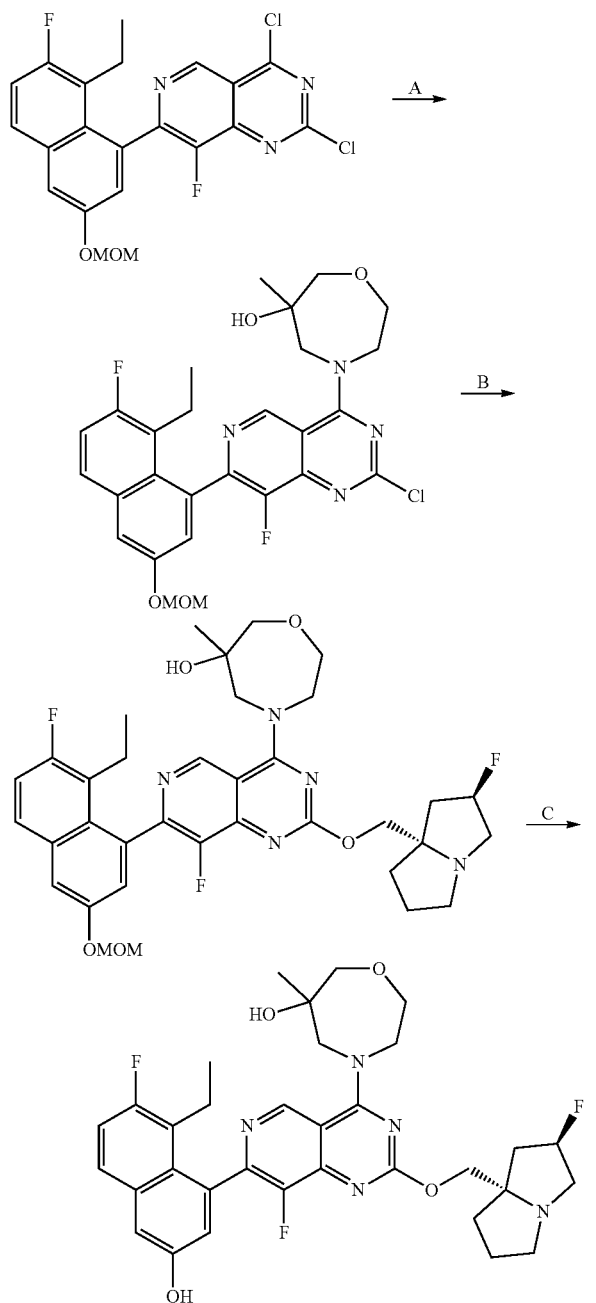

Step A. 4-[2-chloro-7-[8-ethyl-7-fluoro-3-(methoxymethoxy)-1-naphthyl]-8-fluoro-pyrido[4,3-d]pyrimidin-4-yl]-6-methyl-1,4-oxazepan-6-ol: To a mixture of 2,4-dichloro-7-[8-ethyl-7-fluoro-3-(methoxymethoxy)-1-naphthyl]-8-fluoro-pyrido[4,3-d]pyrimidine (189 mg, 420 μmol) and DIEA (217 mg, 1.68 mmol, 292 μL) in dichloromethane (2 mL) was added 6-methyl-1,4-oxazepan-6-ol (49.5 mg, 378 μmol) at −40° C. and the mixture was stirred at −40° C. for 20 mins. After completion, the mixture was quenched by water (8 mL) and filtered. Then the mixture was extracted with dichloromethane (8 mL×2). The combined organic layer was dried over $Na_2SO_4$. The mixture was filtered and concentrated in vacuum. The residue was purified by reversed phase flash chromatography [water (0.1% formic acid)/acetonitrile] to give 4-[2-chloro-7-[8-ethyl-7-fluoro-3-(methoxymethoxy)-1-naphthyl]-8-fluoro-pyrido[4,3-d]pyrimidin-4-yl]-6-methyl-1,4-oxazepan-6-ol (103 mg, 44% yield). Yellow solid. LCMS (ESI, M+1): m/z 545.2.

Step B. 4-(7-(8-ethyl-7-fluoro-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol: A mixture of 4-[2-chloro-7-[8-ethyl-7-fluoro-3-(methoxymethoxy)-1-naphthyl]-8-fluoro-pyrido[4,3-d]pyrimidin-4-yl]-6-methyl-1,4-oxazepan-6-ol (103 mg, 189 μmol), ((2R,7aS)-2-fluorotetrahydro-1H-pyrrolizin-7a(5H)-yl)methanol (90.3 mg, 567 μmol), DIEA (73.3 mg, 567 μmol, 98.8 μL) and 4 Å molecular sieves (10 mg) in dioxane (1 mL) was stirred at 90° C. for 21 h. After completion, the mixture was filtered and concentrated in vacuum. The residue was purified by reversed phase flash chromatography [water (0.1% formic acid)/acetonitrile] to the title compound (92.0 mg, 73% yield). Yellow solid. LCMS (ESI, M+1): m/z 668.3.

Step C. 4-(7-(8-ethyl-7-fluoro-3-hydroxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol: To a mixture of 4-(7-(8-ethyl-7-fluoro-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol (84.0 mg, 125.8 μmol) in dichloromethane (0.5 mL) was added TFA (770 mg, 6.75 mmol, 0.5 mL) at 0° C. and the mixture was stirred at 25° C. for 0.5 h. After completion, the mixture was concentrated in vacuum. The pH value was adjusted to 9 with saturated $NaHCO_3$ solution and the mixture was extracted with ethyl acetate twice. The combined organic layer was dried over $Na_2SO_4$ and filtered. The residue was concentrated in vacuum. The residue was purified by prep-HPLC (Shim-pack C18 150*25*10 um; mobile phase: [water (0.225% formic acid)-ACN]; B %: 19%-39%, 10 min) to afford the title compound (26.9 mg, 33% yield, 0.2 formic acid salt). White solid. $^1$H NMR (400 MHz, METHANOL-d4): δ 9.61-9.56 (m, 1H), 7.68 (dd, J=5.6, 8.8 Hz, 1H), 7.33-7.30 (m, 1H), 7.25 (t, J=9.2 Hz, 1H), 7.06 (dd, J=2.4, 13.6 Hz, 1H), 5.54-5.37 (m, 1H), 4.63-4.44 (m, 5H), 4.25-4.14 (m, 1H), 4.07-3.85 (m, 3H), 3.74-3.66 (m, 2H), 3.65-3.56 (m, 2H), 3.29-3.23 (m, 1H), 2.60-2.37 (m, 3H), 2.33-2.03 (m, 5H), 1.28 (d, J=2.4 Hz, 3H), 0.84-0.76 (m, 3H). LCMS (ESI, M+1): m/z 624.3.

Example 64

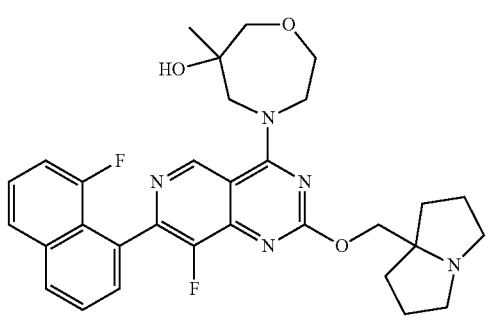 [SMILES: CC1(O)COCCN(c2nc(OCC34CCCN3CCC4)nc3c(F)c(-c4cccc5cccc(F)c45)ncc23)C1]

227

4-(8-fluoro-7-(8-fluoronaphthalen-1-yl)-2-((hexa-
hydro-1H-pyrrolizin-7a-yl)methoxy)pyrido[4,3-d]
pyrimidin-4-yl)-6-methyl-1,4-oxazepan-6-ol

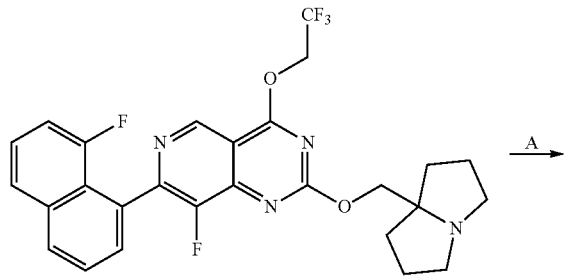

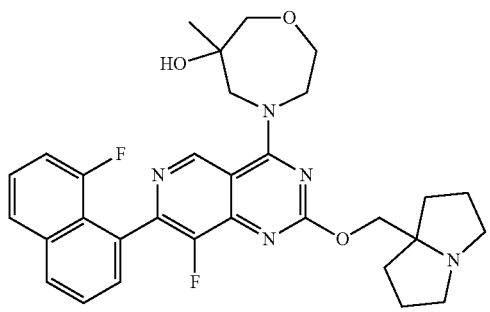

228

Example 65

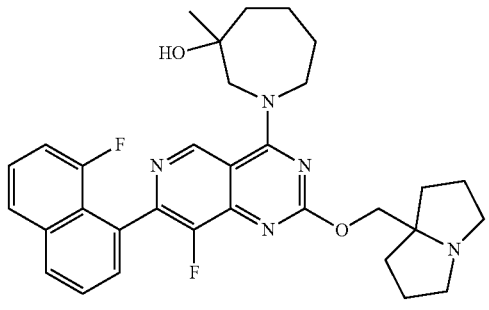 [SMILES: CC1(O)CCCCN(c2nc(OCC34CCCN3CCC4)nc3c(F)c(-c4cccc5cccc(F)c45)ncc23)C1]

1-(8-fluoro-7-(8-fluoronaphthalen-1-yl)-2-((hexa-
hydro-1H-pyrrolizin-7a-yl)methoxy)pyrido[4,3-d]
pyrimidin-4-yl)-3-methylazepan-3-ol

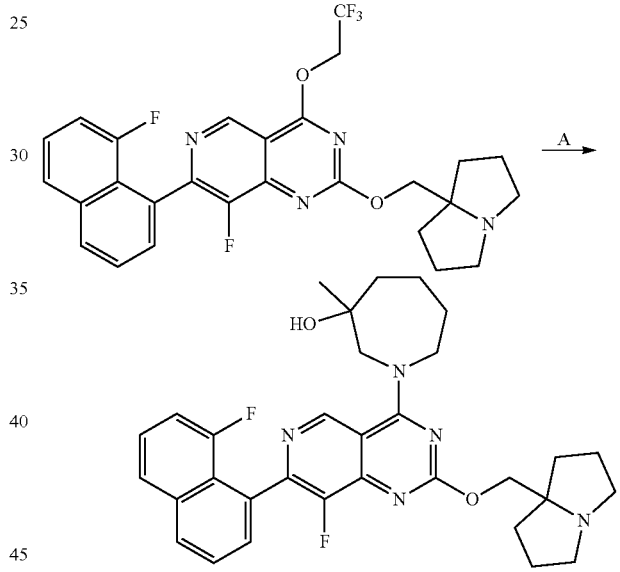

Step A. 4-(8-fluoro-7-(8-fluoronaphthalen-1-yl)-2-((hexahydro-1H-pyrrolizin-7a-yl) methoxy)pyrido[4,3-d]pyrimidin-4-yl)-6-methyl-1,4-oxazepan-6-ol: To the mixture of 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d]pyrimidine (30 mg, 56 µmol), 6-methyl-1,4-oxazepan-6-ol (15 mg, 113 µmol) and 4 Å molecular sieves (5.0 mg) in DMF (0.5 mL) was added DIEA (22 mg, 169 mmol). The mixture was stirred at 40° C. for 12 hours. After completion, the reaction mixture was filtered and purified by prep-HPLC (column: Phenomenex luna C18 150×25 mm×10 µm; mobile phase: [water (0.225% formic acid)-ACN]; B %: 15%-45%, 10 min) and (column: Phenomenex Gemini-NX C18 75×30 mm×3 µm; mobile phase: [water (10 mM NH$_4$HCO$_3$)-ACN]; B %: 25%-55%, 8 min) to afford 4-(8-fluoro-7-(8-fluoronaphthalen-1-yl)-2-((hexahydro-1H-pyrrolizin-7a-yl) methoxy)pyrido[4,3-d]pyrimidin-4-yl)-6-methyl-1,4-oxazepan-6-ol (3.93 mg, 12% yield). Yellow solid; 1H NMR (400 MHz, CHLOROFORM-d): δ 9.29 (d, J=2.4 Hz, 1H), 8.04-8.00 (m, 1H), 7.76 (d, J=8.0 Hz, 1H), 7.67-7.44 (m, 3H), 7.14 (br dd, J=7.6, 12.8 Hz, 1H), 5.64-5.21 (m, 1H), 4.73-4.61 (m, 1H), 4.56-4.43 (m, 1H), 4.39-4.22 (m, 2H), 4.05-3.80 (m, 3H), 3.76-3.52 (m, 3H), 3.26-3.08 (m, 2H), 2.79-2.57 (m, 2H), 2.14-2.01 (m, 2H), 1.93-1.84 (m, 4H), 1.81-1.74 (m, 2H), 1.42-1.34 (m, 3H); LCMS (ESI, M+1): m/z 562.2.

Step A. 1-(8-fluoro-7-(8-fluoronaphthalen-1-yl)-2-((hexahydro-1H-pyrrolizin-7a-yl) methoxy)pyrido[4,3-d]pyrimidin-4-yl)-3-methylazepan-3-ol: 8-fluoro-7-(8-fluoronaphthalen-1-yl)-2-((hexahydro-1H-pyrrolizin-7a-yl) methoxy)-4-(2,2,2-trifluoroethoxy)pyrido[4,3-d]pyrimidine (50.0 mg, 94.3 µmol, 1.0 equiv.), DIEA (60.9 mg, 471 µmol, 82.1 µL, 5.0 equiv.) and 4 Å molecular sieves (5.00 mg) in DMF (1.0 mL) was added 3-methylazepan-3-ol (24.4 mg, 189 µmol, 2.0 equiv.). The mixture was stirred at 40° C. for 12 h. Upon completion, the reaction solution was filtered and purified by prep-HPLC [Phenomenex luna C18 150×25 mm×10 µm; A: water (0.225% formic acid formic acid), B: ACN, B %: 19%-49% over 10 min] to afford 1-(8-fluoro-7-(8-fluoronaphthalen-1-yl)-2-((hexahydro-1H-pyrrolizin-7a-yl)methoxy)pyrido[4,3-d]pyrimidin-4-yl)-3-methylazepan-3-ol (12.6 mg, 15% yield). Off-white solid; 1H NMR (400 MHz, METHANOL-d$_4$) δ 9.45 (br d, J=8.4 Hz, 1H), 8.54 (s, 1H), 8.11 (br d, J=8.4 Hz, 1H), 7.85 (d, J=8.4 Hz, 1H), 7.73-7.65 (m, 1H), 7.65-7.57 (m, 1H), 7.56-7.48 (m, 1H), 7.23-7.14 (m, 1H), 4.57-4.51 (m, 1H), 4.50-4.38 (m, 2H), 4.37-4.24 (m, 1H), 3.98-3.81 (m, 2H), 3.50-3.38 (m, 2H), 3.11-2.97 (m, 2H), 2.29-2.13 (m, 3H), 2.13-1.98 (m, 5H), 1.98-1.88 (m, 3H), 1.87-1.67 (m, 3H), 1.42-1.31 (m, 3H); LCMS (ESI, M+1): m/z 560.2.

Example 66

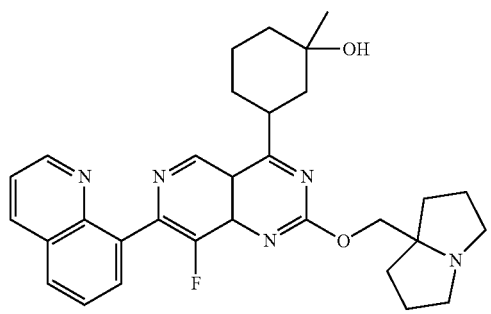 [SMILES: CC1(O)CCCC(C2=NC(OCC34CCCN3CCC4)=NC3C(F)=C(c4cccc5cccnc45)N=CC23)C1]

1-(8-fluoro-2-((hexahydro-1H-pyrrolizin-7a-yl)
methoxy)-7-(quinolin-8-yl)pyrido[4,3-d]pyrimidin-
1-yl)-3-methylpiperidin-3-ol

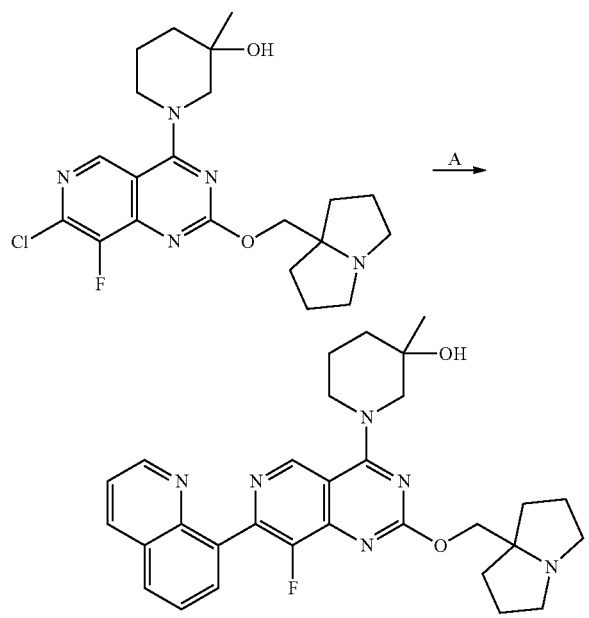

Step A. 1-(8-fluoro-2-((hexahydro-1H-pyrrolizin-7a-yl)methoxy)-7-(quinolin-8-yl) pyrido[4,3-d]pyrimidin-4-yl)-3-methylpiperidin-3-ol: To a mixture of 1-(7-chloro-8-fluoro-2-((hexahydro-1H-pyrrolizin-7a-yl)methoxy)pyrido[4,3-d]pyrimidin-4-yl)-3-methylpiperidin-3-ol (100 mg, 229 µmol), quinolin-8-ylboronic acid (79.4 mg, 459 µmol, 79.4 µL), Na₂CO₃ (72.9 mg, 688 µmol) and tetrabutylammonium bromide (74.0 mg, 229 µmol) in 1,2-dimethoxyethane (3.0 mL), EtOH (3.0 mL) and water (1.0 mL) was added Pd(PPh₃)₄ (53.0 mg, 45.9 µmol, 0.2 equiv.). The mixture was stirred at 80° C. for 12 h. Upon completion, the mixture reaction was diluted water (5.0 mL) and was extracted with EtOAc (3×5.0 mL). The combined organic layer was dried over anhydrous Na₂SO₄. The mixture was filtered and concentrated in vacuum. The reaction was purified by prep-HPLC [Phenomenex Gemini-NX C18 75×30 mm×3 µm; A: water (0.225% formic acid formic acid), B: ACN, B %: 8%-38% over 7 min] to afford 1-(8-fluoro-2-((hexahydro-1H-pyrrolizin-7a-yl)methoxy)-7-(quinolin-8-yl)pyrido[4,3-d]pyrimidin-4-yl)-3-methylpiperidin-3-ol (7.25 mg, 5.8% yield). White solid; ¹H NMR (400 MHz, METHANOL-d4) δ 9.29 (s, 1H), 8.85-8.79 (m, 1H), 8.54 (s, 1H), 8.50-8.45 (m, 1H), 8.15 (d, J=8.0 Hz, 1H), 7.98-7.71 (m, 1H), 7.83-7.76 (m, 1H), 7.63-7.57 (m, 1H), 4.59 (br d, J=12.8 Hz, 3H), 4.34 (br d, J=13.2 Hz, 1H), 3.72-3.62 (m, 1H), 3.52-3.39 (m, 3H), 3.10-2.98 (m, 2H), 2.27-2.19 (m, 2H), 2.16-1.91 (m, 7H), 1.89-1.75 (m, 3H), 1.29 (s, 3H); LCMS (ESI, M+1): m/z 529.3.

Example 67

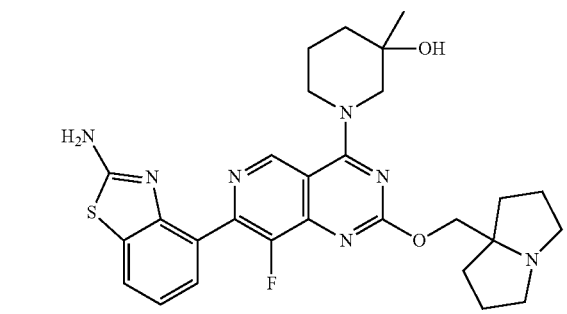 [SMILES: CC1(O)CCCN(c2nc(OCC34CCCN3CCC4)nc3c(F)c(-c4cccc5sc(N)nc45)ncc23)C1]

1-(7-(2-aminobenzo[d]thiazol-4-yl)-8-fluoro-2-
((hexahydro-1H-pyrrolizin-7a-yl) methoxy)pyrido[4,
3-d]pyrimidin-4-yl)-3-methylpiperidin-3-ol

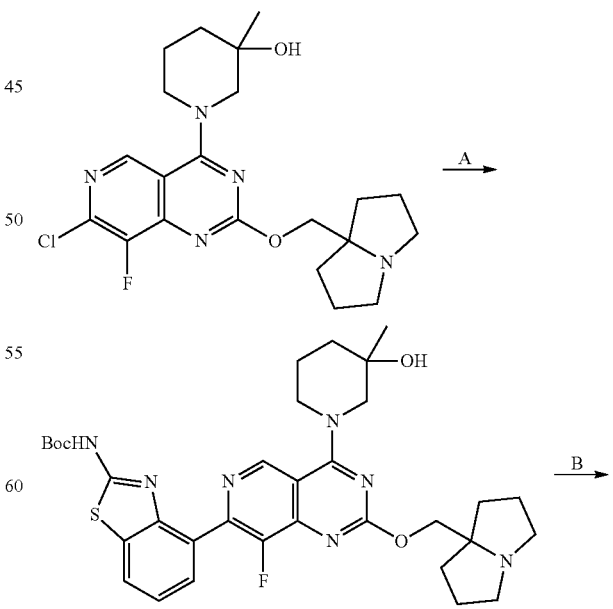

231

-continued

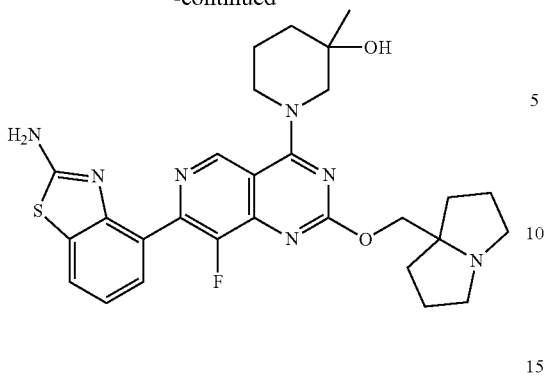

Step A. tert-butyl (4-(8-fluoro-2-((hexahydro-1H-pyrrolizin-7a-yl)methoxy)-4-(3-hydroxy-3-methylpiperidin-1-yl)pyrido[4,3-d]pyrimidin-7-yl)benzo[d]thiazol-2-yl)carbamate: To a mixture of 1-(7-chloro-8-fluoro-2-((hexahydro-1H-pyrrolizin-7a-yl)methoxy)pyrido[4,3-d]pyrimidin-4-yl)-3-methylpiperidin-3-ol (150 mg, 344 µmol), (2-((tert-butoxycarbonyl)amino)benzo[d]thiazol-4-yl)boronic acid (202 mg, 688 µmol) and K₃PO₄ (1.5 M, 688 µL) in THF (2.0 mL) was added BrettPhos Pd G3 (31.2 mg, 34.4 µmol). The mixture was stirred at 60° C. for 16 h. After completion, water (10 mL) was added and the mixture was extracted with EtOAc (2×10 mL). The combined organic layer was dried over Na₂SO₄. The mixture was filtered and concentrated. The residue was purified by reversed phase flash chromatography (C18, water (0.1% formic acid)/ACN) affording tert-butyl (4-(8-fluoro-2-((hexahydro-1H-pyrrolizin-7a-yl)methoxy)-4-(3-hydroxy-3-methylpiperidin-1-yl)pyrido[4,3-d]pyrimidin-7-yl) benzo[d]thiazol-2-yl)carbamate (190 mg, 79% yield). Yellow solid; LCMS (ESI, M+1): m/z 650.3.

Step B. 1-(7-(2-aminobenzo[d]thiazol-4-yl)-8-fluoro-2-((hexahydro-1H-pyrrolizin-7a-yl)methoxy)pyrido[4,3-d]pyrimidin-4-yl)-3-methylpiperidin-3-ol: To a solution of tert-butyl (4-(8-fluoro-2-((hexahydro-1H-pyrrolizin-7a-yl)methoxy)-4-(3-hydroxy-3-methylpiperidin-1-yl)pyrido[4,3-d]pyrimidin-7-yl)benzo[d]thiazol-2-yl)carbamate (90.0 mg, 139 µmol) in dichloromethane (1.0 mL) was added TFA (1.54 g, 13.5 mmol, 1.0 mL). The mixture was stirred at 20° C. for 0.5 h. After completion, the pH of the mixture was adjusted to ~7 with saturated NaHCO₃ aqueous solution. The mixture was extracted with EtOAc (2×10 mL). The combined organic layer was dried over Na₂SO₄. The mixture was filtered and concentrated. The residue was purified by prep-HPLC [Phenomenex luna C18 150×25 mm×10 µm; A: water (0.225% formic acid), B: ACN, B %: 9%-39% over 10 min], followed by prep-HPLC [Water s Xbridge 150×5 mm×5 µm; A: water (10 mM NH₄HCO₃), B: ACN, B %: 20%-50% over 10 min] to afford 1-(7-(2-aminobenzo[d]thiazol-4-yl)-8-fluoro-2-((hexahydro-1H-pyrrolizin-7a-yl)methoxy)pyrido[4,3-d]pyrimidin-4-yl)-3-methylpiperidin-3-ol (9.54 mg, 12% yield). Yellow solid; ¹H NMR (400 MHz, METHANOL-d4) δ 9.26 (s, 1H), 7.77 (dd, J=1.2, 8.0 Hz, 1H), 7.45 (d, J=6.8 Hz, 1H), 7.24 (t, J=8.0 Hz, 1H), 4.66-4.56 (m, 3H), 4.33 (br d, J=13.2 Hz, 1H), 3.76-3.60 (m, 3H), 3.49-3.39 (m, 1H), 3.30-3.24 (m, 2H), 2.39-2.28 (m, 2H), 2.27-2.07 (m, 7H), 1.92-1.73 (m, 3H), 1.29 (s, 3H); LCMS (ESI, M+1): m/z 550.1.

232

Example 68

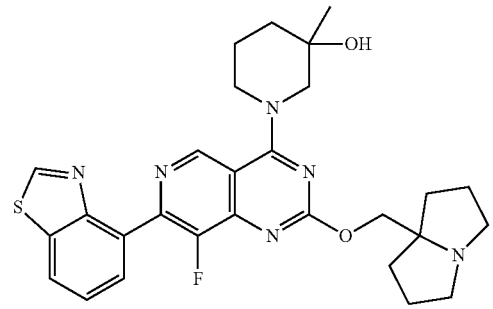 [SMILES: CC1(O)CCCN(c2nc(OCC34CCCN3CCC4)nc3c(F)c(-c4cccc5scnc45)ncc23)C1]

1-(7-(benzo[d]thiazol-4-yl)-8-fluoro-2-((hexahydro-1H-pyrrolizin-7a-yl)methoxy)pyrido[4,3-d]pyrimidin-4-yl)-3-methylpiperidin-3-ol

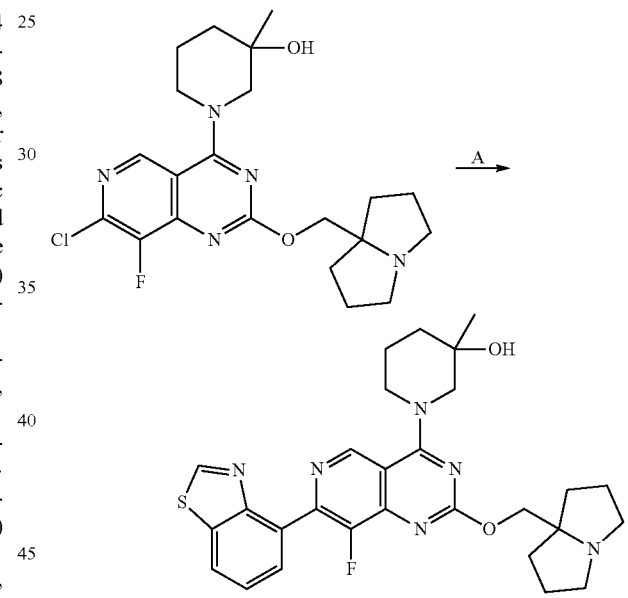

Step A. 1-(7-(benzo[d]thiazol-4-yl)-8-fluoro-2-((hexahydro-1H-pyrrolizin-7a-yl) methoxy)pyrido[4,3-d]pyrimidin-4-yl)-3-methylpiperidin-3-ol: A mixture of 1-(7-chloro-8-fluoro-2-((hexahydro-1H-pyrrolizin-7a-yl)methoxy) pyrido[4,3-d]pyrimidin-4-yl)-3-methylpiperidin-3-ol (100 mg, 229 µmol), benzo[d]thiazol-4-ylboronic acid (53.4 mg, 298 µmol), K₃PO₄ (1.5 M, 0.5 mL) and [2-(2-aminophenyl) phenyl]palladium(1+); bis (1-adamantyl)-butyl-phosphane; methanesulfonate (25.1 mg, 34.4 µmol) in THF (2.00 mL) was degassed and purged with N₂ for 3 times, and then the mixture was stirred at 60° C. for 10 hours under N₂ atmosphere. Upon completion, the reaction mixture was diluted with water (10 mL) and extracted with ethyl acetate (3×10 mL). The combined organic layers were washed with brine (50 mL) and dried over Na₂SO₄. The mixture was filtered and concentrated under reduced pressure to give a residue. The residue was purified by prep-HPLC (column: Phenomenex luna C18 150×25 mm×10 µm; mobile phase: [water (0.225% formic acid formic acid)-ACN]; B %: 11%-

41%, 10 min) to give 1-(7-(benzo[d]thiazol-4-yl)-8-fluoro-2-((hexahydro-1H-pyrrolizin-7a-yl)methoxy)pyrido[4,3-d]pyrimidin-4-yl)-3-methylpiperidin-3-ol (52.32 mg, 42% yield). Yellow solid; ¹H NMR (400 MHz, METHANOL-d4) δ 9.36-9.25 (m, 2H), 8.53 (s, 1H), 8.27 (dd, J=0.8 Hz, 8.0 Hz, 1H), 7.79 (dd, J=0.8 Hz, 7.2 Hz, 1H), 7.69 (t, J=8.0 Hz, 1H), 4.67-4.59 (m, 3H), 4.40-4.30 (m, 1H), 3.72-3.62 (m, 3H), 3.48-3.39 (m, 1H), 3.30-3.20 (m, 2H), 2.36-2.28 (m, 2H), 2.27-2.05 (m, 7H), 1.90-1.74 (m, 3H), 1.29 (s, 3H); LCMS (ESI, M+1): m/z 535.3.

Example 69

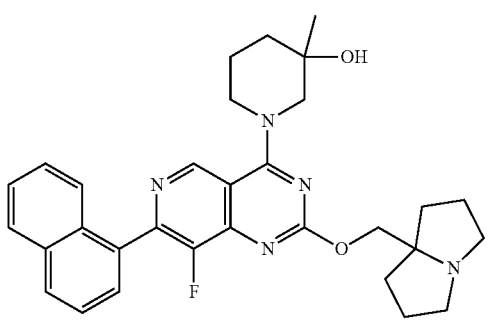 [SMILES: CC1(O)CCCN(c2nc(OCC34CCCN3CCC4)nc3c(F)c(-c4cccc5ccccc45)ncc23)C1]

1-(8-fluoro-2-((hexahydro-1H-pyrrolizin-7a-yl)methoxy)-7-(naphthalen-1-yl)pyrido[4,3-d]pyrimidin-4-yl)-3-methylpiperidin-3-ol

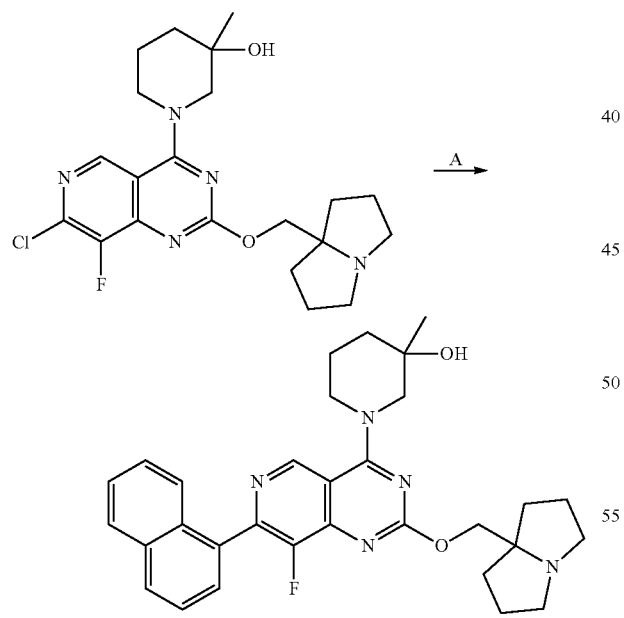

Step A. 1-(8-fluoro-2-((hexahydro-1H-pyrrolizin-7a-yl)methoxy)-7-(naphthalen-1-yl)pyrido[4,3-d]pyrimidin-4-yl)-3-methylpiperidin-3-ol: 1-(7-chloro-8-fluoro-2-((hexahydro-1H-pyrrolizin-7a-yl)methoxy)pyrido[4,3-d]pyrimidin-4-yl)-3-methylpiperidin-3-ol (50.0 mg, 115 μmo), naphthalen-1-ylboronic acid (39.5 mg, 229 μmol) and K₃PO₄ (1.50 M in water, 229 μL) in THF (1.0 mL) was added cataCXium-A-Pd-G3 (8.35 mg, 11.5 μmol). The mixture was stirred at 60° C. for 12 h. Upon completion, the reaction mixture was diluted water (2.0 mL) and was extracted with EtOAc (3×2 mL). The combined organic layer was dried over Na₂SO₄. The mixture was filtered and concentrated in vacuum. The residue was purified by prep-HPLC [Phenomenex luna C18 150×25 mm×10 μm; A: water (0.225% formic acid formic acid), B: ACN, B %: 17/6-47% over 10 min] to afford 1-(8-fluoro-2-((hexahydro-1H-pyrrolizin-7a-yl)methoxy)-7-(naphthalen-1-yl)pyrido[4,3-d]pyrimidin-4-yl)-3-methylpiperidin-3-ol (14.9 mg, 24% yield). Yellow solid; ¹H NMR (400 MHz, METHANOL-d4) δ 9.34 (s, 1H), 8.52 (s, 1H), 8.09-8.04 (m, 1H), 8.01 (d, J=8.4 Hz, 1H), 7.70 (br d, J=8.8 Hz, 1H), 7.67-7.62 (m, 2H), 7.59-7.53 (m, 1H), 7.52-7.46 (m, 1H), 4.61-4.55 (m, 4H), 4.40-4.34 (m, 1H), 3.72-3.62 (m, 3H), 3.50-3.39 (m, 1H), 3.28-3.22 (m, 1H), 2.38-2.28 (m, 2H), 2.27-2.04 (m, 7H), 1.92-1.74 (m, 3H), 1.30 (s, 3H); LCMS (ESI, M+1): m/z 528.3.

Example 70

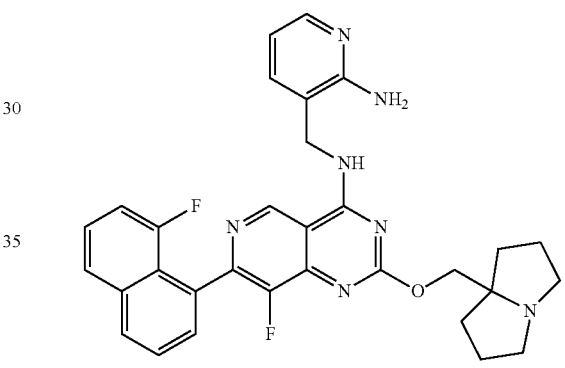

N-((2-aminopyridin-3-yl)methyl)-8-fluoro-7-(8-fluoronaphthalen-1-yl)-2-((hexahydro-1H-pyrrolizin-7a-yl)methoxy)pyrido[4,3-d]pyrimidin-4-amine

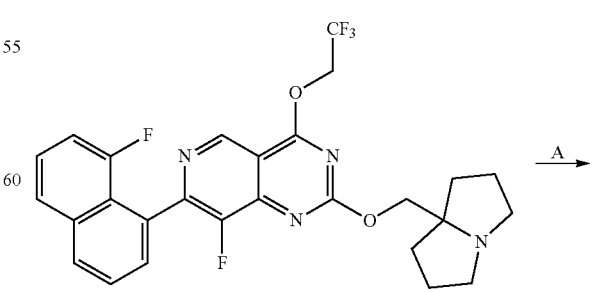

235
-continued

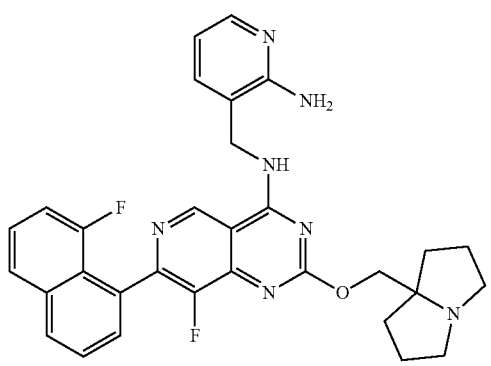 [SMILES: Nc1ncccc1CNc1nc(OCC23CCCN2CCC3)nc2c(F)c(-c3cccc4cccc(F)c34)ncc12]

Step A. N-((2-aminopyridin-3-yl)methyl)-8-fluoro-7-(8-fluoronaphthalen-1-yl)-2-((hexahydro-1H-pyrrolizin-7a-yl)methoxy)pyrido[4,3-d]pyrimidin-4-amine: To a solution of 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d]pyrimidine (30 mg, 56.55 μmol) and 3-(aminomethyl)pyridin-2-amine (34.8 mg, 283 μmol) in DMF (3 mL) were added DIPEA (21.9 mg, 170 μmol) and 4 Å molecular sieves (50 mg). The mixture was stirred at 40° C. for 12 hours. The mixture was filtered and purified by prep-HPLC (column: Unisil 3-100 C18 Ultra 150×50 mm×3 μm; mobile phase: [water (0.225% formic acid)-ACN]; B %: 15%-35%, 10 min) to give N-((2-aminopyridin-3-yl) methyl)-8-fluoro-7-(8-fluoronaphthalen-1-yl)-2-((hexahydro-1H-pyrrolizin-7a-yl) methoxy)pyrido[4,3-d]pyrimidin-4-amine (11.1 mg, 35% yield, 2 FORMIC ACID) as white solid. $^1$H NMR (400 MHz, DMSO-d$_6$): δ 9.57-9.26 (m, 2H), 8.30 (br s, 2H), 8.19 (br d, J=8.4 Hz, 1H), 7.98-7.85 (m, 2H), 7.80-7.69 (m, 1H), 7.65-7.52 (m, 2H), 7.47-7.36 (m, 1H), 7.35-7.22 (m, 1H), 6.56 (dd, J=5.0, 7.2 Hz, 1H), 6.06-5.88 (m, 2H), 4.65-4.55 (m, 2H), 4.16-4.02 (m, 3H), 3.02-2.87 (m, 3H), 1.97-1.66 (m, 7H), 1.64-1.49 (m, 2H); LCMS (ESI, M+1): m/z 554.2.

Example 71

236

1-(7-(3-chloro-2-cyclopropyl-5-hydroxyphenyl)-8-fluoro-2-(((tetrahydro-1H-pyrrolizin-7a(5H)-yl)methoxy)pyrido[4,3-d]pyrimidin-4-yl)-3-methylpiperidin-3-ol

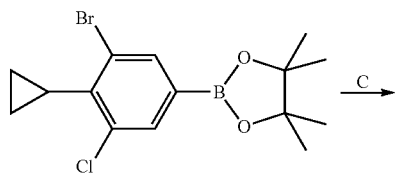

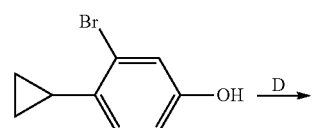

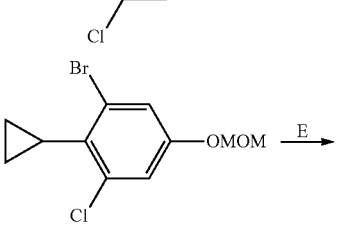

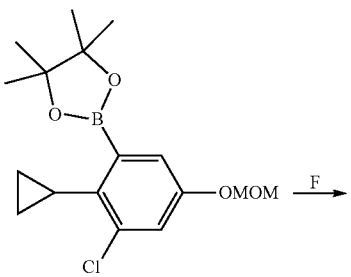

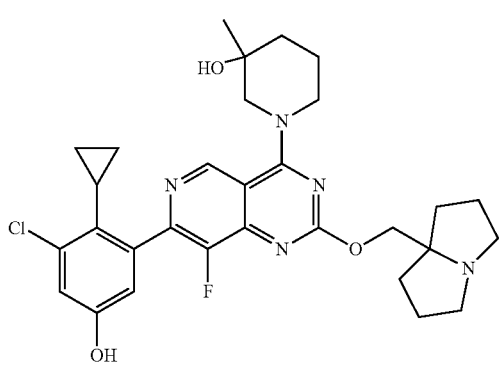 [SMILES: CC1(O)CCCN(c2nc(OCC34CCCN3CCC4)nc3c(F)c(-c4cc(O)cc(Cl)c4C4CC4)ncc23)C1]

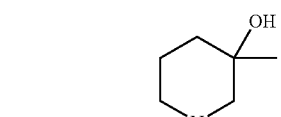

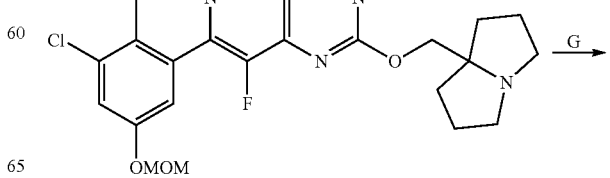

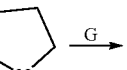

-continued

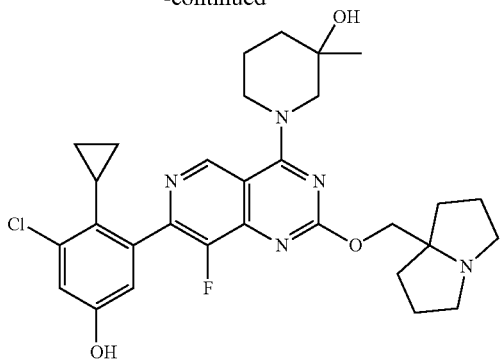

Step A. 1-bromo-3-chloro-2-cyclopropyl-benzene: A mixture of cyclopropylboronic acid (1.62 g, 18.91 mmol), 1-bromo-3-chloro-2-iodo-benzene (2 g, 6.30 mmol), $K_3PO_4$ (4.82 g, 22.7 mmol), and Pd(dppf)Cl$_2$ (461 mg, 630 μmol) in 1,4-dioxane (12 mL) and water (3 mL) was degassed and purged with $N_2$ for 3 times. The mixture was stirred at 100° C. for 7 hours under $N_2$ atmosphere. Upon completion, the reaction mixture was extracted with ethyl acetate (10 mL×2). The combined organic layers were washed with brine 15 mL and dried over $Na_2SO_4$. The mixture was filtered and concentrated under reduced pressure to give a residue. The residue was purified by column chromatography (Silica gel, Petroleum ether/Ethyl acetate=I/O) to give 1-bromo-3-chloro-2-cyclopropyl-benzene as a colorless liquid (1.6 g, 88% yield); $^1$H NMR (400 MHz, CDCl$_3$) δ=7.38 (d, J=8.0 Hz, 1H), 7.22 (d, J=8.0 Hz, 1H), 6.91 (t, J=8.0 Hz, 1H), 2.31 (tt, J=5.4, 8.5 Hz, 1H), 1.69 (tt, J=5.8, 8.4 Hz, 1H), 1.29-1.16 (m, 1H), 1.15-1.06 (m, 3H), 0.84-0.74 (m, 2H), 0.74-0.66 (m, 3H).

Step B. 2-(3-bromo-5-chloro-4-cyclopropyl-phenyl-4,4,5,5-tetramethyl-1,3,2-dioxaborolane: A mixture of 4,4,5,5-tetramethyl-1,3,2-dioxaborolane (995 mg, 7.77 mmol, 1.13 mL), 1-bromo-3-chloro-2-cyclopropyl-benzene (600 mg, 2.59 mmol), [Ir(OMe)(COD)]2 (172 mg, 259 μmol) and 4-tert-butyl-2-(4-tert-butyl-2-pyridyl)pyridine (83.5 mg, 311 μmol) in hexane (10 mL) was degassed and purged with $N_2$ for 3 times. The reaction mixture was stirred at 60° C. for 3 hours under $N_2$ atmosphere. The reaction mixture was concentrated under reduced pressure to remove solvent. The residue was purified by column chromatography (Silica gel, Petroleum ether/Ethyl acetate=50/1) to give 2-(3-bromo-5-chloro-4-cyclopropyl-phenyl)-4,4,5,5-tetramethyl-1,3,2-dioxaborolane (782 mg, 84% yield) as a colorless oil; $^1$H NMR (400 MHz, CDCl$_3$) δ=7.79 (s, 1H), 7.63 (s, 1H), 1.71 (tt, J=5.8, 8.5 Hz, 1H), 1.26 (s, 12H), 1.15-1.09 (m, 2H), 0.72-0.68 (m, 2H).

Step C. 3-bromo-5-chloro-4-cyclopropyl-phenol: To a solution of 2-(3-bromo-5-chloro-4-cyclopropyl-phenyl)-4,4,5,5-tetramethyl-1,3,2-dioxaborolane (1.12 g, 3.13 mmol) in water (4 mL) and THF (8 mL) were added AcOH (12.1 g, 200 mmol, 11.5 mL) and water 2 (2.05 g, 18.1 mmol, 1.74 mL, 30% purity). The mixture was stirred at 0° C. for 1 hour. The reaction mixture was quenched with $Na_2S_2O_3$ (10% aq, 40 mL) at 0° C. The mixture was extracted with ethyl acetate 60 mL (30 mL×2). The combined organic layers were washed with brine 100 mL and dried over $Na_2SO_4$. The mixture was filtered and concentrated under reduced pressure to give a residue. The residue was purified by column chromatography (Silica gel, Petroleum ether/Ethyl acetate-10/1) to give 3-bromo-5-chloro-4-cyclopropyl-phenol as a colorless oil (700 mg, 90% yield); $^1$H NMR (400 MHz, CDCl$_3$) δ=6.93 (d, J=2.6 Hz, 1H), 6.77 (d, J=2.6 Hz, 1H), 5.73-5.49 (m, 1H), 1.64-1.55 (m, 1H), 1.08-1.00 (m, 2H), 0.67-0.60 (m, 2H).

Step D. 1-bromo-3-chloro-2-cyclopropyl-5-(methoxymethoxy)benzene: To a solution of chloro(methoxy)methane (1.62 g, 20.12 mmol, 1.53 mL), 3-bromo-5-chloro-4-cyclopropyl-phenol (1.2 g, 4.85 mmol) and DIEA (1.88 g, 14.5 mmol, 2.53 mL) in DCM (15 mL) was added chloro(methoxy)methane (1.62 g, 20.1 mmol, 1.53 mL) at 0° C. The reaction mixture was stirred at 25° C. for 2 hours. The reaction mixture was quenched with water (10 mL) at 0° C. The mixture was extracted with EtOAc (10 mL×3). The combined organic layers were washed with brine (30 mL) and dried over $Na_2SO_4$. The mixture was filtered and concentrated under reduced pressure to give a residue. The residue was purified by column chromatography (Silica gel, Petroleum ether/Ethyl acetate=30/1) to give 1-bromo-3-chloro-2-cyclopropyl-5-(methoxymethoxy)benzene as a colorless oil (923 mg, 65% yield); $^1$H NMR (400 MHz, CDCl$_3$) δ=7.20 (d, J=2.6 Hz, 1H), 7.04 (d, J=2.5 Hz, 1H), 5.12 (s, 2H), 3.47 (s, 3H), 1.70 (tt, J=5.7, 8.4 Hz, 1H), 1.17-1.11 (m. 2H), 0.76-0.69 (m, 2H).

Step E. 2-[3-chloro-2-cyclopropyl-5-(methoxymethoxy)phenyl]-4,4,5,5-tetramethyl-1,3,2-dioxaborolane: To a mixture of 1-bromo-3-chloro-2-cyclopropyl-5-(methoxymethoxy)benzene (300 mg, 1.03 mmol), KOAc (303 mg, 3.09 mmol) and 4,4,5,5-tetramethyl-2-(4,5,5-trimethyl-4-methyl-1,3,2-dioxaborolan-2-yl)-1,3,2-dioxaborolane (521 mg, 2.06 mmol) in dioxane (4.5 mL) was added Pd(dppf)Cl$_2$ (75.37 mg, 103 μmol). The mixture was stirred at 100° C. for 1 hour. Upon completion, to the reaction mixture was added water (5 mL) and the mixture was extracted with ethyl acetate 15 mL (3×5 mL). The organic layer was dried over by anhydrous $Na_2SO_4$, filtered and concentrated. The residue was purified by prep-TLC (Silica gel, Petroleum ether/Ethyl acetate=15:1) to give 2-[3-chloro-2-cyclopropyl-5-(methoxymethoxy)phenyl]-4,4,5,5-tetramethyl-1,3,2-dioxaborolane as a colorless oil (135 mg, 39% yield); $^1$H NMR (400 MHz, CDCl$_3$) d=7.11-7.08 (m, 2H), 5.14 (s, 2H), 3.46 (s, 3H), 1.98 (tt, J=5.6, 8.5 Hz, 1H), 1.38 (s, 12H), 1.01-0.95 (m, 2H), 0.55-0.50 (m, 2H).

Step F. 1-(7-(3-chloro-2-cyclopropyl-5-(methoxymethoxy)phenyl)-8-fluoro-2-((tetrahydro-1H-pyrrolizin-7a(5H)-yl)methoxy)pyrido[4,3-d]pyrimidin-4-yl)-3-methylpiperidin-3-ol: To a mixture of 2-[3-chloro-2-cyclopropyl-5-(methoxymethoxy)phenyl]-4,4,5,5-tetramethyl-1,3,2-dioxaborolane (77.7 mg, 229 μmol), 1-(7-chloro-8-fluoro-2-((hexahydro-1H-pyrrolizin-7a-yl)methoxy)pyrido[4,3-d]pyrimidin-4-yl)-3-methylpiperidin-3-ol (50 mg, 115 μmol) and $K_3PO_4$ (1.5 M in water, 229.40 μL) in THF (0.5 mL) was added cataCXium-A-Pd-G3 (8.35 mg, 11.5 μmol). The mixture was degassed and purged with $N_2$ for 3 times. The mixture was stirred at 60° C. for 2.5 hours. The reaction mixture was diluted with water (5 mL) and the mixture was extracted with ethyl acetate (3×5 mL). The organic layer was dried over $Na_2SO_4$, filtered and concentrated. The residue was purified by prep-TLC (Silica gel, DCM:MeOH=10:1) to give the title compound as a brown oil (43 mg, 61% yield); $^1$H NMR (400 MHz, CDCl$_3$) δ=9.15-9.13 (m, 1H), 7.20 (d, J=2.5 Hz, 1H), 7.08-7.06 (m, 1H), 5.19-5.16 (m, 2H), 4.46-4.39 (m, 2H), 4.39-4.34 (m, 3H), 3.55-3.50 (m, 1H), 3.49 (s, 2H), 3.47 (s, 3H), 3.40 (d, J=13.5 Hz, 1H), 3.30 (br d, J=6.6 Hz, 2H), 2.72 (td, J=6.8, 10.4 Hz, 2H), 2.21-2.11 (m, 3H), 1.97-1.91 (m, 6H), 1.79-1.71 (m, 4H), 1.70-1.64 (m, 1H), 0.67 (br s, 2H), 0.19-0.06 (m, 2H).

Step G. 1-(7-(3-chloro-2-cyclopropyl-5-hydroxyphenyl)-8-fluoro-2-((tetrahydro-1H-pyrrolizin-7a(5H)-yl)methoxy)pyrido[4,3-d]pyrimidin-4-yl)-3-methylpiperidin-3-ol: To a solution of 1-(7-(3-chloro-2-cyclopropyl-5-(methoxymethoxy)phenyl)-8-fluoro-2-((tetrahydro-1H-pyrrolizin-7a(5H)-yl)methoxy)pyrido[4,3-d]pyrimidin-4-yl)-3-methylpiperidin-3-ol (40 mg, 65.3 μmol) in MeCN (0.8 mL) was added HCV/EtOAc (4 M, 1.8 mL). The mixture was stirred at 20° C. for 0.5 hour. After completion, the mixture was concentrated to give a residue. The residue was purified by prep-HPLC (FA condition, column: Phenomenex luna C18 150×25 mm×10 μm; mobile phase: [water (0.225% formic acid formic acid)-ACN]; B %: 16%-46%, 11 min) to give the title compound (19.68 mg, 48% yield, FA salt); $^1$H NMR (400 MHz, METHANOL-d4) δ=9.26 (s, 1H), 8.53 (br s, 1H), 6.98 (d, J=2.5 Hz, 1H), 6.80 (d, J=2.6 Hz, H), 4.61 (s, 2H), 4.58 (br s, 1H), 4.33 (br d, J=13.5 Hz, 1H), 3.68-3.59 (m, 3H), 3.43 (br t, J=11.0 Hz, 1H), 3.27-3.20 (m, 2H), 2.35-2.26 (m, 2H), 2.25-2.02 (m, 8H), 1.91-1.75 (m, 4H), 1.32-1.28 (m, 3H), 0.71-0.56 (m, 2H), 0.15-0.00 (m, 2H). LCMS (ESI, M+1): m/z 568.4.

Example 72

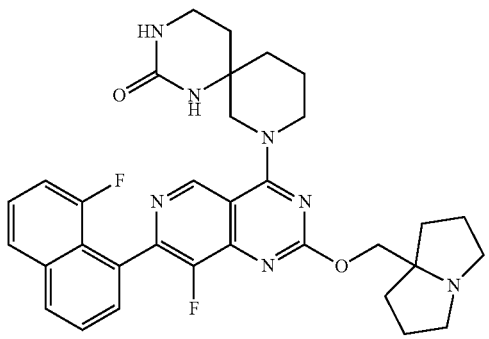 [SMILES: O=C1NCCC2(CCCN(c3nc(OCC45CCCN4CCC5)nc4c(F)c(-c5cccc6cccc(F)c56)ncc34)C2)N1]

8-(8-fluoro-7-(8-fluoronaphthalen-1-yl)-2-((tetrahydro-1H-pyrrolizin-7a(5H)-yl) methoxy)pyrido[4,3-d]pyrimidin-4-yl)-1,3,8-triazaspiro[5.5]undecan-2-one

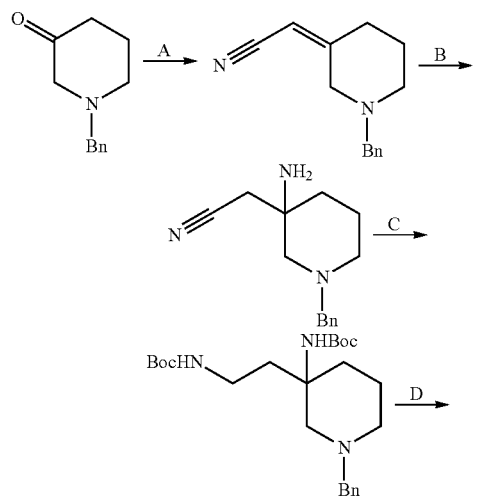

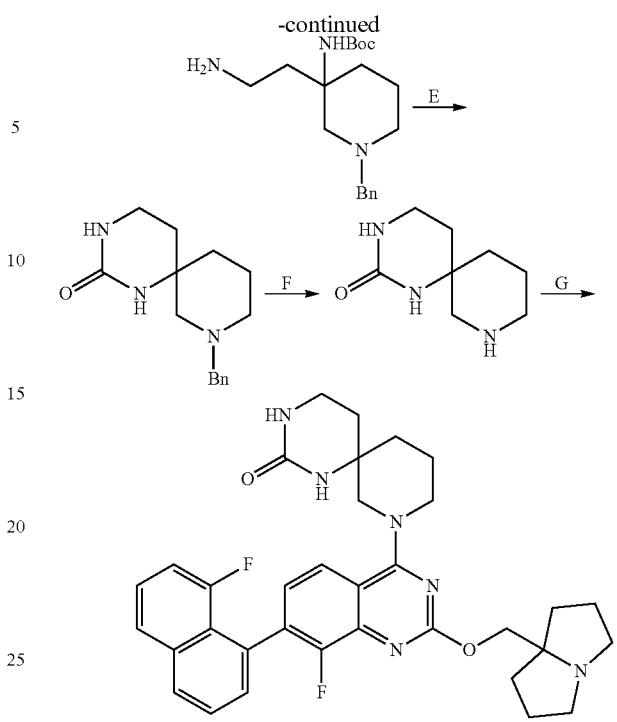

Step A. 2-(1-benzylpiperidin-3-ylidene)acetonitrile: A mixture of 2-diethoxyphosphorylacetonitrile (9.27 g, 52.3 mmol, 8.42 mL), K$_2$CO$_3$ (8.89 g, 64.3 mmol) in THF (25 mL) was stirred for 10 min at 25° C. and 20 min at 70° C. under N$_2$ atmosphere. The reaction mixture was cooled to 25° C. A mixture of 1-benzylpiperidin-3-one (10 g, 52.84 mmol) and K$_2$CO$_3$ (7.30 g, 52.84 mmol) in THF (25 mL) was added into the mixture and the reaction was stirred at 70° C. for further 18 hours. The mixture was diluted with water (350 mL) and extracted with ethyl acetate (200 mL×2). The combined organic layers were dried over Na$_2$SO$_4$ and concentrated to give a residue. The residue was purified by column chromatography (Silica gel, Petroleum ether/Ethyl acetate=10/1 to 4/1) to give 2-(1-benzyl-3-piperidylidene)acetonitrile (7.8 g, crude) as a yellow oil. $^1$H NMR (400 MHz, CDCl$_3$) δ=7.27 (br s, 5H), 5.17-5.01 (m, 1H), 4.09 (dq, J=1.5, 7.1 Hz, 1H), 3.65-3.47 (m, 2H), 2.96 (s, 2H), 2.64-2.39 (m, 4H), 2.07-1.95 (m, 1H), 1.84-1.58 (m, 2H). LCMS (ESI, M+1): m/z 213.2.

Step B. 2-(3-amino-1-benzyl-3-piperidyl)acetonitrile: To a mixture of 2-(1-benzyl-3-piperidylidene)acetonitrile (4 g, 18.8 mmol) in MeOH (6 mL) was added ammonium; hydroxide (39.6 g, 339 mmol, 43.5 mL, 30% purity). The mixture was heated to 80° C. and stirred for 18 hours in a sealed tube. The reaction mixture was concentrated under reduced pressure to give 2-(3-amino-1-benzyl-3-piperidyl)acetonitrile (3.5 g, crude) as a yellow oil. $^1$H NMR (400 MHz, CDCl$_3$) δ=7.31-7.09 (m, 5H), 3.50-3.33 (m, 2H), 2.58-2.11 (m, 8H), 1.76-1.29 (m, 4H). LCMS (ESI, M+1): m/z 230.1.

Step C. tert-butyl N-[1-benzyl-3-[2-(tert-butoxycarbonylamino)ethyl]-3-piperidyl]carbamate: To a mixture of 2-(3-amino-1-benzyl-3-piperidyl)acetonitrile (4.0 g, 17.4 mmol), tert-butoxycarbonyl tert-butyl carbonate (15.2 g, 69.8 mmol, 16.0 mL) and NiCl$_2$.6 WATER (2.07 g, 8.72 mmol) in MeOH (40 mL) was added NaBH$_4$ (3.35 g, 88.5 mmol) at 0° C. in portions. The reaction mixture was stirred at 27° C. for 3 hours under N$_2$ atmosphere. The mixture was quenched with saturated NH₄Cl solution at 25° C. and diluted with brine (80 mL). The mixture was extracted with ethyl acetate (80 mL×3). The combined organic layers were dried over Na₂SO₄, then filtered and concentrated to give a residue. The residue was purified by column chromatography (Silica gel, Petroleum ether/Ethyl acetate=0 to 20/1) to give tert-butyl N-[1-benzyl-3-[2-(tert-butoxycarbonylamino)ethyl]-3-piperidyl]carbamate (2.2 g, 25% yield) as a colorless liquid. ¹H NMR (400 MHz, CDCl₃) δ=7.34-7.12 (m, 5H), 5.12-4.99 (m, 1H), 4.78-4.66 (m, 1H), 4.63-4.42 (m, 3H), 3.45-3.31 (m, 2H), 3.18-3.01 (m, 1H), 3.01-2.87 (m, 1H), 2.71-2.60 (m, 2H), 2.26-2.02 (m, 2H), 1.94-1.73 (m, 2H), 1.68-1.47 (m, 2H), 1.40-1.36 (m, 23H), 1.36-1.33 (m, 8H). LCMS (ESI, M+1): m/z 434.5.

Step D. 3-(2-aminoethyl)-1-benzyl-piperidin-3-amine: A mixture of tert-butyl N-[1-benzyl-3-[2-(tert-butoxycarbonylamino)ethyl]-3-piperidyl]carbamate (500 mg, 1.15 mmol) and HCl/EtOAc (4 M, 7.21 mL) was stirred at 25° C. for 18 hours. The reaction mixture was concentrated under reduced pressure to give 3-(2-aminoethyl)-1-benzyl-piperidin-3-amine (250 mg, crude, HCl) as a white solid. ¹H NMR (400 MHz, METHANOL-d4) δ=7.79-7.63 (m, 2H), 7.56-7.29 (m, 3H), 4.57-4.35 (m, 2H), 3.69-3.42 (m, 3H), 3.25-2.99 (m, 4H), 3.24-2.95 (m, 3H), 2.22-2.03 (m, 4H), 2.00-1.94 (m, 3H). LCMS (ESI, M+1): m/z 234.0.

Step E. 8-benzyl-1,3,8-triazaspiro[5.5]undecan-2-one: To a mixture of 3-(2-aminoethyl)-1-benzyl-piperidin-3-amine (250 mg, 926 μmol, HCl) in toluene (25 mL) was added TEA (281 mg, 2.78 mmol, 387 μL) and di(imidazol-1-yl)methanone (300 mg, 1.85 mmol). The reaction mixture was stirred at 80° C. for 16 hours. The reaction mixture was concentrated under reduced pressure to remove toluene. The residue was diluted with brine 5 mL and extracted with EtOAc (5 mL×3). The combined organic layers were dried over Na₂SO₄ and filtered. The mixture was concentrated to give a residue. The residue was purified by prep-HPLC (column: Phenomenex luna C18 150×25 mm×10 μm; mobile phase: [water (0.1% formic acid)-ACN]; B %: 2%-32%, 10 min) to give 8-benzyl-1,3,8-triazaspiro[5.5]undecan-2-one (70 mg, 269.91 μmol, 29% yield) as a white solid. ¹H NMR (400 MHz, METHANOL-d4) δ=7.62-7.46 (m, 5H), 7.44-7.27 (m, 1H), 4.48-4.28 (m, 2H), 3.59-3.38 (m, 2H), 3.28-3.12 (m, 2H), 3.09-2.72 (m, 3H), 2.27-2.19 (m, 1H), 2.31-2.16 (m, 1H), 2.14-1.57 (m, 9H). LCMS (ESI, M+1): m/z 260.2.

Step F. 1,3,8-triazaspiro[5.5]undecan-2-one: To a mixture of 8-benzyl-1,3,8-triazaspiro[5.5]undecan-2-one (70 mg, 270 μmol) in MeOH (1 mL) was added Pd/C (34.5 mg, 32.4 μmol, 10% purity). The reaction mixture was stirred at 25° C. for 16 hours under H₂ (15 psi). The reaction mixture was filtered and concentrated under reduced pressure to give 1,3,8-triazaspiro[5.5]undecan-2-one (45 mg, crude) as a colorless oil. ¹H NMR (400 MHz, METHANOL-d₄) δ=3.29-3.22 (m, 3H), 3.21-3.03 (m, 4H), 2.92-2.84 (m, 1H), 2.92-2.78 (m, 1H), 2.06-1.83 (m, 5H), 1.82-1.67 (m, 2H). LCMS (ESI, M+1): m/z 170.1.

Step G. 8-(8-fluoro-7-(8-fluoronaphthalen-1-yl)-2-((tetrahydro-1H-pyrrolizin-7a(5H)-yl)methoxy)pyrido[4,3-d]pyrimidin-4-yl)-1,3,8-triazaspiro[5.5]undecan-2-one: To a mixture of 1,3,8-triazaspiro[5.5]undecan-2-one (45 mg, 266 μmol) and 8-fluoro-7-(8-fluoronaphthalen-1-yl)-2-((tetrahydro-1H-pyrrolizin-7a(5H)-yl)methoxy)-4-(2,2,2-trifluoroethoxy) pyrido[4,3-d]pyrimidine (155 mg, 292 μmol) in DMF (3 mL) was added DIEA (103 mg, 798 μmol, 139 μL) and 4 Å molecular sieves (100 mg) in one portion at 25° C. The mixture was heated to 40° C. and stirred for 16 hours under N₂ atmosphere. The mixture was filtered and concentrated to give a residue. The residue was purified by prep-HPLC (column: Phenomenex Luna C18 150×25 mm×10 μm; mobile phase: [water (0.225% formic acid)-ACN]; B %: 12%-42%, 11 min) to give the title compound (9.06 mg, 5.63% yield) as an off-white solid. ¹H NMR (400 MHz, DMSO-d₆) δ=9.13 (d, J=1.9 Hz, 1H), 8.28 (s, 1H), 8.21-8.14 (m, 1H), 7.92 (d, J=7.6 Hz, 1H), 7.74 (dd, J=7.2, 8.2 Hz, 1H), 7.64-7.52 (m, 2H), 7.30 (dd, J=7.4, 13.6 Hz, 1H), 4.32-4.19 (m, 2H), 4.05-3.80 (m, 3H), 3.79-3.66 (m, 1H), 3.24-3.05 (m, 4H), 2.86-2.75 (m, 2H), 2.04-1.69 (m, 14H), 1.65-1.52 (m, 1H). LCMS (ESI, M+1): m/z 600.2.

Example 73

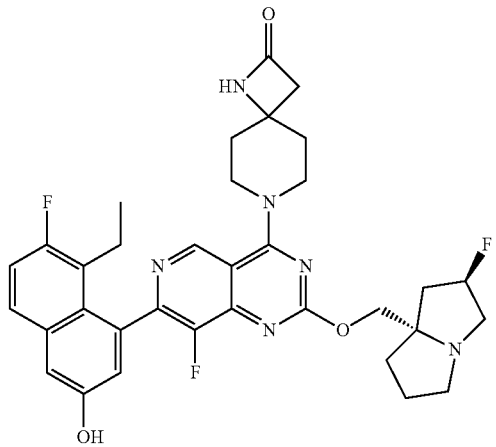 [SMILES: CCc1c(F)ccc2cc(O)cc(-c3ncc4c(N5CCC6(CC5)CC(=O)N6)nc(OC[C@@]56CCCN5C[C@H](F)C6)nc4c3F)c12]

7-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,7-diazaspiro[3.5]nonan-2-one

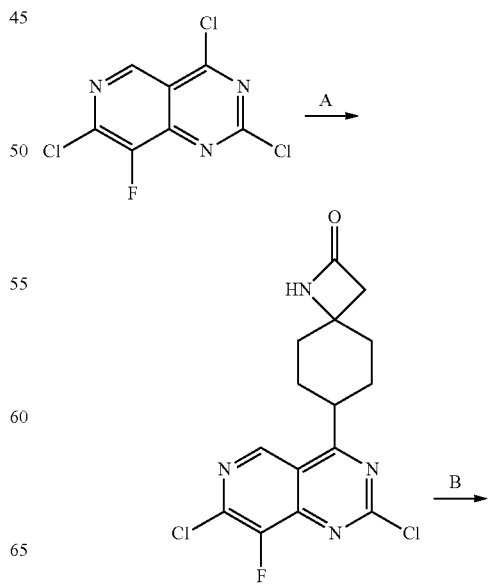

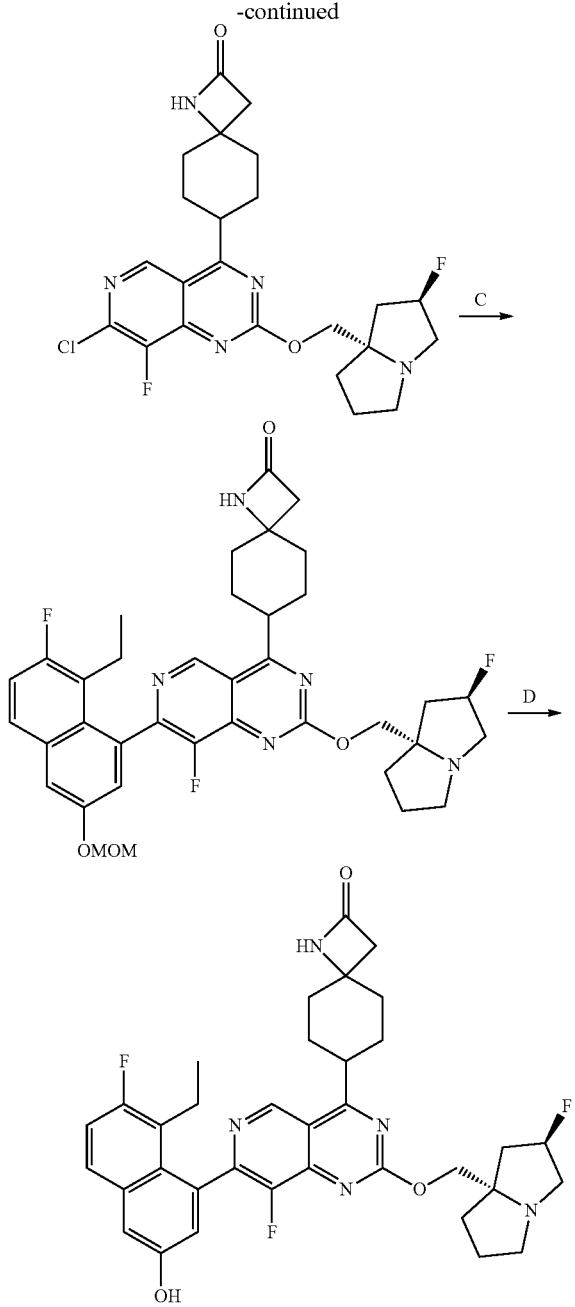

Step A. 7-(2,7-dichloro-8-fluoropyrido[4,3-d]pyrimidin-4-yl)-1,7-diazaspiro[3.5]nonan-2-one: To a solution of 2,4,7-trichloro-8-fluoropyrido[4,3-d]pyrimidine (400 mg, 1.58 mmol), DIEA (614 mg, 4.75 mmol) and 4 Å molecular sieves (10 mg) in DCM (8.0 mL) was added 1,7-diazaspiro[3.5]nonan-2-one (244 mg, 1.74 mmol) at −40° C. The mixture was stirred at −40° C. for 1 hour. The mixture was quenched with water (10 mL) and separated. The aqueous layer was extracted with EtOAc (2×10 mL). The combined organic layer was dried over anhydrous Na$_2$SO$_4$. The mixture was filtered and concentrated under reduced pressure to give 7-(2,7-dichloro-8-fluoropyrido[4,3-d]pyrimidin-4-yl)-1,7-diazaspiro[3.5]nonan-2-one (350 mg, crude) as yellow solid. (M+1). LCMS (ESI, M+1): m/z 356.1.

Step B. 7-(7-chloro-8-fluoro-2-(((2R,7aS)-2-fluorohexahydro-1H-pyrrolizin-7a-yl) methoxy)pyrido[4,3-d]pyrimidin-4-yl)-1,7-diazaspiro[3.5]nonan-2-one: To a solution of 7-(2,7-dichloro-8-fluoropyrido[4,3-d]pyrimidin-4-yl)-1,7-diazaspiro[3.5]nonan-2-one (300 mg, 842 μmol), 4 Å molecular sieves (50 mg) and DIEA (326 mg, 2.53 mmol) in dioxane (6.0 mL) was added ((2R,7aS)-2-fluorohexahydro-1H-pyrrolizin-7a-yl)methanol (161 mg, 1.01 mmol). The mixture was stirred at 90° C. for 12 hours. The mixture was quenched with water (10 mL) and extracted with EtOAc (2×10 mL). The combined organic layer was dried over anhydrous Na$_2$SO$_4$, filtered and concentrated. The residue was purified by reversed phase flash chromatography (C18, water (0.1% formic acid)-ACN) affording 7-(7-chloro-8-fluoro-2-(((2R,7aS)-2-fluorohexahydro-1H-pyrrolizin-7a-yl)methoxy)pyrido[4,3-d]pyrimidin-4-yl)-1,7-diazaspiro[3.5]nonan-2-one (150 mg, 311 μmol, 37% yield over two steps, 99.3% purity) as yellow solid. LCMS (ESI, M+1): m/z 479.2.

Step C. 7-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,7-diazaspiro[3.5]nonan-2-one: To a mixture of 7-(7-chloro-8-fluoro-2-(((2R,7aS)-2-fluorohexahydro-1H-pyrrolizin-7a-yl)methoxy)pyrido[4,3-d]pyrimidin-4-yl)-1,7-diazaspiro[3.5]nonan-2-one (90.0 mg, 188 μmol), 2-(8-ethyl-7-fluoro-3-(methoxymethoxy)naphthalen-1-yl)-4,4,5,5-tetramethyl-1,3,2-dioxaborolane (135 mg, 376 μmol) and Cs$_2$CO$_3$ (1.5 M, 376 μL) in methoxycyclopentane (2.0 mL) was added cataCXium-A-Pd-G3 (27.4 mg, 37.6 μmol). The mixture was stirred at 100° C. for 3 hours. The mixture was quenched with water (5 mL) and extracted with EtOAc (2×5 mL). The combined organic layer was dried over anhydrous Na$_2$SO$_4$. The mixture was filtered and concentrated under reduced pressure to give a residue. The residue was purified by reversed phase flash chromatography (C18, water (0.1% formic acid)/ACN) affording 7-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,7-diazaspiro[3.5]nonan-2-one (100 mg, 78% yield) as yellow solid. LCMS (ESI, M+1): m/z 677.3.

Step D. 7-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,7-diazaspiro[3.5]nonan-2-one: To a solution of 7-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,7-diazaspiro[3.5]nonan-2-one (90 mg, 133 μmol) in DCM (1.5 mL) was added TFA (2.31 g, 20.3 mmol, 1.50 mL). The mixture was stirred at 20° C. for 0.5 hour. The mixture was concentrated. The residue was purified by prep-HPLC [Water s Xbridge 150×25 mm×5 μm; A: water (10 mM NH$_4$HCO$_3$), B: ACN, B %: 30%-60/over 10 min) to afford 7-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,7-diazaspiro[3.5]nonan-2-one (16.7 mg, 19% yield) as white solid. $^1$H NMR (400 MHz, METHANOL-d$_4$): δ 9.06 (s, 1H), 7.68 (dd, J=6.0, 8.8 Hz, 1H), 7.31 (d, J=2.8 Hz, 1H), 7.26 (t, J=9.6 Hz, 1H), 7.05 (d, J=2.4 Hz, 1H), 5.39-5.23 (m, 1H), 4.79-4.65 (m, 1H), 4.37-4.23 (m, 2H), 4.22-4.13 (m, 1H), 4.09-3.98 (m, 1H), 4.22-3.97 (m, 1H), 3.29-3.16 (m, 1H), 3.29-3.15 (m, 2H), 3.05-2.98 (m, 1H), 2.87 (s, 2H), 2.57-2.42 (m, 1H), 2.41-2.28 (m, 1H), 2.26-2.20 (m, 1H), 2.19-2.04 (m, 5H), 2.03-1.83 (m, 4H), 0.80 (br t, J=7.6 Hz, 3H); LCMS (ESI, M+1): m/z 633.3.

Example 74

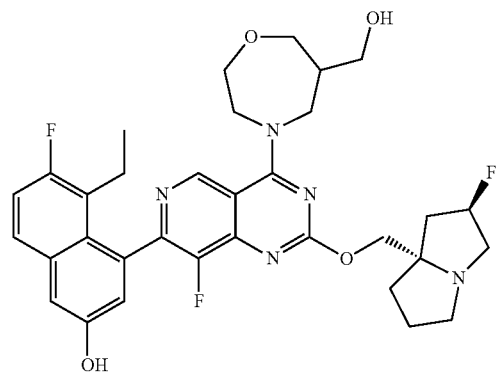 [SMILES: CCc1c(F)ccc2cc(O)cc(-c3ncc4c(N5CCOCC(CO)C5)nc(OC[C@@]56CCCN5C[C@H](F)C6)nc4c3F)c12]

5-ethyl-6-fluoro-4-(8-fluoro-2-(((2R,7aS)-2-fluoro-tetrahydro-1H-pyrrolizin-7a(5H)-yl)methoxy)-4-(6-(hydroxymethyl)-1,4-oxazepan-4-yl)pyrido[4,3-d]pyrimidin-7-yl)naphthalen-2-ol

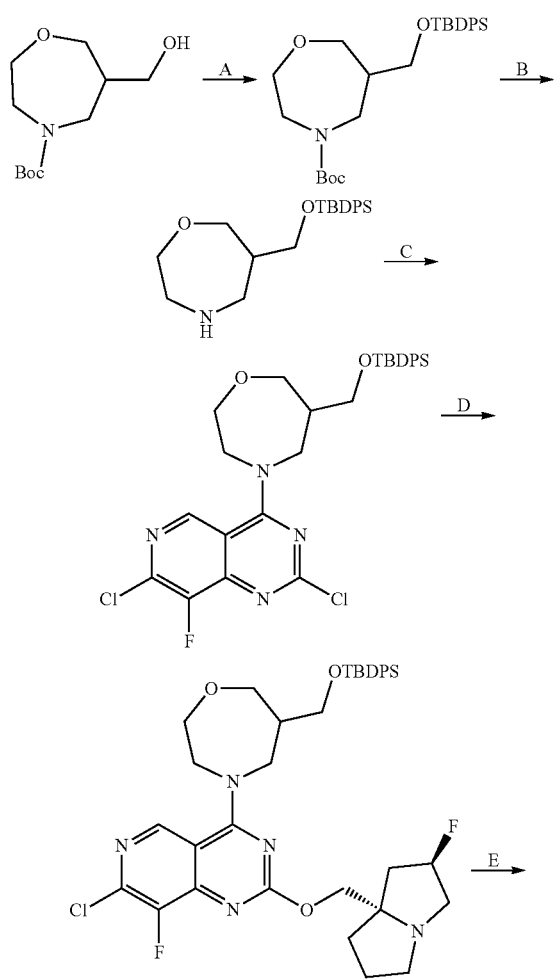

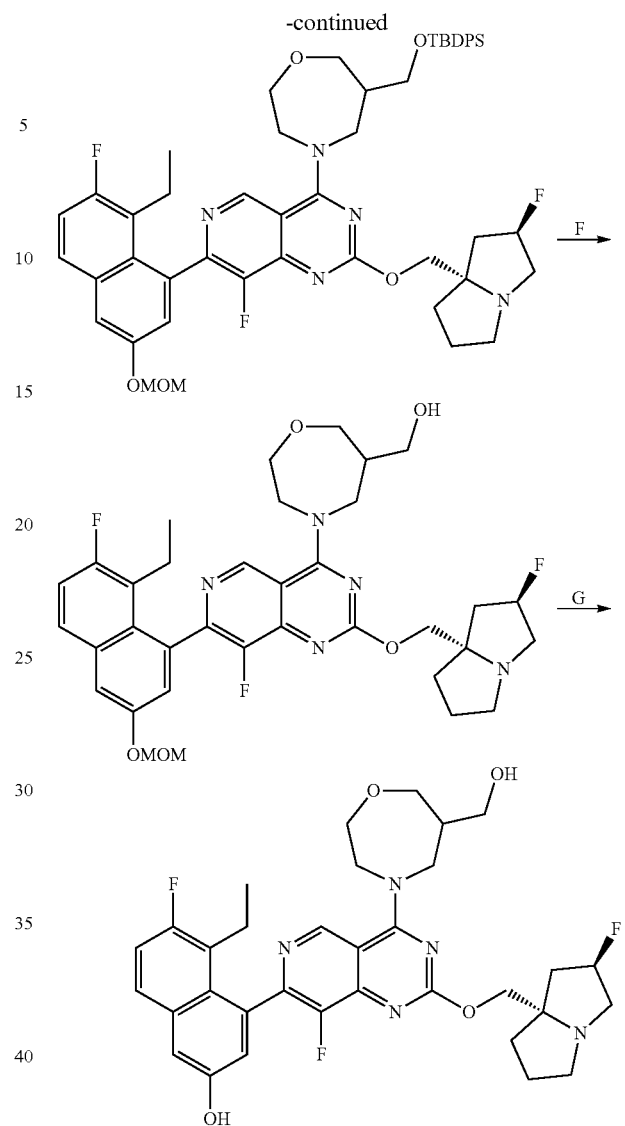

Step A. tert-butyl 6-(((tert-butyldiphenylsilyl)oxy)methyl)-1,4-oxazepane-4-carboxylate: To a solution of tert-butyl 6-(hydroxymethyl)-1,4-oxazepane-4-carboxylate (750 mg, 3.24 mmol) in THF (20 mL) were added imidazole (662 mg, 9.73 mmol) and TBDPSCl (1.34 g, 4.86 mmol, 1.25 mL) at 0° C. The mixture was stirred at 25° C. for 2 hours. The reaction mixture was diluted with water (100 mL) and extracted with ethyl acetate (3×50 mL). The combined organic layers were dried over $Na_2SO_4$, filtered and concentrated to give a residue. The residue was purified by reversed phase flash chromatography [water (0.1% formic acid)/acetonitrile] to give tert-butyl 6-(((tert-butyldiphenylsilyl)oxy)methyl)-1,4-oxazepane-4-carboxylate (1.10 g, 71% yield) as yellow oil. $^1$H NMR (400 MHz, $CDCl_3$) δ 7.74-7.60 (m, 4H), 7.50-7.32 (m, 6H), 3.85-3.56 (m, 8H), 3.41-3.21 (m, 1H), 3.19-3.01 (m, 1H), 2.41-2.20 (m, 1H), 1.52-1.39 (m, 9H), 1.06 (s, 9H). LCMS (ESI, M−55): m/z 414.2.

Step B. 6-(((tert-butyldiphenylsilyl)oxy)methyl)-1,4-oxazepane: To a solution of tert-butyl 6-(((tert-butyldiphenylsilyl)oxy)methyl)-1,4-oxazepane-4-carboxylate (900 mg, 1.92 mmol) in DCM (5 mL) was added TFA (13.9 g, 121 mmol, 9.00 mL) at 0° C. The mixture was stirred at 0° C. for 1 hour. The reaction mixture was concentrated under reduced pressure to remove solvent. The residue was diluted with water 10 mL and pH was adjusted to 8 with NaHCO$_3$. The mixture was extracted with ethyl acetate (3×20 mL). The combined organic layers were dried over Na$_2$SO$_4$ and filtered. The mixture was concentrated to give 6-(((tert-butyl diphenylsilyl)oxy)methyl)-1,4-oxazepane (700 mg, crude) as yellow solid. LCMS (ESI, M+1): m/z 370.3.

Step C. 6-(((tert-butyldiphenylsilyl)oxy)methyl)-4-(2,7-dichloro-8-fluoropyrido[4,3-d]pyrimidin-4-yl)-1,4-oxazepane: To a solution of 2,4,7-trichloro-8-fluoropyrido[4,3-d]pyrimidine (500 mg, 1.98 mmol) in DCM (10 mL) were added DIEA (768 mg, 5.94 mmol, 1.03 mL) and 6-(((tert-butyldiphenylsilyl)oxy)methyl)-1,4-oxazepane (439 mg, 1.19 mmol) at −40° C. The mixture was stirred at −40° C. for 0.5 hour. The reaction mixture was diluted with water (20 mL) and extracted with DCM (3×20 mL). The combined organic layers were dried over Na$_2$SO$_4$, filtered and concentrated to give a residue. The residue was purified by reversed phase flash chromatography [water (0.1% formic acid)/acetonitrile] to give 6-(((tert-butyl diphenylsilyl)oxy)methyl)-4-(2,7-dichloro-8-fluoropyrido[4,3-d]pyrimidin-4-yl)-1,4-oxazepane (700 mg, 60% yield); Yellow solid. LCMS (ESI, M+1): m/z 585.2.

Step D. 6-(((tert-butyldiphenylsilyl)oxy)methyl)-4-(7-chloro-8-fluoro-2-(((2R,7aS)-2-fluorohexahydro-1H-pyrrolizin-7a-yl)methoxy)pyrido[4,3-d]pyrimidin-4-yl)-1,4-oxazepane: To a solution of 6-(((tert-butyldiphenylsilyl)oxy)methyl)-4-(2,7-dichloro-8-fluoropyrido[4,3-d]pyrimidin-4-yl)-1,4-oxazepane (680 mg, 1.16 mmol) in dioxane (8 mL) were added DIEA (450 mg, 3.48 mmol), 4 Å molecular sieves (300 mg) and ((2R,7aS)-2-fluorohexahydro-1H-pyrrolizin-7a-yl)methanol (370 mg, 2.32 mmol). The mixture was stirred at 95° C. for 12 hours. After completion, the reaction mixture was filtered and concentrated under reduced pressure to give a residue. The crude product was triturated with DMF (10 mL) at 20° C. for 1 hour to give 6-(((tert-butyldiphenylsilyl)oxy)methyl)-4-(7-chloro-8-fluoro-2-(((2R,7aS)-2-fluorohexahydro-1H-pyrrolizin-7a-yl)methoxy)pyrido[4,3-d]pyrimidin-4-yl)-1,4-oxazepane (550 mg, 63% yield) as yellow solid. LCMS (ESI, M+1): m/z 708.4.

Step E. 6-(((tert-butyldiphenylsilyl)oxy)methyl)-4-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,4-oxazepane: To a solution of 6-(((tert-butyl diphenylsilyl)oxy)methyl)-4-(7-chloro-8-fluoro-2-(((2R,7aS)-2-fluorohexahydro-1H-pyrrolizin-7a-yl)methoxy)pyrido[4,3-d]pyrimidin-4-yl)-1,4-oxazepane (500 mg, 706 μmol) and 2-(8-ethyl-7-fluoro-3-(methoxymethoxy)naphthalen-1-yl)-4,4,5,5-tetramethyl-1,3,2-dioxaborolane (381 mg, 1.06 mmol) in methoxycyclopentane (8 mL) were added K$_3$PO$_4$ (1.5 M, 1.41 mL) and cataCXium-A-Pd-G3 (77.1 mg, 106 μmol). The mixture was stirred at 90° C. for 2 hours. The reaction mixture was diluted with water (10 mL) and extracted with ethyl acetate (3×10 mL). The combined organic layers were dried over Na$_2$SO$_4$, filtered and concentrated to give a residue. The residue was purified by reversed phase flash chromatography [water (0.1% formic acid)/acetonitrile] to give 6-(((tert-butyldiphenylsilyl)oxy)methyl)-4-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,4-oxazepane (500 mg, 67% yield) as yellow solid. LCMS (ESI, M+1): m/z 906.5.

Step F. (4-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,4-oxazepan-6-yl)methanol: To a solution of 6-(((tert-butyldiphenylsilyl)oxy)methyl)-4-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,4-oxazepane (300 mg, 285 μmol, 86% purity) in DMF (5 mL) was added CsF (432 mg, 2.85 mmol). The mixture was stirred at 25° C. for 2 hours. The reaction mixture was filtered and purified by reversed phase flash chromatography (C18, 0.1% formic acid in water, 0-60% ACN) to give (4-(7-(8-ethyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)-1,4-oxazepan-6-yl)methanol (180 mg, 91% yield); Yellow solid. LCMS (ESI, M+1): m/z 668.3.

Step G. 5-ethyl-6-fluoro-4-(8-fluoro-2-(((2R,7aS)-2-fluorohexahydro-1H-pyrrolizin-7a-yl)methoxy)-4-(6-(hydroxymethyl)-1,4-oxazepan-4-yl)pyrido[4,3-d]pyrimidin-7-yl) naphthalen-2-ol: To a solution of (4-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy) pyrido[4,3-d]pyrimidin-4-yl)-1,4-oxazepan-6-yl)methanol (100 mg, 150 μmol) in ACN (1 mL) was added HCl-dioxane (4.0 M, 2 mL). The mixture was stirred at 25° C. for 0.5 hour. After The reaction mixture was concentrated under reduced pressure to give a residue. The residue was purified by prep-HPLC (column: water s Xbridge 150×25 mm×5 μm; mobile phase: [water (10 mM NH$_4$HCO$_3$)-ACN]; B %: 32%-62%, 10 min) to give 5-ethyl-6-fluoro-4-(8-fluoro-2-(((2R,7aS)-2-fluorohexahydro-1H-pyrrolizin-7a-yl) methoxy)-4-(6-(hydroxymethyl)-1,4-oxazepan-4-yl) pyrido[4,3-d]pyrimidin-7-yl)naphthalen-2-ol (58.0 mg, 62% yield); White solid. $^1$H NMR (400 MHz, METHANOL-d$_4$) δ 9.19 (d, J=4.4 Hz, 1H), 7.67 (dd, J=6.0, 9.2 Hz, 1H), 7.30 (d, J=2.4 Hz, 1H), 7.25 (t, J=9.2 Hz, 1H), 7.06 (dd, J=2.4, 10.0 Hz, 1H), 5.41-5.19 (m, 1H), 4.59 (br s, 1H), 4.46-4.22 (m, 3H), 4.16-3.91 (m, 4H), 3.89-3.74 (m, 1H), 3.70-3.55 (m, 3H), 3.36-3.12 (m, 3H), 3.05-2.96 (m, 1H), 2.56-2.42 (m, 2H), 2.40-2.07 (m, 4H), 2.04-1.85 (m, 3H), 0.86-0.73 (m, 3H). LCMS (ESI, M+1): m/z 624.4.

Example 75

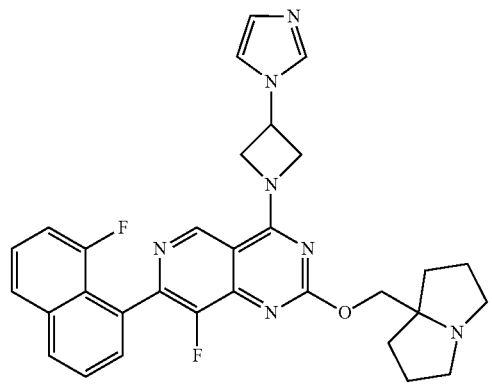 [SMILES: Fc1c(-c2cccc3cccc(F)c23)ncc2c(N3CC(n4ccnc4)C3)nc(OCC34CCCN3CCC4)nc12]

249

4-(3-(1H-imidazol-1-yl)azetidin-1-yl)-8-fluoro-7-(8-fluoronaphthalen-1-yl)-2-((hexahydro-1H-pyrrolizin-7a-yl)methoxy)pyrido[4,3-d]pyrimidine

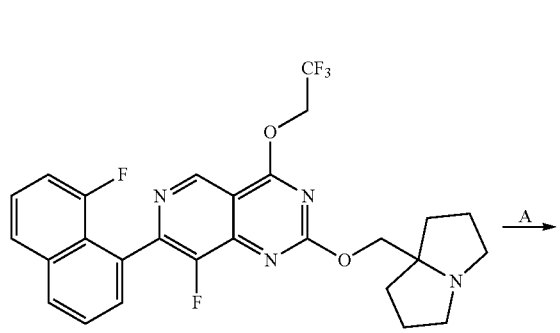

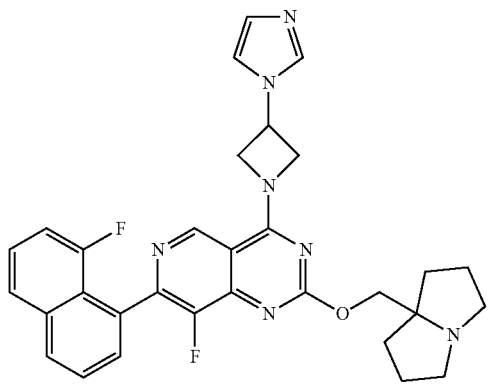

Step A. 4-(3-(1H-imidazol-1-yl)azetidin-1-yl)-8-fluoro-7-(8-fluoronaphthalen-1-yl)-2-((hexahydro-1H-pyrrolizin-7a-yl)methoxy)pyrido[4,3-d]pyrimidine: A mixture of 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d] pyrimidine (50.0 mg, 94.0 μmol) in DMF (0.5 mL) was added 4 Å molecular sieves (50.0 mg, 94.0 μmol), DIEA (48.7 mg, 377 μmol), 1-(azetidin-3-yl)imidazole (15.0 mg, 94.0 μmol, HCl salt) and stirred at 40° C. for 16 hours under N₂ atmosphere. The mixture solution was filtered and purified by reverse-phase preparatory HPLC (15% to 25% water/ACN with 0.225% formic acid formic acid over 7 minutes) to give 4-(3-(1H-imidazol-1-yl)azetidin-1-yl)-8-fluoro-7-(8-fluoronaphthalen-1-yl)-2-((hexahydro-1H-pyrrolizin-7a-yl) methoxy)pyrido[4,3-d]pyrimidine (10.81 mg, 20% yield). $^1$H NMR (400 MHz CDCl$_3$): δ 8.94 (s, 1H), 8.04-7.99 (m, 1H), 7.79-7.72 (m, 2H), 7.68-7.62 (m, 1H), 7.61-7.57 (m, 1H), 7.47 (m, 1H), 7.29 (br s, 1H), 7.24 (s, 1H), 7.14 (dd, J=7.6, 12.8 Hz, 1H), 5.31-5.27 (m, 1H), 5.19 (m, 2H), 4.82 (m, 2H), 4.54 (s, 2H), 3.61-3.42 (m, 2H), 2.88-2.73 (m, 2H), 2.26 (m, 2H), 2.08-2.01 (m, 4H), 1.87-1.82 (m, 2H); LCMS (ESI, M+1): m/z 554.3

250

Example 76

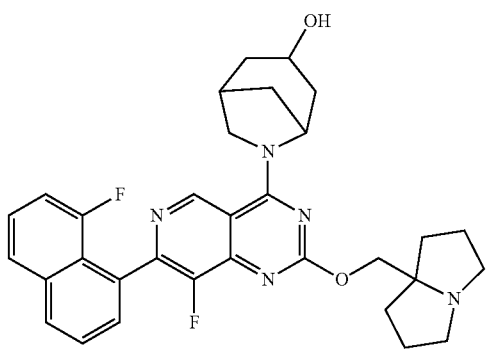 [SMILES: OC1CC2CC(C1)N(c1nc(OCC34CCCN3CCC4)nc3c(F)c(-c4cccc5cccc(F)c45)ncc13)C2]

6-(8-fluoro-7-(8-fluoronaphthalen-1-yl)-2-((hexahydro-1H-pyrrolizin-7a-yl)methoxy)pyrido[4,3-d]pyrimidin-4-yl)-6-azabicyclo[3.2.1]octan-3-ol

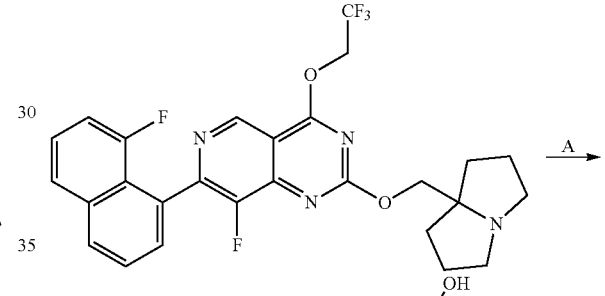

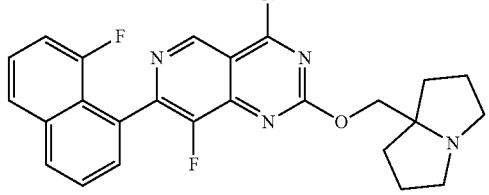

Step A. 6-(8-fluoro-7-(8-fluoronaphthalen-1-yl)-2-((hexahydro-1H-pyrrolizin-7a-yl) methoxy)pyrido[4,3-d] pyrimidin-4-yl)-6-azabicyclo[3.2.1]octan-3-ol: 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d] pyrimidine (100 mg, 189 μmol), DIEA (122 mg, 943 μmol) and 4 Å molecular sieves (10.0 mg) in DMF (5.0 mL) was added 6-azabicyclo[3.2.1]octan-3-ol (48.0 mg, 377 μmol). The mixture was stirred at 40° C. for 12 hours. The reaction mixture was diluted water (5.0 mL) and was extracted with EtOAc (3×5.0 mL). The combined organic layer was dried over anhydrous Na₂SO₄. The mixture was filtered and concentrated under reduced pressure to give a residue. The reaction was purified by prep-HPLC [Phenomenex Synergi C18 150×25 mm×10 μm; A: water (0.225% formic acid formic acid), B: ACN, B %: 12%-42%] to afford 6-(8-fluoro-7-(8-fluoronaphthalen-1-yl)-2-((hexahydro-1H-pyrrolizin- 7a-yl)methoxy)pyrido[4,3-d]pyrimidin-4-yl)-6-azabicyclo[3.2.1]octan-3-ol (3.89 mg, 4% yield) as yellow solid. $^1$H NMR (400 MHz, METHANOL-d$_4$): δ 9.43-9.24 (m, 1H), 8.61-8.44 (m, 1H), 8.17-8.03 (m, 1H), 7.86 (d, J=8.4 Hz, 1H), 7.75-7.65 (m, 1H), 7.63-7.48 (m, 2H), 7.23-7.14 (m, 1H), 5.07-4.97 (m, 1H), 4.64-4.59 (m, 2H), 4.55 (br s, 1H), 4.41-4.34 (m, 1H), 4.3-4.22 (m, 1H), 4.15 (br d, J=2.0 Hz, 1H), 3.65-3.53 (m, 2H), 3.26-3.10 (m, 2H), 2.81 (br s, 1H), 2.75-2.57 (m, 1H), 2.38-1.97 (m, 1H), 1.90-1.81 (m, 1H); LCMS (ESI, M+1): m/z 558.2

Example 77

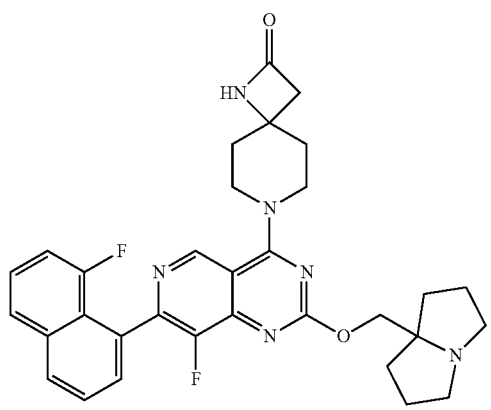 [SMILES: O=C1CC2(CCN(c3nc(OCC45CCCN4CCC5)nc4c(F)c(-c5cccc6cccc(F)c56)ncc34)CC2)N1]

7-(8-fluoro-7-(8-fluoronaphthalen-1-yl)-2-((hexahydro-1H-pyrrolizin-7a-yl)methoxy)pyrido[4,3-d]pyrimidin-4-yl)-1,7-diazaspiro[3.5]nonan-2-one

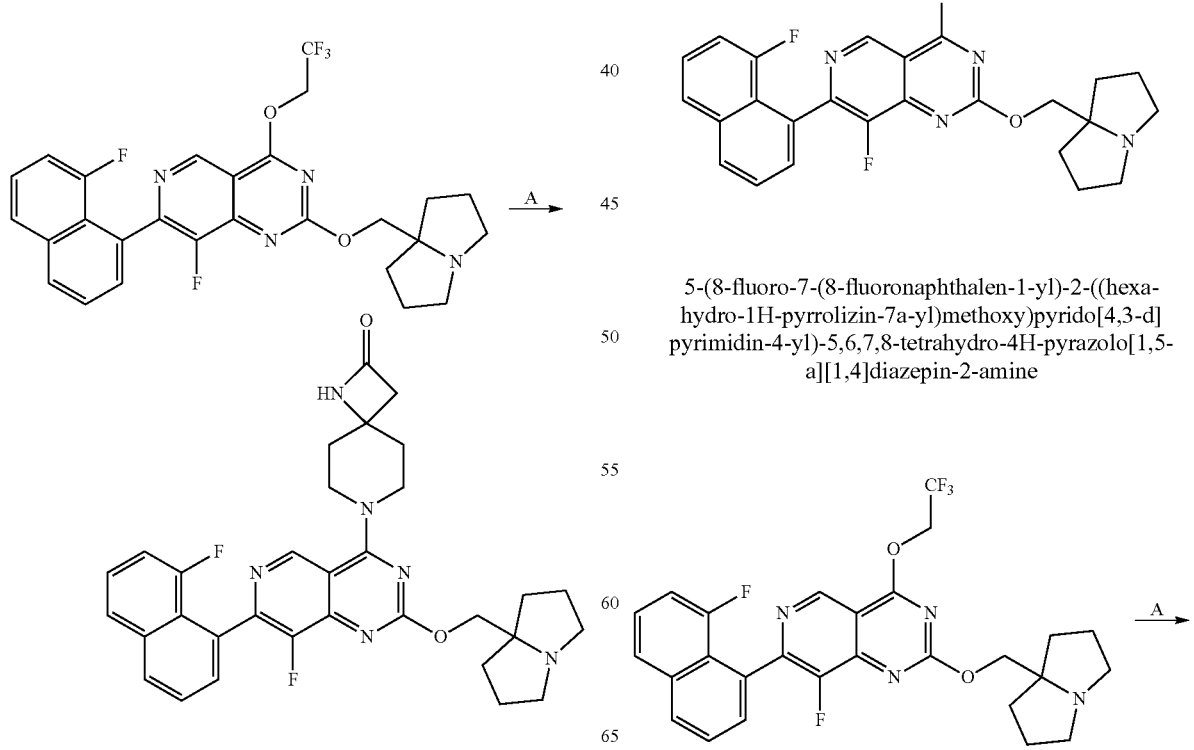

Step A. 7-(8-fluoro-7-(8-fluoronaphthalen-1-yl)-2-((hexahydro-1H-pyrrolizin-7a-yl) methoxy)pyrido[4,3-d]pyrimidin-4-yl)-1,7-diazaspiro[3.5]nonan-2-one: 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d]pyrimidine (100 mg, 189 μmol), DIEA (122 mg, 943 μmol) and 4 Å molecular sieves (10 mg) in DMF (5 mL) was added 1,7-diazaspiro[3.5]nonan-2-one (50.0 mg, 357 μmol). The mixture was stirred at 40° C. for 12 hours. The reaction mixture was diluted water (5.0 mL) and extracted with EtOAc (3×5.0 mL). The combined organic layer was dried over anhydrous Na$_2$SO$_4$. The mixture was filtered and concentrated under reduced pressure to give a residue. The reaction was purified by prep-HPLC [Phenomenex Synergi C18 150×25 mm×10 μm; A: water (0.225% formic acid formic acid), B: ACN, B %: 11%-41%] to afford 7-(8-fluoro-7-(8-fluoronaphthalen-1-yl)-2-((hexahydro-1H-pyrrolizin-7a-yl)methoxy)pyrido[4,3-d]pyrimidin-4-yl)-1,7-diazaspiro[3.5]nonan-2-one (16.0 mg, 14% yield) as yellow solid. $^1$H NMR (400 MHz, METHANOL-d$_4$): δ 9.10 (s, 1H), 8.52 (br s, 1H), 8.12 (br d, J=8.4 Hz, 1H), 7.86 (d, J=8.0 Hz, 1H), 7.74-7.68 (m, 1H), 7.62 (dd, J=0.8, 7.2 Hz, 1H), 7.57-7.50 (m, 1H), 7.24-7.15 (m, 1H), 4.63 (s, 2H), 4.29-4.14 (m, 2H), 4.12-4.00 (m, 2H), 3.72-3.57 (m, 2H), 3.27-3.17 (m, 2H), 2.87 (s, 2H), 2.36-2.26 (m, 2H), 2.24-2.12 (m, 4H), 2.11-2.01 (m, 6H); LCMS (ESI, M+1): m/z 571.3

Example 78

5-(8-fluoro-7-(8-fluoronaphthalen-1-yl)-2-((hexahydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-amine

253

-continued

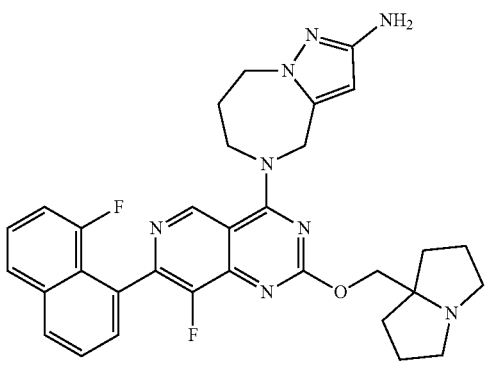

Step A. 5-(8-fluoro-7-(8-fluoronaphthalen-yl)-2-((hexahydro-1H-pyrrolizin-7a-yl) methoxy)pyrido[4,3-d]pyrimidin-4-yl)-5,6,7,8-tetrahydro-4H-pyrazolo[1,5-a][1,4]diazepin-2-amine: To the mixture of 8-fluoro-7-(8-fluoronaphthalen-1-yl)-2-((hexahydro-1H-pyrrolizin-7a-yl) methoxy)-4-(2,2,2-trifluoroethoxy)pyrido[4,3-d]pyrimidine (42 mg, 79 µmol), 5,6,7,8-tetrahydro-4H-pyrazolo[1,5-a][1,4]diazepin-2-amine (18 mg, 119 µmol) and 4 Å molecular sieves (40 mg, 79 µmol) in DMF (0.6 mL) was added DIEA (31 mg, 237 µmol). The mixture was stirred at 40° C. for 12 hours. The reaction mixture was filtered and purified by prep-HPLC (column: Phenomenex luna C18 150×25 mm×10 µm; mobile phase: [water (0.225% formic acid)-ACN]; B %: 10%-40%, 10 min) to afford 5-(8-fluoro-7-(8-fluoronaphthalen-1-yl)-2-((hexahydro-1H-pyrrolizin-7a-yl) methoxy)pyrido[4,3-d]pyrimidin-4-yl)-5,6,7,8-tetrahydro-4H-pyrazolo[1,5-a][1,4]diazepin-2-amine (5.57 mg, 11% yield, 0.422 FA) as white solid. $^1$H NMR (400 MHz, METHANOL-d$_4$): δ 9.23 (s, 1H), 8.55 (s, 1H), 8.13 (br d, J=8.8 Hz, 1H), 7.86 (d, J=8.4 Hz, 1H), 7.71 (dd, J=7.2, 8.0 Hz, 1H), 7.61 (dd, J=1.2, 7.2 Hz, 1H), 7.54 (dt, J=5.2, 8.0 Hz, 1H), 7.24-7.13 (m, 1H), 5.79 (s, 1H), 5.17-5.06 (m, 2H), 4.49 (s, 2H), 4.38 (br t, J=5.6 Hz, 2H), 4.28-4.19 (m, 2H), 3.48-3.39 (m, 2H), 3.10-2.96 (m, 2H), 2.43-2.32 (m, 2H), 2.25-2.16 (m, 2H), 2.15-2.02 (m, 4H), 2.00-1.89 (m, 2H); LCMS (ESI, M+1): m/z 583.2

Example 79

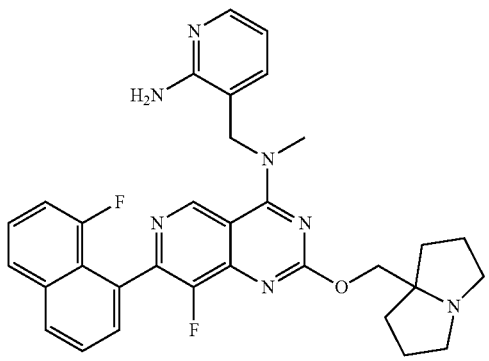 [SMILES: CN(Cc1cccnc1N)c1nc(OCC23CCCN2CCC3)nc2c(F)c(-c3cccc4cccc(F)c34)ncc12]

254

N-((2-aminopyridin-3-yl)methyl)-8-fluoro-7-(8-fluoronaphthalen-1-yl)-N-methyl-2-((tetrahydro-1H-pyrrolizin-7a(5H)-yl)methoxy)pyrido[4,3-d]pyrimidin-4-amine

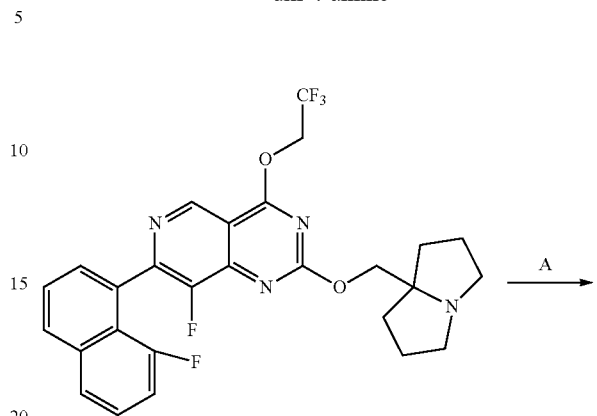

Step A: N-((2-aminopyridin-3-yl)methyl)-8-fluoro-7-(8-fluoronaphthalen-1-yl)-N-methyl-2-((tetrahydro-1H-pyrrolizin-7a(5H)-yl)methoxy)pyrido[4,3-d]pyrimidin-4-amine: To a solution of 8-fluoro-7-(8-fluoronaphthalen-1-yl)-2-((tetrahydro-1H-pyrrolizin-7a(5H)-yl) methoxy)-4-(2,2,2-trifluoroethoxy)pyrido[4,3-d]pyrimidine (100 mg, 189 µmol, 1.0 equiv.), DIEA (122 mg, 943 µmol, 164 µL, 5.0 equiv.) and 4 Å molecular sieves (50 mg) in DMF (1.0 mL) was added 3-((methylamino)methyl)pyridin-2-amine (51.7 mg, 377 µmol, 2.0 equiv.). The mixture was stirred at 40° C. for 12 h. Upon completion, the reaction solution was filtered and purified by prep-HPLC [Phenomenex Gemini-NX C18 75×30 mm×3 µm; A: water (0.225% formic acid formic acid), B: ACN, B %: 8%-38% over 7 min] to afford the title compound (6.38 mg, 6% yield, 99% purity). White solid; $^1$H NMR (400 MHz, METHANOL-d$_4$) δ=9.22 (s, 1H), 8.48 (br d, J=0.4 Hz, 1H), 8.12 (br d, J=8.2 Hz, 1H), 7.99-7.91 (m, 1H), 7.85 (d, J=8.0 Hz, 1H), 7.75-7.66 (m, 1H), 7.63-7.58 (m, 1H), 7.57-7.50 (m, 2H), 7.24-7.13 (m, 1H), 6.79-6.67 (m, 1H), 5.00 (s, 2H), 4.59 (s, 2H), 3.71-3.61 (m, 5H), 3.30-3.22 (m, 2H), 2.31-2.17 (m, 4H), 2.16-2.01 (m, 4H); LCMS [ESI, M+1]: 568.4.

Example 80

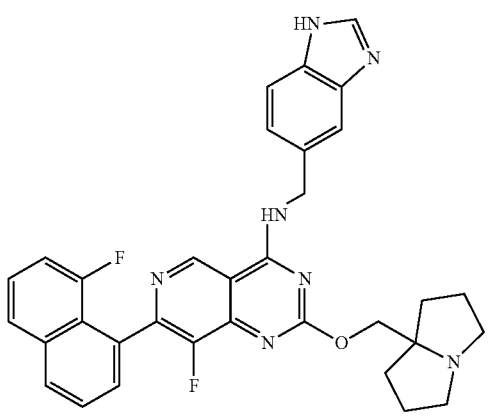 [SMILES: Fc1c(-c2cccc3cccc(F)c23)ncc2c(NCc3ccc4[nH]cnc4c3)nc(OCC34CCCN3CCC4)nc12]

N-((1H-benzo[d]imidazol-5-yl)methyl)-8-fluoro-7-(8-fluoronaphthalen-1-yl)-2-((hexahydro-1H-pyrrolizin-7a-yl)methoxy)pyrido[4,3-d]pyrimidin-4-amine

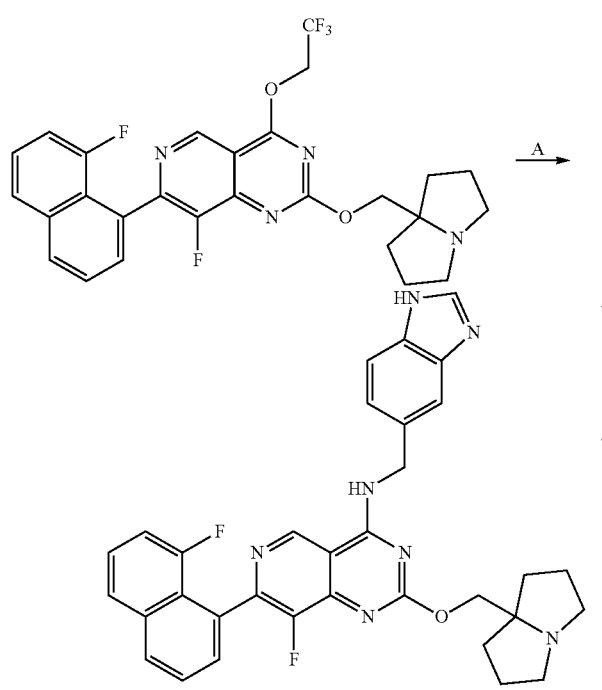

Step A. N-((1H-benzo[d]imidazol-5-yl)methyl)-8-fluoro-7-(8-fluoronaphthalen-1-yl)-2-((hexahydro-1H-pyrrolizin-7a-yl)methoxy)pyrido[4,3-d]pyrimidin-4-amine: 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d] pyrimidine (100 mg, 189 μmol), DIEA (122 mg, 943 μmol) and 4 Å molecular sieves (10 mg) in DMF (1.0 mL) was added (1H-benzo[d]imidazol-5-yl)methanamine (55.5 mg, 377 μmol). The mixture was stirred at 40° C. for 12 hours. The reaction solution was filtered and purified by prep-HPLC [Phenomenex Gemini-NX C18 75×30 mm×3 μm; A: water (0.225% formic acid formic acid), B: ACN, B %: 8%-38% over 7 min] to afford N-((1H-benzo[d]imidazol-5-yl)methyl)-8-fluoro-7-(8-fluoronaphthalen-1-yl)-2-((hexahydro-1H-pyrrolizin-7a-yl)methoxy)pyrido[4,3-d]pyrimidin-4-amine (41.0 mg, 38% yield) as white solid. $^1$H NMR (400 MHz, METHANOL-$d_4$): δ 9.27 (s, 1H), 8.55 (br s, 1H), 8.19 (s, 1H), 8.11 (br d, J=8.4 Hz, 1H), 7.85 (d, J=8.0 Hz, 1H), 7.75-7.67 (m, 2H), 7.64-7.57 (m, 2H), 7.56-7.49 (m, 1H), 7.43-7.38 (m, 1H), 7.23-7.14 (m, 1H), 5.03 (s, 2H), 4.55 (s, 2H), 3.63-3.52 (m, 2H), 3.24-3.13 (m, 2H), 2.26-2.18 (m, 2H), 2.17-2.11 (m, 2H), 2.10-2.02 (m, 2H), 2.01-1.93 (m, 2H); LCMS (ESI, M+1): m/z 578.2

Example 81

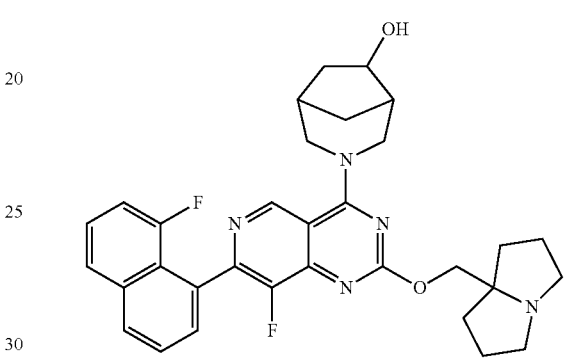

3-(8-fluoro-7-(8-fluoronaphthalen-1-yl)-2-((hexahydro-1H-pyrrolizin-7a-yl)methoxy)pyrido[4,3-d]pyrimidin 4-yl)-3-azabicyclo[3.2.1]octan-6-ol

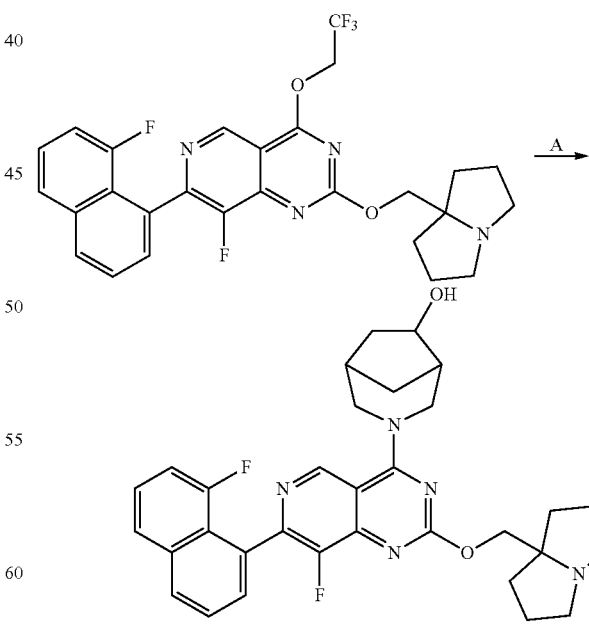

Step A. 3-(8-fluoro-7-(8-fluoronaphthalen-1-yl)-2-((hexahydro-1H-pyrrolizin-7a-yl) methoxy)pyrido[4,3-d]pyrimidin-4-yl-3-azabicyclo[3.2.1]octan-6-ol: To the mixture of 8-fluoro-7-(8-fluoronaphthalen-1-yl)-2-((hexahydro- 1H-pyrrolizin-7a-yl)methoxy)-4-(2,2,2-trifluoroethoxy) pyrido[4,3-d]pyrimidine (50 mg, 94 μmol), 3-azabicyclo [3.2.1]octan-6-ol (26 mg, 207 μmol) and 4 Å molecular sieves (40 mg) in DMF (1 mL) was added DIEA (49 mg, 377 μmol) The mixture was stirred at 40° C. for 16 hours. The reaction mixture was filtered and purified by prep-HPLC (column: water s Xbridge 150×25 mm×5 μm; mobile phase: [water (10 mM NH$_4$HCO$_3$)-ACN]; B %: 27%-57%, 10 min) to afford 3-(8-fluoro-7-(8-fluoronaphthalen-1-yl)-2-((hexahydro-1H-pyrrolizin-7a-yl)methoxy)pyrido[4,3-d]pyrimidin-4-yl)-3-azabicyclo[3.2.1]octan-6-ol (12.5 mg, 23% yield) as white solid. $^1$H NMR (400 MHz, DMSO-d$_6$): δ 9.32 (d, J=12.4 Hz, 1H), 8.17 (br d, J=8.0 Hz, 1H), 7.93 (d, J=8.0 Hz, 1H), 7.73 (dt, J=3.2, 7.6 Hz, 1H), 7.67-7.52 (m, 2H), 7.35-7.24 (m, 1H), 4.84-4.66 (m, 2H), 4.59 (m, 1H), 4.16 (br d, J=2.4 Hz, 1H), 4.08-3.96 (m, 2H), 3.72 (br t, J=12.4 Hz, 1H), 2.95-2.88 (m, 2H), 2.56-2.53 (m, 2H), 2.33 (br s, 1H), 2.17-2.04 (m, 2H), 1.88 (m, 2H), 1.83-1.70 (m, 5H), 1.69-1.61 (m, 1H), 1.61-1.49 (m, 2H), 1.26 (br d, J=13.2 Hz, 1H); LCMS (ESI, M+1): m/z 558.3

Example 82

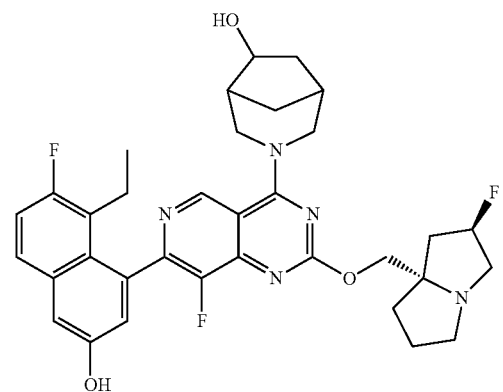 [SMILES: CCc1c(F)ccc2cc(O)cc(-c3ncc4c(N5CC6CC(O)C(C6)C5)nc(OC[C@@]56CCCN5C[C@H](F)C6)nc4c3F)c12]

3-(7-(8-ethyl-7-fluoro-3-hydroxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3-azabicyclo[3.2.1]octan-6-ol

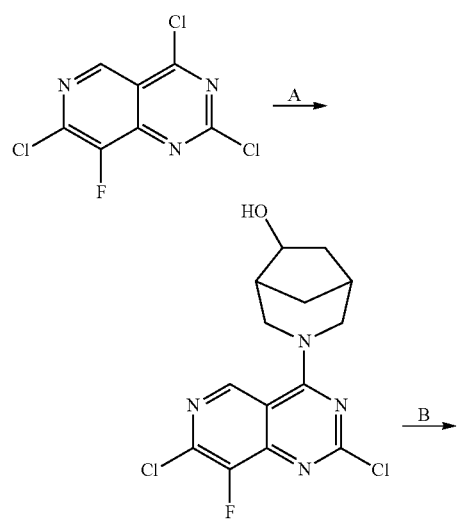


Step A. 3-(2,7-dichloro-8-fluoropyrido[4,3-d]pyrimidin-4-yl)-3-azabicyclo[3.2.1]octan-6-ol: To a solution of 2,4,7-trichloro-8-fluoropyrido[4,3-d]pyrimidine (150 mg, 594 μmol), DIPEA (231 mg, 1.79 mmol) in DCM (1.5 mL) was added 3-azabicyclo[3.2.1]octan-6-ol (54.0 mg, 330 μmol, HCl). DIPEA (231 mg, 1.79 mmol) in DMF (1.0 mL) was dropwise added at −40° C. The mixture was stirred at −40° C. for 1.5 h. The reaction mixture was diluted with water (20 mL) and extracted DCM (10 mL×3). The combined organic phase was dried with anhydrous Na$_2$SO$_4$ and filtered. The mixture was concentrated under reduced pressure to give a residue. The residue was purified by column chromatography (Silica gel, Petroleum ether/Ethyl acetate=5/1 to 1.5/1). TLC (PE/EA=1/1, Rf=0.41) to afford 3-(2,7-dichloro-8-fluoropyrido[4,3-d]pyrimidin-4-yl)-3-azabicyclo[3.2.1]octan-6-ol (90 mg, 31% yield) as a yellow solid; LCMS (ESI, M+1): m/z 343.0.

Step B. 3-(7-chloro-8-fluoro-2-(((2R,7aS)-2-fluorohexahydro-1H-pyrrolizin-7a-yl) methoxy)pyrido[4,3-d]pyrimidin-4-yl)-3-azabicyclo[3.2.1]octan-6-ol: A mixture of 3-(2,7-dichloro-8-fluoropyrido[4,3-d]pyrimidin-4-yl)-3-azabicyclo[3.2.1]octan-6-ol (90 mg, 262 μmol), ((2R,7aS)-

2-fluorohexahydro-1H-pyrrolizin-7a-yl)methanol (50 mg, 314 μmol), 4 Å molecular sieves (20 mg), DIPEA (102 mg, 792 μmol) in dioxane (1.0 mL) was degassed and purged with $N_2$ for 3 times. The mixture was stirred at 95° C. for 16 h under $N_2$ atmosphere. After completion, the reaction mixture was filtered and concentrated under reduced pressure to give a residue. The residue was purified by reversed phase flash chromatography [water (0.1% formic acid)/acetonitrile=3/1] to afford 3-(7-chloro-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol (96 mg, 71% yield) as a yellow gum; LCMS (ESI, M+1): m/z 466.1.

Step C. 3-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol: A mixture of 3-(7-chloro-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol (96 mg, 206 μmol), and $K_3PO_4$ (1.5 M in water, 412 μL) in THF (2.0 mL) was degassed and purged with $N_2$ for 3 times. 2-(8-ethyl-7-fluoro-3-(methoxymethoxy)naphthalen-1-yl)-4,4,5,5-tetramethyl-1,3,2-dioxaborolane (112 mg, 311 μmol) was added. Then CataCXium A Pd G3 (15 mg, 20.6 μmol) was added into the reaction mixture. The mixture was stirred at 65° C. for 4 h under $N_2$ atmosphere. After completion, the reaction mixture was diluted with water (3.0 mL) and extracted with ethyl acetate (1.0 mL×4). The combined organic phase was dried over anhydrous $Na_2SO_4$ and filtered. The mixture was concentrated under reduced pressure to give a residue. The residue was purified by reversed phase flash chromatography [water (0.1% formic acid)/acetonitrile=13/7] to afford 3-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol (104 mg, 75% yield) as a yellow oil; LCMS (ESI, M+1): m/z 664.3.

Step D. 3-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol: To a solution of 3-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol (99 mg, 149 μmol) in MeCN (4.0 mL) was added HCl/dioxane (4 M, 2.0 mL) at 0° C. The mixture was stirred between 0° C. and 10° C. for 0.5 h. After completion, the reaction mixture was quenched with saturated $NaHCO_3$ aqueous (10 mL). The mixture was extracted with ethyl acetate (10 mL×4). The combined organic phase was dried over anhydrous $Na_2SO_4$ and filtered. The mixture was concentrated under reduced pressure to give a residue. The residue was purified by prep-HPLC [Water s Xbridge 150× 25 mm×5 gm; A: water (10 mM $NH_4HCO_3$), B: ACN, B %: 41%-71% over 10 min] to afford 3-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol (33.5 mg, 36% yield) as a white solid; $^1$H NMR (400 MHz, METHANOL-$d_4$) δ 9.25-9.01 (m, 1H), 7.70-7.62 (m 1H), 7.30 (d, J=2.8 Hz, 1H), 7.27-7.20 (m, 1H), 7.09-7.01 (m, 1H), 5.41-5.19 (m, 1H), 5.04-4.97 (m, 1H), 4.77-4.73 (m, 1H), 4.38-4.16 (m, 3H), 3.97-3.68 (m, 1H), 3.54-3.39 (m, 1H), 3.29-3.07 (m, 3H), 3.04-2.81 (m, 1H), 2.58-2.28 (m, 3H), 2.28-2.11 (m, 5H), 2.03-1.85 (m, 4H), 1.85-1.76 (m, 1H), 1.40 (br d, J=13.6 Hz, 1H), 0.83-0.75 (m, 3H). F NMR (376 MHz, METHANOL-$d_4$) δ=-121, -139, -173. LCMS (ESI, M+1): m/z 620.3.

Example 83

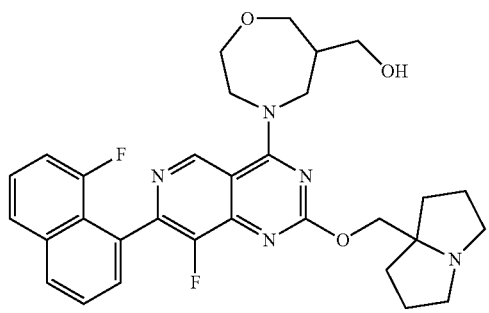 [SMILES: OCC1COCCN(c2nc(OCC34CCCN3CCC4)nc3c(F)c(-c4cccc5cccc(F)c45)ncc23)C1]

(4-(8-fluoro-7-(8-fluoronaphthalen-1-yl)-2-((hexahydro-1H-pyrrolizin-7a-yl)methoxy)pyrido[4,3-d]pyrimidin-4-yl)-1,4-oxazepan-6-yl)methanol


Step A. 6-((((tert-butyldiphenylsilyl)oxy)methyl)-4-(8-fluoro-7-(8-fluoronaphthalen-1-yl)-2-((hexahydro-1H-pyrrolizin-7a-yl)methoxy))pyrido[4,3-d]pyrimidin-4-yl)-1,4-oxazepane: 8-fluoro-7-(8-fluoronaphthalen-1-yl)-2-((hexahydro-1H-pyrrolizin-7a-yl) methoxy)-4-(2,2,2- trifluoroethoxy)pyrido[4,3-d]pyrimidine (100 mg, 189 µmol), 6-(((tert-butyl diphenylsilyl)oxy)methyl)-1,4-oxazepane (153 mg, 377 µmol, HCl) and 4 Å molecular sieves (10.0 mg) in DMF (1 mL) was added DIEA (73.1 mg, 566 µmol). The mixture was stirred at 40° C. for 12 hours. The reaction mixture was diluted water (5 mL) and was extracted with EtOAc (3×5.0 mL). The combined organic layer was dried over anhydrous Na₂SO₄, filtered and concentrated in vacuum. The residue was purified by reversed phase flash chromatography (C18, water (0.1% formic acid)/ACN) to afford 6-(((tert-butyldiphenylsilyl)oxy)methyl)-4-(8-fluoro-7-(8-fluoronaphthalen-1-yl)-2-((hexahydro-1H-pyrrolizin-7a-yl)methoxy)pyrido[4,3-d]pyrimidin-4-yl)-1,4-oxazepane (46.0 mg, 29.8% yield) as colorless oil. LCMS (ESI, M+1): m/z 800.4.

Step B. (4-(8-fluoro-7-(8-fluoronaphthalen-1-yl)-2-((hexahydro-1H-pyrrolizin-7a-yl) methoxy)pyrido[4,3-d]pyrimidin-4-yl)-1,4-oxazepan-6-yl)methanol: 6-(((tert-butyl diphenylsilyl)oxy)methyl)-4-(8-fluoro-7-(8-fluoronaphthalen-1-yl)-2-((hexahydro-1H-pyrrolizin-7a-yl)methoxy) pyrido[4,3-d]pyrimidin-4-yl)-1,4-oxazepane (45.0 mg, 56.3 µmol) in DMF (1 mL) was added CsF (85.4 mg, 562 µmol). The mixture was stirred at 25° C. for 12 hours. The reaction solution was filtered and purified by prep-HPLC [Phenomenex Gemini-NX C18 75×30 mm×3 µm; A: water (0.225% formic acid), B: ACN; B %: 12%-42% over 7 min] to afford (4-(8-fluoro-7-(8-fluoronaphthalen-1-yl)-2-((hexahydro-1H-pyrrolizin-7a-yl)methoxy)pyrido[4,3-d]pyrimidin-4-yl)-1,4-oxazepan-6-yl)methanol (9.78 mg, 30.7% yield) as yellow solid. ¹H NMR (400 MHz, METHANOL-d₄): δ 9.24 (s, 1H), 8.54 (s, 1H), 8.12 (d, J=8.4 Hz, 1H), 7.86 (d, J=8.0 Hz, 1H), 7.75-7.67 (m, 1H), 7.66-7.57 (m, 1H), 7.57-7.50 (m, 1H), 7.24-7.15 (m, 1H), 4.66 (br d, J=14.0 Hz, 1H), 4.55-4.55 (m, 1H), 4.55-4.39 (m, 2H), 4.19-3.92 (m, 4H), 3.84 (dd, J=10.0, 14.0 Hz, 1H), 3.68-3.55 (m, 3H), 3.52-3.40 (m, 2H), 3.12-2.99 (m, 2H), 2.59-2.44 (m, 1H), 2.28-2.17 (m, 2H), 2.16-2.02 (m, 4H), 2.00-1.92 (m, 2H); LCMS (ESI, M+1): m/z 562.3.

Example 84

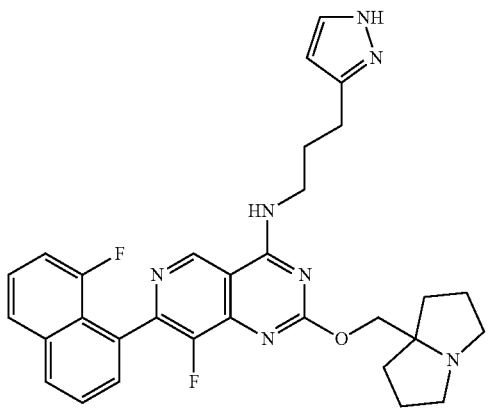 [SMILES: Fc1c(-c2cccc3cccc(F)c23)ncc2c(NCCCc3cc[nH]n3)nc(OCC34CCCN3CCC4)nc12]

N-(3-(1H-pyrazol-3-yl) propyl)-8-fluoro-7-(8-fluoronaphthalen-1-yl)-2-((hexahydro-1H-pyrrolizin-7a-yl) methoxy)pyrido[4,3-d] pyrimidin-4-amine

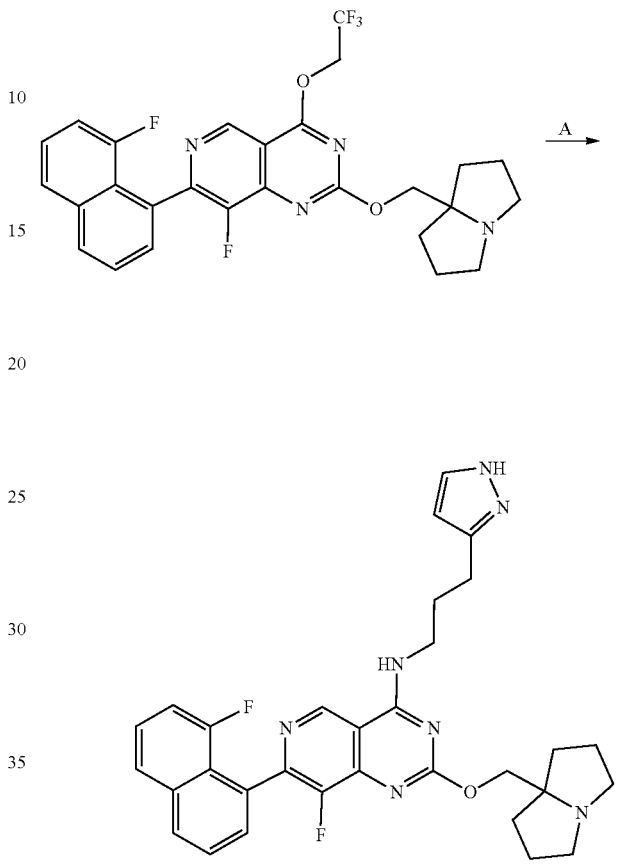

Step A. N-(3-(1H-pyrazol-3-yl)propyl)-8-fluoro-7-(8-fluoronaphthalen-1-yl)-2-((hexahydro-1H-pyrrolizin-7a-yl)methoxy)pyrido[4,3-d]pyrimidin-4-amine: To a solution of 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d]pyrimidine (50 mg, 94.2 µmol), 3-(1H-pyrazol-3-yl)propan-1-amine (18.7 mg, 94.2 µmol, 2 HCl salt) and 4 Å molecular sieves (50 mg) in DMF (0.5 mL) was added DIEA (60.9 mg, 471 µmol). The mixture was stirred at 40° C. for 16 hours under N₂. The mixture was filtered through a pad of Celite. The filtrate was poured into 10 mL water and extracted with ethyl acetate (10 mL×2). The combined organic phase was dried over anhydrous Na₂SO₄ and concentrated in vacuum. The residue was purified by reverse-phase preparatory HPLC (20% to 40% water/ACN with 0.225% formic acid formic acid over 10 minutes) to give N-(3-(1H-pyrazol-3-yl)propyl)-8-fluoro-7-(8-fluoronaphthalen-1-yl)-2-((hexahydro-1H-pyrrolizin-7a-yl) methoxy) pyrido[4,3-d]pyrimidin-4-amine (2.08 mg, 3.67% yield). LCMS (ESI, M+1): m/z 556.3. ¹H NMR (400 MHz, METHANOL-d₄) δ: 9.17 (s, 1H), 8.63-8.47 (m, 1H), 8.13 (br d, J=8.0 Hz, 1H), 7.86 (d, J=8.0 Hz, 1H), 7.75-7.67 (m, 1H), 7.59 (d, J=6.4 Hz, 1H), 7.57-7.47 (m, 2H), 7.23-7.15 (m, 1H), 6.21 (d, J=2.0 Hz, 1H), 4.58 (br s, 2H), 3.76 (m, 2H), 3.67-3.57 (m, 2H), 3.27-3.16 (m, 2H), 2.84 (t, J=7.6 Hz, 2H), 2.66 (s, 1H), 2.35-2.03 (m, 10H).

Example 85

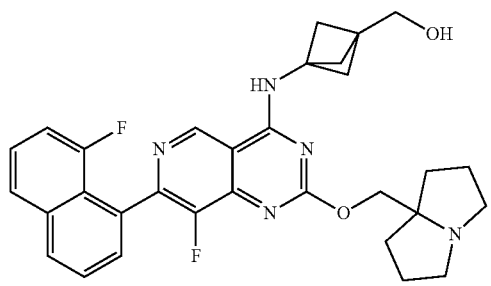 [SMILES: OCC12CC(Nc3nc(OCC45CCCN4CCC5)nc4c(F)c(-c5cccc6cccc(F)c56)ncc34)(C1)C2]

(3-((8-fluoro-7-(8-fluoronaphthalen-1-yl)-2-((hexa-hydro-1H-pyrrolizin-7a-yl)methoxy)pyrido[4,3-d]pyrimidin-4-yl)amino)bicyclo[1.1.1]pentan-1-yl)methanol

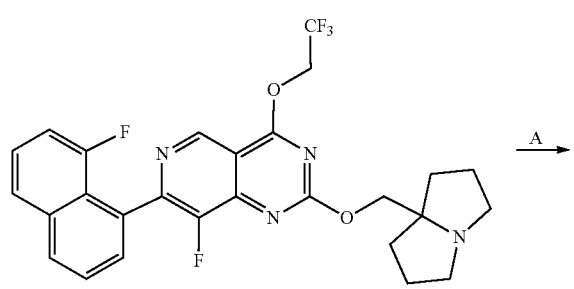

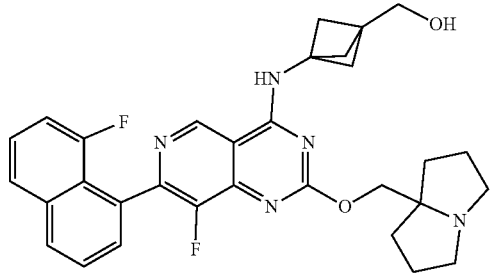

Step A. (3-((8-fluoro-7-(8-fluoronaphthalen-1-yl)-2-((hexahydro-1H-pyrrolizin-7a-yl)methoxy)pyrido[4,3-d]pyrimidin-4-yl)amino)bicyclo[1.1.1]pentan-1-yl)methanol: To a solution of (3-amino-1-bicyclo[1.1.1]pentanyl)methanol (9.60 mg, 84.8 μmol) and 4 Å molecular sieves (20 mg) in DMF (1.0 mL) were added DIEA (36.5 mg, 283 μmol, 49.2 μL) and 8-fluoro-7-(8-fluoronaphthalen-1-yl)-2-((tetrahydro-1H-pyrrolizin-7a(5H)-yl)methoxy)-4-(2,2,2-trifluoroethoxy) pyrido[4,3-d]pyrimidine (30 mg, 56.5 μmol). The mixture was stirred at 40° C. for 12 hours. Upon completion, The reaction mixture was filtered through Celite and the filtrate was concentrated. The residue was purified by prep-HPLC (column: water s Xbridge 150×25 mm×5 μm; mobile phase: [water (10 mM NH₄HCO₃)-ACN]; B %: 32%-62%, 10 min) to afford (3-((8-fluoro-7-(8-fluoronaphthalen-1-yl)-2-((hexahydro-1H-pyrrolizin-7a-yl)methoxy)pyrido[4,3-d]pyrimidin-4-yl)amino)bicyclo[1.1.1]pentan-1-yl)methanol (9.82 mg, 32% yield) as a white solid. LCMS (ESI, M+1): m/z 544.2.

Example 86

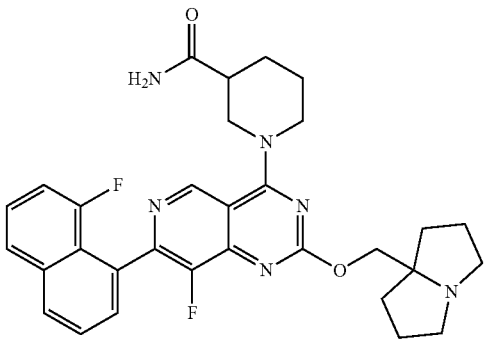 [SMILES: NC(=O)C1CCCN(c2nc(OCC34CCCN3CCC4)nc3c(F)c(-c4cccc5cccc(F)c45)ncc23)C1]

1-(8-fluoro-7-(8-fluoronaphthalen-1-yl)-2-((hexa-hydro-1H-pyrrolizin-7a-yl)methoxy)pyrido[4,3-d]pyrimidin-4-yl)piperidine-3-carboxamide

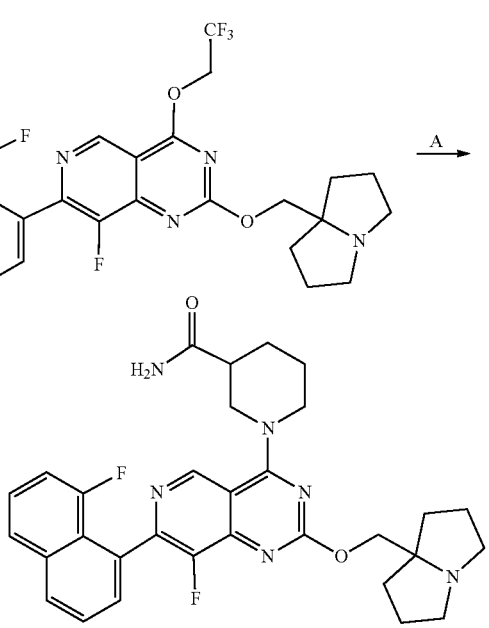

Step A. 1-(8-fluoro-7-(8-fluoronaphthalen-yl)-2-((hexa-hydro-1H-pyrrolizin-7a-yl) methoxy)pyrido[4,3-d]pyrimidin-4-yl)piperidine-3-carboxamide: To a solution of 8-fluoro-7-(8-fluoronaphthalen-1-yl)-2-((tetrahydro-1H-pyrrolizin-7a(5H)-yl)methoxy)-4-(2,2,2-trifluoroethoxy) pyrido[4,3-d]pyrimidine (30 mg, 56.6 μmol), DIEA (21.9 mg, 169 μmol, 29.6 μL) and 4 Å molecular sieves (1.0 mg) in DMF (1.0 mL) was added (3R)-piperidine-3-carboxamide (14.5 mg, 113 μmol). The mixture was stirred at 40° C. for 2 hours. After completion, the mixture was concentrated at 20° C. The residue was purified by prep-HPLC (column: Shim-pack C18 Ultra 150×25 mm×10 um; A: water (0.225% formic acid formic acid), B: ACN, B %: 17%-37% over 10 min) to afford 1-(8-fluoro-7-(8-fluoronaphthalen-1-yl)-2-((hexahydro-1H-pyrrolizin-7a-yl) methoxy)pyrido[4,3-d]pyrimidin-4-yl)piperidine-3-carboxamide (8.41 mg, 26% yield, 98.2% purity). Yellow solid; LCMS (ESI, M+1): m/z 559.3.

Example 87

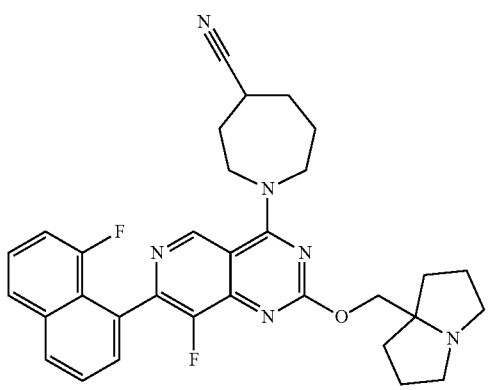 [SMILES: N#CC1CCCN(c2nc(OCC34CCCN3CCC4)nc3c(F)c(-c4cccc5cccc(F)c45)ncc23)CC1]

1-(8-fluoro-7-(8-fluoronaphthalen-1-yl)-2-((hexahydro-1H-pyrrolizin-7a-yl)methoxy)pyrido[4,3-d]pyrimidin-4-yl)azepane-4-carbonitrile

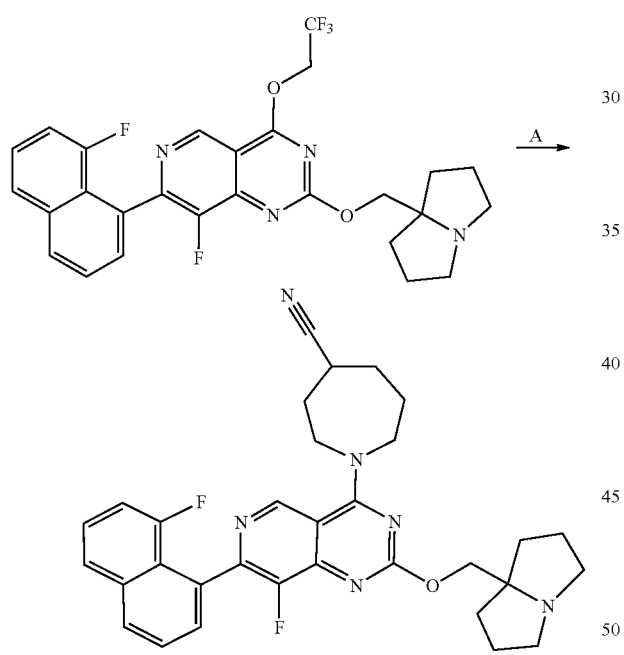

Step A. 1-(8-fluoro-7-(8-fluoronaphthalen-1-yl)-2-((hexahydro-1H-pyrrolizin-7a-yl) methoxy)pyrido[4,3-d]pyrimidin-4-yl)azepane-4-carbonitrile: To a solution of 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (30.0 mg, 56.6 μmol), DIEA (21.9 mg, 169 μmol, 29.5 μL) and 4 Å molecular sieves (1.0 mg) in DMF (1.0 mL) was added (4R)-azepane-4-carbonitrile (14.1 mg, 113 μmol HCl). The mixture was stirred at 40° C. for 12 hours. After completion, the mixture was concentrated at 20° C. The residue was purified by prep-HPLC [column: water s Xbridge C18 150×25 mm×5 μm; A: water (10 mM NH$_4$HCO$_3$), B: ACN, B %: 30%-60% over 9 min] to afford 1-(8-fluoro-7-(8-fluoronaphthalen-1-yl)-2-((hexahydro-1H-pyrrolizin-7a-yl) methoxy)pyrido[4,3-d]pyrimidin-4-yl)azepane-4-carbonitrile (3.64 mg, 12% yield, 100% purity). Yellow solid; LCMS (ESI, M+1): m/z 555.2.

Example 88

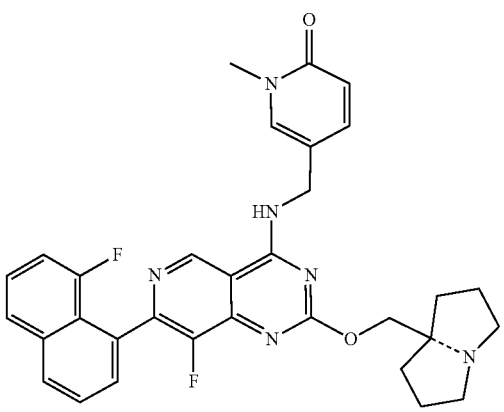

5-(((8-fluoro-7-(8-fluoronaphthalen-1-yl)-2-((hexahydro-1H-pyrrolizin-7a-yl) methoxy)pyrido[4,3-d]pyrimidin-4-yl)amino)methyl)-methylpyridin-2(1H)-one

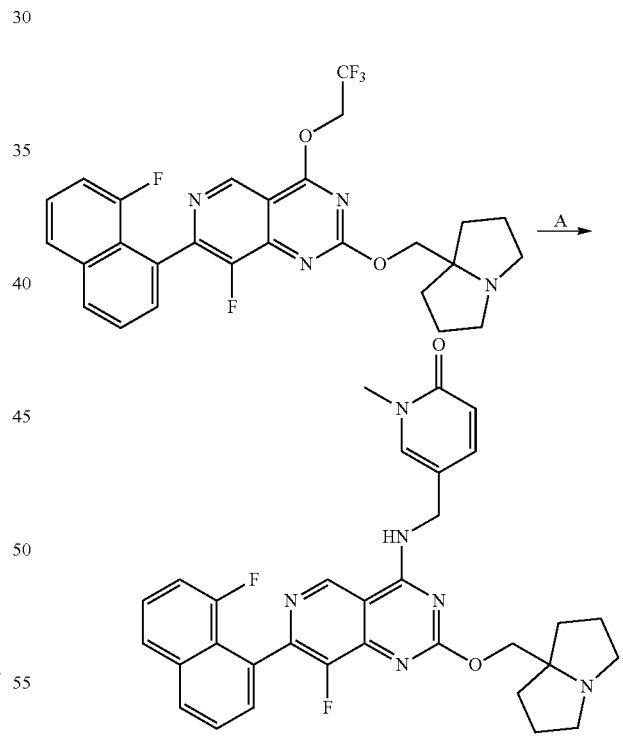

Step A. 5-(((8-fluoro-7-(8-fluoronaphthalen-1-yl)-2-((hexahydro-1H-pyrrolizin-7a-yl)methoxy)pyrido[4,3-d]pyrimidin-4-yl)amino)methyl)-1-methylpyridin-2 (1H)-one: To a mixture of 8-fluoro-7-(8-fluoronaphthalen-1-yl)-2-((tetrahydro-1H-pyrrolizin-7a(5H)-yl) methoxy)-4-(2,2,2-trifluoroethoxy)pyrido[4,3-d]pyrimidine (30.0 mg, 56.5 μmol) and 5-(aminomethyl)-1-methyl-pyridin-2-one (19.7 mg, 113 μmol, HCl) in DMF (1.0 mL) was added DIEA (29.2 mg, 226 μmol) and 4 Å molecular sieves (30 mg) in one portion at 25° C. under $N_2$. The mixture was stirred at 40° C. for 12 hours. The reaction mixture was filtered and purified by prep-HPLC (column: Phenomenex Gemini-NX C18 75*30 mm*3 µm; mobile phase: [water (0.225% formic acid)-ACN]; B %: 15%-45%, 7 min) to afford 5-(((8-fluoro-7-(8-fluoronaphthalen-1-yl)-2-((hexahydro-1H-pyrrolizin-7a-yl)methoxy)pyrido[4,3-d]pyrimidin-4-yl)amino) methyl)-1-methylpyridin-2 (1H)-one (12.3 mg, 22% yield); Off-white solid. LCMS (ESI, M+1): m/z 569.3.

Example 89

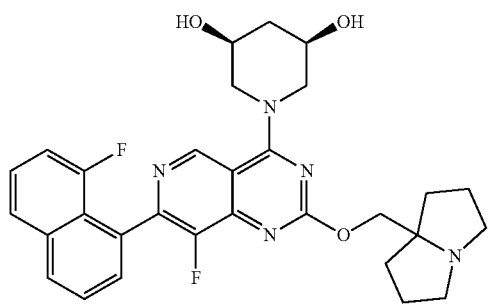 [SMILES: O[C@@H]1C[C@H](O)CN(c2nc(OCC34CCCN3CCC4)nc3c(F)c(-c4cccc5cccc(F)c45)ncc23)C1]

(3S,5R)-1-(8-fluoro-7-(8-fluoronaphthalen-1-yl)-2-((hexahydro-1 H-pyrrolizin-7a-yl)methoxy)pyrido[4,3-d]pyrimidin-4-yl)piperidine-3,5-diol

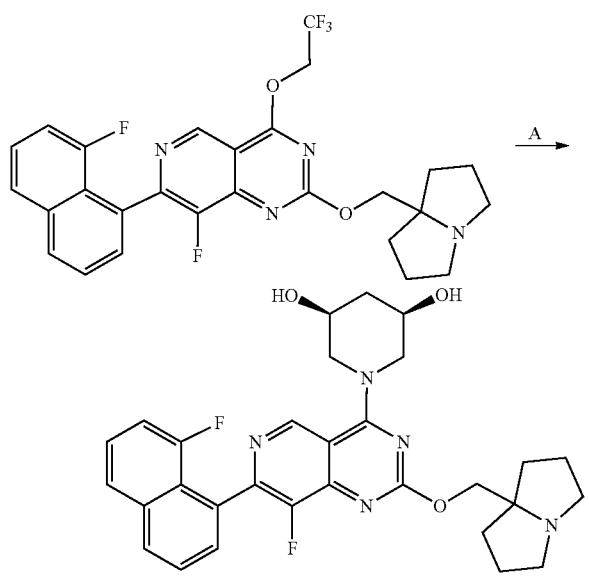

Step A. (3S,5R)-1-(8-fluoro-7-(8-fluoronaphthalen-1-yl)-2-((hexahydro-1H-pyrrolizin-7a-yl)methoxy)pyrido[4,3-d]pyrimidin-4-yl)piperidine-3,5-diol: To a solution of (3S, 5R)-piperidine-3,5-diol (9.94 mg, 84.8 µmol) and 4 Å molecular sieves (20 mg) in DMF (1.0 mL) were added DIEA (36.5 mg, 283 µmol, 49.2 LL) and 8-fluoro-7-(8-fluoronaphthalen-1-yl)-2-((tetrahydro-1H-pyrrolizin-7a (5H)-yl)methoxy)-4-(2,2,2-trifluoroethoxy)pyrido[4,3-d] pyrimidine (30 mg, 56.5 µmol). The mixture was stirred at 40° C. for 12 hours. Upon completion, the reaction mixture was filtered through Celite and the filtrate was concentrated. The residue was purified by prep-HPLC (column: water s Xbridge 150×25 mm×5 µm; mobile phase: [water (10 mM $NH_4HCO_3$)-ACN]; B %: 25%-55%, 0 min) to afford (3S, 5R)-1-(8-fluoro-7-(8-fluoronaphthalen-1-yl)-2-((hexahydro-1H-pyrrolizin-7a-yl)methoxy)pyrido[4,3-d]pyrimidin-4-yl)piperidine-3,5-diol (13.03 mg, 42% yield, 100% purity) as a white solid. LCMS (ESI, M+1): m/z 548.2.

Example 90

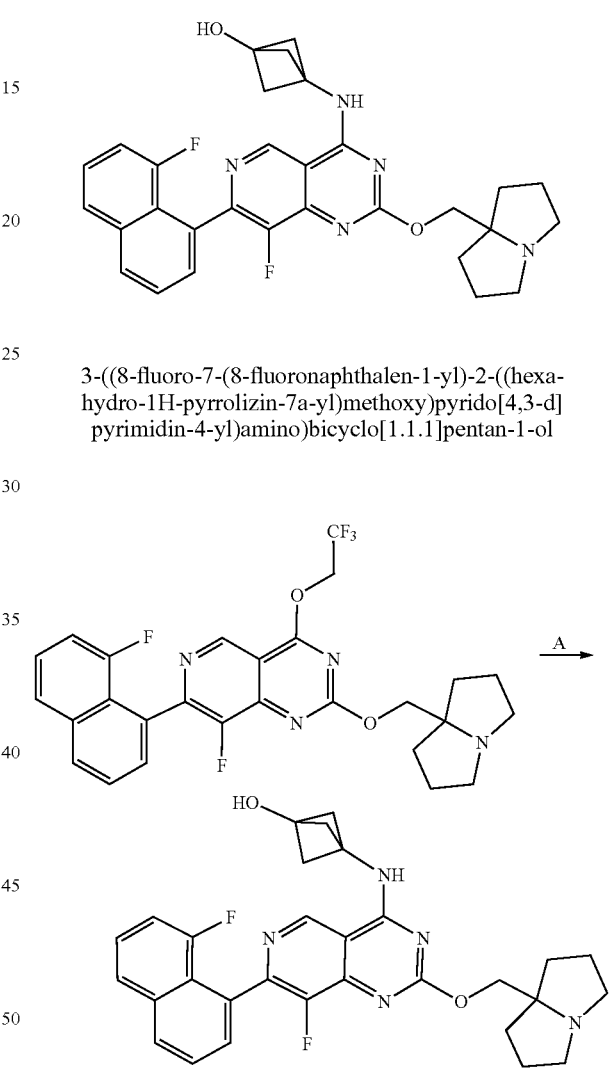

3-((8-fluoro-7-(8-fluoronaphthalen-1-yl)-2-((hexahydro-1H-pyrrolizin-7a-yl)methoxy)pyrido[4,3-d]pyrimidin-4-yl)amino)bicyclo[1.1.1]pentan-1-ol Step A. 3-((8-fluoro-7-(8-fluoronaphthalen-1-yl)-2-((hexahydro-1H-pyrrolizin-7a-yl) methoxy)pyrido[4,3-d] pyrimidin-4-yl)amino)bicyclo[1.1.1]pentan-1-ol: To a solution of 8-fluoro-7-(8-fluoronaphthalen-1-yl)-2-((tetrahydro-1H-pyrrolizin-7a(5H)-yl)methoxy)-4-(2,2,2-trifluoroethoxy) pyrido[4,3-d]pyrimidine (30.0 mg, 56.5 µmol) in DMF (1.0 mL) were added DIEA (29.2 mg, 226 µmol, 39.4 µL), 4 Å molecular sieves (10 mg), and 3-aminobicyclo[1.1.1]pentan-1-ol (11.2 mg, 113 µmol). The mixture was stirred at 40° C. for 12 hours. The reaction mixture was filtered and purified by prep-HPLC (column: Phenomenex luna C18 150*25 mm*10 µm; mobile phase: [water (0.225% formic acid)-ACN]; B %: 15%-45%, 10 min) to afford 3-((8-fluoro-7-(8-fluoronaphthalen-1-yl)-2-((hexahydro-1H-pyrrolizin-7a-yl)methoxy)pyrido[4,3-d]pyrimidin-4-yl) amino)bicyclo[1.1.1]pentan-1-ol (6.53 mg, 12.3 μmol, 100% purity); White solid. LCMS (ESI, M+J): m/z 530.3.

Example 91

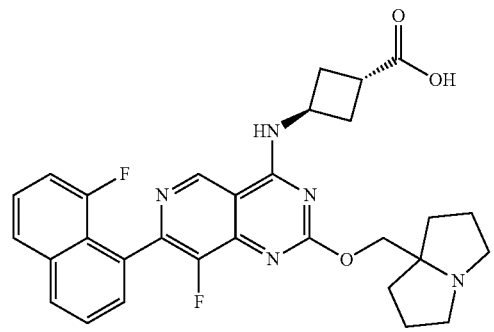 [SMILES: O=C(O)[C@H]1C[C@H](Nc2nc(OCC34CCCN3CCC4)nc3c(F)c(-c4cccc5cccc(F)c45)ncc23)C1]

trans-3-((8-fluoro-7-(8-fluoronaphthalen-1-yl)-2-((tetrahydro-1H-pyrrolizin-7a(5H)-yl) methoxy) pyrido[4,3-d]pyrimidin-4-yl)amino)cyclobutane-1-carboxylic acid

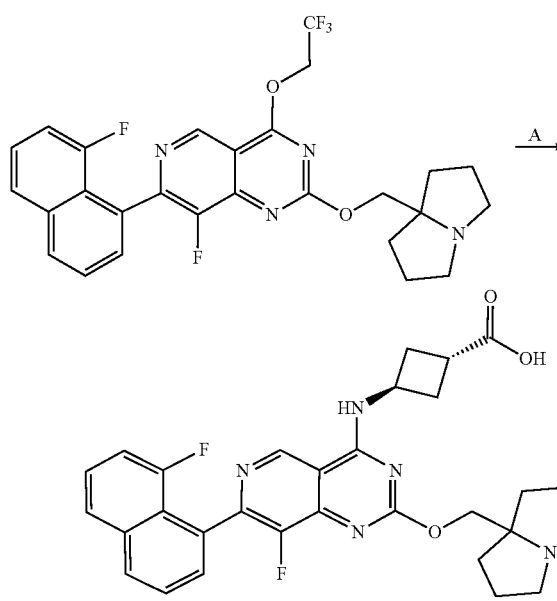

Step A. trans-3-((8-fluoro-7-(8-fluoronaphthalen-1-yl)-2-((hexahydro-1H-pyrrolizin-7a-yl)methoxy)pyrido[4,3-d]pyrimidin-4-yl)amino)cyclobutanecarboxylic acid: To a mixture of trans-3-aminocyclobutanecarboxylic acid (9 mg, 59.4 μmol, HCl), DIPEA (49.0 mg, 379 μmol) and 4 Å molecular sieves (10 mg) in DMSO (0.8 mL) was added 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d]pyrimidine (20 mg, 37.7 μmol). The mixture was stirred at 40° C. for 39 hours under $N_2$ atmosphere. The reaction mixture was filtered and purified by prep-HPLC (column: water s Xbridge 150×25 mm×5 um; mobile phase: [water (10 mM $NH_4HCO_3$)-ACN]; B %: 14%-44%, 10 minutes) to give the product as white solid (7.35 mg, 35% yield). LCMS (ESI, M+1): m/z 546.3.

Example 92

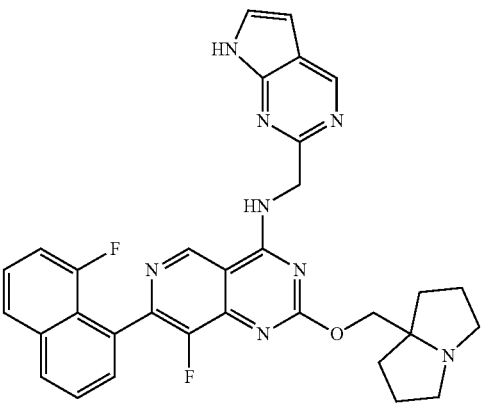 [SMILES: Fc1c(-c2cccc3cccc(F)c23)ncc2c(NCc3ncc4cc[nH]c4n3)nc(OCC34CCCN3CCC4)nc12]

N-((7H-pyrrolo[2,3-d]pyrimidin-2-yl)methyl)-8-fluoro-7-(8-fluoronaphthalen-1-yl)-2-((hexahydro-1H-pyrrolizin-7a-yl)methoxy)pyrido[4,3-d]pyrimidin-4-amine

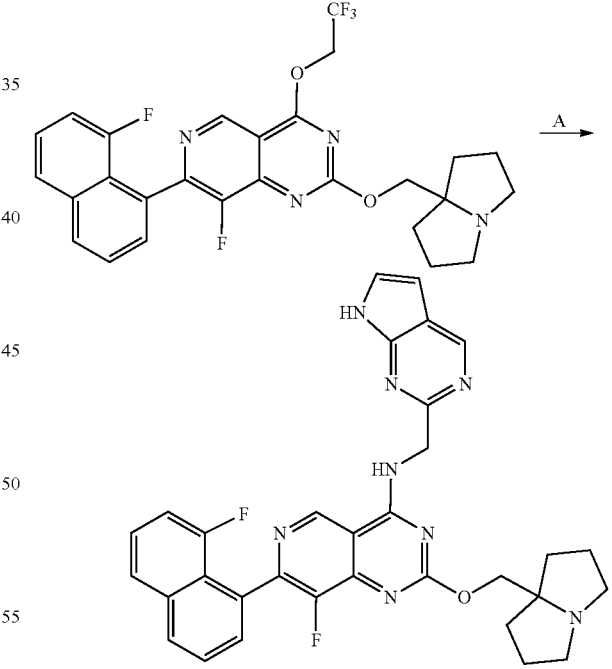

Step A. N-((7H-pyrrolo[2,3-d]pyrimidin-2-yl)methyl)-8-fluoro-7-(8-fluoronaphthalen-1-yl)-2-((hexahydro-1H-pyrrolizin-7a-yl)methoxy)pyrido[4,3-d]pyrimidin-4-amine: To a solution of 7H-pyrrolo[2,3-d]pyrimidin-2-ylmethanamine (12.6 mg, 84.8 μmol) and 4 Å molecular sieves (20 mg) in DMF (1.0 mL) were added DIEA (36.5 mg, 283 μmol, 49.25 μL) and 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine. The mixture was stirred at 40° C. for 12 hours. Upon completion, the reaction mixture was filtered and purified by prep-HPLC (column: water s Xbridge 150×25 mm×5 µm; mobile phase: [water (10 mM NH$_4$HCO$_3$)-ACN]; B %: 30%-60%, 10 min) to afford N-((7H-pyrrolo[2,3-d]pyrimidin-2-yl)methyl)-8-fluoro-7-(8-fluoronaphthalen-1-yl)-2-((hexahydro-1H-pyrrolizin-7a-yl)methoxy)pyrido[4,3-d]pyrimidin-4-amine (13.53 mg, 41.3% yield, 100% purity) as an off-white solid. 1H NMR (400 MHz, METHANOL-d$_4$) δ=9.31 (s, 1H), 8.95 (s, 1H), 8.12 (br d, J=8.1 Hz, 1H), 7.86 (d, J=8.2 Hz, 1H), 7.71 (t, J=7.7 Hz, 1H), 7.61 (d, J=6.6 Hz, 1H), 7.54 (dt, J=5.0, 7.9 Hz, 1H), 7.44 (d, J=3.5 Hz, 1H), 7.20 (dd, J=7.8, 13.0 Hz, 1H), 6.64 (d, J=3.5 Hz, 1H), 5.19-5.08 (m, 2H), 4.24 (s, 2H), 3.29-3.21 (m, 2H), 2.97-2.84 (m, 2H), 2.06-1.92 (m, 4H), 1.90-1.72 (m, 4H). LCMS (ESI, M+1): m/z 579.3.

Example 93

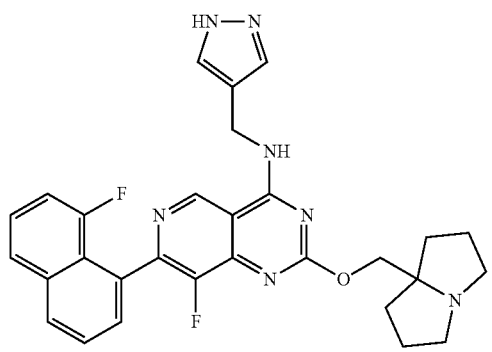 [SMILES: Fc1c(-c2cccc3cccc(F)c23)ncc2c(NCc3cn[nH]c3)nc(OCC34CCCN3CCC4)nc12]

N-((1H-pyrazol-4-yl)methyl)-8-fluoro-7-(8-fluoronaphthalen-1-yl)-2-((hexahydro-1H-pyrrolizin-7a-yl)methoxy)pyrido[4,3-d]pyrimidin-4-amine Step A. N-((1H-pyrazol-4-yl)methyl)-8-fluoro-7-(8-fluoronaphthalen-1-yl)-2-((hexahydro-1H-pyrrolizin-7a-yl)methoxy)pyrido[4,3-d]pyrimidin-4-amine: A mixture of 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (30.0 mg, 56.5 µmol) and 1H-pyrazol-4-ylmethanamine (19.2 mg, 113 µmol, 2 HCl) in DMF (1 mL) was added DIEA (29.2 mg, 226 µmol) and 4 Å molecular sieves (30 mg) in one portion at 25° C. under N$_2$. The mixture was stirred at 40° C. for 12 hours. The reaction mixture was filtered and the filtrate was purified. The residue was purified by prep-HPLC (column: Phenomenex Gemini-NX C18 75*30 mm*3 µm; mobile phase: [water (0.225% formic acid)-ACN]; B %: 15%-45%, 7 min) to afford N-((1H-pyrazol-4-yl)methyl)-8-fluoro-7-(8-fluoronaphthalen-1-yl)-2-((hexahydro-1H-pyrrolizin-7a-yl)methoxy)pyrido[4,3-d]pyrimidin-4-amine (2.14 mg, 6.6% yield); Yellow solid. LCMS (ESI, M+1): m/z 528.3.

Example 94

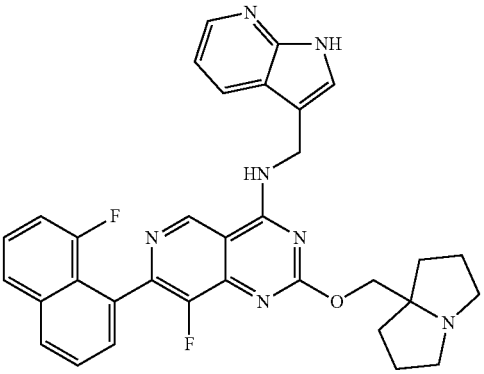 [SMILES: Fc1c(-c2cccc3cccc(F)c23)ncc2c(NCc3c[nH]c4ncccc34)nc(OCC34CCCN3CCC4)nc12]

N-((1H-pyrrolo[2,3-b]pyridin-3-yl)methyl)-8-fluoro-7-(8-fluoronaphthalen-1-yl)-2-((tetrahydro-1H-pyrrolizin-7a(5H)-yl)methoxy)pyrido[4,3-d]pyrimidin-4-amine

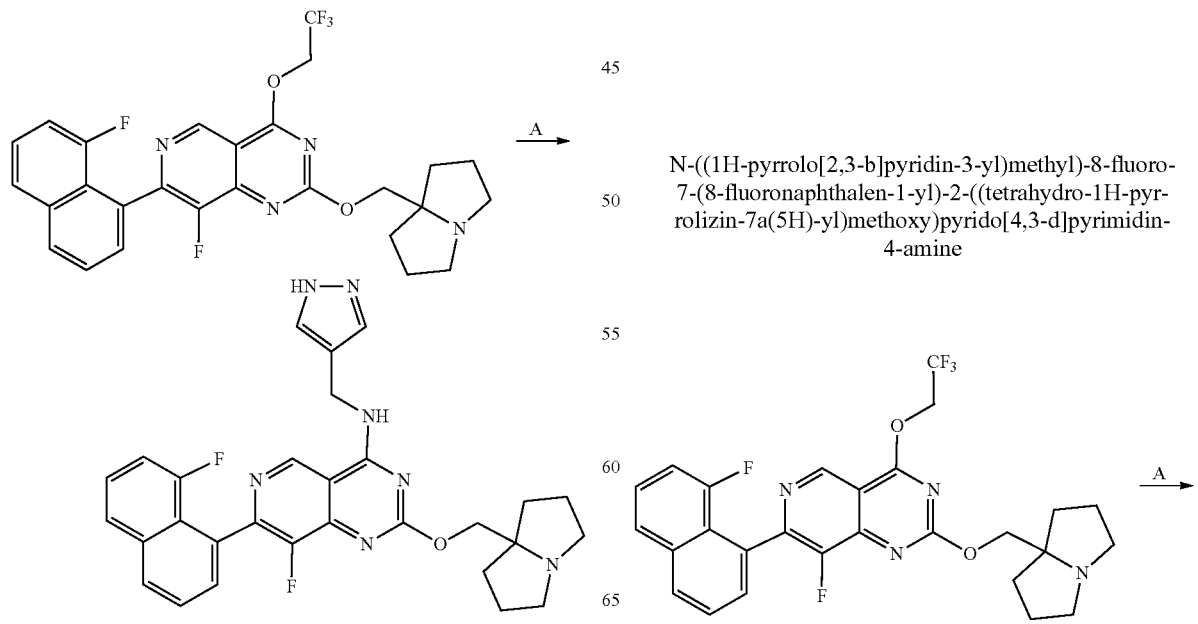

273

-continued

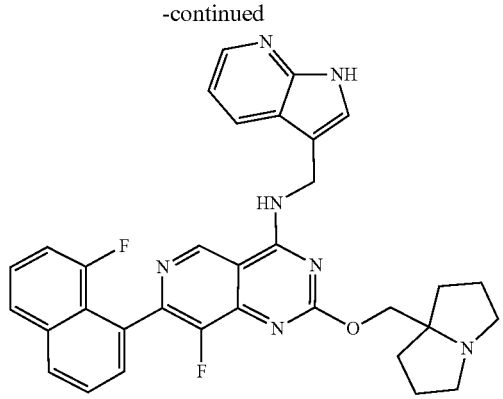

Step A. N-((1H-pyrrolo[2,3-b]pyridin-3-yl)methyl)-8-fluoro-7-(8-fluoronaphthalen-1-yl)-2-((tetrahydro-1H-pyrrolizin-7a(5H)-v)methoxy)pyrido[4,3-d]pyrimidin-4-amine: A mixture of 8-fluoro-7-(8-fluoronaphthalen-1-yl)-2-((tetrahydro-1H-pyrrolizin-7a(5H)-yl) methoxy)-4-(2,2,2-trifluoroethoxy)pyrido[4,3-d]pyrimidine (50.0 mg, 86.6 µmol, formic acid salt), 1H-pyrrolo[2,3-b]pyridin-3-ylmethanamine (28.6 mg, 130 µmol, 2 HCl), DIEA (78.3 mg, 606 µmol, 105 µL) and 4 Å molecular sieves (10 mg) in DMF (0.5 mL) was stirred at 40° C. for 16 hours. After completion, the mixture was filtered and purified by prep-HPLC (column: water s Xbridge 150×25 mm×5 µm; mobile phase: [water (10 mM NH$_4$HCO$_3$)-ACN]; B %: 33%-63%, 8 min) to afford the title compound, 18% yield). White Solid. $^1$H NMR (400 MHz, CDCl$_3$-d): δ 9.33-9.22 (m, 1H), 8.83 (s, 1H), 8.33 (br dd, J=4.0, Hz, 1H), 8.00 (br dd, J=8.0, 18.8 Hz, 2H), 7.72 (d, J=7.6 Hz, 1H), 7.62-7.57 (m, 1H), 7.56-7.52 (m, 1H), 7.46-7.40 (m, 2H), 7.13-7.06 (m, 2H), 6.54-6.37 (m, 1H), 5.09-5.01 (m, 2H), 4.33 (s, 2H), 3.19-3.09 (m, 2H), 2.71-2.61 (m, 2H), 2.18-2.09 (m, 2H), 1.93-1.86 (m, 4H), 1.73-1.69 (m, 2H). LCMS (EST, M+1): m/z 578.3.

Example 95

274

3-((8-fluoro-7-(8-fluoronaphthalen-1-yl)-2-((hexahydro-1H-pyrrolizin-7a-yl)methoxy)pyrido[4,3-d]pyrimidin-4-yl)amino)thietane1,1-dioxide

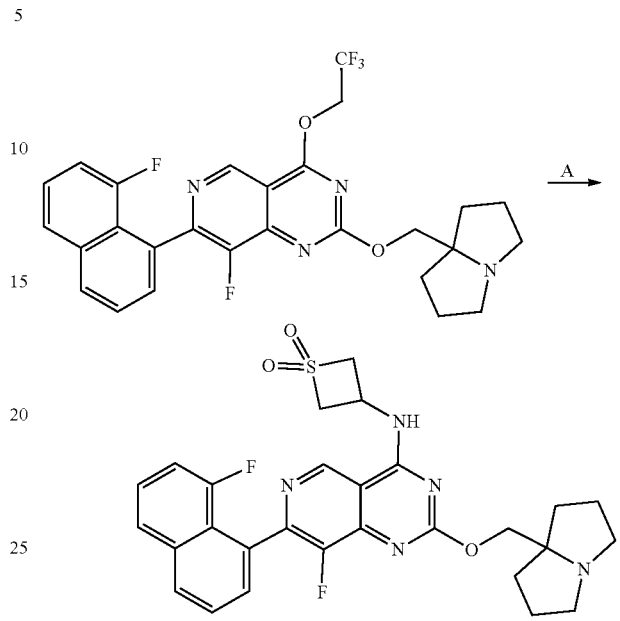

Step A. 3-4 (8-fluoro-7-(8-fluoronaphthalen-1-yl)-2-((hexahydro-1H-pyrrolizin-7a-yl) methoxy)pyrido[4,3-d]pyrimidin-4-yl amino)thietane1,1-dioxide: To a solution of 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (30.0 mg, 56.5 µmol) in DMF (1 mL) was added DIEA (29.2 mg, 226 µmol, 39.4 µL), 4 Å molecular sieves (10 mg), 1,1-dioxothietan-3-amine (13.7 mg, 113 µmol). The mixture was stirred at 60° C. for 12 hr. The reaction mixture was filtered and purified by prep-HPLC (column: Phenomenex luna C18 150×25 mm×10 µm; mobile phase: [water (0.225% formic acid)-ACN]; B %: 11%-47%, 11 min) to afford 3-((8-fluoro-7-(8-fluoronaphthalen-1-yl)-2-((hexahydro-1H-pyrrolizin-7a-yl)methoxy) pyrido[4,3-d]pyrimidin-4-yl) amino)thietane1,1-dioxide (3.25 mg, 5.89 µmol, 10% yield, 100% purity); White solid. LCMS (ESI, M+1): m/z 552.2.

Example 96

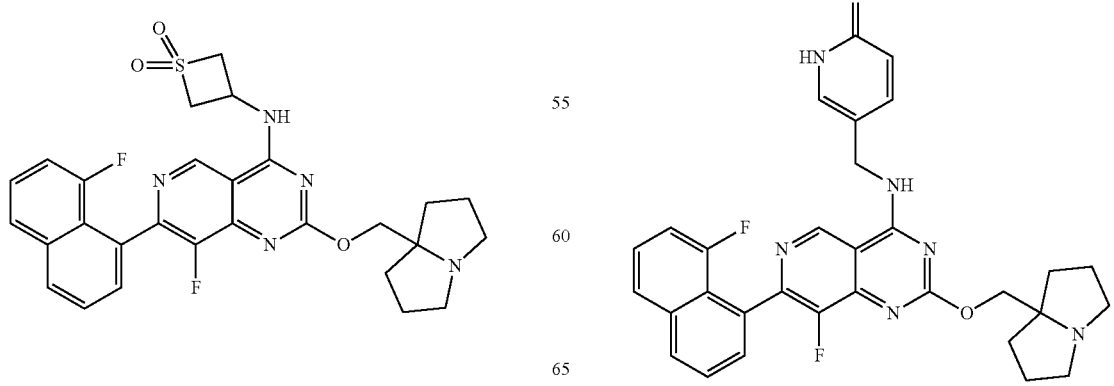

5-(((8-fluoro-7-(8-fluoronaphthalen-1-yl)-2-((hexahydro-1H-pyrrolizin-7a-yl) methoxy)pyrido[4,3-d]pyrimidin-4-yl)amino)methyl)pyridin-2 (1H)-one Example 97

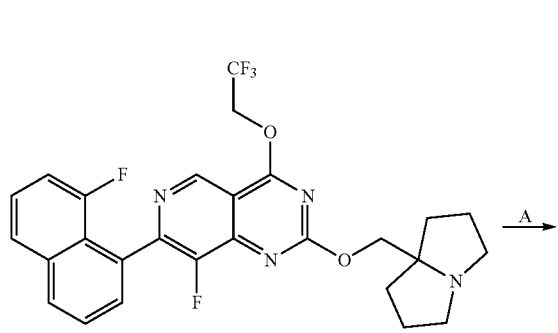

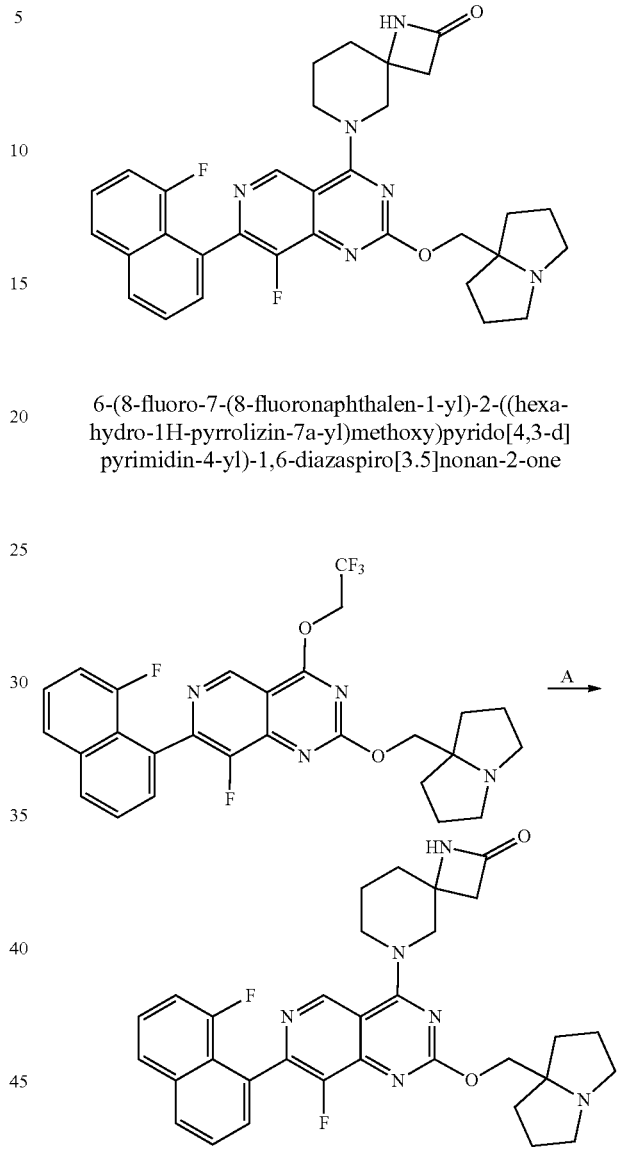

6-(8-fluoro-7-(8-fluoronaphthalen-1-yl)-2-((hexahydro-1H-pyrrolizin-7a-yl)methoxy)pyrido[4,3-d]pyrimidin-4-yl)-1,6-diazaspiro[3.5]nonan-2-one Step A. 5-(((8-fluoro-7-(8-fluoronaphthalen-1-yl)-2-((hexahydro-1H-pyrrolizin-7a-yl)methoxy)pyrido[4,3-d]pyrimidin-4-yl)amino)methyl)pyridin-2 (1H)-one: To a mixture of 5-(aminomethyl)-1H-pyridin-2-one (10.53 mg, 84.83 µmol) and 4 Å molecular sieves (20 mg) in DMF (1 mL) were added DIEA (36.54 mg, 282.75 µmol, 49.25 µL) and 8-fluoro-7-(8-fluoronaphthalen-1-yl)-2-((tetrahydro-1H-pyrrolizin-7a(5H)-yl)methoxy)-4-(2,2,2-trifluoroethoxy) pyrido[4,3-d]pyrimidine (30 mg, 56.55 µmol). The mixture was stirred at 40° C. for 12 hours. Upon completion, the reaction mixture was filtered. The residue was purified by prep-HPLC (column: water s Xbridge 150×25 mm×5 µm; mobile phase: [water (10 mM $NH_4HCO_3$)-ACN]; B %: 23%-53%, 10 min) to afford 5-(((8-fluoro-7-(8-fluoronaphthalen-1-yl)-2-((hexahydro-1H-pyrrolizin-7a-yl)methoxy)pyrido[4,3-d]pyrimidin-4-yl)amino)methyl)pyridin-2 (1H)-one (8.11 mg, 26% yield, 100% purity) as a white solid. $^1$H NMR (400 MHz, METHANOL-$d_4$) δ=9.15 (s, 1H), 8.11 (br d, J=7.8 Hz, 1H), 7.85 (d, J=8.1 Hz, 1H), 7.76 (dd, J=2.5, 9.4 Hz, 1H), 7.69 (t, J=7.7 Hz, 1H), 7.64-7.49 (m, 3H), 7.18 (dd, J=7.6, 13.0 Hz, 1H), 6.57 (d, J=9.4 Hz, 1H), 4.69 (s, 2H), 4.28 (s, 2H), 3.14-3.05 (m, 2H), 2.72 (td, J=6.5, 10.4 Hz, 2H), 2.06 (td, J=6.1, 12.1 Hz, 2H), 1.97-1.82 (m, 4H), 1.80-1.71 (m, 2H). LCMS (ESI, M+1): m/z 555.3.

Step A. 6-(8-fluoro-7-(8-fluoronaphthalen-1-yl)-2-((hexahydro-1H-pyrrolizin-7a-yl) methoxy)pyrido[4,3-d]pyrimidin-4-yl)-1,6-diazaspiro[3.5]nonan-2-one: A solution of 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d]pyrimidine (30 mg, 56.55 µmol) in DMF (1 mL) was added DIEA (29.3 mg, 226 µmol, 39.4 µL), 4 Å molecular sieves (10 mg) and 1,6-diazaspiro[3.5]nonan-2-one (15.8 mg, 113 µmol). The mixture was stirred at 60° C. for 2 hours. After completion, the mixture was filtered and concentrated in vacuum. The residue was purified by prep-HPLC (column: Phenomenex luna C18 150×40 mm×15 µL; mobile phase: [water (0.225% formic acid)-ACN]; B %: 15%-45%, 10 min) to give 6-(8-fluoro-7-(8-fluoronaphthalen-1-yl)-2-((hexahydro-1H-pyrrolizin-7a-yl)methoxy)pyrido[4,3-d]pyrimidin-4-yl)-1,6-diazaspiro[3.5]nonan-2-one (9.11 mg, 28% yield); White solid. $^1$H NMR (400 MHz, METHANOL-$d_4$) δ 9.14 (s, 1H), 8.53 (br s, 1H), 8.13 (br d, J=8.4 Hz, 1H), 7.87 (d, J=8.4 Hz, 1H), 7.71 (t, J=7.6 Hz, 1H), 7.62 (d, J=7.2 Hz, 1H), 7.58-7.49 (m, 1H), 7.25-7.15 (m, 1H), 4.60-7.57 (m, 2H), 4.48-4.27 (m, 2H), 4.03 (t, J=12.8 Hz, 1H), 3.95-3.80 (m, 1H), 3.66-3.52 (m, 2H), 3.25-3.10 (m, 2H), 2.97-2.87 (m, 1H), 2.83-2.74 (m, 1H), 2.35-2.23 (m, 2H), 2.23-2.09 (m, 5H), 2.09-1.96 (m, 5H). LCMS (ESI, M+1): m/z 571.2.

Example 98

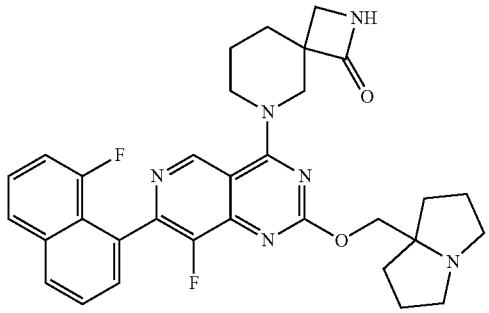 [SMILES: O=C1NCC12CCCN(c1nc(OCC34CCCN3CCC4)nc3c(F)c(-c4cccc5cccc(F)c45)ncc13)C2]

6-(8-fluoro-7-(8-fluoronaphthalen-1-yl)-2-((tetrahydro-1H-pyrrolizin-7a(5H)-yl) methoxy)pyrido[4,3-d]pyrimidin-4-yl)-2,6-diazaspiro[3.5]nonan-1-one mm×5 μm; mobile phase: [water (10 mM NH$_4$HCO$_3$)-ACN]; B %: 32%-62%, 10 min) to afford the title compound (5.18 mg, 8.91 μmol, 16% yield, 98.1% purity); White solid. LCMS (ESI, M+1): m/z 571.3.

Example 99

8-fluoro-7-(8-fluoronaphthalen-1-yl)-2-((hexahydro-1H-pyrrolizin-7a-yl)methoxy)-N-(1-methyl-1H-indazol-6-yl)pyrido[4,3-d]pyrimidin-4-amine

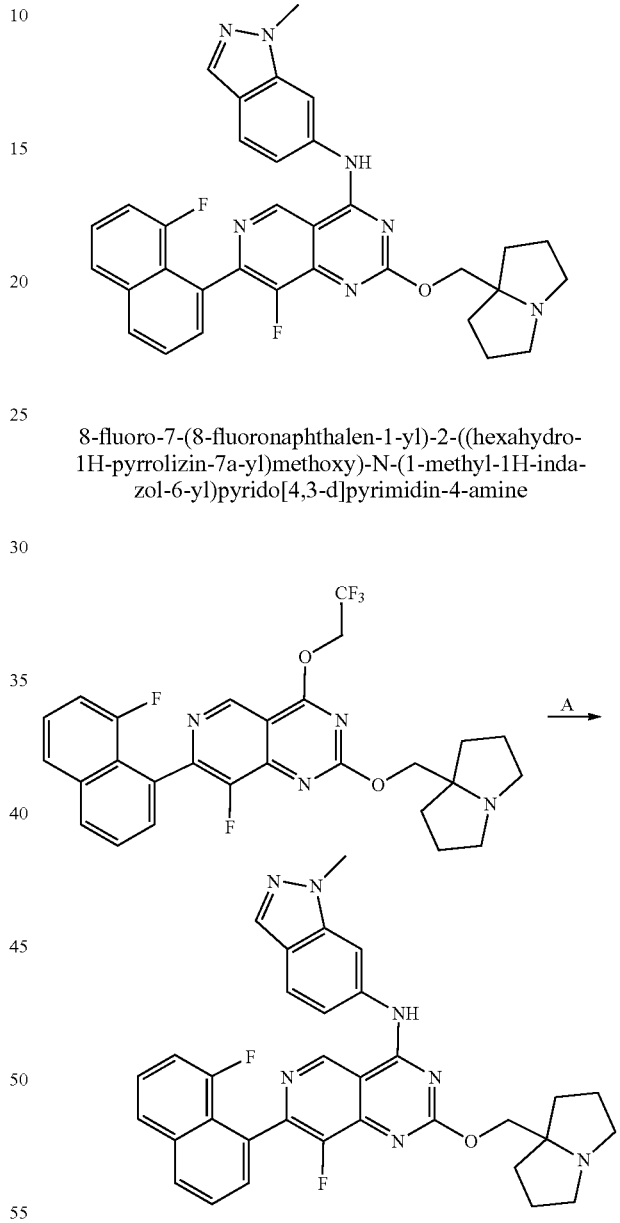

Step A. (S)-6-(8-fluoro-7-(8-fluoronaphthalen-1-yl)-2-((hexahydro-1H-pyrrolizin-7a-yl)methoxy)pyrido[4,3-d]pyrimidin-4-yl)-2,6-diazaspiro[3.5]nonan-1-one: To a solution 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (30.0 mg, 56.5 μmol) in DMF (1 mL) was added DIEA (29.2 mg, 226 μmol, 39.4 μL), 4 Å molecular sieves (10 mg) and (4R)-2,8-diazaspiro[3.5]nonan-3-one (15.8 mg, 113 μmol, 2.0 equiv.). The mixture was stirred at 40° C. for 12 hr. The reaction mixture was filtered and the filtrate was concentrated. The residue was purified by prep-HPLC (column: waters Xbridge 150×25

Step A. 8-fluoro-7-(8-fluoronaphthalen-1-yl)-2-((hexahydro-1H-pyrrolizin-7a-yl) methoxy)-N-(1-methyl-1H-indazol-6-yl)pyrido[4,3-d]pyrimidin-4-amine: To a mixture of 1-methylindazol-6-amine (11.1 mg, 75.4 μmol) in THF (1 mL) was added NaH (4.52 mg, 113 μmol, 60% purity) in one portion at 0° C. under N$_2$ for 15 minutes. Then 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (20.0 mg, 37.7 μmol) was added at 0° C. The mixture was stirred at 0° C. for 15 minutes. The residue was quenched with saturated NH$_4$Cl aqueous solution (0.1 mL)

dropwise, and then filtered. The filtrate was concentrated in vacuum. The residue was purified by prep-HPLC (column: Phenomenex Gemini-NX C18 75×30 mm×3 μm; mobile phase: [water (0.225% formic acid)-ACN]; B %: 18%-48%, 7 min) to afford 8-fluoro-7-(8-fluoronaphthalen-1-yl)-2-((hexahydro-1H-pyrrolizin-7a-yl)methoxy)-N-(1-methyl-1H-indazol-6-yl)pyrido[4,3-d]pyrimidin-4-amine (5.29 mg, 22% yield); Off-white solid. LCMS (ESI, M+1): m/z 578.4.

Example 100

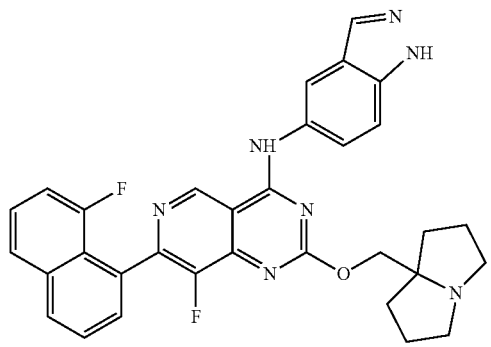 [SMILES: N=Cc1cc(Nc2nc(OCC34CCCN3CCC4)nc3c(F)c(-c4cccc5cccc(F)c45)ncc23)ccc1N]

8-fluoro-7-(8-fluoronaphthalen-1-yl)-2-((hexahydro-1H-pyrrolizin-7a-yl)methoxy)-N-(1H-indazol-5-yl)pyrido[4,3-d]pyrimidin-4-amine

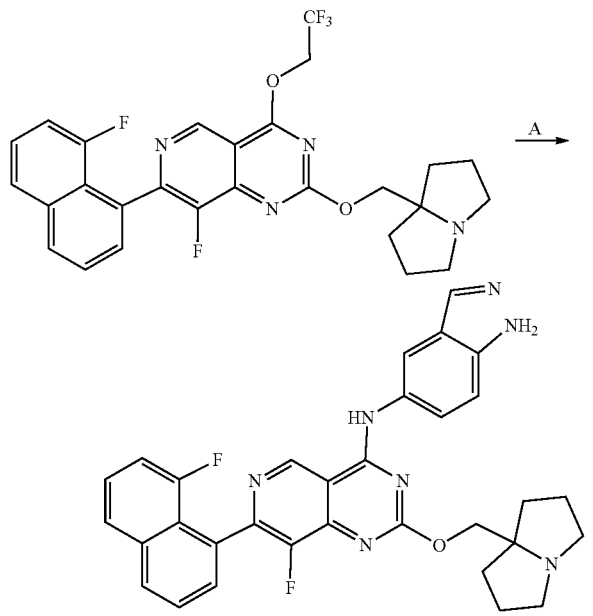

Step A. 8-fluoro-7-(8-fluoronaphthalen-1-yl)-2-((hexahydro-1H-pyrrolizin-7a-yl) methoxy)-N-(1H-indazol-5-yl)pyrido[4,3-d]pyrimidin-4-amine: To the mixture of 1H-indazol-5-amine (6.93 mg, 52.0 μmol), 4 Å MS (5 mg) in THF (0.5 mL) was added LiHMDS (1 M, 105 μL) at 0° C. After 0.5 hour, to the mixture was added 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (20.0 mg, 34.7 μmol, formic acid salt). The mixture was stirred at 20° C. for 14 hours. The reaction mixture was diluted with sat. NH₄Cl (3 mL) and extracted with ethyl acetate twice. The combined organic phase was washed with brine (5 mL), dried over anhydrous sodium sulfate. The mixture was filtered and concentrated to give a residue. The residue was purified by prep-HPLC (column: Phenomenex Gemini—NX C18 75×30 mm×3 μm; mobile phase: [water (10 mM NH₄HCO₃)-ACN]; B %: 40%-70%, 8 min) to afford 8-fluoro-7-(8-fluoronaphthalen-1-yl)-2-((hexahydro-1H-pyrrolizin-7a-yl)methoxy)-N-(1H-indazol-5-yl)pyrido[4,3-d]pyrimidin-4-amine (3.98 mg, 20% yield). Yellow Solid; LCMS (ESI, M+1): m/z 564.4.

Synthesis of Example 101 to 131: A mixture of 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine or 7-(8-chloronaphthalen-1-yl)-8-fluoro-2-((tetrahydro-1H-pyrrolizin-7a(5H)-yl) methoxy)-4-(2,2,2-trifluoroethoxy)pyrido[4,3-d]pyrimidine (0.04 mmol, 1 equiv.), amine (HNR₁R₂, 2 equiv.) and DIEA (3 eq or 5/7 eq for amine hydro/dihydro chlorides) in DMSO (1 mL) was heated with stirring at 40° C. for 16 hours. The resulting solution was cooled to room temperature and subjected to HPLC purification (deionized water/HPLC-grade acetonitrile or methanol, ammonia) to give the product.

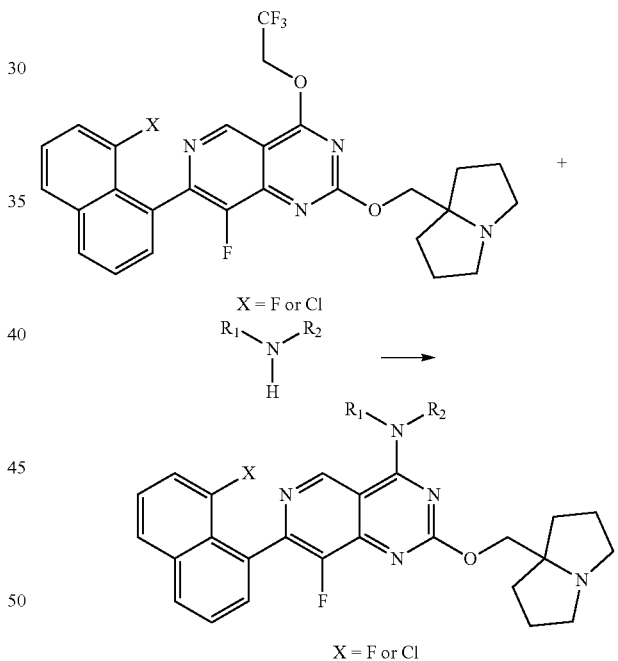

TABLE 1

Mass Spectrum Data of Example 103 to 131

| Example No. | Obs. M + 1 | Example No. | Obs. M + 1 |
|---|---|---|---|
| 101 | 570 | 117 | 562.2 |
| 102 | 561.2 | 118 | 557.4 |
| 103 | 589 | 119 | 558.2 |
| 104 | 584.1 | 120 | 566.2 |
| 105 | 575.1 | 121 | 580.2 |
| 106 | 574.2 | 122 | 580.2 |
| 107 | 562.2 | 123 | 514.2 |
| 108 | 599.2 | 124 | 567.2 |

TABLE 1-continued

Mass Spectrum Data of Example 103 to 131

| Example No. | Obs. M + 1 | Example No. | Obs. M + 1 |
| --- | --- | --- | --- |
| 109 | 598.1 | 125 | 580.2 |
| 110 | 547 | 126 | 569.2 |
| 111 | 548.4 | 127 | 566 |
| 112 | 546.4 | 128 | 581.2 |
| 113 | 546.4 | 129 | 546.2 |
| 114 | 542.2 | 130 | 560.2 |
| 115 | 543.2 | 131 | 582.2 |
| 116 | 560.2 | | |

Example 101

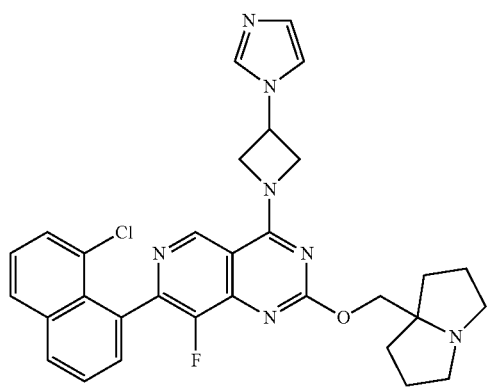 [SMILES: Fc1c(-c2cccc3cccc(Cl)c23)ncc2c(N3CC(n4ccnc4)C3)nc(OCC34CCCN3CCC4)nc12]

4-(3-(1H-imidazol-1-yl)azetidin-1-yl)-7-(8-chloronaphthalen-1-yl)-8-fluoro-2-((tetrahydro-1H-pyrrolizin-7a(5H)-yl)methoxy)pyrido[4,3-d]pyrimidine Example 102

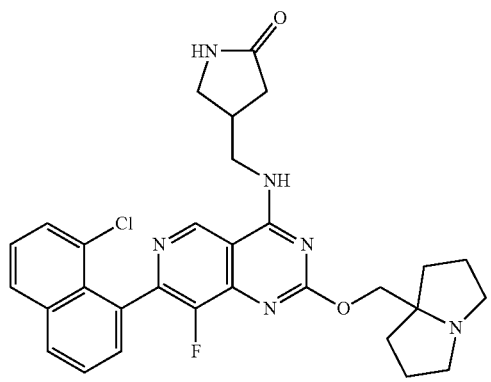 [SMILES: O=C1CC(CNc2nc(OCC34CCCN3CCC4)nc3c(F)c(-c4cccc5cccc(Cl)c45)ncc23)CN1]

4-(((7-(8-chloronaphthalen-1-yl)-8-fluoro-2-((tetrahydro-1H-pyrrolizin-7a(5H)-yl) methoxy)pyrido[4,3-d]pyrimidin-4-yl)amino)methyl)pyrrolidin-2-one Example 103

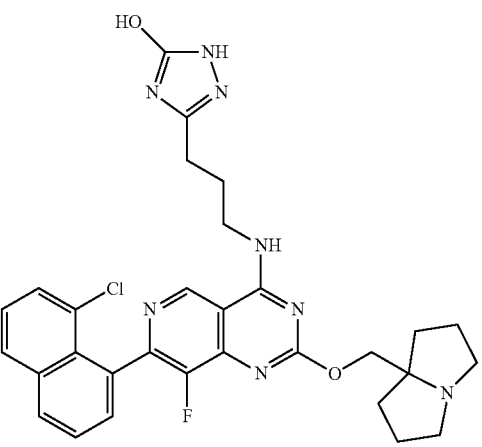 [SMILES: Oc1nc(CCCNc2nc(OCC34CCCN3CCC4)nc3c(F)c(-c4cccc5cccc(Cl)c45)ncc23)n[nH]1]

3-(3-((7-(8-chloronaphthalen-1-yl)-8-fluoro-2-((tetrahydro-1H-pyrrolizin-7a(5H)-yl) methoxy)pyrido[4,3-d]pyrimidin-4-yl)amino)propyl)-1H-1,2,4-triazol-5-ol Example 104

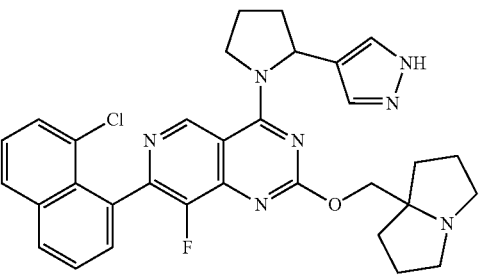 [SMILES: Fc1c(-c2cccc3cccc(Cl)c23)ncc2c(N3CCCC3c3cn[nH]c3)nc(OCC34CCCN3CCC4)nc12]

4-(2-(1H-pyrazol-4-yl)pyrrolidin-1-yl)-7-(8-chloronaphthalen-1-yl)-8-fluoro-2-((tetrahydro-1H-pyrrolizin-7a(5H)-yl)methoxy)pyrido[4,3-d]pyrimidine Example 105

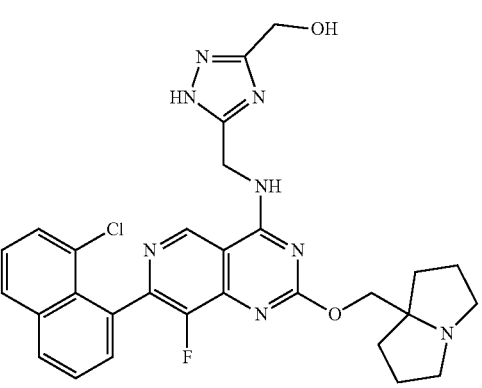 [SMILES: OCc1n[nH]c(CNc2nc(OCC34CCCN3CCC4)nc3c(F)c(-c4cccc5cccc(Cl)c45)ncc23)n1]

(5-(((7-(8-chloronaphthalen-1-yl)-8-fluoro-2-((tetra-hydro-1H-pyrrolizin-7a(5H)-yl) methoxy)pyrido[4,3-d]pyrimidin-4-yl)amino)methyl)-1H-1,2,4-triazol-3-yl)methanol Example 106

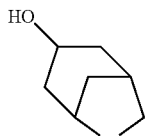
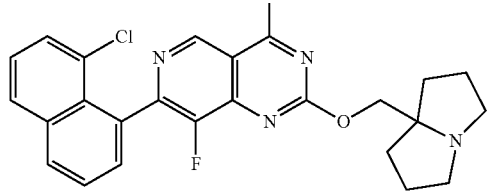

6-(7-(8-chloronaphthalen-1-yl)-8-fluoro-2-((tetra-hydro-1H-pyrrolizin-7a(5H)-yl) methoxy)pyrido[4,3-d]pyrimidin-4-yl)-6-azabicyclo[3.2.1]octan-3-ol Example 107

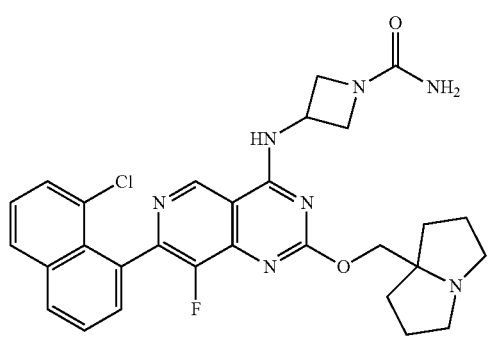 [SMILES: NC(=O)N1CC(Nc2nc(OCC34CCCN3CCC4)nc3c(F)c(-c4cccc5cccc(Cl)c45)ncc23)C1]

3-(((7-(8-chloronaphthalen-1-yl)-8-fluoro-2-((tetra-hydro-1H-pyrrolizin-7a(5H)-yl) methoxy)pyrido[4,3-d]pyrimidin-4-yl)amino)azetidine-1-carboxamide Example 108

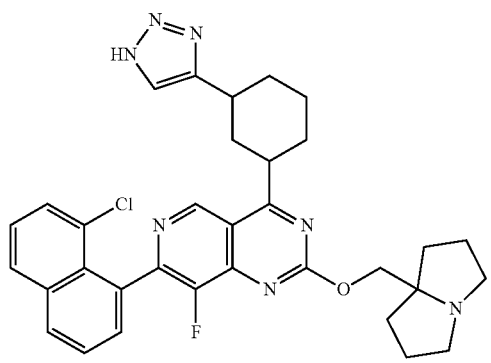 [SMILES: Fc1c(-c2cccc3cccc(Cl)c23)ncc2c(C3CCCC(c4c[nH]nn4)C3)nc(OCC34CCCN3CCC4)nc12]

4-(3-(1H-1,2,3-triazol-4-yl)piperidin-1-yl)-7-(8-chloronaphthalen-1-yl)-8-fluoro-2-((tetrahydro-1H-pyrrolizin-7a(5H)-yl)methoxy)pyrido[4,3-d]pyrimidine Example 109

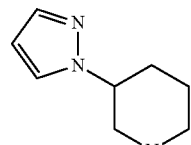
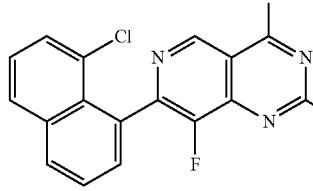

4-(3-(1H-pyrazol-1-yl)piperidin-1-yl)-7-(8-chloronaphthalen-1-yl)-8-fluoro-2-((tetrahydro-1H-pyrrolizin-7a(5H)-yl)methoxy)pyrido[4,3-d]pyrimidine Example 110

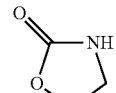
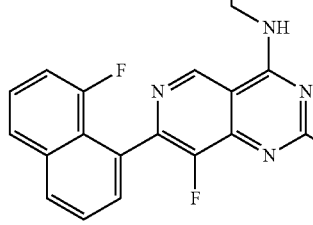

5-(((8-fluoro-7-(8-fluoronaphthalen-1-yl)-2-((tetra-hydro-1H-pyrrolizin-7a(5H)-yl) methoxy)pyrido[4,3-d]pyrimidin-4-yl)amino)methyl)oxazolidin-2-one Example 111

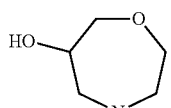
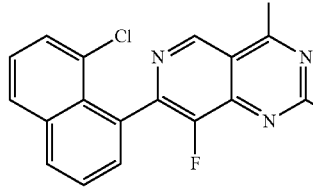

4-(8-fluoro-7-(8-fluoronaphthalen-1-yl)-2-((tetra-hydro-1H-pyrrolizin-7a(5H)-yl) methoxy)pyrido[4,3-d]pyrimidin-4-yl)-1,4-oxazepan-6-ol Example 112

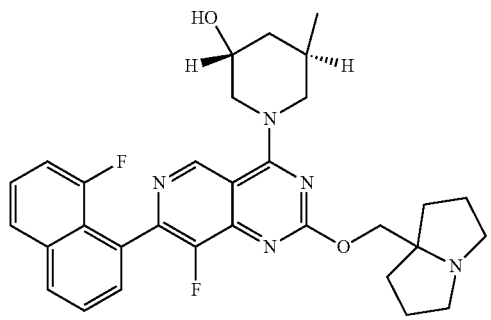 [SMILES: C[C@@H]1C[C@@H](O)CN(c2nc(OCC34CCCN3CCC4)nc3c(F)c(-c4cccc5cccc(F)c45)ncc23)C1]

(3R,5R)-1-(8-fluoro-7-(8-fluoronaphthalen-1-yl)-2-((tetrahydro-1H-pyrrolizin-7a(5H)-yl) methoxy) pyrido[4,3-d]pyrimidin-4-yl)-5-methylpiperidin-3-ol Example 113

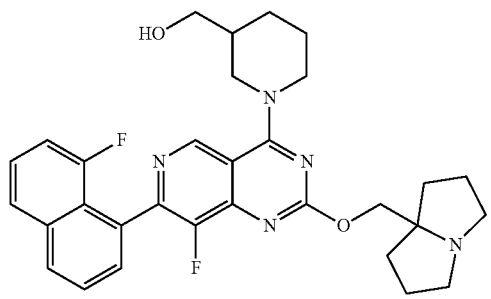 [SMILES: OCC1CCCN(c2nc(OCC34CCCN3CCC4)nc3c(F)c(-c4cccc5cccc(F)c45)ncc23)C1]

(1-(8-fluoro-7-(8-fluoronaphthalen-1-yl)-2-((tetra-hydro-1H-pyrrolizin-7a(5H)-yl) methoxy)pyrido[4,3-d]pyrimidin-4-yl)piperidin-3-yl)methanol Example 114

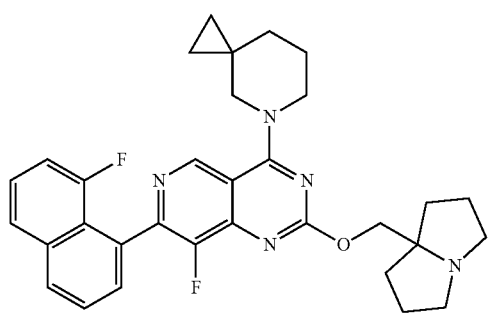 [SMILES: Fc1c(-c2cccc3cccc(F)c23)ncc2c(N3CCCC4(CC4)C3)nc(OCC34CCCN3CCC4)nc12]

8-fluoro-7-(8-fluoronaphthalen-1-yl)-4-(5-azaspiro [2.5]octan-5-yl)-2-((tetrahydro-1H-pyrrolizin-7a (5H)-yl)methoxy)pyrido[4,3-d]pyrimidine Example 115

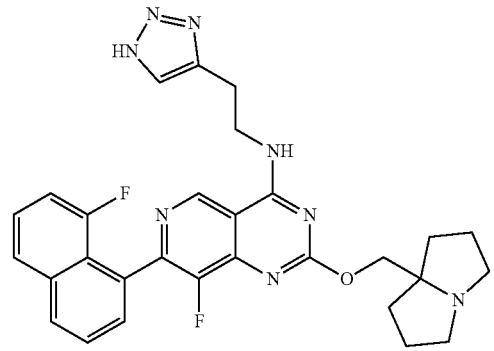 [SMILES: Fc1c(-c2cccc3cccc(F)c23)ncc2c(NCCc3c[nH]nn3)nc(OCC34CCCN3CCC4)nc12]

N-(2-(1H-1,2,3-triazol-4-yl)ethyl)-8-fluoro-7-(8-fluoronaphthalen-1-yl)-2-((tetrahydro-1H-pyrrolizin-7a(5H)-yl)methoxy)pyrido[4,3-d]pyrimidin-4-amine Example 116

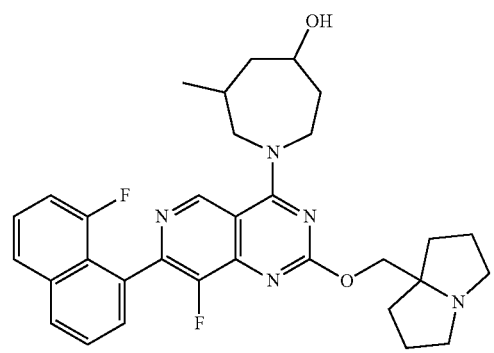 [SMILES: CC1CC(O)CCN(c2nc(OCC34CCCN3CCC4)nc3c(F)c(-c4cccc5cccc(F)c45)ncc23)C1]

1-(8-fluoro-7-(8-fluoronaphthalen-1-yl)-2-((tetra-hydro-1H-pyrrolizin-7a(5H)-yl) methoxy)pyrido[4,3-d]pyrimidin-4-yl)-6-methylazepan-4-ol Example 117

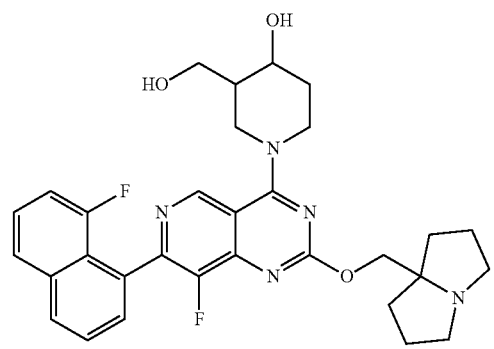 [SMILES: OCC1CN(c2nc(OCC34CCCN3CCC4)nc3c(F)c(-c4cccc5cccc(F)c45)ncc23)CCC1O]

287

1-(8-fluoro-7-(8-fluoronaphthalen-1-yl)-2-((tetra-hydro-1H-pyrrolizin-7a(5H)-yl) methoxy)pyrido[4,3-d]pyrimidin-4-yl)-3-(hydroxymethyl)piperidin-4-ol Example 118

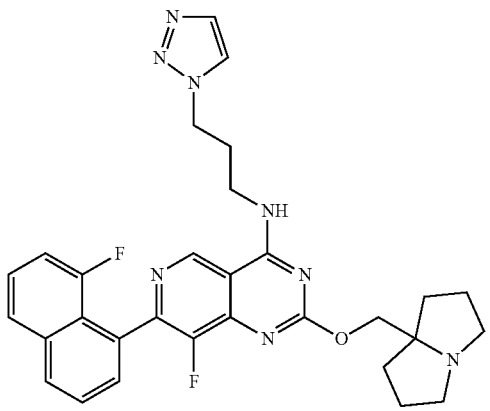 [SMILES: Fc1c(-c2cccc3cccc(F)c23)ncc2c(NCCCn3ccnn3)nc(OCC34CCCN3CCC4)nc12]

288

N-(3-(1H-tetrazol-1-yl)propyl)-8-fluoro-7-(8-fluoronaphthalen-1-yl)-2-((tetrahydro-1H-pyrrolizin-7a(5H)-yl)methoxy)pyrido[4,3-d]pyrimidin-4-amine Example 120

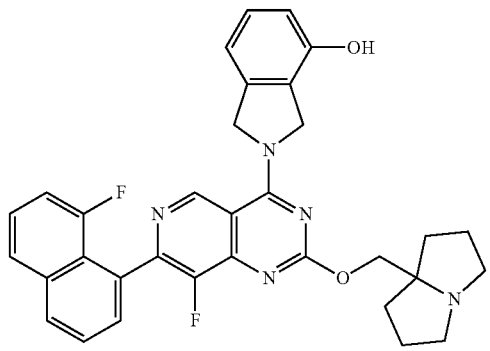

N-(3-(1H-1,2,3-triazol-1-yl)propyl)-8-fluoro-7-(8-fluoronaphthalen-1-yl)-2-((tetrahydro-1H-pyrrolizin-7a(5H)-yl)methoxy)pyrido[4,3-d]pyrimidin-4-amine Example 119

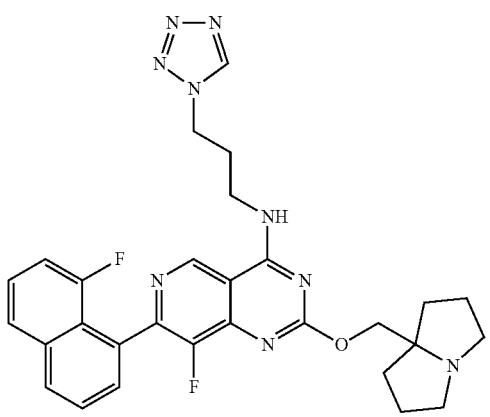 [SMILES: Fc1c(-c2cccc3cccc(F)c23)ncc2c(NCCCn3cnnn3)nc(OCC34CCCN3CCC4)nc12]

2-(8-fluoro-7-(8-fluoronaphthalen-1-yl)-2-((tetrahydro-1H-pyrrolizin-7a(5H)-yl) methoxy)pyrido[4,3-d]pyrimidin-4-yl)isoindolin-4-ol Example 121

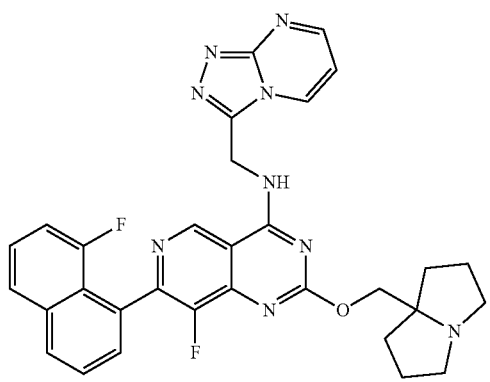 [SMILES: Fc1c(-c2cccc3cccc(F)c23)ncc2c(NCc3nnc4ncccn34)nc(OCC34CCCN3CCC4)nc12]

289

N-([1,2,4]triazolo[4,3-a]pyrimidin 3 ylmethyl) 8-fluoro-7-(8-fluoronaphthalen-1-yl)-2-((tetrahydro-1H-pyrrolizin-7a(5H)-yl)methoxy)pyrido[4,3-d]pyrimidin-4-amine Example 122

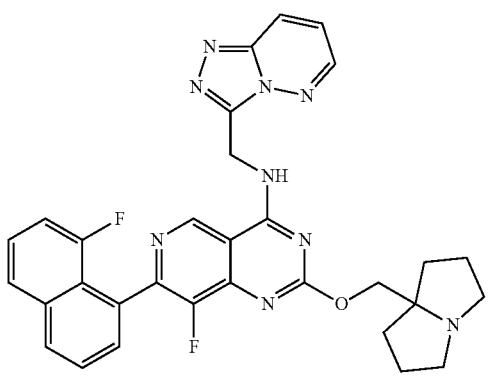 [SMILES: Fc1c(-c2cccc3cccc(F)c23)ncc2c(NCc3nnc4cccnn34)nc(OCC34CCCN3CCC4)nc12]

290

4-(3,6-dihydropyridin-1 (2H)-yl)-8-fluoro-7-(8-fluoronaphthalen-1-yl)-2-((tetrahydro-1H-pyrrolizin-7a(5H)-yl)methoxy)pyrido[4,3-d]pyrimidine Example 124

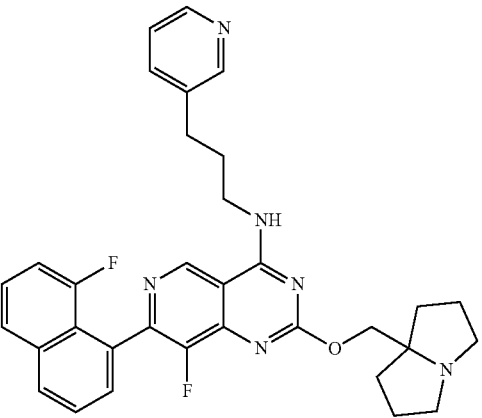

N-([1,2,4]triazolo[4,3-b]pyridazin-3-ylmethyl)-8-fluoro-7-(8-fluoronaphthalen-1-yl)-2-((tetrahydro-1H-pyrrolizin-7a(5H)-yl)methoxy)pyrido[4,3-d]pyrimidin-4-amine Example 123

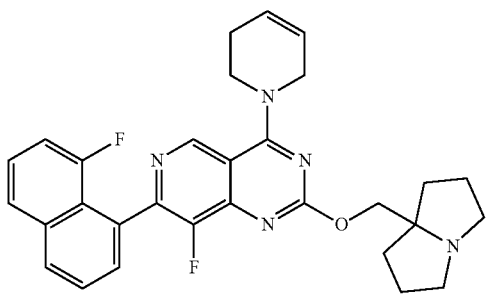 [SMILES: Fc1c(-c2cccc3cccc(F)c23)ncc2c(N3CC=CCC3)nc(OCC34CCCN3CCC4)nc12]

8-fluoro-7-(8-fluoronaphthalen-1-yl)-N-(3-(pyridin-3-yl)propyl)-2-((tetrahydro-1H-pyrrolizin-7a(5H)-yl)methoxy)pyrido[4,3-d]pyrimidin-4-amine Example 125

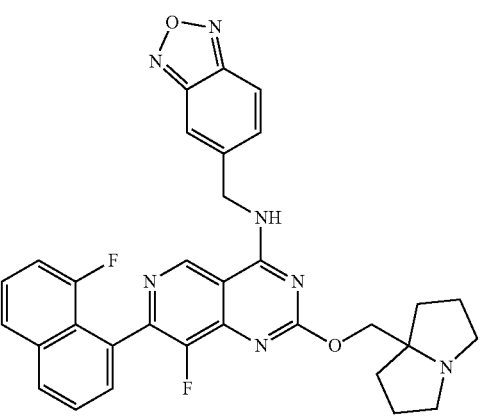 [SMILES: Fc1c(-c2cccc3cccc(F)c23)ncc2c(NCc3ccc4nonc4c3)nc(OCC34CCCN3CCC4)nc12]

291

N-(benzo[c][1,2,5]oxadiazol-5-ylmethyl)-8-fluoro-7-(8-fluoronaphthalen-1-yl)-2-((tetrahydro-1H-pyrrolizin-7a(5H)-yl)methoxy)pyrido[4,3-d]pyrimidin-4-amine Example 126

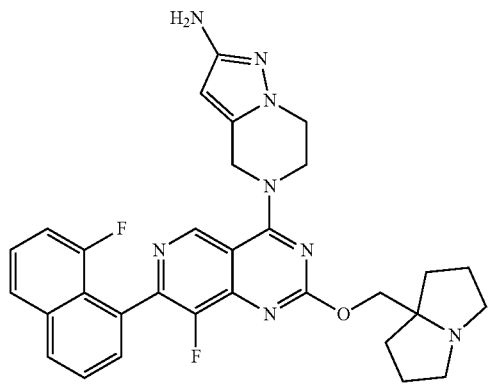 [SMILES: Nc1cc2n(n1)CCN(c1nc(OCC34CCCN3CCC4)nc3c(F)c(-c4cccc5cccc(F)c45)ncc13)C2]

292

3-(((8-fluoro-7-(8-fluoronaphthalen-1-yl)-2-((tetrahydro-1H-pyrrolizin-7a(5H)-yl) methoxy)pyrido[4,3-d]pyrimidin-4-yl)amino)methyl)thietane 1,1-dioxide Example 128

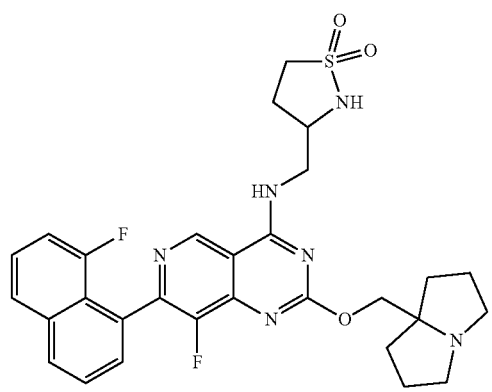

5-(8-fluoro-7-(8-fluoronaphthalen-1-yl)-2-((tetrahydro-1H-pyrrolizin-7a(5H)-yl) methoxy)pyrido[4,3-d]pyrimidin-4-yl)-4,5,6,7-tetrahydropyrazolo[1,5-a]pyrazin-2-amine Example 127

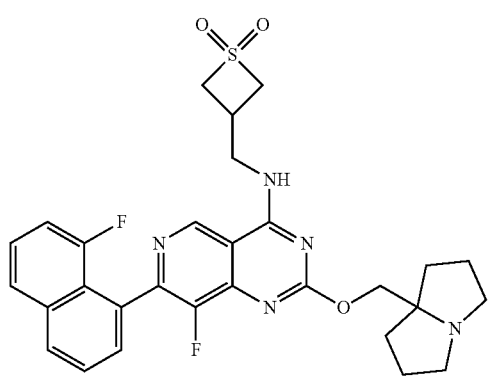 [SMILES: O=S1(=O)CC(CNc2nc(OCC34CCCN3CCC4)nc3c(F)c(-c4cccc5cccc(F)c45)ncc23)C1]

(R)-3-(((8-fluoro-7-(8-fluoronaphthalen-1-yl)-2-((tetrahydro-1H-pyrrolizin-7a(5H)-yl) methoxy) pyrido[4,3-d]pyrimidin-4-yl)amino)methyl)isothiazolidine 1,1-dioxide Example 129

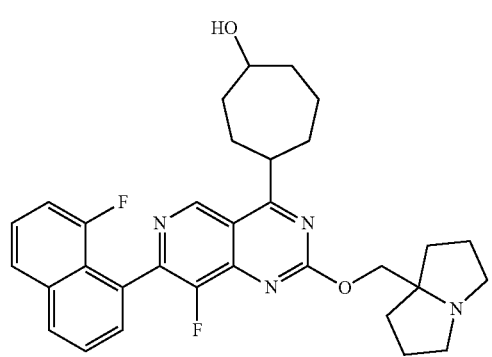 [SMILES: OC1CCCC(c2nc(OCC34CCCN3CCC4)nc3c(F)c(-c4cccc5cccc(F)c45)ncc23)CC1]

293

1-(8-fluoro-7-(8-fluoronaphthalen-1-yl)-2-((tetra-hydro-1H-pyrrolizin-7a(5H)-yl) methoxy)pyrido[4,3-d]pyrimidin-4-yl)azepan-4-ol Example 130

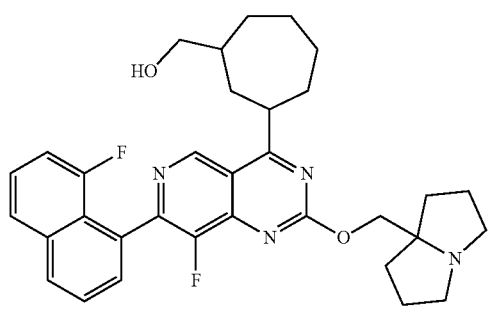 [SMILES: OCC1CCCCC(c2nc(OCC34CCCN3CCC4)nc3c(F)c(-c4cccc5cccc(F)c45)ncc23)C1]

(1-(8-fluoro-7-(8-fluoronaphthalen-1-yl)-2-((tetra-hydro-1H-pyrrolizin-7a(5H)-yl) methoxy)pyrido[4,3-d]pyrimidin-4-yl)azepan-3-yl)methanol Example 131

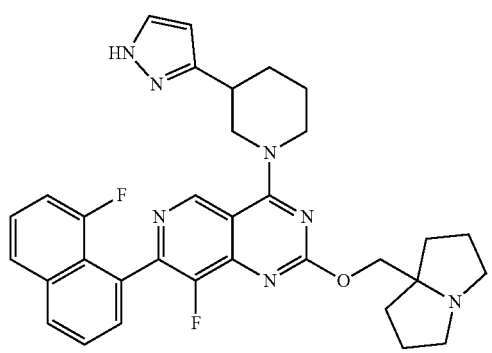 [SMILES: Fc1c(-c2cccc3cccc(F)c23)ncc2c(N3CCCC(c4cc[nH]n4)C3)nc(OCC34CCCN3CCC4)nc12]

4-(3-(1H-pyrazol-3-yl)piperidin-1-yl)-8-fluoro-7-(8-fluoronaphthalen-1-yl)-2-((tetrahydro-1H-pyrrolizin-7a(5H)-yl)methoxy)pyrido[4,3-d]pyrimidine Example 132

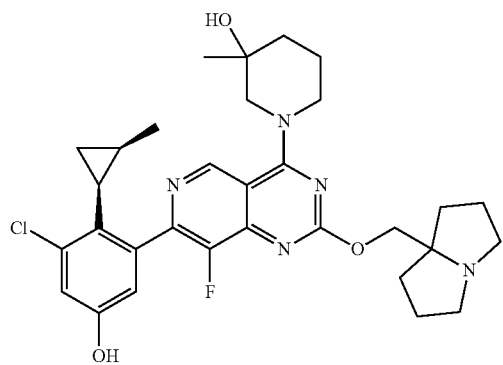 [SMILES: C[C@@H]1C[C@@H]1c1c(Cl)cc(O)cc1-c1ncc2c(N3CCCC(C)(O)C3)nc(OCC34CCCN3CCC4)nc2c1F]

294

1-(7-(3-chloro-5-hydroxy-2-((1S,2R)-2-methylcyclopropyl)phenyl)-8-fluoro-2-((tetrahydro-1H-pyrrolizin-7a(5H)-yl)methoxy)pyrido[4,3-d]pyrimidin-4-yl)-3-methylpiperidin-3-ol

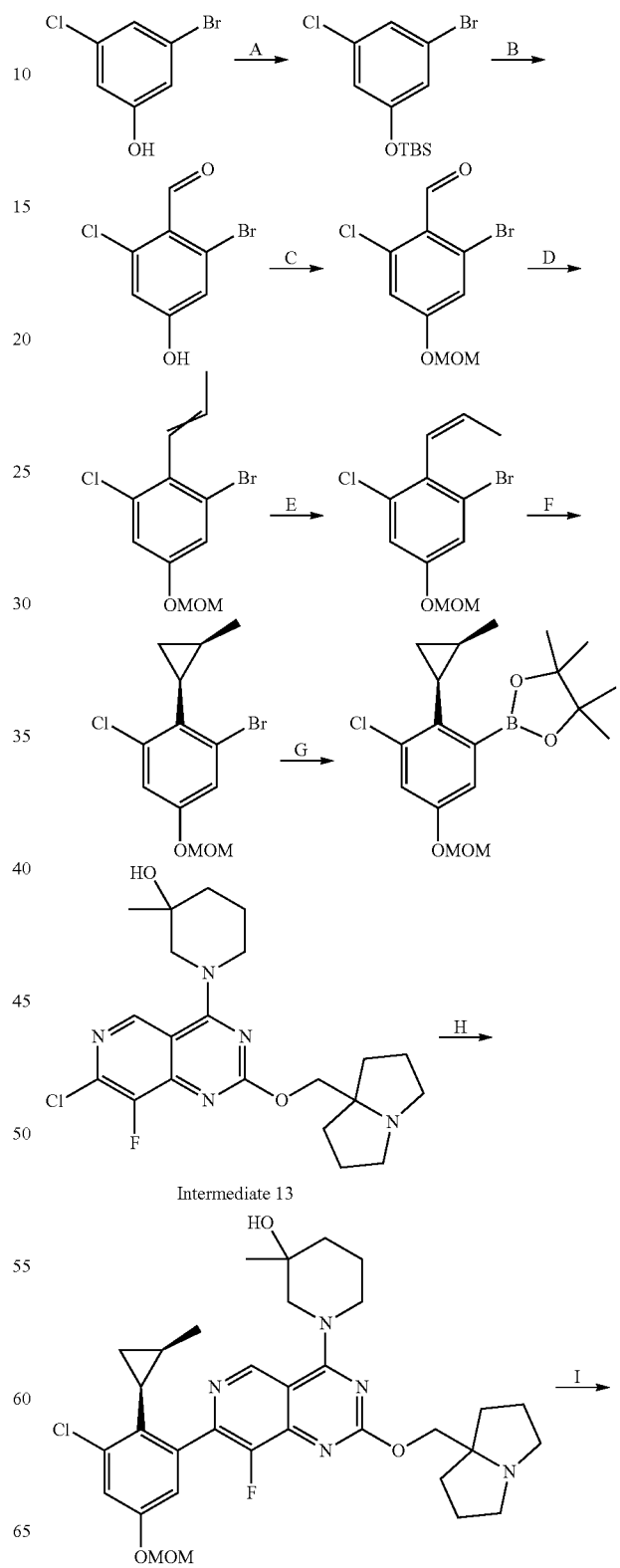

Intermediate 13

-continued

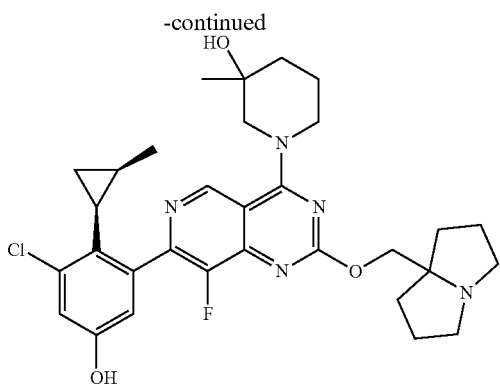

Step A. (3-bromo-5-chloro-phenoxy)-tert-butyl-dimethyl-silane: To the mixture of 3-bromo-5-chlorophenol (50 g, 1.0 equiv.) and imidazole (36.1 g, 2.2 equiv.) in DMF (250 mL) was added TBSCl (40 g, 1.1 equiv.) at 0° C. The reaction was stirred and allowed to warm up to 25° C. over the course of 15 hours. The mixture was diluted with water (3 L) and extracted with ethyl acetate (400 mL×2). The combined organic layers were washed with saturated aqueous NH$_4$Cl solution (150 mL), dried over anhydrous Na$_2$SO$_4$, concentrated, and purified by silica gel column chromatography (petroleum ether) to afford the title compound (89.5 g, crude) as a colorless oil; $^1$H NMR (400 MHz, DMSO-d$_6$) δ=7.31 (d, J=1.6 Hz, 1H), 7.03 (t, J=1.2 Hz, 1H), 6.94 (d, J=2.0 Hz, 1H), 0.94 (s, 9H), 0.21 (s, 6H).

Step B. 2-bromo-6-chloro-4-hydroxy-benzaldehyde: To the solution of (3-bromo-5-chloro-phenoxy)-tert-butyl-dimethyl-silane (84.5 g, crude) in THF (850 mL) was added LDA (2 M in hexane, 184 mL) dropwise at −65° C. The reaction was stirred at −65° C. for 2 hours. DMF (40.5 mL) was added dropwise at −65° C. and the reaction was stirred at −65° C. for 0.1 hour. The mixture was quenched with 1.5N aqueous HCl solution between −65° C. and 0° C. until the pH was 2-3 and then extracted with ethyl acetate (300 mL×3). The combined organic layers were dried over anhydrous Na$_2$SO$_4$ and concentrated. The residue was dispersed in petroleum ether/ethyl acetate 20:1 (210 mL), stirred for 0.5 hour and filtered. The filter cake was washed with petroleum ether (50 mL) and dried under reduced pressure to afford the title compound (42.7 g, 86% yield over two steps) as a light yellow solid; $^1$H NMR (400 MHz, DMSO-d$_6$) δ=11.38 (br s, 1H), 10.13 (s, 1H), 7.11 (d, J=2.4 Hz, 1H), 6.95 (d, J=2.0 Hz, 1H); LCMS (ESI, M+1): m/z=236.9.

Step C. 2-bromo-6-chloro-4-(methoxymethoxy)benzaldehyde: To the solution of 2-bromo-6-chloro-4-hydroxy-benzaldehyde (49 g, 1 equiv.) and DIEA (54.2 g, 2.0 equiv.) in DCM (500 mL) was added MOMCl (21.8 g, 1.3 equiv.) dropwise at 0° C. under N$_2$ atmosphere. The reaction was stirred between 0° C. and 15° C. for 1 hour. The mixture was quenched with saturated aqueous NaHCO$_3$ solution (100 mL) and water (100 mL) maintaining the temperature below 10° C. The organic layer was washed with saturated aqueous NH$_4$Cl solution (200 mL×5) and water (100 mL), dried over anhydrous Na$_2$SO$_4$, concentrated and purified by silica gel column chromatography (petroleum ether/ethyl acetate 5:1 to 9:2) to afford the title compound (56 g, 94% yield) as a white solid; $^1$H NMR (400 MHz, DMSO-4) δ=10.18 (s, 1H), 7.42 (d, J=2.4 Hz, 1H), 7.29 (d, J=2.4 Hz, 1H), 5.36 (s, 2H), 3.40 (s, 3H).

Step D. 1-bromo-3-chloro-5-(methoxymethoxy)-2-(prop-1-en-1-yl)benzene: To the mixture of ethyl(triphenyl)phosphonium bromide (59.8 g, 1.5 equiv.) in THF (350 mL) was added t-BuOK (1 M in THF, 140 mL, 1.3 equiv.) dropwise at 0° C. The mixture was stirred between 0 and 10° C. for 1 hour. A solution of 2-bromo-6-chloro-4-(methoxymethoxy)benzaldehyde (30 g, 1.0 equiv.) in THF (300 mL) was added dropwise maintaining the temperature below 10° C. The mixture was stirred between 0 and 10° C. for 0.5 hour. The mixture was quenched with water (200 mL) maintaining the temperature below 10° C. The mixture was concentrated and extracted with ethyl acetate (100 mL×3). The combined organic layers were dried over anhydrous Na$_2$SO$_4$, concentrated and purified by silica gel column chromatography (petroleum ether) to afford the title compound (30 g, 95% yield) as a light yellow liquid.

Step E. 1-bromo-3-chloro-5-(methoxymethoxy)-2-[(Z)-prop-1-enyl]benzene: 1-bromo-3-chloro-5-(methoxymethoxy)-2-(prop-1-en-1-yl)benzene (30 g, 1 equiv.) was purified by prep-HPLC [column: Phenomenex luna C18 (250×70 mm, 10 um); mobile phase: [water (0.225% Formic acid)-ACN] B %: 80%-100%, 13 min) to afford the title compound (11.5 g, 38% yield) as a light yellow liquid; $^1$H NMR (400 MHz, chloroform-d) δ=7.24 (d, J=2.4 Hz, 1H), 7.10 (d, J=2.4 Hz, 1H), 6.20-6.18 (m, 1H), 5.94 (qd, J=6.8, 11.2 Hz, 1H), 5.15 (s, 2H), 3.49 (s, 3H), 1.58-1.56 (m, 3H).

Step F. cis-1-bromo-3-chloro-5-(methoxymethoxy)-2-(2-methylcyclopropyl)benzene: To a solution of ZnEt$_2$ (1 M in n-hexane, 175 mL, 6 equiv.) in DCM (180 mL) was added TFA (20.0 g, 6 equiv.) in DCM (20 mL) dropwise at −40° C. The reaction was stirred at −40° C. for 30 minutes. A solution of CH$_2$I$_2$ (46.9 g, 6 equiv.) in DCM (10 mL) was added dropwise at −40° C. and the reaction was stirred at −40° C. for 30 minutes. l-bromo-3-chloro-5-(methoxymethoxy)-2-[(Z)-prop-1-enyl]benzene (8.5 g, 1.0 equiv.) in DCM (10 mL) was added dropwise at −40° C. and the reaction was stirred and allowed to warm up to 25° C. for 16 hours. The mixture was quenched with saturated aqueous NaHCO$_3$ solution maintaining the temperature below 10° C. until pH 7-8. The mixture was filtered through a pad of celite. The filter cake was washed with DCM (100 mL×2). The layers of the filtrate were separated, and the aqueous layer was extracted with DCM (100 mL×3). The combined organic layers were dried over anhydrous Na$_2$SO$_4$, concentrated and purified reversed phase flash chromatography (mobile phase: [water (0.1% Formic acid)/ACN 1:9]) to afford the title compound (1.5 g, 16% yield) as a yellow oil; $^1$H NMR (400 MHz, chloroform-d) δ=7.22 (d, J=2.4 Hz, 1H), 7.06 (d, J=2.4 Hz, 1H), 5.13 (s, 2H), 3.48 (s, 3H), 1.82 (dt, J=6.8, 8.4 Hz, 1H), 1.58-1.56 (m, 2H), 1.54-1.37 (m, 1H), 0.85 (d, J=6.0 Hz, 3H).

Step G. cis-2-[3-chloro-5-(methoxymethoxy)-2-(2-methylcyclopropyl)phenyl]-4,4,5,5-tetramethyl-1,3,2-dioxaborolane: To a mixture of cis-1-bromo-3-chloro-5-(methoxymethoxy)-2-(2-methylcyclopropyl)benzene (1.4 g, 1.0 equiv.), 4,4,5,5-tetramethyl-2-(4,4,5,5-tetramethyl-1,3,2-dioxaborolan-2-yl)-1,3,2-dioxaborolane (2.33 g, 2.0 equiv.) and KOAc (1.57 g, 3.5 equiv.) in dioxane (22 mL) was added Pd(dppf)Cl$_2$ (336 mg, 0.1 equiv.). The reaction was stirred 80° C. for 5 hours under N$_2$ atmosphere. The reaction mixture was diluted with water (100 mL) and extracted with ethyl acetate (20 mL×4). The combined organic layers were dried over anhydrous Na$_2$SO$_4$, concentrated and purified by silica gel column chromatography [petroleum ether/ethyl acetate 30:1 to 10:1]. The crude product was purified again by reversed phase flash chromatography (mobile phase: [water (0.1% Formic acid)]) to afford the title compound (0.4 g, crude) as a light yellow oil; $^1$H NMR (400 MHz, chloroform-d) δ=7.13-7.10 (m, 2H), 5.16-5.15 (m, 2H), 3.48-3.46 (m, 3H), 2.11-2.05 (m, 1H), 1.53-1.51 (m, 1H), 1.39-1.36 (m, 12H), 1.28-1.25 (m, 2H), 0.72 (d, J=6.0 Hz, 3H); LCMS (ESI, M+1): m/z=353.2.

Step H. cis-1-[7-[3-chloro-5-(methoxymethoxy)-2-(2-methylcyclopropyl)phenyl]-8-fluoro-2-((tetrahydro-1H-pyrrolizin-7a(5H)-yl)methoxy)pyrido[4,3-d]pyrimidin-4-yl]-3-methyl-piperidin-3-ol: A mixture of 1-[7-chloro-8-fluoro-2-((tetrahydro-1H-pyrrolizin-7a(5H)-yl) methoxy) pyrido[4,3-d]pyrimidin-4-yl]-3-methyl-piperidin-3-ol, Intermediate 13 (65 mg, 1.0 equiv.), cis-2-[3-chloro-5-(methoxymethoxy)-2-(2-methylcyclopropyl)phenyl]-4,4,5,5-tetramethyl-1,3,2-dioxaborolane (95 mg, crude), cat-aCXium A Pd G3 (17 mg, 0.15 equiv.) and $K_3PO_4$ (1.5 M in water, 300 μL, 3 equiv.) in methoxycyclopentane (1.5 mL) was stirred at 90° C. for 1 hours under $N_2$ atmosphere. The mixture was diluted with water (1 mL) and extracted with ethyl acetate (2 mL×4). The combined organic layers were concentrated and purified by reversed phase flash chromatography (Mobile phase: [water (0.1% formic acid)/acetonitrile 1:1] to afford the title compound (69 mg, 70% yield) as a brown solid; LCMS (ESI, M+1): m/z=626.4.

Step I. 1-(7-(3-chloro-5-hydroxy-2-((1S,2R)-2-methylcyclopropyl)phenyl)-8-fluoro-2-((tetrahydro-1H-pyrrolizin-7a (5H)-yl)methoxy)pyrido[4,3-d]pyrimidin-4-yl)-3-methylpiperidin-3-ol: To the solution of cis-1-[7-[3-chloro-5-(methoxymethoxy)-2-(2-methylcyclopropyl)phenyl]-8-fluoro-2-((tetrahydro-1H-pyrrolizin-7a(5H)-yl) methoxy) pyrido[4,3-d]pyrimidin-4-yl]-3-methyl-piperidin-3-ol (69 mg, 1.0 equiv.) in MeCN (2 mL) was added HCl in dioxane (4 M, 1.5 mL) dropwise at 0° C. The reaction was stirred at 0° C. for 0.5 hour. The mixture was concentrated at room temperature. The residue was dissolved in ethyl acetate (20 mL) and water (5 mL). The pH of the mixture was adjusted to 8 with $NaHCO_3$ solid maintaining the temperature below 5° C. The mixture was extracted with ethyl acetate (10 mL×4). The combined organic layers were dried over anhydrous $Na_2SO_4$, concentrated and purified by prep-HPLC (column: water s Xbridge 150×25 mm×Sum; mobile phase: [water (10 mM $NH_4HCO_3$)/CAN], B %: 29%-59%, 9 min] to afford the title compound (24.9 mg, 37% yield) as a white solid; $^1$H NMR (400 MHz, methanol-d4) δ=9.21-9.17 (m, 1H), 7.00-6.94 (m, 1H), 6.81-6.76 (m, 1H), 4.51 (d, J=12 Hz, 1H), 4.28-4.25 (m, 3H), 3.66-3.59 (m, 1H), 3.46-3.44 (m, 1H), 3.11-3.09 (m, 2H), 2.73 (td, J=6.4, 10.4 Hz, 2H), 2.09-2.06 (m, 3H), 1.94-1.87 (m, 6H), 1.79-1.74 (m, 4H), 1.28-1.27 (m, 3H), 1.21-1.04 (m, 1H), 0.82 (br s, 1H), 0.65 (br d, J=5.6 Hz, 3H), 0.52-0.15 (m, 1H); LCMS (ESI, M+1): m/z=582.4.

yl)-8-Example 133

7-(7-(8-ethyl-7-fluoro-3-hydroxy)naphthalen-1-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decan-2-one

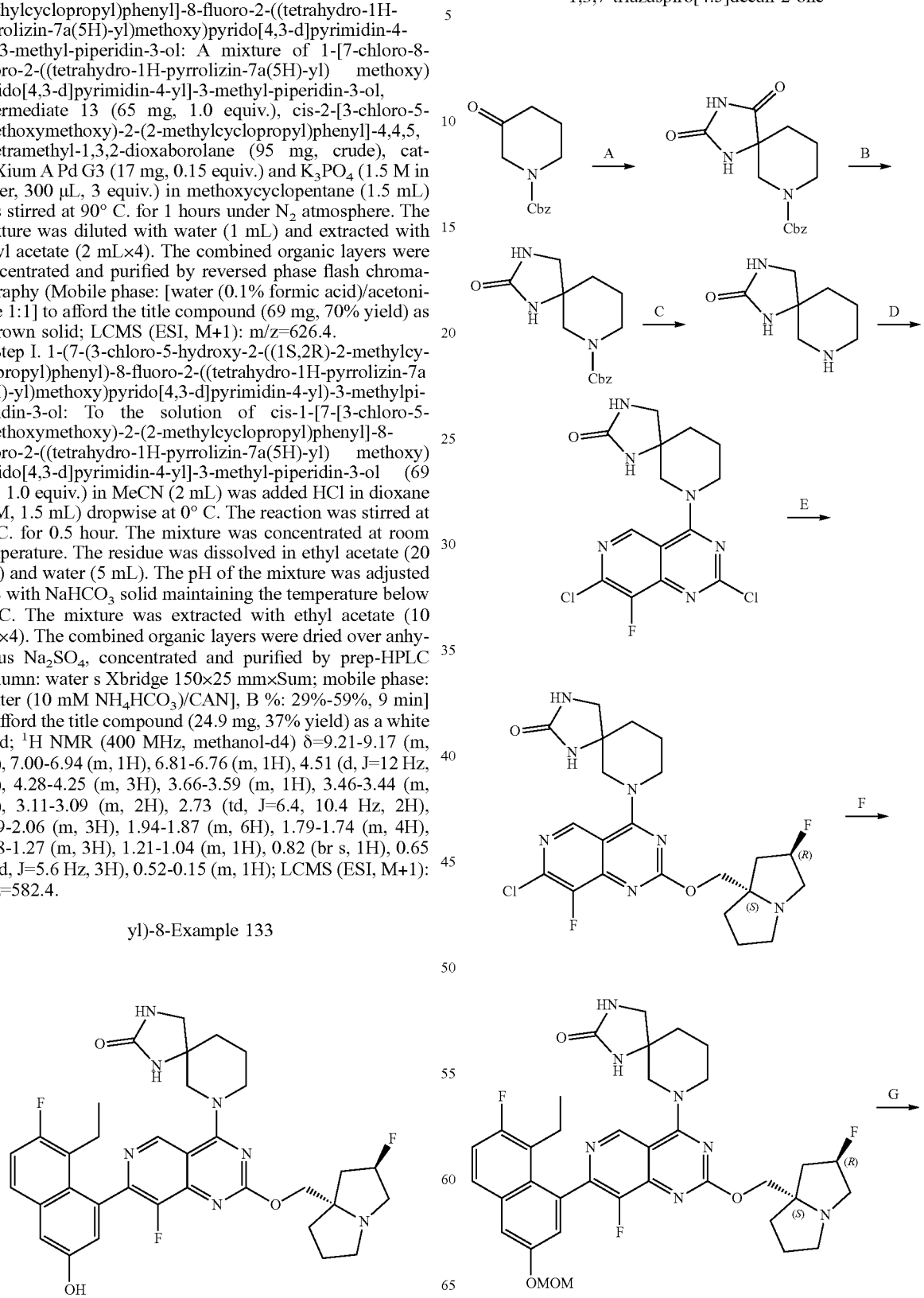

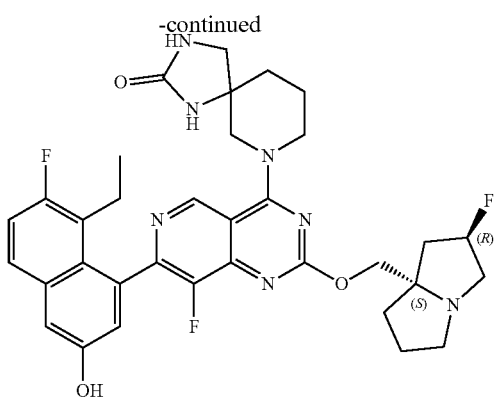

Step A. benzyl 2,4-dioxo-1,3,7-triazaspiro[4.5]decane-7-carboxylate: To the mixture of benzyl 3-oxopiperidine-1-carboxylate (7.00 g, 1.0 equiv.), (NH₄)₂CO₃ (8.65 g, 3.0 equiv.) in EtOH (35 mL) and water (35 mL) was added KCN (2.93 g, 1.5 equiv.), the reaction was stirred at 85° C. for 16 hours. The reaction was cooled to 25° C. and concentrated. The residue was diluted with water (300 mL), extracted with ethyl acetate (300 mL×3). The combined organic phase was washed with brine (100 mL), dried over anhydrous sodium sulfate, concentrated to give the title compound (6.70 g, 63% yield) as a white solid; $^1$H NMR (400 MHz, methanol-d4) δ 7.42-7.19 (m, 5H), 5.19-4.97 (m, 2H), 3.84 (br s, 2H), 3.54-3.34 (m, 1H), 3.26-3.06 (m, 1H), 2.10-1.94 (m, 1H), 1.91-1.50 (m, 3H); LCMS (ESI, M+Na): m/z=326.1.

Step B. Benzyl 2-oxo-1,3,7-triazaspiro[4.5]decane-7-carboxylate: To the solution of benzyl 2,4-dioxo-1,3,7-triazaspiro[4.5]decane-7-carboxylate (1.00 g, 1.0 equiv.) in THF (20 mL) was added BH₃-THF (1 M in THF, 19.8 mL, 6.0 equiv.) at 0° C. The reaction was then stirred at 80° C. for 2 hours. The mixture was quenched by addition of MeOH (20 mL) slowly at 0° C. and stirred at 20° C. for 0.5 hour and then concentrated. The residue was purified reversed phase flash chromatography (C18, mobile phase: [water (0.1% formic acid)/acetonitrile]) to provide the title compound (800 mg, 82% yield) as a yellow solid; LCMS (ESI, M+1): m/z=290.1.

Step C. 1,3,7-triazaspiro[4.5]decan-2-one: To a solution of benzyl 2-oxo-1,3,7-triazaspiro[4.5]decane-7-carboxylate (480 mg, 1.0 equiv.) in t-BuOH (8 mL) was added Pd(OH)₂C (70 mg, 10% purity) under N₂. The suspension was degassed and purged with H₂ several times. The reaction was stirred under H₂ (15 psi) at 20° C. for 2 hours. The mixture was filtered and concentrated to give the title compound (255 mg, crude) as a white solid.

Step D. 7-(2,7-dichloro-8-fluoropyrido[4,3-d]pyrimidin-4-yl)-1,3,7-triazaspiro[4.5]decan-2-one: To a mixture of 2,4,7-trichloro-8-fluoropyrido[4,3-d]pyrimidine (500 mg, 1.0 equiv.), DIEA (768 mg, 3.0 equiv.) in dichloromethane (8 mL) was added 1,3,7-triazaspiro[4.5]decan-2-one (250 mg, 0.8 equiv.) at −40° C. The reaction was stirred at −40° C. for 0.5 hour. The mixture was diluted with dichloromethane (10 mL) and water (10 mL), extracted with dichloromethane (5 mL). The combined organic phase was washed with brine (8 mL), dried over anhydrous sodium sulfate, concentrated to give the title compound (650 mg, crude) as a yellow solid.

Step E. 7-(7-chloro-8-fluoro-2-(((2R,7aS)-2-fluorohexahydro-1H-pyrrolizin-7a-yl) methoxy)pyrido[4,3-d]pyrimidin-4-yl)-1,3,7-triazaspiro[4.5]decan-2-one: To the mixture of 7-(2,7-dichloro-8-fluoropyrido[4,3-d]pyrimidin-4-yl)-1,3,7-triazaspiro[4.5]decan-2-one (650 mg, crude), ((2R,7aS)-2-fluorohexahydro-1H-pyrrolizin-7a-yl)methanol (502 mg), 4 Å molecular sieves (300 mg) in dioxane (7 mL) was added DIEA (679 mg). The reaction was stirred at 90° C. for 12 hours. The reaction mixture was diluted with ethyl acetate (15 mL) and water (10 mL). The aqueous layer was extracted with ethyl acetate (15 mL). The combined organic phase was washed with brine (20 mL), dried over anhydrous sodium sulfate, concentrated and purified reversed phase flash chromatography (C18, mobile phase: [water (0.1% formic acid)/acetonitrile]) to give the title compound (405 mg, 38% yield over three steps) as a yellow solid; $^1$H NMR (400 MHz, chloroform-d) δ 8.74-8.40 (m, 1H), 5.47-5.21 (m, 1H), 4.61-4.12 (m, 4H), 3.97-2.74 (m, 8H), 2.51-2.05 (m, 4H), 2.01-1.56 (m, 6H); LCMS (ESI, M+1): m/2=494.2.

Step F. 7-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decan-2-one: To a mixture of 7-(7-chloro-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decan-2-one (210 mg, 1.0 equiv.), 2-(8-ethyl-7-fluoro-3-(methoxymethoxy)naphthalen-1-yl)-4,4,5,5-tetramethyl-1,3,2-dioxaborolane (184 mg, 1.2 equiv.), K₃PO₄ (1.5 M in water, 3.0 equiv.) in THF (3 mL) was added CataCXium A Pd G3 (31.0 mg, 0.1 equiv.) under N₂. The reaction was stirred at 60° C. for 28 hours. The reaction mixture was diluted with ethyl acetate (15 mL) and water (10 mL). The aqueous layer was extracted with ethyl acetate (15 mL). The combined organic phase was washed with brine (10 mL), dried over anhydrous sodium sulfate, concentrated and purified by reversed phase flash chromatography (mobile phase: [water (0.1% formic acid)/acetonitrile]) and prep-HPLC [column: Phenomenex Gemini-NX C18 75×30 mm×3 μm; mobile phase: [water (0.05% ammonia hydroxide v/v)]/ACN], B %: 28%-58%, 10 min] to give the title compound (9.00 mg, 3% yield) as a white solid; LCMS (ESI, M+1): m/z=692.4.

Step G. 7-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decan-2-one: To the solution of 7-(7-(8-ethyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)-1,3,7-triazaspiro[4.5]decan-2-one (8.00 mg, 1.0 equiv.) in MeOH (1 mL) was added HCl.dioxane (4 M, 2 mL) at 0° C., the mixture was stirred at 0° C. for 0.5 hour. The mixture was concentrated, pH was adjusted to 7 by NaHCO₃ and MeOH (1 mL) was added. The residue was purified by prep-HPLC [column: Shim-pack C18 150×25×10 μm; mobile phase: [water (0.225% formic acid formic acid)/ACN], B %: 15%-45%, 10 min] to afford the title compound (6.07 mg, 78% yield, 0.50 formic acid) as a white solid; $^1$H NMR (400 MHz, methanol-d₄) δ=9.13 (s, 1H), 7.75-7.61 (m, 1H), 7.36-7.19 (m, 2H), 7.05 (t, J=3.2 Hz, 1H), 5.56-5.34 (m, 1H), 4.59-4.45 (m, 2H), 4.43-4.14 (m, 2H), 4.07-3.86 (m, 2H), 3.74-3.49 (m, 3H), 3.46-3.34 (m, 2H), 3.27-3.21 (m, 1H), 2.63-2.35 (m, 3H), 2.32-2.11 (m, 4H), 2.10-1.79 (m, 5H), 0.90-0.73 (m, 3H); LCMS (ESI, M+1): m/z=648.3.

Example 134

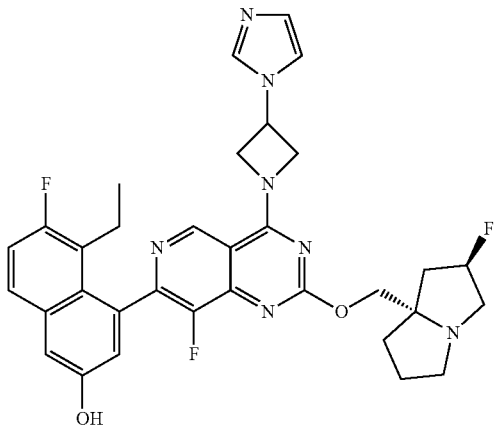 [SMILES: CCc1c(F)ccc2cc(O)cc(-c3ncc4c(N5CC(n6ccnc6)C5)nc(OC[C@@]56CCCN5C[C@H](F)C6)nc4c3F)c12]

4-(4-(3-(1H-imidazol-1-yl)azetidin-1-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol

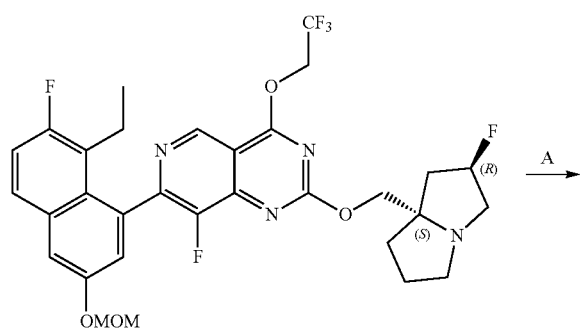

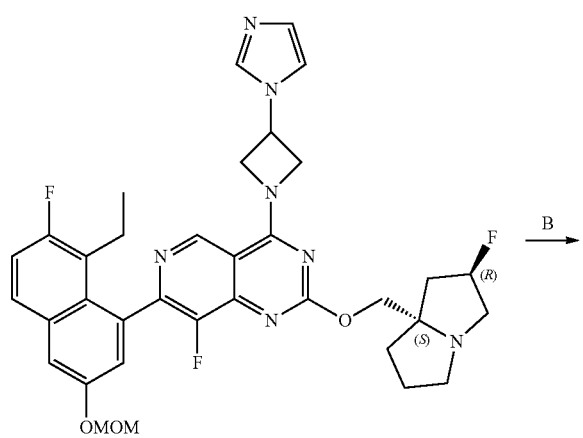

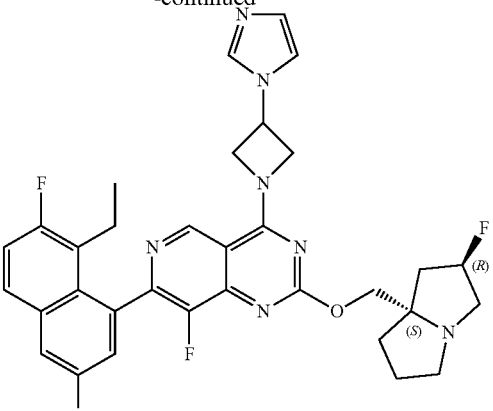

Step A. 4-(3-(1H-imidazol-1-yl)azetidin-1-yl)-7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidine: To the solution of 7-(8-ethyl-7-fluoro-3-(methoxymethoxy)naphthalen-1-yl)-8-fluoro-2-(((2R,7aS)-2-fluorohexahydro-1H-pyrrolizin-7a-yl) methoxy)-4-(2,2,2-trifluoroethoxy)pyrido[4,3-d]pyrimidine (60.0 mg, 1.0 equiv.) and DIEA (60.9 mg, 5.0 equiv.) in DMF (2.0 mL) was added 1-(azetidin-3-yl)imidazole (18.1 mg, 1.20 equiv., HCl salt). The mixture was stirred at 40° C. for 12 hours. The mixture treated with water (5 mL) and extracted with ethyl acetate (3×5 mL). The organic layer was washed with brine (2×10 mL), dried over anhydrous sodium sulfate, filtered and concentrated to afford the title compound (60 mg, crude) as a yellow liquid; LCMS (ESI, M+1): m/z=660.3.

Step B. 4-(4-(3-(III-imidazol-1-yl)azetidin-1-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol: To the solution of 4-(3-(1H-imidazol-1-yl)azetidin-1-yl)-7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidine (50.0 mg, 1.0 equiv.) in DCM (0.5 mL) was added TFA (7.70 g, 891 equiv.). The reaction was stirred at 20° C. for 0.5 hour. The mixture was concentrated. The residue was purified by prep-HPLC [column: Phenomenex Gemini-NX C18 75×30 mm×3 μm; mobile phase: [water (10 mM NH$_4$HCO$_3$)/ACN], B %: 34/a-64%, 8 min] to afford the title compound (9.23 mg, 19% yield over two steps) as a white solid; $^1$H NMR (400 MHz, methanol-d4) δ 8.96 (s, 1H), 7.97 (s, 1H), 7.68 (dd, J=5.6, 8.8 Hz, 1H), 7.58 (s, 1H), 7.30 (d, J=2.4 Hz, 1H), 7.25 (t, J=9.6 Hz, 1H), 7.11 (s, 1H), 7.04 (d, J=2.4 Hz, 1H), 5.55-5.45 (m, 1H), 5.41-4.90 (m, 5H), 4.38-4.23 (m, 2H), 3.29-3.13 (m, 3H), 3.05-2.96 (m, 1H), 2.56-2.43 (m, 1H), 2.39-2.19 (m, 2H), 2.18-2.08 (m, 2H), 2.05-1.83 (m, 3H), 0.79 (t, J=7.2 Hz, 3H); LCMS (ESI, M+1): m/z=616.4.

Example 135

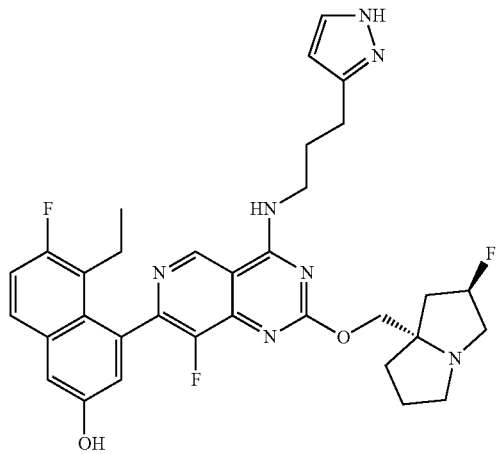 [SMILES: CCc1c(F)ccc2cc(O)cc(-c3ncc4c(NCCCc5cc[nH]n5)nc(OC[C@@]56CCCN5C[C@H](F)C6)nc4c3F)c12]

4-(4-((3-(1H-pyrazol-3-yl)propyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol

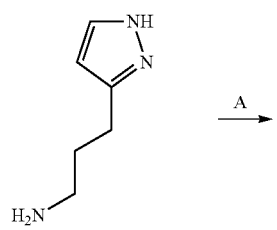

A →

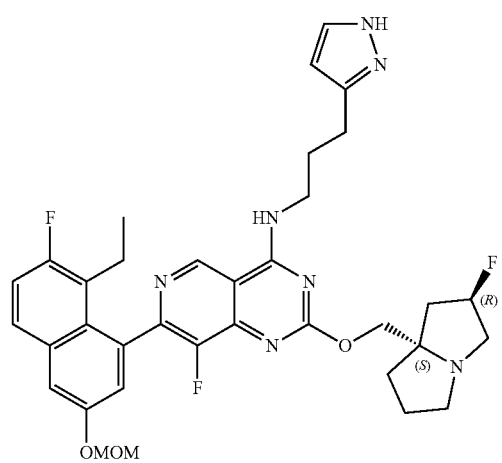

B →

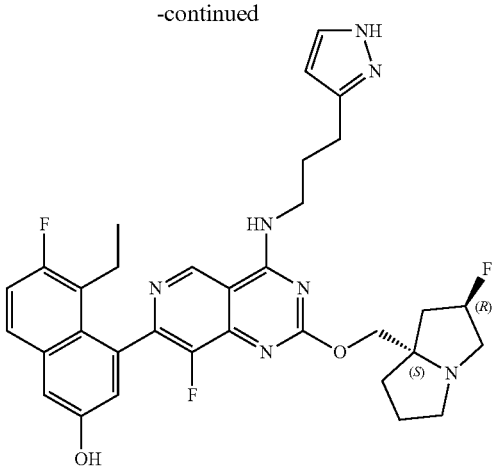

Step A. N-(3-(1H-pyrazol-3-yl)propyl)-7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-amine: To a solution of 7-(8-ethyl-7-fluoro-3-(methoxymethoxy)naphthalen-1-yl)-8-fluoro-2-(((2R$^7$aS)-2-fluorohexahydro-1H-pyrrolizin-7a-yl) methoxy)-4-(2,2,2-trifluoroethoxy)pyrido[4,3-d]pyrimidine (50 mg, 1.0 equiv.) and 3-(1H-pyrazol-3-yl)propan-1-amine (14.7 mg, 1.5 equiv.) in DMF (2 mL) was added DIEA (50.8 mg, 5 equiv.). The mixture was stirred at 40° C. for 16 hours. The mixture was poured into water (10 mL) and extracted with ethyl acetate (10 mL×2). The combined organic phase was dried over anhydrous $Na_2SO_4$, filtered and concentrated in vacuum to afford the title compound (40 mg, 77% yield) as a yellow solid; LCMS (ESI, M+1): m/z=662.4.

Step B. 4-(4-((3-(1H-pyrazol-3-ylpropyl)amino)-8-fluoro-2-(((2R$^7$aS)-2-fluorohexahydro-1H-pyrrolizin-7a-yl)methoxy)pyrido[4,3-d]pyrimidin-7-yl)-5-ethyl-6-fluoronaphthalen-2-ol: To a solution of N-(3-(1H-pyrazol-3-yl)propyl)-7-(8-ethyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-amine (40 mg, 1.0 equiv.) in ACN (2 mL) was added HCl.dioxane (4 M, 1.36 mL, 90 equiv.). The mixture was stirred at 0° C. for 1 hour. The mixture was concentrated in vacuum. The residue was purified by Prep-HPLC [column: water s Xbridge 150×25 mm×5 μm; mobile phase: [water (10 mM $NH_4HCO_3$)/ACN], B %: 35/0-65%, 8 min) to afford the title compound (13.7 mg, 34% yield) as a white solid; $^1$HNMR (400 MHz, methanol-d4) S=9.12 (s, 1H), 7.67 (dd, J=5.6, 9.2 Hz, 1H), 7.50 (br s, 1H), 7.30 (d, J=2.4 Hz, 1H), 7.25 (t, J=9.2 Hz, 1H), 7.04 (d, J=2.4 Hz, 1H), 6.20 (d, J=1.6 Hz, 1H), 5.43-5.24 (m, 1H), 4.38-4.24 (m, 2H), 3.75 (t, J=7.2 Hz, 2H), 3.25 (br s, 1H), 3.11-3.00 (m, 1H), 2.83 (t, J=7.2 Hz, 2H), 2.54-1.86 (m, 12H), 0.79 (t, J=7.2 Hz, 3H). LCMS (ESI, M+1): m/z=618.3.

Example 136

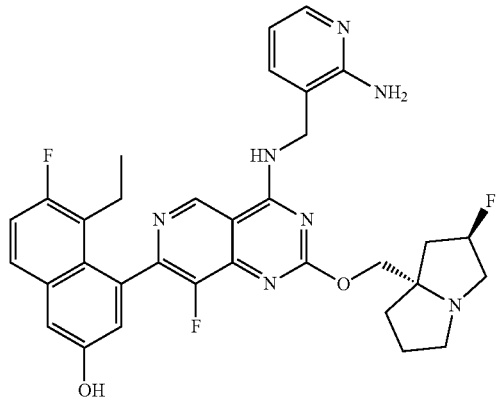 [SMILES: CCc1c(F)ccc2cc(O)cc(-c3ncc4c(NCc5cccnc5N)nc(OC[C@@]56CCCN5C[C@H](F)C6)nc4c3F)c12]

4-(4-(((2-aminopyridin-3-yl)methyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol

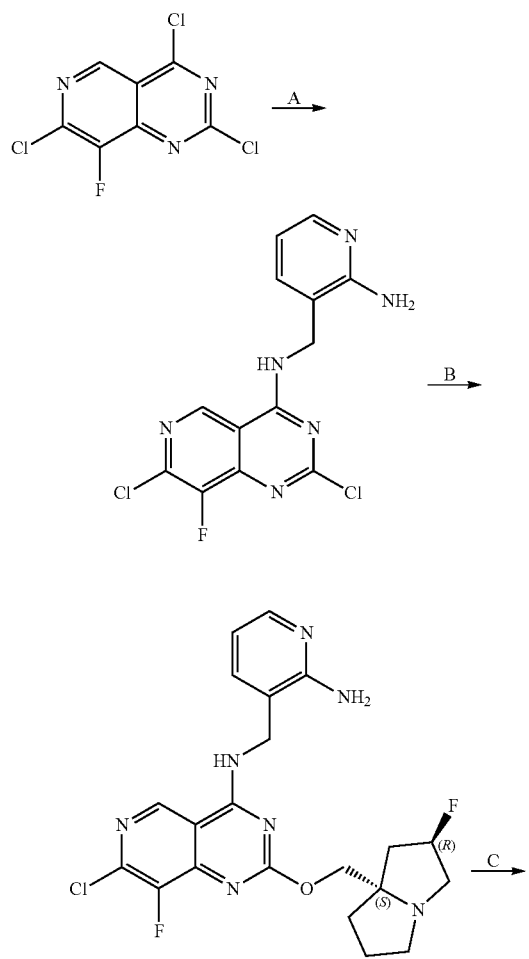

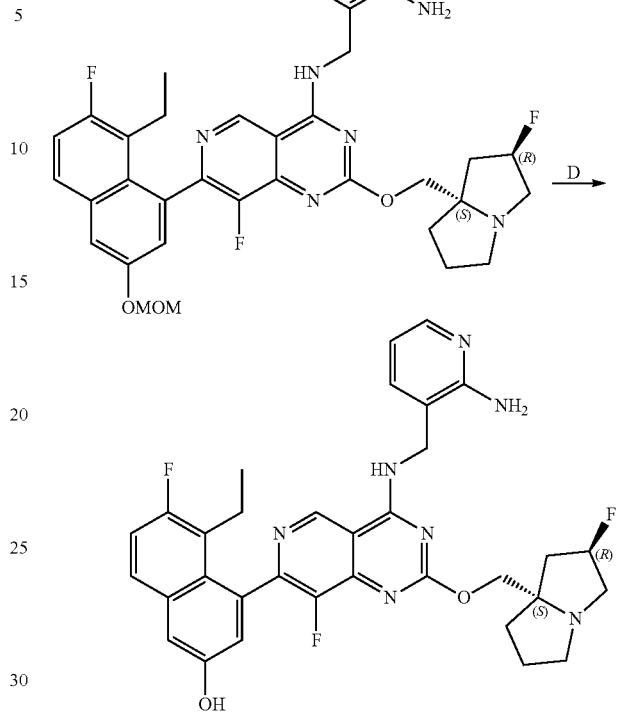

Step A. N-((2-aminopyridin-3-yl)methyl)-2,7-dichloro-8-fluoropyrido[4,3-d]pyrimidin-4-amine: To a mixture of 2,4,7-trichloro-8-fluoropyrido[4,3-d]pyrimidine (300 mg, 1.0 equiv.), DIEA (461 mg, 3.0 equiv) and 4 Å molecular sieves (20 mg) in DCM (5 mL) was added 3-(aminomethyl)pyridin-2-amine (205 mg, 1.4 equiv.) at −40° C. The mixture was stirred at −40° C. for 1 hour. The mixture was poured into water (10 mL) and the aqueous layer was extracted with ethyl acetate (2×10 mL). The combined organic layer was dried over anhydrous $Na_2SO_4$, filtered and concentrated to afford the title compound (150 mg, 37% yield) as a yellow solid; LCMS (ESI, M+1): m/z=339.1.

Step B. $N_4$ (2-aminopyridin-3-yl)methyl)-7-chloro-8-fluoro-2-(((2R,7aS)-2-fluorohexahydro-1H-pyrrolizin-7a-yl)methoxy)pyrido[4,3-d]pyrimidin-4-amine: To a mixture of N-((2-aminopyridin-3-yl)methyl)-2,7-dichloro-8-fluoropyrido[4,3-d]pyrimidin-4-amine (150 mg, 1.0 equiv.), 4 Å molecular sieves (15 mg) and DIEA (172 mg, 3.0 equiv.) in dioxane (3 mL) was added ((2R,7aS)-2-fluorohexahydro-1H-pyrrolizin-7a-yl)methanol (84.5 mg, 1.2 equiv.). The reaction was stirred at 90° C. for 12 hours. The mixture was poured into water (10 mL) and extracted with ethyl acetate (2×10 mL). The combined organic layer was dried over anhydrous $Na_2SO_4$, filtered and concentrated. The residue was purified by reversed phase flash column chromatography (C18, mobile phase: [water (0.1% formic acid)/acetonitrile]) to afford the title compound (50 mg, 24% yield) as a yellow solid; LCMS (ESI, M+1): m/z=462.2.

Step C. N-((2-aminopyridin-3-yl)methyl)-7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-amine: To a mixture of N-((2-aminopyridin-3-yl)methyl)-7-chloro-8-fluoro-2-(((2R,7aS)-2-fluorohexahydro-1H-pyrrolizin-7a-yl)

methoxy)pyrido[4,3-d]pyrimidin-4-amine (50 mg, 1.0 equiv.), 2-(8-ethyl-7-fluoro-3-(methoxymethoxy)naphthalen-1-yl)-4,4,5,5-tetramethyl-1,3,2-dioxaborolane (78.0 mg, 2.0 equiv.) and $Cs_2CO_3$ (1.5 M in water, 216 μL, 3.0 equiv.) in methoxycyclopentane (2.0 mL) was added cataCXium-A-Pd-G3 (15.8 mg, 0.2 equiv.). The reaction was stirred at 100° C. for 3 hours. The mixture was poured into water (5 mL) and extracted with ethyl acetate (2×5 mL). The combined organic layers were dried over $Na_2SO_4$, filtered and concentrated. The residue was purified reversed phase flash column chromatography (C18, mobile phase: [water (0.1% formic acid)/acetonitrile]) to afford the title compound (40 mg, 56% yield) as a yellow solid; LCMS (ESI, M+1): m/z=660.3.

Step D. 4-(4-(((2-aminopyridin-3-yl)methyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol: To a mixture of N-((2-aminopyridin-3-yl)methyl)-7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-amine (25.0 mg, 1.0 equiv.) in DCM (1 mL) was added TFA (1.54 g, 356 equiv.). The reaction was stirred at 20° C. for 1 hour. The mixture was concentrated. The residue was purified by prep-HPLC [column: Phenomenex Gemini-NX C18 75×30 mm×3 μm; mobile phase: [water (0.225% formic acid)/ACN], B %: 8%-38%, 7 min] to afford the title compound (7.44 mg, 32% yield) as a white solid; $^1$H NMR (400 MHz, methanol-$d_4$) δ=9.22 (s, 1H), 8.55-8.38 (m, 1H), 7.92 (br d, J=5.2 Hz, 1H), 7.68 (dd, J=6.0, 8.8 Hz, 1H), 7.62 (d, J=7.2 Hz, 1H), 7.31 (d, J=2.8 Hz, 1H), 7.25 (t, J=9.2 Hz, 1H), 7.04 (s, 1H), 6.71 (dd, J=5.2, 7.2 Hz, 1H), 5.57-5.32 (m, 1H), 4.76 (br s, 2H), 4.56-4.45 (m, 2H), 3.74-3.58 (m, 3H), 3.29-3.23 (m, 1H), 2.60-2.38 (m, 3H), 2.36-2.24 (m, 1H), 2.23-2.11 (m, 3H), 2.10-1.96 (m, 1H), 0.78 (t, J=7.2 Hz, 3H); LCMS (ESI, M+1): m/z=616.4.

Example 137

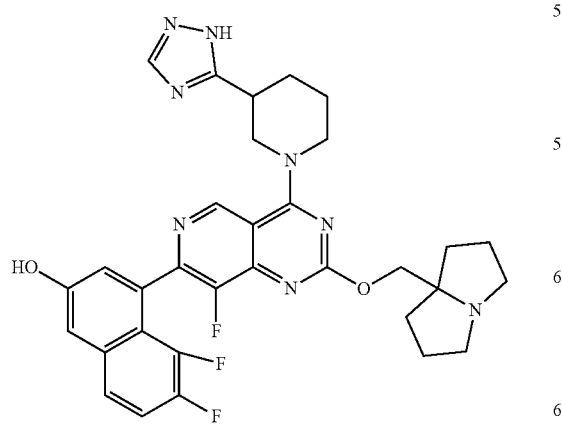

4-(4-(3-(1H-1,2,4-triazol-5-yl)piperidin-1-yl)-8-fluoro-2-((hexahydro-1H-pyrrolizin-7a-yl)methoxy)pyrido[4,3-d]pyrimidin-7-yl)-5,6-difluoronaphthalen-2-ol

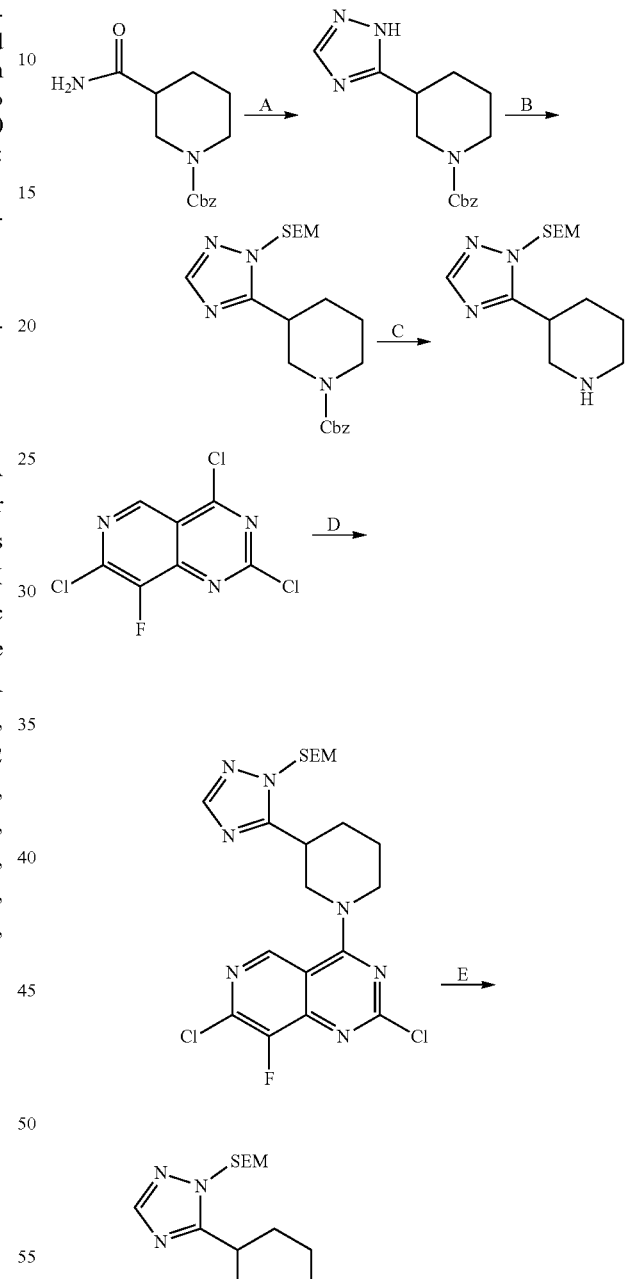

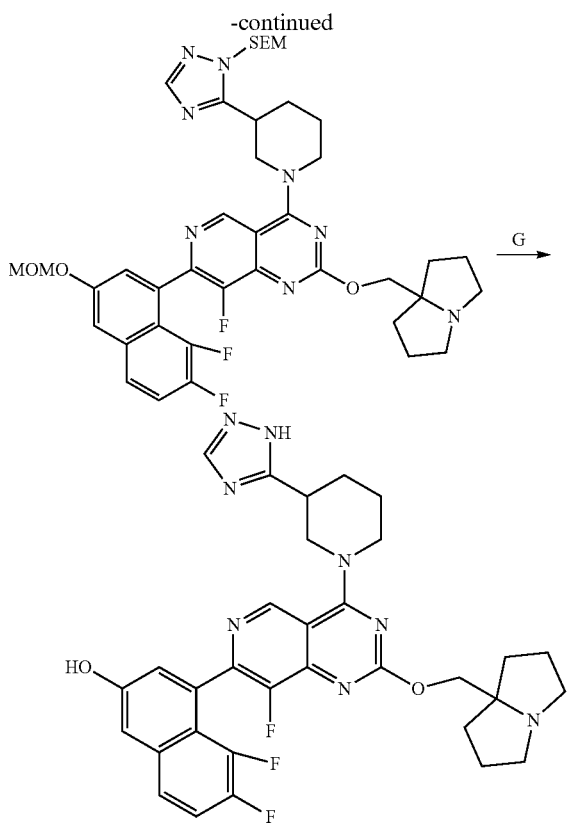

Step A. benzyl 3-(1H-1,2,4-triazol-5-ylpiperidine-1-carboxylate: A mixture of benzyl 3-carbamoylpiperidine-1-carboxylate (5.0 g, 1.0 equiv.) in DMF-DMA (45.4 g, 20.0 equiv.) was heated to 110° C. for 2 hours. After removal of the volatiles, the residue was re-dissolved in AcOH (30 mL) and treated with N₂H₄-WATER (1.17 g, 1.20 equiv.). The reaction was heated to 90° C. for 1 hour. The mixture was concentrated under reduced pressure to remove AcOH. The residue was diluted with water (50 mL) and extracted with ethyl acetate (3×50 mL). The combined organic layers were dried over anhydrous sodium sulfate, concentrated, and purified by reversed phase flash chromatography (C18, mobile phase: [water (0.1% formic acid)/ACN, 0-100%]) to afford the title compound (5.30 g, 97% yield) as a white solid; LCMS (ESI, M+1): m/z=287.2.

Step B. benzyl 3-(1-((2-(trimethylsilyl)ethoxy)methyl)-1H-1,2,4-triazol-5-yl) piperidine-1-carboxylate: To a solution of benzyl 3-(1H-1,2,4-triazol-5-yl)piperidine-1-carboxylate (4.40 g, 1.0 equiv.) in THF (40 mL) was added NaH (1.23 g, 60% purity, 2.0 equiv.). The mixture was stirred at 0° C. for 0.5 hour before SEM-CI (3.84 g, 1.50 equiv.) was added at 0° C. The mixture was stirred at 0° C. for 1 hour. The reaction mixture was quenched by addition of water (50 mL) at 0° C., and extracted with ethyl acetate (3×50 mL). The combined organic layers were dried over anhydrous sodium sulfate, concentrated, and purified by reversed phase flash chromatography (C18, mobile phase: [water (0.1% formic acid)/ACN, 0-100%]) to afford the title compound (3.30 g, 49% yield) as a yellow liquid; LCMS (ESI, M+1): m/z=417.3.

Step C. 3-(1-((2-(trimethylsilyl)ethoxy)methyl)-1H-1,2,4-triazol-5-yl)piperidine: To a solution of benzyl 3-(1-((2-(trimethylsilyl)ethoxy)methyl)-1H-1,2,4-triazol-5-yl)piperidine-1-carboxylate (3.00 g, 1.0 equiv.) in MeOH (20 mL) was added Pd/C (300 mg, 10% purity). The suspension was degassed in vacuum and purged with H₂ several times. The reaction was stirred under H₂ (15 psi) at 25° C. for 1 hour. The mixture was filtered and the filtrate was concentrated to afford the title compound (1.80 g, crude) as a colourless liquid.

Step D. 2,7-dichloro-8-fluoro 1 (3 (1 ((2 (trimethylsilyl)ethoxy)methyl) 1H 1,2,4-triazol-5-yl)piperidin-1-yl)pyrido[4,3-d]pyrimidine: To a solution of 3-(1-((2-(trimethylsilyl)ethoxy)methyl)-1H-1,2,4-triazol-5-yl)piperidine (1.51 g, 0.90 equiv.) in DCM (15 mL) was added DIEA (2.30 g, 3.0 equiv.) and 2,4,7-trichloro-8-fluoropyrido[4,3-d]pyrimidine (1.50 g, 1.0 equiv.) at −60° C. The mixture was stirred at −60° C. for 0.5 hour. The reaction mixture was diluted with water (20 mL) and extracted with DCM (3×20 mL). The combined organic layers were dried over anhydrous sodium sulfate, concentrated, and purified by reversed phase flash chromatography (C18, mobile phase: [water (0.1% formic acid)/ACN, 0-100%]) to afford the title compound (2.30 g, 81% yield over two steps) as a yellow solid; LCMS (ESI, M+1): m/z=498.2.

Step E. 7-chloro-8-fluoro-2-((hexahydro-1H-pyrrolizin-7a-yl)methoxyl-4-(3-(1-((2-(trimethylsilyl)ethoxy)methyl)-1H-1,2,4-triazol-5-ylpiperidin-1-yl)pyrido[4,3-d]pyrimidine: To a solution of 2,7-dichloro-8-fluoro-4-(3-(1-((2-(trimethylsilyl)ethoxy)methyl)-1H-1,2,4-triazol-5-yl)piperidin-1-yl)pyrido[4,3-d]pyrimidine (2.00 g, 1.0 equiv.) in dioxane (8 mL). was added DIEA (1.56 g, 3.0 equiv.), 4 Å molecular sieves (500 mg) and (hexahydro-1H-pyrrolizin-7a-yl)methanol (1.13 g, 2.0 equiv.). The reaction was stirred at 95° C. for 12 hours. The mixture was filtered. The filtrate was concentrated, and purified by reversed phase flash chromatography (C18, mobile phase: [water (0.1% formic acid)/ACN, 0-100%]) to afford the title compound (1.60 g, 66% yield) as a yellow solid; LCMS (ESI, M+1): m/z=603.3.

Step F. 7-(7,8-difluoro-3-(methoxymethoxy)naphthalen-1-yl)-8-fluoro-2-((hexahydro-1H-pyrrolizin-7a-yl)methoxy)-4-(3-(1-((2-(trimethylsilyl)ethoxy)methyl)-1H-1,2,4-triazol-5-yl)piperidin-1-yl)pyrido[4,3-d]pyrimidine: To a mixture of 7-chloro-8-fluoro-2-((hexahydro-1H-pyrrolizin-7a-yl)methoxy)-4-(3-(1-((2-(trimethylsilyl)ethoxy)methyl)-1H-1,2,4-triazol-5-yl)piperidin-1-yl)pyrido[4,3-d]pyrimidine (500 mg, 1.0 equiv.) and 2-(7,8-difluoro-3-(methoxymethoxy)naphthalen-1-yl)-4,4,5,5-tetramethyl-1,3,2-dioxaborolane (580 mg, 2.0 equiv.) in THF (10 mL) was added K₃PO₄ (1.5 M, 3.0 equiv.) and CataCXium A Pd G3 (90.5 mg, 0.15 equiv.). The mixture was stirred at 60° C. for 2 hours. The reaction mixture was diluted with water (10 mL) and extracted with ethyl acetate (3×10 mL). The combined organic layers were dried over anhydrous sodium sulfate, and purified by reversed phase flash chromatography (C18, mobile phase: [water (0.1% formic acid)/ACN, 0-100%]) to afford the title compound (400 mg, 58% yield) as a yellow solid; LCMS (ESI, M+1): m/z=791.4.

Step G. 4-(4-(3-(1H-1,2,4-triazol-5-yl)piperidin-1-yl)-8-fluoro-2-((hexahydro-1H-pyrrolizin-7a-yl)methoxy)pyrido[4,3-d]pyrimidin-7-yl)-5,6-difluoronaphthalen-2-ol: To a solution of 7-(7,8-difluoro-3-(methoxymethoxy)naphthalen-1-yl)-8-fluoro-2-((hexahydro-1H-pyrrolizin-7a-yl)methoxy)-4-(3-(1-((2-(trimethylsilyl)ethoxy)methyl)-1H-1,2,4-triazol-5-yl) piperidin-1-yl)pyrido[4,3-d]pyrimidine (200 mg, 1.0 equiv.) in DCM (1.0 mL) was added TEA (1.45 g, 56.8 equiv.). The reaction was stirred at 25° C. for 2 hours. The reaction mixture was concentrated under reduced pressure to remove solvent. The residue was diluted with water (10 mL) and pH was adjusted to 8 with aqueous Na₂CO₃. The mixture was extracted with DCM (3×10 mL). The combined organic layers were dried over anhydrous sodium sulfate, concentrated, and purified by reversed phase flash chromatography [column: Phenomenex Gemini-NX C18 75×30 mm×3 μm; mobile phase: [water (0.225% formic acid)/CAN]; B %: 20%-30%, 7 min] to afford the title compound (46.8 mg, 27% yield) as a white solid; ¹H NMR (400 MHz, methanol-d4) δ 9.12 (s, 1H), 8.33 (s, 1H), 7.77-7.66 (m, 1H), 7.61-7.50 (m, 1H), 7.43-7.35 (m, 1H), 7.28-7.20 (m, 1H), 4.77-4.63 (m, 1H), 4.51-4.40 (m, 1H), 4.39-4.26 (m, 2H), 3.57-3.51 (m, 1H), 3.30-3.17 (m, 3H), 2.94-2.81 (m, 2H), 2.27-2.17 (m, 1H), 2.08-1.72 (m, 12H). LCMS (ESI, M+1): m/z=617.3.

Example 138

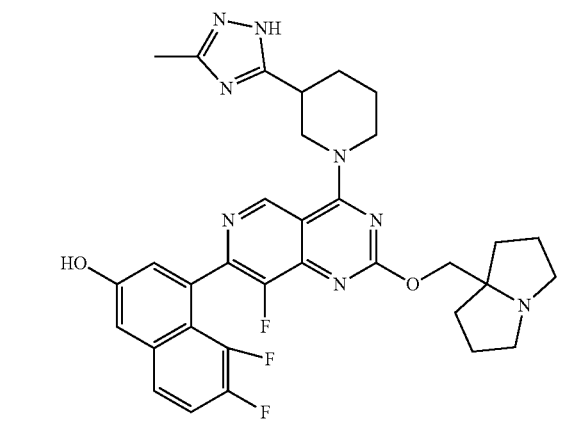 [SMILES: Cc1n[nH]c(C2CCCN(c3nc(OCC45CCCN4CCC5)nc4c(F)c(-c5cc(O)cc6ccc(F)c(F)c56)ncc34)C2)n1]

5,6-difluoro-4-(8-fluoro-2-((hexahydro-1H-pyr-rolizin-7a-yl)methoxy)-4-(3-(3-methyl-1H-1,2,4-triazol-5-yl)piperidin-1-yl)pyrido[4,3-d]pyrimidin-7-yl)naphthalen-2-ol

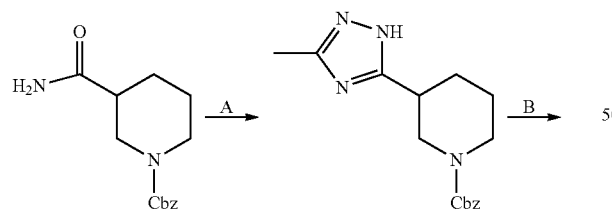

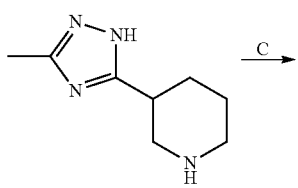

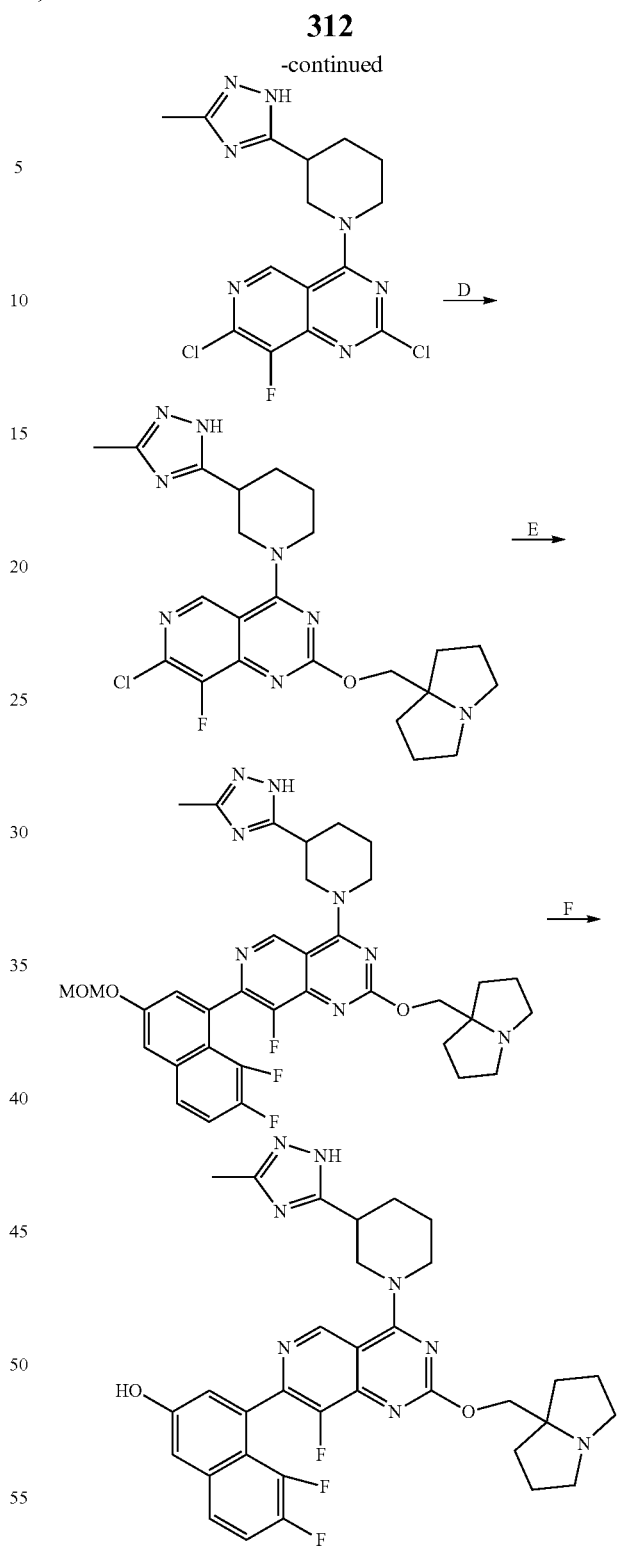

Step A. benzyl 3-(3-methyl-1H-1,2,4-triazol-5-yl)piperi-dine-t-carboxylate: A mixture of benzyl 3-carbamoylpiperi-dine-1-carboxylate (1.50 g, 1.0 equiv.) in 1,1-dimethoxy-N,N-dimethyl-ethanamine (15.2 g, 20.0 equiv.) was heated at 110° C. for 2 hours. After removal of the volatiles, the residue was re-dissolved in AcOH (3 mL). hydrazine hydrate (438 mg, 1.50 equiv.) was added, and the reaction was heated to 90° C. for 1 hour. The mixture was concentrated under reduced pressure to remove AcOH. The residue was diluted with water (10 mL) and extracted with ethyl acetate (3×10 mL). The combined organic layers were washed with brine (50 mL), dried over anhydrous sodium sulfate, concentrated, and purified by silica gel column chromatography (petroleum ether/ethyl acetate 10:1 to 1:1) to afford the title compound (1.50 g, 87% yield) as a yellow liquid; $^1$H NMR (400 MHz, CDCl$_3$) δ 7.39-7.28 (m, 5H), 5.21-5.07 (m, 2H), 4.40-4.18 (m, 1H), 4.11-3.88 (m, 1H), 3.34-2.82 (m, 3H), 2.39 (s, 3H), 2.18-2.08 (m, 1H), 1.93-1.49 (m, 3H). LCMS (ESI, M+1): m/z=301.2.

Step B. 3-(3-methyl-1H-1,2,4-triazol-5-yl)piperidine: To a solution of benzyl 3-(3-methyl-1H-1,2,4-triazol-5-yl)piperidine-1-carboxylate (1.50 g, 1.0 equiv.) in MeOH (20 mL) was added Pd/C (200 mg, 10% purity) under N$_2$. The suspension was degassed in vacuum and purged with H$_2$ several times. The mixture was stirred under H$_2$ (15 psi) at 25° C. for 2 hours. The reaction mixture was filtered and the filtrate was concentrated to afford the title compound (800 mg, crude) as a by yellow liquid.

Step C. 2,7-dichloro-8-fluoro-4-(3-(3-methyl-1H-1,2,4-triazol-5-yl)piperidin-1-yl) pyrido[4,3-d]pyrimidine: To a solution of 3-(3-methyl-1H-1,2,4-triazol-5-yl)piperidine (592 mg, 1.50 equiv.) in THF (20 mL) was added DIEA (921 mg, 3.0 equiv.) and 2,4,7-trichloro-8-fluoropyrido[4,3-d]pyrimidine (600 mg, 1.0 equiv.) at −60° C. The mixture was stirred at −60° C. for 0.5 hour. The reaction mixture was diluted with water (20 mL) and extracted with ethyl acetate (3×20 mL). The combined organic layers were dried over anhydrous sodium sulfate, concentrated, and purified by reversed phase flash chromatography (C18, mobile phase: [water (0.1% formic acid)/ACN, 0-100%]) to afford the title compound (600 mg, 66% yield) as yellow liquid; $^1$H NMR (400 MHz, CDCl$_3$) δ 8.92 (s, 1H), 4.65 (br dd, J=3.2, 13.2 Hz, 1H), 4.50-4.39 (m, 1H), 3.94 (dd, J=9.2, 13.2 Hz, 1H), 3.74-3.62 (m, 1H), 3.32-3.20 (m, 1H), 2.48 (s, 3H), 2.37-2.26 (m, 1H), 2.19-2.10 (m, 1H), 2.04-1.98 (m, 1H), 1.92-1.79 (m, 1H); LCMS (ESI, M+1): m/z=382.1.

Step D. 7-chloro-8-fluoro-2-((hexahydro-1H-pyrrolizin-7a-yl)methoxyl-4-(3-(3-methyl-1H-1,2,4-triazol-5-ylpiperidin-1-yl)pyrido[4,3-d]pyrimidine: To a solution of 2,7-dichloro-8-fluoro-4-(3-(3-methyl-1H-1,2,4-triazol-5-yl) piperidin-1-yl)pyrido[4,3-d]pyrimidine (600 mg, 1.0 equiv.) in dioxane (6 mL) was added DIEA (609 mg, 3.0 equiv.) and (hexahydro-1H-pyrrolizin-7a-yl)methanol (665 mg, 3.0 equiv.). The reaction mixture was stirred at 95° C. for 3 hours. The reaction mixture was diluted with water (20 mL) and extracted with ethyl acetate (3×20 mL). The combined organic layers were dried over anhydrous sodium sulfate, concentrated, and purified by reversed phase flash chromatography (C18, mobile phase: [water (0.1% formic acid)/ACN, 0-20%]) to afford the title compound (400 mg, 47% yield) as a yellow solid; LCMS (EST, M+1): m/z=487.3.

Step E. 7-(7,8-difluoro-3-(methoxymethoxy)naphthalen-1-yl)-8-fluoro-2-((hexahydro-1H-pyrrolizin-7a-yl) methoxy)-4-(3-(3-methyl-1H-1,2,4-triazol-5-yl)piperidin-1-yl) pyrido[4,3-d]pyrimidine: To a solution of 7-chloro-8-fluoro-2-((hexahydro-1H-pyrrolizin-7a-yl) methoxy)-4-(3-(3-methyl-1H-1,2,4-triazol-5-yl)piperidin-1-yl)pyrido[4,3-d]pyrimidine (200 mg, 1.0 equiv.) and 2-(7,8-difluoro-3-(methoxymethoxy)naphthalen-1-yl)-4,4,5,5-tetramethyl-1,3,2-dioxaborolane (288 mg, 2.0 equiv.) in methoxycyclopentane (6.0 mL) was added K$_3$PO$_4$ (1.5 M, 3.0 equiv.) and CataCXium A Pd G3 (44.9 mg, 0.15 equiv.). The reaction was stirred at 90° C. for 2 hours. The mixture was diluted with water (10 mL) and extracted with ethyl acetate (3×10 mL). The combined organic layers were dried over anhydrous sodium sulfate, concentrated, and purified by reversed phase flash chromatography (C18, mobile phase: [water (0.1% formic acid)/ACN, 0-20%]) to afford the title compound (80 mg, 29% yield) as a yellow solid; LCMS (ESI, M+1): m/z=675.4.

Step F. 5,6-difluoro-4-(8-fluoro-2-((hexahydro-1H-pyrrolizin-7a-yl)methoxy)-4-(3-(3-methyl-1H-1,2,4-triazol-5-yl)piperidin-1-yl)pyrido[4,3-d]pyrimidin-7-yl)naphthalen-2-ol: To a solution of 5,6-difluoro-4-(8-fluoro-2-((hexahydro-1H-pyrrolizin-7a-yl)methoxy)-4-(3-(3-methyl-1H-1,2,4-triazol-5-yl)piperidin-1-yl)pyrido[4,3-d]pyrimidin-7-yl)naphthalen-2-ol (80.0 mg, 1.0 equiv.) in ACN (1 mL) was added HCl.dioxane (4.0 M, 72.0 equiv.). The reaction was stirred at 25° C. for 0.5 hour. The mixture was concentrated and purified by reversed phase HPLC [column: Phenomenex Luna C18 150×25 mm×10 μm; mobile phase: water (0.225% formic acid)/ACN; B %: 12/a-42%, 10 min] to afford the title compound (29.5 mg, 39% yield) as a white solid; $^1$H NMR (400 MHz, methanol-d4) δ=9.14 (s, 1H), 8.54 (s, 1H), 7.66-7.59 (m, 1H), 7.45-7.37 (m, 1H), 7.36-7.31 (m, 1H), 7.29-7.22 (m, 1H), 4.62-4.51 (m, 3H), 3.79-3.66 (m, 2H), 3.65-3.56 (m, 2H), 3.28-3.15 (m, 3H), 2.41 (s, 3H), 2.34-2.25 (m, 3H), 2.24-2.00 (m, 9H), 1.97-1.86 (m, 1H). LCMS (ESI, M+1): m/z=631.3.

Example 139

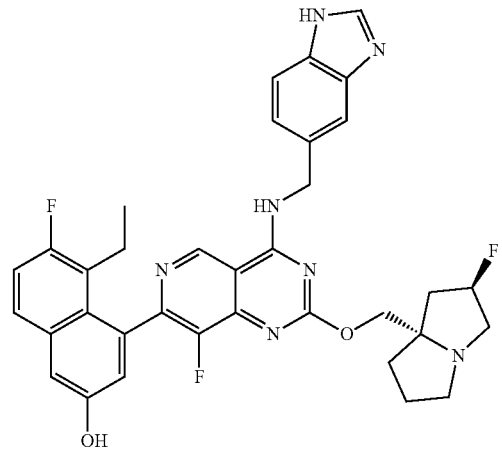 [SMILES: CCc1c(F)ccc2cc(O)cc(-c3ncc4c(NCc5ccc6[nH]cnc6c5)nc(OC[C@@]56CCCN5C[C@H](F)C6)nc4c3F)c12]

4-(4-(((1H-benzo[d]imidazol-5-yl)methyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 134. $^1$H NMR (400 MHz, methanol-d4) δ=9.23 (s, 1H), 8.52 (br d, J=1.2 Hz, 1H), 8.18 (s, 1H), 7.72 (s, 1H), 7.70-7.60 (m, 2H), 7.41 (dd, J=1.2, 8.4 Hz, 1H), 7.32-7.22 (m, 2H), 7.04 (d, J=2.8 Hz, 1H), 5.40-5.22 (m, 1H), 5.03 (br d, J=1.2 Hz, 2H), 4.42-4.28 (m, 2H), 3.51-3.34 (m, 3H), 3.18-2.99 (m, 1H), 2.50-2.38 (m, 1H), 2.30-2.09 (m, 4H), 2.07-1.99 (m, 2H), 1.96-1.81 (m, 1H), 0.79 (t, J=7.6 Hz, 3H); LCMS (ESI, M+1): m/z=640.3.

Example 140

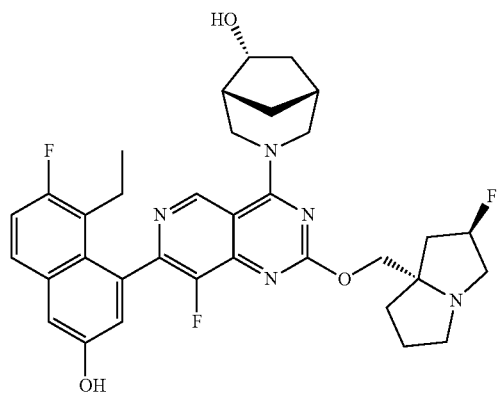 [SMILES: CCc1c(F)ccc2cc(O)cc(-c3ncc4c(N5C[C@@H]6C[C@H](C5)[C@H](O)C6)nc(OC[C@@]56CCCN5C[C@H](F)C6)nc4c3F)c12]

3-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol

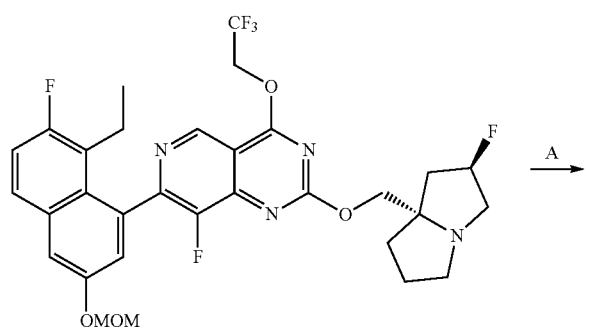

A ⟶

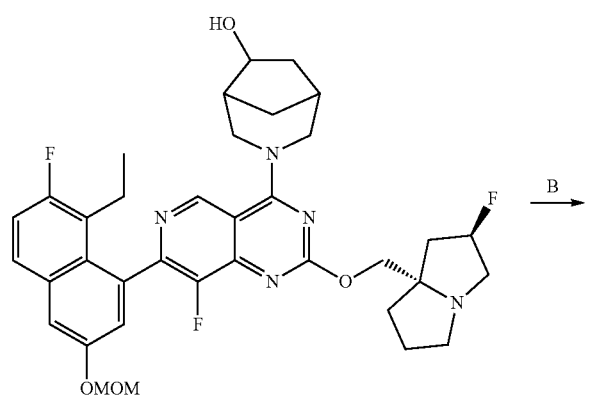

B ⟶

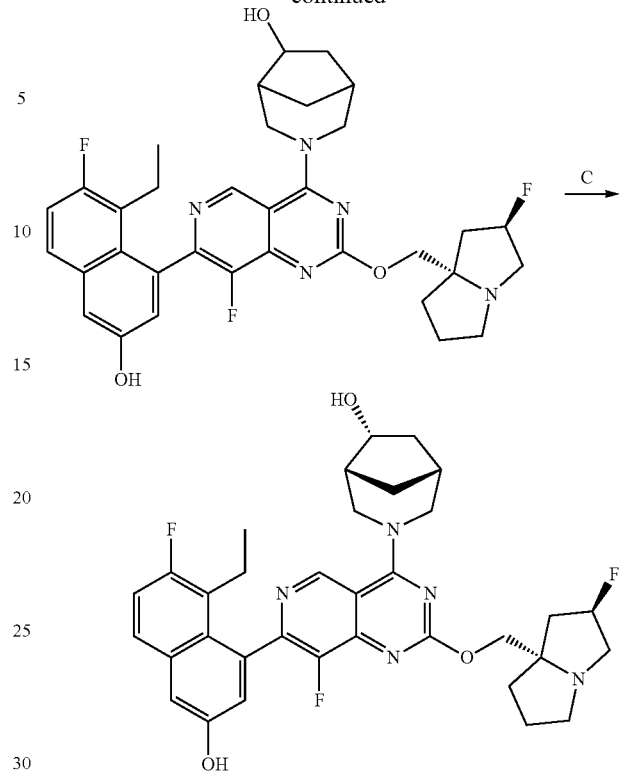

Step A. 3-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol: A mixture of 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-4-(2,2,2-trifluoroethoxy) pyrido[4,3-d]pyrimidine (130 mg, 1.0 equiv., 1.7 FORMIC ACID), 3-azabicyclo[3.2.1]octan-6-ol (60 mg, 2.0 equiv., HCl), DIPEA (200 μL, 6.3 equiv.), 4 Å molecular sieves (30 mg) in DMF (1.0 mL) was degassed and stirred at 40° C. for 15 hours. The mixture was filtered. The filtrate was purified reversed phase flash chromatography (mobile phase: [water (0.1% formic acid)/acetonitrile 11:9]) to afford the title compound (115 mg, 89% yield) as a yellow oil; LCMS (ESI, M+1): m/z=664.3.

Step B. 3-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol: To a solution of 3-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol (142 mg, 1.0 equiv.) in MeCN (3.0 mL) was added HCl.dioxane (4 M, 1.5 mL). The reaction was stirred at 0° C. for 0.5 hour. The mixture was quenched with saturated aqueous NaHCO$_3$ (15 mL) and extracted with ethyl acetate (15 mL×4). The combined organic phase was dried over anhydrous Na$_2$SO$_4$, concentrated and purified by prep-HPLC [column: Water s Xbridge 150×25 mm×5 μm; mobile phase: [water (10 mM NH$_4$HCO$_3$)/ACN]; B %: 41%-71%, 9 min] to afford the title compound (49.1 mg, 36% yield) as a white solid.

Step C 3-(7-(8-ethyl-7-fluoro-3-hydroxy)naphthalen-1-yl)-8-fluoro-2-(((2R,7aS)-2-fluorohexahydro-1H-pyrrolizin-7a-yl)methoxyl)pyrido[4,3-d]pyrimidin-4-yl)-3- azabicyclo [3.2.1]octan-6-ol: 3-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol (72 mg, 1 equiv.) was purified by SFC (column: DAICEL CHIRALPAK AD (250 mm×30 mm, 10 μm); mobile phase: [IPA-ACN]; B %: 35%-35%, 30 minutes) to give the crude product as the second eluting peak. The crude product was further re-purified by prep-HPLC [column: Waters Xbridge 150×25 mm×5 μm; mobile phase: [water (10 mM NH$_4$HCO$_3$)/ACN]; B %: 43%-73%, 10 min] to afford the title compound (13.6 mg, 18% yield) as a white solid; SFC: >99% ee, Chiralpak AD-3 50×4.6 mm I.D., 3 μm column A: IPA+ACN (0.05% DEA), B: CO2, 3 mL/min, t$_R$: 0.900 min; $^1$H NMR (400 MHz, methanol-d$_4$) δ=9.24 (d, J=19.6 Hz, 1H), 7.67 (dd, J=6.0, 2.8 Hz, 1H), 7.31-7.30 (m, 1H), 7.26-7.21 (m, 1H), 7.09-7.03 (m, 1H), 5.39 (d, J=53.2 Hz, 1H), 5.00-4.78 (m, 1H), 4.45-4.42 (m, 1H), 4.35-4.31 (m, 3H), 3.80 (br dd, J=12.8, 18.8 Hz, 1H), 3.57-3.50 (m, 1H), 3.49-3.34 (m, 3H), 3.22-3.09 (m, 1H), 2.51-2.36 (m, 3H), 2.34-2.18 (m, 4H), 2.16-1.88 (m, 5H), 1.86-1.75 (m, 1H), 1.45-1.26 (m, 1H), 0.83-0.76 (m, 3H); LCMS (ESI, M+1): m/z=620.3.

Example 141

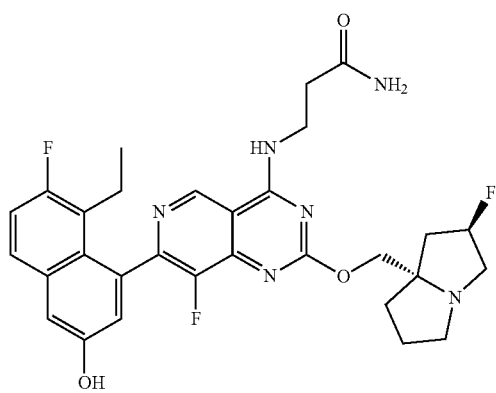 [SMILES: CCc1c(F)ccc2cc(O)cc(-c3ncc4c(NCCC(N)=O)nc(OC[C@@]56CCCN5C[C@H](F)C6)nc4c3F)c12]

3-((7-(8-ethyl-7-fluoro-3-hydroxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)propenamide The title compound was synthesized according to the procedure described for example 134. $^1$H NMR (400 MHz, METHANOL-d$_4$) δ=9.13 (s, 1H), 7.67 (dd, J=6.0, 9.2 Hz, 1H), 7.30 (d, J=2.8 Hz, 1H), 7.24 (t, J=9.6 Hz, 1H), 7.03 (d, J=2.4 Hz, 1H), 5.42-5.22 (m, 1H), 4.41-4.24 (m, 2H), 4.02-3.90 (m, 2H), 3.27-3.13 (m, 3H), 3.05-2.98 (m, 1H), 2.71 (t, J=6.4 Hz, 2H), 2.50 (br s, 1H), 2.39-2.19 (m, 2H), 2.18-2.10 (m, 2H), 2.04-1.90 (m, 3H), 0.78 (t, J=7.2 Hz, 3H); LCMS (ESI, M+1): m/z=581.3.

Example 142

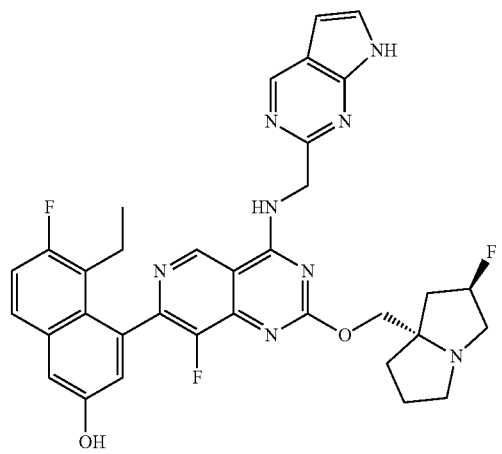 [SMILES: CCc1c(F)ccc2cc(O)cc(-c3ncc4c(NCc5ncc6cc[nH]c6n5)nc(OC[C@@]56CCCN5C[C@H](F)C6)nc4c3F)c12]

4-(4-(((7H-pyrrolo[2,3-d]pyrimidin-2-yl)methyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 61. $^1$H NMR (400 MHz, methanol-d4): =9.31 (s, 1H), 8.95 (s, 1H), 8.51 (br s, 1H), 7.69 (dd, J=5.6, 8.8 Hz, 1H), 7.49-7.43 (m, 1H), 7.35-7.30 (m, 1H), 7.26 (t, J=9.6 Hz, 1H), 7.06 (s, 1H), 6.65 (d, J=3.6 Hz, 1H), 5.35-5.19 (m, 1H), 5.13 (s, 2H), 4.16-4.08 (m, 1H), 4.24-4.06 (m, 1H), 3.49-3.34 (m, 2H), 3.14-3.00 (m, 1H), 2.57-2.44 (m, 1H), 2.07-1.91 (m, 4H), 2.35-1.89 (m, 3H), 1.86-1.73 (m, 1H), 0.82 (br t, J=6.8 Hz, 3H); LCMS (ESI, M+1): m/z=641.3.

Example 143

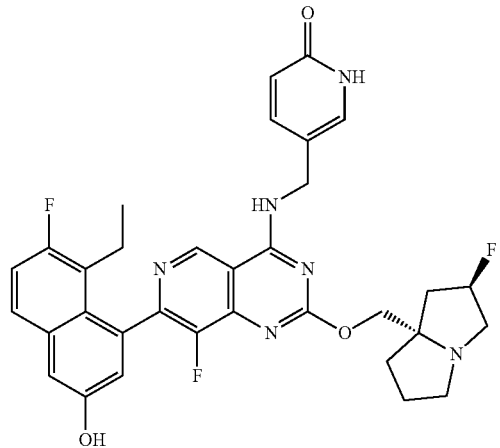 [SMILES: CCc1c(F)ccc2cc(O)cc(-c3ncc4c(NCc5ccc(=O)[nH]c5)nc(OC[C@@]56CCCN5C[C@H](F)C6)nc4c3F)c12]

5-((((7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl) amino)methyl)pyridin-2 (1H)-one The title compound was synthesized according to the procedure described for example 135. $^1$HNMR (400 MHz, methanol-d₄) δ=9.23 (s, 1H), 7.77 (dd, J=2.4, 9.2 Hz, 1H), 7.69 (dd, J=6.0, 9.2 Hz, 1H), 7.61 (d, J=2.0 Hz, 1H), 7.32 (d, J=2.4 Hz, 1H), 7.26 (t, J=9.2 Hz, 1H), 7.04 (d, J=2.4 Hz, 1H), 6.58 (d, J=9.2 Hz, 1H), 5.70-5.49 (m, 1H), 4.78-4.65 (m, 4H), 4.12-3.84 (m, 3H), 3.53-3.43 (m, 1H), 2.80-2.53 (m, 2H), 2.51-2.30 (m, 4H), 2.24-2.07 (m, 2H), 0.78 (t, J=7.6 Hz, 3H); LCMS (ESI, M+1): m/z=617.3.

Example 144

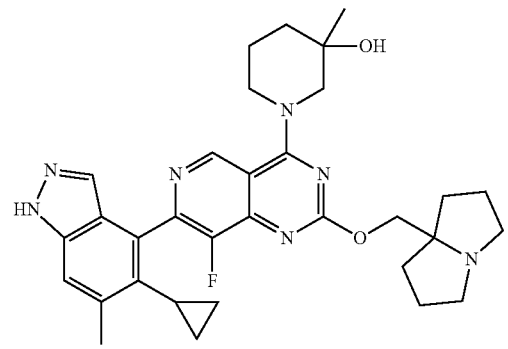 [SMILES: Cc1cc2[nH]ncc2c(-c2ncc3c(N4CCCC(C)(O)C4)nc(OCC45CCCN4CCC5)nc3c2F)c1C1CC1]

1-(7-(5-cyclopropyl-6-methyl-1H-indazol-4-yl)-8-fluoro-2-((tetrahydro-1H-pyrrolizin-7a(5H)-yl)methoxy)pyrido[4,3-d]pyrimidin-4-yl)-3-methylpiperidin-3-ol

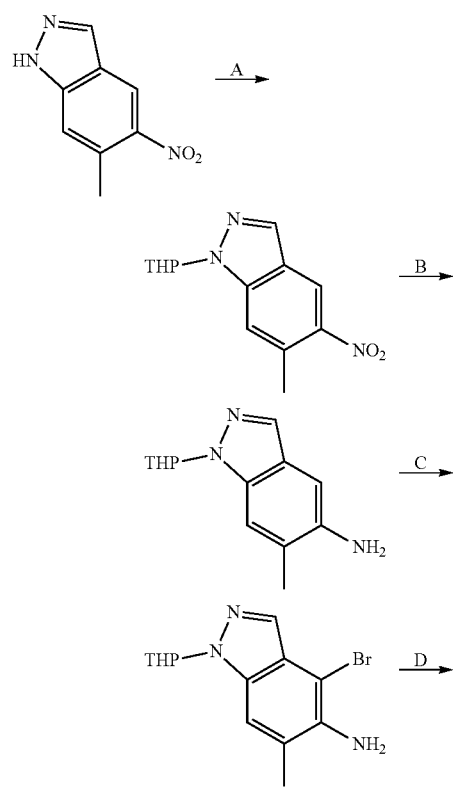

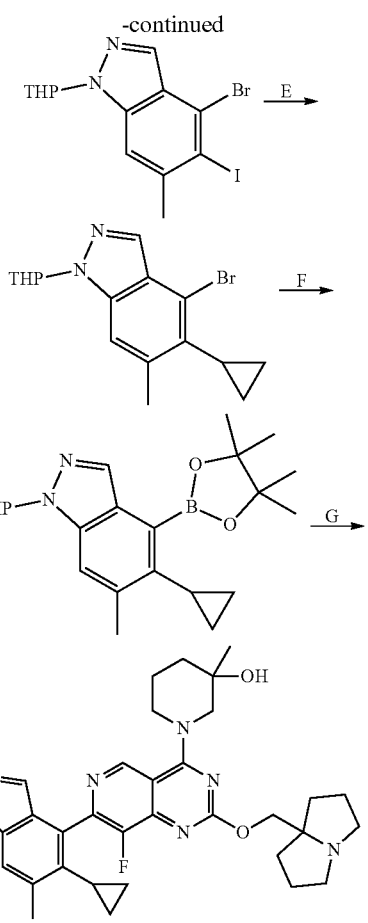

Step A. 6-methyl-5-nitro-1-tetrahydropyran-2-yl)-indazole: To a solution of 6-methyl-5-nitro-1H-indazole (8.60 g, 1 equiv.) in DCM (86 mL) was added THP (12.5 g, 3 equiv.), TsOH (834 mg, 0.1 equiv.) and resulting mixture was stirred at 20° C. for 2 hours under N₂ atmosphere. The mixture was diluted with water (100 mL) and extracted with ethyl acetate (2×100 mL). The combined organic layers were washed with brine (1×100 mL), dried over anhydrous sodium sulfate, concentrated and purified by flash silica gel chromatography (ethyl acetate/petroleum 0 to 20%) to afford the title compound (12 g, 95% yield) as a yellow solid; ¹HNMR (400 MHz, CDCl₃) δ 8.49 (s, 1H), 8.12 (s, 1H), 7.49 (s, 1H), 5.73 (dd, J=2.7, 9.2 Hz, 1H), 4.08-3.95 (m, 1H), 3.81-3.72 (m, 1H), 2.74 (s, 3H), 2.59-2.46 (m, 1H), 2.21-2.06 (m, 2H), 1.85-1.69 (m, 3H).

Step B. 6-methyl-1-tetrahydropyran-2-yl)-indazol-5-amine: To a mixture of 6-methyl-5-nitro-1-tetrahydropyran-2-yl)-indazole (6.00 g, 1 equiv.) and NH₄Cl (4.91 g, 91.9 mmol, 4 equiv.) in EtOH (50 mL) and water (10 mL) was added iron powder (6.41 g, 5 equiv.). The reaction was stirred at 80° C. for 3 hours. The mixture was filtered to remove solids. The filtrate was concentrated in vacuum. The residue was diluted with water (30 mL) and filtered. Then the filter cake was triturated with petroleum ether/ethyl acetate 50:1 (20 mL) at 25° C. for 30 min to afford the title compound (3.7 g, 70% yield) as a light red solid; $^1$HNMR (400 MHz, CDCl$_3$) δ 7.81 (s, 1H), 7.32 (s, 1H), 6.94 (s, 1H), 5.64 (dd, J=2.8, 9.2 Hz, 1H), 4.10-3.97 (m, 1H), 3.81-3.70 (m, 1H), 3.69-3.45 (m, 2H), 2.64-2.47 (m, 1H), 2.35 (s, 3H), 2.22-2.01 (m, 2H), 1.83-1.72 (m, 2H), 1.70-1.61 (m, 1H).

Step C. 4-bromo-6-methyl-1-tetrahydropyran-2-yl)-indazol-5-amine: To a solution of 6-methyl-1-tetrahydropyran-2-yl)-indazol-5-amine (4.50 g, 1 equiv.) in THF (130 mL) was added NBS (3.81 g, 1.1 equiv.). The reaction was stirred at 25° C. for 2 hours under N$_2$ atmosphere. The mixture was diluted with water (150 mL) and extracted with ethyl acetate (2×150 mL). The combined organic layers were washed with brine (1 x 150 mL), dried over anhydrous sodium sulfate, concentrated and purified by flash silica gel chromatography (ethyl acetate/petroleum ether 0 to 50%) to afford the title compound (3.5 g, 57% yield) as a yellow solid; $^1$HNMR (400 MHz, CDCl$_3$) δ 7.83 (s, 1H), 7.29 (s, 1H), 5.63 (dd, J=2.8, 9.2 Hz, 1H), 4.07-3.90 (m, 3H), 3.82-3.67 (m, 1H), 2.60-2.47 (m, 1H), 2.38 (d, J=0.8 Hz, 3H), 2.20-2.02 (m, 2H), 1.83-1.63 (m, 3H).

Step D. 4-bromo-5-iodo-6-methyl-1-tetrahydropyran-2-yl)-indazole: To a solution of 4-bromo-6-methyl-1-tetrahydropyran-2-yl)-indazol-5-amine (1.80 g, 1 equiv.) in THF (20 mL) was added CuI (1.33 g, 1.2 equiv.), CH$_2$I$_2$ (77.7 g, 50 equiv.) and isopentyl nitrite (2.04 g, 3 equiv.). The reaction was stirred at 70° C. for 2 hours. The mixture was diluted with water (100 mL), extracted with ethyl acetate (2×200 mL). The combined organic layer was washed with brine (100 mL), dried over anhydrous sodium sulfate, concentrated and purified by reversed phase flash chromatography (mobile phase: [water (0.1% formic acid)/acetonitrile]). The desired fractions were collected, neutralized with solid NaHCO$_3$ (5 g), concentrated in vacuum to remove acetonitrile, and extracted with dichloromethane (2×100 mL). The combined organic layer was washed with brine (100 mL), dried over anhydrous sodium sulfate, concentrated and purified by column chromatography (Silica gel, ethyl acetate/petroleum ether 3/1) to afford the title compound (1.4 g, 53% yield) as a yellow solid; LCMS (ESI, M+1): m/z=421.0.

Step E. 4-bromo-5-cyclopropyl-6-methyl-1-tetrahydropyran-2-yl)-indazole: A mixture of 4-bromo-5-iodo-6-methyl-1-tetrahydropyran-2-yl)-indazole (500 mg, 1 equiv.), cyclopropylboronic acid (112 mg, 1.1 equiv.), K$_2$CO$_3$ (492 mg, 3 equiv.) and Pd(dppf)Cl$_2$ (86.9 mg, 0.1 equiv.) in dioxane (10 mL) and water (3 mL) was stirred at 90° C. for 24 hours under N$_2$. The mixture was diluted with ethyl acetate (40 mL), washed with brine (20 mL), dried over anhydrous sodium sulfate, concentrated and purified by reversed phase flash chromatography (mobile phase: [water (0.1% formic acid)/acetonitrile]) twice to afford the title compound (350 mg, 80% yield) as a yellow oil; LCMS (ESI, M+1): m/z=337.0.

Step F. 5-cyclopropyl-6-methyl-1-tetrahydropyran-2-yl)-4-(4,4,5,5-tetramethyl-1,3,2-dioxaborolan-2-yl)indazole: A mixture of 4-bromo-5-cyclopropyl-6-methyl-1-tetrahydropyran-2-yl)-indazole (140 mg, 1 equiv.), 4,4,5,5-tetramethyl-1,3,2-dioxaborolane (107 mg, 2 equiv.), PCy$_3$ Pd G2 (24.7 mg, 0.1 equiv.), TEA (169 mg, 4 equiv.) in dioxane (1 mL) was stirred at 70° C. for 1 hour under N$_2$. The mixture was concentrated in vacuum. The residue was purified by reversed phase flash chromatography (mobile phase: [water (0.1% formic acid)/acetonitrile]) to afford the title compound (35 mg, 19% yield) as a yellow oil; LCMS (ESI, M+1): m/z=383.3.

Step G: 1-[7-(5-cyclopropyl-6-methyl-1-tetrahydropyran-2-yl)-indazol-4-yl)-8-fluoro-2-((tetrahydro-1H-pyrrolizin-7a(5H)-yl)methoxy)pyrido[4,3-d]pyrimidin-4-yl]-3-methyl-piperidin-3-ol: A mixture of 1-(7-chloro-8-fluoro-2-((hexahydro-1H-pyrrolizin-7a-yl) methoxy)pyrido[4,3-d]pyrimidin-4-yl)-3-methylpiperidin-3-ol (40 mg, 1 equiv.), 5-cyclopropyl-6-methyl-1-tetrahydropyran-2-yl)-4-(4,4,5,5-tetramethyl-1,3,2-dioxaborolan-2-yl) indazole (28.1 mg, 0.8 equiv.), CataCXium A Pd G3 (6.68 mg, 0.1 equiv.), K$_3$PO$_4$ (1.5 M in water, 3 equiv.) in THF (1 mL) was stirred at 60° C. for 8 hours. The mixture was concentrated and purified by reversed phase flash chromatography (mobile phase: [water (0.1% formic acid)/acetonitrile]) to afford the title compound (16 mg, 23% yield) as a yellow oil.

Step H. 1-(7-(5-cyclopropyl-6-methyl-1H-indazol-4-yl)-8-fluoro-2-((tetrahydro-1H-pyrrolizin-7a(5H)-yl)methoxy) pyrido[4,3-d]pyrimidin-4-yl)-3-methylpiperidin-3-ol: To a solution of 1-[7-(5-cyclopropyl-6-methyl-1-tetrahydropyran-2-yl)-indazol-4-yl)-8-fluoro-2-((tetrahydro-1H-pyrrolizin-7a(5H)-yl)methoxy)pyrido[4,3-d]pyrimidin-4-yl]-3-methyl-piperidin-3-ol (14 mg, 1 equiv.) in MeCN (0.5 mL) was added HCl-dioxane (4 M, 131 equiv.). The reaction was stirred at 20° C. for 0.5 hour. The mixture was concentrated in vacuum, neutralized with saturated NaHCO$_3$ solution (0.5 mL), purified by reversed phase flash chromatography (mobile phase: [water (0.1% formic acid)/acetonitrile]) and then prep-HPLC [column: Phenomenex Synergi C18 150×25 mm×10 μm; mobile phase: [water (0.225% formic acid)/ACN] B %: 9%-39%, 10 min] to afford the title compound (2.89 mg, 23% yield) as a white solid; $^1$H NMR (400 MHz, CDCl$_3$-d) δ 9.36 (br d, J=4.4 Hz, 1H), 8.55 (br s, 1H), 7.74 (br s, 1H), 7.52 (s, 1H), 4.69-4.54 (m, 3H), 4.38 (br dd, J=4.4, 12.8 Hz, 1H), 3.72-3.61 (m, 1H), 3.58-3.45 (m, 3H), 3.13 (br dd, J=4.0, 4.8 Hz, 2H), 2.69 (s, 3H), 2.27 (br dd, J=6.0, 12.0 Hz, 2H), 2.22-1.97 (m, 8H), 1.94-1.77 (m, 3H), 1.33 (br d, J=7.6 Hz, 3H), 0.92-0.53 (m, 2H), 0.25--0.02 (m, 2H); LCMS (ESI, M+1): m/z=572.4.

Example 145

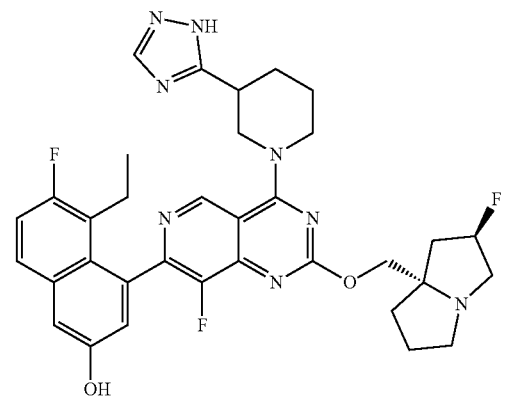 [SMILES: CCc1c(F)ccc2cc(O)cc(-c3ncc4c(N5CCCC(c6ncn[nH]6)C5)nc(OC[C@@]56CCCN5C[C@H](F)C6)nc4c3F)c12]

4-(4-(3-(1H-1,2,4-triazol-5-yl)piperidin-1-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 134. $^1$H NMR (400 MHz, CDCl$_3$) δ=13.99-13.61 (m, 1H), 10.16-9.75 (m, 1H), 9.16-9.02 (m, 1H), 7.83-7.69 (m, 1H), 7.41-7.26 (m, 2H), 7.09-6.96 (m, 1H), 5.38-5.16 (m, 1H), 4.82-4.61 (m, 1H), 4.53-4.34 (m, 1H), 4.23-4.00 (m, 2H), 3.78-3.53 (m, 2H), 3.13-2.99 (m, 3H), 2.88-2.79 (m, 1H), 2.45-2.29 (m, 2H), 2.27-1.69 (m, 12H), 0.81-0.66 (m, 3H). LCMS (ESI, M+1): m/z=645.3.

Example 146

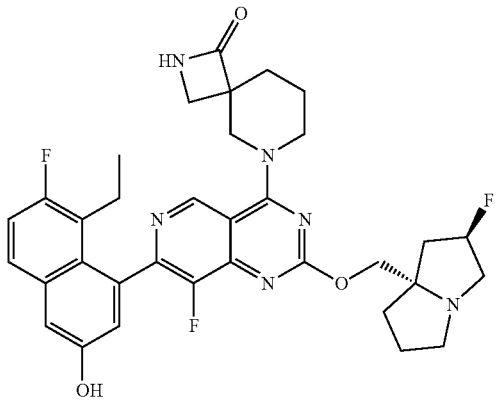 [SMILES: CCc1c(F)ccc2cc(O)cc(-c3ncc4c(N5CCCC6(CNC6=O)C5)nc(OC[C@@]56CCCN5C[C@H](F)C6)nc4c3F)c12]

6-(7-(8-ethyl-7-fluoro-3-hydroxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2,6-diazaspiro[3.5]nonan-1-one The title compound was synthesized according to the procedure described for example 134. $^1$H NMR (400 MHz, methanol-d$_4$) δ 9.07 (s, 1H), 7.68 (dd, J=5.6, 8.8 Hz, 1H), 7.30 (d, J=2.8 Hz, 1H), 7.25 (t, J=9.2 Hz, 1H), 7.06 (t, J=2.0 Hz, 1H), 5.40-5.23 (m, 1H), 4.41-4.32 (m, 2H), 4.31-4.18 (m, 2H), 4.16-3.96 (m, 2H), 3.38-3.33 (m, 1H), 3.29-3.25 (m, 2H), 3.24-3.18 (m, 2H), 3.08-3.00 (m, 1H), 2.52-2.41 (m, 1H), 2.40-2.27 (m, 1H), 2.25-1.99 (m, 8H), 1.95-1.86 (m, 2H), 0.80 (br t, J=7.2 Hz, 3H); $^{19}$F NMR (376 MHz, methanol-d4) δ −121.158, −138.976, −173.778; LCMS (ESI, M+1): m/z=633.4.

Example 147

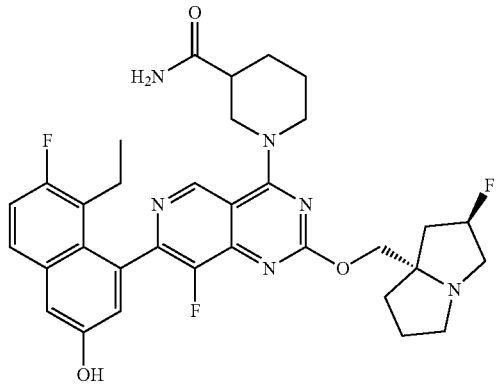 [SMILES: CCc1c(F)ccc2cc(O)cc(-c3ncc4c(N5CCCC(C(N)=O)C5)nc(OC[C@@]56CCCN5C[C@H](F)C6)nc4c3F)c12]

1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)piperidine-3-carboxamide The title compound was synthesized according to the procedure described for example 134. $^1$H NMR (400 MHz, DMSO-d$_6$) δ=9.93 (br s, 1H), 9.09 (s, 1H), 7.76 (dd, J=6.0, 9.2 Hz, 1H), 7.45 (br d, J=4.4 Hz, 1H), 7.39-7.29 (m, 2H), 7.03 (d, J=2.4 Hz, 1H), 6.97 (br s, 1H), 5.40-5.15 (m, 1H), 4.55-4.42 (m, 1H), 4.41-4.31 (m, 1H), 4.19-4.10 (m, 1H), 4.09-4.01 (m, 1H), 3.58-3.42 (m, 2H), 3.17-3.04 (m, 1H), 3.16-3.03 (m, 1H), 3.01 (s, 1H), 2.88-2.76 (m, 1H), 2.66-2.54 (m, 2H), 2.22-2.09 (m, 2H), 2.08-1.95 (m, 3H), 1.93-1.82 (m, 2H), 1.81-1.66 (m, 4H), 0.72 (t, J=7.2 Hz, 3H); LCMS (ESI, M+1): m/z=621.3.

Example 148

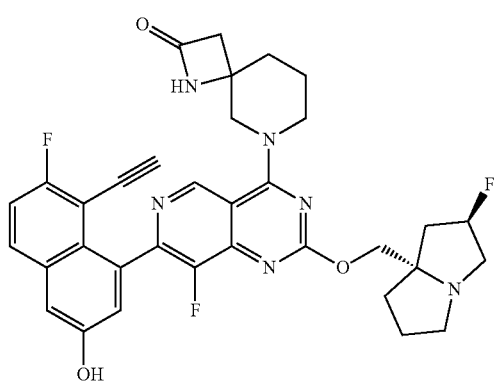 [SMILES: C#Cc1c(F)ccc2cc(O)cc(-c3ncc4c(N5CCCC6(CC(=O)N6)C5)nc(OC[C@@]56CCCN5C[C@H](F)C6)nc4c3F)c12]

325

6-(7-(8-ethynyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,6-diazaspiro[3.5]nonan-2-one

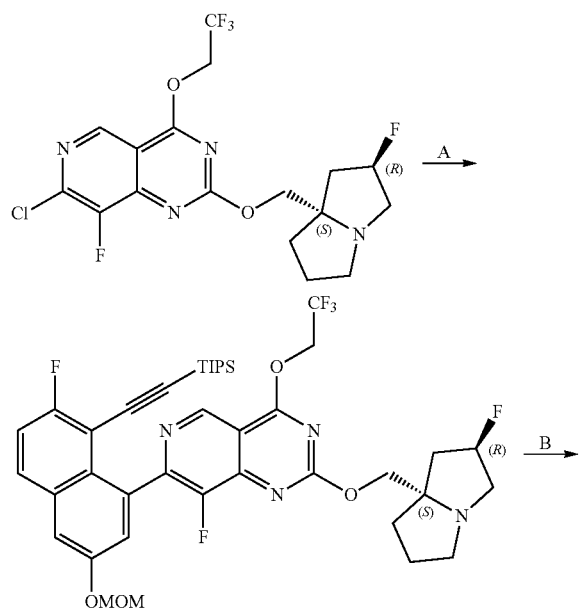

326

-continued

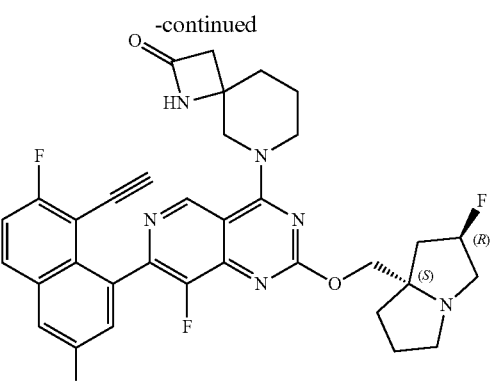

Step A: 8-fluoro-7-(7-fluoro-3-(methoxymethoxy)-8-((triisopropylsilyl) ethynyl)naphthalen-1-yl)-2-(((2R,7aS)-2-fluorohexahydro-1H-pyrrolizin-7a-yl) methoxy)-4-(2,2,2-trifluoroethoxy)pyrido[4,3-d]pyrimidine: To a mixture of 7-chloro-8-fluoro-2-(((2R,7aS)-2-fluorohexahydro-1H-pyrrolizin-7a-yl)methoxy)-4-(2,2,2-trifluoroethoxy) pyrido[4,3-d]pyrimidine (410 mg, 1.0 equiv., formic acid salt), ((2-fluoro-6-(methoxymethoxy)-8-(4,4,5,5-tetramethyl-1,3,2-dioxaborolan-2-yl)naphthalen-1-yl) ethynyl) triisopropylsilane (563 mg, 1.3 equiv.) and $Cs_2CO_3$ (1.5 M in water, 1.69 mL, 3.0 equiv.) in methoxycyclopentane (5.1 mL) was added CataCXium A Pd G3 (61.6 mg, 0.1 equiv.) under $N_2$. The reaction was de-gassed and then heated to 100° C. for 1 hour under $N_2$. The mixture was poured into saturated $NH_4Cl$ solution (10 mL). Then the mixture was diluted with ethyl acetate (10 mL) and layers were separated. The aqueous phase was extracted with ethyl acetate (10 mL). The combined organic layer was washed with brine (10 mL), dried over $Na_2SO_4$, filtered and concentrated in vacuum. The residue was purified by reversed phase flash chromatography [water (0.1% formic acid)/acetonitrile] to afford the title compound (547 mg, 76% yield, formic acid salt) as a brown oil; $^1$H NMR (400 MHz, $CDCl_3$A-d)=9.31-9.27 (m, 1H), 7.81 (dd, J=5.6, 9.2 Hz, 1H), 7.55 (d, J=2.4 Hz, 1H), 7.37-7.28 (m, 2H), 5.69-5.43 (m, 1H), 5.36-5.23 (m, 3H), 5.01-4.79 (m, 2H), 4.30-4.17 (m, 1H), 3.70-3.56 (m, 1H), 3.54-3.50 (m, 3H), 3.32 (br s, 1H), 2.92-2.72 (m, 2H), 2.68-2.55 (m, 2H), 2.42-2.29 (m, 4H), 0.95-0.80 (m, 18H), 0.70-0.44 (m, 3H); LCMS (ESI, M+1): m/z=789.3.

Step B: 6-(8-fluoro-7-(7-fluoro-3-(methoxymethoxy)-8-((triisopropylsilyl) ethynyl)naphthalen-1-yl)-2-(((2R,7aS)-2-fluorohexahydro-1H-pyrrolizin-7a-yl) methoxy)pyrido[4,3-d]pyrimidin-4-yl)-1,6-diazaspiro[3,5]nonan-2-one: A mixture of 7-chloro-8-fluoro-2-(((2R,7aS)-2-fluorohexahydro-1H-pyrrolizin-7a-yl)methoxy)-4-(2,2,2-trifluoroethoxy) pyrido[4,3-d]pyrimidine (0.1 g, 1.0 equiv., formic acid salt), 1,8-diazaspiro[3.5]nonan-2-one (58.8 mg, 3.5 equiv.), DIEA (46.4 mg, 3.0 equiv.) and 4 Å molecular sieves (10 mg) in DMF (1 mL) was stirred at 40-60° C. for 105 hours. The mixture was filtered and the filtrate was purified by reversed phase flash chromatography (mobile phase: [water (0.1% formic acid)/acetonitrile]) to afford the title compound (27 mg, 26% yield) as a yellow solid; LCMS (ESI, M+1): m/z=829.5.

Step C: 6-(7-(8-ethynyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,6-diazaspiro[3.5]nonan-2-one: A mixture of 6-(8-fluoro-7-(7-fluoro-3-(methoxymethoxy)-8-((triisopropylsilyl) ethynyl)naphthalen-1-yl)-2-(((2R,7aS)-2-fluorohexahydro- 1H-pyrrolizin-7a-yl) methoxy)pyrido[4,3-d]pyrimidin-4-yl)-1,6-diazaspiro[3.5]nonan-2-one (27.0 mg, 1.0 equiv.) and CsF (74.2 mg, 15 equiv.) in DMF (0.5 mL) was stirred at 25° C. for 1 hour. The mixture was purified by reversed phase flash chromatography (mobile phase: [water (0.1% formic acid)/acetonitrile]) to afford the title compound (15.0 mg, 68% yield) as a yellow solid; LCMS (ESI, M+1): m/z=673.3.

Step D: 6-(7-(8-ethynyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,6-diazaspiro[3.5]nonan-2-one: A mixture of 6-(7-(8-ethynyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)-1,6-diazaspiro[3.5]nonan-2-one (15.0 mg, 1.0 equiv.) and TFA (462 mg, 182 equiv.) in dichloromethane (0.3 mL) was stirred at 25° C. for 0.5 hour. The mixture was concentrated in vacuum and the pH value was adjusted to around 8 with ice-cold saturated $Na_2CO_3$ solution. The mixture was diluted with ethyl acetate/methanol 7:1 (8 mL) and the layers were separated. The aqueous phase was extracted with ethyl acetate (6 mL). The combined organic layers were washed with brine (8 mL), dried over $Na_2SO_4$, filtered and concentrated in vacuum. The residue was purified by prep-HPLC [column: water s Xbridge 150×25 mm×5 μm; mobile phase: [water (10 mM $NH_4HCO_3$)/ACN] B %: 29%-59%, 9 min] to afford the title compound (4.50 mg, 31% yield) as a yellow solid; $^1$H NMR (400 MHz, methanol-d4) δ=9.03 (d, J=6.4 Hz, 1H), 7.87 (dd, J=5.6, 9.2 Hz, 1H), 7.37-7.30 (m, 2H), 7.22 (d, J=2.4 Hz, 1H), 5.41-5.25 (m, 1H), 4.46-4.23 (m, 4H), 4.05-3.96 (m, 1H), 3.88-3.64 (m, 1H), 3.41-3.32 (m, 3H), 3.26-3.02 (m, 2H), 2.92-2.73 (m, 2H), 2.41-2.23 (m, 2H), 2.19-2.09 (m, 2H), 2.04-1.92 (m, 6H); $^{19}$F NMR (376 MHz, methanol-d4) δ=−111.662, −139.984, −173.693; LCMS (ESI, M+1): m/z=629.3.

Example 149

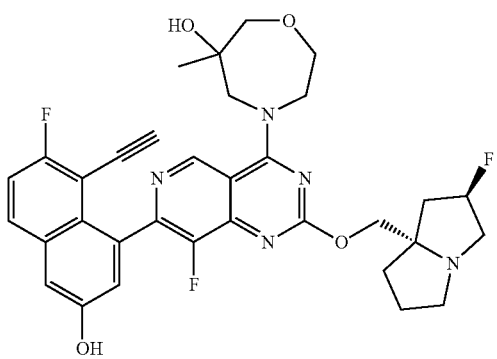 [SMILES: C#Cc1c(F)ccc2cc(O)cc(-c3ncc4c(N5CCOCC(C)(O)C5)nc(OC[C@@]56CCCN5C[C@H](F)C6)nc4c3F)c12]

4-(7-(8-ethynyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol The title compound was synthesized according to the procedure described for example 24. $^1$H NMR (400 MHz, methanol-d4) δ=9.49-9.36 (m, 1H), 7.88-7.83 (m, 1H), 7.36-7.29 (m, 2H), 7.22 (dd, J=2.4, 10.0 Hz, 1H), 5.39-5.22 (m, 1H), 4.64-4.45 (m, 2H), 4.35-4.16 (m, 3H), 4.05-3.84 (m, 3H), 3.74-3.61 (m, 2H), 3.47-3.41 (m, 1H), 3.29-3.11 (m, 3H), 3.06-2.98 (m, 1H), 2.40-2.18 (m, 2H), 2.17-2.09 (m, 1H), 2.05-1.95 (m, 2H), 1.94-1.85 (m, 1H), 1.27 (d, J=13.6 Hz, 3H); $^{19}$F NMR (376 MHz, methanol-d4) δ=−111.763, −139.876, −173.658; LCMS (ESI, M+1): m/z=620.3.

Example 150

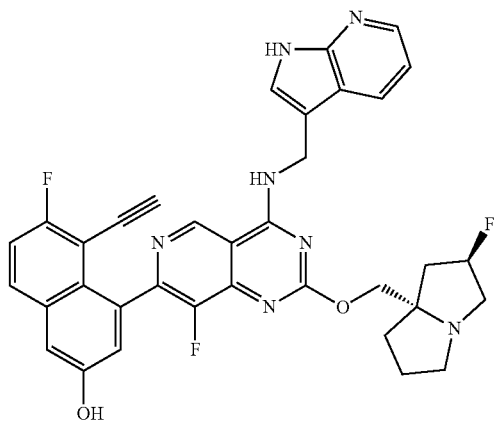 [SMILES: C#Cc1c(F)ccc2cc(O)cc(-c3ncc4c(NCc5c[nH]c6ncccc56)nc(OC[C@@]56CCCN5C[C@H](F)C6)nc4c3F)c12]

4-(4-(((1H-pyrrolo[2,3-b]pyridin-3-yl)methyl)amino)-8-fluoro-2-(((2R,7aS)-2-fluorohexahydro-1H-pyrrolizin-7a-yl)methoxy)pyrido[4,3-d]pyrimidin-7-yl)-5-ethynyl-6-fluoronaphthalen-2-ol The title compound was synthesized according to the procedure described for example 24. $^1$H NMR (400 MHz, CD3OD) δ 9.12 (s, 1H), 8.22 (s, 1H), 8.21-8.19 (m, 1H), 7.87-8.82 (m, 1H), 7.54 (s, 1H), 7.35-7.28 (m, 2H), 7.21-7.09 (m, 2H), 5.39-5.20 (d, J=56.4 Hz, 1H), 5.12-5.00 (m, 2H), 4.38-4.26 (m, 2H), 3.30-3.11 (m, 4H), 3.09-2.92 (m, 1H), 2.39-2.25 (m, 1H), 2.24-2.18 (m, 1H), 2.17-2.08 (m, 1H), 2.04-1.93 (m, 2H), 1.93-1.82 (m, 1H); LCMS (ESI, M+1): m/z=636.4.

Example 151

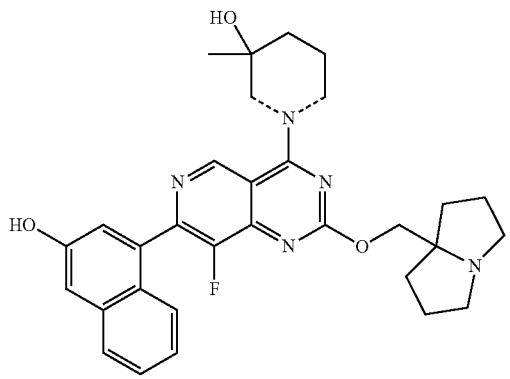

1-(8-fluoro-7-(3-hydroxy)naphthalen-1-yl)-2-((tetra-hydro-1H-pyrrolizin-7a(5H)-yl) methoxy)pyrido[4,3-d]pyrimidin-4-yl)-3-methylpiperidin-3-ol

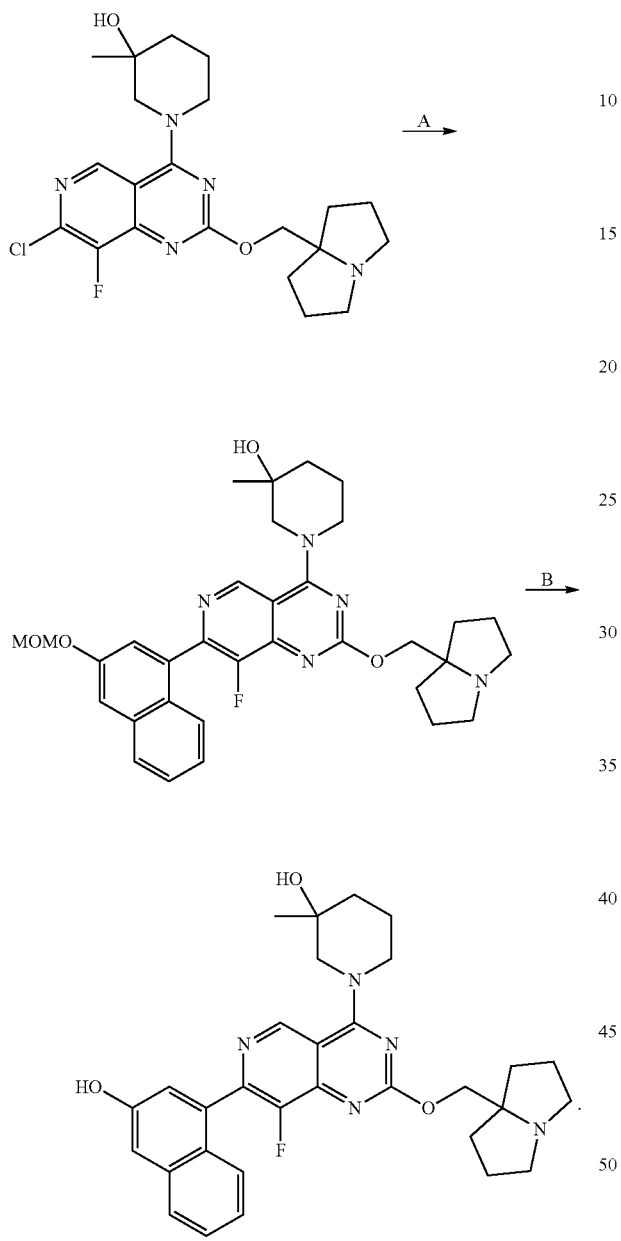

dried over Na$_2$SO$_4$, filtered, concentrated and purified by silica gel column chromatography (ethyl acetate and then NH$_4$OH/MeOH 1:1000) to afford the title compound as a brown liquid (45 mg, 67% yield); LCMS (ESI, M+1): m/z=588.3.

Step B. 1-(8-fluoro-7-(3-hydroxynaphthalen-1-yl)-2-((tetrahydro-1H-pyrrolizin-7a(5H)-yl)methoxy)pyrido[4,3-d]pyrimidin-4-yl)-3-methylpiperidin-3-ol: To a solution of 1-[8-fluoro-2-((tetrahydro-1H-pyrrolizin-7a(5H)-yl)methoxy)-7-[4-(methoxymethoxy)-2-naphthyl]pyrido[4,3-d]pyrimidin-4-yl]-3-methyl-piperidin-3-ol (45 mg, 76.57 μmol, 1 equiv.) in MeCN (0.5 mL) was added HCl/dioxane (4 M, 0.5 mL, 26.12 equiv.) at 0° C. The reaction was stirred at 0° C. for 0.5 hour. The mixture was concentrated under reduced pressure and purified by prep-HPLC (column: Phenomenex Luna C18 150×25 mm×10 μm; mobile phase: [water (0.225% formic acid)/ACN]; B %: 7%-37%, 11.5 min) to afford the title compound as a yellow oil (26.86 mg, 59% yield, formic acid salt); $^1$H NMR (400 MHz, METHANOL-d$_4$) δ=9.33 (s, 1H), 8.55 (s, 1H), 7.79 (d, J=8.4 Hz, 1H), 7.56 (br d, J=8.0 Hz, 1H), 7.46 (dt, J=1.0, 7.6 Hz, 1H), 7.32 (d, J=2.4 Hz, 1H), 7.30-7.24 (m, 2H), 4.66 (s, 3H), 4.38 (br d, J=13.5 Hz, 1H), 3.72-3.62 (m, 3H), 3.53-3.40 (m, 1H), 3.28-3.21 (m, 2H), 2.33 (ddd, J=3.2, 6.7, 12.4 Hz, 2H), 2.25-2.07 (m, 7H), 1.89-1.76 (m, 3H), 1.34-1.28 (m, 3H), 1.31 (s, 3H); $^{19}$F NMR (377 MHz, METHANOL-d$_4$) δ=−140.42; LCMS (ESI, M+1): m/z=544.5.

Example 152

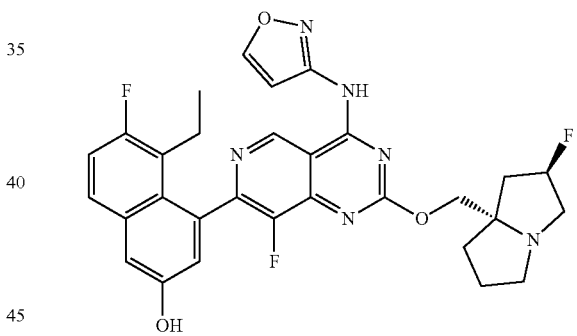

5-ethyl-6-fluoro-4-(8-fluoro-2-(((2R,7aS)-2-fluoro-hexahydro-1H-pyrrolizin-7a-yl)methoxy)-4-(isoxazol-3-ylamino)pyrido[4,3-d]pyrimidin-7-yl)naphthalen-2-ol Step A. 1-[8-fluoro-2-((tetrahydro-1H-pyrrolizin-7a(5H)-yl)methoxy)-7-[4-(methoxymethoxy)-2-naphthyl]pyrido[4,3-d]pyrimidin-4-yl]-3-methyl-piperidin-3-ol: To a solution of 1-(7-chloro-8-fluoro-2-((hexahydro-1H-pyrrolizin-7a-yl)methoxy)pyrido[4,3-d]pyrimidin-4-yl)-3-methylpiperidin-3-ol (50 mg, 1.0 equiv.), 2-[3-(methoxymethoxy)-1-naphthyl]-4,4,5,5-tetramethyl-1,3,2-dioxaborolane (72.1 mg, 2.0 equiv.) and K$_3$PO$_4$ (1.5 M in water, 3.0 equiv.) in THF (0.5 mL) was added CataCXium A Pd G3 (8.35 mg, 0.1 equiv.). The mixture was degassed and stirred at 60° C. for 2 hours. Upon reaction completion, the mixture was diluted with water (5 mL) and extracted with ethyl acetate (5 mL×3). The combined organic layers were washed with brine 20 mL, The title compound was synthesized according to the procedure described for example 134. $^1$H NMR (400 MHz, METHANOL-d$_4$) δ=9.50 (s, 1H), 8.70 (d, J=1.6 Hz, 1H), 8.47 (br s, 1H), 7.69 (dd, J=6.0, 9.2 Hz, 1H), 7.32 (d, J=2.8 Hz, 1H), 7.30-7.22 (m, 2H), 7.07 (d, J=2.4 Hz, 1H), 5.56-5.31 (m, 1H), 4.60-4.45 (m, 2H), 3.67-3.47 (m, 3H), 3.28-3.17 (m, 1H), 2.60-2.37 (m, 3H), 2.36-2.24 (m, 1H), 2.23-2.11 (m, 3H), 2.09-1.96 (m, 1H), 0.80 (t, J=7.2 Hz, 3H); LCMS (ESI, M+1): m/z=577.2.

331

Example 153

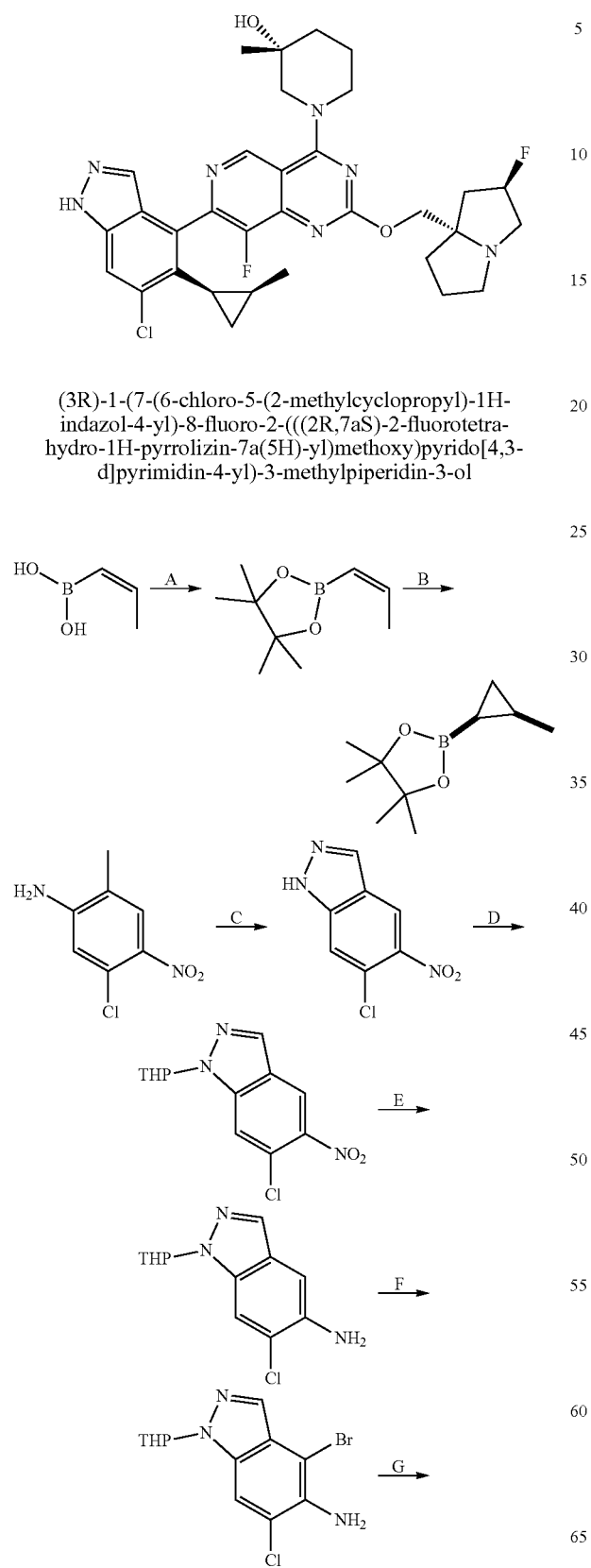

(3R)-1-(7-(6-chloro-5-(2-methylcyclopropyl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-ol

332

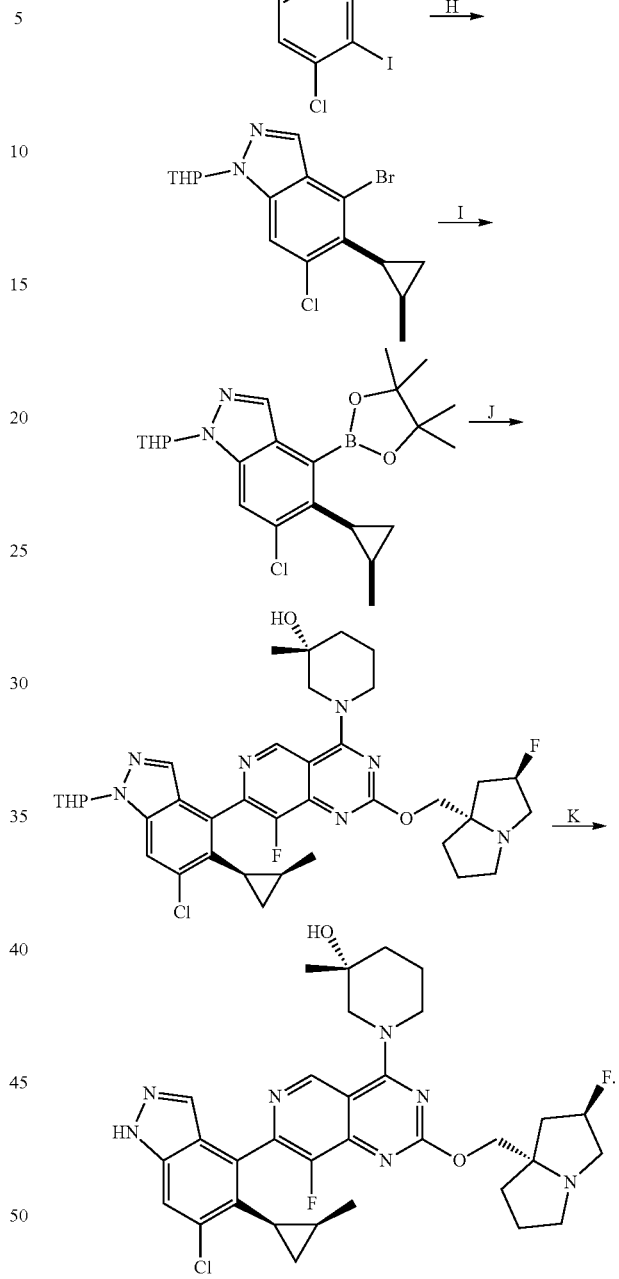

Step A. 4,4,5,5-tetramethyl-2-[(Z)-prop-1-enyl]-1,3,2-dioxaborolane: A mixture of [(Z)-prop-1-enyl]boronic acid (3.00 g, 1 equiv.), pinacol (4.13 g, 1 equiv.) and MgSO$_4$ (12.6 g, 3 equiv.) in DCM (30 mL) was stirred at 20° C. for 12 hours. After reaction completion, the mixture was filtered and concentrated in vacuum to afford the title compound (5 g, 85% yield) as a yellow liquid. $^1$H NMR (400 MHz, CDCl$_3$-d) S 6.59-6.39 (m, 1H), 5.39-5.27 (m, 1H), 1.97 (dd, J=1.6, 6.8 Hz, 3H), 1.32-1.25 (m, 12H).

Step B. rac-4,4,5,5-tetramethyl-2-[2-methylcyclopropyl]-1,3,2-dioxaborolane: To a solution of ZnEt$_2$ (2 M in hexane, 3 equiv.) in DCM (10 mL) was added TFA (4.07 g, 3 equiv.) at −40° C. After stirred at −40° C. for 10 mins, CH$_2$I$_2$ (9.56 g, 3 equiv.) was added into the mixture. The reaction was stirred at −40° C. for 10 mins, 4,4,5,5-tetramethyl-2-[(Z)-prop-1-enyl]-1,3,2-dioxaborolane (2.00 g, 1 equiv.) was added into the mixture. The reaction was stirred at 25° C. for 16 hours. After reaction completion, the mixture was diluted with DCM (100 mL) and filtered. The filtrate was washed with water (100 mL) and brine (100 mL), dried over anhydrous sodium sulfate, filtered and concentrated in vacuum to afford the title compound (2.00 g, 92% yield) as a yellow oil and used into next step without further purification. $^1$H NMR (400 MHz, CDCl$_3$-d) δ 1.23 (d, J=7.6 Hz, 12H), 1.15-1.11 (m, 3H), 1.10-1.03 (m, 1H), 0.80-0.71 (m, 1H), 0.40-0.30 (m, 1H), −0.10 (dt, J=6.8, 9.2 Hz, 1H).

Step C. 6-chloro-5-nitro-1H-indazole: To a solution of 5-chloro-2-methyl-4-nitro-aniline (10.0 g, 1 equiv.) in AcOH (300 mL) was added dropwise the solution of NaNO$_2$ (4.07 g, 1.1 equiv.) in water (40 mL) at 0° C. The reaction was stirred at 25° C. for 2 hours. After completion, the mixture was poured into 1000 mL water and filtered. The filter cake was washed by 1000 mL water, then dried in vacuum to afford the title compound (8 g, 76% yield) as a yellow solid. $^1$H NMR (400 MHz, CDCl$_3$) δ 8.44 (s, 1H), 8.25 (s, 1H), 7.71 (s, 1H).

Step D. 6-chloro-5-nitro-1-tetrahydropyran-2-yl)-indazole: To a solution of 6-chloro-5-nitro-1H-indazole (6.6 g, 1 equiv.) in DCM (60 mL) was added TsOH·H$_2$O (635 mg, 0.1 equiv.), then 3,4-dihydro-2H-pyran (8.43 g, 3 equiv.) slowly at 25° C. The mixture was stirred at 25° C. for 1 hour before being concentrated in vacuum and purified by flash silica gel chromatography (ethyl acetate in petroleum ether 0-30%) to afford the title compound (7.20 g, 76% yield) as a yellow solid. $^1$H NMR (400 MHz, CDCl$_3$) δ 8.38 (s, 1H), 8.15 (s, 1H), 7.81 (s, 1H), 5.73 (dd, J=2.4, 8.9 Hz, 1H), 4.06-3.97 (m, 1H), 3.82-3.71 (m, 1H), 2.55-2.41 (m, 1H), 2.22-2.08 (m, 2H), 1.90-1.64 (m, 4H).

Step E. 6-chloro-1-tetrahydropyran-2-yl)-indazol-5-amine: To a solution of 6-chloro-5-nitro-1-tetrahydropyran-2-yl)-indazole (7.2 g, 1 equiv.) in EtOH (80 mL) and water (16 mL) was added NH$_4$Cl (5.74 g, 4.2 equiv.) and iron powder (5.99 g, 4.2 equiv.). The reaction was stirred at 80° C. for 6 hours. After completion, the mixture was filtered, the filtrate was concentrated and purified by flash silica gel chromatography (ethyl acetate in petroleum ether 0-30%) to afford the title compound (6 g, 93% yield) as a yellow solid. $^1$H NMR (400 MHz, CDCl$_3$) δ 7.80 (s, 1H), 7.59 (s, 1H), 7.00 (s, 1H), 5.59 (dd, J=2.4, 9.3 Hz, 1H), 4.06-3.92 (m, 3H), 3.80-3.69 (m, 1H), 2.58-2.44 (m, 1H), 2.18-2.05 (m, 2H), 1.81-1.57 (m, 4H).

Step F. 4-bromo-6-chloro-1-tetrahydropyran-2-yl)-indazol-5-amine: To a solution of 6-chloro-1-tetrahydropyran-2-yl)-indazol-5-amine (6.10 g, 1 equiv.) in THF (120 mL) was added NBS (5.18 g, 1.2 equiv.). The reaction was stirred at 25° C. for 2 hours. After completion, the mixture was filtered and the filtrate was concentrated in vacuum and purified by flash silica gel chromatography (ethyl acetate in petroleum ether 0-30%) to afford the title compound (3 g, 34% yield) as a yellow solid. $^1$H NMR (400 MHz, CDCl$_3$) δ 7.83 (d, J=0.8 Hz, 1H), 7.59 (s, 1H), 5.60 (dd, J=2.8, 9.2 Hz, 1H), 4.37 (br s, 2H), 4.04-3.96 (m, 1H), 3.80-3.66 (m, 1H), 2.52-2.41 (m, 1H), 2.22-2.09 (m, 2H), 1.84-1.66 (m, 4H).

Step G. 4-bromo-6-chloro-5-iodo-1-tetrahydropyran-2-yl)-indazole: A reaction mixture of 4-bromo-6-chloro-1-tetrahydropyran-2-yl)-indazol-5-amine (2.40 g, 1 equiv.), CuI (1.80 g, 1.3 equiv.), isopentyl nitrite (2.55 g, 3 equiv.) and CH$_2$I$_2$ (97.2 g, 50 equiv.) in THF (20 mL) was stirred at 70° C. for 2 hours. After completion, the mixture was diluted with water (100 mL), extracted with ethyl acetate (2×200 mL). The combined organic layers were washed with brine (100 mL), dried over anhydrous sodium sulfate, concentrated in vacuum and purified by reversed phase flash chromatography (mobile phase: [water (0.1% formic acid)/acetonitrile]). The desired fractions were collected, neutralized with solid NaHCO$_3$ (5 g), concentrated in vacuum to remove acetonitrile, and extracted with ethyl acetate (2×50 mL). The combined organic layer was washed with brine (50 mL), dried over anhydrous Na$_2$SO$_4$, concentrated and purified by silica gel column chromatography (ethyl acetate in petroleum ether 30%) to afford the title compound (1.05 g, 32% yield) as a yellow solid. LCMS (ESI, M−84): m/z=358.8.

Step H. 4-bromo-6-chloro-5-[2-methylcyclopropyl]-1-tetrahydropyran-2-yl-indazole: To a solution of 4-bromo-6-chloro-5-iodo-1-tetrahydropyran-2-yl)-indazole (500 mg, 1 equiv.), 4,4,5,5-tetramethyl-2-[2-methylcyclopropyl]-1,3,2-dioxaborolane (309 mg, 1.5 equiv.) in dioxane (10 mL) and water (3 mL) was added K$_2$CO$_3$ (469 mg, 3 equiv.) and Pd(dppf)Cl$_2$ (82.9 mg, 0.1 equiv.). The reaction was stirred at 90° C. for 12 hours. After completion, the mixture was diluted with ethyl acetate (40 mL), washed with brine (20 mL), dried over anhydrous sodium sulfate, concentrated and purified by reversed phase flash chromatography (mobile phase: [water (0.1% formic acid)/acetonitrile]) to afford the title compound (90 mg, 21% yield) as a yellow oil. LCMS (ESI, M−84): m/z=286.9.

Step I. 6-chloro-5-[2-methylcyclopropyl]-1-tetrahydropyran-2-yl)-4-(4,4,5,5-tetramethyl-1,3,2-dioxaborolan-2-yl) indazole: A reaction mixture of 4-bromo-6-chloro-5-[2-methylcyclopropyl]-1-tetrahydropyran-2-yl)-indazole (80 mg, 1 equiv.), 4,4,5,5-tetramethyl-1,3,2-dioxaborolane (83.1 mg, 3 equiv.), TEA (131 mg, 6 equiv.), Pd(OAc)$_2$ (4.86 mg, 0.1 equiv.) in dioxane (2 mL) was stirred at 70° C. for 5 hours. After completion, the mixture was concentrated in vacuum and purified by reversed phase flash chromatography (C18, mobile phase: [water (0.1% formic acid)/acetonitrile]) to afford the title compound (70 mg, 78% yield) as a yellow liquid. LCMS (ESI, M+1): m/z=417.1.

Step J. (3R)-1-(7-(6-chloro-5-(2-methylcyclopropyl)-1-(tetrahydro-2H-pyran-2-yl)-1H-indazol-4-yl)-8-fluoro-2-(((2R,7aS)-2-fluorotetrahydro-1H-pyrrolizin-7a(5H)-yl) methoxy)pyrido[4,3-d]pyrimidin-4-yl)-3-methylpiperidin-3-ol: A reaction mixture of (R)-1-(7-chloro-8-fluoro-2-(((2R,7aS)-2-fluorohexahydro-1H-pyrrolizin-7a-yl) methoxy)pyrido[4,3-d]pyrimidin-4-yl)-3-methylpiperidin-3-ol (40 mg, 1 equiv.), 6-chloro-5-[2-methylcyclopropyl]-1-tetrahydropyran-2-yl)-4-(4,4,5,5-tetramethyl-1,3,2-dioxaborolan-2-yl)indazole (36.7 mg, 1 equiv.), CataCXium A Pd G3 (6.42 mg, 0.1 equiv.) and K$_3$PO$_4$ (1.5 M in water, 3 equiv.) in THF (1 mL) was stirred at 60° C. for 2 hours. After completion, the mixture was concentrated and purified by reversed phase flash chromatography (C18, mobile phase: [water (0.1% formic acid)/acetonitrile]) to afford the title compound (7 mg, 11% yield) as a yellow solid. LCMS (ESI, M+1): m/z=708.3.

Step K. (3R)-1-(7-(6-chloro-5-(2-methylcyclopropyl)-1H-indazol-4-yl)-8-fluoro-2-(((2R,7aS)-2-fluorotetrahydro-1H-pyrrolizin-7a(5H)-yl)methoxy)pyrido[4,3-d]pyrimidin-4-yl)-3-methylpiperidin-3-ol: A reaction mixture of (3R)-1-(7-(6-chloro-5-(2-methylcyclopropyl)-1-(tetrahydro-2H-pyran-2-yl)-1H-indazol-4-yl)-8-fluoro-2-(((2R,7aS)-2-fluorotetrahydro-1H-pyrrolizin-7a(5H)-yl)methoxy)pyrido [4,3-d]pyrimidin-4-yl)-3-methylpiperidin-3-ol (7 mg, 1 equiv.) in HCl/dioxane (4 M, 142 equiv.) and MeCN (0.1 mL) was stirred at 15° C. for 10 mins. After reaction completion, the mixture was concentrated in vacuum and purified by reversed phase flash chromatography (C18, mobile phase: [water (0.1% formic acid)/acetonitrile]) and then re-purified by prep-HPLC: [column: Phenomenex luna C18 150×25 mm×10 um; mobile phase: [water (0.225% formic acid)/CAN]; B %: 18%-48%, 10 min] to afford the title compound (1.75 mg, 27% yield) as a white solid. $^1$H NMR (400 MHz, CDCl$_3$-d) δ 9.36-9.25 (m, 1H), 8.57-8.46 (m, 1H), 8.17-7.68 (m, 2H), 5.46-5.28 (m, 1H), 4.91 (br d, J=1.2 Hz, 1H), 4.64-4.52 (m, 1H), 4.46-4.23 (m, 3H), 3.70-3.63 (m, 1H), 3.63-3.57 (m, 1H), 3.55-3.34 (m, 4H), 3.17-3.09 (m, 1H), 2.49-2.27 (m, 2H), 2.26-2.03 (m, 5H), 2.02-1.75 (m, 5H), 1.36-1.22 (m, 4H), 1.18 (t, J=7.2 Hz, 2H), 0.71-0.64 (m, 3H). LCMS (ESI, M+1): m/z=624.3.

Example 154

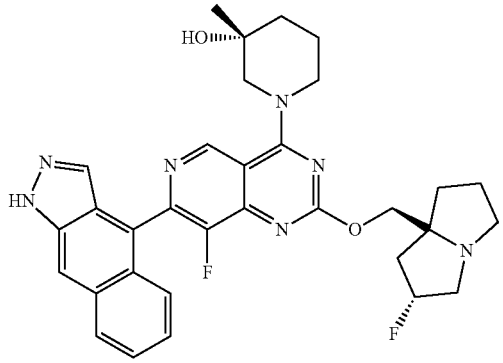

(3R)-1-(7-(1H-benzo[f]indazol-4-yl)-8-fluoro-2-((((2R,7aS)-2-fluorohexahydro-1H-pyrrolizin-7a-yl)methoxy)pyrido[4,3-d]pyrimidin-4-yl)-3-methylpiperidin-3-ol

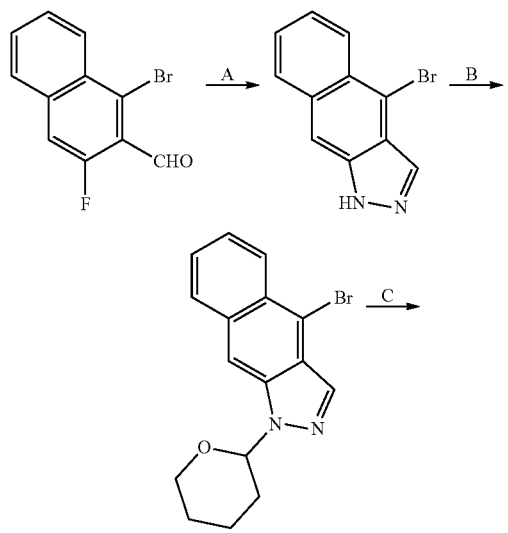

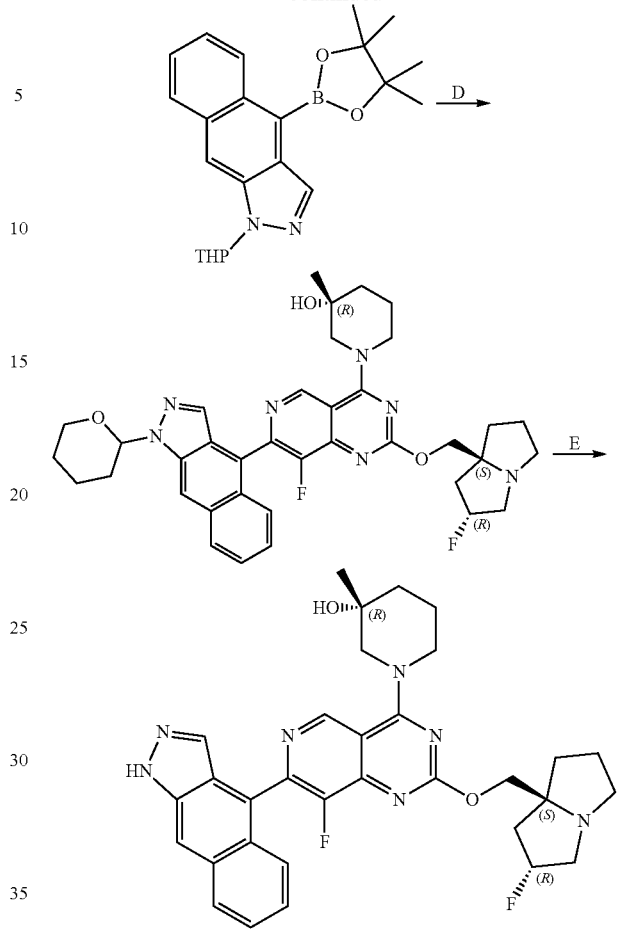

Step A. 4-bromo-1H-benzo[f]indazole: To a mixture of 1-bromo-3-fluoro-2-naphthaldehyde (500 mg, 1.00 equiv.) in dimethyl sulfoxide (5.00 mL) was added hydrazine hydrate (0.60 g, 582 μL, 98.0% purity, 5.9 equiv.) and diisopropylethylamine (2.04 g, 2.75 mL, 8.00 equiv.) in one portion under nitrogen. The reaction was stirred at 130° C. for 8 hours. The reaction mixture was concentrated under reduced pressure and purified by prep-HPLC (column: Phenomenex luna C18 150×25 mm×10 μm; mobile phase: [water (0.225% formic acid)/ACN]; B %: 44%-74%, 10 min) to give the title compound (150 mg, 30% yield) as a white solid. $^1$H NMR (400 MHz, CD3OD) δ=8.32-8.25 (m, 2H), 8.03 (s, 1H), 8.00-7.93 (m, 1H), 7.51-7.44 (m, 2H); LCMS (EST, M+1): m/z=247.1.

Step B. 4-bromo-1-(tetrahydro-2H-pyran-2-yl)-1H-benzo[f]indazole: To a solution of 4-bromo-1H-benzo[f]indazole (150 mg, 1.0 equiv.) and 3,4-dihydro-2H-pyran (153 mg, 167 μL, 3.0 equiv.) in dichloromethane (2.00 mL) was added 4-methylbenzenesulfonic acid hydrate (5.23 mg, 0.05 equiv.) in one portion at 25° C. under nitrogen. The reaction was stirred at 25° C. for 12 hours. The reaction mixture was concentrated under reduced pressure and purified by prep-TLC (silica gel, petroleum ether/ethyl acetate 4:1) to give the title compound (180 mg, 543 μmol, 89.5% yield, 100% purity) as a yellow solid. LCMS (ESI, M+1): m/z=330.9.

Step C. 1-(tetrahydro-2H-pyran-2-yl)-4-(4,4,5,5-tetramethyl-1,3,2-dioxaborolan-2-yl)-1H-benzo[f]indazole: To a solution of 4-bromo-1-(tetrahydro-2H-pyran-2-yl)-1H-benzo[f]indazole (180 mg, 1.0 equiv.) and 4,4,4',4',5,5,5',5'- octamethyl-2,2'-bi(1,3,2-dioxaborolane) (166 mg, 1.2 equiv.) in dioxane (3.00 mL) was added potassium acetate (160 mg, 3.00 equiv.), Pd(dppf)Cl₂ (39.8 mg, 0.1 equiv.), then the mixture was degassed and stirred at 90° C. for 1 hour under nitrogen. After completion, the reaction mixture was concentrated under reduced pressure and purified by prep-TLC (silica gel, petroleum ether/ethyl acetate 4:1) to give the title compound (150 mg, 54% yield) as a yellow solid. LCMS (ESI, M+1): m/z=379.3.

Step D. (3R)-1-(8-fluoro-2-(((2R,7aS)-2-fluorohexahydro-1H-pyrrolizin-7a-yl) methoxyl-7-(1-(tetrahydro-2H-pyran-2-yl)-1H-benzo[f]indazol-4-yl)pyrido[4,3-d]pyrimidin-4-yl)-3-methylpiperidin-3-ol: To a mixture of 1-(tetrahydro-2H-pyran-2-yl)-4-(4,4,5,5-tetramethyl-1,3,2-dioxaborolan-2-yl)-1H-benzo[f]indazole (150 mg, 1.0 equiv.) and (R)-1-(7-chloro-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (180 mg, 1.0 equiv.) in toluene (3.00 mL) was added CataCXium A Pd G3 (43.3 mg, 0.15 equiv.), potassium phosphate (1.5 M, 793 μL, 3.0 equiv.), the reaction mixture was degassed and purged with nitrogen for 3 times, then it was stirred at 90° C. for 2 hours under nitrogen. The reaction mixture was concentrated under reduced pressure and purified by prep-TLC (silica gel, petroleum ether/ethyl acetate 4:1) to give the title compound (200 mg, 36% yield) as a yellow solid. LCMS (ESI, M+1): m/z=670.5.

Step E. (3R)-1-(7-(1H-benzo[f]indazol-4-yl)-8-fluoro-2-(((2R,7aS)-2-fluorohexahydro-1H-pyrrolizin-7a-yl) methoxy)pyrido[4,3-d]pyrimidin-4-yl)-3-methylpiperidin-3-ol: To a mixture of (3R)-1-(8-fluoro-2-(((2R,7aS)-2-fluorohexahydro-1H-pyrrolizin-7a-yl) methoxy)-7-(1-(tetrahydro-2H-pyran-2-yl)-1H-benzo[f]indazol-4-yl)pyrido[4,3-d]pyrimidin-4-yl)-3-methylpiperidin-3-ol (200 mg, 47.5% purity, 1.0 equiv.) in dichloromethane (4.00 mL) was added trifluoroacetic acid (6.16 g, 4.00 mL, equiv.) in one portion at 0° C. under nitrogen. The reaction was stirred at 20° C. for 10 min. The reaction mixture was concentrated under reduced pressure and purified by prep-HPLC (column: Phenomenex luna C18 150×25 mm×10 um; mobile phase: [water (0.225% formic acid)/ACN]; B %: 8%-38%, 10 min) to give the title compound (27.9 mg, 32% yield, formic acid salt) as a yellow solid. ¹H NMR (400 MHz, CD3OD) δ=9.41 (d, J=9.2 Hz, 1H), 8.45 (s, 1H), 8.21 (s, 1H), 8.11-8.00 (m, 2H), 7.80 (d, J=8.8 Hz, 1H), 7.54-7.46 (m, 1H), 7.41-7.32 (m, 1H), 5.67-5.33 (m, 1H), 4.72-4.62 (m, 1H), 4.62-4.48 (m, 2H), 4.39 (d, J=13.6 Hz, 1H), 3.84-3.54 (m, 4H), 3.52-3.39 (m, 1H), 3.29-3.25 (m, 1H), 2.68-2.38 (m, 2H), 2.37-2.28 (m, 1H), 2.28-2.13 (m, 3H), 2.12-1.98 (m, 1H), 1.94-1.72 (m, 3H), 1.31 (s, 3H); ¹⁹F NMR (377 MHz, CD3OD) δ=-139.13, δ=-173.98; LCMS (ESI, M+1): m/z=586.3.

Example 155

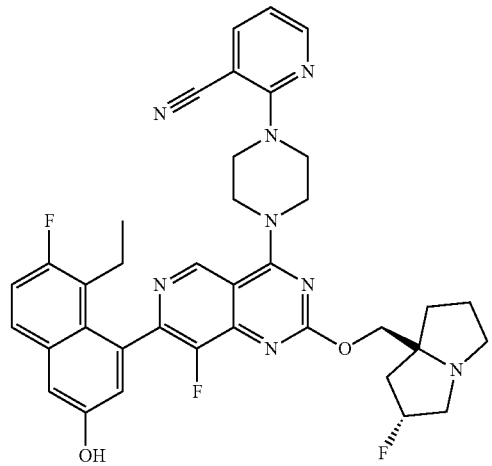

2-(4-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)piperazin-1-yl) nicotinonitrile The title compound was synthesized according to the procedure described for example 134. ¹H NMR (400 MHz, METHANOL-d₄) 5-9.17 (s, 1H), 8.40 (dd, J=1.6, 4.8 Hz, 1H), 7.98 (dd, J=1.6, 7.6 Hz, 1H), 7.66 (dd, J=5.6, 9.2 Hz, 1H), 7.33-7.18 (m, 2H), 7.06 (d, J=2.4 Hz, 1H), 6.91 (dd, J=4.8, 7.6 Hz, 1H), 5.41-5.18 (m, 1H), 4.40-4.20 (m, 6H), 4.08-3.95 (m, 4H), 3.29-3.11 (m, 3H), 3.05-2.91 (m, 1H), 2.55-2.43 (m, 1H), 2.40-2.28 (m, 1H), 2.27-2.11 (m, 4H), 2.05-1.96 (m, 2H), 0.80 (br t, J=7.2 Hz, 3H); LCMS (ESI, M+1): m/z=681.4.

Example 156

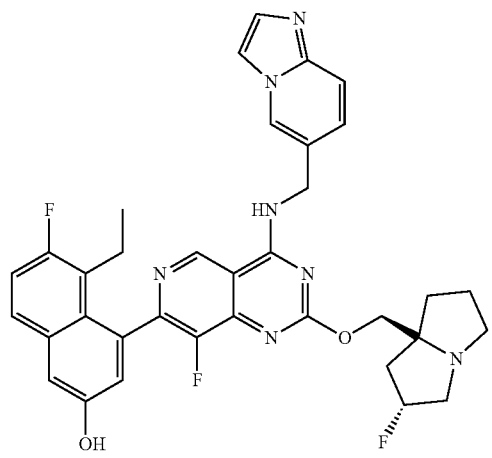

5-ethyl-6-fluoro-4-(8-fluoro-2-(((2R,7aS)-2-fluoro-hexahydro-1H-pyrrolizin-7a-yl)methoxy)-4-((imidazo[1,2-a]pyridin-6-ylmethyl)amino)pyrido[4,3-d]pyrimidin-7-yl)naphthalen-2-ol The title compound was synthesized according to the procedure described for example 135. ¹H NMR (400 MHz, METHANOL-d₄): δ=9.20 (s, 1H), 8.60 (s, 1H), 8.55 (s, 1H), 7.85 (s, 1H), 7.68 (dd, J=6.0, 9.2 Hz, 1H), 7.60-7.53 (m, 2H), 7.45 (dd, J=1.6, 9.2 Hz, 1H), 7.30 (d, J=2.8 Hz, 1H), 7.25 (t, J=9.2 Hz, 1H), 7.04 (d, J=2.4 Hz, 1H), 5.34-5.16 (m, 1H), 4.92 (br d, J=4.4 Hz, 3H), 4.59 (br s, 2H), 4.32-4.19 (m, 2H), 3.26-3.12 (m, 3H), 2.98 (dt, J=6.0, 9.6 Hz, 1H), 2.54-2.42 (m, 1H), 2.34-1.89 (m, 7H), 1.87-1.73 (m, 1H), 0.79 (t, J=7.6 Hz, 3H); LCMS (ESI, M+1): m/z=640.3.

Example 157

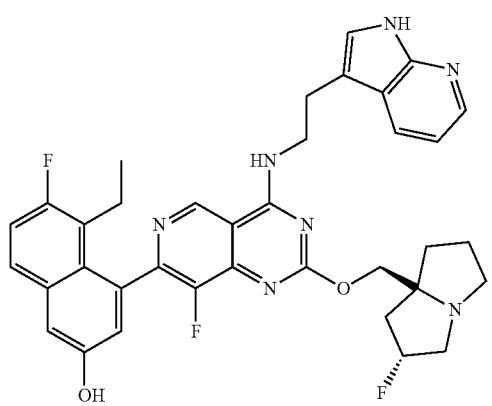

4-(4-((2-(1H-pyrrolo[2,3-b]pyridin-3-yl)ethyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 135. ¹H NMR (400 MHz, CD3OD): δ 9.07 (s, 1H), 8.20-8.16 (dd, J=1.6, 4.8 Hz, 1H), 8.13-8.07 (dd, J=1.6, 7.6 Hz, 1H), 7.71-7.66 (dd, J=5.6, 8.8 Hz, 1H), 7.33-7.29 (m, 2H), 7.26 (t, J=9.2 Hz, 1H), 7.10-7.01 (m, 2H), 5.43-5.20 (m, 1H), 4.31-4.18 (m, 2H), 4.09-3.94 (m, 2H), 3.29-3.12 (m, 5H), 3.07-2.97 (m, 1H), 2.54-2.41 (m, 1H), 2.38-2.25 (m, 1H), 2.25-2.19 (m, 1H), 2.18-2.08 (m, 2H), 2.05-1.95 (m, 2H), 1.95-1.84 (m, 1H), 0.84-0.76 (dt, J=2.0, 7.6 Hz, 3H); LCMS (ESI, M+1): m/z=654.3.

Example 158

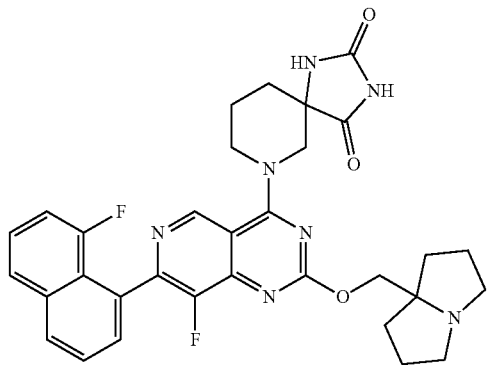 [SMILES: O=C1NC(=O)C2(CCCN(c3nc(OCC45CCCN4CCC5)nc4c(F)c(-c5cccc6cccc(F)c56)ncc34)C2)N1]

7-(8-fluoro-7-(8-fluoronaphthalen-1-yl)-2-((hexahydro-1H-pyrrolizin-7a-yl)methoxy)pyrido[4,3-d]pyrimidin-4-yl)-1,3,7-triazaspiro[4.5]decane-2,4-dione

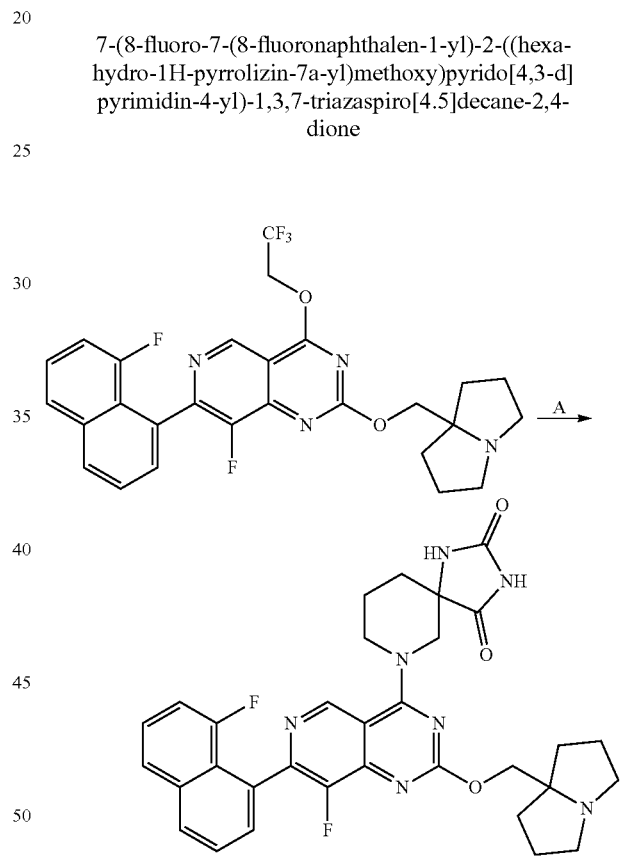

Step A. 7-(8-fluoro-7-(8-fluoronaphthalen-1-yl)-2-((hexahydro-1H-pyrrolizin-7a-yl) methoxy)pyrido[4,3-d]pyrimidin-4-yl)-1,3,7-triazaspiro[4.5]decane-2,4-dione: To a solution of 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d]pyrimidine (150 mg, 1.0 equiv.), 1,3,7-triazaspiro[4.5]decane-2,4-dione (76.5 mg, 1.6 equiv.) in DMF (1 mL) was added DIEA (183 mg, 5.0 equiv.). The reaction was stirred at 40° C. for 10 hours. The mixture was filtered to give a residue. The residue was purified by prep-HPLC (column: Phenomenex Gemini-NX C18 75×30 mm×3 um; mobile phase: [water (10 mM NH₄HCO₃)/ACN]; B %: 20%-50%, 8 min) and lyophilized to afford the title compound (75.13 mg, 42% yield) as a white solid; ¹H NMR (400 MHz, METHANOL-d₄) δ=9.10 (s, 1H), 8.11 (br d, J=8.8 Hz, 1H), 7.84 (d, J=8.0 Hz, 1H), 7.73-7.65 (m, 1H), 7.63-7.58 (m, 1H), 7.56-7.48 (m, 1H), 7.23-7.14 (m, 1H), 4.62 (br d, J=13.2 Hz, 1H), 4.53-4.41 (m, 1H), 4.35-4.20 (m, 2H), 3.85-3.62 (m, 2H), 3.18-3.05 (m, 2H), 2.78-2.66 (m, 2H), 2.31-2.17 (m, 1H), 2.13-1.99 (m, 4H), 1.98-1.83 (m, 5H), 1.80-1.67 (m, 2H); LCMS (ESI, M+1): m/z=600.3.

Example 159

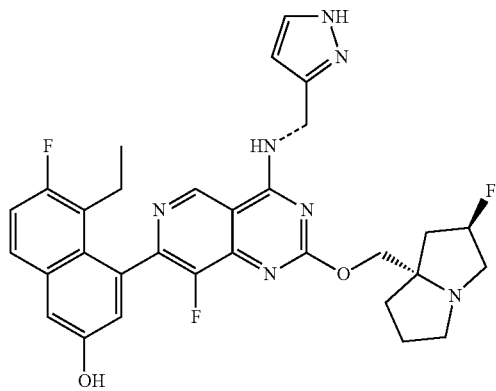

4-(4-(((1H-pyrazol-3-yl)methyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 135. ¹H NMR (400 MHz, METHANOL-d₄) δ=9.18 (s, 1H), 7.70-7.60 (m, 2H), 7.30 (d, J=2.8 Hz, 1H), 7.25 (t, J=9.6 Hz, 1H), 7.04 (d, J=2.8 Hz, 1H), 6.39 (br s, 1H), 5.37-5.21 (m, 1H), 4.94 (s, 2H), 4.29 (q, J=10.4 Hz, 2H), 3.25-3.12 (m, 3H), 3.04-2.97 (m, 1H), 2.53-2.42 (m, 1H), 2.27-2.20 (m, 1H), 2.16-2.08 (m, 2H), 2.03-1.83 (m, 4H), 0.79 (t, J=7.2 Hz, 3H); LCMS (ESI, M+1): m/z=590.3.

Example 160

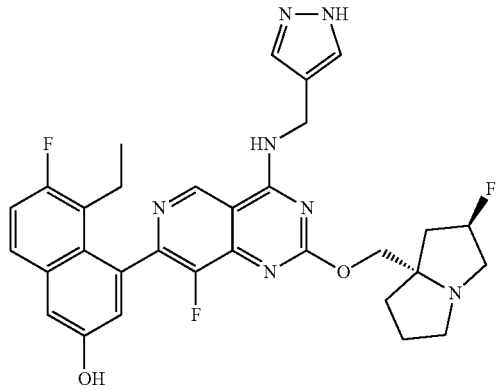 [SMILES: CCc1c(F)ccc2cc(O)cc(-c3ncc4c(NCc5cn[nH]c5)nc(OC[C@@]56CCCN5C[C@H](F)C6)nc4c3F)c12]

4-(4-(((1H-pyrazol-4-yl)methyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 134. ¹H NMR (400 MHz, METHANOL-d₄) δ=9.13 (s, 1H), 7.73 (br s, 2H), 7.67 (dd, J=5.6, 8.8 Hz, 1H), 7.29 (d, J=2.4 Hz, 1H), 7.24 (t, J=9.2 Hz, 1H), 7.04 (d, J=2.4 Hz, 1H), 5.46-5.16 (m, 1H), 4.80 (s, 2H), 4.44-4.22 (m, 2H), 3.29-3.13 (m, 3H), 3.05-2.97 (m, 1H), 2.53-2.40 (m, 1H), 2.39-2.19 (m, 2H), 2.18-2.07 (m, 2H), 2.05-1.94 (m, 2H), 1.94-1.82 (m, 1H), 0.78 (t, J=7.6 Hz, 3H); LCMS (ESI, M+1): m/z=590.3.

Example 161

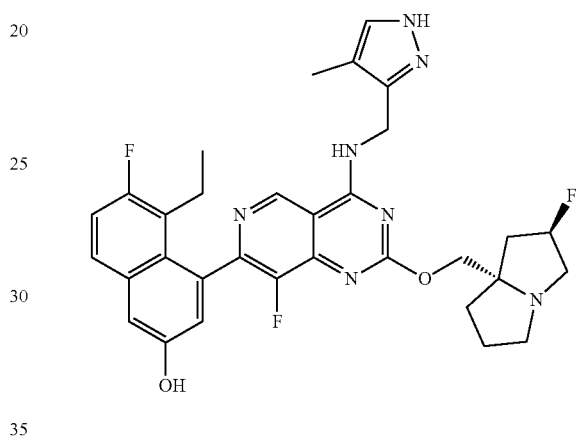

5-ethyl-6-fluoro-4-(8-fluoro-2-(((2R,7aS)-2-fluoro-hexahydro-1H-pyrrolizin-7a-yl)methoxy)-4-(((4-methyl-1H-pyrmzol-3-yl)methyl)amino)pyrido[4,3-d]pyrimidin-7-yl)naphthalen-2-ol

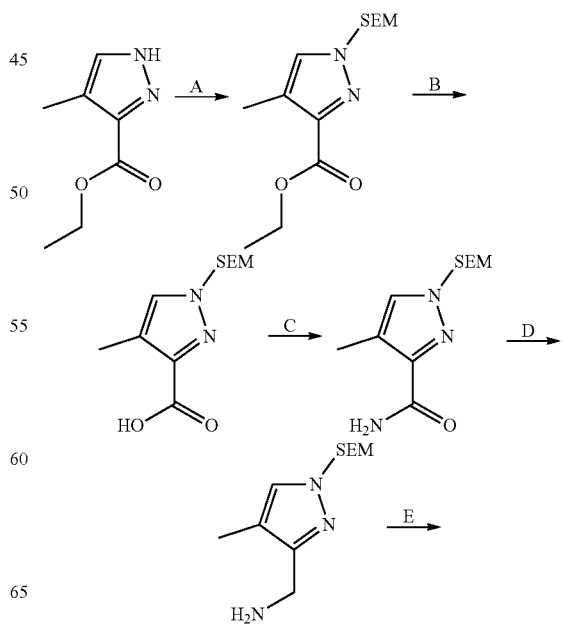

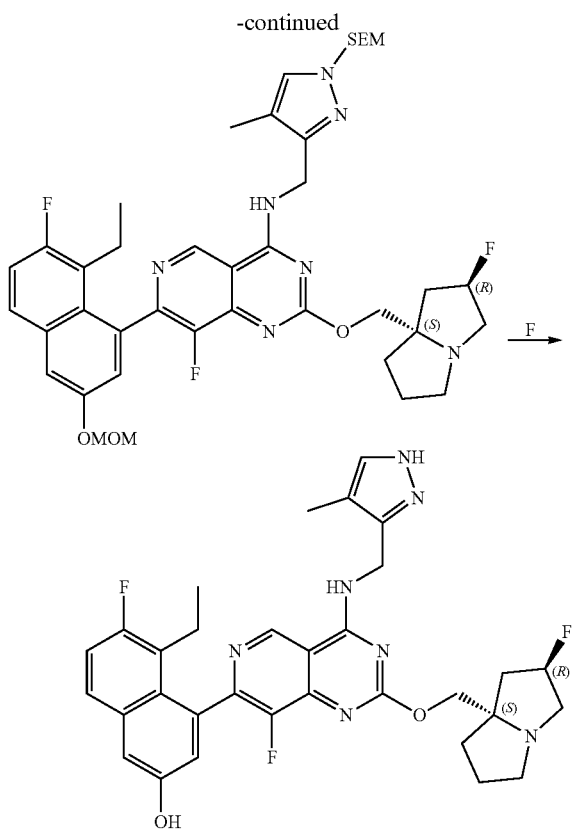

Step A. ethyl 4-methyl-1-((2-(trimethylsilyl)ethoxy)methyl)-1H-pyrazole-3-carboxylate: To a solution of ethyl 4-methyl-1H-pyrazole-3-carboxylate (1.50 g, 1.0 equiv.) in THF (15 mL) was added NaH (428 mg, 60% purity, 1.1 equiv.) at 0° C. The mixture was stirred at 0° C. for 30 minutes. Then SEMCl (1.92 g, 1.2 equiv.) was added to the mixture. The reaction was stirred at 20° C. for 1 hour. Upon reaction completion, the mixture was quenched by addition of water (20 mL) at 0° C., then extracted with ethyl acetate (40 mL×3). The combined organic layers were washed with brine (80 mL), dried over anhydrous sodium sulfate, concentrated and purified by silica gel column chromatography (petroleum ether/ethyl acetate 20:1 to 5:1) to afford the title compound (2.15 g, 65% yield) as a yellow liquid; $^1$H NMR (400 MHz, CDCl$_3$): δ 7.44-7.39 (d, J=0.8 Hz, 1H), 5.42 (s, 2H), 4.46-4.32 (dd, J=7.2, 14.0 Hz, 2H), 3.58-3.48 (m, 2H), 2.31-2.27 (d, J=0.8 Hz, 3H), 1.42-1.35 (t, J=7.2 Hz, 3H), 0.93-0.85 (m, 2H), −0.02-0.08 (m, 9H); LCMS (ESI, M+1): m/z=285.2.

Step B. 4-methyl-1-((2-(trimethylsilyl)ethoxy)methyl)-1H-pyrazole-3-carboxylic acid: To a solution of ethyl 4-methyl-1-((2-(trimethylsilyl) ethoxy)methyl)-1H-pyrazole-3-carboxylate (2.0 g, 1.0 equiv.) in EtOH (18.0 mL) was added LiOH hydrate (885 mg, 3.0 equiv.) and water (6.0 mL), The reaction was stirred at 20° C. for 2 hours. Upon completion, the reaction mixture was concentrated under reduced pressure to remove EtOH. The residue was diluted with HCl (30 mL, 1 M) and extracted with ethyl acetate (20 mL×3). The combined organic layers were washed with brine (50 mL), dried over anhydrous sodium sulfate, filtered and concentrated under reduced pressure to afford the title compound (1.70 g, 93% yield) as a yellow solid; $^1$H NMR (400 MHz, CDCl$_3$): δ 7.44 (s, 1H), 5.46 (s, 2H), 3.62-3.51 (m, 2H), 2.38-2.27 (m, 3H), 0.97-0.83 (m, 2H), 0.04-0.09 (m, 9H).

Step C. 4-methyl-1-((2-(trimethylsilyl) ethoxy)methyl)-1H-pyrazole-3-carboxamide: To a solution of 4-methyl-1-((2-(trimethylsilyl)ethoxy)methyl)-1H-pyrazole-3-carboxylic acid (1.50 g, 1.0 equiv.) and NH$_4$Cl (1.5 g, 5.0 equiv.) in DMF (20.0 mL) was added HATU (4.50 g, 2.0 equiv.) and DIEA (6.12 g, 8.0 equiv.). The reaction was stirred at 40° C. for 2 hours. Upon completion, the mixture was diluted with water (50 mL) and extracted with ethyl acetate (20 mL×3). The combined organic layers were washed with brine (40 mL), dried over anhydrous sodium sulfate, filtered, concentrated and purified by reversed phase flash chromatography [C18, mobile phase: [water (0.1% formic acid)/acetonitrile]) to afford the title compound (1.40 g, 81% yield) as a yellow liquid; $^1$H NMR (400 MHz, DMSO-D$_6$): δ 7.71 (d, J=0.8 Hz, 1H), 7.35-7.06 (m, 2H), 5.35 (s, 2H), 3.56-3.47 (m, 2H), 2.22-2.14 (d, J=0.4 Hz, 3H), 0.88-0.75 (m, 2H), −0.02-0.11 (m, 9H).

Step D. (4-methyl-1-((2-(trimethylsilylethoxy)methyl)-1H-pyrazol-3-yl) methanamine: A mixture of 4-methyl-1-((2-(trimethylsilyl)ethoxy)methyl)-1H-pyrazole-3-carboxamide (1.30 g, 1.0 equiv.) and THF (15 mL) was degassed and purged with N$_2$ for 3 times, and then the mixture was stirred at 0° C. for 5 minutes under N$_2$ atmosphere. Following that LiAlH$_4$ (386 mg, 2.0 equiv.) was added into the mixture in portions during a period of 10 minutes. The mixture was stirred at 40° C. for 2 hours. Upon completion, the mixture was quenched by addition of saturated sodium sulfate (386 μL) at 0° C., filtered and the filtrate was diluted with water (10 mL) and extracted with ethyl acetate (10 mL×3). The combined organic layers were washed with brine (20 mL), dried over anhydrous sodium sulfate, concentrated and purified by reversed phase flash chromatography (C18, mobile phase: [water (0.1% formic acid)/acetonitrile]) to afford the title compound (1.10 g, 87% yield) as a yellow solid; $^1$H NMR (400 MHz, CD3OD): δ 7.47 (s, 1H), 5.31 (s, 2H), 3.75 (s, 2H), 3.56-3.50 (m, 2H), 2.07 (s, 3H), 0.89-0.84 (m, 2H), −0.01-0.07 (m, 9H).

Step E. 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-N((4-methyl-1-((2-(trimethylsilyl)ethoxy)methyl-1H-pyrazol-3-yl)methyl)pyrido[4,3-d]pyrimidin-4-amine: To a solution of (4-methyl-1-((2-(trimethylsilyl)ethoxy)methyl)-1H-pyrazol-3-yl) methanamine (150 mg, 1.0 equiv.) and 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-4-(2,2,2-trifluoroethoxy) pyrido[4,3-d]pyrimidine (395 mg, 1.0 equiv.) in DMF (3 mL) was added DIEA (401 mg, 541 μL, 5.0 equiv.) and 4 Å molecular sieves (50 mg). The reaction was stirred at 40° C. for 2 hours. Upon completion, the mixture was diluted with water (10 mL) and extracted with ethyl acetate (10 mL×3). The combined organic layers were washed with brine (20 mL), dried over anhydrous sodium sulfate. The mixture was filtered and concentrated and purified by reversed phase flash chromatography (C18, mobile phase: [water (0.1% formic acid)/acetonitrile)] to afford the title compound (100 mg, 20.2% yield) as a yellow oil; LCMS (ESI, M+1): m/z=778.5.

Step F. 5-ethyl-6-fluoro-4-(8-fluoro-2-(((2R,7aS)-2-fluorohexahydro-1H-pyrrolizin-7a-yl)methoxy-4-(((4-methyl-1H-pyrazol-3-yl)methyl)amino)pyrido[4,3-d]pyrimidin-7-yl)naphthalen-2-ol: To a solution of 7-(8-ethyl-7-fluoro-3-(methoxymethoxy) naphthalen-1-yl)-8-fluoro-2-(((2R,7aS)-2-fluorohexahydro-1H-pyrrolizin-7a-yl)methoxy)-N-((4-methyl-1-((2-(trimethylsilyl)ethoxy)methyl)-1H-pyrazol-3-yl)methyl)pyrido[4,3-d]pyrimidin-4-amine (90.0 mg, 1.0 equiv.) in DCM (1 mL) was added TFA (769 mg, 499 μL, 58 equiv.). The mixture was stirred at 20° C. for 0.5 hour. Upon reaction completion, the mixture was concentrated under reduced pressure to remove DCM, the residue was diluted with water (10 mL) and pH was adjusted to 9 with solid Na$_2$CO$_3$. Then the mixture was extracted with ethyl acetate (10 mL×3) and the combined organic layers were washed with brine (20 mL), dried over anhydrous sodium sulfate, concentrated and purified by prep-HPLC [column: waters Xbridge 150×25 mm×5 µm; mobile phase: [water (10 mM NH$_4$HCO$_3$)/ACN]; B %: 42%-72%, 10 minutes] to afford the title compound (16 mg, 52.6% yield, 98.2% purity) as a yellow solid; $^1$H NMR (400 MHz, CD3OD): δ 9.22-9.15 (d, J=0.8 Hz, 1H), 7.71-7.64 (dd, J=5.6, 9.2 Hz, 1H), 7.41 (s, 1H), 7.31-7.26 (d, J=2.4 Hz, 1H), 7.26-7.20 (t, J=9.2 Hz, 1H), 7.06-7.03 (d, J=2.0 Hz, 1H), 5.38-5.17 (m, 1H), 4.89 (s, 2H), 4.34-4.23 (m, 2H), 3.29-3.11 (m, 3H), 3.04-2.94 (m, 1H), 2.53-2.39 (m, 1H), 2.37-2.06 (m, 7H), 2.02-1.83 (m, 3H), 0.78 (t, J=7.2 Hz, 3H); LCMS (ESI, M+1): m/z=604.4.

Example 162

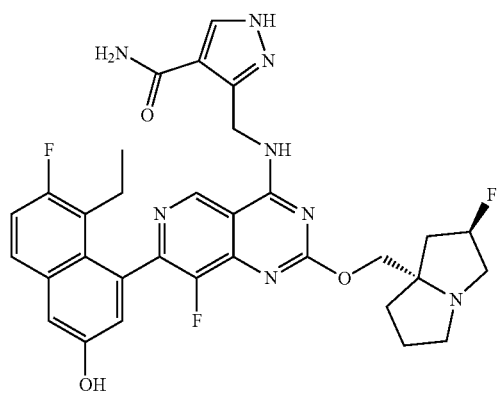 [SMILES: CCc1c(F)ccc2cc(O)cc(-c3ncc4c(NCc5n[nH]cc5C(N)=O)nc(OC[C@@]56CCCN5C[C@H](F)C6)nc4c3F)c12]

3-(((7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)-1H-pyrazole-4-carboxamide

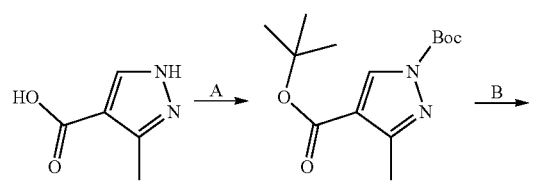

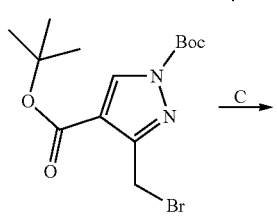

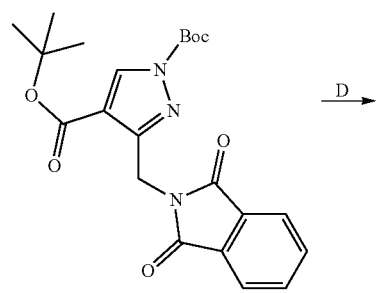

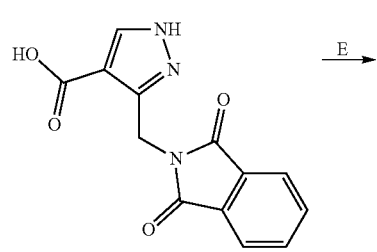

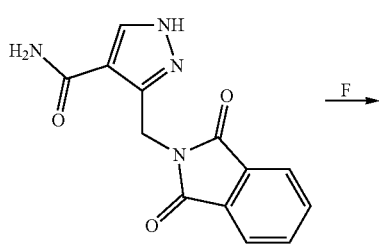

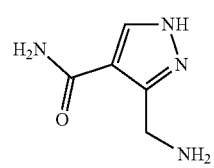

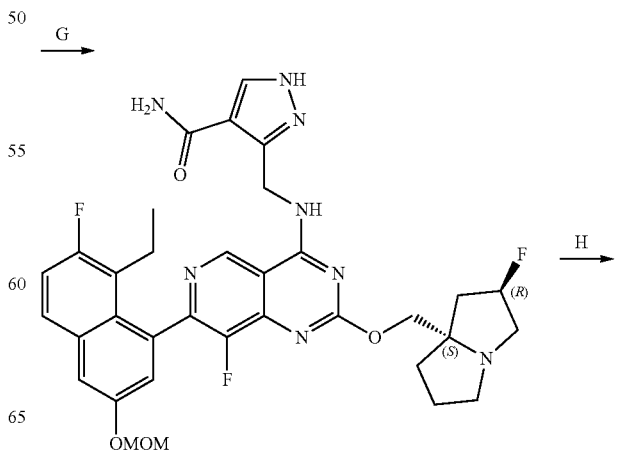

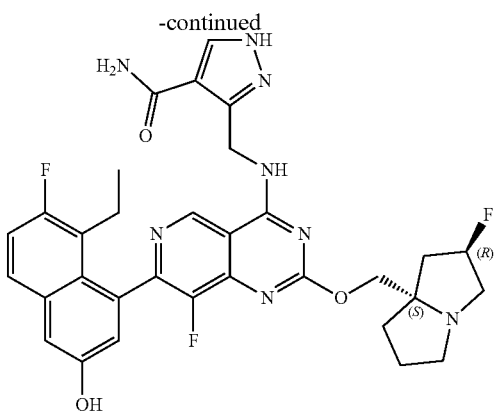

Step A. di-tert-butyl 3-methyl-1H-pyrazole-1,4-dicarboxylate: To a solution of 3-methyl-1H-pyrazole-4-carboxylic acid (4.50 g, 1.0 equiv.) in 2-methylpropan-2-ol (34.9 g, 13.2 equiv.) was added DMAP (872 mg, 0.2 equiv.) and Boc₂O (31.1 g, 4.0 equiv.) under nitrogen. The reaction was stirred at 40° C. for 12 hours. The reaction mixture was filtered, concentrated and purified by reversed phase flash chromatography (C18, mobile phase: [water (0.1% formic acid)/ACN], 0-70% ACN) to afford the title compound (6.0 g, 59% yield) as a white solid; $^{1}$H NMR (400 MHz, METHANOL-d₄) δ=8.44 (s, 1H), 2.44 (s, 3H), 1.65 (s, 9H), 1.57 (s, 9H). LCMS (ESI, M−55): m/z=227.2.

Step B. di-tert-butyl 3-methyl-1H-pyrazole-1,4-dicarboxylate: To a solution of ditert-butyl 3-methylpyrazole-1,4-dicarboxylate (3.0 g, 1.0 equiv.) in CCl₄ (20 mL) was added NBS (2.27 g, 1.20 equiv.) and AIBN (523 mg, 0.3 equiv.) under nitrogen. The mixture was stirred at 80° C. for 12 hours. The reaction mixture was filtered, concentrated and purified by column chromatography (Silica gel, Petroleum ether/Ethyl acetate 1:0 to 50:1) to afford the title compound (3.0 g, 65% purity, 51% yield) as a colorless liquid; LCMS (ESI, M−99): m/z=261.0.

Step C. di-tert-butyl 3-((1,3-dioxoisoindolin-2-yl)methyl)-1H-pyrazole-1,4-dicarboxylate: To a solution of di-tert-butyl 3-(bromomethyl)pyrazole-1,4-dicarboxylate (2.80 g, 65% purity, 1.0 equiv.) in DMF (20 mL) was added (1,3-dioxoisoindolin-2-yl)potassium (1.87 g, 2.0 equiv.). The reaction was stirred at 100° C. for 2 hours. The reaction mixture was filtered, concentrated and purified by reversed phase flash chromatography (C18, mobile phase: [water (0.1% formic acid)/ACN], 0-40% ACN) to afford the title compound (1.10 g, 55% yield) as a red solid; LCMS (ESI, M−155): m/z=272.1.

Step D. 3-((1,3-dioxoisoindolin-2-yl)methyl)-1H-pyrazole-4-carboxylic acid: To a solution of di-tert-butyl 3-[(1,3-dioxoisoindolin-2-yl)methyl]pyrazole-1,4-dicarboxylate (1.10 g, 1.0 equiv.) in DCM (10 mL) was added TFA (15.4 g, 52.5 equiv.) under nitrogen. The mixture was stirred at 20° C. for 2 hours. The reaction mixture was filtered and concentrated to afford the title compound (0.9 g, crude, TFA salt) as a yellow solid; LCMS (ESI, M+1): m/z=272.1.

Step E. 3-((1,3-dioxoisoindolin-2-yl)methyl)-1H-pyrazole-4-carboxamide: To a solution of 3-[(1,3-dioxoisoindolin-2-yl)methyl]-1H-pyrazole-4-carboxylic acid (100 mg, 1.0 equiv.) in DMF (2 mL) was added DIEA (476 mg, 10.0 equiv.), HATU (420 mg, 3.0 equiv.) and NH₄Cl (98.6 mg, 5.0 equiv.) under nitrogen. The reaction was stirred at 40° C. for 12 hours. The reaction mixture was filtered, the filtrate was concentrated and purified by reversed phase flash chromatography (C18, mobile phase: [water (0.1% formic acid)/ACN], 0-40% ACN) to afford the title compound (30 mg, 30% yield) as a red solid; LCMS (ESI, M+1): m/z=271.1.

Step F. 3-(aminomethyl)-1H-pyrazole-4-carboxamide: To a solution of 3-[(1,3-dioxoisoindolin-2-yl)methyl]-1H-pyrazole-4-carboxamide (20.0 mg, 1.0 equiv.) in EtOH (0.5 mL) was added hydrazine hydrate (37.8 mg, 10.0 equiv.). The reaction was stirred at 40° C. for 1 hour. The reaction mixture was filtered and the filtrate was concentrated to afford the title compound (5.0 mg, crude) as a yellow solid; LCMS (ESI, M+23): m/z=163.1.

Step G. 3-(((7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)-1H-pyrazole-4-carboxamide: To a solution of 7-(8-ethyl-7-fluoro-3-(methoxymethoxy)naphthalen-1-yl)-8-fluoro-2-(((2R,7aS)-2-fluorohexahydro-1H-pyrrolizin-7a-yl) methoxy)-4-(2,2,2-trifluoroethoxy)pyrido[4,3-d]pyrimidine (60.0 mg, 1.0 equiv., 0.5 formic acid salt) and DIEA (35.3 mg, 3.0 equiv.) in DMF (1 mL) was added 4 Å MS (20.0 mg) and 3-(aminomethyl)-1H-pyrazole-4-carboxamide (12.7 mg, 1.0 equiv.). The reaction was stirred at 40° C. for 12 hours. The reaction mixture was filtered, concentrated and purified by prep-TLC [Silica gel, DCM/MeOH 10:1] to afford the title compound (50.0 mg, 80% yield) as a light yellow solid; LCMS (ESI, M+1): m/z=677.1.

Step H. 3-(((7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl) amino) methyl)-1H-pyrazole-4-carboxamide: To a solution of 3-(((7-(8-ethyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)amino) methyl)-1H-pyrazole-4-carboxamide (40.0 mg, 1.0 equiv.) in MeOH (0.5 mL) was added HCl in MeOH (4 M, 0.5 mL). The reaction was stirred at 20° C. for 0.5 hour. The reaction mixture filtered, concentrated and purified by reversed phase flash chromatography [column: Phenomenex Gemini-NX C18 75*30 mm*3 um; mobile phase: [water (0.225% formic acid)/ACN]; B %: 12%-42%, 7 min] to afford the title compound (8.14 mg, 20% yield) as a white solid; $^{1}$H NMR (400 MHz, methanol-d4) δ 9.20 (d, J=1.6 Hz, 1H), 8.51 (br s, 1H), 8.16 (br s, 1H), 7.68 (dd, J=6.0, 9.2 Hz, 1H), 7.31 (d, J=2.4 Hz, 1H), 7.25 (t, J=9.2 Hz, 1H), 7.05 (t, J=2.8 Hz, 1H), 5.50-5.33 (m, 1H), 5.19 (s, 2H), 4.54-4.35 (m, 2H), 3.69-3.43 (m, 3H), 3.21 (br d, J=5.4 Hz, 1H), 2.57-2.32 (m, 3H), 2.30-2.10 (m, 4H), 2.05-1.94 (m, 1H), 0.78 (dt, J=2.0, 7.2 Hz, 3H). LCMS (ESI, M+1): m/z=633.3.

Example 163

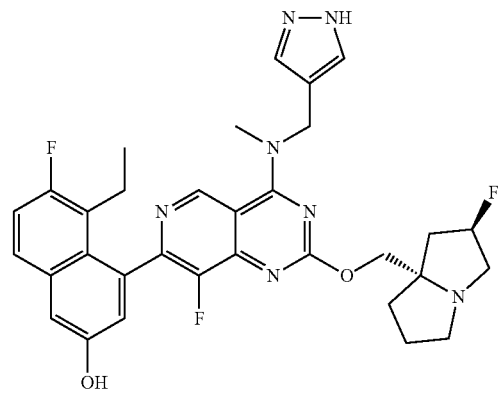 [SMILES: CCc1c(F)ccc2cc(O)cc(-c3ncc4c(N(C)Cc5cn[nH]c5)nc(OC[C@@]56CCCN5C[C@H](F)C6)nc4c3F)c12]

4-(4-(((1H-pyrazol-4-yl)methyl)(methyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 134. $^1$H NMR (400 MHz, METHANOL-d$_4$) δ=9.21 (s, 1H), 7.77 (br d, J=2.0 Hz, 2H), 7.67 (dd, J=6.0, 9.2 Hz, 1H), 7.30 (d, J=2.4 Hz, 1H), 7.24 (t, J=9.4 Hz, 1H), 7.05 (d, J=2.8 Hz, 1H), 5.39-5.21 (m, 1H), 5.06 (s, 2H), 4.39-4.23 (m, 2H), 3.59 (s, 3H), 3.27-3.12 (m, 3H), 3.06-2.93 (m, 1H), 2.53-2.42 (m, 1H), 2.38-2.20 (m, 2H), 2.19-2.09 (m, 2H), 2.03-1.85 (m, 3H), 0.80 (t, J=7.2 Hz, 3H); LCMS (ESI, M+1): m/z=604.3.

Example 164

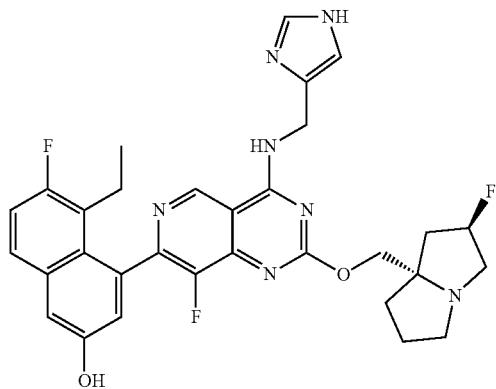 [SMILES: CCc1c(F)ccc2cc(O)cc(-c3ncc4c(NCc5c[nH]cn5)nc(OC[C@@]56CCCN5C[C@H](F)C6)nc4c3F)c12]

4-(4-(((1H-imidazol-4-yl)methyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 134. $^1$H NMR (400 MHz, METHANOL-d$_4$) δ=9.18 (s, 1H), 7.70-7.64 (m, 2H), 7.30 (d, J=2.4 Hz, 1H), 7.24 (t, J=9.2 Hz, 1H), 7.15 (s, 1H), 7.04 (d, J=2.8 Hz, 1H), 5.38-5.21 (m, 1H), 4.77-4.45 (m, 2H), 4.36-4.26 (m, 2H), 3.28-3.13 (m, 3H), 3.06-2.96 (m, 1H), 2.51-2.41 (m, 1H), 2.38-2.19 (m, 2H), 2.18-2.10 (m, 2H), 2.03-1.86 (m, 3H), 0.78 (t, J=7.2 Hz, 3H); LCMS (ESI, M+1): m/z=590.2.

Example 165

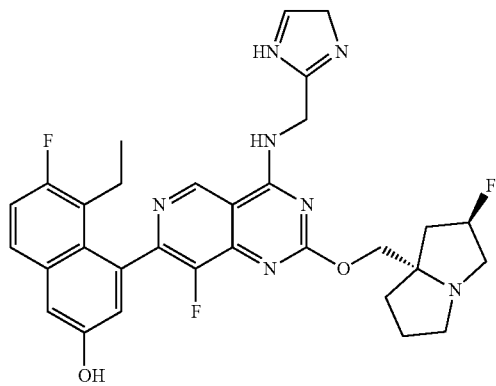 [SMILES: CCc1c(F)ccc2cc(O)cc(-c3ncc4c(NCC5=NCC=N5)nc(OC[C@@]56CCCN5C[C@H](F)C6)nc4c3F)c12]

4-(4-(((1H-imidazol-2-yl)methyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 135. $^1$H NMR (400 MHz, METHANOL-d$_4$) δ=9.20 (s, 1H), 7.68 (dd, J=6.0, 9.2 Hz, 1H), 7.30 (d, J=2.8 Hz, 1H), 7.25 (t, J=9.6 Hz, 1H), 7.09-6.97 (m, 3H), 5.38-5.19 (m, 1H), 4.94 (d, J=4.4 Hz, 2H), 4.28-4.15 (m, 2H), 3.29-3.12 (m, 3H), 3.06-2.95 (m, 1H), 2.54-2.41 (m, 1H), 2.35-2.06 (m, 4H), 2.03-1.83 (m, 3H), 0.79 (t, J=7.2 Hz, 3H); LCMS (ESI, M+1): m/z=590.3.

Example 166

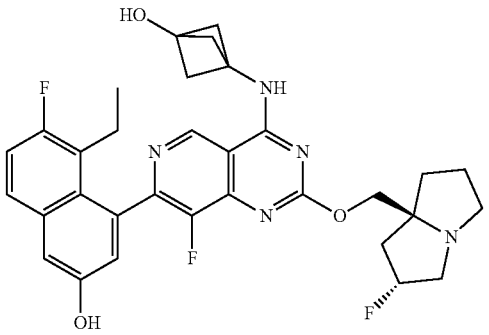 [SMILES: CCc1c(F)ccc2cc(O)cc(-c3ncc4c(NC56CC(O)(C5)C6)nc(OC[C@@]56CCCN5C[C@H](F)C6)nc4c3F)c12]

3-((7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)amino)bicyclo[1.1.1]pentan-1-ol The title compound was synthesized according to the procedure described for example 135. $^1$H NMR (400 MHz, methanol-d4) δ 9.24 (s, 1H), 7.68 (dd, J=5.6, 8.8 Hz, 1H), 7.32 (d, J=2.4 Hz, 1H), 7.25 (t, J=9.2 Hz, 1H), 7.04 (d, J=2.0 Hz, 1H), 5.67-5.51 (m, 1H), 4.71 (qd, J=4.4, 12.0 Hz, 2H), 4.10-3.85 (m, 3H), 3.54-3.44 (m, 1H), 2.80-2.56 (m, 2H), 2.45 (s, 6H), 2.43-2.31 (m, 4H), 2.28-2.07 (m, 2H), 0.77 (br t, J=6.4 Hz, 3H); LCMS (EST, M+1): m/z=592.3.

Example 167

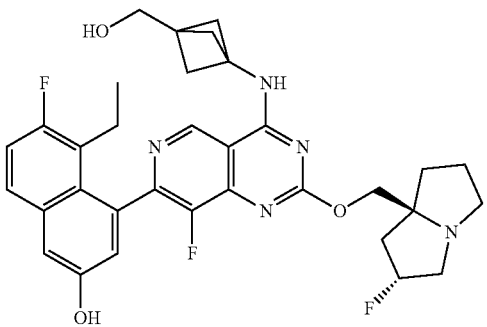 [SMILES: CCc1c(F)ccc2cc(O)cc(-c3ncc4c(NC56CC(CO)(C5)C6)nc(OC[C@@]56CCCN5C[C@H](F)C6)nc4c3F)c12]

351

5-ethyl-6-fluoro-4-(8-fluoro-2-(((2R,7aS)-2-fluoro-hexahydro-1H-pyrrolizin-7a-yl)methoxy)-4-((3-(hydroxymethyl)bicyclo[1.1.1]pentan-1-yl)amino)pyrido[4,3-d]pyrimidin-7-yl) naphthalen-2-ol The title compound was synthesized according to the procedure described for example 135. $^1$H NMR (400 MHz, METHANOL-d4): δ=9.24 (s, 1H), 7.69 (dd, J=6.0, 9.2 Hz, 1H), 7.32 (d, J=2.8 Hz, 1H), 7.26 (t, J=9.6 Hz, 1H), 7.04 (d, J=2.4 Hz, 1H), 5.66-5.51 (m, 1H), 4.76-4.62 (m, 2H), 4.11-3.86 (m, 3H), 3.73 (s, 2H), 3.54-3.43 (m, 1H), 2.79-2.59 (m, 2H), 2.49-2.30 (m, 5H), 2.28 (s, 5H), 2.21-2.07 (m, 2H), 0.78 (br t, J=6.8 Hz, 3H); LCMS (ESI, M+1): m/z=606.3.

Example 168

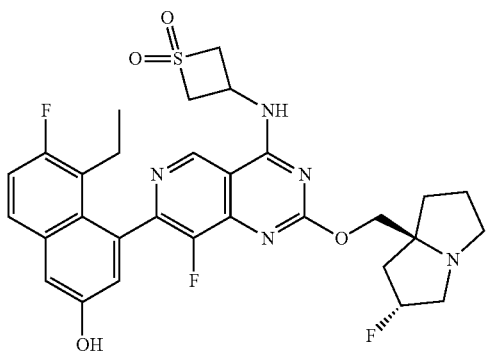 [SMILES: CCc1c(F)ccc2cc(O)cc(-c3ncc4c(NC5CS(=O)(=O)C5)nc(OC[C@@]56CCCN5C[C@H](F)C6)nc4c3F)c12]

3-((7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)amino)thietane 1,1-dioxide The title compound was synthesized according to the procedure described for example 134. $^1$H NMR (400 MHz, CD$_3$OD) δ 9.28 (s, 1H), 7.68 (dd, J=6.0, 9.2 Hz, 1H), 7.31 (d, J=2.8 Hz, 1H), 7.25 (t, J=9.6 Hz, 1H), 7.04 (d, J=2.4 Hz, 1H), 5.43-5.18 (m, 1H), 4.98-4.91 (m, 1H), 4.79-4.67 (m, 2H), 4.53-4.40 (m, 2H), 4.38-4.22 (m, 2H), 3.29-3.19 (m, 3H), 3.03 (dt, J=5.6, 9.2 Hz, 1H), 2.50-2.39 (m, 1H), 2.38-2.20 (m, 2H), 2.19-2.09 (m, 2H), 2.06-1.87 (m, 3H), 0.78 (t, J=7.2 Hz, 3H). LCMS (ESI, M+1): m/z=614.3.

Example 169

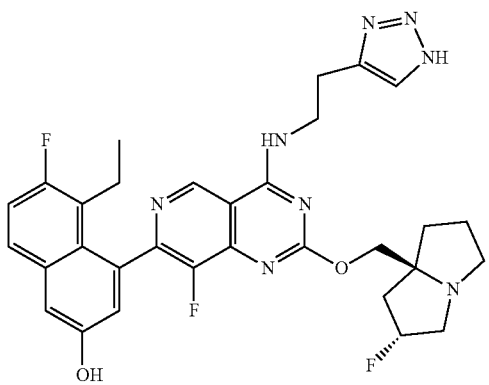 [SMILES: CCc1c(F)ccc2cc(O)cc(-c3ncc4c(NCCc5c[nH]nn5)nc(OC[C@@]56CCCN5C[C@H](F)C6)nc4c3F)c12]

352

4-(4-((2-(1H-1,2,3-triazol-4-yl)ethyl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 135. $^1$H NMR (400 MHz, METHANOL-d$_4$): δ=9.10 (s, 1H), 7.69 (s, 1H), 7.68-7.63 (m, 1H), 7.30 (d, J=2.8 Hz, 1H), 7.24 (t, J=9.2 Hz, 1H), 7.04 (d, J=2.4 Hz, 1H), 5.40-5.22 (m, 1H), 4.34-4.23 (m, 2H), 4.05-3.95 (m, 2H), 3.28-3.10 (m, 5H), 3.07-2.95 (m, 1H), 2.49-2.12 (m, 5H), 2.03-1.88 (m, 3H), 0.79 (t, J=7.2 Hz, 3H); LCMS (ESI, M+1): m/z=605.2.

Example 170

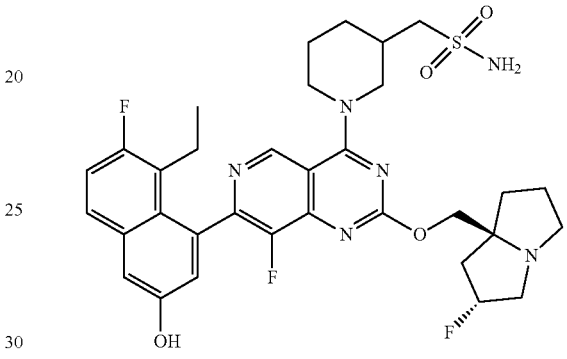

1-(1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)piperidin-3-yl)methanesulfonamide The title compound was synthesized according to the procedure described for example 135. $^1$H NMR (400 MHz, methanol-d$_4$) δ 9.08 (s, 1H), 7.67 (dd, J=5.6, 8.8 Hz, 1H), 7.30 (d, J=2.8 Hz, 1H), 7.24 (t, J=9.2 Hz, 1H), 7.05 (dd, J=2.4, 6.0 Hz, 1H), 5.40-5.23 (m, 1H), 5.03-4.93 (m, 1H), 4.60-4.50 (m, 1H), 4.41-4.26 (m, 2H), 3.68-3.55 (m, 1H), 3.43-3.34 (m, 1H), 3.30-3.07 (m, 5H), 3.06-2.97 (m, 1H), 2.56-2.43 (m, 2H), 2.41-2.08 (m, 5H), 2.04-1.89 (m, 4H), 1.86-1.74 (m, 1H), 1.68-1.55 (m, 1H), 0.80 (q, J=6.8 Hz, 3H); $^{19}$F NMR (376 MHz, methanol-d$_4$) δ=−121.192, −138.964, −173.392; LCMS (ESI, M+1): m/z=671.3.

Example 171

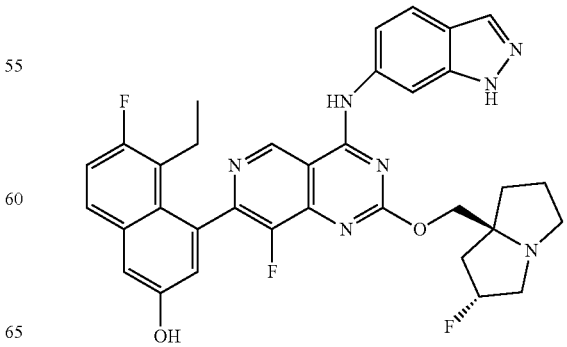

4-(4-((1H-indazol-6-yl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol

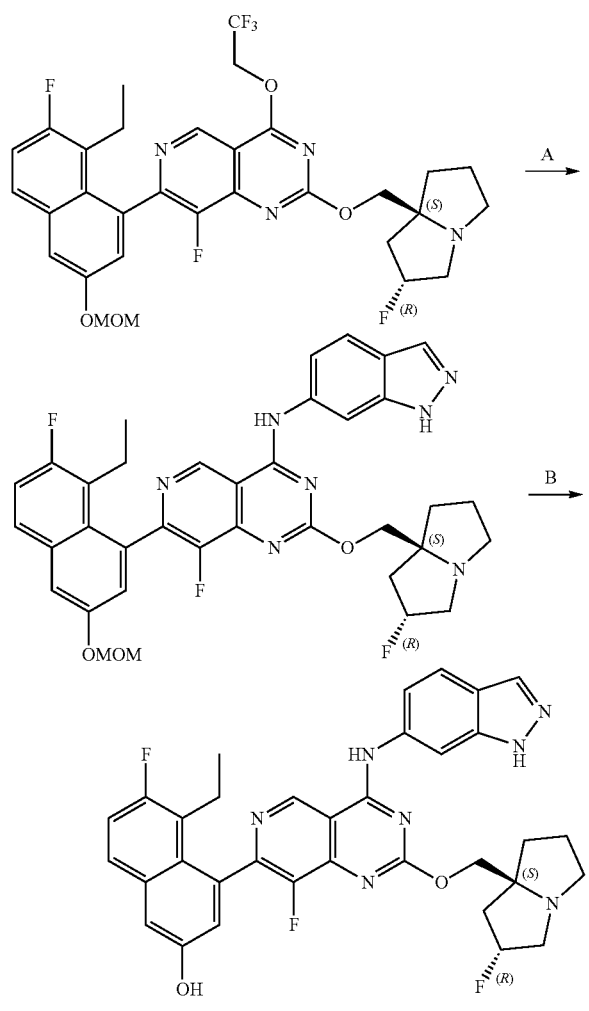

Step A. 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-N-(1H-indazol-6-yl)pyrido[4,3-d]pyrimidin-4-amine: To a solution of 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-4-(2,2,2-trifluoroethoxy) pyrido[4,3-d]pyrimidine (200 mg, 1.0 equiv.) and 1H-indazol-6-amine (41.8 mg, 1.0 equiv.) in DMF (2 mL) was added 4 Å MS (50 mg) and t-BuONa (60.4 mg, 2.0 equiv.). The mixture was stirred at 0° C. for 0.5 hour. Upon reaction completion, the mixture was quenched with water (10 mL) and extracted with ethyl acetate (3×10 mL). The combined organic layers were washed with brine (20 mL), dried over anhydrous sodium sulfate, concentrated, and purified by reversed phase flash chromatography (C18, mobile phase: [water (0.1% formic acid)/ACN]) to afford the title compound (80 mg, 29% yield) as a yellow solid; LCMS (ESI, M+1): m/z=670.3.

Step B. 4-(4-((1H-indazol-6-yl)amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol: To a solution of 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-N-(1H-indazol-6-yl)pyrido[4,3-d]pyrimidin-4-amine (90 mg, 1.0 equiv.) in DCM (1 mL) was added TFA (1.15 g, 750 µL, 90 equiv.). The mixture was stirred at 0° C. for 0.5 hour. The reaction mixture was concentrated under reduced pressure to remove TFA. The residue was dissolved in water (5 mL), neutralized with solid $Na_2CO_3$, then extracted with ethyl acetate (3×5 mL). The combined organic layers were washed with brine (20 mL), dried over anhydrous sodium sulfate, concentrated and purified by prep-HPLC [column: waters Xbridge 150×25 mm×5 µm; mobile phase: [water (10 mM $NH_4HCO_3$)/ACN]; B %: 39%-69%, 9 min] to afford the title compound (12 mg, 17% yield) as a white solid. $^1$H NMR (400 MHz, $CD_3OD$): δ 9.65 (s, 1H), 8.42 (s, 1H), 8.13 (s, 1H), 7.91-7.87 (d, J=8.4 Hz, 1H), 7.82-7.76 (dd, J=6.0, 10.2 Hz, 1H), 7.64-7.57 (dd, J=0.8, 8.4 Hz, 1H), 7.43-7.31 (m, 2H), 7.16-7.13 (d, J=2.4 Hz, 1H), 5.49-5.20 (m, 1H), 4.41-4.22 (m, 3H), 3.27-3.15 (m, 3H), 3.06-2.93 (m, 1H), 2.55-2.45 (m, 1H), 2.35-2.11 (m, 4H), 2.03-1.82 (m, 3H), 0.86 (t, J=7.2 Hz, 3H). LCMS (ESI, M+1): m/z=626.3.

Example 172

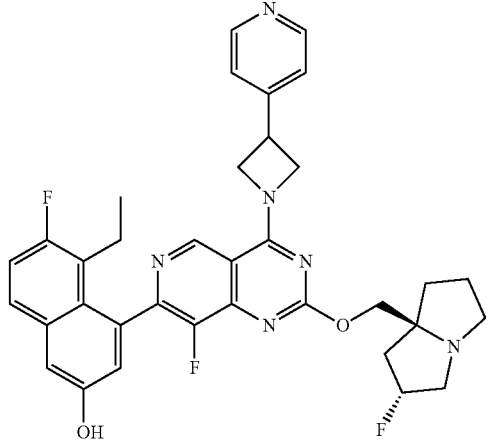 [SMILES: CCc1c(F)ccc2cc(O)cc(-c3ncc4c(N5CC(c6ccncc6)C5)nc(OC[C@@]56CCCN5C[C@H](F)C6)nc4c3F)c12]

5-ethyl-6-fluoro-4-(8-fluoro-2-(((2R,7aS)-2-fluorohexahydro-1H-pyrrolizin-7a-yl)methoxy)-4-(3-(pyridin-4-yl)azetidin-1-yl)pyrido[4,3-d]pyrimidin-7-yl)naphthalen-2-ol The title compound was synthesized according to the procedure described for example 135. $^1$H NMR (400 MHz, DMSO-$d_6$) δ 9.94 (s, 1H), 9.01 (s, 1H), 8.58 (br d, J=4.8 Hz, 2H), 7.77 (dd, J=6.4, 8.6 Hz, 1H), 7.55 (br d, J=4.8 Hz, 2H), 7.39-7.30 (m, 2H), 7.00 (s, 1H), 5.40-5.15 (m, 2H), 5.03-4.72 (m, 211), 4.47-4.27 (m, 1H), 4.24-4.11 (m, 2H), 4.09-4.00 (m, 1H), 3.08 (br d, J=9.2 Hz, 2H), 3.01 (br s, 1H), 2.87-2.76 (m, 1H), 2.41-2.31 (m, 1H), 2.15-2.07 (m, 2H), 2.06-1.95 (m, 2H), 1.87-1.73 (m, 3H), 0.73 (br t, J=7.2 Hz, 3H); LCMS [ESI, M+1]: 627.4

Example 173

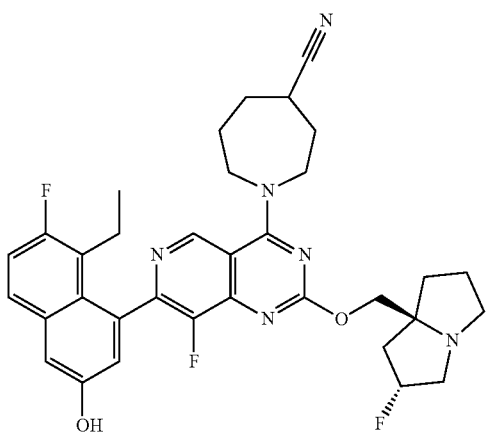 [SMILES: CCc1c(F)ccc2cc(O)cc(-c3ncc4c(N5CCCC(C#N)CC5)nc(OC[C@@]56CCCN5C[C@H](F)C6)nc4c3F)c12]

1-(7-(8-ethyl-7-fluoro-3-hydroxy)naphthalen-1-yl)-
8-fluoro-2-(((2R,7aS)-2-fluorohexahydro-1H-pyr-
rolizin-7a-yl)methoxy)pyrido[4,3-d]pyrimidin-4-yl)
azepane-4-carbonitrile The title compound was synthesized according to the procedure described for example 134. $^1$H NMR (400 MHz, methanol-$d_4$) δ=9.15 (s, 1H), 7.67 (dd, J=5.6, 8.8 Hz, 1H), 7.30 (d, J=2.8 Hz, 1H), 7.25 (t, J=9.2 Hz, 1H), 7.06 (dd, J=2.8, 5.2 Hz, 1H), 5.40-5.22 (m, 1H), 4.40-3.95 (m, 6H), 3.29-3.12 (m, 4H), 3.10-2.95 (m, 1H), 2.55-2.44 (m, 1H), 2.41-2.20 (m, 5H), 2.19-2.06 (m, 3H), 2.05-1.86 (m, 5H), 0.87-0.71 (m, 3H); LCMS (ESI, M+1): m/z=617.3.

Example 174

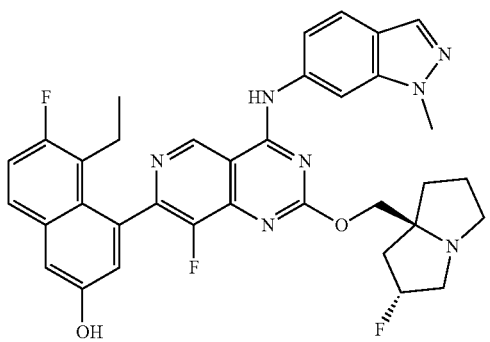 [SMILES: CCc1c(F)ccc2cc(O)cc(-c3ncc4c(Nc5ccc6cnn(C)c6c5)nc(OC[C@@]56CCCN5C[C@H](F)C6)nc4c3F)c12]

5-ethyl-6-fluoro-4-(8-fluoro-2-(((2R,7aS)-2-fluoro-
hexahydro-1H-pyrrolizin-7a-yl)methoxy)-4-((1-
methyl-1H-indazol-6-yl)amino)pyrido[4,3-d]pyrimi-
din-7-yl)naphthalen-2-ol The title compound was synthesized according to the procedure described for example 171. $^1$H NMR (400 MHz, METHANOL-$d_4$) δ=9.49 (s, 1H), 8.31 (s, 1H), 8.02 (d, J=0.8 Hz, 1H), 7.82 (d, J=8.4 Hz, 1H), 7.69 (dd, J=6.0, 9.2 Hz, 1H), 7.51 (dd, J=1.6, 8.8 Hz, 1H), 7.32 (d, J=2.4 Hz, 1H), 7.26 (t, J=9.2 Hz, 1H), 7.09 (d, J=2.8 Hz, 1H), 5.37-5.18 (m, 1H), 4.41-4.24 (m, 2H), 4.11 (s, 3H), 3.26- 3.14 (m, 3H), 2.99 (dt, J=5.6, 9.6 Hz, 1H), 2.58-2.44 (m, 1H), 2.37-2.20 (m, 2H), 2.18-2.03 (m, 2H), 2.02-1.82 (m, 3H), 0.82 (t, J=7.2 Hz, 3H); LCMS (ESI, M+1): m/z=640.2.

Example 175

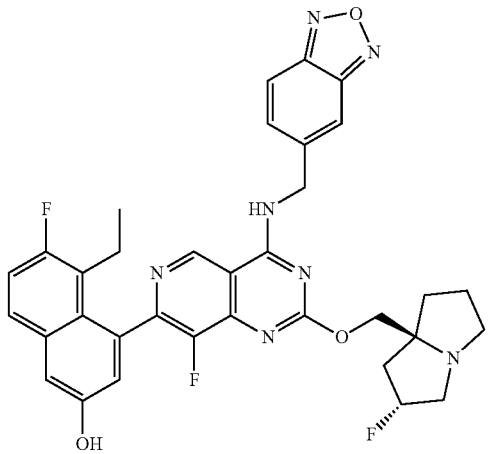 [SMILES: CCc1c(F)ccc2cc(O)cc(-c3ncc4c(NCc5ccc6nonc6c5)nc(OC[C@@]56CCCN5C[C@H](F)C6)nc4c3F)c12]

4-(4-((benzo[c][1,2,5]oxadiazol-5-ylmethyl)amino)-
8-fluoro-2-(((2R,7aS)-2-fluorohexahydro-1H-pyr-
rolizin-7a-yl)methoxy)pyrido[4,3-d]pyrimidin-7-yl)-
5-ethyl-6-fluoronaphthalen-2-ol The title compound was synthesized according to the procedure described for example 135. $^1$H NMR (400 MHz, methanol-$d_4$) δ 9.23 (s, 1H), 7.97-7.88 (m, 2H), 7.71-7.61 (m, 2H), 7.30 (d, J=2.8 Hz, 1H), 7.25 (t, J=9.2 Hz, 1H), 7.05 (d, J=2.4 Hz, 1H), 5.34-5.13 (m, 1H), 5.04-4.94 (m, 2H), 4.27-4.14 (m, 2H), 3.25-3.08 (m, 3H), 3.01-2.90 (m, 1H), 2.55-2.40 (m, 1H), 2.30-2.11 (m, 3H), 2.10-1.89 (m, 3H), 1.84-1.70 (m, 1H), 0.80 (br t, J=7.2 Hz, 3H); LCMS [ESI, M+1]: 642.3.

Example 176

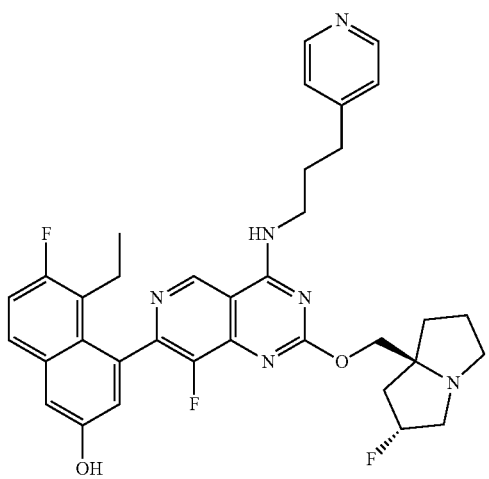 [SMILES: CCc1c(F)ccc2cc(O)cc(-c3ncc4c(NCCCc5ccncc5)nc(OC[C@@]56CCCN5C[C@H](F)C6)nc4c3F)c12]

5-ethyl-6-fluoro-4-(8-fluoro-2-(((2R,7aS)-2-fluoro-hexahydro-1H-pyrrolizin-7a-yl)methoxy)-4-((3-(pyridin-4-yl)propyl)amino)pyrido[4,3-d]pyrimidin-7-yl)naphthalen-2-ol The title compound was synthesized according to the procedure described for example 134. $^1$H NMR (400 MHz, METHANOL-d$_4$) δ=9.09 (s, 1H), 8.41 (d, J=6.0 Hz, 2H), 7.67 (dd, J=6.0, 9.2 Hz, 1H), 7.37 (d, J=6.0 Hz, 2H), 7.30 (d, J=2.8 Hz, 1H), 7.24 (t, J=9.2 Hz, 1H), 7.04 (d, J=2.8 Hz, 1H), 5.39-5.22 (m, 1H), 4.32-4.21 (m, 2H), 3.80-3.72 (m, 2H), 3.27-3.13 (m, 3H), 3.05-2.97 (m, 1H), 2.86 (t, J=7.6 Hz, 2H), 2.53-2.42 (m, 1H), 2.38-2.20 (m, 2H), 2.19-2.09 (m, 4H), 2.03-1.85 (m, 3H), 0.79 (t, J=7.2 Hz, 3H); LCMS (ESI, M+1): m/z=629.3.

Example 177

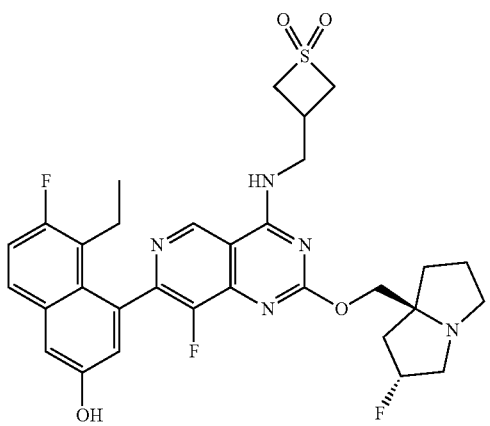 [SMILES: CCc1c(F)ccc2cc(O)cc(-c3ncc4c(NCC5CS(=O)(=O)C5)nc(OC[C@@]56CCCN5C[C@H](F)C6)nc4c3F)c12]

3-(((7-(8-ethyl-7-fluoro-3-hydroxy)naphthalen-1-yl)-8-fluoro-2-(((2R,7aS)-2-fluorohexahydro-1H-pyr-rolizin-7a-yl)methoxy)pyrido[4,3-d]pyrimidin-4-yl)amino)methyl)thietane1,1-dioxide The title compound was synthesized according to the procedure described for example 135. $^1$H NMR (400 MHz, DMSO-d$_6$): δ 9.27 (s, 1H), 9.23-9.11 (m, 1H), 8.18 (s, 1H), 7.76 (dd, J=6.0, 8.8 Hz, 1H), 7.41-7.28 (m, 2H), 6.99 (d, J=2.4 Hz, 1H), 5.38-5.19 (m, 1H), 4.35 (br t, J=11.2 Hz, 2H), 4.19-4.03 (m, 4H), 3.94-3.76 (m, 2H), 3.15-3.08 (m, 2H), 3.05-2.95 (m, 2H), 2.89-2.79 (m, 1H), 2.28-1.96 (m, 5H), 1.90-1.70 (m, 3H), 0.81-0.64 (m, 3H); LCMS (ESI, M+1): m/z=628.

Example 178

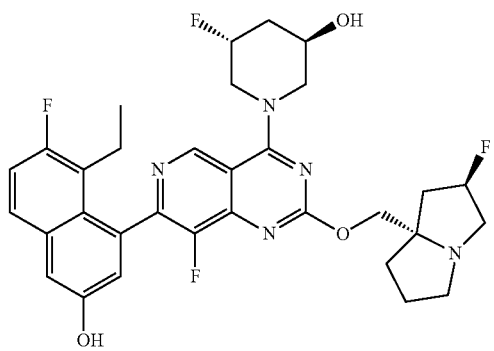 [SMILES: CCc1c(F)ccc2cc(O)cc(-c3ncc4c(N5C[C@H](O)C[C@@H](F)C5)nc(OC[C@@]56CCCN5C[C@H](F)C6)nc4c3F)c12]

(3R,5R)-1-(7-(8-ethyl-7-fluoro-3-hydroxy)naphtha-len-1-yl)-8-fluoro-2-(((2R,7aS)-2-fluorohexahydro-1H-pyrrolizin-7a-yl)methoxy)pyrido[4,3-d]pyrimi-din-4-yl)-5-fluoropiperidin-3-ol The title compound was synthesized according to the procedure described for example 135. $^1$H NMR (400 MHz, CD3OD): δ 9.14-9.12 (d, J=6.8 Hz, 1H), 7.71-7.63 (dd, J=6.0, 9.2 Hz, 1H), 7.32-7.29 (d, J=2.8 Hz, 1H), 7.28-7.21 (t, J=9.6 Hz, 1H), 7.08-7.01 (m, 1H), 5.54 (s, 1H), 5.40 (s, 1H), 5.37 (s, 1H), 5.24 (s, 1H), 4.98 (s, 1H), 4.46-4.15 (m, 5H), 3.82-3.76 (dd, J=2.0, 11.6 Hz, 1H), 3.29-3.10 (m, 3H), 3.08-2.96 (m, 1H), 2.56-2.40 (m, 3H), 2.40-2.10 (m, 4H), 2.05-1.85 (m, 3H), 0.86-0.74 (td, J=7.4, 19.2 Hz, 3H); LCMS (ESI, M+1): m/z=612.3.

Example 179

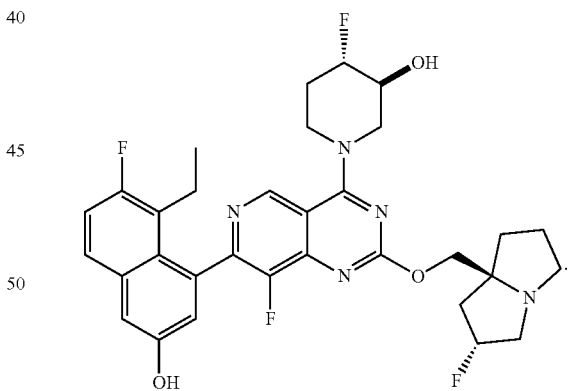

(3S,4S)-1-(7-(8-ethyl-7-fluoro-3-hydroxy)naphtha-len-1-yl)-8-fluoro-2-(((2R,7aS)-2-fluorohexahydro-1H-pyrrolizin-7a-yl)methoxy)pyrido[4,3-d]pyrimi-din-4-yl)-4-fluoropiperidin-3-ol The title compound was synthesized according to the procedure described for example 135 except for HCl-MeOH (4 M, 49.2 equiv.) was used in the deprotection step. $^1$H NMR (400 MHz, methanol-d$_4$) δ=9.24 (dd, J=1.2, 6.4 Hz, 1H), 8.49 (s, 1H), 7.68 (dd, J=6.0, 9.2 Hz, 1H), 7.35-7.19 (m, 1H), 7.06 (t, J=2.8 Hz, 1H), 5.55-5.28 (m, 1H), 4.79-4.60

(m, 1H), 4.55-4.38 (m, 2H), 4.32-4.12 (m, 2H), 4.11-3.88 (m, 3H), 3.69-3.41 (m, 3H), 3.21 (dt, J=5.6, 9.6 Hz, 1H), 2.56-2.23 (m, 5H), 2.22-2.08 (m, 3H), 2.07-1.92 (m, 2H), 0.80 (br t, J=7.2 Hz, 3H); LCMS (ESI, M+1): m/z=612.2.

Example 180

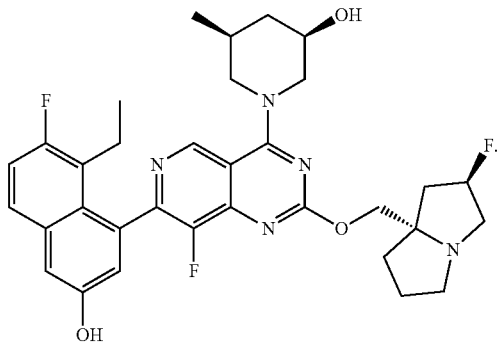 [SMILES: CCc1c(F)ccc2cc(O)cc(-c3ncc4c(N5C[C@@H](C)C[C@@H](O)C5)nc(OC[C@@]56CCCN5C[C@H](F)C6)nc4c3F)c12]

(3R,5S)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-5-methylpiperidin-3-ol The title compound was synthesized according to the procedure described for example 135 except for HCl/EtOAc (4 M, 1.0 mL, 27 equiv.) was used in the deprotection step. ¹H NMR (400 MHz, METHANOL-d₄) δ=9.05 (d, J=1.6 Hz, 1H), 7.68 (dd, J=6.0, 9.2 Hz, 1H), 7.38-7.15 (m, 2H), 7.06 (s, 1H), 5.44-5.15 (m, 1H), 4.81-4.72 (m, 1H), 4.55 (br d, J=12.8 Hz, 1H), 4.38-4.18 (m, 2H), 3.88 (br dd, J=4.4, 10.4 Hz, 1H), 3.29-3.12 (m, 3H), 3.09-2.90 (m, 3H), 2.54-2.10 (m, 6H), 2.06-1.86 (m, 4H), 1.35-1.21 (m, 1H), 1.06 (d, J=6.5 Hz, 3H), 0.80 (br t, J=7.3 Hz, 3H); LCMS (ESI, M+1): m/z=608.4.

Example 181

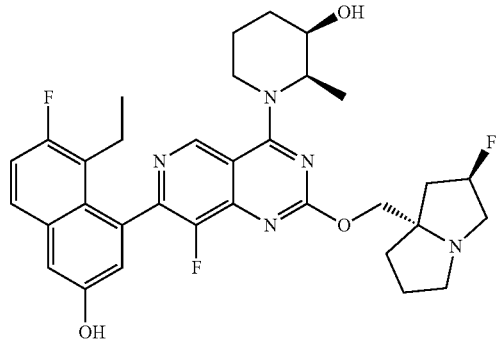 [SMILES: CCc1c(F)ccc2cc(O)cc(-c3ncc4c(N5CCC[C@@H](O)[C@H]5C)nc(OC[C@@]56CCCN5C[C@H](F)C6)nc4c3F)c12]

(2R,3R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2-methylpiperidin-3-ol

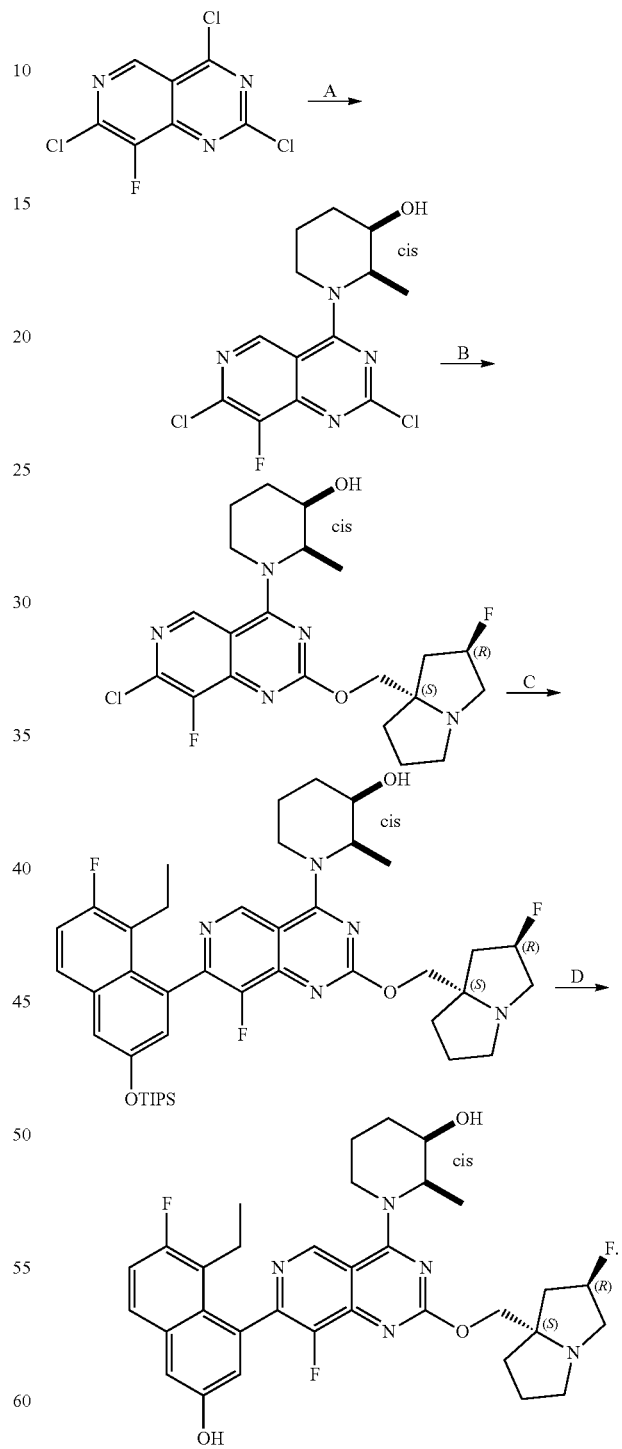

Step A. (2R,3R)-1-(2,7-dichloro-8-fluoropyrido[4,3-d]pyrimidin-4-yl)-2-methylpiperidin-3-ol: To a mixture of 2,4,7-trichloro-8-fluoropyrido[4,3-d]pyrimidine (450 mg, 1.0 equiv.), DIEA (2.30 g, 10 equiv.) and 4 Å molecular sieves (45 mg) in DMAc (4 mL) was added (2R,3R)-2-methylpiperidin-3-ol (135 mg, 0.5 equiv., HCl) at 15° C. The reaction was stirred at 15° C. for 1 hour. The mixture was filtered and the filtrate was purified by reversed phase flash chromatography (mobile phase: [water (0.1% formic acid)/acetonitrile]). The desired fractions were collected, neutralized with NaHCO$_3$ solid, concentrated in vacuum to remove acetonitrile, and extracted with ethyl acetate (2×20 mL). The combined organic layer was washed with brine (15 mL) dried over anhydrous sodium sulfate, concentrated in vacuum to afford the title compound (265 mg, 44% yield) as a red solid; $^1$H NMR (400 MHz, DMSO-d$_6$) δ=8.90 (s, 1H), 5.12 (d, J=4.0 Hz, 1H), 4.92 (br s, 1H), 4.25 (br d, J=11.6 Hz, 1H), 3.77-3.67 (m, 1H), 3.46 (br s, 1H), 1.82-1.58 (m, 4H), 1.31 (br d, J=6.8 Hz, 3H); LCMS (ESI, M+1): m/z=331.0.

Step B. (2R,3R)-1-(7-chloro-8-fluoro-2-(((2R,7aS)-2-fluorohexahydro-1H-pyrrolizin-7a-yl)methoxy)pyrido[4,3-d]pyrimidin-4-yl)-2-methylpiperidin-3-ol: A mixture of (2R,3R)-1-(2,7-dichloro-8-fluoropyrido[4,3-d]pyrimidin-4-yl)-2-methylpiperidin-3-ol (257 mg, 1.0 equiv.), ((2R,7aS)-2-fluorohexahydro-1H-pyrrolizin-7a-yl)methanol (371 mg, 3.0 equiv.), DIEA (501 mg, 5.0 equiv.) and 4 Å molecular sieves (30 mg) in dioxane (3 mL) was stirred at 90° C. for 14 hours. The mixture was filtered and the filtrate was concentrated, purified by reversed phase flash chromatography (mobile phase: [water (0.1% formic acid)/acetonitrile]). The desired fractions were collected, neutralized with NaHCO$_3$ solid, extracted with ethyl acetate (2×40 mL). The combined organic layer was washed with brine (40 mL), dried over anhydrous Na$_2$SO$_4$, and concentrated in vacuum to afford the title compound (296 mg, 74% yield) as a yellow solid; LCMS (ESI, M+1): m/z=454.1.

Step C. (2R,3R)-1-(7-(8-ethyl-7-fluoro-3-((triisopropylsilyl)oxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2-methylpiperidin-3-ol: To a mixture of (2R,3R)-1-(7-chloro-8-fluoro-2-(((2R,7aS)-2-fluorohexahydro-1H-pyrrolizin-7a-yl)methoxy)pyrido[4,3-d]pyrimidin-4-yl)-2-methylpiperidin-3-ol (100 mg, 1.0 equiv.), ((5-ethyl-6-fluoro-4-(4,4,5,5-tetramethyl-1,3,2-dioxaborolan-2-yl)naphthalen-2-yl)oxy)triisopropylsilane (156 mg, 1.5 equiv.) and Cs$_2$CO$_3$ (144 mg, 2.0 equiv.) in dioxane (1.5 mL) and water (0.5 mL) was added Pd(PPh$_3$)$_4$ (25.5 mg, 0.1 equiv.) under N$_2$. The mixture was de-gassed and stirred at 100° C. for 8 hours under N$_2$. The mixture was diluted with water (3 mL) and extracted with ethyl acetate (3×3 mL). The combined organic layers were washed with brine (5 mL), dried over Na$_2$SO$_4$, concentrated in vacuum. The residue was purified by reversed phase flash chromatography (mobile phase: [water (0.1% formic acid)/acetonitrile]). The desired fractions were collected neutralized with NaHCO$_3$ solid, concentrated in vacuum to remove acetonitrile, and extracted with ethyl acetate (15 mL). The combined organic layer was washed with brine (15 mL), dried over anhydrous Na$_2$SO$_4$, concentrated in vacuum to afford the title compound (53.0 mg, 31% yield) as a yellow solid; LCMS (ESI, M+1): m/z=764.3.

Step D. (2R,3R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-2-methylpiperidin-3-ol: A mixture of (2R,3R)-1-(7-(8-ethyl-7-fluoro-3-((triisopropylsilyl) oxy)naphthalen-1-yl)-8-fluoro-2-(((2R,7aS)-2-fluorohexahydro-1H-pyrrolizin-7a-yl) methoxy)pyrido[4,3-d]pyrimidin-4-yl)-2-methylpiperidin-3-ol (50.0 mg, 1.0 equiv.) and CsF (99.4 mg, 10 equiv.) in DMF (0.6 mL) was stirred at 15° C. for 1 hour. The mixture was filtered and the filtrate was purified by reversed phase flash chromatography (mobile phase: [water (0.1% formic acid)/acetonitrile]). The desired fractions were collected, neutralized with solid NaHCO$_3$, concentrated in vacuum to remove acetonitrile and extracted with ethyl acetate (2×10 mL). The combined organic layer was washed with brine (15 mL), dried over anhydrous Na$_2$SO$_4$ and concentrated in vacuum. The residue was purified by prep-HPLC [Waters Xbridge 150×25 mm×5 μm; mobile phase: [water (10 mM NH$_4$HCO$_3$)/ACN]; B %: 39%-69%, 9 min] twice to afford the title compound (22.0 mg, 55% yield) as a white solid; $^1$H NMR (400 MHz, methanol-d$_4$) δ=8.97 (d, J=2.8 Hz, 1H), 7.67 (dd, J=5.6, 8.8 Hz, 1H), 7.30 (d, J=2.4 Hz, 1H), 7.24 (t, J=9.2 Hz, 1H), 7.05 (dd, J=2.4, 6.8 Hz, 1H), 5.30 (d, J=54.4 Hz, 1H), 5.11-5.02 (m, 1H), 4.40 (br d, J=13.6 Hz, 1H), 4.34-4.21 (m, 2H), 3.96-3.88 (m, 1H), 3.58-3.47 (m, 1H), 3.29-3.13 (m, 3H), 3.06-2.96 (m, 1H), 2.55-2.43 (m, 1H), 2.38-2.10 (m, 4H), 2.03-1.95 (m, 2H), 1.94-1.79 (m, 5H), 1.45 (t, J=6.0 Hz, 3H), 0.85-0.75 (m, 3H); $^{19}$F NMR (376 MHz, methanol-d$_4$) δ=−121.191, −138.888, −173.675; LCMS (ESI, M+1): m/z=608.3.

Example 182

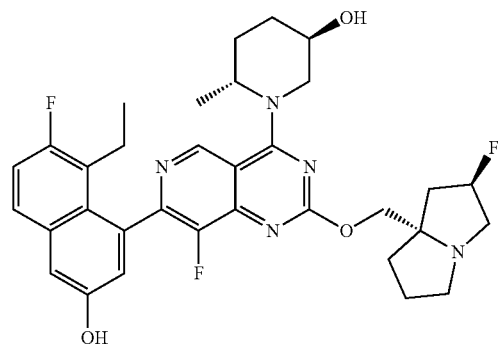 [SMILES: CCc1c(F)ccc2cc(O)cc(-c3ncc4c(N5C[C@H](O)CC[C@H]5C)nc(OC[C@@]56CCCN5C[C@H](F)C6)nc4c3F)c12]

(3R,6R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methylpiperidin-3-ol

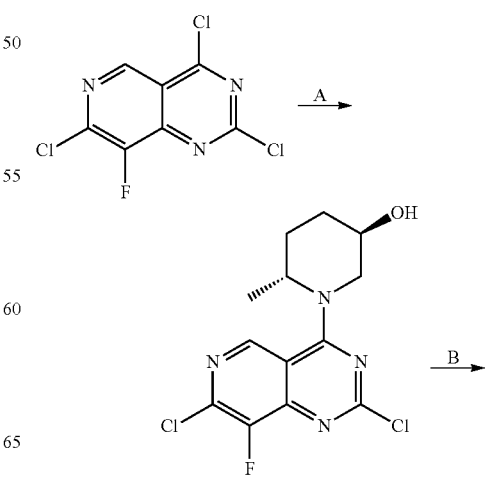

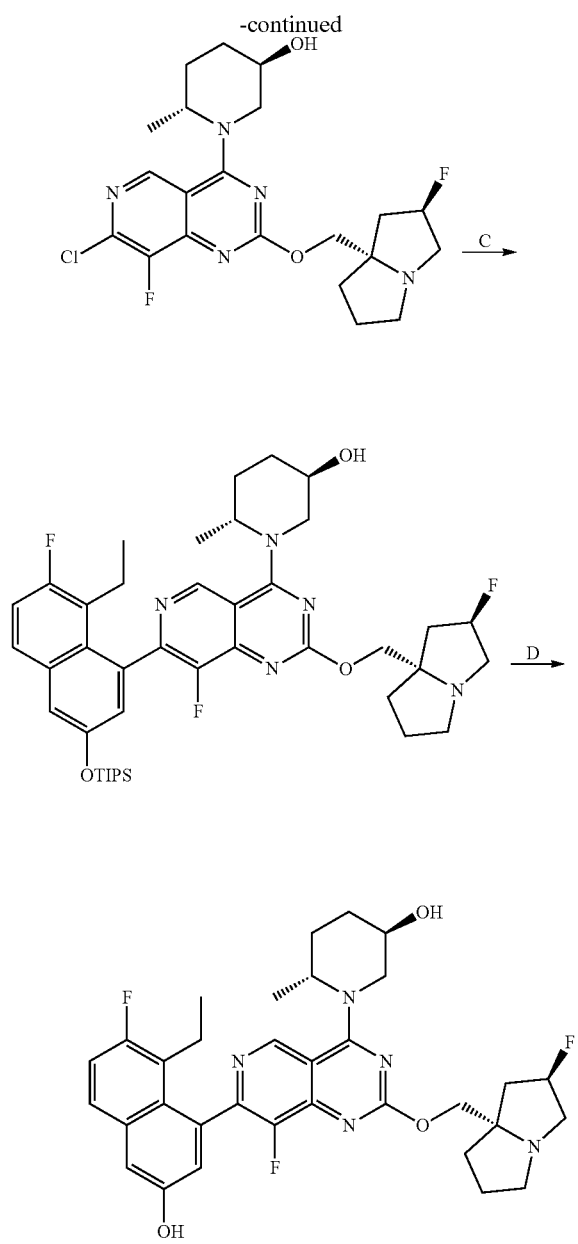

Step A. (3R,6R)-1-(2,7-dichloro-8-fluoropyrido[4,3-d]pyrimidin-4-yl)-6-methylpiperidin-3-ol: To a solution of 2,4,7-trichloro-8-fluoropyrido[4,3-d]pyrimidine (200 mg, 1.0 equiv.) and (3R,6R)-6-methylpiperidin-3-ol (84.1 mg, 0.7 equiv., HCl) in DMAc (4 mL) was added DIEA (307 mg, 414 μL, 3 equiv.) and 4 Å molecular sieves (300 mg). The reaction was stirred at 20° C. for 2 hours. The mixture was diluted with water (10 mL) and extracted with ethyl acetate (10 mL×3). The combined organic layers were washed with brine (20 mL), dried over anhydrous sodium sulfate, and concentrated in vacuum. The residue was purified by reversed phase flash chromatography (mobile phase: [water (0.1% formic acid)/acetonitrile]) to afford the title compound (205 mg, 78% yield) as a yellow solid; $^1$H NMR (400 MHz, DMSO-D$_6$): δ 9.32 (s, 1H), 5.13-4.96 (m, 2H), 4.28-4.21 (d, J=13.6 Hz, 1H), 4.00 (s, 1H), 3.76-3.68 (d, J=14.0 Hz, 1H), 2.24-2.14 (m, 1H), 2.03-1.92 (m, 1H), 1.64-1.55 (d, J=12.8 Hz, 1H), 1.47-1.40 (m, 1H), 1.37-1.30 (d, J=6.8 Hz, 3H); LCMS (ESI, M+1): m/z=331.1.

Step B. (3R,6R)-1-(7-chloro-8-fluoro-2-(((2R,7aS)-2-fluorohexahydro-1H-pyrrolizin-7a-yl)methoxy)pyrido[4,3-d]pyrimidin-4-yl)-6-methylpiperidin-3-ol: To a solution of (3R,6R)-1-(2,7-dichloro-8-fluoropyrido[4,3-d]pyrimidin-4-yl)-6-methylpiperidin-3-ol (205 mg, 1.0 equiv.) and ((2R,7aS)-2-fluorohexahydro-1H-pyrrolizin-7a-yl)methanol (296 mg, 3.0 equiv.) in DMF (5 mL) was added DIEA (400 mg, 539 μL, 5.0 equiv.) and 4 Å molecular sieves (400 mg). The reaction was stirred at 90° C. for 12 hours. The mixture was purified by reversed phase flash chromatography (mobile phase: [water (0.1% formic acid)/acetonitrile]) to afford the title compound (210 mg, 71.0% yield) as a yellow solid; LCMS (ESI, M+1): m/z=454.1.

Step C. (3R,6R)-14 (74(8-ethyl-7-fluoro-3-((triisopropylsilyl)oxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methylpiperidin-3-ol: A mixture of (3R,6R)-1-(7-chloro-8-fluoro-2-(((2R,7aS)-2-fluorohexahydro-1H-pyrrolizin-7a-yl)methoxy)pyrido[4,3-d]pyrimidin-4-yl)-6-methylpiperidin-3-ol (190 mg, 1.0 equiv.), ((5-ethyl-6-fluoro-4-(4,4,5,5-tetramethyl-1,3,2-dioxaborolan-2-yl)naphthalen-2-yl)oxy)triisopropylsilane (395 mg, 2.0 equiv.), K$_3$PO$_4$ (1.5 M, 3.0 equiv.) and CataCXium A Pd G3 (30.5 mg, 0.1 equiv.) in THF (3 mL) was degassed and stirred at 60° C. for 2 hours under N$_2$ atmosphere. The mixture was diluted with water (20 mL) and extracted with ethyl acetate (20 mL×3). The combined organic layers were washed with brine (30 mL), dried over anhydrous sodium sulfate, concentrated under reduced pressure. The residue was purified by reversed phase flash chromatography (mobile phase: [water (0.1% formic acid)/acetonitrile]) to afford the title compound (210 mg, 63% yield) as a black solid; LCMS (ESI, M+1): m/z=764.4.

Step D. (3R,6R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methylpiperidin-3-ol: To a solution of (3R,6R)-1-(7-(8-ethyl-7-fluoro-3-((triisopropylsilyl) oxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methylpiperidin-3-ol (100 mg, 1.0 equiv.) in DMF (2 mL) was added CsF (199 mg, 10 equiv.). The reaction was stirred at 40° C. for 1 hour. The mixture was diluted with water (10 mL) and extracted with ethyl acetate (10 mL×3). The combined organic layers were washed with brine (20 mL), dried over anhydrous sodium sulfate, filtered and concentrated in vacuum. The residue was purified by prep-HPLC [column: Phenomenex Gemini-NX C18 75×30 mm×3 μm; mobile phase: [water (10 mM NH$_4$HCO$_3$)/ACN]; B %: 34-64%, 8 minutes] to afford the title compound (72 mg, 90% yield) as a white solid; $^1$H NMR (400 MHz, CD3OD): δ 9.41-9.32 (d, J=4.4 Hz, 1H), 7.69-7.64 (dd, J=5.6, 8.8 Hz, 1H), 7.32-7.29 (d, J=2.0 Hz, 1H), 7.27-7.21 (t, J=9.6 Hz, 1H), 7.07-7.03 (dd, J=2.4, 6.8 Hz, 1H), 5.42-5.21 (d, J=54.4 Hz, 1H), 5.20-5.12 (m, 1H), 4.86 (s, 9H), 4.52-4.44 (d, J=14.4 Hz, 1H), 4.34-4.23 (m, J=10.5 Hz, 2H), 4.13 (s, 1H), 3.84-3.76 (m, 1H), 3.29-3.16 (m, 3H), 3.05-2.97 (m, 1H), 2.57-2.08 (m, 7H), 2.04-1.73 (m, 4H), 1.59-1.52 (m, 1H), 1.48-1.44 (m, 3H), 0.84-0.77 (t, J=7.2 Hz, 3H); LCMS (ESI, M+1): m/z=608.3.

Example 183

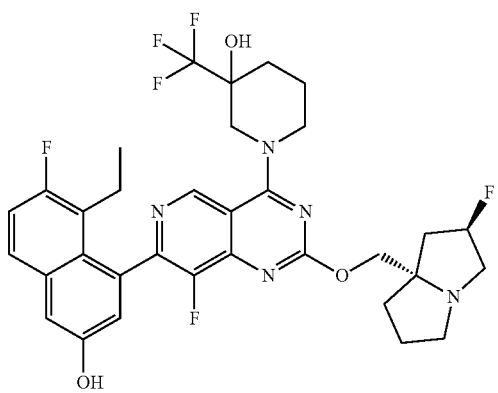 [SMILES: CCc1c(F)ccc2cc(O)cc(-c3ncc4c(N5CCCC(O)(C(F)(F)F)C5)nc(OC[C@@]56CCCN5C[C@H](F)C6)nc4c3F)c12]

1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-(trifluoromethyl)piperidin-3-ol The title compound was synthesized according to the procedure described for example 135. $^1$H NMR (400 MHz, methanol-$d_4$) δ=9.21 (dd, J=3.2, 14.8 Hz, 1H), 7.67 (dd, J=5.8, 8.9 Hz, 1H), 7.30 (d, J=2.4 Hz, 1H), 7.25 (t, J=9.2 Hz, 1H), 7.07 (t, J=2.4 Hz, 1H), 5.30 (d, J=54.4 Hz, 1H), 4.72-4.64 (m, 2H), 4.35-4.25 (m, 2H), 3.72 (t, J=14.4 Hz, 1H), 3.37 (t, J=12.8 Hz, 1H), 3.28-3.18 (m, 3H), 3.01 (dt, J=5.2, 9.2 Hz, 1H), 2.24-2.20 (m, 6H), 2.07-1.90 (m, 6H), 0.80 (dt, J=3.2, 7.2 Hz, 3H); F NMR (400 MHz, methanol-$d_4$) δ=−84.2, −121, −139, −174; LCMS (ESI, M+1): m/z=662.4.

Example 184

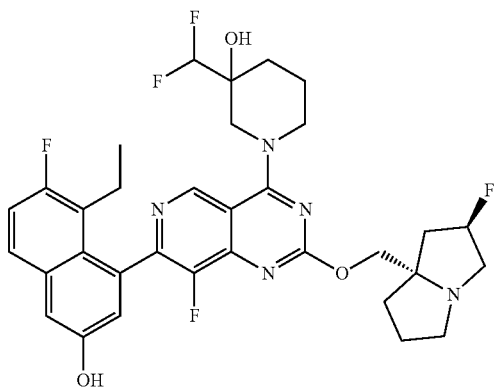 [SMILES: CCc1c(F)ccc2cc(O)cc(-c3ncc4c(N5CCCC(O)(C(F)F)C5)nc(OC[C@@]56CCCN5C[C@H](F)C6)nc4c3F)c12]

3-(difluoromethyl)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)piperidin-3-ol The title compound was synthesized according to the procedure described for example 135. $^1$H NMR (400 MHz, METHANOL-$d_4$) δ=9.25 (dd, J=2.4, 6.8 Hz, 1H), 8.50 (br s, 1H), 7.68 (dd, J=6.0, 8.8 Hz, 1H), 7.32-7.22 (m, 2H), 7.06 (d, J=2.4 Hz, 1H), 5.96-5.60 (m, 1H), 5.52-5.31 (m, 1H), 4.69 (br d, J=13.2 Hz, 1H), 4.57-4.40 (m, 3H), 3.78-3.64 (m, 1H), 3.64-3.45 (m, 3H), 3.45-3.37 (m, 1H), 3.25-3.15 (m, 1H), 2.54-2.31 (m, 3H), 2.29-2.09 (m, 5H), 2.06-1.85 (m, 4H), 0.85-0.74 (m, 3H); LCMS (ESI, M+1): m/z=644.3.

Example 185

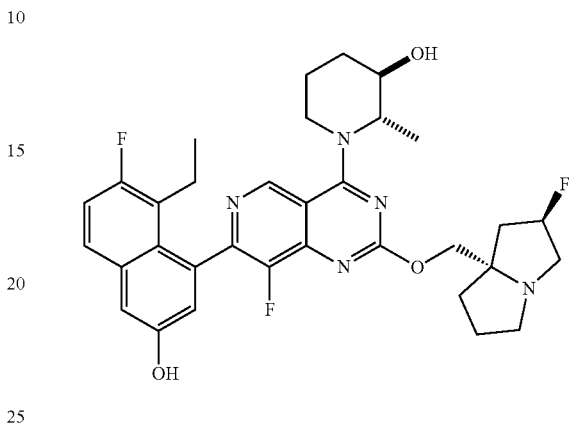

(2S,3R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-7-methylpiperidin-3-ol The title compound was synthesized according to the procedure described for example 182. $^1$H NMR (400 MHz, methanol-$d_4$): δ ppm 0.74-0.86 (m, 3H) 1.55 (m, 3H) 1.61-1.72 (m, 1H) 1.77-2.04 (m, 4H) 2.04-2.39 (m, 6H) 2.41-2.56 (m, 1H) 2.96-3.05 (m, 1H) 3.12-3.29 (m, 3H) 3.14-3.27 (m, 3H) 3.47-3.63 (m, 1H) 3.82-3.96 (m, 1H) 4.18-4.39 (m, 2H) 4.49-4.59 (m, 1H) 4.88-5.11 (m, 1H) 5.21-5.39 (m, 1H) 7.05 (dd, J=16.8, 2.8 Hz, 1H) 7.21-7.28 (m, 1H) 7.29-7.32 (m, 1H) 7.67 (dd, J=8.8, 6.4 Hz, 1H) 9.03 (t, J=2.4 Hz, 1H); LCMS (ESI, M+1): m/z=608.2.

Example 186

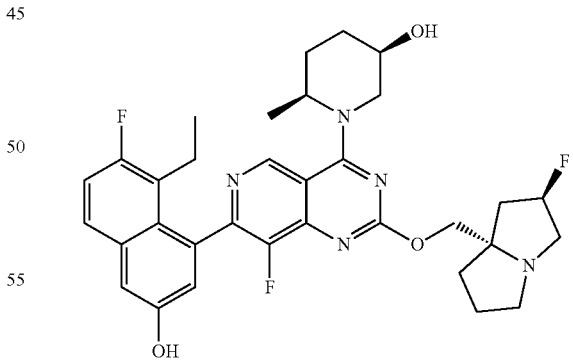

(3R,6S)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methylpiperidin-3-ol The title compound was synthesized according to the procedure described for example 182 except for BrettPhos- Pd-G3 (0.1 equiv.) was used instead of cataCXium A Pd G3 in step C. ¹H NMR (400 MHz, CHLOROFORM-d): δ=8.99-8.72 (m, 1H), 8.54 (s, 1H), 7.59-7.43 (m, 1H), 7.25-6.78 (m, 3H), 5.50-5.26 (m, 1H), 4.84-4.64 (m, 2H), 4.61-4.40 (m, 2H), 3.91-3.60 (m, 3H), 3.49-3.34 (m, 1H), 3.21-2.96 (m, 2H), 2.64-2.33 (m, 4H), 2.22-2.03 (m, 4H), 1.92 (br s, 4H), 1.51 (br t, J=6.8 Hz, 3H), 0.85-0.73 (m, 3H); LCMS (ESI, M+1): m/z=608.2.

Example 187

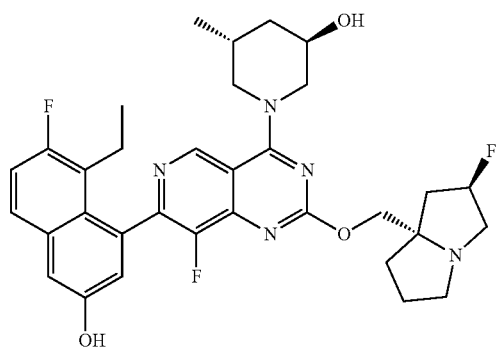 [SMILES: CCc1c(F)ccc2cc(O)cc(-c3ncc4c(N5C[C@H](C)C[C@@H](O)C5)nc(OC[C@@]56CCCN5C[C@H](F)C6)nc4c3F)c12]

(3R,5R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-5-methylpiperidin-3-ol The title compound was synthesized according to the procedure described for example 135. ¹H NMR (400 MHz, methanol-d₄) δ 9.22 (dd, J=2.8, 8.4 Hz, 1H), 7.67 (dd, J=6.0, 8.8 Hz, 1H), 7.30 (d, J=2.4 Hz, 1H), 7.24 (t, J=9.2 Hz, 1H), 7.08-7.04 (m, 1H), 5.39-5.19 (m, 1H), 4.69-4.50 (m, 2H), 4.37-4.21 (m, 2H), 4.15 (br s, 1H), 3.64 (br d, J=14.0 Hz, 1H), 3.29-3.16 (m, 3H), 3.06-2.92 (m, 2H), 2.51-2.33 (m, 2H), 2.29-2.10 (m, 4H), 2.04-1.86 (m, 4H), 1.63-1.51 (m, 1H), 1.03 (br d, J=6.4 Hz, 3H), 0.85-0.76 (m, 3H); ¹⁹F NMR (400 MHz, methanol-d₄) δ−121.176, −139.194, −173.708; LCMS (ESI, M+1): m/z=608.3.

Example 188

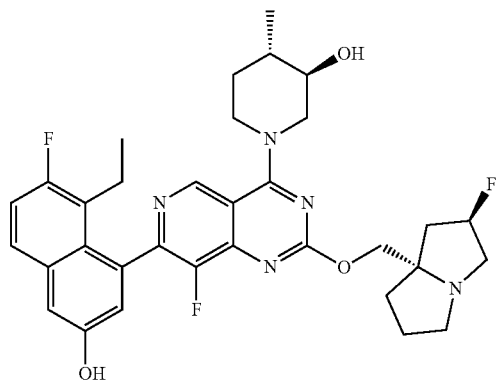 [SMILES: CCc1c(F)ccc2cc(O)cc(-c3ncc4c(N5CC[C@H](C)[C@@H](O)C5)nc(OC[C@@]56CCCN5C[C@H](F)C6)nc4c3F)c12]

(3R,4S)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-4-methylpiperidin-3-ol The title compound was synthesized according to the procedure described for example 135. ¹H NMR (400 MHz, METHANOL-d₄) δ=9.06 (d, J=2.0 Hz, 1H), 7.67 (dd, J=6.0, 9.2 Hz, 1H), 7.34-7.19 (m, 2H), 7.05 (t, J=2.4 Hz, 1H), 5.42-5.19 (m, 1H), 4.75-4.63 (m, 1H), 4.57 (br d, J=13.6 Hz, 1H), 4.36-4.19 (m, 2H), 3.54-3.35 (m, 2H), 3.28-3.12 (m, 4H), 3.01 (dt, J=5.6, 9.2 Hz, 1H), 2.54-2.40 (m, 1H), 2.39-2.09 (m, 4H), 2.05-1.84 (m, 4H), 1.78-1.65 (m, 1H), 1.55-1.40 (m, 1H), 1.14 (d, J=6.4 Hz, 3H), 0.87-0.72 (m, 3H); LCMS (ESI, M+1): m/z=608.4.

Example 189

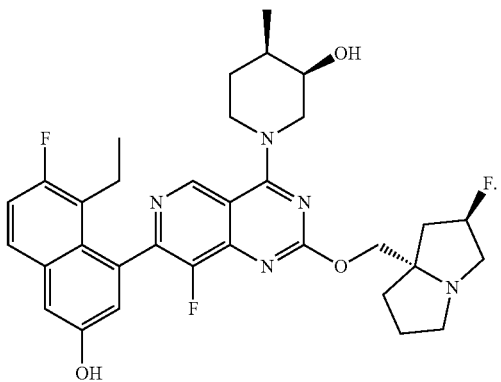 [SMILES: CCc1c(F)ccc2cc(O)cc(-c3ncc4c(N5CC[C@@H](C)[C@@H](O)C5)nc(OC[C@@]56CCCN5C[C@H](F)C6)nc4c3F)c12]

(3R,4R)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-4-methylpiperidin-3-ol

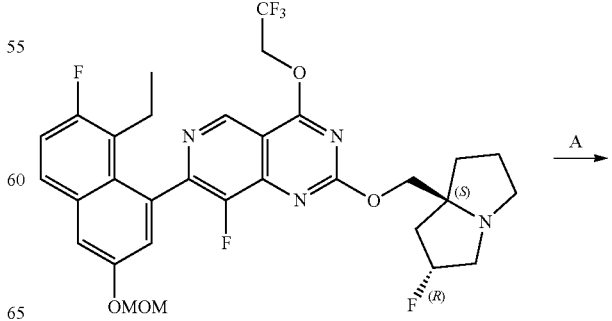

369

-continued

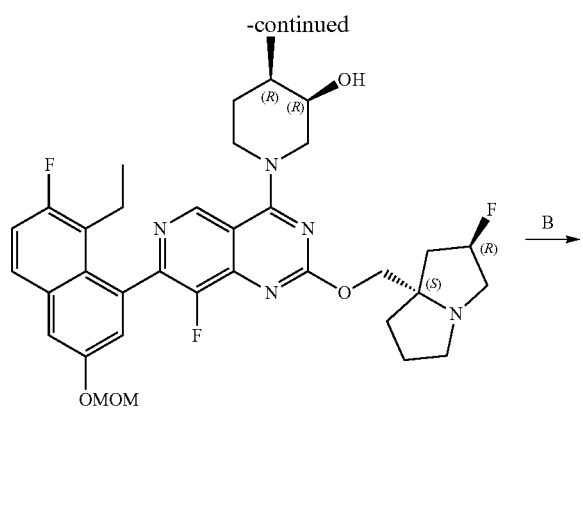

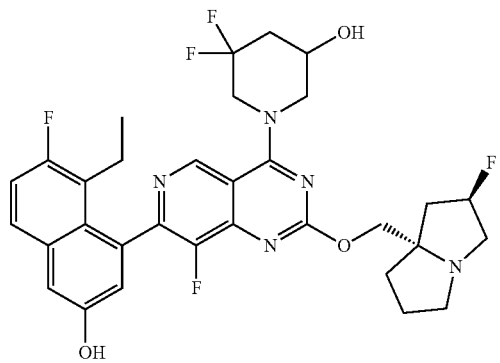 [SMILES: CCc1c(F)ccc2cc(O)cc(-c3ncc4c(N5CC(O)CC(F)(F)C5)nc(OC[C@@]56CCCN5C[C@H](F)C6)nc4c3F)c12]

The title compound was synthesized according to the procedure described for example 135. $^1$H NMR (400 MHz, methanol-d$_4$) δ=9.30 (dd, J=2.8, 9.2 Hz, 1H), 8.50 (s, 1H), 7.68 (dd, J=6.0, 9.2 Hz, 1H), 7.37-7.18 (m, 2H), 7.13-6.99 (m, 1H), 5.52-5.33 (m, 1H), 4.81-4.69 (m, 2H), 4.53-4.38 (m, 2H), 3.91 (br s, 1H), 3.67-3.45 (m, 4H), 3.35 (br d, J=3.6 Hz, 1H), 3.21 (dt, J=5.6, 10.0 Hz, 1H), 2.56-2.32 (m, 3H), 2.30-2.10 (m, 4H), 2.07-1.83 (m, 3H), 1.66 (br d, J=12.2 Hz, 1H), 1.07 (d, J=6.4 Hz, 3H), 0.85-0.75 (m, 3H); LCMS (ESI, M+1): m/z=608.4.

Example 190

370

1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-5,5-difluoropiperidin-3-ol

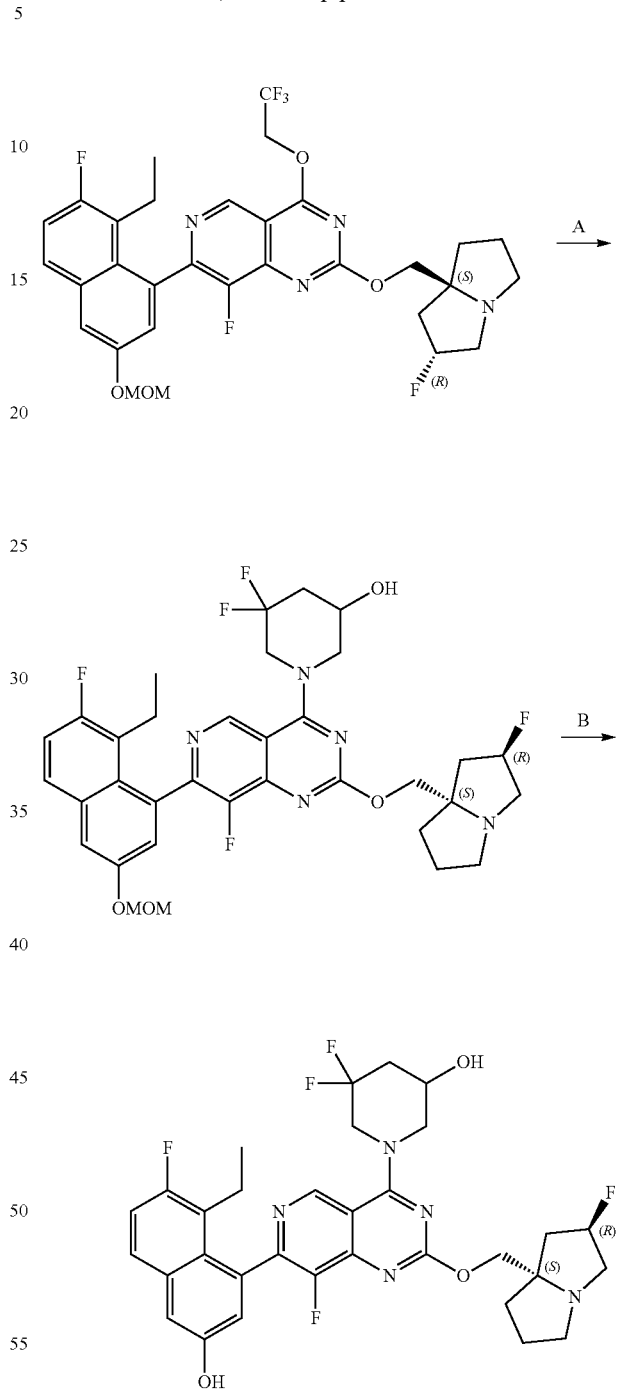

The title compound was synthesized according to the procedure described for example 135. $^1$H NMR (400 MHz, METHANOL-d$_4$): δ=9.26 (dd, J=1.2, 10.8 Hz, 1H), 7.68 (dd, J=6.0, 9.2 Hz, 1H), 7.31 (d, J=2.8 Hz, 1H), 7.25 (t, J=9.6 Hz, 1H), 7.07 (t, J=2.4 Hz, 1H), 5.40-5.21 (m, 1H), 4.46-4.32 (m, 3H), 4.31-4.13 (m, 3H), 3.78-3.59 (m, 1H), 3.28-3.13 (m, 3H), 3.01 (dt, J=5.6, 9.6 Hz, 1H), 2.63-2.38 (m, 2H), 2.33-2.10 (m, 5H), 2.05-1.89 (m, 3H), 0.80 (t, J=7.2 Hz, 3H); LCMS (ESI, M+1): m/z=630.2.

Example 191

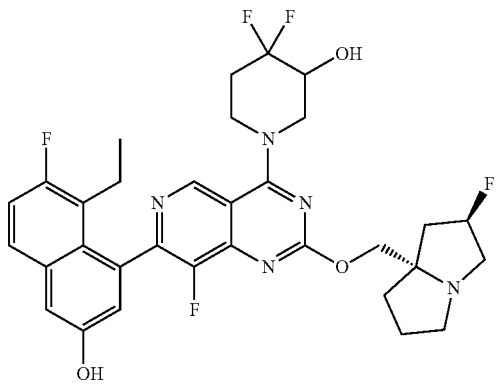 [SMILES: CCc1c(F)ccc2cc(O)cc(-c3ncc4c(N5CCC(F)(F)C(O)C5)nc(OC[C@@]56CCCN5C[C@H](F)C6)nc4c3F)c12]

1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-4,4-difluoropiperidin-3-ol The title compound was synthesized according to the procedure described for example 135. $^1$H NMR (400 MHz, methanol-d) 0.79 (t, J=7.2 Hz, 3H) 1.87-2.04 (m, 3H) 2.11-2.38 (m, 5H) 2.41-2.62 (m, 2H) 3.01 (m, 1H) 3.16-3.29 (m, 3H) 3.61-3.70 (m, 1H) 3.96-4.07 (m, 2H) 4.25-4.37 (m, 2H) 4.38-4.60 (m, 2H) 5.21-5.39 (m, 1H) 7.06 (dd, J=4.4, 2.4 Hz, 1H) 7.25 (t, J=9.2 Hz, 1H) 7.30 (d, J=2.8 Hz, 1H) 7.68 (dd, J=8.8, 5.6 Hz, 1H) 9.28 (dd, J=9.6, 2.0 Hz, 1H); $^{19}$F NMR (400 MHz, DMSO-d$_6$) δ−110.901, −121.183, −138.993, 173.712. LCMS (ESI, M+1): m/z=630.3.

Example 192

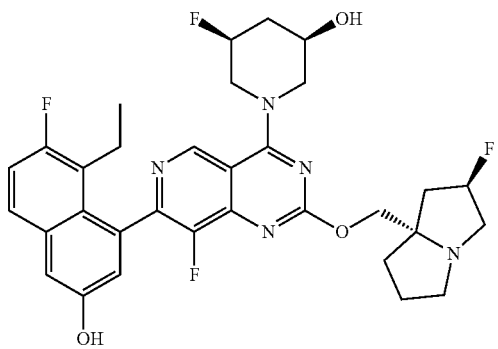 [SMILES: CCc1c(F)ccc2cc(O)cc(-c3ncc4c(N5C[C@H](O)C[C@H](F)C5)nc(OC[C@@]56CCCN5C[C@H](F)C6)nc4c3F)c12]

(3R,5S)-1-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-5-fluoropiperidin-3-ol

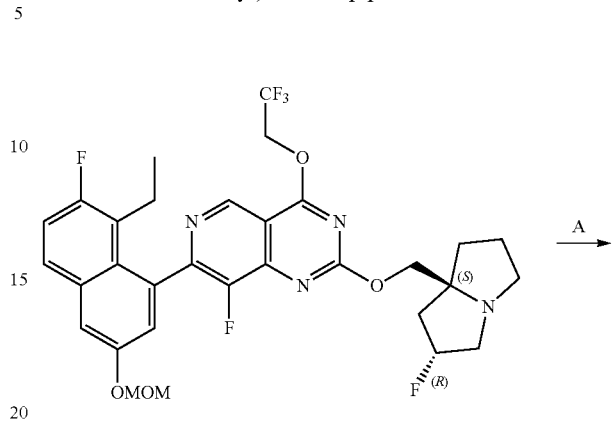

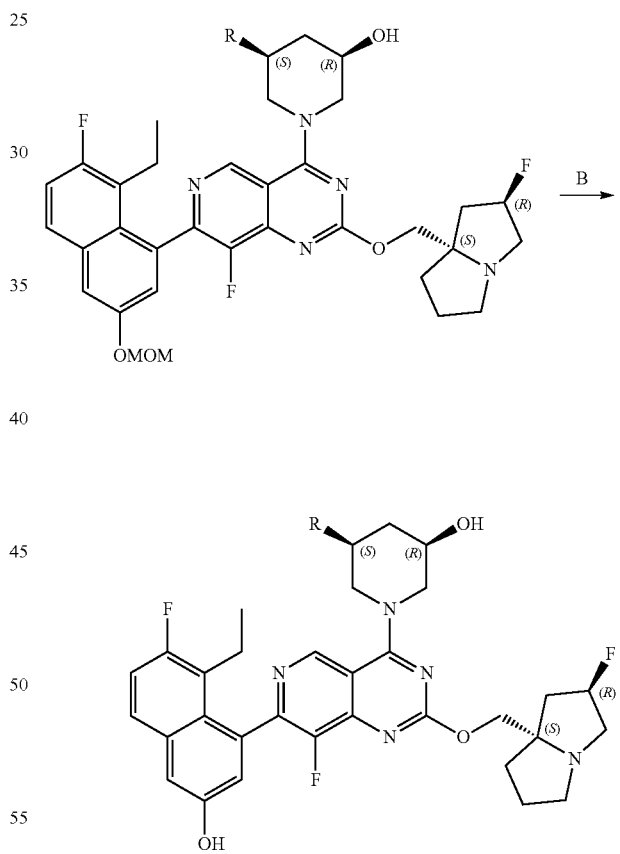

The title compound was synthesized according to the procedure described for example 135. $^1$H NMR (400 MHz, METHANOL-d$_4$) 6-9.36 (d, J=5.8 Hz, 1H), 8.48 (br s, 1H), 7.68 (dd, J=5.8, 9.2 Hz, 1H), 7.35-7.19 (m, 1H), 7.06 (t, J=2.8 Hz, 1H), 5.55-5.32 (m, 1H), 5.08-4.91 (m, 1H), 4.58-4.43 (m, 2H), 4.43-4.28 (m, 1H), 4.25-3.95 (m, 4H), 3.72-3.46 (m, 3H), 3.24 (dt, J=5.6, 10.0 Hz, 1H'), 2.60-2.24 (m, 5H), 2.23-1.95 (m, 5H), 0.80 (dt, J=2.0, 7.2 Hz, 3H); LCMS (ESI, M+1): m/z=612.3.

Example 193

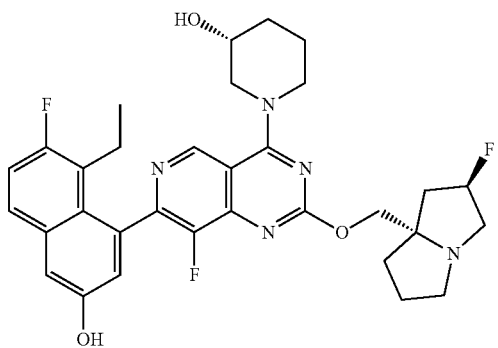 [SMILES: CCc1c(F)ccc2cc(O)cc(-c3ncc4c(N5CCC[C@@H](O)C5)nc(OC[C@@]56CCCN5C[C@H](F)C6)nc4c3F)c12]

(R)-1-(7-(8-ethyl-7-fluoro-3-hydroxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-ol The title compound was synthesized according to the procedure described for example 135. $^1$H NMR (400 MHz, methanol-$d_4$)=9.18-9.08 (m, 1H), 7.73-7.61 (m, 1H), 7.32-7.28 (m, 1H), 7.27-7.19 (m, 1H), 7.08-7.03 (m, 1H), 5.39-5.20 (m, 1H), 4.36-4.29 (m, 1H), 4.28-4.19 (m, 2H), 4.08-3.91 (m, 3H), 3.87-3.74 (m, 1H), 3.29-3.12 (m, 3H), 3.06-2.95 (m, 1H), 2.56-2.41 (m, 1H), 2.40-1.84 (m, 10H), 1.82-1.67 (m, 2H), 0.86-0.74 (m, 3H). LCMS (ESI, M+1): m/z=594.2.

Example 194

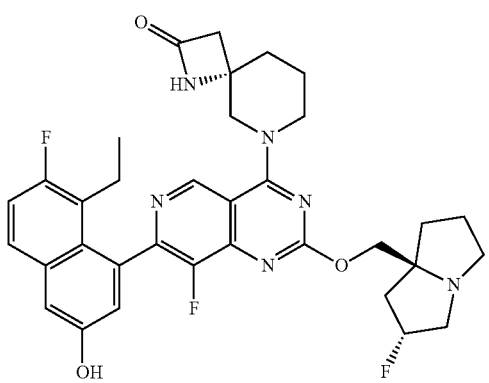 [SMILES: CCc1c(F)ccc2cc(O)cc(-c3ncc4c(N5CCC[C@]6(CC(=O)N6)C5)nc(OC[C@@]56CCCN5C[C@H](F)C6)nc4c3F)c12]

(S)-6-(7-(8-ethyl-7-fluoro-3-hydroxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1,6-diazaspiro[3.5]nonan-2-one

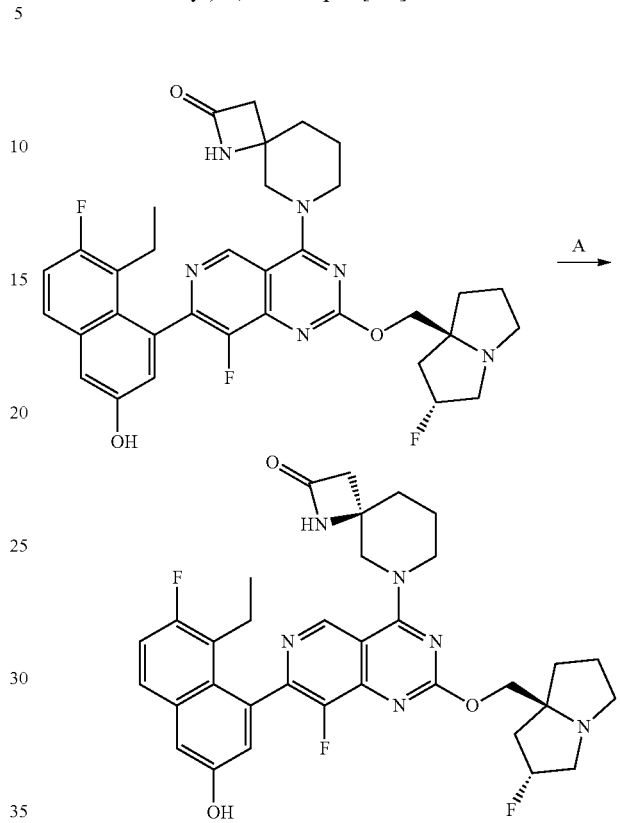

6-(7-(8-ethyl-7-fluoro-3-hydroxy)naphthalen-1-yl)-8-fluoro-2-(((2R,7aS)-2-fluorotetrahydro-1H-pyrrolizin-7a (5H)-yl methoxy)pyrido[4,3-d]pyrimidin-4-yl)-1,6-diazaspiro[3.5]nonan-2-one: The title compound was synthesized according to the procedure described for example 134. LCMS (ESI, M+1): m/z=633.3.

Step A. (S)-6-(7-(8-ethyl-7-fluoro-3-hydroxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1, 6-diazaspiro[3.5]nonan-2-one: Stereoisomeric mixture 6-(7-(8-ethyl-7-fluoro-3-hydroxy)naphthalen-1-yl)-8-fluoro-2-(((2R,7aS)-2-fluorotetrahydro-1H-pyrrolizin-7a(5H)-yl) methoxy)pyrido[4,3-d]pyrimidin-4-yl)-1,6-diazaspiro[3.5] nonan-2-one (70 mg, 1.0 equiv.) was separated by SFC [column: Daicel Chiralpak as (250 mm×30 mm, 10 um); mobile phase: [CO$_2$/0.1% NH$_3$·H$_2$O in MeOH] 45%-45%; 25 min]. The desired fractions of product (2$^{nd}$ eluting peak) were collected and concentrated in vacuum to give an impure product. The impure product was purified by prep-HPLC [column: Unisil 3-100 C18 Ultra 150×50 mm×3 um; mobile phase: [water (0.225% formic acid)/ACN]; B %: 15%-45%, 10 min]. The desired fractions were collected and concentrated in vacuum to remove ACN. The aqueous layer was lyophilized to afford title compound (8.09 mg, 11% yield, 0.1 formic acid salt) as a white solid; LCMS (ESI, M+1): m/z=633.4; SFC: 97.2% ee Chiralpak AS-3 50×4.6 mm I.D., 3 um column A: 60% MeOH+40% ACN (w/0.05% DEA), B: CO$_2$, 3 mL/min, 220 nm, t$_R$: 2.070 min; $^1$H NMR (400 MHz, MeOD): δ 9.09 (s, 1H), 7.68 (dd, J=5.6, 8.8 Hz, 1H), 7.31 (d, J=2.4 Hz, 1H), 7.25 (t, J=9.6 Hz, 1H), 7.08-7.04 (m, 1H), 5.44-5.23 (m, 1H), 4.47-4.23 (m, 4H), 3.99 (t, J=11.6 Hz, 1H), 3.90-3.68 (m, 1H), 3.42-3.35 (m, 1H), 3.28-3.20 (m, 1H), 3.16-3.00 (m, 1H), 2.95-2.84 (m, 1H), 2.80-2.71 (m, 1H), 2.56-2.24 (m, 3H), 2.24-1.86 (m, 10H), 0.79 (t, J=7.6 Hz, 3H).

Example 195

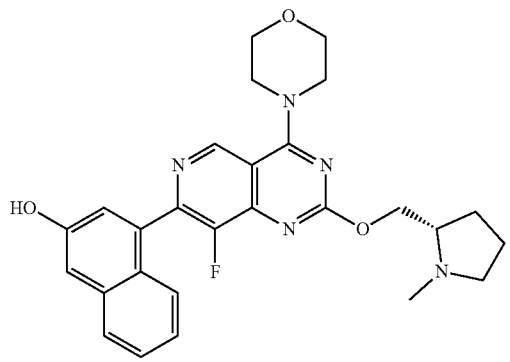 [SMILES: CN1CCC[C@H]1COc1nc(N2CCOCC2)c2cnc(-c3cc(O)cc4ccccc34)c(F)c2n1]

(S)-4-(8-fluoro-2-((1-methylpyrrolidin-2-yl)methoxy)-4-morpholinopyrido[4,3-d]pyrimidin-7-yl)naphthalen-2-ol

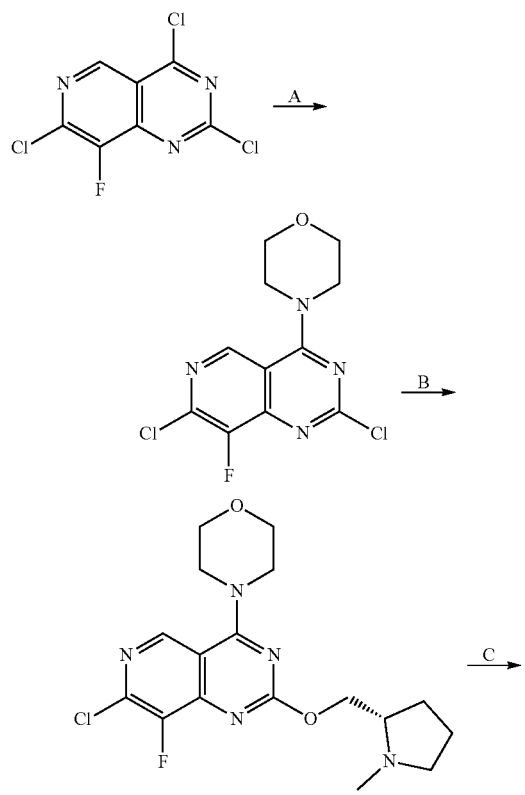

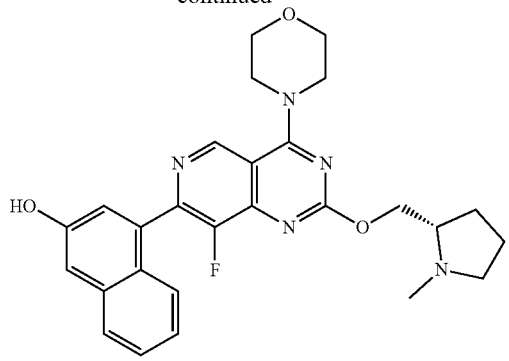

Step A. 4-(2,7-dichloro-8-fluoro-pyrido[4,3-d]pyrimidin-4-yl)morpholine: To a solution of 2,4,7-trichloro-8-fluoro-pyrido[4,3-d]pyrimidine (600 mg, 2.38 mmol, 1.0 equiv.) in DCM (10.0 mL) were added DIEA (921 mg, 7.13 mmol, 1.24 mL, 3.0 equiv.) and 4 Å molecular sieves (200 mg). The mixture was stirred at 25° C. for 10 minutes. Then a solution of morpholine (103 mg, 1.19 mmol, 104 µL, 0.5 equiv.) in DCM (2.0 mL) was added dropwise at −40° C. The mixture was stirred at −40° C. for 0.5 h. After completion, the reaction mixture was filtered and the filtrate was concentrated. The residue was purified by silica gel chromatography (petroleum ether/ethyl acetate 30:1 to 1:1) to afford the title compound (310 mg, 84% yield) as a yellow solid; $^1$H NMR (400 MHz, CDCl$_3$): δ 8.87 (s, 1H), 4.13-4.07 (m, 4H), 3.92-3.86 (m, 4H); LCMS [ESI, M+1]: 303.1.

Step B. 4-[7-chloro-8-fluoro-2-[[(2S)-1-methylpyrrolidin-2-yl]methoxy]pyrido[4,3-d]pyrimidin-4-yl]morpholine: To a solution of 4-(2,7-dichloro-8-fluoro-pyrido[4,3-d]pyrimidin-4-yl)morpholine (530 mg, 1.75 mmol, 1.0 equiv.) in dioxane (10.0 mL) were added DIEA (678 mg, 5.25 mmol, 914 µL, 3.0 equiv.) and [(2S)-1-methylpyrrolidin-2-yl]methanol (604 mg, 5.25 mmol, 623 µL, 3.0 equiv.). The mixture was stirred at 60° C. for 1.5 hrs. After completion, water (10.0 mL) was added and the mixture was extracted with ethyl acetate (3×10.0 mL). The combined the organic layers were dried over Na$_2$SO$_4$ and concentrated. The residue was purified by reversed phase flash chromatography (mobile phase: [water (0.1% formic acid)/acetonitrile]) to afford the title compound (480 mg, 67% yield) as a yellow solid; $^1$H NMR (400 MHz, CDCl$_3$): δ 8.73 (s, 1H), 4.52 (dd, J=4.8, 10.8 Hz, 1H), 4.33 (dd, J=6.8, 10.8 Hz, 1H), 4.01-3.95 (m, 4H), 3.88-3.81 (m, 4H), 3.13-3.06 (m, 1H), 2.74-2.64 (m, 1H), 2.48 (s, 3H), 2.31-2.25 (m, 1H), 2.09-2.03 (m, 1H), 1.88-1.71 (m, 3H); LCMS [ESI, M+1]: 382.1.

Step C. 4-[8-fluoro-2-[[(2S)-1-methylpyrrolidin-2-yl]methoxy]-4-morpholino-pyrido[4,3-d]pyrimidin-7-yl]naphthalen-2-ol: To a solution of 4-[7-chloro-8-fluoro-2-[[(2S)-1-methylpyrrolidin-2-yl]methoxy]pyrido[4,3-d]pyrimidin-4-yl]morpholine (150 mg, 393 µmol, 1.0 equiv.) and 4-(4,4,5,5-tetramethyl-1,3,2-dioxaborolan-2-yl)naphthalen-2-ol (127 mg, 471 µmol, 1.2 equiv.) in THF (3.0 mL) was added CataCXium A Pd G3 (28.6 mg, 39.3 µmol, 0.1 equiv.) and K$_3$PO$_4$ (1.5 M in water, 786 µL, 3.0 equiv.). The mixture was stirred at 60° C. for 2 hrs. After reaction completion, water (5.0 mL) was added and the mixture was extracted with ethyl acetate (3×5.0 mL). Combined organic layers were dried over anhydrous Na$_2$SO$_4$ and concentrated. The residue was purified by reversed phase flash chromatography (mobile phase: [water (0.1% formic acid)/acetonitrile]). The desired fractions were collected, neutralized with solid NaHCO$_3$, and concentrated in vacuum to remove ACN. The aqueous phase was extracted with ethyl acetate (2×10.0 mL). The combined organic phase was dried over anhydrous Na₂SO₄, filtered and concentrated in vacuum. Then the residue was purified by prep-HPLC (column: Phenomenex Gemini-NX C18 75×30 mm×3 μm, mobile phase: [water (10 mM NH₄HCO₃)/ACN]; B %: 22%-52%, 8 min) to afford the title compound (51.1 mg, 26% yield) as a yellow solid; ¹H NMR (400 MHz, DMSO-d⁶): δ 10.21-10.00 (m, 1H), 9.22 (s, 1H), 7.80 (d, J=8.4 Hz, 1H), 7.54 (br d, J=8.4 Hz, 1H), 7.47-7.40 (m, 1H), 7.29 (d, J=2.0 Hz, 1H), 7.26-7.21 (m, 2H), 4.41 (dd, J=4.4, 10.8 Hz, 1H), 4.23 (dd, J=6.4, 10.8 Hz, 1H), 4.05-3.97 (m, 4H), 3.84-3.75 (m, 4H), 2.99-2.90 (m, 1H), 2.64-2.54 (m, 1H), 2.35 (s, 3H), 2.17 (q, J=8.8 Hz, 1H), 2.02-1.88 (m, 1H), 1.74-1.57 (m, 3H); HRMS (ESI+) calcd for $C_{27}H_{29}FN_5O_3$*(M+H*): 490.2249, found 490.2235.

Example 196

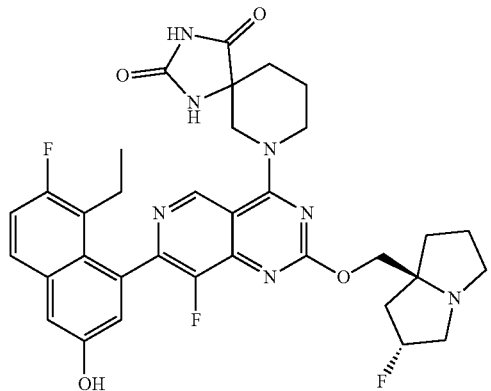 [SMILES: CCc1c(F)ccc2cc(O)cc(-c3ncc4c(N5CCCC6(C5)NC(=O)NC6=O)nc(OC[C@@]56CCCN5C[C@H](F)C6)nc4c3F)c12]

7-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decane-2,4-dione The title compound was synthesized according to the procedure described for example 134. ¹H NMR (400 MHz, CD3OD) δ (ppm)=9.18-9.04 (m, 1H), 7.67 (dd, J=5.6, 8.8 Hz, 1H), 7.30 (d, J=2.4 Hz, 1H), 7.24 (t, J=9.6 Hz, 1H), 7.06 (d, J=2.8 Hz, 1H), 5.40-5.15 (m, 1H), 4.69-4.57 (m, 1H), 4.55-4.39 (m, 1H), 4.35-4.17 (m, 2H), 3.88-3.63 (m, 2H), 3.29-3.12 (m, 3H), 3.06-2.94 (m, 1H), 2.56-2.30 (m, 2H), 2.29-2.07 (m, 5H), 2.05-1.87 (m, 5H), 0.79 (q, J=7.8 Hz, 3H). LCMS (ESI, M+1): 662.4.

Example 197

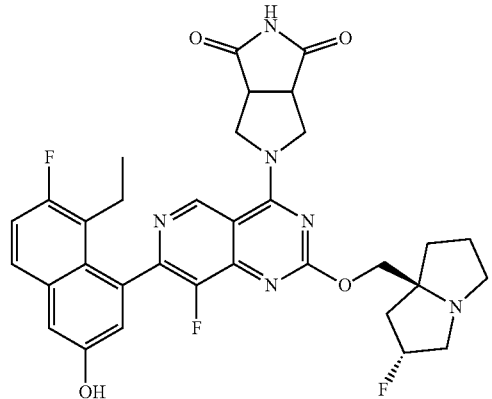 [SMILES: CCc1c(F)ccc2cc(O)cc(-c3ncc4c(N5CC6C(=O)NC(=O)C6C5)nc(OC[C@@]56CCCN5C[C@H](F)C6)nc4c3F)c12]

5-(7-(8-ethyl-7-fluoro-3-hydroxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)tetrahydropyrrolo[3,4-c]pyrrole-1,3(2H, 3aH)-dione The title compound was synthesized according to the procedure described for example 135. ¹H NMR (400 MHz, MeOD) δ 9.29 (s, 1H), 7.68 (dd, J=6.0, 9.2 Hz, 1H), 7.31 (d, J=2.4 Hz, 1H), 7.25 (t, J=9.2 Hz, 1H), 7.06 (d, J=2.8 Hz, 1H), 5.57-5.37 (m, 1H), 4.68-4.60 (m, 2H), 4.59-4.48 (m, 2H), 4.40-4.30 (m, 2H), 3.80-3.55 (m, 5H), 2.67-1.97 (m, 9H), 0.78 (br t, J=7.2 Hz, 3H). LCMS (ESI, M+1): m/z=633.3.

Example 198

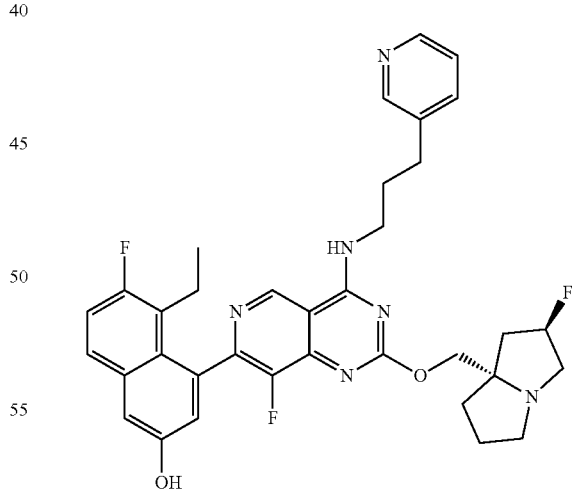

5-ethyl-6-fluoro-4-(8-fluoro-2-(((2R,7aS)-2-fluorohexahydro-1H-pyrrolizin-7a-yl)methoxy)-4-((3-(pyridin-3-yl)propyl)amino)pyrido[4,3-d]pyrimidin-7-yl)naphthalen-2-ol The title compound was synthesized according to the procedure described for example 134. ¹H NMR (400 MHz, CD3OD-d₄) δ 9.10 (s, 1H), 8.46 (d, J=2.0 Hz, 1H), 8.36 (dd, J=1.6, 5.2 Hz, 1H), 7.79 (br d, J=8.0 Hz, 1H), 7.66 (dd, J=6.0, 9.2 Hz, 1H), 7.37 (dd, J=4.8, 8.0 Hz, 1H), 7.28 (d, J=2.8 Hz, 1H), 7.25 (s, 1H), 7.03 (d, J=2.8 Hz, 1H), 5.45-5.18 (m, 1H), 4.35-4.19 (m, 2H), 3.76 (br t, J=7.2 Hz, 2H), 3.28-3.12 (m, 3H), 3.01 (dt, J=5.6, 9.4 Hz, 1H), 2.85 (t, J=7.6 Hz, 2H), 2.52-2.38 (m, 1H), 2.38-2.19 (m, 2H), 2.19-2.07 (m, 4H), 2.03-1.82 (m, 3H), 0.79 (t, J=7.2 Hz, 3H); LCMS (ESI, M+1): m/z=629.3.

Example 199

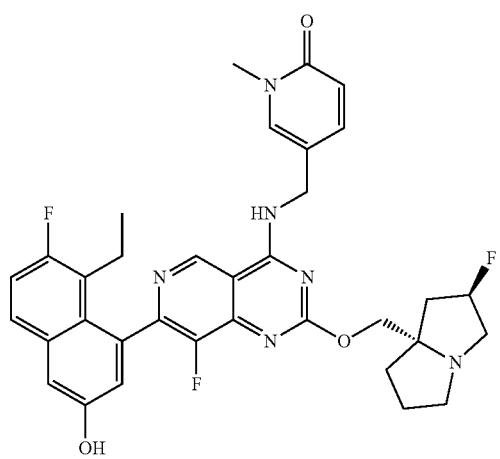 [SMILES: CCc1c(F)ccc2cc(O)cc(-c3ncc4c(NCc5ccc(=O)n(C)c5)nc(OC[C@@]56CCCN5C[C@H](F)C6)nc4c3F)c12]

5-(((7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)-1-methylpyridin-2 (1H)-one The title compound was synthesized according to the procedure described for example 135. ¹H NMR (400 MHz, CD₃OD-d₄) δ 9.15 (s, 1H), 7.81 (s, 1H), 7.74-7.61 (m, 2H), 7.34-7.17 (m, 2H), 7.03 (d, J=2.4 Hz, 1H), 6.57 (d, J=9.2 Hz, 1H), 5.41-5.17 (m, 1H), 4.67 (s, 2H), 4.37-4.19 (m, 2H), 3.59 (s, 3H), 3.28-3.15 (m, 3H), 3.01 (dt, J=6.0, 9.2 Hz, 1H), 2.53-2.39 (m, 1H), 2.37-2.18 (m, 2H), 2.18-2.07 (m, 2H), 2.04-1.94 (m, 2H), 1.93-1.81 (m, 1H), 0.78 (t, J=7.2 Hz, 3H); LCMS (ESI, M+1): m/z=631.3.

Example 200

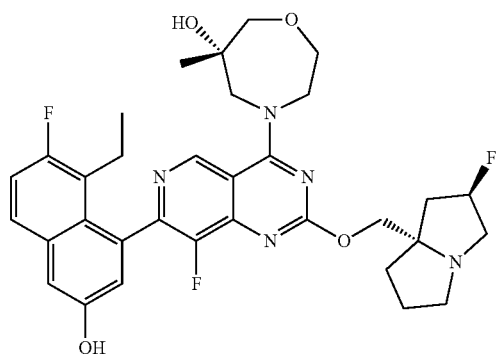 [SMILES: CCc1c(F)ccc2cc(O)cc(-c3ncc4c(N5CCOC[C@@](C)(O)C5)nc(OC[C@@]56CCCN5C[C@H](F)C6)nc4c3F)c12]

(S)-4-(7-(8-ethyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol

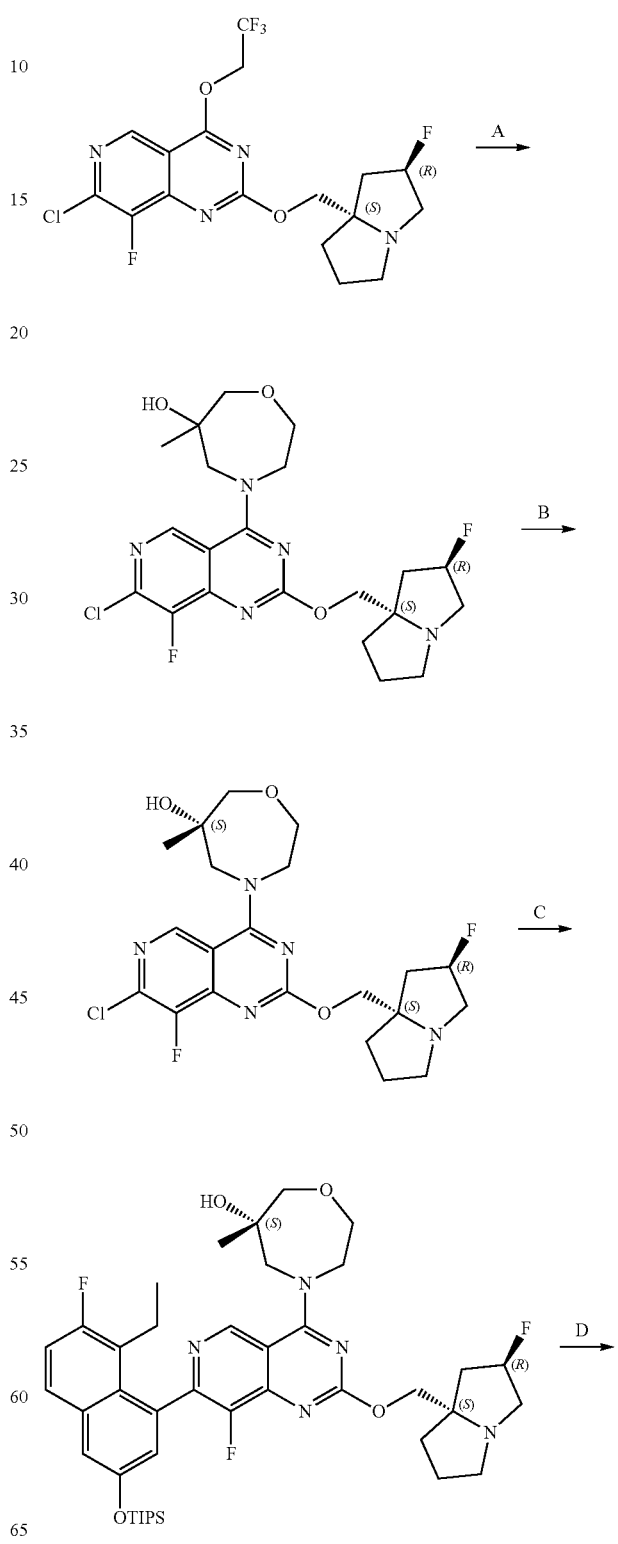

-continued

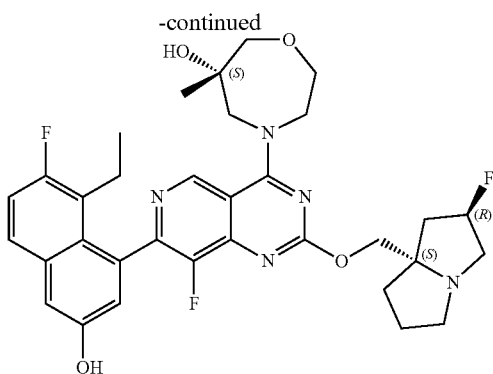

Step A. 4-(7-chloro-8-fluoro-2-((((2R,7aS)-2-fluorohexahydro-1H-pyrrolizin-7a-yl) methoxy)pyrido[4,3-d]pyrimidin-4-yl)-6-methyl-1,4-oxazepan-6-ol: A mixture of 6-methyl-1,4-oxazepan-6-ol (2.66 g, 1.0 equiv.), 4 Å molecular sieves (850 mg) and DIEA (10.5 g, 4.0 equiv.) in DMF (90 mL) was stirred at 15° C. for 0.5 hour. Then 7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (8.90 g, 1.0 equiv.) was added into the above mixture and the mixture was stirred at 40° C. for 4 hours. The mixture was filtered. The filtrate was diluted with ethyl acetate (120 mL) and water (200 mL), extracted with ethyl acetate (2×50 mL) and dichloromethane/methanol=10/1 (2×50 mL). The combined organic layers were dried over $Na_2SO_4$, concentrated and purified by reversed phase flash chromatography (mobile phase: [water (0.1% formic acid)/acetonitrile]) twice. The desired fractions were collected, neutralized with solid $NaHCO_3$, concentrated in vacuum to remove acetonitrile, and extracted with ethyl acetate (3×500 mL). The combined organic phase was dried over anhydrous $Na_2SO_4$ and concentrated in vacuum to afford the title compound (6.63 g, 68% yield) as a yellow solid; $^1H$ NMR (400 MHz, methanol-$d_4$) δ=9.34 (d, J=2.0 Hz, 1H), 5.38-5.21 (m, 1H), 4.52 (td, J=5.2, 14.4 Hz, 1H), 4.43 (dd, J=3.6, 14.8 Hz, 1H), 4.33-4.19 (m, 2H), 4.17-4.09 (m, 1H), 3.98 (ddd, J=3.6, 6.0, 12.4 Hz, 1H), 3.91 (d, J=15.2 Hz, 1H), 3.86-3.78 (m, 1H), 3.71-3.60 (m, 2H), 3.28-3.16 (m, 3H), 3.05-2.97 (m, 1H), 2.36-2.23 (m, 1H), 2.23-2.17 (m, 1H), 2.16-2.08 (m, 1H), 2.03-1.94 (m, 2H), 1.93-1.83 (m, 1H), 1.25 (s, 3H); LCMS (ESI, M+1): m/z=470.1.

Step B. (S)-4-(7-chloro-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol: 4-(7-chloro-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol (7.38 g) was separated by SFC [column: DAICEL CHIRALPAK IG (250 mm×50 mm, 10 um); mobile phase: [0.1% $NH_3 \times H_2O$ in $EtOH/CO2$]; 45%-45%, 8.7; 300 min]. The first peak was collected and concentrated in vacuum to afford the title compound (3.24 g, 43% yield) as a white solid; $^1H$ NMR (400 MHz, methanol-$d_4$) δ=9.33 (s, 1H), 5.39-5.21 (m, 1H), 4.52 (td, J=5.2, 14.4 Hz, 1H), 4.43 (d, J=14.8 Hz, 1H), 4.31-4.21 (m, 2H), 4.17-4.09 (m, 1H), 3.98 (ddd, J=4.0, 6.4, 12.8 Hz, 1H), 3.90 (d, J=14.8 Hz, 1H), 3.82 (ddd, J=4.0, 7.2, 14.4 Hz, 1H), 3.65 (q, J=12.8 Hz, 2H), 3.29-3.15 (m, 3H), 3.05-2.95 (m, 1H), 2.36-2.23 (m, 1H), 2.23-2.17 (m, 1H), 2.16-2.07 (m, 1H), 2.03-1.93 (m, 2H), 1.93-1.82 (m, 1H), 1.25 (s, 3H); SFC: >99% ee, Chiralpak IG-3 50×4.6 mm I.D., 3 μm column; A: 60% EtOH+40% ACN (w/0.05% DEA), B: $CO_2$, 3 mL/min, 220 nm, $t_R$: 1.072 min; LCMS (ESI, M+1): m/z=470.1.

Step C. (S)-4-(7-(8-ethyl-7-fluoro-3-((triisopropylsilyl)oxy)naphthalen-yl)-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol: To a mixture of (S)-4-(7-chloro-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol (1.47 g, 1.0 equiv.), ((5-ethyl-6-fluoro-4-(4,4,5,5-tetramethyl-1,3,2-dioxaborolan-2-yl)naphthalen-2-yl)oxy)triisopropylsilane (1.92 g, 1.3 equiv.) and $K_3PO_4$ (1.5 M in water, 6.26 mL, 3.0 equiv.) in methoxycyclopentane (19 mL) was added CataCXium A Pd G3 (228 mg, 0.1 equiv.) under $N_2$. The reaction was degassed and stirred at 90° C. for 3 hours under $N_2$. The mixture was diluted with water (20 mL) and extracted with ethyl acetate (20 mL). The organic layer was concentrated in vacuum and purified by reversed phase flash chromatography (mobile phase: [water (0.1% formic acid)/acetonitrile]). The desired fractions were collected and neutralized with $NaHCO_3$ solid, concentrated in vacuum to remove acetonitrile, and extracted with ethyl acetate (2×80 mL). The combined organic layer was washed with brine (60 mL). The organic phase was dried over anhydrous $Na_2SO_4$ and concentrated in vacuum to afford the title compound (2.08 g, 77% yield) as a white solid; LCMS (ESI, M+1): m/z=780.5.

Step D. (S)-4-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol: A mixture of (S)-4-(7-(8-ethyl-7-fluoro-3-((triisopropylsilyl) oxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol (1.97 g, 1.0 equiv.) and CsF (5.75 g, 15 equiv.) in DMF (10 mL) was stirred at 15° C. for 1 hour. After completion, the mixture was filtered and the filtrate was purified by reversed phase flash chromatography (mobile phase: [water (0.1% formic acid)/acetonitrile]). The desired fractions were collected and lyophilized to afford the title compound (1.28 g, 75% yield, formic acid salt) as a white solid; $^1H$ NMR (400 MHz, methanol-$d_4$) 5-9.58 (s, 1H), 7.67 (dd, J=5.6, 9.2 Hz, 1H), 7.32-7.29 (m, 1H), 7.25 (t, J=9.2 Hz, 1H), 7.06 (dd, J=2.4, 18.4 Hz, 1H), 5.46 (br d, J=52.8 Hz, 1H), 4.62-4.50 (m, 4H), 4.24-4.14 (m, 1H), 4.06-3.82 (m, 3H), 3.80-3.54 (m, 5H), 3.30-3.23 (m, 1H), 2.63-2.27 (m, 4H), 2.26-2.01 (m, 4H), 1.27 (s, 3H), 0.80 (q, J=8.0 Hz, 3H); $^{19}F$ NMR (376 MHz, methanol-$d_4$) δ=−121.041, −139.083, −173.810; SFC: >99% ee, Chiralpak IG-3 50×4.6 mm I.D., 3 μm column, A: 60% IPA+40% ACN (w/0.05% DEA), B: $CO_2$, 3 mL/min, 220 nm, $t_R$: 2.337 min; LCMS (ESI, M+1): m/z=624.3.

Example 201

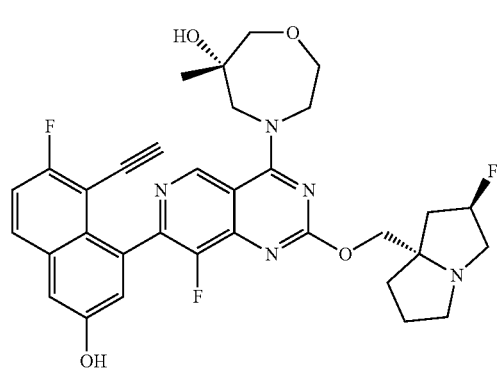 [SMILES: C#Cc1c(F)ccc2cc(O)cc(-c3ncc4c(N5CCOC[C@@](C)(O)C5)nc(OC[C@@]56CCCN5C[C@H](F)C6)nc4c3F)c12]

383

(S)-4-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol

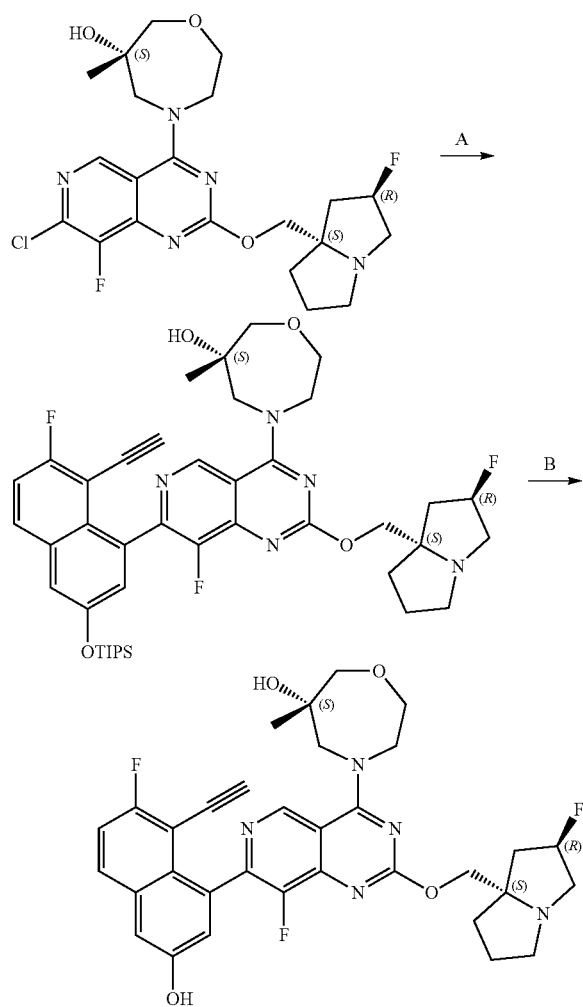

Step A. (S)-4-(8-fluoro-7-(7-fluoro-8-((triisopropylsilyl)ethynyl)-3-((triisopropylsilyloxy)naphthalen-1-yl)-2-(((2R,7aS)-2-fluorohexahydro-1H-pyrrolizin-7a-yl) methoxy)pyrido[4,3-d]pyrimidin-4-yl)-6-methyl-1,4-oxazepan-6-ol: To a mixture of (S)-4-(7-chloro-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol (1.47 g, 1.0 equiv.), ((6-fluoro-4-(4,4,5,5-tetramethyl-1,3,2-dioxaborolan-2-yl)-5-((triisopropylsilyl)ethynyl)naphthalen-2-yl)oxy)triisopropylsilane (2.54 g, 1.3 equiv.) and $K_3PO_4$ (1.5 M in water, 6.26 mL, 3.0 equiv.) in THF (19 mL) was added CataCXium A Pd G3 (228 mg, 0.1 equiv.) under $N_2$. The reaction was de-gassed and stirred at 60° C. for 3 hours under $N_2$. The mixture was diluted with water (20 mL), extracted with ethyl acetate (20 mL), concentrated in vacuum, and purified by reversed phase flash chromatography (mobile phase: [water (0.1% formic acid)/acetonitrile]). The desired fractions were collected and concentrated in vacuum to afford the title compound (2.12 g, 70% yield) as a yellow solid; LCMS (ESI, M+1): m/z=932.6.

384

Step B. (S)-4-(7-(8-ethynyl-7-fluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol: A mixture of (S)-4-(8-fluoro-7-(7-fluoro-8-((triisopropylsilyl) ethynyl)-3-((triisopropylsilyl)oxy)naphthalen-1-yl)-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol (1.87 g, 1.0 equiv.) and CsF (4.57 g, 15 equiv.) in DMF (10 mL) was stirred at 15° C. for 7 hours. The mixture was filtered and the filtrate was purified by reversed phase flash chromatography (mobile phase: [water (0.1% formic acid)/acetonitrile]). The desired fractions were collected and lyophilized to afford the title compound (1.19 g, 89% yield, formic acid salt) as a yellow solid; $^1$H NMR (400 MHz, methanol-$d_4$) δ-9.56-9.43 (m, 1H), 7.86 (ddd, J=1.6, 5.6, 8.8 Hz, 1H), 7.37-7.29 (m, 2H), 7.23 (dd, J=2.4, 9.6 Hz, 1H), 5.56-5.39 (m, 1H), 4.69-4.51 (m, 4H), 4.29-4.17 (m, 1H), 4.05-3.85 (m, 3H), 3.81-3.59 (m, 5H), 3.45 (d, J=11.6 Hz, 1H), 3.30-3.25 (m, 1H), 2.64-2.40 (m, 2H), 2.36-2.28 (m, 1H), 2.26-2.16 (m, 2H), 2.13-2.01 (m, 1H), 1.28 (d, J=14.0 Hz, 3H); $^{19}$F NMR (376 MHz, methanol-$d_4$) δ=−111.749, −140.066, −173.900; SFC: >99% ee, Chiralpak IE-3 50×4.6 mm I.D., 3 um; A: heptane (0.05% DEA); B: EtOH (0.05% DEA); Gradient: 25% B in A; 1 mL/min, 254 nm, $t_R$: 4.443 min; LCMS (ESI, M+1): m/z=620.1.

Example 202

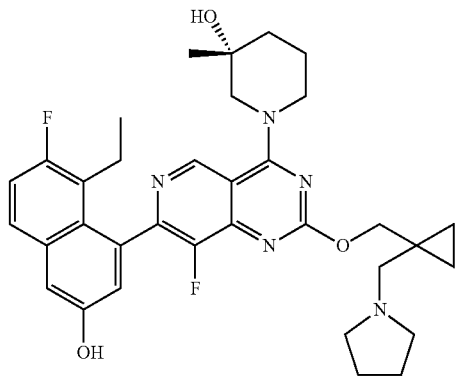 [SMILES: CCc1c(F)ccc2cc(O)cc(-c3ncc4c(N5CCC[C@@](C)(O)C5)nc(OCC5(CN6CCCC6)CC5)nc4c3F)c12]

(3R)-1-[7-(8-ethyl-7-fluoro-3-hydroxy-1-naphthyl)-8-fluoro-2-[[1-(pyrrolidin-1-ylmethyl)cyclopropyl]methoxy]pyrido[4,3-d]pyrimidin-4-yl]-3-methyl-piperidin-3-ol

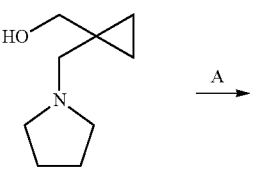

385
-continued

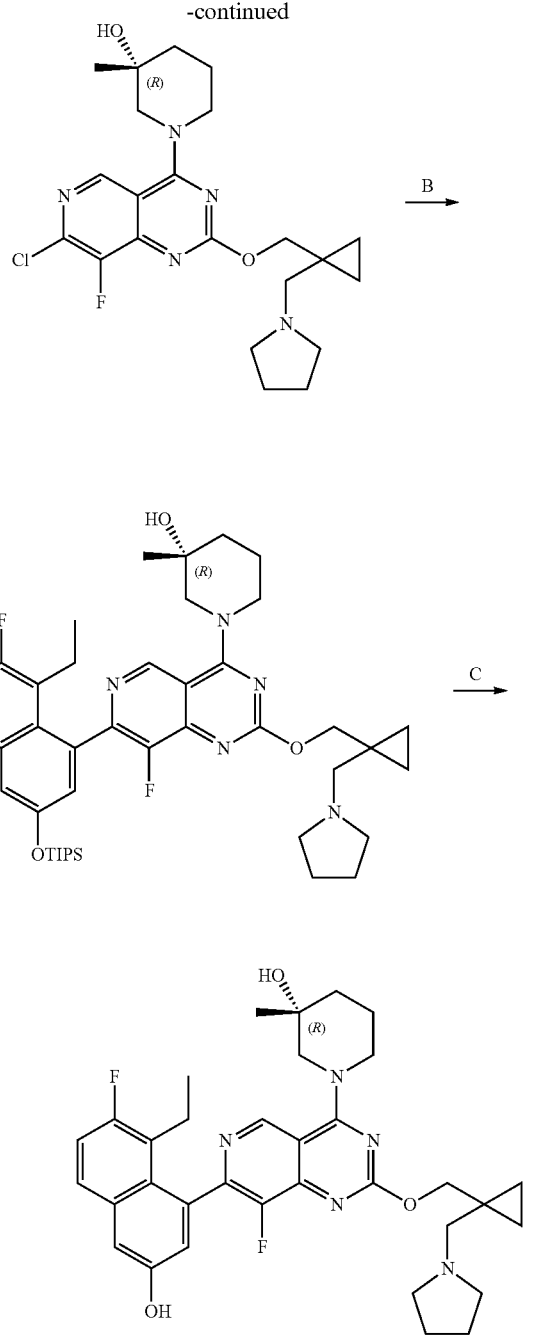

Step A. (3R)-[7-chloro-8-fluoro-2-[[1-(pyrrolidin-1-ylmethyl)cyclopropyl]methoxy]pyrido[4,3-d]pyrimidin-4-yl]-3-methyl-piperidin-3-ol: A mixture of (R)-1-(2,7-dichloro-8-fluoropyrido[4,3-d]pyrimidin-4-yl)-3-methylpiperidin-3-ol (150 mg, 1 equiv.), [1-(pyrrolidin-1-ylmethyl)cyclopropyl]methanol (141 mg, 2.0 equiv.), DIPEA (178 mg, 3 equiv.) and 4 Å molecular sieves (50 mg) in dioxane (1.5 mL) was stirred at 95° C. for 12 hours under $N_2$ atmosphere. The reaction mixture was filtered. The filter cake was washed with DCM (20 mL). The filtrate was concentrated and purified by reversed phase flash chromatography [water (0.1% formic acid)/acetonitrile 7:3] to afford the title compound (130 mg, 62% yield) as a light yellow gum; LCMS (ESI, M+1): m/z=450.2.

386

Step B. (3R)-1-[7-(8-ethyl-7-fluoro-3-triisopropylsilyloxy-1-naphthyl]-8-fluoro-2-[[1-(pyrrolidin-1-ylmethyl)cyclopropyl]methoxy]pyrido[4,3-d]pyrimidin-4-yl]-3-methyl-piperidin-3-ol: A mixture of (3R)-1-[7-chloro-8-fluoro-2-[[1-(pyrrolidin-1-ylmethyl)cyclopropyl]methoxy]pyrido[4,3-d]pyrimidin-4-yl]-3-methyl-piperidin-3-ol (130 mg, 1 equiv.), ((5-ethyl-6-fluoro-4-(4,4,5,5-tetramethyl-1,3,2-dioxaborolan-2-yl)naphthalen-2-yl) oxy)triisopropylsilane (165 mg, 1.2 equiv.), CataCXium A (22 mg, 0.1 equiv.) and $K_3PO_4$ (1.5 M in water, 0.6 mL, 3.1 equiv.) in methoxycyclopentane (2.4 mL) was degassed and purged with $N_2$ for 3 times. The mixture was stirred at 90° C. for 2.5 hours. The reaction mixture was diluted with water (1 mL), extracted with ethyl acetate (3 mL×4), dried over anhydrous $Na_2SO_4$ and concentrated to afford the title compound (300 mg, crude) as a red gum; LCMS (ESI, M+1): m/z=760.5.

Step C. (3R)-1-[7-(8-ethyl-7-fluoro-3-hydroxy-1-naphthyl)-8-fluoro-2-[[1-(pyrrolidin-1-yl)methyl)cyclopropyl]methoxy]pyrido[4,3-d]pyrimidin-4-yl]-3-methyl-piperidin-3-ol: A mixture of (3R)-1-[7-(8-ethyl-7-fluoro-3-triisopropylsilyloxy-1-naphthyl)-8-fluoro-2-[[1-(pyrrolidin-1-ylmethyl)cyclopropyl]methoxy]pyrido[4,3-d]pyrimidin-4-yl]-3-methyl-piperidin-3-ol (300 mg, crude) and CsF (300 mg) in DMF (2.5 mL) was stirred at 25° C. for 13 hours. The reaction mixture was filtered. The filtrate was purified by reversed phase flash chromatography [water (0.1% formic acid)/acetonitrile 13:7] and prep-HPLC [column: water s Xbridge 150×25 mm×Sum; mobile phase: [water (10 mM $NH_4HCO_3$)/CAN]; B %: 33%-66%, 9 minutes] to give a crude product. The crude product was purified by prep-HPLC [column: Phenomenex Gemini-NX C18 75×30 mm×3 um; mobile phase: [water (0.225% formic acid)/ACN]; B %: 20%-50%, 7 minutes] to afford the title compound (60.7 mg, 33% yield over two steps, 0.58 formic acid salt) as a white solid; $^1$H NMR (400 MHz, methanol-$d_4$) δ=9.23 (d, J=3.2 Hz, 1H), 7.68 (dd, J=6.0, 9.2 Hz, 1H), 7.31 (d, J=2.4 Hz, 1H), 7.25 (t, J=9.6 Hz, 1H), 7.06 (s, 1H), 4.54 (br d, J=12.4 Hz, 1H), 4.48-4.42 (m, 2H), 4.29 (t, J=11.2 Hz, 1H), 3.61 (q, J=13.6 Hz, 1H), 3.45-3.43 (m, 1H), 3.17-3.08 (m, 6H), 2.45-2.42 (m, 1H), 2.19-2.17 (m, 2H), 1.98 (br s, 4H), 1.85-1.76 (m, 3H), 1.29 (d, J=9.2 Hz, 3H), 0.85-0.75 (m, 7H); LCMS (ESI, M+1): m/z=604.3.

Example 203

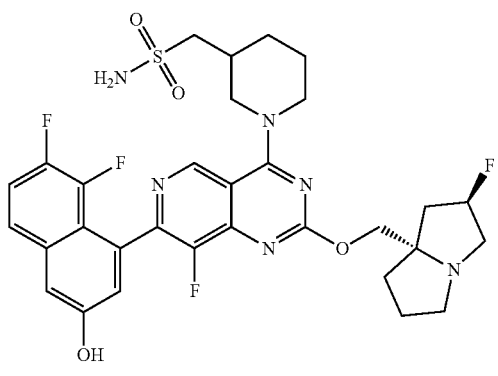 [SMILES: NS(=O)(=O)CC1CCCN(c2nc(OC[C@@]34CCCN3C[C@H](F)C4)nc3c(F)c(-c4cc(O)cc5ccc(F)c(F)c45)ncc23)C1]

1-(1-(7-(7,8-difluoro-3-hydroxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3, yl)methanesulfonamide

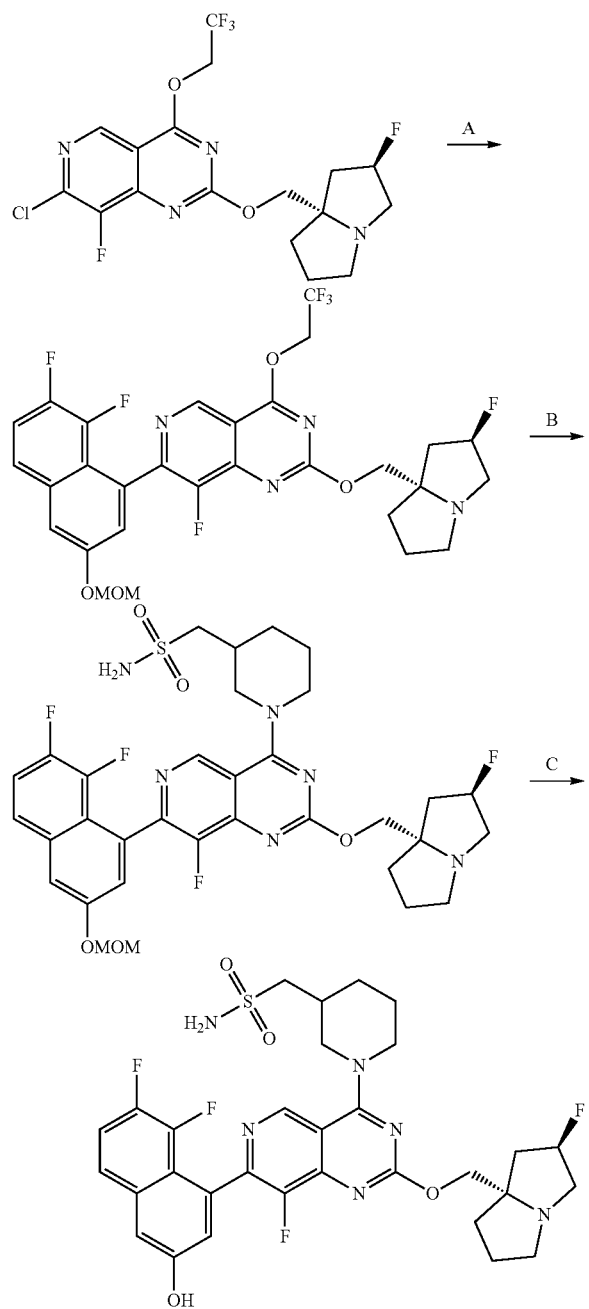

Step A. 7-(7,8-difluoro-3-(methoxymethoxy)naphthalen-1-yl)-8-fluoro-2-(((2R,7aS)-2-fluorotetrahydro-1H-pyrrolizin-7a(5H)-yl)methoxy)-4-(2,2,2-trifluoroethoxy) pyrido[4,3-d]pyrimidine: To a mixture of 7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (300 mg, 1.0 equiv.), 2-(7,8-difluoro-3-(methoxymethoxy)naphthalen-1-yl)-4,4,5,5-tetramethyl-1,3,2-dioxaborolane (359 mg, 1.5 equiv.) and K$_3$PO$_4$ (1.5 M in water, 1.37 mL, 3.0 equiv.) in THF (5 mL) was added CataCXium A Pd G3 (49.8 mg, 0.1 equiv.) under N$_2$. The reaction was de-gassed and stirred at 60° C. for 1 hour under N$_2$. The mixture was diluted with water (10 mL), extracted with ethyl acetate (2×8 mL), washed with brine (10 mL), dried over Na$_2$SO$_4$, concentrated, and purified by reversed phase flash chromatography [water (0.1% formic acid)/acetonitrile]. The desired fractions were collected, neutralized with NaHCO$_3$ solid, and extracted with ethyl acetate (2×25 mL). The combined organic phase was washed with brine (30 mL), dried over anhydrous Na$_2$SO$_4$ and concentrated in vacuum to afford the title compound (323 mg, 73% yield, 0.5 formic acid salt) as a yellow solid; $^1$H NMR (400 MHz, chloroform-d) δ=9.29 (s, 1H), 7.59 (br dd, J=4.4, 9.2 Hz, 1H), 7.56-7.52 (m, 1H), 7.41-7.38 (m, 1H), 7.37-7.31 (m, 1H), 5.69-5.43 (m, 1H), 5.36-5.28 (m, 2H), 5.20-5.06 (m, 2H), 5.04-4.95 (m, 1H), 4.87-4.69 (m, 1H), 4.23-4.15 (m, 1H), 4.12-3.96 (m, 1H), 3.64-3.49 (m, 4H), 3.35-3.26 (m, 1H), 2.91-2.69 (m, 1H), 2.63-2.36 (m, 3H), 2.35-2.28 (m, 2H); LCMS (ESI, M+1): m/z=627.1.

Step B. (1-(7-(7,8-difluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl) piperidin-3-yl)methanesulfonamide: A mixture of piperidin-3-ylmethanesulfonamide (65.9 mg, 2.0 equiv.), DIEA (95.5 mg, 4.0 equiv.) and 4 Å molecular sieves (20 mg) in DMF (1.5 mL) was stirred at 15° C. for 0.5 hour. Then 7-(7,8-difluoro-3-(methoxymethoxy)naphthalen-1-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (120 mg, 0.5 formic acid salt) was added into the above mixture and the resulting was stirred at 40° C. for 14 hours. The mixture was filtered and the filtrate was purified by reversed phase flash chromatography [water (0.1% formic acid)/acetonitrile]. The desired fractions were collected, neutralized with NaHCO$_3$ solid, concentrated in vacuum to remove acetonitrile, and extracted with ethyl acetate (2×15 mL). The combined organic phase was washed with brine (15 mL), dried over anhydrous Na$_2$SO$_4$ and concentrated in vacuum to afford the title compound (120 mg, 90% yield) as a yellow solid; LCMS (ESI, M+1, M/2+1): m/z=705.3, 353.2.

Step C. 1-(1-(7-(7,8-difluoro-3-hydroxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)piperidin-3-yl) methanesulfonamide: To a mixture of (1-(7-(7,8-difluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)piperidin-3-yl) methanesulfonamide (60.0 mg, 1.0 equiv.) in MeCN (0.5 mL) was added HCl.dioxane (4 M, 1.0 mL, 47 equiv.) at 0° C. and the mixture was stirred at 0° C. for 0.5 hour. The mixture was concentrated in vacuum, neutralized with saturated NaHCO$_3$ solution, extracted with ethyl acetate (2×8 mL), concentrated in vacuum and purified by prep-HPLC [column: PhenomenexSynergi C18 150×25 mm×10 um; mobile phase: [water (0.225% formic acid)/ACN]; B %: 8%-38%, 10 min]. The desired fraction was collected and lyophilized to afford the title compound (30.4 mg, 51% yield, 0.6 formic acid salt) as a white solid; $^1$H NMR (400 MHz, methanol-d$_4$) δ=9.13 (s, 1H), 7.62 (br dd, J=4.4, 8.8 Hz, 1H), 7.44-7.36 (m, 1H), 7.34 (s, 1H), 7.25 (dd, J=2.0, 15.2 Hz, 1H), 5.48 (br d, J=52.8 Hz, 1H), 5.18-5.05 (m, 1H), 4.73-4.47 (m, 3H), 3.85-3.55 (m, 4H), 3.36 (br s, 1H), 3.29-3.10 (m, 3H), 2.68-2.36 (m, 4H), 2.25-2.01 (m, 4H), 1.96-1.87 (m, 1H), 1.83-1.54 (m, 2H); $^{19}$F NMR (376 MHz, methanol-d₄) δ=−141.320, −145.127, −146.874, −173.734; LCMS (ESI, M+1, M/2+1): m/z=661.3, 331.2.

Example 204

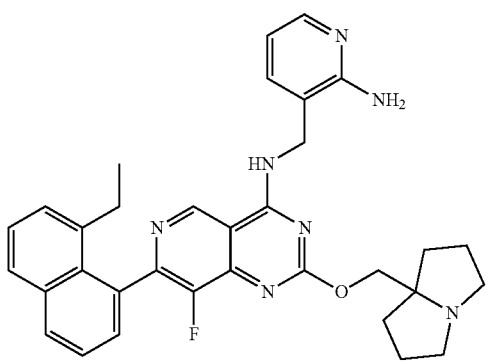 [SMILES: CCc1cccc2cccc(-c3ncc4c(NCc5cccnc5N)nc(OCC56CCCN5CCC6)nc4c3F)c12]

N-((2-aminopyridin-3-yl)methyl)-7-(8-ethylnaphthalen-1-yl)-8-fluoro-2-((hexahydro-1H-pyrrolizin-7a-yl)methoxy)pyrido[4,3-d]pyrimidin-4-amine

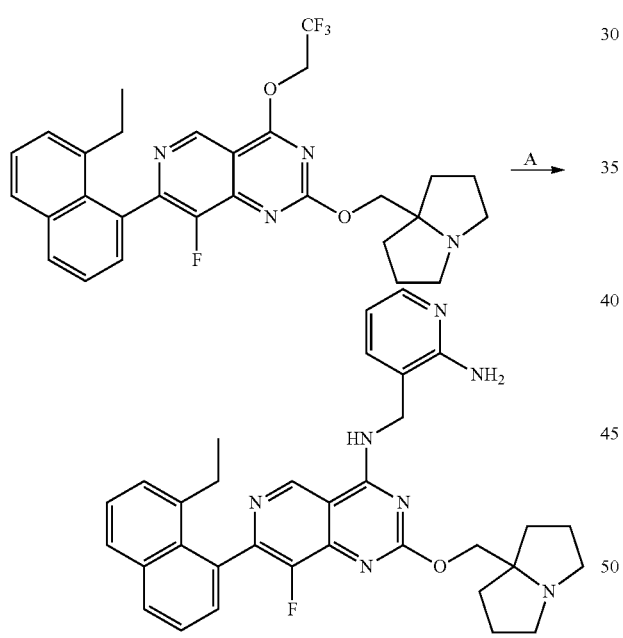

Step A. N-((2-aminopyridin-3-yl methyl)-7-(8-ethylnaphthalen-1-yl)-8-fluoro-2-((hexahydro-1H-pyrrolizin-7a-yl) methoxy)pyrido[4,3-d]pyrimidin-4-amine: To a solution of 7-(8-ethylnaphthalen-1-yl)-8-fluoro-2-((hexahydro-1H-pyrrolizin-7a-yl)methoxy)-4-(2,2,2-trifluoroethoxy) pyrido[4,3-d]pyrimidine (60.0 mg, 1.0 equiv.), 3-(aminomethyl)pyridin-2-amine (27.3 mg, 2.0 equiv.) and 4 Å molecular sieves (10 mg) in DMF (0.5 mL) was added DIEA (71.7 mg, 5.0 equiv.). The reaction was stirred at 40° C. for 72 hours. The mixture was filtered and the filter cake was washed with DMF (1 mL). The filtrate was purified by prep-HPLC [column: Phenomenex Gemini-NX C18 75×30 mm×3 μm; mobile phase: [water (0.225% formic acid), ACN]; B %: 18%-28%, 7 min] to afford title compound (24.2 mg, 39% yield) as an off-white solid; ¹H NMR (400 MHz, methanol-d₄) δ=9.24 (s, 1H), 8.61-8.29 (m, 1H), 8.06 (d, J=7.2 Hz, 1H), 7.94-7.90 (m, 1H), 7.87 (d, J=7.6 Hz, 1H), 7.64 (dd, J=1.2, 7.2 Hz, 1H), 7.57 (t, J=7.6 Hz, 1H), 7.52-7.46 (m, 1H), 7.45-7.38 (m, 2H), 6.72 (dd, J=5.2, 7.2 Hz, 1H), 4.77 (s, 2H), 4.65 (s, 2H), 3.72-3.62 (m, 21H), 3.30-3.22 (m, 2H), 2.45-2.37 (m, 1H), 2.36-2.26 (m, 3H), 2.26-2.12 (m, 4H), 2.11-2.04 (m, 2H), 0.91 (t, J=7.6 Hz, 3H); LCMS (ESI, M+1): m/z=564.2.

Example 205

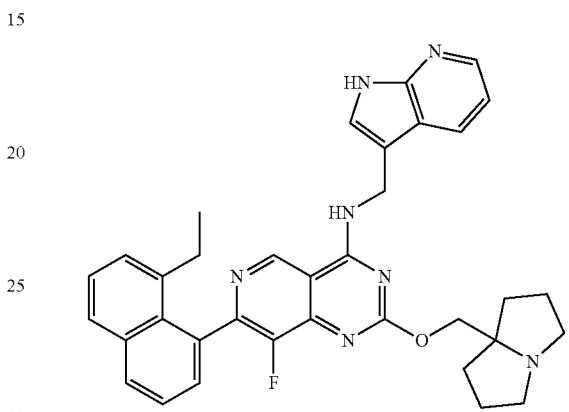

N-((1H-pyrrolo[2,3-b]pyridin-3-yl)methyl)-7-(8-ethylnaphthalen-1-yl)-8-fluoro-2-((hexahydro-1H-pyrrolizin-7a-yl)methoxy)pyrido[4,3-d]pyrimidin-4-amine The title compound was synthesized according to the procedure described for example 204. ¹H NMR (400 MHz, METHANOL-d₄) δ=9.15 (s, 1H), 8.23-8.17 (m, 2H), 8.06-8.00 (m, 1H), 7.85 (d, J=8.0 Hz, 1H), 7.57-7.52 (m, 2H), 7.50-7.45 (m, 1H), 7.43-7.36 (m, 2H), 7.15-7.11 (m, 1H), 5.13-5.02 (m, 2H), 4.39 (s, 2H), 3.15 (br dd, J=5.6, 9.6 Hz, 2H), 2.84-2.73 (m, 2H), 2.44-2.23 (m, 2H), 2.10 (ddd, J=2.4, 6.4, 12.4 Hz, 2H), 2.00-1.87 (m, 4H), 1.84-1.76 (m, 2H), 0.90 (t, J=7.5 Hz, 3H); LCMS (ESI, M+1): m/z=588.4.

Example 206

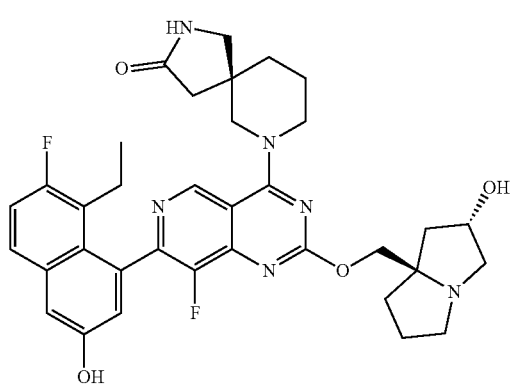 [SMILES: CCc1c(F)ccc2cc(O)cc(-c3ncc4c(N5CCC[C@]6(CNC(=O)C6)C5)nc(OC[C@]56CCCN5C[C@@H](O)C6)nc4c3F)c12]

391

(S)-7-(7-(8-ethyl-7-fluoro-3-hydroxy)naphthalen-1-yl)-8-fluoro-2-(((2S,7aR)-2-hydroxyhexahydro-1H-pyrrolizin-7a-yl)methoxy)pyrido[4,3-d]pyrimidin-4-yl)-2,7-diazaspiro[4.5]decan-3-one

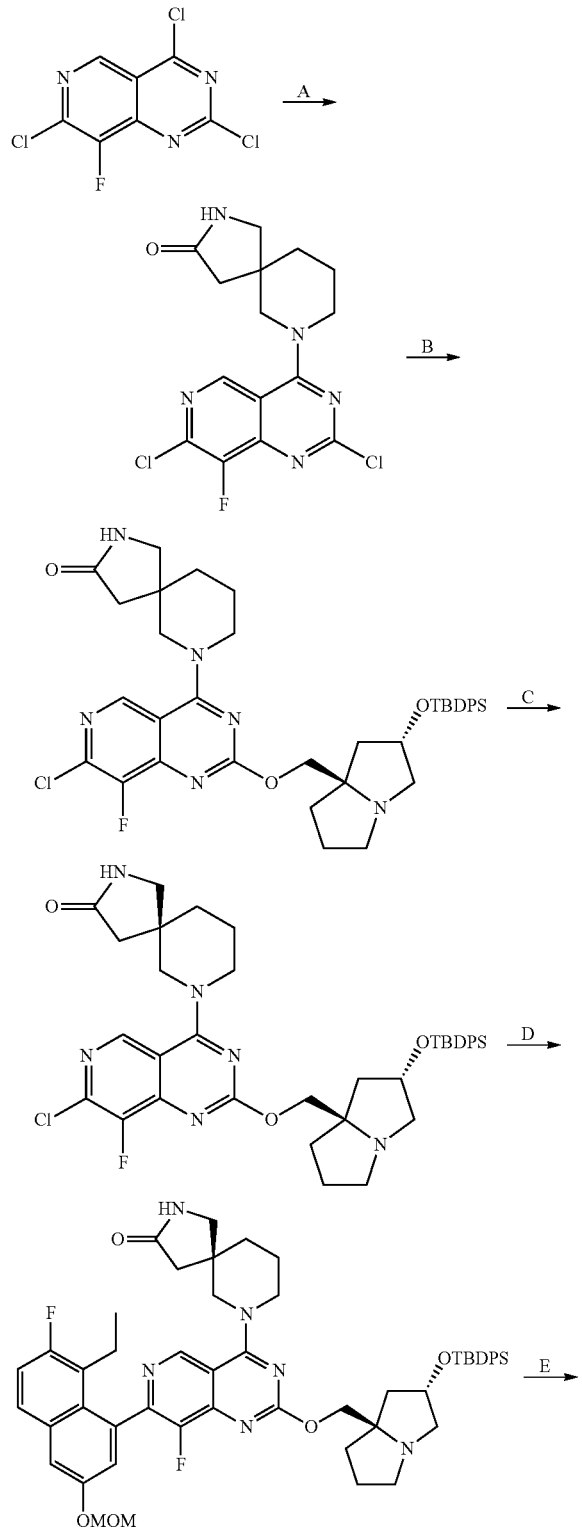

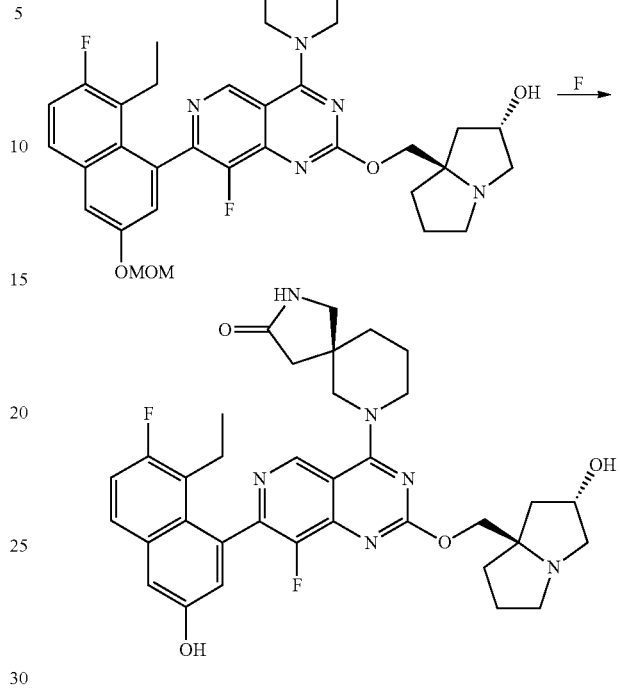

-continued

Step A. 7-(2,7-dichloro-8-fluoropyrido[4,3-d]pyrimidin-4-yl)-2,7-diazaspiro[4.5]decan-3-one: To a solution of 2,9-diazaspiro[4.5]decan-3-one (3.36 g, 1.0 equiv.) in DMF (50 mL) was added DIEA (8.45 g, 11.38 mL, 3.0 equiv.) and 2,4,7-trichloro-8-fluoro-pyrido[4,3-d]pyrimidine (5.5 g, 1.0 equiv.). The reaction was stirred at −40° C. for 3 hours. The mixture was diluted with water 50 mL and extracted with ethyl acetate 150 mL (50 mL×3). The combined organic layers were washed with brine 300 mL, dried over Na$_2$SO$_4$, concentrated, and purified by reversed phase flash chromatography (Silica gel, DCM/MeOH 10:1) to afford the title compound (7.00 g, 87% yield) as a yellow solid.

Step B. 7-(2-(((2S,7aR)-2-((tert-butyldiphenylsilyl)oxy)hexahydro-1H-pyrrolizin-7a-yl)methoxy)-7-chloro-8-fluoropyrido[4,3-d]pyrimidin-4-yl)-2,7-diazaspiro[4.5]decan-3-one: To a solution of 7-(2,7-dichloro-8-fluoro-pyrido[4,3-d]pyrimidin-4-yl)-2,7-diazaspiro[4.5]decan-3-one (3.00 g, 1.0 equiv.) and DIPEA (5.24 g, 7.06 mL, 5.0 equiv.) in dioxane (30 mL) was added ((2S,7aR)-2-((tert-butyldiphenylsilyl)oxy)tetrahydro-1H-pyrrolizin-7a(5H)-yl)methanol (3.21 g, 1.0 equiv.). The reaction was stirred at 100° C. for 6 hours. The mixture was diluted with water (10 mL) and extracted with ethyl acetate (5 mL×3). The combined organic layers were washed with brine (20 mL), dried over Na$_2$SO$_4$, concentrated, and purified by prep-HPLC (mobile phase: [water (0.1% formic acid)/acetonitrile]; 5-70%) to afford the title compound (1.63 g, 15% yield) as a yellow solid. $^1$H NMR (400 MHz, CDCl$_3$) δ=8.76 (d, J=4.8 Hz, 1H), 7.66-7.64 (m, 1H), 7.66-7.58 (m, 3H), 7.51-7.36 (m, 6H), 4.74-4.52 (m, 2H), 4.35 (dd, J=18.8, 10.9 Hz, 1H), 4.27-3.66 (m, 6H), 3.61-3.27 (m, 3H), 3.19-2.96 (m, 2H), 2.53-2.09 (m, 8H), 1.91-1.65 (m, 4H), 1.09 (s, 9H); LCMS (ESI, M+1): m/z=729.3.

Step C. (S)-7-(2-(((2S,7aR)-2-((tert-butyldiphenylsilyl)oxy)hexahydro-1H-pyrrolizin-7a-yl)methoxy)-7-chloro-8-fluoropyrido[4,3-d]pyrimidin-4-yl)-2,7-diazaspiro[4.5]decan-3-one: 7-(2-(((2S,7aR)-2-((tert-butyldiphenylsilyl)oxy)hexahydro-1H-pyrrolizin-7a-yl)methoxy)-7-chloro-8-fluoropyrido[4,3-d]pyrimidin-4-yl)-2,7-diazaspiro[4.5]decan-3-one (3.80 g) was purified by chiral prep-HPLC (column: DAICEL CHIRALCEL OD (250 mm×30 mm, 10 μm); mobile phase: [0.1% NH$_3$H$_2$O/MeOH]; B %: 50%-50%, 4.5; 180 min) to give the title compound (1.7 g, 32% yield, 98.9% ee) as a light-yellow solid. $^1$H NMR (400 MHz, CDCl$_3$) δ=8.62 (s, 1H), 7.59-7.54 (m, 4H), 7.34-7.24 (m, 6H), 4.49-4.40 (m, 1H), 4.13-3.83 (m, 6H), 3.65-3.59 (m, 1H), 3.30 (d, J=7.0 Hz, 3H), 3.04 (s, 3H), 2.18-1.98 (m, 8H), 1.80-1.71 (m, 4H), 0.98 (s, 9H); LCMS (ESI, M+1): m/z=729.3.

Step D. (S)-7-(2-(((2S,7aR)-2-((tert-butyldiphenylsilyl)oxy)hexahydro-1H-pyrrolizin-7a-yl)methoxy)-7-(8-ethyl-7-fluoro-3-(methoxymethoxy)naphthalen-1-yl)-8-fluoro-pyrido[4,3-d]pyrimidin-4-yl)-2,7-diazaspiro[4.5]decan-3-one: A mixture of 2-(8-ethyl-7-fluoro-3-(methoxymethoxy)naphthalen-1-yl)-4,4,5,5-tetramethyl-1,3,2-dioxaborolane (356 mg, 2.0 equiv.), (S)-7-(2-(((2S,7aR)-2-((tert-butyldiphenylsilyl)oxy)hexahydro-1H-pyrrolizin-7a-yl) methoxy)-7-chloro-8-fluoropyrido[4,3-d]pyrimidin-4-yl)-2,7-diazaspiro[4.5]decan-3-one (500 mg, 1.0 equiv.), CataCXium A Pd G3 (35.95 mg, 0.1 equiv.) and K$_3$PO$_4$ (1.5 M, 987 μL, 3.0 equiv.) in THF (1 mL) was degassed and stirred at 60° C. for 2 hours under nitrogen atmosphere. The mixture was diluted with water (5 mL) and extracted with ethyl acetate (5 mL×2). The combined organic layers were washed with brine (20 mL), dried over Na$_2$SO$_4$, concentrated and purified by column chromatography (silica gel, DCM/MeOH 1:1) to afford (349 mg, 76% yield) as an orange oil. LCMS (ESI, M+1): m/z=927.8.

Step E. (S)-7-(7-(8-ethyl-7-fluoro-3-(methoxymethoxy)naphthalen-1-yl)-8-fluoro-2-(((2S,7aR)-2-hydroxyhexahydro-1H-pyrrolizin-7a-yl)methoxy)pyrido[4,3-d]pyrimidin-4-yl)-2,7-diazaspiro[4.5]decan-3-one: To a solution of (S)-7-(2-(((2S,7aR)-2-((tert-butyl diphenylsilyl)oxy)hexahydro-1H-pyrrolizin-7a-yl)methoxy)-7-(8-ethyl-7-fluoro-3-(methoxymethoxy)naphthalen-1-yl)-8-fluoropyrido[4,3-d]pyrimidin-4-yl)-2,7-diazaspiro[4.5]decan-3-one (100 mg, 1.0 equiv.) in DMF (1 mL) was added CsF (246 mg, 15 equiv.), the reaction was stirred at 40° C. for 16 hours. The mixture was diluted with ethyl acetate (5 mL), washed with brine (15 mL), dried over Na$_2$SO$_4$, concentrated, and purified by column chromatography (Silica gel, Ethyl acetate/MeOH (0.1% NH$_4$OH) 0-100%) to afford the title compound (51 mg, 69% yield) as a yellow solid. $^1$H NMR (400 MHz, CDCl$_3$) δ=9.03-8.90 (m, 1H), 7.67 (dd, J=8.8, 6.0, Hz, 1H), 7.51 (d, J=2.8 Hz, 1H), 7.25-7.17 (m, 2H), 5.31-5.26 (m, 2H), 4.68 (d, J=5.2 Hz, 1H), 4.49-4.34 (m, 1H), 4.22 (d, J=7.2 Hz, 1H), 4.09 (s, 1H), 3.89 (br s, 1H), 3.76 (t, J=14.4 Hz, 2H), 3.50 (s, 3H), 3.50-3.40 (m, 2H), 3.22 (d, J=9.6 Hz, 1H), 3.05-2.91 (m, 1H), 2.84-2.69 (m, 1H), 2.55-2.42 (m, 2H), 2.41-2.14 (m, 5H), 1.94-1.82 (m, 7H), 0.84 (dt, J=7.4, 2.8 Hz, 4H); LCMS (ESI, M+1): m/z=689.6.

Step F. (S)-7-(7-(8-ethyl-7-fluoro-3-hydroxy)naphthalen-1-yl)-8-fluoro-2-(((2S,7aR)-2-hydroxyhexahydro-1H-pyrrolizin-7a-yl)methoxy)pyrido[4,3-d]pyrimidin-4-yl)-2,7-diazaspiro[4.5]decan-3-one: To a solution of (S)-7-(7-(8-ethyl-7-fluoro-3-(methoxymethoxy)naphthalen-1-yl)-8-fluoro-2-(((2S,7aR)-2-hydroxyhexahydro-1H-pyrrolizin-7a-yl)methoxy)pyrido[4,3-d]pyrimidin-4-yl)-2,7-diazaspiro[4.5]decan-3-one (37.00 mg, 1.0 equiv.) in MeCN (0.4 mL) was added HCl/dioxane (4 M, 376 μL, 28 equiv.). The mixture was stirred at 0° C. for 0.5 hour. The mixture was concentrated and purified by prep-HPLC (column: Phenomenex luna C18 150×25 mm×10 μm; mobile phase: [water (0.225% formic acid)/ACN]; B %: 14%-44%, 11.5 min) to afford the title compound (16.7 mg, 47% yield, 96.7% ee, formic acid salt) as a yellow solid. $^1$H NMR (400 MHz, CD3OD) δ=9.12 (s, 1H), 8.58-8.48 (m, 1H), 7.73-7.64 (m, 1H), 7.31 (d, J=2.8 Hz, 1H), 7.26 (t, J=9.2 Hz, 1H), 7.05 (t, J=3.2 Hz, 1H), 4.66 (s, 1H), 4.56 (dd, J=11.8, 2.4 Hz, 1H), 4.51-4.37 (m, 2H), 4.36-4.20 (m, 1H), 4.12-3.95 (m, 1H), 3.83-3.59 (m, 3H), 3.57-3.43 (m, 1H), 3.29-3.19 (m, 3H), 2.51-2.09 (m, 10H), 1.94-1.83 (m, 4H), 0.85-0.75 (m, 3H); $^{19}$F NMR (377 MHz, CD3OD) δ=−121.09, −139.15; LCMS (ESI, M+1): m/z=645.5.

Example 207

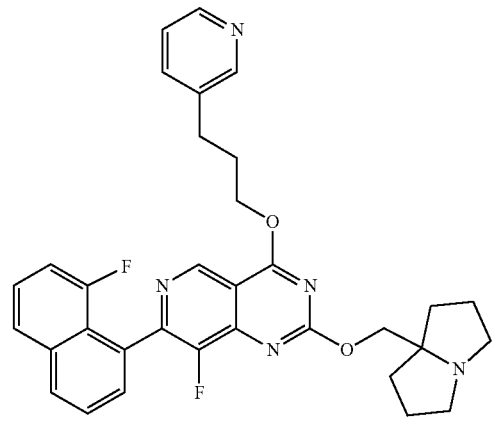 [SMILES: Fc1c(-c2cccc3cccc(F)c23)ncc2c(OCCCc3cccnc3)nc(OCC34CCCN3CCC4)nc12]

8-fluoro-7-(8-fluoronaphthalen-1-yl)-4-(3-(pyridin-3-yl)propoxy)-2-((tetrahydro-1H-pyrrolizin-7a(5H)-yl)methoxy)pyrido[4,3-d]pyrimidine Step A: 8-fluoro-7-(8-fluoronaphthalen-1-yl)-4-(3-(pyridin-3-yl)propoxy)-2-((tetrahydro-1H-pyrrolizin-7a(5H)-yl)methoxy)pyrido[4,3-d]pyrimidine: To a mixture of 3-(pyridin-3-yl)propan-1-ol (1.5 equiv.) and 4 A molecular sieves (20 mg) in THF (2 mL) was added LiHMDS (1 M, 141 μL, 1.5 equiv.) at 0° C. After addition, the mixture was stirred at 0° C. for 20 minutes, and then 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (50 mg, I equiv.) was added at 0° C. The resulting mixture was stirred at 20° C. for 40 minutes. The reaction mixture was quenched with saturated aqueous NH$_4$Cl (3 mL) and extracted with ethyl acetate (3×5 mL) The combined organic layers were dried over Na$_2$SO$_4$, filtered, and concentrated under reduced pressure to give a residue. The residue was purified by prep-HPLC (column: Shim-pack C18 150×25×10 um; mobile phase: [water (0.225% formic acid)/ACN]; B %: 31%-51%, 10 min) and lyophilized to afford the title compound. LCMS (ESI, M+1): m/z 568.4.

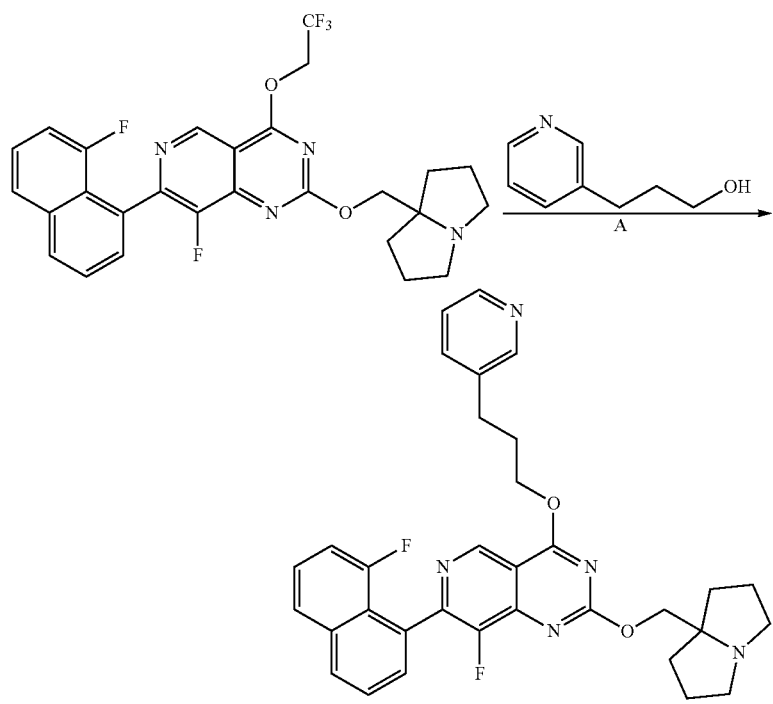
Example 208 to 223 were synthesized according to the procedure described for example 34.
TABLE 2
Mass Spectrum Data of Example 208 to 223
| Example No. | Obs. M + 1 | Example No. | Obs. M + 1 |
|---|---|---|---|
| 208 | 578.3 | 216 | 618.3 |
| 209 | 619.3 | 217 | 586.3 |
| 210 | 591.2 | 218 | 564.3 |
| 211 | 568.3 | 219 | 543.2 |
| 212 | 592.3 | 220 | 558.3 |
| 213 | 565.3 | 221 | 609.2 |
| 214 | 579.2 | 222 | 584.3 |
| 215 | 542.3 | 223 | 592.2 |
8-fluoro-7-(8-fluoronaphthalen-1-yl)-N-(imidazo[1,2-a]pyridin-6-ylmethyl)-2-((tetrahydro-1H-pyrrolizin-7a(5H)-yl)methoxy)pyrido[4,3-d]pyrimidin-4-amine
Example 209
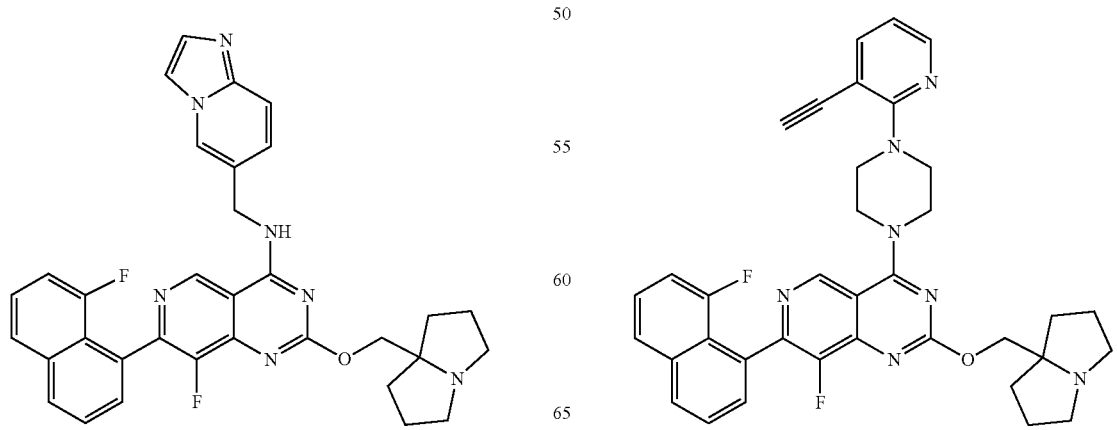

397

2-(4-(8-fluoro-7-(8-fluoronaphthalen-1-yl)-2-((tetra-hydro-1H-pyrrolizin-7a(5H)-yl) methoxy)pyrido[4,3-d]pyrimidin-4-yl)piperazin-1-yl)nicotinonitrile Example 210

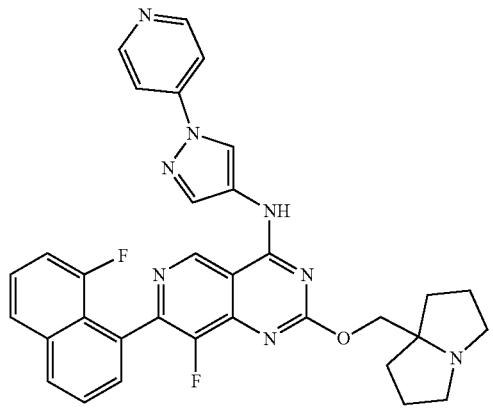 [SMILES: Fc1c(-c2cccc3cccc(F)c23)ncc2c(Nc3cnn(-c4ccncc4)c3)nc(OCC34CCCN3CCC4)nc12]

398

N1-(8-fluoro-7-(8-fluoronaphthalen-1-yl)-2-((tetra-hydro-1H-pyrrolizin-7a(5H)-yl) methoxy)pyrido[4,3-d]pyrimidin-4-yl)-N₂-(pyridin-3-yl)ethane-1,2-diamine Example 212

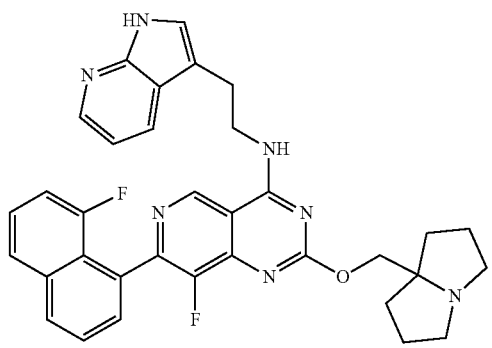

8-fluoro-7-(8-fluoronaphthalen-1-yl)-N-(1-(pyridin-4-yl)-1H-pyrazol-4-yl)-2-((tetrahydro-1H-pyrrolizin-7a(5H)-yl)methoxy)pyrido[4,3-d]pyrimidin-4-amine Example 211

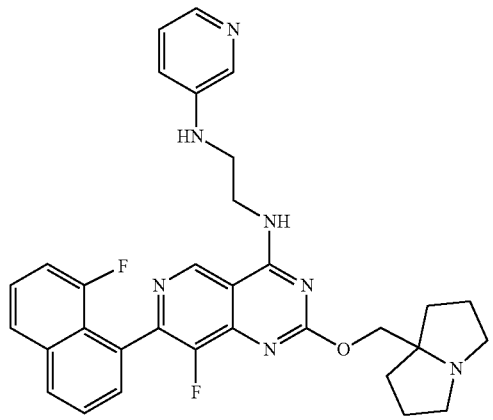 [SMILES: Fc1c(-c2cccc3cccc(F)c23)ncc2c(NCCNc3cccnc3)nc(OCC34CCCN3CCC4)nc12]

N-(2-(1H-pyrrolo[2,3-b]pyridin-3-yl)ethyl)-8-fluoro-7-(8-fluoronaphthalen-1-yl)-2-((tetrahydro-1H-pyrrolizin-7a(5H)-yl)methoxy)pyrido[4,3-d]pyrimidin-4-amine Example 213

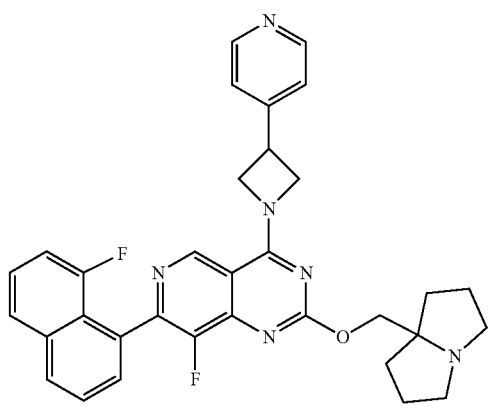 [SMILES: Fc1c(-c2cccc3cccc(F)c23)ncc2c(N3CC(c4ccncc4)C3)nc(OCC34CCCN3CCC4)nc12]

399

8-fluoro-7-(8-fluoronaphthalen-1-yl)-4-(3-(pyridin-4-yl)azetidin-1-yl)-2-((tetrahydro-1H-pyrrolizin-7a(5H)-yl)methoxy)pyrido[4,3-d]pyrimidine Example 214

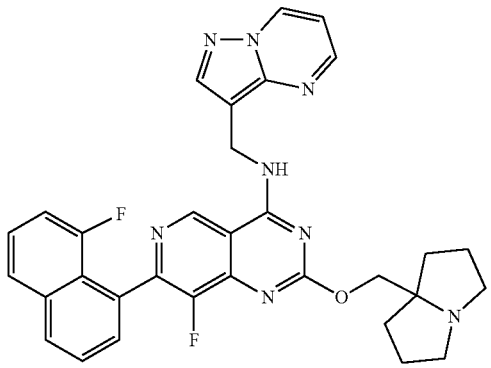 [SMILES: Fc1c(-c2cccc3cccc(F)c23)ncc2c(NCc3cnn4cccnc34)nc(OCC34CCCN3CCC4)nc12]

8-fluoro-7-(8-fluoronaphthalen-1-yl)-N-(pyrazolo[1,5-a]pyrimidin-3-ylmethyl)-2-((tetrahydro-1H-pyrrolizin-7a(5H)-yl)methoxy)pyrido[4,3-d]pyrimidin-4-amine

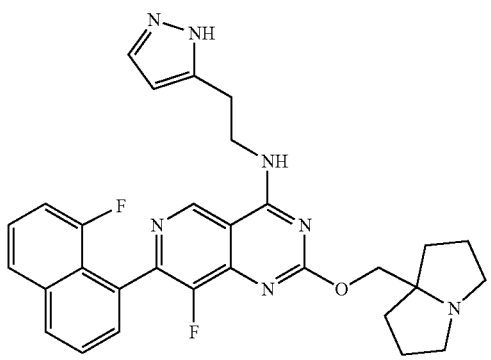 [SMILES: Fc1c(-c2cccc3cccc(F)c23)ncc2c(NCCc3ccn[nH]3)nc(OCC34CCCN3CCC4)nc12]

N-(2-(1H-pyrazol-5-yl)ethyl)-8-fluoro-7-(8-fluoronaphthalen-1-yl)-2-((tetrahydro-1H-pyrrolizin-7a(5H)-yl)methoxy)pyrido[4,3-d]pyrimidin-4-amine Example 216

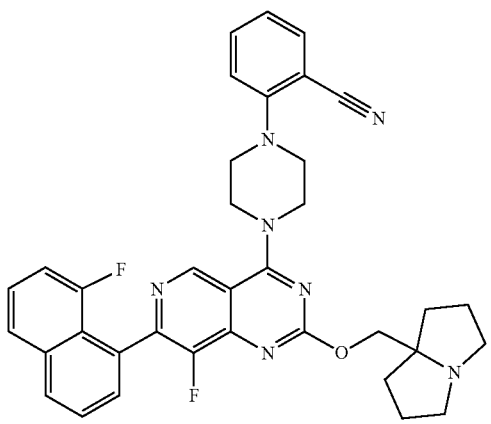 [SMILES: N#Cc1ccccc1N1CCN(c2nc(OCC34CCCN3CCC4)nc3c(F)c(-c4cccc5cccc(F)c45)ncc23)CC1]

400

2-(4-(8-fluoro-7-(8-fluoronaphthalen-1-yl)-2-((tetrahydro-1H-pyrrolizin-7a(5H)-yl) methoxy)pyrido[4,3-d]pyrimidin-4-yl)piperazin-1-yl)benzonitrile Example 217

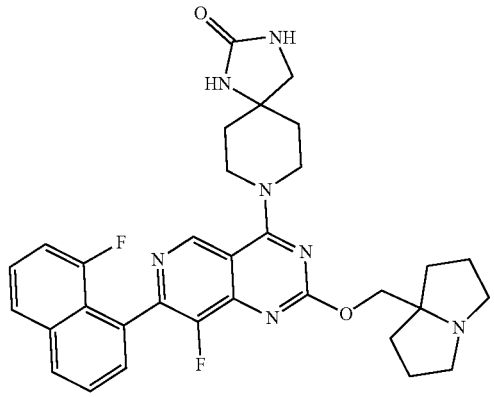 [SMILES: O=C1NCC2(CCN(c3nc(OCC45CCCN4CCC5)nc4c(F)c(-c5cccc6cccc(F)c56)ncc34)CC2)N1]

8-(8-fluoro-7-(8-fluoronaphthalen-1-yl)-2-((tetrahydro-1H-pyrrolizin-7a(5H)-yl) methoxy)pyrido[4,3-d]pyrimidin-4-yl)-1,3,8-triazaspiro[4.5]decan-2-one Example 218

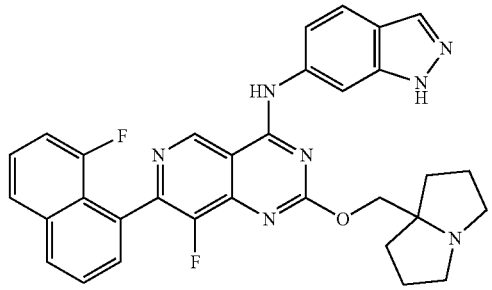 [SMILES: Fc1c(-c2cccc3cccc(F)c23)ncc2c(Nc3ccc4cn[nH]c4c3)nc(OCC34CCCN3CCC4)nc12]

8-fluoro-7-(8-fluoronaphthalen-1-yl)-N-(1H-indazol-6-yl)-2-((tetrahydro-1H-pyrrolizin-7a(5H)-yl)methoxy)pyrido[4,3-d]pyrimidin-4-amine Example 219

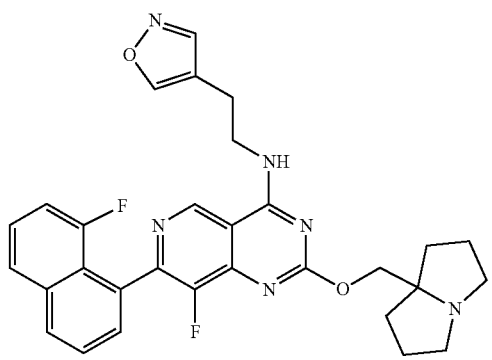 [SMILES: Fc1c(-c2cccc3cccc(F)c23)ncc2c(NCCc3cnoc3)nc(OCC34CCCN3CCC4)nc12]

401

8-fluoro-7-(8-fluoronaphthalen-1-yl)-N-(2-(isoxazol-4-yl)ethyl)-2-((tetrahydro-1H-pyrrolizin-7a(5H)-yl) methoxy)pyrido[4,3-d]pyrimidin-4-amine Example 220

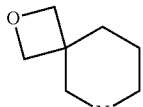
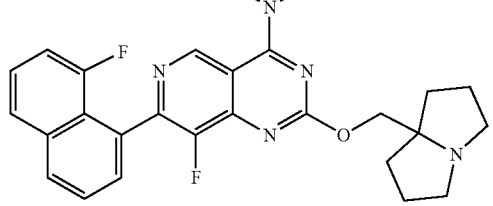

6-(8-fluoro-7-(8-fluoronaphthalen-1-yl)-2-((tetrahydro-1H-pyrrolizin-7a(5H)-yl) methoxy)pyrido[4,3-d]pyrimidin-4-yl)-2-oxa-6-azaspiro[3.5]nonane Example 221

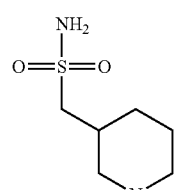
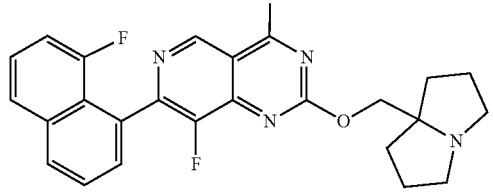

1-(1-(8-fluoro-7-(8-fluoronaphthalen-1-yl)-2-((tetrahydro-1H-pyrrolizin-7a(5H)-yl) methoxy)pyrido[4,3-d]pyrimidin-4-yl)piperidin-3-yl)methanesulfonamide Example 222

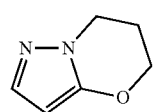
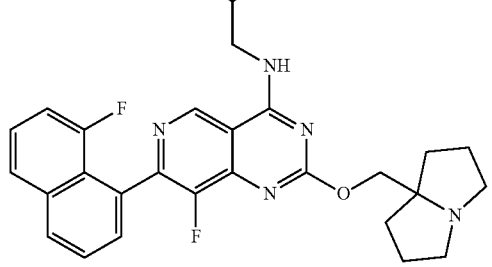

402

N-((6,7-dihydro-5H-pyrazolo[5,1-b][1,3]oxazin-3-yl)methyl)-8-fluoro-7-(8-fluoronaphthalen-1-yl)-2-((tetrahydro-1H-pyrrolizin-7a(5H)-yl)methoxy)pyrido[4,3-d]pyrimidin-4-amine Example 223

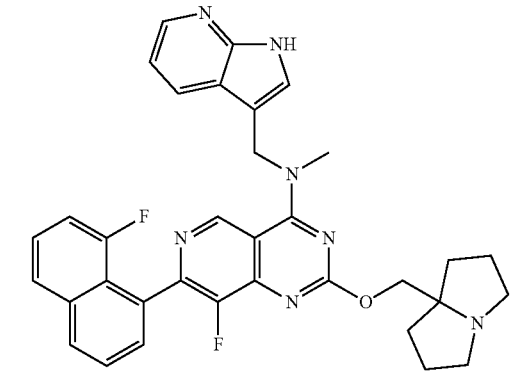 [SMILES: CN(Cc1c[nH]c2ncccc12)c1nc(OCC23CCCN2CCC3)nc2c(F)c(-c3cccc4cccc(F)c34)ncc12]

N-((1H-pyrrolo[2,3-b]pyridin-3-yl)methyl)-8-fluoro-7-(8-fluoronaphthalen-1-yl)-N-methyl-2-((tetrahydro-1H-pyrrolizin-7a(5H)-yl)methoxy)pyrido[4,3-d]pyrimidin-4-amine Example 224

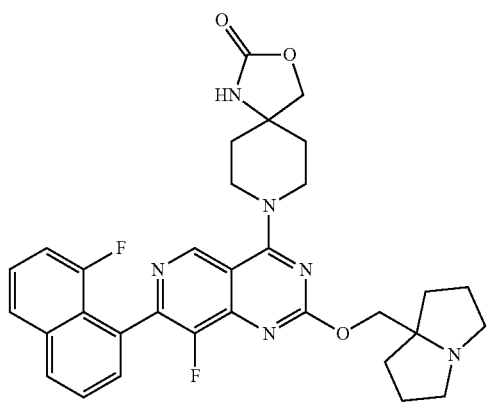 [SMILES: O=C1NC2(CCN(c3nc(OCC45CCCN4CCC5)nc4c(F)c(-c5cccc6cccc(F)c56)ncc34)CC2)CO1]

8-(8-fluoro-7-(8-fluoronaphthalen-1-yl)-2-((tetrahydro-1H-pyrrolizin-7a(5H)-yl) methoxy)pyrido[4,3-d]pyrimidin-4-yl)-3-oxa-1,8-diazaspiro[4.5]decan-2-one The title compound was synthesized according to the procedure described for example 85. LCMS (ESI, M+1): m/z 587.3.

Example 225

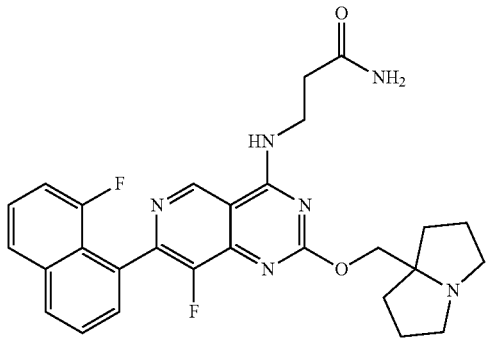 [SMILES: NC(=O)CCNc1nc(OCC23CCCN2CCC3)nc2c(F)c(-c3cccc4cccc(F)c34)ncc12]

3-((8-fluoro-7-(8-fluoronaphthalen-1-yl)-2-((hexa-hydro-1H-pyrrolizin-7a-yl)methoxy)pyrido[4,3-d]pyrimidin-4-yl)amino)propanamide The title compound was synthesized according to the procedure described for example 84. $^1$H NMR (400 MHz, MeOD-$d_4$) δ 9.17 (s, 1H), 8.12 (br d, J=8.2 Hz, 1H), 7.86 (d, J=8.2 Hz, 1H), 7.70 (t, J=7.6 Hz, 1H), 7.59 (d, J=6.6 Hz, 1H), 7.57-7.50 (m, 1H), 7.19 (dd, J=7.6, 13.0 Hz, 1H), 4.66-4.54 (m, 2H), 4.07-3.89 (m, 2H), 3.60-3.48 (m, 2H), 3.19-3.07 (m, 2H), 2.71 (t, J=6.8 Hz, 2H), 2.33-2.23 (m, 2H), 2.21-2.06 (m, 4H), 2.05-1.95 (m, 2H); LCMS (ESI, M+1): m/z=519.1.

Example 226

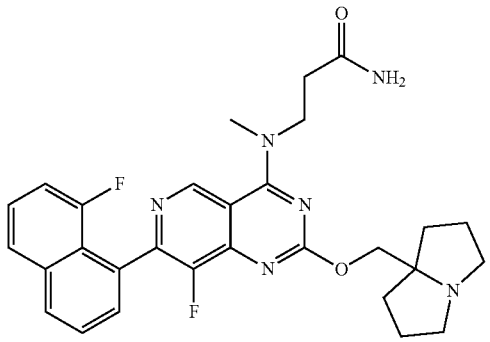 [SMILES: CN(CCC(N)=O)c1nc(OCC23CCCN2CCC3)nc2c(F)c(-c3cccc4cccc(F)c34)ncc12]

3-((8-fluoro-7-(8-fluoronaphthalen-1-yl)-2-((hexa-hydro-1H-pyrrolizin-7a-yl)methoxy)pyrido[4,3-d]pyrimidin-4-yl)(methyl)amino)propanamide The title compound was synthesized according to the procedure described for example 84. $^1$H NMR (400 MHz, DMSO-$d_6$) δ 9.26 (s, 1H), 8.20 (s, 1H), 8.18 (d, J=8.6 Hz, 1H), 7.93 (d, J=8.2 Hz, 1H), 7.78-7.68 (m, 1H), 7.65-7.54 (m, 2H), 7.52-7.42 (m, 1H), 7.33-7.28 (m, 1H), 7.01-6.88 (m, 1H), 4.13 (s, 2H), 4.06-4.05 (d, J=6.2 Hz, 2H), 3.53 (s, 3H), 3.02-2.97 (m, 2H), 2.63-2.61 (m, 3H), 1.93-1.89 (dd, J=5.5, 11.5 Hz, 3H), 1.87-1.74 (m, 5H), 1.68-1.57 (m, 2H); LCMS (ESI, M+1): m/z=533.2.

Example 227

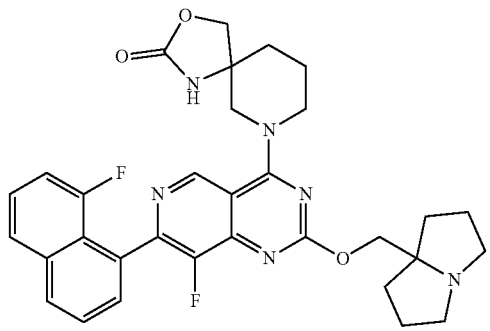 [SMILES: O=C1NC2(CCCN(c3nc(OCC45CCCN4CCC5)nc4c(F)c(-c5cccc6cccc(F)c56)ncc34)C2)CO1]

7-(8-fluoro-7-(8-fluoronaphthalen-1-yl)-2-((hexa-hydro-1H-pyrrolizin-7a-yl) methoxy)pyrido[4,3-d]pyrimidin-4-yl)-3-oxa-1,7-diazaspiro[4.5]decan-2-one

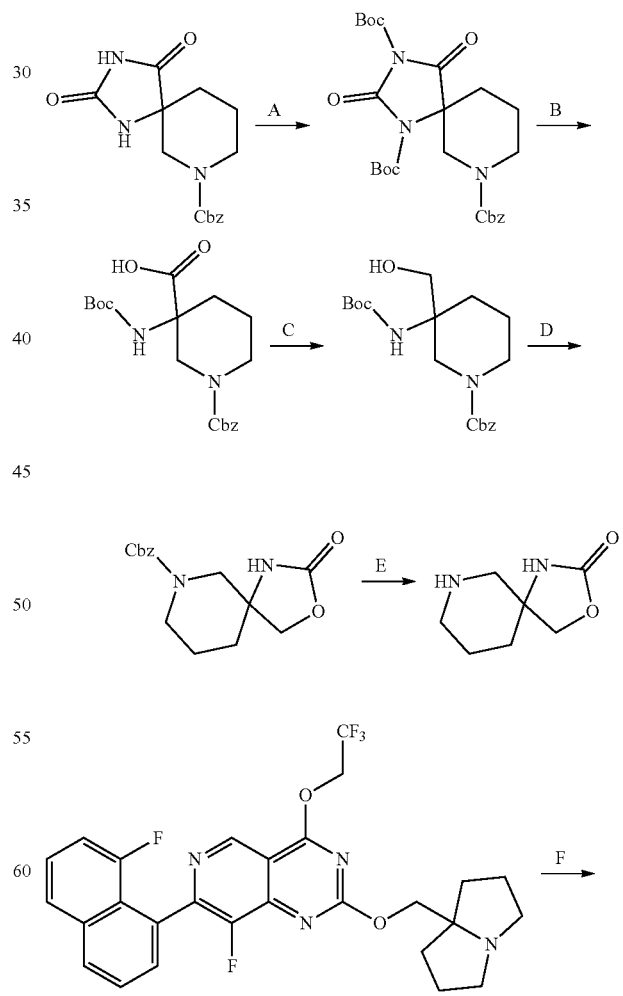

-continued

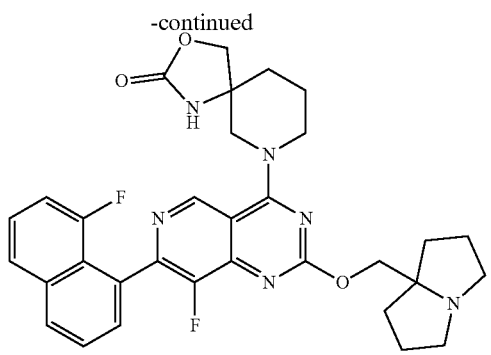

Step A. 7-benzyl 1,3-di-tert-butyl 2,4-dioxo-1,3,7-triazaspiro[4.5]decane-1,3,7-tricarboxylate: A mixture of benzyl 2,4-dioxo-1,3,7-triazaspiro[4.5]decane-7-carboxylate (3 g, 1 equiv.), (Boc)₂O (8.63 g, 4 equiv.), TEA (1.0 g, 1 equiv.) and DMAP (31 mg, 0.03 equiv.) in DME (100 mL) was stirred at 25° C. for 18 hours. The reaction mixture was concentrated to give a yellow solid. The solid was dispersed in isopropyl ether (20 mL) and the mixture was stirred for 10 minutes. The mixture was filtered and the solid was dried under reduced pressure to afford the tittle compound (4 g, crude) as a light-yellow solid; LCMS [ESI, M+H]: m/z=504.3.

Step B. 1-((benzyloxycarbonyl)-3-((tert-butoxycarbonyl)amino)piperidine-3-carboxylic acid: To a solution of 7-benzyl 1,3-di-tert-butyl 2,4-dioxo-1,3,7-triazaspiro[4.5]decane-1,3,7-tricarboxylate (2 g, 1 equiv.) in THF (20 mL) was added LiOH·H₂O (1 M in water, 31.8 mL, 8 equiv.) at 25° C. The mixture was stirred at 25° C. for 18 hours. The pH of the reaction mixture was adjusted to 10 with 2N HCl while maintaining the reaction mixture temperature below 5° C. (Boc)₂O (4 mL) was added and the mixture was stirred at 25° C. for 18 hours. The pH of the reaction mixture was adjusted to 3-4 with 2N HCl while maintaining the reaction mixture temperature below 5° C. The mixture was extracted with ethyl acetate (4×30 mL). The combined organic layer was dried over anhydrous Na₂SO₄, concentrated and purified by reversed phase flash chromatography [water (0.1% formic acid)/acetonitrile 1:1] to afford the tittle compound (1.9 g, crude) as a brown gum; LCMS [ESI, M−55]: m/z=323.3.

Step C. benzyl 3-((tert-butoxycarbonyl)amino)-3-(hydroxymethyl)piperidine-1-carboxylate: To a solution of 1-((benzyloxy)carbonyl)-3-((tert-butoxycarbonyl)amino)piperidine-3-carboxylic acid (1.9 g, crude) in THF (30 mL) was added LiAlH₄ (250 mg, 1.3 equiv.) at 0° C. under N₂ atmosphere. The mixture was stirred at 20° C. for 15 hours. The reaction mixture was quenched with Na₂SO₄·10H₂O (2 g) and saturated aqueous NaHCO₃ (0.1 mL) at 0° C. Na₂SO₄ (3 g) was added and the mixture was stirred for 5 minutes. The mixture was filtered through a pad of Celite and the filter cake was washed with ethyl acetate/methanol 10:1 (20 mL) and methanol (100 mL). The filtrate was concentrated and purified by reversed phase flash chromatography [water (0.1% formic acid)/acetonitrile 1:4] to afford the tittle compound (0.69 g, crude) as a white gum; LCMS [ESI, M−55]: m/z=309.2.

Step D. benzyl 2-oxo-3-oxa-1,7-diazaspiro[4.5]decane-7-carboxylate: To a solution of benzyl 3-((tert-butoxycarbonyl)amino)-3-(hydroxymethyl)piperidine-1-carboxylate (0.69 g, crude) in DMF (10 mL) was added NaH (60% in mineral oil, 114 mg, 1.5 equiv.) in portions at 0° C. The mixture was stirred at 20° C. for 16 hours. The mixture was quenched with water (150 mL) at 0° C. and extracted with ethyl acetate (3×20 mL). The combined organic layers were dried over anhydrous Na₂SO₄, concentrated and purified by reversed phase flash chromatography [water (0.1% formic acid)/acetonitrile 1:1] to afford the tittle compound (270 mg, crude) as a white gum; LCMS [ESI, M−55]: m/z=291.2.

Step E. 3-oxa-1,7-diazaspiro[4.5]decan-2-one: To a solution of benzyl 2-oxo-3-oxa-1,7-diazaspiro[4.5]decane-7-carboxylate (270 mg, 1 equiv.) in CF₃COOH (9 mL) was added Pd(OH)₂ (40 mg, 10% purity) under N₂ atmosphere. The mixture was degassed and purged with H₂ for 3 times. The mixture was stirred at 20° C. for 2 hours under H₂ atmosphere (15 psi). The reaction mixture was filtered through a pad of Celite. The filter cake was washed with THF/MeOH 1:1 (30 mL). The combined organic phase was concentrated under reduced pressure. The residue was washed with THF (5 mL×5) and the combined THF phase was concentrated to afford the tittle compound (145 mg, 36% yield over five steps) as a colorless oil.

Step F. 7-(8-fluoro-7-(8-fluoronaphthalen-1-yl)-2-((hexahydro-1H-pyrrolizin-7a-yl) methoxy)pyrido[4,3-d]pyrimidin-4-yl)-3-oxa-1,7-diazaspiro[4.5]decan-2-one: A mixture of 8-fluoro-7-(8-fluoronaphthalen-1-yl)-2-((hexahydro-1H-pyrrolizin-7a-yl)methoxy)-4-(2,2,2-trifluoroethoxy) pyrido[4,3-d]pyrimidine (200 mg, 1 equiv.), 3-oxa-1,7-diazaspiro[4.5]decan-2-one (145 mg, 2.5 equiv.), DIPEA (171 mg, 3.5 equiv.) and 4 Å molecular sieves (40 mg) in DMF (2 mL) was stirred at 40° C. for 18 hours under N₂ atmosphere. The reaction mixture was filtered. The filtrate was purified by reversed phase flash chromatography [water (0.1% formic acid)/acetonitrile 7:3] and then prep-HPLC [column: Waters Xbridge 150×25 mm×5 μm; mobile phase: [water (10 mM NH₄HCO₃)/ACN]; B %: 13%-43%, 10 minutes] to afford the tittle compound (82.6 mg, 36% yield) as a white solid; ¹H NMR (400 MHz, DMSO-d6) δ=9.09 (d, J=1.6 Hz, 1H), 8.41 (br s, 1H), 8.18 (br d, J=8.4 Hz, 1H), 7.94 (d, J=8.4 Hz, 1H), 7.74-7.62 (m, 1H), 7.59-7.58 (m, 2H), 7.31 (dd, J=7.2, 12.8 Hz, 1H), 4.29-4.05 (m, 6H), 3.69-3.66 (m, 2H), 2.94-2.89 (m, 2H), 2.59-2.51 (m, 2H), 1.89-1.77 (m, 10H), 1.61-1.58 (m, 2H); LCMS [ESI, M+H]: m/z=587.4.

Example 228

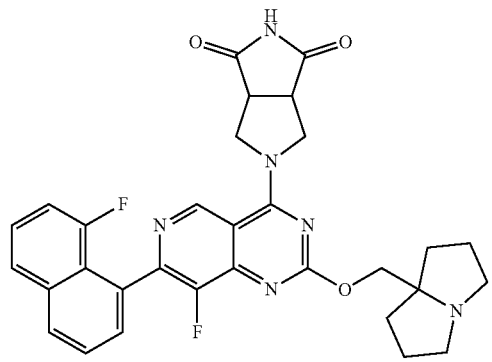 [SMILES: O=C1NC(=O)C2CN(c3nc(OCC45CCCN4CCC5)nc4c(F)c(-c5cccc6cccc(F)c56)ncc34)CC12]

5-(8-fluoro-7-(8-fluoronaphthalen-1-yl)-2-((hexahydro-1H-pyrrolizin-7a-yl) methoxy)pyrido[4,3-d]pyrimidin-4-yl)tetrahydropyrrolo[3,4-c]pyrrole-1,3(2H,3aH)-dione The title compound was synthesized according to the procedure described for example 84. ¹H NMR (400 MHz, METHANOL-d$_4$) δ=9.29 (s, 1H), 8.12 (br d, J=7.6 Hz, 1H), 7.85 (br d, J=8.0 Hz, 1H), 7.70 (br t, J=7.6 Hz, 1H), 7.61 (br d, J=7.2 Hz, 1H), 7.57-7.48 (m, 1H), 7.18 (br dd, J=7.6, 12.8 Hz, 1H), 4.64 (br d, J=13.2 Hz, 2H), 4.56 (s, 2H), 4.35 (br d, J=3.6 Hz, 2H), 3.78-3.76 (m, 2H), 3.60-3.47 (m, 2H), 3.20-3.07 (m, 2H), 2.26 (td, J=6.4, 12.4 Hz, 2H), 2.11 (ddd, J=6.4, 12.4, 18.8 Hz, 4H), 2.01 (br dd, J=6.4, 12.8 Hz, 2H) LCMS [ESI, M+1]: m/z=571.2

Example 229

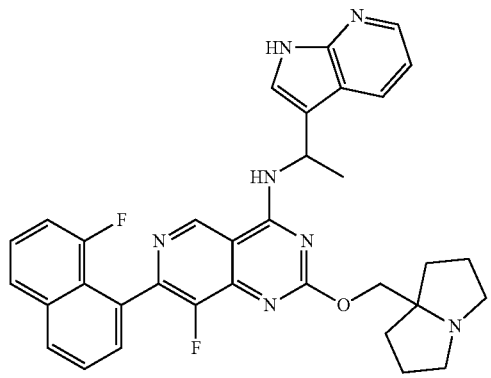 [SMILES: CC(Nc1nc(OCC23CCCN2CCC3)nc2c(F)c(-c3cccc4cccc(F)c34)ncc12)c1c[nH]c2ncccc12]

N-(1-(1H-pyrrolo[2,3-b]pyridin-3-yl)ethyl)-8-fluoro-7-(8-fluoronaphthalen-1-yl)-2-((tetrahydro-1H-pyrrolizin-7a(5H)-yl)methoxy)pyrido[4,3-d]pyrimidin-4-amine The title compound was synthesized according to the procedure described for example 84. $^1$H NMR (400 MHz, methanol-d4) δ 9.29 (d, J=3.2 Hz, 1H), 8.23-8.09 (m, 3H), 7.86 (d, J=8.2 Hz, 1H), 7.70 (td, J=4.4, 7.6 Hz, 1H), 7.62-7.49 (m, 2H), 7.23-7.07 (m, 2H), 6.10-6.00 (m, 11H), 4.64-4.51 (m, 2H), 3.64-3.52 (m, 2H), 3.24-3.14 (m, 2H), 2.29-1.95 (m, 8H), 1.86 (dd, J=3.2, 6.8 Hz, 3H); $^{19}$F NMR (376 MHz, methanol-d4) δ=−115.427, −141.83; LCMS [ESI, M+1, M/2+1]: m/z=592.3, 296.7.

Example 230

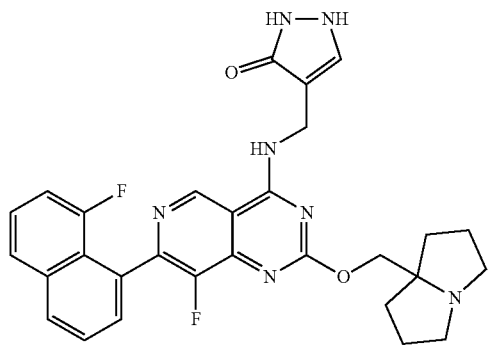 [SMILES: O=c1[nH][nH]cc1CNc1nc(OCC23CCCN2CCC3)nc2c(F)c(-c3cccc4cccc(F)c34)ncc12]

4-(((8-fluoro-7-(8-fluoronaphthalen-1-yl)-2-((hexahydro-1H-pyrrolizin-7a-yl)methoxy)pyrido[4,3-d]pyrimidin-4-yl)amino)methyl)-1H-pyrazol-3(2H)-one

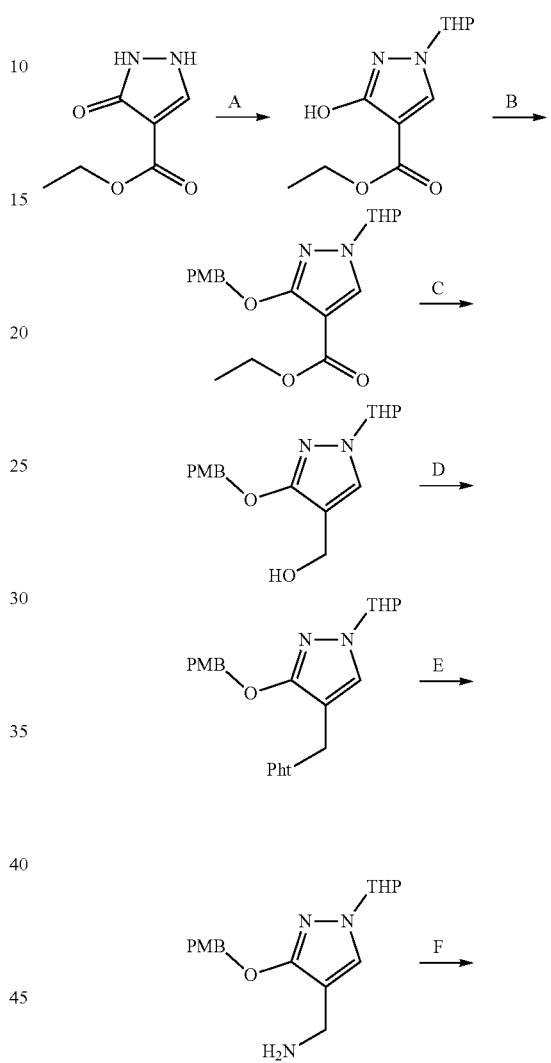

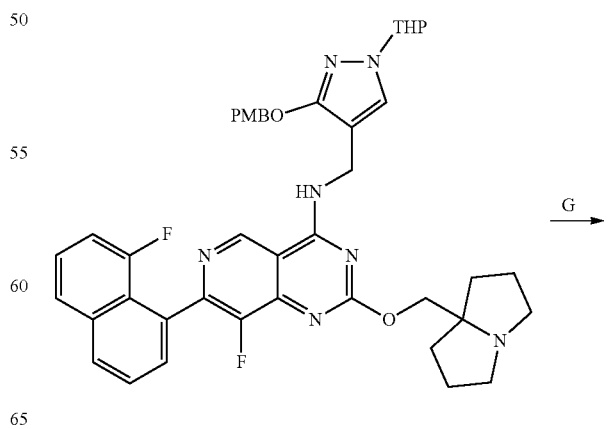

-continued

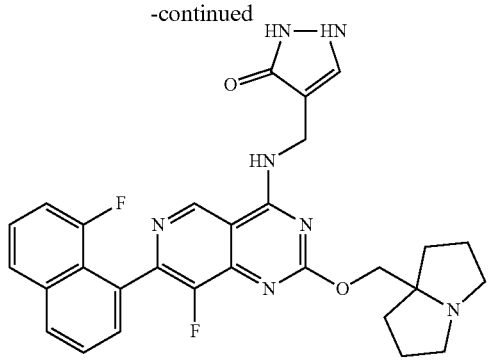

Step A. Ethyl 3-hydroxy-1-(tetrahydro-2H-pyran-2-yl)-1H-pyrazole-4-carboxylate: A mixture of ethyl 3-oxo-2,3-dihydro-1H-pyrazole-4-carboxylate (2 g, 1 equiv.) in DCM (20 mL), DHP (3.31 g, 3 equiv.), TosOH (220 mg, 0.1 equiv.) was stirred at 25° C. for 2 hours under $N_2$ atmosphere. The mixture was diluted with water (50 mL) and extracted with ethyl acetate (2×50 mL). The combined organic layers were washed with brine (50 mL), dried over sodium sulfate, concentrated and purified by silica gel column chromatography [petroleum ether/ethyl acetate] to afford the title compound (2.5 g, 80% yield) as a yellow solid; $^1$H NMR (400 MHz, DMSO-$d_6$) δ=10.42 (s, 1H), 8.10 (s, 1H), 5.20 (dd, J=2.4, 9.6 Hz, 1H), 4.15 (q, J=7.2 Hz, 2H), 3.92 (m, 1H), 3.65-3.50 (m, 1H), 1.99 (br s, 1H), 1.93-1.79 (m, 2H), 1.60 (m, 1H), 1.55-1.45 (m, 2H), 1.23 (t, J=7.2 Hz, 3H); LCMS (ESI, M+Na): m/z=263.0.

Step B. Ethyl 3-((4-methoxybenzyl)oxy)-1-(tetrahydro-2H-pyran-2-yl)-1H-pyrazole-4-carboxylate: To a mixture of ethyl 3-hydroxy-1-(tetrahydro-2H-pyran-2-yl)-1H-pyrazole-4-carboxylate (800 mg, 1 equiv.), $K_2CO_3$ (920 mg, 2 equiv.) in DMF (12 mL) was added PMBCl (626 mg, 1.2 equiv.). The mixture was stirred at 60° C. for 16 hours under $N_2$ atmosphere. The mixture was diluted with water (20 mL) and extracted with ethyl acetate (2×20 mL). The combined organic layers were washed with brine (20 mL), dried over sodium sulfate, concentrated and purified by silica gel column chromatography [petroleum ether/ethyl acetate] to afford the title compound (1.0 g, 75.6% yield) as a white solid; $^1$H NMR (400 MHz, DMSO-$d_6$) δ=8.25 (s, 1H), 7.40 (d, J=8.8 Hz, 2H), 6.95 (d, J=8.8 Hz, 2H), 5.28 (dd, J=2.4, 10.0 Hz, 1H), 5.16 (s, 2H), 4.15 (q, J=7.2 Hz, 2H), 3.97-3.89 (m, 1H), 3.76 (s, 3H), 3.64-3.56 (m, 1H), 2.13-2.02 (m, 1H), 1.96-1.83 (m, 2H), 1.70-1.57 (m, 1H), 1.56-1.48 (m, 2H), 1.25-1.19 (m, 3H); LCMS (ESI, M+1): m/z=361.1.

Step C. (3-((4-methoxybenzyl)oxy)-1-(tetrahydro-2H-pyran-2-yl)-1H-pyrazol-4-yl)methanol: To a solution of ethyl 3-((4-methoxybenzyl)oxy)-1-(tetrahydro-2H-pyran-2-yl)-1H-pyrazole-4-carboxylate (1 g, J equiv.) in THF (20 mL) was added LiAlH$_4$ (316 mg, 3 equiv.) at 0° C. and the mixture was stirred at 25° C. for 30 minutes. The mixture was quenched with saturated aqueous NH$_4$Cl (10 mL) and extracted with ethyl acetate (3×20 mL). The combined organic layers were washed with brine (20 mL), dried over Na$_2$SO$_4$ and concentrated to afford the title compound (0.7 g, 69.4% yield) as a white solid; $^1$HNMR (400 MHz, DMSO-$d_6$) δ=7.60 (s, 1H), 7.38 (d, J=8.8 Hz, 2H), 6.93 (d, J=8.8 Hz, 2H), 5.18-5.12 (m, 1H), 5.08 (s, 2H), 4.68 (s, 1H), 4.19 (d, J=5.2 Hz, 2H), 3.88 (br s, 1H), 3.75 (s, 3H), 3.61-3.53 (m, 1H), 2.09-2.00 (m, 1H), 1.91 (br d, J=1.6 Hz, 1H), 1.86-1.77 (m, 1H), 1.70-1.56 (m, 1H), 1.54-1.47 (m, 2H); LCMS (ESI, M+1): m/z=319.2.

Step D. 2-((3-((4-methoxybenzyl)oxy)-1-(tetrahydro-2H-pyran-2-yl)-1H-pyrazol-4-yl)methyl)isoindoline-1,3-dione: A solution of DIAD (381 mg, 1.5 equiv.), PPh$_3$ (494 mg, 1.5 equiv.) in THF (8 mL) was stirred at 0° C. for 30 minutes. A solution of (3-((4-methoxybenzyl)oxy)-1-(tetrahydro-2H-pyran-2-yl)-1H-pyrazol-4-yl)methanol (400 mg, 1 equiv.) and isoindoline-1,3-dione (277 mg, 1.5 equiv.) in THF (8 mL) was added at 0° C. and the mixture was stirred at 25° C. for 1 hour. The filtrate was diluted with water (15 mL) and extracted with ethyl acetate (2×15 mL). The combined organic layers were washed with brine (15 mL), dried over sodium sulfate, concentrated and purified by silica gel column chromatography [petroleum ether/ethyl acetate] to afford the title compound (150 mg, 22.1% yield) as a colorless oil; LCMS (ESI, M+Na): m/z=447.9.

Step E. (3-((4-methoxybenzyl)oxy)-1-(tetrahydro-2H-pyran-2-yl)-1H-pyrazol-4-yl)methanamine: A solution of 2-((3-((4-methoxybenzyl)oxy)-1-(tetrahydro-2H-pyran-2-yl)-1H-pyrazol-4-yl)methyl)isoindoline-1,3-dione (50 mg, 1 equiv.) and N$_2$H$_4$·H$_2$O (237 mg, 98% purity, 41 equiv.) in EtOH (1 mL) was stirred at 40° C. for 16 hours. The mixture was concentrated and triturated with ethyl acetate (10 mL) for 10 minutes to afford the title compound (30 mg, 82.1% yield) as a colorless oil; $^1$H NMR (400 MHz, DMSO-$d_6$) δ=8.92 (br s, 2H), 7.55 (s, 1H), 7.37 (d, J=8.4 Hz, 2H), 6.93 (d, J=8.4 Hz, 2H), 5.15-5.11 (m, 1H), 5.07 (s, 2H), 3.87 (br d, J=1.6 Hz, 1H), 3.75 (s, 3H), 3.61-3.52 (m, 1H), 3.40 (s, 2H), 2.07-1.92 (m, 2H), 1.86-1.79 (m, 1H), 1.69-1.58 (m, 1H), 1.54-1.45 (m, 2H); LCMS (ESI, M+1): m/z=318.2.

Step F. 8-fluoro-7-(8-fluoronaphthalen-1-yl)-2-((hexahydro-JH-pyrrolizin-7a-yl)methoxy)-N-((3-((4-methoxybenzyl)oxy)-1-(tetrahydro-2H-pyran-2-yl)-1H-pyrazol-4-yl)methyl)pyrido[4,3-d]pyrimidin-4-amine: A mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (40 mg, 1 equiv.), DIEA (39.0 mg, 4 equiv.), (3-((4-methoxybenzyl)oxy)-1-(tetrahydro-2H-pyran-2-yl)-1H-pyrazol-4-yl)methanamine (23.9 mg, 1 equiv.) and 4 Å molecular sieves (50 mg) in DMF (0.5 mL) was stirred at 40° C. for 16 hours under $N_2$ atmosphere. The mixture was filtered and purified by reverse phase flash chromatography to afford the title compound (25 mg, 35.1% yield) as a yellow oil; LCMS [ESI, M+1]: m/z=748.3.

Step G. 4-((8-fluoro-7-(8-fluoronaphthalen-1-yl)-2-((hexahydro-1H-pyrrolizin-7a-yl)methoxy)pyrido[4,3-d]pyrimidin-4-yl)amino)methyl)-1H-pyrazol-3(2H)-one: To a solution of 8-fluoro-7-(8-fluoronaphthalen-1-yl)-2-((hexahydro-1H-pyrrolizin-7a-yl)methoxy)-N-((3-((4-methoxybenzyl)oxy)-1-(tetrahydro-2H-pyran-2-yl)-1H-pyrazol-4-yl)methyl)pyrido[4,3-d]pyrimidin-4-amine (20 mg, 1 equiv.) in DCM (1 mL) was added TFA (770 mg, 252 equiv.) at 0° C. and the mixture was stirred at 20° C. for 16 hours under $N_2$ atmosphere. The mixture was concentrated and purified by prep-HPLC [column: Phenomenex luna C18 150×25 mm×10 μm; mobile phase: [water (0.225% formic acid)/ACN]; B %: 14%-44%, 10 minutes] to afford the title compound (10.5 mg, 63.6% yield) as a white solid. $^1$HNMR (400 MHz, METHANOL-$d_4$) δ=9.19 (s, 1H), 8.11 (br d, J=8.4 Hz, 1H), 7.85 (d, J=8.4 Hz, 1H), 7.69 (t, J=7.6 Hz, 1H), 7.59 (dd, J=1.2, 7.2 Hz, 1H), 7.56-7.47 (m, 2H), 7.18 (dd, J=7.6, 13.2 Hz, 1H), 4.71 (s, 2H), 4.56 (s, 2H), 3.75 (m, 2H), 3.31-3.26 (m, 2H), 2.40-2.31 (m, 2H), 2.29-2.16 (m, 4H), 2.11 (m, 2H); LCMS (ESI, M+1): m/z=544.2.

Example 231

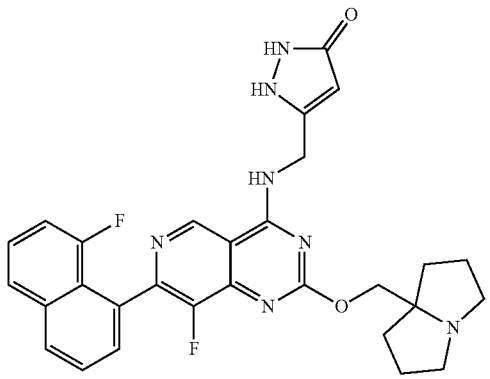 [SMILES: O=c1cc(CNc2nc(OCC34CCCN3CCC4)nc3c(F)c(-c4cccc5cccc(F)c45)ncc23)[nH][nH]1]

5-(((8-fluoro-7-(8-fluoronaphthalen-1-yl)-2-((hexa-hydro-1H-pyrrolizin-7a-yl)methoxy)pyrido[4,3-d]pyrimidin-4-yl)amino)methyl)-1H-pyrazol-3(2H)-one The title compound was synthesized according to the procedure described for example 85. $^1$H NMR (400 MHz, DMSO-d$_6$) δ=11.78-11.35 (m, 1H), 9.79-9.16 (m, 3H), 8.17 (br d, J=8.0 Hz, 1H), 7.93 (d, J=8.0 Hz, 1H), 7.76-7.70 (m, 1H), 7.63-7.55 (m, 2H), 7.30 (dd, J=7.6, 13.2 Hz, 1H), 5.65-5.23 (m, 1H), 4.70 (br s, 2H), 4.06 (s, 2H), 2.95-2.89 (m, 2H), 2.56-2.52 (m, 2H), 1.92-1.84 (mi, 2H), 1.82-1.71 (m, 4H), 1.60-1.52 (m, 2H); $^{19}$F NMR (400 MHz, DMSO-d$_6$) δ−113.230, −141.701; LCMS (ESI, M+1): m/z=544.3.

Example 232

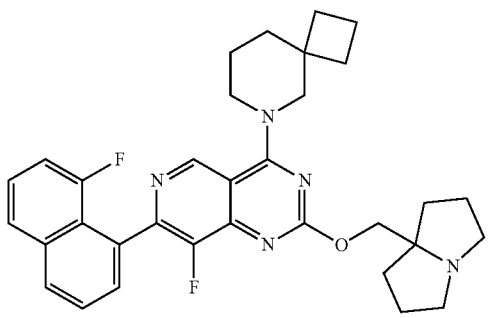 [SMILES: Fc1c(-c2cccc3cccc(F)c23)ncc2c(N3CCCC4(CCC4)C3)nc(OCC34CCCN3CCC4)nc12]

8-fluoro-7-(8-fluoronaphthalen-1-yl)-2-((hexahydro-1H-pyrrolizin-7a-yl)methoxy)-4-(6-azaspiro[3.5]nonan-6-yl)pyrido[4,3-d]pyrimidine The title compound was synthesized according to the procedure described for example 84. $^1$HNMR (400 MHz, METHANOL-d$_4$) δ=9.10 (s, 1H), 8.12 (br d, J=8.0 Hz, 1H), 7.86 (d, J=8.4 Hz, 1H), 7.74-7.67 (m, 1H), 7.62 (d, J=7.2 Hz, 1H), 7.57-7.50 (m, 1H), 7.19 (dd, J=7.6, 13.2 Hz, 1H), 4.56 (s, 2H), 4.13-3.93 (m, 4H), 3.51 (br s, 2H), 3.18-3.06 (m, 2H), 2.30-2.21 (m, 2H), 2.20-2.05 (m, 4H), 2.04-1.93 (m, 4H), 1.90-1.76 (m, 8H) LCMS [ESI, M+1]: m/z=556.4

Example 233

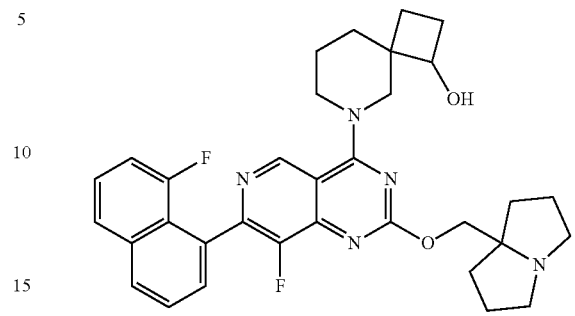

6-(8-fluoro-7-(8-fluoronaphthalen-1-yl)-2-((tetra-hydro-1H-pyrrolizin-7a(5H)-yl)methoxy)pyrido[4,3-d]pyrimidin-4-yl)-6-azaspiro[3.5]nonan-1-ol The title compound was synthesized according to the procedure described for example 85. $^1$H NMR (400 MHz, methanol-d4) δ 9.13-9.02 (m, 1H), 8.11 (br d, J=8.4 Hz, 1H), 7.85 (d, J=8.0 Hz, 1H), 7.73-7.67 (m, 1H), 7.61 (br d, J=7.2 Hz, 1H), 7.53 (dt, J=4.8, 8.0 Hz, 1H), 7.19 (br dd, J=7.6, 13.2 Hz, 1H), 4.49-4.37 (m, 0.5H), 4.35-4.27 (m, 2H), 4.21-3.80 (m, 4.5H), 3.16-3.06 (m, 2H), 2.79-2.66 (m, 2H), 2.31-2.21 (m, 1H), 2.13-1.82 (m, 10H), 1.81-1.59 (m, 4H), 1.53-1.31 (m, 1H); LCMS [ESI, M+1]: 572.3.

Example 234

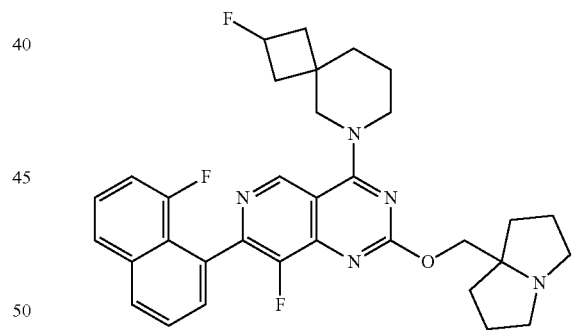

8-fluoro-4-(2-fluoro-6-azaspiro[3.5]nonan-6-yl)-7-(8-fluoronaphthalen-1-yl)-2-((hexahydro-1H-pyrrolizin-7a-yl)methoxy)pyrido[4,3-d]pyrimidine The title compound was synthesized according to the procedure described for example 84. $^1$H NMR (400 MHz, METHANOL-d$_4$) δ=9.05 (d, J=8.4 Hz, 1H), 8.12 (d, J=8.4 Hz, 1H), 7.86 (d, J=8.0 Hz, 1H), 7.71 (t, J=7.6 Hz, 1H), 7.68 (d, J=8.0 Hz, 1H), 7.54-7.49 (m, 11H), 7.25-7.21 (m, 1H), 5.26-5.00 (m, 1H), 4.34 (d, J=16.0 Hz, 2H), 4.11-3.95 (m, 4H), 3.40-3.12 (m, 2H), 2.85-2.70 (m, 2H), 2.50-2.35 (m, 1H), 2.27-2.22 (m, 1H), 2.18-2.05 (m, 3H), 2.04-1.75 (m, 11H); LCMS (ESI, M+1): m/z=574.4.

Example 235

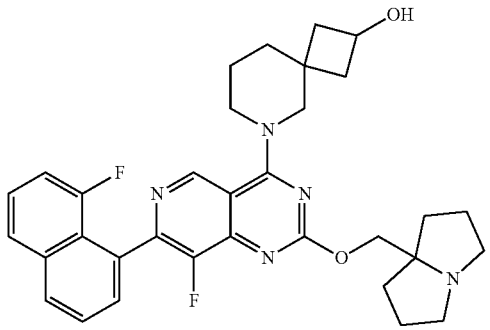 [SMILES: OC1CC2(CCCN(c3nc(OCC45CCCN4CCC5)nc4c(F)c(-c5cccc6cccc(F)c56)ncc34)C2)C1]

6-(8-fluoro-7-(8-fluoronaphthalen-1-yl)-2-((hexa-hydro-1H-pyrrolizin-7a-yl)methoxy)pyrido[4,3-d]pyrimidin-4-yl)-6-azaspiro[3.5]nonan-2-ol The title compound was synthesized according to the procedure described for example 84. $^1$H NMR (400 MHz, METHANOL-d$_4$) δ 9.09 (d, J=6.8 Hz, 1H), 8.54 (s, 1H), 8.12 (br d, J=8.0 Hz, 1H), 7.86 (d, J=8.4 Hz, 1H), 7.74-7.67 (m, 1H), 7.62 (d, J=6.8 Hz, 1H), 7.53 (dt, J=5.2, 8.0 Hz, 1H), 7.19 (dd, J=7.6, 12.8 Hz, 1H), 4.54 (d, J=8.0 Hz, 2H), 4.40-4.20 (m, 1H), 4.17-3.92 (m, 4H), 3.60-3.42 (m, 2H), 3.21-2.98 (m, 2H), 2.38-2.19 (m, 4H), 2.10 (tdd, J=6.8, 13.2, 19.6 Hz, 4H), 2.03-1.94 (m, 2H), 1.88-1.77 (m, 5H), 1.77-1.66 (m, 1H); LCMS [ESI, M+1]: m/z=572.2.

Example 236

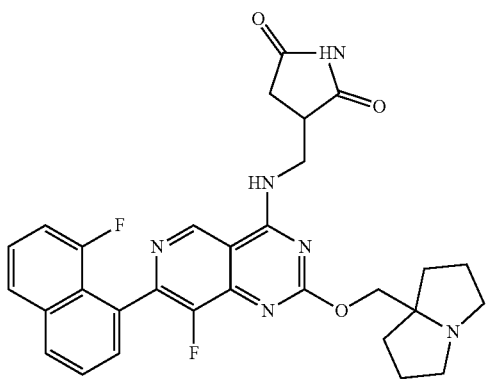 [SMILES: O=C1CC(CNc2nc(OCC34CCCN3CCC4)nc3c(F)c(-c4cccc5cccc(F)c45)ncc23)C(=O)N1]

3-(((8-fluoro-7-(8-fluoronaphthalen-1-yl)-2-((hexa-hydro-1H-pyrrolizin-7a-yl)methoxy)pyrido[4,3-d]pyrimidin-4-yl)amino)methyl)pyrrolidine-2,5-dione The title compound was synthesized according to the procedure described for example 85. $^1$H NMR (400 MHz, METHANOL-d$_4$) δ=9.19 (s, 1H), 8.11 (d, J=8.4 Hz, 1H), 7.86 (d, J=8.0 Hz, 1H), 7.76 (t, J=7.6 Hz, 1H), 7.60 (d, J=7.2 Hz, 1H), 7.54-7.52 (m, 1H), 7.21-7.18 (m, 1H), 4.61-4.59 (m, 2H), 4.24-4.12 (m, 1H), 4.05-3.90 (m, 1H), 3.60-3.40 (m, 3H), 3.20-3.08 (m, 2H), 3.00-2.88 (m, 1H), 2.80-2.62 (m, 1H), 2.40-2.27 (m, 2H), 2.21-2.07 (m, 4H), 2.04-1.90 (m, 2H); LCMS (ESI, M+1): m/z=559.2.

Example 237

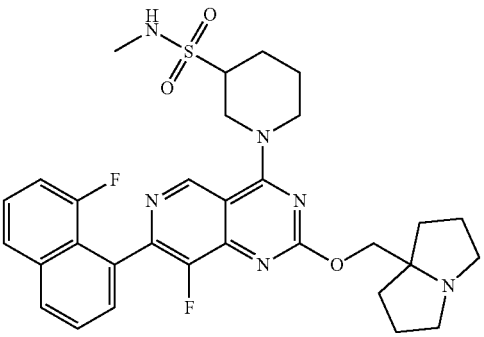 [SMILES: CNS(=O)(=O)C1CCCN(c2nc(OCC34CCCN3CCC4)nc3c(F)c(-c4cccc5cccc(F)c45)ncc23)C1]

1-(8-fluoro-7-(8-fluoronaphthalen-1-yl)-2-((hexa-hydro-1H-pyrrolizin-7a-yl)methoxy)pyrido[4,3-d]pyrimidin-4-yl)-N-methylpiperidine-3-sulfonamide The title compound was synthesized according to the procedure described for example 84. $^1$H NMR (400 MHz, methanol-d4) δ=9.13 (s, 1H), 8.12 (br d, J=8.0 Hz, 1H), 7.86 (d, J=8.0 Hz, 1H), 7.70-7.68 (m, 1H), 7.63-7.60 (m, 1H), 7.53 (dt, J=5.2, 8.0 Hz, 1H), 7.21-7.18 (m, 1H), 4.95 (br d, J=12.4 Hz, 1H), 4.56 (s, 3H), 3.69-3.68 (m, 3H), 3.47-3.45 (m, 2H), 3.09-3.06 (m, 2H), 2.79 (d, J=2.4 Hz, 3H), 2.24-2.22 (m, 3H), 2.12-1.97 (m, 8H), 1.86-1.75 (m, 1H). LCMS [ESI, M+1]: m/z=609.3.

Example 238

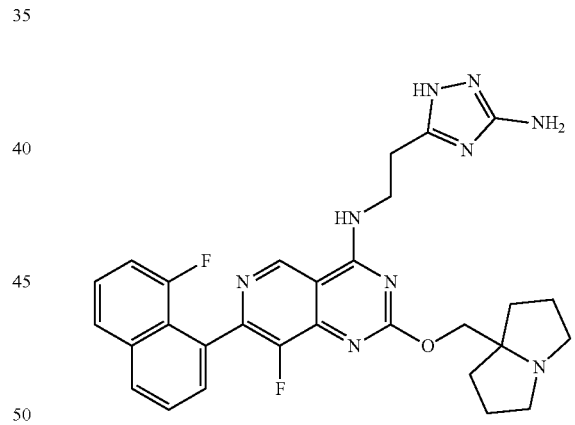

N-(2-(3-amino-1H-1,2,4-triazol-5-yl)ethyl)-8-fluoro-7-(8-fluoronaphthalen-1-yl)-2-((hexahydro-1H-pyr-rolizin-7a-yl)methoxy)pyrido[4,3-d]pyrimidin-4-amine The title compound was synthesized according to the procedure described for example 84. $^1$NMR (400 MHz, METHANOL-d$_4$) δ=9.16 (s, 1H), 8.53 (br s, 1H), 8.12 (br d, J=8.8 Hz, 1H), 7.86 (d, J=7.6 Hz, 1H), 7.70 (dd, J=7.2, 8.4 Hz, 1H), 7.61-7.49 (m, 2H), 7.19 (ddd, J=1.2, 7.6, 13.2 Hz, 1H), 4.63 (d, J=1.2 Hz, 2H), 4.01 (dt, J=2.8, 6.8 Hz, 2H), 3.71-3.60 (m, 2H), 3.27-3.19 (m, 2H), 3.00 (t, J=6.8 Hz, 2H), 2.33 (br dd, J=6.4, 12.4 Hz, 2H), 2.25-2.13 (m, 4H), 2.09 (br dd, J=6.4, 12.4 Hz, 2H) LCMS [ESI, M+1]: m/z=558.4

Example 239

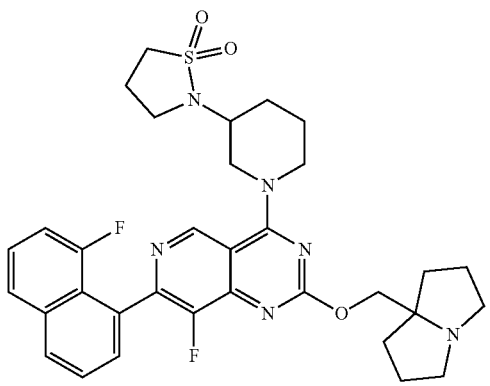 [SMILES: O=S1(=O)CCCN1C1CCCN(c2nc(OCC34CCCN3CCC4)nc3c(F)c(-c4cccc5cccc(F)c45)ncc23)C1]

2-(1-(8-fluoro-7-(8-fluoronaphthalen-1-yl)-2-((hexa-hydro-1H-pyrrolizin-7a-yl)methoxy)pyrido[4,3-d]pyrimidin-4-yl)piperidin-3-yl)isothiazolidine 1,1-dioxide The title compound was synthesized according to the procedure described for example 84. $^1$H NMR (400 MHz, METHANOL-d$_4$) δ=9.13 (d, J=3.2 Hz, 1H), 8.12 (d, J=8.4 Hz, 1H), 7.86 (d, J=8.4 Hz, 1H), 7.70 (dt, J=8.0, 3.6 Hz, 1H), 7.66-7.57 (m, 1H), 7.53 (dt, J=8.0, 4.8 Hz, 1H), 7.19 (ddd, J=12.4 Hz, 7.6, 4.8, 1H), 4.93 (d, J=10.8 Hz, 1H), 4.69-4.56 (m, 2H), 4.47 (dd, J=11.6, 6.6 Hz, 1H), 3.88-3.77 (m, 1H), 3.69-3.58 (m, 1H), 3.53-3.37 (m, 5H), 3.28-3.17 (m, 2H), 3.06-2.97 (m, 2H), 2.39 (quin, J=7.0 Hz, 2H), 2.31-2.22 (m, 2H), 2.13-2.03 (m, 5H), 2.00 (d, J=11.6 Hz, 2H), 1.97-1.87 (m, 2H), 1.84-1.70 (m, 1H); $^{19}$F NMR (377 MHz, CD3OD) δ−115.32, −141.27; LCMS: [ESI, M+1]$^+$: 635.5.

Example 240

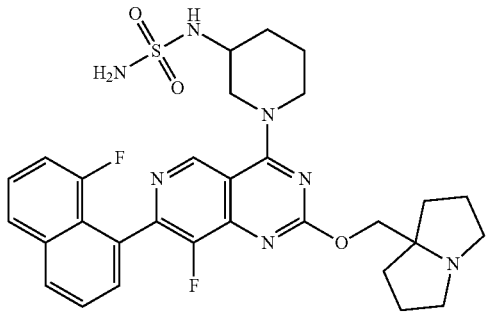 [SMILES: NS(=O)(=O)NC1CCCN(c2nc(OCC34CCCN3CCC4)nc3c(F)c(-c4cccc5cccc(F)c45)ncc23)C1]

8-fluoro-7-(8-fluoronaphthalen-1-yl)-2-(1,2,3,5,6,7-hexahydropyrrolizin-8-ylmethoxy)-4-[3-(sulfamoy-lamino)piperidin-1-yl]pyrido[4,3-d]pyrimidine The title compound was synthesized according to the procedure described for example 84. $^1$H NMR (400 MHz, METHANOL-d$_4$) δ=9.18 (s, 1H), 8.56 (s, 1H), 8.14 (br d, J=8.4 Hz, 1H), 7.88 (d, J=8.4 Hz, 1H), 7.78-7.69 (m, 1H), 7.63 (dd, J=7.2, 10.2 Hz, 1H), 7.55 (dt, J=5.2, 8.0 Hz, 1H), 7.21 (ddd, J=2.8, 7.6, 12.8 Hz, 1H), 4.78 (br d, J=16.4 Hz, 1H), 4.68-4.54 (m, 2H), 4.53-4.40 (m, 1H), 3.80-3.63 (m, 2H), 3.61-3.45 (m, 3H), 3.19-3.04 (m, 2H), 2.35-2.23 (m, 2H), 2.22-2.05 (m, 5H), 2.05-1.93 (m, 3H), 1.84-1.70 (m, 2H); LCMS (ESI, M+1): m/z=610.4.

Example 241

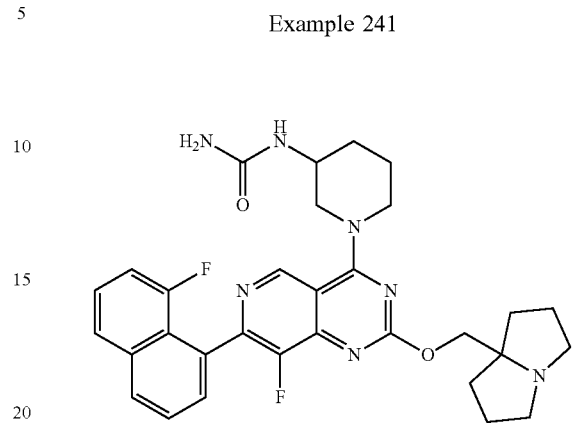

1-(1-(8-fluoro-7-(8-fluoronaphthalen-1-yl)-2-((hexa-hydro-1H-pyrrolizin-7a-yl)methoxy)pyrido[4,3-d]pyrimidin-4-yl)piperidin-3-yl)urea The title compound was synthesized according to the procedure described for example 84. $^1$H NMR (400 MHz, METHANOL-d$_4$) δ=9.18 (d, J=1.6 Hz, 1H), 8.12 (br d, J=8.4 Hz, 1H), 7.86 (d, J=8.4 Hz, 1H), 7.73-7.67 (m, 1H), 7.65-7.59 (m, 1H), 7.53 (dt, J=4.8, 8.0 Hz, 1H), 7.19 (dd, J=7.6, 12.8 Hz, 1H), 4.72-4.64 (m, 1H), 4.63-4.56 (m, 1H), 4.55-4.43 (m, 1H), 4.42-4.29 (m, 1H), 3.96-3.74 (m, 2H), 3.73-3.54 (m, 3H), 3.25-3.15 (m, 2H), 2.37-2.26 (m, 2H), 2.24-2.11 (m, 4H), 2.11-1.93 (m, 4H), 1.89-1.66 (m, 2H); LCMS [ESI, M+1]: m/z=574.4.

Example 242

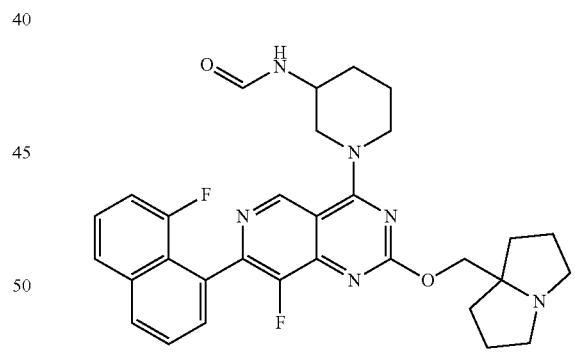

N-(1-(8-fluoro-7-(8-fluoronaphthalen-1-yl)-2-((hexa-hydro-1H-pyrrolizin-7a-yl)methoxy)pyrido[4,3-d]pyrimidin-4-yl)piperidin-3-yl)formamide

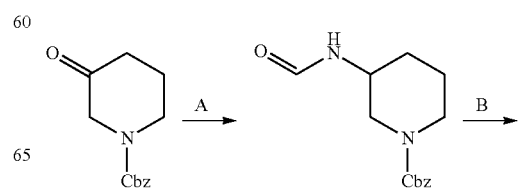

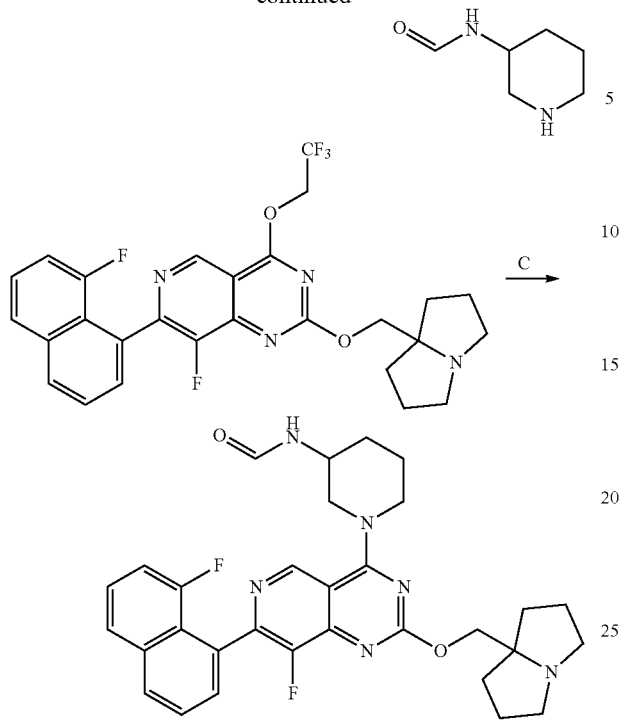

Step A. Benzyl 3-formamidopiperidine-1-carboxylate: A mixture of benzyl 3-oxopiperidine-1-carboxylate (500 mg, 1.0 equiv.), formamide (2.49 g, 25.7 equiv.), ammonium formate (3.30 g, 24.4 equiv.) and formic acid (2.44 g, 2 mL, 98% purity, 24.2 equiv.) was stirred at 160° C. for 7 hours. The reaction mixture was diluted with water (20.0 mL), and then was extracted with ethyl acetate (30 mL×2). The combined organic layers were dried over anhydrous sodium sulfate, filtered and concentrated in vacuum. The crude product was purified by reversed phase flash chromatography (water (0.1% formic acid)-ACN) to afford the title compound (198 mg, 34% yield) as a yellow oil; $^1$H NMR (400 MHz, DMSO-$d_6$) δ=8.12 (br d, J=6.4 Hz, 1H), 7.96 (s, 1H), 7.47-7.25 (m, 5H), 5.16-4.99 (m, 2H), 3.85-3.45 (m, 3H), 3.16-2.74 (m, 2H), 1.87-1.60 (m, 2H), 1.52-1.30 (m, 2H); LCMS (ESI, M+1): m/z=263.0.

Step B. N-(piperidin-3-yl)formamide: To a solution of benzyl 3-formamidopiperidine-1-carboxylate (140 mg, 1.0 equiv.) in MeOH (10 mL) was added NH$_3$·MeOH (1 mL, 20% purity) and Pd/C (10.0 mg, 10% purity) under N$_2$. The suspension was degassed in vacuum and purged with H$_2$ several times. The mixture was stirred under H$_2$ (15 psi) at 15° C. for 1 hour. The mixture was filtered and the filtrate was concentrated in vacuum to afford the title compound (77.0 mg, crude) as a colorless solid.

Step C. N-(1-(8-fluoro-7-(8-fluoronaphthalen-1-yl)-2-((hexahydro-1H-pyrrolizin-7a-yl)methoxy)pyrido[4,3-d]pyrimidin-4-yl)piperidin-3-yl)formamide: A mixture of N-(piperidin-3-yl)formamide (72.5 mg, 2.0 equiv.), DIEA (110 mg, 3.0 equiv.) and 4 Å molecular sieves (100 mg) in DMF (5 mL) was stirred at 15° C. for 0.5 hour. Then to the mixture was added 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (150 mg, 1.0 equiv.) at 15° C. The mixture was stirred at 40° C. for 14 hours. The mixture was diluted with water (10 mL) and extracted with ethyl acetate (15 mL). The organic layer was washed with water (2×10 mL), dried over sodium sulfate, filtered and concentrated in vacuum. The residue was purified by prep-HPLC (column: Phenomenex Luna C18 150×25 mm×10 μm; mobile phase: water (0.225% formic acid, v/v)/ACN]B %: 16%-46%, 10 min) and lyophilized to afford the title compound (66.2 mg, 38% yield) as a white solid; $^1$H NMR (400 MHz, DMSO-$d_6$) δ=9.16 (d, J=3.2 Hz, 1H), 8.35 (br d, J=7.6 Hz, 1H), 8.26 (s, 1H), 8.18 (br d, J=8.4 Hz, 1H), 8.02 (s, 1H), 7.93 (d, J=8.0 Hz, 1H), 7.74 (dt, J=2.4, 8.0 Hz, 1H), 7.68-7.55 (m, 2H), 7.36-7.25 (m, 1H), 4.32-4.13 (m, 4H), 4.09-3.99 (m, 1H), 3.68-3.44 (m, 2H), 3.08-2.97 (m, 2H), 2.72-2.59 (m, 2H), 2.02-1.89 (m, 4H), 1.88-1.73 (m, 5H), 1.71-1.59 (m, 3H); LCMS (ESI, M+1): m/z=559.3.

Example 243

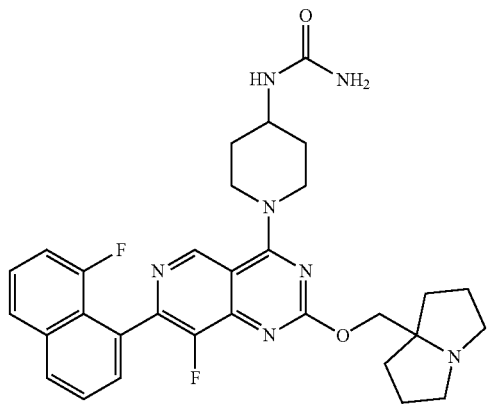 [SMILES: NC(=O)NC1CCN(c2nc(OCC34CCCN3CCC4)nc3c(F)c(-c4cccc5cccc(F)c45)ncc23)CC1]

1-(1-(8-fluoro-7-(8-fluoronaphthalen-1-yl)-2-((hexahydro-1H-pyrrolizin-7a-yl)methoxy)pyrido[4,3-d]pyrimidin-4-yl)piperidin-4-yl)urea The title compound was synthesized according to the procedure described for example 84. $^1$H NMR (400 MHz, METHANOL-$d_4$) δ=9.09 (s, 1H), 8.12 (br d, J=8.4 Hz, 1H), 7.86 (d, J=8.4 Hz, 1H), 7.75-7.67 (m, 1H), 7.61 (d, J=6.8 Hz, 1H), 7.53 (dt, J=5.2, 8.0 Hz, 1H), 7.19 (dd, J=7.6, 13.2 Hz, 1H), 4.70-4.53 (m, 4H), 3.99-3.85 (m, 1H), 3.68-3.51 (m, 4H), 3.18 (td, J=6.0, 11.6 Hz, 2H), 2.37-2.22 (m, 2H), 2.20-1.96 (m, 8H), 1.68 (q, J=11.2 Hz, 2H); LCMS [ESI, M+1]: m/z=574.4.

Example 244

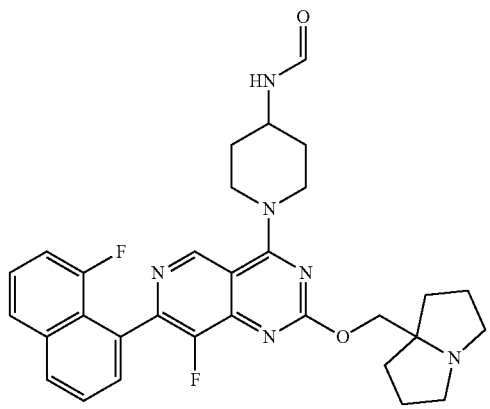 [SMILES: O=CNC1CCN(c2nc(OCC34CCCN3CCC4)nc3c(F)c(-c4cccc5cccc(F)c45)ncc23)CC1]

N-(1-(8-fluoro-7-(8-fluoronaphthalen-1-yl)-2-((hexa-hydro-1H-pyrrolizin-7a-yl)methoxy)pyrido[4,3-d]pyrimidin-4-yl)piperidin-4-yl)formamide The title compound was synthesized according to the procedure described for example 84. $^1$H NMR (400 MHz, DMSO-$d_6$) δ=9.09 (s, 1H), 8.27-8.16 (m, 3H), 8.02 (s, 1H), 7.94 (d, J=8.4 Hz, 1H), 7.78-7.70 (m, 1H), 7.66-7.55 (m, 2H), 7.31 (dd, J=7.6, 13.2 Hz, 1H), 4.53-4.39 (m, 2H), 4.20 (s, 2H), 4.13-4.00 (m, 1H), 3.57 (br t, J=11.2 Hz, 2H), 3.18-3.02 (m, 2H), 2.77-2.64 (m, 2H), 2.04-1.93 (m, 4H), 1.92-1.77 (m, 4H), 1.72-1.55 (m, 4H); LCMS (ESI, M+1): m/z=559.3.

Example 245

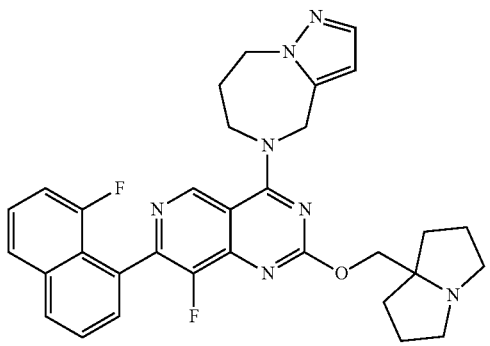 [SMILES: Fc1c(-c2cccc3cccc(F)c23)ncc2c(N3CCCn4nccc4C3)nc(OCC34CCCN3CCC4)nc12]

4-(7,8-dihydro-4H-pyrazolo[1,5-a][1,4]diazepin-5(6H)-yl)-8-fluoro-7-(8-fluoronaphthalen-1-yl)-2-((hexahydro-1H-pyrrolizin-7a-yl)methoxy)pyrido[4,3-d]pyrimidine The title compound was synthesized according to the procedure described for example 84. $^1$H NMR (400 MHz, CD3OD-$d_6$) δ=9.19 (s, 1H), 8.12 (d, J=8.4 Hz, 1H), 7.85 (d, J=8.4 Hz, 1H), 7.73-7.67 (m, 1H), 7.61 (d, J=7.2 Hz, 1H), 7.53 (dt, J=8.0, 5.2 Hz, 1H), 7.42 (d, J=2.0 Hz, 1H), 7.19 (dd, J=13.2, 8.0 Hz, 1H), 6.48 (d, J=1.6 Hz, 1H), 5.34-5.18 (m, 2H), 4.55-4.49 (m, 2H), 4.42 (t, J=5.2 Hz, 2H), 4.32 (s, 2H), 3.21-3.13 (m, 2H), 2.85-2.74 (m, 2H), 2.45-2.37 (m, 2H), 2.08 (dd, J=12.4, 6.8 Hz, 2H), 2.01-1.87 (m, 4H), 1.84-1.75 (m, 2H); $^{19}$F NMR (377 MHz, CD$_3$OD) δ=-115.18, -140.71; LCMS (ESI, M+1): m/z=568.3.

Example 246

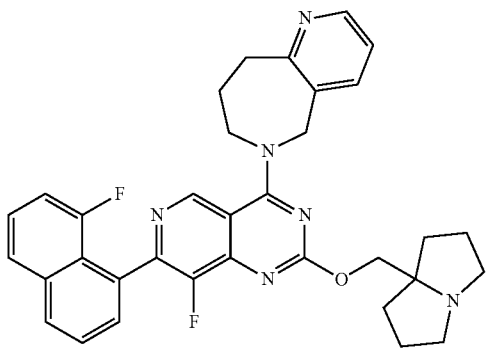 [SMILES: Fc1c(-c2cccc3cccc(F)c23)ncc2c(N3CCCc4ncccc4C3)nc(OCC34CCCN3CCC4)nc12]

6-(8-fluoro-7-(8-fluoronaphthalen-1-yl)-2-((hexa-hydro-1H-pyrrolizin-7a-yl)methoxy)pyrido[4,3-d]pyrimidin-4-yl)-6,7,8,9-tetrahydro-5H-pyrido[3,2-c]azepine The title compound was synthesized according to the procedure described for example 84. $^1$H NMR (400 MHz, CD$_{30}$D) δ=9.14 (s, 1H), 8.36 (dd, J=4.8, 1.2 Hz, 1H), 8.11 (br d, J=8.4 Hz, 1H), 7.99 (d, J=6.8 Hz, 1H), 7.85 (d, J=8.4 Hz, 1H), 7.73-7.64 (m, 1H), 7.64-7.57 (m, 1H), 7.53 (dt, J=7.6, 4.8 Hz, 1H), 7.32 (dd, J=7.6, 4.8 Hz, 1H), 7.19 (dd, J=12.8, 7.6 Hz, 1H), 5.34-5.14 (m, 2H), 4.49-4.37 (m, 2H), 4.33-4.22 (m, 2H), 3.29-3.20 (m, 4H), 2.93-2.84 (m, 2H), 2.41-2.31 (m, 2H), 2.15-1.81 (m, 8H); $^{19}$F NMR (377 MHz, CD$_{30}$D) δ=-115.23. -140.94; LCMS (ESI, M+1): m/z=579.2.

Example 247

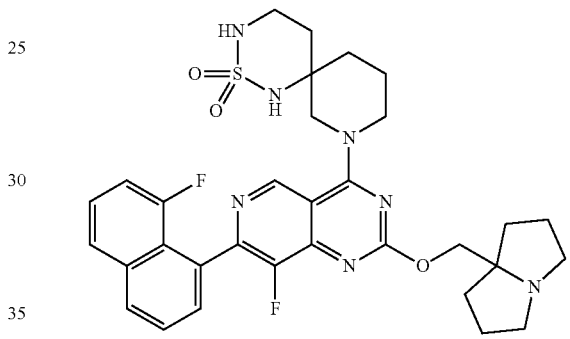

8-(8-fluoro-7-(8-fluoronaphthalen-1-yl)-2-((hexa-hydro-1H-pyrrolizin-7a-yl)methoxy) pyrido[4,3-d]pyrimidin-4-yl)-2-thia-1,3,8-triazaspiro[5.5]unde-cane 2,2-dioxide

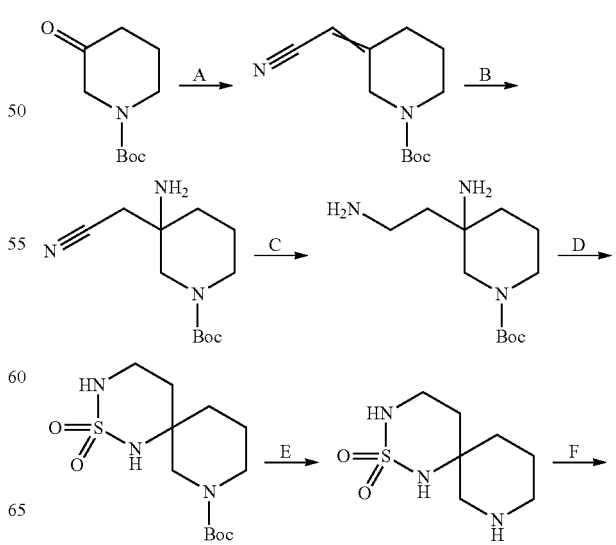

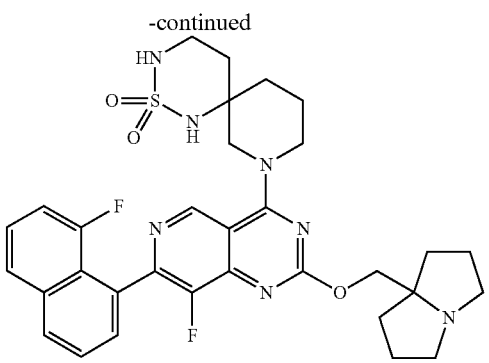

Step A. Tert-butyl 3-(cyanomethylene)piperidine-1-carboxylate: To a solution of 2-diethoxyphosphorylacetonitrile (10.7 g, 1.20 equiv.) in 2-MeTHF (45 mL) was added K$_2$CO$_3$ (8.32 g, 1.20 equiv.). The mixture was stirred at 20° C. for 1 hours, then tert-butyl 3-oxopiperidine-1-carboxylate (10.0 g, 50.2 mmol, 1.0 equiv.) was added to the mixture. The mixture was stirred at 70° C. for 13 hours. After completion, the reaction mixture was diluted with water (40 ml.) and extracted with ethyl acetate (20 mL×3). The combined organic layers were washed with brine (20.00 mL×2), dried over Na$_2$SO$_4$, concentrated and purified by silica gel column chromatography [Petroleum ether/Ethyl acetate 5:1 to 4:1] to afford the title compound (9.0 g, 81% yield) as a yellow oil; $^1$H NMR (400 MHz, CDCl$_3$) δ=5.24-5.15 (m, 1H), 4.25-3.97 (m, 2H), 3.51-3.47 (m, 2H), 2.64-2.38 (m, 2H), 1.76-1.71 (m, 2H), 1.48-1.44 (m, 9H).

Step B. tert-butyl 3-amino-3-(cyanomethyl)piperidine-1-carboxylate: The mixture of tert-butyl 3-(cyanomethylene)piperidine-1-carboxylate (4.0 g, 1.0 equiv.) and NH$_4$OH (20.0 g, 21.98 mL, 30% purity, 9.51 equiv.) in MeOH (6.00 mL) was stirred at 90° C. for 4 hours in a sealed tube. After completion, the mixture was concentrated to remove MeOH and then the residue was extracted with ethyl acetate (120 mL×3). The combined organic phase was washed with brine (100 mL×3), dried with anhydrous Na$_2$SO$_4$, concentrated and purified by silica gel column chromatography [petroleum ether/ethyl acetate 1:0 to 1:10 then dichloromethane/methyl alcohol 10:1] to afford the title compound (550 mg, 13% yield) as a yellow oil. $^1$H NMR (400 MHz, CD3OD) δ=3.56-3.52 (m, 2H), 3.32-3.00 (m, 2H), 2.65-2.54 (m, 2H), 1.80-1.71 (m, 2H), 1.66-1.53 (m, 2H), 1.49 (s, 9H).

Step C. tert-butyl 3-amino-3-(2-aminoethyl)piperidine-1-carboxylate: A mixture of tert-butyl 3-amino-3-(cyanomethyl)piperidine-1-carboxylate (200 mg, 1.0 equiv.), NH$_4$OH (97.6 mg, 107 µL, 30% purity, 1.0 equiv.) and Raney Nickel (7.16 mg, 0.10 equiv.) in MeOH (5 mL) was stirred at 35° C. for 12 hours under H$_2$ (50 psi). After completion, the mixture was filtered and concentrated to afford the title compound (160 mg, 79% yield) as a yellow gum; $^1$H NMR (400 MHz, CD3OD) δ=3.32-3.21 (m, 2H), 3.20-2.95 (m, 2H), 2.69-2.66 (m, 2H), 1.39-1.36 (m, 15H).

Step D. tert-butyl 2-thia-1,3,8-triazaspiro[5.5]undecane-8-carboxylate 2,2-dioxide: A mixture of tert-butyl 3-amino-3-(2-aminoethyl)piperidine-1-carboxylate (160 mg, 1.00 equiv.) and sulfamide (94.8 mg, 1.50 equiv.) in pyridine (0.30 mL) was stirred at 110° C. for 12 hours under N$_2$ atmosphere. After completion, the mixture was concentrated and purified by prep-HPLC [column: Phenomenex luna CIS 150×25 mm×10 um; mobile phase: [water (0.225% formic acid)/ACN]; B %: 22%-52%, 10 min] to afford the title compound (80.0 mg, 40% yield) as a yellow gum; $^1$H NMR (400 MHz, CD3OD) δ=4.22-4.12 (m, 1H), 3.62-3.56 (m, 2H), 3.48-3.42 (m, 1H), 3.16-3.12 (m, 2H), 1.95-1.41 (m, 15H).

Step E. 2-thia-1,3,8-triazaspiro[5.5]undecane 2,2-dioxide: A mixture of tert-butyl 2-thia-1,3,8-triazaspiro[5.5]undecane-8-carboxylate 2,2-dioxide (20.0 mg, 1.00 equiv.) and TFA (231 mg, 30.9 equiv.) in DCM (0.5 mL) was stirred at 20° C. for 1 hour. After reaction completion, the mixture was concentrated to remove DCM to afford the title compound (20.0 mg, crude, TFA salt) as a yellow oil.

Step E. 8-(8-fluoro-7-(8-fluoronaphthalen-1-yl)-2-((hexahydro-1H-pyrrolizin-7a-yl)methoxy)pyrido[4,3-d]pyrimidin-4-yl)-2-thia-1,3,8-triazaspiro[5.5]undecane 2,2-dioxide: A mixture of 2-thia-1,3,8-triazaspiro[5.5]undecane 2,2-dioxide (20.0 mg, 1.00 equiv., TFA), 8-fluoro-7-(8-fluoro-1-naphthyl)-2-(1,2,3,5,6,7-hexahydropyrrolizin-8-yl-methoxy)-4-(2,2,2-trifluoroethoxy) pyrido[4,3-d]pyrimidine (33.2 mg, 1.00 equiv.), DIPEA (32.4 mg, 4.00 equiv.) and 4 Å molecular sieves (10.0 mg, 1.00 equiv.) in DMF (1.00 mL) was stirred at 40° C. for 12 hours under N$_2$. After reaction completion, the mixture was concentrated and purified by prep-HPLC [column: Phenomenex Luna C18 150× 25 mm×10 um; mobile phase: [water (0.225% formic acid)/ACN]; B %: 13%-43%, 10 min] to afford the title compound (2.50 mg, 5.7% yield) as an off-white solid; $^1$H NMR (400 MHz, CD3OD) δ=9.15 (d, J=2.8 Hz, 1H), 8.14 (d, J=8.8 Hz, 1H), 7.88 (d, J=8.0 Hz, 1H), 7.73-7.69 (m, 1H), 7.64 (t, J=7.2 Hz, 1H), 7.57-7.55 (m, 1H), 7.22-7.20 (m, 1H), 4.66-4.53 (m, 3H), 4.42-4.20 (m, 2H), 4.01-3.81 (m, 1H), 3.75-3.45 (m, 4H), 3.23-3.13 (m, 2H), 2.37-2.02 (m, 10H), 1.90-1.72 (m, 3H), 1.61-1.50 (m, 1H); LCMS (ESI, M+1): m/z=636.0.

Example 248

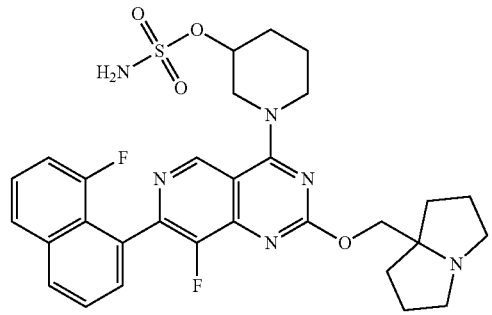

1-(8-fluoro-7-(8-fluoronaphthalen-1-yl)-2-((tetrahydro-1H-pyrrolizin-7a(5H)-yl)methoxy)pyrido[4,3-d]pyrimidin-4-yl)piperidin-3-yl sulfamate

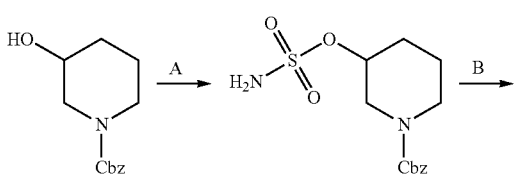

-continued

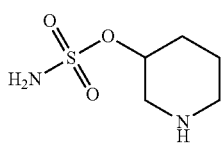

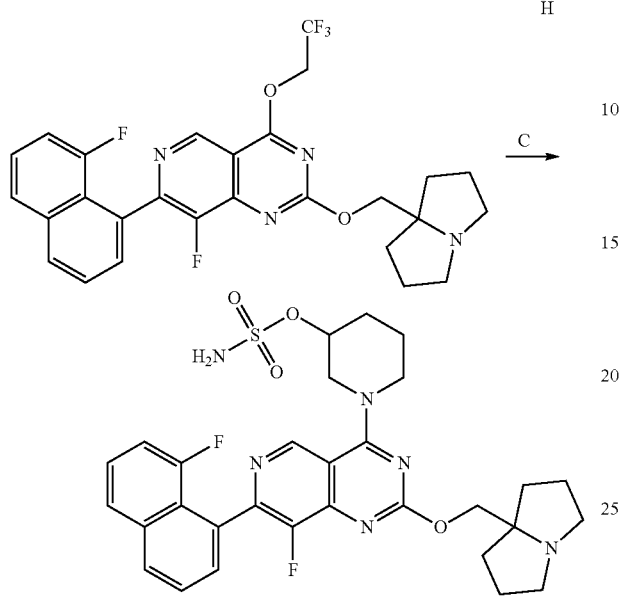

Step A. benzyl 3-(sulfamoyloxy)piperidine-1-carboxylate: To a solution of benzyl 3-hydroxypiperidine-1-carboxylate (500 mg, 1.0 equiv.) and sulfamoyl chloride (442 mg, 1.8 equiv.) in DCM (10 mL) was added TEA (1.08 g, 1.48 mL, 5.0 equiv.), the mixture was stirred at 15° C. for 8 hours. After completion, the reaction mixture was diluted with water (10 mL) and extracted with DCM (20 mL). The organic layer was dried over $Na_2SO_4$, filtered and concentrated under reduced pressure to give a residue. The residue was purified by prep-HPLC (column: Waters Xbridge C18 150×50 mm×10 μm; mobile phase: [water (10 mM $NH_4HCO_3$)/ACN], B %: 24%-54%, 11 min) to afford the title compound (230 mg, 33% yield) as a light yellow oil; LCMS [ESI, M+1]: m/z=315.2.

Step B. piperidin-3-yl sulfamate: To a mixture of benzyl 3-(sulfamoyloxy)piperidine-1-carboxylate (100 mg, 1.0 equiv.) in MeOH (2 mL) was added Pd/C (100 mg, 10% purity), the reaction was stirred at 15° C. for 2 hours under $H_2$ atmosphere (15 psi). After completion, the reaction mixture was filtered and concentrated under reduced pressure to afford the title compound (59 mg, crude) as a light yellow solid.

Step C. 1-(8-fluoro-7-(8-fluoronaphthalen-1-yl)-2-((hexahydro-1H-pyrrolizin-7a-yl)methoxy)pyrido[4,3-d]pyrimidin-4-yl)piperidin-3-yl sulfamate: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50.0 mg, 1.0 equiv.), piperidin-3-yl sulfamate (25.5 mg, 1.5 equiv.) in DMF (1 mL) was added DIEA (36.5 mg, 49.2 μL, 3.0 equiv.), the reaction was stirred at 40° C. for 4 hours. After completion, the reaction mixture was filtered to give a residue and the residue was purified by reversed-phase flash chromatography (water (0.1% formic acid)-ACN) and then prep-HPLC (column: Phenomenex Synergi C18 150×25 mm×10 μm; mobile phase: water (0.225% formic acid)/ACN], B %: 13%-43%, 10 min) and lyophilized to afford the title compound (3.85 mg, 6% yield over two steps) as a white solid; $^1$H NMR (400 MHz, methanol-d4): δ=9.15 (s, 1H), 8.53 (s, 1H), 8.13 (br d, J=8.8 Hz, 1H), 7.86 (d, J=8.4 Hz, 1H), 7.74-7.68 (m, 1H), 7.64-7.59 (m, 1H), 7.57-7.50 (m, 1H), 7.24-7.15 (m, 1H), 4.62 (br s, 2H), 4.39-3.99 (m, 3H), 3.52-3.37 (m, 4H), 3.16-3.00 (m, 2H), 2.31-2.17 (m, 3H), 2.10 (br dd, J=6.0, 12.4 Hz, 8H), 1.87-1.74 (m, 1H); LCMS [ESI, M+1]: m/z=611.3.

Example 249

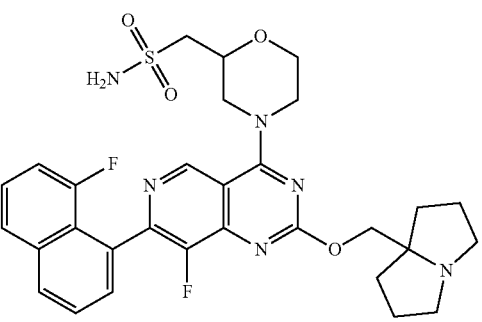 [SMILES: NS(=O)(=O)CC1CN(c2nc(OCC34CCCN3CCC4)nc3c(F)c(-c4cccc5cccc(F)c45)ncc23)CCO1]

1-(4-(8-fluoro-7-(8-fluoronaphthalen-1-yl)-2-((tetrahydro-1H-pyrrolizin-7a(5H)-yl)methoxy)pyrido[4,3-d]pyrimidin-4-yl)morpholin-2-yl)methanesulfonamide

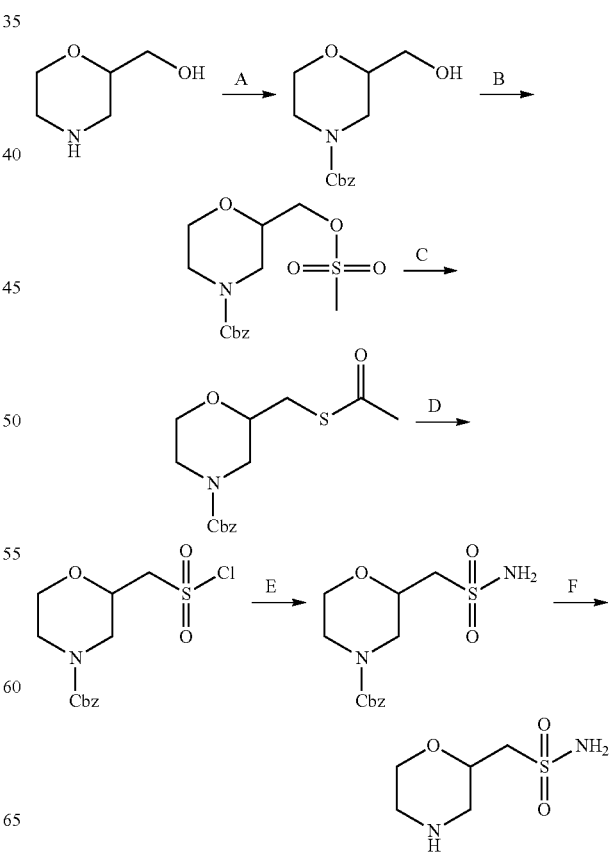

-continued

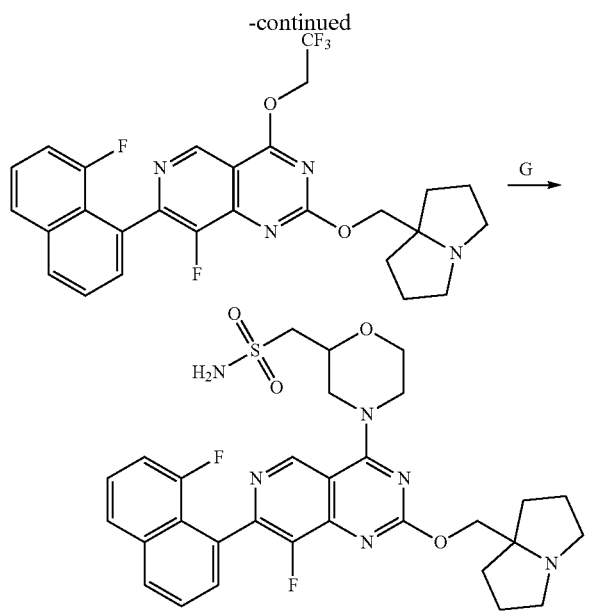

Step A. benzyl 2-(hydroxymethyl)morpholine-4-carboxylate: A mixture of morpholin-2-ylmethanol (1 g, 1 equiv., HCl salt) and NaHCO$_3$(1.37 g, 2.5 equiv.) in water (10 mL) and THF (10 mL) was stirred at 20° C. for 0.1 hour. Benzyl carbonochloridate (1.20 g, 1.1 equiv.) was added dropwise and the mixture was stirred at 20° C. for 16 hours. The mixture was diluted with water (30 mL) and extracted with ethyl acetate (10 mL×4). The combined organic layers were dried over anhydrous Na$_2$SO$_4$, concentrated and purified by reversed phase flash chromatography [water (0.1% formic acid)/acetonitrile 3:1] to afford the tittle compound (1.18 g, 71% yield) as a yellow oil; $^1$H NMR (400 MHz, methanol-d4) δ=7.37-7.31 (m, 5H), 5.14 (s, 2H), 4.02 (br d, J=13.2 Hz, 1H), 3.91 (br d, J=12.8 Hz, 2H), 3.56-3.43 (m, 4H), 3.01 (br s, 1H), 2.78 (br s, 1H); LCMS [ESI, M+Na]: m/z=274.2.

Step B. benzyl 2-(((methylsulfonyl)oxy)methyl)morpholine-4-carboxylate: To a solution of benzyl 2-(hydroxymethyl)morpholine-4-carboxylate (1.18 g, 1 equiv) and TEA (1.02 g, 2.1 equiv.) in DCM (15 mL) was added MsCl (1.03 g, 1.9 equiv.) dropwise at 0° C. The mixture was stirred at 10° C. for 1 hour. The mixture was quenched with saturated aqueous NaHCO$_3$(20 mL) at 0° C. The DCM phase was separated. The aqueous phase was extracted with DCM (20 mL). The combined organic layers were washed with saturated aqueous NH$_4$Cl (20 mL), brine (20 mL), dried over Na$_2$SO$_4$ and concentrated to afford the title compound (1.65 g, crude) as a light yellow oil.

Step C. benzyl 2-((acetylthio)methyl)morpholine-4-carboxylate: A mixture of benzyl 2-(((methylsulfonyl)oxy)methyl)morpholine-4-carboxylate (1.65 g, crude) and acetylsulfanylpotassium (660 mg, 1.2 equiv.) in DMF (20 mL) was stirred at 95° C. for 1.5 hours. The mixture was diluted with ethyl acetate (30 mL), water (300 mL) and brine (30 mL). The mixture was extracted with ethyl acetate (4×20 mL). The organic layer was washed with brine (3×20 mL), dried over Na$_2$SO$_4$, concentrated and purified by reversed phase flash chromatography [water (0.1% formic acid)/acetonitrile 1:9] to afford the title compound (1.15 g, 79% yield over two steps) as a light-yellow liquid; LCMS (ESI, M+Na): m/z=332.1.

Step D. benzyl 2-((chlorosulfonyl)methyl)morpholine-4-carboxylate: To a solution of benzyl 2-((acetylthio)methyl)morpholine-4-carboxylate (1.15 g, 1 equiv.) in AcOH (18 mL) and water (2 mL) was added NCS (1.62 g, 3.3 equiv.) portion wise. The mixture was poured into water (100 mL). The mixture was extracted with ethyl acetate (4×20 mL). The combined organic layers were washed with water (50 mL), saturated aqueous NaHCO$_3$(3×30 mL), brine (20 mL), dried over anhydrous Na$_2$SO$_4$ and concentrated to afford the title compound (1.4 g, crude) as a light-yellow oil.

Step E. benzyl 2-(sulfonylmethyl)morpholine-4-carboxylate: Benzyl 2-((chlorosulfonyl)methyl)morpholine-4-carboxylate (1.4 g, crude) in THF (15 mL) was added into NH$_3$—H$_2$O (20 mL, 25% purity) dropwise maintaining the temperature below 5° C. The mixture was stirred between 5 and 15° C. for 0.5 hour. The mixture was diluted with water (150 mL) and extracted with DCM (4×15 mL). The combined organic layers were dried over anhydrous Na$_2$SO$_4$, concentrated and purified by reversed phase flash chromatography [water (0.1% formic acid)/acetonitrile 8:17] to afford the title compound (1 g, 85% yield over two steps) as a white solid; $^1$H NMR (400 MHz, chloroform-d) δ=7.40-7.32 (m, 5H), 5.15 (br s, 2H), 4.96 (br s, 2H), 4.14-3.94 (m, 4H), 3.63 (br t, J=10.8 Hz, 1H), 3.31-3.25 (m, 2H), 3.05 (br s, 1H), 2.83 (br s, 1H); LCMS [ESI, M+Na]: m/z=315.1.

Step F. morpholin-2-ylmethanesulfonamide: To a solution of benzyl 2-(sulfonylmethyl)morpholine-4-carboxylate (300 mg, 1 equiv.) in MeOH (10 mL) was added Pd/C (60 mg, 10% purity) under N$_2$ atmosphere. The mixture was degassed and purged with H$_2$. The mixture was stirred at 10° C. for 2.5 hours under H$_2$ atmosphere (15 psi) before being filtered through a pad of Celite. The filter cake was washed with THF/MeOH 1:1 (20 mL). The combined filtrate was concentrated to afford the title compound (180 mg, 100% yield, crude) as a white solid; $^1$H NMR (400 MHz, DMSO-d$_6$) δ=6.79 (br s, 2H), 3.80-3.71 (m, 1H), 3.70 (td, J=2.4, 11.2 Hz, 1H), 3.45 (dt, J=3.2, 10.8 Hz, 1H), 3.34 (br s, 1H), 3.10-3.06 (m, 2H), 2.90 (dd, J=2.0, 12.0 Hz, 1H), 2.64-2.62 (m, 2H), 2.41 (br dd, J=10.0, 12.0 Hz, 1H).

Step G. 1-(4-(8-fluoro-7-(8-fluoronaphthalen-1-yl)-2-((hexahydro-1H-pyrrolizin-7a-yl)methoxy)pyrido[4,3-d]pyrimidin-4-yl)morpholin-2-yl)methanesulfonamide: A mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (80 mg, 1 equiv.), morpholin-2-ylmethanesulfonamide (55 mg, crude), DIPEA (58.6 mg, 3.0 equiv.) and 4 Å molecular sieves (20 mg) in DMF (1 mL) was stirred at 40° C. for 14 hours under N$_2$ atmosphere. The mixture was filtered. The filtrate was purified by prep-HPLC [column: Phenomenex Gemini-NX C18 75×30 mm×3 µm; mobile phase: [water (0.225% formic acid)-ACN]; B %: 12%-42%, 7 minutes] to afford the title compound (29.7 mg, 30% yield, 0.5 formic acid salt) as a white solid; $^1$H NMR (400 MHz, methanol-d4) δ=9.16 (s, 1H), 8.12 (br d, J=8.0 Hz, 1H), 7.86 (d, J=8.4 Hz, 11H), 7.71-7.64 (m, 1H), 7.61 (dd, J=7.2, 14.8 Hz, 1H), 7.53 (dt, J=5.6, 7.6 Hz, 1H), 7.19 (br dd, J=7.6, 13.2 Hz, 1H), 5.02 (br t, J=14.0 Hz, 1H), 4.63 (br dd, J=6.4, 12.0 Hz, 1H), 4.55-4.46 (m, 2H), 4.31-4.18 (m, 1H), 4.05 (br d, J=10.8 Hz, 1H), 3.82-3.73 (m, 2H), 3.54-3.43 (m, 5H), 3.17-3.03 (m, 2H), 2.29 (td, J=6.4, 12.8 Hz, 2H), 2.14-2.10 (m, 4H), 2.04-1.99 (m, 2H); LCMS [ESI, M+1]: m/z=611.4.

Example 250

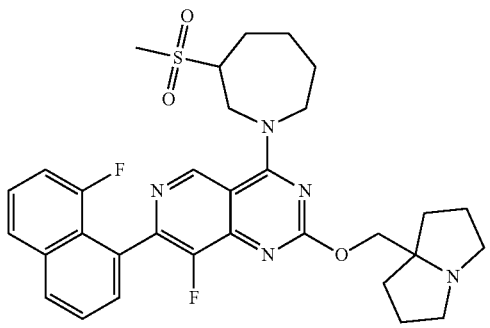 [SMILES: CS(=O)(=O)C1CCCCN(c2nc(OCC34CCCN3CCC4)nc3c(F)c(-c4cccc5cccc(F)c45)ncc23)C1]

8-fluoro-7-(8-fluoronaphthalen-1-yl)-2-((hexahydro-1H-pyrrolizin-7a-yl)methoxy)-4-(3-(methylsulfonyl)azepan-1-yl)pyrido[4,3-d]pyrimidine

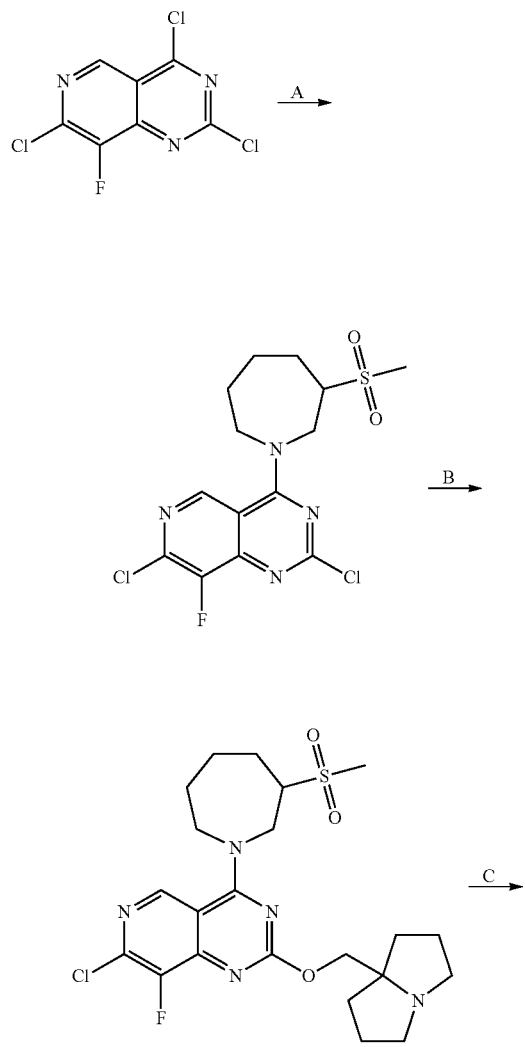

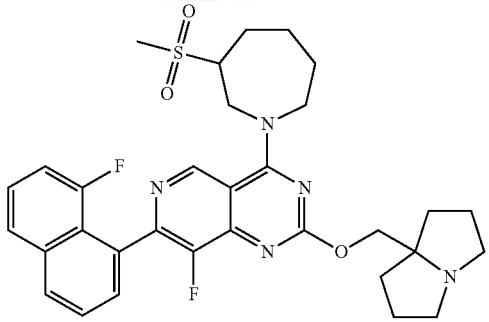

Step A. 2,7-dichloro-8-fluoro-4-(3-(methylsulfonyl)azepan-1-yl)pyrido[4,3-d]pyrimidine: To a solution of 2,4,7-trichloro-8-fluoro-pyrido[4,3-d]pyrimidine (215 mg, 1.0 equiv.), 3-methylsulfonyl)azepane (200 mg, 1.1 equiv., HCl) in THF (1 mL) was added DIEA (550 mg, 5.0 equiv.) at −40° C. The mixture was stirred at −40° C. for 2 hours. The mixture was diluted with water (20 mL) and extracted with EtOAc (3×20 mL). The combined organic layers were dried over anhydrous sodium sulfate, concentrated to afford the title compound (500 mg, crude) as a yellow solid; LCMS (ESI, M+1): m/z=393.3.

Step B. 7-chloro-8-fluoro-2-((hexahydro-1H-pyrrolizin-7a-yl)methoxy)-4-(3-(methylsulfonyl)azepan-1-yl)pyrido[4,3-d]pyrimidine: To a solution of 2,7-dichloro-8-fluoro-4-(3-methylsulfonyl)azepan-1-yl)pyrido[4,3-d]pyrimidine (470 mg, 1.0 equiv.), 1,2,3,5,6,7-hexahydropyrrolizin-8-yl-methanol (337 mg, 2.0 equiv.) and 4 Å molecular sieves (200 mg) in dioxane (2.5 mL) was added DIEA (463 mg, 3.0 equiv.). The reaction was stirred at 95° C. for 16 hours. The mixture was diluted with water (20 mL) and extracted with EtOAc (3×20 mL). The combined organic layers were dried over anhydrous sodium sulfate, concentrated, and purified by reversed phase flash chromatography [C18, water (0.1% formic acid)/ACN] to afford the title compound (180 mg, 29.9% yield) as a yellow solid; LCMS (ESI, M+1): m/z=498.1.

Step C. 8-fluoro-7-(8-fluoronaphthalen-1-yl)-2-((hexahydro-1H-pyrrolizin-7a-yl)methoxy)-4-(3-(methylsulfonyl)azepan-1-yl)pyrido[4,3-d]pyrimidine: To a solution of 7-chloro-8-fluoro-2-(1,2,3,5,6,7-hexahydropyrrolizin-8-yl-methoxy)-4-(3-methylsulfonyl)azepan-1-yl)pyrido[4,3-d]pyrimidine (100 mg, 1.0 equiv.), Cs$_2$CO$_3$ (1.5 M, 402 µL, 3.0 equiv.) and cataCXium® A Pd G3 (14.6 mg, 0.1 equiv.) in methoxycyclopentane (1.5 mL) was added 2-(8-fluoro-1-naphthyl)-4,4,5,5-tetramethyl-1,3,2-dioxaborolane (71.0 mg, 1.3 equiv.). The reaction was stirred at 90° C. for 3 hours. The mixture was diluted with water (20 mL) and extracted with EtOAc (3×20 mL). The combined organic layers were dried over anhydrous sodium sulfate, concentrated, and purified by reversed phase flash chromatography [C18, water (0.1% formic acid)/ACN] to give a crude product. The crude product was purified by prep-HPLC [column: Phenomenex Gemini-NX C18 75×30 mm×3 µm; mobile phase: [water (0.225% formic acid)/ACN]; B %: 18%-48%, 7 min] and lyophilized to afford the title compound (21.4 mg, 17% yield) as a light yellow solid; $^1$H NMR (400 MHz, methanol-d4) δ=9.22 (s, 1H), 8.11 (d, J=8.4 Hz, 1H), 7.85 (d, J=8.0 Hz, 1H), 7.75-7.65 (m, 1H), 7.65-7.49 (m, 2H), 7.25-7.10 (m, 1H), 4.93 (br d, J=13.6 Hz, 1H), 4.57-4.44 (m, 2H), 4.33-4.21 (m, 1H), 4.20-4.05 (m, 1H), 3.91-3.71 (m, 2H), 3.36-3.31 (m, 1H), 3.30-3.26 (m, 1H), 3.15 (d, J=2.0 Hz, 3H), 2.99-2.85 (m, 2H), 2.40-2.28 (m, 1H), 2.27-2.14 (m, 3H), 2.14-2.02 (m, 3H), 2.02-1.92 (m, 3H), 1.91-1.78 (m, 3H), 1.52-1.36 (m, 1H); LCMS (ESI, M+1): m/z=608.0.

Example 251

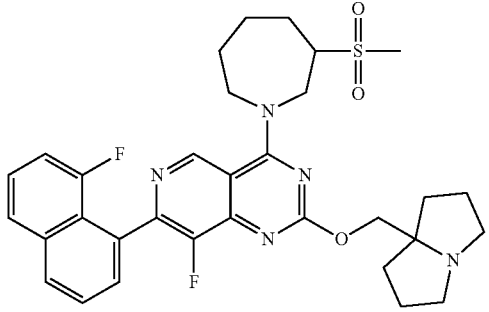 [SMILES: CS(=O)(=O)C1CCCCN(c2nc(OCC34CCCN3CCC4)nc3c(F)c(-c4cccc5cccc(F)c45)ncc23)C1]

8-fluoro-7-(8-fluoronaphthalen-1-yl)-2-((hexahydro-1H-pyrrolizin-7a-yl)methoxy)-4-(3-(methylsulfonyl)azocan-1-yl)pyrido[4,3-d]pyrimidine The title compound was synthesized according to the procedure described for example 250. ¹H NMR (400 MHz, methanol-d4) δ=9.25 (d, J=0.8 Hz, 1H), 8.12 (br d, J=8.4 Hz, 1H), 7.86 (d, J=8.0 Hz, 1H), 7.75-7.67 (m, 1H), 7.61 (dd, J=4.4, 6.8 Hz, 1H), 7.53 (dt, J=5.2, 8.0 Hz, 1H), 7.25-7.12 (m, 1H), 5.12 (br d, J=12.4 Hz, 1H), 4.64-4.51 (m, 3H), 3.98-3.79 (m, 3H), 3.47-3.36 (m, 2H), 3.12 (s, 3H), 3.07-2.97 (m, 2H), 2.52-2.38 (m, 1H), 2.27-2.18 (m, 2H), 2.16-2.08 (m, 3H), 2.07-2.00 (m, 4H), 2.00-1.88 (m, 3H), 1.88-1.69 (m, 2H), 1.59-1.45 (m, 1H); LCMS (ESI, M+1): m/z=622.2.

Example 252

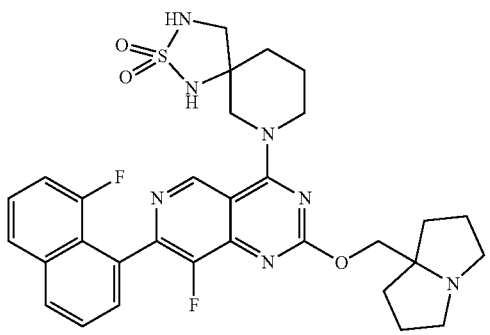 [SMILES: O=S1(=O)NCC2(CCCN(c3nc(OCC45CCCN4CCC5)nc4c(F)c(-c5cccc6cccc(F)c56)ncc34)C2)N1]

7-(8-fluoro-7-(8-fluoronaphthalen-1-yl)-2-((tetrahydro-1H-pyrrolizin-7a(5H)-yl)methoxy)pyrido[4,3-d]pyrimidin-4-yl)-2-thia-1,3,7-triazaspiro[4.5]decane 2,2-dioxide

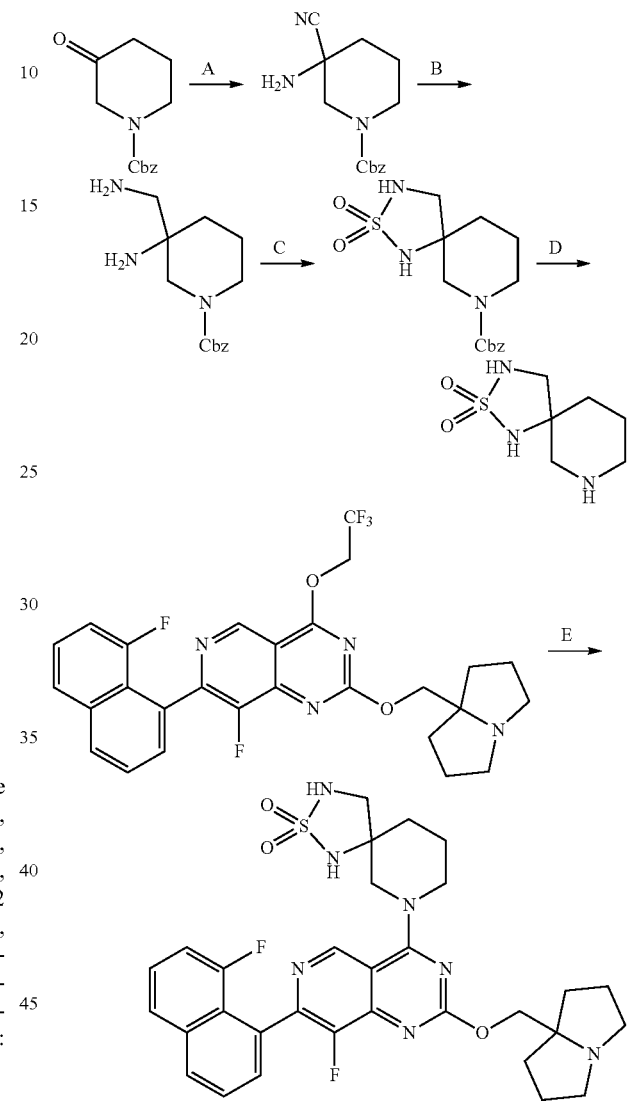

Step A. benzyl 3-amino-3-cyano-piperidine-1-carboxylate: A mixture of benzyl 3-oxopiperidine-1-carboxylate (10.0 g, 1.0 equiv.) and NH₄Cl (9.17 g, 4.0 equiv.) in isopropyl alcohol (60 mL) and NH—H₂O (120 mL) was added KCN (10.1 g, 3.61 equiv.) in one portion at 25° C. under N₂. The mixture was stirred at 25° C. for 12 hours. The reaction mixture was poured into water (150 mL), and the aqueous phase was extracted with ethyl acetate (3×50 mL). The combined organic phase was washed with brine (100 mL), and dried with anhydrous Na₂SO₄, filtered and concentrated in vacuum. The residue was purified by column chromatography (Silica gel, Petroleum ether/Ethyl acetate 20:1 to 0:1) to afford the title compound (10.0 g, 89% yield) as a yellow oil; LCMS (ESI, 2M+1): m/z=519.2.

Step B. benzyl 3-amino-3-(aminomethyl)piperidine-1-carboxylate: A mixture of benzyl 3-amino-3-cyano-piperidine-1-carboxylate (200 mg, 1.0 equiv.), NH₃-MeOH (1.00 mL, 20% purity, 1.0 equiv.) in MeOH (5 mL) and Raney Ni (30.0 mg) was stirred at 25° C. for 5 hours under H₂ atmosphere (15 psi). The reaction mixture was filtered and concentrated under reduced pressure to give a residue. The residue was purified by prep-HPLC [column: Waters Xbridge 150×25 mm×5 μm; mobile phase: [water (10 mM NH₄HCO₃)/ACN], B %: 9%-39%, 10 min] and lyophilized to afford the title compound (100 mg, 45% yield) as a colorless oil; ¹H NMR (400 MHz, chloroform-d₄) δ=7.38-7.30 (m, 5H), 5.23-5.03 (m, 2H), 3.45 (br s, 3H), 3.19 (br d, J=13.2 Hz, 1H), 2.78-2.63 (m, 1H), 2.49 (d, J=13.2 Hz, 1H), 1.66-1.40 (m, 4H).

Step C. benzyl 2-thia-1,3,7-triazaspiro[4.5]decane-7-carboxylate 2,2-dioxide: To a refluxing solution of sulfamide (109 mg, 10.0 equiv.) in Pyridine (2 mL) was added benzyl 3-amino-3-(aminomethyl)piperidine-1-carboxylate (30.0 mg, 1.0 equiv.). The resulting mixture was stirred at 120° C. for further 12 hours under nitrogen. The reaction mixture was concentrated under reduced pressure to give a residue. The residue was purified by prep-HPLC [column: Phenomenex Gemini-NX C18 75×30 mm×3 μm; mobile phase: water (0.225% formic acid),/ACN], B %: 22%-52%, 7 min] and lyophilized to afford the title compound (15.0 mg, 40% yield) as a yellow solid; ¹H NMR (400 MHz, chloroform-d4) δ=7.35 (s, 5H), 5.62 (br d, J=0.8 Hz, 1H), 5.13 (br s, 2H), 5.03 (br s, 1H), 3.65 (br d, J=12.0 Hz, 1H), 3.58-3.31 (m, 4H), 3.22-3.11 (m, 11H), 1.95-1.84 (m, 1H), 1.81-1.67 (m, 2H), 1.54 (br dd, J=2.8, 7.2 Hz, 1H).

Step D. 2λ⁶-thia-1,3,9-triazaspiro[4.5]decane 2,2-dioxide: To a mixture of benzyl 2,2-dioxo-2λ⁶-thia-1,3,9-triazaspiro[4.5]decane-9-carboxylate (15.0 mg, 1.0 equiv.) in MeOH (2 mL) was added Pd/C (3.00 mg, 10% purity) and then the mixture was stirred at 25° C. for 1 hour under H₂ atmosphere (15 psi). The mixture was filtered and concentrated under reduced pressure to afford the title compound (17.0 mg, crude) as a yellow solid.

Step E. 7-(8-fluoro-7-(8-fluoronaphthalen-1-yl)-2-((tetrahydro-1H-pyrrolizin-7a(5H)-yl)methoxy)pyrido[4,3-d]pyrimidin-4-yl)-2-thia-1,3,7-triazaspiro[4.5]decane 2,2-dioxide: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (15.0 mg, 1.0 equiv.) in DMF (1.0 mL) was added DIEA (11.0 mg, 3.0 equiv.) and 2λ⁶-thia-1,3,9-triazaspiro[4.5]decane 2,2-dioxide (16.2 mg, 3.0 equiv.). The mixture was stirred at 45° C. for 12 hours. The reaction mixture was filtered and concentrated under reduced pressure. The residue was purified by prep-HPLC [column: Phenomenex C18 75×30 mm×3 μm; mobile phase: [water (0.1% formic acid)/ACN]B %: 15%-45%, 7 min] and lyophilized to afford the title compound (4.74 mg, 26% yield) as a white solid; ¹H NMR (400 MHz, methanol-d) 6-9.14 (s, 1H), 8.12 (br d, J=8.4 Hz, 1H), 7.86 (d, J=8.0 Hz, 1H), 7.76-7.66 (m, 1H), 7.61 (t, J=5.2 Hz, 1H), 7.54 (dt, J=4.8, 7.6 Hz, 1H), 7.19 (dd, J=7.6, 13.2 Hz, 1H), 4.68-4.58 (m, 2H), 4.55-4.33 (m, 2H), 3.90-3.72 (m, 2H), 3.56-3.39 (m, 3H), 3.28-3.19 (m, 1H), 3.16-3.04 (m, 2H), 2.26 (td, J=6.4, 12.4 Hz, 2H), 2.17-1.89 (m, 10H); LCMS (ESI, M+1): m/z=622.3.

Example 253

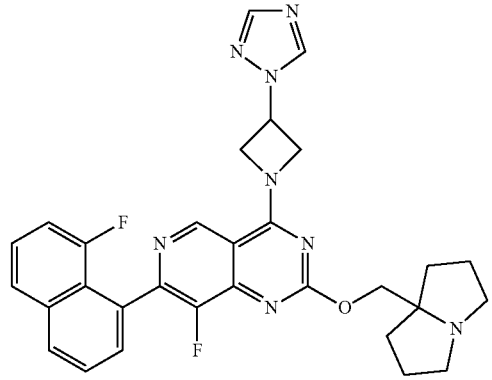 [SMILES: Fc1c(-c2cccc3cccc(F)c23)ncc2c(N3CC(n4cncn4)C3)nc(OCC34CCCN3CCC4)nc12]

4-(3-(1H-1,2,4-triazol-1-yl)azetidin-1-yl)-8-fluoro-7-(8-fluoronaphthalen-1-yl)-2-((hexahydro-1H-pyrrolizin-7a-yl)methoxy)pyrido[4,3-d]pyrimidine The title compound was synthesized according to the procedure described for example 84. ¹H NMR (400 MHz, METHANOL-d₄) δ=8.96 (s, 1H), 8.28 (s, 1H), 8.10 (d, J=8.4 Hz, 1H), 7.84 (t, J=4.0 Hz, 2H), 7.72-7.66 (m, 1H), 7.60 (dd, J=0.8, 7.2 Hz, 1H), 7.52 (dt, J=5.2, 8.0 Hz, 1H), 7.18 (dd, J=7.6, 13.2 Hz, 1H), 5.90-5.78 (m, 1H), 5.55-4.94 (m, 4H), 4.43 (s, 2H), 3.37-3.32 (m, 2H), 2.97-2.86 (m, 2H), 2.20-2.11 (m, 2H), 2.09-1.90 (m, 4H), 1.90-1.81 (m, 2H); ¹⁹F NMR (377 MHz, METHANOL-d₄) δ=-115.14, -140.68; LCMS (ESI, M+1): m/z=555.3.

Example 254

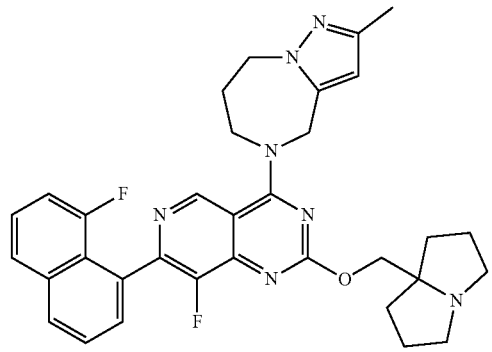 [SMILES: Cc1cc2n(n1)CCCN(c1nc(OCC34CCCN3CCC4)nc3c(F)c(-c4cccc5cccc(F)c45)ncc13)C2]

8-fluoro-7-(8-fluoronaphthalen-1-yl)-2-((hexahydro-1H-pyrrolizin-7a-yl)methoxy)-4-(2-methyl-7,8-dihydro-4H-pyrazolo[1,5-a][1,4]diazepin-5(6H)-yl)pyrido[4,3-d]pyrimidine The title compound was synthesized according to the procedure described for example 84. ¹H NMR (400 MHz, METHANOL-d₄) 8=9.25 (s, 1H), 8.13 (br d, J=8.0 Hz, 1H), 7.87 (d, J=8.0 Hz, 1H), 7.71 (t, J=8.0 Hz, 1H), 7.62 (dd, J=0.8, 7.2 Hz, 1H), 7.58-7.50 (m, 1H), 7.20 (dd, J=7.2, 13.2 Hz, 1H), 6.26 (s, 1H), 5.29-5.14 (m, 2H), 4.71-4.61 (m, 2H), 4.49-4.37 (m, 4H), 3.76-3.65 (m, 2H), 3.37-3.32 (m, 1H), 3.30-3.26 (m, 1H), 2.46-2.37 (m, 2H), 2.36-2.29 (m, 2H), 2.28-2.07 (m, 9H); LCMS (ESI, M+1): m/z=582.3.

Example 255

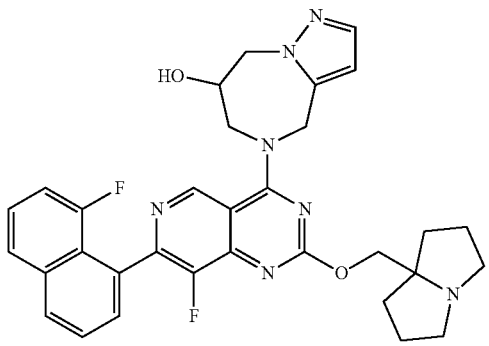 [SMILES: OC1CN(c2nc(OCC34CCCN3CCC4)nc3c(F)c(-c4cccc5cccc(F)c45)ncc23)Cc2ccnn2C1]

5-(8-fluoro-7-(8-fluoronaphthalen-1-yl)-2-((hexahydro-1H-pyrrolizin-7a-yl)methoxy)pyrido[4,3-d]pyrimidin-4-yl)-5,6,7,8-tetrahydro-4H-pyrazolo[1,5-a][1,4]diazepin-7-ol The title compound was synthesized according to the procedure described for example 85. $^1$H NMR (400 MHz, METHANOL-d$_4$) δ=9.42 (d, J=16.0 Hz, 1H), 8.11 (d, J=8.0 Hz, 1H), 7.85 (d, J=8.0 Hz, 1H), 7.70 (t, J=7.2 Hz, 1H), 7.64-7.58 (m, 1H), 7.57-7.49 (m, 1H), 7.43 (d, J=1.6 Hz, 1H), 7.22-7.15 (m, 1H), 6.60-6.50 (m, 1H), 5.60-5.45 (m, 1H), 5.14-5.00 (m, 1H), 4.67-4.55 (m, 2H), 4.54-4.44 (m, 1H), 4.43-4.27 (m, 4H), 3.20-3.09 (m, 21H), 2.82-2.73 (m, 2H), 2.15-2.04 (m, 2H), 2.02-1.85 (m, 4H), 1.84-1.74 (m, 2H); LCMS (ESI, M+1): m/z=584.3.

Example 256

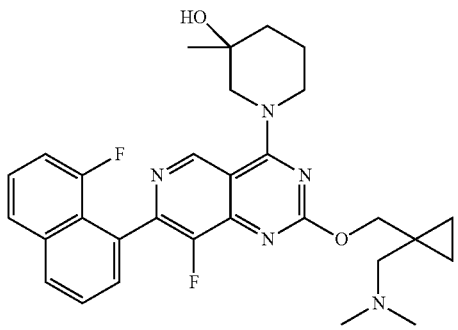 [SMILES: CN(C)CC1(COc2nc(N3CCCC(C)(O)C3)c3cnc(-c4cccc5cccc(F)c45)c(F)c3n2)CC1]

1-(2-((1-(((dimethylamino)methyl)cyclopropyl)methoxy)-8-fluoro-7-(8-fluoronaphthalen-1-yl)pyrido[4,3-d]pyrimidin-4-yl)-3-methylpiperidin-3-ol

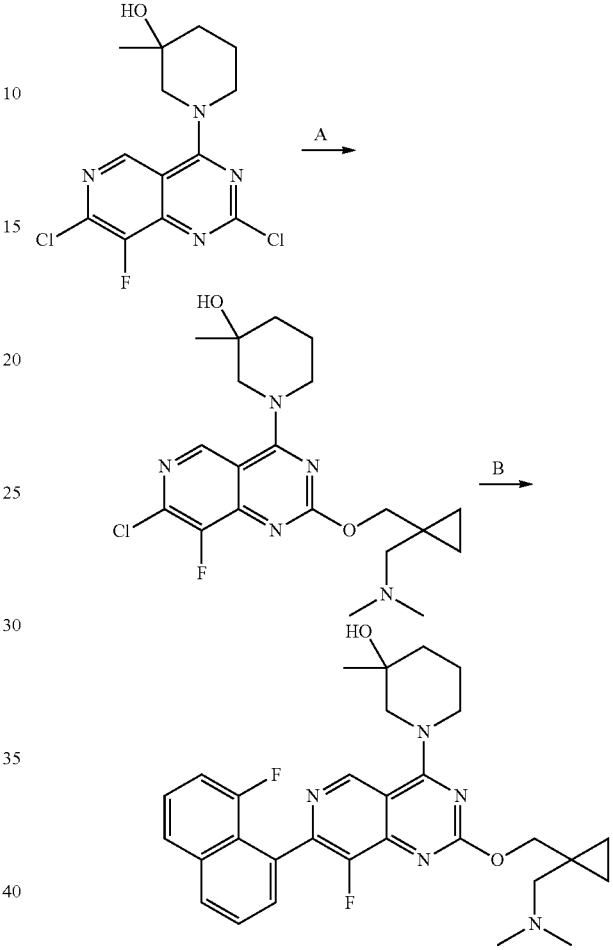

Step A. 1-(7-chloro-2-((1-(((dimethylamino)methyl)cyclopropyl)methoxyl-8-fluoropyrido[4,3-d]pyrimidin-4-yl)-3-methylpiperidin-3-ol: A mixture of 1-(2,7-dichloro-8-fluoropyrido[4,3-d]pyrimidin-4-yl)-3-methylpiperidin-3-ol (200 mg, 1 equiv.), (1-((dimethylamino)methyl)cyclopropyl)methanol (78 mg, 1 equiv.), DIPEA (195 mg, 2.5 equiv.) and 4 Å molecular sieves (40 mg) in dioxane (2.5 mL) was stirred at 90° C. for 14 hours under N$_2$ atmosphere. The reaction mixture was filtered. The filter cake was washed with DCM (20 mL). The combined organic phase was concentrated and purified by reversed phase flash chromatography [water (0.1% formic acid)/acetonitrile 3:1] to afford the tittle compound (65 mg, 24% yield) as a light yellow solid; LCMS (ESI, M+1): m/z=424.3.

Step B. 1-(2-((1-(((dimethylamino)methyl)cyclopropyl)methoxy)-8-fluoro-7-(8-fluoronaphthalen-1-yl)pyrido[4,3-d]pyrimidin-4-yl)-3-methylpiperidin-3-ol: A mixture of 1-(7-chloro-2-((1-(((dimethylamino)methyl)cyclopropyl)methoxy)-8-fluoropyrido[4,3-d]pyrimidin-4-yl)-3-methylpiperidin-3-ol (65 mg, 1 equiv.), 2-(8-fluoronaphthalen-1-yl)-4,4,5,5-tetramethyl-1,3,2-dioxaborolane (50 mg, 184 μmol, 1.2 equiv.), cataCXium® A Pd G3 (12 mg, 0.1 equiv.) and K$_3$PO$_4$ (1.5 M in water, 307 μL, 3 equiv.) in methoxycyclopentane (1.5 mL) was degassed and stirred at 90° C. for 3 hours. The mixture was diluted with water (1 mL) and extracted with ethyl acetate (4×2 mL). The organic layer was dried over anhydrous Na$_2$SO$_4$ and concentrated to give a residue. The residue was purified by reversed phase flash chromatography [water (0.1% formic acid)/acetonitrile 13:7] and then prep-HPLC [column: waters Xbridge 150×25 mm×5 µm; mobile phase: [water (10 mM NH$_4$HCO$_3$)/ACN]; B %: 43%-73%, 9 minutes] to afford the title compound (47.5 mg, 57% yield) as a white solid; $^1$H NMR (400 MHz, METHANOL-d$_4$) δ=9.20 (d, J=5.2 Hz, 1H), 8.11 (d, J=8.4 Hz, 1H), 7.85 (d, J=8.4 Hz, 1H), 7.70 (t, J=7.6 Hz, 1H), 7.62-7.52 (m, 1H), 7.53 (dt, J=5.2, 8.0 Hz, 1H), 7.19 (dd, J=8.0, 12.8 Hz, 1H), 4.51 (br dd, J=4.4, 9.6 Hz, 1H), 4.39-4.36 (m, 2H), 4.26 (br d, J=13.2 Hz, 1H), 3.63 (dd, J=2.0, 13.2 Hz, 1H), 3.49-3.46 (m, 1H), 2.46-2.44 (m, 2H), 2.30 (s, 6H), 2.18-2.14 (m, 1H), 1.85-1.75 (m, 3H), 1.29 (d, J=5.6 Hz, 3H), 0.75-0.72 (m, 2H), 0.54-0.52 (m, 2H); 19F NMR (400 MHz, methanol-d$_4$) δ=−115, −141; LCMS (ESI, M+1): 534.4.

Example 257

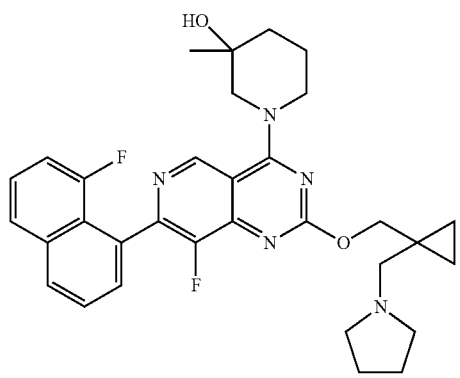 [SMILES: CC1(O)CCCN(c2nc(OCC3(CN4CCCC4)CC3)nc3c(F)c(-c4cccc5cccc(F)c45)ncc23)C1]

1-(8-fluoro-7-(8-fluoronaphthalen-1-yl)-2-((1-(pyrrolidin-1-ylmethyl)cyclopropyl)methoxy)pyrido[4,3-d]pyrimidin-4-yl)-3-methylpiperidin-3-ol

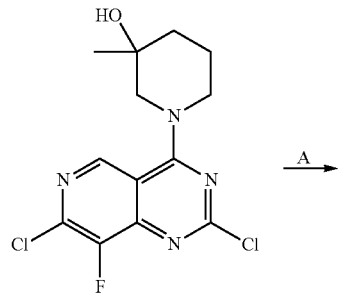

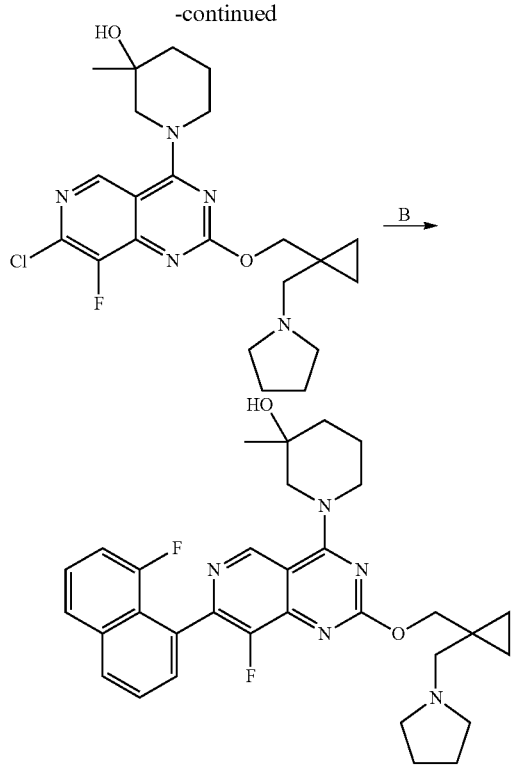

Step A. 1-(7-chloro-8-fluoro-2-((1-(pyrrolidin-1-ylmethyl)cyclopropyl)methoxy)pyrido[4,3-d]pyrimidin-4-yl)-3-methyl)piperidin-3-ol: To a solution of 1-(2,7-dichloro-8-fluoropyrido[4,3-d]pyrimidin-4-yl)-3-methylpiperidin-3-ol (200 mg, 1.0 equiv.), (1-(pyrrolidin-1-ylmethyl)cyclopropyl)methanol (140 mg, 1.5 equiv.), 4 Å molecular sieves (10.0 mg) in dioxane (1.5 mL) was added DIEA (234 mg, 315 µL, 3.0 equiv.). The reaction was stirred at 95° C. for 12 hours. After completion, the reaction mixture was diluted with water (1 mL) and extracted with Ethyl acetate (2 mL). The combined organic layer was dried over anhydrous Na$_2$SO$_4$, filtered and concentrated under reduced pressure to give a residue. The residue was purified by reversed-phase flash chromatography (water (0.1% formic acid)/ACN) to afford the title compound (93.0 mg, 33% yield) as a yellow oil; LCMS [ESI, M+1]: m/z=450.1.

Step B. 1-(8-fluoro-7-(8-fluoronaphthalen-1-yl)-2-((1-(pyrrolidin-1-ylmethyl)cyclopropyl)methoxy)pyrido[4,3-d]pyrimidin-4-yl)-3-methylpiperidin-3-ol: To a solution of 1-(7-chloro-8-fluoro-2-((1-(pyrrolidin-1-ylmethyl)cyclopropyl)methoxy)pyrido[4,3-d]pyrimidin-4-yl)-3-methylpiperidin-3-ol (50.0 mg, 1.0 equiv.), 2-(8-fluoronaphthalen-1-yl)-4,4,5,5-tetramethyl-1,3,2-dioxaborolane (36.3 mg, 1.2 equiv.), K$_3$PO$_4$ (1.5 M, 222 µL, 3.0 equiv.) in Methoxycyclopentane (1 mL) was added CataCXium A Pd G3 (8.09 mg, 11.1 µmol, 0.1 equiv.) under N$_2$. The reaction was stirred at 90° C. for 2 hours. After completion, the reaction mixture was diluted with water (1 mL) and extracted with Ethyl acetate (2 mL). The combined organic layer was dried over anhydrous Na$_2$SO$_4$, filtered and concentrated under reduced pressure to give a residue. The crude product was purified by reversed-phase flash chromatography (water (0.1% formic acid)/ACN) and prep-HPLC (column: Phenomenex Synergi C18 150×25 mm×10 µm; mobile phase: [water (0.225% formic acid)/ACN] B %: 12%-42%, 10 min) and lyophilized to afford the title compound (19.9 mg, 32% yield) as a yellow solid; ¹H NMR (400 MHz, methanol-d4): δ 9.23 (d, J=8.0 Hz, 1H), 8.54 (s, 1H), 8.12 (br d, J=8.4 Hz, 1H), 7.86 (d, J=8.0 Hz, 1H), 7.73-7.68 (m, 1H), 7.61 (dt, J=1.2, 8.0 Hz, 1H), 7.56-7.51 (i, 1H), 7.20 (ddd, J=1.6, 7.6, 13.2 Hz, 11H), 4.58-4.46 (m, 2H), 4.43-4.37 (m, 1H), 4.30 (br d, J=13.2 Hz, 1H), 3.62 (dd, J=2.0, 13.2 Hz, 1H), 3.43 (br t, J=11.6 Hz, 1H), 3.30-3.05 (m, 6H), 2.22-2.10 (m, 1H), 2.00 (br s, 4H), 1.88-1.74 (m, 3H), 1.29 (d, J=4.4 Hz, 3H), 0.90-0.75 (m, 4H); LCMS [ESI, M+1]: m/z=560.2.

Example 258

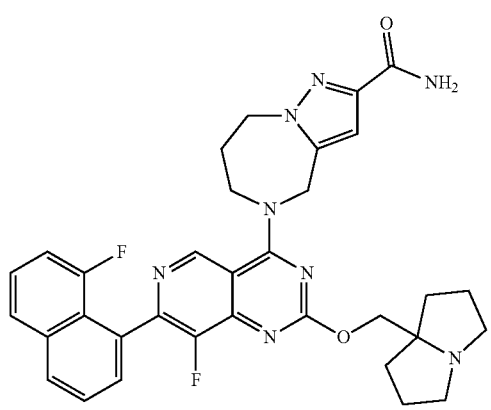 [SMILES: NC(=O)c1cc2n(n1)CCCN(c1nc(OCC34CCCN3CCC4)nc3c(F)c(-c4cccc5cccc(F)c45)ncc13)C2]

5-(8-fluoro-7-(8-fluoronaphthalen-1-yl)-2-((hexahydro-1H-pyrrolizin-7a-yl)methoxy)pyrido[4,3-d]pyrimidin-4-yl)-5,6,7,8-tetrahydro-4H-pyrazolo[1,5-a][1,4]diazepine-2-carboxamide

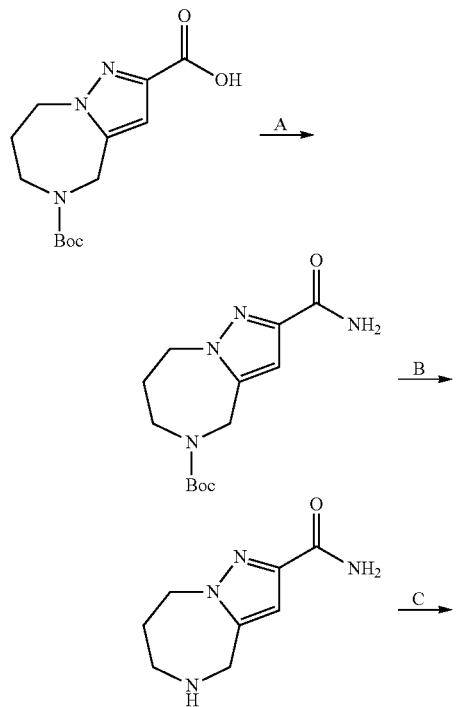

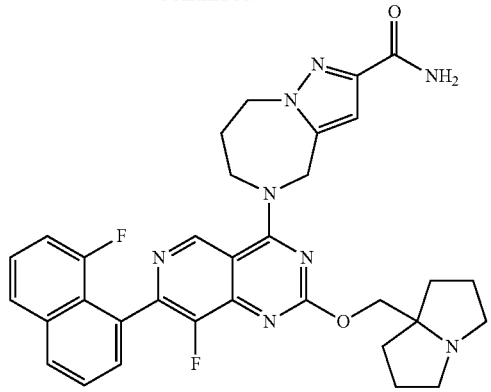

Step A. tert-butyl-2-carbamoyl-7,8-dihydro-4H-pyrazolo[1,5-a][1,4]diazepine-(6H)-carboxylate: To a solution of 5-tert-butoxycarbonyl-4,6,7,8-tetrahydropyrazolo[1,5-a][1,4]diazepine-2-carboxylic acid (1.00 g, 1.0 equiv.), TEA (2.16 g, 6.0 equiv.) and HATU (2.70 g, 2.0 equiv.) in THF (10 mL) was added NH₄Cl (570 mg, 3.0 equiv.). The mixture was stirred at 25° C. for 12 hours. The mixture was diluted with water (10 mL) and extracted with ethyl acetate (3×10 mL). The combined organic layers were dried over anhydrous sodium sulfate, concentrated and purified by reversed phase flash chromatography [C18, water (0.1% formic acid)/ACN] to afford the title compound (800 g, 80% yield) as a yellow solid; LCMS (ESI, M+1): m/z=281.2.

Step B. 5,6,7,8-tetrahydro-4H-pyrazolo[1,5-a][1,4]diazepine-2-carboxamide: To a solution of tert-butyl 2-carbamoyl-4,6,7,8-tetrahydropyrazolo[1,5-a][1,4]diazepine-5-carboxylate (800 mg, 1.0 equiv.) in MeCN (8 mL) was added HCl.dioxane (4 M, 16 mL, 22 equiv.) at 0° C. The reaction was stirred at 0° C. for 0.5 hour. The mixture was concentrated to afford the title compound (800 mg, crude, HCl) as a yellow solid; LCMS (ESI, M+1): m/z=180.1.

Step C. 5-(8-fluoro-7-(8-fluoronaphthalen-1-yl)-2-((hexahydro-1H-pyrrolizin-7a-yl)methoxy)pyrido[4,3-d]pyrimidin-4-yl)-5,6,7,8-tetrahydro-4H-pyrazolo[1,5-a][1,4]diazepine-2-carboxamide: To a mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 1.0 equiv.), 5,6,7,8-tetrahydro-4H-pyrazolo[1,5-a][1,4]diazepine-2-carboxamide (408 mg, 10 equiv., HCl) and 4 Å molecular sieves (10 mg) in DMF (0.5 mL) was added DIEA (487 mg, 20 equiv.). The reaction was stirred at 40° C. for 24 hours. The residue was filtered and purified by prep-HPLC [column: Phenomenex Gemini-NX C18 75×30 mm×3 μm; mobile phase: water (0.225% formic acid)/ACN] B %: 15%-45%, 7 minutes] to afford the title compound (15.2 mg, 13% yield) as a white solid; ¹H NMR (400 MHz, methanol-d₄) δ=9.27-9.16 (m, 1H), 8.12 (d, J=8.4 Hz, J H), 7.86 (d, J=8.0 Hz, 1H), 7.74-7.67 (m, 1H), 7.61 (dd, J=1.2, 7.2 Hz, 1H), 7.53 (dt, J=4.8, 8.0 Hz, 1H), 7.24-7.14 (m, 1H), 6.88 (s, 1H), 5.35-5.16 (m, 2H), 4.58-4.45 (m, 6H), 3.56-3.43 (m, 2H), 3.17-3.04 (m, 2H), 2.57-2.35 (m, 2H), 2.28-2.19 (m, 2H), 2.18-2.03 (m, 4H), 2.02-1.92 (m, 2H); LCMS (ESI, M+1): m/z=611.2.

Example 259

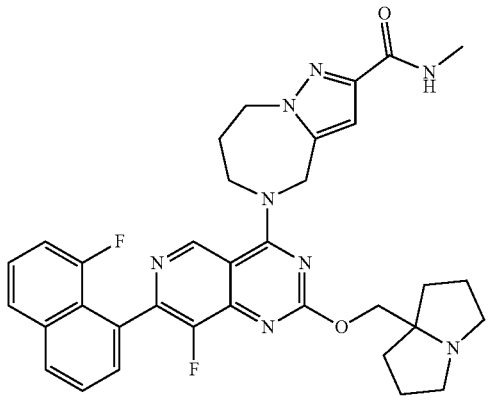 [SMILES: CNC(=O)c1cc2n(n1)CCCN(c1nc(OCC34CCCN3CCC4)nc3c(F)c(-c4cccc5cccc(F)c45)ncc13)C2]

5-(8-fluoro-7-(8-fluoronaphthalen-1-yl)-2-((hexahydro-1H-pyrrolizin-7a-yl)methoxy)pyrido[4,3-d]pyrimidin-4-yl)-N-methyl-5,6,7,8-tetrahydro-4H-pyrazolo[1,5-a][1,4]diazepine-2-carboxamide

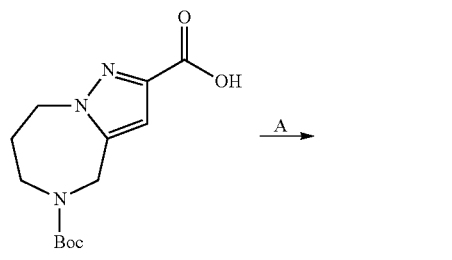

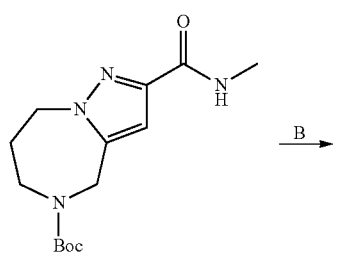

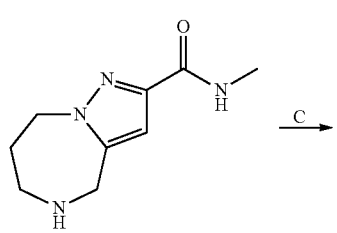

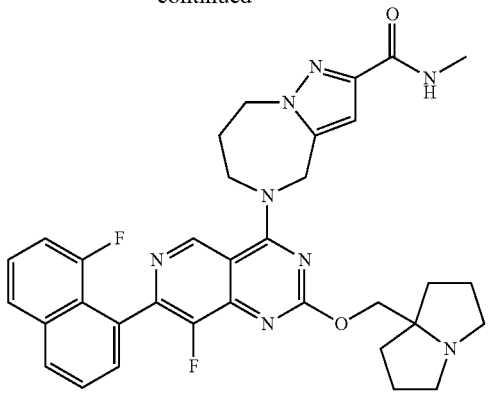

Step A. tert-butyl-2-(methylcarbamoyl)-7,8-dihydro-4H-pyrazolo[1,5-a][1,4]diazepine-5(6H)-carboxylate: To a solution of 5-tert-butoxycarbonyl-4,6,7,8-tetrahydropyrazolo[1,5-a][1,4]diazepine-2-carboxylic acid (1.00 g, 1.0 equiv.), TEA (2.16 g, 6.0 equiv.) and HATU (2.70 g, 2.0 equiv.) in THF (10 mL) was added methylamine (720 mg, 3.0 equiv., HCl). The reaction was stirred at 25° C. for 3 hours. The mixture was diluted with water (10 mL) and extracted with ethyl acetate (3×10 mL). The combined organic layers were dried over anhydrous sodium sulfate, concentrated and purified by reversed phase flash chromatography [C18, water (0.1% formic acid)/ACN] to afford the title compound (900 g, 83% yield) as a yellow solid; LCMS (ESI, M+1): m/z=295.0.

Step B. N-methyl-5,6,7,8-tetrahydro-4H-pyrazolo[1,5-a][1,4]diazepine-2-carboxamide: To a solution of tert-butyl-2-(methylcarbamoyl)-4,6,7,8-tetrahydropyrazolo[1,5-a][1,4]diazepine-5-carboxylate (900 mg, 1.0 equiv.) in MeCN (9 mL) was added HCl.dioxane (4 M, 18 mL, 23 equiv.) at 0° C. The reaction was stirred at 0° C. for 0.5 hour. The mixture was concentrated to afford the title compound (900 mg, crude) as a yellow solid; LCMS (ESI, M+): m/z=194.2.

Step C. 5-(8-fluoro-7-(8-fluoronaphthalen-1-yl)-2-((hexahydro-1H-pyrrolizin-7a-yl)methoxy)pyrido[4,3-d]pyrimidin-4-yl)-N-methyl-5,6,7,8-tetrahydro-4H-pyrazolo[1,5-a][1,4]diazepine-2-carboxamide: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 1.0 equiv.), N-methyl-5,6,7,8-tetrahydro-4H-pyrazolo[1,5-a][1,4]diazepine-2-carboxamide (435 mg, 10 equiv., HCl) and 4 Å molecular sieves (10 mg) in DMF (0.5 mL) was added DIEA (487 mg, 20 equiv.). The reaction was stirred at 40° C. for 12 hours. The residue was filtered and purified by prep-HPLC [column: Phenomenex Gemini-NX C18 75×30 mm×3 µm; mobile phase: water (0.225% formic acid)/ACN] B %: 15%-45%, 7 minutes] to afford the title compound (60.1 mg, 50% yield) as a yellow solid; $^1$H NMR (400 MHz, methanol-$d_4$) δ=9.22 (s, 1H), 8.12 (br d, J=8.4 Hz, 1H), 7.86 (d, J=8.4 Hz, 1H), 7.70 (t, J=7.6 Hz, 1H), 7.61 (d, J=7.2 Hz, 1H), 7.53 (dt, J=5.2, 8.0 Hz, 1H), 7.19 (dd, J=7.6, 13.2 Hz, 1H), 6.84 (s, 1H), 5.37-5.13 (m, 2H), 4.56 (s, 2H), 4.54-4.42 (m, 4H), 3.65-3.54 (m, 2H), 3.20 (td, J=6.0, 11.6 Hz, 2H), 2.88 (s, 3H), 2.45 (br s, 2H), 2.33-2.23 (m, 2H), 2.23-2.09 (m, 4H), 2.09-2.00 (m, 2H); LCMS (ESI, M+1): m/z=625.1.

Example 260

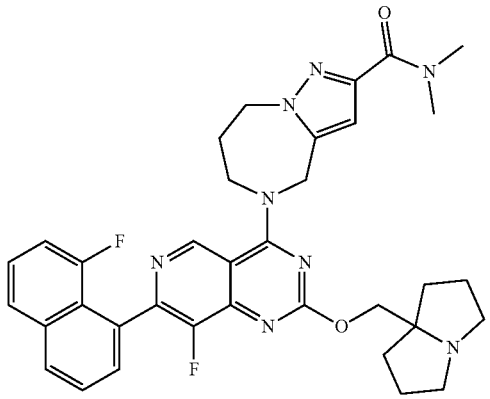 [SMILES: CN(C)C(=O)c1cc2n(n1)CCCN(c1nc(OCC34CCCN3CCC4)nc3c(F)c(-c4cccc5cccc(F)c45)ncc13)C2]

5-(8-fluoro-7-(8-fluoronaphthalen-1-yl)-2-((hexahydro-1H-pyrrolizin-7a-yl)methoxy)pyrido[4,3-d]pyrimidin-4-yl)-N,N-dimethyl-5,6,7,8-tetrahydro-4H-pyrazolo[1,5-a][1,4]diazepine-2-carboxamide

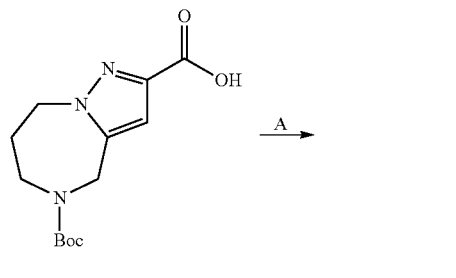 A →

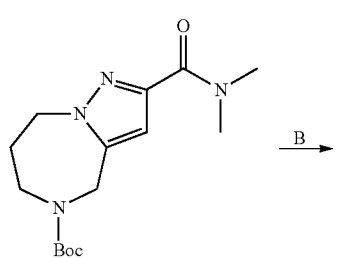 B →

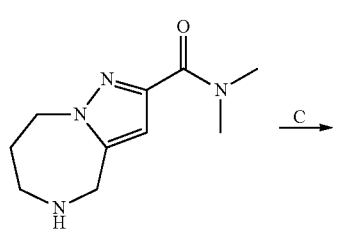 C →

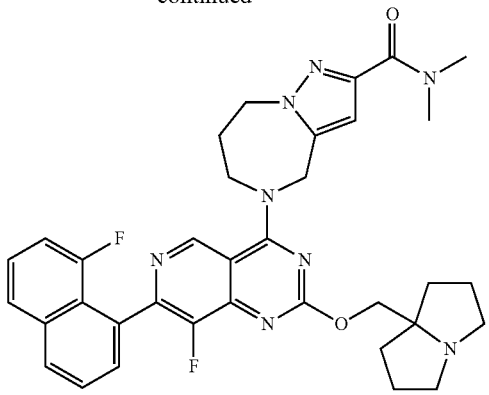

Step A. tert-butyl-2-(dimethylcarbamoyl)-7,8-dihydro-4H-pyrazolo[1,5-a][1,4]diazepine-5(6H)-carboxylate: To a solution of 5-tert-butoxycarbonyl-4,6,7,8-tetrahydropyrazolo[1,5-a][1,4]diazepine-2-carboxylic acid (1.00 g, 1.0 equiv.), TEA (1.08 g, 3.0 equiv.) and HATU (2.70 g, 7.11 mmol, 2.0 equiv.) in THF (10 mL) was added dimethylamine (2 M in THF, 2.0 equiv.). The mixture was stirred at 25° C. for 12 hours. The mixture was diluted with water (10 mL) and extracted with ethyl acetate (3×10 mL). The combined organic layers were dried over anhydrous sodium sulfate, concentrated and purified by reversed phase chromatography [C18, water (0.1% formic acid)/ACN] to afford the title compound (1.00 g, 89% yield) as a yellow solid; LCMS (ESI, M+1): m/z=309.0.

Step B. N,N-dimethyl-5,6,7,8-tetrahydro-4H-pyrazolo[1,5-a][1,4]diazepine-2-carboxamide: To a solution of tert-butyl-2-(dimethylcarbamoyl)-7,8-dihydro-4H-pyrazolo[1,5-a][1,4]diazepine-5(6H)-carboxylate (1.00 g, 1.0 equiv.) in MeCN (10 mL) was added HCl.dioxane (4 M, 20 mL, 25 equiv.) at 0° C. The reaction was stirred at 0° C. for 0.5 hour. The mixture was concentrated to afford the title compound (1.00 g, crude, HCl) as a yellow liquid; LCMS (ESI, M+): m/z=208.3.

Step C. 5-(8-fluoro-7-(8-fluoronaphthalen-1-yl)-2-((hexahydro-1H-pyrrolizin-7a-yl)methoxy)pyrido[4,3-d]pyrimidin-4-yl)-N,N-dimethyl-5,6,7,8-tetrahydro-4H-pyrazolo[1,5-a][1,4]diazepine-2-carboxamide: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 1.0 equiv.), N,N-dimethyl-5,6,7,8-tetrahydro-4H-pyrazolo[1,5-a][1,4]diazepine-2-carboxamide (461 mg, 10 equiv., HCl) and 4 Å molecular sieves (10 mg) in DMF (0.5 mL) was added DIEA (487 mg, 20 equiv.). The reaction was stirred at 40° C. for 24 hours. The mixture was filtered and purified by prep-HPLC [column: Phenomenex Gemini-NX C18 75×30 mm×3 μm; A: water (0.225% formic acid)/ACN] B %: 15%-45%, 7 minutes] to afford the title compound (7.28 mg, 6.02% yield) as a white solid; $^1$H NMR (400 MHz, methanol-$d_4$) δ=9.19 (s, 1H), 8.12 (d, J=8.4 Hz, 1H), 7.85 (d, J=8.0 Hz, 1H), 7.74-7.66 (m, 1H), 7.61 (dd, J=1.2, 7.2 Hz, 1H), 7.53 (dt, J=4.8, 8.0 Hz, 1H), 7.23-7.13 (m, 1H), 6.79 (s, 1H), 5.38-5.15 (m, 2H), 4.58-4.52 (m, 2H), 4.46 (br t, J=4.8 Hz, 2H), 4.36 (s, 3H), 3.29-3.20 (m, 2H), 3.08 (s, 3H), 2.94-2.80 (m, 2H), 2.50-2.38 (m, 2H), 2.18-2.08 (m, 2H), 2.06-1.91 (m, 4H), 1.90-1.79 (m, 2H); LCMS (ESI, M+1): m/z=639.1.

Example 261

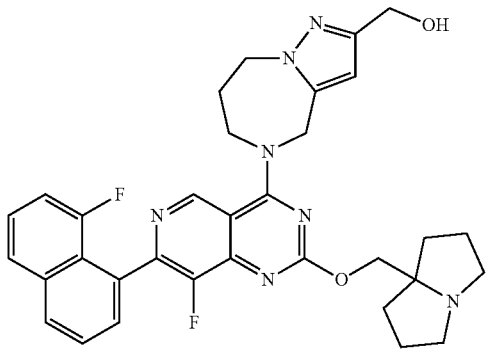 [SMILES: OCc1cc2n(n1)CCCN(c1nc(OCC34CCCN3CCC4)nc3c(F)c(-c4cccc5cccc(F)c45)ncc13)C2]

(5-(8-fluoro-7-(8-fluoronaphthalen-1-yl)-2-((hexa-hydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-yl)methanol The title compound was synthesized according to the procedure described for example 84. $^1$H NMR (400 MHz, methanol-$d_4$) δ=9.24 (s, 1H), 8.13 (br d, J=8.0 Hz, 1H), 7.86 (d, J=8.3 Hz, 1H), 7.75-7.66 (m, 1H), 7.61 (d, J=7.2 Hz, 1H), 7.54 (dt, J=5.2, 8.0 Hz, 1H), 7.19 (dd, J=7.6, 13.2 Hz, 1H), 6.46 (s, 1H), 5.3-5.17 (m, 2H), 4.56 (d, J=17.6 Hz, 4H), 4.44 (br d, J=6.0 Hz, 4H), 3.64-3.56 (m, 2H), 3.20 (td, J=6.0, 11.6 Hz, 2H), 2.42 (br s, 2H), 2.33-2.25 (m, 2H), 2.25-2.18 (m, 1H), 2.18-2.09 (m, 3H), 2.09-2.01 (m, 2H); LCMS (ESI, M+1): m/z=598.3.

Example 262

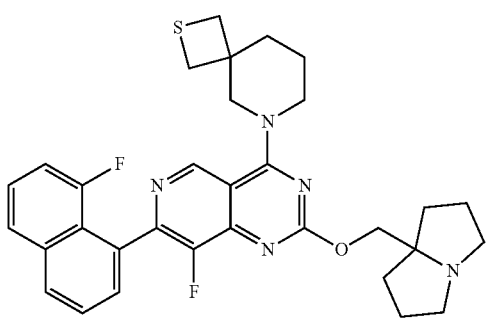 [SMILES: Fc1c(-c2cccc3cccc(F)c23)ncc2c(N3CCCC4(CSC4)C3)nc(OCC34CCCN3CCC4)nc12]

6-(8-fluoro-7-(8-fluoronaphthalen-1-yl)-2-((hexa-hydro-1H-pyrrolizin-7a-yl)methoxy)pyrido[4,3-d]pyrimidin-4-yl)-2-thia-6-azaspiro[3.5]nonane The title compound was synthesized according to the procedure described for example 84. $^1$H NMR (400 MHz, METHANOL-$d_4$) δ=9.14 (s, 1H), 8.12 (br d, J=8.4 Hz, 1H), 7.86 (d, J=8.0 Hz, 1H), 7.72-7.69 (m, 1H), 7.62 (dd, J=0.8, 7.2 Hz, 1H), 7.53 (dt, J=5.2, 8.0 Hz, 1H), 7.19 (dd, J=7.2, 13.2 Hz, 1H), 4.57 (s, 2H), 4.43-4.36 (m, 2H), 4.02 (br dd, J=4.4, 6.0 Hz, 2H), 3.46-3.43 (m, 2H), 3.16 (d, J=9.2 Hz, 2H), 3.06-3.03 (m, 2H), 2.90 (t, J=9.2 Hz, 2H), 2.22-2.17 (m, 2H), 2.15-2.05 (m, 4H), 1.97-1.93 (m, 4H), 1.83-1.77 (m, 2H); LCMS (ESI, M+1): m/z=574.3.

Example 263

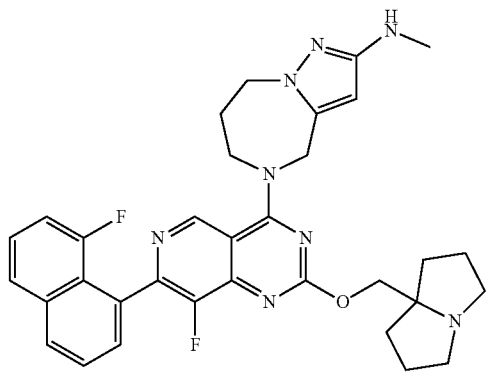 [SMILES: CNc1cc2n(n1)CCCN(c1nc(OCC34CCCN3CCC4)nc3c(F)c(-c4cccc5cccc(F)c45)ncc13)C2]

5-(8-fluoro-7-(8-fluoronaphthalen-1-yl)-2-((tetra-hydro-1H-pyrrolizin-7a(5H)-yl)methoxy)pyrido[4,3-d]pyrimidin-4-yl)-N-methyl-5,6,7,8-tetrahydro-4H-pyrazolo[1,5-a][1,4]diazepin-2-amine

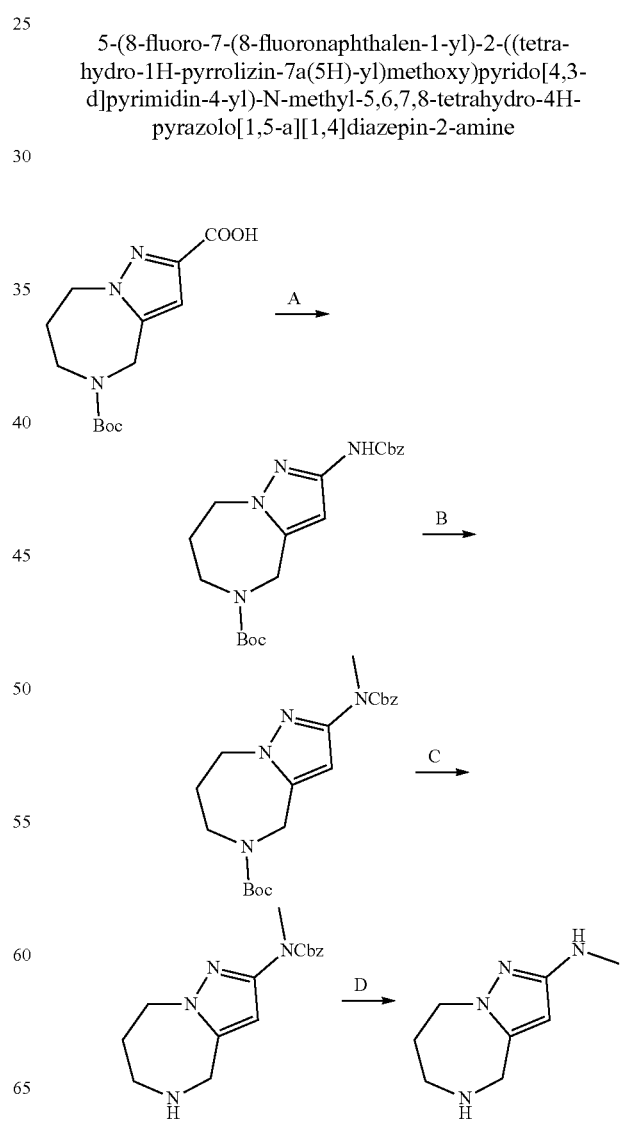

-continued

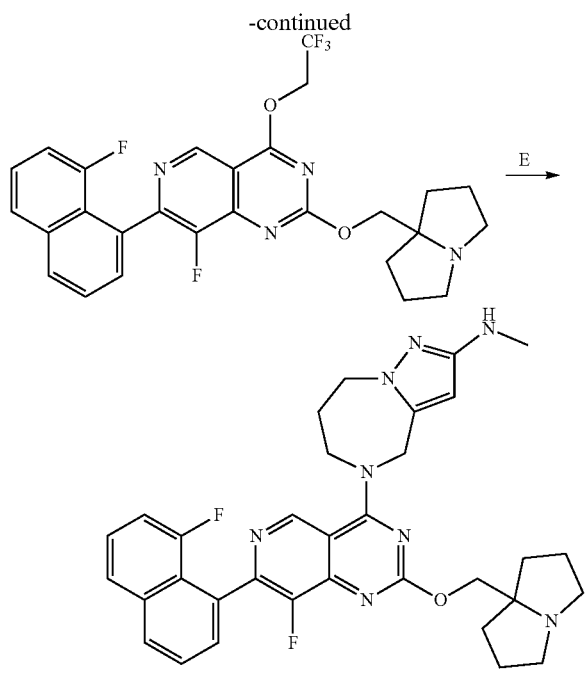

Step A. tert-butyl 2-(benzyloxycarbonylamino)-4,6,7,8-tetrahydropyrazolo[1,5-a][1,4]diazepine-5-carboxylate: A mixture of 5-tert-butoxycarbonyl-4,6,7,8-tetrahydropyrazolo[1,5-a][1,4]diazepine-2-carboxylic acid (500 mg, 1.0 equiv.), 4 Å MS (300 mg) and TEA (539 mg, 3.0 equiv.) in toluene (5 mL) and BnOH (1.15 g, 6.0 equiv.) was stirred at 110° C. for 0.5 hour under nitrogen. And then the mixture was cooled to 15° C. and DPPA (734 mg, 1.5 equiv.) was added at 15° C. The mixture was stirred at 110° C. for 5 hours. The reaction mixture was diluted with water (15 mL) and extracted with ethyl acetate (3×20 mL). The combined organic layers were washed with brine (20 mL), and dried over sodium sulfate, filtered and concentrated under reduced pressure to give a residue. The residue was purified by reversed phase flash chromatography [C18, water (0.1% formic acid)/ACN] to afford the title compound (400 mg, 42% yield) as a gray solid; LCMS (ESI, M+1): m/z=387.2.

Step B. tert-butyl 2-(benzyloxycarbonyl(methyl)amino)-4,6,7,8-tetrahydropyrazolo[1,5-a][1,4]diazepin-5-carboxylate: A mixture of tert-butyl 2-(benzyloxycarbonylamino)-4,6,7,8-tetrahydropyrazolo[1,5-a][1,4]diazepine-5-carboxylate (100 mg, 1.0 equiv.) in DMF (3 mL) was added K$_2$CO$_3$ (179 mg, 5.0 equiv.) and MeI (220 mg, 6.0 equiv.). The mixture was stirred at 50° C. for 3 hours. The reaction mixture was quenched with saturated NH$_4$Cl solution (20 mL). The mixture was extracted with ethyl acetate (2×10 mL). The combined organic extracts were washed with brine (10 ml), dried over sodium sulfate, filtered and concentrated under reduced pressure. The residue was purified by column chromatography (Silica gel, Petroleum ether/Ethyl acetate 20:1 to 1:1) to afford the title compound (85.0 mg, 82% yield) as a yellow oil; LCMS (ESI, M+1): m/z=401.3.

Step C. benzyl N-methyl-N-(5,6,7,8-tetrahydro-4H-pyrazolo[1,5-a][1,4]diazepin-2-yl)carbamate: To a solution of tert-butyl 2-[benzyloxycarbonyl(methyl)amino]-4,6,7,8-tetrahydropyrazolo[1,5-a][1,4]diazepine-5-carboxylate (85.0 mg, 1.0 equiv.) in MeCN (1 mL) was added HCl.dioxane (4 M, 0.5 mL, 9.42 equiv.). The mixture was stirred at 25° C. for 2 hours. The reaction mixture was concentrated under reduced pressure to give a residue. The pH of the mixture was adjusted to 8 with saturated NaHCO$_3$ solution and the resulting was extracted with ethyl acetate (15 mL×3). The combined organic layers were washed with brine (5 mL), dried over sodium sulfate, filtered and concentrated under reduced pressure to afford the title compound (60.0 mg, 94% yield) as a yellow solid.

Step D. N-methyl-5,6,7,8-tetrahydro-4H-pyrazolo[1,5-a][1,4]diazepin-2-amine: To a mixture of benzyl N-methyl-N-(5,6,7,8-tetrahydro-4H-pyrazolo[1,5-a][1,4]diazepin-2-yl)carbamate (60.0 mg, 1.0 equiv.) in MeOH (3 mL) was added Pd/C (15.0 mg, 10% purity). The mixture was stirred at 25° C. for 2 hours under H$_2$ atmosphere (15 psi) before being filtered and concentrated under reduced pressure to give a residue. The residue was purified by prep-TLC (Silica gel, DCM/MeOH 5:1) to afford the title compound (32.0 mg, 88% yield) as a yellow solid; $^1$H NMR (400 MHz, chloroform-d) δ=5.41 (s, 1H), 4.24-4.11 (m, 2H), 3.78 (s, 2H), 3.21-3.09 (m, 2H), 2.80 (s, 3H), 1.82-1.74 (m, 2H); LCMS [ESI, M+1]: m/z=167.3.

Step E. 5-[8-fluoro-7-(8-fluoro-1-naphthyl)-2-(1,2,3,5,6,7-hexahydropyrrolizin-8-yl)methoxy)pyrido[4,3-d]pyrimidin-4-yl]-N-methyl-4,6,7,8-tetrahydropyrazolo[1,5-a][1,4]diazepin-2-amine: To a solution of N-methyl-5,6,7,8-tetrahydro-4H-pyrazolo[1,5-a][1,4]diazepin-2-amine (31.3 mg, 10 equiv.), 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (10.0 mg, 1.0 equiv.), DIEA (7.31 mg, 3.0 equiv.) in DMF (0.05 mL) was degassed and stirred at 50° C. for 12 hours under N$_2$ atmosphere. The reaction mixture was filtered and concentrated under reduced pressure. The residue was purified by prep-HPLC [column: Phenomenex C 18 75×30 mm×3 μm; mobile phase: water (0.1% formic acid)/ACN], B %: 12%-42%, 7 min] to afford the title compound (3.84 mg, 33% yield) as a white solid; $^1$H NMR (400 MHz, METHANOL-d$_4$): δ=9.23 (s, 1H), 8.12 (br d, J=8.4 Hz, 1H), 7.86 (d, J=8.4 Hz, 1H), 7.71 (t, J=7.2 Hz, 1H), 7.63-7.59 (m, 1H), 7.53 (dt, J=4.8, 8.0 Hz, 1H), 7.19 (dd, J=8.0, 13.2 Hz, 1H), 5.77 (s, 1H), 5.18-5.06 (m, 2H), 4.45 (s, 2H), 4.37 (br s, 2H), 4.30-4.21 (m, 2H), 3.41-3.34 (m, 2H), 3.03-2.93 (m, 2H), 2.77 (s, 3H), 2.39 (br s, 2H), 2.17 (br dd, J=6.0, 12.0 Hz, 2H), 2.04 (dt, J=6.4, 13.2 Hz, 4H), 1.91 (br dd, J=6.8, 12.8 Hz, 2H); LCMS [ESI, M+1]: m/z=597.4.

Example 264

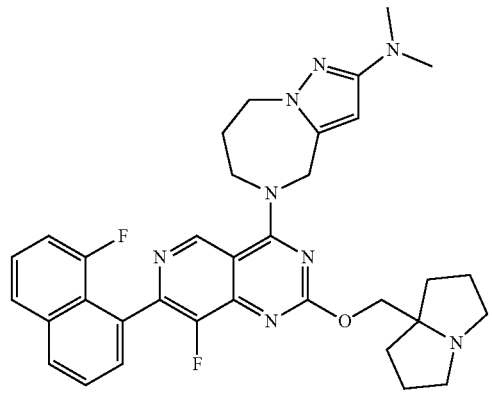 [SMILES: CN(C)c1cc2n(n1)CCCN(c1nc(OCC34CCCN3CCC4)nc3c(F)c(-c4cccc5cccc(F)c45)ncc13)C2]

5-(8-fluoro-7-(8-fluoronaphthalen-1-yl)-2-((hexa-hydro-1H-pyrrolizin-7a-yl)methoxy)pyrido[4,3-d]pyrimidin-4-yl)-N,N-dimethyl-5,6,7,8-tetrahydro-4H-pyrazolo[1,5-a][1,4]diazepin-2-amine

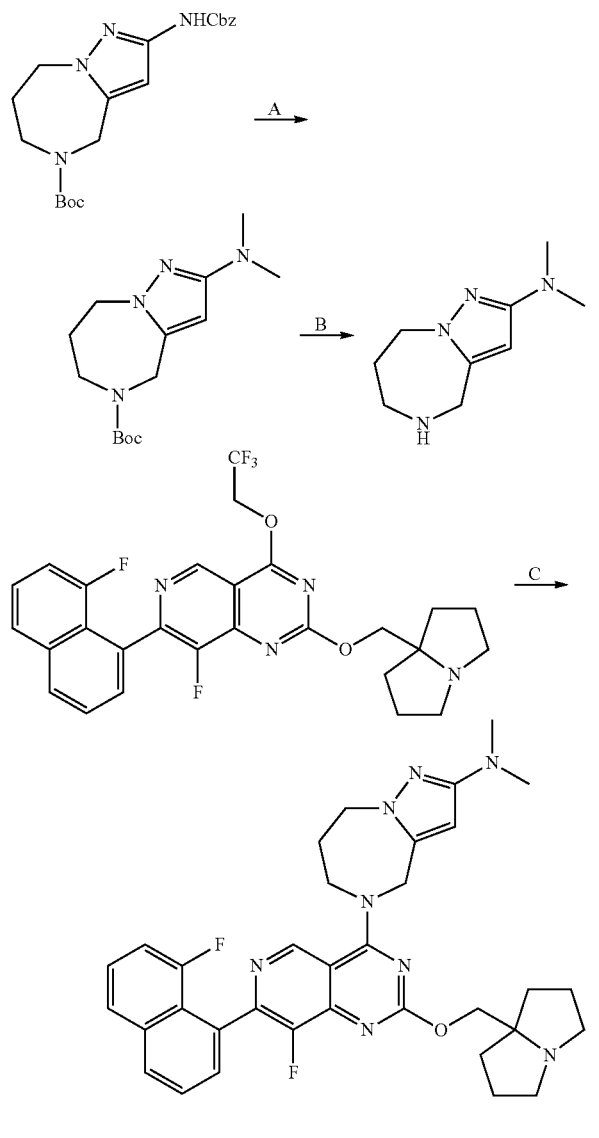

Step A. tert-butyl 2-(dimethylamino)-7,8-dihydro-4H-pyrazolo[1,5-a]diazepine-5(6H)-carboxylate: To a solution of tert-butyl-2-(((benzyloxy)carbonyl)amino)-7,8-dihydro-4H-pyrazolo[1,5-a][1,4]diazepine-5(6H)-carboxylate (589 mg, 1.0 equiv.) and HCHO (371 mg, 37% purity, 3.0 equiv.) in MeOH (20.0 mL) was added Pd/C (500 mg, 10% purity) under $N_2$. The mixture was degassed and purged with $H_2$ for 3 times, and then stirred at 25° C. for 1 hour under $H_2$ (15 psi). The mixture was filtered, the filtrate was concentrated in vacuum. The crude product was purified by reversed phase flash chromatography [C18, water (0.1% formic acid)/ACN] to afford the tittle compound (202 mg, 43% yield) as a yellow oil. LCMS (ESI, M+1): m/z=281.2.

Step B. N,N-dimethyl-5,6,7,8-tetrahydro-4H-pyrazolo[1,5-a][1,4]diazepin-2-amine: To a solution of tert-butyl 2-(dimethylamino)-7,8-dihydro-4H-pyrazolo[1,5-a][1,4]diazepine-5(6H)-carboxylate (170 mg, 1.0 equiv.) in MeCN (3.00 mL) was added HCl-dioxane (4 M, 6.00 mL, 39.6 equiv.). The mixture was stirred at 25° C. for 0.5 hour. The mixture was concentrated in vacuum to afford the tittle compound (131 mg, crude, HCl) as a white solid.

Step C. 5-(8-fluoro-7-(8-fluoronaphthalen-1-yl)-2-((hexahydro-1H-pyrrolizin-7a-yl)methoxy)pyrido[4,3-d]pyrimidin-4-yl)-N,N-dimethyl-5,6,7,8-tetrahydro-4H-pyrazolo[1,5-a][1,4]diazepin-2-amine: To a mixture of N,N-dimethyl-5,6,7,8-tetrahydro-4H-pyrazolo[1,5-a][1,4]diazepin-2-amine (129 mg, 4.5 equiv., HCl) and DIEA (170 mg, 10.0 equiv.) was added 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (70.0 mg, 1.0 equiv.) and DMF (0.5 mL). The mixture was stirred at 50° C. for 14 hours. The mixture was diluted with DMF (1.5 mL) and purified by reversed phase flash chromatography [C18, water (0.1% formic acid)/ACN] and further purified by prep-HPLC (column: Phenomenex luna C18 150×25 mm×10 μm; mobile phase: water (0.1% formic acid)/ACN] B %: 15%-45%, 10 mins) to afford the tittle compound (10.2 mg, 2.7% yield over two steps) as a white solid; $^1$H NMR (400 MHz, methanol-$d_4$) δ=9.23 (s, 1H), 8.12 (br d, J=8.4 Hz, 1H), 7.86 (d, J=8.0 Hz, 1H), 7.74-7.67 (m, 1H), 7.61 (dd, J=0.8, 6.8 Hz, 1H), 7.53 (dt, J=4.8, 8.0 Hz, 1H), 7.19 (ddd, J=0.8, 7.6, 13.2 Hz, 1H), 5.90 (s, 1H), 5.21-5.06 (m, 2H), 4.43-4.33 (m, 4H), 4.32-4.24 (m, 2H), 3.29-3.23 (m, 2H), 2.96-2.86 (m, 2H), 2.81 (s, 6H), 2.45-2.32 (m, 2H), 2.20-2.08 (m, 2H), 2.07-1.92 (m, 4H), 1.91-1.80 (m, 2H); LCMS (ESI, M+1): m/z=611.4.

Example 265

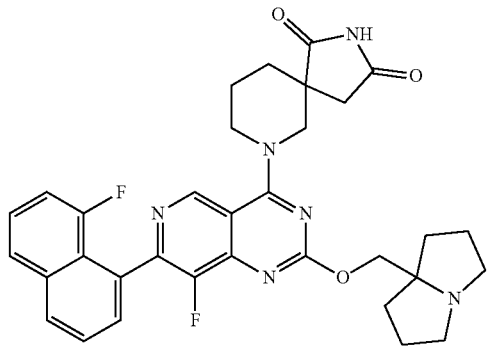 [SMILES: O=C1CC2(CCCN(c3nc(OCC45CCCN4CCC5)nc4c(F)c(-c5cccc6cccc(F)c56)ncc34)C2)C(=O)N1]

7-(8-fluoro-7-(8-fluoronaphthalen-1-yl)-2-((hexa-hydro-1H-pyrrolizin-7a-yl)methoxy)pyrido[4,3-d]pyrimidin-4-yl)-2,7-diazaspiro[4.5]decane-1,3-dione The title compound was synthesized according to the procedure described for example 84. $^1$H NMR (400 MHz, METHANOL-$d_4$) δ=9.12 (d, J=2.4 Hz, 1H), 8.13 (d, J=8.4 Hz, 1H), 7.86 (d, J=8.0 Hz, 1H), 7.74-7.68 (m, 1H), 7.62 (ddd, J=0.8, 7.2, 10.8 Hz, 1H), 7.54 (dt, J=5.2, 8.0 Hz, 1H), 7.19 (ddd, J=1.6, 7.6, 13.2 Hz, 1H), 4.66 (br dd, J=6.0, 13.2 Hz, 1H), 4.52 (s, 2H), 4.42 (br dd, J=5.2, 12.8 Hz, 1H), 3.95 (dt, J=3.2, 10.4 Hz, 1H), 3.82 (d, J=13.2 Hz, 1H), 3.59-3.47 (m, 2H), 3.18-3.08 (m, 2H), 2.97 (dd, J=12.0, 18.0 Hz, 1H), 2.68 (d, J=18.0 Hz, 1H), 2.30-2.19 (m, 3H), 2.17-2.04 (m, 5H), 2.04-1.83 (m, 4H); LCMS [ESI, M+1]: m/z=599.4.

Example 266

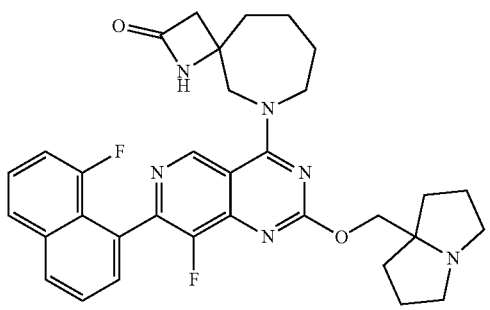 [SMILES: O=C1CC2(CCCCN(c3nc(OCC45CCCN4CCC5)nc4c(F)c(-c5cccc6cccc(F)c56)ncc34)C2)N1]

6-(8-fluoro-7-(8-fluoronaphthalen-1-yl)-2-((hexa-hydro-1H-pyrrolizin-7a-yl)methoxy)pyrido[4,3-d]pyrimidin-4-yl)-1,6-diazaspiro[3.6]decan-2-one

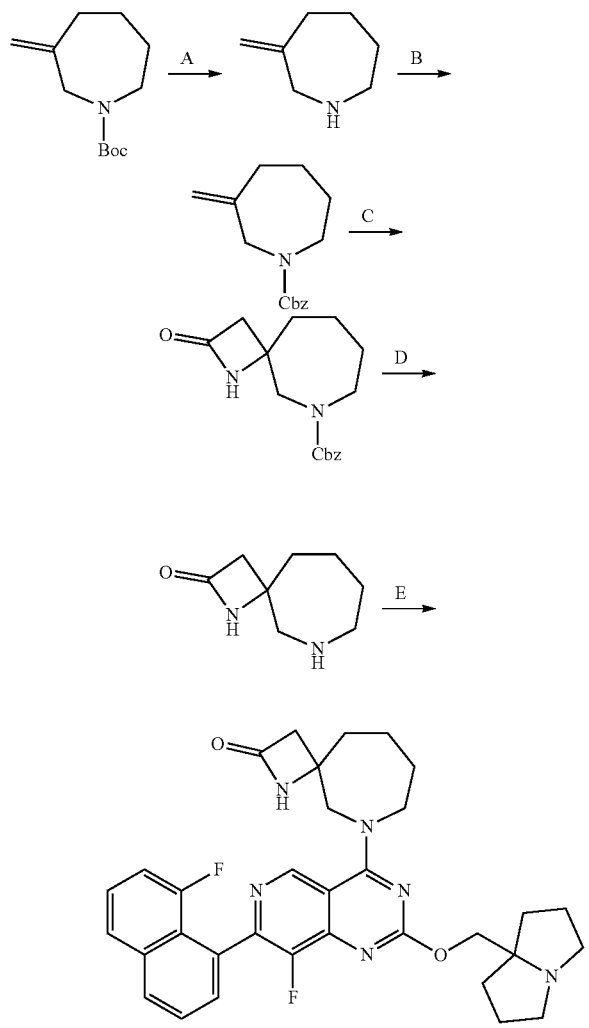

Step A. 3-methyleneazepane: To a solution of tert-butyl 3-methyleneazepane-1-carboxylate (1.50 g, 1.0 equiv.) in MeCN (5 mL) was added HCl.dioxane (4 M, 10.0 mL, 5.63 equiv.). The mixture was stirred at 20° C. for 1 hour. After completion, the residue was concentrated to afford the title compound (1.50 g, crude, HCl) as a white solid.

Step B. benzyl 3-methyleneazepane-1-carboxylate: To a solution of 3-methyleneazepane (1.50 g, 1.0 equiv., HCl) and DIEA (6.57 g, 5.0 equiv.) in dichloromethane (20.0 mL) was added CbzCl (2.60 g, 1.50 equiv.). The mixture was stirred at 20° C. for 3 hours. The residue was concentrated to afford the title compound (2.70 g, crude) as a yellow solid.

Step C. benzyl 2-oxo-1,6-diazaspiro[3.6]decane-6-carboxylate: To a solution of benzyl 3-methyleneazepane-1-carboxylate (2.70 g, 1.0 equiv.) in toluene (60.0 mL) was added a solution of sulfurisocyanatidic chloride (1.71 g, 1.10 equiv.) in toluene (20.0 mL) dropwise at 0° C. After addition the mixture was stirred at 20° C. for 20 hours. After reaction completion, the mixture was slowly added to a vigorously stirred solution of $Na_2SO_3$ (3.0 g) and $K_2CO_3$ (20 g) in water (60.0 mL). The mixture was stirred at 20° C. for 4 hours. Then the mixture was extracted with ethyl acetate (3×15 mL). The organic layer was dried over $Na_2SO_4$, filtered and concentrated. The residue was purified by column chromatography ($Al_2O_3$, petroleum ether/ethyl acetate 10:1 then ethyl acetate/methanol 10:1) to afford the title compound (1.20 g, three steps 36% yield) as a yellow oil; $^1$H NMR (400 MHz, CHLOROFORM-d) δ=7.46-7.29 (m, 5H), 5.26-5.02 (m, 2H), 3.87-3.52 (m, 3H), 3.36-3.15 (m, 1H), 2.98-2.59 (m, 2H), 1.96-1.70 (m, 4H), 1.65-1.43 (m, 2H); LCMS (ESI, M−41, 2M+1): m/z=247.1, 577.4.

Step D. 1,6-diazaspiro[3.6]decan-2-one: To a solution of benzyl 2-oxo-1,6-diazaspiro[3.6]decane-6-carboxylate (200 mg, 1.0 equiv.) in MeOH (5.0 mL) was added Pd/C (50 mg, 10% purity) under $N_2$. The suspension was degassed in vacuum and purged with $H_2$ several times. The mixture was stirred under $H_2$ (15 Psi) at 20° C. for 12 hours. The mixture was filtered and concentrated to afford the title compound (120 mg, crude) as a yellow oil.

Step E. 6-(8-fluoro-7-(8-fluoronaphthalen-1-yl)-2-((hexa-hydro-1H-pyrrolizin-7a-yl)methoxy)pyrido[4,3-d]pyrimi-din-4-yl)-1,6-diazaspiro[3.6]decan-2-one: To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (65.0 mg, 1.0 equiv.) and DIEA (110 mg, 149 µL, 7.0 equiv.) in DMF (2 mL) was added 1,6-diazaspiro[3.6]decan-2-one (94.5 mg, 5.0 equiv.). The mixture was stirred at 40° C. for 12 hours. After reaction completion, the mixture was filtered and purified by prep-HPLC (column: Phenomenex luna C18 150×25 mm×10 µm; mobile phase: [water (0.1% formic acid)/ACN], B %: 20%.-50%, 7 min) to afford the title compound (32.1 mg, 43% yield over two steps) as a white solid; $^1$H NMR (400 MHz, METHANOL-$d_4$) δ=9.22 (d, J=4.0 Hz, 1H), 8.12 (d, J=8.4 Hz, 1H), 7.85 (d, J=8.0 Hz, 1H), 7.70 (dd, J=7.2, 8.0 Hz, 1H), 7.63-7.58 (m, 1H), 7.56-7.50 (m, 1H), 7.19 (dd, J=7.6, 12.8 Hz, 1H), 4.85-4.78 (m, 2H), 4.46-4.35 (m, 2H), 4.32-4.22 (m, 11H), 4.21-4.05 (m, 2H), 3.38-3.33 (m, 1H), 3.10 (dd, J=3.6, 14.8 Hz, 1H), 2.98-2.89 (m, 2H), 2.82 (dd, J=3.6, 14.8 Hz, 1H), 2.25-2.09 (m, 4H), 2.08-1.94 (m, 6H), 1.94-1.84 (m, 3H), 1.83-1.72 (m, 1H); LCMS (ESI, M+1): m/z=585.4.

Example 267

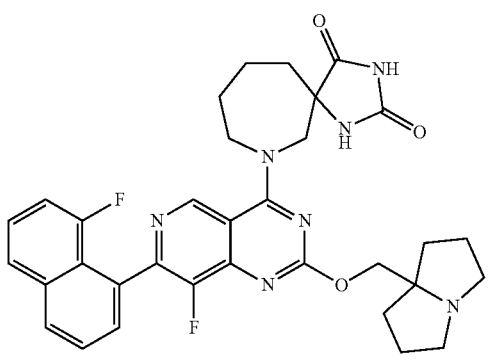 [SMILES: O=C1NC(=O)C2(CCCCN(c3nc(OCC45CCCN4CCC5)nc4c(F)c(-c5cccc6cccc(F)c56)ncc34)C2)N1]

7-(8-fluoro-7-(8-fluoronaphthalen-1-yl)-2-((hexa-hydro-1H-pyrrolizin-7a-yl)methoxy)pyrido[4,3-d]pyrimidin-4-yl)-1,3,7-triazaspiro[4.6]undecane-2,4-dione

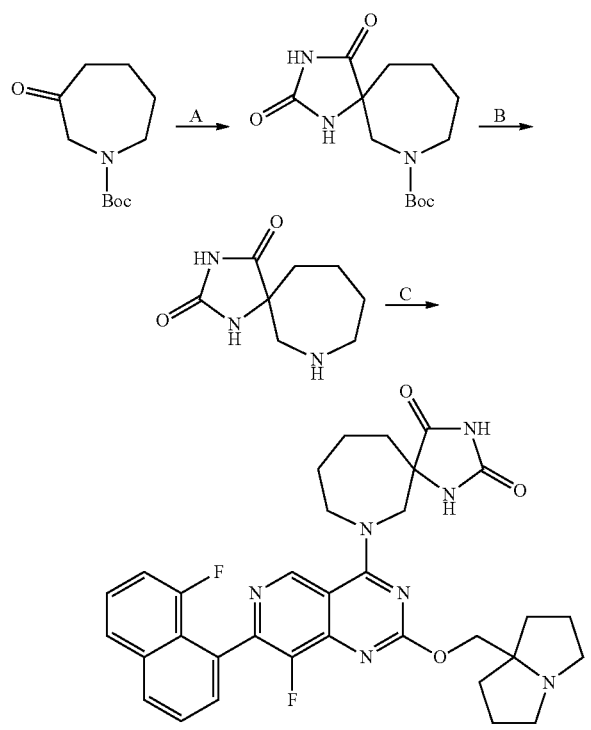

Step A. tert-butyl 2,4-dioxo-1,3,7-triazaspiro[4.6]undecane-7-carboxylate: To a solution of tert-butyl 3-oxoazepane-1-carboxylate (2.00 g, 1.0 equiv.), $(NH_4)_2CO_3$ (2.70 g, 3.0 equiv.) in EtOH (10 mL) and water (10 mL) was added KCN (1.12 g, 1.8 equiv.). The reaction was stirred at 85° C. for 16 hours. The mixture was diluted with water (20 mL) and extracted with ethyl acetate (3×20 mL). The combined organic layers were dried over anhydrous sodium sulfate and concentrated to afford the title compound (2.20 g, 83% yield) as a white solid; $^1$H NMR (400 MHz, dimethylsulfoxide-$d_6$) δ=11.39-9.68 (m, 1H), 7.97-7.52 (m, 1H), 3.45 (s, 2H), 3.29-3.12 (m, 2H), 1.82-1.65 (m, 3H), 1.64-1.47 (m, 3H), 1.45-1.31 (m, 9H); LCMS (ESI, M+1): m/z=284.0.

Step B. 1,3,7-triazaspiro[4.6]undecane-2,4-dione: To a solution of tert-butyl 2,4-dioxo-1,3,7-triazaspiro[4.6]undecane-7-carboxylate (500 mg, 1.0 equiv.) in MeCN (5 mL) was added HCl.dioxane (4 M, 2.5 mL, 5.6 equiv.) at 0° C. The reaction was stirred at 0° C. for 0.5 hour. The mixture was concentrated to afford the title compound (500 mg, crude, HCl salt) as a yellow liquid; LCMS (ESI, M+): m/z=183.1.

Step C. 7-(8-fluoro-7-(8-fluoronaphthalen-1-yl)-2-((hexahydro-1H-pyrrolizin-7a-yl)methoxy)pyrido[4,3-d]pyrimidin-4-yl)-1,3,7-triazaspiro[4.6]undecane-2,4-dione: A mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 1.0 equiv.), 1,3,7-triazaspiro[4.6]undecane-2,4-dione (345 mg, 10 equiv.), DIEA (487 mg, 20 equiv.) and 4 Å molecular sieves (10 mg) in DMF (0.5 mL) was stirred at 40° C. for 24 hours. The residue was filtered and purified by prep-HPLC [column: Phenomenex Gemini-NX C18 75×30 mm×3 μm; mobile phase: [water (0.225% formic acid)/ACN] B %: 15%-45%, 7 minutes] to afford the title compound (32.7 mg, 52.9 μmol, 28% yield) as a white solid; $^1$H NMR (400 MHz, methanol-$d_4$) δ=9.30 (d, J=5.6 Hz, 1H), 8.13 (d, J=8.4 Hz, 1H), 7.86 (d, J=8.0 Hz, 1H), 7.75-7.68 (m, 1H), 7.65-7.59 (m, 1H), 7.54 (dt, J=5.2, 8.0 Hz, 1H), 7.20 (dd, J=7.2, 13.2 Hz, 1H), 4.98 (dd, J=11.6, 14.2 Hz, 1H), 4.60-4.47 (m, 2H), 4.43-4.28 (m, 1H), 4.20-4.00 (m, 2H), 3.61 (qd, J=6.0, 11.6 Hz, 2H), 3.24-3.10 (m, 2H), 2.32-2.19 (m, 4H), 2.19-2.08 (m, 6H), 2.07-1.98 (m, 2H), 1.95-1.70 (m, 2H); LCMS (ESI, M+1): m/z=614.1.

Example 268

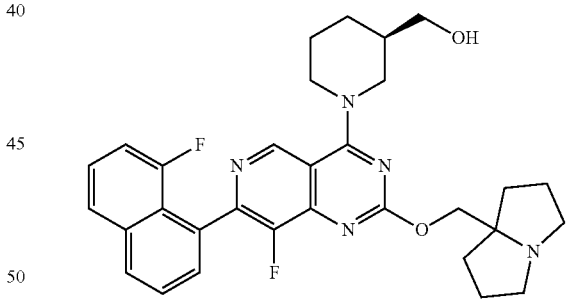

(R)-(1-(8-fluoro-7-(8-fluoronaphthalen-1-yl)-2-((hexahydro-1H-pyrrolizin-7a-yl)methoxy)pyrido[4,3-d]pyrimidin-4-yl)piperidin-3-yl)methanol The title compound was synthesized according to the procedure described for example 84. $^1$H NMR (400 MHz, METHANOL-$d_4$) δ=9.10 (s, 1H), 8.11 (br d, J=8.0 Hz, 1H), 7.85 (d, J=8.0 Hz, 1H), 7.70 (t, J=7.6 Hz, 1H), 7.61 (d, J=7.2 Hz, 1H), 7.52 (dt, J=5.2, 8.0 Hz, 1H), 7.18 (dd, J=7.6, 13.2 Hz, 1H), 4.76-4.58 (m, 2H), 4.47 (s, 2H), 3.60 (dd, J=4.8, 11.2 Hz, 1H), 3.53-3.44 (m, 2H), 3.42-3.32 (m, 3H), 3.03-2.94 (m, 2H), 2.24-2.14 (m, 2H), 2.12-1.98 (m, 5H), 1.98-1.88 (m, 4H), 1.84-1.73 (m, 1H), 1.53-1.41 (m, 1H); LCMS [ESI, M+1]: m/z=546.3.

Example 269

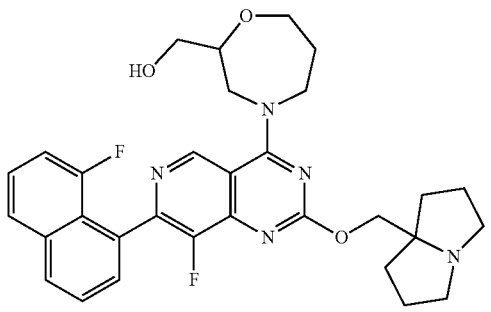 [SMILES: OCC1CN(c2nc(OCC34CCCN3CCC4)nc3c(F)c(-c4cccc5cccc(F)c45)ncc23)CCCO1]

(4-(8-fluoro-7-(8-fluoronaphthalen-1-yl)-2-((hexa-hydro-1H-pyrrolizin-7a-yl)methoxy)pyrido[4,3-d]pyrimidin-4-yl)-1,4-oxazepan-2-yl)methanol The title compound was synthesized according to the procedure described for example 84. ¹H NMR (400 MHz, methanol-d₄) δ=9.22 (s, 1H), 8.12 (br d, J=8.0 Hz, 1H), 7.86 (d, J=8.0 Hz, 1H), 7.71 (dt, J=2.8, 7.2 Hz, 1H), 7.65-7.57 (m, 1H), 7.54 (dt, J=5.2, 8.0 Hz, 1H), 7.24-7.14 (m, 1H), 4.70-4.64 (m, 11H), 4.63-4.55 (m, 2H), 4.39-4.29 (m, 1H), 4.28-4.20 (m, 1H), 4.16 (td, J=4.0, 12.8 Hz, 1H), 4.00-3.91 (m, 1H), 3.84-3.73 (m, 1H), 3.73-3.64 (m, 2H), 3.64-3.53 (m, 3H), 3.23-3.13 (m, 2H), 2.36-2.22 (m, 3H), 2.20-2.08 (m, 5H), 2.06-1.99 (m, 2H); LCMS (ESI, M+1): m/z=562.3.

Example 270

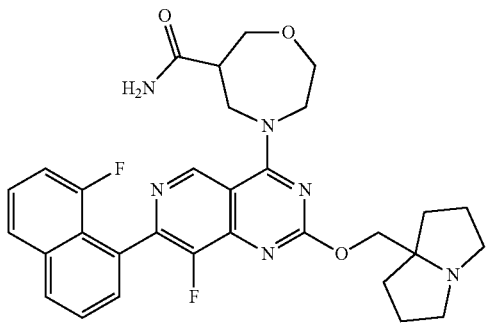 [SMILES: NC(=O)C1COCCN(c2nc(OCC34CCCN3CCC4)nc3c(F)c(-c4cccc5cccc(F)c45)ncc23)C1]

4-(8-fluoro-7-(8-fluoronaphthalen-1-yl)-2-((hexa-hydro-1H-pyrrolizin-7a-yl)methoxy)pyrido[4,3-d]pyrimidin-4-yl)-1,4-oxazepane-6-carboxamide The title compound was synthesized according to the procedure described for example 84. ¹H NMR (400 MHz, methanol-d₄) δ=9.22 (s, 1H), 8.13 (br d, J=8.4 Hz, 1H), 7.87 (d, J=8.0 Hz, 1H), 7.71 (dt, J=2.8, 7.6 Hz, 1H), 7.66-7.58 (m, 1H), 7.54 (dt, J=5.2, 7.6 Hz, 1H), 7.19 (td, J=6.8, 13.2 Hz, 1H), 4.73-4.66 (m, 1H), 4.60 (br s, 2H), 4.44-4.33 (m, 1H), 4.26-4.05 (m, 5H), 3.93-3.79 (m, 1H), 3.72-3.59 (m, 2H), 3.28-3.18 (m, 3H), 2.37-2.25 (m, 2H), 2.25-2.12 (m, 4H), 2.12-2.02 (m, 2H); LCMS (EST, M+1): m/z=575.2.

Example 271

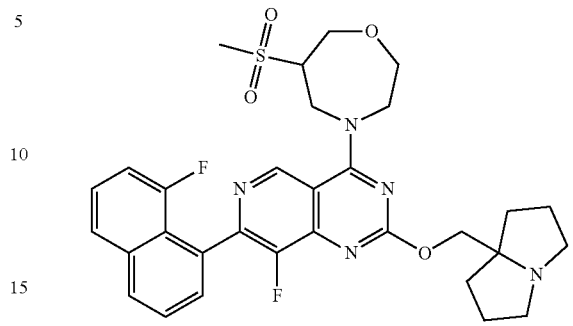

4-(8-fluoro-7-(8-fluoronaphthalen-1-yl)-2-((hexa-hydro-1H-pyrrolizin-7a-yl)methoxy)pyrido[4,3-d]pyrimidin-4-yl)-6-(methylsulfonyl)-1,4-oxazepane

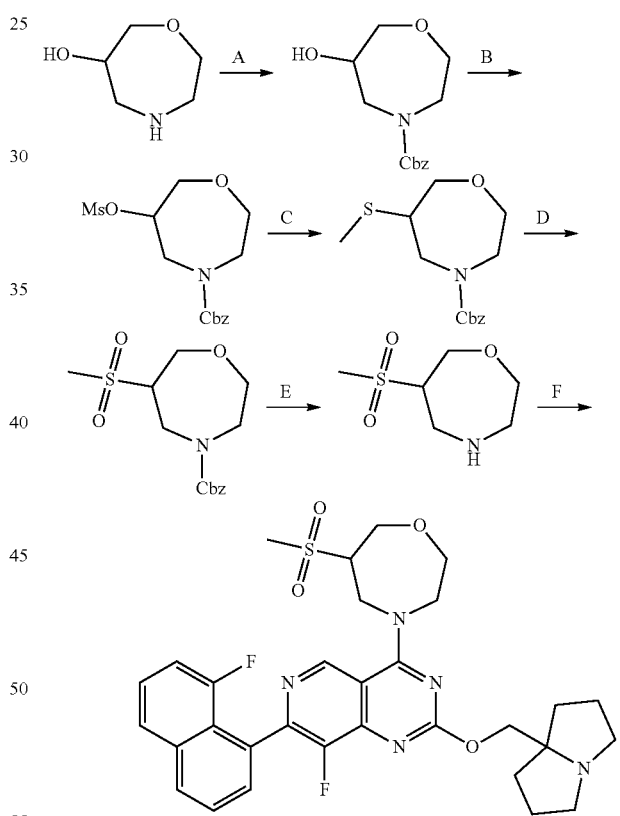

Step A. benzyl 6-hydroxy-1,4-oxazepane-4-carboxylate: To a solution of 1,4-oxazepan-6-ol (539 mg, 1.0 equiv.) and DIEA (1.78 g, 3.0 equiv.) in DCM (10 mL) at 0° C. was added CbzCl (1.18 g, 1.5 equiv.). The mixture was stirred at 0° C. for 1 hour and then warmed to 25° C. for 12 hours. The reaction mixture was diluted with ethyl acetate (10 mL) and water (20 mL), and the aqueous layer was extracted with ethyl acetate (10 mL). The combined organic phase was washed with brine (10 mL), dried over anhydrous sodium sulfate, filtered and concentrated in vacuum. The residue was purified by reversed phase flash chromatography [water (0.1% formic acid)/acetonitrile]. The desired fractions were collected, neutralized with solid NaHCO$_3$, and concentrated in vacuum to remove acetonitrile. The aqueous layer was extracted with ethyl acetate (2×8 mL). The combined organic layers were dried over anhydrous sodium sulfate and concentrated in vacuum to afford the title compound (660 mg, 56.40% yield) as a yellow oil; $^1$H NMR (400 MHz, DMSO) δ=7.43-7.27 (m, 5H), 5.09 (s, 2H), 5.03-4.96 (m, 1H), 3.89-3.43 (m, 7H), 3.32-3.19 (m, 1H), 3.09 (dt, J=8.0, 13.9 Hz, 1H); LCMS (ESI, M+1): m/z=252.2.

Step B. benzyl 6-((methylsulfonyl)oxy)-1,4-oxazepane-4-carboxylate: To a solution mixture of benzyl 6-hydroxy-1,4-oxazepane-4-carboxylate (400 mg, 1.0 equiv.) and TEA (483 mg, 3.0 equiv.) in DCM (8 mL) at 0° C. was added MsCl (645 mg, 3.5 equiv.). The mixture was stirred at 0° C. for 1 hour. The mixture was quenched with water (20 mL) and extracted with dichloromethane (2×8 mL). The combined organic layers were dried over anhydrous sodium sulfate, filtered and concentrated in vacuum to afford the title compound (524 mg, crude) as a yellow solid which was used to next step without further purification.

Step C. benzyl 6-(methylthio)-1,4-oxazepane-4-carboxylate: To a solution of benzyl 6-((methylsulfonyl)oxy)-1,4-oxazepane-4-carboxylate (524 mg, 1.0 equiv.) in DMF (10 mL) at 0° C. was added MeSNa (335 mg, 3.0 equiv.). The reaction mixture was heated to 60° C. for 2 hours. The mixture was diluted with ethyl acetate (8 mL) and water (15 mL), and the aqueous layer was extracted with ethyl acetate (8 mL). The combined organic phase was washed with brine (10 mL), dried over anhydrous sodium sulfate, filtered and concentrated in vacuum. The residue was purified by reversed phase flash chromatography [water (0.1% formic acid)/acetonitrile]. The desired fractions were collected, neutralized with solid NaHCO$_3$ and concentrated in vacuum to remove acetonitrile. The aqueous layer was extracted with ethyl acetate (2×5 mL). The combined organic layers were dried over anhydrous sodium sulfate, filtered and concentrated in vacuum to afford the title compound (175 mg, 39.0% yield) as a yellow oil; $^1$H NMR (400 MHz, DMSO) δ=7.42-7.28 (m, 5H), 5.14-5.04 (m, 2H), 3.98-3.82 (m, 2H), 3.75-3.62 (m, 3H), 3.53 (m, 1H), 3.43-3.32 (m, 1H), 3.30-3.22 (m, 1H), 2.99-2.83 (m, 1H), 2.10 (s, 1H), 2.08-1.97 (m, 2H) LCMS (ESI, M+1): m/z=282.1.

Step D. benzyl 6-(methylsulfonyl)-1,4-oxazepane-4-carboxylate: To a solution of benzyl 6-methylsulfanyl-1,4-oxazepane-4-carboxylate (170 mg, 1.0 equiv.) in DCM (3 mL) was added m-CPBA (368 mg, 3.0 equiv.) at 0° C. The reaction mixture was stirred at 25° C. for 2 hours. The mixture was quenched with saturated Na$_2$SO$_3$ solution (10 mL). The organic phase was separated, and then washed with NaHCO$_3$(10 mL) and brine (10 mL). The organic phase was dried over anhydrous sodium sulfate, filtered and concentrated in vacuum to give a residue. The residue was purified by reversed phase flash chromatography [water (0.1% formic acid)/acetonitrile]. The desired fractions were collected and neutralized with solid NaHCO$_3$, and concentrated in vacuum to remove acetonitrile. The aqueous layer was extracted with ethyl acetate (2×5 mL). The combined organic layers were dried over anhydrous sodium sulfate and concentrated in vacuum to afford the title compound (144 mg, 76.0% yield) as a colorless oil; $^1$H NMR (400 MHz, DMSO) δ=7.45-7.29 (m, 5H), 5.17-5.08 (m, 2H), 4.20-4.09 (m, 2H), 3.85-3.75 (m, 2H), 3.67-3.48 (m, 3H), 3.42-3.34 (m, 1H), 3.30-3.21 (m, 1H), 2.98 (br d, J=16.0 Hz, 3H); LCMS (ESI, M+1): m/z=314.0.

Step E. 6-(methylsulfonyl)-1,4-oxazepane: To a mixture of benzyl 6-(methylsulfonyl)-1,4-oxazepane-4-carboxylate (130 mg, 1.0 equiv.) in MeOH (3 mL) was added Pd/C (20 mg, 10% purity) under N$_2$. The suspension was degassed in vacuum and purged with H$_2$ for three times. The mixture was stirred at 25° C. under H$_2$ (15 Psi) for 3 hours. The mixture was filtered and the filtrate was concentrated in vacuum to afford the title compound (74 mg, crude) as a colorless oil; $^1$H NMR (400 MHz, METHANOL-d$_4$) δ=4.33-4.25 (m, 1H), 4.13 (dd, J=5.6, 13.6 Hz, 1H), 3.87-3.80 (m, 1H), 3.66-3.58 (m, 11H), 3.48-3.38 (m, 2H), 3.28-3.19 (m, 1H), 2.99-2.95 (m, 3H), 2.95-2.86 (m, 2H).

Step F. 4-(8-fluoro-7-(8-fluoronaphthalen-1-yl)-2-((hexahydro-1H-pyrrolizin-7a-yl)methoxy)pyrido[4,3-d]pyrimidin-4-yl)-6-(methylsulfonyl)-1,4-oxazepane: To a solution of 6-(methylsulfonyl)-1,4-oxazepane (54.1 mg, 2.9 equiv.) in DMF (0.3 mL) were added DIEA (40.4 mg, 3.0 equiv.), 4 Å molecular sieves (10 mg) and 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (60 mg, 1.0 equiv., formic acid salt). The reaction mixture was stirred at 40° C. for 12 hours. The mixture was filtered. The filtrate was purified by prep-HPLC [column: Phenomenex Luna C18 150×25 mm×10 um; mobile phase: [water (0.1% formic acid)/acetonitrile] B %: 12/.-42%, 10 min] to afford the title compound (25.4 mg, 39.3% yield) as a white solid; $^1$H NMR (400 MHz, methanol-d)$_{6=9.22}$ (s, 1H), 8.54 (br s, 1H), 8.12 (br d, J=8.4 Hz, 1H), 7.86 (d, J=8.0 Hz, 1H), 7.71 (dt, J=3.8, 7.6 Hz, 1H), 7.62 (dd, J=7.2, 19.8 Hz, 11H), 7.57-7.49 (m, 1H), 7.23-7.14 (m, 1H), 5.18-5.05 (m, 1H), 4.72-4.65 (m, 2H), 4.53-4.41 (m, 1H), 4.32 (td, J=4.8, 12.4 Hz, 1H), 4.24-4.10 (m, 5H), 4.05 (br d, J=3.2 Hz, 1H), 3.63-3.52 (m, 2H), 3.23-3.14 (m, 2H), 3.11 (s, 3H), 2.37-2.23 (m, 2H), 2.21-2.08 (m, 4H), 2.07-1.98 (m, 2H); LCMS (ESI, M+1): m/z=610.3.

Example 272

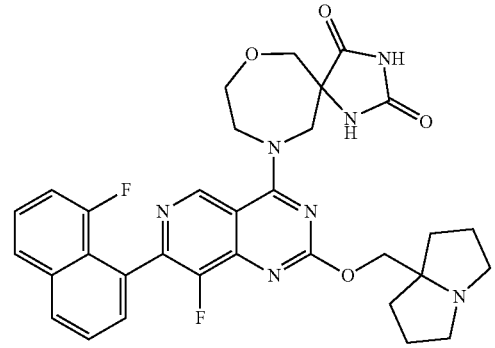 [SMILES: O=C1NC(=O)C2(COCCN(c3nc(OCC45CCCN4CCC5)nc4c(F)c(-c5cccc6cccc(F)c56)ncc34)C2)N1]

10-(8-fluoro-7-(8-fluoronaphthalen-1-yl)-2-((hexahydro-1H-pyrrolizin-7a-yl)methoxy)pyrido[4,3-d]pyrimidin-4-yl)-7-oxa-1,3,10-triazaspiro[4.6]undecane-2,4-dione

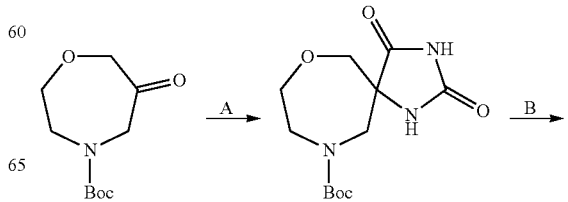


Step A. tert-butyl 2,4-dioxo-10-oxa-1,3,7-triazaspiro[4.6]undecane-7-carboxylate: To a solution of tert-butyl 6-oxo-1,4-oxazepane-4-carboxylate (2.00 g, 1.0 equiv.) and (NH$_4$)$_2$CO$_3$ (2.68 g, 3.0 equiv.) in EtOH (10 mL) and water (10 mL) was added KCN (907 mg, 1.5 equiv.). The reaction was stirred at 85° C. for 16 hours. The mixture was diluted with water (50 mL) and extracted with ethyl acetate (3×50 mL). The combined organic layers were dried over anhydrous sodium sulfate and concentrated to afford the title compound (2.40 g, 90% yield) as a white solid; $^1$H NMR (400 MHz, dimethylsulfoxide-d$_6$) δ=11.55-9.81 (m, 1H), 8.23-8.09 (m, 1H), 3.82-3.62 (m, 5H), 3.61-3.47 (m, 2H), 3.46-3.41 (m, 1H), 1.44-1.34 (m, 9H); LCMS (ESI, M−100): m/z=186.2.

Step B. 7-oxa-1,3,10-triazaspiro[4.6]undecane-2,4-dione: To a solution of tert-butyl 2,4-dioxo-10-oxa-1,3,7-triazaspiro[4.6]undecane-7-carboxylate (500 mg, 1.0 equiv.) in MeCN (2.5 mL) was added HCl.dioxane (4 M, 5 mL, 11.4 equiv.) at 0° C. The mixture was stirred at 0° C. for 0.5 hour. The mixture was concentrated to afford the title compound (450 mg, crude, HCl) as a white liquid; LCMS (ESI, M+1): m/z=186.2.

Step C. 10-(8-fluoro-7-(8-fluoronaphthalen-1-yl)-2-((hexahydro-1H-pyrrolizin-7a-yl)methoxy)pyrido[4,3-d]pyrimidin-4-yl)-7-oxa-1,3,10-triazaspiro[4.6]undecane-2,4-dione: A mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 1.0 equiv.), 10-oxa-1,3,7-triazaspiro[4.6]undecane-2,4-dione (349 mg, 10 equiv.), DIEA (487 mg, 20 equiv.) and 4 Å molecular sieves (10 mg) in DMF (0.5 mL) was stirred at 40° C. for 96 hours. The residue was filtered and purified by prep-HPLC [column: Phenomenex C18 75×30 mm×3 µm; mobile phase: [water (0.1% formic acid)/acetonitrile]; B %: 12%-42%, 7 minutes] to afford the title compound (68.0 mg, 58% yield) as a yellow solid; $^1$H NMR (400 MHz, methanol-d$_4$) δ=9.28 (d, J=2.9 Hz, 1H), 8.13 (d, J=8.3 Hz, 1H), 7.86 (d, J=8.1 Hz, 1H), 7.75-7.67 (m, 1H), 7.66-7.58 (m, 1H), 7.54 (dt, J=5.2, 8.0 Hz, 11H), 7.19 (dd, J=7.6, 13.2 Hz, 1H), 5.04 (dd, J=14.4, 17.6 Hz, 1H), 4.59-4.54 (m, 1H), 4.53-4.47 (m, 11H), 4.46-4.37 (m, 1H), 4.36-4.31 (m, 1H), 4.31-4.24 (m, 2H), 4.24-4.16 (m, 1H), 4.11-3.99 (m, 1H), 3.89 (d, J=12.6 Hz, 1H), 3.66-3.52 (m, 2H), 3.24-3.10 (m, 2H), 2.32-2.21 (m, 2H), 2.15 (quind, J=7.2, 13.6 Hz, 4H), 2.09-1.97 (m, 2H); LCMS (ESI, M+1): m/z=616.4.

Example 273

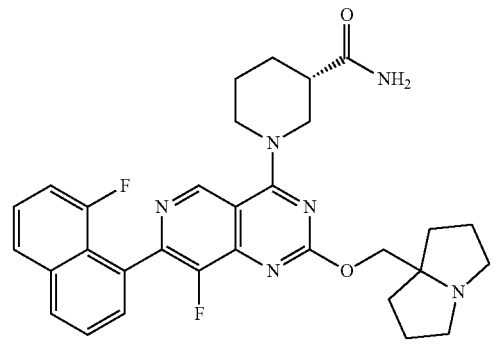 [SMILES: NC(=O)[C@H]1CCCN(c2nc(OCC34CCCN3CCC4)nc3c(F)c(-c4cccc5cccc(F)c45)ncc23)C1]

(S)-1-(8-fluoro-7-(8-fluoronaphthalen-1-yl)-2-((hexahydro-1H-pyrrolizin-7a-yl)methoxy)pyrido[4,3-d]pyrimidin-4-yl)piperidine-3-carboxamide The title compound was synthesized according to the procedure described for example 84. $^1$H NMR (400 MHz, methanol-d$_4$) δ=9.10 (s, 1H), 8.53 (s, 1H), 8.12 (br d, J=8.4 Hz, 1H), 7.86 (d, J=8.4 Hz, 1H), 7.74-7.67 (m, 1H), 7.61 (d, J=7.2 Hz, 1H), 7.54 (dt, J=5.2, 8.0 Hz, 1H), 7.19 (dd, J=7.6, 13.2 Hz, 1H), 4.73-4.62 (m, 1H), 4.60-4.56 (m, 2H), 4.56-4.46 (m, 1H), 3.74-3.50 (m, 4H), 3.21-3.10 (m, 2H), 2.82-2.72 (m, 1H), 2.33-2.22 (m, 2H), 2.21-2.07 (m, 5H), 2.07-1.92 (m, 4H), 1.92-1.77 (m, 1H); HPLC:>99% ee, Chiralcel IC-3 50×4.6 mm I.D., 3 µm Mobile phase:A=Heptane; B=40% EtOH (0.05% DEA), Flow rate:1 mL/min, 254 nm, t$_R$=6.421 min; LCMS [ESI, M−55]: m/z=559.3.

Example 274

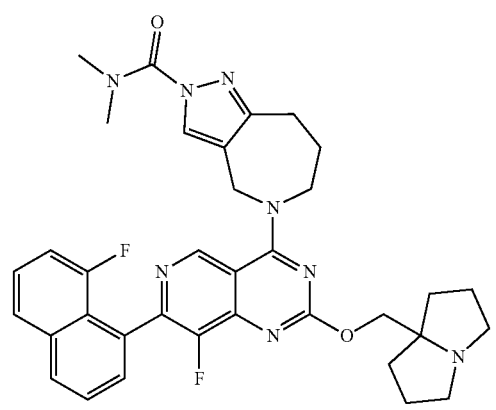 [SMILES: CN(C)C(=O)n1cc2c(n1)CCCN(c1nc(OCC34CCCN3CCC4)nc3c(F)c(-c4cccc5cccc(F)c45)ncc13)C2]

5-(8-fluoro-7-(8-fluoronaphthalen-1-yl)-2-((hexahydro-1H-pyrrolizin-7a-yl)methoxy)pyrido[4,3-d]pyrimidin-4-yl)-N,N-dimethyl-5,6,7,8-tetrahydropyrazolo[4,3-c]azepine-2(4H)-carboxamide

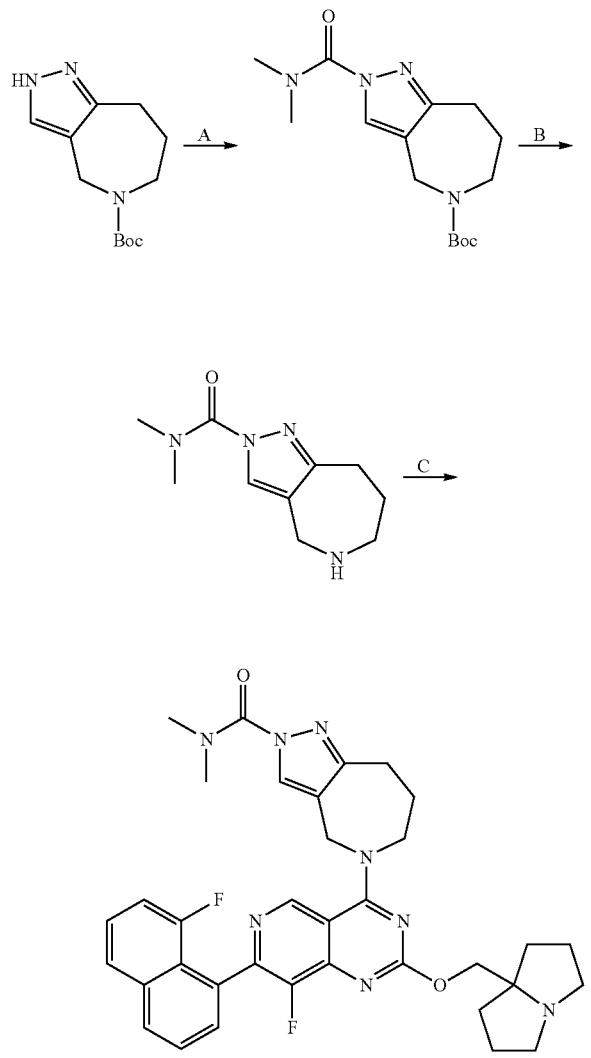

Step A. tert-butyl 2-(dimethylcarbamoyl-4,6,7,8-tetrahydropyrazolo[4,3-c]azepine-5(2H)-carboxylate: A solution of tert-butyl 4,6,7,8-tetrahydropyrazolo[4,3-c]azepine-5(2H)-carboxylate (890 mg, 1.0 equiv.) in THF (18 mL) was added NaH (300 mg, 2.0 equiv.) at 0° C. and the mixture was stirred at 0° C. for 0.5 hour. Then NN-dimethylcarbamoyl chloride (605 mg, 1.5 equiv.) was added into the mixture and the resulting was stirred at 25° C. for 2 hours. The mixture was quenched with water (50 ml) at 0° C. and extracted with ethyl acetate (20 mL×2). The combined organic layers were dried over anhydrous sodium sulfate, filtered and concentrated in vacuum to give a residue. The residue was purified by column chromatography (silica gel, petroleum ether/ethyl acetate 10:1 to 3:1) to afford the title compound (860 mg, 74.4% yield) as a yellow solid; $^1$H NMR (400 MHz, CHLOROFORM-d) δ=7.88 (br s, 1H), 4.42-4.24 (m, 2H), 3.75-3.60 (m, 2H), 3.33-3.13 (m, 6H), 2.94-2.84 (m, 2H), 1.91-1.77 (m, 2H), 1.50-1.33 (m, 9H).

Step B. N,N-dimethyl-5,6,7,8-tetrahydropyrazolo[4,3-c]azepine-2(4H)-carboxamide: To a solution of tert-butyl 2-(dimethylcarbamoyl)-4,6,7,8-tetrahydropyrazolo[4,3-c]azepine-5(2H)-carboxylate (860 mg, 1.0 equiv.) in ACN (5 mL) at 0° C. was added HCl.dioxane (4 M, 14.3 equiv.). The reaction mixture was stirred at 0° C. for 0.5 hour. The mixture was concentrated in vacuum to afford the title compound (682 mg, crude, HCl) as a yellow solid; $^1$H NMR (400 MHz, methanol-$d_4$) δ=8.15 (s, 1H), 4.29 (s, 2H), 3.57-3.52 (m, 2H), 3.19 (br s, 6H), 3.05-2.95 (m, 2H), 2.09-2.02 (m, 2H).

Step C. 5-(8-fluoro-7-(8-fluoronaphthalen-1-yl)-2-((hexahydro-1H-pyrrolizin-7a-yl)methoxy)pyrido[4,3-d]pyrimidin-4-yl)-N,N-dimethyl-5,6,7,8-tetrahydropyrazolo[4,3-c]azepine-2(4H-carboxamide: To a solution of N,N-dimethyl-5,6,7,8-tetrahydropyrazolo[4,3-c]azepine-2(4H)-carboxamide (46.1 mg, 2.4 equiv.) in DMF (0.5 mL) were added DIEA (60.9 mg, 5.0 equiv.), 4 Å molecular sieves (5 mg) and 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (50 mg, 1.0 equiv.). The reaction mixture was stirred at 40° C. for 12 hours. The mixture was filtered and the filtrate was purified by prep-HPLC [column: Phenomenex Synergi Polar-RP 100×25 mm×4 um; mobile phase: [water (0.01% TFA)/acetonitrile]; B %: 35%-55% over 7 min]. The desired fractions were collected and concentrated in vacuum to remove acetonitrile. The mixture was lyophilized to give a residue. The residue was re-purified by prep-HPLC (column: Phenomenex C18 75×30 mm×3 um; mobile phase: [water (0.1% formic acid)/acetonitrile]; B %: 18%-48%, 7 min]. The desired fractions were collected and lyophilized to afford the title compound (10.2 mg, 16.8% yield) as a yellow solid; $^1$H NMR (400 MHz, methanol-$d_4$) δ=9.15 (s, 1H), 8.54 (s, 1H), 8.23 (s, 1H), 8.11 (br d, J=8.4 Hz, 1H), 7.85 (d, J=8.4 Hz, 1H), 7.74-7.66 (m, 1H), 7.60 (dd, J=0.8, 7.2 Hz, 1H), 7.52 (dt, J=5.2, 8.0 Hz, 1H), 7.18 (dd, J=7.2, 13.2 Hz, 1H), 5.20-5.03 (m, 2H), 4.46-4.39 (m, 2H), 4.36 (s, 2H), 3.29-3.23 (m, 2H), 3.18 (br s, 5H), 3.05-2.98 (m, 2H), 2.87 (td, J=6.4, 10.8 Hz, 2H), 2.31-2.23 (m, 2H), 2.19-2.08 (m, 2H), 1.98 (tq, J=6.4, 12.6 Hz, 4H), 1.89-1.79 (m, 2H); LCMS (ESI, M+1): m/z=639.4.

Example 275

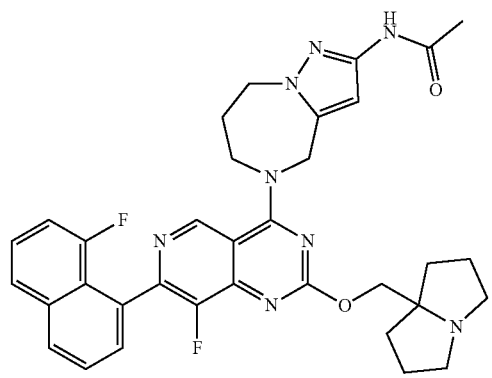 [SMILES: CC(=O)Nc1cc2n(n1)CCCN(c1nc(OCC34CCCN3CCC4)nc3c(F)c(-c4cccc5cccc(F)c45)ncc13)C2]

N-(5-(8-fluoro-7-(8-fluoronaphthalen-1-yl)-2-((hexa-hydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-yl)acetamide

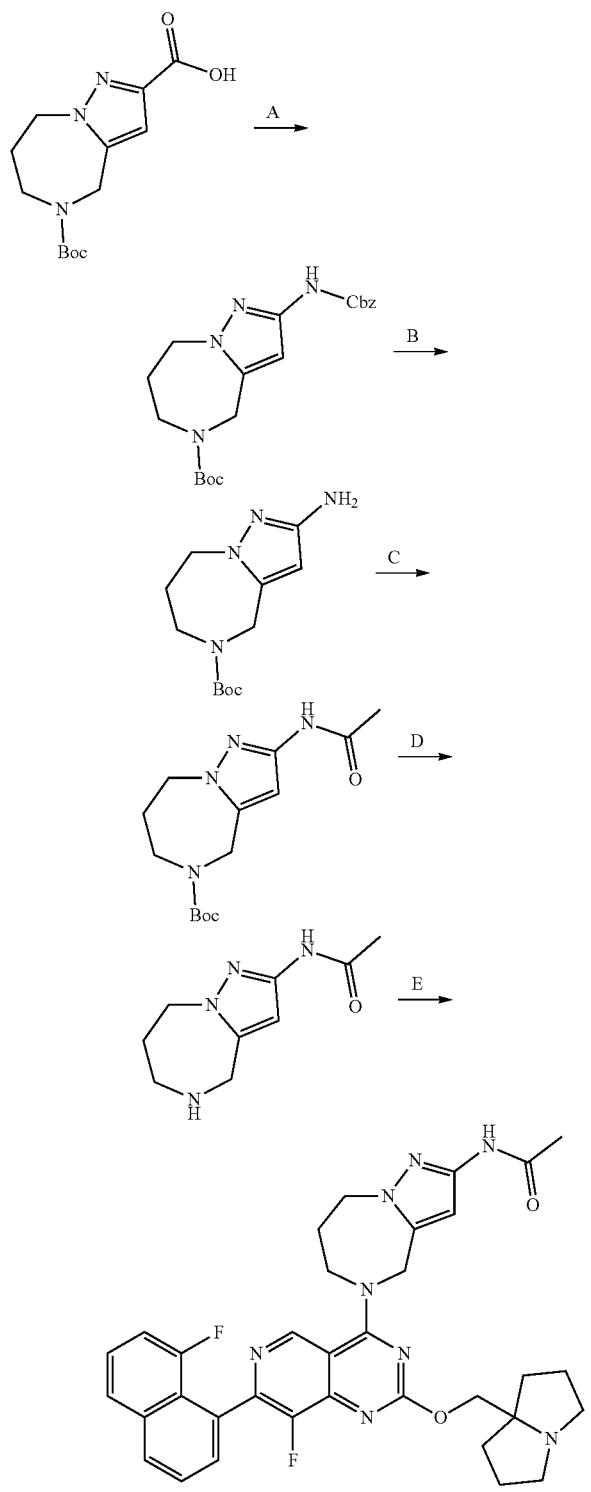

Step A. tert-butyl 2-(((benzyloxy)carbonyl)amino)-7,8-dihydro-4H-pyrazolo[1,5-a][1,4]diazepine-5(6H)-carboxy-late: A mixture of 5-tert-butoxycarbonyl-4,6,7,8-tetrahydro-pyrazolo[1,5-a][1,4]diazepine-2-carboxylic acid (3 g, 1.0 equiv.), 4 Å molecular sieves (1.00 g), TEA (3.24 g, 3.0 equiv.) and BnOH (6.92 g, 6.0 equiv.) in toluene (50 mL) was stirred at 110° C. for 0.5 hour under nitrogen. Then the mixture was cooled to 15° C. and DPPA (4.40 g, 1.5 equiv.) was added at 15° C. The mixture was stirred at 110° C. for 5 hours. The reaction mixture was diluted with ethyl acetate (70 mL) and water (200 mL), and extracted with ethyl acetate (50 mL). The combined organic phase was washed with brine (50 mL), dried over anhydrous sodium sulfate, filtered and concentrated in vacuum to give a residue. The residue was purified by column chromatography (Silica gel, petroleum ether/ethyl acetate 10:1 to 1:1) to afford the title compound (2.1 g, 50.0% yield) as a yellow solid; LCMS [ESI, M−55]: m/z=387.3.

Step B. tert-butyl 2-amino-7,8-dihydro-4H-pyrazolo[1,5-a][1,4]diazepine-5(6H)-carboxylate: tert-butyl2-(benzy-loxycarbonylamino)-4,6,7,8-tetrahydropyrazolo[1,5-a][1,4]diazepine-5-carboxylate (470 mg, 1.0 equiv.) was dissolved in MeOH (10 mL) and charged with $N_2$. To the solution was added Pd/C (50 mg, 10% purity) under nitrogen. The mixture was stirred at 25° C. for 12 hours under $H_2$ (15 psi). The mixture was filtered and the filtrate was concentrated in vacuum. The residue was purified by reversed phase flash chromatography [water (0.1% formic acid)/acetonitrile]. The desired fractions were collected, neutralized with solid $NaHCO_3$ and concentrated in vacuum to remove acetoni-trile. The aqueous layer was extracted with ethyl acetate (2×15 mL). The combined organic layers were dried over anhydrous sodium sulfate, filtered and concentrated in vacuum to afford the title compound (270 mg, 84.9% yield) as a yellow oil; $^1$H NMR (400 MHz, CHLOROFORM-d) δ=5.66-5.45 (m, 1H), 4.41-4.26 (m, 2H), 4.21-4.16 (m, 2H), 3.76-3.40 (m, 4H), 1.90-1.83 (m, 2H), 1.42 (s, 9H); LCMS [ESI, M+1]: 253.1.

Step C. tert-butyl 2-acetamido-7,8-dihydro-4H-pyrazolo[1,5-a][1,4]diazepine-5(6H)-carboxylate: To a solution of tert-butyl 2-amino-4,6,7,8-tetrahydropyrazolo[1,5-a][1,4]di-azepine-5-carboxylate (270 mg, 1.0 equiv.) in DCM (2 mL) were added TEA (325 mg, 3.0 equiv.) and acetylchloride (126 mg, 1.5 equiv.) at 0° C. The reaction mixture was stirred at 0° C. for 0.5 hour. The reaction mixture was diluted with ethyl acetate (15 mL) and water (30 mL), and extracted with ethyl acetate (10 mL). The combined organic phase was washed with brine (15 mL), dried over anhydrous sodium sulfate, filtered and concentrated in vacuum. The residue was purified by reversed phase flash chromatography [water (0.1% formic acid)/acetonitrile]. The desired fractions were collected and neutralized with solid $NaHCO_3$ and concentrated in vacuum to remove acetonitrile. The aqueous layer was extracted with ethyl acetate (2×10 mL). The combined organic layers were dried over anhydrous sodium sulfate, filtered and concentrated in vacuum to afford the title compound (273 mg, 85.8% yield) as a white solid; LCMS [ESI, M+1]: 295.2.

Step D. N-(5,6,7,8-tetrahydro-4H-pyrazolo[1,5-a][1,4]di-azepin-2-yl)acetamide: To a solution of tert-butyl 2-acet-amido-4,6,7,8-tetrahydropyrazolo[1,5-a][1,4]diazepine-5-carboxylate (310 mg, 1.0 equiv.) in dioxane (1.5 mL) at 0° C. was added HCl.dioxane (4 M, 11 equiv.). The reaction mixture was stirred at 0° C. for 0.5 hour. The mixture was concentrated in vacuum to afford the title compound (200 mg, crude) as a yellow solid; $^1$H NMR (400 MHz, methanol-$d_4$) δ=6.45 (s, 1H), 4.45 (s, 2H), 4.34-4.26 (m, 2H), 3.70 (br d, J=4.4 Hz, 2H), 2.09 (s, 3H), 1.83 (br s, 2H).

Step E. N-(5-(8-fluoro-7-(8-fluoronaphthalen-1-yl)-2-((hexahydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-yl)acetamide: A mixture of N-(5,6,7,8-tetrahydro-4H-pyrazolo[1,5-a][1,4]diazepin-2-yl)acetamide (110 mg, 2.0 equiv.), DIEA (183 mg, 5.0 equiv.) and 4 Å molecular sieves (20 mg) in DMF (1 mL) were stirred at 25° C. for 0.5 hour. Then 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (150 mg, 1.0 equiv.) was added into the reaction mixture and the resulting was stirred at 40° C. for 12 hours. The mixture was filtered and the filtrate was purified by prep-HPLC [column: Unisil 3-100 C18 Ultra 150×50 mm×3 um; mobile phase: [water (0.1% formic acid)/acetonitrile], B %: 5%-35%, 10 min]. The desired fraction was collected and lyophilized to afford the title compound (26.8 mg, 15.1% yield) as a white solid; $^1$H NMR (400 MHz, methanol-$d_4$) δ=9.22 (s, 1H), 8.54 (s, 1H), 8.12 (br d, J=8.4 Hz, 1H), 7.86 (d, J=8.0 Hz, 1H), 7.73-7.67 (m, 1H), 7.61 (dd, J=1.2, 7.2 Hz, 1H), 7.53 (dt, J=5.2, 8.0 Hz, 1H), 7.19 (ddd, J=0.8, 7.6, 13.2 Hz, 1H), 6.71 (s, 1H), 5.27-5.12 (m, 2H), 4.52 (s, 2H), 4.46 (br t, J=5.2 Hz, 2H), 4.37-4.29 (m, 2H), 3.56-3.45 (m, 2H), 3.15-3.05 (m, 2H), 2.48-2.38 (m, 2H), 2.30-2.20 (m, 2H), 2.19-2.03 (m, 7H), 2.03-1.92 (m, 2H); LCMS (ESI, M+1): m/z=625.4.

Example 276

(5-(8-fluoro-7-(8-fluoronaphthalen-1-yl)-2-((hexahydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-yl)(morpholino)methanone

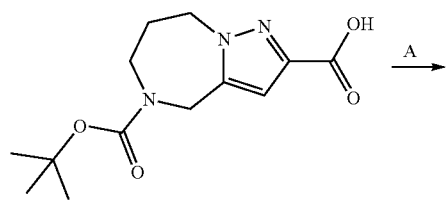

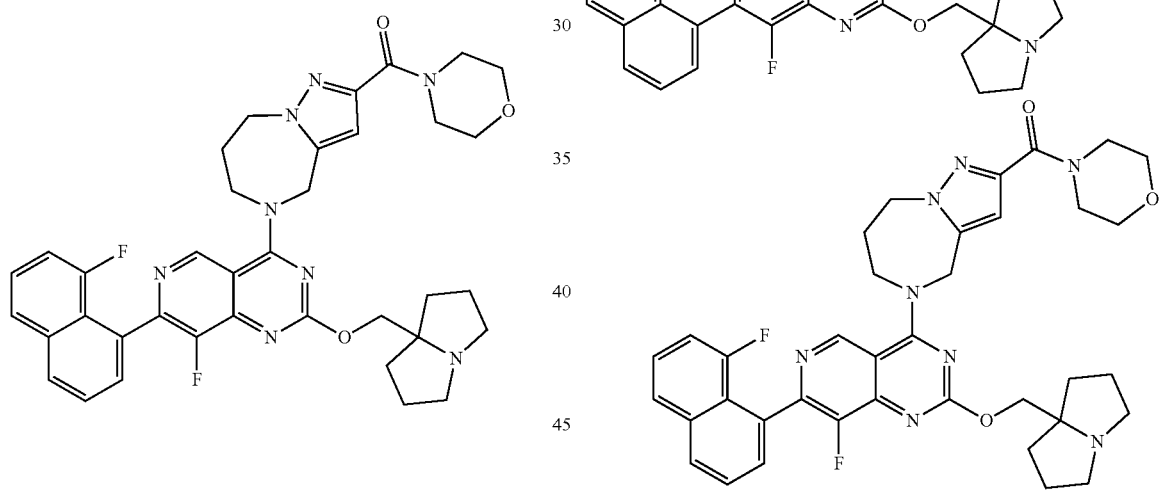

Step A. tert-butyl 2-(morpholine-4-carbonyl)-7,8-dihydro-4H-pyrazolo[1,5-a][1.4]diazepine-5(6H)-carboxylate: To a solution of 5-tert-butoxycarbonyl-4,6,7,8-tetrahydropyrazolo[1,5-a][1,4]diazepine-2-carboxylic acid (300 mg, 1.0 equiv.), morpholine (278 mg, 3.0 equiv.) and DIEA (1.65 g, 12 equiv.) in ethyl acetate (3 mL) was added T3P (2.04 g, 6.0 equiv.) at 0° C. The mixture was stirred at 0-25° C. for 2 hours. The mixture was concentrated under reduced pressure to give a residue and the residue was purified by reversed phase flash chromatography [C18, water (0.1% formic acid)/ACN] to afford the title compound (320 mg, 85% yield) as a white oil; LCMS (ESI, M+1): m/z=351.3.

Step B. morpholino(5,6,7,8-tetrahydro-4H-pyrazolo[1,5-a][1,4]diazepin-2-yl)methanone: To a solution of tert-butyl 2-(morpholine-4-carbonyl)-4,6,7,8-tetrahydropyrazolo[1,5-a][1,4]diazepine-5-carboxylate (310 mg, 1.0 equiv.) in MeCN (3 mL) was added HCl-dioxane (4 M, 6.8 equiv.) at 0° C. The mixture was stirred at 0-25° C. for 0.5 hour. The mixture was concentrated under reduced pressure to afford the title compound (215 mg, crude) as a white solid;

Step C. (5-(8-fluoro-7-(8-fluoronaphthalen-1-yl)-2-((hexahydro-1H-pyrrolizin-7a-yl methoxy)pyrido[4,3-d]pyrimidin-4-yl)-5,6,7,8-tetrahydro-4H-pyrazolo[1,5-a][1,4]diazepin-2-yl)(morpholino)methanone: To a solution of morpholino(5,6,7,8-tetrahydro-4H-pyrazolo[1,5-a][1,4]diazepin-2-yl)methanone (212 mg, 3.0 equiv.) in DMF (3 mL) was added DIEA (219 mg, 6.0 equiv.) and 4 Å molecular sieves (40 mg). 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (150 mg, 1.0 equiv.). The mixture was stirred at 40° C. for 16 hours. DIEA (365 mg, 10 equiv.) was added, the mixture was stirred at 40° C. for 20 hours. The reaction mixture was filtered and purified by reversed phase flash chromatography [C18, water (0.1% formic acid)/ACN] and re-purified by prep-HPLC [column: Phenomenex luna C18 150×25 mm×10 µm, mobile phase: [water (0.1% formic acid)/acetonitrile], B %: 22%-52%, 7 min] and lyophilized to afford the title compound (8.66 mg, 4.3% yield) as a yellow solid; $^1$H NMR (400 MHz, METHANOL-&) δ=9.20 (s, 1H), 8.12 (d, J=8.4 Hz, 1H), 7.85 (d, J=8.0 Hz, 1H), 7.72-7.67 (m, 1H), 7.61 (dd, J=1.2, 7.2 Hz, 1H), 7.53 (dt, J=4.8, 8.0 Hz, 1H), 7.19 (ddd, J=0.8, 7.6, 13.2 Hz, 1H), 6.80 (s, 1H), 5.33-5.21 (m, 2H), 4.56-4.51 (m, 2H), 4.50-4.45 (m, 2H), 4.44 (s, 2H), 4.04 (br s, 2H), 3.75-3.65 (m, 6H), 3.42-3.34 (m, 2H), 3.03-2.95 (m, 2H), 2.48-2.39 (m, 2H), 2.23-2.15 (m, 2H), 2.10-1.97 (m, 4H), 1.96-1.88 (m, 2H), 1.37-1.31 (m, 2H); LCMS [ESI, M+1]: 681.4.

Example 277

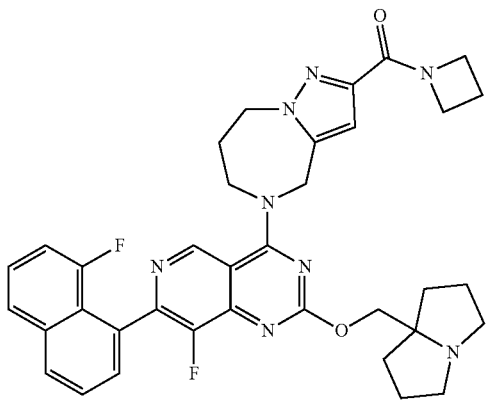 [SMILES: O=C(c1cc2n(n1)CCCN(c1nc(OCC34CCCN3CCC4)nc3c(F)c(-c4cccc5cccc(F)c45)ncc13)C2)N1CCC1]

azetidin-1-yl(5-(8-fluoro-7-(8-fluoronaphthalen-1-yl)-2-((hexahydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-yl)methanone The title compound was synthesized according to the procedure described for example 276. $^1$H NMR (400 MHz, methanol-d$_4$): δ=9.21 (s, 1H), 8.53 (s, 1H), 8.12 (br d, J=8.4 Hz, 1H), 7.86 (d, J=8.0 Hz, 1H), 7.70 (t, J=7.6 Hz, 1H), 7.61 (d, J=7.2 Hz, 1H), 7.53 (dt, J=5.2, 8.0 Hz, 1H), 7.19 (dd, J=7.6, 13.2 Hz, 1H), 6.84 (s, 1H), 5.32-5.19 (m, 2H), 4.60 (br t, J=7.6 Hz, 2H), 4.55-4.44 (m, 6H), 4.16 (br t, J=7.6 Hz, 2H), 3.60-3.50 (m, 2H), 3.20-3.11 (m, 2H), 2.47-2.33 (m, 4H), 2.30-2.22 (m, 2H), 2.20-2.08 (m, 4H), 2.06-1.97 (m, 2H); LCMS [ESI, M+1]: m/z=651.5.

Example 278

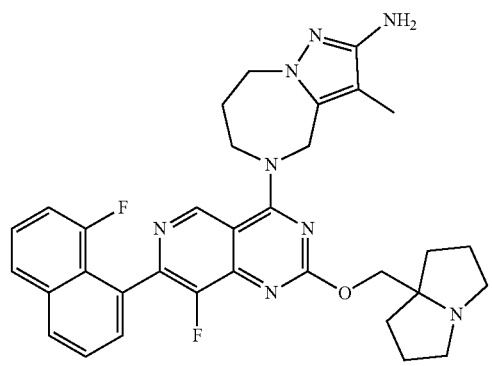 [SMILES: Cc1c(N)nn2c1CN(c1nc(OCC34CCCN3CCC4)nc3c(F)c(-c4cccc5cccc(F)c45)ncc13)CCC2]

5-(8-fluoro-7-(8-fluoronaphthalen-1-yl)-2-((hexahydro-1H-pyrrolizin-7a-yl)methoxy)pyrido[4,3-d]pyrimidin-4-yl)-3-methyl-5,6,7,8-tetrahydro-4H-pyrazolo[1,5-a][1,4]diazepin-2-amine

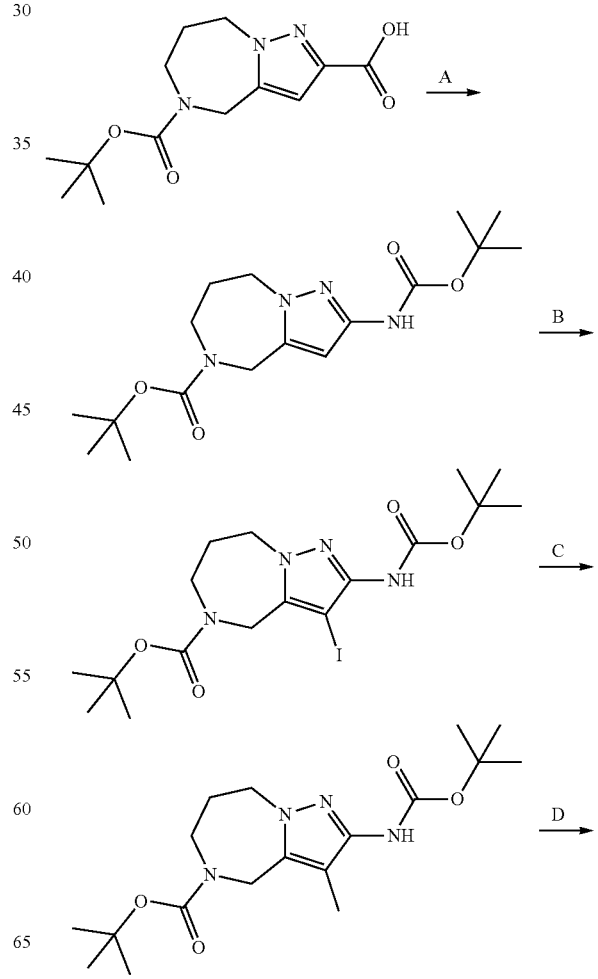

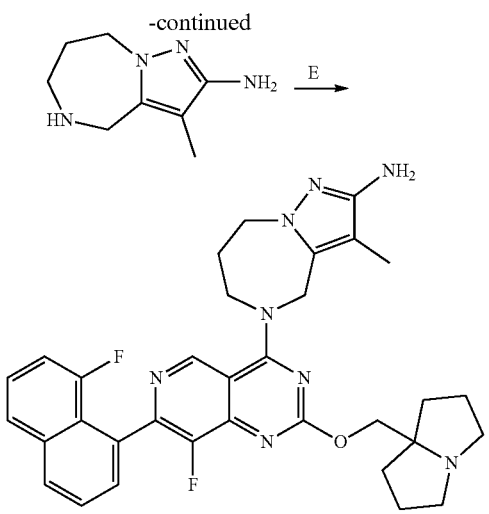

Step A. tert-butyl 2-((tert-butoxycarbonyl)amino)-7,8-dihydro-4H-pyrazolo[1,5-a][1,4]diazepine-5(6H)-carboxylate: A mixture of 5-(tert-butoxycarbonyl)-5,6,7,8-tetrahydro-4H-pyrazolo[1,5-a][1,4]diazepine-2-carboxylic acid (2.00 g, 1.0 equiv.), 4 Å molecular sieves (2.00 g) and TEA (2.16 g, 3.0 equiv.) in toluene (20 mL) and 2-methylpropan-2-ol (15.5 g, 29.4 equiv.) was stirred at 110° C. for 0.5 hour under nitrogen. The mixture was cooled to 25° C. and DPPA (2.93 g, 1.5 equiv.) was added at 25° C. The mixture was stirred at 110° C. for 5 hours before being quenched by addition of water (30 mL) and extracted with ethyl acetate (80 mL). The organic layer was dried over anhydrous sodium sulfate, concentrated, and purified by reversed-phase HPLC [water (0.1% formic acid)/ACN] to afford the title compound (1.50 g, 60% yield) as a yellow solid; LCMS (ESI, M+1): m/z=353.1.

Step B. tert-butyl 2-((tert-butoxycarbonyl)amino)-3-iodo-7,8-dihydro-4H-pyrazolo[1,5-a][1,4]diazepine-5(6H)-carboxylate: To a solution of tert-butyl 2-((tert-butoxycarbonyl)amino)-7,8-dihydro-4H-pyrazolo[1,5-a][1,4]diazepine-5(6H)-carboxylate (1.50 g, 1.0 equiv.) in MeCN (50 mL) was added NIS (1.92 g, 2.0 equiv.) at 25° C., The mixture was stirred at 25° C. for 1 hour. The mixture was concentrated in vacuum. The crude product was purified by reversed phase flash chromatography [water (0.1% formic acid)/ACN] to afford the title compound (1.90 g, 93% yield) as a yellow solid; LCMS (ESI, M+1): 479.2.

Step C. tert-butyl 2-((tert-butoxycarbonyl)amino)-3-methyl-7,8-dihydro-4H-pyrazolo[1,5-a][1,4]diazepine-5(6H)-carboxylate: A mixture of tert-butyl 2-((tert-butoxycarbonyl)amino)-3-iodo-7,8-dihydro-4H-pyrazolo[1,5-a][1,4]diazepine-5(6H)-carboxylate (1.90 g, 1.0 equiv.), 2,4,6-trimethyl-1,3,5,2,4,6-trioxatriborinane (3.5 M, 2.27 mL, 2.0 equiv.), CataCXium A Pd G3 (578 mg, 0.2 equiv.) and $K_3PO_4$ (1.5 M, 7.94 mL, 3.0 equiv.) in THF (80 mL) was degassed and stirred at 60° C. for 24 hours under $N_2$ atmosphere. The mixture was quenched by addition of water (100 mL) and extracted with ethyl acetate (2×60 mL). The combined organic layers were dried over $Na_2SO_4$, and concentrated. The crude product was purified by reversed phase flash chromatography [water (0.1% formic acid)/ACN] to afford the title compound (900 mg, 46% yield) as a yellow solid; LCMS (ESI, M+1): 367.2.

Step D. 3-methyl-5,6,7,8-tetrahydro-4H-pyrazolo[1,5-a][1,4]diazepin-2-amine: To a solution of tert-butyl 2-((tert-butoxycarbonyl)amino)-3-methyl-7,8-dihydro-4H-pyrazolo[1,5-a][1,4]diazepine-5(6H)-carboxylate (300 mg, 1.0 equiv.) in MeCN (1 mL) was added HCl-dioxane (4 M, 2 mL, 9.77 equiv.) at 25° C. The mixture was stirred at 25° C. for 0.5 hour. The mixture was concentrated in vacuum. The residue was diluted with MeOH (5 mL), treated with solid $NaHCO_3$ (1 g), filtered and the filtrate was concentrated in vacuum to afford the title compound (210 mg, crude, 2HCl) as a yellow solid; LCMS (ESI, M+1): m/z=167.2.

Step E. 5-(8-fluoro-7-(8-fluoronaphthalen-1-yl)-2-((hexahydro-1H-pyrrolizin-7a-yl)methoxy)pyrido[4,3-d]pyrimidin-4-yl)-3-methyl-5,6,7,8-tetrahydro-4H-pyrazolo[1,5-a][1,4]diazepin-2-amine: To a mixture of 3-methyl-5,6,7,8-tetrahydro-4H-pyrazolo[1,5-a][1,4]diazepin-2-amine (75.2 mg, 4.0 equiv.) and DIEA (73.1 mg, 5.0 equiv.) was added 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (60.0 mg, 1.0 equiv.) and DMF (0.5 mL). The mixture was stirred at 40° C. for 14 hours. The mixture was filtered and the filtrate was purified by reversed phase flash chromatography [water (0.1% formic acid)/ACN], and further re-purified by prep-HPLC (column: Phenomenex Luna C18 150×25 mm×10 μm; mobile phase: [water (0.1% formic acid)/ACN], B %: 11%-41%, 10 min) to afford the title compound (2.05 mg, 2.9% yield) as an off-white solid; $^1$H NMR (400 MHz, methanol-$d_4$) δ=9.15 (s, 1H), 8.53 (br s, 1H), 8.13 (br d, J=8.4 Hz, 1H), 7.86 (d, J=8.4 Hz, 1H), 7.71 (t, J=7.2 Hz, 1H), 7.61 (d, J=6.4 Hz, 1H), 7.54 (dt, J=5.2, 8.0 Hz, 1H), 7.19 (dd, J=8.0, 13.2 Hz, 1H), 5.17-5.12 (m, 2H), 4.59 (br s, 2H), 4.40-4.35 (m, 2H), 4.23-4.19 (m, 2H), 3.65-3.55 (m, 2H), 3.25-3.18 (m, 2H), 2.41-2.04 (m, 10H), 2.04 (s, 3H); LCMS (ESI, M+1): m/z=597.4.

Example 279

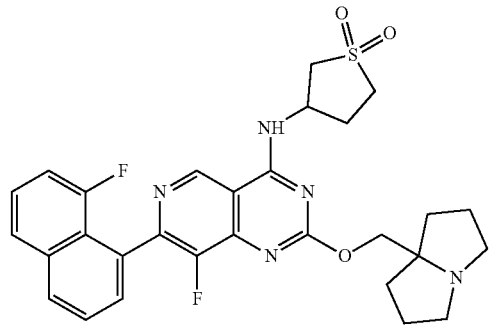 [SMILES: O=S1(=O)CCC(Nc2nc(OCC34CCCN3CCC4)nc3c(F)c(-c4cccc5cccc(F)c45)ncc23)C1]

3-((8-fluoro-7-(8-fluoronaphthalen-1-yl)-2-((hexahydro-1H-pyrrolizin-7a-yl)methoxy)pyrido[4,3-d]pyrimidin-4-yl)amino)tetrahydrothiophene 1,1-dioxide The title compound was synthesized according to the procedure described for example 85. $^1$H NMR (400 MHz, methanol-$d_4$) δ ppm 9.26-9.24 (m, 1H), 9.25 (s, 1H), 8.12 (br d, J=8.2 Hz, 1H), 7.85 (d, J=8.2 Hz, 1H), 7.73-7.67 (m, 11H), 7.59 (d, J=6.8 Hz, 11H), 7.53 (m, 7.9 Hz, 1H), 7.19 (dd, J=7.2, 13.2 Hz, 1H), 5.23-5.14 (m, 1H), 4.32 (s, 2H), 3.81-3.72 (m, 1H), 3.49-3.40 (m, 1H), 3.30-3.22 (m, 2H), 3.16-3.07 (m, 2H), 2.81-2.70 (m, 3H), 2.56-2.44 (m, 1H), 2.15-2.03 (m, 2H), 1.96-1.92 (m, 4H), 1.82-1.72 (m, 2H). HPLC:>99%. SFC: Chiralcel OD-3 50×4.6 mm I.D., 3 μm column A: 40% (MeOH:ACN=4:1) (w/0.05% DEA), B: CO2, 3 mL/min, 220 nm. LCMS [ESI, M+1]: m/z=566.2.

Example 280

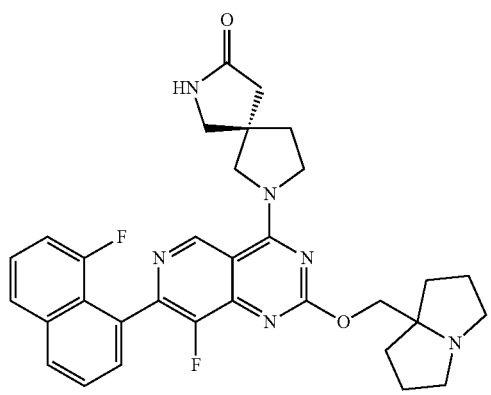 [SMILES: O=C1C[C@@]2(CCN(c3nc(OCC45CCCN4CCC5)nc4c(F)c(-c5cccc6cccc(F)c56)ncc34)C2)CN1]

(S)-7-(8-fluoro-7-(8-fluoronaphthalen-1-yl)-2-((hexahydro-1H-pyrrolizin-7a-yl)methoxy)pyrido[4,3-d]pyrimidin-4-yl)-2,7-diazaspiro[4.4]nonan-3-one The title compound was synthesized according to the procedure described for example 85. LCMS (ESI, M+1): m/z=571.3.

Example 281

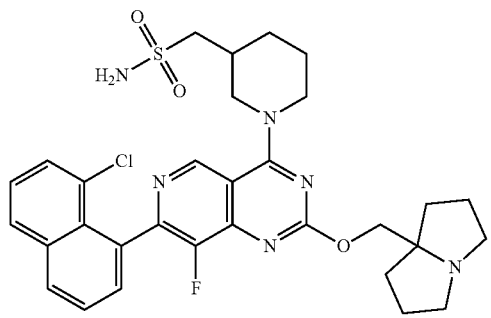 [SMILES: NS(=O)(=O)CC1CCCN(c2nc(OCC34CCCN3CCC4)nc3c(F)c(-c4cccc5cccc(Cl)c45)ncc23)C1]

1-(1-(7-(8-chloronaphthalen-1-yl)-8-fluoro-2-((tetrahydro-1H-pyrrolizin-7a(5H)-yl)methoxy)pyrido[4,3-d]pyrimidin-4-yl)piperidin-3-yl)methanesulfonamide

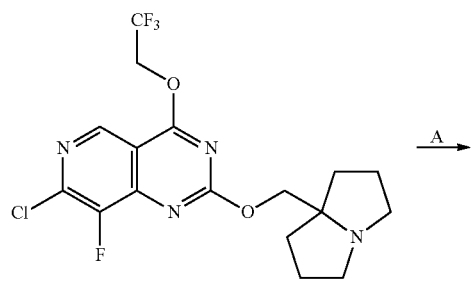

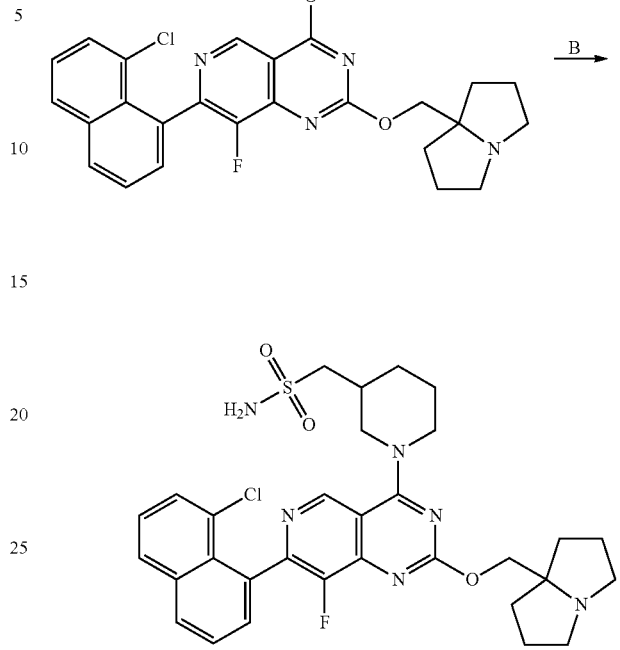

Step A. 7-(8-chloronaphthalen-1-yl)-8-fluoro-2-((hexahydro-1H-pyrrolizin-7a-yl)methoxy)-4-(2,2,2-trifluoroethoxy)pyrido[4,3-d]pyrimidine: To a mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (200 mg, 1.0 equiv.), (8-chloronaphthalen-1-yl)trimethylstannane (464 mg, 1.43 mmol, 3.0 equiv.), CuI (27.2 mg, 0.3 equiv.) and BINAP (59.2 mg, 0.2 equiv.) in toluene (8 mL) was added Pd(dppf)Cl₂ (34.8 mg, 0.1 equiv.) under N₂. The reaction was de-gassed and stirred at 90° C. for 2 hours under N₂. The mixture was filtered and purified by reversed phase flash chromatography [C18, water (0.1% formic acid)/ACN] to afford the title compound (156 mg, 25% yield) as a yellow solid; LCMS (ESI, M+1): m/z=547.1.

Step B. 1-(1-(7-(8-chloronaphthalen-1-yl)-8-fluoro-2-((tetrahydro-)H-pyrrolizin-7a(5H)-yl)methoxy)pyrido[4,3-d]pyrimidin-4-yl)piperidin-3-yl)methanesulfonamide: To a solution of 7-(8-chloronaphthalen-1-yl)-8-fluoro-2-((hexahydro-1H-pyrrolizin-7a-yl)methoxy)-4-(2,2,2-trifluoroethoxy)pyrido[4,3-d]pyrimidine (40.0 mg, 1.0 equiv.), piperidin-3-ylmethanesulfonamide (26.1 mg, 2.0 equiv.) and DIEA (28.4 mg, 3.0 equiv.) in DMF (0.5 mL) was added 4 Å molecular sieves (10 mg). The reaction was stirred at 40° C. for 2 hours. The mixture was filtered and purified by prep-HPLC [column: Waters Xbridge 150×25 mm×5 µm; mobile phase: [water (10 mM NH₄HCO₃)/ACN] B %: 42%-72%, 8 min] and lyophilized to afford the title compound (13.8 mg, 29% yield) as a white solid; ¹H NMR (400 MHz, methanol-d₄) δ=9.08 (s, 1H), 8.13 (d, J=8.0 Hz, 1H), 8.01 (d, J=7.6 Hz, 1H), 7.69 (dt, J=2.0, 7.6 Hz, 1H), 7.63-7.58 (m, 2H), 7.50 (t, J=7.6 Hz, 1H), 4.99 (br d, J=11.2 Hz, 1H), 4.56 (br d, J=13.6 Hz, 1H), 4.47-4.36 (m, 2H), 3.70-3.58 (m, 1H), 3.39-3.33 (m, 1H), 3.29-3.21 (m, 2H), 3.21-3.09 (m, 2H), 2.90-2.81 (m, 2H), 2.58-2.46 (m, 1H), 2.22-2.08 (m, 3H), 2.04-1.90 (m, 5H), 1.87-1.74 (m, 3H), 1.68-1.56 (m, 1H); ¹⁹F NMR (400 MHz, methanol-d₄) δ=−139.695; LCMS (ESI, M+1): m/z=625.2.

Example 282

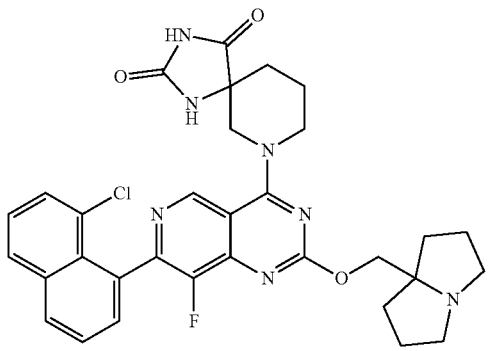 [SMILES: O=C1NC(=O)C2(CCCN(c3nc(OCC45CCCN4CCC5)nc4c(F)c(-c5cccc6cccc(Cl)c56)ncc34)C2)N1]

7-(7-(8-chloronaphthalen-1-yl)-8-fluoro-2-((hexa-hydro-1H-pyrrolizin-7a-yl)methoxy)pyrido[4,3-d]pyrimidin-4-yl)-1,3,7-triazaspiro[4.5]decane-2,4-dione The title compound was synthesized according to the procedure described for example 281. $^1$H NMR (400 MHz, METHANOL-$d_4$) δ=9.09 (d, J=3.6 Hz, 1H), 8.14 (d, J=7.9 Hz, 1H), 8.01 (d, J=8.0 Hz, 1H), 7.68 (t, J=5.6 Hz, 1H), 7.63-7.57 (m, 2H), 7.50 (t, J=5.2 Hz, 13.6 Hz, 1H), 4.63 (dd, J=5.2, 13.2 Hz, 1H), 4.48-4.45 (m, 1H), 4.37-4.30 (m, 2H), 3.85-3.68 (m, 2H), 3.25-3.14 (m, 2H), 2.89-2.74 (m, 2H), 2.31-2.19 (m, 1H), 2.18-2.00 (m, 4H), 1.99-1.87 (m, 5H), 1.85-1.76 (m, 2H); LCMS (EST, M+1): m/z=616.2.

Example 283

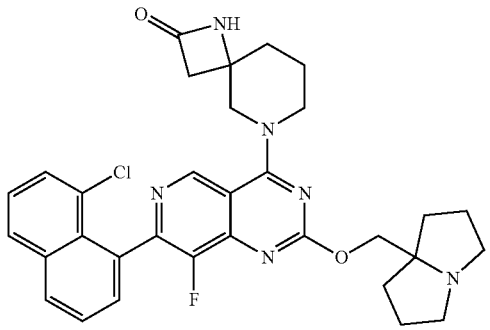 [SMILES: O=C1CC2(CCCN(c3nc(OCC45CCCN4CCC5)nc4c(F)c(-c5cccc6cccc(Cl)c56)ncc34)C2)N1]

6-(7-(8-chloronaphthalen-1-yl)-8-fluoro-2-((tetra-hydro-1H-pyrrolizin-7a(5H)-yl)methoxy)pyrido[4,3-d]pyrimidin-4-yl)-1,6-diazaspiro[3.5]nonan-2-one The title compound was synthesized according to the procedure described for example 281. $^1$H NMR (400 MHz, METHANOL-$d_4$) δ=9.07 (s, 1H), 8.14 (dd, J=1.2, 8.0 Hz, 1H), 8.04-7.98 (m, 1H), 7.72-7.65 (m, 1H), 7.63-7.57 (m, 2H), 7.54-7.48 (m, 1H), 4.38 (d, J=13.6 Hz, 1H), 4.34-4.22 (m, 3H), 3.99 (d, J=13.2 Hz, 1H), 3.88-3.70 (m, 1H), 3.16-3.04 (m, 2H), 2.92-2.86 (m, 11H), 2.80-2.65 (m, 3H), 2.18-2.01 (m, 4H), 2.01-1.84 (m, 6H), 1.80-1.69 (m, 2H); LCMS (ESI, M+1): m/z=587.2.

Example 284

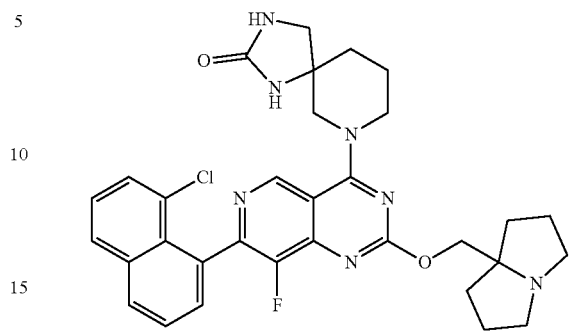

7-(7-(8-chloronaphthalen-1-yl)-8-fluoro-2-((hexa-hydro-1H-pyrrolizin-7a-yl)methoxy)pyrido[4,3-d]pyrimidin-4-yl)-1,3,7-triazaspiro[4.5]decan-2-one The title compound was synthesized according to the procedure described for example 281. $^1$H NMR (400 MHz, METHANOL-$d_4$) δ=9.14 (s, 1H), 8.16-8.14 (d, J=8.0 Hz, 1H), 8.2 (d, J=8.0 Hz, 1H), 7.70 (t, J=7.2 Hz, 1H), 7.66-7.57 (m, 2H), 7.54-7.50 (t, J=8.0 Hz, 1H), 4.81 (s, 1H), 4.65-4.50 (m, 3H), 4.38-4.21 (m, 1H), 4.04-3.81 (m, 2H), 3.61-3.55 (m, 2H), 3.45-3.41 (m, 1H), 3.22-3.08 (m, 2H), 2.32-2.23 (m, 2H), 2.18-2.14 (m, 4H), 2.08-1.94 (m, 5H), 1.94-1.80 (m, 1H); LCMS (ESI, M+1): m/z=602.3.

Example 285

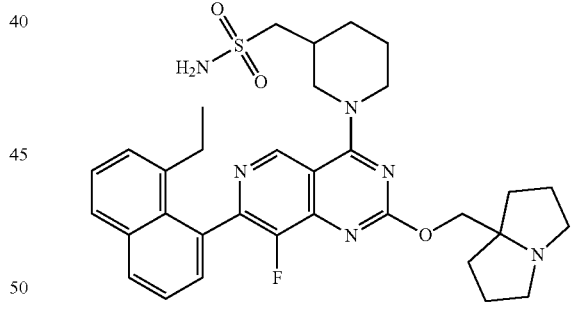

1-(1-(7-(8-ethylnaphthalen-1-yl)-8-fluoro-2-((tetrahydro-1H-pyrrolizin-7a(5H)-yl)methoxy)pyrido[4,3-d]pyrimidin-4-yl)piperidin-3-yl)methanesulfonamide The title compound was synthesized according to the procedure described for example 204. $^1$H NMR (400 MHz, METHANOL-$d_4$) δ=9.08 (s, 1H), 8.04 (d, J=8.0 Hz, 1H), 7.86 (d, J=8.0 Hz, 1H), 7.59-7.52 (m, 1H), 7.51-7.38 (m, 3H), 4.99-4.88 (m, 1H), 4.60-4.50 (m, 1H), 4.37-4.27 (m, 2H), 3.66-3.51 (m, 1H), 3.48-3.33 (m, 1H), 3.22-3.08 (m, 4H), 2.76-2.67 (m, 2H), 2.55-2.29 (m, 3H), 2.10 (dd, J=6.4, 5.2 Hz, 3H), 1.98-1.86 (m, 5H), 1.82-1.70 (m, 3H), 1.67-1.58 (m, 1H), 0.93 (dd, J=7.6, 2.0 Hz, 3H); $^{19}$F NMR (377 MHz, METHANOL-$d_4$) δ−134.15, −147.26. LCMS (ESI, M+1): m/z=619.2.

Example 286

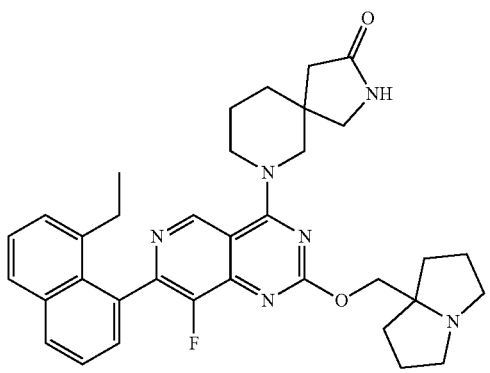 [SMILES: CCc1cccc2cccc(-c3ncc4c(N5CCCC6(CNC(=O)C6)C5)nc(OCC56CCCN5CCC6)nc4c3F)c12]

7-(7-(8-ethylnaphthalen-1-yl)-8-fluoro-2-((hexa-hydro-1H-pyrrolizin-7a-yl)methoxy)pyrido[4,3-d]pyrimidin-4-yl)-2,7-diazaspiro[4.5]decan-3-one The title compound was synthesized according to the procedure described for example 204. $^1$H NMR (400 MHz, METHANOL-d$_4$) δ=9.10 (s, 1H), 8.05 (dd, J=1.2, 8.0 Hz, 1H), 7.87 (d, J=7.6 Hz, 1H), 7.59-7.54 (m, 1H), 7.52-7.47 (m, 1H), 7.46-7.39 (m, 2H), 4.54-4.38 (m, 2H), 4.54-3.98 (m, 2H), 3.95-3.79 (m, 1H), 3.46-3.35 (m, 2H), 3.34 (br s, 1H), 3.30-3.24 (m, 2H), 3.01 (br d, J=9.2 Hz, 2H), 2.49-2.17 (m, 6H), 2.07 (td, J=6.3, 12.4 Hz, 4H), 1.91 (br s, 6H), 0.93 (q, J=7.6 Hz, 3H). LCMS [ESI, M+1]: m/z=595.4.

Example 287

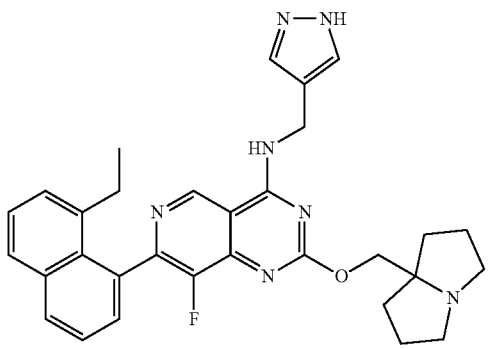 [SMILES: CCc1cccc2cccc(-c3ncc4c(NCc5cn[nH]c5)nc(OCC56CCCN5CCC6)nc4c3F)c12]

N-((1H-pyrazol-4-yl)methyl)-7-(8-ethylnaphthalen-1-yl)-8-fluoro-2-((hexahydro-1H-pyrrolizin-7a-yl)methoxy)pyrido[4,3-d]pyrimidin-4-amine The title compound was synthesized according to the procedure described for example 204. $^1$H NMR (400 MHz, dimethylsulfoxide-d$_6$) δ=9.36 (br t, J=5.2 Hz, 1H), 8.07 (d, J=7.6 Hz, 11H), 7.91 (d, J=8.0 Hz, 11H), 7.67 (s, 2H), 7.57 (t, J=7.6 Hz, 11H), 7.51 (t, J=7.6 Hz, 1H), 7.39 (t, J=7.6 Hz, 2H), 4.66 (br d, J=5.2 Hz, 2H), 4.16 (s, 2H), 3.05-2.97 (m, 2H), 2.69-2.58 (m, 2H), 2.41-2.17 (m, 3H), 2.00-1.90 (m, 2H), 1.88-1.75 (m, 4H), 1.68-1.58 (m, 2H), 0.83 (t, J=7.6 Hz, 3H); LCMS (ESI, M+1): m/z=538.3.

Example 288

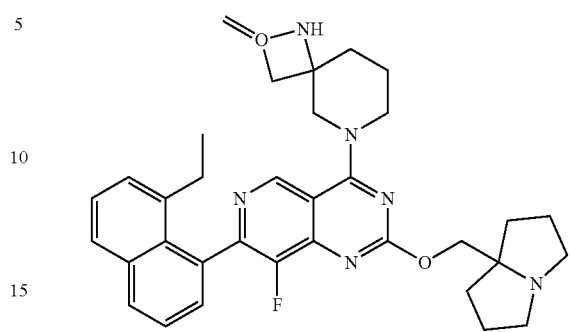

6-(7-(8-ethylnaphthalen-1-yl)-8-fluoro-2-((hexa-hydro-1H-pyrrolizin-7a-yl)methoxy)pyrido[4,3-d]pyrimidin-4-yl)-1,6-diazaspiro[3.5]nonan-2-one The title compound was synthesized according to the procedure described for example 204. $^1$H NMR (400 MHz, dimethylsulfoxide-d$_6$) δ=8.58 (br d, J=7.6 Hz, 1H), 8.08 (d, J=7.6 Hz, 1H), 7.92 (d, J=8.0 Hz, 1H), 7.63-7.55 (m, 11H), 7.52 (t, J=7.6 Hz, 1H), 7.45 (br d, J=7.2 Hz, 1H), 7.39 (d, J=7.2 Hz, 1H), 4.28-4.12 (m, 4H), 3.94-3.79 (m, 2H), 3.09-3.00 (m, 2H), 2.88-2.76 (m, 1H), 2.71-2.60 (m, 3H), 2.45-2.20 (m, 3H), 2.02-1.92 (m, 3H), 1.91-1.74 (m, 7H), 1.70-1.60 (m, 2H), 0.85 (t, J=7.6 Hz, 3H); LCMS (ESI, M+1): m/z=581.1.

Example 289

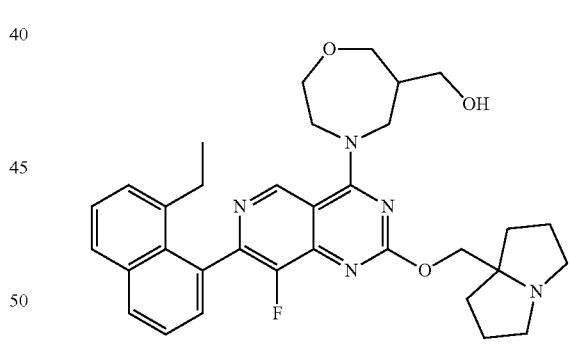

(4-(7-(8-ethylnaphthalen-1-yl)-8-fluoro-2-((hexa-hydro-1H-pyrrolizin-7a-yl)methoxy)pyrido[4,3-d]pyrimidin-4-yl)-1,4-oxazepan-6-yl)methanol The title compound was synthesized according to the procedure described for example 204. $^1$H NMR (400 MHz, METHANOL-d$_4$): δ=9.26-9.21 (m, 1H), 8.53 (s, 1H), 8.05 (d, J=8.0 Hz, 1H), 7.87 (d, J=8.0 Hz, 1H), 7.61-7.53 (m, 1H), 7.52-7.36 (m, 3H), 4.71-4.53 (m, 3H), 4.47-4.37 (m, 1H), 4.18-3.93 (m, 4H), 3.89-3.77 (m, 1H), 3.71-3.49 (m, 5H), 3.19-3.08 (m, 2H), 2.56-2.22 (m, 5H), 2.19-1.96 (m, 6H), 0.98 (br s, 3H); LCMS [ESI, M+1]: m/z=572.2.

Example 290

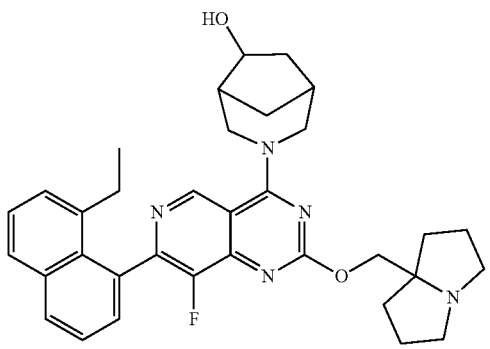 [SMILES: CCc1cccc2cccc(-c3ncc4c(N5CC6CC(O)C(C6)C5)nc(OCC56CCCN5CCC6)nc4c3F)c12]

3-(7-(8-ethylnaphthalen-1-yl)-8-fluoro-2-((hexahydro-1H-pyrrolizin-7a-yl)methoxy)pyrido[4,3-d]pyrimidin-4-yl)-3-azabicyclo[3,2,1]octan-6-ol The title compound was synthesized according to the procedure described for example 204. ¹H NMR (400 MHz, methanol-d₄) δ 9.23-9.06 (m, 1H), 8.04 (d, J=8.4 Hz, 1H), 7.86 (d, J=8.4 Hz, 1H), 7.59-7.53 (m, 1H), 7.51-7.37 (m, 3H), 5.01-4.92 (m, 1H), 4.84-4.76 (m, 1H), 4.36-4.26 (m, 3H), 3.78 (br dd, J=7.6, 11.6 Hz, 1H), 3.53-3.45 (m, 1H), 3.20-3.08 (m, 2H), 2.81-2.72 (m, 2H), 2.47-2.17 (m, 5H), 2.15-2.06 (m, 2H), 2.02-1.85 (m, 5H), 1.85-1.74 (m, 3H), 1.45-1.27 (m, 1H), 0.95-0.89 (m, 3H); LCMS [ESI, M+1]: m/z=568.4.

Example 291

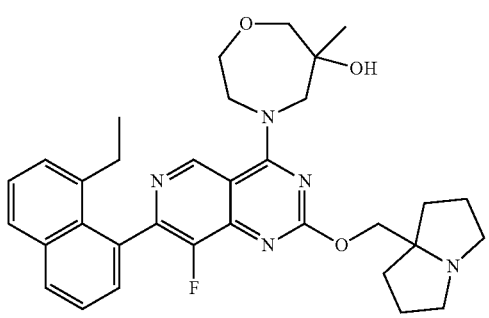 [SMILES: CCc1cccc2cccc(-c3ncc4c(N5CCOCC(C)(O)C5)nc(OCC56CCCN5CCC6)nc4c3F)c12]

4-(7-(8-ethylnaphthalen-1-yl)-8-fluoro-2-((hexahydro-1H-pyrrolizin-7a-yl)methoxy)pyrido[4,3-d]pyrimidin-4-yl)-6-methyl-1,4-oxazepan-6-ol The title compound was synthesized according to the procedure described for example 204 except for water (10 mM NH₄HCO₃)/ACN was used as a mobile phase for prep-HPLC. ¹H NMR (400 MHz, methanol-d₄) δ−9.53 (d, J=5.2 Hz, 1H), 8.07-8.03 (m, 1H), 7.88-7.84 (m, 1H), 7.59-7.53 (m, 1H), 7.51-7.38 (m, 3H), 4.61-4.49 (m, 2H), 4.35-4.26 (m, 2H), 4.23-4.14 (m, 1H), 4.07-3.86 (m, 3H), 3.74-3.63 (m, 2H), 3.16-3.07 (m, 2H), 2.79-2./0 (m, 2H), 2.49-2.30 (m, 2H), 2.14-2.03 (m, 2H), 2.00-1.83 (m, 4H), 1.82-1.73 (m, 2H), 1.28 (d, J=3.2 Hz, 3H), 0.97-0.89 (m, 3H); LCMS [ESI, M+1]: m/z=572.2

Example 292

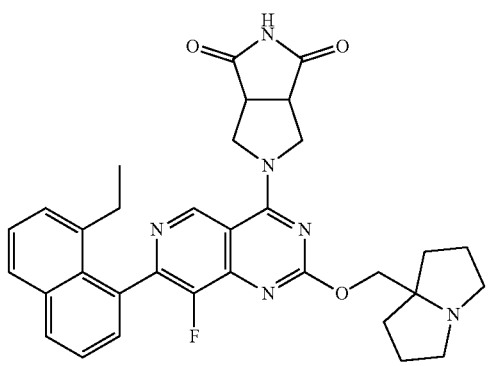 [SMILES: CCc1cccc2cccc(-c3ncc4c(N5CC6C(=O)NC(=O)C6C5)nc(OCC56CCCN5CCC6)nc4c3F)c12]

5-(7-(8-ethylnaphthalen-1-yl)-8-fluoro-2-((hexahydro-1H-pyrrolizin-7a-yl)methoxy)pyrido[4,3-d]pyrimidin-4-yl)tetrahydropyrrolo[3,4-c]pyrrole-1,3(2H,3aH)-dione The title compound was synthesized according to the procedure described for example 204. ¹H NMR (400 MHz, methanol-d₄) δ=9.32-9.23 (m, 1H), 8.05 (dd, J=1.2, 8.4 Hz, 1H), 7.86 (d, J=7.6 Hz, 11H), 7.57 (t, J=7.6 Hz, 1H), 7.51-7.46 (m, 1H), 7.44 (dd, J=1.2, 7.2 Hz, 1H), 7.40 (d, J=7.2 Hz, 11H), 4.65 (br d, J=12.4 Hz, 2H), 4.48-4.42 (m, 2H), 4.40-4.29 (m, 2H), 3.80-3.58 (m, 2H), 3.36-3.32 (m, 1H), 3.29 (br s, 1H), 3.01-2.85 (m, 2H), 2.48-2.26 (m, 2H), 2.17 (dtd, J=2.4, 6.4, 12.4 Hz, 2H), 2.11-2.04 (m, 1H), 2.04-2.00 (m, 2H), 1.99-1.93 (m, 1H), 1.93-1.83 (m, 2H), 0.96-0.87 (m, 3H); LCMS (ESI, M+1): m/z=581.1.

Example 293

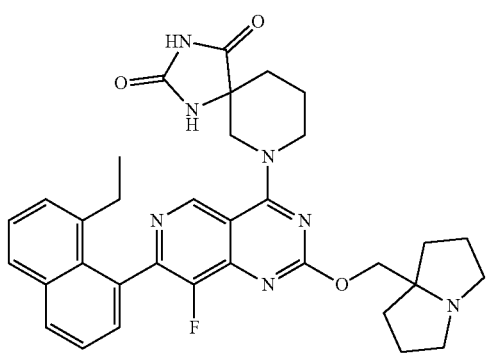 [SMILES: CCc1cccc2cccc(-c3ncc4c(N5CCCC6(C5)NC(=O)NC6=O)nc(OCC56CCCN5CCC6)nc4c3F)c12]

7-(7-(8-ethylnaphthalen-1-yl)-8-fluoro-2-((hexahydro-1H-pyrrolizin-7a-yl)methoxy)pyrido[4,3-d]pyrimidin-4-yl)-1,3,7-triazaspiro[4.5]decane-2,4-dione The title compound was synthesized according to the procedure described for example 291. ¹H NMR (400 MHz, METHANOL-d₄) δ=9.11-9.10 (m, 1H), 8.05-8.03 (d, J=7.2 Hz, 1H), 7.87-7.85 (d, J=8.0 Hz, 1H), 7.58-7.54 (m, 1H), 7.50-7.38 (m, 3H), 4.65-4.60 (m, 1H), 4.54-4.39 (m, 1H), 4.37-4.27 (m, 2H), 3.89-3.80 (m, 1H), 3.77-3.68 (m, 1H), 3.24-3.08 (m, 2H), 2.79-2.73 (m, 2H), 2.50-2.29 (m, 2H), 2.28-2.19 (m, 1H), 2.16-2.00 (m, 4H), 1.99-1.88 (m, 5H), 1.83-1.72 (m, 2H), 0.94-0.88 (m, 3H); LCMS [EST, M+1]: m/z=610.3.

Example 294

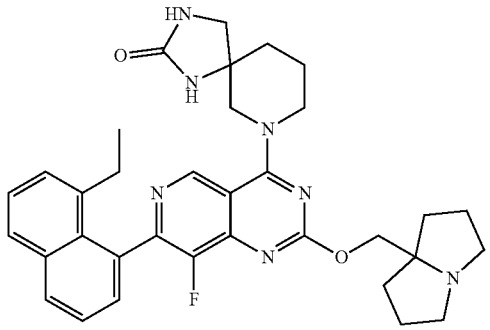 [SMILES: CCc1cccc2cccc(-c3ncc4c(N5CCCC6(CNC(=O)N6)C5)nc(OCC56CCCN5CCC6)nc4c3F)c12]

7-(7-(8-ethylnaphthalen-1-yl)-8-fluoro-2-((hexahydro-1H-pyrrolizin-7a-yl)methoxy)pyrido[4,3-d]pyrimidin-4-yl)-1,3,7-triazaspiro[4.5]decan-2-one The title compound was synthesized according to the procedure described for example 204. ¹H NMR (400 MHz, methanol-d₄) δ=9.14 (d, J=1.6 Hz, 11H), 8.05 (dd, J=0.8, 8.0 Hz, 1H), 7.87 (d, J=8.0 Hz, 1H), 7.59-7.55 (m, 1H), 7.51-7.47 (m, 1H), 7.46-7.38 (m, 2H), 4.68-4.36 (m, 3H), 4.41-4.33 (m, 1H), 4.30-4.17 (m, 1H), 4.07-3.80 (m, 2H), 3.66-3.51 (m, 2H), 3.42 (dd, J=4.2, 9.6 Hz, 1H), 3.22-3.10 (m, 2H), 2.47-2.32 (m, 2H), 2.32-2.25 (m, 2H), 2.19-2.11 (m, 4H), 2.07-1.94 (m, 5H), 1.90-1.86 (m, 1H), 0.95-0.90 (m, 3H); LCMS [ESI, M+1]: m/z=596.3.

Example 295

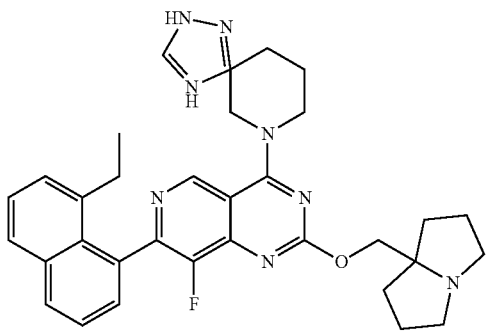

4-(3-(1H-1,2,4-triazol-3-yl)piperidin-1-yl)-7-(8-ethylnaphthalen-1-yl)-8-fluoro-2-((hexahydro-1H-pyrrolizin-7a-yl)methoxy)pyrido[4,3-d]pyrimidine The title compound was synthesized according to the procedure described for example 291. ¹H NMR (400 MHz, CD3OD, 298 K) δ (ppm)=9.09 (d, J=2.4 Hz, 1H), 8.25 (d, J=4.4 Hz, 1H), 8.07-8.00 (m, 1H), 7.86 (d, J=7.6 Hz, 1H), 7.56 (t, J=7.6 Hz, 1H), 7.52-7.37 (m, 3H), 4.55 (br t, J=12.0 Hz, 1H), 4.35-4.24 (m, 2H), 3.87-3.65 (m, 2H), 3.41-3.33 (m, 1H), 3.14-3.06 (m, 2H), 2.73 (m, 2H), 2.47-2.26 (m, 3H), 2.14-2.01 (m, 4H), 2.01-1.70 (m, 8H), 0.92 (t, J=7.2 Hz, 3H); LCMS (ESI, M+1): m/z=593.3.

Example 296

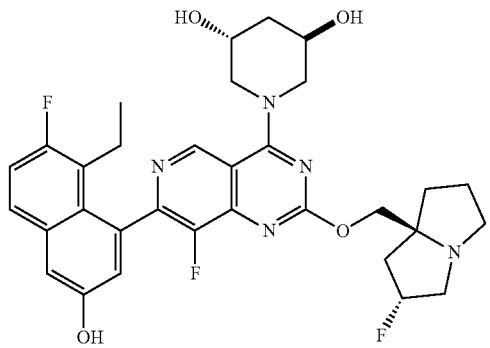 [SMILES: CCc1c(F)ccc2cc(O)cc(-c3ncc4c(N5C[C@H](O)C[C@@H](O)C5)nc(OC[C@@]56CCCN5C[C@H](F)C6)nc4c3F)c12]

(3R,5R)-1-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)piperidine-3,5-diol The title compound was synthesized according to the procedure described for example 135. ¹H NMR (400 MHz, methanol-d₄) δ=9.24 (dd, J=2.8, 7.2 Hz, 1H), 7.67 (dd, J=5.6, 8.8 Hz, 1H), 7.30 (d, J=2.8 Hz, 1H), 7.24 (t, J=9.2 Hz, 1H), 7.05 (dd, J=2.4, 8.8 Hz, 1H), 5.39-5.22 (m, 1H), 4.37-4.31 (m, 1H), 4.30-4.19 (m, 5H), 3.84-3.75 (m, 2H), 3.21 (br d, J=19.6 Hz, 3H), 3.01 (m, 1H), 2.54-2.42 (m, 1H), 2.39-2.12 (m, 4H), 2.04-1.88 (m, 5H), 0.84-0.76 (m, 3H). ¹⁹F NMR (376 MHz, METHANOL-d₄) δ=−121.237, −139.064, −173.716. HPLC:>99%. LCMS (ESI, M+1): m/z=610.2.

Example 297

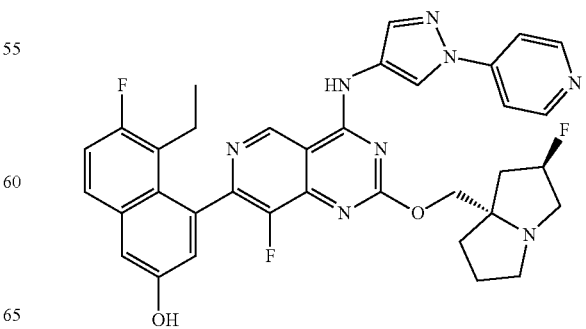

5-ethyl-6-fluoro-4-(8-fluoro-2-(((2R,7aS)-2-fluoro-hexahydro-1H-pyrrolizin-7a-yl)methoxy)-4-((1-(pyridin-4-yl)-1H-pyrazol-4-yl)amino)pyrido[4,3-d]pyrimidin-7-yl)naphthalen-2-ol

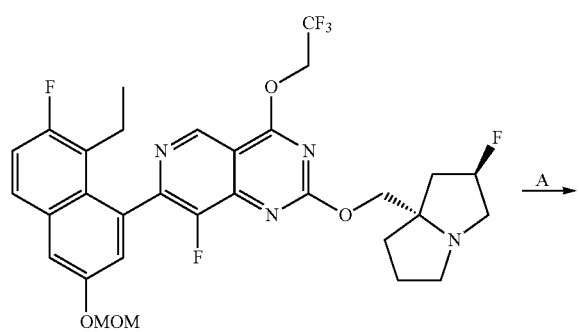

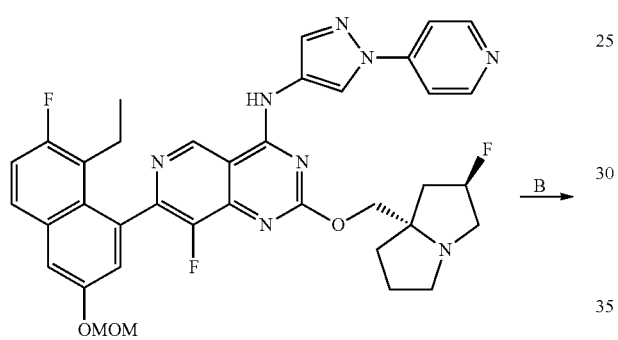

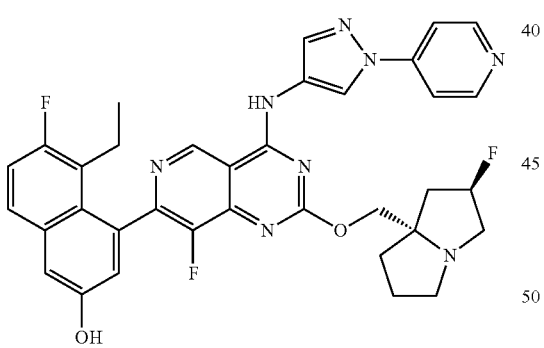

Step A. 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-N-(1-(pyridin-4-yl)-1H-pyrazol-4-yl)pyrido[4,3-d]pyrimidin-4-amine: To the mixture of 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (143 mg, 1.0 equiv.), 1-(pyridin-4-yl)-1H-pyrazol-4-amine (110 mg, 2.5 equiv., HCl), 4 Å molecular sieves (50.0 mg) in DMAC (1.5 mL) was added CsF (340 mg, 10.0 equiv.), and the mixture was stirred at 40° C. for 14 hours. After reaction completion, the mixture was filtered and diluted with water (10 mL), extracted with ethyl acetate (2×20 mL), dried over anhydrous sodium sulfate, filtered and concentrated. The residue was purified by reversed-phase flash chromatography [water (0.1% formic acid)/acetonitrile] to afford the title compound (106 mg, 62% yield over two steps) as a yellow solid; LCMS [ESI, M+1]: m/z=697.2.

Step B. 5-ethyl-6-fluoro-4-(8-fluoro-2-(((2R,7aS)-2-fluorohexahydro-1H-pyrrolizin-7a-yl)methoxy-4-((1-(pyridin-4-yl)-1H-pyrazol-4-yl)amino)pyrido[4,3-d]pyrimidin-7-yl)naphthalen-2-ol: To a solution of 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-N-(1-(pyridin-4-yl)-1H-pyrazol-4-yl)pyrido[4,3-d]pyrimidin-4-amine (50.0 mg, 1.0 equiv.) in ACN (1 mL) was added HCl.dioxane (4 M, 2 mL, 111.5 equiv.) at 0° C. The reaction was stirred at 0° C. for 0.5 hour. After reaction completion, the mixture was concentrated under reduced pressure to give a residue. pH was adjusted with sat. aq. NaHCO$_3$ to 9 and the mixture was extracted with ethyl acetate (3×2 mL). The combined organic layers were dried over anhydrous Na$_2$SO$_4$, filtered and concentrated. The residue was purified by prep-HPLC (column: Waters Xbridge 150×25 mm×5 μm; mobile phase: [water (10 mM NH$_4$HCO$_3$)/ACN,] B %: 45%-75%, 10 min) and lyophilized to afford the title compound (14.9 mg, 31% yield) as an off-white solid; $^1$H NMR (400 MHz, methanol-d$_4$): δ=9.39 (s, 1H), 9.06 (s, 1H), 8.67-8.61 (m, 2H), 8.23 (s, 1H), 7.93-7.88 (m, 2H), 7.69 (dd, J=5.6, 9.2 Hz, 1H), 7.32 (d, J=2.8 Hz, 1H), 7.26 (t, J=9.6 Hz, 1H), 7.08 (d, J=2.8 Hz, 1H), 5.43-5.24 (m, 1H), 4.50-4.36 (m, 2H), 3.29-3.20 (m, 3H), 3.12-2.97 (m, 1H), 2.54-2.23 (m, 3H), 2.22-1.93 (m, 5H), 0.81 (t, J=7.6 Hz, 3H); LCMS [ESI, M+1]: m/z=653.3.

Example 298

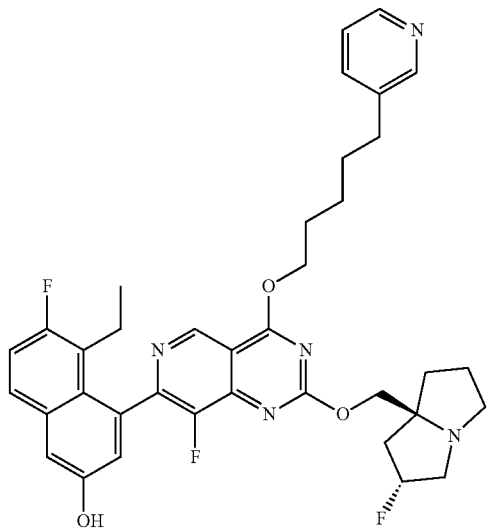 [SMILES: CCc1c(F)ccc2cc(O)cc(-c3ncc4c(OCCCCCc5cccnc5)nc(OC[C@@]56CCCN5C[C@H](F)C6)nc4c3F)c12]

5-ethyl-6-fluoro-4-(8-fluoro-2-(((2R,7aS)-2-fluoro-hexahydro-1H-pyrrolizin-7a-yl)methoxy)-4-(3-(pyridin-3-yl)propoxy)pyrido[4,3-d]pyrimidin-7-yl)naphthalen-2-ol

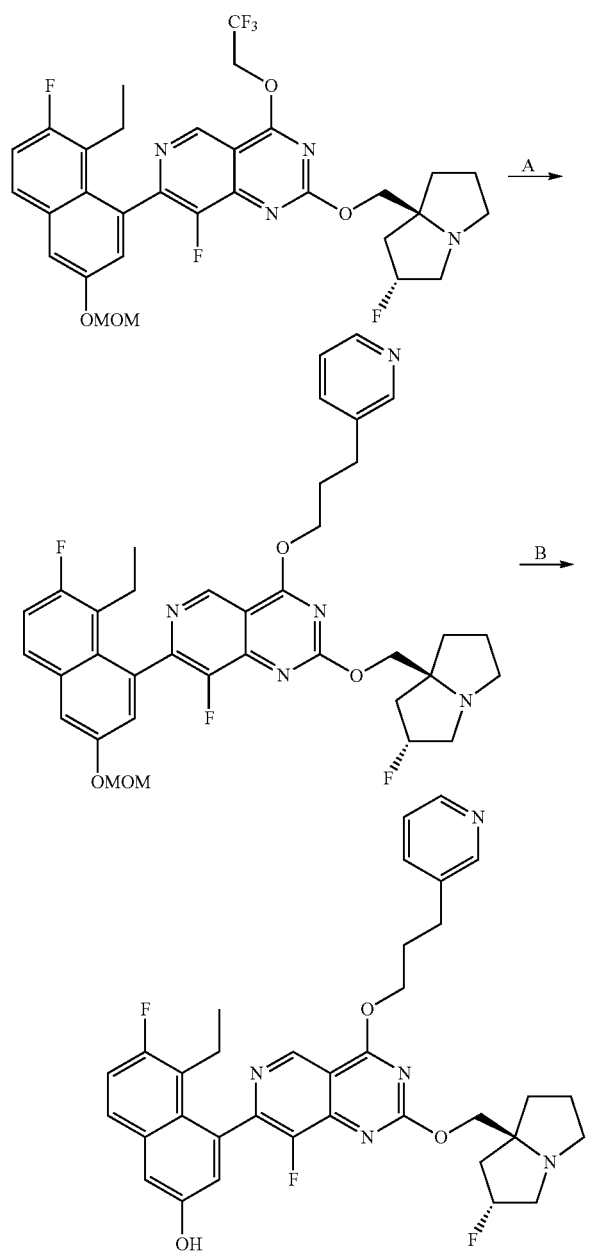

Step A. 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-4-(3-(pyridin-3-yl)propoxy)pyrido[4,3-d]pyrimidine: To a mixture of 3-(pyridin-3-yl)propan-1-ol (15.1 mg, 110 μmol, 14.2 μL, 1.5 equiv.) and 4 Å molecular sieves (5 mg) in THF (1 mL) was added LiHMDS (1.0 M in THF, 220 μL, 3.0 equiv.) at −40° C. and the mixture was stirred at −40° C. for 0.5 hour. Then 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (50.0 mg, 73.3 μmol, 1.0 equiv., formic acid salt) in THF (0.5 mL) was added into the above mixture and the mixture was stirred at 25° C. for 1 hour. The mixture was quenched by water (3 mL) at 0° C. The mixture was diluted with ethyl acetate (4 mL), the layers were separated and the aqueous phase was extracted with ethyl acetate (2×5 ML). The combined organic layers were dried over Na$_2$SO$_4$, filtered and concentrated in vacuum. The residue was purified by reversed phase flash chromatography [water (0.1% formic acid)/acetonitrile] to afford the title compound (35.0 mg, 64% yield) as a yellow solid; LCMS (ESI, M+1): m/z=674.3.

Step B. 5-ethyl-6-fluoro-4-(8-fluoro-2-(((2R,7aS)-2-fluorohexahydro-1H-pyrrolizin-7a-yl)methoxy)-4-(3-(pyridin-3-yl)propoxy)pyrido[4,3-d]pyrimidin-7-yl)naphthalen-2-ol: To a mixture of 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-4-(3-(pyridin-3-yl)propoxy)pyrido[4,3-d]pyrimidine (60.0 mg, 89.1 μmol, 1.0 equiv.) in dichloromethane (0.60 mL) was added TFA (924 mg, 91 equiv.) at 0° C. and the mixture was stirred at 0-25° C. for 1.5 hours. The mixture was concentrated in vacuum and the pH value was adjusted to 8 with saturated NaHCO$_3$ solution. The mixture was diluted with ethyl acetate (4 mL) then separated. The aqueous layer was extracted with ethyl acetate (2×4 mL) and the combined organic layers were washed with brine (4 mL) and dried over Na$_2$SO$_4$. The mixture was filtered and concentrated in vacuum. The mixture was purified by prep-HPLC [column: Waters Xbridge 150×25 mm×5 um; mobile phase: water (10 mM NH$_4$HCO$_3$)/ACN], B %: 43%-73%, 9 min] to afford the title compound (13.3 mg, 23% yield) as a white solid; $^1$H NMR (400 MHz, methanol-d$_4$) δ=9.05 (s, 1H), 8.37 (dd, J=1.6, 4.8 Hz, 1H), 7.82 (br d, J=7.6 Hz, 1H), 7.68 (dd, J=5.6, 8.8 Hz, 1H), 7.38 (dd, J=4.8, 7.6 Hz, 1H), 7.31 (d, J=3.0 Hz, 1H), 7.26 (t, J=9.2 Hz, 1H), 7.05 (s, 1H), 5.38-5.22 (m, 1H), 4.75 (t, J=6.0 Hz, 2H), 4.35 (q, J=10.4 Hz, 2H), 3.29-3.17 (m, 3H), 3.05-2.95 (m, 3H), 2.49-2.39 (m, 1H), 2.38-2.26 (m, 3H), 2.24-2.19 (m, 1H), 2.17-2.09 (m, 2H), 2.04-1.96 (m, 2H), 1.94-1.86 (m, 1H), 0.77 (t, J=7.2 Hz, 3H); $^{19}$F NMR (376 MHz, methanol-d$_4$) δ=a −121.108, −138.808, −173.817; SFC condition: Column: Chiralcel 01-3 50×4.6 mm I.D., 3 um; Mobile phase: Phase A for CO$_2$, and Phase B for MeOH (0.05% DEA); Gradient elution: MeOH (0.05% DEA) in CO$_2$ from 5% to 40%; Flow rate: 3 mL/min; Detector: PDA; Column Temp: 35° C.; Back Pressure: 100 Bar; LCMS (ESI, M+1): m/z=630.3.

Example 299

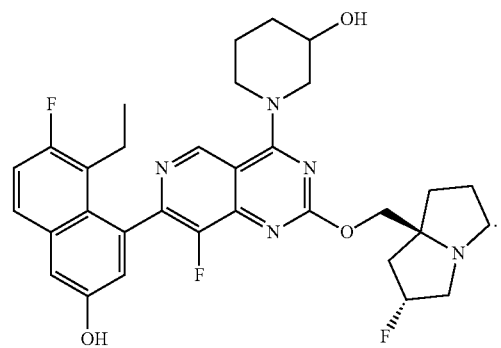 [SMILES: CCc1c(F)ccc2cc(O)cc(-c3ncc4c(N5CCCC(O)C5)nc(OC[C@@]56CCCN5C[C@H](F)C6)nc4c3F)c12]

483

1-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)piperidin-3-ol The title compound was synthesized according to the procedure described for example 135. $^1$H NMR (400 MHz, METHANOL-d$_4$) δ=9.21-9.13 (m, 1H), 7.68 (dd, J=6.0, 9.2 Hz, 1H), 7.31 (d, J=2.4 Hz, 1H), 7.25 (t, J=9.6 Hz, 1H), 7.09-7.02 (m, 1H), 5.51-5.32 (m, 1H), 4.52-4.37 (m, 2H), 4.27-4.19 (m, 1H), 4.13-3.94 (m, 3H), 3.93-3.83 (m, 1H), 3.64-3.41 (m, 3H), 3.24-3.14 (m, 1H), 2.56-2.30 (m, 3H), 2.28-2.05 (m, 6H), 2.03-1.95 (m, 1H), 1.84-1.69 (m, 2H), 0.84-0.75 (m, 3H); LCMS (ESI, M+1): m/z=594.3.

Example 300

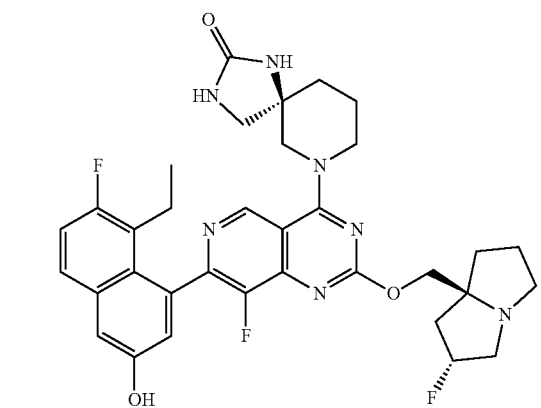 [SMILES: CCc1c(F)ccc2cc(O)cc(-c3ncc4c(N5CCC[C@@]6(CNC(=O)N6)C5)nc(OC[C@@]56CCCN5C[C@H](F)C6)nc4c3F)c12]

(R)-7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7triazaspiro[4.5]decan-2-one

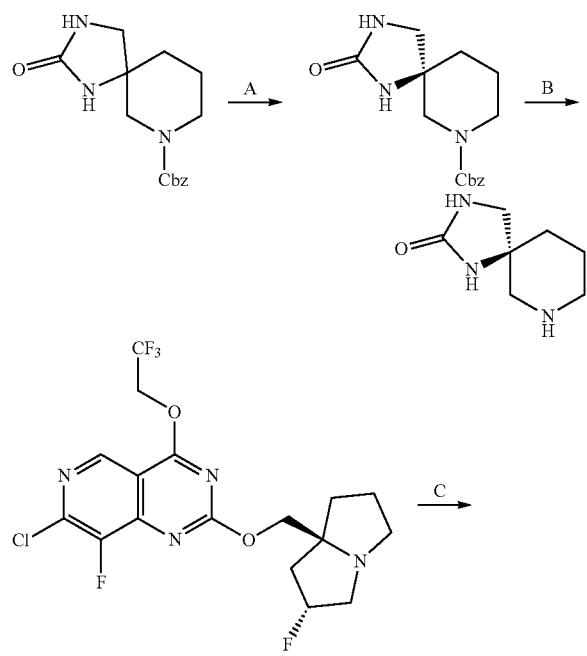

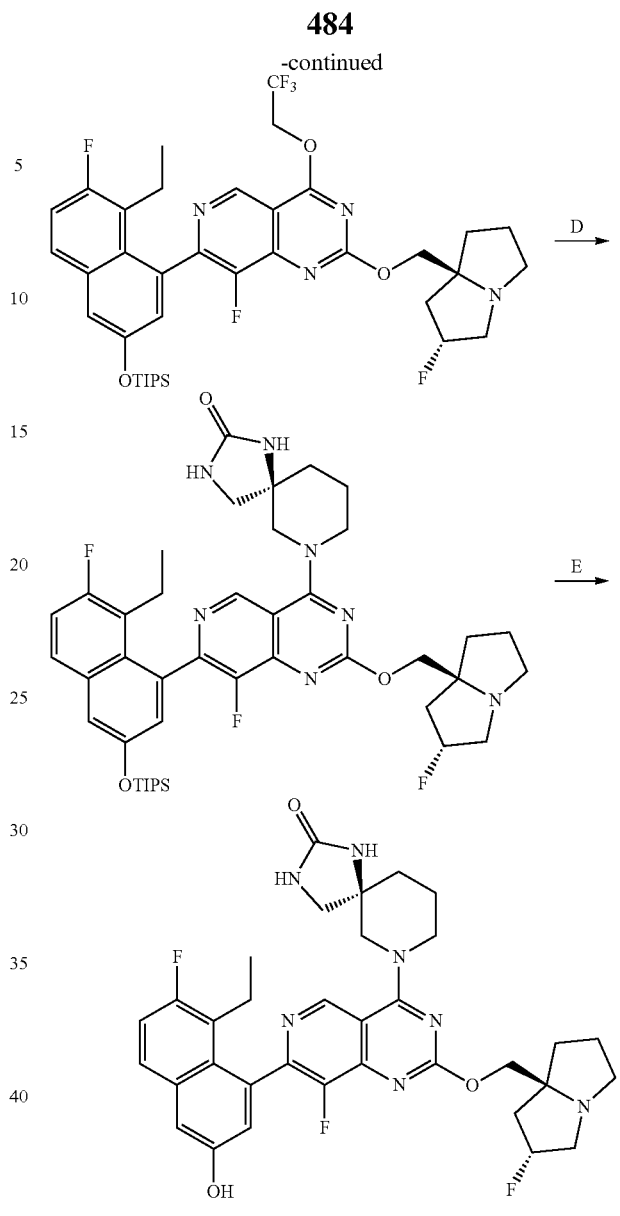

Step A. (R)-benzyl 2-oxo-1,3,7-triazaspiro[4.5]decane-7-carboxylate: SFC separation of benzyl 2-oxo-1,3,7-triazaspiro[4.5]decane-7-carboxylate (650 mg) [column: DAICEL CHIRALPAK AY-H (250 mm*30 mm, 10 um); mobile phase: water (0.1% NH$_4$OH)-EtOH]; B %: 50%-50%, 4.8 min; 110 min]. The crude product was purified by reversed phase flash chromatography [C18, water (0.1% formic acid)/ACN] to afford the title compound (200 mg, 54% yield) as a white solid; $^1$H NMR (400 MHz, DMSO-d$_6$) δ=7.43-7.27 (m, 5H), 6.65 (s, 1H), 6.21 (s, 1H), 5.07 (br s, 2H), 3.59-3.43 (m, 2H), 3.18-2.91 (m, 4H), 1.71-1.52 (m, 3H), 1.47-1.30 (m, 1H).

Step B. (S)-1,3,7-triazaspiro[4.5]decan-2-one: To a solution of benzyl (R)-benzyl 2-oxo-1,3,7-triazaspiro[4.5]decane-7-carboxylate (200 mg, 1.0 equiv.) in MeOH (30 mL) was added Pd/C (50.0 mg, 10% purity) under N$_2$. The mixture was stirred at 10° C. for 2 hours under H$_2$ (15 psi). The reaction mixture was filtered and concentrated to afford the title compound (120 mg, crude) as a white solid; $^1$H NMR (400 MHz, DMSO-d$_6$) δ=6.36 (s, 1H), 6.08 (br s, 1H), 3.18-3.13 (m, 4H), 2.96 (d, J=8.8 Hz, 1H), 2.20-2.10 (m, 1H), 1.64-1.41 (m, 4H).

Step C. 7-(8-ethyl-7-fluoro-3-((triisopropylsilyl)oxy) naphthalen-1-yl)-8-fluoro-2-(((2R,7aS)-2-fluorohexahydro-1H-pyrrolizin-7a-yl)methoxy-4-(2,2,2-trifluoroethoxy) pyrido[4,3-d]pyrimidine: To a solution of 7-chloro-8-fluoro-2-(((2R,7aS)-2-fluorohexahydro-1H-pyrrolizin-7a-yl) methoxy)-4-(2,2,2-trifluoroethoxy)pyrido[4,3-d]pyrimidine (1.0 g, 1.0 equiv.), CataCXium A Pd G3 (166 mg, 0.1 equiv.) and ((5-ethyl-6-fluoro-4-(4,4,5,5-tetramethyl-1,3,2-dioxaborolan-2-yl)naphthalen-2-yl)oxy)triisopropylsilane (1.29 g, 1.20 equiv.) in THF (17 mL) was added $K_3PO_4$ (1.5 M, 3.0 equiv.) under $N_2$. The mixture was stirred at 60° C. for 1 hour. The reaction mixture was diluted with saturated $NH_4Cl$ (20 mL), the aqueous phase was extracted with ethyl acetate (3×10 mL). The combined organic phase was washed with brine (15 mL), dried with anhydrous $Na_2SO_4$, concentrated and purified by column chromatography [Silica gel, Petroleum ether/Ethyl acetate 1:0 to 3:1] to afford the title compound (crude) as a yellow solid; LCMS (ESI, M+1): m/z=749.4.

Step D. (R)-7-(7-(8-ethyl-7-fluoro-3-((triisopropylsilyl) oxy)naphthalen-1-yl)-8-fluoro-2-(((2R,7aS)-2-fluorohexahydro-1H-pyrrolizin-7a-yl methoxy)pyrido[4,3-d]pyrimidin-4-yl)-1,3,7-triazaspiro[4.5]decan-2-one: To a solution of 7-(8-ethyl-7-fluoro-3-((triisopropylsilyl)oxy)naphthalen-1-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (380 mg, 1.0 equiv.), 4 Å molecular sieves (200 mg) and (S)-1,3,7-triazaspiro[4.5]decan-2-one (78.7 mg, 1.0 equiv.) in DMF (4.0 mL) was added DIEA (197 mg, 3.0 equiv.).The mixture was stirred at 40° C. for 12 hours. The reaction mixture was filtered. The crude product was purified by reversed phase flash chromatography [C18, water (0.1% formic acid)/ACN] to afford the title compound (180 mg, 44% yield) as a brown solid; LCMS (ESI, M+1): m/z=804.3.

Step E. (R)-7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decan-2-one: To a solution of (R)-7-(7-(8-ethyl-7-fluoro-3-((triisopropylsilyl)oxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro [4.5]decan-2-one (180 mg, 1.0 equiv.) in DMF (1.0 mL) was added CsF (340 mg, 10 equiv.). The mixture was stirred at 10° C. for 0.5 hour. The reaction mixture was filtered and purified by prep-HPLC [Waters Xbridge 150×25 mm×5 um; mobile phase: water (10 mM $NH_4HCO_3$)-ACN; B %: 34%-64%, 9 min] to afford the title compound (125 mg, 86% yield) as a white solid; $^1$H NMR (400 MHz, CD3OD) δ=9.11 (d, J=4.0 Hz, 1H), 7.68 (dd, J=6.0, 9.2 Hz, 1H), 7.30 (d, J=2.4 Hz, 1H), 7.25 (t, J=9.6 Hz, 1H), 7.05 (d, J=2.8 Hz, 1H), 5.40-5.21 (m, 1H), 4.33-4.24 (m, 2H), 4.18-3.84 (m, 4H), 3.47-3.38 (m, 1H), 3.28-3.14 (m, 3H), 3.05-2.96 (m, 1H), 2.55-2.08 (m, 5H), 2.06-1.81 (m, 7H), 0.87-0.72 (m, 3H); LCMS (ESI, M+1): m/z=648.2.

Example 301

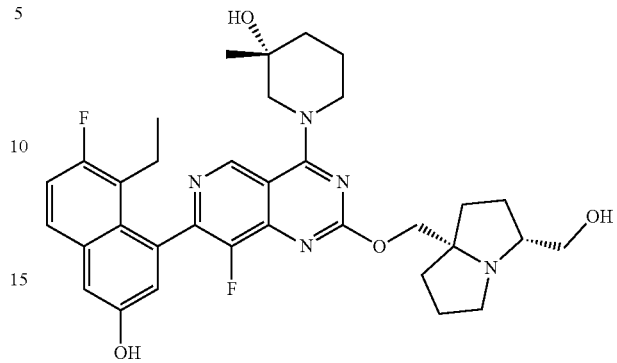

(R)-1-(7-(8-ethyl-7-fluoro-3-hydroxynaphthalen-1-yl)-8-fluoro-2-(((3R,7aS)-3-(hydroxymethyl)tetrahydro-1H-pyrrolizin-7a(5H)-yl)methoxy)pyrido[4,3-d]pyrimidin-4-yl)-3-methylpiperidin-3-ol

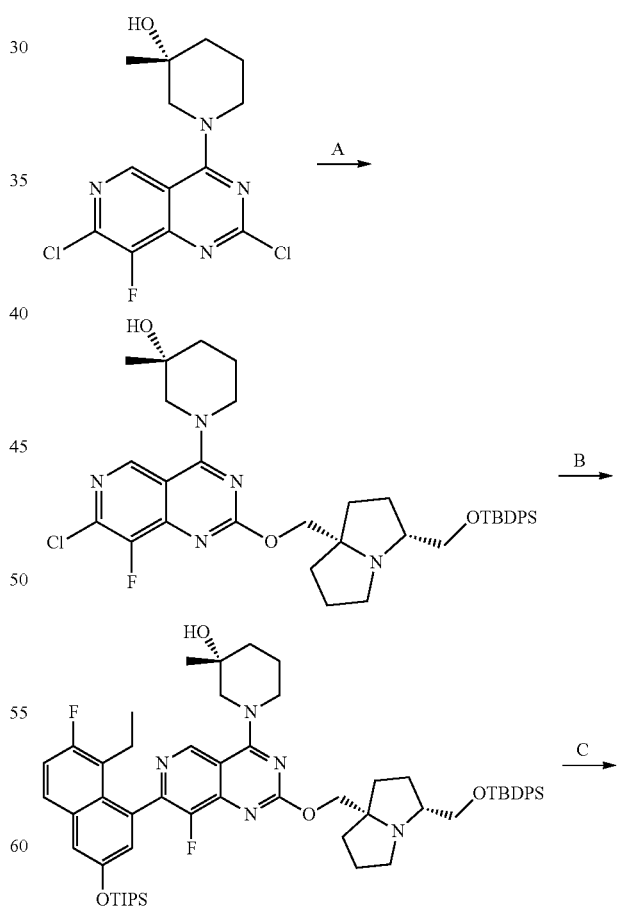

-continued

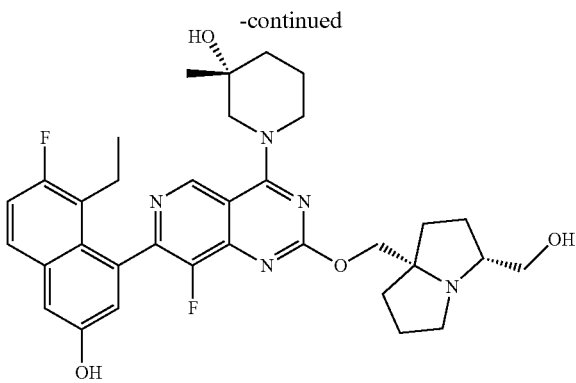

Step A. (R)-1-(2-(((3R,7aS)-3-(((tert-butyldiphenylsilyl)oxy)methyl)hexahydro-1H-pyrrolizin-7a-yl)methoxy)-7-chloro-8-fluoropyrido[4,3-d]pyrimidin-4-yl)-3-methylpiperidin-3-ol: To a mixture of ((3R,7aR)-3-(((tert-butyldiphenylsilyl)oxy)methyl)hexahydro-1H-pyrrolizin-7a-yl)methanol (408 mg, 1.1 equiv.) and 4 Å molecular sieves (30 mg) in toluene (3 mL) was added t-BuONa (261 mg, 3.0 equiv.) at 0° C. The reaction was stirred at 0° C. for 10 mins. Then (R)-1-(2,7-dichloro-8-fluoropyrido[4,3-d]pyrimidin-4-yl)-3-methylpiperidin-3-ol (300 mg, 906 μmol, 1.0 equiv.) was added. The reaction was stirred at 0° C. for 1 hour. The mixture was quenched with water (4 mL) at 0° C. and extracted with ethyl acetate (3×8 mL). The combined organic layers were dried over anhydrous sodium sulfate, concentrated, and purified by reversed phase flash chromatography [water (0.1% formic acid)/acetonitrile]. The desired fractions were collected, neutralized with solid NaHCO$_3$, concentrated in vacuum to remove acetonitrile, and extracted with dichloromethane (2×20 mL). The combined organic layer was washed with brine (20 mL), dried over anhydrous Na$_2$SO$_4$, and concentrated in vacuum to afford the title compound (580 mg, 89% yield) as a brown solid; $^1$H NMR (400 MHz, methanol-d$_4$) δ 8.97 (s, 1H), 7.74-7.67 (m, 4H), 7.45-7.35 (m, 6H), 4.44 (br d, J=13.2 Hz, 1H), 4.23-4.14 (m, 3H), 3.70-3.57 (m, 2H), 3.52 (d, J=13.2 Hz, 1H), 3.30-3.25 (m, 1H), 3.04-2.88 (m, 2H), 2.83-2.73 (m, 1H), 2.19-2.12 (m, 1H), 2.10-2.02 (m, 2H), 1.93-1.83 (m, 3H), 1.81-1.73 (m, 3H), 1.72-1.60 (m, 3H), 1.22 (s, 3H), 1.04 (s, 9H); LCMS [ESI, M+1]: m/z=704.2.

Step B. (R)-1-(2-(((3R,7aS)-3-(((tert-butyldiphenylsilyl)oxy methylhexahydro-1H-pyrrolizin-7a-yl)methoxy)-7-(8-ethyl-7-fluoro-3-((triisopropylsilyl)oxy)naphthalen-1-yl)-8-fluoropyrido[4,3-d]pyrimidin-4-yl)-3-methylpiperidin-3-ol: To a solution of (R)-1-(2-(((3R,7aR)-3-(((tert-butyldiphenylsilyl)oxy)methyl)hexahydro-1H-pyrrolizin-7a-yl)methoxy)-7-chloro-8-fluoropyrido[4,3-d]pyrimidin-4-yl)-3-methylpiperidin-3-ol (530 mg, 1.0 equiv.), ((5-ethyl-6-fluoro-4-(4,4,5,5-tetramethyl-1,3,2-dioxaborolan-2-yl)naphthalen-2-yl)oxy)triisopropylsilane (462 mg, 1.3 equiv.) and K$_3$PO$_4$ (1.5 M in water, 1.50 mL, 3.0 equiv.) in methoxycyclopentane (4.6 mL) was added CataCXium A Pd G3 (54.8 mg, 0.1 equiv.) under N$_2$. The reaction was stirred at 90° C. for 2.5 hours. The layers of the mixture were separated and the aqueous phase was extracted with ethyl acetate (2×5 mL). The combined organic layers were concentrated and purified by reversed phase flash chromatography [water (0.1% formic acid)/acetonitrile]. The desired fractions were collected, neutralized with solid NaHCO$_3$, concentrated in vacuum to remove acetonitrile, and extracted with dichloromethane (2×15 mL). The combined organic layers were washed with brine (15 mL), dried over anhydrous Na$_2$SO$_4$, and concentrated in vacuum to afford the title compound (193 mg, 23% yield) as a brown solid; LCMS [ESI, M+1, M/2+1]: m/z=1014.7, 508.1.

Step C. (R 1-(7-(8-ethyl-7-fluoro-3-hydroxynaphthalen-1-yl)-8-fluoro-2-(((3R,7aS)-3-(hydroxymethyl)hexahydro-1H-pyrrolizin-7a-yl)methoxy)pyrido[4,3-d]pyrimidine-4-yl)-3-methylpiperidin-3-ol: To a mixture of (R)-1-(2-(((3R,7aR)-3-(((tert-butyldiphenylsilyl)oxy)methyl)hexahydro-1H-pyrrolizin-7a-yl)methoxy)-7-(8-ethyl-7-fluoro-3-((triisopropylsilyl)oxy)naphthalen-1-yl)-8-fluoropyrido[4,3-d]pyrimidin-4-yl)-3-methylpiperidin-3-ol (163 mg, 1.0 equiv.) in DMF (0.8 mL) was added CsF (366 mg, 15 equiv.). The reaction was stirred at 20° C. for 15 hours. The mixture was filtered and the filtrate was purified by reversed phase flash chromatography [water (0.1% formic acid)/acetonitrile]. The desired fractions were collected, neutralized with solid NaHCO$_3$, concentrated in vacuum to remove acetonitrile, and extracted with dichloromethane (2×15 mL). The combined organic layer was washed with brine (15 mL), dried over anhydrous Na$_2$SO$_4$, and concentrated in vacuum. The residue was purified by prep-HPLC [column: Waters Xbridge 150×25 mm×5 μm; mobile phase: [water (10 mM NH$_4$HCO$_3$)-AC,] B %: 35%-65%, 8 min] and lyophilized to afford the title compound (46.7 mg, 47% yield) as a yellow solid; $^1$H NMR (400 MHz, methanol-d$_4$) δ 9.20 (d, J=1.2 Hz, 1H), 7.67 (dd, J=5.6, 8.8 Hz, 1H), 7.30 (d, J=2.8 Hz, 1H), 7.25 (t, J=9.2 Hz, 11H), 7.06 (t, J=2.0 Hz, 1H), 4.54 (br d, J=12.4 Hz, 1H), 4.34-4.24 (m, 3H), 3.68-3.59 (m, 1H), 3.59-3.52 (m, 2H), 3.50-3.42 (m, 0.1H), 3.13-3.01 (m, 1H), 2.98-2.84 (m, 2H), 2.54-2.41 (m, 1H), 2.26-2.11 (m, 3H), 2.06-1.99 (m, 1H), 1.98-1.92 (m, 2H), 1.92-1.84 (m, 2H), 1.83-1.66 (m, 5H), 1.29 (d, J=10.0 Hz, 3H), 0.82 (q, J=7.2 Hz, 3H); $^{19}$F NMR (376 MHz, methanol-d$_4$) δ−121.198, −139.196; SFC: >99% ee, (S,S)Whelk-O1 100×4.6 mm I.D., 3.5 μm column, A: CO$_2$,B: 40% [IPA+ACN (w/0.05% DEA)], 3 mL/min, 220 nm, t$_R$: 1.705 min; LCMS [ESI, M+1, M/2+1]: m/z=620.2, 310.7.

Example 302

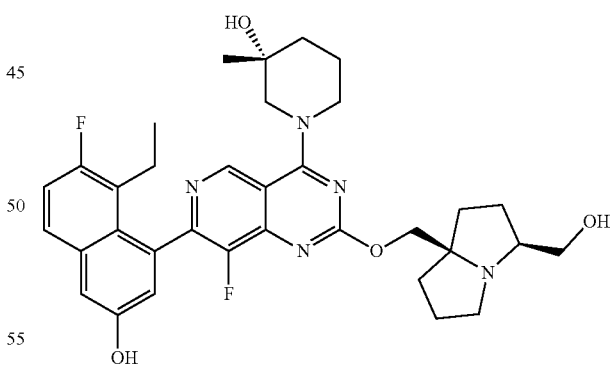

(R)-1-(7-(8-ethyl-7-fluoro-3-hydroxynaphthalen-1-yl)-8-fluoro-2-(((3S,7aR)-3-(hydroxymethyl)tetrahydro-1H-pyrrolizin-7a(5H)-yl)methoxy)pyrido[4,3-d]pyrimidin-4-yl)-3-methylpiperidin-3-ol The title compound was synthesized according to the procedure described for example 301. $^1$H NMR (400 MHz, methanol-d$_4$) δ ppm=9.21 (s, 1H), 7.68 (dd, J=9.2, 6.0 Hz, 1H), 7.30 (d, J=2.8 Hz, 1H), 7.28-7.21 (m, 1H), 7.08-7.04

(m, 1H), 4.55 (br d, J=13.2 Hz, 1H), 4.40-4.20 (m, 3H), 3.68-3.59 (m, 1H), 3.59-3.50 (m, 2H), 3.50-3.40 (m, 1H), 3.16-3.06 (m, 1H), 3.02-2.87 (m, 2H), 2.48 (qd, J=7.2, 14.4 Hz, 1H), 2.28-2.10 (m, 3H), 2.09-2.02 (m, 1H), 2.01-1.94 (m, 2H), 1.93-1.88 (m, 1H), 1.88-1.67 (m, 6H), 1.34-1.24 (m, 3H), 0.82 (q, J=7. Hz, 3H); HPLC:>99% ee, Chiralcel IC-3 50×4.6 mm I.D., 3 μm column A: 50% (MeOH:ACN=4:1) (w/0.05% DEA), B: CO₂, 3 mL/min, 220 nm, t$_R$: 0.519 min; LCMS (ESI, M+1): m/z=620.2.

Example 303

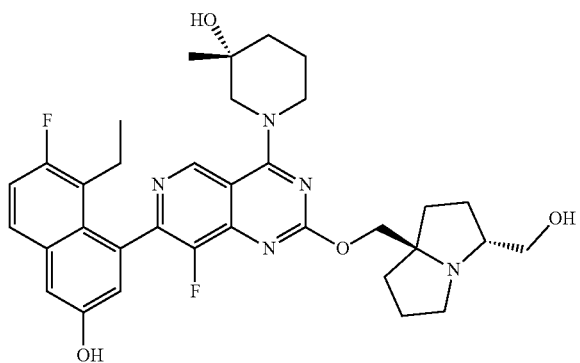 [SMILES: CCc1c(F)ccc2cc(O)cc(-c3ncc4c(N5CCC[C@@](C)(O)C5)nc(OC[C@]56CCCN5[C@@H](CO)CC6)nc4c3F)c12]

(R)-1-(7-(8-ethyl-7-fluoro-3-hydroxynaphthalen-1-yl)-8-fluoro-2-(((3R,7aR)-3-(hydroxymethyl)hexa-hydro-1H-pyrrolizin-7a-yl)methoxy)pyrido[4,3-d]pyrimidin-4-yl)-3-methylpiperidin-3-ol The title compound was synthesized according to the procedure described for example 301. ¹H NMR (400 MHz, methanol-d₄) δ=9.21 (s, 1H), 7.67 (dd, J=6.0, 8.8 Hz, 1H), 7.30 (d, J=2.8 Hz, 1H), 7.25 (t, J=9.6 Hz, 1H), 7.06 (t, J=2.4 Hz, 1H), 4.56 (br d, J=12.8 Hz, 1H), 4.42-4.36 (m, 1H), 4.35-4.26 (m, 2H), 3.85 (dd, J=6.8, 11.2 Hz, 1H), 3.73 (dd, J=6.0, 11.2 Hz, 1H), 3.68-3.55 (m, 1H), 3.51-3.36 (m, 2H), 3.06-2.96 (m, 1H), 2.93-2.81 (m, 1H), 2.55-2.40 (m, 1H), 2.29-2.11 (m, 3H), 2.09-1.97 (m, 1H), 1.95-1.83 (m, 5H), 1.82-1.65 (m, 4H), 1.29 (d, J=10.4 Hz, 3H), 0.87-0.75 (m, 3H); LCMS (ESI, M+1): m/z=620.4.

Example 304

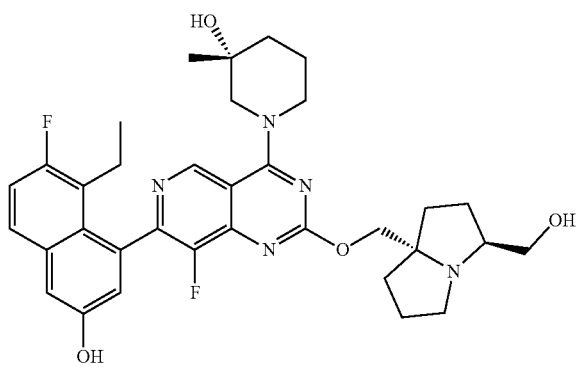 [SMILES: CCc1c(F)ccc2cc(O)cc(-c3ncc4c(N5CCC[C@@](C)(O)C5)nc(OC[C@@]56CCCN5[C@H](CO)CC6)nc4c3F)c12]

(R)-1-(7-(8-ethyl-7-fluoro-3-hydroxynaphthalen-1-yl)-8-fluoro-2-(((3S,7aS)-3-(hydroxymethyl)hexa-hydro-1H-pyrrolizin-7a-yl)methoxy)pyrido[4,3-d]pyrimidin-4-yl)-3-methylpiperidin-3-ol The title compound was synthesized according to the procedure described for example 301. ¹H NMR (400 MHz, methanol-d₄) δ=9.22 (s, 1H), 7.67 (dd, J=6.0, 9.2 Hz, 1H), 7.37-7.18 (m, 2H), 7.06 (s, 1H), 4.61-4.51 (m, 1H), 4.49-4.39 (m, 1H), 4.39-4.24 (m, 2H), 3.88-3.79 (m, 1H), 3.79-3.70 (m, 1H), 3.69-3.56 (m, 1H), 3.52-3.42 (m, 2H), 3.15-3.03 (m, 1H), 3.02-2.86 (m, 11H), 2.57-2.38 (m, 1H), 2.29-2.12 (m, 3H), 2.11-2.02 (m, 1H), 1.99-1.84 (m, 5H), 1.84-1.69 (m, 4H), 1.35-1.25 (m, 3H), 0.90-0.72 (m, J=7.2, 3H); LCMS (ESI, M+1): m/z=620.2.

Example 305

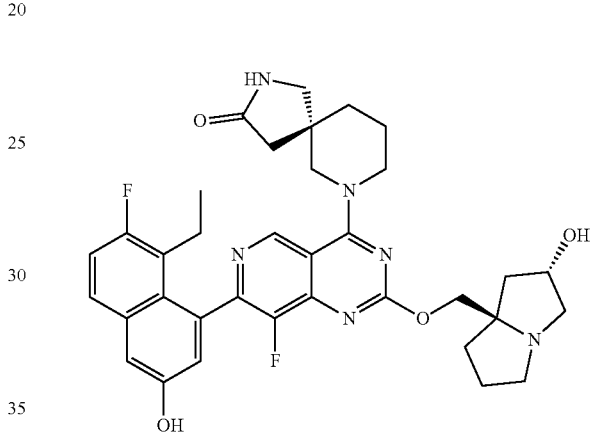

(R)-7-(7-(8-ethyl-7-fluoro-3-hydroxynaphthalen-1-yl)-8-fluoro-2-(((2S,7aR)-2-hydroxytetrahydro-1H-pyrrolizin-7a(5H)-yl)methoxy)pyrido[4,3-d]pyrimidin-4-yl)-2,7-diazaspiro[4.5]decan-3-one The title compound was synthesized according to the procedure described for example 206 except for second eluted peak ((R)-7-(2-(((2S,7aR)-2-((tert-butyldiphenylsilyl)oxy)hexahydro-1H-pyrrolizin-7a-yl)methoxy)-7-chloro-8-fluoropyrido[4,3-d]pyrimidin-4-yl)-2,7-diazaspiro[4.5]decan-3-one) was collected during chiral prep HPLC in step C and carried through steps D, E and F. ¹H NMR (400 MHz, METHANOL-d₄) δ=9.15 (s, H), 7.69 (dd, J=9.2, 6.0 Hz, 1H), 7.32 (d, J=2.4 Hz, 11H), 7.26 (t, J=9.2 Hz, 1H), 7.05 (dd, J=2.8, 4.4 Hz, 1H), 4.74-4.68 (m, 1H), 4.65-4.52 (m, 3H), 4.45-4.29 (m, 1H), 4.10-3.94 (m, 1H), 3.88-3.79 (m, 2H), 3.75-3.60 (m, 2H), 3.41 (d, J=12 Hz, 1H), 3.29 (s, 2H), 2.58-2.19 (m, 10H), 1.97-1.82 (m, 4H), 0.86-0.76 (m, 3H); ¹⁹F NMR (377 MHz, MeOD) δ=121.08, 139.33; LCMS (ESI, M+1): m/z=645.1

Example 306

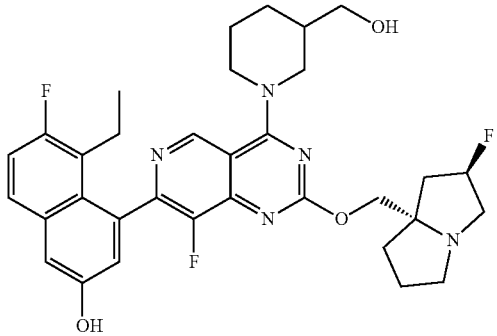 [SMILES: CCc1c(F)ccc2cc(O)cc(-c3ncc4c(N5CCCC(CO)C5)nc(OC[C@@]56CCCN5C[C@H](F)C6)nc4c3F)c12]

5-ethyl-6-fluoro-4-(8-fluoro-2-(((2R,7aS)-2-fluoro-hexahydro-1H-pyrrolizin-7a-yl)methoxy)-4-(3-(hydroxymethyl)piperidin-1-yl)pyrido[4,3-d]pyrimidin-7-yl)naphthalen-2-ol The title compound was synthesized according to the procedure described for example 134. $^1$H NMR (400 MHz, METHANOL-d$_4$): δ=9.08 (s, 1H), 7.67 (dd, J=6.0, 9.2 Hz, 1H), 7.30 (d, J=2.8 Hz, 1H), 7.28-7.22 (m, 1H), 7.06 (s, 1H), 5.41-5.20 (m, 1H), 4.76-4.64 (m, 1H), 4.63-4.50 (m, 1H), 4.37-4.20 (m, 2H), 3.63-3.56 (m, 1H), 3.54-3.44 (m, 2H), 3.38-3.33 (m, 1H), 3.29-3.12 (m, 3H), 3.01 (dt, J=5.6, 9.6 Hz, 1H), 2.51-2.09 (m, 5H), 2.05-1.78 (m, 7H), 1.55-1.41 (m, 1H), 0.81 (t, J=7.6 Hz, 3H); LCMS [ESI, M+1]: m/z=608.3.

Example 307

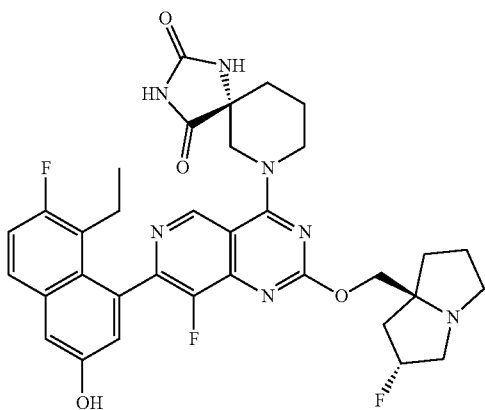 [SMILES: CCc1c(F)ccc2cc(O)cc(-c3ncc4c(N5CCC[C@]6(C5)NC(=O)NC6=O)nc(OC[C@@]56CCCN5C[C@H](F)C6)nc4c3F)c12]

(R)-7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decane-2,4-dione

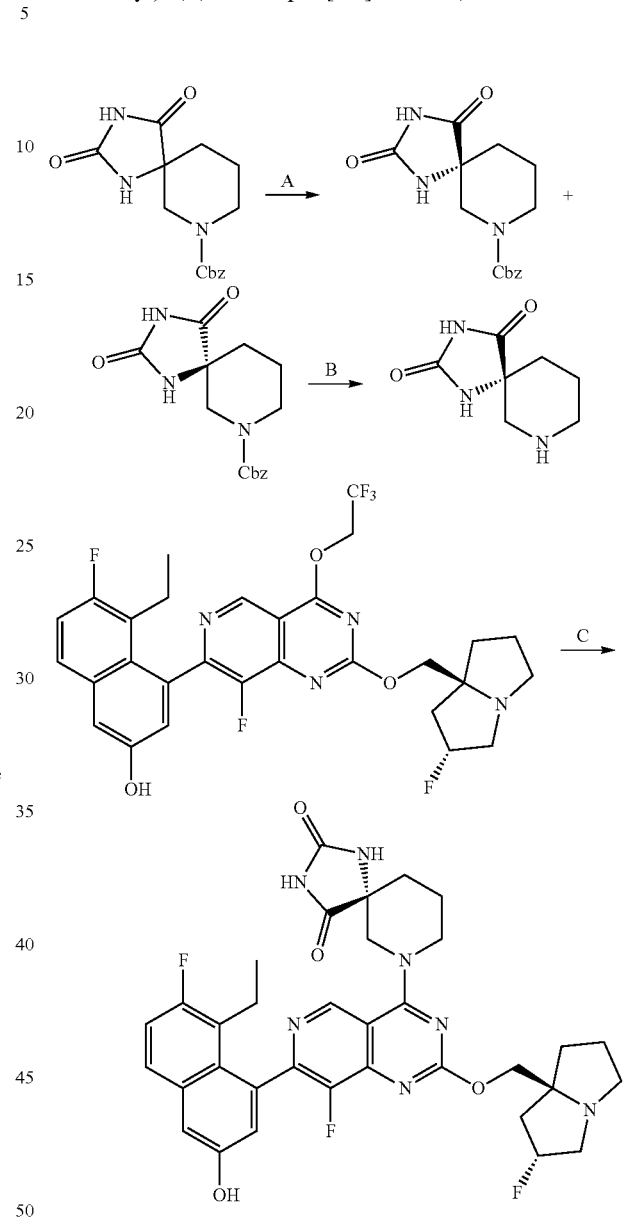

Step A. (R-benzyl 2,4-dioxo-1,3,7-triazaspiro[4.5]decane-7-carboxylate: Enantiomers of benzyl 2,4-dioxo-1,3,7-triazaspiro[4.5]decane-7-carboxylate were separated by chiral SFC [DAICEL CHIRALPAK IG (250 mm*30 mm, 10 um); A: 0.1% NH$_3$×H$_2$O B: MeOH, B %: 45%-45% over 4.3 min; 150 min] to afford the title compound (200 mg, 50% yield) as a yellow liquid; LCMS (ESI, M+1): m/z=304.3.

Step B. (R)-1,3,7-triazaspiro[4.5]decane-2,4-dione: To a solution of benzyl 2-oxo-1,3,9-triazaspiro[4.5]decane-9-carboxylate (200 mg, 1.0 equiv.) in MeOH (10 mL) was added Pd/C (200 mg, 10% purity) under N$_2$. The suspension was degassed in vacuum and purged with H$_2$ several times. The reaction was stirred under H$_2$ (15 psi) at 20° C. for 2 hours. The reaction mixture was filtered and the filtrate was concentrated to afford the title compound (150 mg, 71% yield) as a colorless liquid; LCMS (ESI, M+1): m/z=170.2.

493

Step C. (R)-7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decane-2,4-dione: To a solution of 5-ethyl-6-fluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (80.0 mg, 1.0 equiv.), (R)-1,3,7-triazaspiro[4.5]decane-2,4-dione (45.7 mg, 2.0 equiv.) and 4 Å molecular sieves (10 mg) in DMF (1 mL) was added DIEA (52.3 mg, 3.0 equiv.). The mixture was stirred at 40° C. for 12 hours and then concentrated. The residue was purified by prep-HPLC [column: Phenomenex Gemini-NX C18 75×30 mm×3 μm; mobile phase: water (0.225% formic acid)/ACN] B %: 15%-45%, 7 min] and lyophilized to afford the title compound (49.0 mg, 54.6% yield) as a white solid; $^1$H NMR (400 MHz, methanol-d$_4$) δ=9.14 (d, J=6.4 Hz, 1H), 7.68 (dd, J=6.0, 9.2 Hz, 1H), 7.31 (d, J=2.8 Hz, 1H), 7.26 (t, J=9.6 Hz, 1H), 7.06 (d, J=2.4 Hz, 1H), 5.56-5.31 (m, 1H), 4.64 (br t, J=12.8 Hz, 1H), 4.53-4.36 (m, 3H), 3.90-3.71 (m, 2H), 3.70-3.58 (m, 1H), 3.58-3.45 (m, 2H), 3.28-3.18 (m, 1H), 2.57-2.46 (m, 1H), 2.45-2.33 (m, 2H), 2.33-2.21 (m, 2H), 2.07 (br s, 4H), 2.06-1.90 (m, 3H), 0.90-0.70 (m, 3H); LCMS (ESI, M+1): m/z=662.3.

Example 308

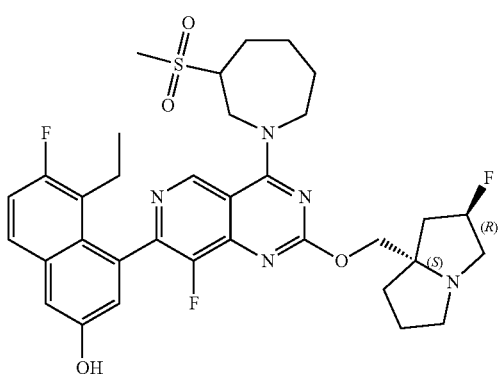

5-ethyl-6-fluoro-4-(8-fluoro-2-(((2R,7aS)-2-fluoro-hexahydro-1H-pyrrolizin-7a-yl)methoxy)-4-(3-(methylsulfonyl)azepan-1-yl)pyrido[4,3-d]pyrimidin-7-yl)naphthalen-2-ol The title compound was synthesized according to the procedure described for example 135. $^1$H NMR (400 MHz, methanol-d$_4$) δ=9.24 (dd, J=2.0, 3.2 Hz, 1H), 7.68 (dd, J=6.0, 9.2 Hz, 1H), 7.33-7.21 (m, 2H), 7.04 (dd, J=2.4, 14.4 Hz, 1H), 5.55-5.28 (m, 1H), 5.05-4.92 (m, 1H), 4.64-4.46 (m, 2H), 4.36-4.23 (m, 1H), 4.21-4.04 (m, 1H), 3.97-3.73 (m, 2H), 3.65-3.39 (m, 3H), 3.25-3.15 (m, 1H), 3.14-3.08 (m, 3H), 2.61-2.41 (m, 2H), 2.40-2.23 (m, 4H), 2.21-1.99 (m, 6H), 1.93-1.80 (m, 1H), 1.56-1.36 (m, 1H), 0.94-0.66 (m, 3H); LCMS (ESI, M+1): m/z=670.3.

494

Example 309

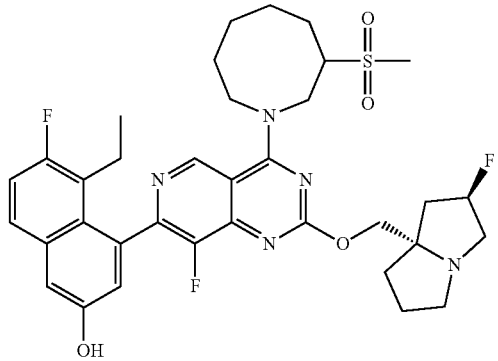 [SMILES: CCc1c(F)ccc2cc(O)cc(-c3ncc4c(N5CCCCCC(S(C)(=O)=O)C5)nc(OC[C@@]56CCCN5C[C@H](F)C6)nc4c3F)c12]

5-ethyl-6-fluoro-4-(8-fluoro-2-(((2R,7aS)-2-fluoro-hexahydro-1H-pyrrolizin-7a-yl)methoxy)-4-(3-(methylsulfonyl)azocan-1-yl)pyrido[4,3-d]pyrimidin-7-yl)naphthalen-2-ol

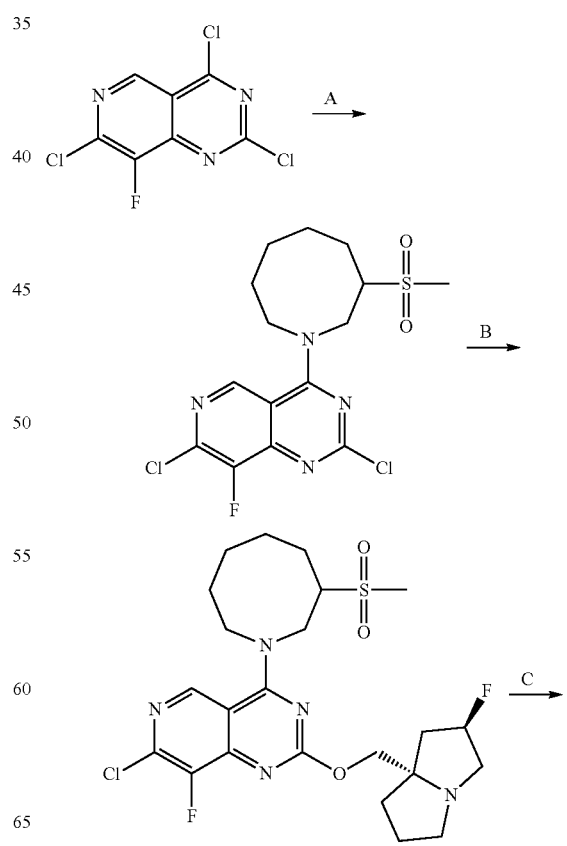

-continued

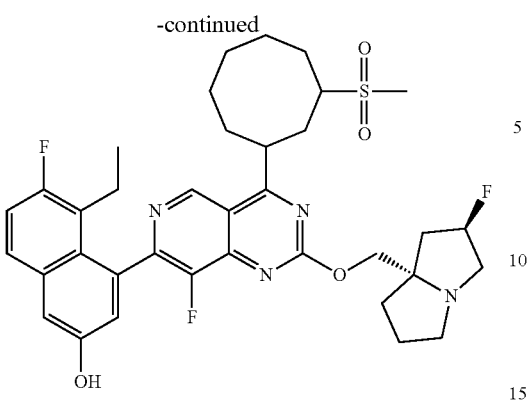

Step A. 2,7-dichloro-8-fluoro-4-(3-(methylsulfonyl)azocan-1-yl)pyrido[4,3-d]pyrimidine: To a solution of 2,4,7-trichloro-8-fluoro-pyrido[4,3-d]pyrimidine (130 mg, 1 equiv.), 3-methylsulfonylazocane (129.00 mg, 1.1 equiv., HCl) in THF (1.5 mL) was added DIEA (333 mg, 5.0 equiv.). The mixture was stirred at −40° C. for 2 hours. The mixture was diluted with water (20 mL) and extracted with EtOAc (3×20 mL). The combined organic layers were dried over anhydrous sodium sulfate, concentrated to afford the title compound (220 mg, crude) as a yellow solid; LCMS (ESI, M+1): m/z=407.0.

Step B. 7-chloro-8-fluoro-2-(((2R,7aS)-2-fluorohexahydro-1H-pyrrolizin-7a-yl)methoxy)-4-(34methylsulfonyl)azocan-1-yl)pyrido[4,3-d]pyrimidine: To a solution of 2,7-dichloro-8-fluoro-4-(3-methylsulfonylazocan-1-yl)pyrido[4,3-d]pyrimidine (210 mg, 1.0 equiv.), ((2R,7aS)-2-fluorohexahydro-1H-pyrrolizin-7a-yl)methanol (164 mg, 2.0 equiv.) and 4 Å MOLECULAR SIEVES (100 mg) in dioxane (1.5 mL) was added DIEA (200 mg, 3.0 equiv.). The reaction was stirred at 95° C. for 12 hours. The mixture was diluted with water (20 mL) and extracted with EtOAc (3×20 mL). The combined organic layers were dried over anhydrous sodium sulfate, concentrated, and purified by reversed phase flash chromatography [C18, water (0.1% formic acid)/ACN] to afford the title compound (90.0 mg, 32.5% yield) as a yellow solid; LCMS (ESI, M+1): m/z=530.1.

Step C. 5-ethyl-6-fluoro-4-(8-fluoro-2-(((2R,7aS)-2-fluorohexahydro-1H-pyrrolizin-7a-yl)methoxy)-4-(3-(methylsulfonyl)azocan-1-yl)pyrido[4,3-d]pyrimidin-7-yl)naphthalen-2-ol: To a solution of 7-chloro-8-fluoro-2-(((2R,7aS)-2-fluorohexahydro-1H-pyrrolizin-7a-yl)methoxy)-4-(3-(methylsulfonyl)azocan-1-yl)pyrido[4,3-d]pyrimidine (80.0 mg, 1.0 equiv.), Cs$_2$CO$_3$ (1.5 M, 302 μL, 3.0 equiv.) and CataCXium A Pd G3 (11.0 mg, 0.1 equiv.) in methoxycyclopentane (1 mL) was added 5-ethyl-6-fluoro-4-(4,4,5,5-tetramethyl-1,3,2-dioxaborolan-2-yl)naphthalen-2-ol (62.0 mg, 1.3 equiv.). The reaction was stirred at 95° C. for 3 hours. The mixture was diluted with water (20 mL) and extracted with EtOAc (3×20 mL). The combined organic layers were dried over anhydrous sodium sulfate, concentrated, and purified by reversed phase flash chromatography [C18, water (0.1% formic acid)/ACN] to give a crude product. The crude product was purified by prep-HPLC [column: Phenomenex Gemini-NX C18 75×30 mm×3 μm; mobile phase: water (0.225% formic acid)/ACN] B %: 18%-48%, 7 min] and lyophilized to afford the title compound (28.4 mg, 26.8% yield,) as a yellow solid; $^1$H NMR (400 MHz, methanol-d$_4$) δ=9.23 (d, J=4.3 Hz, 1H), 7.68 (dd, J=6.0, 9.2 Hz, 1H), 7.34-7.18 (m, 2H), 7.05 (d, J=2.0 Hz, 1H), 5.47-5.25 (m, 1H), 5.19-5.07 (m, 1H), 4.59 (dt, J=4.8, 9.6 Hz, 1H), 4.48-4.32 (m, 2H), 3.96-3.74 (m, 3H), 3.48-3.33 (m, 2H), 3.26 (br s, 1H), 3.15-3.03 (m, 4H), 2.53-2.32 (m, 3H), 2.30-2.21 (m, 1H), 2.20-2.13 (m, 2H), 2.11-1.91 (m, 7H), 1.89-1.68 (m, 2H), 1.57-1.41 (m, 1H), 0.86-0.70 (m, 3H); LCMS (ESI, M+1): m/z=684.3.

Example 310

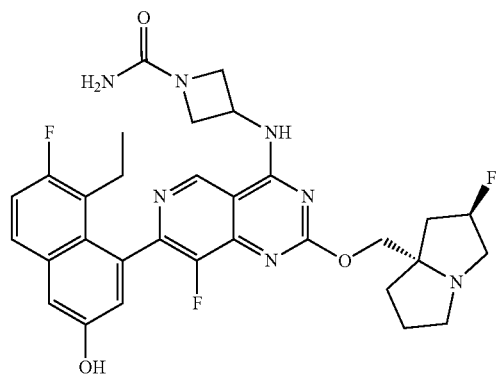 [SMILES: CCc1c(F)ccc2cc(O)cc(-c3ncc4c(NC5CN(C(N)=O)C5)nc(OC[C@@]56CCCN5C[C@H](F)C6)nc4c3F)c12]

3-((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)azetidine-1-carboxamide The title compound was synthesized according to the procedure described for example 135. $^1$H NMR (400 MHz, methanol-d$_4$) δ=9.29 (s, 1H), 8.43 (s, 1H), 7.82-7.63 (m, 1H), 7.44-7.19 (m, 2H), 7.15-6.98 (m, 1H), 5.63-5.38 (m, 1H), 5.02-4.97 (m, 1H), 4.64-4.48 (m, 2H), 4.41 (br t, J=8.0 Hz, 2H), 4.30-4.13 (m, 2H), 3.93-3.60 (m, 3H), 2.74-2.00 (m, 9H), 0.91-0.70 (m, 3H); LCMS (ESI, M+1): m/z=608.2.

Example 311

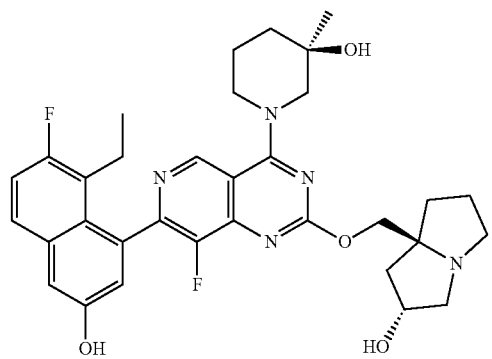 [SMILES: CCc1c(F)ccc2cc(O)cc(-c3ncc4c(N5CCC[C@@](C)(O)C5)nc(OC[C@@]56CCCN5C[C@H](O)C6)nc4c3F)c12]

(2R,7aS)-7a-(((7-(8-ethyl-7-fluoro-3-hydroxynaph-thalen-1-yl)-8-fluoro-4-((R)-3-hydroxy-3-methylpip-eridin-1-yl)pyrido[4,3-d]pyrimidin-2-yl)oxy)methyl) hexahydro-1H-pyrrolizin-2-ol

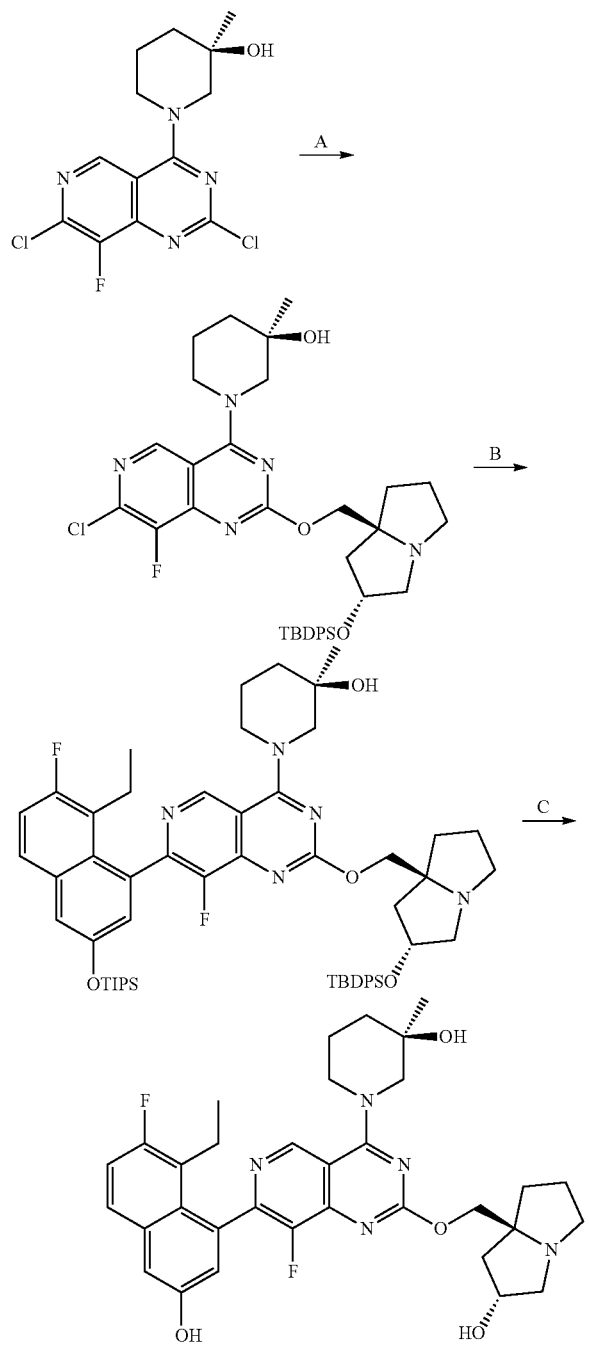

Step A. (R)-1-(2-(((2R,7aS)-2-((tert-butyldiphenylsilyl) oxy)hexahydro-1H-pyrrolizin-7a-yl)methoxyl-7-chloro-8-fluoropyrido[4,3-d]pyrimidin-4-yl)-3-methylpiperidin-3-ol: To a solution of (R)-1-(2,7-dichloro-8-fluoropyrido[4,3-d] pyrimidin-4-yl)-3-methylpiperidin-3-ol (146 mg, 1.0 equiv.) in dioxane (2 mL) were added ((2S,7aR)-2-((tert-butyldi-phenylsilyl)oxy)tetrahydro-1H-pyrrolizin-7a(5H)-yl)metha-nol (209 mg, 1.2 equiv.), DIEA (171 mg, 3.0 equiv.) and 4 Å molecular sieves (15 mg). The reaction was stirred at 90° C. for 16 hours. The mixture was filtered and the filtrate was purified by reversed phase flash chromatography [water (0.1% formic acid)/acetonitrile]. The desired fractions were collected, neutralized with solid NaHCO$_3$ and concentrated in vacuum to remove acetonitrile. Then the mixture was extracted with ethyl acetate (30 mL). The organic phase was washed with brine (30 mL), dried over anhydrous sodium sulfate, filtered and concentrated to afford the title compound (171 mg, 48% yield) as a yellow oil; $^1$H NMR (400 MHz, methanol-d$_4$) δ=8.98 (s, 1H), 7.65-7.65 (m, 1H), 7.65-7.64 (m, 1H), 7.70-7.61 (m, 2H), 7.47-7.30 (m, 6H), 4.64-4.51 (m, 3H), 4.21-4.13 (m, 2H), 3.54-3.47 (m, 1H), 3.27-3.18 (m, 2H), 3.16-3.03 (m, 3H), 2.16-2.04 (m, 4H), 1.92-1.59 (m, 6H), 1.24 (s, 3H), 1.08-1.03 (m, 9H).

Step B. (R)-1(2-(((2R,7aS)-2-((tert-butyldiphenylsilyl) oxy)hexahydro-1H-pyrrolizin-7a-yl)methoxy)-7-(8-ethyl-7-fluoro-3-((triisopropylsilyl)oxy)naphthalen-1-yl)-8-fluoro-pyrido[4,3-d]pyrimidin-4-yl)-3-methylpyridin-3-ol: A mixture of (R)-1-(2-(((2R,7aS)-2-((tert-butyldiphenylsilyl) oxy)hexahydro-1H-pyrrolizin-7a-yl)methoxy)-7-chloro-8-fluoropyrido[4,3-d]pyrimidin-4-yl)-3-methylpiperidin-3-ol (205 mg, 1.0 equiv.), ((5-ethyl-6-fluoro-4-(4,4,5,5-tetram-ethyl-1,3,2-dioxaborolan-2-yl)naphthalen-2-yl)oxy)triiso-propylsilane (168 mg, 1.2 equiv.), K$_3$PO$_4$ (1.5 M in water, 3.0 equiv.) and CataCXium A Pd G3 (21.6 mg, 0.1 equiv.) in methoxycyclopentane (2 mL) was de-gassed and stirred at 90° C. for 2 hours under N$_2$. The mixture was filtered and the filtrate was purified by reversed phase flash chromatography [water (0.1% formic acid)/acetonitrile]. The desired fractions were collected and neutralized with solid NaHCO$_3$, concentrated in vacuum to remove acetonitrile. Then the mixture was diluted with ethyl acetate (20 mL) and water (30 mL), extracted with ethyl acetate (10 mL). The combined organic phase was washed with brine (20 mL), dried over anhydrous sodium sulfate, filtered and concentrated to afford the title compound (160 mg, 54% yield) as a yellow solid; $^1$H NMR (400 MHz, methanol-d$_4$) δ=9.21 (d, J=3.4 Hz, 1H), 7.78-7.72 (m, 1H), 7.69-7.62 (m, 4H), 7.45-7.26 (m, 8H), 7.09 (dd, J=2.4, 5.6 Hz, 1H), 4.61-4.54 (m, 1H), 4.44 (br d, J=13.2 Hz, 1H), 4.28-4.13 (m, 3H), 3.64-3.49 (m, 1H), 3.21-3.12 (m, 3H), 2.87-2.79 (m, 1H), 2.55-2.42 (m, 1H), 2.13 (br d, J=7.6 Hz, 4H), 1.99-1.66 (m, 6H), 1.39-1.30 (m, 3H), 1.29-1.21 (m, 5H), 1.14 (dd, J=2.0, 7.2 Hz, 18H), 1.08-1.04 (m, 9H), 0.81 (t, J=7.2 Hz, 3H); LCMS [ESI, M/2+1]: m/z=501.0.

Step C. (2R,7aS)-7a-(((7-(8-ethyl-7-fluoro-3-hy-droxynaphthalen-1-yl)-8-fluoro-4-((R)-3-hydroxy-3-meth-ylpiperidin-1-yl)pyrido[4,3-d]pyrimidin-2-yl)oxy)methyl) hexahydro-1H-pyrrolizin-2-ol: A solution of (R)-1-(2-(((2R, 7aS)-2-((tert-butyldiphenylsilyl)oxy)hexahydro-1H-pyrrolizin-7a-yl)methoxy)-7-(8-ethyl-7-fluoro-3-((triisopropylsilyl)oxy)naphthalen-1-yl)-8-fluoropyrido[4, 3-d]pyrimidin-4-yl)-3-methylpiperidin-3-ol (120 mg, 1.0 equiv.) and CsF (273 mg, 15 equiv.) in DMF (0.6 mL) was stirred at 18° C. for 7 hrs. The mixture was filtered and the filtrate was purified by reversed phase flash chromatography [water (0.1% formic acid)/acetonitrile]. The desired fractions were collected and lyophilized to afford the title compound (39 mg, 53% yield) as a white solid; $^1$H NMR (400 MHz, CD3OD, 298K) δ=9.24 (s, 1H), 8.54 (br s, 1H), 7.68 (br dd, J=5.6, 8.4 Hz, 1H), 7.31 (br d, J=2.4 Hz, 1H), 7.25 (br t, J=9.2 Hz, 11H), 7.05 (br s, 1H), 4.67-4.56 (m, 2H), 4.54-4.41 (m, 2H), 4.38-4.27 (m, 1H), 3.68-3.41 (m, 5H), 3.17-3.03 (m, 1H), 2.51-2.41 (m, 2H), 2.32-2.16 (m, 5H), 2.11-1.98 (m, 2H), 1.93-1.74 (m, 3H), 1.30 (br d, J=9.2 Hz, 3H), 0.90-0.75 (m, 3H); SFC analysis: Column: Chiralpak AS-3 50×4.6 mm I.D., 3 um; Mobile phase: Phase A for CO$_2$, and Phase B for MEOH (0.05% DEA); Gradient elution: B in A from 5% to 40%; Flow rate: 3 mL/min; Detector: DAD; Column Temp: 35° C.; Back Pressure: 100 Bar; LCMS [EST, M+1]: m/z=606.3.

Example 312

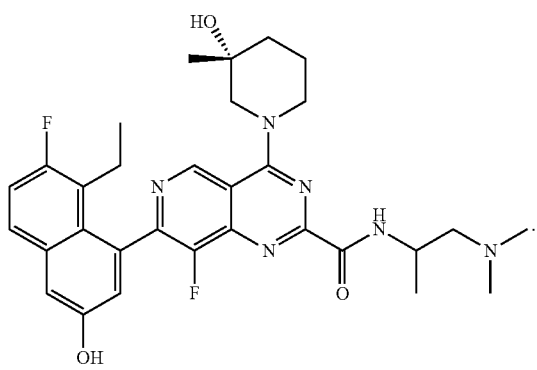 [SMILES: CCc1c(F)ccc2cc(O)cc(-c3ncc4c(N5CCC[C@@](C)(O)C5)nc(C(=O)NC(C)CN(C)C)nc4c3F)c12]

N-(1-(dimethylamino)propan-7.-yl)-7-(R-ethyl-7-fluoro-3-hydroxynaphthalen-1-yl)-8-fluoro-4-((R)-3-hydroxy-3-methylpiperidin-1-yl)pyrido[4,3-d]pyrimidine-2-carboxamide

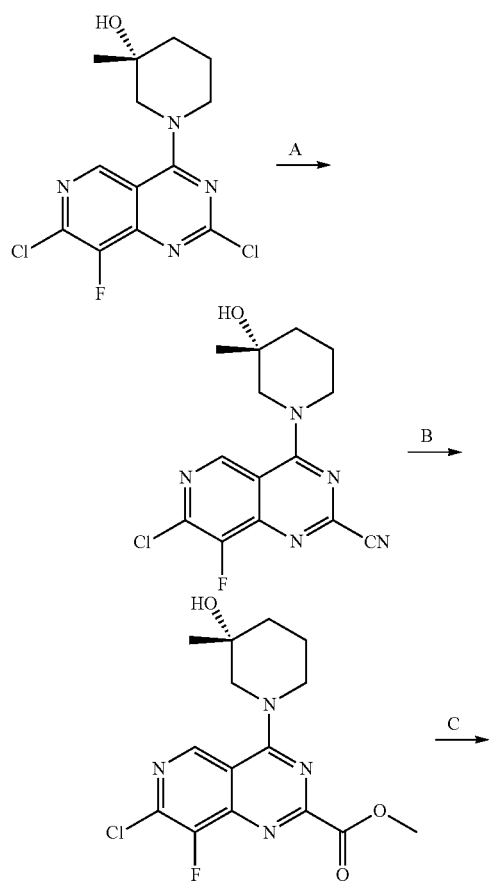

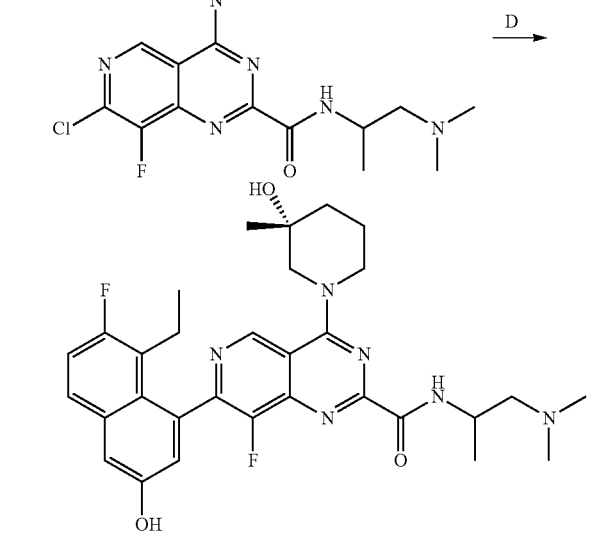

Step A. (R)-7-chloro-8-fluoro-4-(3-hydroxy-3-methylpiperidin-1-yl)pyrido[4,3-d]pyrimidine-2-carbonitrile: To a mixture of (R)-1-(2,7-dichloro-8-fluoropyrido[4,3-d]pyrimidin-4-yl)-3-methylpiperidin-3-ol (800 mg, 1.0 equiv.), NaCN (280 mg, 2.4 equiv.) and DABCO (27.1 mg, 0.1 equiv.) in DMSO (10 mL) was stirred at 60° C. for 12 hours. After reaction completion, the mixture was diluted with ethyl acetate (20 mL) and extracted with water (3×10 mL). The organic layer was washed with brine (20 mL), dried over anhydrous Na$_2$SO$_4$, filtered and concentrated under reduced pressure to give a residue. Te residue was purified by reversed-phase flash chromatography (water (0.1% formic acid)-ACN) to afford the title compound (170 mg, 19% yield) as a black brown oil. LCMS [ESI, M+1]: m/z=322.2.

Step B. (R)-methyl 7-chloro-8-fluoro-4-(3-hydroxy-3-methylpiperidin-1-yl)pyrido[4,3-d]pyrimidine-2-carboxylate: To a solution of (R)-7-chloro-8-fluoro-4-(3-hydroxy-3-methylpiperidin-1-yl)pyrido[4,3-d]pyrimidine-2-carbonitrile (170 mg, 1.0 equiv.) in MeOH (0.5 mL) was added HCl-MeOH (4 M, 5 mL, 37.8 equiv.). The mixture was stirred at 50° C. for 1 hour. After completion, the reaction mixture was concentrated under reduced pressure to give a residue, diluted sat. aq. NaHCO$_3$ to adjust the pH to 9, extracted with ethyl acetate (3×5 mL), dried over anhydrous Na$_2$SO$_4$, filtered and concentrated to afford the title compound (143 mg, crude) as a black brown oil; LCMS [ESI, M+1]: m/z=355.2.

Step C. 7-chloro-N-(1-(dimethylamino)propan-2-yl)-8-fluoro-4-((R)-3-hydroxy-3-methylpiperidin-1-yl)pyrido[4,3-d]pyrimidine-2-carboxamide: To a solution of (R)-methyl 7-chloro-8-fluoro-4-(3-hydroxy-3-methylpiperidin-1-yl)pyrido[4,3-d]pyrimidine-2-carboxylate (135 mg, 1.0 equiv.) in MeOH (0.5 mL) was added N1,N1-dimethylpropane-1,2-diamine (777 mg, 20.0 equiv.). The reaction was stirred at 25° C. for 1 hour. After completion, the reaction mixture was filtered. The filtrate was purified by reversed-phase flash chromatography (water (0.1% formic acid)-ACN) to afford the title compound (33 mg, 20% yield over two steps) as a yellow oil; LCMS [EST, M+1]: m/z=425.2.

Step D. N-(1-(dimethylamino)propan-2-yl)-7-(8-ethyl-7-fluoro-3-hydroxynaphthalen-1-yl)-8-fluoro-4-((R)-3-hydroxy-3-methylpiperidin-1-yl)pyrido[4,3-d]pyrimidine-2-carboxamide: To a mixture of 7-chloro-N-(1-(dimethylamino)propan-2-yl)-8-fluoro-4-((R)-3-hydroxy-3-methylpiperidin-1-yl)pyrido[4,3-d]pyrimidine-2-carboxamide (15.0 mg, 1.0 equiv.), 5-ethyl-6-fluoro-4-(4,4,5,5-tetramethyl-1,3,2-dioxaborolan-2-yl)naphthalen-2-ol (14.5 mg, 1.3 equiv.), $K_3PO_4$ (1.5 M, 70.6 μL, 3.0 equiv.) in methoxycyclopentane (1 mL) was added CataCXium A Pd G3 (2.57 mg, 0.1 equiv.). The reaction was stirred at 90° C. for 2 hours. After reaction completion, the mixture was quenched by water (2 mL) and extracted with ethyl acetate (5 mL). The combined organic layer was dried over anhydrous $Na_2SO_4$, filtered and concentrated under reduced pressure to give a residue. The residue was purified by prep-HPLC (column: Phenomenex Synergi C18 150×25 mm×10 μm; mobile phase: water (0.1% formic acid)/ACN, B %: 9%-39%, 10 min) and lyophilized to afford the title compound (6.75 mg, 33% yield) as a white solid; $^1$H NMR (400 MHz, methanol-$d_4$): δ=9.41 (dd, J=3.2, 4.8 Hz, 1H), 8.53 (s, 1H), 7.70 (dd, J=5.6, 9.2 Hz, 1H), 7.33 (d, J=2.4 Hz, 1H), 7.27 (t, J=9.2 Hz, 1H), 7.11-7.08 (m, 1H), 4.78 (br d, J=13.6 Hz, 1H), 4.44 (br s, 2H), 3.63-3.45 (m, 2H), 3.04-2.92 (m, 1H$_4$), 2.76-2.68 (m, 1H), 2.56 (s, 6H), 2.49-2.37 (m, 1H), 2.28-2.11 (m, 2H), 1.93-1.75 (m, 3H), 1.36-1.29 (m, 6H), 0.84-0.76 (m, 3H); LCMS [ESI, M+1]: m/z=579.4.

Example 313

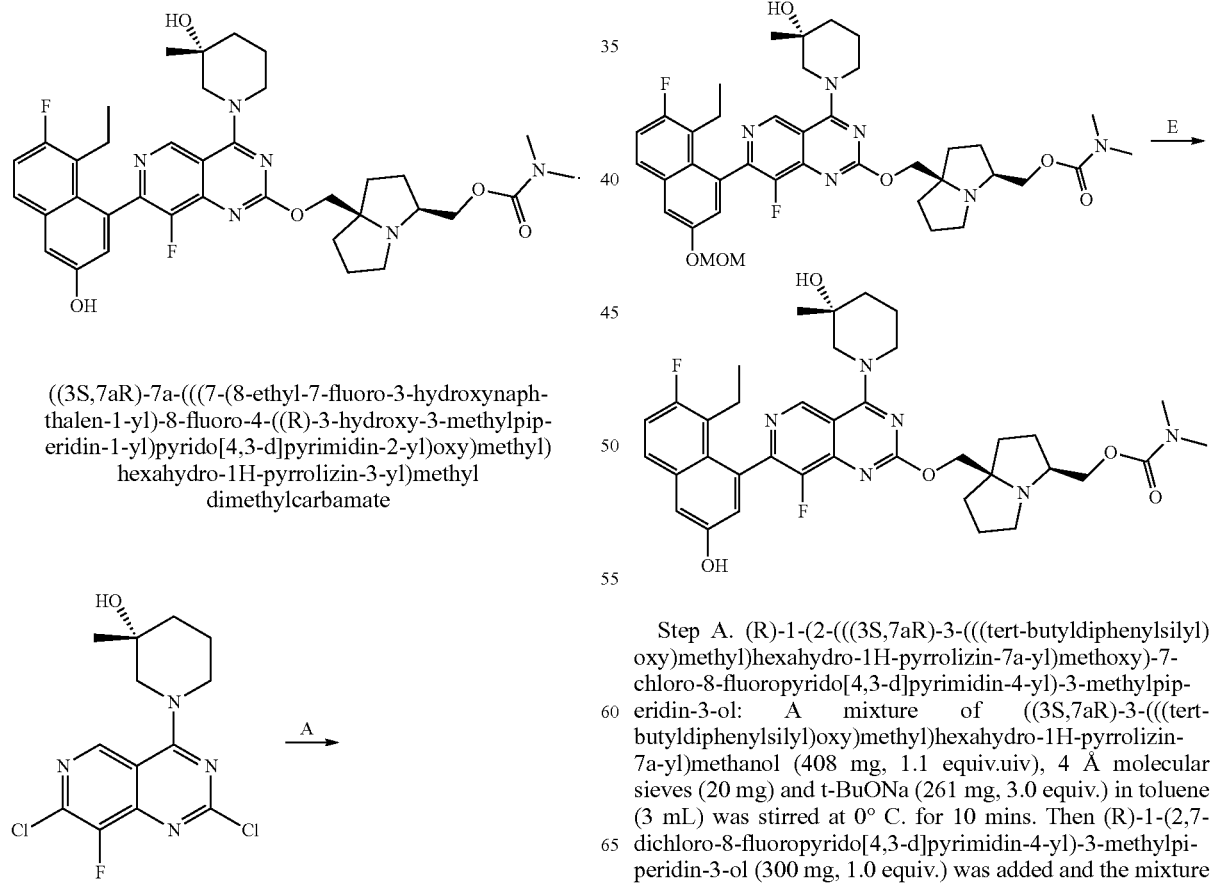

((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl dimethylcarbamate Step A. (R)-1-(2-(((3S,7aR)-3-(((tert-butyldiphenylsilyl)oxy)methyl)hexahydro-1H-pyrrolizin-7a-yl)methoxy)-7-chloro-8-fluoropyrido[4,3-d]pyrimidin-4-yl)-3-methylpiperidin-3-ol: A mixture of ((3S,7aR)-3-(((tert-butyldiphenylsilyl)oxy)methyl)hexahydro-1H-pyrrolizin-7a-yl)methanol (408 mg, 1.1 equiv.uiv), 4 Å molecular sieves (20 mg) and t-BuONa (261 mg, 3.0 equiv.) in toluene (3 mL) was stirred at 0° C. for 10 mins. Then (R)-1-(2,7-dichloro-8-fluoropyrido[4,3-d]pyrimidin-4-yl)-3-methylpiperidin-3-ol (300 mg, 1.0 equiv.) was added and the mixture was stirred at 0° C. for 1 hour. The reaction mixture was quenched by water (40 mL) at 0° C. and extracted with ethyl acetate (3×20 mL). Then the combined organic phase was washed with brine (20 mL), dried over anhydrous sodium sulfate, filtered and concentrated in vacuum. The residue was purified by reversed phase flash chromatography [water (0.1% formic acid)/acetonitrile]. The desired fractions were collected, neutralized with solid NaHCO₃ and concentrated in vacuum to remove acetonitrile. The aqueous layer was extracted with ethyl acetate (3×30 mL). The combined organic layers were dried over anhydrous sodium sulfate and concentrated in vacuum to afford the title compound (484 mg, 66.4% yield) as a black solid; LCMS (ESI, M+1): m/z=704.2.

Step B. (R)-1-(2-(((3S,7aR)-3-(((tert-butyldiphenylsilyl)oxy)methyl)hexahydro-1H-pyrrolizin-7a-yl)methoxy)-7-(8-ethyl-7-fluoro-3-(methoxymethoxy)naphthalen-1-yl)-8-fluoropyrido[4,3-d]pyrimidin-4-yl)-3-methylpiperidin-3-ol: To a solution of (R)-1-(2-(((3S,7aR)-3-(((tert-butyldiphenylsilyl)oxy)methyl)hexahydro-1H-pyrrolizin-7a-yl)methoxy)-7-chloro-8-fluoropyrido[4,3-d]pyrimidin-4-yl)-3-methylpiperidin-3-ol (495 mg, 1.0 equiv.) in methoxycyclopentane (8 mL) was added 2-(8-ethyl-7-fluoro-3-(methoxymethoxy)naphthalen-1-yl)-4,4,5,5-tetramethyl-1,3,2-dioxaborolane (329 mg, 1.3 equiv.), K₃PO₄ (1.5 M in water, 3.0 equiv.) and CataCXium A Pd G3 (51.2 mg, 0.1 equiv.) at 18° C. under N2. The mixture was de-gassed and then heated to 90° C. for 3 hours. The reaction mixture was diluted with ethyl acetate (30 mL) and water (50 mL), the aqueous phase was extracted with ethyl acetate (20 mL). The combined organic phase was washed with brine (20 mL), dried over anhydrous sodium sulfate and concentrated in vacuum to give a residue. The residue was purified by reversed phase flash chromatography [water (0.1% formic acid)/acetonitrile]. The desired fractions were collected, neutralized with solid NaHCO₃ and concentrated in vacuum to remove ACN. Then the mixture was extracted with ethyl acetate (20 mL×2). The combined organic phase was dried over anhydrous sodium sulfate and concentrated to afford the title compound (327 mg, 48.8% yield,) as a yellow solid; LCMS (ESI, M+1): m/z=902.3.

Step C. (R)-1-(7-(8-ethyl-7-fluoro-3-(methoxymethoxy)naphthalen-1-yl)-8-fluoro-2-(((3S,7aR)₃-(hydroxymethyl)hexahydro-1H-pyrrolizin-7a-yl)methoxy)pyrido[4,3-d]pyrimidin-4-yl)-3-methylpiperidin-3-ol: To a solution of (R)-1-(2-(((3S,7aR)-3-(((tert-butyldiphenylsilyl)oxy)methyl)hexahydro-1H-pyrrolizin-7a-yl)methoxy)-7-(8-ethyl-7-fluoro-3-(methoxymethoxy)naphthalen-1-yl)-8-fluoropyrido[4,3-d]pyrimidin-4-yl)-3-methylpiperidin-3-ol (200 mg, 1.0 equiv.) in DMF (2 mL) was added CsF (505 mg, 15 equiv.). The reaction mixture was stirred at 40° C. for 12 hrs. The reaction mixture was diluted with ethyl acetate (15 mL) and water (30 mL), the aqueous phase was extracted with ethyl acetate (10 mL). The combined organic phase was washed with brine (10 mL), dried over anhydrous sodium sulfate, filtered and concentrated in vacuum to give a residue. The residue was purified by reversed phase flash chromatography [water (0.1% formic acid)/acetonitrile]. The desired fractions were collected and neutralized with solid NaHCO₃ and concentrated in vacuum to remove acetonitrile. Then the mixture was diluted with ethyl acetate (20 mL×2), dried over anhydrous sodium sulfate and concentrated to afford the title compound (107 mg, 72.6% yield) as a yellow solid.

Step D. ((3S,7aR)-7a-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yloxy)methyl)hexahydro-1H-pyrrolizin-3-yl)methyl dimethylcarbamate: To a solution of (R)-1-(7-(8-ethyl-7-fluoro-3-(methoxymethoxy)naphthalen-1-yl)-8-fluoro-2-(((3S,7aR)-3-(hydroxymethyl)hexahydro-1H-pyrrolizin-7a-yl)methoxy)pyrido[4,3-d]pyrimidin-4-yl)-3-methylpiperidin-3-ol (107 mg, 1.0 equiv.) in THF (1 mL) was added NaH (12.9 mg, 2.0 equiv.) at 0° C. After stirring at 0° C. for 0.5 hour, N,N-dimethylcarbamoyl chloride (34.7 mg, 2.0 equiv.) in THF (1 mL) was added to the above mixture and the reaction was stirred at 0° C. for 2 hours. The mixture was quenched with water (10 mL) and extracted with ethyl acetate (8 mL×2). The combined organic layers were washed with brine (10 mL), dried over anhydrous sodium sulfate, filtered and concentrated in vacuum to give a residue. The residue was purified by prep-HPLC [column: Water s Xbridge 150×25 mm×5 μm; mobile phase: water (10 mM NH₄HCO₃)/ACN; B %: 56%-86%, 8 min]. The desired fraction was collected and lyophilized to afford the title compound (64 mg, 53.5% yield) as white solid; LCMS (ESI, M+1): m/z=735.5.

Step E. ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl dimethylcarbamate: To a solution of ((3S,7aR)-7a-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl dimethylcarbamate (59 mg, 1.0 equiv.) in ACN (0.2 mL) was added HCl.dioxane (4 M, 20 equiv.) at 0° C. The mixture was stirred at 0° C. for 0.5 hour. The mixture was concentrated in vacuum to give a residue. The residue was purified by reversed phase flash chromatography [water (0.1% formic acid)/acetonitrile]. The desired fractions were collected and neutralized with solid NaHCO₃, and concentrated in vacuum to remove acetonitrile. Then the mixture was diluted with ethyl acetate (20 mL×2), dried over anhydrous sodium sulfate and concentrated in vacuum. Then the residue was purified by SFC (REGIS(S,S)WHELK-O1(250 mm×25 mm, 10 μm); A: [0.1% NH₃H₂O ErOH]; B %: 50%-50%,4.0 min; 30 min). The desired fraction was collected and concentrated in vacuum to afford the title compound (19.9 mg, 16% yield) as a yellow solid; ¹H NMR (400 MHz, METHANOL-d₄) δ=9.18 (s, 1H), 8.55 (s, 1H), 7.62 (dd, J=6.0, 9.0 Hz, 1H), 7.23 (d, J=2.4 Hz, 1H), 7.22 (s, 1H), 7.04 (t, J=2.6 Hz, 1H), 4.59-4.44 (m, 1H), 4.32-4.20 (m, 3H), 4.11-4.02 (m, 1H), 4.00-3.92 (m, 1H), 3.70-3.56 (m, 1H), 3.51-3.43 (m, 1H), 3.10-2.99 (m, 2H), 2.98-2.86 (m, 6H), 2.85-2.77 (m, 1H), 2.55-2.39 (m, 1H), 2.23-2.13 (m, 3H), 2.07-1.99 (m, 1H), 1.98-1.84 (m, 4H), 1.83-1.72 (m, 4H), 1.71-1.62 (m, 1H), 1.29 (d, J=10.8 Hz, 3H), 0.81 (q, J=7.2 Hz, 3H); ¹⁹F NMR (400 MHz, DMSO, 273 K) δ=−122.415, −139.163; HPLC:>99% ee, Chiralcel ID-3 100×4.6 mm I.D., 3 μm column A: 20% (IPA/ACN=4/1) (w/0.05% DEA), B: Heptane (0.05% DEA), 254 nm, t_R: 0.817 min; LCMS [ESI, M+1]: m/z=691.5.

Example 314

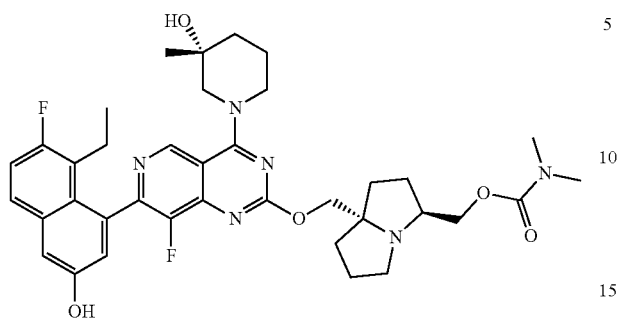

((3S,7aS)-7a-(((7-(8-ethyl-7-fluoro-3-hydroxynaph-thalen-1-yl)-8-fluoro-4-((R)-3-hydroxy-3-methylpip-eridin-1-yl)pyrido[4,3-d]pyrimidin-2-yl)oxy)methyl)hexahydro-1H-pyrrolizin-3-yl)methyl dimethylcarbamate The title compound was synthesized according to the procedure described for example 313. $^1$H NMR (400 MHz, METHANOL-$d_4$) δ=9.24-9.19 (m, 1H), 7.71-7.65 (m, 1H), 7.32-7.29 (m, 1H), 7.28-7.22 (m, 1H), 7.07 (t, J=2.4 Hz, 1H), 4.58-4.51 (m, 1H), 4.42-4.38 (m, 1H), 4.35-4.25 (m, 4H), 3.69-3.59 (m, 1H), 3.52-3.48 (m, 3H), 2.98-2.91 (m, 6H), 2.90-2.82 (m, 1H), 2.55-2.42 (m, 1H), 2.28-2.12 (m, 3H), 2.07-1.98 (m, 1H), 1.94-1.84 (m, 5H), 1.83-1.75 (m, 3H), 1.74-1.65 (m, 1H), 1.29 (d, J=10.0 Hz, 3H), 0.86-0.77 (m, 3H); LCMS (ESI, M+1): m/z=691.5.

Example 315

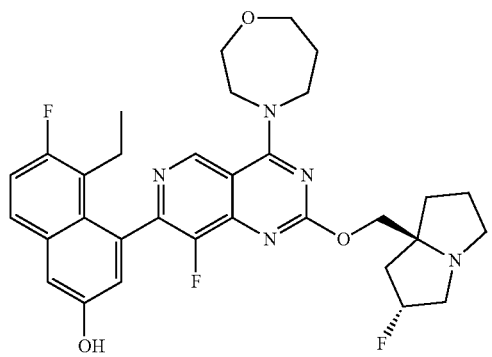 [SMILES: CCc1c(F)ccc2cc(O)cc(-c3ncc4c(N5CCCOCC5)nc(OC[C@@]56CCCN5C[C@H](F)C6)nc4c3F)c12]

5-ethyl-6-fluoro-4-(8-fluoro-2-(((2R,7aS)-2-fluoro-hexahydro-1H-pyrrolizin-7a-yl)methoxy)-4-(1,4-oxazepan-4-yl)pyrido[4,3-d]pyrimidin-7-yl)naphtha-len-2-ol The title compound was synthesized according to the procedure described for example 135. $^1$H NMR (400 MHz, methanol-$d_4$) δ=9.19 (s, 1H), 7.69 (dd, J=6.0, 9.2 Hz, 1H), 7.32 (d, J=2.8 Hz, 1H), 7.26 (t, J=9.6 Hz, 1H), 7.06 (d, J=2.8 Hz, 1H), 5.64-5.42 (m, 1H), 4.67-4.55 (m, 2H), 4.36-4.20 (m, 4H), 4.05 (t, J=4.8 Hz, 2H), 3.98-3.71 (m, 5H), 3.44-3.34 (m, 1H), 2.72-2.50 (m, 2H), 2.50-2.33 (m, 2H), 2.32-2.24 (m, 2H), 2.23-2.05 (m, 4H), 0.80 (dt, J=1.6, 7.6 Hz, 3H); LCMS (ESI, M+1): m/z=594.3.

Example 316

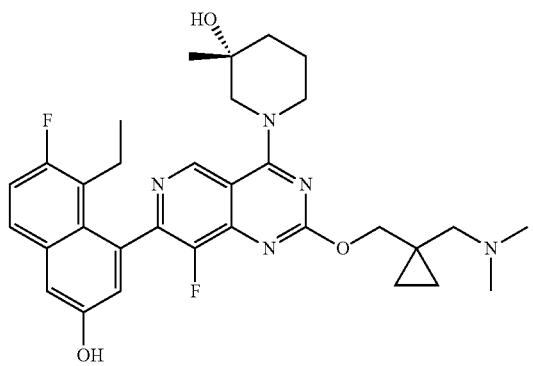 [SMILES: CCc1c(F)ccc2cc(O)cc(-c3ncc4c(N5CCC[C@@](C)(O)C5)nc(OCC5(CN(C)C)CC5)nc4c3F)c12]

(R)-1-(2-((1-((dimethylamino)methyl)cyclopropyl)methoxy)-7-(8-ethyl-7-fluoro-3-hydroxynaphthalen-1-yl)-8-fluoropyrido[4,3-d]pyrimidin-4-yl)-3-meth-ylpiperidin-3-ol

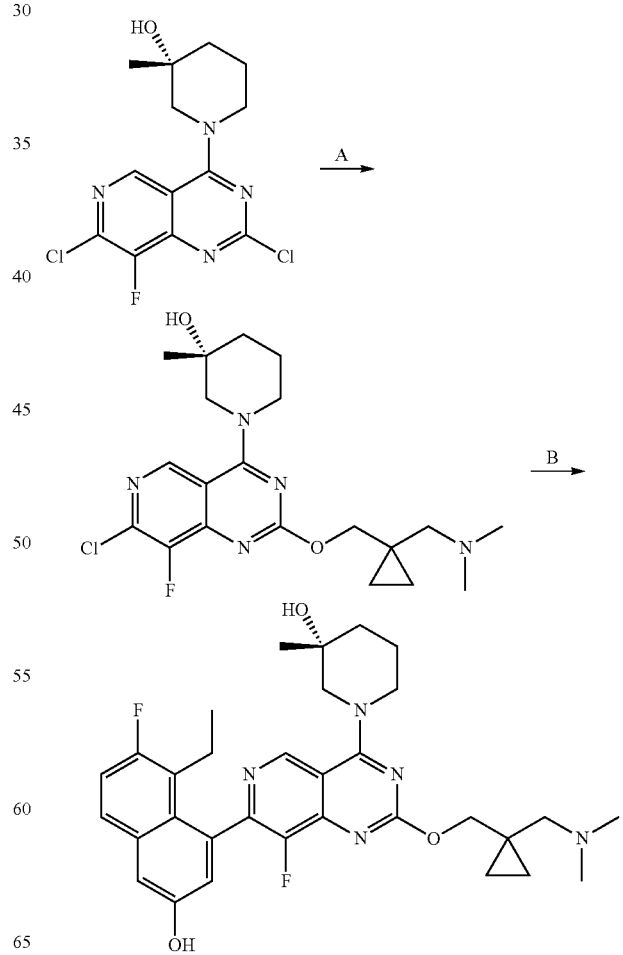

Step A. (R)-1-(7-chloro-2-((1-((dimethylamino)methyl)cyclopropyl)methoxy)-8-fluoropyrido[4,3-d]pyrimidin-4-yl)-3-methylpiperidin-3-ol: To a solution of (R)-1-(2,7-dichloro-8-fluoropyrido[4,3-d]pyrimidin-4-yl)-3-methylpiperidin-3-ol (350 mg, 1.0 equiv.) and (1-((dimethylamino)methyl)cyclopropyl)methanol (205 mg, 1.5 equiv.) in DMF (4 mL) was added DIEA (410 mg, 3.0 equiv.) and 4 Å molecular sieves (110 mg). The mixture was stirred at 40° C. for 12 hours. The mixture was filtered and purified by reversed phase flash chromatography [C18, water (0.1% formic acid)-ACN] to afford the title compound (360 mg, 80% yield) as a yellow solid; LCMS [ESI, M+1]: m/z=424.2.

Step B. (R)-1-(2-((1-((dimethylamino)methyl)cyclopropyl)methoxy)-7-(8-ethyl-7-fluoro-3-hydroxynaphthalen-1-yl)-8-fluoropyrido[4,3-d]pyrimidin-4-yl)-3-methylpiperidin-3-ol: A mixture of (R)-1-(7-chloro-2-((1-((dimethylamino)methyl)cyclopropyl)methoxy)-8-fluoropyrido[4,3-d]pyrimidin-4-yl)-3-methylpiperidin-3-ol (50 mg, 1.0 equiv.), 5-ethyl-6-fluoro-4-(4,4,5,5-tetramethyl-1,3,2-dioxaborolan-2-yl)naphthalen-2-ol (44.7 mg, 1.2 equiv.), $K_3PO_4$ (1.5 M, 236 ILL, 3.0 equiv.) and CataCXium A Pd G3 (8.59 mg, 0.1 equiv.) in methoxycyclopentane (1 mL) was degassed and stirred at 90° C. for 2 hours under N2 atmosphere. The mixture was diluted with water (5 mL) and extracted with ethyl acetate (4×5 mL). The combined organic layers were dried over anhydrous $Na_2SO_4$, concentrated and purified by prep-HPLC [column: Water s Xbridge 150×25 mm×5 μm; mobile phase: water (10 mM $NH_4HCO_3$)/ACN; B %: 44%-74%, 10 min] to afford the title compound (24.6 mg, 36% yield) as a yellow solid; $^1$H NMR (400 MHz, METHANOL-$d_4$) δ=9.21 (s, 1H), 7.69-7.66 (m, 1H), 7.30 (d, J=2.8 Hz, 1H), 7.27-7.22 (m, 1H), 7.05 (d, J=2.4 Hz, 1H), 4.54-4.50 (m, 1H), 4.44-4.34 (m, 2H), 4.27 (t, J=12.8 Hz, 1H), 3.70-3.55 (m, 1H), 3.52-3.40 (m, 1H), 2.62-2.41 (m, 3H), 2.36 (s, 6H), 2.25-2.10 (m, 2H), 1.93-1.71 (m, 3H), 1.29 (d, J=10.4 Hz, 3H), 0.84-0.78 (m, 3H), 0.77-0.72 (m, 2H), 0.63-0.50 (m, 2H); LCMS [ESI, M+1]: m/z=578.4.

Example 317

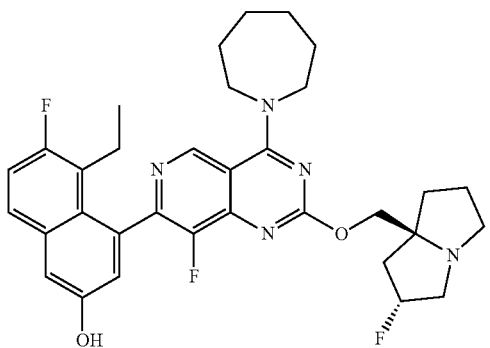 [SMILES: CCc1c(F)ccc2cc(O)cc(-c3ncc4c(N5CCCCCC5)nc(OC[C@@]56CCCN5C[C@H](F)C6)nc4c3F)c12]

4-(4-(azepan-1-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol

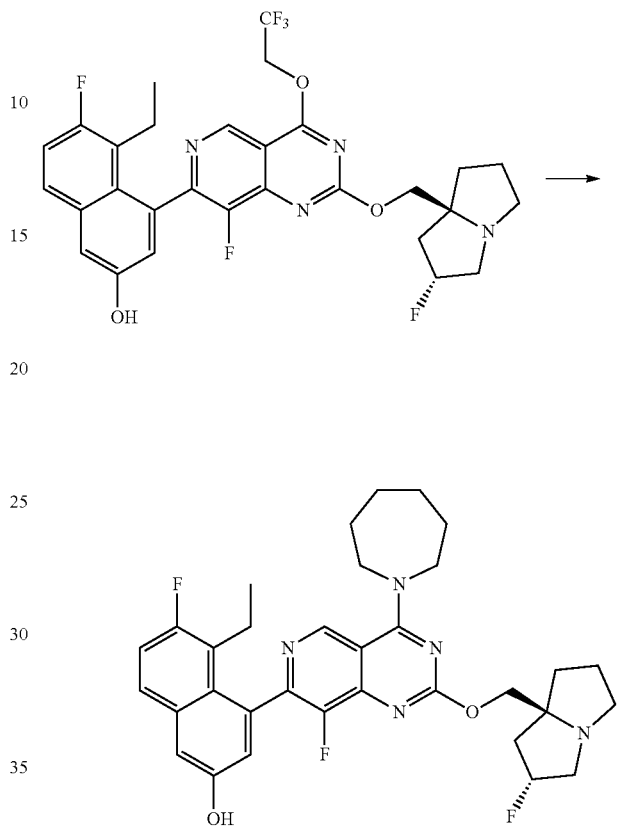

4-(4-(azepan-1-yl)-8-fluoro-2-(((2R,7aS)-2-fluorohexahydro-H-pyrrolizin-7a-yl)methoxy)pyrido[4,3-d]pyrimidin-7-yl)-5-ethyl-6-fluoronaphthalen-2-ol: To a solution of 5-ethyl-6-fluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (100 mg, 1.0 equiv.) and azepane (25.1 mg, 1.5 equiv) in DMF (1 mL) were added DIEA (65.4 mg, 3 equiv.) and 4 Å molecular sieves (30 mg). The mixture was stirred at 40° C. for 12 hours. The mixture was filtered and the filtrated was purified by prep-HPLC [column: Water s Xbridge 150×25 mm×5 μm; mobile phase: [water (10 mM $NH_4HCO_3$)/ACN] B %: 60%-90%, 10 min) to afford the tittle compound (49.1 mg, 47% yield) as a yellow solid; $^1$H NMR (400 MHz, METHANOL-$d_4$)=9.13 (s, H), 7.69-7.65 (m, 1H), 7.30 (d, J=2.6 Hz, 1H), 7.24 (t, J=9.6 Hz, 1H), 7.06 (d, J=2.4 Hz, 1H), 5.40-5.20 (m, 1H), 4.35-4.21 (m, 2H), 4.17-4.03 (m, 4H), 3.30-3.20 (m, 2H), 3.20-3.13 (m, 1H), 3.05-2.95 (m, 1H), 2.52-2.46 (m, 1H), 2.38-2.10 (m, 4H), 2.08-1.95 (m, 6H), 1.93-1.82 (m, 1H), 1.73-1.71 (s, 4H), 0.82-0.78 (m, 3H); LCMS [ESI, M+1]: m/z=592.3.

Example 318

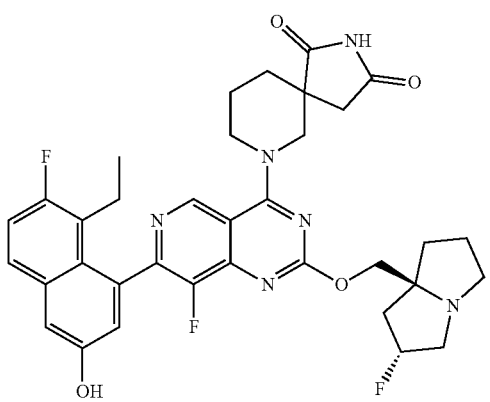 [SMILES: CCc1c(F)ccc2cc(O)cc(-c3ncc4c(N5CCCC6(CC(=O)NC6=O)C5)nc(OC[C@@]56CCCN5C[C@H](F)C6)nc4c3F)c12]

7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decane-1,3-dione The title compound was synthesized according to the procedure described for example 135. $^1$H NMR (400 MHz, METHANOL-$d_4$) δ=9.10 (d, J=1.6 Hz, 1H), 7.68 (dd, J=6.0, 9.2 Hz, 1H), 7.31 (d, J=2.4 Hz, 1H), 7.25 (t, J=9.2 Hz, 1H), 7.06 (dd, J=2.4, 4.8 Hz, 1H), 5.51-5.30 (m, 1H), 4.67-4.59 (m, 1H), 4.52-4.32 (m, 3H), 4.01-3.89 (m, 1H), 3.89-3.77 (m, 1H), 3.64-3.39 (m, 3H), 3.23-3.12 (m, 1H), 2.95 (dd, J=14.4, 18.0 Hz, 1H), 2.67 (d, J=18.0 Hz, 1H), 2.53-2.29 (m, 3H), 2.27-1.79 (m, 9H), 0.87-0.72 (m, 3H); LCMS [ESI, M+1]: m/z=661.4.

Example 319

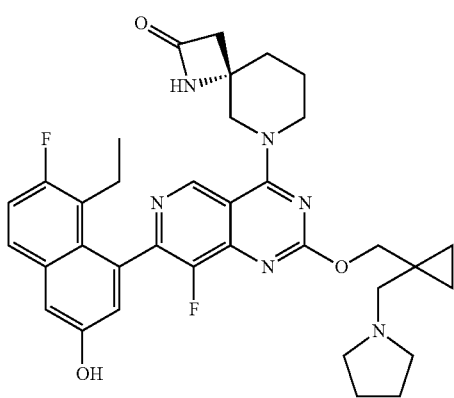 [SMILES: CCc1c(F)ccc2cc(O)cc(-c3ncc4c(N5CCC[C@]6(CC(=O)N6)C5)nc(OCC5(CN6CCCC6)CC5)nc4c3F)c12]

(S)-6-(7-(8-ethyl-7-fluoro-3-hydroxynaphthalen-1-yl)-8-fluoro-2-((1-(pyrrolidin-1-ylmethyl)cyclopropyl)methoxy)pyrido[4,3-d]pyrimidin-4-yl)-1,6-diazaspiro[3.5]nonan-2-one The title compound was synthesized according to the procedure described for example 309 except for K$_3$PO$_4$ was used in step C instead of Cs$_2$CO$_3$. $^1$H NMR (400 MHz, METHANOL-$d_4$) δ=9.07 (s, 1H), 7.69-7.65 (m, 1H), 7.30 (d, J=2.8 Hz, 1H), 7.25 (t, J=12.4 Hz, 1H), 7.06-7.04 (m, 1H), 4.45-4.39 (m, 2H), 4.38-4.21 (m, 2H), 4.02-3.96 (m, 1H), 3.85-3.70 (m, 1H), 2.92-2.86 (m, 1H), 2.76-2.73 (m, 1H), 2.69-2.55 (m, 6H), 2.53-2.38 (m, 1H), 2.23-2.14 (m, 1H), 2.13-2.08 (m, 1H), 2.06-1.99 (m, 1H), 1.98-1.91 (m, 2H), 1.83-1.81 (m, 4H), 0.82-0.77 (m, 3H), 0.74-0.68 (m, 2H), 0.59-0.52 (m, 2H); LCMS [ESI, M+1]: m/z=629.3.

Example 320

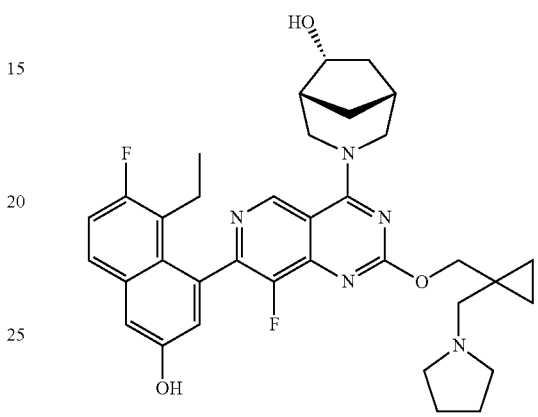

(1R,5R,6R)-3-(7-(8-ethyl-7-fluoro-3-hydroxynaphthalen-1-yl)-8-fluoro-2-((1-(pyrrolidin-1-ylmethyl)cyclopropyl)methoxy)pyrido[4,3-d]pyrimidin-4-yl)-3-azabicyclo[3,2,1]octan-6-ol The title compound was synthesized according to the procedure described for example 309. $^1$H NMR (400 MHz, METHANOL-$d_4$) δ=9.29-9.19 (m, 1H), 8.54 (s, 1H), 7.68 (dd, J=6.0, 8.8 Hz, 1H), 7.30 (d, J=2.4 Hz, 1H), 7.28-7.21 (m, 1H), 7.06 (dd, J=2.4, 15.2 Hz, 1H), 4.98 (br d, J=13.2 Hz, 1H), 4.82-4.68 (m, 1H), 4.51-4.37 (m, 2H), 4.36-4.27 (m, 1H), 3.85-3.71 (m, 1H), 3.55-3.38 (m, 1H), 3.23-2.95 (m, 6H), 2.56-2.35 (m, 2H), 2.31-2.11 (m, 3H), 2.04-1.88 (m, 5H), 1.82 (br s, 1H), 1.37-1.36 (m, 1H), 0.89-0.68 (m, 7H); LCMS [ESI, M+1]: 616.4.

Example 321

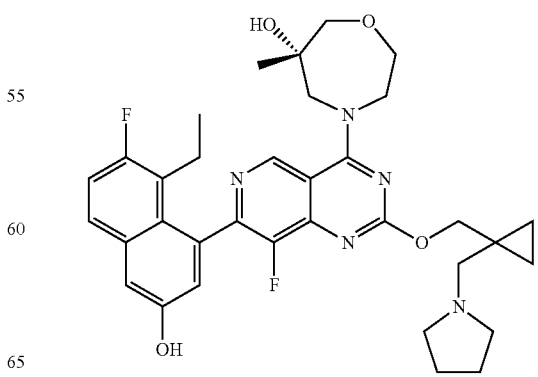

(S)-4-(7-(8-ethyl-7-fluoro-3-hydroxynaphthalen-1-yl)-8-fluoro-2-((1-(pyrrolidin-1-ylmethyl)cyclopropyl)methoxy)pyrido[4,3-d]pyrimidin-4-yl)-6-methyl-1,4-oxazepan-6-ol The title compound was synthesized according to the procedure described for example 309. $^1$H NMR (400 MHz, METHANOL-$d_4$) δ=9.59 (d, J=5.6 Hz, 1H), 7.69 (dd, J=5.6, 9.2 Hz, 1H), 7.32 (d, J=2.0 Hz, 1H), 7.26 (t, J=9.6 Hz, 1H), 7.06 (dd, J=2.4, 14.2 Hz, 1H), 4.63-4.52 (m, 2H), 4.51-4.42 (m, 2H), 4.25-4.15 (m, 1H), 4.07-3.84 (m, 3H), 3.74-3.64 (m, 2H), 3.60-3.42 (m, 3H), 3.35 (s, 3H), 2.55-2.40 (m, 1H), 2.29-2.15 (m, 1H), 2.14-2.04 (m, 4H), 1.28 (d, J=2.0 Hz, 3H), 0.98-0.85 (m, 4H), 0.84-0.76 (m, 3H); LCMS (ESI, M+1): m/z=620.3.

Example 322

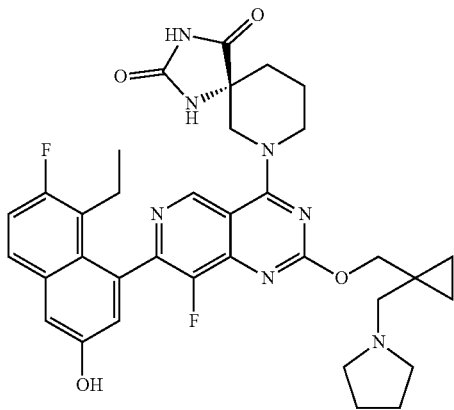 [SMILES: CCc1c(F)ccc2cc(O)cc(-c3ncc4c(N5CCC[C@]6(C5)NC(=O)NC6=O)nc(OCC5(CN6CCCC6)CC5)nc4c3F)c12]

(R)-7-(7-(8-ethyl-7-fluoro-3-hydroxynaphthalen-1-yl)-8-fluoro-2-((1-(pyrrolidin-1-ylmethyl)cyclopropyl)methoxy)pyrido[4,3-d]pyrimidin-4-yl)-1,3,7-triazaspiro[4.5]decane-2,4-dione

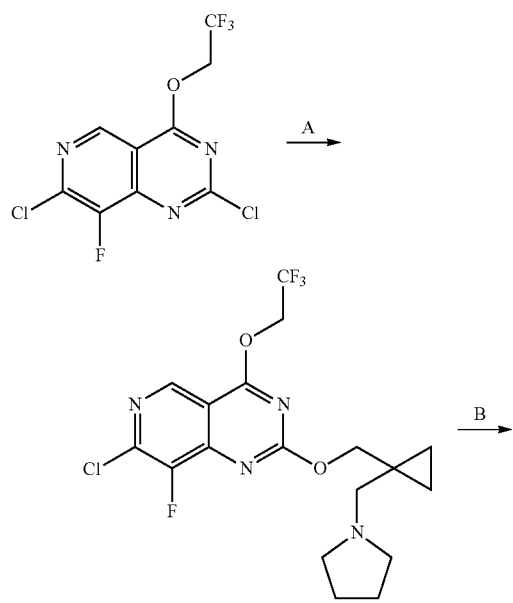

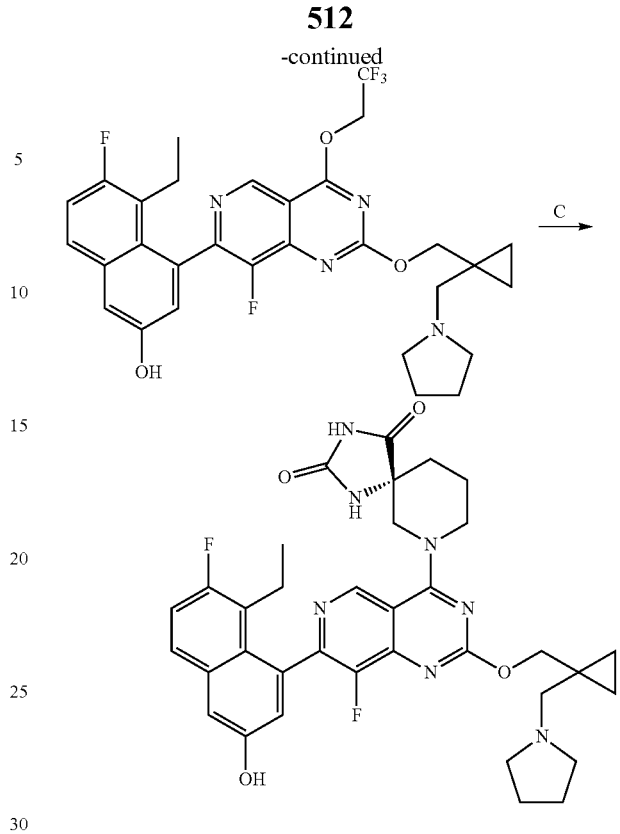

Step A. 7-chloro-8-fluoro-2-((1-(pyrrolidin-1-yl)methyl)cyclopropyl)methoxy)-4-(2,2,2-trifluoroethoxy)pyrido[4,3-d]pyrimidine: To a suspension of 2,7-dichloro-8-fluoro-4-(2,2,2-trifluoroethoxy)pyrido[4,3-d]pyrimidine (3.00 g, 1.0 equiv.) and 4 Å molecular sieves (3.0 g) in THF (600 mL) was added a solution of [1-(pyrrolidin-1-ylmethyl)cyclopropyl]methanol (1.47 g, 1.0 equiv.) and DIEA (3.68 g, 3.0 equiv.) in THF (120 mL) at 0° C. The mixture was stirred at 0° C. for 1 hour, then 20° C. for 2 hours. The mixture was quenched by addition of brine (200 mL) and extracted with ethyl acetate (3×100 mL). The combined organic layers were dried over anhydrous sodium sulfate, concentrated and purified by reversed phase flash chromatography [C18, water (0.1% formic acid)/ACN] to afford the title compound (260 mg, 12% yield) as a yellow solid; LCMS (ESI, M+1): m/z=435.0.

Step B. 5-ethyl-6-fluoro-4-(8-fluoro-2-((1-(pyrrolidin-1-yl)methyl)cyclopropyl)methoxy)-4-(2,2,2-trifluoroethoxy)pyrido[4,3-d]pyrimidin-7-yl)naphthalen-2-ol: To a mixture of 7-chloro-8-fluoro-2-[[1-(pyrrolidin-1-ylmethyl)cyclopropyl]methoxy]-4-(2,2,2-trifluoroethoxy)pyrido[4,3-d]pyrimidine (200 mg, 1.0 equiv.), 5-ethyl-6-fluoro-4-(4,4,5,5-tetramethyl-1,3,2-dioxaborolan-2-yl)naphthalen-2-ol (218 mg, 1.5 equiv.) and Cs$_2$CO$_3$ (1.5 M, 920 µL, 3.0 equiv.) in methoxycyclopentane (3 mL) was added CataCXium A Pd G3 (33.5 mg, 0.10 equiv.). The reaction mixture was stirred at 90° C. for 3 hours. The mixture was diluted with water (10 mL) and extracted with ethyl acetate (3×10 mL). The combined organic layers were dried over anhydrous sodium sulfate, concentrated and purified by reversed phase flash chromatography [C18, water (0.1% formic acid)/ACN] to afford the title compound (160 mg, 57% yield) as a yellow solid; LCMS (ESI, M+1): m/z=589.2.

Step C. (R)-7-(7-(8-ethyl-7-fluoro-3-hydroxynaphthalen-1-yl)-8-fluoro-2-((1-(pyrrolidin-1-yl)methyl)cyclopropyl)methoxy)pyrido[4,3-d]pyrimidin-4-yl)-1,3,7-triazaspiro

[4.5]decane-2,4-dione: To a solution of 5-ethyl-6-fluoro-4-[8-fluoro-2-[[1-(pyrrolidin-1-ylmethyl)cyclopropyl]methoxy]-4-(2,2,2-trifluoroethoxy)pyrido[4,3-d]pyrimidin-7-yl]naphthalen-2-ol (100 mg, 1.0 equiv.), (5R)-1,3,9-triazaspiro[4.5]decane-2,4-dione (57.5 mg, 2.0 equiv.) and 4 Å molecular sieves (10 mg) in DMF (1 mL) was added DIEA (110 mg, 5.0 equiv.). The reaction was stirred at 40° C. for 12 hours. The residue was filtered and washed with DMF (1 mL), and purified by prep-HPLC [column: Phenomenex C18 75×30 mm×3 μm; mobile phase: water (0.1% formic acid)/ACN; B %: 15%-45%, 7 min] and lyophilized to afford the title compound (47.9 mg, 43% yield) as a yellow solid; $^1$H NMR (400 MHz, methanol-$d_4$) δ=9.14 (d, J=10.0 Hz, 1H), 7.69 (dd, J=6.0, 8.4 Hz, 1H), 7.32 (t, J=2.0 Hz, 1H), 7.26 (t, J=9.6 Hz, 1H), 7.06 (dd, J=2.8, 7.2 Hz, 1H), 4.60 (br t, J=14.2 Hz, 3H), 4.50-4.29 (m, 3H), 3.91-3.80 (m, 1H), 3.80-3.56 (m, 1H), 3.30-3.25 (m, 2H), 3.20 (s, 2H), 2.57-2.29 (m, 1H), 2.29-2.10 (m, 2H), 2.10-1.98 (m, 5H), 1.97 (br d, J=3.6 Hz, 2H), 0.95-0.84 (m, 2H), 0.83-0.69 (m, 5H); LCMS (ESI, M+1): m/z=658.3.

Example 323

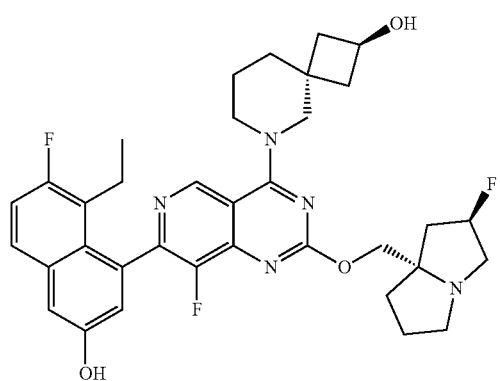 [SMILES: CCc1c(F)ccc2cc(O)cc(-c3ncc4c(N5CCC[C@]6(C5)C[C@H](O)C6)nc(OC[C@@]56CCCN5C[C@H](F)C6)nc4c3F)c12]

trans-(2R,4r)-6-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azaspiro[3.5]nonan-2-ol

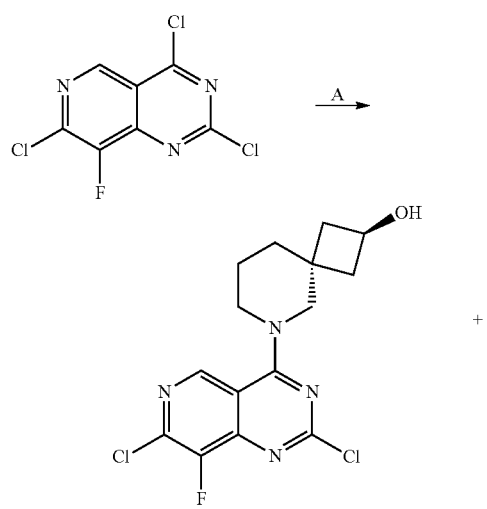

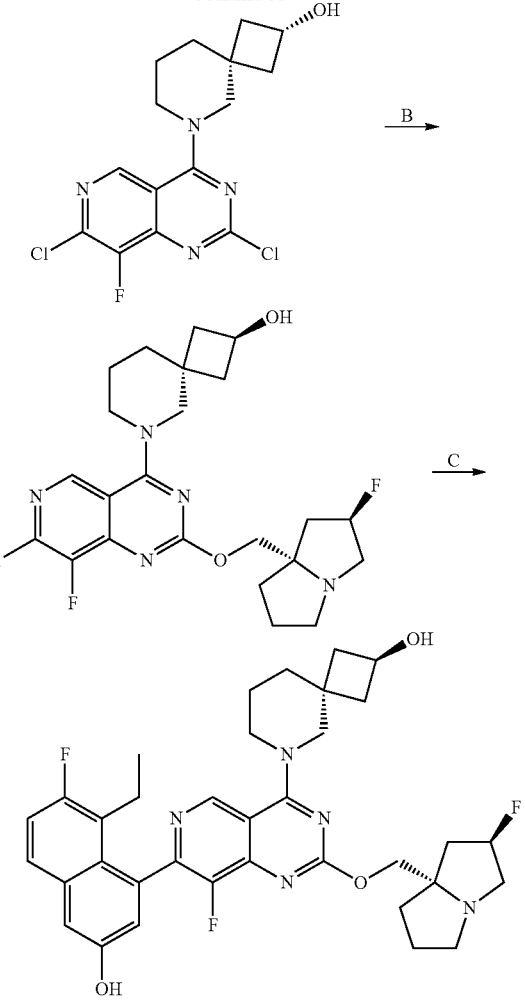

Step A. 6-(2,7-dichloro-8-fluoro-pyrido[4,3-d]pyrimidin-4-yl)-6-azaspiro[3.5]nonan-2-ol: To a solution of 2,4,7-trichloro-8-fluoro-pyrido[4,3-d]pyrimidine (2.0 g, 1.0 equiv.) in DCM (50 mL) was added DIEA (5.12 g, 6.90 mL, 5.0 equiv.) and 6-azaspiro[3.5]nonan-2-ol (1.13 g, 0.8 equiv., HCl). The reaction was stirred at −40° C. for 0.5 hour. The mixture was diluted with water (20 mL) and the layers were separated. The aqueous phase was extracted with ethyl acetate (2×10 mL). Combined the organic layers were dried over anhydrous $Na_2SO_4$ and concentrated. The residue was purified by silica gel chromatography (petroleum ether/ethyl acetate 50:1 to 1:1). The product was further purified by chiral SFC separation (DAICEL CHIRALPAK AY-H (250 mm×30 mm, 10 μm); mobile phase: [0.1% NH3·H2O EtOH]; B %: 60%-60%, 8.5; 80 min) to afford (2s,4r)-6-(2,7-dichloro-8-fluoropyrido[4,3-d]pyrimidin-4-yl)-6-azaspiro[3.5]nonan-2-ol (trans product) as the first eluting peak (650 mg) as a yellow solid; $^1$H NMR (400 MHz, dimethylsulfoxide-d6) δ 8.98 (s, 1H), 5.07-4.99 (d, J=6.2 Hz, 1H), 4.16-4.05 (m, 1H), 3.87-3.94 (m, 4H), 2.20-2.10 (m, 2H), 1.74-1.62 (m, 4H), 1.58-1.50 (m, 2H); LCMS [ESI, M+1]: 357.0. The product was purified by SFC separation (DAICEL CHIRALPAK AY-H (250 mm×30 mm, 10 μm); mobile phase: [0.1% NH3·H2O EtOH]; B %: 60%-60%, 8.5; 80 min) to afford the (2r,4s)-6-(2,7-dichloro-8-fluoropyrido[4,3-d]pyrimidin-4-yl)-6-azaspiro[3.5]nonan-2-ol, (cis product) as the second eluting peak (650 mg) as a yellow solid; ¹H NMR (400 MHz, dimethylsulfoxide-d6) δ 9.03 (s, 1H), 4.97 (d, J=6.4 Hz, 1H), 4.12-4.02 (m, 1H), 3.94 (s, 2H), 3.90-3.85 (m, 2H), 2.08-1.99 (m, 2H), 1.74-1.67 (br s, 4H), 1.65-1.59 (m, 2H); LCMS [ESI, M+1]: m/z=357.1.

Step B. (2R,4r)-6-(7-chloro-8-fluoro-2-(((2R,7aS)-2-fluorotetrahydro-1H-pyrrolizin-7a(5H)-yl)methoxy)pyrido[4,3-d]pyrimidin-4-yl)-6-azaspiro[3.5]nonan-2-ol: To a solution of (2s,4r)-6-(2,7-dichloro-8-fluoro-pyrido[4,3-d]pyrimidin-4-yl)-6-azaspiro[3.5]nonan-2-ol (100 mg, 1.0 equiv.) in dioxane (2.0 mL) was added DIEA (108 mg, 146 μL, 3.0 equiv.) and ((2R,7aS)-2-fluorohexahydro-1H-pyrrolizin-7a-yl)methanol (66.8 mg, 1.5 equiv.). The reaction was stirred at 90° C. for 16 hours. The mixture was concentrated in vacuum. The residue was purified by reversed phase flash chromatography [water (0.1% formic acid)/acetonitrile]. The desired fractions were collected and neutralized with solid NaHCO₃, concentrated in vacuum to remove ACN. The aqueous phase was extracted with ethyl acetate (2×6.0 mL). The combined organic phase was dried with anhydrous Na₂SO₄, filtered and concentrated in vacuum to afford the title compound (100 mg, 71% yield) as a yellow solid; ¹H NMR (400 MHz, chloroform-d) δ 8.73 (s, 1H), 5.44-5.21 (m, 1H), 4.43 (quin, J=7.2 Hz, 1H), 4.38-4.27 (m, 2H), 3.86-3.80 (m, 4H), 3.48-3.21 (m, 3H), 3.08-2.97 (m, 1H), 2.38-2.27 (m, 4H), 2.26-2.19 (m, 2H), 2.03-1.94 (m, 3H), 1.81-1.72 (m, 5H); LCMS [ESI, M+1]: m/z=480.3.

Step C. trans-(2R,4r)-6-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azaspiro[3.5]nonan-2-ol: A mixture of (2R,4r)-6-(7-chloro-8-fluoro-2-(((2R,7aS)-2-fluorotetrahydro-1H-pyrrolizin-7a(5H)-yl)methoxy)pyrido[4,3-d]pyrimidin-4-yl)-6-azaspiro[3.5]nonan-2-ol (60 mg, 1.0 equiv.), 5-ethyl-6-fluoro-4-(4,4,5,5-tetramethyl-1,3,2-dioxaborolan-2-yl)naphthalen-2-ol (47.4 mg, 1.2 equiv.), K₃PO₄ (1.5 M, 250 μL, 3.0 equiv.) and cataCXium-A-Pd-G3 (9.10 mg, 0.1 equiv.) in THF (1.5 mL) was degassed and purged with N2 for 3 times, and then the reaction was stirred at 60° C. for 2 hours under N2 atmosphere. The mixture was diluted with water (2.0 mL) and extracted with ethyl acetate (3×2.0 mL). The combined organic layers were dried over anhydrous Na₂SO₄ and concentrated. The residue was purified by reversed phase flash chromatography [water (0.1% formic acid)/acetonitrile]. The desired fractions were collected and concentrated in vacuum to remove ACN. The aqueous layers was lyophilized. The residue was purified by prep-HPLC [Unisil 3-100 C18 Ultra 150×50 mm×3 μm; mobile phase: water (0.1% formic acid)/ACN, B %: 14%-44% over 15 min]. The desired fractions were collected and lyophilized to afford the title compound (9.89 mg, 11% yield, 0.62FORMIC ACID) as a white solid; ¹H NMR (400 MHz, methanol-d₄) δ 9.07 (s, 11H), 7.72-7.72 (m, 1H), 7.31 (d, J=2.8 Hz, 1H), 7.29-7.22 (m, 1H), 7.07 (d, J=2.4 Hz, 11H), 5.49-5.30 (m, 1H), 4.49-4.43 (m, 1H), 4.42-4.37 (m, 11H), 4.32-4.24 (m, 1H), 4.18-4.08 (m, 2H), 4.03-3.86 (m, 2H), 3.59-3.38 (m, 3H), 3.21-3.10 (m, 1H), 2.53-2.46 (m, 1H), 2.44-2.29 (m, 3H), 2.28-2.19 (m, 2H), 2.18-2.07 (m, 3H), 2.05-1.95 (m, 1H), 1.86-1.78 (m, 4H), 1.74-1.65 (m, 2H), 0.84-0.77 (m, 3H); LCMS [ESI, M+1]: m/z=634.4.

Example 324

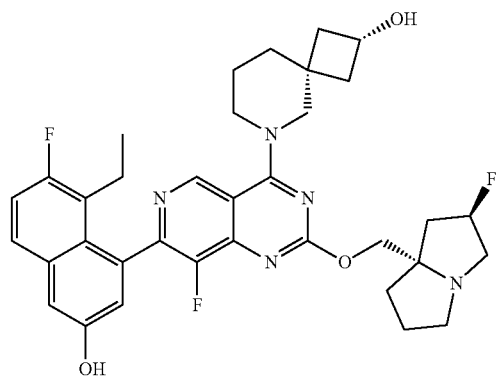 [SMILES: CCc1c(F)ccc2cc(O)cc(-c3ncc4c(N5CCC[C@]6(C5)C[C@@H](O)C6)nc(OC[C@@]56CCCN5C[C@H](F)C6)nc4c3F)c12]

cis-(2S,4s)-6-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azaspiro[3.5]nonan-2-ol The title compound was synthesized according to the procedure described for example 323 except using second eluting peak from chiral SFC separation (step A) in further steps B and C. ¹H NMR (400 MHz, methanol-d₄) δ=9.06 (s, 1H), 7.67 (dd, J=5.6, 8.8 Hz, 1H), 7.30 (d, J=2.4 Hz, 11H), 7.25 (t, J=9.2 Hz, 1H), 7.07 (d, J=2.4 Hz, 1H), 5.40-5.22 (m, 1H), 4.36-4.20 (m, 3H), 4.12-3.91 (m, 4H), 3.30-3.11 (m, 3H), 3.06-2.96 (m, 1H), 2.55-2.42 (m, 1H), 2.38-2.11 (m, 6H), 2.04-1.88 (m, 3H), 1.86-1.72 (m, 6H), 0.81 (br t, J=6.4 Hz, 3H); ¹⁹F NMR (376 MHz, methanol-d₄) δ=−121.085, −138.973, −173.678; SFC: >99% ee, Chiralpak IF-3 50×4.6 mm I.D., 3 μm column, A: CO₂, B: 30% MeOH (w/0.05% DEA), 3 mL/min, 220 nm, ta: 3.449 min; LCMS (ESI, M+1): m/z=634.3.

Example 325

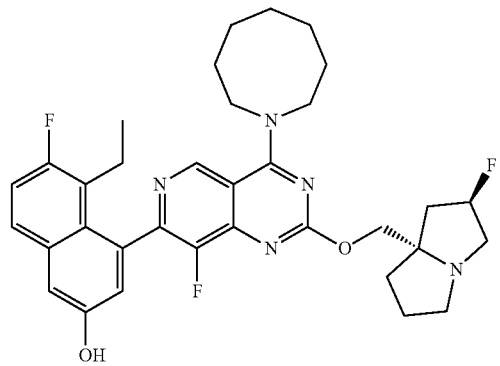 [SMILES: CCc1c(F)ccc2cc(O)cc(-c3ncc4c(N5CCCCCCC5)nc(OC[C@@]56CCCN5C[C@H](F)C6)nc4c3F)c12]

4-(4-(azocan-1-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 135. ¹H NMR (400 MHz, DMSO-d₆) δ=9.96-9.90 (m, 1H), 9.16-9.08 (m, 11H), 7.76

(dd, J=6.0, 9.1 Hz, 1H), 7.39-7.29 (m, 2H), 7.03 (d, J=2.4 Hz, 1H), 5.42-5.18 (m, 1H), 4.23-3.95 (m, 6H), 3.18-3.01 (m, 3H), 2.90-2.80 (m, 1H), 2.43-2.34 (m, 1H), 2.21-2.05 (m, 3H), 2.04-1.85 (m, 6H), 1.84-1.75 (m, 2H), 1.62 (br d, J=5.2 Hz, 4H), 1.57-1.47 (m, 2H), 0.77-0.67 (m, 3H); LCMS (ESI, M+1): m/z=606.4.

Example 326

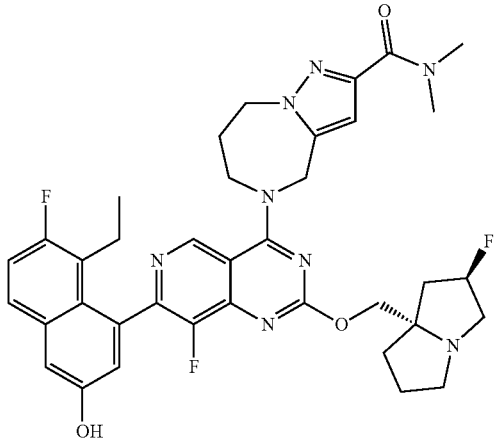 [SMILES: CCc1c(F)ccc2cc(O)cc(-c3ncc4c(N5CCCn6nc(C(=O)N(C)C)cc6C5)nc(OC[C@@]56CCCN5C[C@H](F)C6)nc4c3F)c12]

5-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-N,N-dimethyl-5,6,7,8-tetrahydro-4H-pyrazolo[1,5-a][1,4]diazepine-2-carboxamide The title compound was synthesized according to the procedure described for example 135. ¹H NMR (400 MHz, methanol-d₄) δ=9.21 (s, 1H), 7.68 (dd, J=5.6, 9.2 Hz, 1H), 7.31 (d, J=2.8 Hz, 1H), 7.25 (t, J=9.6 Hz, 1H), 7.05 (d, J=2.8 Hz, 1H), 6.76 (s, 1H), 5.50-5.19 (m, 3H), 4.66-4.52 (m, 4H), 4.52-4.33 (m, 4H), 3.52-3.43 (m, 2H), 3.34 (s, 3H), 3.23-3.13 (m, 1H), 3.08 (s, 3H), 2.52-2.42 (m, 3H), 2.36 (br dd, J=9.2, 14.0 Hz, 1H), 2.31-2.21 (m, 1H), 2.20-2.07 (m, 3H), 2.06-1.93 (m, 1H), 0.90-0.67 (m, 3H); LCMS (ESI, M+1): m/z=701.3.

Example 327

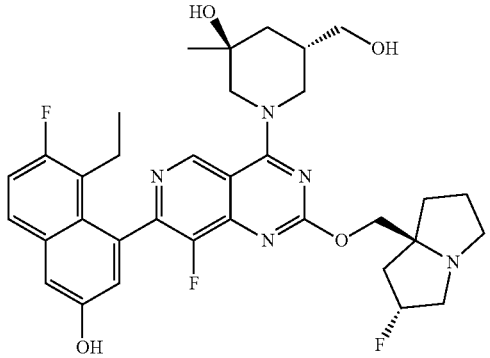 [SMILES: CCc1c(F)ccc2cc(O)cc(-c3ncc4c(N5C[C@@H](CO)C[C@](C)(O)C5)nc(OC[C@@]56CCCN5C[C@H](F)C6)nc4c3F)c12]

(3RS,5RS)-1-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-5-(hydroxymethyl)-3-methylpiperidin-3-ol

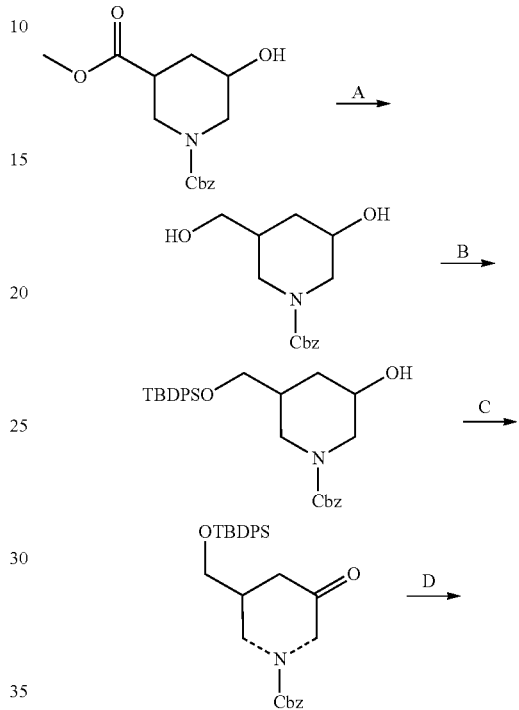

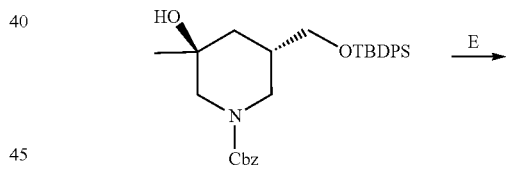

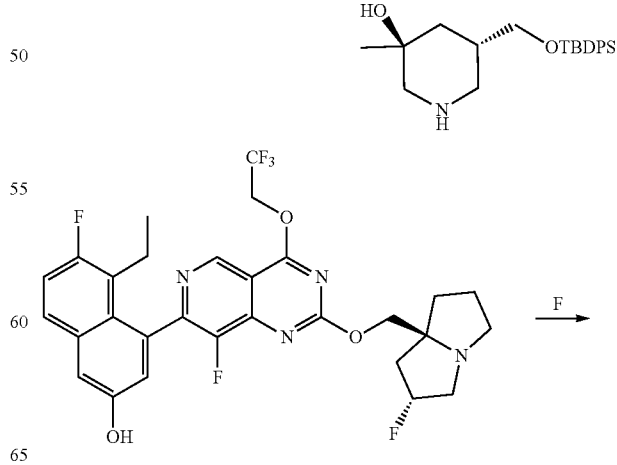

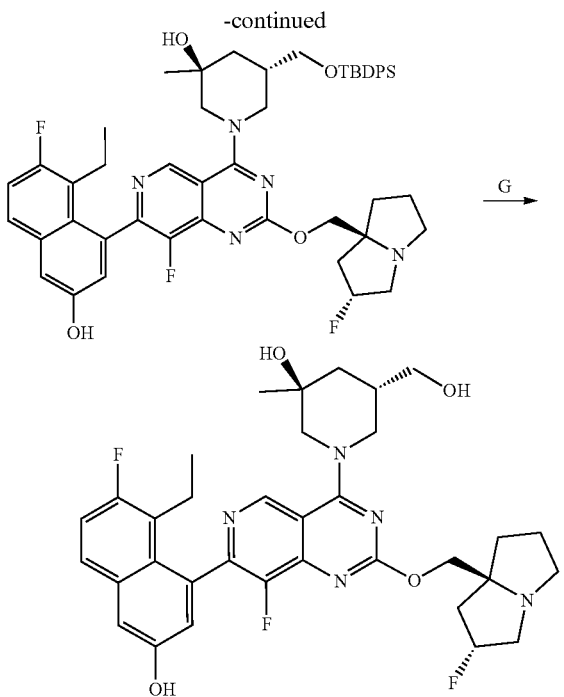

Step A. benzyl 3-hydroxy-5-(hydroxymethyl)piperidine-1-carboxylate: To a solution of 1-benzyl 3-methyl 5-hydroxypiperidine-1,3-dicarboxylate (5.00 g, 1.0 equiv.) in THF (100 mL) was added LiAlH$_4$ (970 mg, 1.5 equiv.) under N$_2$ at −40° C. The reaction was stirred at −40° C. for 0.5 hour. The reaction mixture was quenched with water (970.5 mg), 15% NaOH aqueous (970.5 mg), and water (3×970.5 mg) at 0° C. sequentially, then filtered. The filter cake was washed with ethyl acetate (2×25 mL), the filtrate was concentrated to give title compound (4.41 g, crude) as a colorless oil; LCMS (ESI, M+1): m/z=266.2.

Step B. benzyl 3-(((tert-butyldiphenylsilyl)oxy)methyl)-5-hydroxypiperidine-1-carboxylate: To a solution of benzyl 3-hydroxy-5-(hydroxymethyl)piperidine-1-carboxylate (4.41 g, 1.0 equiv.) in DCM (45 mL) was added imidazole (2.26 g, 2.0 equiv.) and TBDPSCl (5.48 g, 1.2 equiv.) at 0° C. The reaction mixture was stirred at 25° C. for 1 hour. The mixture was quenched by addition of water (50 mL), and extracted with DCM (3×50 mL). The combined organic layers were dried over anhydrous sodium sulfate, concentrated and purified by reversed-phase flash chromatography (water (0.1% formic acid)-ACN) to give title compound (4.50 g, 52% yield) as a yellow oil; LCMS (ESI, M+1): m/z=504.4.

Step C. benzyl 3-(((tert-butyldiphenylsilyl)oxy)methyl)-5-oxopiperidine-1-carboxylate: To a solution of benzyl 3-(((tert-butyldiphenylsilyl)oxy)methyl)-5-hydroxypiperidine-1-carboxylate (4.50 g, 1.0 equiv.) in DCM (50 mL) was added Dess-Martin reagent (7.58 g, 2.0 equiv.). The reaction mixture was stirred at 25° C. for 12 hours. The reaction mixture was quenched by addition of saturated sodium sulfite solution (300 mL) and filtered, then extracted with DCM (150 mL). The organic layer was dried over anhydrous sodium sulfate and purified by column chromatography (Silica gel, Petroleum ether/Ethyl acetate 20:1 to 3:1) to give the title compound (2.90 g, 64% yield) as a yellow oil; LCMS (ESI, M+1): m/z=502.1.

Step D. (3RS,5RS)-benzyl 5-(((tert-butyldiphenylsilyl)oxy)methyl)-3-hydroxy-3-methylpiperidine-1-carboxylate: To a solution of benzyl 3-(((tert-butyldiphenylsilyl)oxy)methyl)-5-oxopiperidine-1-carboxylate (2.90 g, 1.0 equiv.) in THF (20 mL) was added MeMgBr (3 M, 1.2 equiv.) at 0° C. The reaction mixture was stirred at 0° C. for 0.5 hour. The reaction mixture was quenched by addition of water (20 mL) at 0° C., extracted with ethyl acetate (3×20 mL). The combined organic layer was dried over anhydrous sodium sulfate, concentrated and purified by reversed-phase flash chromatography (water (0.1% formic acid)-ACN) and then column chromatography (Silica gel, Petroleum ether/Ethyl acetate 20:1 to 1:1) to produce a yellow oil, which was further separated by SFC (column: DAICEL CHIRALPAK IC (250 mm×30 mm, 5 µm); mobile phase: [0.1% NH$_3$H$_2$O IPA]; B %: 35%-35%, 4.2; 60 min) and (column: REGIS (S,S)WHELK-O1 (250 mm×25 mm, 10 µm); mobile phase: [0.1% NH$_3$H$_2$O IPA]; B %: 30%-30%, 7.4; 50 min) to give the title compound (30.0 mg, 1% yield) as a yellow oil; LCMS (ESI, M+23): m/z=540.4.

Step E. (3S,5S)-5-(((tert-butyldiphenylsilyl)oxy)methyl)-3-methylpiperidin-3-ol: To a suspension of Pd/C (80 mg, 10% purity) in MeOH (1 mL) was added (3RS,5RS)-5-(((tert-butyldiphenylsilyl)oxy)methyl)-3-methylpiperidin-3-ol (30 mg, 57.95 µmol, 1.0 equiv.) under N$_2$. The suspension was degassed in vacuum and purged with H$_2$ several times. The mixture was stirred under H$_2$ (15 psi) at 25° C. for 2 hours. The reaction mixture was filtered, the filtrate was concentrated under reduced pressure to give the title compound (15 mg, crude) as a white solid.

Step F. (3S,5S)-5-(((tert-butyldiphenylsilyl)oxy)methyl)-1-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a mixture of 5-ethyl-6-fluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (20.0 mg, 1.0 equiv.), (3RS,5RS)-5-(((tert-butyldiphenylsilyl)oxy)methyl)-3-methylpiperidin-3-ol (12.9 mg, 1 equiv.), 4 Å molecular sieves (10 mg) in DMF (0.5 mL) was added DIEA (4.36 mg, 1.0 equiv.). The mixture was stirred at 40° C. for 2 hours. The reaction mixture was filtered to give a solution which was purified by reversed-phase flash chromatography (C18, water (0.1% formic acid)/ACN) to give the title compound (20.0 mg, 53% yield) as a yellow solid. LCMS (ESI, M+1): m/z=876.2.

Step G. (3RS,5RS)-1-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-5-(hydroxymethyl)-3-methylpiperidin-3-ol:
To a solution of (3RS,5RS)-5-(((tert-butyldiphenylsilyl)oxy)methyl)-1-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (20 mg, 1.0 equiv.) in DMF (0.5 mL) was added CsF (34.7 mg, 10 equiv.). The reaction was stirred at 25° C. for 2 hours. The reaction mixture was filtered to give a solution which was purified by prep-HPLC (column: Phenomenex Luna C18 150×25 mm×10 µm; mobile phase: water (0.1% formic acid)/ACN, B %: 10%-40%, 10 min) and lyophilized to afford the title compound (6.56 mg, 43% yield) as a white solid; $^1$H NMR (400 MHz, methanol-d$_4$): δ=9.27 (s, 1H), 8.51 (s, 1H), 7.68 (dd, J=5.6, 9.2 Hz, 1H), 7.31 (d, J=2.4 Hz, 1H), 7.25 (t, J=9.2 Hz, 1H), 7.06 (dd, J=2.4, 8.0 Hz, 1H), 5.50-5.33 (m, 1H), 4.68-4.56 (m, 2H), 4.53-4.39 (m, 2H), 3.65-3.44 (m, 5H), 3.43-3.34 (m, 1H), 3.22-2.87 (m, 2H), 2.54-2.33 (m, 4H), 2.29-2.09

(m, 4H), 2.05-1.80 (m, 2H), 1.46 (dt, J=5.2, 13.2 Hz, 1H), 1.31 (d, J=6.4 Hz, 3H), 0.86-0.76 (m, 3H); LCMS (ESI, M+1): m/z=638.4.

Example 328

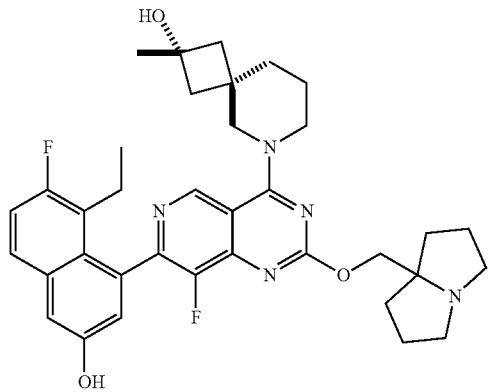

trans-6-(7-(8-ethyl-7-fluoro-3-hydroxynaphthalen-1-yl)-8-fluoro-2-((hexahydro-1H-pyrrolizin-7a-yl)methoxy)pyrido[4,3-d]pyrimidin-4-yl)-2-methyl-6-azaspiro[3.5]nonan-2-ol

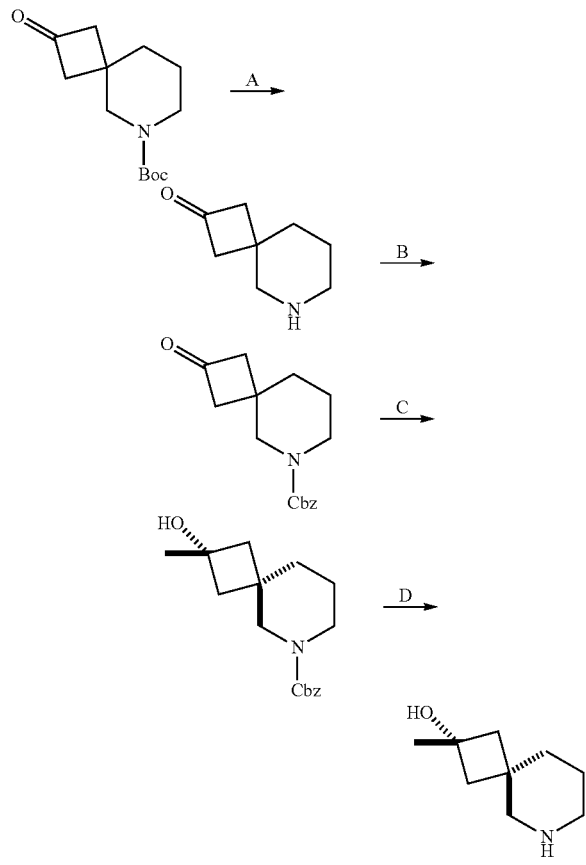

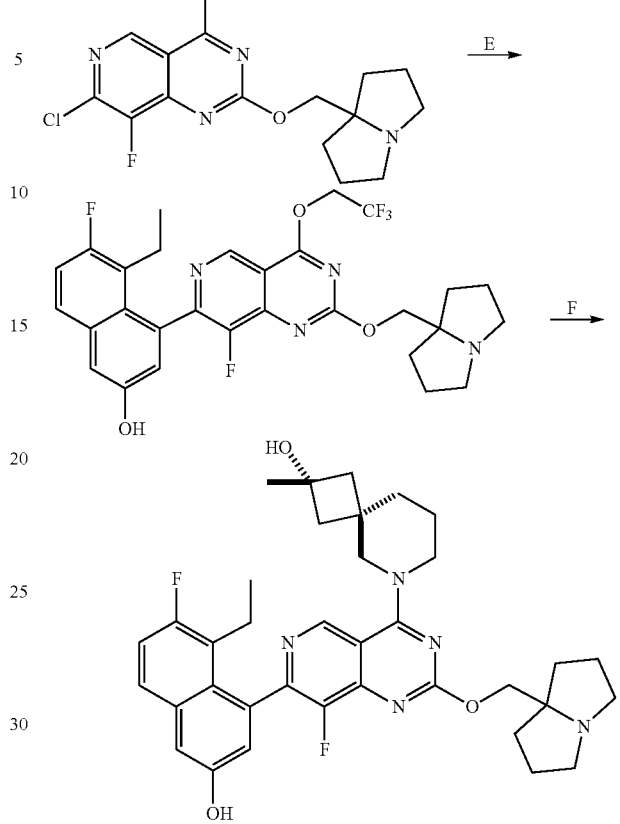

Step A. 6-azaspiro[3.5]nonan-2-one: To a solution of tert-butyl 2-oxo-6-azaspiro[3.5]nonane-6-carboxylate (1.00 g, 1.0 equiv.) in MeCN (5 mL) was added HCl.dioxane (4 M, 9.57 equiv.). The mixture was stirred at 25° C. for 0.5 hour. The mixture was concentrated in vacuum to afford the title compound (734 mg, crude, HCl salt) as a yellow oil.

Step B. benzyl 2-oxo-6-azaspiro[3.5]nonane-6-carboxylate: To a mixture of 6-azaspiro[3.5]nonan-2-one (3.67 g, 1.0 equiv., HCl) in ethyl acetate (50 mL) was added TEA (10.6 g, 5.0 equiv.) and CbzCl (5.35 g, 1.5 equiv.) at 25° C. The mixture was stirred at 25° C. for 12 hours. The mixture was diluted with water (50 mL) and extracted with ethyl acetate (2×60 mL). The combined organic layers were dried over sodium sulfate, filtered and concentrated in vacuum. The crude product was purified by reversed phase flash chromatography (water (0.1% formic acid)-ACN) to afford the title compound (4.70 g, 81% yield over two steps) as a yellow oil; $^1$H NMR (400 MHz, chloroform-d) δ=7.40-7.29 (m, 5H), 5.14 (s, 2H), 3.60-3.45 (m, 4H), 2.97-2.75 (m, 2H), 2.74-2.65 (m, 2H), 1.82-1.74 (m, 2H), 1.61 (br s, 2H); LCMS (ESI, M+1): m/z=274.1.

Step C. trans-benzyl 2-hydroxy-2-methyl-6-azaspiro[3.5]nonane-6-carboxylate: To a solution of benzyl 2-oxo-6-azaspiro[3.5]nonane-6-carboxylate (500 mg, 1.0 equiv.) in acetonitrile (10 mL) was added MeMgBr (3 M, 1.22 mL, 2.0 equiv.) at 0° C. The reaction was stirred at 0° C. for 0.5 hours. The mixture was quenched by addition of water (10 mL) and extracted with ethyl acetate (2×10 mL). The combined organic layers were dried over Na$_2$SO$_4$, concentrated and purified by reversed phase flash chromatography (water (0.1% formic acid)-ACN), and stereoisomers were further separated by SFC (column: daicel chiralpak IG 250 mm×30 mm×10 μm; mobile phase: 0.1% NH$_3$—H$_2$O in IPA—CO$_2$, 40%, 2.6 min over 40 min) to afford the title compound (100 mg, 19% yield) as a colorless oil; LCMS (ESI, M+1): m/z=290.2.

Step D. trans-2-methyl-6-azaspiro[3.5]nonan-2-ol: To a solution of trans-benzyl 2-hydroxy-2-methyl-6-azaspiro [3.5]nonane-6-carboxylate (100 mg, 1.0 equiv.) in MeOH (5 mL) was added Pd(OH)$_2$/C (20.0 mg, 20% purity) under N2. The mixture was degassed and purged with H$_2$ for 3 times, and then stirred at 25° C. for 0.5 hours under H$_2$ (15 psi). The mixture was filtered and the filtrate was concentrated to afford the title compound (60.0 mg, crude) as a colorless oil.

Step E. 5-ethyl-6-fluoro-4-(8-fluoro-2-((hexahydro-1H-pyrrolizin-7a-yl)methoxy)-4-(2,2,2-trifluoroethoxy)pyrido[4,3-d]pyrimidin-7-yl)naphthalen-2-ol: A mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (420 mg, 1.0 equiv.), 5-ethyl-6-fluoro-4-(4,4,5,5-tetramethyl-1,3,2-dioxaborolan-2-yl)naphthalen-2-ol (410 mg, 1.3 equiv.), CataCXium A Pd G3 (145 mg, 0.2 equiv.) and Cs$_2$CO$_3$ (1.5 M, 2.00 mL, 3.0 equiv.) in methoxycyclopentane (15 mL) were degassed and stirred at 100° C. for 3 hours under N2 atmosphere. The mixture was diluted with water (20 mL) and extracted with ethyl acetate (30 mL). The organic layer was dried over sodium sulfate, filtered and concentrated in vacuum. The crude product was purified by reversed phase flash chromatography (water (0.1% formic acid)-ACN), to afford the title compound (210 mg, 32% yield) as a yellow solid; LCMS (ESI, M+1): m/z=575.3.

Step F. trans-6-(7-(8-ethyl-7-fluoro-3-hydroxynaphthalen-1-yl)-8-fluoro-2-((hexahydro-1H-pyrrolizin-7a-yl)methoxy)pyrido[4,3-d]pyrimidin-4-yl)-2-methyl-6-azaspiro[3.5]nonan-2-ol: To a solution of 5-ethyl-6-fluoro-4-(8-fluoro-2-((tetrahydro-1H-pyrrolizin-7a(5H)-yl)methoxy)-4-(2,2,2-trifluoroethoxy)pyrido[4,3-d]pyrimidin-7-yl)naphthalen-2-ol (100 mg, 1.0 equiv.) and trans-2-methyl-6-azaspiro[3.5]nonan-2-ol (54.0 mg, 2.0 equiv.) in DMF (2 mL) was added 4 Å molecular sieves (20 mg) and DIEA (67.5 mg, 3.0 equiv.). The mixture was stirred at 40° C. for 14 hours. The mixture was filtered and the filtrate was purified by prep-HPLC (column: Waters Xbridge 150×25 mm×5 μm; mobile phase: water (10 mM NH$_4$HCO$_3$)-ACN, B %: 48%-78%, 10 min) to afford the title compound (35.7 mg, 31% yield) as a yellow solid; $^1$H NMR (400 MHz, methanol-d$_4$) δ=9.05 (s, 1H), 7.68 (dd, J=6.0, 9.2 Hz, 1H), 7.30 (d, J=2.4 Hz, 1H), 7.25 (t, J=9.2 Hz, 1H), 7.06 (d, J=2.4 Hz, 1H), 4.34-4.26 (m, 2H), 4.21-4.11 (m, 2H), 3.99 (d, J=12.8 Hz, 1H), 3.90-3.78 (m, 1H), 3.17-3.06 (m, 2H), 2.57-2.43 (m, 1H), 2.20-2.02 (m, 4H), 1.98-1.86 (m, 9H), 1.86-1.73 (m, 4H), 1.36 (s, 3H), 0.81 (t, J=7.2 Hz, 3H); LCMS (ESI, M+1): m/z=630.5.

Example 329

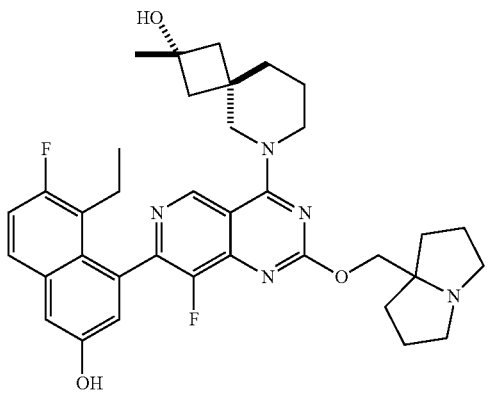

cis-6-(7-(8-ethyl-7-fluoro-3-hydroxynaphthalen-1-yl)-8-fluoro-2-((hexahydro-1H-pyrrolizin-7a-yl)methoxy)pyrido[4,3-d]pyrimidin-4-yl)-2-methyl-6-azaspiro[3.5]nonan-2-ol The title compound was synthesized according to the procedure described for example 328 except for using the other eluting peak from SFC separation in step C in further steps D and F. $^1$H NMR (400 MHz, methanol-d$_4$) δ=9.09 (s, 1H), 7.67 (dd, J=6.0, 9.2 Hz, 1H), 7.30 (d, J=2.8 Hz, 1H), 7.24 (t, J=9.6 Hz, 1H), 7.06 (d, J=2.4 Hz, 1H), 4.31 (s, 2H), 4.22-4.12 (m, 2H), 4.07-3.91 (m, 2H), 3.17-3.04 (m, 2H), 2.81-2.69 (m, 2H), 2.55-2.40 (m, 1H), 2.27-2.03 (m, 3H), 2.02-1.86 (m, 8H), 1.86-1.71 (m, 6H), 1.33 (s, 3H), 0.81 (t, J=7.2 Hz, 3H); LCMS (ESI, M+1): m/z=630.5.

Example 330

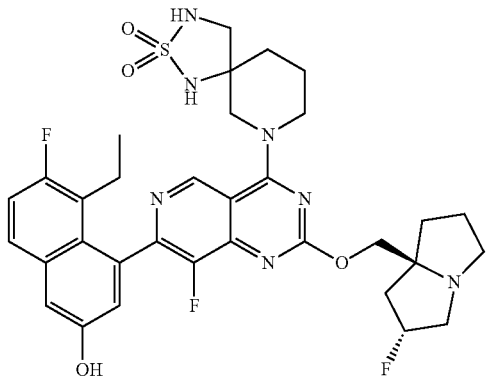 [SMILES: CCc1c(F)ccc2cc(O)cc(-c3ncc4c(N5CCCC6(CNS(=O)(=O)N6)C5)nc(OC[C@@]56CCCN5C[C@H](F)C6)nc4c3F)c12]

7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2-thia-1,3,7-triazaspiro[4.5]decane 2,2-dioxide

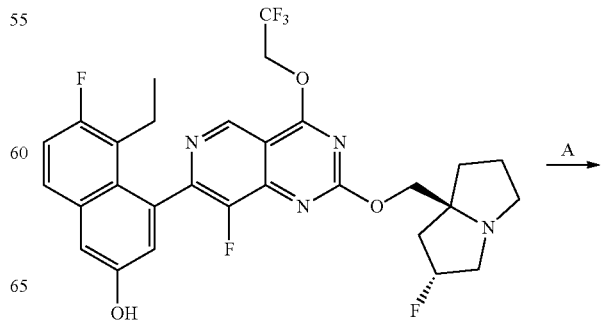

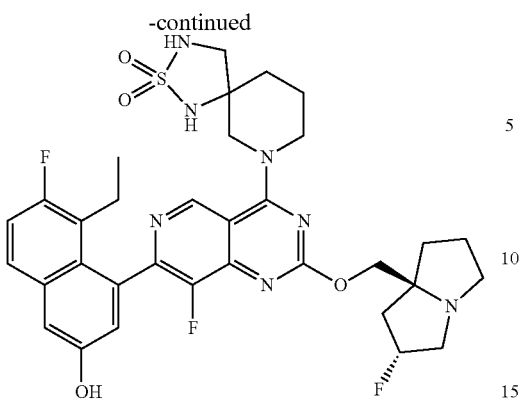

Step A. 7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2-thia-1,3,7-triazaspiro[4.5]decane 2,2-dioxide: To a mixture of 5-ethyl-6-fluoro-4-(8-fluoro-2-(((2R,7aS)-2fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (50.0 mg, 1.0 equiv.), 2$\lambda^6$-thia-1,3,9-triazaspiro[4.5]decane 2,2-dioxide (32.3 mg, 2.0 equiv.) and 4 Å molecular sieves (10 mg, 1.0 equiv.) in DMF (0.5 mL) was added DIEA (32.7 mg, 3.0 equiv.). The reaction was stirred at 40° C. for 12 hours. The residue was filtered and washed with DMF (1 mL). The filtrate was purified by prep-HPLC [column: Phenomenex C18 75×30 mm×3 µm; mobile phase: water (0.1% formic acid)/ACN] B %: 15%-45%, 7 min] and lyophilized to afford the title compound (26.4 mg, 45% yield) as a white solid; $^1$H NMR (400 MHz, methanol-$d_4$) δ=9.14 (s, 1H), 7.68 (ddd, J=3.2, 5.6, 9.2 Hz, 1H), 7.31 (d, J=2.8 Hz, 1H), 7.26 (dt, J=1.6, 9.6 Hz, 11H), 7.04 (t, J=3.2 Hz, 1H), 5.62-5.38 (m, 1H), 4.79-4.61 (m, 3H), 4.59-4.42 (m, 2H), 3.88-3.74 (m, 2H), 3.74-3.60 (m, 3H), 3.41 (td, J=2.4, 12.0 Hz, 1H), 3.22 (dd, J=1.6, 12.4 Hz, 1H), 2.71-2.49 (m, 2H), 2.48-2.30 (m, 2H), 2.28-2.15 (m, 3H), 2.15-2.00 (m, 3H), 2.00-1.81 (m, 2H), 0.80 (t, J=7.6 Hz, 3H); LCMS (ESI, M+1): m/z=684.4.

Example 331

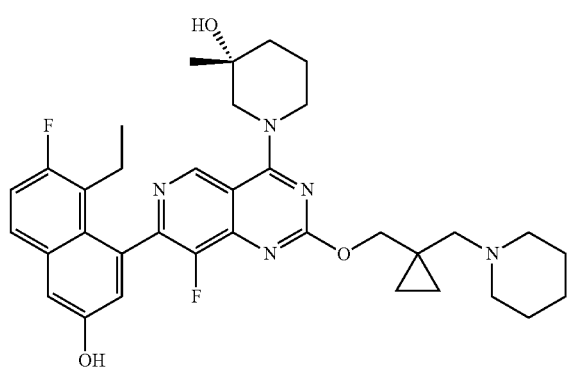 [SMILES: CCc1c(F)ccc2cc(O)cc(-c3ncc4c(N5CCC[C@@](C)(O)C5)nc(OCC5(CN6CCCCC6)CC5)nc4c3F)c12]

(R)-1-(7-(8-ethyl-7-fluoro-3-hydroxynaphthalen-1-yl)-8-fluoro-2-((1-(piperidin-1-ylmethyl)cyclopropyl)methoxy)pyrido[4,3-d]pyrimidin-4-yl)-3-methylpiperidin-3-ol The title compound was synthesized according to the procedure described for example 309. $^1$H NMR (400 MHz, chloroform-d) δ=9.22 (s, 1H), 8.54 (s, 1H), 7.65 (s, 1H), 7.31 (s, 11H), 7.29-7.22 (m, 1H), 7.03 (br d, J=1.2 Hz, 11H), 4.55 (br d, J=13.2 Hz, 11H), 4.48-4.41 (m, 2H), 4.35-4.25 (m, 1H), 3.69-3.57 (m, 1H), 3.50-3.41 (m, 2H), 3.13-2.79 (m, 5H), 2.55-2.38 (m, 1H), 2.26-2.12 (m, 2H), 1.86-1.75 (m, 6H), 1.66-1.53 (m, 2H), 1.29 (d, J=10.4 Hz, 3H), 0.89-0.78 (m, 5H), 0.75-0.66 (m, 2H); LCMS [ESI, M+1] m/z=618.4.

Example 332

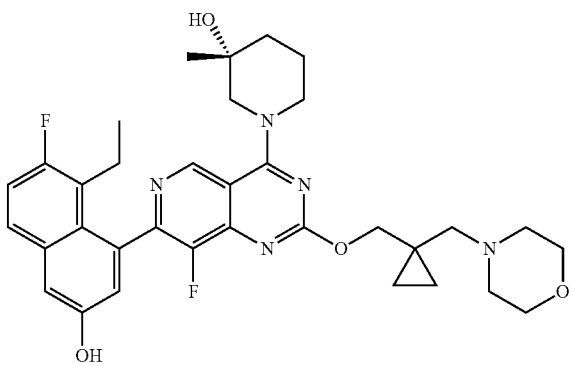 [SMILES: CCc1c(F)ccc2cc(O)cc(-c3ncc4c(N5CCC[C@@](C)(O)C5)nc(OCC5(CN6CCOCC6)CC5)nc4c3F)c12]

(R)-1-(7-(8-ethyl-7-fluoro-3-hydroxynaphthalen-1-yl)-8-fluoro-2-((1-(morpholinomethyl)cyclopropyl)methoxy)pyrido[4,3-d]pyrimidin-4-yl)-3-methylpiperidin-3-ol The title compound was synthesized according to the procedure described for example 309. $^1$H NMR (400 MHz, METHANOL-$d_4$) δ=9.25 (s, 1H), 8.59-8.47 (m, 1H), 7.74-7.66 (m, 1H), 7.36-7.22 (m, 21H), 7.08 (br d, J=19.1 Hz, 1H), 4.41 (s, 3H), 4.33-4.23 (m, 1H), 3.72-3.61 (m, 5H), 3.53-3.46 (m, 1H), 2.62-2.52 (m, 4H), 2.51-2.43 (m, 3H), 2.29-2.12 (m, 2H), 1.96-1.72 (m, 3H), 1.33-1.29 (m, 3H), 0.89-0.79 (m, 3H), 0.78-0.71 (m, 2H), 0.47 (s, 2H); LCMS [ESI, M+1] m/z=620.1.

Example 333

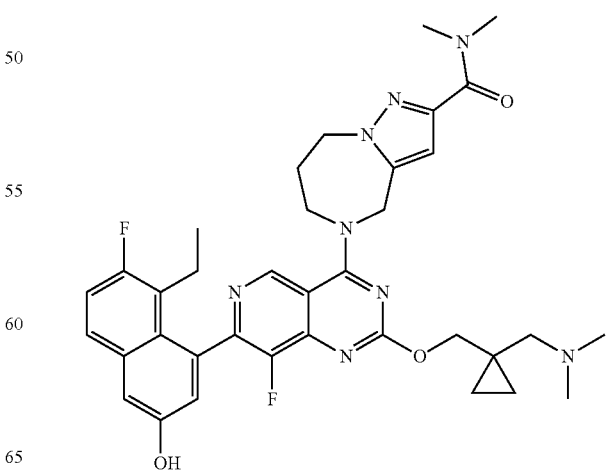

527

5-(2-((1-(((dimethylamino)methyl)cyclopropyl)methoxy)-7-(8-ethyl-7-fluoro-3-hydroxynaphthalen-1-yl)-8-fluoropyrido[4,3-d]pyrimidin-4-yl)-N,N-dimethyl-5,6,7,8-tetrahydro-4H-pyrazolo[1,5-a][1,4]diazepine-2-carboxamide The title compound was synthesized according to the procedure described for example 319. ¹H NMR (400 MHz, methanol-d₄) δ=9.16 (s, 1H), 7.67 (dd, J=6.0, 9.2 Hz, 1H), 7.29 (d, J=2.8 Hz, 1H), 7.24 (t, J=9.2 Hz, 1H), 7.04 (d, J=2.4 Hz, 1H), 6.72 (s, 1H), 5.37-5.17 (m, 2H), 4.58-4.54 (m, 2H), 4.48-4.32 ((m, 4H), 3.33 (s, 3H), 3.13-3.02 (m, 3H), 2.50-2.37 (m, 511), 2.31 (s, 6H), 2.21-2.11 (m, 1H), 0.78 (t, J=7.2 Hz, 3H), 0.75-0.70 (m, 2H), 0.56-0.51 (m, 2H); LCMS (ESI, M+1): m/z=671.1.

Example 334

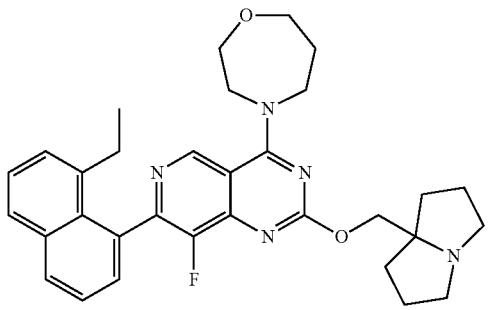 [SMILES: CCc1cccc2cccc(-c3ncc4c(N5CCCOCC5)nc(OCC56CCCN5CCC6)nc4c3F)c12]

4-(7-(8-ethylnaphthalen-1-yl)-8-fluoro-2-((hexahydro-1H-pyrrolizin-7a-yl)methoxy)pyrido[4,3-d]pyrimidin-4-yl)-1,4-oxazepane The title compound was synthesized according to the procedure described for example 204. ¹H NMR (400 MHz, METHANOL-d₄) δ=9.19-9.15 (m, 1H), 8.09-8.04 (m, 1H), 7.91-7.85 (m, 1H), 7.62-7.55 (m, 1H), 7.53-7.39 (m, 3H), 4.40-4.34 (m, 2H), 4.33-4.23 (m, 4H), 4.11-4.04 (m, 2H), 3.92-3.84 (m, 2H), 3.27-3.17 (m, 2H), 2.89-2.80 (m, 2H), 2.51-2.31 (m, 2H), 2.27-2.19 (m, 2H), 2.18-2.09 (m, 2H), 2.05-1.90 (m, 4H), 1.88-1.79 (m, 2H), 1.00-0.91 (m, 3H); LCMS (ESI, M+1): m/z=542.2.

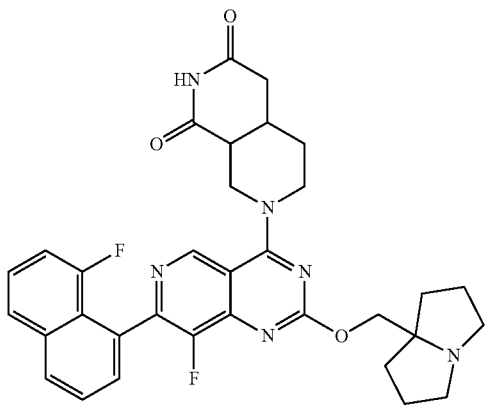 [SMILES: O=C1CC2CCN(c3nc(OCC45CCCN4CCC5)nc4c(F)c(-c5cccc6cccc(F)c56)ncc34)CC2C(=O)N1]

528

7-(8-fluoro-7-(8-fluoronaphthalen-1-yl)-2-((hexahydro-1H-pyrrolizin-7a-yl)methoxy)pyrido[4,3-d]pyrimidin-4-yl)hexahydro-2,7-naphthyridine-1,3(2H,4H)-dione

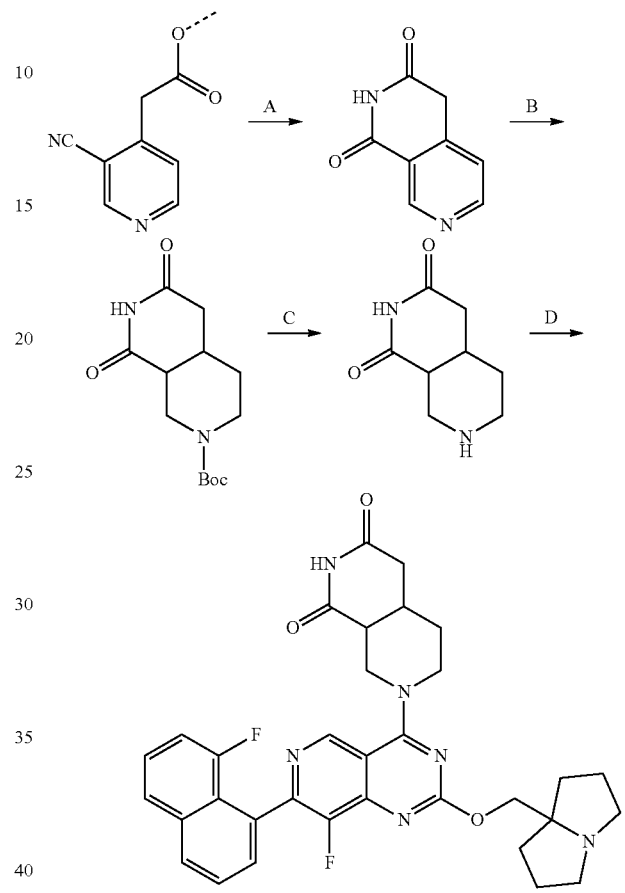

Step A. 4H-2,7-naphthyridine-1,3-dione: A mixture of methyl 2-(3-cyano-4-pyridyl)acetate (500 mg, 1.0 equiv.), (1E)-acetaldehyde oxime (838 mg, 5.0 equiv.) and RhCl(PPh₃)₃ (263 mg, 0.1 equiv.) in toluene (15 mL) was degassed and stirred at 110° C. for 2 hours under N₂ atmosphere. The mixture was concentrated under reduced pressure and then diluted with water (20 mL). The mixture was refluxed at 100° C. for 1 hour. After cooling to 20° C., the mixture was filtered. The filter cake was triturated with EtOAc (10 mL) and MeOH (10 mL) to afford the title compound (300 mg, 52.2% yield) as a white solid; ¹H NMR (400 MHz, DMSO-d₆) δ=12.41-11.59 (m, 1H), 10.52 (br s, 1H), 8.19 (s, 1H), 7.36 (br d, J=7.2 Hz, 1H), 6.66 (br d, J=7.2 Hz, 1H), 5.14 (s, 1H) LCMS (ESI, M+1): m/z=163.0.

Step B. tert-butyl 6,8-dioxooctahydro-2,7-naphthyridine-2(1H)-carboxylate: A mixture of 4H-2,7-naphthyridine-1,3-dione (400 mg, 1.0 equiv.), Boc₂O (1.62 g, 3.0 equiv.) and Pd/C (50 mg, 10% purity) in MeOH (10 mL) was degassed and purged with H₂ for 3 times before being stirred at 60° C. for 6 hours under H₂ atmosphere (1 atm). The mixture was filtered and concentrated under reduced pressure to afford the title compound (400 mg, crude) as a green oil; LCMS (ESI, M+1): m/z=269.0.

Step C. hexahydro-2,7-naphthyridine-1,3(2H,4H)-dione: A mixture of tert-butyl 6,8-dioxo-1,3,4,4a,5,8a-hexahydro- 2,7-naphthyridine-2-carboxylate (400 mg, 1.0 equiv.) in DCM (3 mL) and TFA (1 mL) was stirred at 25° C. for 2 hours under $N_2$ atmosphere. The mixture was concentrated under reduced pressure to give a residue. The residue was purified by prep-HPLC [column: Waters Atlantis T3 150×30 mm×5 μm; mobile phase: mobile phase: water (0.1% formic acid)/ACN; B %: 1%-20%, 10 min] to afford the title compound (100 mg, 25% yield) as a green oil; $^1$H NMR (400 MHz, METHANOL-$d_4$) δ=4.06-3.93 (m, 1H), 3.51-3.33 (m, 1H), 3.23-3.16 (m, 1H), 3.12-2.90 (m, 2H), 2.80-2.64 (m, 1H), 2.62-2.35 (m, 2H), 2.11-1.83 (m, 1H), 1.70-1.48 (m, 1H); LCMS (ESI, M+1): m/z=169.2.

Step D. 7-(8-fluoro-7-(8-fluoronaphthalen-1-yl)-2-((hexahydro-1H-pyrrolizin-7a-yl)methoxy)pyrido[4,3-d]pyrimidin-4-yl)hexahydro-2,7-naphthyridine-1,3(2H,4H)-dione: A mixture of 4a,5,6,7,8,8a-hexahydro-4H-2,7-naphthyridine-1,3-dione (63.0 mg, 2.0 equiv.), 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 1.0 equiv.), DIEA (243 mg, 10.0 equiv.) and 4 Å molecular sieves (10 mg) in DMF (0.01 mL) was stirred at 40° C. for 48 hours under $N_2$ atmosphere. The mixture was filtered. The residue was purified by prep-HPLC (neutral condition) to afford the title compound (6.2 mg, 5.3% yield) as an off-white solid; $^1$H NMR (400 MHz, METHANOL-$d_4$) δ=9.13 (s, 1H), 8.54 (s, 1H), 8.13 (br d, J=8.4 Hz, 1H), 7.87 (d, J=8.4 Hz, 1H), 7.76-7.67 (m, 1H), 7.62 (d, J=7.2 Hz, 1H), 7.54 (dt, J=5.2, 7.8 Hz, 1H), 7.20 (dd, J=8.2, 13.2 Hz, 1H), 5.24 (br d, J=14.0 Hz, 1H), 4.84-4.79 (m, 1H), 4.59 (s, 2H), 3.61-3.42 (m, 3H), 3.40-3.33 (m, 1H), 3.22-3.10 (m, 2H), 2.84-2.66 (m, 2H), 2.55-2.44 (m, 1H), 2.41-2.23 (m, 3H), 2.22-2.11 (m, 3H), 2.10-1.98 (m, 4H), 1.76-1.53 (m, 1H); LCMS (ESI, M+1): m/z=599.4.

Example 336

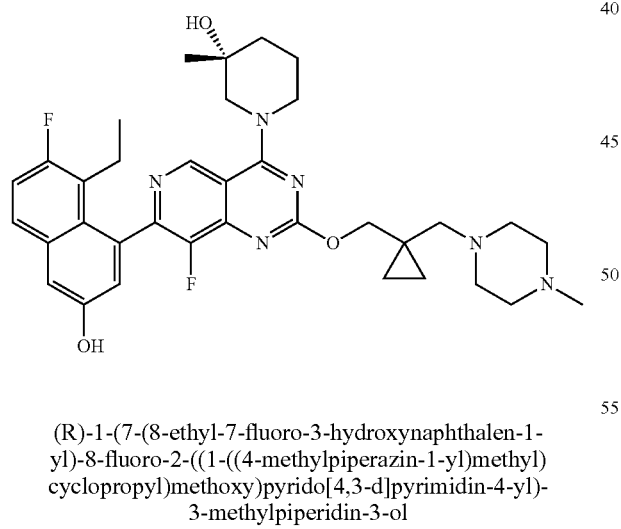

(R)-1-(7-(8-ethyl-7-fluoro-3-hydroxynaphthalen-1-yl)-8-fluoro-2-((1-((4-methylpiperazin-1-yl)methyl)cyclopropyl)methoxy)pyrido[4,3-d]pyrimidin-4-yl)-3-methylpiperidin-3-ol The title compound was synthesized according to the procedure described for example 309. $^1$H NMR (400 MHz, METHANOL-$d_4$) δ=9.20 (d, J=4.0 Hz, 1H), 7.68 (dd, J=8.8, 6.0 Hz, 1H), 7.32-7.30 (m, 1H), 7.25 (t, J=9.6 Hz, 1H), 7.09-7.01 (m, 1H), 4.56-4.38 (m, 3H), 4.29-4.26 (m, 1H), 3.68-3.60 (m, 1H), 3.51-3.40 (m, 1H), 3.10-2.38 (m, 14H), 2.27-2.08 (m, 2H), 1.91-1.71 (m, 3H), 1.31-1.26 (m, 3H), 0.85-0.81 (m, 3H), 0.79-0.76 (m, 2H), 0.55-0.53 (m, 2H); LCMS (ESI, M+1): m/z=633.5;

Example 337

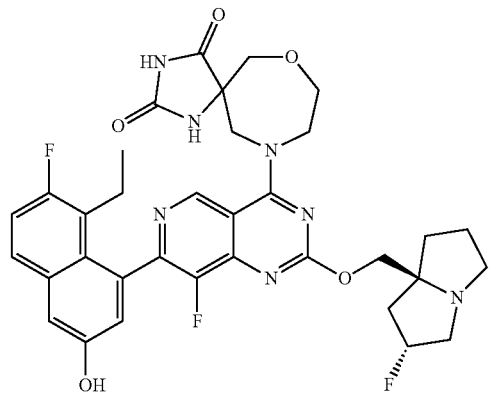 [SMILES: CCc1c(F)ccc2cc(O)cc(-c3ncc4c(N5CCOCC6(C5)NC(=O)NC6=O)nc(OC[C@@]56CCCN5C[C@H](F)C6)nc4c3F)c12]

10-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-7-oxa-1,3,10-triazaspiro[4.6]undecane-2,4-dione The title compound was synthesized according to the procedure described for example 330. $^1$H NMR (400 MHz, METHANOL-d) δ=9.35 (d, J=1.6 Hz, 1H), 7.76 (dd, J=6.0, 8.8 Hz, 1H), 7.39 (d, J=2.8 Hz, 1H), 7.34 (t, J=9.6 Hz, 1H), 7.13 (dd, J=2.4, 7.2 Hz, 1H), 5.63-5.42 (m, 1H), 5.20-5.00 (m, 1H), 4.62-4.25 (m, 7H), 4.18-4.09 (m, 1H), 4.02-3.96 (m, 1H), 3.81-3.50 (m, 3H), 3.36-3.25 (m, 1H), 2.69-2.39 (m, 3H), 2.38-2.06 (m, 5H), 0.96-0.82 (m, 3H); LCMS (ESI, M+1): m/z=678.1.

Example 338

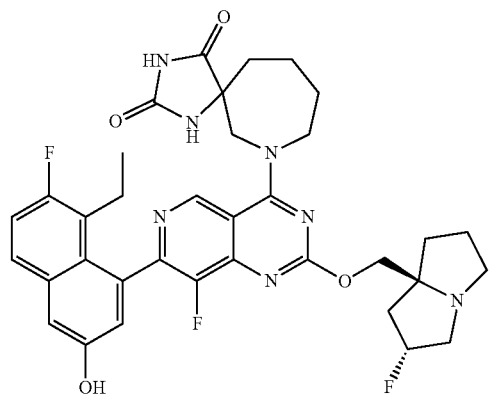 [SMILES: CCc1c(F)ccc2cc(O)cc(-c3ncc4c(N5CCCCC6(C5)NC(=O)NC6=O)nc(OC[C@@]56CCCN5C[C@H](F)C6)nc4c3F)c12]

7-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1,3,7-triazaspiro[4.6]undecane-2,4-dione The title compound was synthesized according to the procedure described for example 330. $^1$H NMR (400 MHz, methanol-d₄) δ=9.28 (t, J=3.2 Hz, 1H), 7.68 (dd, J=5.6, 8.8 Hz, 1H), 7.32-7.24 (m, 2H), 7.05 (d, J=2.4 Hz, 1H), 5.54-5.33 (m, 1H), 5.00-4.95 (m, 1H), 4.52-4.40 (m, 3H), 4.21-4.05 (m, 2H), 3.63-3.61 (m, 3H), 3.26 (br d, J=5.2 Hz, 1H), 2.50-2.45 (m, 3H), 2.20-2.11 (m, 9H), 1.88-1.84 (m, 2H), 0.84-0.77 (m, 3H); LCMS (ESI, M+1): m/z=676.3.

Example 339

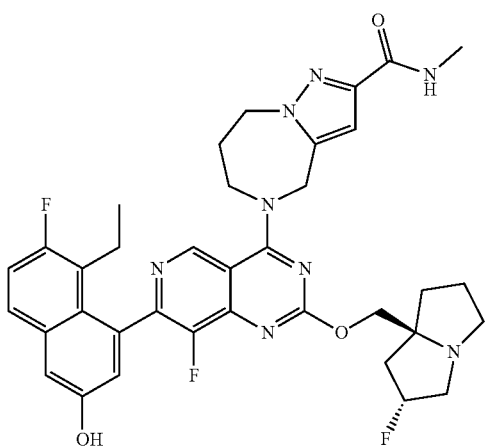 [SMILES: CCc1c(F)ccc2cc(O)cc(-c3ncc4c(N5CCCn6nc(C(=O)NC)cc6C5)nc(OC[C@@]56CCCN5C[C@H](F)C6)nc4c3F)c12]

5-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-N-methyl-5,6,7,8-tetrahydro-4H-pyrazolo[1,5-a][1,4]diazepine-2-carboxamide The title compound was synthesized according to the procedure described for example 330. ¹H NMR (400 MHz, METHANOL-d₄) δ=9.19 (s, 1H), 7.67 (dd, J=5.6, 9.2 Hz, 1H), 7.33-7.20 (m, 2H), 7.05 (d, J=2.4 Hz, 1H), 6.82 (s, 1H), 5.52-5.12 (m, 3H), 4.60-4.30 (m, 6H), 3.65-3.38 (m, 3H), 3.18 (dt, J=5.6, 9.2 Hz, 1H), 2.88 (s, 3H), 2.57-2.21 (m, 6H), 2.20-1.92 (m, 4H), 0.78 (t, J=7.6 Hz, 3H); LCMS (ESI, M+1): m/z=687.1.

Example 340

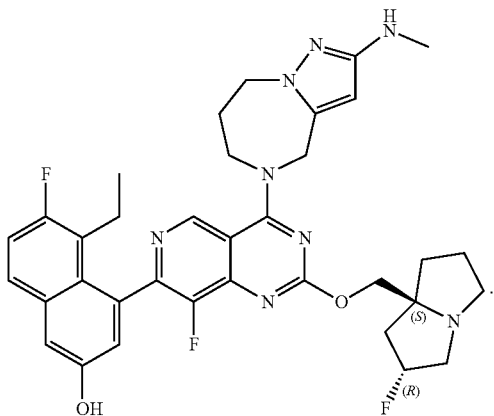

5-ethyl-6-fluoro-4-(8-fluoro-2-(((2R,7aS)-2-fluoro-hexahydro-1H-pyrrolizin-7a-yl)methoxy)-4-(2-(methylamino)-7,8-dihydro-4H-pyrazolo[1,5-a][1,4]diazepin-5(6H)-yl)pyrido[4,3-d]pyrimidin-7-yl)naphthalen-2-ol The title compound was synthesized according to the procedure described for example 135. ¹H NMR (400 MHz, methanol-d₄) δ=9.21 (s, 1H), 7.67 (dd, J=6.0, 9.2 Hz, 1H), 7.30 (d, J=2.8 Hz, 1H), 7.25 (t, J=9.6 Hz, 1H), 7.06 (d, J=2.8 Hz, 1H), 5.75 (s, 1H), 5.32 (d, J=54.4, 1H), 5.17-5.03 (m, 2H), 4.39-4.25 (m, 6H), 3.36 (br d, J=2.8 Hz, 1H), 3.26-3.25 (m, 2H), 3.06 (dt, J=6.0, 9.6 Hz, 1H), 2.76 (s, 3H), 2.49-2.46 (m, 1H), 2.38-2.03 (m, 6H), 2.02-1.87 (m, 3H), 0.79 (t, J=7.2 Hz, 3H); LCMS (ESI, M+1): m/z=659.4.

Example 341

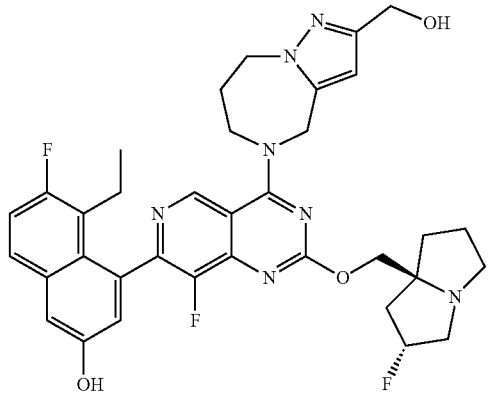 [SMILES: CCc1c(F)ccc2cc(O)cc(-c3ncc4c(N5CCCn6nc(CO)cc6C5)nc(OC[C@@]56CCCN5C[C@H](F)C6)nc4c3F)c12]

5-ethyl-6-fluoro-4-(8-fluoro-2-(((2R,7aS)-2-fluoro-hexahydro-1H-pyrrolizin-7a-yl)methoxy)-4-(2-(hydroxymethyl)-7,8-dihydro-4H-pyrazolo[1,5-a][1,4]diazepin-5(6H)-yl)pyrido[4,3-d]pyrimidin-7-yl)naphthalen-2-ol The title compound was synthesized according to the procedure described for example 330. ¹H NMR (400 MHz, METHANOL-d₄) δ=9.24-9.16 (m, 1H), 7.68 (dd, J=5.6, 8.8 Hz, 1H), 7.34-7.19 (m, 2H), 7.06 (d, J=2.4 Hz, 1H), 6.44 (s, 1H), 5.51-5.33 (m, 1H), 5.32-5.06 (m, 2H), 4.73-4.24 (m, 8H), 3.72-3.40 (m, 3H), 3.26-3.15 (m, 1H), 2.58-2.21 (m, 6H), 2.19-1.96 (m, 4H), 0.78 (br t, J=7.2 Hz, 3H); LCMS (ESI, M+1): m/z=660.1.

Example 342

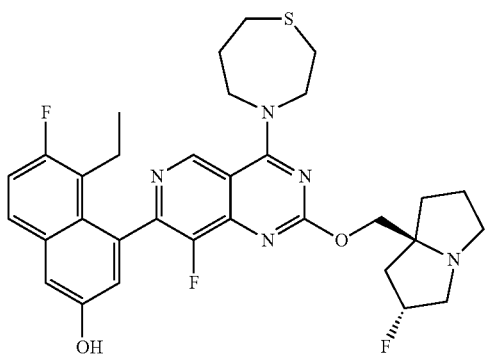 [SMILES: CCc1c(F)ccc2cc(O)cc(-c3ncc4c(N5CCCSCC5)nc(OC[C@@]56CCCN5C[C@H](F)C6)nc4c3F)c12]

5-ethyl-6-fluoro-4-(8-fluoro-2-(((2R,7aS)-2-fluoro-hexahydro-1H-pyrrolizin-7a-yl)methoxy)-4-(1,4-thiazepan-4-yl)pyrido[4,3-d]pyrimidin-7-yl)naphthalen-2-ol The title compound was synthesized according to the procedure described for example 330. $^1$H NMR (400 MHz, Methanol-d$_4$) δ ppm 0.81 (td, J=7.2, 1.6 Hz, 3H) 1.86-2.00 (m, 1H) 2.01-2.11 (m, 2H) 2.13-2.25 (m, 2H) 2.27-2.56 (m, 5H) 2.79 (t, J=6.0 Hz, 2H) 3.10 (dt, J=9.2, 4.8 Hz, 1H) 3.16 (br t, J=5.6 Hz, 2H) 3.35-3.51 (m, 2H) 4.23-4.43 (m, 6H) 4.61 (br s, 1H) 5.27-5.46 (m, 1H) 7.07 (d, J=2.4 Hz, 1H) 7.21-7.29 (m, 1H) 7.31 (d, J=2.4 Hz, 1H) 7.68 (dd, J=9.2, 6.0 Hz, 1H) 8.53 (s, 1H) 9.16 (s, 1H); LCMS (ESI, M+1): m/z=610.3

Example 343

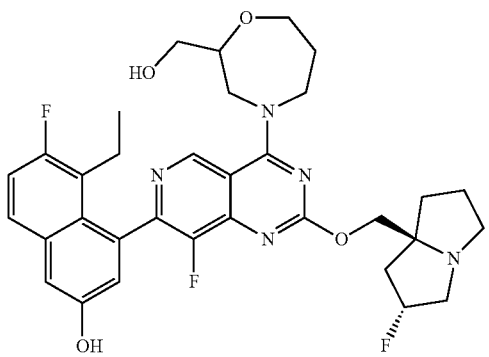 [SMILES: CCc1c(F)ccc2cc(O)cc(-c3ncc4c(N5CCCOC(CO)C5)nc(OC[C@@]56CCCN5C[C@H](F)C6)nc4c3F)c12]

5-ethyl-6-fluoro-4-(8-fluoro-2-(((2R,7aS)-2-fluoro-tetrahydro-1H-pyrrolizin-7a(5H)-yl)methoxy)-4-(2-(hydroxymethyl)-1,4-oxazepan-4-yl)pyrido[4,3-d]pyrimidin-7-yl)naphthalen-2-ol The title compound was synthesized according to the procedure described for example 330. $^1$H NMR (400 MHz, methanol-d$_4$) δ=9.20 (d, J=2.8 Hz, 1H), 8.55 (s, 1H), 7.70 (dd, J=6.0, 9.2 Hz, 1H), 7.33 (d, J=2.8 Hz, 1H), 7.27 (t, J=9.6 Hz, 1H), 7.08 (dd, J=2.4, 8.8 Hz, 1H), 5.48-5.29 (m, 1H), 4.74-4.56 (m, 4H), 4.48-4.29 (m, 3H), 4.28-4.12 (m, 2H), 4.04-3.89 (m, 1H), 3.74-3.58 (m, 3H), 3.19-3.07 (m, 1H), 3.13-2.64 (m, 1H), 2.60-1.93 (m, 10H), 2.55-1.90 (m, 1H), 0.87-0.77 (m, 3H); LCMS (ESI, M+1):m/z=624.4

Example 344

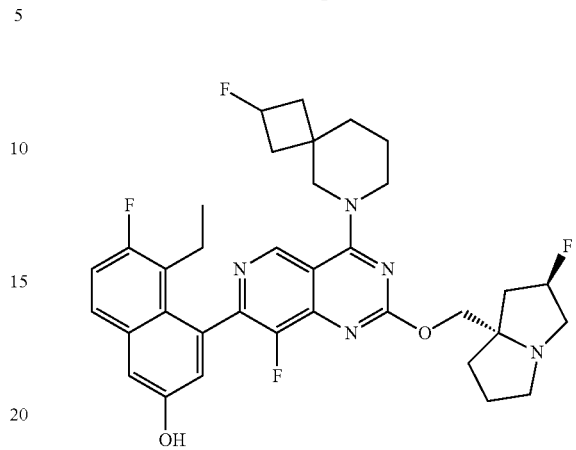

5-ethyl-6-fluoro-4-(8-fluoro-4-(2-fluoro-6-azaspiro[3.5]nonan-6-yl)-2-(((2R,7aS)-2-fluorohexahydro-1H-pyrrolizin-7a-yl)methoxy)pyrido[4,3-d]pyrimidin-7-yl)naphthalen-2-ol The title compound was synthesized according to the procedure described for example 330. $^1$H NMR (400 MHz, chloroform-d) δ=9.06-8.97 (m, 1H), 7.58-7.51 (m, 1H), 7.23-6.87 (m, 3H), 5.96-5.73 (m, 1H), 5.45-5.09 (m, 3H), 4.66-4.48 (m, 2H), 4.43-4.19 (m, 2H), 3.44-2.93 (m, 6H), 2.57-2.35 (m, 3H), 2.25-2.16 (m, 2H), 2.03-1.85 (m, 4H), 1.82-1.62 (m, 5H), 0.89-0.74 (m, 3H); LCMS (ESI, M+1): m/z=636.3.

Example 345

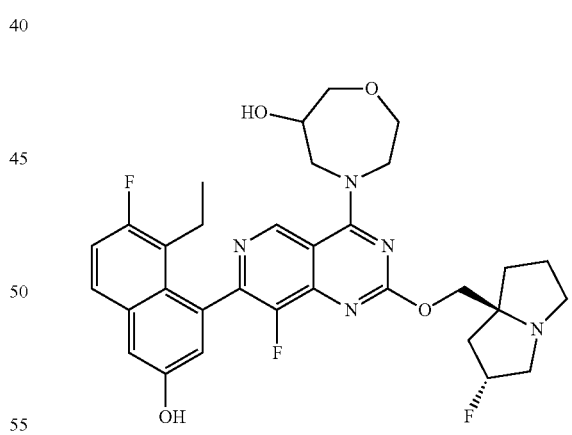

4-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1,4-oxazepan-6-ol The title compound was synthesized according to the procedure described for example 330. $^1$H NMR (400 MHz, METHANOL-d$_4$) δ=9.33 (d, J=11.6 Hz, 1H), 8.55 (s, 1H), 7.67 (dd, J=6.0, 9.2 Hz, 1H), 7.30 (d, J=2.8 Hz, 1H), 7.25 (t, J=9.6 Hz, 1H), 7.06 (d, J=2.4 Hz, 1H), 5.37 (br s, 1H), 4.46-4.39 (m, 1H), 4.37-4.21 (m, 5H), 4.17-4.00 (m, 3H), 4.00-3.89 (m, 1H), 3.79-3.67 (m, 1H), 3.24 (br s, 1H), 3.18 (s, 11H), 3.01 (dt, J=6.0, 9.6 Hz, 11H), 2.56-2.45 (m, 1H), 2.36-2.11 (m, 4H), 2.08-1.81 (m, 4H), 0.87-0.73 (m, 3H); LCMS (ESI, M+1):m/z=610.4.

Example 346

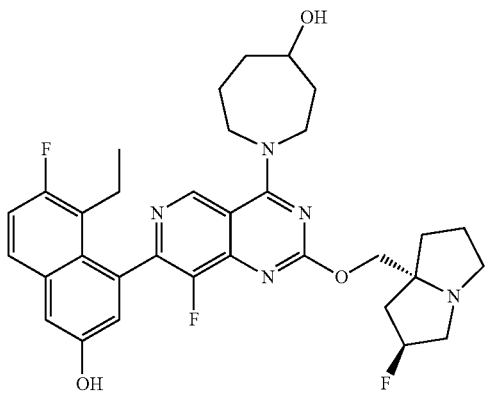 [SMILES: CCc1c(F)ccc2cc(O)cc(-c3ncc4c(N5CCCC(O)CC5)nc(OC[C@]56CCCN5C[C@@H](F)C6)nc4c3F)c12]

1-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)azepan-4-ol The title compound was synthesized according to the procedure described for example 330. $^1$H NMR (400 MHz, MeOH-d$_4$) δ=9.17 (s, 1H), 8.49 (br s, 1H), 7.68 (dd, J=6.0, 9.2 Hz, 1H), 7.31 (d, J=2.8 Hz, 1H), 7.25 (t, J=9.6 Hz, 1H), 7.05 (d, J=2.8 Hz, 1H), 5.51-5.33 (m, 1H), 4.52-4.46 (m, 1H), 4.44-4.37 (m, 1H), 4.25-4.17 (m, 11H), 4.25-4.15 (m, 1H), 4.13 (br t, J=5.6 Hz, 1H), 4.06-3.95 (m, 2H), 3.67-3.45 (m, 3H), 3.25-3.17 (m, 1H), 2.55-2.35 (m, 3H), 2.34-2.18 (m, 4H), 2.17-2.05 (m, 3H), 2.02-1.84 (m, 3H), 1.83-1.70 (m, 1H), 0.80 (t, J=7.2 Hz, 3H). LCMS (ESI, M+1): m/z=608.1

Example 347

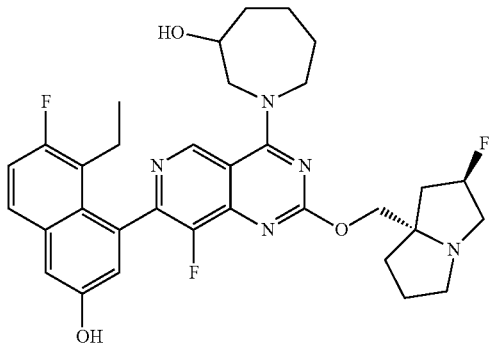 [SMILES: CCc1c(F)ccc2cc(O)cc(-c3ncc4c(N5CCCCC(O)C5)nc(OC[C@@]56CCCN5C[C@H](F)C6)nc4c3F)c12]

1-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)azepan-3-ol

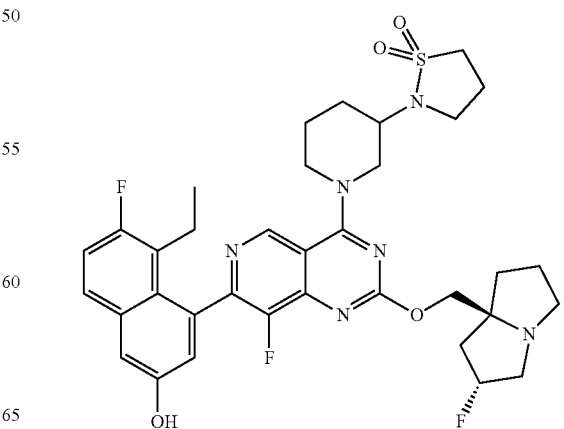

The title compound was synthesized according to the procedure described for example 330. $^1$H NMR (400 MHz, METHANOL-d$_4$) δ=9.35-9.18 (m, 1H), 8.56-8.41 (m, 1H), 7.68 (dd, J=6.0, 8.8 Hz, 1H), 7.36-7.19 (m, 2H), 7.05 (dd, J=2.8, 4.4 Hz, 1H), 5.53-5.31 (m, 1H), 4.59 (s, 1H), 4.54-4.37 (m, 3H), 4.19 (td, J=4.0, 8.4 Hz, 1H), 4.14 (t, J=6.4 Hz, 1H), 3.88-3.76 (m, 1H), 3.46 (s, 3H), 3.26-3.18 (m, 1H), 2.54-1.92 (m, 12H), 1.68 (d, J=10.8 Hz, 1H), 1.55-1.40 (m, 1H), 0.88-0.72 (m, 3H); LCMS [ELSD, M+1]: m/z=608.1

Example 348

2-(1-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)isothiazolidine 1,1-dioxide The title compound was synthesized according to the procedure described for example 330. ¹H NMR (400 MHz, DMSO-d₆) δ=9.09 (s, 1H), 7.76 (br dd, J=6.0, 8.8 Hz, 1H), 7.44-7.25 (m, 2H), 7.02 (br s, 11H), 5.47-5.11 (m, 1H), 4.60 (br t, J=13.6 Hz, 1H), 4.50-4.35 (m, 1H), 4.21-4.03 (m, 2H), 3.71-3.59 (m, 2H), 3.22 (br d, J=3.6 Hz, 3H), 3.14-2.94 (m, 4H), 2.86-2.65 (m, 2H), 2.37-2.30 (m, 1H), 2.29-2.19 (m, 2H), 2.18-2.08 (m, 2H), 2.03 (br d, J=16.4 Hz, 3H), 1.94-1.71 (m, 6H), 0.72 (q, J=7.2 Hz, 3H); LCMS (ESI, M+1): m/z=697.4.

Example 349

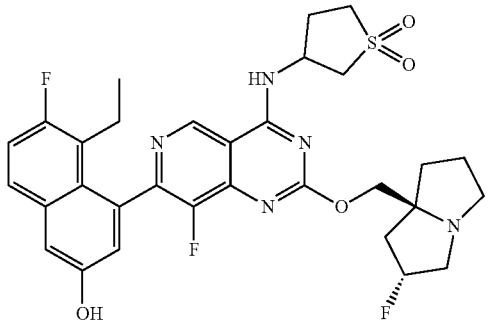 [SMILES: CCc1c(F)ccc2cc(O)cc(-c3ncc4c(NC5CCS(=O)(=O)C5)nc(OC[C@@]56CCCN5C[C@H](F)C6)nc4c3F)c12]

3-((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)tetrahydrothiophene 1,1-dioxide The title compound was synthesized according to the procedure described for example 330. ¹H NMR (400 MHz, DMSO-d₆) δ=9.36 (d, J=2.0 Hz, 1H), 9.10 (br d, J=6.8 Hz, 1H), 8.35 (s, 1H), 7.77 (dd, J=6.0, 9.2 Hz, 1H), 7.41-7.28 (m, 2H), 6.99 (d, J=2.4 Hz, 1H), 5.41-5.17 (m, 1H), 5.14-5.02 (m, 1H), 4.23-4.03 (m, 2H), 3.76-3.59 (m, 2H), 3.06-2.98 (m, 2H), 2.86-2.78 (m, 1H), 2.72-2.65 (m, 2H), 2.35-2.29 (m, 3H), 2.13-1.97 (m, 4H), 1.95-1.68 (m, 4H), 0.71 (t, J=7.6 Hz, 3H), LCMS (ESI, M+1): m/z=628.2.

Example 350

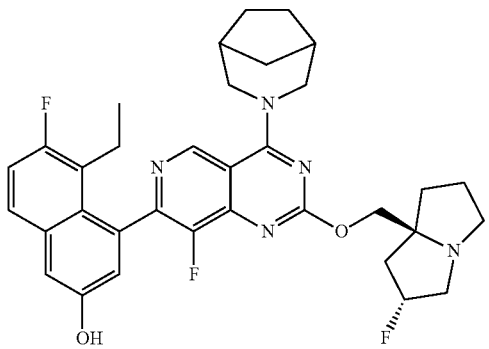 [SMILES: CCc1c(F)ccc2cc(O)cc(-c3ncc4c(N5CC6CCC(C6)C5)nc(OC[C@@]56CCCN5C[C@H](F)C6)nc4c3F)c12]

4-(4-(3-azabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 330. LCMS (ESI, M+1): m/z=604.0.

Example 351

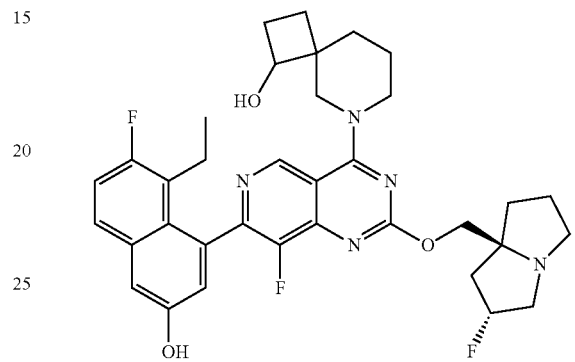

6-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azaspiro[3.5]nonan-1-ol The title compound was synthesized according to the procedure described for example 330. ¹H NMR (400 MHz, METHANOL-d₄) δ=9.14 (d, J=6.0 Hz, 1H), 8.61-8.44 (m, 1H), 7.75-7.62 (m, 1H), 7.31 (d, J=2.4 Hz, 11H), 7.25 (t, J=9.6 Hz, 1H), 7.07 (t, J=3.2 Hz, 1H), 5.49-5.27 (m, 1H), 4.52-4.27 (m, 3H), 4.25-4.11 (m, 1H), 4.10-3.81 (m, 3H), 3.57-3.37 (m, 3H), 3.20-3.08 (m, 1H), 2.55-2.16 (m, 6H), 2.14-2.05 (m, 2H), 2.00-1.84 (m, 4H), 1.83-1.72 (m, 2H), 1.72-1.55 (m, 1H), 1.38-1.30 (m, 1H), 0.86-0.74 (m, 3H). LCMS (ESI, M+1): m/z=634.5.

Example 352

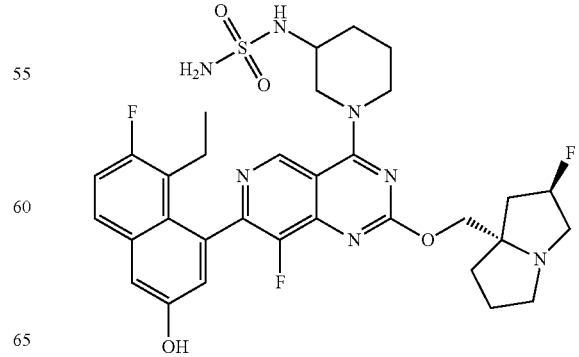

7-(8-ethyl-7-fluoro-3-hydroxy-1-naphthyl)-8-fluoro-2-(((2R,7aS)-2-fluorohexahydro-1H-pyrrolizin-7a-yl)methoxy)-4-[3-(sulfamoylamino)-1-piperidyl]pyrido[4,3-d]pyrimidine The title compound was synthesized according to the procedure described for example 330. $^1$H NMR (400 MHz, METHANOL-$d_4$) δ=9.12 (s, 1H), 7.69-7.60 (m, 1H), 7.28 (d, J=2.4 Hz, 1H), 7.23 (t, J=9.2 Hz, 1H), 7.05 (t, J=3.2 Hz, 1H), 5.41-5.20 (m, 1H), 4.79-4.67 (m, 1H), 4.46-4.23 (m, 3H), 3.75-3.60 (m, 2H), 3.58-3.45 (m, 1H), 3.28-3.11 (m, 3H), 3.04-2.95 (m, 1H), 2.57-2.43 (m, 1H), 2.41-2.12 (m, 5H), 2.05-1.87 (m, 4H), 1.85-1.67 (m, 2H), 0.87-0.73 (m, 3H); LCMS [ESI, M+1]: m/z=672.2.

Example 353

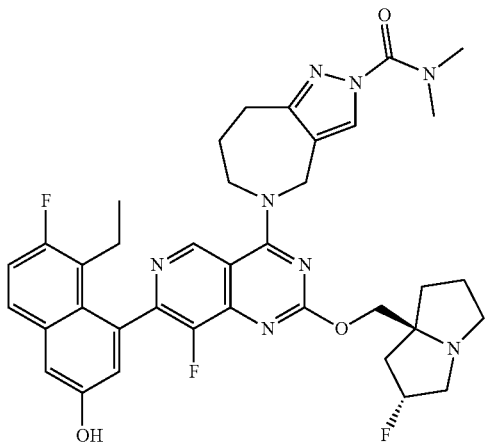 [SMILES: CCc1c(F)ccc2cc(O)cc(-c3ncc4c(N5CCCc6nn(C(=O)N(C)C)cc6C5)nc(OC[C@@]56CCCN5C[C@H](F)C6)nc4c3F)c12]

5-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-N,N-dimethyl-5,6,7,8-tetrahydropyrazolo[4,3-c]azepine-2(4H)-carboxamide The title compound was synthesized according to the procedure described for example 330. $^1$H NMR (400 MHz, DMSO-$d_6$) δ=9.97 (s, 1H), 9.16 (s, 1H), 8.20 (s, 1H), 7.76 (dd, J=6.0, 9.2 Hz, 11H), 7.38-7.31 (m, 2H), 7.01 (d, J=2.4 Hz, 11H), 5.46-5.26 (m, 11H), 5.12-5.00 (m, 2H), 4.32 (br s, 5H), 3.10 (br s, 6H), 2.99-2.82 (m, 3H), 2.43-1.74 (m, 1H), 1.23 (s, 1H), 0.70 (t, J=7.2 Hz, 3H); LCMS (ESI, M+1): m/z=701.4.

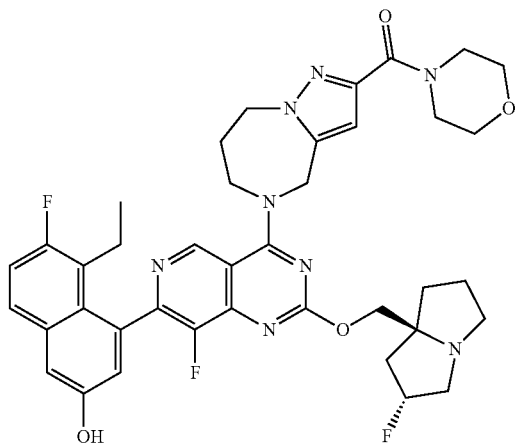 [SMILES: CCc1c(F)ccc2cc(O)cc(-c3ncc4c(N5CCCn6nc(C(=O)N7CCOCC7)cc6C5)nc(OC[C@@]56CCCN5C[C@H](F)C6)nc4c3F)c12]

(5-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-yl)(morpholino)methanone The title compound was synthesized according to the procedure described for example 330. $^1$H NMR (400 MHz, CD3OD) δ=9.25 (s, 1H), 7.75-7.65 (m, 11H), 7.32 (d, J=2.4 Hz, 1H), 7.26 (t, J=9.2 Hz, 1H), 7.05 (d, J=2.4 Hz, 1H), 6.79 (s, 1H), 5.68-5.51 (m, 1H), 5.38-5.30 (m, 1H), 5.28-5.20 (m, 1H), 4.83-4.75 (m, 2H), 4.73-4.59 (m, 2H), 4.53 (br d, J=5.6 Hz, 2H), 4.12-4.03 (m, 2H), 3.95-3.87 (m, 2H), 3.77-3.64 (m, 6H), 3.52-3.42 (m, 1H), 2.83-2.05 (m, 11H), 0.78 (t, J=7.2 Hz, 3H); LCMS (ESI, M+1): m/z=743.3.

Example 355

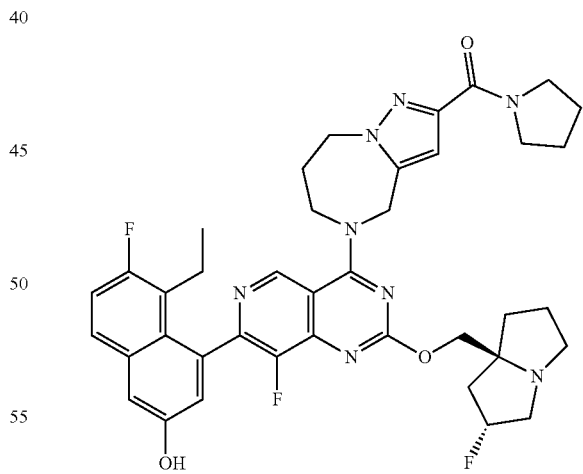

(5-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-5,6,7,8-tetrahydro-4H-pyrazolo[1,5-a][1,4]diazepin-2-yl)(pyrrolidin-1-yl)methanone The title compound was synthesized according to the procedure described for example 330. $^1$H NMR (400 MHz, CD3OD) δ=9.24 (s, 1H), 7.73-7.65 (m, 1H), 7.32 (d, J=2.4 Hz, 1H), 7.26 (t, J=9.2 Hz, 1H), 7.05 (d, J=2.4 Hz, 1H), 6.85 (s, 1H), 5.65-5.43 (m, 1H), 5.39-5.19 (m, 2H), 4.59-4.42 (m, 6H), 3.98-3.87 (m, 2H), 3.81-3.71 (m, 2H), 3.60 (t, J=6.8 Hz, 2H), 2.71-2.06 (m, 11H), 2.03-1.81 (m, 5H), 0.78 (t, J=7.2 Hz, 3H); LCMS [ESI, M+1]: m/z=727.4.

Example 356

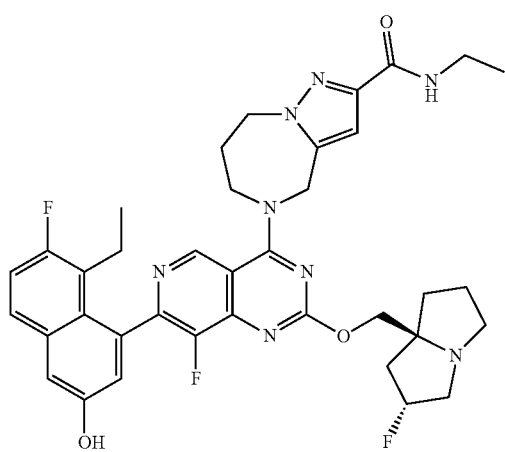 [SMILES: CCNC(=O)c1cc2n(n1)CCCN(c1nc(OC[C@@]34CCCN3C[C@H](F)C4)nc3c(F)c(-c4cc(O)cc5ccc(F)c(CC)c45)ncc13)C2]

N-ethyl-5-(7-(8-ethyl-7-fluoro-3-hydroxynaphtha-len-1-yl)-8-fluoro-2-(((2R,7aS)-2-fluorohexahydro-1H-pyrrolizin-7a-yl)methoxy)pyrido[4,3-d]pyrimidin-4-yl)-5,6,7,8-tetrahydro-4H-pyrazolo[1,5-a][1,4]diazepine-2-carboxamide The title compound was synthesized according to the procedure described for example 330. $^1$H NMR (400 MHz, DMSO-d$_4$) δ=9.94 (s, 1H), 9.20 (s, 1H), 8.09 (br t, J=6.0 Hz, 1H), 7.83-7.69 (m, 1H), 7.39-7.30 (m, 2H), 7.00 (d, J=2.4 Hz, 1H), 6.65 (s, 1H), 5.53-5.00 (m, 3H), 4.56-4.47 (m, 2H), 4.42-4.25 (m, 2H), 4.22-3.96 (m, 2H), 3.27-3.15 (m, 3H), 3.13-2.74 (m, 3H), 2.33 (br s, 2H), 2.21-1.97 (m, 5H), 1.88-1.73 (m, 3H), 1.05 (t, J=7.2 Hz, 3H), 0.70 (br t, J=7.2 Hz, 3H); LCMS (ESI, M+1): m/z=701.1.

Example 357

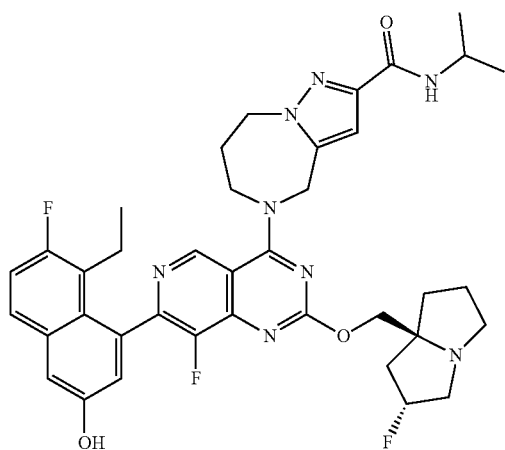 [SMILES: CCc1c(F)ccc2cc(O)cc(-c3ncc4c(N5CCCn6nc(C(=O)NC(C)C)cc6C5)nc(OC[C@@]56CCCN5C[C@H](F)C6)nc4c3F)c12]

5-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-N-isopropyl-5,6,7,8-tetrahydro-4H-pyrazolo[1,5-a][1,4]diazepine-2-carboxamide The title compound was synthesized according to the procedure described for example 330. $^1$H NMR (400 MHz, DMSO-d$_6$) δ=11.09-10.83 (m, 1H), 9.27 (s, 1H), 7.81-7.73 (m, 2H), 7.40-7.32 (m, 2H), 7.02 (d, J=2.4 Hz, 1H), 6.77 (s, 1H), 5.68-5.50 (m, 1H), 5.36-5.19 (m, 2H), 4.64-4.38 (m, 6H), 4.09-4.00 (m, 1H), 3.91-3.84 (m, 1H), 3.17-3.08 (m, 1H), 2.23-2.00 (m, 5H), 1.29-1.24 (m, 7H), 1.12 (d, J=6.4 Hz, 6H), 0.70 (t, J=7.2 Hz, 3H); LCMS (ESI, M+1): m/z=715.5.

Example 358

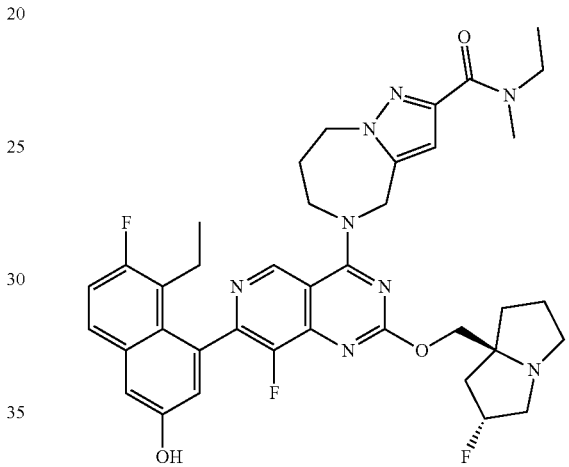

N-ethyl-5-(7-(8-ethyl-7-fluoro-3-hydroxynaphtha-len-1-yl)-8-fluoro-2-(((2R,7aS)-2-fluorotetrahydro-1H-pyrrolizin-7a(5H)-yl)methoxy)pyrido[4,3-d]pyrimidin-4-yl)-N-methyl-5,6,7,8-tetrahydro-4H-pyrazolo[1,5-a][1,4]diazepine-2-carboxamide The title compound was synthesized according to the procedure described for example 330. $^1$H NMR (400 MHz, METHANOL-d$_4$) δ=9.26 (s, 1H), 8.09 (s, 1H), 7.69 (dd, J=6.0, 9.0 Hz, 1H), 7.32 (d, J=2.8 Hz, 1H), 7.26 (t, J=9.6 Hz, 1H), 7.05 (d, J=2.4 Hz. 1H), 6.76 (br d, J=4.0 Hz, 1H), 5.70-5.48 (m, 1H), 5.37-5.19 (m, 2H), 4.76-4.43 (m, 6H), 4.03-3.73 (m, 3H), 4.05-3.70 (m, 1H), 3.62-3.43 (m, 2H), 3.06 (s, 11H), 2.84-2.02 (m, 11H), 1.22 (td, J=7.2, 11.8 Hz, 3H), 0.78 (br t, J=7.2 Hz, 3H); LCMS (ESI, M+1):m/z=715.5

Example 359

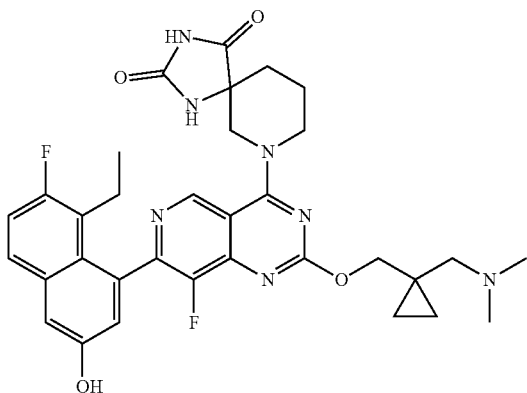 [SMILES: CCc1c(F)ccc2cc(O)cc(-c3ncc4c(N5CCCC6(C5)NC(=O)NC6=O)nc(OCC5(CN(C)C)CC5)nc4c3F)c12]

7-(2-((1-(((dimethylamino)methyl)cyclopropyl)
methoxy)-7-(8-ethyl-7-fluoro-3-hydroxynaphthalen-
1-yl)-8-fluoropyrido[4,3-d]pyrimidin-4-yl)-1,3,7-
triazaspiro[4.5]decane-2,4-dione

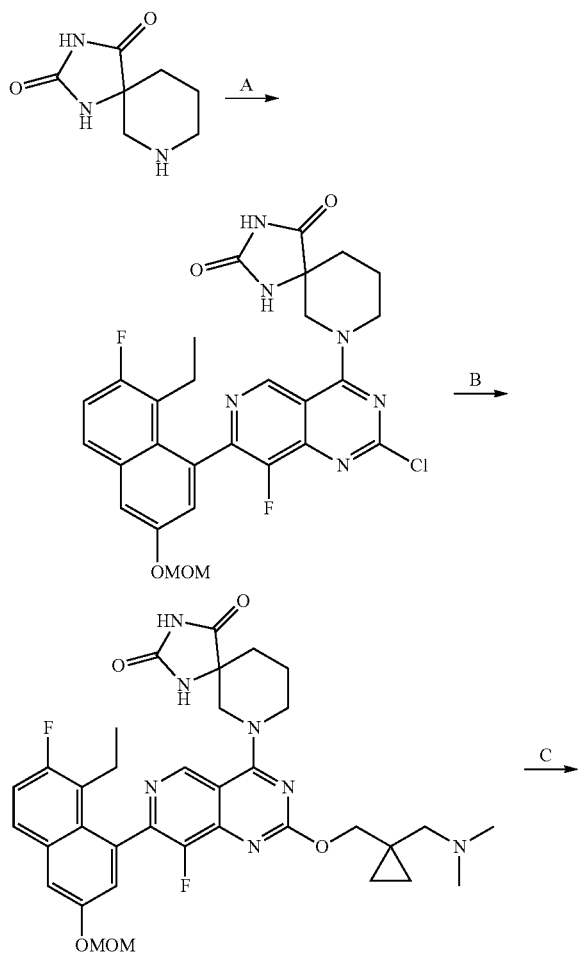

Step A. 7-(2-chloro-7-(8-ethyl-7-fluoro-3-(methoxymethoxy)naphthalen-1-yl)-8-fluoropyrido[4,3-d]pyrimidin-4-yl)-1,3,7-triazaspiro[4.5]decane-2,4-dione: To a solution of 2,4-dichloro-7-(8-ethyl-7-fluoro-3-(methoxymethoxy)naphthalen-1-yl)-8-fluoropyrido[4,3-d]pyrimidine (200 mg, 1.0 equiv.) in DCM (2 mL) was added DIEA (172 mg, 3.0 equiv.) and 1,3,7-triazaspiro[4.5]decane-2,4-dione (75.2 mg, 1.0 equiv.) at −40° C. The reaction mixture was stirred at −40° C. for 1 hour. The mixture was poured dropwise into ice-cold saturated NH$_4$Cl solution (8 mL). Then the mixture was extracted with ethyl acetate (2×5 mL). The combined organic layers were washed with brine (5 mL), dried over anhydrous sodium sulfate, filtered and concentrated in vacuum to give a residue. The residue was purified by reversed phase flash chromatography [water (0.1% formic acid)/acetonitrile]. The desired fractions were collected and neutralized with solid NaHCO$_3$, and concentrated in vacuum to remove acetonitrile. The aqueous layer was extracted with ethyl acetate (10 mL×2). The combined organic layers were dried over anhydrous sodium sulfate, filtered and concentrated in vacuum to afford the title compound (170 mg, 64.7% yield) as a white solid; LCMS (ESI, M+1): m/z=583.2.

Step B. 7-(2-((1-(((dimethylamino)methyl)cyclopropyl)methoxy)-7-(8-ethyl-7-fluoro-3-(methoxymethoxy)naphthalen-1-yl)-8-fluoropyrido[4,3-d]pyrimidin-4-yl)-1,3,7-triazaspiro[4.5]decane-2,4-dione: To a solution of 7-(2-chloro-7-(8-ethyl-7-fluoro-3-(methoxymethoxy)naphthalen-1-yl)-8-fluoropyrido[4,3-d]pyrimidin-4-yl)-1,3,7-triazaspiro[4.5]decane-2,4-dione (170 mg, 1.0 equiv.) in THF (2 mL) were added (1-((dimethylamino)methyl)cyclopropyl)methanol (113 mg, 3.0 equiv.), DIEA (113 mg, 3.0 equiv.) and 4 Å molecular sieves (10 mg). The reaction mixture was stirred at 40° C. for 12 hours. The mixture was filtered. The filter cake was triturated with dichloromethane/methanol 10:1 (10 mL) at 25° C. for 15 mins to afford the title compound (140 mg, 68.5% yield) as a white solid; LCMS (EST, M+1): m/z=676.4.

Step C. 7-(2-((1-(((dimethylamino)methyl)cyclopropyl)methoxy)-7-(8-ethyl-7-fluoro-3-hydroxynaphthalen-1-yl)-8-fluoropyrido[4,3-d]pyrimidin-4-yl)-1,3,7-triazaspiro[4.5]decane-2,4-dione: To a solution of 7-(2-((1-(((dimethylamino)methyl)cyclopropyl)methoxy)-7-(8-ethyl-7-fluoro-3-(methoxymethoxy)naphthalen-1-yl)-8-fluoropyrido[4,3-d]pyrimidin-4-yl)-1,3,7-triazaspiro[4.5]decane-2,4-dione (130 mg, 1.0 equiv.) in MeCN (1 mL) was added HCl.dioxane (4 M, 6.0 equiv.) at 0° C. The reaction mixture was stirred at 0° C. for 1 hour. The mixture was concentrated in vacuum to give a residue. The residue was purified by reversed phase flash chromatography [water (0.1% formic acid)/acetonitrile]. The desired fractions were collected and lyophilized to afford the title compound (92.7 mg, 69.1% yield, formic acid salt) as a white solid; $^1$H NMR (400 MHz, methanol-$d_4$) δ=9.14 (d, J=4.0 Hz, 1H), 8.50 (br s, 1H), 7.69 (dd, J=6.0, 9.2 Hz, 1H), 7.32 (d, J=2.4 Hz, 1H), 7.26 (t, J=9.2 Hz, 1T), 7.06 (d, J=2.4 Hz, 1H), 4.70-4.53 (m, 2H), 4.45-4.38 (m, 2H), 3.95-3.74 (m, 2H), 3.23-3.09 (m, 2H), 2.87 (s, 6H), 2.55-2.35 (m, 1H), 2.32-2.03 (m, 3H), 2.03-1.89 (m, 2H), 1.00-0.90 (m, 2H), 0.87-0.71 (m, 5H); LCMS (ESI, M+1): m/z=632.4.

Example 360

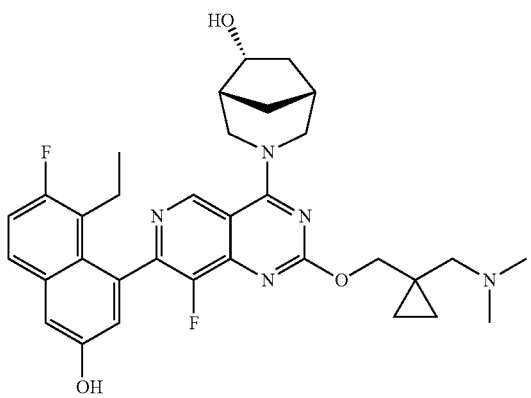 [SMILES: CCc1c(F)ccc2cc(O)cc(-c3ncc4c(N5C[C@@H]6C[C@H](C5)[C@H](O)C6)nc(OCC5(CN(C)C)CC5)nc4c3F)c12]

(1R,5R,6R)-3-(2-((1-((dimethylamino)methyl)cyclopropyl)methoxy)-7-(8-ethyl-7-fluoro-3-hydroxynaphthalen-1-yl)-8-fluoropyrido[4,3-d]pyrimidin-4-yl)-3-azabicyclo[3,2,1]octan-6-ol The title compound was synthesized according to the procedure described for example 359 except for TsOH (10 equiv.) in DCM was used in step C. $^1$H NMR (400 MHz, METHANOL-$d_4$) δ=9.28-9.18 (m, 1H), 7.67 (dd, J=5.6, 8.8 Hz, 1H), 7.34-7.28 (m, 1H), 7.27-7.20 (m, 1H), 7.06 (dd, J=2.8, 13.2 Hz, 1H), 4.63-4.51 (m, 2H), 4.37 (s, 2H), 4.35-4.28 (m, 1H), 3.82-3.7 (m, 1H), 3.52-3.43 (m, 1H), 2.55-2.44 (m, 3H), 2.423-2.38 (m, 1H), 2.37-2.29 (m, 6H), 2.28-2.10 (m, 3H), 1.96-1.88 (m, 1H), 1.85-1.77 (m, 11H), 1.46-1.37 (m, 1H), 0.85-0.76 (m, 3H), 0.76-0.70 (m, 2H), 0.57-0.49 (m, 2H); LCMS (ESI, M+1): m/z=590.2.

Example 361

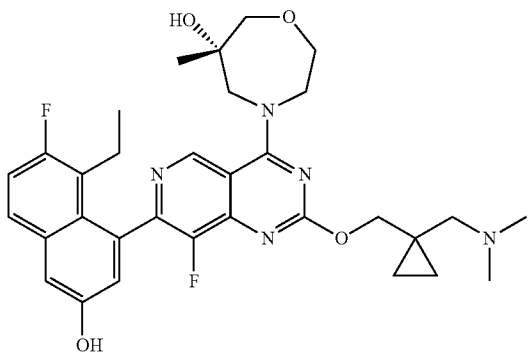 [SMILES: CCc1c(F)ccc2cc(O)cc(-c3ncc4c(N5CCOC[C@@](C)(O)C5)nc(OCC5(CN(C)C)CC5)nc4c3F)c12]

(S)-4-(2-((1-((dimethylamino)methyl)cyclopropyl)methoxy)-7-(8-ethyl-7-fluoro-3-hydroxynaphthalen-1-yl)-8-fluoropyrido[4,3-d]pyrimidin-4-yl)-6-methyl-1,4-oxazepan-6-ol The title compound was synthesized according to the procedure described for example 360. $^1$H NMR (400 MHz, METHANOL-$d_4$) δ=9.53 (d, J=4.4 Hz, 1H), 7.67 (dd, J=6.0, 8.98 Hz, 1H), 7.33-7.19 (m, 2H), 7.10-7.00 (m, 1H), 4.57-4.44 (m, 2H), 4.39 (dd, J=5.6, 10.4 Hz, 2H), 4.24-4.13 (m, 1H), 4.08-3.94 (m, 2H), 3.93-3.84 (m, 1H), 3.74-3.61 (m, 2H), 2.5-2.40 (m, 3H), 2.31 (s, 6H), 2.24-2.13 (m, 1H), 1.27 (d, J=2.8 Hz, 3H), 0.84-0.76 (m, 3H), 0.76-0.69 (m, 2H), 0.57-0.51 (m, 2H); LCMS (ESI, M+1): m/z=594.1.

Example 362

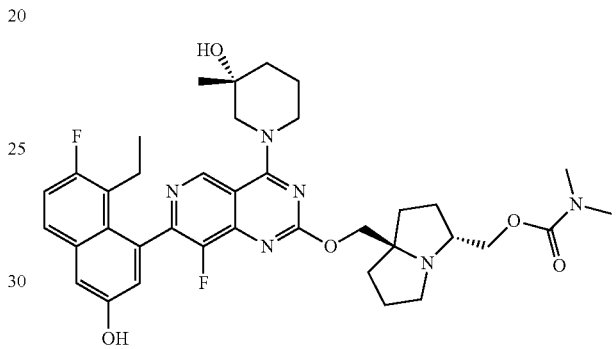

((3R,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl dimethylcarbamate

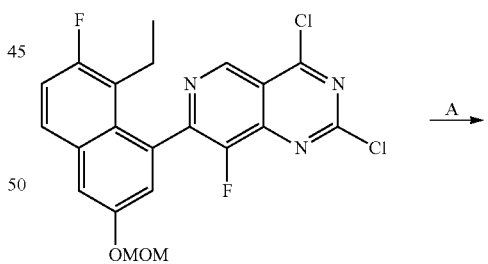

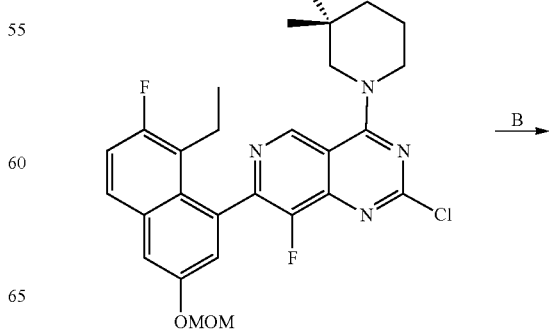

-continued

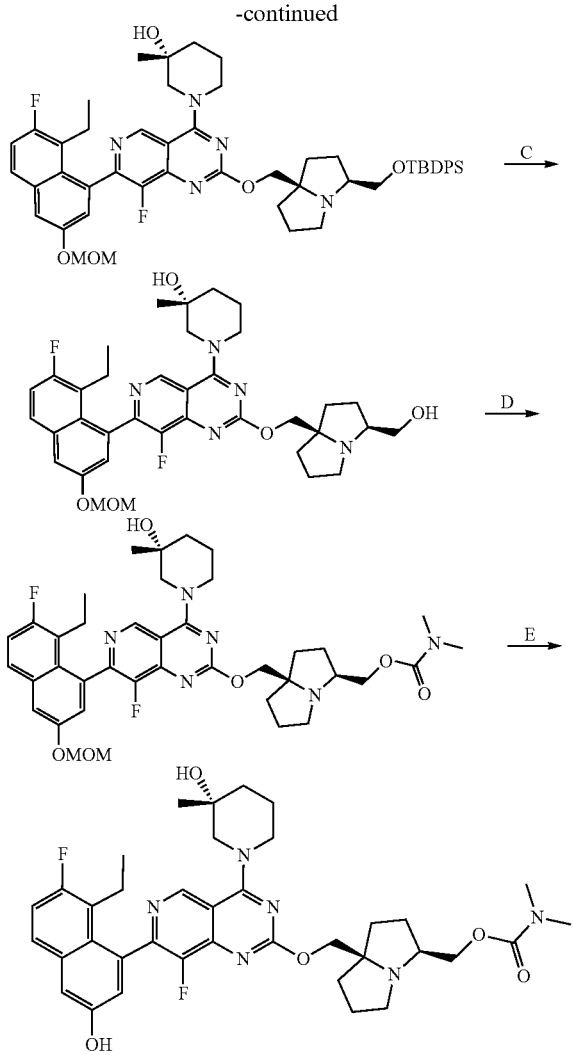

Step A. (R)-1-(2-chloro-7-(8-ethyl-7-fluoro-3-(methoxymethoxy)naphthalen-1-yl)-8-fluoropyrido[4,3-d]pyrimidin-4-yl)-3-methylpiperidin-3-ol: To a solution of 2,4-dichloro-7-[8-ethyl-7-fluoro-3-(methoxymethoxy)-1-naphthyl]-8-fluoro-pyrido[4,3-d]pyrimidine (5.00 g, 1.0 equiv.) in DCM (50 mL) were added 4 Å molecular sieves (30 mg, 1.0 equiv.), DIEA (7.18 g, 5.0 equiv.) and (3R)-3-methylpiperidin-3-ol (1.85 g, 1.1 equiv., HCl) at −40° C. The reaction mixture was stirred at −40° C. for 15 mins. The reaction mixture was diluted with DCM (30 mL) and water (40 mL), and extracted with DCM (20 mL). The combined organic phase was washed with brine (20 mL), dried over anhydrous sodium sulfate, filtered and concentrated in vacuum. The residue was purified by reversed phase flash chromatography [water (0.1% formic acid)/acetonitrile]. The desired fractions were collected and neutralized with solid NaHCO₃, and concentrated in vacuum to remove acetonitrile. The aqueous layer was extracted with ethyl acetate (2×20 mL). The combined organic layers were dried over anhydrous sodium sulfate, filtered and concentrated in vacuum to afford the title compound (4.9 g, 81.4% yield) as an off-yellow solid; LCMS (ESI, M+1): m/z=529.2.

Step B. (R)-1-(2-(((3R,7aR)-3-(((tert-butyldiphenylsilyl)oxy)methyl)hexahydro-1H-pyrrolizin-7a-yl methoxy)-7-(8-ethyl-7-fluoro-3-(methoxymethoxy)naphthalen-1-yl)-8-fluoropyrido[4,3-d]pyrimidin-4-yl)-3-methylpiperidin-3-ol: To a solution of ((3R,7aR)-3-(((tert-butyldiphenylsilyl)oxy)methyl)hexahydro-1H-pyrrolizin-7a-yl)methanol (465 mg, 1.2 equiv.) in toluene (5 mL) were added 4 Å molecular sieves (20 mg) and t-BuONa (273 mg, 3.0 equiv.) at 0° C. and the resulting mixture was stirred for 10 minutes. Then (R)-1-(2-chloro-7-(8-ethyl-7-fluoro-3-(methoxymethoxy)naphthalen-1-yl)-8-fluoropyrido[4,3-d]pyrimidin-4-yl)-3-methylpiperidin-3-ol (500 mg, 1.0 equiv.) was added and the mixture was stirred at 0° C. for 1 hour. The reaction mixture was diluted with ethyl acetate (15 mL) and water (20 mL), and extracted with ethyl acetate (10 mL). The combined organic phase was washed with brine (10 mL), dried over anhydrous sodium sulfate, filtered and concentrated in vacuum to give a residue. The residue was purified by reversed phase flash chromatography [water (0.1% formic acid)/acetonitrile]. The desired fractions were collected and neutralized with solid NaHCO₃, and concentrated in vacuum to remove acetonitrile. The aqueous layer was extracted with ethyl acetate (10 mL×2). The combined organic layers were dried over anhydrous sodium sulfate, filtered and concentrated in vacuum to afford the title compound (600 mg, 67.5% yield) as a yellow solid; $^1$H NMR (400 MHz, methanol-d4) 5-9.22 (d, J=2.2 Hz, 1H), 7.80 (dd, J=5.6, 9.2 Hz, 1H), 7.69 (qd, J=1.8, 6.0 Hz, 4H), 7.62 (d, J=2.8 Hz, 1H), 7.47-7.38 (m, 6H), 7.31 (t, J=9.2 Hz, 1H), 7.22 (t, J=3.2 Hz, 1H), 5.33 (s, 2H), 4.65-4.48 (m, 2H), 4.42-4.23 (m, 3H), 3.97 (dd, J=5.6, 10.8 Hz, 1H), 3.90-3.78 (m, 1H), 3.69-3.55 (m, 1H), 3.53-3.39 (m, 5H), 2.96-2.82 (m, 2H), 2.58-2.42 (m, 1H), 2.29-2.06 (m, 3H), 1.96-1.73 (m, 8H), 1.71-1.60 (m, 1H), 1.31-1.26 (m, 3H), 1.08-1.03 (m, 9H), 0.82 (dt, J=4.8, 7.2 Hz, 3H); LCMS (ESI, M+1): m/z=902.6.

Step C. (R)-1-(7-(8-ethyl-7-fluoro-3-(methoxymethoxy)naphthalen-1-yl)-8-fluoro-2-(((3R,7aR)-3-(hydroxymethyl)hexahydro-1H-pyrrolizin-7a-yl)methoxy)pyrido[4,3-d]pyrimidin-4-yl)-3-methylpiperidin-3-ol: To a solution of (R)-1-(2-(((3R,7aR)-3-(((tert-butyldiphenylsilyl)oxy)methyl)hexahydro-1H-pyrrolizin-7a-yl)methoxy)-7-(8-ethyl-7-fluoro-3-(methoxymethoxy)naphthalen-1-yl)-8-fluoropyrido[4,3-d]pyrimidin-4-yl)-3-methylpiperidin-3-ol (300 mg, 1.0 equiv.) in DMF (3 mL) was added CsF (758 mg, 15 equiv.). The reaction mixture was stirred at 40° C. for 12 hours. The mixture was filtered and the filtrate was purified by reversed phase flash chromatography [water (0.1% formic acid)/acetonitrile]. The desired fractions were collected and neutralized with solid NaHCO₃, and concentrated in vacuum to remove acetonitrile. The aqueous layer was extracted with ethyl acetate (5 mL×2). The combined organic layers were dried over anhydrous sodium sulfate, and concentrated in vacuum to afford the title compound (190 mg, 85.5% yield) as a yellow solid; LCMS (ESI, M+1): m/z=664.4.

Step D. ((3R,7aR)-7a-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl dimethylcarbamate: To a solution of (R)-1-(7-(8-ethyl-7-fluoro-3-(methoxymethoxy)naphthalen-1-yl)-8-fluoro-2-(((3R,7aR)-3-(hydroxymethyl)hexahydro-1H-pyrrolizin-7a-yl)methoxy)pyrido[4,3-d]pyrimidin-4-yl)-3-methylpiperidin-3-ol (190 mg, 1.0 equiv.) in THF (2 mL) was added NaH (22.9 mg, 60% purity, 2.0 equiv.) at 0° C. After stirring at 0° C. for 0.5 hour, N,N-dimethylcarbamoyl chloride (46.17 mg, 1.5 equiv.) in THF (1 mL) was added and the resulting was stirred at 0° C. for 2 hours. The mixture was quenched with water (10 ml) and extracted with ethyl acetate (2×10 mL). The combined organic layers were dried over anhydrous sodium sulfate, filtered and concentrated in vacuum. The residue was purified by reversed phase flash chromatography [water (0.1% formic acid)/acetonitrile]. The desired fractions were collected and neutralized with solid NaHCO₃, and concentrated in vacuum to remove acetonitrile. The aqueous layer was extracted with ethyl acetate (2×8 mL). The combined organic layers were dried over anhydrous sodium sulfate, and concentrated in vacuum to give a residue. Then the residue was purified by prep-TLC (silica gel, DCM/MeOH 10:1) to afford the title compound (45 mg, 21.4% yield) as a yellow solid; LCMS (ESI, M+1): m/z=735.6.

Step E. ((3R,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yloxy)methyl)hexahydro-1H-pyrrolizin-3-yl)methyl dimethylcarbamate: To a solution of ((3R,7aR)-7a-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl dimethylcarbamate (32 mg, 1.0 equiv.) in MeCN (0.3 mL) was added HCl.dioxane (4 M, 55 equiv.) at 0° C. The reaction mixture was stirred at 0° C. for 0.5 hour. The mixture was concentrated in vacuum. The residue was purified by reversed phase flash chromatography [water (0.1% formic acid)/acetonitrile]. The desired fractions were collected and lyophilized to afford the title compound (15.6 mg, 45.4% yield, formic acid salt) as a white solid; ¹H NMR (400 MHz, methanol-d4) δ=9.26-9.21 (m, 1H), 8.55 (s, 1H), 7.68 (dd, J=6.0, 9.2 Hz, 1H), 7.34-7.20 (m, 2H), 7.06 (s, 1H), 4.82-4.70 (m, 2H), 4.52-4.22 (m, 3H), 4.14-3.97 (m, 1H), 3.88-3.74 (m, 1H), 3.69-3.54 (m, 1H), 3.52-3.35 (m, 1H), 3.34-2.30 (m, 2H), 2.95-2.91 (m, 5H), 2.51-2.40 (m, 1H), 2.35-2.09 (m, 4H), 2.07-1.89 (d, J=14. Hz, 5H), 1.86-1.67 (m, 4H), 1.29 (d, J=9.2 Hz, 3H), 0.86-0.74 (m, 3H); LCMS (ESI, M+1): m/z=691.4.

Example 363

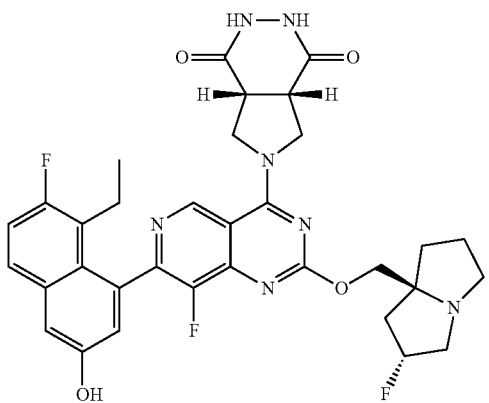 [SMILES: CCc1c(F)ccc2cc(O)cc(-c3ncc4c(N5C[C@@H]6C(=O)NNC(=O)[C@@H]6C5)nc(OC[C@@]56CCCN5C[C@H](F)C6)nc4c3F)c12]

(4aR,7aS)-6-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)hexahydro-1H-pyrrolo[3,4-d]pyridazine-1,4(4aH)-dione

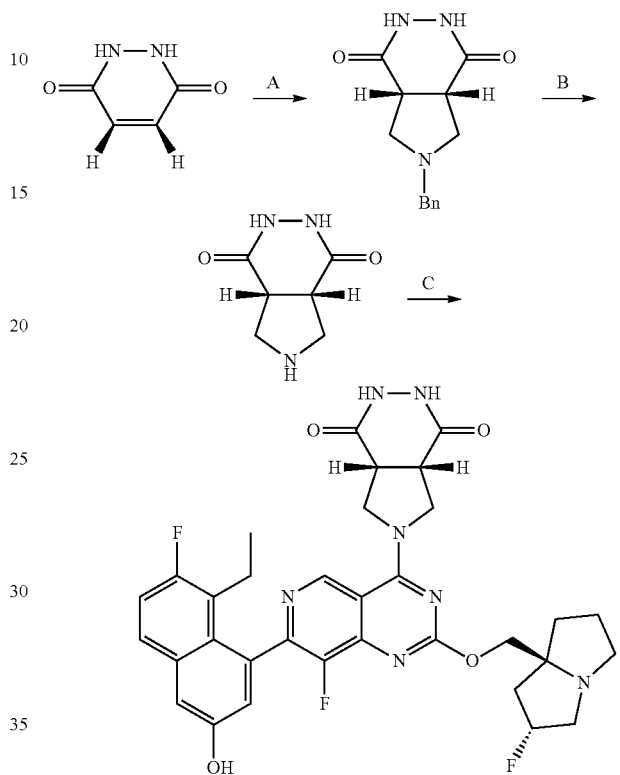

Step A. (4aR,7aS)-6-benzylhexahydro-1H-pyrrolo[3,4-d]pyridazine-1,4(4aH)-dione: To a solution of 1,2-dihydropyridazine-3,6-dione (10.0 g, 1.0 equiv.) in dichloromethane (90.0 mL) was added N-benzyl-1-methoxy-N-((trimethylsilyl)methyl)methanamine (42.4 g, 2.0 equiv.) at 0° C. The resulting mixture was stirred at 0° C. for 5 minutes, then TFA (1.02 g, 0.1 equiv.) in dichloromethane (10 mL) was added dropwise at 0° C. The resulting mixture was stirred at 25° C. for 2 hours. The mixture was quenched by addition of water (50 mL) and extracted with EtOAc (3×100 mL). The combined organic layers were washed with brine (3×50 mL), dried over anhydrous sodium sulfate, concentrated and triturated with dichloromethane/methyl alcohol 10:1 (3×100 mL) at 25° C. for 30 minutes and filtered to afford the title compound (10 g, crude) as a yellow solid; ¹H NMR (400 MHz, DMSO-d₆) δ 7.36-7.26 (m, 5H), 4.59 (d, J=13.2 Hz, 1H), 4.31 (d, J=12.8 Hz, 1H), 3.21-3.10 (m, 2H), 3.01-2.91 (m, 2H), 2.75 (dt, J=8.0, 9.6 Hz, 2H).

Step B. (4aR,7aS)-hexahydro-1H-pyrrolo[3,4-d]pyridazine-1,4(4aH)-dione: To a suspension of Pd/C (0.20 g, 10% purity) in MeOH (40.0 mL) was added (4aR,7aS)-6-benzylhexahydro-1H-pyrrolo[3,4-d]pyridazine-1,4(4aH)-dione (1.00 g, 1.0 equiv.) under N₂ atmosphere. The suspension was degassed and purged with H₂ for 3 times. The mixture was stirred under H₂ (15 Psi) at 25° C. for 1 hour. The mixture was filtered and concentrated to afford the title compound (0.23 g, 36% yield over two steps) as a yellow solid; ¹H NMR (400 MHz, DMSO-d4) δ 3.15-3.10 (m, 2H), 2.92-2.88 (m, 1H), 2.88-2.85 (m, 11H), 2.83-2.75 (m, 2H).

Step C. (4aR,7aS)-6-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)hexahydro-1H-pyrrolo[3,4-d]pyridazine-1,4(4aH)-dione: To a solution of 5-ethyl-6-fluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (150 mg, 1.0 equiv.) in DMF (2.0 mL) were added (4aR,7aS)-hexahydro-1H-pyrrolo[3,4-d]pyridazine-1,4(4aH)-dione (58.9 mg, 1.5 equiv.), DIEA (98.1 mg, 3.0 equiv.) and 4 Å molecular sieves (70 mg). The mixture was stirred at 40° C. for 16 hours. After reaction completion, the mixture was filtered and purified by prep-HPLC [column: Waters Xbridge 150×25 mm×5 μm; mobile phase: water (10 mM NH$_4$HCO$_3$)-ACN, B %: 30%-50%, 9 min] and re-purified by prep-HPLC [column: Waters Xbridge 150×25 mm×5 μm; mobile phase: water (10 mM ammonium hydroxide)-ACN, B %: 7%-37%, 9 min] to afford the title compound (16.9 mg, 10% yield, 99.2% purity) as a white solid; $^1$H NMR (400 MHz, Methanol-d4) δ 9.29 (s, 1H), 7.68 (dd, J=5.6, 9.2 Hz, 1H), 7.31 (d, J=2.8 Hz, 1H), 7.25 (t, J=9.6 Hz, 1H), 7.07 (d, J=2.8 Hz, 1H), 5.43-5.21 (m, 1H), 4.51-4.21 (m, 6H), 3.58-3.46 (m, 2H), 3.31-3.16 (m, 3H), 3.03 (dt, J=5.6, 9.2 Hz, 1H), 2.55-2.42 (m, 1H), 2.42-2.11 (m, 4H), 2.07-1.85 (m, 3H), 0.81 (t, J=7.2 Hz, 3H); LCMS (ESI, M+1): m/z=648.4.

Example 364

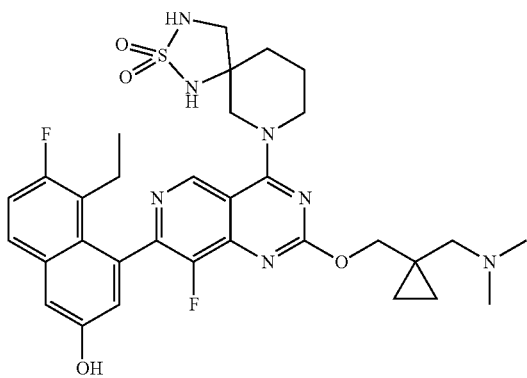 [SMILES: CCc1c(F)ccc2cc(O)cc(-c3ncc4c(N5CCCC6(CNS(=O)(=O)N6)C5)nc(OCC5(CN(C)C)CC5)nc4c3F)c12]

7-(2-((1-((dimethylamino)methyl)cyclopropyl)methoxy)-7-(8-ethyl-7-fluoro-3-hydroxynaphthalen-1-yl)-8-fluoropyrido[4,3-d]pyrimidin-4-yl)-2-thia-1,3,7-triazaspiro[4.5]decane 2,2-dioxide

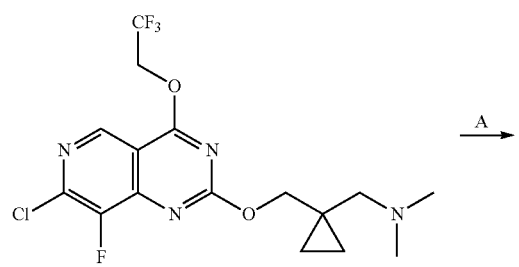

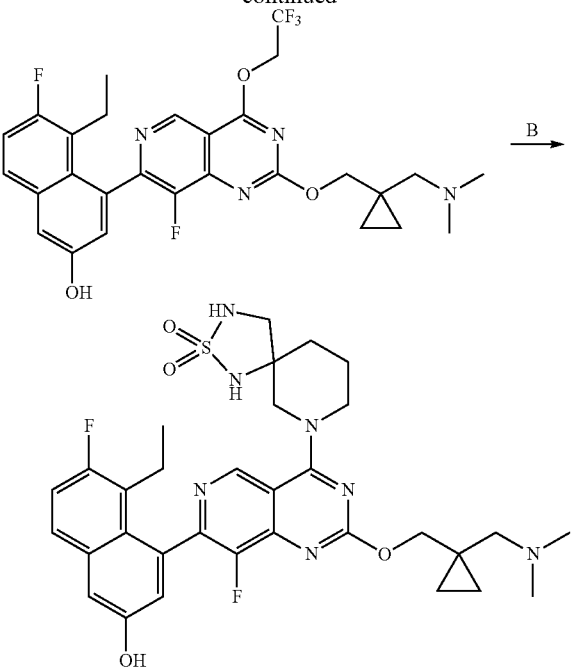

Step A. 4-(2-((1-((dimethylamino)methylcyclopropyl)methoxyl-8-fluoro-4-(2,2,2-trifluoroethoxy)pyrido[4,3-d]pyrimidin-7-yl)-5-ethyl-6-fluoronaphthalen-2-ol: To a mixture of 1-(1-(((7-chloro-8-fluoro-4-(2,2,2-trifluoroethoxy)pyrido[4,3-d]pyrimidin-2-yl)oxy)methyl)cyclopropyl)-N,N-dimethylmethanamine (500 mg, 1.0 equiv.), 5-ethyl-6-fluoro-4-(4,4,5,5-tetramethyl-1,3,2-dioxaborolan-2-yl)naphthalen-2-ol (464 mg, 1.2 equiv.), K$_3$PO$_4$ (1.5 M, 2.45 mL, 3.0 equiv.) in methoxycyclopentane (5 mL) was added CataCXium A Pd G3 (89.0 mg, 0.1 equiv.). The reaction mixture was stirred at 90° C. for 2 hours under N$_2$ atmosphere. The reaction mixture was quenched by addition of water (5 mL), and extracted with ethyl acetate (15 mL). The combined organic layer was dried over anhydrous sodium sulfate, concentrated and purified by reversed-phase flash chromatography (water (0.1% formic acid)-ACN) to give title compound (333 mg, 47% yield) as a yellow solid; LCMS (ESI, M+1): m/z=563.3.

Step B. 7-(2-((1-((dimethylamino)methyl)cyclopropyl)methoxyl-7-(8-ethyl-7-fluoro-3-hydroxynaphthalen-1-yl)-8-fluoropyrido[4,3-d]pyrimidin-4-yl)-2-thia-1,3,7-triazaspiro[4.5]decane 2,2-dioxide: To a mixture of 4-(2-((1-((dimethylamino)methyl)cyclopropyl)methoxy)-8-fluoro-4-(2,2,2-trifluoroethoxy)pyrido[4,3-d]pyrimidin-7-yl)-5-ethyl-6-fluoronaphthalen-2-ol (170 mg, 1.0 equiv.), 2-thia-1,3,7-triazaspiro[4.5]decane 2,2-dioxide (69.3 mg, 1.2 equiv.), 4 Å molecular sieves (20.0 mg) in DMF (2 mL) was added DIEA (195 mg, 5.0 equiv.). The reaction mixture was stirred at 40° C. for 12 hours. The reaction mixture was filtered. The filtrate was purified by prep-HPLC (column: Phenomenex Synergi C18 150×25 mm×10 μm; mobile phase: [water (0.1% formic acid)-ACN]; B %: 13%-43%, 10 min) and lyophilized to afford title compound (141 mg, 69% yield) as a white solid; $^1$H NMR (400 MHz, METHANOL-d$_4$): δ=9.12 (s, 1H), 8.52 (s, 1H), 7.68 (ddd, J=3.2, 5.6, 9.2 Hz, 1H), 7.31 (d, J=1.6 Hz, 1H), 7.28-7.22 (m, 1H), 7.03 (dd, J=2.4, 10.0 Hz, 1H), 4.59 (br t, J=12.0 Hz, 1H), 4.51-4.38 (m, 3H), 3.85-3.73 (m, 1H), 3.72-3.60 (m, 1H), 3.37 (dd, J=12.0, 14.4 Hz, 1H), 3.20 (d, J=12.0 Hz, 1H), 3.15-3.05 (m, 2H), 2.83 (s, 6H), 2.49 (ddd, J=6.4, 7.6, 14.4 Hz, 1H), 2.26-2.11 (m, 1H), 2.08-1.99 (m, 2H), 1.97-1.81 (m, 2H), 0.93 (s, 2H), 0.83-0.75 (m, 5H) LCMS(ESI, M+1): m/z=654.0.

Example 365

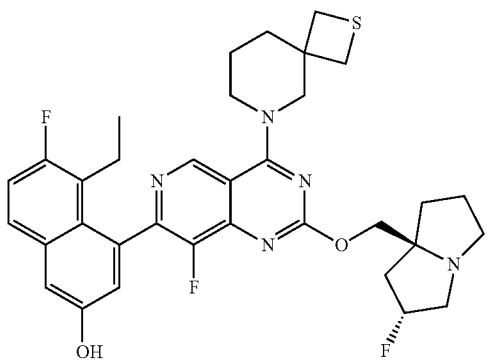 [SMILES: CCc1c(F)ccc2cc(O)cc(-c3ncc4c(N5CCCC6(CSC6)C5)nc(OC[C@@]56CCCN5C[C@H](F)C6)nc4c3F)c12]

5-ethyl-6-fluoro-4-(8-fluoro-2-(((2R,7aS)-2-fluoro-hexahydro-1H-pyrrolizin-7a-yl)methoxy)-4-(2-thia-6-azaspiro[3.5]nonan-6-yl)pyrido[4,3-d]pyrimidin-7-yl)naphthalen-2-ol The title compound was synthesized according to the procedure described for example 330. $^1$H NMR (400 MHz, METHANOL-d$_4$) δ=9.15 (s, 1H), 7.68 (dd, J=6.0, 9.2 Hz, 1H), 7.31 (d, J=2.8 Hz, 1H), 7.25 (t, J=9.6 Hz, 1H), 7.07 (d, J=2.4 Hz, 1H), 5.52-5.32 (m, 1H), 4.63-4.41 (m, 3H), 4.30 (dd, J=13.2, 19.2 Hz, 1H), 4.18-4.04 (m, 1H), 3.93 (qd, J=6.4, 12.8 Hz, 1H), 3.64-3.40 (m, 3H), 3.24-3.11 (m, 3H), 2.95-2.78 (m, 2H), 2.55-2.30 (m, 3H), 2.28-2.09 (m, 4H), 2.06-1.87 (m, 3H), 1.77 (q, J=5.6 Hz, 2H), 0.80 (t, J=7.2 Hz, 3H); LCMS (ESI, M+1): m/z=636.4.

Example 366

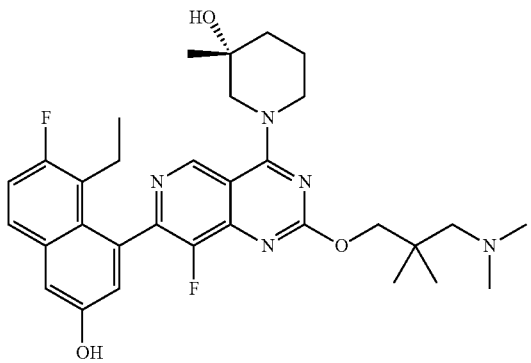

(R)-1-(2-(3-(dimethylamino)-2,2-dimethylpropoxy)-7-(8-ethyl-7-fluoro-3-hydroxynaphthalen-1-yl)-8-fluoropyrido[4,3-d]pyrimidin-4-yl)-3-methylpiperidin-3-ol The title compound was synthesized according to the procedure described for example 309. $^1$H NMR (400 MHz, methanol-d$_4$) δ=9.24 (d, J=2.0 Hz, 1H), 8.55-8.49 (m, 1H), 7.68 (dd, J=5.8, 9.2 Hz, 1H), 7.31 (d, J=2.8 Hz, 1H), 7.26 (t, J=9.6 Hz, 1H), 7.06 (t, J=2.0 Hz, 1H), 4.34 (s, 2H), 4.33-4.28 (m, 1H), 3.69-3.59 (m, 1H), 3.55-3.38 (m, 2H), 3.02 (br s, 2H), 2.76 (br s, 6H), 2.52-2.42 (m, 1H), 2.24-2.13 (m, 2H), 1.89-1.77 (m, 3H), 1.30 (d, J=9.8 Hz, 3H), 1.18 (s, 6H), 0.81 (q, J=7.6 Hz, 3H); LCMS [ESI, M+1]: m/z=580.3.

Example 367

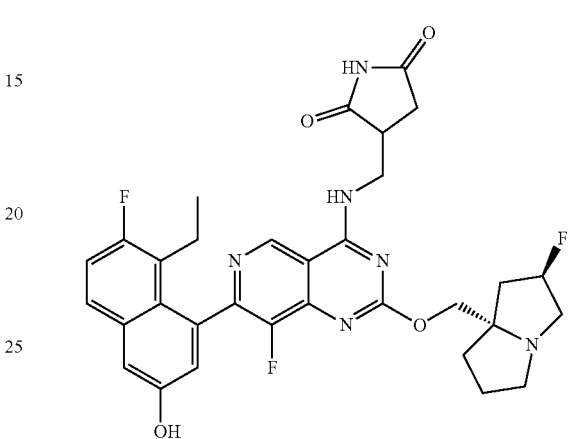

3-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)pyrrolidine-2,5-dione The title compound was synthesized according to the procedure described for example 330. $^1$H NMR (400 MHz, methanol-d$_4$) δ=9.21-9.18 (m, 1H), 8.47 (s, 1H), 7.69 (dd, J=6.0, 9.2 Hz, 1H), 7.31 (d, J=2.8 Hz, 11H), 7.26 (t, J=9.6 Hz, 1H), 7.06-7.02 (m, 1H), 5.58-5.37 (m, 1H), 4.60-4.46 (m, 3H), 4.19-4.08 (m, 1H), 4.03-3.93 (m, 1H), 3.80-3.54 (m, 3H), 3.51-3.41 (m, 11H), 3.01-2.88 (m, 1H), 2.74 (dd, J=4.8, 18.2 Hz, 11H), 2.62-2.28 (m, 4H), 2.24-2.04 (m, 4H), 0.79 (t, J=7.2 Hz, 3H) LCMS [ESI, M+1]: m/z=621.3.

Example 368

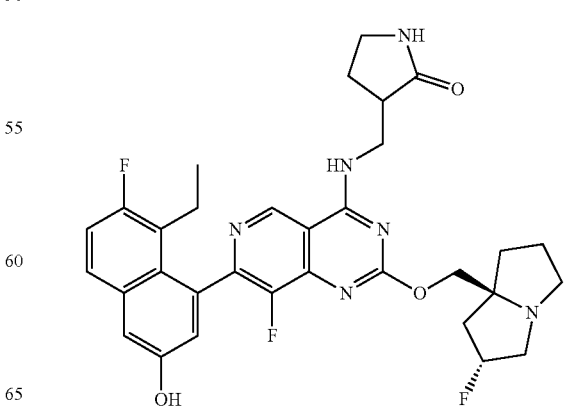

3-(((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)methyl)pyrrolidin-2-one The title compound was synthesized according to the procedure described for example 330. $^1$H NMR (400 MHz, MeOD-d$_4$) δ=9.15 (s, 1H), 7.68 (dd, J=5.6, 8.8 Hz, 1H), 7.30 (d, J=2.4 Hz, 1H), 7.25 (t, J=9.2 Hz, 1H), 7.04 (d, J=2.4 Hz, 1H), 5.42-5.22 (m, 1H), 4.33 (q, J=10.8 Hz, 2H), 4.04 (dd, J=6.0, 13.6 Hz, 1H), 3.83 (dd, J=8.0, 13.2 Hz, 1H), 3.46-3.33 (m, 3H), 3.27-3.11 (m, 3H), 3.06-2.91 (m, 2H), 2.54-.28 (m, 3H), 2.27-1.82 (m, 8H), 0.79 (t, J=7.2 Hz, 3H); $^{19}$F NMR (400 MHz, MeOD-d$_4$) δ=−121.18 (br s, 1F), −139.08 (br s, 1F), −173.55 (br t, J=14.2 Hz, 1F); LCMS (ESI, M+1): m/z=607.3.

Example 369

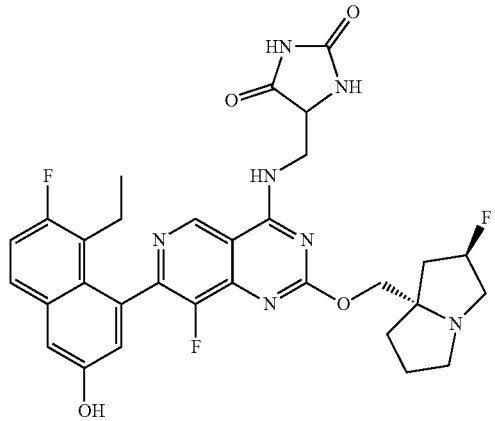 [SMILES: CCc1c(F)ccc2cc(O)cc(-c3ncc4c(NCC5NC(=O)NC5=O)nc(OC[C@@]56CCCN5C[C@H](F)C6)nc4c3F)c12]

5-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)imidazolidine-2,4-dione The title compound was synthesized according to the procedure described for example 330. $^1$H NMR (400 MHz, METHANOL-d$_4$) δ=9.19 (s, 1H), 8.49 (br s, 1H), 7.68 (dd, J=6.0, 8.8 Hz, 1H), 7.31 (d, J=2.4 Hz, 1), 7.25 (t, J=9.2 Hz, 1H), 7.04 (s, 1H), 5.58-5.34 (m, 1H), 4.66-4.51 (m, 4H), 4.14 (td, J=4.4, 13.6 Hz, 1H), 4.05-3.94 (m, 1H), 3.75-3.50 (m, 3H), 2.61-2.27 (m, 4H), 2.24-1.98 (m, 4H), 0.78 (br t, J=7.2 Hz, 3H); LCMS (ESI, M+1): m/z=622.3.

Example 370

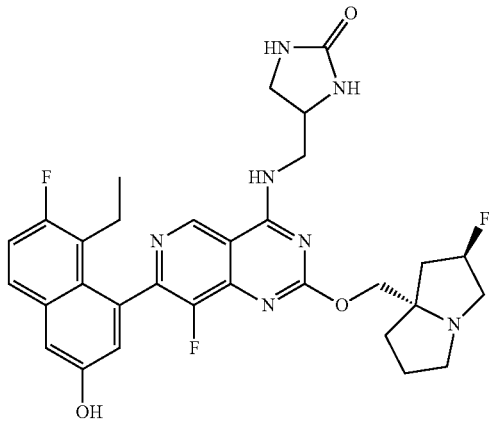 [SMILES: CCc1c(F)ccc2cc(O)cc(-c3ncc4c(NCC5CNC(=O)N5)nc(OC[C@@]56CCCN5C[C@H](F)C6)nc4c3F)c12]

4-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)imidazolidin-2-one The title compound was synthesized according to the procedure described for example 330. $^1$H NMR (400 MHz, methanol-d$_4$) δ=9.22-9.17 (m, 1H), 8.48 (br s, 1H), 7.68 (dd, J=6.0, 9.2 Hz, 1H), 7.31 (d, J=2.4 Hz, 1H), 7.26 (br t, J=9.2 Hz, 1H), 7.04 (br s, 1H), 5.56-5.40 (m, 1H), 4.64-4.48 (m, 3H), 4.24-4.10 (m, 1H), 4.05-3.89 (m, 1H), 3.81-3.58 (m, 4H), 3.44-3.35 (m, 1H), 2.58-2.09 (m, 9H), 0.78 (br t, J=6.0 Hz, 3H); LCMS (ESI, M+1): m/z=608.3.

Example 371

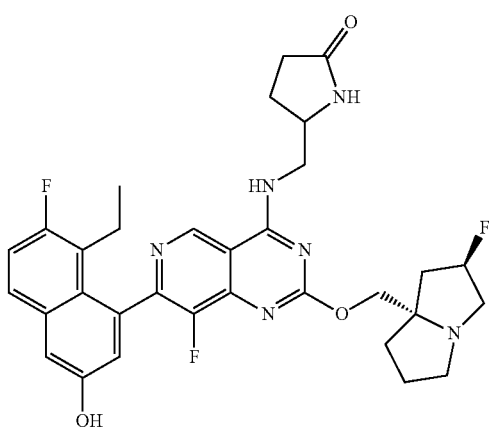 [SMILES: CCc1c(F)ccc2cc(O)cc(-c3ncc4c(NCC5CCC(=O)N5)nc(OC[C@@]56CCCN5C[C@H](F)C6)nc4c3F)c12]

5-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)pyrrolidin-2-one The title compound was synthesized according to the procedure described for example 330. $^1$H NMR (400 MHz, methanol-d$_4$) δ=9.22 (s, 1H), 8.45 (s, 1H), 7.71 (dd, J=6.0, 9.2 Hz, 1H), 7.34 (d, J=2.8 Hz, 1H), 7.28 (t, J=9.6 Hz, 1H), 7.05 (d, J=2.4 Hz, 1H), 5.74-5.32 (m, 1H), 4.66-4.50 (m, 3H), 4.13 (br s, 1H), 3.96-3.66 (m, 5H), 2.70-2.45 (m, 4H), 2.43-2.33 (m, 3H), 2.31-2.20 (m, 2H), 2.19-1.98 (m, 3H), 0.81 (br t, J=7.2 Hz, 3H) LCMS [ESI, M+1]: m/z=607.3.

Example 372

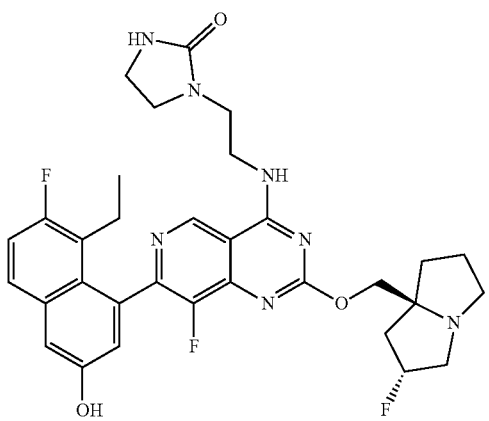 [SMILES: CCc1c(F)ccc2cc(O)cc(-c3ncc4c(NCCN5CCNC5=O)nc(OC[C@@]56CCCN5C[C@H](F)C6)nc4c3F)c12]

1-(2-((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)ethyl)imidazolidin-2-one The title compound was synthesized according to the procedure described for example 330. $^1$H NMR (400 MHz, DMSO-$d_6$) δ=10.13-9.76 (m, 1H), 9.24 (s, 1H), 9.12 (s, 1H), 7.76 (dd, J=6.0, 8.8 Hz, 1H), 7.41-7.29 (m, 2H), 7.00 (s, 1H), 6.34 (s, 1H), 5.45-5.16 (m, 1H), 4.22-4.12 (m, 1H), 4.12-4.03 (m, 1H), 3.82-3.70 (m, 1H), 3.69-3.58 (m, 1H), 3.55-3.45 (m, 2H), 3.41 (s, 1H), 3.28-3.21 (m, 2H), 3.16-3.06 (m, 2H), 3.05-2.98 (m, 1H), 2.89-2.78 (m, 1H), 2.44-2.25 (m, 2H), 2.18-1.97 (m, 4H), 1.89-1.75 (m, 3H), 0.72-0.68 (m, 3H); LCMS (ESI, M+1): m/z=622.1.

Example 373

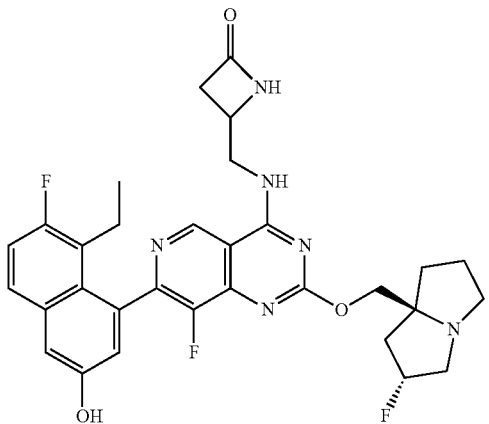 [SMILES: CCc1c(F)ccc2cc(O)cc(-c3ncc4c(NCC5CC(=O)N5)nc(OC[C@@]56CCCN5C[C@H](F)C6)nc4c3F)c12]

Example 374

4-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)azetidin-2-one

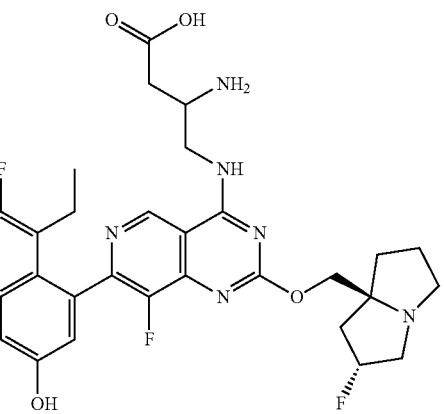

3-amino-4-((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino) butanoic Acid

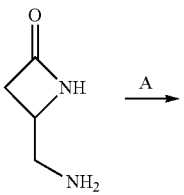

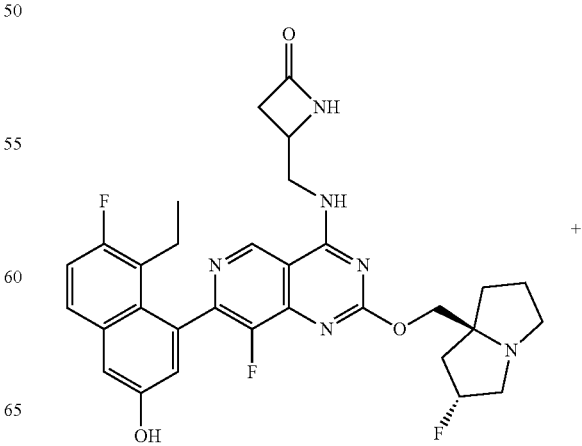

559

-continued

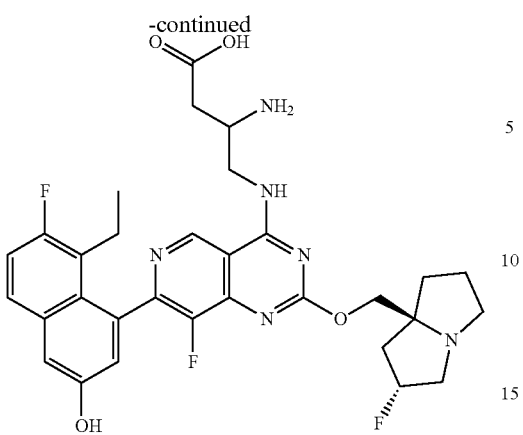

Step A. 4-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)azetidin-2-one and 3-amino-4-((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)butanoic acid: To a solution of 5-ethyl-6-fluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (60.0 mg, 1.0 equiv.) in N,N-dimethylformamide (1.00 mL) was added 4 Å molecular sieves (30.0 mg), diisopropylethylamine (39.3 mg, 3.0 equiv.) and 4-(aminomethyl)azetidin-2-one (20.3 mg, 2.0 equiv.). The mixture was stirred at 40° C. for 16 hours. The mixture was filtered. The filtrate was purified by prep-HPLC [column: 3_Phenomenex Luna C18 75×30 mm×3 μm; mobile phase: water (0.1% HCl)-acetonitrile; B %: 23%-43%, 7 minutes] and prep-HPLC [column: water s Xbridge 150×25 mm×5 μm; mobile phase: water (ammonium bicarbonate)-acetonitrile; B %: 34%-64%, 9 min] to afford 4-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)azetidin-2-one (7.14 mg, 11% yield) as a white solid (second eluting peak); $^1$H NMR (400 MHz, MeOD-d$_4$) δ=9.15 (s, 1H), 7.68 (dd, J=5.6, 8.8 Hz, 1H), 7.30 (d, J=2.8 Hz, 1H), 7.25 (t, J=9.2 Hz, 1H), 7.04 (d, J=2.4 Hz, 1H), 5.40-5.20 (m, 2H), 4.70-4.51 (m, 2H), 4.39-4.24 (m, 2H), 4.07 (br d, J=1.6 Hz, 1H), 4.02-3.85 (m, 2H), 3.27-3.17 (m, 3H), 3.17-3.09 (m, 1H), 3.07-2.97 (m, 1H), 2.87-2.79 (m, 1H), 2.55-2.29 (m, 2H), 2.29-2.08 (m, 4H), 2.04-1.84 (m, 4H), 0.79 (br t, J=7.2 Hz, 3H); LCMS (ESI, M+1): m/z=593.3; and 3-amino-4-((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)butanoic acid (11.8 mg, 17.5% yield) as white solid (first eluting peak); $^1$H NMR (400 MHz, MeOD-d$_4$) δ=9.17 (s, 11H), 7.68 (dd, J=6.0, 9.2 Hz, 1H), 7.31 (d, J=2.8 Hz, 1H), 7.25 (t, J=9.6 Hz, 1H), 7.04 (d, J=2.4 Hz, 1H), 5.44-5.22 (m, 1H), 4.42-4.31 (m, 2H), 4.00-3.88 (m, 2H), 3.84-3.73 (m, 1H), 3.42-3.33 (m, 1H), 3.26 (br d, J=7.6 Hz, 1H), 3.12-3.00 (m, 1H), 2.66-2.56 (m, 1H), 2.53-2.35 (m, 3H), 2.33-2.10 (m, 4H), 2.09-1.88 (m, 4H), 0.78 (t, J=7.2 Hz, 3H); LCMS (ESI, M+1): m/z=611.1.

560

Example 375

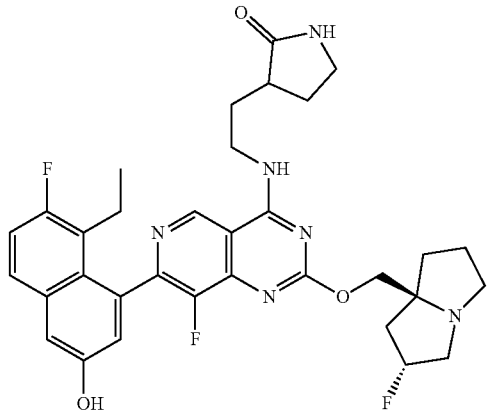 [SMILES: CCc1c(F)ccc2cc(O)cc(-c3ncc4c(NCCC5CCNC5=O)nc(OC[C@@]56CCCN5C[C@H](F)C6)nc4c3F)c12]

3-(2-((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)ethyl)pyrrolidin-2-one The title compound was synthesized according to the procedure described for example 330. $^1$H NMR (400 MHz, MeOD-d$_4$) δ=9.18 (s, 1H), 7.68 (dd, J=6.0, 8.8 Hz, 1H), 7.31 (d, J=2.4 Hz, 1H), 7.25 (t, J=9.2 Hz, 1H), 7.05 (d, J=2.4 Hz, 1H), 5.51-5.30 (m, 1H), 4.55-4.39 (m, 2H), 3.93-3.69 (m, 2H), 3.67-3.43 (m, 3H), 3.42-3.34 (m, 2H), 3.26-3.13 (m, 1H), 2.64-2.51 (m, 1H), 2.51-2.38 (m, 3H), 2.38-2.19 (m, 3H), 2.19-2.08 (m, 3H), 2.07-1.78 (m, 3H), 1.40-1.35 (m, 11H), 0.78 (t, J=7.2 Hz, 3H); LCMS (ESI, M+1): m/z=621.1.

Example 376

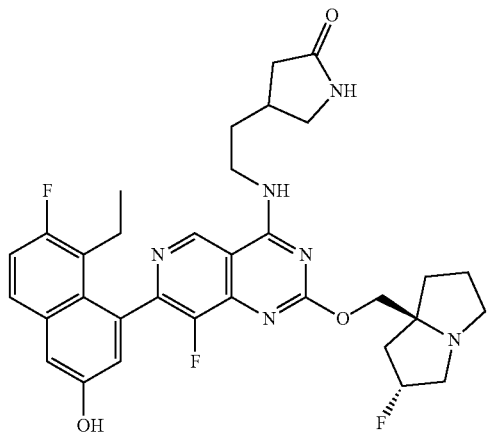 [SMILES: CCc1c(F)ccc2cc(O)cc(-c3ncc4c(NCCC5CNC(=O)C5)nc(OC[C@@]56CCCN5C[C@H](F)C6)nc4c3F)c12]

4-(2-((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)ethyl)pyrrolidin-2-one The title compound was synthesized according to the procedure described for example 330. $^1$H NMR (400 MHz, MeOD) δ=9.18 (s, 1H), 8.45 (s, 1H), 7.68 (dd, J=5.6, 9.2 Hz, 1H), 7.34-7.30 (m, 1H), 7.25 (t, J=9.2 Hz, 1H), 7.05 (s, 1H), 5.68-5.38 (m, 1H), 4.64-4.52 (m, 3H), 3.90-3.66 (m, 5H), 3.61 (dd, J=8.0, 9.6 Hz, 1H), 3.15 (dd, J=6.8, 9.2 Hz, 1H), 2.73-2.31 (m, 6H), 2.30-2.03 (m, 5H), 2.02-1.87 (m, 2H), 0.78 (t, J=7.2 Hz, 3H); LCMS (ESI, M+1): m/z=621.3.

Example 377

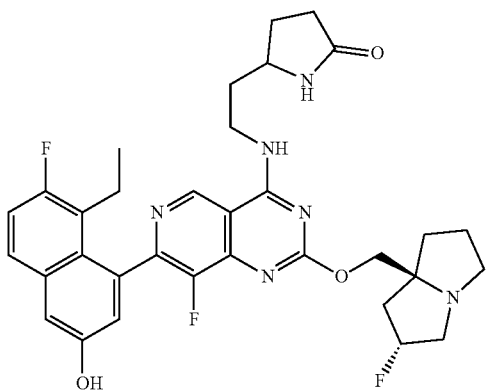 [SMILES: CCc1c(F)ccc2cc(O)cc(-c3ncc4c(NCCC5CCC(=O)N5)nc(OC[C@@]56CCCN5C[C@H](F)C6)nc4c3F)c12]

5-(2-((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)ethyl)pyrrolidin-2-one The title compound was synthesized according to the procedure described for example 330. ¹H NMR (400 MHz, MeOD) δ=9.12 (s, 1H), 7.68 (dd, J=6.0, 9.2 Hz, 1H), 7.30 (d, J=2.4 Hz, 1H), 7.25-7.22 (m, 1H), 7.03 (d, J=2.4 Hz, 1H), 5.44-5.21 (m, 1H), 4.60 (s, 2H), 4.41-4.26 (m, 2H), 3.90-3.70 (m, 3H), 3.23 (s, 1H), 3.04-3.03 (m, 1H), 2.53-2.21 (m, 6H), 2.20-2.09 (m, 2H), 2.06-1.86 (m, 6H), 0.80-0.76 (m, 3H); LCMS (ESI, M+1): m/z=621.3.

Example 378

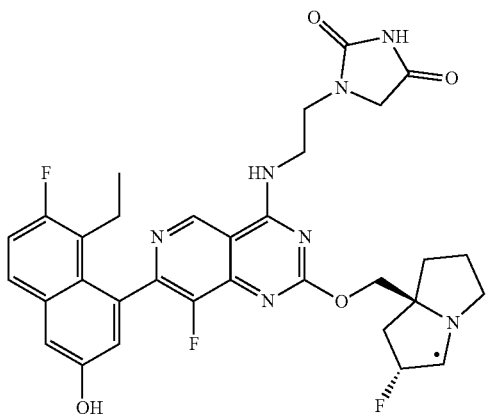 [SMILES: CCc1c(F)ccc2cc(O)cc(-c3ncc4c(NCCN5CC(=O)NC5=O)nc(OC[C@@]56CCCN5C[C@H](F)C6)nc4c3F)c12]

1-(2-((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)ethyl)imidazolidine-2,4-dione The title compound was synthesized according to the procedure described for example 330. ¹H NMR (400 MHz, METHANOL-d₄) δ=9.11 (s, 1H), 8.48 (s, 1H), 7.69-7.66 (m, 1H), 7.31 (d, J=2.8 Hz, 1H), 7.27-7.22 (m, 11H), 7.04 (d, J=2.8 Hz, 11H), 5.54-5.40 (m, 1H), 4.57-4.55 (m, 11H), 4.50-4.49 (m, 1H), 4.18 (t, J=5.6 Hz, 11H), 3.83-3.70 (m, 2H), 3.62-3.27 (m, 5H), 3.31-3.27 (m, 1H), 2.46-2.45 (m, 1H), 2.41-2.18 (m, 6H), 2.16-2.05 (m, 11H), 0.78 (t, J=7.2 Hz, 3H); LCMS (ESI, M+1): m/z=636.4.

Example 379

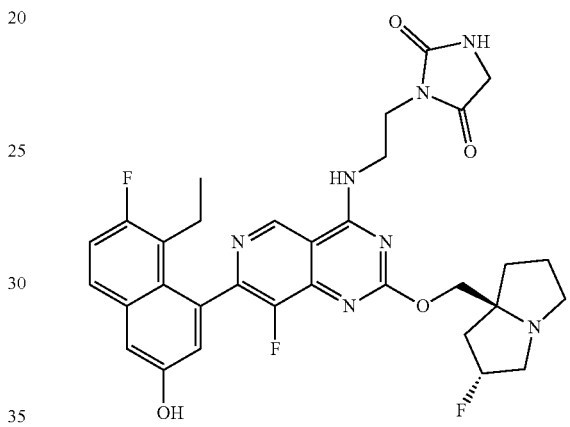

3-(2-((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)ethyl)imidazolidine-2,4-dione The title compound was synthesized according to the procedure described for example 330. ¹H NMR (400 MHz, MeOD) δ=9.07 (s, 1H), 8.50 (s, 1H), 7.68 (dd, J=9.2, 6.0 Hz, 1H), 7.31 (d, J=2.4 Hz, 1H), 7.25 (t, J=9.6 Hz, 1H), 7.04 (d, J=2.0 Hz, 1H), 5.56-5.34 (m, 1H), 4.59-4.48 (m, 2H), 3.99-3.84 (m, 6H), 3.72 (s, 1H), 3.57-3.47 (m, 2H), 3.26-3.18 (m, 1H), 2.64-2.24 (m, 4H), 2.21-2.00 (m, 4H), 0.78 (t, J=7.2 Hz, 3H); LCMS (ESI, M+1): m/z=636.3.

Example 380

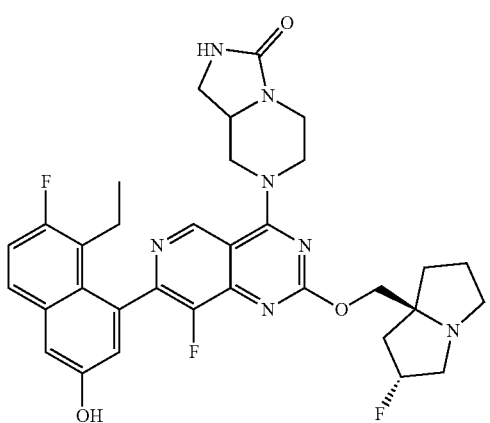 [SMILES: CCc1c(F)ccc2cc(O)cc(-c3ncc4c(N5CCN6C(=O)NCC6C5)nc(OC[C@@]56CCCN5C[C@H](F)C6)nc4c3F)c12]

7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)hexahydroimidazo[1,5-a]pyrazin-3(2H)-one The title compound was synthesized according to the procedure described for example 330. $^1$H NMR (400 MHz, METHANOL-d$_4$) δ=9.13 (s, 11H), 7.70 (dd, J=5.9, 9.0 Hz, 11H), 7.33 (d, J=2.4 Hz, 1H), 7.27 (t, J=9.2 Hz, 1H), 7.07 (t, J=2.4 Hz, 11H), 5.49-5.24 (m, 1H), 4.77-4.58 (m, 3H), 4.46-4.29 (m, 2H), 4.17-4.05 (m, 1H), 3.95 (br d, J=12.4 Hz, 1H), 3.73-3.61 (m, 1H), 3.52-3.39 (m, 3H), 3.31-3.19 (m, 3H), 3.16-3.04 (m, 1H), 2.57-2.46 (m, 1H), 2.45-2.26 (m, 2H), 2.24-2.13 (m, 2H), 2.11-2.01 (m, 2H), 2.00-1.89 (m, 1H), 0.81 (t, J=7.2 Hz, 3H); LCMS (EST, M+1): m/z=634.3.

Example 381

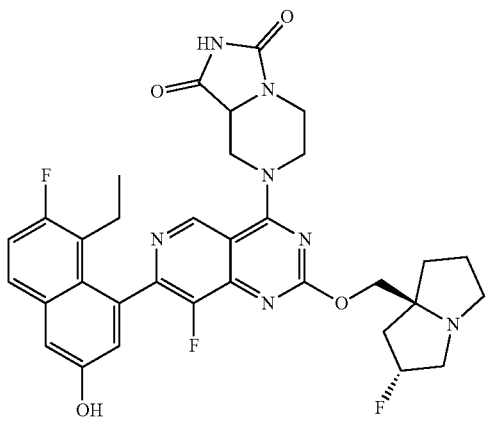 [SMILES: CCc1c(F)ccc2cc(O)cc(-c3ncc4c(N5CCN6C(=O)NC(=O)C6C5)nc(OC[C@@]56CCCN5C[C@H](F)C6)nc4c3F)c12]

7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)tetrahydroimidazo[1,5-a]pyrazine-1,3(2H,5H)-dione The title compound was synthesized according to the procedure described for example 330. $^1$H NMR (400 MHz, MeOD-d$_4$) δ=9.15 (s, 1H), 8.50 (s, 1H), 7.68 (dd, J=6.0, 9.2 Hz, 1H), 7.31 (d, J=2.4 Hz, 1H), 7.26 (t, J=9.2 Hz, 1H), 7.06 (d, J=2.4 Hz, 1H), 5.53-5.24 (m, 1H), 4.63 (d, J=12.4 Hz, 1H), 4.53-4.37 (m, 3H), 4.16 (d, J=13.2 Hz, 1H), 3.68-3.52 (m, 2H), 3.52-3.46 (m, 1H), 3.43-3.35 (m, 4H), 3.19-3.08 (m, 1H), 2.57-2.28 (m, 3H), 2.27-2.15 (m, 2H), 2.13-2.03 (m, 2H), 2.03-1.94 (m, 1H), 0.80 (dt, J=2.4, 7.2 Hz, 3H); LCMS (ESI, M+1): m/z=648.2.

Example 382

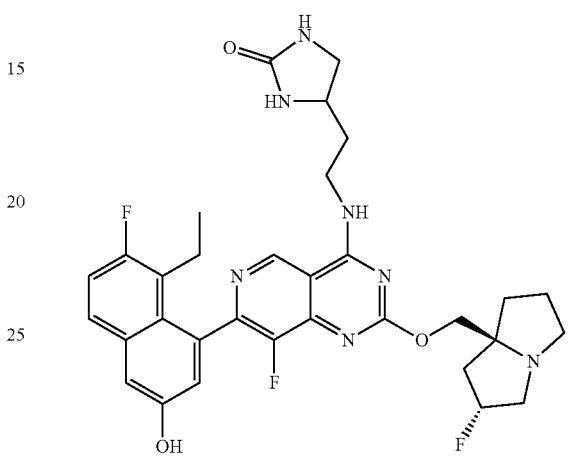

4-(2-((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)ethyl) imidazolidin-2-one The title compound was synthesized according to the procedure described for example 330. $^1$H NMR (400 MHz, METHANOL-d$_4$) δ=9.15 (s, 1H), 8.47 (s, 1H), 7.68 (dd, J=6.0, 9.2 Hz, 11H), 7.31 (d, J=2.8 Hz, 1H), 7.25 (t, J=10.0 Hz, 1H), 7.04 (d, J=2.4 Hz, 11H), 5.59-5.35 (m, 1H), 4.64-4.47 (m, 2H), 3.98-3.88 (m, 1H), 3.86-3.77 (m, 2H), 3.76-3.53 (m, 4H), 3.26-3.20 (m, 1H), 2.66-2.52 (m, 1H), 2.50-2.40 (m, 2H), 2.38-2.28 (m, 1H), 2.26-2.13 (m, 3H), 2.12-2.05 (m, 1H), 2.04-1.94 (m, 2H), 0.78 (t, J=7.2 Hz, 3H). LCMS (ESI, M+1): m/z=622.1.

Example 383

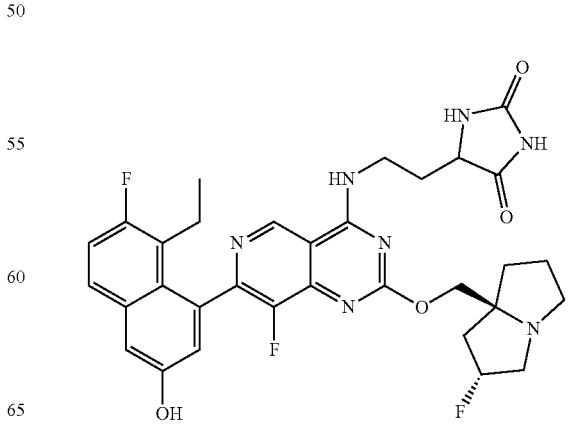

5-(2-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)ethyl) imidazolidine-2,4-dione The title compound was synthesized according to the procedure described for example 330. $^1$H NMR (400 MHz, METHANOL-$d_4$) δ=9.13 (d, J=4.0 Hz, 1H), 8.46 (s, 1H), 7.68 (dd, J=6.0, 9.2 Hz, 1H), 7.31 (d, J=2.4 Hz, 1H), 7.25 (t, J=9.2 Hz, 1H), 7.03 (t, J=3.2 Hz, 1H), 5.63-5.40 (m, 1H), 4.69-4.48 (m, 3H), 4.31-4.24 (m, 1H), 4.15-3.92 (m, 1H), 3.89-3.80 (m, 1H), 3.77-3.62 (m, 3H), 2.71-2.54 (m, 1H), 2.49-2.35 (m, 3H), 2.31-2.19 (m, 4H), 2.18-2.08 (m, 2H), 0.79 (q, J=6.8 Hz, 3H); LCMS (ESI, M+1): m/z=636.3

Example 384

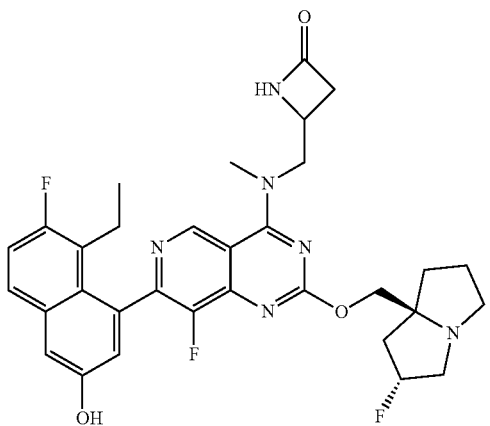 [SMILES: CCc1c(F)ccc2cc(O)cc(-c3ncc4c(N(C)CC5CC(=O)N5)nc(OC[C@@]56CCCN5C[C@H](F)C6)nc4c3F)c12]

4-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)methyl)amino)methyl)azetidin-2-one The title compound was synthesized according to the procedure described for example 330. $^1$H NMR (400 MHz, DMSO-d) δ=10.21-9.90 (m, 1H), 9.28 (s, 1H), 8.18 (br d, J=4.8 Hz, 1H), 7.80-7.72 (m, 1H), 7.40-7.29 (m, 2H), 7.01 (d, J=2.4 Hz, 1H), 5.38-5.17 (m, 1H), 4.17-4.01 (m, 5H), 3.62 (s, 3H), 3.14-2.97 (m, 4H), 2.84-2.74 (m, 2H), 2.30-1.92 (m, 4H), 1.93-1.90 (m, 1H), 1.89-1.74 (m, 3H), 0.73 (t, J=7.2 Hz, 3H); LCMS (ESI, M+1): m/z=607.4.

Example 385

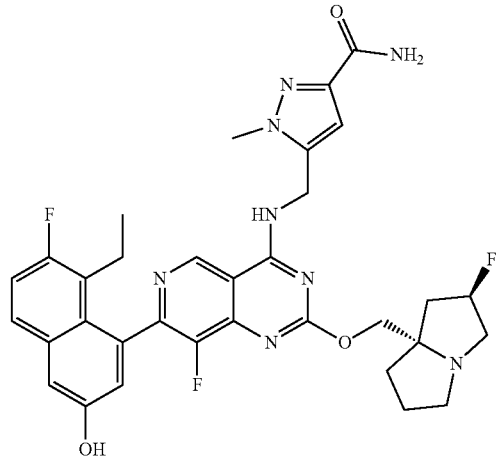 [SMILES: CCc1c(F)ccc2cc(O)cc(-c3ncc4c(NCc5cc(C(N)=O)nn5C)nc(OC[C@@]56CCCN5C[C@H](F)C6)nc4c3F)c12]

5-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)-1-methyl-1H-pyrazole-3-carboxamide The title compound was synthesized according to the procedure described for example 330. $^1$H NMR (400 MHz, DMSO-$d_6$) δ=9.92 (s, 1H), 9.50 (m, 1H), 9.34 (s, 1H), 8.13 (s, 1H), 7.76 (m, 1H), 7.41 (s, 1H), 7.38-7.29 (m, 2H), 7.20-7.12 (m, 1H), 6.99 (d, J=2.4 Hz, 1H), 6.66 (s, 1H), 5.42-5.20 (m, 1H), 4.93-4.74 (m, 2H), 4.24-4.07 (m, 2H), 3.98 (s, 3H), 3.17-3.05 (m, 3H), 2.91-2.84 (m, 1H), 2.36-2.30 (m, 1H), 2.20-1.99 (m, 4H), 1.89-1.74 (m, 3H), 0.71 (t, J=7.2 Hz, 3H); LCMS (ESI, M+1): m/z=647.1

Example 386

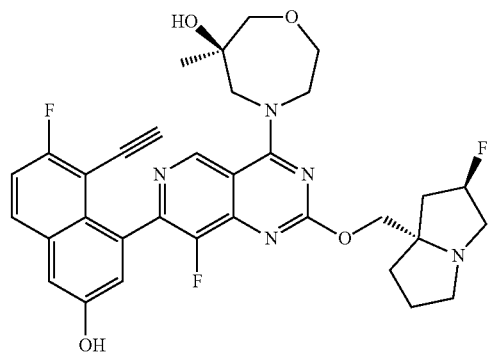 [SMILES: C#Cc1c(F)ccc2cc(O)cc(-c3ncc4c(N5CCOC[C@](C)(O)C5)nc(OC[C@@]56CCCN5C[C@H](F)C6)nc4c3F)c12]

567

(R)-4-(7-(8-ethynyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol

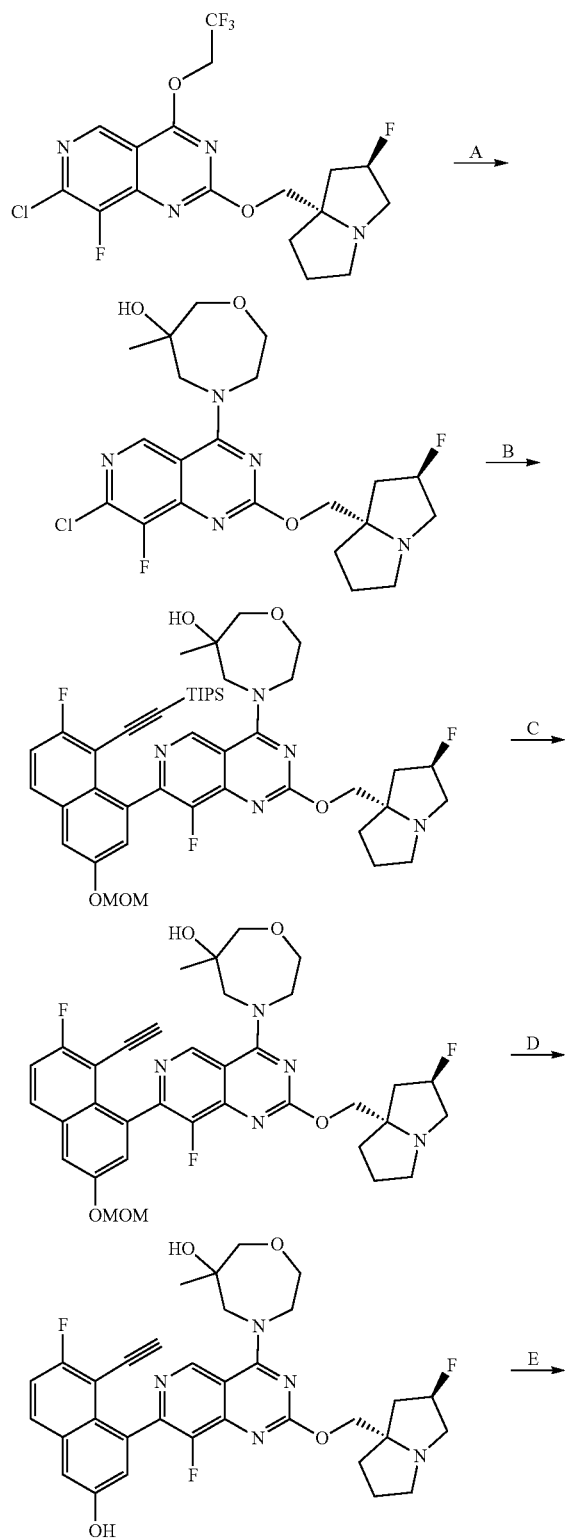

568

-continued

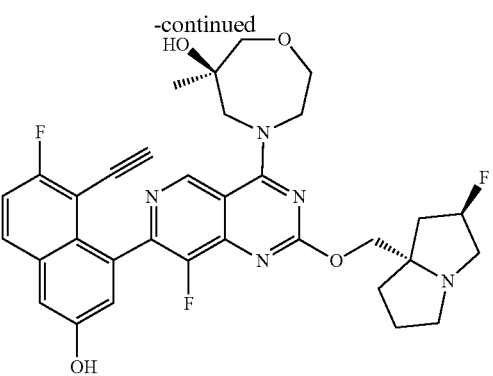

Step A. 4-(7-chloro-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol: A mixture of 6-methyl-1,4-oxazepan-6-ol (117 mg, 1.3 equiv.), 4 Å molecular sieves (30 mg) and DIEA (353 mg, 4.0 equiv.) in DMF (3 mL) was stirred at 15° C. for 0.5 hour. Then 7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (300 mg, 1.0 equiv.) was added into the above mixture and the mixture was stirred at 40° C. for 4 hours. After reaction completion, the mixture was filtered and the filtrate was purified by reversed phase flash chromatography [water (0.1% formic acid)/acetonitrile]. The desired fractions were collected, neutralized with solid NaHCO$_3$ and concentrated in vacuum to remove acetonitrile. The aqueous phase was extracted with ethyl acetate (2×15 mL). The combined organic phase was washed with brine (20 mL), dried over anhydrous Na$_2$SO$_4$, concentrated in vacuum to afford the title compound (210 mg, 62% yield) as a white solid; $^1$H NMR (400 MHz, DMSO-d$_6$) δ=9.31 (s, 1H), 5.27 (br d, J=53.6 Hz, 1H), 5.15 (s, 1H), 4.37-4.26 (m, 1H), 4.20-4.11 (m, 2H), 4.08-3.96 (m, 3H), 3.95-3.89 (m, 1H), 3.82-3.73 (m, 1H), 3.57-3.48 (m, 2H), 3.11-2.99 (m, 3H), 2.87-2.78 (m, 1H), 2.13-2.03 (m, 2H), 2.01-1.94 (m, 1H), 1.88-1.72 (m, 3H), 1.13 (s, 3H); LCMS [ESI, M+1]: 470.1.

Step B. 4-(8-fluoro-7-(7-fluoro-3-(methoxymethoxy)-8-((triisopropylsilyl)ethynyl)naphthalen-1-yl)-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol: To a mixture of 4-(7-chloro-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol (190 mg, 1.0 equiv.), ((2-fluoro-6-(methoxymethoxy)-8-(4,4,5,5-tetramethyl-1,3,2-dioxaborolan-2-yl)naphthalen-1-yl)ethynyl)triisopropylsilane (311 mg, 1.5 equiv.) and K$_3$PO$_4$ (1.5 M in water, 809 μL, 3.0 equiv.) in THF (2.4 mL) was added CataCXium A·Pd G3 (29.5 mg, 0.1 equiv.) under N$_2$. The mixture was degassed and stirred at 60° C. for 2.5 hours under N$_2$. After completion, the mixture was diluted with water (5 mL) and extracted with ethyl acetate (2×6 mL). The combined organic layers were concentrated in vacuum. The residue was purified by reversed phase flash chromatography [water (0.1% formic acid)/acetonitrile]. The desired fractions were collected and neutralized with solid NaHCO$_3$, concentrated in vacuum to remove acetonitrile. The aqueous phase was extracted with ethyl acetate (25 mL). The combined organic phase was washed with brine (20 mL), dried over anhydrous Na$_2$SO$_4$, concentrated in vacuum to afford the title compound (316 mg, 89% yield) as a yellow solid; LCMS [ESI, M+1, M/2+1]: 820.3, 410.9.

Step C. 4-(7-(8-ethynyl-7-fluoro-3-(methoxymethoxy) naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol: A mixture of 4-(8-fluoro-7-(7-fluoro-3-(methoxymethoxy)-8-((triisopropylsilyl)ethynyl)naphthalen-1-yl)-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol (320 mg, 1.0 equiv.) and CsF (889 mg, 15 equiv.) in DMF (1.6 mL) was stirred at 25° C. for 2 hours. After reaction completion, the mixture was filtered and the filtrate was purified by reversed phase flash chromatography [water (0.1% formic acid)/acetonitrile]. The desired fractions were collected, neutralized with solid $NaHCO_3$ and concentrated in vacuum to remove acetonitrile. The mixture was extracted with ethyl acetate (20 mL). The organic phase was washed with brine (20 mL), dried over anhydrous $Na_2SO_4$, concentrated in vacuum to afford the title compound (242 mg, 92% yield) as a yellow solid; $^1$H NMR (400 MHz, DMSO-$d_6$) δ=9.39 (d, J=47.2 Hz, 1H), 8.10 (dd, J=6.0, 9.2 Hz, 1H), 7.74 (d, J=2.4 Hz, 1H), 7.55 (t, J=8.8 Hz, 1H), 7.39 (dd, J=1.6, 9.2 Hz, 1H), 5.38 (s, 2H), 5.36-5.08 (m, 2H), 4.42-4.31 (m, 1H), 4.20-4.05 (m, 4H), 4.02-3.93 (m, 2H), 3.90-3.79 (m, 1H), 3.63-3.49 (m, 2H), 3.44 (s, 3H), 3.30 (br s, 1H), 3.15-3.00 (m, 3H), 2.87-2.79 (m, 1H), 2.15-2.03 (m, 2H), 1.99 (s, 1H), 1.88-1.73 (m, 3H), 1.19-1.16 (m, 3H); $^{19}$F NMR (376 MHz, DMSO-$d_6$) δ=−108.987, −140.166, −172.173; LCMS [ESI, M+1, M/2+1]: 664.3, 332.7.

Step D. 4-(7-(8-ethynyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol: To a mixture of 4-(7-(8-ethynyl-7-fluoro-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol (260 mg, 1.0 equiv.) in dichloromethane (1 mL) was added TFA (1.54 g, 34 equiv.) at 0° C. and the mixture was stirred at 0-15° C. for 2 hours. After reaction completion, the mixture was concentrated in vacuum. The residue was neutralized with saturated $NaHCO_3$ solution and extracted with ethyl acetate (2×8 mL). The combined organic layers were washed with brine (10 mL), dried over anhydrous $Na_2SO_4$ and concentrated in vacuum. The residue was purified by reversed phase flash chromatography [water (0.1% formic acid)/acetonitrile]. The desired fractions were collected and neutralized with $NaHCO_3$ solid, concentrated in vacuum to remove acetonitrile. The mixture was extracted with ethyl acetate (2×20 mL) and the combined organic phase was washed with brine (25 mL), dried over anhydrous $Na_2SO_4$. The mixture was concentrated in vacuum to afford the title compound (177 mg, 70% yield) as a yellow solid; LCMS [ESI, M+1]: 620.2.

Step E. (R)-4-(7-(8-ethynyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol: Stereoisomers of 4-(7-(8-ethynyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-methyl-1,4-oxazepan-6-ol (177 mg) were separated by SFC (column: DAICEL CHIRALPAK AD (250 mm×30 mm, 10 um); mobile phase: A: [0.1% NH3·H2O-IPA], B: $CO_2$, B %: 35%-35%, 6.8 min over 90 min). Both peaks were further re-purified by prep-HPLC [column: Waters Xbridge 150×25 mm×5 μm; mobile phase: water (10 mM $NH_4HCO_3$)-ACN; B %: 30%-60%, 8 min] followed by another prep-HPLC [column: PhenomenexGemini-NX C18 75×30 mm×3 μm; mobile phase: water (0.05% ammonia hydroxide v/v)-ACN, B %: 25%-55%, 7 min] to afford the title compound (peak 2) (35.1 mg, 19% yield) as an orange solid; SFC: 97.4%: Chiralpak IE-3 50×4.6 mm I.D., 3 μm; A: Heptane (0.05% DEA); B: 25% EtOH (0.05% DEA); 1 mL/min; 220 nm, $t_R$: 6.204 min; $^1$H NMR (400 MHz, methanol-$d_4$) δ=9.42 (d, J=43.2 Hz, 1H), 7.88-7.81 (m, 1H), 7.36-7.29 (m, 2H), 7.22 (dd, J=2.4, 10.4 Hz, 1H), 5.30 (br d, J=54.0 Hz, 1H), 4.64-4.43 (m, 2H), 4.35-4.15 (m, 3H), 4.07-3.83 (m, 3H), 3.75-3.56 (m, 2H), 3.48-3.41 (m, 1H), 3.29-3.13 (m, 3H), 3.05-2.97 (m, 1H), 2.38-2.18 (m, 2H), 2.16-2.08 (m, 1H), 2.04-1.95 (m, 2H), 1.94-1.83 (m, 1H), 1.27 (d, J=13.6 Hz, 3H); LCMS (ESI, M+1): m/z=620.3.

Example 387

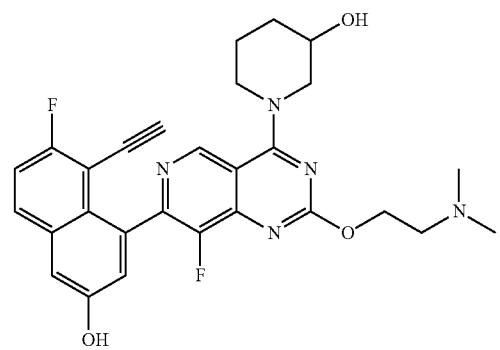 [SMILES: C#Cc1c(F)ccc2cc(O)cc(-c3ncc4c(N5CCCC(O)C5)nc(OCCN(C)C)nc4c3F)c12]

1-(2-(2-(dimethylamino)ethoxy)-7-(8-ethynyl-7-fluoro-3-hydroxynaphthalen-1-yl)-8-fluoropyrido[4,3-d]pyrimidin-4-yl)piperidin-3-ol

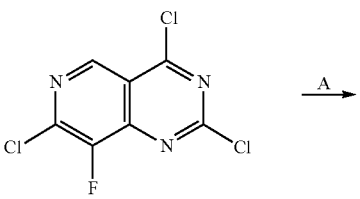

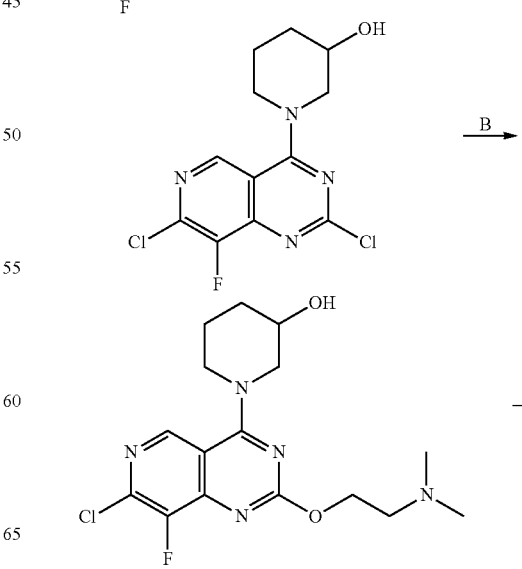

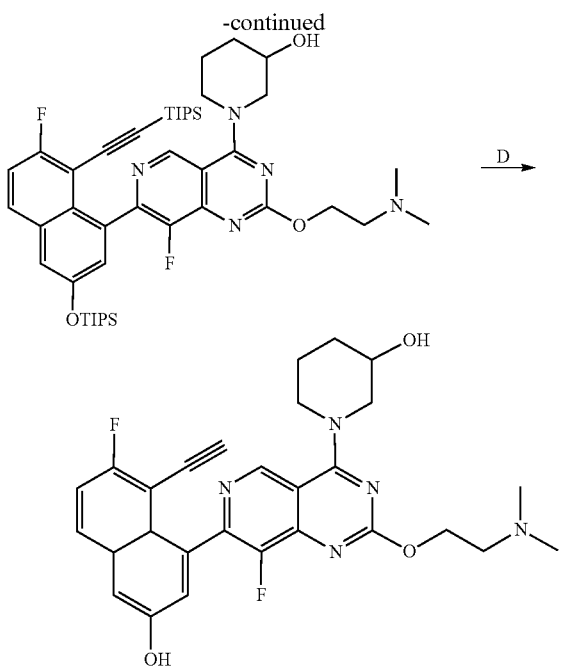

Step A. 1-(2,7-dichloro-8-fluoropyrido[4,3-d]pyrimidin-4-yl)piperidin-3-ol: A solution of 2,4,7-trichloro-8-fluoropyrido[4,3-d]pyrimidine (200 mg, 1.0 equiv.), DIEA (512 mg, 5.0 equiv.) and 4 Å molecular sieves (20 mg) in DCM (4 mL) at 18° C. under $N_2$ was de-gassed and piperidin-3-ol was added dropwise at −40° C. (218 mg, 2.0 equiv., HCl) under $N_2$. The reaction was stirred at −40° C. for 15 minutes. The mixture was quenched with water (20 mL) and extracted with ethyl acetate (2×20 mL). The combined organic layers were dried over anhydrous sodium sulfate, concentrated in vacuum to give a residue and the residue was purified by reversed phase flash chromatography [C18, water (0.1% formic acid)-ACN] to afford the title compound (193 mg, 77% yield) as a yellow solid. LCMS (ESI, M+1): m/z=316.9.

Step B. 1-(7-chloro-2-(2-(dimethylamino)ethoxy)-8-fluoropyrido[4,3-d]pyrimidin-4-yl)piperidin-3-ol: A stirred mixture of 1-(2,7-dichloro-8-fluoropyrido[4,3-d]pyrimidin-4-yl)piperidin-3-ol (129 mg, 1.0 equiv.), DIEA (157 mg, 3.0 equiv.) and 2-(dimethylamino) ethanol (366 mg, 10 equiv.) was heated to 90° C. for 3 hours. The mixture was diluted with ethyl acetate (10 mL) and water (20 mL). The aqueous phase was extracted with ethyl acetate (20 mL), the combined organic phase was washed with brine (10 mL), dried over anhydrous sodium sulfate, filtered, concentrated and the residue was purified by reversed phase flash chromatography [C18, water (0.1% formic acid)-ACN] to afford the title compound (126 mg, 84% yield) as a yellow solid. LCMS (ESI, M+1): m/z=370.1.

Step C. 1-(2-(2-(dimethylamino)ethoxy)-8-fluoro-7-(7-fluoro-8-((triisopropylsilyl)ethynyl-3-((triisopropylsilyl)oxy)naphthalen-1-yl)pyrido[4,3-d]pyrimidin-4-ylpiperidin-3-ol: A mixture of ((6-fluoro-4-(4,4,5,5-tetramethyl-1,3,2-dioxaborolan-2-yl)-5-((triisopropylsilyl)ethynyl)naphthalen-2-yl)oxy)triisopropylsilane (243 mg, 1.2 equiv.), 1-(7-chloro-2-(2-(dimethylamino)ethoxy)-8-fluoropyrido[4,3-d]pyrimidin-4-yl)piperidin-3-ol (120 mg, 1.0 equiv.), $Cs_2CO_3$ (1.5 M in water, 3.0 equiv.) and CataCXium A Pd G3 (24 mg, 0.1 equiv.) in methoxycyclopentane (4 mL) was de-gassed and attired at 90° C. for 2.5 hours under $N_2$. The mixture was diluted with ethyl acetate (10 mL) and water (20 mL). The aqueous phase was extracted with ethyl acetate (10 mL), the combined organic phase was washed with brine (15 mL), dried over anhydrous sodium sulfate, filtered and concentrated to give a residue and the residue was purified by reversed phase flash chromatography [C18, water (0.1% formic acid)-ACN] to afford the title compound (115 mg, 42% yield) as a yellow solid; LCMS (ESI, M+1): m/z=832.4.

Step D. 1-(2-(2-(dimethylamino)ethoxy)-7-(8-ethynyl-7-fluoro-3-hydroxynaphthalen-1-yl)-8-fluoropyrido[4,3-d]pyrimidin-4-yl)piperidin-3-ol: A mixture of 1-(2-(2-(dimethylamino)ethoxy)-8-fluoro-7-(7-fluoro-8-((triisopropylsilyl)ethynyl)-3-((triisopropylsilyl)oxy)naphthalen-1-yl)pyrido[4,3-d]pyrimidin-4-yl)piperidin-3-ol (60 mg, 1.0 equiv.) and CsF (164 mg, 15 equiv.) in DMF (0.6 mL) was stirred at 18° C. for 12 hours. After reaction completion, the mixture was filtered and the filtrate was purified by prep-HPLC (column: Waters Xbridge 150×25 mm×5 μm; mobile phase: water (10 mM $NH_4HCO_3$)-ACN, B %: 24%-54%, 7 min) to afford the title compound (5.3 mg, 14% yield) as a white solid; $^1H$ NMR (400 MHz, CD3OD, 298 K) δ (ppm)=9.12-9.02 (m, 1H), 7.85 (dd, J=5.6, 8.8 Hz, 1H), 7.36-7.28 (m, 2H), 7.22 (dd, J=2.4, 10.4 Hz, 1H), 4.66-4.59 (m, 2H), 4.29-4.17 (m, 1H), 4.14-3.76 (m, 4H), 3.50-3.38 (m, 1H), 2.84 (t, J=5.6 Hz, 2H), 2.37 (s, 6H), 2.18-2.01 (m, 2H), 1.84-1.68 (m, 2H) LCMS [ESI, M+1]: m/z=520.2.

Example 388

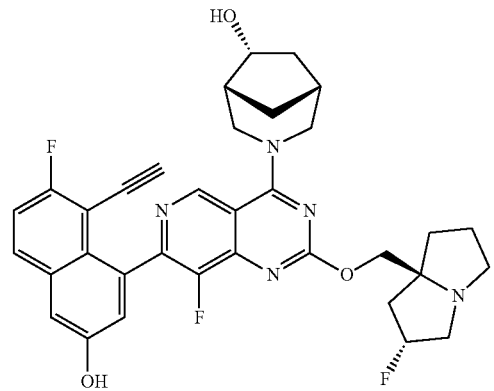 [SMILES: C#Cc1c(F)ccc2cc(O)cc(-c3ncc4c(N5C[C@@H]6C[C@H](C5)[C@H](O)C6)nc(OC[C@@]56CCCN5C[C@H](F)C6)nc4c3F)c12]

(1R,5R,6R)-3-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3,2,1]octan-6-ol

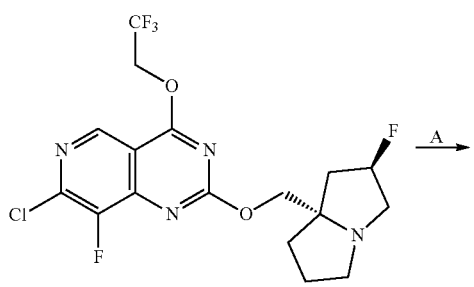

-continued

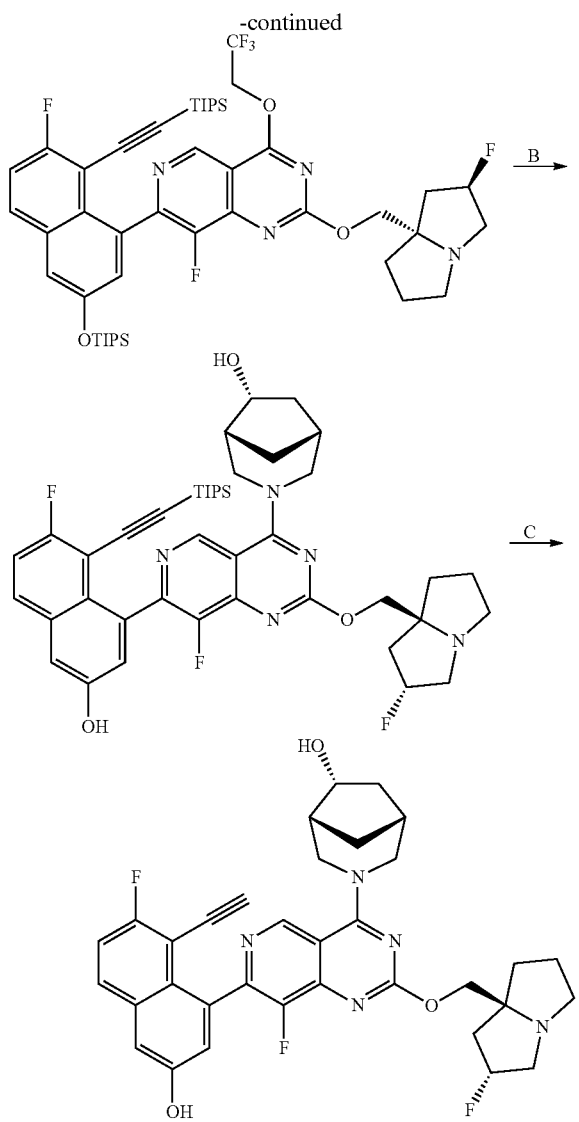

Step A. 8-fluoro-7-(7-fluoro-8-((triisopropylsilyl)ethynyl)-3-((triisopropylsilyl)oxy)naphthalen-1-yl)-2-(((2R,7aS)-2-fluorohexahydro-1H-pyrrolizin-7a-yl)methoxy)-4-(2,2,2-trifluoroethoxy)pyrido[4,3-d]pyrimidine: A mixture of 7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (130 mg, 1.0 equiv.), ((6-fluoro-4-(4,4,5,5-tetramethyl-1,3,2-dioxaborolan-2-yl)-5-((triisopropylsilyl)ethynyl)naphthalen-2-yl)oxy) triisopropylsilane (204 mg, 1.1 equiv.), Cs$_2$CO$_3$ (1.5 M in water, 3.0 equiv.) and CataCXium A Pd G3 (21.6 mg, 0.1 equiv.) in methoxycyclopentane (2 mL) was de-gassed and stirred at 100° C. for 2.5 hours under N$_2$. The reaction mixture was diluted with ethyl acetate (15 mL) and water (30 mL). The aqueous phase was extracted with ethyl acetate (10 mL), the combined organic phase was washed with brine (15 mL), dried over anhydrous sodium sulfate, filtered and concentrated in vacuum. The residue was purified by reversed phase flash chromatography [water (0.1% formic acid)/acetonitrile]. The desired fractions were collected and neutralized with solid NaHCO$_3$, concentrated in vacuum to afford the title compound (260 mg, 97% yield) as a yellow oil; LCMS (ESI, M+1): m/z=901.3.

Step B. 3-(8-fluoro-7-(7-fluoro-3-hydroxy-8-((triisopropylsilyl)ethynyl)naphthalen-1-yl)-2-(((2R,7aS)-2-fluorotetrahydro-1H-pyrrolizin-7a(5H)-yl)methoxy)pyrido[4,3-d]pyrimidin-4-yl)-3-azabicyclo[3.2.1]octan-6-ol: A solution of 8-fluoro-7-(7-fluoro-8-((triisopropylsilyl)ethynyl)-3-((triisopropylsilyl)oxy)naphthalen-1-yl)-2-(((2R,7aS)-2-fluorohexahydro-1H-pyrrolizin-7a-yl)methoxy)-4-(2,2,2-trifluoroethoxy)pyrido[4,3-d]pyrimidine (260 mg, 1.0 equiv.), (1R,5R,6R)-3-azabicyclo[3,2,1]octan-6-ol (47.7 mg, 1.3 equiv.), DIEA (112 mg, 3.0 equiv.) and 4 Å molecular sieves (20 mg) in DMF (3 mL) was stirred at 40° C. for 12 hrs. Additional amounts of (1R,5R,6R)-3-azabicyclo[3,2,1]octan-6-ol (25.7 mg, 0.7 equiv.) and DIEA (37.3 mg, 1.0 equiv.) were introduced into the reaction mixture and the resulting was stirred at 40° C. for 12 hrs. The mixture was filtered and the filtrate was purified by reversed phase flash chromatography [water (0.1% formic acid)/acetonitrile]. The desired fractions were collected and neutralized with solid NaHCO$_3$, concentrated in vacuum to remove ACN. The aqueous phase was extracted with ethyl acetate (10 mL×2). The combined organic phase was dried with anhydrous Na$_2$SO$_4$, filtered and concentrated in vacuum to afford the title compound (110 mg, 44% yield) as a white solid; LCMS (ESI, M+1): m/z=772.3.

Step C. (1R,5R,6R)-3-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3,2,1]octan-6-ol: To a solution of 3-(8-fluoro-7-(7-fluoro-3-hydroxy-8-((triisopropylsilyl)ethynyl)naphthalen-1-yl)-2-(((2R,7aS)-2-fluorotetrahydro-1H-pyrrolizin-7a(5H)-yl)methoxy)pyrido[4,3-d]pyrimidin-4-yl)-3-azabicyclo[3,2,1]octan-6-ol (100 mg, 1.0 equiv.) in DMF (1 mL) was added CsF (295 mg, 15 equiv.). The reaction was stirred at 20° C. for 12 hours. The mixture was filtered and the filtrate was purified by prep-HPLC [column: Water s Xbridge 150×25 mm×5 µm; mobile phase: water (10 mM NH$_4$HCO$_3$)-ACN, B %: 38%-68%, 9 min] and lyophilized to afford the title compound (33.8 mg, 42% yield) as a yellow solid; $^1$H NMR (400 MHz, CD3SOCD3, 298 K) δ (ppm)=10.58-9.93 (m, 1H), 9.36-9.01 (m, 1H), 8.00-7.91 (m, 1H), 7.49-7.34 (m, 2H), 7.26-7.13 (m, 1H), 5.37-5.17 (m, 1H), 5.10-4.54 (m, 2H), 4.51-4.05 (m, 3H), 4.01-3.94 (m, 1H), 3.93-3.86 (m, 1H), 3.77-3.63 (m, 1H), 3.23 (br d, J=12.8 Hz, 1H), 3.14-2.97 (m, 3H), 2.86-2.77 (m, 1H), 2.32 (s, 1H), 2.18-1.92 (m, 5H), 1.92-1.58 (m, 5H), 1.33-1.20 (m, 1H); LCMS (ESI, M+1): m/z=616.2

Example 389

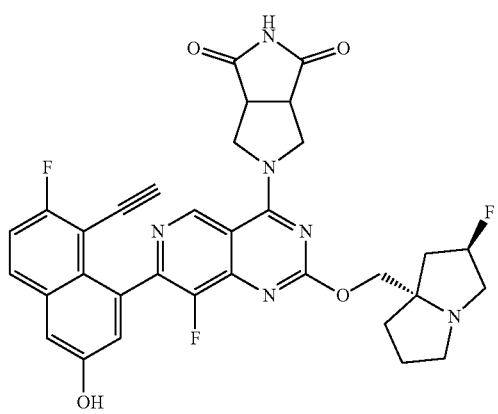

575

5-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)tetrahydropyrrolo[3,4-c]pyrrole-1,3(2H,3aH)-dione The title compound was synthesized according to the procedure described for example 388. $^1$H NMR (400 MHz, methanol-$d_4$) δ 9.23 (s, 1H), 7.90-7.83 (m, 1H), 7.38-7.28 (m, 2H), 7.23 (d, J=2.4 Hz, 1H), 5.55-5.36 (m, 1H), 4.76-4.73 (m, 1H), 4.65-4.61 (m, 1H), 4.56-4.46 (m, 2H), 4.41-4.33 (m, 1H), 4.31-4.22 (m, 1H), 3.79-3.71 (m, 2H), 3.71-3.52 (m, 3H), 3.36-3.33 (m, 1H), 3.26-3.24 (m, 1H), 2.60-2.37 (m, 2H), 2.34-2.26 (m, 1H), 2.24-2.14 (m, 2H), 2.11-1.99 (m, 1H); LCMS (ESI, M+1): m/z=629.3.

Example 390

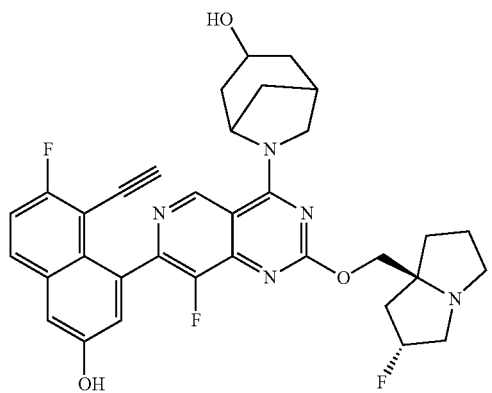 [SMILES: C#Cc1c(F)ccc2cc(O)cc(-c3ncc4c(N5CC6CC(O)CC5C6)nc(OC[C@@]56CCCN5C[C@H](F)C6)nc4c3F)c12]

6-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azabicyclo[3,2,1]octan-3-ol

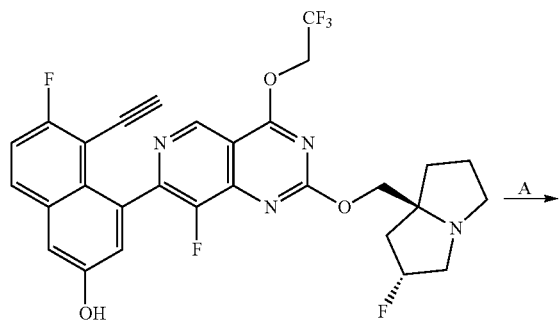

576

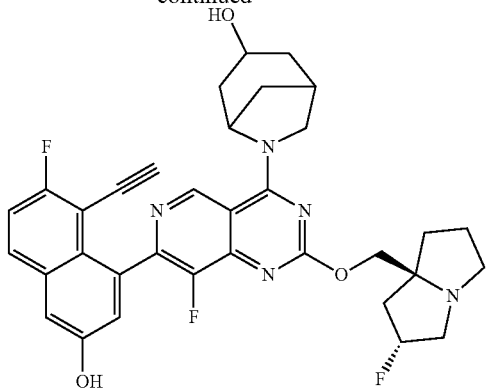

Step A. 6-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azabicyclo[3.2.1]octan-3-ol: To a solution of 5-ethynyl-6-fluoro-4-(8-fluoro-2-(((2R,7aS)-2-fluorohexahydro-1H-pyrrolizin-7a-yl)methoxy)-4-(2,2,2-trifluoroethoxy)pyrido[4,3-d]pyrimidin-7-yl)naphthalen-2-ol (100 mg, 1.0 equiv.) and 4 Å molecular sieves (20.0 mg) in DMF (1 mL) was added DIEA (371 mg, 0.50 mL, 16.9 equiv.) and 6-azabicyclo[3,2,1]octan-3-ol (123 mg, 3.0 equiv., TFA). The mixture was stirred at 40° C. for 12 hours. The mixture was filtered and the filtrate was purified by prep-HPLC (column: Phenomenex luna C18 150×25 mm×10 μm; mobile phase: [water (0.1% formic acid)-ACN]; B %: 12%-42%, 10.5 min) to afford the title compound (15.6 mg, 14% yield) as a yellow solid; $^1$H NMR (400 MHz, METHANOL-d) δ=9.27-9.10 (m, 1H), 7.84 (dd, J=5.6, 8.4 Hz, 1H), 7.36-7.27 (m, 2H), 7.27-7.17 (m, 1H), 5.40-5.21 (m, 1H), 4.97 (br s, 1H), 4.40-4.18 (m, 4H), 4.16-4.05 (m, 1H), 3.27-3.12 (m, 3H), 3.07-2.95 (m, 1H), 2.82-2.53 (m, 2H), 2.40-2.27 (m, 1H), 2.26-2.11 (m, 3H), 2.07-1.95 (m, 4H), 1.95-1.85 (m, 2H), 1.84-1.62 (m, 2H); LCMS (ESI, M+1): m/z=616.5.

Example 391

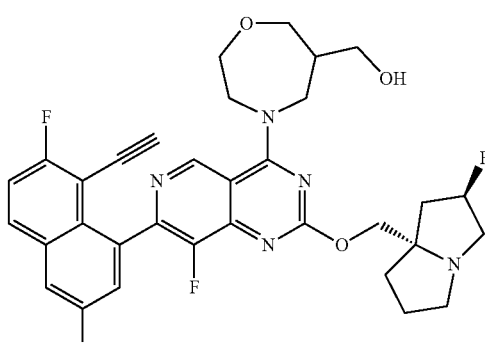

5-ethynyl-6-fluoro-4-(8-fluoro-2-(((2R,7aS)-2-fluorohexahydro-1H-pyrrolizin-7a-yl)methoxy)-4-(6-(hydroxymethyl)-1,4-oxazepan-4-yl)pyrido[4,3-d]pyrimidin-7-yl)naphthalen-2-ol The title compound was synthesized according to the procedure described for example 390. 1H NMR (400 MHz, METHANOL-d₄) δ=9.19 (d, J=14.4 Hz, 1H), 8.51 (br s, 11H), 7.89 (dd, J=5.6, 9.2 Hz, 1H), 7.38 (d, J=2.4 Hz, 1H), 7.35 (t, J=9.2 Hz, 1H), 7.24 (dd, J=2.4, 10.8 Hz, 1H), 5.55-5.34 (m, 1H), 4.74-4.54 (m, 2H), 4.53-4.48 (m, 1H), 4.48-4.30 (m, 2H), 4.20-4.10 (m, 2H), 4.09 (br s, 2H), 3.94-3.77 (m, 1H), 3.70-3.61 (m, 3H), 3.60-3.48 (m, 3H), 3.29-3.20 (m, 1H), 2.59-2.34 (m, 3H), 2.32-2.22 (m, 1H), 2.21-2.11 (m, 2H), 2.10-1.97. (m, 1H); LCMS (ESI, M+1): m/z=620.3.

Example 392

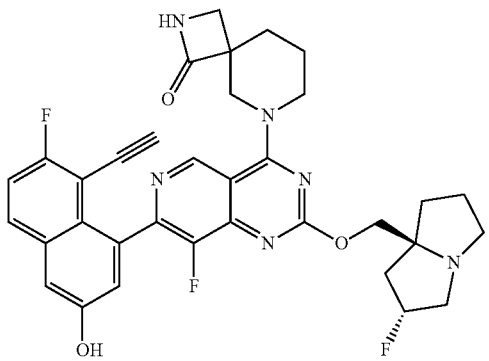 [SMILES: C#Cc1c(F)ccc2cc(O)cc(-c3ncc4c(N5CCCC6(CNC6=O)C5)nc(OC[C@@]56CCCN5C[C@H](F)C6)nc4c3F)c12]

6-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2,6-diazaspiro[3.5]nonan-1-one The title compound was synthesized according to the procedure described for example 390. ¹H NMR (400 MHz, METHANOL-d₄) δ=9.01 (d, J=8.0 Hz, 1H), 7.85 (dd, J=5.6, 9.2 Hz, 1H), 7.36-7.27 (m, 2H), 7.23 (dd, J=2.4, 6.4 Hz, 1H), 5.40-5.20 (m, 1H), 4.43-4.27 (m, 3H), 4.26-4.19 (m, 1H), 4.13-3.98 (m, 1H), 3.85-3.60 (m, 1H), 3.42-3.33 (m, 1H), 3.29-3.12 (m, 5H), 3.00 (dt, J=5.6, 9.2 Hz, 1H), 2.39-2.26 (m, 1H), 2.24-2.02 (m, 5H), 2.02-1.82 (m, 4H); LCMS (ESI, M+1): m/z=629.5.

Example 393

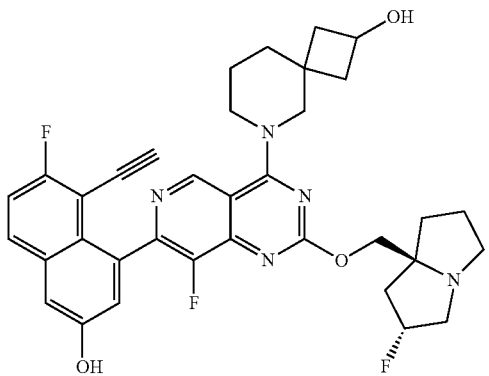 [SMILES: C#Cc1c(F)ccc2cc(O)cc(-c3ncc4c(N5CCCC6(CC(O)C6)C5)nc(OC[C@@]56CCCN5C[C@H](F)C6)nc4c3F)c12]

6-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azaspiro[3.5]nonan-2-ol The title compound was synthesized according to the procedure described for example 390. 1H NMR (400 MHz, METHANOL-d₄) δ=9.05-8.96 (m, 1H), 7.86 (dd, J=5.6, 9.2 Hz, 1H), 7.43-7.28 (m, 1H), 7.39-7.26 (m, 1H), 7.24-7.18 (m, 1H), 5.45-5.15 (m, 1H), 4.36-4.30 (m, 1H), 4.39-4.17 (m, 1H), 4.16-4.09 (m, 1H), 4.06 (br s, 1H), 4.02-3.95 (m, 1H), 3.95-3.84 (m, 1H), 3.47-3.35 (m, 1H), 3.28-3.12 (m, 3H), 3.06-2.98 (m, 1H), 2.39-2.32 (m, 1H), 2.32-2.26 (m, 1H), 2.25-2.11 (m, 3H), 2.05-1.96 (m, 2H), 1.96-1.67 (m, 5H); LCMS (ESI, M+1): m/z=630.4.

Example 394

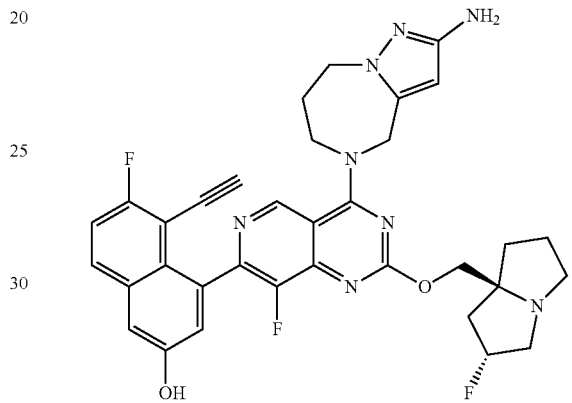

4-(4-(2-amino-7,8-dihydro-4H-pyrazolo[1,5-a][1,4]diazepin-5(6H)-yl)-8-fluoro-2-(((2R,7aS)-2-fluorohexahydro-1H-pyrrolizin-7a-yl)methoxy)pyrido[4,3-d]pyrimidin-7-yl)-5-ethynyl-6-fluoronaphthalen-2-ol The title compound was synthesized according to the procedure described for example 390. 1H NMR (400 MHz, METHANOL-d₄) δ=9.19 (s, 1H), 8.47 (s, 1H), 7.87 (dd, J=5.6, 9.2 Hz, 1H), 7.36 (d, J=2.4 Hz, 1H), 7.36-7.30 (m, 1H), 7.22 (d, J=2.4 Hz, 1H), 5.79 (s, 1H), 5.53-5.34 (m, 1H), 5.18-5.03 (m, 2H), 4.54-4.41 (m, 2H), 4.38 (br d, J=4.8 Hz, 2H), 4.25 (br dd, J=4.0, 5.6 Hz, 2H), 3.70-3.47 (m, 3H), 3.40 (d, J=2.4 Hz, 1H), 3.24 (dt, J=6.0, 9.6 Hz, 1H), 2.55-2.43 (m, 1H), 2.39 (br d, J=4.0 Hz, 311), 2.32-2.23 (m, 1H), 2.23-2.12 (m, 2H), 2.09-1.98 (m, 1H); LCMS (ESI, M+1): m/z=641.2

Example 395

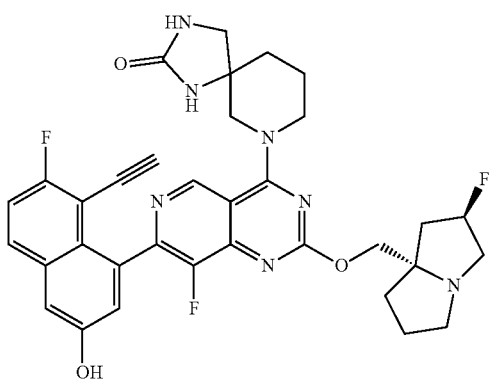 [SMILES: C#Cc1c(F)ccc2cc(O)cc(-c3ncc4c(N5CCCC6(CNC(=O)N6)C5)nc(OC[C@@]56CCCN5C[C@H](F)C6)nc4c3F)c12]

7-(7-(8-ethynyl-7-fluoro-3-hydroxynaphthalen-1-yl)-8-fluoro-2-(((2R,7aS)-2-fluorohexahydro-1H-pyr-rolizin-7a-yl)methoxy)pyrido[4,3-d]pyrimidin-4-yl)-1,3,7-triazaspiro[4.5]decan-2-one The title compound was synthesized according to the procedure described for example 390. $^1$H NMR (400 MHz, METHANOL-d$_4$) δ=9.06 (s, 1H), 8.51 (br s, 1H), 7.86 (ddd, J=1.6, 5.6, 9.2 Hz, 1H), 7.39-7.26 (m, 2H), 7.22 (dd, J=2.4, 4.4 Hz, 1H), 5.52-5.29 (m, 1H), 4.52-4.36 (m, 2H), 4.36-4.28 (m, 1H), 4.25-3.98 (m, 2H), 3.97-3.78 (m, 1H), 3.63-3.49 (m, 1H), 3.49-3.40 (m, 3H), 3.40-3.36 (m, 1H), 3.28 (br d, J=2.0 Hz, 1H), 3.21-3.11 (m, 1H), 2.53-2.30 (m, 2H), 2.30-2.18 (m, 1H), 2.16-1.94 (m, 6H), 1.92-1.82 (m, 1H). LCMS (ESI, M+1): m/z=644.2.

Example 396

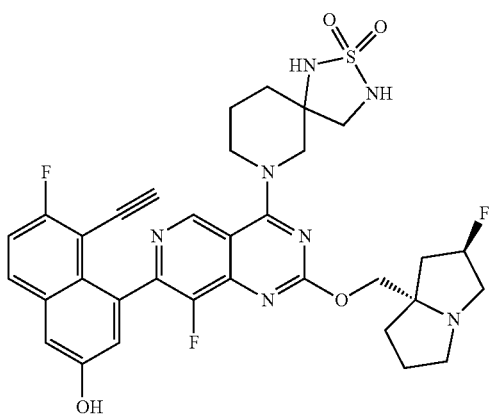 [SMILES: C#Cc1c(F)ccc2cc(O)cc(-c3ncc4c(N5CCCC6(CNS(=O)(=O)N6)C5)nc(OC[C@@]56CCCN5C[C@H](F)C6)nc4c3F)c12]

7-(7-(8-ethynyl-7-fluoro-3-hydroxynaphthalen-1-yl)-8-fluoro-2-(((2R,7aS)-2-fluorohexahydro-1H-pyr-rolizin-7a-yl)methoxy)pyrido[4,3-d]pyrimidin-4-yl)-2-thia-1,3,7-triazaspiro[4.5]decane 2,2-dioxide The title compound was synthesized according to the procedure described for example 390. $^1$H NMR (400 MHz, METHANOL-d$_4$) δ=9.19 (d, J=14.4 Hz, 1H), 8.51 (br s, 1H), 7.89 (dd, J=5.6, 9.2 Hz, 1H), 7.38 (d, J=2.4 Hz, 1H), 7.35 (t, J=9.2 Hz, 1H), 7.24 (dd, J=2.4, 10.8 Hz, 1H), 5.55-5.34 (m, 1H), 4.74-4.54 (m, 2H), 4.53-4.48 (m, 1H), 4.48-4.30 (m, 2H), 4.20-4.10 (m, 2H), 4.09 (br s, 2H), 3.94-3.77 (m, 1H), 3.70-3.61 (m, 3H), 3.60-3.48 (m, 3H), 3.29-3.20 (m, 1H), 2.59-2.34 (m, 3H), 2.32-2.22 (m, 1H), 2.21-2.11 (m, 2H), 2.10-1.97 (m, 1H); LCMS (ESI, M+1): m/z=680.2.

Example 397

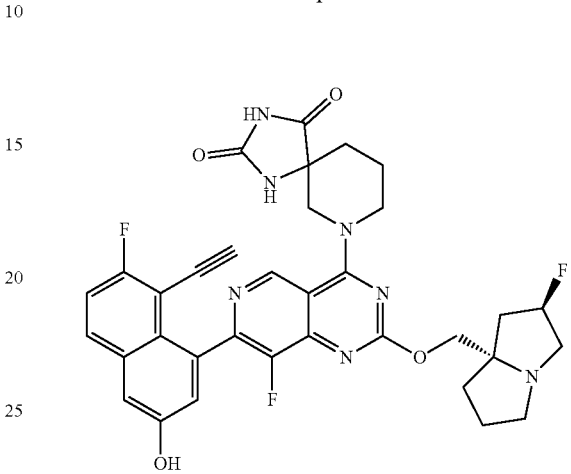

7-(7-(8-ethynyl-7-fluoro-3-hydroxynaphthalen-1-yl)-8-fluoro-2-(((2R,7aS)-2-fluorohexahydro-1H-pyr-rolizin-7a-yl)methoxy)pyrido[4,3-d]pyrimidin-4-yl)-1,3,7-triazaspiro[4.5]decane-2,4-dione The title compound was synthesized according to the procedure described for example 390. $^1$H NMR (400 MHz, METHANOL-d$_4$) δ 9.05 (d, J=6.4 Hz, 1H), 7.86 (dd, J=6.0, 9.2 Hz, 1H), 7.37-7.29 (m, 2H), 7.23 (dd, J=2.4, 4.8 Hz, 1H), 5.38-5.22 (m, 1H), 4.64-4.58 (m, 1H), 4.56-4.49 (m, 1H), 4.45-4.13 (m, 3H), 3.97-3.56 (m, 3H), 3.23-3.12 (m, 2H), 3.05-2.96 (m, 1H), 2.37-2.23 (m, 2H), 2.23-2.13 (m, 2H), 2.12-2.03 (m, 2H), 2.03-1.91 (m, 4H). LCMS (ESI, M+1): m/z=658.4.

Example 398

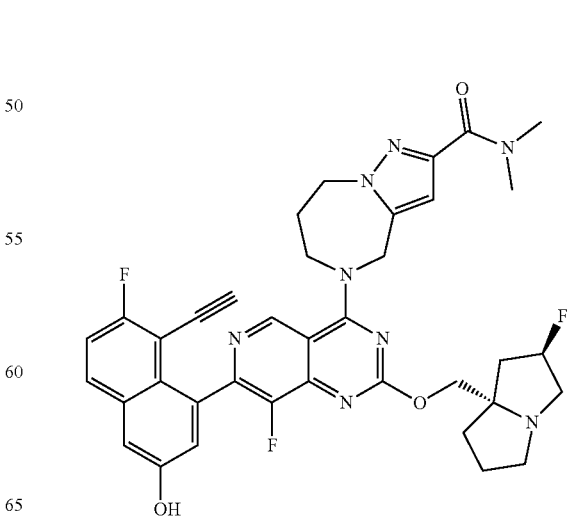

581

5-(7-(8-ethynyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-N,N-dimethyl-5,6,7,8-tetrahydro-4H-pyrazolo[1,5-a][1,4]diazepine-2-carboxamide The title compound was synthesized according to the procedure described for example 390. $^1$H NMR (400 MHz, METHANOL-$d_4$) δ=9.14 (s, 1H), 7.88 (dd, J=5.6, 9.2 Hz, 1H), 7.38-7.31 (m, 2H), 7.23 (d, J=2.4 Hz, 1H), 6.79 (s, 1H), 5.42-5.19 (m, 3H), 4.61-4.55 (m, 2H), 4.46 (br t, J=5.6 Hz, 2H), 4.35-4.21 (m, 2H), 3.43 (d, J=4.8 Hz, 1H), 3.36 (s, 2H), 3.28-3.14 (m, 3H), 3.10 (s, 3H), 3.06-2.98 (m, 1H), 2.46 (br s, 2H), 2.07-1.84 (m, 4H), 2.37-1.84 (m, 3H); LCMS (ESI, M+1): m/z=697.3.

Example 399

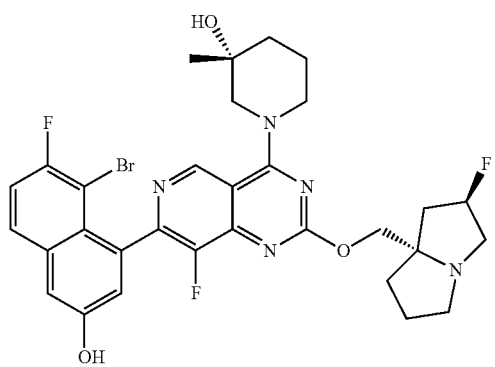 [SMILES: C[C@@]1(O)CCCN(c2nc(OC[C@@]34CCCN3C[C@H](F)C4)nc3c(F)c(-c4cc(O)cc5ccc(F)c(Br)c45)ncc23)C1]

(R)-1-(7-(8-bromo-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol

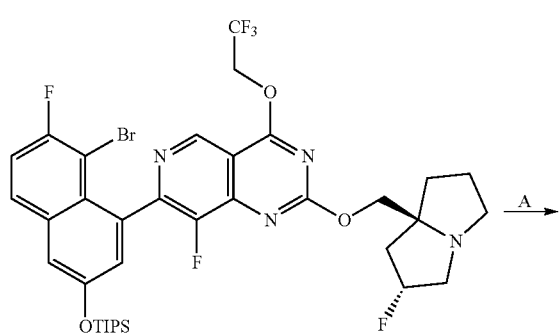

582

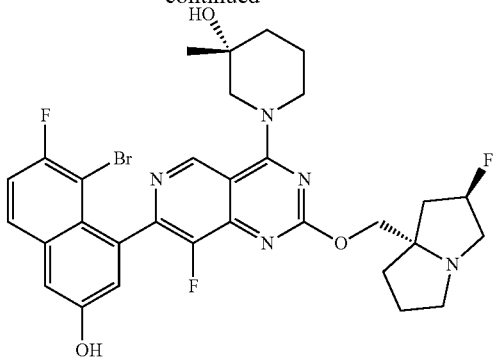

Step A. (S)-1-(7-(8-bromo-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a solution of 7-(8-bromo-7-fluoro-3-((triisopropylsilyl)oxy)naphthalen-1-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (100 mg, 1.0 equiv.) in DMF (0.5 mL) were added DIEA (129 mg, 8.0 equiv.), 4 Å molecular sieves (5 mg, 1.00 equiv.) and (3R)-3-methylpiperidin-3-ol (28.4 mg, 1.97 equiv.). The mixture was stirred at 40° C. for 12 hours. The reaction mixture was filtered and the filtrate was purified by prep-HPLC (column: Phenomenex Luna C18 150×25 mm×10 μm; mobile phase: [water (0.1% formic acid)-ACN]; B %: 16%-46%, 8 min) and lyophilized to afford the title compound (13.2 mg, 16% yield) as a brown solid; $^1$H NMR (400 MHz, METHANOL-$d_4$) δ=9.23 (d, J=11.2 Hz, 1H), 8.61-8.38 (m, 1H), 7.91-7.82 (m, 1H), 7.41-7.33 (m, 2H), 7.24 (dd, J=2.8, 4.4 Hz, 1H), 5.52-5.35 (m, 1H), 4.59 (br d, J=13.2 Hz, 1H), 4.54-4.40 (m, 2H), 4.33 (br dd, J=5.6, 13.2 Hz, 1H), 3.73-3.59 (m, 2H), 3.59-3.51 (m, 2H), 3.49-3.41 (m, 1H), 3.28-3.19 (m, 1H), 2.60-2.33 (m, 2H), 2.32-2.24 (m, 1H), 2.23-2.09 (m, 3H), 2.07-1.98 (m, 1H), 1.90-1.73 (m, 3H), 1.30 (d, J=6.4 Hz, 3H); LCMS (ESI, M+1): m/z=658.2.

Example 400

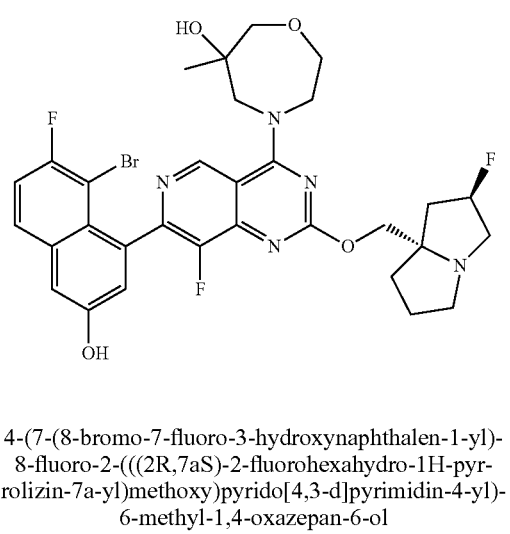

4-(7-(8-bromo-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol The title compound was synthesized according to the procedure described for example 399. $^1$H NMR (400 MHz, METHANOL-d₄) δ=9.54 (dd, J=2.8, 12.0 Hz, 1H), 8.51 (s, 1H), 7.86 (ddd, J=1.2, 5.6, 9.2 Hz, 1H), 7.43-7.32 (m, 2H), 7.24 (dd, J=2.4, 14.4 Hz, 1H), 5.48-5.28 (m, 1H), 4.59-4.49 (m, 2H), 4.48-4.33 (m, 2H), 4.23-4.14 (m, 1H), 4.06-3.87 (m, 3H), 3.75-3.63 (m, 2H), 3.55-3.36 (m, 3H), 3.21-3.09 (m, 1H), 2.49-2.28 (m, 2H), 2.26-2.18 (m, 1H), 2.14-2.04 (m, 2H), 2.03-1.92 (m, 1H), 1.28 (s, 3H). LCMS (ESI, M+1): m/z=674.2.

Example 401

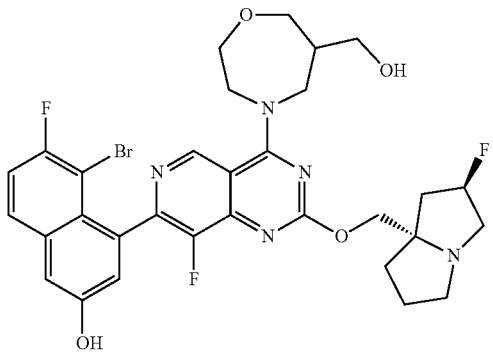 [SMILES: OCC1COCCN(c2nc(OC[C@@]34CCCN3C[C@H](F)C4)nc3c(F)c(-c4cc(O)cc5ccc(F)c(Br)c45)ncc23)C1]

5-bromo-6-fluoro-4-(8-fluoro-2-(((2R,7aS)-2-fluoro-hexahydro-1H-pyrrolizin-7a-yl)methoxy)-4-(6-(hydroxymethyl)-1,4-oxazepan-4-yl)pyrido[4,3-d]pyrimidin-7-yl)naphthalen-2-ol The title compound was synthesized according to the procedure described for example 399. ¹H NMR (400 MHz, METHANOL-d₄) 5-9.34-9.16 (m, 1H), 8.59-8.46 (m, 1H), 7.88 (dd, J=5.6, 9.2 Hz, 1H), 7.46-7.34 (m, 2H), 7.27 (dd, J=2.4, 11.2 Hz, 1H), 5.54-5.35 (m, 1H), 4.67 (dt, J=4.4, 9.2 Hz, 1H), 4.60-4.39 (m, 3H), 4.21-3.94 (m, 4H), 3.92-3.78 (m, 1H), 3.69-3.44 (m, 6H), 3.28-3.17 (m, 1H), 2.35 (br s, 3H), 2.31-1.98 (m, 4H); LCMS (ESI, M+1): m/z=674.2.

Example 402

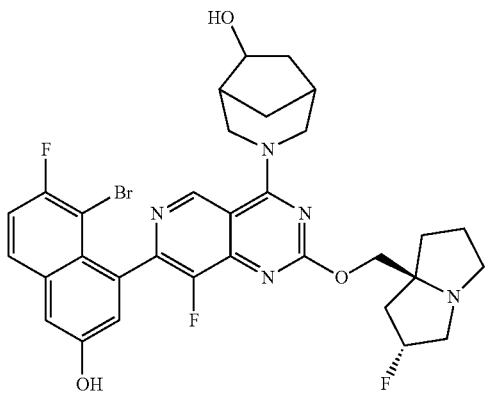 [SMILES: Oc1cc(-c2ncc3c(N4CC5CC(O)C(C5)C4)nc(OC[C@@]45CCCN4C[C@H](F)C5)nc3c2F)c2c(Br)c(F)ccc2c1]

3-(7-(8-bromo-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-azabicyclo[3.2.1]octan-6-ol The title compound was synthesized according to the procedure described for example 399. ¹HNMR (400 MHz, METHANOL-d₄) δ=9.32-9.20 (m, 1H), 8.59-8.47 (m, 1H), 7.88 (ddd, J=1.2, 5.6, 9.2 Hz, 1H), 7.41 (d, J=2.4 Hz, 1H), 7.40-7.35 (m, 1H), 7.26 (dd, J=2.4, 16.8 Hz, 1H), 5.53-5.35 (m, 1H), 5.03 (br d, J=9.6 Hz, 1H), 4.80 (br s, 1H), 4.54-4.47 (m, 1H), 4.46-4.38 (m, 1H), 4.38-4.30 (m, 1H), 3.91-3.74 (m, 1H), 3.71-3.43 (m, 4H), 3.28-3.18 (m, 1H), 2.59-2.37 (m, 3H), 2.36-2.21 (m, 3H), 2.21-2.11 (m, 2H), 2.09-1.92 (m, 2H), 1.89-1.78 (m, 1H), 1.45-1.35 (m, 1H); LCMS (ESI, M+1): nm/z=670.1.

Example 403

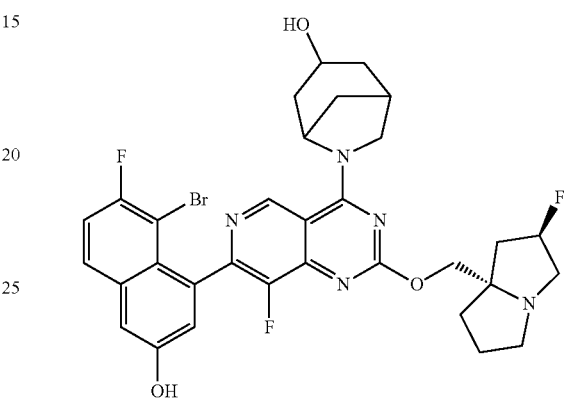

6-(7-(8-bromo-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azabicyclo[3.2.1]octan-3-ol The title compound was synthesized according to the procedure described for example 399. ¹H NMR (400 MHz, METHANOL-d₄) δ=9.30 (br d, J=7.2 Hz, 11H), 8.50 (s, 1H), 7.86 (dd, J=5.6, 9.2 Hz, 1H), 7.34 (s, 2H), 7.29-7.19 (m, 1H), 5.53-5.35 (m, 1H), 5.00 (br s, 1H), 4.55-4.34 (m, 3H), 4.31-4.24 (m, 1H), 4.14 (br s, 1H), 3.74-3.52 (m, 3H), 3.27-3.21 (m, 1H), 2.84-2.58 (m, 2H), 2.55 (br s, 1H), 2.45-2.26 (m, 2H), 2.17 (br dd, J=5.2, 9.2 Hz, 3H), 2.10-1.98 (m, 3H), 1.94-1.76 (m, 2H). LCMS (ESI, M+1): m/z=670.2.

Example 404

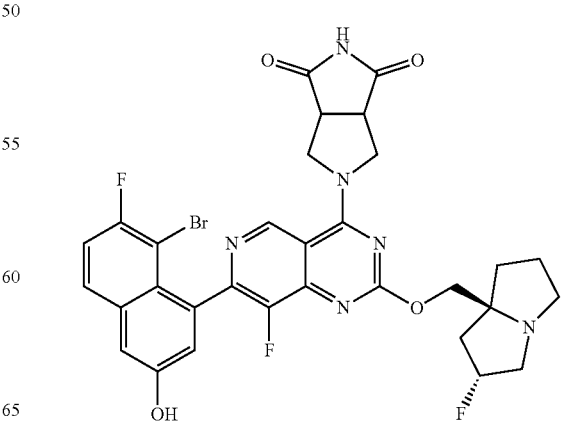

5-(7-(8-bromo-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)tetrahydropyrrolo[3,4-c]pyrrole-1,3(2H,3aH)-dione The title compound was synthesized according to the procedure described for example 399. $^1$H NMR (400 MHz, METHANOL-d$_4$) δ=9.26 (s, 1H), 8.51 (br s, 1H), 7.86 (dd, J=5.6, 9.2 Hz, 1H), 7.40-7.33 (m, 2H), 7.24 (d, J=2.4 Hz, 1H), 5.47-5.29 (m, 1H), 4.64 (br t, J=12.0 Hz, 2H), 4.47-4.42 (m, 1H), 4.41-4.30 (m, 3H), 3.81-3.72 (m, 2H), 3.57-3.45 (m, 1H), 3.45-3.35 (m, 2H), 3.20-3.10 (m, 1H), 2.51-2.30 (m, 2H), 2.29-2.17 (m, 1H), 2.15-2.05 (m, 2H), 2.04-1.93 (m, 1H); LCMS (ESI, M+1): m/z=682.9.

Example 405

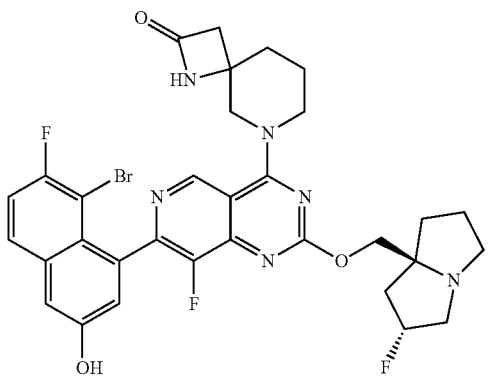 [SMILES: O=C1CC2(CCCN(c3nc(OC[C@@]45CCCN4C[C@H](F)C5)nc4c(F)c(-c5cc(O)cc6ccc(F)c(Br)c56)ncc34)C2)N1]

6-(7-(8-bromo-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,6-diazaspiro[3.5]nonan-2-one The title compound was synthesized according to the procedure described for example 399. $^1$H NMR (400 MHz, METHANOL-d$_4$) δ=9.11 (s, 1H), 8.45 (br s, 1H), 7.87 (br dd, J=5.8, 8.0 Hz, 1H), 7.43-7.33 (m, 2H), 7.25 (br s, 1H), 5.58-5.34 (m, 1H), 4.63-4.26 (m, 4H), 4.09-3.96 (m, 1H), 3.92-3.54 (m, 4H), 3.29-3.22 (m, 1H), 2.99-2.72 (m, 2H), 2.62-2.25 (m, 3H), 2.23-1.92 (m, 7H) LCMS (ESI, M+1): m/z=683.2.

Example 406

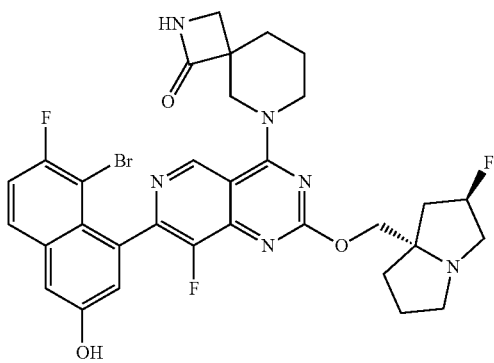 [SMILES: O=C1NCC12CCCN(c1nc(OC[C@@]34CCCN3C[C@H](F)C4)nc3c(F)c(-c4cc(O)cc5ccc(F)c(Br)c45)ncc13)C2]

6-(7-(8-bromo-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2,6-diazaspiro[3.5]nonan-1-one The title compound was synthesized according to the procedure described for example 399. $^1$H NMR (400 MHz, METHANOL-d$_4$) δ=9.09 (d, J=2.0 Hz, 1H), 8.49 (br d, J=2.4 Hz, 1H), 7.86 (dd, J=5.6, 9.2 Hz, 1H), 7.42-7.33 (m, 2H), 7.25 (t, J=3.2 Hz, 1H), 5.57-5.28 (m, 1H), 4.54-4.27 (m, 4H), 4.26-3.91 (m, 2H), 3.70-3.45 (m, 3H), 3.29-3.17 (m, 3H), 2.57-2.35 (m, 2H), 2.32-2.08 (m, 6H), 2.07-1.89 (m, 2H); LCMS (ESI, M+1): m/z=683.2.

Example 407

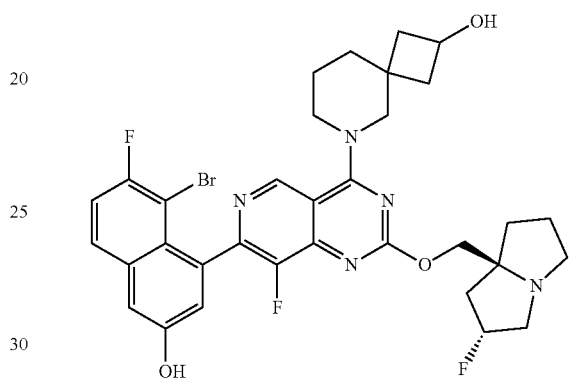

6-(7-(8-bromo-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azaspiro[3.5]nonan-2-ol The title compound was synthesized according to the procedure described for example 399. $^1$H NMR (400 MHz, METHANOL-d$_4$) δ=9.11-9.05 (m, 11H), 8.54-8.43 (m, 1H), 7.91-7.82 (m, 1H), 7.43-7.31 (m, 2H), 7.30-7.22 (m, 1H), 5.52-5.36 (m, 1H), 4.56-4.44 (m, 2H), 4.32-4.24 (m, 1H), 4.15-3.95 (m, 4H), 3.69-3.50 (m, 3H), 3.27-3.19 (m, 1H), 2.53-2.15 (m, 7H), 2.09-2.00 (m, 11H), 1.88-1.72 (m, 6H); LCMS (ESI, M+1): m/z=684.2.

Example 408

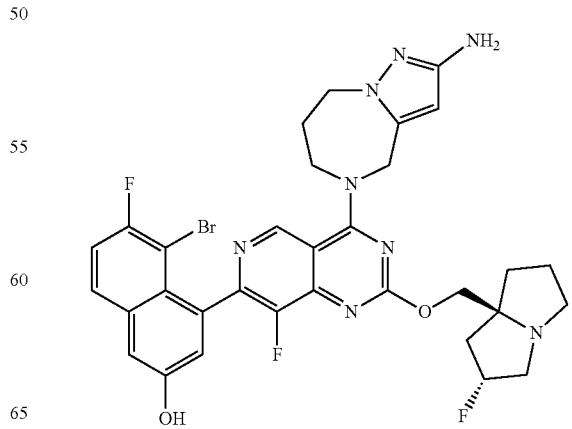

4-(4-(2-amino-7,8-dihydro-4H-pyrazolo[1,5-a][1,4]
diazepin-5(6H)-yl)-8-fluoro-2-(((2R,7aS)-2-fluoro-
hexahydro-1H-pyrrolizin-7a-yl)methoxy)pyrido[4,3-
d]pyrimidin-7-yl)-5-bromo-6-fluoronaphthalen-2-ol The title compound was synthesized according to the procedure described for example 399. $^1$H NMR (400 MHz, METHANOL-d$_4$) δ=9.20 (s, 1H), 7.87-7.83 (m, 1H), 7.42-7.33 (m, 2H), 7.25 (d, J=2.0 Hz, 1H), 5.78 (s, 1H), 5.51-5.33 (m, 1H), 5.19-5.01 (m, 2H), 4.51-4.39 (m, 2H), 4.38-4.32 (m, 2H), 4.27-4.18 (m, 2H), 3.65-3.42 (m, 3H), 3.25-3.15 (m, 11H), 2.54-2.41 (m, 1H), 2.40-2.30 (m, 3H), 2.30-2.21 (m, 1H), 2.19-2.09 (m, 2H), 2.07-1.96 (m, 1H); LCMS (ESI, M+1): m/z=695.2.

Example 409

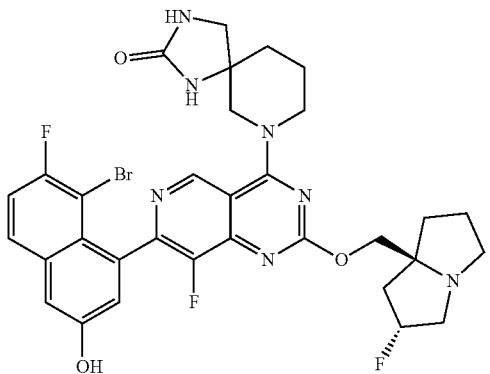 [SMILES: O=C1NCC2(CCCN(c3nc(OC[C@@]45CCCN4C[C@H](F)C5)nc4c(F)c(-c5cc(O)cc6ccc(F)c(Br)c56)ncc34)C2)N1]

7-(7-(8-bromo-7-fluoro-3-hydroxynaphthalen-1-yl)-
8-fluoro-2-(((2R,7aS)-2-fluorohexahydro-1H-pyr-
rolizin-7a-yl)methoxy)pyrido[4,3-d]pyrimidin-4-yl)-
1,3,7-triazaspiro[4.5]decan-2-one The title compound was synthesized according to the procedure described for example 399. $^1$H NMR (400 MHz, METHANOL-d$_4$) δ=9.09 (s, 1H), 7.91-7.79 (m, 1H), 7.46-7.31 (m, 2H), 7.24 (s, 11H), 5.44-5.19 (m, 11H), 4.37-4.23 (m, 2H), 4.19-4.06 (m, 2H), 4.05-3.89 (m, 2H), 3.52-3.34 (m, 2H), 3.27-3.18 (m, 3H), 3.05-2.96 (m, 1H), 2.39-2.12 (m, 3H), 2.05-1.84 (m, 7H); LCMS (ESI, M+1): m/z=698.1.

Example 410

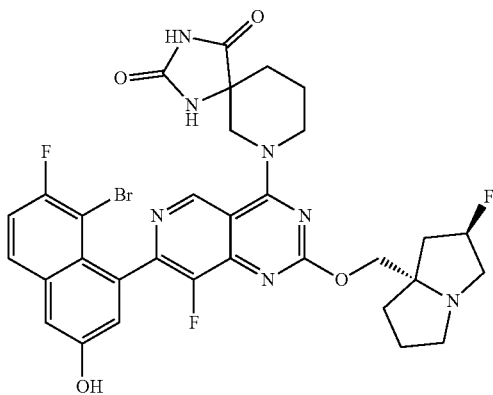 [SMILES: O=C1NC(=O)C2(CCCN(c3nc(OC[C@@]45CCCN4C[C@H](F)C5)nc4c(F)c(-c5cc(O)cc6ccc(F)c(Br)c56)ncc34)C2)N1]

7-(7-(8-bromo-7-fluoro-3-hydroxynaphthalen-1-yl)-
8-fluoro-2-(((2R,7aS)-2-fluorohexahydro-1H-pyr-
rolizin-7a-yl)methoxy)pyrido[4,3-d]pyrimidin-4-yl)-
1,3,7-triazaspiro[4.5]decane-2,4-dione The title compound was synthesized according to the procedure described for example 399. $^1$H NMR (400 MHz, METHANOL-d$_4$) δ=9.09 (s, 1H), 7.85 (dd, J=6.0, 8.8 Hz, 1H), 7.40-7.20 (m, 3H), 5.45-5.15 (m, 11H), 4.54-4.40 (m, 2H), 4.31-4.18 (m, 2H), 3.86-3.70 (m, 2H), 3.23-3.16 (m, 2H), 3.13-2.93 (m, 2H), 2.39-2.17 (m, 4H), 2.16-2.08 (m, 2H), 2.03-1.98 (m, 2H), 1.95-1.88 (m, 2H). LCMS (ESI, M+1): m/z=712.0.

Example 411

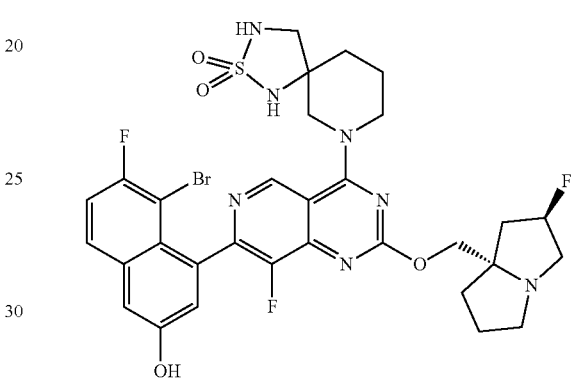

7-(7-(8-bromo-7-fluoro-3-hydroxynaphthalen-1-yl)-
8-fluoro-2-(((2R,7aS)-2-fluorohexahydro-1H-pyr-
rolizin-7a-yl)methoxy)pyrido[4,3-d]pyrimidin-4-yl)-
2-thia-1,3,7-triazaspiro[4.5]decane 2,2-dioxide The title compound was synthesized according to the procedure described for example 399. $^1$H NMR (400 MHz, METHANOL-d$_4$) δ=9.11 (d, J=7.2 Hz, 1H), 8.54-8.43 (m, 1H), 7.86 (td, J=5.2, 9.2 Hz, 1H), 7.41-7.31 (m, 2H), 7.23 (t, J=2.0 Hz, 1H), 5.57-5.34 (m, 1H), 4.65 (br dd, J=4.0, 14.4 Hz, 1H), 4.62-4.53 (m, 1H), 4.52-4.41 (m, 2H), 3.85-3.76 (m, 1H), 3.74-3.50 (m, 4H), 3.45-3.38 (m, 1H), 3.28-3.18 (m, 2H), 2.62-2.38 (m, 2H), 2.38-2.27 (m, 1H), 2.22-2.13 (m, 2H), 2.12-2.00 (m, 3H), 1.99-1.83 (m, 2H); LCMS (ESI, M+1): m/z=734.1.

Example 412

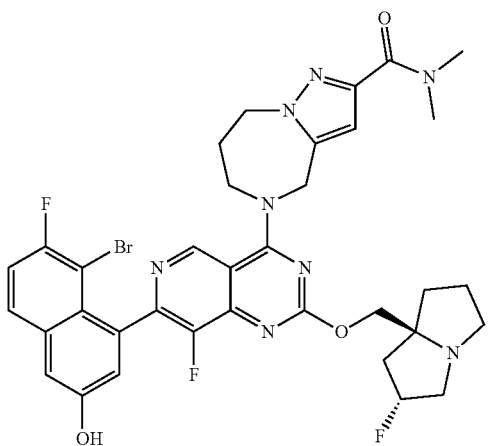

5-(7-(8-bromo-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-N,N-dimethyl-5,6,7,8-tetrahydro-4H-pyrazolo[1,5-a][1,4]diazepine-2-carboxamide The title compound was synthesized according to the procedure described for example 399. $^1$H NMR (400 MHz, methanol-$d_4$) δ=9.19 (s, 1H), 8.52 (br s, 1H), 7.86 (dd, J=5.4, 8.8 Hz, 1H), 7.43-7.33 (m, 2H), 7.24 (d, J=2.4 Hz, 1H), 6.76 (s, 1H), 5.46-5.19 (m, 3H), 4.60 (br s, 4H), 4.42-4.30 (m, 2H), 3.54-3.45 (m, 1H), 3.42-3.36 (m, 2H), 3.34 (s, 3H), 3.21-3.11 (m, 1H), 3.11-3.06 (m, 31H), 2.51-2.50 (m, 1H), 2.18-2.16 (m, 11H), 2.50-2.16 (m, 5H), 2.13-1.92 (m, 3H); LCMS (ESI, M+1): m/z=751.0.

Example 413

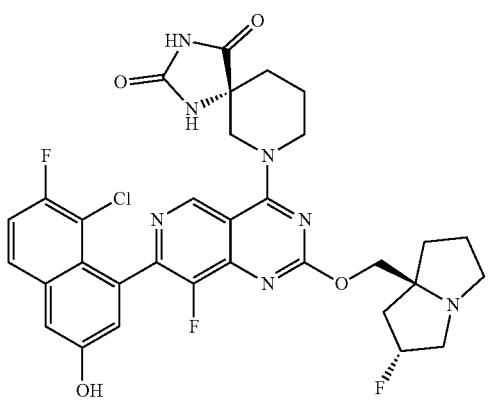 [SMILES: O=C1NC(=O)[C@]2(CCCN(c3nc(OC[C@@]45CCCN4C[C@H](F)C5)nc4c(F)c(-c5cc(O)cc6ccc(F)c(Cl)c56)ncc34)C2)N1]

(R)-7-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decane-2,4-dione

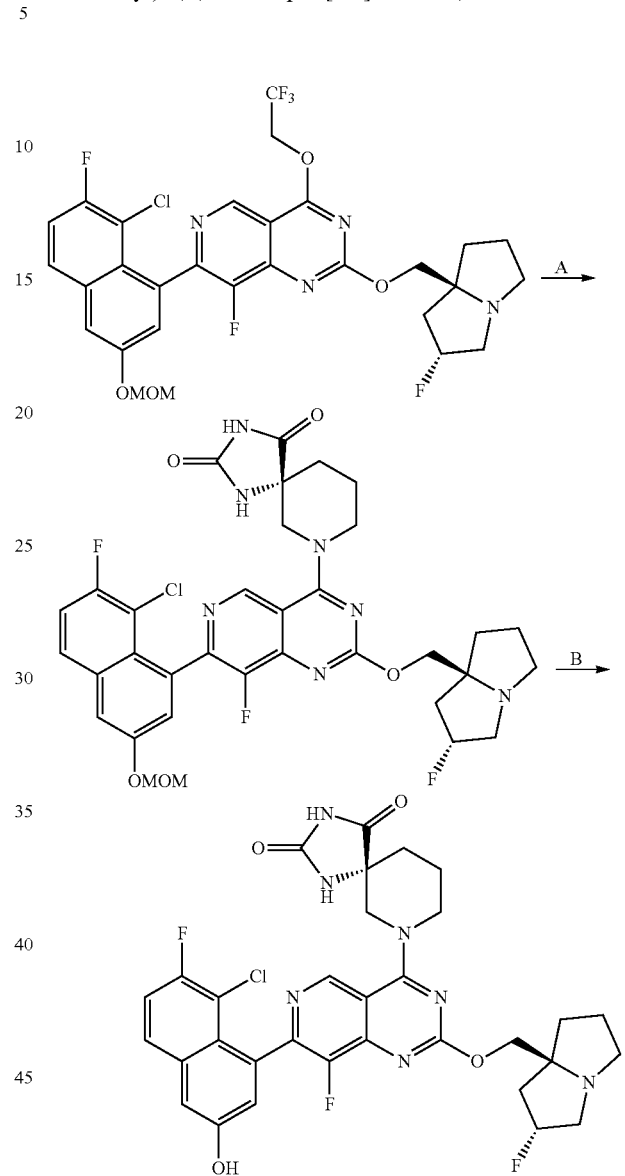

Step A. (R)-7-(7-(8-chloro-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decane-2,4-dione: To a mixture of 7-(8-chloro-7-fluoro-3-(methoxymethoxy)naphthalen-1-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (100 mg, 1.0 equiv.), (5R)-1,3,9-triazaspiro[4.5]decane-2,4-dione (78.9 mg, 3.0 equiv.) and 4 Å molecular sieves (10 mg) in DMF (1 mL) was added DIEA (100 mg, 5.0 equiv.). The reaction was stirred at 40° C. for 12 hours. The residue was filtered and purified by reversed phase flash chromatography [C18, water (0.1% formic acid)/ACN] to afford the title compound (110 mg, 92% yield) as a yellow solid; LCMS (EST, M+1): m/z=712.3.

Step B. (R)-7-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decane-2,4-dione: To a solution of (R)-7-(7-(8-chloro-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decane-2,4-dione (50 mg, 1.0 equiv.) in DCM (2 mL) and MeOH (2 mL) was added TsOH (121 mg, 10 equiv.). The reaction was stirred at 10° C. for 12 hours. The residue was filtered and purified by prep-HPLC [column: Phenomenex C18 75×30 mm×3 μm; mobile phase: water (0.1% formic acid)/ACN] B %: 10%-40%, 7 min] and lyophilized to afford the title compound (20.0 mg, 41% yield) as a white solid; $^1$H NMR (400 MHz, methanol-$d_4$) δ=9.15 (d, J=14.8 Hz, 1H), 7.83 (ddd, J=1.6, 5.6, 9.2 Hz, 1H), 7.52-7.29 (m, 2H), 7.27-7.17 (m, 1H), 5.64-5.43 (m, 1H), 4.77-4.28 (m, 6H), 3.95-3.67 (m, 4H), 3.44-3.32 (m, 1H), 2.72-2.52 (m, 1H), 2.51-2.29 (m, 2H), 2.29-2.05 (m, 4H), 2.05-1.87 (m, 2H); LCMS (ESI, M+1): m/z=668.2.

Example 414

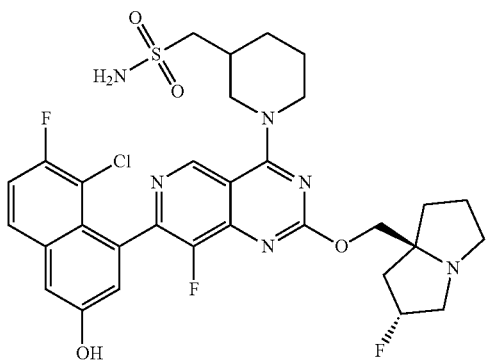

1-(1-(7-(8-chloro-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperidin-3-yl)methanesulfonamide The title compound was synthesized according to the procedure described for example 413 except for HCl.dioxane in MeCN was added in step B. $^1$H NMR (400 MHz, DMSO-d6) δ=9.06 (d, J=2.0 Hz, 1H), 7.92 (dd, J=6.0, 9.2 Hz, 1H), 7.55 (t, J=8.8 Hz, 1H), 7.41 (d, J=2.4 Hz, 1H), 7.19 (s, 1H), 7.03-6.70 (m, 2H), 5.38-5.17 (m, 1H), 4.70-4.53 (m, 1H), 4.45-4.31 (m, 1H), 4.19-4.00 (m, 2H), 3.16-3.03 (m, 4H), 3.03-2.96 (m, 2H), 2.86-2.78 (m, 1H), 2.42-2.34 (m, 1H), 2.33 (m, 1H), 2.20-2.09 (m, 11H), 2.09-1.98 (m, 3H), 1.92-1.69 (m, 5H), 1.60-1.45 (m, 1H); LCMS (ESI, M+1): m/z=677.3.

Example 415

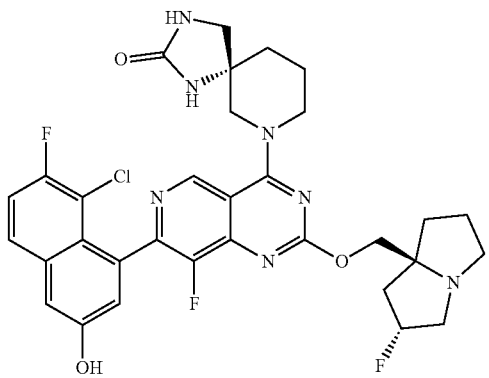 [SMILES: O=C1NC[C@]2(CCCN(c3nc(OC[C@@]45CCCN4C[C@H](F)C5)nc4c(F)c(-c5cc(O)cc6ccc(F)c(Cl)c56)ncc34)C2)N1]

(S)-7-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decan-2-one The title compound was synthesized according to the procedure described for example 413. $^1$H NMR (400 MHz, methanol-$d_4$) δ=9.14 (d, J=7.2 Hz, 1H), 7.85-7.66 (m, 1H), 7.47-7.31 (m, 2H), 7.25-7.18 (m, 1H), 5.65-5.33 (m, 1H), 4.63-4.54 (m, 2H), 4.39 (br t, J=13.2 Hz, 1H), 4.31-4.16 (m, 1H), 4.05-3.63 (m, 5H), 3.47-3.34 (m, 2H), 2.73-2.45 (m, 2H), 2.43 (br d, J=4.4 Hz, 5H), 2.09-1.76 (m, 4H); LCMS (ESI, M+1): m/z=654.2.

Example 416

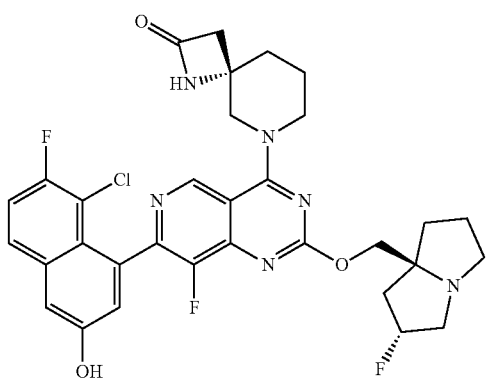 [SMILES: O=C1C[C@]2(CCCN(c3nc(OC[C@@]45CCCN4C[C@H](F)C5)nc4c(F)c(-c5cc(O)cc6ccc(F)c(Cl)c56)ncc34)C2)N1]

(S)-6-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,6-diazaspiro[3.5]nonan-2-one

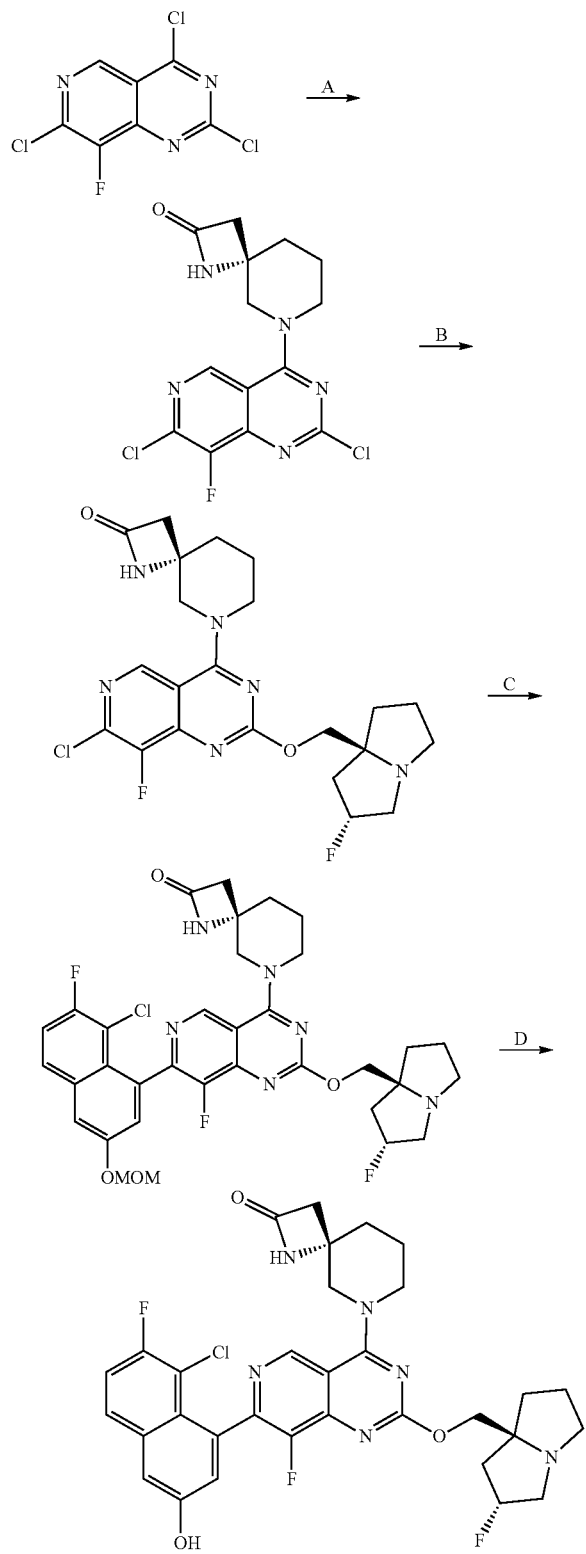

Step A. (S)-6-(2,7-dichloro-8-fluoropyrido[4,3-d]pyrimidin-4-yl)-1,6-diazaspiro[3.5]nonan-2-one: To a solution of 2,4,7-trichloro-8-fluoropyrido[4,3-d]pyrimidine (500 mg, 1.0 equiv.), (S)-1,6-diazaspiro[3.5]nonan-2-one (138 mg, 0.5 equiv.) in DCM (5 mL) was added DIEA (767 mg, 1.03 mL, 3.0 equiv.). The mixture was stirred at −40° C. for 0.5 hour. After reaction completion, the mixture was concentrated under reduced pressure to give a residue. The crude product was purified by reversed-phase flash chromatography (water (0.1% formic acid)-ACN) to afford the title compound (330 mg, 46% yield) as a white solid; LCMS [ESI, M+1]: m/z=356.1.

Step B. (S)-6-(7-chloro-8-fluoro-2-(((2R,7aS)-2-fluorohexahydro-1H-pyrrolizin-7a-yl)methoxyl)pyrido[4,3-d]pyrimidin-4-yl)-1,6-diazaspiro[3.5]nonan-2-one: To a mixture of (S)-6-(2,7-dichloro-8-fluoropyrido[4,3-d]pyrimidin-4-yl)-1,6-diazaspiro[3.5]nonan-2-one (300 mg, 1.0 equiv.), ((2R,7aS)-2-fluorohexahydro-1H-pyrrolizin-7a-yl)methanol (268 mg, 2.0 equiv.), 4 Å molecular sieves (10.0 mg, 1.0 equiv.) in dioxane (3 mL) was added DIEA (544 mg, 733 μL, 5.0 equiv.). The reaction was stirred at 90° C. for 12 hours. After completion, the reaction mixture was quenched by addition of water (3 mL), and extracted with Ethyl acetate (10 mL). The combined organic layer was dried over anhydrous Na₂SO₄, filtered and concentrated under reduced pressure to give a residue. The crude product was purified by reversed-phase flash chromatography (water (0.1% formic acid)-ACN) to afford the title compound (210 mg, 52% yield) as a yellow solid; LCMS [ESI, M+1]: m/z=479.1.

Step C. (S)-6-(7-(8-chloro-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,6-diazaspiro[3.5]nonan-2-one: To a solution of (S)-6-(7-chloro-8-fluoro-2-(((2R,7aS)-2-fluorohexahydro-1H-pyrrolizin-7a-yl)methoxy)pyrido[4,3-d]pyrimidin-4-yl)-1,6-diazaspiro[3.5]nonan-2-one (130 mg, 1.0 equiv.), (8-chloro-7-fluoro-3-(methoxymethoxy)naphthalen-1-yl)trimethylstannane (328 mg, 3.0 equiv.) in toluene (3 mL) was added Pd(dppf)Cl2 (19.8 mg, 0.1 equiv.), BINAP (33.8 mg, 0.2 equiv.), CuI (15.5 mg, 0.3 equiv.) under N₂. The reaction was stirred at 90° C. for 2 hours under N₂. After reaction completion, the mixture was quenched by addition of water (3 mL), and then extracted with Ethyl acetate (6 mL). The organic layer was dried over anhydrous Na₂SO₄, filtered and concentrated under reduced pressure to give a residue. The crude product was purified by reversed-phase flash chromatography (water (0.1% formic acid)-ACN) to afford the title compound (57.0 mg, 17% yield) as a green oil; LCMS [ESI, M+1]: m/z=683.4.

Step D. (S)-6-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,6-diazaspiro[3.5]nonan-2-one: To a solution of (S)-6-(7-(8-chloro-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-1,6-diazaspiro[3.5]nonan-2-one (52.0 mg, 1.0 equiv.) in DCM (0.5 mL) was added TFA (770 mg, 0.5 mL, 88 equiv.) at 0° C. The reaction was stirred at 0° C. for 0.5 hour. After reaction completion, the mixture was concentrated under reduced pressure to give a residue. The pH of the residue was adjusted to 9 with sat. aq. NaHCO₃ and the resulting mixture was extracted with DCM (3×2 mL), dried over anhydrous Na₂SO₄, filtered and concentrated to give a residue. The residue was purified by prep-HPLC (column: Phenomenex Synergi C18 150×25 mm×10 μm; mobile phase: [water (0.1% formic acid)-ACN]; B %: 8%-38%, 10 min) and lyophilized to afford the title compound (26.3 mg, 49% yield, formic acid salt) as a white solid; ¹H NMR (400 MHz, methanol-d₄): δ=9.10 (d, J=3.2 Hz, 1H), 8.49 (br s, 1H), 7.82 (dd, J=5.6, 9.2 Hz, 1H), 7.43-7.37 (m, 2H), 7.22 (d, J=2.4 Hz, 1H), 5.49-5.32 (m, 1H), 4.47-4.37 (m, 3H), 4.36-4.26 (m, 1H), 3.99 (dd, J=2.8, 13.2 Hz, 1H), 3.86-3.75 (m, 1H), 3.62-3.43 (m, 3H), 3.18 (dt, J=5.6, 9.6 Hz, 1H), 2.91 (dd, J=6.8, 14.8 Hz, 1H), 2.79-2.73 (m, 1H), 2.53-2.33 (m, 2H), 2.31-2.21 (m, 1H), 2.17-2.08 (m, 3H), 2.06-1.90 (m, 4H); LCMS [ESI, M+1]: m/z=638.9.

Example 417

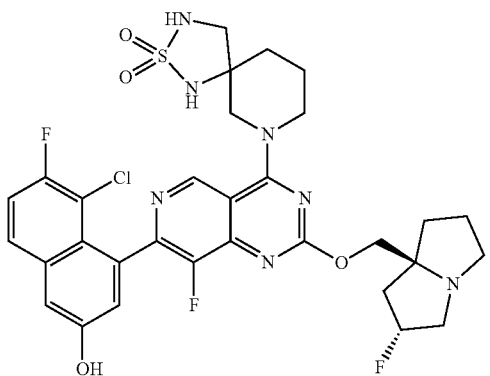 [SMILES: O=S1(=O)NCC2(CCCN(c3nc(OC[C@@]45CCCN4C[C@H](F)C5)nc4c(F)c(-c5cc(O)cc6ccc(F)c(Cl)c56)ncc34)C2)N1]

7-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2-thia-1,3,7-triazaspiro[4.5]decan 2,2-dioxide The title compound was synthesized according to the procedure described for example 414. ¹H NMR (400 MHz, METHANOL-d₄) δ=9.19-9.05 (m, 1H), 7.81 (ddd, J=3.6, 5.6, 9.2 Hz, 1H), 7.43-7.35 (m, 2H), 7.24-7.19 (m, 1H), 5.58-5.33 (m, 1H), 4.73-4.55 (m, 2H), 4.55-4.25 (m, 3H), 3.90-3.67 (m, 2H), 3.66-3.45 (m, 3H), 3.44-3.33 (m, 1H), 3.29-3.19 (m, 2H), 2.61-2.37 (m, 2H), 2.36-2.25 (m, 1H), 2.22-2.12 (m, 2H), 2.11-1.99 (m, 3H), 1.95-1.79 (m, 2H); LCMS (ESI, M+1): m/z=690.2.

Example 418

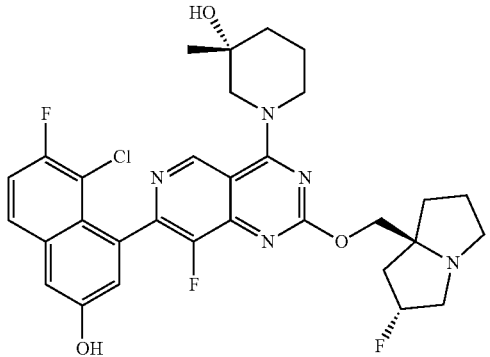 [SMILES: C[C@@]1(O)CCCN(c2nc(OC[C@@]34CCCN3C[C@H](F)C4)nc3c(F)c(-c4cc(O)cc5ccc(F)c(Cl)c45)ncc23)C1]

(R)-1-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol The title compound was synthesized according to the procedure described for example 414. ¹H NMR (400 MHz, METHANOL-d₄) δ=9.23 (s, 1H), 8.49 (br s, 1H), 7.85-7.79 (m, 1H), 7.44-7.35 (m, 2H), 7.22 (t, J=2.8 Hz, 1H), 5.57-5.29 (m, 1H), 4.60 (br s, 2H), 4.54-4.50 (m, 1H), 4.47-4.41 (m, 1H), 4.37-4.28 (m, 1H), 3.73-3.63 (m, 1H), 3.62-3.55 (m, 2H), 3.50-3.41 (m, 1H), 3.28-3.19 (m, 1H), 2.60-2.38 (m, 2H), 2.36-2.25 (m, 1H), 2.21-2.12 (m, 3H), 2.08-1.98 (m, 1H), 1.90-1.75 (m, 3H), 1.30 (d, J=8.4 Hz, 3H); LCMS (ESI, M+1): m/z=614.3.

Example 419

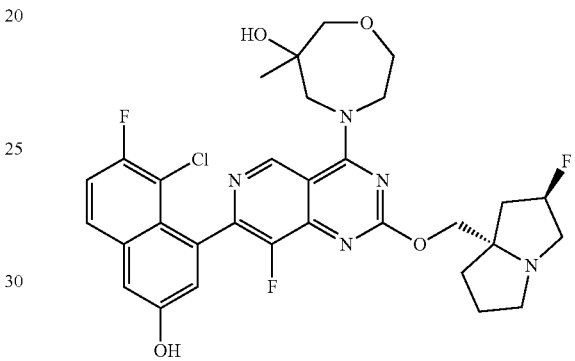

4-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol

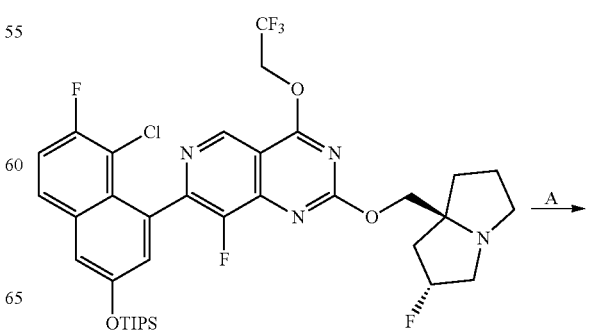

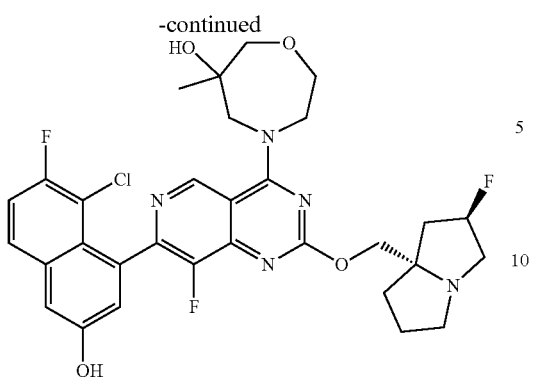

Step A. 4-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-methyl-1,4-oxazepan-6-ol: To a mixture of 7-(8-chloro-7-fluoro-3-((triisopropylsilyl)oxy)naphthalen-1-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (126 mg, 1 equiv.) and 4 Å MS (15 mg) in DMF (0.5 mL) was added DIEA (172 mg, 8 equiv.) and 6-methyl-1,4-oxazepan-6-ol (83.9 mg, 3 equiv., HCl). The mixture was stirred at 40° C. for 12 hr. The reaction mixture was filtered and purified by prep-HPLC (column: 3_Phenomenex Luna C18 75×30 mm×3 um; mobile phase: [water (0.1% formic acid)-ACN]; B %: 8%-38%, 10 min) to afford the title compound (28.7 mg, 25% yield) as a white solid; $^1$H NMR (400 MHz, METHANOL-d4) δ=9.74-9.39 (m, 1H), 8.57-8.42 (m, 1H), 8.01-7.66 (m, 1H), 7.50-7.30 (m, 2H), 7.29-7.12 (m, 1H), 5.50-5.31 (m, 1H), 4.57 (br s, 2H), 4.49-4.37 (m, 2H), 4.25-4.14 (m, 1H), 4.08-3.86 (m, 3H), 3.77-3.63 (m, 2H), 3.51-3.43 (m, 2H), 3.23-3.10 (m, 2H), 2.57-2.41 (m, 1H), 2.38-2.21 (m, 2H), 2.17-1.95 (m, 3H), 1.29 (br s, 3H):LCMS [ESI, M+1]: m/z=630.1.

Example 420

5-chloro-6-fluoro-4-(8-fluoro-2-(((2R,7aS)-2-fluorohexahydro-1H-pyrrolizin-7a-yl)methoxy)-4-(6-(hydroxymethyl)-1,4-oxazepan-4-yl)pyrido[4,3-d]pyrimidin-7-yl)naphthalen-2-ol The title compound was synthesized according to the procedure described for example 413. $^1$H NMR (400 MHz, methanol-d$_4$) δ=9.22 (d, J=6.8 Hz, 1H), 7.85-7.65 (m, 1H), 7.44-7.34 (m, 2H), 7.27-7.17 (m, 1H), 5.62-5.40 (m, 1H), 4.80-4.53 (m, 4H), 4.52-4.31 (m, 1H), 4.18-3.93 (m, 3H), 3.93-3.62 (m, 4H), 3.62-3.53 (m, 2H), 3.41-3.32 (m, 1H), 2.75-2.38 (m, 3H), 2.38-2.13 (m, 4H), 2.13-1.91 (m, 1H); LCMS (ESI, M+1): m/z=630.5.

Example 421

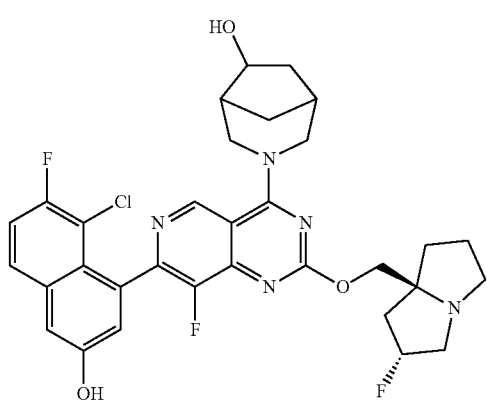 [SMILES: Oc1cc(-c2ncc3c(N4CC5CC(O)C(C5)C4)nc(OC[C@@]45CCCN4C[C@H](F)C5)nc3c2F)c2c(Cl)c(F)ccc2c1]

3-(7-(8-chloro-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3-azabicyclo[3,2,1]octan-6-ol The title compound was synthesized according to the procedure described for example 419. $^1$H NMR (400 MHz, METHANOL-d$_4$) δ=9.25 (dd, J=1.6, 14.8 Hz, 1H), 7.83 (dd, J=5.6, 9.2 Hz, 1H), 7.45-7.36 (m, 2H), 7.23 (dd, J=2.4, 13.6 Hz, 1H), 5.51-5.30 (m, 11H), 4.98 (br s, 1H), 4.83 (br s, 1H), 4.49-4.40 (m, 1H), 4.39-4.29 (m, 2H), 3.85-3.74 (m, 1H), 3.59-3.50 (m, 1H), 3.37 (br s, 3H), 3.21-3.12 (m, 1H), 2.53-2.32 (m, 3H), 2.32-2.18 (m, 3H), 2.16-2.05 (m, 2H), 2.04-1.90 (m, 2H), 1.87-1.78 (m, 11H), 1.40 (br dd, J=2.0, 13.6 Hz, 11H); LCMS [ESI, M+1]: m/z=626.1.

Example 422

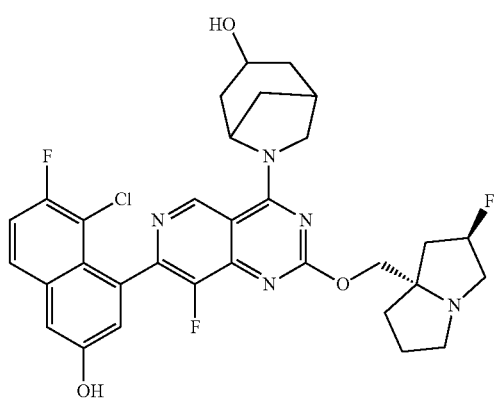 [SMILES: Oc1cc(-c2ncc3c(N4CC5CC(O)CC4C5)nc(OC[C@@]45CCCN4C[C@H](F)C5)nc3c2F)c2c(Cl)c(F)ccc2c1]

6-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azabicyclo[3.2.1]octan-3-ol The title compound was synthesized according to the procedure described for example 419. $^1$H NMR (400 MHz, METHANOL-d₄) δ=9.36-9.14 (m, 1H), 8.49 (br s, 1H), 7.82 (dd, J=5.6, 9.2 Hz, 1H), 7.44-7.34 (m, 2H), 7.24-7.16 (m, 11H), 5.57-5.38 (m, 11H), 5.00 (br s, 1H), 4.61-4.46 (m, 2H), 4.42-4.32 (m, 1H), 4.32-4.19 (m, 1H), 4.14 (br s, 1H), 3.72 (br s, 1H), 3.70-3.57 (m, 2H), 3.27 (br s, 11H), 2.86-2.62 (m, 2H), 2.60-2.48 (m, 11H), 2.45-2.32 (m, 1H), 2.31-2.17 (m, 3H), 2.17-2.10 (m, 1H), 2.10-1.96 (m, 3H), 1.95-1.74 (m, 2H). LCMS [ESI, M+1]: m/z=626.2.

Example 423

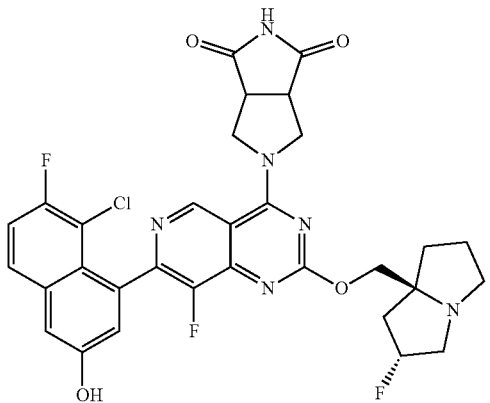 [SMILES: O=C1NC(=O)C2CN(c3nc(OC[C@@]45CCCN4C[C@H](F)C5)nc4c(F)c(-c5cc(O)cc6ccc(F)c(Cl)c56)ncc34)CC12]

5-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)tetrahydropyrrolo[3,4-c]pyrrole-1,3(2H,3aH)-dione The title compound was synthesized according to the procedure described for example 419. ¹H NMR (400 MHz, METHANOL-d₄) δ=9.28 (s, 1H), 8.46 (br s, 1H), 7.82 (dd, J=5.6, 9.2 Hz, 1H), 7.43-7.36 (m, 2H), 7.22 (d, J=2.4 Hz, 11H), 5.54-5.36 (m, 1H), 4.64 (br d, J=13.2 Hz, 2H), 4.60-4.46 (m, 2H), 4.43-4.30 (m, 2H), 3.81-3.55 (m, 3H), 3.69-3.53 (m, 3H), 3.30-3.23 (m, 1H), 2.63-2.37 (m, 2H), 2.36-2.27 (m, 1H), 2.25-2.15 (m, 2H), 2.13-2.00 (m, 1H). LCMS [ESI, M+1]: m/z=639.1.

Example 424

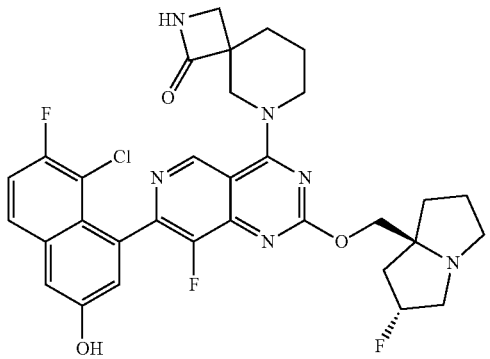 [SMILES: O=C1NCC12CCCN(c1nc(OC[C@@]34CCCN3C[C@H](F)C4)nc3c(F)c(-c4cc(O)cc5ccc(F)c(Cl)c45)ncc13)C2]

6-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2,6-diazaspiro[3.5]nonan-1-one The title compound was synthesized according to the procedure described for example 419. ¹H NMR (400 MHz, METHANOL-d₄) δ=9.08 (s, 11H), 7.83-7.83 (m, 1H), 7.44-7.34 (m, 2H), 7.23 (s, 1H), 5.53-5.34 (m, 11H), 4.55-4.49 (m, 1H), 4.48-4.42 (m, 11H), 4.36-4.28 (m, 2H), 4.21-4.09 (m, 1H), 4.08-3.95 (m, 1H), 3.71-3.59 (m, 1H), 3.59-3.46 (m, 2H), 3.30-3.21 (m, 2H), 3.21-3.18 (m, 1H), 2.59-2.35 (m, 2H), 2.33-2.25 (m, 1H), 2.22-2.12 (m, 4H), 2.12-2.00 (m, 2H), 1.97-1.87 (m, 1H); LCMS [ESI, M+1]: 639.1.

Example 425

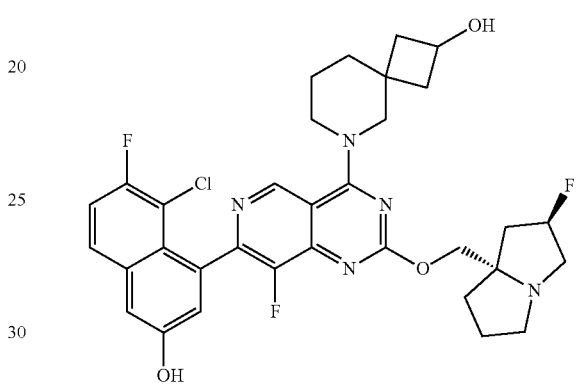

6-(7-(8-chloro-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azaspiro[3.5]nonan-2-ol The title compound was synthesized according to the procedure described for example 419. ¹H NMR (400 MHz, METHANOL-d₄) δ=9.05 (d, J=7.6 Hz, 1H), 8.50 (br s, 1H), 7.80 (dd, J=5.2, 9.2 Hz, 1H), 7.45-7.32 (m, 2H), 7.22 (t, J=2.4 Hz, 1H), 5.55-5.27 (m, 1H), 4.50-4.35 (m, 2H), 4.32-4.22 (m, 1H), 4.12-3.90 (m, 4H), 3.65-3.36 (m, 3H), 3.18 (br d, J=4.5 Hz, 1H), 2.52-2.16 (m, 6H), 2.15-1.96 (m, 3H), 1.84-1.66 (m, 6H); LCMS [ESI, M+1]: m/z=640.2.

Example 426

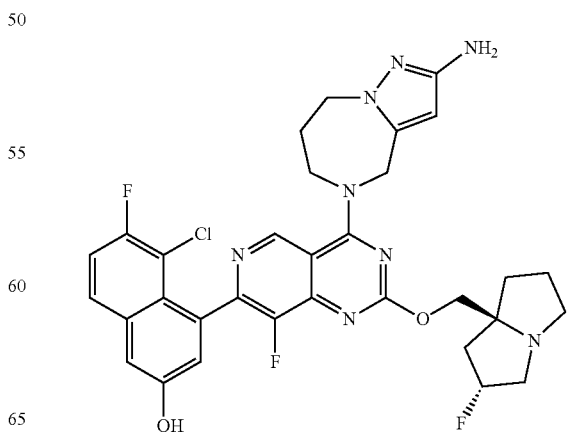

601

4-(4-(2-amino-7,8-dihydro-4H-pyrazolo[1,5-a][1,4]
diazepin-5(6H)-yl)-8-fluoro-2-(((2R,7aS)-2-fluoro-
hexahydro-1H-pyrrolizin-7a-yl)methoxy)pyrido[4,3-
d]pyrimidin-7-yl)-5-chloro-6-fluoronaphthalen-2-ol The title compound was synthesized according to the procedure described for example 419. $^1$H NMR (400 MHz, METHANOL-d$_4$) δ=9.19 (s, 1H), 7.83-7.79 (m, 1H), 7.43-7.34 (m, 2H), 7.22 (d, J=2.4 Hz, 1H), 5.78 (s, 1H), 5.48-5.30 (m, 1H), 5.17-5.01 (m, 2H), 4.45-4.40 (m, 1H), 4.39-4.32 (m, 3H), 4.27-4.21 (m, 2H), 3.56-3.36 (m, 3H), 3.18-3.10 (m, 1H), 2.48-2.29 (m, 4H), 2.28-2.17 (m, 1H), 2.15-2.05 (m, 2H), 2.05-1.92 (m, 1H); LCMS [ESI, M+1]: m/z<651.3.

Example 427

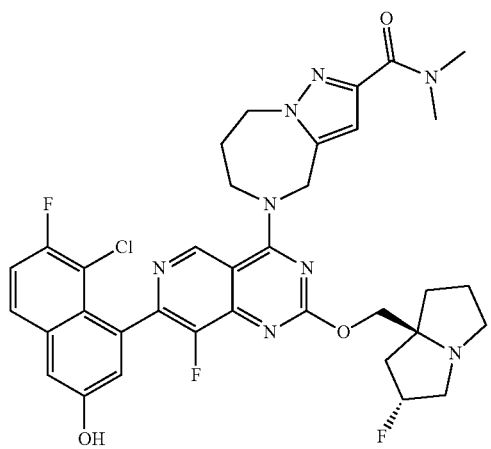 [SMILES: CN(C)C(=O)c1cc2n(n1)CCCN(c1nc(OC[C@@]34CCCN3C[C@H](F)C4)nc3c(F)c(-c4cc(O)cc5ccc(F)c(Cl)c45)ncc13)C2]

5-(7-(8-chloro-7-fluoro-3-hydroxynaphthalen-1-yl)-
8-fluoro-2-(((2R,7aS)-2-fluorohexahydro-1H-pyr-
rolizin-7a-yl)methoxy)pyrido[4,3-d]pyrimidin-4-yl)-
N,N-dimethyl-5,6,7,8-tetrahydro-4H-pyrazolo[1,5-a]
[1,4]diazepine-2-carboxamide The title compound was synthesized according to the procedure described for example 419. $^1$H NMR (400 MHz, METHANOL-d$_4$) δ=9.21 (s, 1H), 8.61-8.44 (m, 1H), 7.83 (dd, J=5.2, 9.2 Hz, 1H), 7.45-7.37 (m, 2H), 7.23 (d, J=2.4 Hz, 1H), 6.78 (s, 1H), 5.52-5.20 (m, 3H), 4.56 (br d, J=6.4 Hz, 2H), 4.51-4.38 (m, 4H), 3.66-3.43 (m, 3H), 3.35 (s, 3H), 3.25-3.17 (m, 1H), 3.10 (s, 3H), 2.55-2.26 (m, 5H), 2.22-1.98 (m, 3H); LCMS [ESI, M+1]: 707.2.

602

Example 428

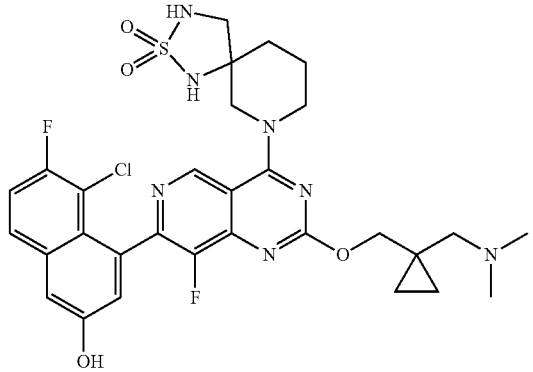 [SMILES: CN(C)CC1(COc2nc(N3CCCC4(CNS(=O)(=O)N4)C3)c3cnc(-c4cc(O)cc5ccc(F)c(Cl)c45)c(F)c3n2)CC1]

7-(7-(8-chloro-7-fluoro-3-hydroxynaphthalen-1-yl)-
2-((1-((dimethylamino)methyl)cyclopropyl)
methoxy)-8-fluoropyrido[4,3-d]pyrimidin-4-yl)-2-
thia-1,3,7-triazaspiro[4.5]decane 2,2-dioxide

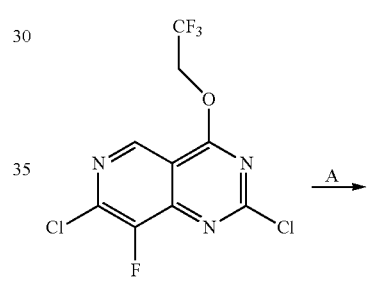

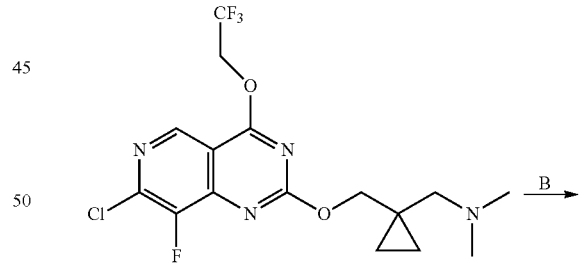

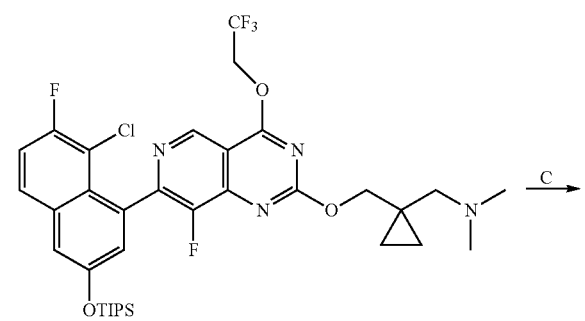

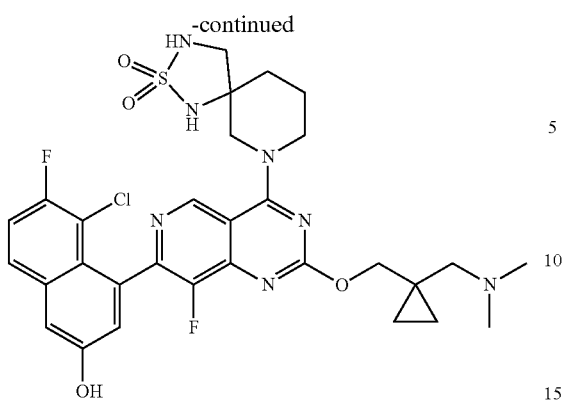

Step A. 1-(1-(((7-chloro-8-fluoro-4(2,2,2-trifluoroethoxy)pyrido[4,3-d]pyrimidin-2-yl)oxy)methyl)cyclopropyl)-N,N-dimethylmethanamine: To a solution of 2,7-dichloro-8-fluoro-4-(2,2,2-trifluoroethoxy)pyrido[4,3-d]pyrimidine (6 g, 1.0 equiv.) and (1-((dimethylamino)methyl)cyclopropyl)methanol (2.21 g, 0.9 equiv.) in THF (60 mL) was added DIEA (7.36 g, 3 equiv.) and 4 Å molecular sieves (I g) at −40° C., The mixture was stirred at −40° C. for 0.5 hour. The mixture was filtered, diluted with water (60 mL) and extracted with ethyl acetate (3×60 mL). The combined organic layers were dried over anhydrous Na$_2$SO$_4$, concentrated and purified by reversed phase flash chromatography [C18, water (0.1% formic acid)—ACN] to afford the title compound (3.0 g, 35% yield) as a yellow solid; LCMS (ESI, M+1): m/z=409.1.

Step B. 1-(1-(((7-(8-chloro-7-fluoro-3-((triisopropylsilyl)oxy)naphthalen-1-yl)-8-fluoro-4-(2,2,2-trifluoroethoxy)pyrido[4,3-d]pyrimidin-2-yl)oxy)methyl)cyclopropyl)-N,N-dimethylmethanamine: A mixture of 1-(1-(((7-chloro-8-fluoro-4-(2,2,2-trifluoroethoxy)pyrido[4,3-d]pyrimidin-2-yl)oxy)methyl)cyclopropyl)-N,N-dimethylmethanamine (500 mg, 1.0 equiv.), ((5-chloro-6-fluoro-4-(trimethylstannyl)naphthalen-2-yl)oxy)triisopropylsilane (1.26 g, 2.0 equiv.), CuI (23.3 mg, 0.1 equiv.), BINAP (152 mg, 0.2 equiv.) and Pd(dppf)Cl$_2$ (89.5 mg, 0.1 equiv.) in toluene (8 mL) was degassed and stirred at 90° C. for 6 hours under N$_2$ atmosphere. The mixture was diluted with water (10 mL) and extracted with ethyl acetate (3×10 mL). The combined organic layers were dried over anhydrous Na$_2$SO$_4$, concentrated and purified by reversed phase flash chromatography [C18, water (0.1% formic acid)—ACN] to afford the title compound (0.5 g, 48% yield) as a yellow oil; LCMS (ESI, M+1): m/z=725.3.

Step C. 7-(7-(8-chloro-7-fluoro-3-hydroxynaphthalen-1-yl)-2-((1-((dimethylamino)methyl)cyclopropyl)methoxy)-8-fluoropyrido[4,3-d]pyrimidin-4-yl)-2-thia-1,3,7-triazaspiro[4.5]decane 2,2-dioxide: To a solution of 1-(1-(((7-(8-chloro-7-fluoro-3-((triisopropylsilyl)oxy)naphthalen-1-yl)-8-fluoro-4-(2,2,2-trifluoroethoxy)pyrido[4,3-d]pyrimidin-2-yl)oxy)methyl)cyclopropyl)-N,N-dimethylmethanamine (157 mg, 1.0 equiv.) and 2-thia-1,3,7-triazaspiro[4.5]decane 2,2-dioxide (58.0 mg, 1.1 equiv.) in DMF (1 mL) were added 4 Å molecular sieves (40 mg) and DIEA (107 mg, 3 equiv.). The mixture was stirred at 60° C. for 12 hours. The mixture was filtered, diluted with water (5 mL) and extracted with ethyl acetate (3×5 mL). The combined organic layers were dried over anhydrous Na$_2$SO$_4$, concentrated and purified by reversed phase flash chromatography [C18, water (0.1% formic acid)-ACN] and prep-HPLC [column: Waters Xbridge 150×25 mm×5 pin; mobile phase: water (NH$_4$HCO$_3$)-ACN; B %: 30%-60%, 10 min] to afford the title compound (16.3 mg, 9% yield) as an off-white solid; $^1$H NMR (400 MHz, METHANOL-d$_4$) δ=9.07 (d, J=2.4 Hz, 1H), 7.82-7.76 (m, 1H), 7.42-7.33 (m, 2H), 7.24-7.16 (m, 1H), 4.50-4.27 (m, 4H), 3.92 (d, J=13.3 Hz, 1H), 3.72 (d, J=13.2 Hz, 1H), 3.41 (d, J=11.6 Hz, 1H), 3.20 (dd, J=3.2, 12.0 Hz, 1H), 2.60-2.54 (m, 1H), 2.42-2.35 (m, 1H), 2.33 (s, 6H), 2.12-1.76 (m, 4H), 0.79-0.70 (m, 2H), 0.58-0.49 (m, 2H). LCMS (ESI, M+1): m/z=660.0.

Example 429

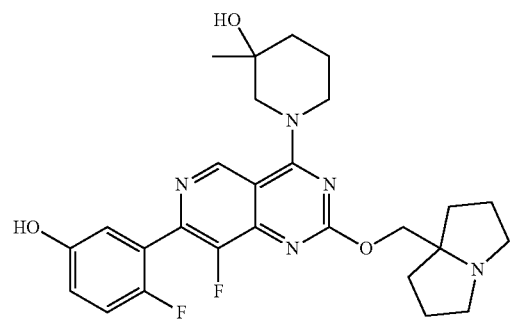

1-(8-fluoro-7-(2-fluoro-5-hydroxyphenyl)-2-((tetrahydro-1H-pyrrolizin-7a(5H)-yl)methoxy)pyrido[4,3-d]pyrimidin-4-yl)-3-methylpiperidin-3-ol

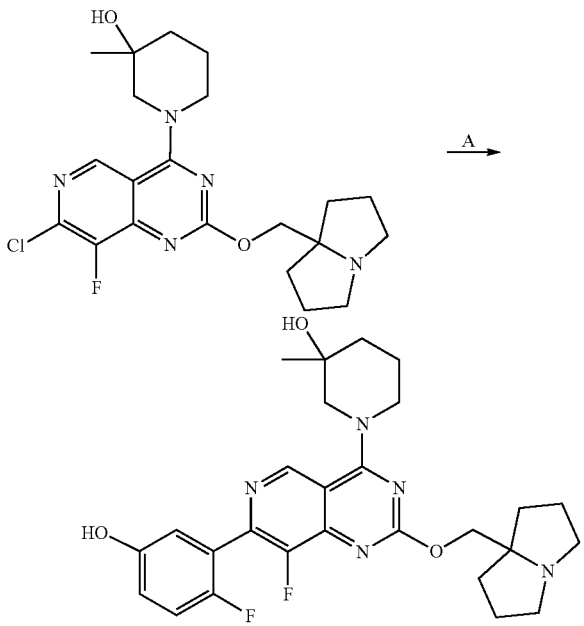

Step A. J-(8-fluoro-7-(2-fluoro-5-hydroxyphenyl)-2-((tetrahydro-1H-pyrrolizin-7a(5H)-yl)methoxy)pyrido[4,3-d]pyrimidin-4-yl)-3-methylpiperidin-3-ol: To a solution of 1-(7-chloro-8-fluoro-2-((hexahydro-1H-pyrrolizin-7a-yl)methoxy)pyrido[4,3-d]pyrimidin-4-yl)-3-methylpiperidin-3-ol (50 mg, 1.0 equiv.), 4-fluoro-3-(4,4,5,5-tetramethyl-1,3,2-dioxaborolan-2-yl)phenol (55 mg, 2 equiv.) and K$_3$PO$_4$ (1.5 M in water, 229 µL, 3 equiv.) in THF (0.5 mL) was added cataCXium-A-Pd-G3 (8.4 mg, 0.1 equiv.). The mixture was degassed and stirred at 60° C. for 2 hours. Upon reaction completion, the mixture was diluted with water (5 mL) and extracted with ethyl acetate (3×5 mL). The combined organic layers were washed with brine (5 mL), dried over Na$_2$SO$_4$, filtered and concentrated under reduced pressure to give a residue. The residue was purified by prep-HPLC [column: Phenomenex luna C18 150×25 mm×10 um; mobile phase: water (0.225% formic acid)-ACN; B: 5%-35%, 11.5 min)] to afford the title compound (37.1 mg, 66.5 μmol, 56.0% yield, formic acid salt) as a white solid; $^1$H NMR (400 MHz, METHANOL-d$_4$) δ=9.26 (s, 1H), 8.50 (br s, 1H), 7.12-7.06 (m, 1H), 7.04 (dd, J=3.0, 5.6 Hz, 1H), 6.93 (td, J=3.6, 8.8 Hz, 1H), 4.64 (s, 2H), 4.60 (br d, J=13.1 Hz, 1H), 4.31 (br d, J=13.3 Hz, 1H), 3.74-3.66 (m, 2H), 3.62 (d, J=13.4 Hz, 1H), 3.44-3.36 (m, 1H), 3.30-3.24 (m, 2H), 2.32 (ddd, J=3.1, 6.8, 12.3 Hz, 2H), 2.27-2.05 (m, 7H), 1.90-1.71 (m, 3H), 1.28 (s, 3H); LCMS(M+H): 512.3.

Example 430

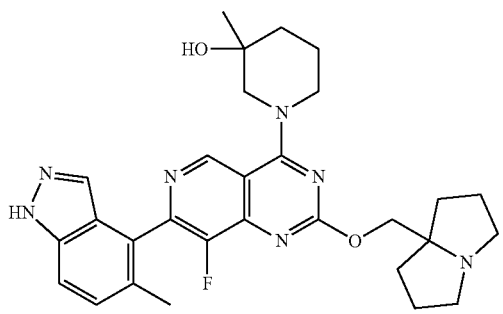 [SMILES: Cc1ccc2[nH]ncc2c1-c1ncc2c(N3CCCC(C)(O)C3)nc(OCC34CCCN3CCC4)nc2c1F]

1-(8-fluoro-2-((hexahydro-1H-pyrrolizin-7a-yl) methoxy)-7-(5-methyl-1H-indazol-4-yl)pyrido[4,3-d]pyrimidin-4-yl)-3-methylpiperidin-3-ol

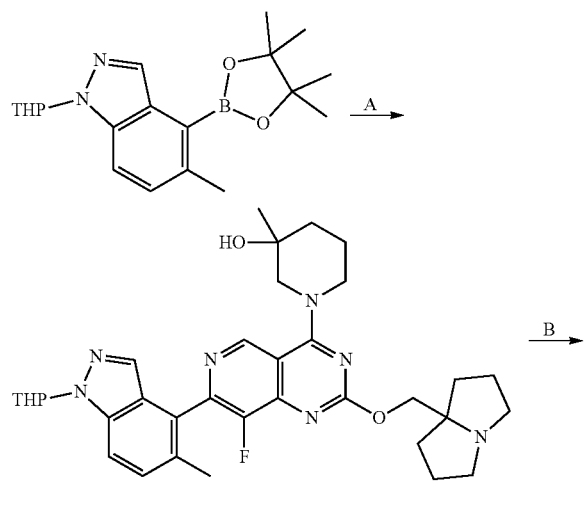

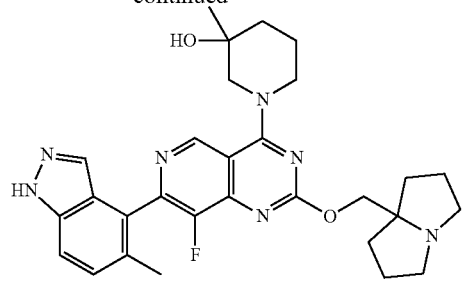

Step A. 1-(8-fluoro-2-((hexahydro-1H-pyrrolizin-7a-yl) methoxy)-7-(5-methyl-1-(tetrahydro-2H-pyran-2-yl)-1H-indazol-4-yl)pyrido[4,3-d]pyrimidin-4-yl)-3-methyl)piperidin-3-ol: To a solution of 1-(7-chloro-8-fluoro-2-((hexahydro-1H-pyrrolizin-7a-yl)methoxy)pyrido[4,3-d]pyrimidin-4-yl)-3-methylpiperidin-3-ol (30 mg, 1 equiv.) in n-BuOH (0.6 mL) was added 5-methyl-1-(tetrahydro-2H-pyran-2-yl)-4-(4,4,5,5-tetramethyl-1,3,2-dioxaborolan-2-yl)-1H-indazole (35.3 mg, 1.5 equiv.), K$_3$PO$_4$ (1.5 M in water, 138 μL, 3 equiv.) and X-Phos-Pd-G4 (5.92 mg, 0.1 equiv.). The mixture was stirred at 60° C. for 2 hours under N$_2$ atmosphere. The mixture was poured into water (5 mL) and extracted with ethyl acetate (3×5 mL). The combined organic layers were washed with brine 5 mL, dried over Na$_2$SO$_4$, concentrated and purified by reverse phase flash chromatography (water (0.225% formic acid)) to afford the title compound (30 mg, 70.5% yield) as a yellow oil; LCMS (ESI, M+1): m/z=616.4.

Step B. 1-(8-fluoro-2-((hexahydro-1H-pyrrolizin-7a-yl) methoxy)-7-(5-methyl-1H-indazol-4-yl)pyrido[4,3-d]pyrimidin-4-yl)-3-methylpiperidin-3-ol: To a mixture of 1-(8-fluoro-2-((hexahydro-1H-pyrrolizin-7a-yl)methoxy)-7-(5-methyl-1-(tetrahydro-2H-pyran-2-yl)-1H-indazol-4-yl) pyrido[4,3-d]pyrimidin-4-yl)-3-methylpiperidin-3-ol (30 mg, 1 equiv.) in MeOH (1 mL) was added HCl.dioxane (4 M, 0.5 mL, 41 equiv.). The mixture was stirred at 25° C. for 2 hours under N$_2$ atmosphere. The mixture was dried with a stream of N$_2$ and purified by prep-HPLC [column: Phenomenex Synergi C18 150×25 mm×10 μm; mobile phase: water (0.225% formic acid)-ACN; B %: 8%-38%, 10 minutes] to afford the title compound (6.31 mg, 22% yield) as an off-white solid; $^1$HNMR (400 MHz, METHANOL-d$_4$) δ=9.34 (s, 1H), 7.71 (s, 1H), 7.61 (d, J=8.4 Hz, 1H), 7.43 (d, J=8.8 Hz, 1H), 4.64 (s, 3H), 4.36 (m, 1H), 3.71-3.58 (m, 3H), 3.44 (br s, 1H), 3.28-3.20 (m, 2H), 2.38-2.27 (m, 5H), 2.25-2.12 (m, 5H), 2.08 (m, 2H), 1.80 (br s, 3H), 1.30 (s, 3H); LCMS (ESI, M+1): m/z=532.3.

Example 431

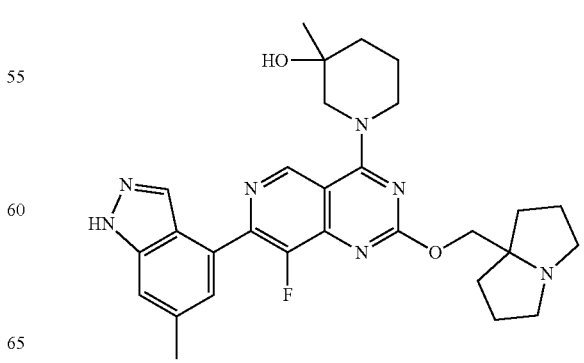

1-(8-fluoro-7-(6-methyl-1H-indazol-4-yl)-2-((tetra-hydro-1H-pyrrolizin-7a(5H)-yl)methoxy)pyrido[4,3-d]pyrimidin-4-yl)-3-methylpiperidin-3-ol The title compound was synthesized according to the procedure described for example 430. ¹HNMR (400 MHz, METHANOL-d₄) δ=9.32 (s, 1H), 8.21 (s, 1H), 7.51 (d, J=13.6 Hz, 2H), 4.58 (s, 3H), 4.36-4.28 (m, 1H), 3.66-3.53 (m, 3H), 3.48-3.37 (m, 1H), 3.22-3.11 (m, 2H), 2.58 (s, 3H), 2.35-2.24 (m, 2H), 2.23-2.08 (m, 5H), 2.04 (s, 2H), 1.91-1.72 (m, 3H), 1.29 (s, 3H); LCMS (ESI, M+1): m/z=532.3.

Example 432

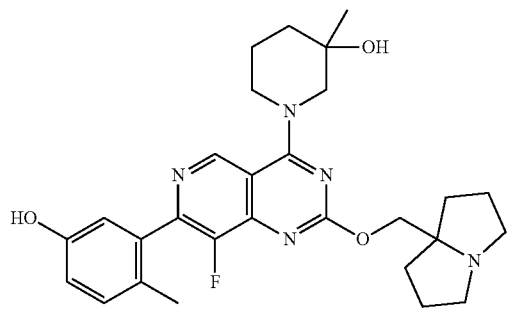 [SMILES: Cc1ccc(O)cc1-c1ncc2c(N3CCCC(C)(O)C3)nc(OCC34CCCN3CCC4)nc2c1F]

1-(8-fluoro-2-((hexahydro-1H-pyrrolizin-7a-yl)methoxy)-7-(5-hydroxy-2-methylphenyl)pyrido[4,3-d]pyrimidin-4-yl)-3-methylpiperidin-3-ol The title compound was synthesized according to the procedure described for example 429. ¹HNMR (400 MHz, METHANOL-d₄) δ=9.24 (s, 1H), 7.17 (d, J=8.4 Hz, 1H), 6.89-6.73 (m, 2H), 4.65 (s, 2H), 4.63-4.56 (m, 1H), 4.35-4.28 (m, 1H), 3.74-3.66 (m, 2H), 3.62 (d, J=13.3 Hz, 1H), 3.45-3.36 (m, 1H), 3.30-3.24 (m, 2H), 2.38-2.28 (m, 2H), 2.26-2.16 (m, 4H), 2.14 (s, 3H), 2.13-2.06 (m, 3H), 1.88-1.74 (m, 3H), 1.29 (s, 3H); LCMS (ESI, M+1): m/z=508.3.

Example 433

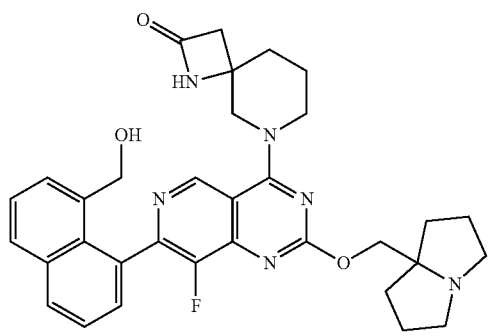 [SMILES: O=C1CC2(CCCN(c3nc(OCC45CCCN4CCC5)nc4c(F)c(-c5cccc6cccc(CO)c56)ncc34)C2)N1]

6-(8-fluoro-2-((hexahydro-1H-pyrrolizin-7a-yl)methoxy)-7-(8-(hydroxymethyl)naphthalen-1-yl)pyrido[4,3-d]pyrimidin-4-yl)-1,6-diazaspiro[3.5]nonan-2-one

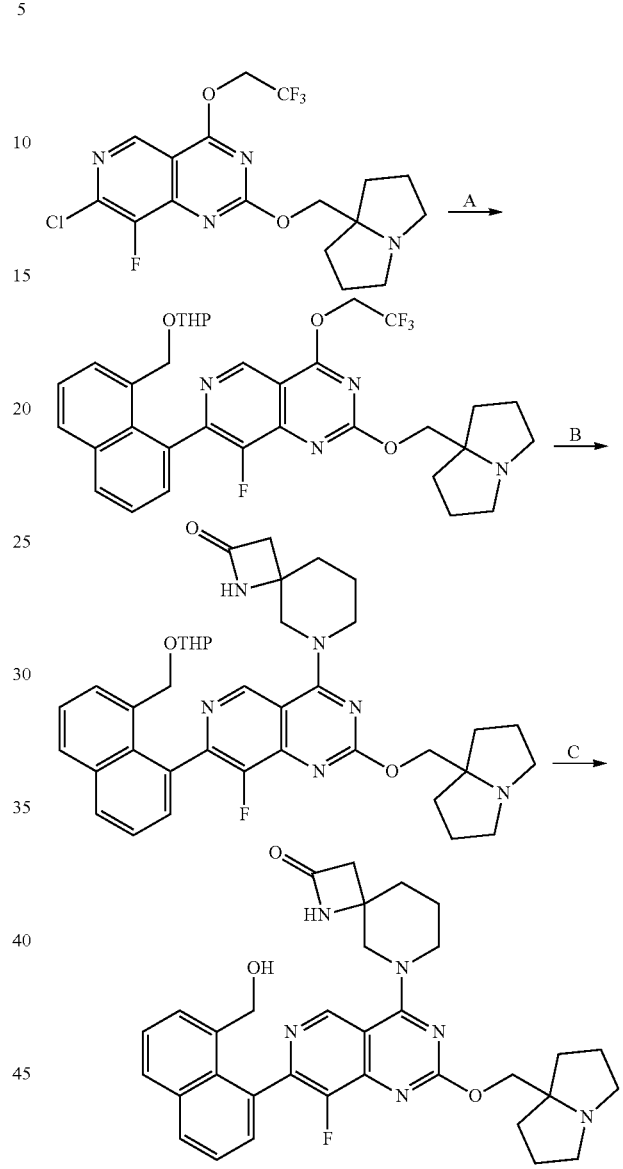

Step A. 8-fluoro-2-((hexahydro-1H-pyrrolizin-7a-yl)methoxy)-7-(R-(((tetrahydro-2H-pyran-2-yl)oxy)methyl)naphthalen-1-yl)-4-(2,2,2-trifluoroethoxy)pyrido[4,3-d]pyrimidine: To a solution of 7-chloro-8-fluoro-2-((tetrahydro-1H-pyrrolizin-7a(5H)-yl)methoxy)-4-(2,2,2-trifluoroethoxy)pyrido[4,3-d]pyrimidine (150 mg, 1 equiv.), 4,4,5,5-tetramethyl-2-(8-(((tetrahydro-2H-pyran-2-yl)oxy)methyl)naphthalen-1-yl)-1,3,2-dioxaborolane (131 mg, 1 equiv.) and Cs₂CO₃ (1.5 M in water, 713 μL, 3 equiv.) in methoxycyclopentane (2.5 mL) was added cataCXium A Pd G3 (26.0 mg, 0.1 equiv.). The mixture was stirred at 90° C. for 3 hours under N₂. The mixture was poured into water (10 mL) and extracted with ethyl acetate (2×10 mL). The combined organic phase was dried over anhydrous Na₂SO₄, concentrated and purified by reversed phase flash chromatography (water (0.225% formic acid)) to afford the title compound (80 mg, 35.8% yield) as a yellow oil; LCMS (ESI, M+1): m/z=627.3

Step B. 6-(8-fluoro-2-((hexahydro-1H-pyrrolizin-7a-yl) methoxy)-7-(8-((((tetrahydro-2H-pyran-2-yl)oxy)methyl) naphthalen-1-yl)pyrido[4,3-d]pyrimidin-4-yl)-1,6-diazaspiro[3.5]nonan-2-one: A mixture of 8-fluoro-2-((hexahydro-1H-pyrrolizin-7a-yl)methoxy)-7-(8-((((tetrahydro-2H-pyran-2-yl)oxy)methyl)naphthalen-1-yl)-4-(2,2,2-trifluoroethoxy)pyrido[4,3-d]pyrimidine (80 mg, 1 equiv.) and 1,6-diazaspiro[3.5]nonan-2-one (21.5 mg, 1.2 equiv.) and DIEA (82.5 mg, 5 equiv.) in DMF (1 mL) was stirred at 40° C. for 2 hours. The mixture was filtered and purified by reversed phase flash chromatography (water (0.225% formic acid)) to afford the title compound (60 mg, 70.5% yield) as a yellow oil; LCMS (EST, M+1): m/z=667.5.

Step C. 6-(8-fluoro-2-((hexahydro-1H-pyrrolizin-7a-yl) methoxy)-7-(8-(hydroxymethyl)naphthalen-1-yl)pyrido[4,3-d]pyrimidin-4-yl)-1,6-diazaspiro[3.5]nonan-2-one: To a solution of 6-(8-fluoro-2-((hexahydro-1H-pyrrolizin-.7a-yl) methoxy)-7-(8-((((tetrahydro-2H-pyran-2-yl)oxy)methyl) naphthalen-1-yl)pyrido[4,3-d]pyrimidin-4-yl)-1,6-diazaspiro[3.5]nonan-2-one (30 mg, 1 equiv.) in EtOH (0.5 mL) was added TsOH·H$_2$O (9.41 mg, 1.1 equiv.). The mixture was stirred at 25° C. for 16 hours. The mixture was poured into water (5 mL). The pH of the mixture was adjusted to 8 with saturated aqueous NaHCO$_3$. The resulting solution was extracted with ethyl acetate (2×5 mL). The combined organic phase was dried over anhydrous Na$_2$SO$_4$, concentrated and purified by prep-HPLC [column: Unisil 3-100 C18 Ultra 150×50 mm×3 μm; mobile phase: water (0.225% formic acid)-ACN; B %: 10%-40%, 10 minutes] to afford the title compound (5.75 mg, 21% yield) as a white solid; $^1$H NMR (400 MHz, MeOD-d$_4$) δ=9.20-9.07 (m, 1H), 8.09 (d, J=7.6 Hz, 1H), 8.02-7.93 (m, 1H), 7.73 (d, J=6.8 Hz, 1H), 7.65-7.54 (m, 2H), 7.48 (d, J=6.8 Hz, 1H), 4.64-4.54 (m, 2H), 4.46-4.22 (m, 4H), 4.05 (m, 1H), 3.98-3.82 (m, 1H), 3.56-3.55 (m, 2H), 3.19-3.13 (m, 2H), 2.97-2.73 (m, 2H), 2.29-2.00 (m, 12H); LCMS (ESI, M+1): m/z=583.5.

Example 434

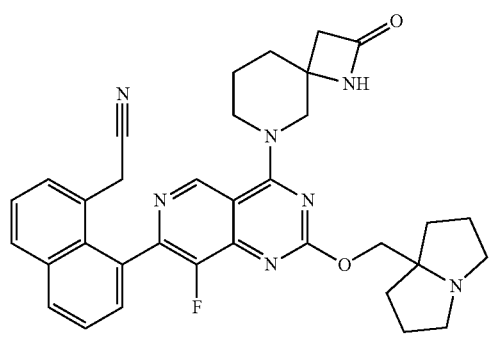 [SMILES: N#CCc1cccc2cccc(-c3ncc4c(N5CCCC6(CC(=O)N6)C5)nc(OCC56CCCN5CCC6)nc4c3F)c12]

2-(8-(8-fluoro-2-((hexahydro-1H-pyrrolizin-7a-yl) methoxy)-4-(2-oxo-1,6-diazaspiro[3.5]nonan-6-yl) pyrido[4,3-d]pyrimidin-7-yl)naphthalen-1-yl)acetonitrile

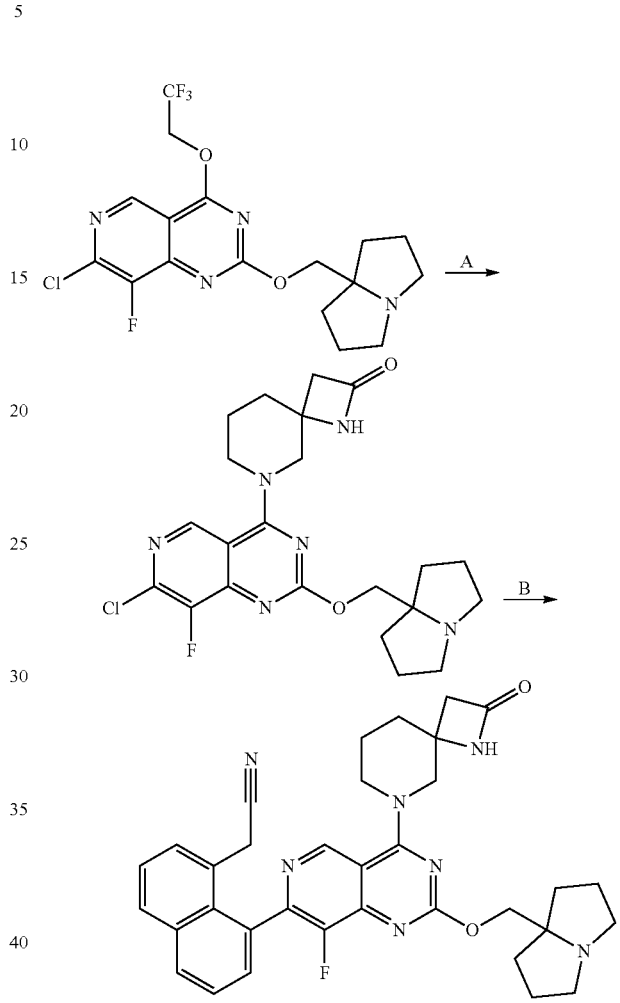

Step A. 6-(7-chloro-8-fluoro-2-((hexahydro-1H-pyrrolizin-7a-yl)methoxy)pyrido[4,3-d]pyrimidin-4-yl)-1,6-diazaspiro[3.5]nonan-2-one: To a solution of 7-chloro-8-fluoro-2-((tetrahydro-1H-pyrrolizin-7a(5H)-yl)methoxy)-4-(2,2,2-trifluoroethoxy)pyrido[4,3-d]pyrimidine (100 mg, 1.0 equiv.), 1,8-diazaspiro[3.5]nonan-2-one (43.3 mg, 1.3 equiv.) in DMF (1.0 mL) was added DIEA (92.1 mg, 3.0 equiv.) and 4 Å molecular sieves (40 mg). The mixture was stirred at 40° C. for 12 hours. The mixture was purified by reversed phase flash chromatography [water (0.1% formic acid)/acetonitrile]. The desired fractions were collected and neutralized with solid NaHCO$_3$, concentrated in vacuum to remove ACN. The aqueous layer was lyophilized to afford title compound (73 mg, 65% yield) as a yellow solid; LCMS (ESI, M+1): m/z=461.1.

Step B. 2-(8-(8-fluoro-2-((hexahydro-1H-pyrrolizin-7a-yl)methoxy)-4-(2-oxo-1,6-diazaspiro[3.5]nonan-6-yl) pyrido[4,3-d]pyrimidin-7-yl)naphthalen-1-yl)acetonitrile: A mixture of 6-(7-chloro-8-fluoro-2-((hexahydro-1H-pyrrolizin-7a-yl)methoxy)pyrido[4,3-d]pyrimidin-4-yl)-1,6-diazaspiro[3.5]nonan-2-one (50 mg, 1.0 equiv.), 2-(8-trimethylstannyl-1-naphthyl)acetonitrile (71.6 mg, 2.0 equiv.) and cataCXium A Pd G3 (7.90 mg, 0.1 equiv.) in DMAC (0.5 mL) was degassed stirred at 90° C. for 3 hours under N₂ atmosphere. The mixture was directly purified by reversed phase flash chromatography [C18, water (0.1% formic acid)/ACN]. The desired fractions were re-purified by prep-HPLC [Waters Xbridge 150×25 mm×5 μm; mobile phase: water (10 mM NH₄HCO₃)-ACN, B %: 34%-64%, 10 min] and lyophilized to afford title compound (16.6 mg, 25% yield) as a white solid; HPLC:>99% cc, Chiralcel OJ-3 50×4.6 mm I.D., 3 μm column A: 60% MeOH+40% ACN (w/0.05% DEA), B: CO₂, 3 mL/min, 220 nm, t$_R$: 1.827 min; ¹H NMR (400 MHz, methanol-d₄) δ=9.07 (s, 1H), 8.56 (s, 1H), 8.18 (d, J=7.2 Hz, 1H), 8.11 (d, J=7.2 Hz, 1H), 7.71-7.65 (m, 2H), 7.65-7.58 (m, 2H), 4.27-4.15 (m, 2H), 4.12-4.04 (m, 2H), 3.96-3.70 (m, 2H), 3.68v3.57 (m, 2H), 2.98-2.89 (m, 2H), 2.86-2.79 (m, 1H), 2.67-2.62 (m, 1H), 2.58-2.53 (m, 2H), 2.03-1.95 (m, 1H), 1.94-1.85 (m, 5H), 1.84-1.79 (m, 4H), 1.62-1.53 (m, 2H); LCMS (ESI, M+1): m/z=592.2.

Example 435

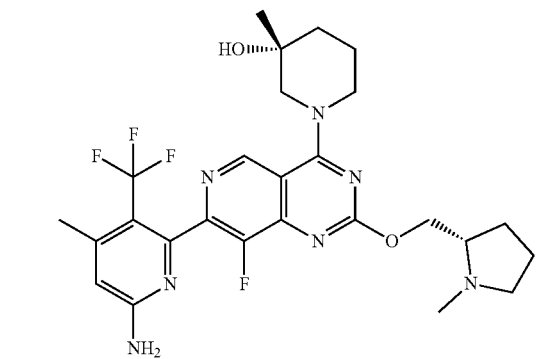 [SMILES: Cc1cc(N)nc(-c2ncc3c(N4CCC[C@@](C)(O)C4)nc(OC[C@@H]4CCCN4C)nc3c2F)c1C(F)(F)F]

(R)-1-(7-(6-amino-4-methyl-3-(trifluoromethyl)pyridin-2-yl)-8-fluoro-2-(((S)-1-methylpyrrolidin-2-yl)methoxy)pyrido[4,3-d]pyrimidin-4-yl)-3-methylpiperidin-3-ol

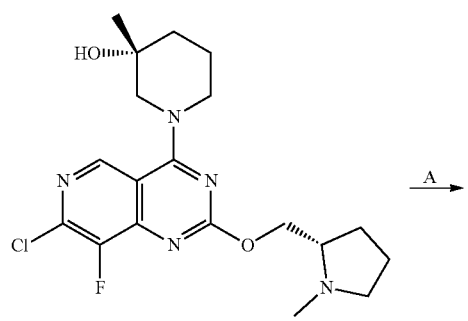

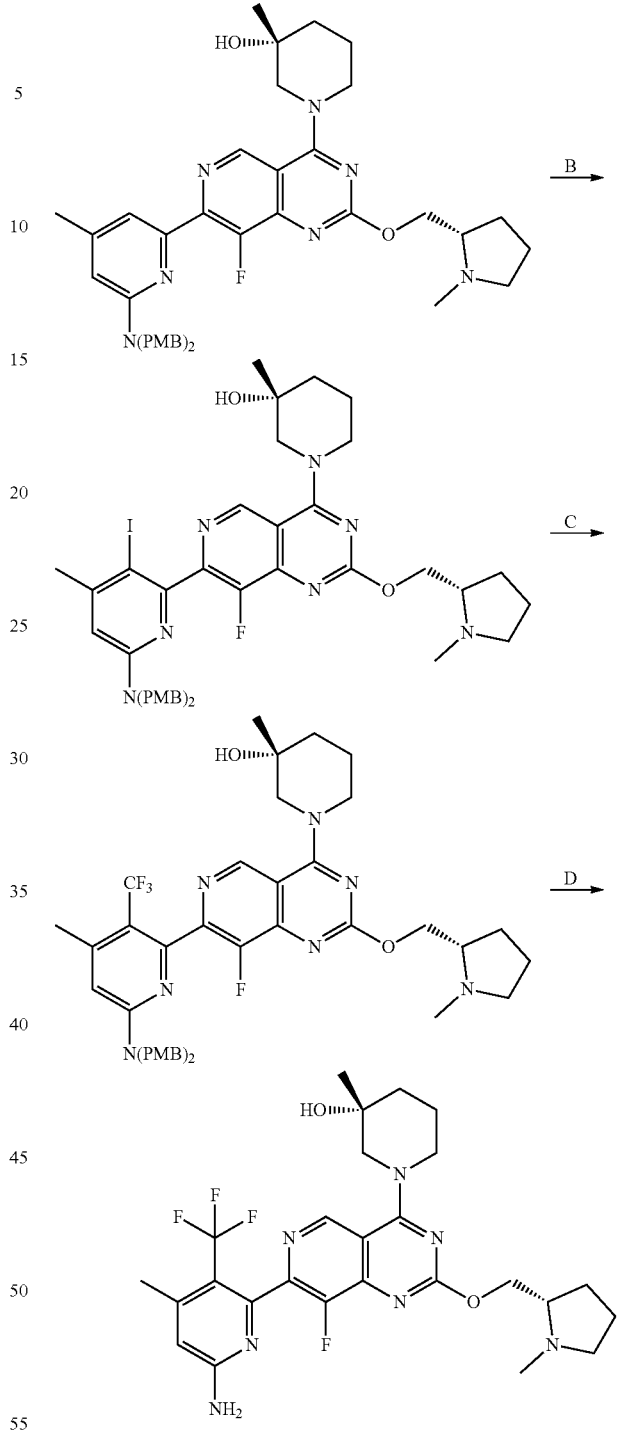

Step A. (R)-1(7-(6-(bis(4-methoxybenzyl)amino)-4-methylpyridin-2-yl)-8-fluoro-2-(((S)-1-methylpyrrolidin-2-yl)methoxy)pyrido[4,3-d]pyrimidin-4-yl)-3-methylpiperidin-3-ol: To a solution of (R)-1-(7-chloro-8-fluoro-2-(((S)-1-methylpyrrolidin-2-yl)methoxy)pyrido[4,3-d]pyrimidin-4-yl)-3-methylpiperidin-3-ol (1.80 g, 1.0 equiv.) in DMAC (20 mL) was added cataCXium A Pd G3 (320 mg, 0.1 equiv.) and N,N-bis[(4-methoxyphenyl)methyl]-4-methyl-6-tributylstannyl-pyridin-2-amine (4.20 g, 1.50 equiv.). The mixture was stirred at 90° C. for 12 hours. The reaction mixture was filtered, concentrated and purified by reversed phase flash chromatography [C18, water (0.1% formic acid)/ACN] to afford the title compound (2.20 g, 69% yield) as a yellow solid; LCMS (ESI, M+1): m/z=722.4.

Step B. (R)-1-(7-(6-(bis(4-methoxybenzyl)amino)-3-iodo-4-methylpyridin-2-yl)-8-fluoro-2-(((S)-1-methylpyrrolidin-2-yl)methoxy)pyrido[4,3-d]pyrimidin-4-yl)-3-methylpiperidin-3-ol: To a solution of (R)-1-(7-(6-(bis(4-methoxybenzyl)amino)-4-methylpyridin-2-yl)-8-fluoro-2-(((S)-1-methylpyrrolidin-2-yl)methoxy)pyrido[4,3-d]pyrimidin-4-yl)-3-methylpiperidin-3-ol (1.0 g, 1.0 equiv.) in AcOH (20 mL) was added dropwise solution of NIS (467 mg, 1.5 equiv.) in AcOH (5 mL). The mixture was stirred at 25° C. for 2 hours. The reaction mixture was filtered and concentrated under reduced pressure to give a residue. The residue was purified by reversed phase flash chromatography [C18, water (0.1% formic acid)/ACN] to afford the title compound (800 mg, 64% yield) as a yellow solid; LCMS (ESI, M+1): m/z=848.3.

Step C. (R)-1-(7-(6-(bis(4-methoxybenzyl)amino)-4-methyl-3-(trifluoromethyl)pyridin-2-yl)-8-fluoro-2-(((S)-1-methylpyrrolidin-2-yl)methoxy)pyrido[4,3-d]pyrimidin-4-yl)-3-methylpiperidin-3-ol: A mixture of CuI (225 mg, 5.0 equiv.) and KF (68.5 mg, 5.0 equiv.) were heated in vacuum with gentle shaking until a greenish color was obtained. To the mixture was added a solution of (R)-1-(7-(6-(bis(4-methoxybenzyl)amino)-3-iodo-4-methylpyridin-2-yl)-8-fluoro-2-(((S)-1-methylpyrrolidin-2-yl)methoxy)pyrido[4,3-d]pyrimidin-4-yl)-3-methylpiperidin-3-ol (200 mg, 1.0 equiv.) and trimethyl(trifluoromethyl)silane (168 mg, 5.0 equiv.) in DMF (3 mL). The mixture was stirred at 20° C. for 3 hours. The reaction mixture was diluted with water (10 mL) and extracted with EtOAc (3×5 mL). The combined organic layers were washed with brine (3×5 mL), dried over anhydrous sodium sulfate, concentrated and purified by reversed phase flash chromatography [C18, water (0.1% formic acid)/ACN] to afford the title compound (60.0 mg, 32% yield) as a yellow solid. LCMS (ESI, M+1): m/z=790.4.

Step D. (R)-1-(7-(6-amino-4-methyl-3-(trifluoromethyl)pyridin-2-yl)-8-fluoro-2-(((S)-1-methylpyrrolidin-2-yl)methoxy)pyrido[4,3-d]pyrimidin-4-yl-3-methylpiperidin-3-ol: A solution of (R)-1-(7-(6-(bis(4-methoxybenzyl)amino)-4-methyl-3-(trifluoromethyl)pyridin-2-yl)-8-fluoro-2-(((S)-1-methylpyrrolidin-2-yl)methoxy)pyrido[4,3-d]pyrimidin-4-yl)-3-methylpiperidin-3-ol (60.0 mg, 1.0 equiv.) in TFA (1 mL) was stirred at 25° C. for 2 hours. The reaction mixture was concentrated. The residue was purified by reversed-phase HPLC [C18, water (0.1% formic acid)/ACN] and further re-purified by prep-HPLC [column: Phenomenex Gemini-NX C18 75×30 mm×3 um; mobile phase: water (0.225% formic acid)-ACN; B %: 12%-42%, 7 min] and lyophilized to afford the title compound (19.3 mg, 46% yield, formic acid salt) as a light yellow solid; $^1$H NMR (400 MHz, methanol-$d_4$) δ=9.21 (s, 1H), 6.63 (s, 1H), 4.80-4.73 (m, 1H), 4.66-4.59 (m, 1H), 4.58-4.50 (m, 1H), 4.29 (br d, J=13.2 Hz, 1H), 3.66-3.50 (m, 3H), 3.47-4.37 (m, 1H), 3.08-2.96 (m, 1H), 2.93 (s, 3H), 2.46 (d, J=1.6 Hz, 3H), 2.38-2.27 (m, 1H), 2.18-1.94 (m, 4H), 1.89-1.72 (m, 3H), 1.28 (s, 3H) LCMS (ESI, M+1): m/z=550.2.

Example 436

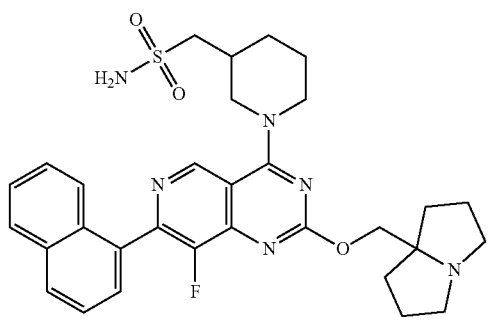 [SMILES: NS(=O)(=O)CC1CCCN(c2nc(OCC34CCCN3CCC4)nc3c(F)c(-c4cccc5ccccc45)ncc23)C1]

(1-(8-fluoro-7-(naphthalen-1-yl)-2-((tetrahydro-1H-pyrrolizin-7a(5H)-yl)methoxy)pyrido[4,3-d]pyrimidin-4-yl)piperidin-3-yl)methanesulfonamide

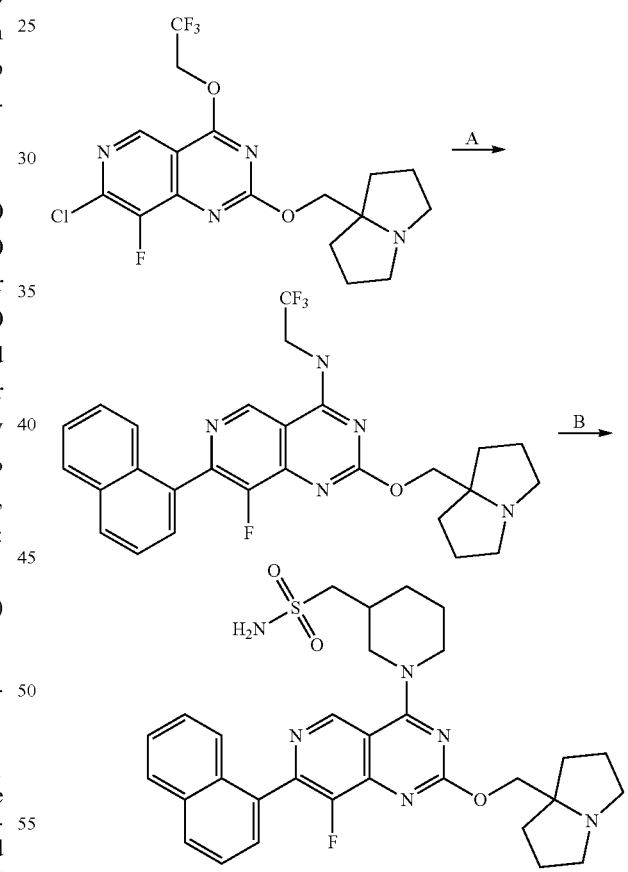

Step A. 8-fluoro-2-((hexahydro-1H-pyrrolizin-7a-yl)methoxyl-7-(naphthalen-1-yl)-4-(2,2,2-trifluoroethoxy)pyrido[4,3-d]pyrimidine: To a solution of 7-chloro-8-fluoro-2-((tetrahydro-1H-pyrrolizin-7a(5H)-yl)methoxy)-4-(2,2,2-trifluoroethoxy)pyrido[4,3-d]pyrimidine (300 mg, 1.0 equiv.), Cs$_2$CO$_3$ (1.5 M, 3.0 equiv.) and naphthalen-1-ylboronic acid (184 mg, 1.5 equiv.) in methoxycyclopentane (5 mL) was added CataCXium A Pd G3 (51.9 mg, 0.1 equiv.) under N$_2$. The reaction was stirred at 90° C. for 2 hours under N₂. The mixture was diluted with water (10 mL) and extracted with ethyl acetate (2×10 mL). The combined organic layers were washed with brine (15 mL), dried over anhydrous sodium sulfate, concentrated and purified by reversed phase flash chromatography [C18, water (0.1% formic acid)/ACN] to afford the title compound (250 mg, 68% yield) as a yellow solid; LCMS (ESI, M+1): m/z=513.2.

Step B. (1-(8-fluoro-7-(naphthalen-1-yl)-2-((tetrahydro-1H-pyrrolizin-7a(5H)-yl)methoxy)pyrido[4,3-d]pyrimidin-4-yl)piperidin-3-yl)methanesulfonamide: To a solution of 8-fluoro-2-((hexahydro-1H-pyrrolizin-7a-yl)methoxy)-7-(naphthalen-1-yl)-4-(2,2,2-trifluoroethoxy)pyrido[4,3-d]pyrimidine (0.10 g, 1.0 equiv.), piperidin-3-ylmethanesulfonamide (69.6 mg, 2.0 equiv.) and DIEA (75.7 mg, 3.0 equiv.) in DMF (0.5 mL) was added 4 Å molecular sieves (10 mg). The reaction was stirred at 40° C. for 12 hours. The mixture was filtered and purified by prep-HPLC [Waters Xbridge 150×25 mm×5 μm; mobile phase: water (10 mM NH₄HCO₃)-ACN, B %: 33%-63%, 2 min] and lyophilized to afford the title compound (66.9 mg, 58% yield) as a white solid; ¹H NMR (400 MHz, methanol-d₄) δ=9.15 (s, 1H), 8.08-8.02 (m, 1H), 7.99 (d, J=8.4 Hz, 1H), 7.71-7.61 (m, 3H), 7.57-7.46 (m, 2H), 4.93 (br d, J=13.6 Hz, 1H), 4.57 (br d, J=12.8 Hz, 1H), 4.37-4.27 (m, 2H), 3.64-3.55 (m, 11H), 3.37 (dd, J=10.4, 13.2 Hz, 1H), 3.23-3.16 (m, 1H), 3.15-3.07 (m, 3H), 2.75-2.67 (m, 2H), 2.57-2.46 (m, 1H), 2.18-2.06 (m, 3H), 1.97-1.85 (m, 5H), 1.84-1.70 (m, 3H), 1.68-1.56 (m, 1H); ¹⁹F NMR (400 MHz, methanol-d₄) δ=−139.847; LCMS [ESI, M+1, M/2+1]: 591.3, 296.2.

Example 437

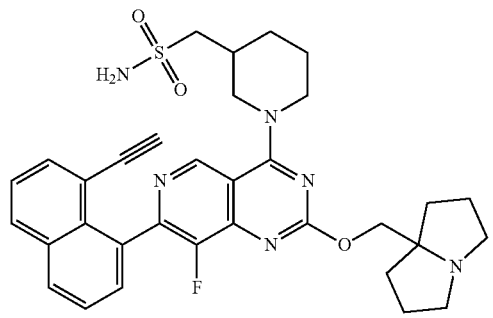 [SMILES: C#Cc1cccc2cccc(-c3ncc4c(N5CCCC(CS(N)(=O)=O)C5)nc(OCC56CCCN5CCC6)nc4c3F)c12]

1-(1-(7-(8-ethynylnaphthalene-1-yl)-8-fluoro-2-((hexahydro-1H-pyrrolizin-7a-yl)methoxy)pyrido[4,3-d]pyrimidin-4-yl)piperidin-3-yl)methanesulfonamide

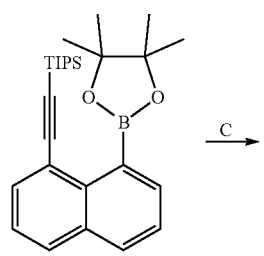

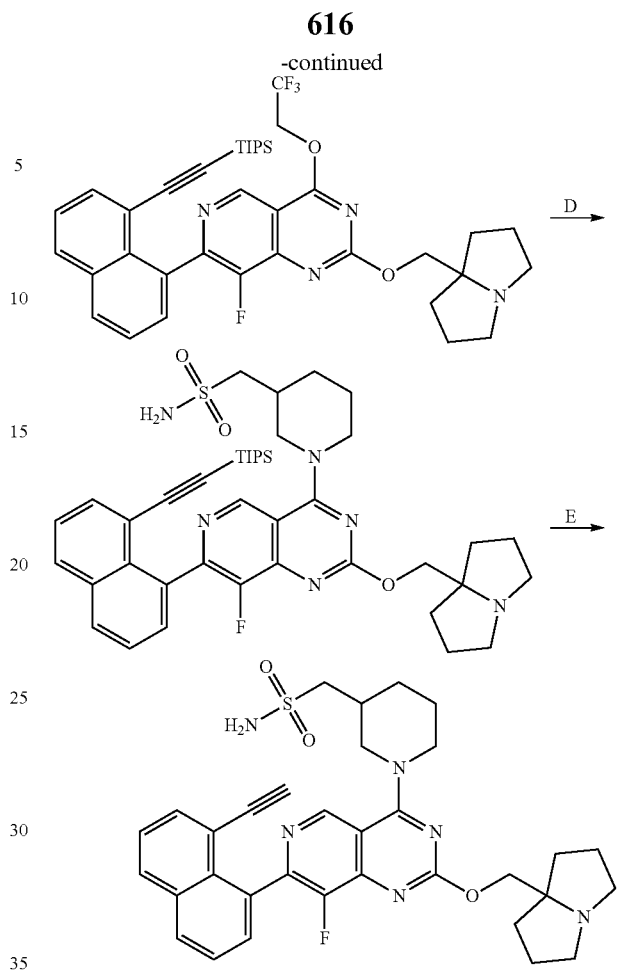

Step A. 8-fluoro-24(hexahydro-1H-pyrrolizin-7a-yl)methoxy)-4-(2,2,2-trifluoroethoxy)-7-(8-((triisopropylsilyl)ethynyl)naphthalen-1-yl)pyrido[4,3-d]pyrimidine: A mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (250 mg, 1.0 equiv.), triisopropyl((8-(4,4,5,5-tetramethyl-1,3,2-dioxaborolan-2-yl)naphthalen-1-yl)ethynyl)silane (310 mg, 1.2 equiv.), CataCXium A Pd G3 (43.3 mg, 0.1 equiv.) and Cs₂CO₃ (1.5 M in water, 1.19 mL, 3.0 equiv.) in methoxycyclopentane (3.5 mL) was degassed and then heated to 90° C. for 3 hours under N₂. The mixture was diluted with EtOAc (50 mL) and water (60 mL). The aqueous layer was extracted with EtOAc (2×40 mL), the combined organic phase was washed with brine (40 mL), dried over anhydrous sodium sulfate, filtered and concentrated in vacuum. The residue was purified by reversed phase flash chromatography [C18, water (0.1% formic acid)-ACN] to afford the title compound (158 mg, 36% yield, 93% purity) as a yellow oil; LCMS (ESI, M+1): m/z=693.3.

Step B. 1(1-(8-fluoro-2-((hexahydro-1H-pyrrolizin-7a-yl)methoxy)-7-(8-((triisopropylsilyl)ethynyl)naphthalen-1-yl)pyrido[4,3-d]pyrimidin-4-yl)piperidin-3-yl)methanesulfonamide: A mixture of piperidin-3-ylmethanesulfonamide (84.9 mg, 2.0 equiv.), DIEA (154 mg, 5.0 equiv.), 8-fluoro-2-((hexahydro-1H-pyrrolizin-7a-yl)methoxy)-4-(2,2,2-trifluoroethoxy)-7-(8-((triisopropylsilyl)ethynyl)naphthalen-1-yl)pyrido[4,3-d]pyrimidine (165 mg, 1.0 equiv.) and 4 Å molecular sieves (10 mg) in DMF (0.5 mL) was stirred at 40° C. for 36 hours. The mixture was filtered and the filtrate was purified by reversed phase flash chromatography [C18, water (0.1% formic acid)-ACN] to afford the title compound (94 mg, 46% yield). Yellow solid; LCMS (ESI, M+1): m/z=771.3.

Step C. 1-(1-(7-(8-ethynylnaphthalen-1-yl)-8-fluoro-2-((hexahydro-1H-pyrrolizin-7a-yl)methoxy)pyrido[4,3-d]pyrimidin-4-yl)piperidin-3-yl)methanesulfonamide: A solution of 1-(1-(8-fluoro-2-((hexahydro-1H-pyrrolizin-7a-yl)methoxy)-7-(8-(((triisopropylsilyl)ethynyl)naphthalen-1-yl)pyrido[4,3-d]pyrimidin-4-yl)piperidin-3-yl)methanesulfonamide (95 mg, 123 μmol, 1.0 equiv.) and CsF (281 mg, 15 equiv.) in DMF (0.5 mL) was stirred at 18° C. for 2 hours. The mixture was filtered and the filtrate was purified by reversed phase flash chromatography [C18, water (0.1% formic acid)-ACN] and re-purified by prep-HPLC [column: Waters Xbridge 150×25 mm×5 μm; mobile phase: water (10 mM NH₄HCO₃)-ACN; B %: 30%-60%, 8 min] to afford the title compound (12.3 mg, 16% yield, 98% purity) as a white solid; $^1$H NMR (400 MHz, METHANOL-d$_4$) δ=9.03 (s, 1H), 8.07 (dd, J=8.0, 18.4 Hz, 2H), 7.77-7.72 (m, 1H), 7.67 (m, 1H), 7.59 (m, 1H), 7.52 (t, J=7.6 Hz, 1H), 4.98-4.90 (m, 1H), 4.61-4.48 (m, 1H), 4.37-4.27 (m, 2H), 3.69-3.51 (m, 1H), 3.50-3.36 (m, 1H), 3.23-3.06 (m, 5H), 2.73 (m, 2H), 2.58-2.43 (m, 1H), 2.18-2.05 (m, 3H), 1.98-1.82 (m, 6H), 1.77-1.72 (m, 2H), 1.69-1.56 (m, 1H); LCMS (ESI, M+1): m/z=615.2

Example 438

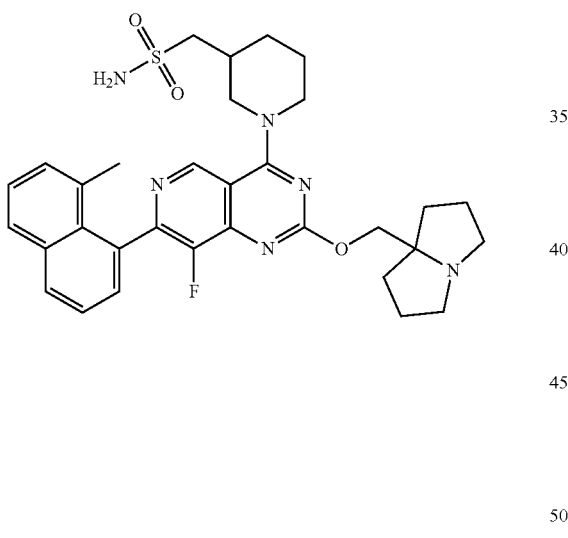

1-(1-(8-fluoro-2-((hexahydro-1H-pyrrolizin-7a-yl)methoxy)-7-(8-methylnaphthalen-1-yl)pyrido[4,3-d]pyrimidin-4-yl)piperidin-3-yl)methanesulfonamide The title compound was synthesized according to the procedure described for example 436. $^1$H NMR (400 MHz, METHANOL-d$_4$) δ=9.08 (s, 1H), 8.04 (d, J=8.0 Hz, 1H), 7.86 (d, J=8.4 Hz, 1H), 7.60-7.53 (m, 1H), 7.48-7.39 (m, 2H), 7.31 (d, J=6.8 Hz, 1H), 5.00-4.89 (m, 1H), 4.57 (dd, J=11.2, 7.6 Hz, 1H), 4.38-4.26 (m, 2H), 3.63-3.53 (m, 1H), 3.43-3.33 (m, 1H), 3.22-3.09 (m, 4H), 2.77-2.69 (m, 2H), 2.56-2.46 (m, 1H), 2.11 (dt, J=12.0, 5.6 Hz, 3H), 2.04 (d, J=5.2 Hz, 3H), 1.92 (td, J=12.0, 6.0 Hz, 5H), 1.82-1.70 (m, 3H), 1.67-1.58 (m, 1H); LCMS (ESI, M+1): m/z 605.3.

Example 439

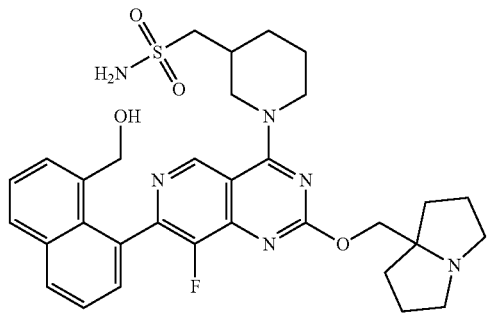 [SMILES: NS(=O)(=O)CC1CCCN(c2nc(OCC34CCCN3CCC4)nc3c(F)c(-c4cccc5cccc(CO)c45)ncc23)C1]

1-(1-(8-fluoro-2-((hexahydro-1H-pyrrolizin-7a-yl)methoxy)-7-(8-(hydroxymethyl)naphthalen-1-yl)pyrido[4,3-d]pyrimidin-4-yl)piperidin-3-yl)methanesulfonamide The title compound was synthesized according to the procedure described for example 433. $^1$H NMR (400 MHz, methanol-d$_4$) δ ppm=9.08 (s, 1H), 8.08 (d, J=8.0 Hz, 1H), 7.95 (d, J=8.2 Hz, 1H), 7.75 (d, J=7.2 Hz, 1H), 7.62-7.53 (m, 2H), 7.44-7.51 (m, 1H), 4.98-4.96 (m, 1H), 4.64-4.52 (m, 1H), 4.42-4.28 (m, 4H), 3.69-3.53 (m, 1H), 3.42-3.34 (m, 1H), 3.25-3.08 (m, 4H), 2.85-2.68 (m, 2H), 2.61-2.44 (m, 1H), 2.15-2.11 (m, 3H), 1.99-1.88 (m, 5H), 1.83-1.73 (m, 3H), 1.68-1.58 (m, 1H); LCMS (ESI, M+1): m/z=621.2.

Example 440

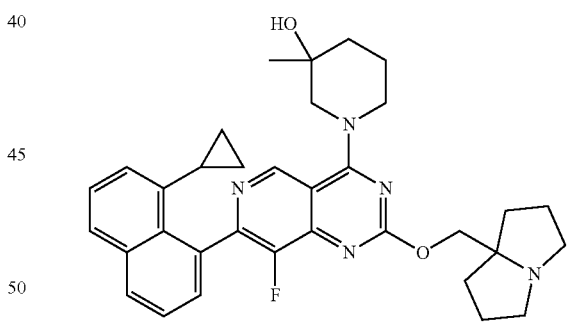

1-(7-(8-cyclopropylnaphthalen-1-yl)-8-fluoro-2-((hexahydro-1H-pyrrolizin-7a-yl)methoxy)pyrido[4,3-d]pyrimidin-4yl)-3-methylpiperidin-3-ol

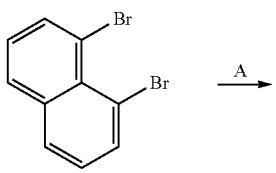

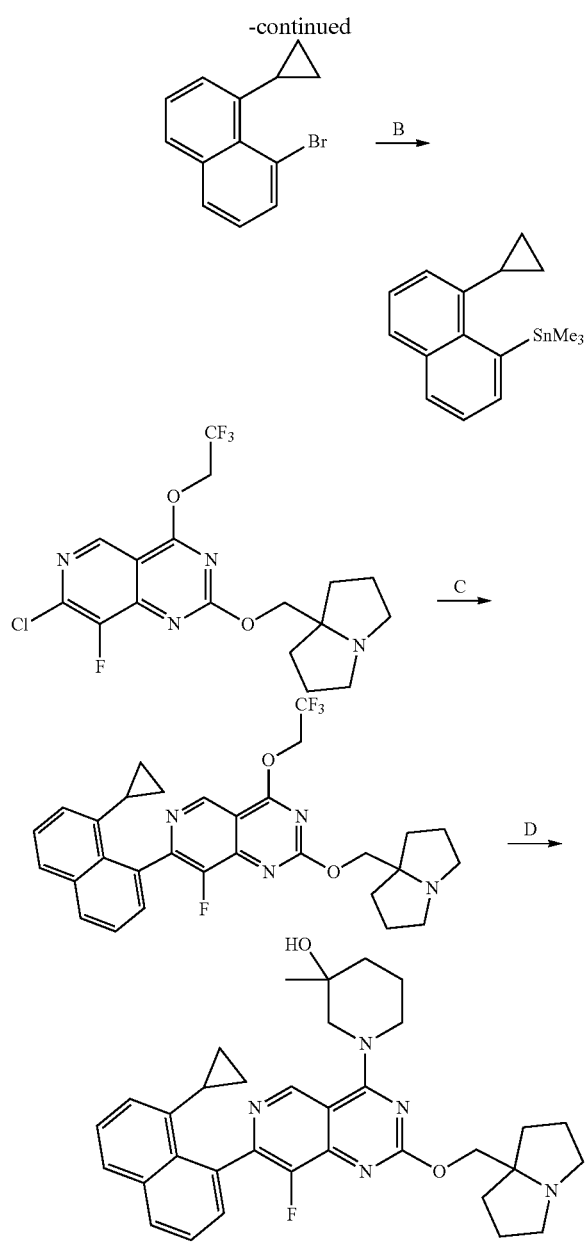

Step A. 1-bromo-8-cyclopropylnaphthalene: To a solution of 1,8-dibromonaphthalene (5.00 g, 1.0 equiv.) in dioxane (45.0 mL) and water (15.0 mL) was added cyclopropylboronic acid (2.25 g, 1.5 equiv.), $K_3PO_4$ (13.4 g, 3.6 equiv.) and Pd(dppf)C12 (640 mg, 0.05 equiv.). The mixture was degassed and stirred at 100° C. for 6 hours. After reaction completion, the mixture was quenched by water (30 mL), and extracted with ethyl acetate (3×50 mL). The combined organic layers were concentrated and purified by purified by reversed phase flash chromatography [C18, water (0.1% formic acid)/ACN] to afford the title compound (2.20 g, 14% yield, 82% purity) as a yellow solid; $^1$H NMR (400 MHz, $CDCl_3$) δ=7.93 (dd, J=1.2, 7.6 Hz, 1H), 7.83 (dd, J=1.2, 8.4 Hz, 1H), 7.74 (d, J=8.0 Hz, 1H), 7.55-7.49 (m, 1H), 7.44-7.37 (m, 1H), 7.33-7.25 (m, 1H), 3.09-2.99 (m, 1H), 1.20-1.13 (m, 2H), 0.96-0.88 (m, 2H).

Step B. (8-cyclopropylnaphthalen-1-yl)trimethylstannane: To a solution of 1-bromo-8-cyclopropylnaphthalene (4.40 g, 1.0 equiv.) in toluene (45.0 mL) were added trimethyl(trimethylstannyl)stannane (31.6 g, 96.6 mmol, 20.0 mL, 5.0 equiv.) and Pd(PPh$_3$)$_4$ (2.06 g, 0.1 equiv.) under $N_2$ atmosphere. The mixture was stirred at 110° C. for 18 h. After reaction completion, the mixture was concentrated under reduced pressure at 40° C. The crude product was purified by column chromatography [Silica gel, petroleum ether] and reversed-phase flash chromatography C18, water (0.1% NH3·H2O)/ACN] to afford the title compound (2.46 g, 42% yield) as a yellow oil; $^1$H NMR (400 MHz, $CDCl_3$) δ=7.87-7.77 (m, 2H), 7.70 (br dd, J=0.8, 8.0 Hz, 1H), 7.45-7.34 (m, 2H), 7.15 (d, J=7.2 Hz, 1H), 2.67-2.43 (m, 1H), 1.16-1.09 (m, 2H), 0.95-0.86 (m, 2H), 0.47-0.32 (m, 9H).

Step C. 7-(8-cyclopropylnaphthalen-1-yl)-8-fluoro-2-((hexahydro-1H-pyrrolizin-7a-yl)methoxy)-4-(2,2,2-trifluoroethoxy)pyrido[4,3-d]pyrimidine: To a reaction mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (500 mg, 1.19 mmol, 1.0 equiv.) in toluene (10.0 mL) was added (8-cyclopropylnaphthalen-1-yl)trimethylstannane (1.18 g, 3.56 mmol, 3.0 equiv.), CuI (67.9 mg, 356 μmol, 0.3 equiv.), BINAP (148 mg, 238 μmol, 0.2 equiv.) and Pd(dppf) C12 (86.9 mg, 119 μmol, 0.1 equiv.). The reaction mixture was stirred at 110° C. for 10 hours under $N_2$ atmosphere. After reaction completion, the mixture was diluted with water (10 mL), then extracted with ethyl acetate (3×30 mL). The combined organic layers were concentrated under reduced pressure at 40° C. The residue was purified by reversed-phase flash chromatography [C18, water (0.1% formic acid)/ACN] to afford the title compound (160 mg, 23% yield) as a yellow solid; $^1$H NMR (400 MHz, $CDCl_3$) δ=9.23 (s, 1H), 7.99 (d, J=8.0 Hz, 1H), 7.83 (t, J=4.8 Hz, 1H), 7.60-7.53 (m, 1H), 7.52-7.48 (m, 1H), 7.44 (d, J=4.8 Hz, 2H), 5.07 (q, J=8.2 Hz, 2H), 4.43 (br s, 2H), 3.27 (br s, 2H), 2.72 (br d, J=6.4 Hz, 2H), 2.12 (br dd, J=5.6, 11.3 Hz, 2H), 1.94 (br s, 4H), 1.81-1.68 (m, 2H), 1.66-1.58 (m, 1H), 0.58 (qd, J=4.9, 9.5 Hz, 1H), 0.51-0.40 (m, 1H), 0.37-0.27 (m, 1H), 0.04-0.09 (m, 1H);

Step D. 1-(7-(8-cyclopropylnaphthalen-1-yl)-8-fluoro-2-((hexahydro-1H-pyrrolizin-7a-yl)methoxy)pyrido[4,3-d]pyrimidin-4-yl)-3-methylpiperidin-3-ol: To a solution of 7-(8-cyclopropylnaphthalen-1-yl)-8-fluoro-2-((hexahydro-1H-pyrrolizin-7a-yl)methoxy)-4-(2,2,2-trifluoroethoxy)pyrido [4,3-d]pyrimidine (140 mg, 1.0 equiv.) in DMF (2.0 mL) were added DIEA (164 mg, 5.0 equiv.) and 3-methylpiperidin-3-ol (58.7 mg, 2.0 equiv.). The mixture was stirred at 40° C. for 16 hours. After reaction completion, the mixture was quenched with water (10 mL), and extracted with ethyl acetate (3×30 mL). The combined organic layers were dried over anhydrous $Na_2SO_4$, filtered, concentrated and purified by prep-HPLC [column: Waters Xbridge 150×25 mm×5 μm; mobile phase: water (10 mM $NH_4HCO_3$)-ACN, B %: 52%-82%, 2 min] to afford the title compound (47.5 mg, 32% yield, 98.5% purity) as a white solid; $^1$H NMR (400 MHz, DMSO-d$_4$) δ=9.18 (d, J=9.6 Hz, 1H), 8.08 (d, J=8.0 Hz, 1H), 7.92 (d, J=8.0 Hz, 1H), 7.65-7.57 (m, 1H), 7.54-7.43 (m, 2H), 7.38 (d, J=7.2 Hz, 1H), 4.72 (d, J=11.6 Hz, 1H), 4.36-4.21 (m, 1H), 4.11-3.93 (m, 3H), 3.68-3.45 (m, 1H), 3.01-2.86 (m, 2H), 2.57-2.52 (m, 2H), 2.05-1.95 (m, 1H), 1.92-1.51 (m, 13H), 1.15 (d, J=9.6 Hz, 3H), 0.56 (dt, J=4.4, 8.8 Hz, 1H), 0.39-0.21 (m, 2H), 0.08-0.10 (m, 1H); LCMS (ESI, M+1): m/z=568.3.

Example 441

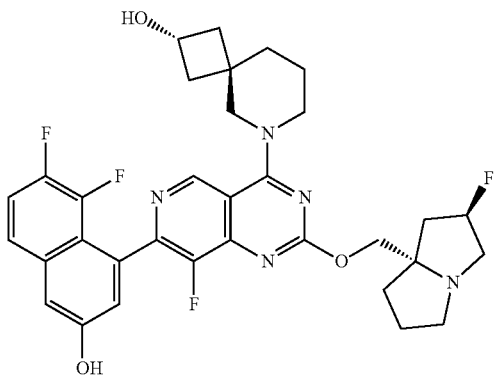 [SMILES: Oc1cc(-c2ncc3c(N4CCC[C@]5(C4)C[C@H](O)C5)nc(OC[C@@]45CCCN4C[C@H](F)C5)nc3c2F)c2c(F)c(F)ccc2c1]

trans-6-(7-(7,8-difluoro-3-hydroxynaphthalen-1-yl)-
8-fluoro-2-(((2R,7aS)-2-fluorohexahydro-1H-pyr-
rolizin-7a-yl)methoxy)pyrido[4,3-d]pyrimidin-4-yl)-
6-azaspiro[3.5]nonan-2-ol Example 442

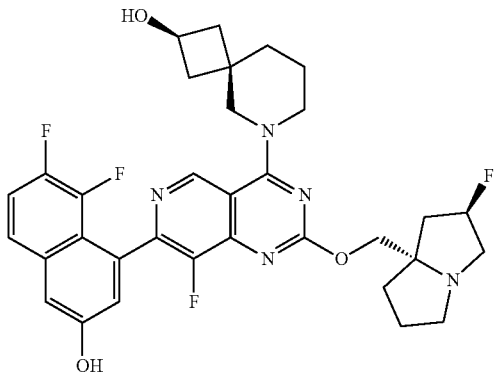 [SMILES: Oc1cc(-c2ncc3c(N4CCC[C@]5(C4)C[C@@H](O)C5)nc(OC[C@@]45CCCN4C[C@H](F)C5)nc3c2F)c2c(F)c(F)ccc2c1]

cis-6-(7-(7,8-difluoro-3-hydroxynaphthalen-1-yl)-8-
fluoro-2-(((2R,7aS)-2-fluorohexahydro-1H-pyr-
rolizin-7a-yl)methoxy)pyrido[4,3-d]pyrimidin-4-yl)-
6-azaspiro[3.5]nonan-2-ol

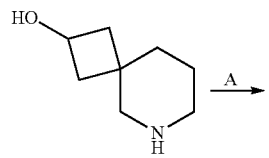

-continued

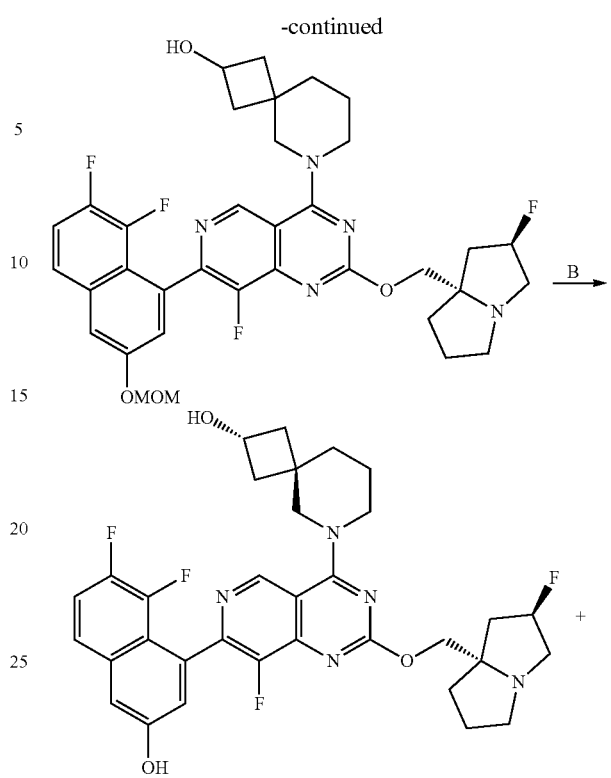

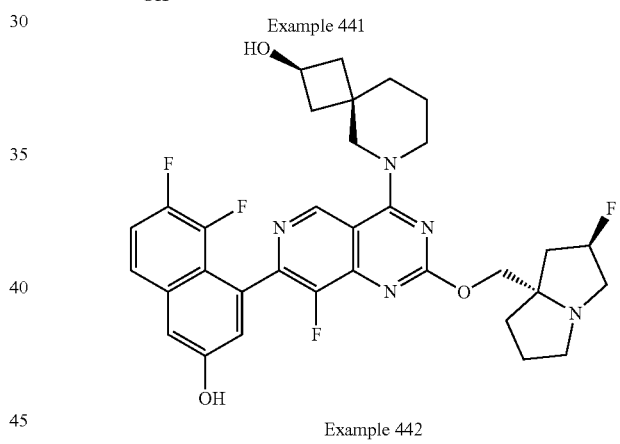

Example 442

Step A. 6-(7-(7,8-difluoro-3-(methoxymethoxy)naphtha-
len-1-yl)-8-fluoro-2-(((2R,7aS)-2-fluorohexahydro-1H-pyr-
rolizin-7a-yl)methoxy)pyrido[4,3-d]pyrimidin-4-yl)-6-
azaspiro[3.5]nonan-2-ol: To a solution of 6-azaspiro[3.5]
nonan-2-ol (317 mg, 5.0 equiv., HCl) in DMF (1.0 mL) was
added 4 Å molecular sieves (20 mg) and DIEA (461 mg, 10
equiv.). The mixture was stirred at 60° C. for 30 minutes
before 7-(7,8-difluoro-3-(methoxymethoxy)naphthalen-1-
yl)-8-fluoro-2-(((2R,7aS)-2-fluorotetrahydro-1H-pyr-
rolizin-7a(5H)-yl)methoxy)-4-(2,2,2-trifluoroethoxy)pyrido
[4,3-d]pyrimidine (240 mg, 1.0 equiv., formic acid salt) was
added. The mixture was stirred at 60° C. for 12 hours. The
reaction mixture was filtered and purified by reversed phase
flash chromatography [C18, water (0.1% formic acid)/ACN]
to afford the title compound (100 mg, 40% yield) as a yellow
solid; LCMS (ESI, M+1): m/z=668.4.

Step B. 6-(7-(7,8-difluoro-3-hydroxynaphthalen-1-yl)-8-
fluoro-2-(((2R,7aS)-2-fluorohexahydro-1H-pyrrolizin-7a-
yl)methoxy)pyrido[4,3-d]pyrimidin-4-yl)-6-azaspiro[3.5]
nonan-2-ol: To a mixture of 6-(7-(7,8-difluoro-3-

623

(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-6-azaspiro[3.5]nonan-2-ol (90.0 mg, 1.0 equiv.) in DCM (0.5 mL) was added TFA (308 mg, 20 equiv.) in one portion at 0° C. under N₂. The mixture was stirred at 0° C. for 1. hour. The reaction mixture was diluted with water (3.0 mL), the aqueous phase was extracted with DCM (3×5 mL). The combined organic phase was washed with brine (10 mL), dried over anhydrous sodium sulfate, concentrated and purified by reversed phase flash chromatography (C18, water (0.1% formic acid)-ACN) and re-purified by prep-HPLC [column: Waters Xbridge 150×25 mm×5 μm; mobile phase: water (10 mM NH₄HCO₃)-ACN, B %: 40%-70%, 10 min] and lyophilized to afford the first eluting peak—Example 441 (6.28 mg, 7.0% yield) as a white solid, $^1$H NMR (400 MHz, methanol-d₄) δ=9.05 (s, 1H), 7.68-7.55 (m, 1H), 7.45-7.36 (m, 1H), 7.33 (t, J=2.4 Hz, 1H), 7.25 (d, J=2.4 Hz, 1H), 5.47-5.18 (m, 1H), 4.39-4.24 (m, 3H), 4.10-3.91 (m, 4H), 3.30-3.18 (m, 3H), 3.10-2.96 (m, 1H), 2.42-2.11 (m, 5H), 2.07-1.90 (m, 3H), 1.85-1.79 (m, 4H), 1.75-1.64 (m, 2H); LCMS (ESI, M+1): m/z=624.2;

and the second eluting peak—Example 442 (8.91 mg, 10% yield) as a white solid. $^1$H NMR (400 MHz, methanol-d₄) δ=9.07 (s, 1H), 7.65-7.57 (m, 1H), 7.45-7.36 (m, 1H), 7.33 (t, J=2.0 Hz, 1H), 7.26-7.22 (m, 1H), 5.48-5.19 (m, 1H), 4.45-4.19 (m, 3H), 4.11-3.93 (m, 4H), 3.45-3.34 (m, 1H), 3.30-3.21 (m, 2H), 3.14-2.97 (m, 1H), 2.46-2.12 (m, 5H), 2.10-1.92 (m, 3H), 1.89-1.72 (m, 6H); LCMS (ESI, M+1): m/z=624.2; LCMS (ESI, M+1): m/z=624.2.

Example 443

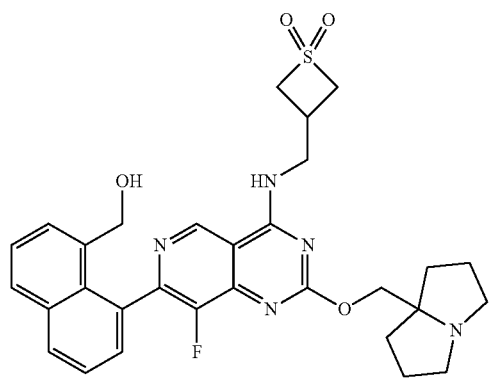 [SMILES: O=S1(=O)CC(CNc2nc(OCC34CCCN3CCC4)nc3c(F)c(-c4cccc5cccc(CO)c45)ncc23)C1]

3-(((8-fluoro-2-((hexahydro-1H-pyrrolizin-7a-yl)methoxy)-7-(8-(hydroxymethyl)naphthalen-1-yl)pyrido[4,3-d]pyrimidin-4-yl)amino)methyl)thietane 1,1-dioxide

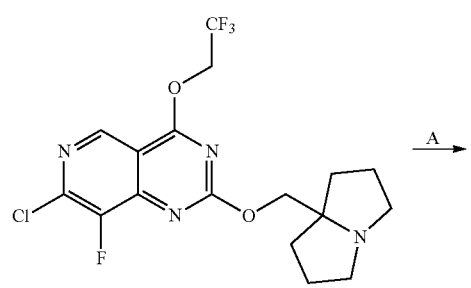

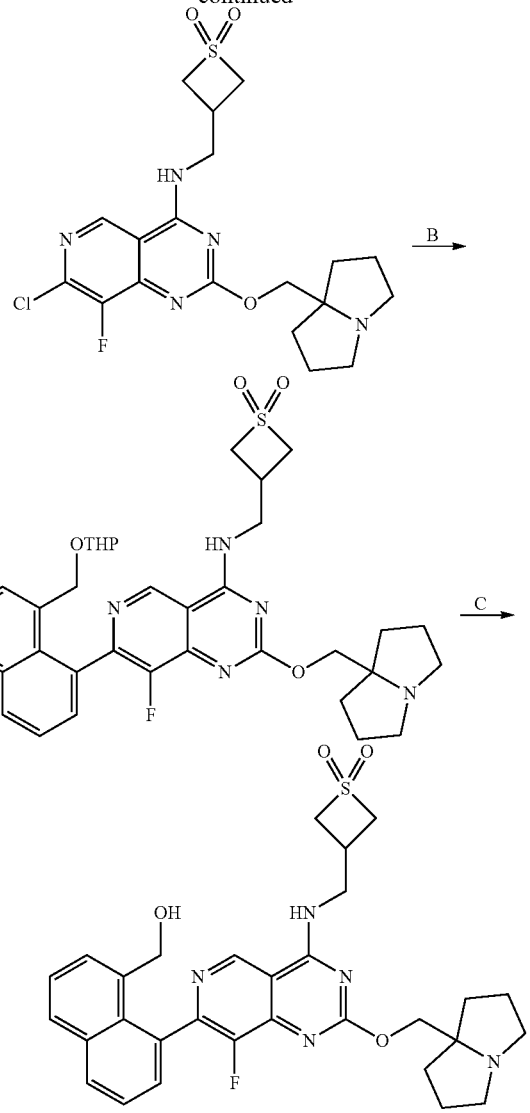

Step A: 3-(((7-chloro-8-fluoro-2-((hexahydro-1H-pyrrolizin-7a-yl)methoxy)pyrido[4,3-d]pyrimidin-4-yl)amino)methyl)thietane 1,1-dioxide: To a solution of 7-chloro-8-fluoro-2-((tetrahydro-1H-pyrrolizin-7a(5H)-yl)methoxy)-4-(2,2,2-trifluoroethoxy)pyrido[4,3-d]pyrimidine (200 mg, 1.0 equiv.) in DMF (2 mL) was added 3-(aminomethyl)thietane 1,1-dioxide (77.1 mg, 1.2 equiv.) and DIEA (307 mg, 5.0 equiv.). The mixture was stirred at 40° C. for 2 hours. The pH of the mixture was adjusted to 7 with 1N HCl and the resulting mixture was filtered. The filter cake was dried in vacuum to give the title compound (140 mg, 65% yield) as a white solid. LCMS (ESI, M+1): 456.2.

Step B: 3-(((8-fluoro-2-((hexahydro-1H-pyrrolizin-7a-yl)methoxy)-7-(8-((((tetrahydro-2H-pyran-2-yl)oxy)methyl)naphthalen-1-yl)pyrido[4,3-d]pyrimidin-4-yl)amino)methyl)thietane 1,1-dioxide: To a solution of 3-(((7-chloro-8-fluoro-2-((hexahydro-1H-pyrrolizin-7a-yl)methoxy)pyrido[4,3-d]pyrimidin-4-yl)amino)methyl)thietane 1,1-dioxide (50 mg, 1.0 equiv.) and 4,4,5,5-tetramethyl-2-(8-((((tetrahydro-2H-pyran-2-yl)oxy)methyl)naphthalen-1-yl)-1,3,2-dioxaborolane (60.6 mg, 1.5 equiv.) in n-BuOH (1.5 mL) was added K₃PO₄ (1.5 M, 3.0 equiv.) and XPhos Pd G3

(9.44 mg, 0.1 equiv.). The mixture was stirred at 60° C. for 2 hours. The mixture was filtered through a pad of celite and concentrated in vacuum. The residue was purified by reversed phase flash chromatography [C18, water (0.1% formic acid)/ACN] and Prep-HPLC [column: Unisil 3-100 C18 Ultra 150×50 mm×3 μm; mobile phase: water (0.225% formic acid)-CAN, B %: 9%-39%, 10 min] to give the title compound (10 mg, 13.8% yield) as a yellow solid. LCMS [ESI, M+1]: 662.0.

Step C: 3-(((8-fluoro-2-((hexahydro-1H-pyrrolizin-7a-yl)methoxy)-7-(8-(hydroxymethyl)naphthalen-1-yl)pyrido[4,3-d]pyrimidin-4-yl)amino)methyl)thietane 1,1-dioxide: To a solution of 3-(((8-fluoro-2-((hexahydro-1H-pyrrolizin-7a-yl)methoxy)-7-(8-((((tetrahydro-2H-pyran-2-yl)oxy)methyl)naphthalen-1-yl)pyrido[4,3-d]pyrimidin-4-yl)amino)methyl)thietane 1,1-dioxide (10 mg, 1.0 equiv.) in MeOH (0.5 mL) was added HCl.dioxane (4 M, 20 equiv.). The mixture was stirred at 25° C. for 1 hour. The mixture was concentrated in vacuum. The residue was purified by Prep-HPLC [column: Unisil 3-100 C18 Ultra 150×50 mm×3 μm; mobile phase: water (0.225% formic acid)-CAN, B %: 9%-39%, 10 min] to give the title compound (2.39 mg, 27% yield) as an off-white solid. $^1$H NMR (400 MHz, MeOD-d4) δ=9.18 (s, 1H), 8.13-8.05 (m, 1H), 7.96 (d, J=7.6 Hz, 1H), 7.73 (d, J=6.4 Hz, 1H), 7.64-7.54 (m, 2H), 7.46 (dd, J=1.2, 7.2 Hz, 1H), 4.72 (s, 2H), 4.36 (m, 2H), 4.29-4.20 (m, 2H), 4.17-4.03 (m, 4H), 3.72-3.63 (m, 2H), 3.28-3.26 (m, 2H), 3.11-2.99 (m, 1H), 2.38-2.07 (m, 8H). LCMS [ESI, M+1]: 578.3.

Example 444

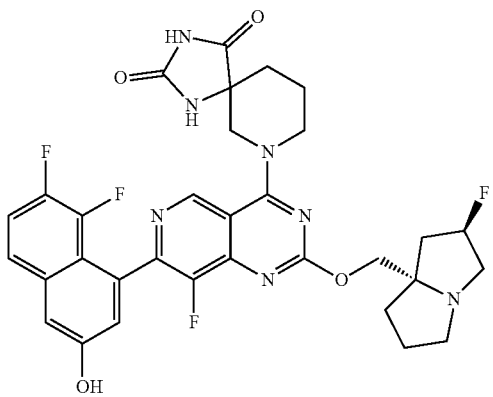 [SMILES: O=C1NC(=O)C2(CCCN(c3nc(OC[C@@]45CCCN4C[C@H](F)C5)nc4c(F)c(-c5cc(O)cc6ccc(F)c(F)c56)ncc34)C2)N1]

7-(7-(7,8-difluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decane-2,4-dione

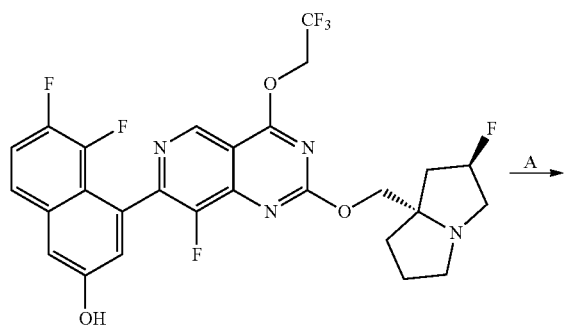

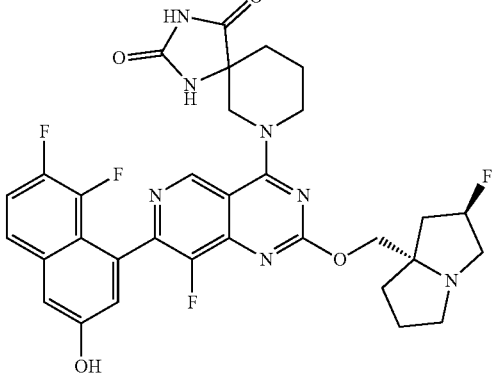

Step A. 7-(7-(7,8-difluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decane-2,4-dione: A mixture of 5,6-difluoro-4-(8-fluoro-2-(((2R,7aS)-2-fluorohexahydro-1H-pyrrolizin-7a-yl)methoxy)-4-(2,2,2-trifluoroethoxy)pyrido[4,3-d]pyrimidin-7-yl)naphthalen-2-ol (60 mg, 1.0 equiv.), 1,3,9-triazaspiro[4.5]decane-2,4-dione (74 mg, 4.25 equiv.), DIEA (40.07 mg, 54 μL, 3.01 equiv.), 4 Å molecular sieves (20 mg) in DMF (1 mL) was degassed and stirred at 40° C. for 18 hours. The mixture was filtered. The filtrate was purified by reversed phase flash chromatography [C18, water (0.1% formic acid)/ACN] to give a crude product. The crude product was re-purified by prep-HPLC (column: Phenomenex luna C18 150×25 mm×10 μm; mobile phase: [water (0.225% formic acid)-ACN]; B %: 11%-41%, 10 min) and lyophilized to give the title compound (34.1 mg, 50% yield) as a white solid; $^1$H NMR (400 MHz, METHANOL-d$_4$) δ=9.20 (s, 1H), 8.50 (s, 1H), 7.62 (dd, J=4.4, 9.2 Hz, 1H), 7.45-7.36 (m, 1H), 7.34 (t, J=2.0 Hz, 1H), 5.50-5.33 (m, 1H), 4.66 (br d, J=13.2 Hz, 1H), 4.56-4.35 (m, 3H), 3.83-3.49 (m, 5H), 3.25-3.14 (m, 1H), 2.56-1.87 (m, 10H); LCMS [ESI, M+1]: 652.3.

Example 445

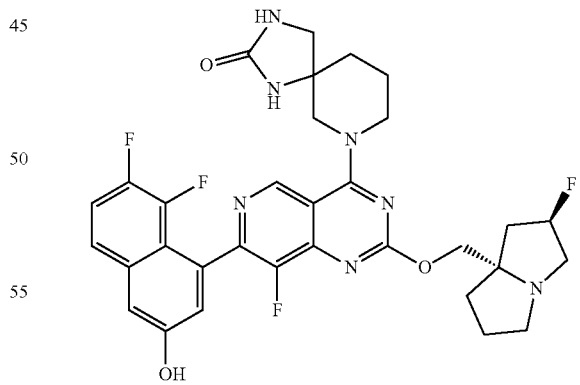

7-(7-(7,8-difluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,3,7-triazaspiro[4.5]decan-2-one The title compound was synthesized according to the procedure described for example 203. $^1$H NMR (400 MHz, DMSO-d$_6$) δ=9.11 (s, 1H), 7.78-7.64 (m, 1H), 7.62-7.45 (m, 1H), 7.37 (s, 1H), 7.24 (s, 1H), 7.00 (br s, 1H), 6.30 (s, 1H), 5.41-5.15 (m, 1H), 4.20-3.91 (m, 4H), 3.78-3.63 (m, 2H), 3.24-2.94 (m, 6H), 2.88-2.75 (m, 1H), 2.20-1.97 (m, 4H), 1.88-1.70 (m, 6H); LCMS (ESI, M+1): m/z=638.2.

Example 446

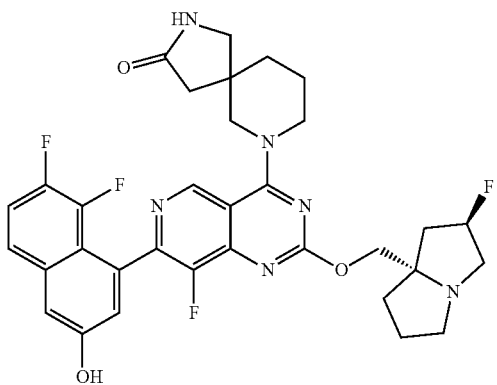 [SMILES: O=C1CC2(CCCN(c3nc(OC[C@@]45CCCN4C[C@H](F)C5)nc4c(F)c(-c5cc(O)cc6ccc(F)c(F)c56)ncc34)C2)CN1]

7-(7-(7,8-difluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2,7-diazaspiro[4.5]decan-3-one The title compound was synthesized according to the procedure described for example 203. $^1$H NMR (400 MHz, methanol-d$_4$) δ=9.07 (s, 1H), 7.67-7.57 (m, 1H), 7.44-7.35 (m, 1H), 7.35-7.31 (m, 1H), 7.26-7.21 (m, 1H), 5.43-5.18 (m, 1H), 4.36-4.19 (m, 2H), 4.17-3.95 (m, 4H), 3.39-3.33 (m, 2H), 3.28-3.16 (m, 3H), 3.06-2.95 (m, 1H), 2.43-2.10 (m, 5H), 2.05-1.82 (m, 7H); LCMS (ESI, M+1): m/z=637.3;

Example 447

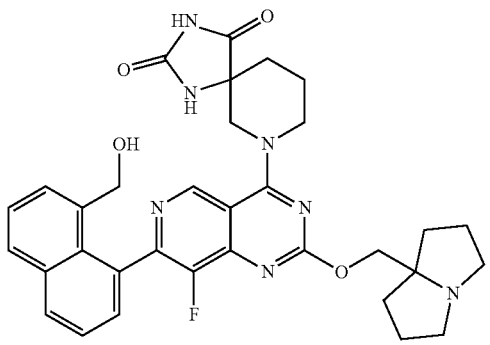 [SMILES: O=C1NC(=O)C2(CCCN(c3nc(OCC45CCCN4CCC5)nc4c(F)c(-c5cccc6cccc(CO)c56)ncc34)C2)N1]

7-(8-fluoro-2-((hexahydro-1H-pyrrolizin-7a-yl)methoxy)-7-(8-(hydroxymethyl)naphthalen-1-yl)pyrido[4,3-d]pyrimidin-4-yl)-1,3,7-triazaspiro[4.5]decane-2,4-dione The title compound was synthesized according to the procedure described for example 433. $^1$H NMR (400 MHz, methanol-d$_4$) δ=9.13-9.07 (m, 1H), 8.08 (dd, J=1.2, 8.0 Hz, 1H), 7.95 (d, J=7.6 Hz, 1H), 7.75 (br d, J=7.2 Hz, 1H), 7.58 (m, 2H), 7.48 (d, J=7.2 Hz, 1H), 4.63 (br d, J=6.8 Hz, 1H), 4.54-4.40 (m, 1H), 4.36-4.22 (m, 4H), 3.85-3.67 (m, 2H), 3.17-3.06 (m, 2H), 2.73 (m, 2H), 2.30-2.19 (m, 1H), 2.14-1.99 (m, 4H), 1.98-1.83 (m, 5H), 1.80-1.71 (m, 2H); LCMS (ESI, M+1): m/z=612.2.

Example 448

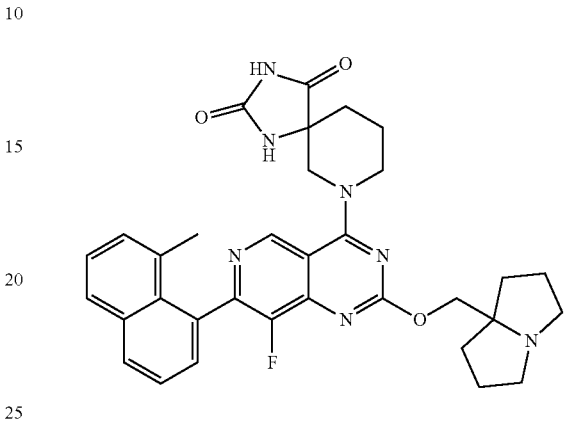

7-(8-fluoro-2-((hexahydro-1H-pyrrolizin-7a-yl)methoxy)-7-(8-methylnaphthalen-1-yl)pyrido[4,3-d]pyrimidin-4-yl)-1,3,7-triazaspiro[4.5]decane-2,4-dione The title compound was synthesized according to the procedure described for example 436. $^1$H NMR (400 MHz, methanol-d$_4$) δ=9.17-9.06 (m, 1H), 8.04 (d, J=8.0 Hz, 1H), 7.86 (d, J=8.0 Hz, 1H), 7.57 (t, J=7.6 Hz, 1H), 7.48-7.40 (m, 2H), 7.35-7.25 (m, 1H), 4.63 (br dd, J=5.6, 13.6 Hz, 1H), 4.52-4.37 (m, 1H), 4.35-4.23 (m, 2H), 3.86-3.64 (m, 2H), 3.17-3.06 (m, 2H), 2.73 (td, J=6.4, 10.4 Hz, 2H), 2.30-2.17 (m, 1H), 2.14-2.02 (m, 5H), 2.02-1.94 (m, 3H), 1.94-1.84 (m, 4H), 1.81-1.72 (m, 2H); LCMS (ESI, M+1): m/z=596.1.

Example 449

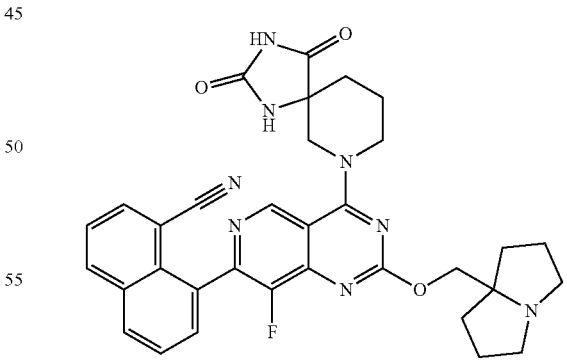

8-(4-(2,4-dioxo-1,3,7-triazaspiro[4.5]decan-7-yl)-8-fluoro-2-((hexahydro-1H-pyrrolizin-7a-yl)methoxy)pyrido[4,3-d]pyrimidin-7-yl)-1-naphthonitrile The title compound was synthesized according to the procedure described for example 436. $^1$H NMR (400 MHz, methanol-d$_4$) δ=9.14 (s, 1H), 8.41-8.35 (m, 1H), 8.27-8.20

(m, 1H), 8.07-8.02 (m, 1H), 7.85-7.78 (m, 2H), 7.73-7.67 (m, 1H), 4.65 (br d, J=13.2 Hz, 1H), 4.55-4.44 (m, 1H), 4.38-4.26 (m, 2H), 3.88-3.66 (m, 2H), 3.22-3.11 (m, 2H), 2.78 (td, J=6.4, 10.4 Hz, 2H), 2.31-2.20 (m, 1H), 2.16-2.02 (m, 4H), 1.99-1.87 (m, 5H), 1.84-1.74 (m, 2H); LCMS (ESI, M+1): m/z=607.2.

Example 450

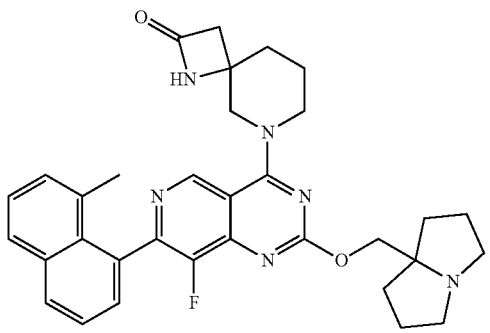 [SMILES: Cc1cccc2cccc(-c3ncc4c(N5CCCC6(CC(=O)N6)C5)nc(OCC56CCCN5CCC6)nc4c3F)c12]

6-(8-fluoro-2-((hexahydro-1H-pyrrolizin-7a-yl)methoxy)-7-(8-methylnaphthalen-1-yl)pyrido[4,3-d]pyrimidin-4-yl)-1,6-diazaspiro[3.5]nonan-2-one The title compound was synthesized according to the procedure described for example 436. $^1$H NMR (400 MHz, methanol-d$_4$) δ=9.13 (d, J=2.4 Hz, 1H), 8.05 (dd, J=1.2, 8.4 Hz, 1H), 7.87 (d, J=8.0 Hz, 1H), 7.63-7.53 (m, 1H), 7.48-7.41 (m, 2H), 7.32 (br d, J=7.2 Hz, 1H), 4.67-4.58 (m, 2H), 4.42 (d, J=13.2 Hz, 1H), 4.37-4.28 (m, 1H), 4.02 (dd, J=4.4, 13.2 Hz, 1H), 3.91-3.82 (m, 1H), 3.70-3.60 (m, 2H), 3.28-3.18 (m, 2H), 2.96-2.87 (m, 1H), 2.82-2.74 (m, 1H), 2.35-2.27 (m, 2H), 2.26-2.14 (m, 4H), 2.13-2.08 (m, 2H), 2.07-2.01 (m, 5H), 1.97 (br dd, J=4.0, 7.6 Hz, 2H); LCMS (ESI, M+1): m/z=567.1.

Example 451

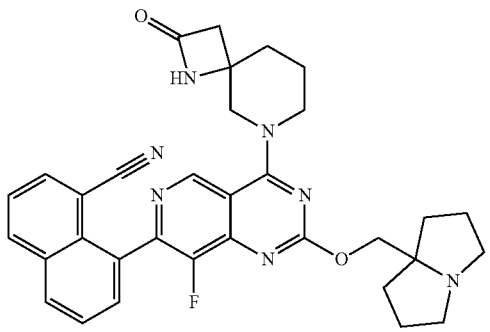 [SMILES: N#Cc1cccc2cccc(-c3ncc4c(N5CCCC6(CC(=O)N6)C5)nc(OCC56CCCN5CCC6)nc4c3F)c12]

8-(8-fluoro-2-((hexahydro-1H-pyrrolizin-7a-yl)methoxy)-4-(2-oxo-1,6-diazaspiro[3.5]nonan-6-yl)pyrido[4,3-d]pyrimidin-7-yl)-1-naphthonitrile The title compound was synthesized according to the procedure described for example 436. $^1$H NMR (400 MHz, methanol-d$_4$) δ=9.11 (s, 1H), 8.40-8.35 (m, 1H), 8.26-8.20 (m, 1H), 8.04 (dd, J=1.2, 7.2 Hz, 1H), 7.85-7.78 (m, 2H), 7.73-7.66 (m, 1H), 4.41-4.18 (m, 4H), 4.09-4.00 (m, 1H), 3.97-3.73 (m, 1H), 3.19-3.09 (m, 2H), 2.81-2.92 (m, 1H), 2.80-2.70 (m, 3H), 2.16-2.03 (m, 4H), 2.01-1.87 (m, 6H), 1.83-1.73 (m, 2H); LCMS (ESI, M+1): m/z=578.3.

Example 452

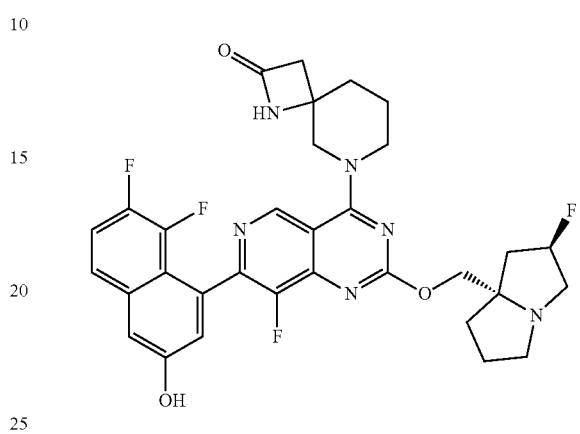

6-(7-(7,8-difluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1,6-diazaspiro[3.5]nonan-2-one The title compound was synthesized according to the procedure described for example 444. $^1$H NMR (400 MHz, methanol-d$_4$) δ=9.09 (s, 1H), 7.65-7.57 (m, 1H), 7.44-7.35 (m, 1H), 7.33 (t, J=2.0 Hz, 1H), 7.26-7.22 (m, 1H), 5.45-5.17 (m, 1H), 4.49-4.20 (m, 4H), 4.03-3.90 (m, 1H), 3.83-3.68 (m, 1H), 3.30-3.14 (m, 3H), 3.06-2.96 (m, 1H), 2.95-2.86 (m, 1H), 2.80-2.71 (m, 1H), 2.40-2.07 (m, 4H), 2.06-1.83 (m, 6H); LCMS (ESI, M+1): m/z=623.2.

Example 453

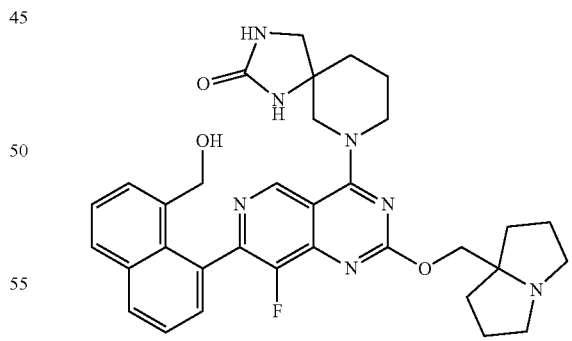

7-(8-fluoro-2-((hexahydro-1H-pyrrolizin-7a-yl)methoxy)-7-(8-(hydroxymethyl)naphthalen-1-yl)pyrido[4,3-d]pyrimidin-4-yl)-1,3,7-triazaspiro[4.5]decan-2-one The title compound was synthesized according to the procedure described for example 433. $^1$H NMR (400 MHz, methanol-d$_4$) δ=9.10 (br d, J=6.4 Hz, 1H), 8.08 (br d, J=6.8

Hz, 1H), 7.95 (br d, J=7.6 Hz, 1H), 7.75 (br s, 1H), 7.63-7.53 (m, 2H), 7.49 (br s, 1H), 4.36-4.22 (m, 4H), 4.15-3.87 (m, 4H), 3.48-3.40 (m, 1H), 3.28 (br s, 1H), 3.16-3.05 (m, 2H), 2.78-2.67 (m, 2H), 2.13-2.02 (m, 2H), 2.01-1.82 (m, 8H), 1.81-1.71 (m, 2H); $^{19}$F NMR (376 MHz, methanol-d$_4$) δ=−139.118; LCMS (ESI, M+1): m/z=598.3.

Example 454

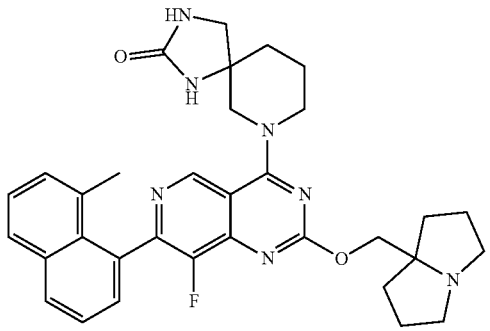 [SMILES: Cc1cccc2cccc(-c3ncc4c(N5CCCC6(CNC(=O)N6)C5)nc(OCC56CCCN5CCC6)nc4c3F)c12]

7-(8-fluoro-2-((hexahydro-1H-pyrrolizin-7a-yl)methoxy)-7-(8-methylnaphthalen-1-yl)pyrido[4,3-d]pyrimidin-4-yl)-1,3,7-triazaspiro[4.5]decan-2-one The title compound was synthesized according to the procedure described for example 436. $^1$H NMR (400 MHz, methanol-d$_4$) δ=9.16 (d, J=2.4 Hz, 1H), 8.06 (dd, J=0.8, 8.4 Hz, 1H), 7.87 (d, J=8.0 Hz, 1H), 7.58 (t, J=7.6 Hz, 1H), 7.50-7.40 (m, 2H), 7.32 (dd, J=3.2, 6.8 Hz, 1H), 4.70-4.65 (m, 1H), 4.61-4.55 (m, 1H), 4.41 (dd, J=8.8, 12.8 Hz, 1H), 4.25 (br dd, J=4.0, 13.2 Hz, 1H), 4.06-3.93 (m, 1H), 3.88 (dd, J=10.4, 12.8 Hz, 1H), 3.74-3.62 (m, 2H), 3.43 (dd, J=1.6, 9.6 Hz, 1H), 3.30-3.21 (m, 3H), 2.37-2.27 (m, 2H), 2.26-2.14 (m, 4H), 2.09 (dd, J=6.4, 12.8 Hz, 2H), 2.03 (d, J=8.8 Hz, 3H), 1.98 (br s, 3H), 1.92-1.84 (m, 1H); LCMS (ESI, M+1): m/z=582.1.

Example 455

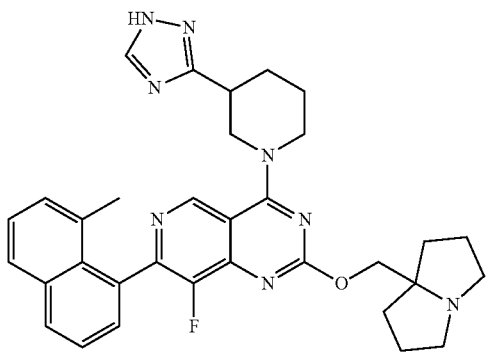 [SMILES: Cc1cccc2cccc(-c3ncc4c(N5CCCC(c6nc[nH]n6)C5)nc(OCC56CCCN5CCC6)nc4c3F)c12]

4-(3-(1H-1,2,4-triazol-3-yl)piperidin-1-yl)-8-fluoro-2-((hexahydro-1H-pyrrolizin-7a-yl)methoxy)-7-(8-methylnaphthalen-1-yl)pyrido[4,3-d]pyrimidine The title compound was synthesized according to the procedure described for example 436. $^1$H NMR (400 MHz, methanol-d$_4$) δ=9.09 (d, J=2.0 Hz, 1H), 8.22 (d, J=4.4 Hz, 1H), 8.08-7.99 (m, 1H), 7.86 (d, J=8.0 Hz, 1H), 7.57 (t, J=7.6 Hz, 1H), 7.48-7.39 (m, 2H), 7.31 (d, J=7.2 Hz, 1H), 4.65-4.50 (m, 1H), 4.35-4.19 (m, 2H), 3.78 (ddd, J=10.4, 13.2, 20.0 Hz, 1H), 3.73-3.64 (m, 1H), 3.42-3.32 (m, 2H), 3.11-3.02 (m, 2H), 2.70 (td, J=6.8, 10.4 Hz, 2H), 2.36-2.27 (m, 1H), 2.15-2.05 (m, 3H), 2.04 (s, 4H), 2.00-1.91 (m, 2H), 1.91-1.86 (m, 2H), 1.86-1.79 (m, 1H), 1.78-1.68 (m, 2H); LCMS (ESI, M+1): m/z=579.1.

Example 456

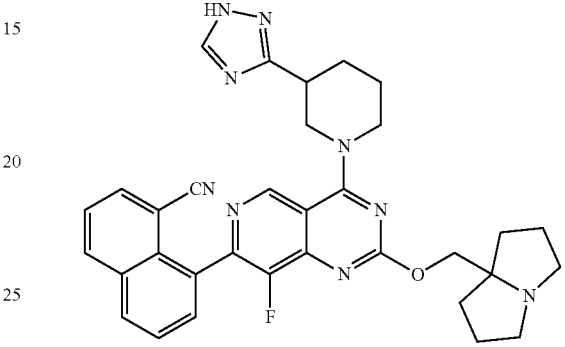

8-(4-(3-(1H-1,2,4-triazol-3-yl)piperidin-1-yl)-8-fluoro-2-((hexahydro-1H-pyrrolizin-7a-yl)methoxy)pyrido[4,3-d]pyrimidin-7-yl)-1-naphthonitrile The title compound was synthesized according to the procedure described for example 436. $^1$H NMR (400 MHz, methanol-d$_4$) δ=9.12 (s, 1H), 8.38-8.36 (m, 1H), 8.29-8.17 (m, 2H), 8.05-8.02 (m, 1H), 7.85-7.77 (m, 2H), 7.71-7.66 (m, 1H), 4.65-4.54 (m, 1H), 4.37-4.26 (m, 2H), 3.79-3.61 (m, 2H), 3.41-3.33 (m, 1H), 3.17-3.06 (m, 2H), 2.77-2.70 (m, 2H), 2.36-2.26 (m, 1H), 2.14-1.82 (m, 10H), 1.81-1.72 (m, 2H); LCMS (ESI, M+1): m/z=590.3.

Example 457

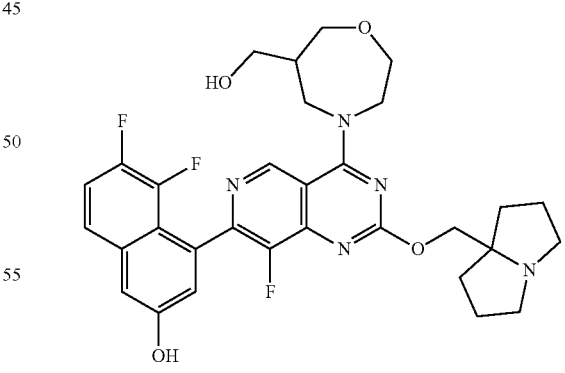

5,6-difluoro-4-(8-fluoro-2-((hexahydro-1H-pyrrolizin-7a-yl)methoxy)-4-(6-(hydroxymethyl)-1,4-oxazepan-4-yl)pyrido[4,3-d]pyrimidin-7-yl)naphthalen-2-ol The title compound was synthesized according to the procedure described for example 203. $^1$H NMR (400 MHz, methanol-d$_4$) δ=9.32-9.20 (m, 1H), 7.63 (br dd, J=4.8, 8.4 Hz, 1H), 7.46-7.39 (m, 1H), 7.38-7.33 (m, 1H), 7.32-7.22 (m, 1H), 4.81-4.64 (m, 3H), 4.52-4.35 (m, 1H), 4.18-4.03 (m, 2H), 4.02-3.94 (m, 1H), 3.88-3.79 (m, 1H), 3.75-3.67 (m, 2H), 3.61-3.53 (m, 2H), 3.35-3.31 (m, 1H), 3.30-3.20 (m, 2H), 3.12-2.97 (m, 1H), 2.40-2.28 (m, 2H), 2.27-2.16 (m, 4H), 2.15-1.99 (m, 3H); LCMS (ESI, M+1): m/z=596.3.

Example 458

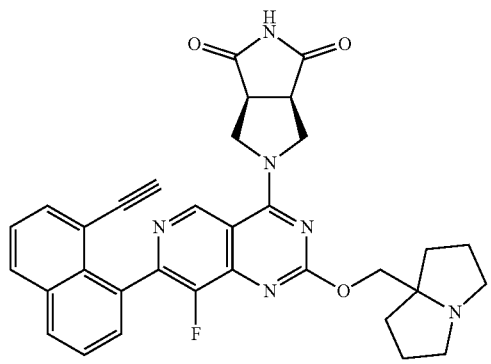 [SMILES: C#Cc1cccc2cccc(-c3ncc4c(N5C[C@@H]6C(=O)NC(=O)[C@@H]6C5)nc(OCC56CCCN5CCC6)nc4c3F)c12]

(3aR,6aS)-5-(7-(8-ethynylnaphthalen-1-yl)-8-fluoro-2-((hexahydro-1H-pyrrolizin-7a-yl)methoxy)pyrido[4,3-d]pyrimidin-4-yl)tetrahydropyrrolo[3,4-c]pyrrole-1,3(2H,3aH)-dione The title compound was synthesized according to the procedure described for example 437. $^1$H NMR (400 MHz, CD3OD) δ=9.24 (s, 1H), 8.58-8.53 (m, 1H), 8.16-8.11 (m, 1H), 8.10-8.05 (m, 1H), 7.78-7.74 (m, 1H), 7.73-7.66 (m, 1H), 7.66-7.60 (m, 1H), 7.58-7.50 (m, 1H), 4.81-4.74 (m, 1H), 4.70-4.60 (m, 1H), 4.42-4.31 (m, 1H), 4.27 (br dd, J=9.2, 12.4 Hz, 1H), 3.81-3.69 (m, 2H), 3.55-3.46 (m, 2H), 3.16-3.05 (m, 3H), 2.34-1.91 (m, 10H); LCMS (ESI, M+1): m/z=577.2.

Example 459

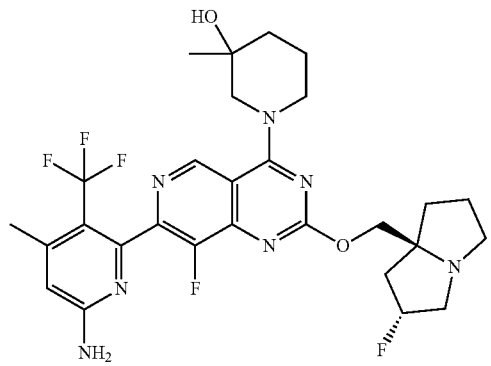 [SMILES: Cc1cc(N)nc(-c2ncc3c(N4CCCC(C)(O)C4)nc(OC[C@@]45CCCN4C[C@H](F)C5)nc3c2F)c1C(F)(F)F]

1-(7-(6-amino-4-methyl-3-(trifluoromethyl)pyridin-2-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol The title compound was synthesized according to the procedure described for example 435 using intermediate 48 instead of intermediate 46 in step A. $^1$H NMR (400 MHz, DMSO-d$_6$) δ=9.13 (s, 1H), 6.78 (s, 2H), 6.50 (s, 1H), 5.40-5.16 (m, 1H), 4.78-4.64 (m, 1H), 4.37-4.25 (m, 1H), 4.15-4.07 (m, 1H), 4.05-3.96 (m, 2H), 3.56 (br d, J=13.2 Hz, 1H), 3.29-3.27 (m, 1H), 3.14-2.99 (m, 3H), 2.87-2.78 (m, 1H), 2.39-2.33 (m, 3H), 2.17-2.09 (m, 11H), 2.06-1.93 (m, 3H), 1.90-1.59 (m, 6H), 1.15 (s, 3H); LCMS (ESI, M+1): m/z=594.2.

Example 460

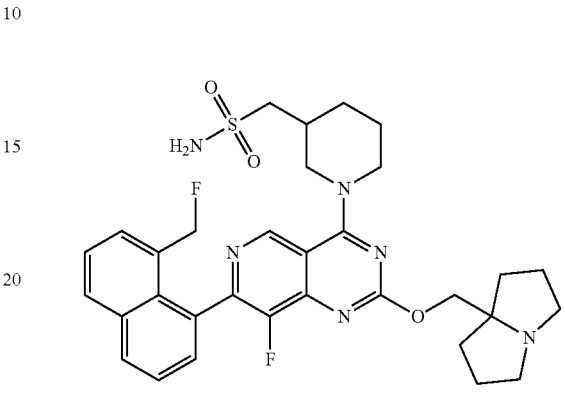

1-(1-(8-fluoro-7-(8-(fluoromethyl)naphthalen-1-yl)-2-((hexahydro-1H-pyrrolizin-7a-yl)methoxy)pyrido[4,3-d]pyrimidin-4-yl)piperidin-3-yl)methanesulfonamide

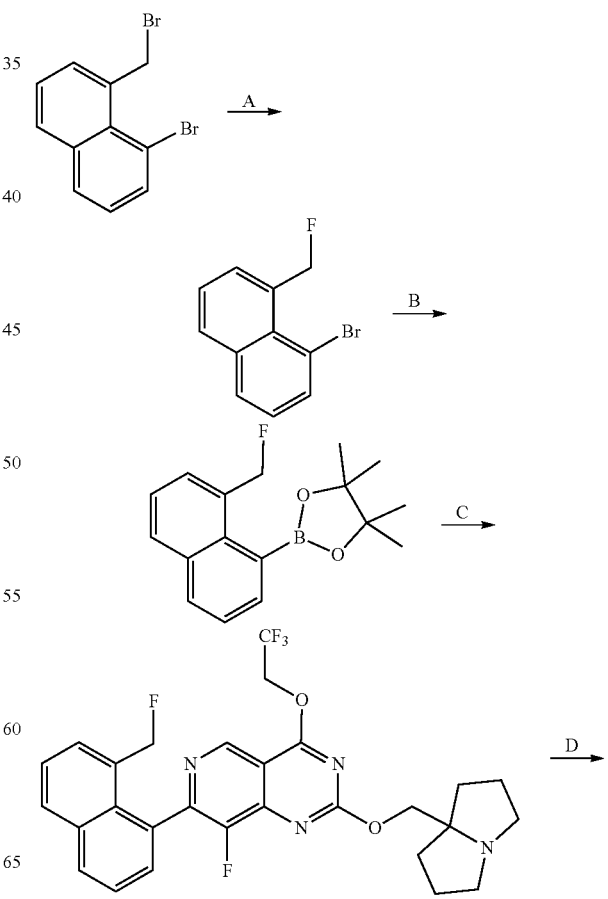

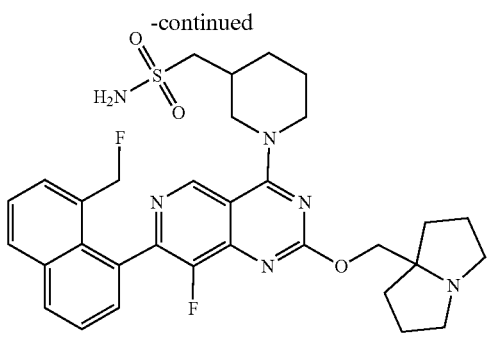

Step A. 1-bromo-8-(fluoromethyl)naphthalene: To a solution of 1-bromo-8-(bromomethyl)naphthalene (2.0 g, 1.0 equiv.) in DMSO (20 mL) was added tetrabutylammonium fluoride trihydrate (10.5 g, 5.0 equiv.). The reaction was stirred at 120° C. for 2 hours. The mixture was diluted with ethyl acetate (30 mL) and water (50 mL) then separated. The aqueous phase was extracted with ethyl acetate (30 mL). The organic layer was washed with brine (3×20 mL) and dried over $Na_2SO_4$, concentrated and purified by column chromatography [silica gel, petroleum ether] to afford the title compound (1.30 g, 78% yield) as a yellow solid; $^1H$ NMR (400 MHz, dimethylsulfoxide-d6) 5-8.10-8.02 (m, 2H), 7.96 (dd, J=1.2, 7.2 Hz, 1H), 7.79 (br d, J=7.2 Hz, 1H), 7.64-7.58 (m, 1H), 7.43 (t, J=7.6 Hz, 1H), 6.32-6.19 (d, J=47.6 Hz, 2H); $^{19}F$ NMR (376 MHz, dimethylsulfoxide-d6) δ–195.731.

Step B. 2-(8-(fluoromethyl)naphthalen-1-yl)-4,4,5,5-tetramethyl-1,3,2-dioxaborolane: To a solution of 1-bromo-8-(fluoromethyl)naphthalene (1.20 g, 1.0 equiv.), 4,4,4',4',5,5,5',5'-octamethyl-2,2'-bi(1,3,2-dioxaborolane) (1.91 g, 1.50 equiv.) and KOAc (1.48 g, 3.0 equiv.) in dioxane (20 mL) was added $Pd(dppf)Cl_2$ (367 mg, 0.1 equiv.) under $N_2$ atm. The reaction was stirred at 90° C. for 1.5 hours. The mixture was diluted with water (10 mL) and extracted with ethyl acetate (2×15 mL). The combined organic layers were washed with brine (20 mL), dried over anhydrous sodium sulfate, concentrated and purified by prep-TLC [Silica gel, petroleum ether/ethyl acetate 100:1] to afford the title compound (1.08 g, 75% yield) as a yellow solid; $^1H$ NMR (400 MHz, chloroform-d) 6-7.93 (dd, J=1.2, 8.0 Hz, 1H), 7.88-7.82 (m, 2H), 7.55-7.43 (m, 3H), 6.15-6.02 (d, J=47.2 Hz, 2H), 1.46 (s, 12H); $^{19}F$ NMR (376 MHz, chloroform-d) δ=–204.598.

Step C. 8-fluoro-7-(8-(fluoromethyl)naphthalen-1-yl)-2-((hexahydro-1H-pyrrolizin-7a-yl)methoxy)-4-(2,2,2-trifluoroethoxy)pyrido[4,3-d]pyrimidine: To a solution of 7-chloro-8-fluoro-2-((tetrahydro-1H-pyrrolizin-7a(5H)-yl)methoxy)-4-(2,2,2-trifluoroethoxy)pyrido[4,3-d]pyrimidine (1.20 g, 1.0 equiv.), 2-(8-(fluoromethyl)naphthalen-1-yl)-4,4,5,5-tetramethyl-1,3,2-dioxaborolane (979 mg, 1.20 equiv.) and $Cs_2CO_3$ (1.5 M, 3.0 equiv.) in methoxycyclopentane (15 mL) was added CataCXium A Pd G3 (208 mg, 0.1 equiv.) under $N_2$. The reaction was stirred at 90° C. for 2 hours under $N_2$. The mixture was diluted with water (10 mL) and extracted with ethyl acetate (2×15 mL). The combined organic layers were dried over anhydrous sodium sulfate, concentrated and purified by reversed phase flash chromatography [C18, water (0.1% formic acid)/ACN] to afford the title compound (0.3 g, 18% yield) as a yellow solid; $^1H$ NMR (400 MHz, chloroform-d) δ 9.26 (s, 1H), 8.05 (dd, J=1.2, 8.0 Hz, 1H), 7.98 (d, J=8.0 Hz, 1H), 7.65-7.59 (m, 2H), 7.59-7.50 (m, 2H), 5.15-5.06 (m, 3H), 5.02 (s, 1H), 4.45 (br s, 2H), 3.40-3.16 (m, 2H), 2.82-2.67 (m, 2H), 2.18-2.08 (m, 2H), 2.02-1.91 (m, 4H), 1.80-1.74 (m, 2H); $^{19}F$ NMR (376 MHz, chloroform-d) δ=–73.277, –136.576; LCMS (ESI, M+1): m/z=545.3.

Step D. 1-(1-(8-fluoro-7-(8-(fluoromethyl)naphthalen-1-yl)-2-((hexahydro-1H-pyrrolizin-7a-yl)methoxy)pyrido[4,3-d]pyrimidin-4-yl)piperidin-3-yl)methanesulfonamide: To a solution of 8-fluoro-7-(8-(fluoromethyl)naphthalen-1-yl)-2-((hexahydro-1H-pyrrolizin-7a-yl)methoxy)-4-(2,2,2-trifluoroethoxy)pyrido[4,3-d]pyrimidine (50.0 mg, 1.0 equiv.), piperidin-3-ylmethanesulfonamide (24.6 mg, 1.5 equiv.) and DIEA (35.6 mg, 3.0 equiv.) in DMF (0.5 mL) was added 4 Å molecular sieves (8 mg). The reaction was stirred at 40° C. for 12 hours. The mixture was filtered and purified by prep-HPLC [column: Waters Xbridge 150×25 mm×5 µm; mobile phase: water (10 mM $NH_4HCO_3$)-ACN, B %: 31%-61%, 8 min]. The desired fraction was collected and concentrated lyophilized to afford the title compound (30.7 mg, 53% yield) as a yellow solid; $^1H$ NMR (400 MHz, methanol-d4) δ=9.10 (s, 1H), 8.12 (dd, J=0.8, 8.0 Hz, 1H), 8.06 (d, J=8.0 Hz, 1H), 7.67-7.62 (m, 2H), 7.61-7.52 (m, 2H), 5.16-5.01 (m, 2H), 4.98 (br d, J=13.6 Hz, 1H), 4.58 (br d, J=12.4 Hz, 1H), 4.44-4.30 (m, 2H), 3.64-3.54 (m, 1H), 3.41-3.33 (m, 1H), 3.23-3.09 (m, 4H), 2.83-2.73 (m, 2H), 2.58-2.46 (m, 1H), 2.19-2.07 (m, 3H), 2.00-1.88 (m, 5H), 1.86-1.73 (m, 3H), 1.68-1.56 (m, 1H); $^{19}F$ NMR (376 MHz, methanol-$d_4$) δ=–138.958, –204.127; LCMS (ESI, M+1): m/z=623.3.

Example 461

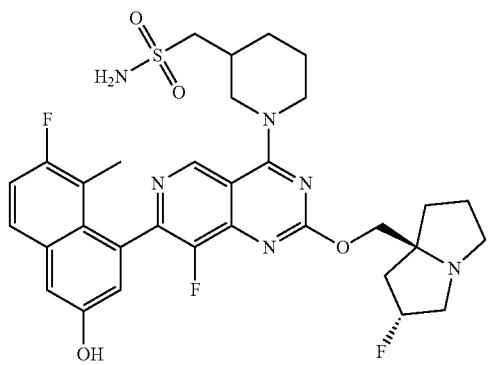 [SMILES: Cc1c(F)ccc2cc(O)cc(-c3ncc4c(N5CCCC(CS(N)(=O)=O)C5)nc(OC[C@@]56CCCN5C[C@H](F)C6)nc4c3F)c12]

1-(1-(8-fluoro-7-(7-fluoro-3-hydroxy-8-methylnaphthalen-1-yl)-2-(((2R,7aS)-2-fluorohexahydro-1H-pyrrolizin-7a-yl)methoxy)pyrido[4,3-d]pyrimidin-4-yl)piperidin-3-yl)methanesulfonamide

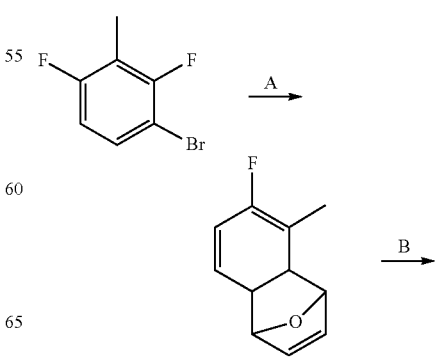

637
-continued
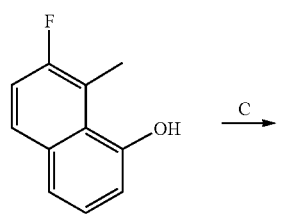
C →
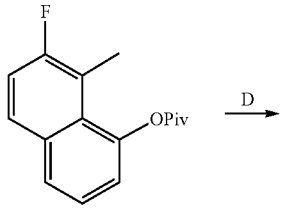
D →
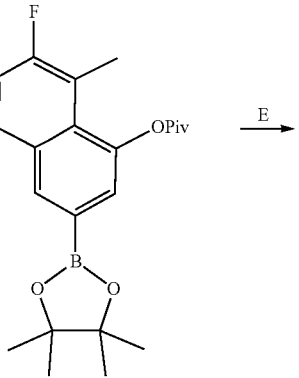
E →
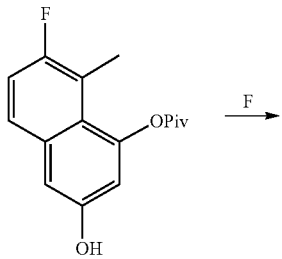
F →
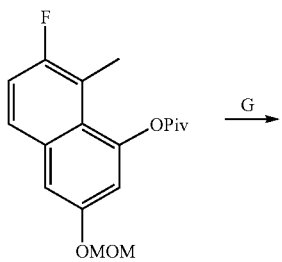
G →
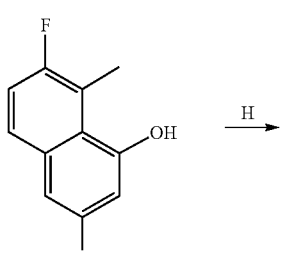
H →
638
-continued
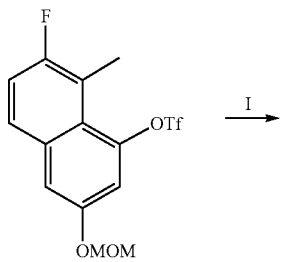
I →
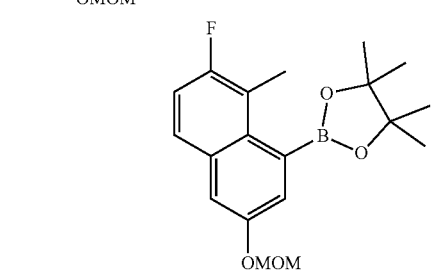
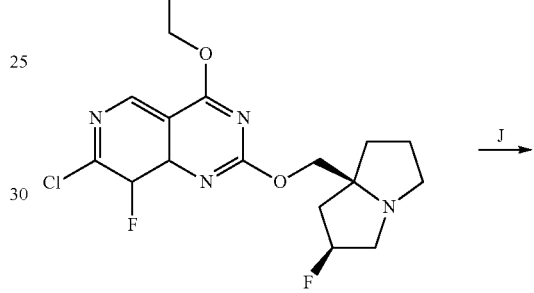
J →
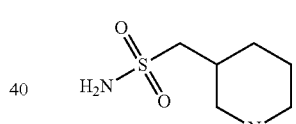
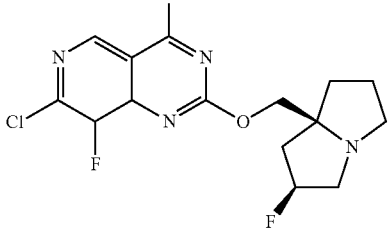
K →
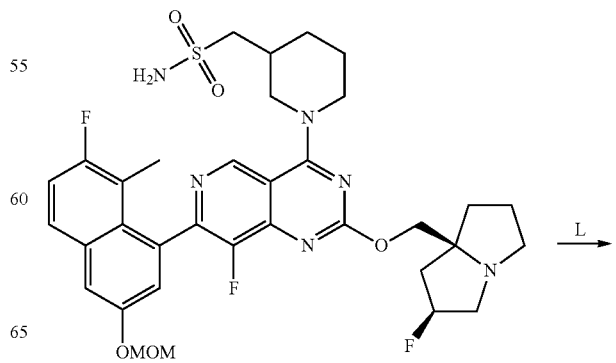
L →

-continued

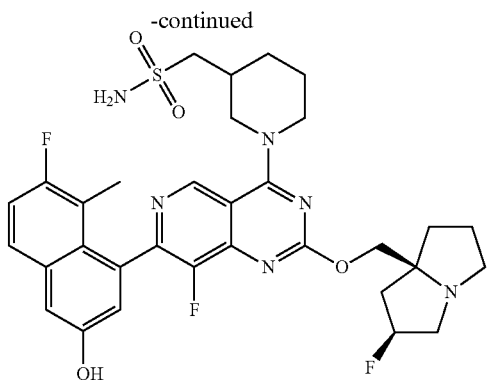

Step A. 6-fluoro-5-methyl-1,4-dihydro-1,4-epoxynaphthalene: To a solution of 1-bromo-2,4-difluoro-3-methylbenzene (80.0 g, 1.0 equiv.) and furan (52.6 g, 2.0 equiv.) in toluene (1000 mL) was added n-BuLi (2.5 M, 185 mL, 1.2equiv.) at −40° C. The mixture was stirred at 15° C. for 16 hours. The mixture was quenched with saturated aqueous NH$_4$Cl (800 mL) and extracted with ethyl acetate (800 mL). The organic phase was concentrated and purified by column chromatography [Silica gel, petroleum ether/ethyl acetate 1:0 to 10:1] to afford the title compound (30.0 g, crude) as a yellow oil.

Step B. 7-fluoro-8-methylnaphthalen-1-ol: To a solution of 6-fluoro-5-methyl-1,4-dihydro-1,4-epoxynaphthalene (30.0 g, 1.0 equiv.) in EtOH (150 mL) was added HCl (150 mL, 36%, 8.9 equiv.). The reaction mixture was stirred at 80° C. for 3 hours. The mixture was concentrated and quenched with saturated aqueous NaHCO$_3$(300 mL) and extracted with ethyl acetate (2×100 mL). The combined organic phase was washed with brine (150 mL), dried, concentrated and purified by column chromatography [Silica gel, petroleum ether/ethyl acetate 100:1 to 10:1] to afford the title compound (10.0 g, 15% yield over two steps) as a yellow oil; $^1$H NMR (400 MHz, CHLOROFORM-d) δ=7.59 (dd, J=5.6, 8.8 Hz, 1H), 7.37 (d, J=8.0 Hz, 1H), 7.24-7.16 (m, 2H), 6.76 (d, J=7.6 Hz, 1H), 5.67 (s, 1H), 2.84 (d, J=2.8 Hz, 3H); LCMS (ESI, M+1): m/z=177.2.

Step C. 7-fluoro-8-methylnaphthalen-1-yl pivalate: To a solution of 7-fluoro-8-methylnaphthalen-1-ol (10.0 g, 1.0 equiv.), DIEA (22.0 g, 3.0 equiv.) in DCM (100 mL) was added 2,2-dimethylpropanoyl chloride (9.58 g, 1.4 equiv.) at 0° C. The reaction mixture was stirred at 0° C. for 1 hour. The mixture was quenched with water (50 mL) and extracted with ethyl acetate (100 mL). The combined organic phase was washed with brine (100 mL), dried over anhydrous Na$_2$SO$_4$, concentrated and purified by column chromatography [Silica gel, petroleum ether/ethyl acetate 50:1 to 20:1] to afford the title compound (10.8 g, 73% yield) as a yellow oil; $^1$H NMR (400 MHz, chloroform-d) δ=7.74-7.65 (m, 2H), 7.39 (t, J=7.6 Hz, 1H), 7.27-7.21 (m, 1H), 7.03 (d, J=7.6 Hz, 1H), 2.64 (d, J=2.4 Hz, 3H), 1.46 (s, 9H).

Step D. 7-fluoro-8-methyl-3-(4,4,5,5-tetramethyl-1,3,2-dioxaborolan-2-yl)naphthalen-1-yl pivalate: To a mixture of 7-fluoro-8-methylnaphthalen-1-yl pivalate (7.00 g, 1.0 equiv.), 4,4,5,5-tetramethyl-2-(4,4,5,5-tetramethyl-1,3,2-dioxaborolan-2-yl)-1,3,2-dioxaborolane (6.83 g, 1.0 equiv.), 4-tert-butyl-2-(4-tert-butyl-2-pyridyl)pyridine (433 mg, 0.06 equiv.) in hexane (240 mL) was added (1,5-Cyclooctadiene)(methoxy)iridium(1) dimer (891 mg, 1.34 mmol, 0.05 equiv.) under N$_2$. The mixture was stirred at 60° C. for 3 hours. The mixture was concentrated and purified by column chromatography [Silica gel, petroleum ether/ethyl acetate 100:1 to 15:1] to afford the title compound (6.00 g, crude) as a white solid.

Step E. 7-fluoro-3-hydroxy-8-methylnaphthalen-1-yl pivalate: To a mixture of 7-fluoro-8-methyl-3-(4,4,5,5-tetramethyl-1,3,2-dioxaborolan-2-yl)naphthalen-1-yl pivalate (6.00 g, 1.0 equiv.), THF (45 mL) and water (21 mL) were added H$_2$O$_2$ (13.4 g, 30% purity, 7.6 equiv.) and AcOH (46.6 g, 50 equiv.) at 10° C. The mixture was stirred at 25° C. for 1 hour. The mixture was quenched with saturated aqueous Na$_2$SO$_3$ (400 mL) and extracted with ethyl acetate (2×100 mL). The combined organic phase was washed with brine (200 mL), dried over anhydrous sodium sulfate, concentrated and purified by column chromatography [Silica gel, petroleum ether/ethyl acetate 20:1 to 5:1] and reversed phase flash chromatography [C18, water (0.1% NH3·H2O)-ACN] to afford the title compound (1.70 g, 23% yield over two steps) as an off-white solid; $^1$H NMR (400 MHz, chloroform-d) δ=7.41 (dd, J=5.6, 8.8 Hz, 1H), 7.16 (t, J=9.2 Hz, 1H), 6.92 (d, J=2.4 Hz, 11H), 6.65 (d, J=2.4 Hz, 1H), 2.58 (d, J=2.0 Hz, 3H), 1.45 (s, 9H).

Step F. 7-fluoro-3-(methoxymethoxy)-8-methylnaphthalen-1-yl pivalate: To a solution of 7-fluoro-3-hydroxy-8-methylnaphthalen-1-yl pivalate (2.30 g, 1.0 equiv.), DIEA (3.23 g, 3.0 equiv.) in DCM (30 mL) was added chloro(methoxy)methane (889 mg, 1.3 equiv.) at 0° C. The mixture was stirred at 20° C. for 1 hour. The mixture was quenched with saturated aqueous NaHCO$_3$(30 mL) and extracted with ethyl acetate (2×30 mL). The combined organic layer was concentrated and purified by column chromatography [Silica gel, petroleum ether/ethyl acetate 20:1 to 5:1] to afford the title compound (2.60 g, 97% yield) as a white solid; $^1$H NMR (400 MHz, chloroform-d) δ=7.57 (dd, J=5.2, 9.0 Hz, 1H), 7.30 (d, J=2.4 Hz, 1H), 7.20 (t, J=9.2 Hz, 1H), 6.79 (d, J=2.4 Hz, 1H), 5.27 (s, 2H), 3.52 (s, 3H), 2.59 (d, J=2.4 Hz, 3H), 1.45 (s, 9H); LCMS (ESI, M+1): m/z=321.2.

Step G. 7-fluoro-3-(methoxymethoxy)-8-methylnaphthalen-1-ol: To a solution of 7-fluoro-3-(methoxymethoxy)-8-methylnaphthalen-1-yl pivalate (2.60 g, 1.0 equiv.) in MeOH (26 mL) was added KOH (1.37 g, 3.0 equiv.). The reaction mixture was stirred at 20° C. for 0.5 hour. The pH of the mixture was to adjusted to 5 with 0.1 N HCl and extracted with ethyl acetate (2×80 mL). The organic phase was concentrated to afford the title compound (1.60 g, 83% yield) as a brown solid; $^1$H NMR (400 MHz, chloroform-d) δ=7.46 (dd, J=5.6, 8.8 Hz, 1H), 7.16 (t, J=9.2 Hz, 1H), 6.96 (d, J=2.4 Hz, 1H), 6.55 (d, J=2.0 Hz, 1H), 5.25 (s, 2H), 3.52 (s, 3H), 2.78 (d, J=2.6 Hz, 3H).

Step H. 7-fluoro-3-(methoxymethoxy)-8-methylnaphthalen-1-yl trifluoromethanesulfonate: To a solution of 7-fluoro-3-(methoxymethoxy)-8-methylnaphthalen-1-ol (1.60 g, 1.0 equiv.), DIEA (2.63 g, 3.0 equiv.) in DCM (25 mL) was added Tf$_2$O (2.48 g, 1.3 equiv.) at −40° C. The mixture was stirred at −40° C. for 0.5 hour. The reaction mixture was diluted with DCM (50 mL) and water (15 mL). The organic phase was washed with brine (20 mL), dried over anhydrous sodium sulfate, concentrated and purified by column chromatography [Silica gel, petroleum ether/ethyl acetate 20:1 to 6:1] to afford the title compound (2.30 g, 89% yield) as a yellow oil; $^1$H NMR (400 MHz, chloroform-d) δ=7.61 (dd, J=5.2, 9.2 Hz, 1H), 7.43 (d, J=2.4 Hz, 1H), 7.32 (d, J=2.0 Hz, 1H), 7.31-7.28 (m, 1H), 7.26 (s, 1H), 5.29 (s, 2H), 3.53 (s, 3H), 2.73 (d, J=2.4 Hz, 3H).

Step I. 2-(7-fluoro-3-(methoxymethoxy)-8-methylnaphthalen-1-yl)-4,4,5,5-tetramethyl-1,3,2-dioxaborolane: To a mixture of 7-fluoro-3-(methoxymethoxy)-8-methylnaphthalen-1-yl trifluoromethanesulfonate (1.00 g, 1.0 equiv.), 4,4, 5,5-tetramethyl-2-(4,4,5,5-tetramethyl-1,3,2-dioxaborolan-2-yl)-1,3,2-dioxaborolane (1.38 g, 2.0 equiv.), AcOK (933 mg, 3.5 equiv.) in dioxane (10 mL) was added Pd(dppf)Cl2 (199 mg, 0.1 equiv.) under $N_2$. The reaction was stirred at 100° C. for 1.5 hours. The mixture was diluted with water (30 mL) and extracted with ethyl acetate (30 mL). The organic phase was washed with brine (20 mL), dried over anhydrous $Na_2SO_4$, concentrated and purified by column chromatography [Silica gel, petroleum ether/ethyl acetate 50:1 to 15:1] to afford the title compound (500 mg, 53% yield) as a colorless oil; $^1$H NMR (400 MHz, chloroform-d) δ=7.57 (dd, J=5.6, 8.8 Hz, 1H), 7.45-7.39 (m, 2H), 7.20 (t, J=9.2 Hz, 1H), 5.32-5.23 (m, 2H), 3.51 (s, 3H), 2.63 (d, J=2.4 Hz, 3H), 1.44 (s, 12H).

Step J. 1-(1-(7-chloro-8-fluoro-2-(((2R,7aS)-2-fluoro-hexahydro-1H-pyrrolizin-7a-yl)methoxy)pyrido[4,3-d]pyrimidin-4-yl)piperidin-3-yl)methanesulfonamide: A mixture of 7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (60.0 mg, 1.0 equiv.), 3-piperidylmethanesulfonamide (26.8 mg, 1.1 equiv.), and DIEA (53.0 mg, 3.0 equiv.) in DMF (1 mL) was stirred at 20° C. for 1 hour. The mixture was filtered and purified by reversed phase flash chromatography [C18, water (0.1% formic acid)/ACN] to afford the title compound (60.0 mg, 82% yield) as a white solid; LCMS (ESI, M+1): m/z=517.3.

Step K. 1-(1-(8-fluoro-7-(7-fluoro-3-(methoxymethoxy)-8-methylnaphthalen-1-yl)-2-(((2R,7aS)-2-fluorohexahydro-1H-pyrrolizin-7a-yl)methoxy)pyrido[4,3-d]pyrimidin-4-yl)piperidin-3-yl)methanesulfonamide: To a mixture of 1-(1-(7-chloro-8-fluoro-2-(((2R,7aS)-2-fluorohexahydro-1H-pyrrolizin-7a-yl)methoxy)pyrido[4,3-d]pyrimidin-4-yl)piperidin-3-yl)methanesulfonamide (60.0 mg, 1.0 equiv.), 2-(7-fluoro-3-(methoxymethoxy)-8-methylnaphthalen-1-yl)-4,4,5,5-tetramethyl-1,3,2-dioxaborolane (48.2 mg, 1.2 equiv.), $K_3PO_4$ (1.5 M in water, 232 μL, 3.0 equiv.) in methoxycyclopentane (1 mL) was added cataCXium A Pd G3 (8.45 mg, 0.1 equiv.) under $N_2$ atmosphere. The reaction mixture was stirred at 90° C. for 2 hours. The reaction mixture was diluted with water (10 mL) and extracted with ethyl acetate (2×15 mL). The combined organic phase was washed with brine (5 mL), dried over anhydrous $Na_2SO_4$, concentrated and purified by reversed phase flash chromatography [C18, water (0.1% formic acid)/ACN] to afford the title compound (42.0 mg, 51% yield) as a yellow solid; LCMS (ESI, M+1): m/z=701.2.

Step L. 1-(1-(8-fluoro-7-(7-fluoro-3-hydroxy-8-methyl-naphthalen-1-yl)-2-(((2R,7aS)-2-fluorohexahydro-1H-pyrrolizin-7a-yl)methoxy)pyrido[4,3-d]pyrimidin-4-yl)piperidin-3-yl)methanesulfonamide: To a solution of (1-(8-fluoro-7-(7-fluoro-3-(methoxymethoxy)-8-methylnaphthalen-1-yl)-2-(((2R,7aS)-2-fluorohexahydro-1H-pyrrolizin-7a-yl)methoxy)pyrido[4,3-d]pyrimidin-4-yl)piperidin-3-yl)methanesulfonamide (39.0 mg, 1.0 equiv.) in ACN (0.5 mL) was added HCl-dioxane (4 M, 1 mL, 72 equiv.) at 0° C. The mixture was stirred at 0° C. for 0.5 hour. The reaction mixture was concentrated at room temperature. The residue was dissolved in ethyl acetate (20 mL) and water (3 mL). The pH of the mixture was adjusted to 8 with solid $NaHCO_3$ while cooling the mixture with ice bath. The mixture was extracted with ethyl acetate (2×15 mL), dried over anhydrous $Na_2SO_4$, concentrated and purified by prep-HPLC [column: Phenomenex Synergi C18 150×25 mm×10 μm; mobile phase: water (0.1% formic acid)-ACN; B %: 10%-40%, 10 minutes] to afford the title compound (22.3 mg, 57% yield, 0.64 formic acid salt) as a white solid; $^1$H NMR (400 MHz, methanol-$d_4$) δ=9.13 (d, J=1.2 Hz, 1H), 7.68 (dd, J=5.6, 8.8 Hz, 1H), 7.31 (d, J=2.4 Hz, 1H), 7.25 (t, J=9.2 Hz, 1H), 7.11 (dd, J=2.8, 8.8 Hz, 1H), 5.57-5.34 (m, 1H), 5.20-5.03 (m, 1H), 4.60-4.44 (m, 3H), 3.76-3.46 (m, 4H), 3.29-3.11 (m, 3H), 2.65-2.30 (m, 4H), 2.23-2.00 (m, 4H), 1.97-1.88 (m, 1H), 1.85-1.71 (m, 4H), 1.70-1.56 (m, 1H); LCMS (ESI, M+1): m/z=657.3.

Example 462

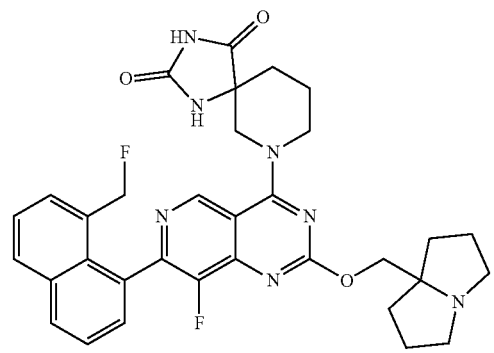 [SMILES: O=C1NC(=O)C2(CCCN(c3nc(OCC45CCCN4CCC5)nc4c(F)c(-c5cccc6cccc(CF)c56)ncc34)C2)N1]

7-(8-fluoro-7-(8-(fluoromethyl)naphthalen-1-yl)-2-((hexahydro-1H-pyrrolizin-7a-yl)methoxy)pyrido[4,3-d]pyrimidin-4-yl)-1,3,7-triazaspiro[4.5]decane-2,4-dione The title compound was synthesized according to the procedure described for example 460. $^1$H NMR (400 MHz, METHANOL-$d_4$) δ=9.17 (s, 1H), 8.19-8.05 (m, 2H), 7.74-7.50 (m, 4H), 5.12 (d, J=47.6 Hz, 2H), 4.68-4.64 (m, 2H), 4.59-4.45 (m, 2H), 3.95-3.80 (m, 2H), 3.76-3.61 (m, 2H), 3.28-3.17 (m, 2H), 2.35-1.96 (m, 12H); LCMS (ESI, M+1): m/z=614.4.

Example 463

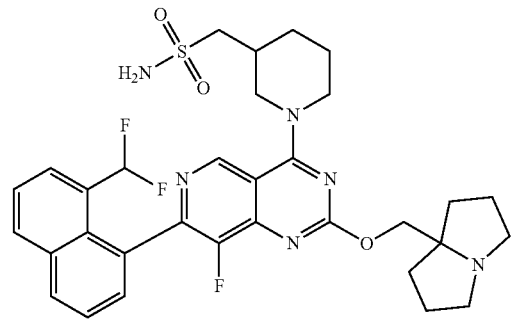 [SMILES: NS(=O)(=O)CC1CCCN(c2nc(OCC34CCCN3CCC4)nc3c(F)c(-c4cccc5cccc(C(F)F)c45)ncc23)C1]

643

1-(1-(7-(8-(difluoromethyl)naphthalen-1-yl)-8-fluoro-2-((hexahydro-1H-pyrrolizin-7a-yl)methoxy)pyrido[4,3-d]pyrimidin-4-yl)piperidin-3-yl)methanesulfonamide

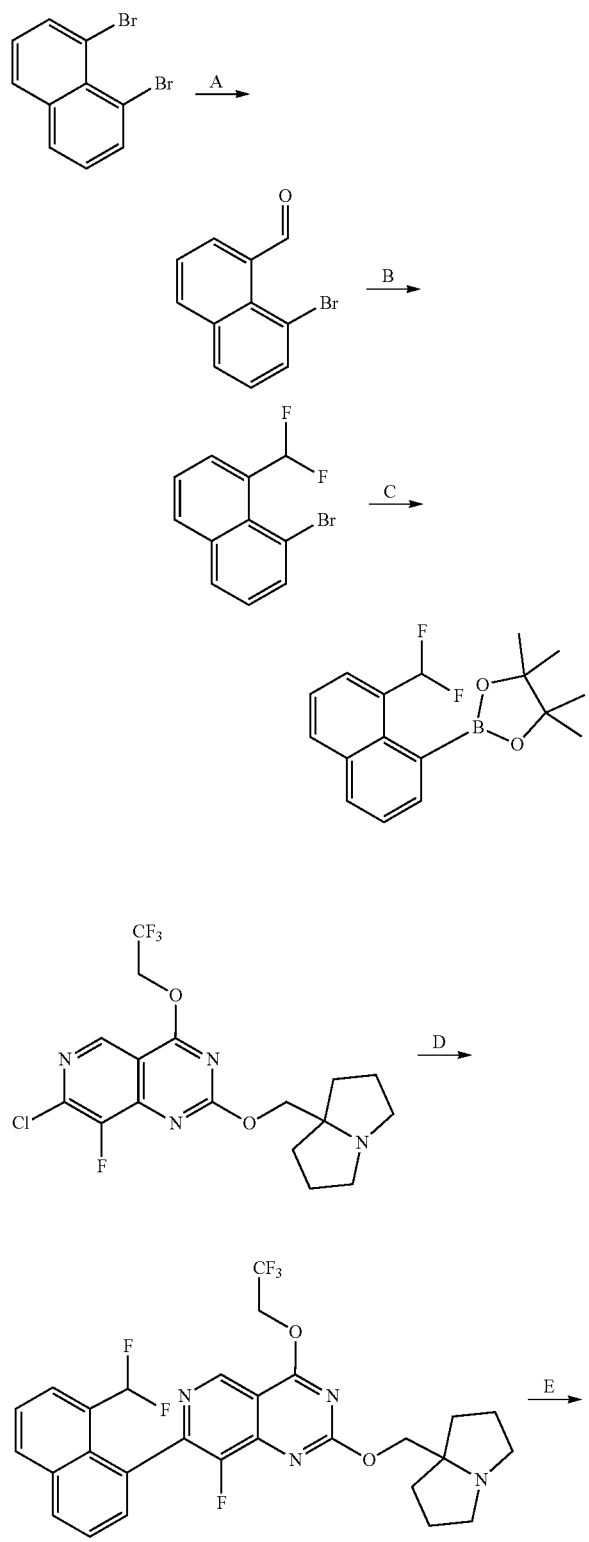

644

-continued

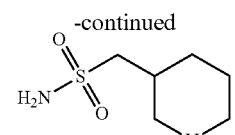

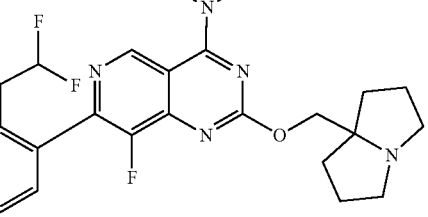

Step A. 8-bromo-1-naphthaldehyde: To a solution of 1,8-dibromonaphthalene (10.0 g, 1.0 equiv.) in THF (200 mL) was added n-BuLi (2.5 M, 18.2 mL, 1.3 equiv.) at −60° C. dropwise under $N_2$atm. After stirring for 5 minutes at −60° C., DMF (25.6 g, 26.9 mL, 10 equiv.) was added dropwise to the mixture. The reaction was warmed up to 25° C. and stirred for another 25 minutes. The mixture was quenched with water (150 mL) and concentrated to remove THF. The residue was extracted with ethyl acetate (2×150 mL). The organic layer was dried over $Na_2SO_4$, concentrated in vacuum. The residue was purified by silica gel chromatography (petroleum ether/ethyl acetate 100:1 to 50:1) to afford the title compound (5.0 g, 61% yield) as a yellow solid; $^1$H NMR (400 MHz, chloroform-d) δ=11.44 (s, 1H), 8.03-7.98 (m, 1H), 7.93-7.87 (m, 3H), 7.57 (t, J=8.0 Hz, 1H), 7.39 (t, J=8.0 Hz, 1H).

Step B. 1-bromo-8-(difluoromethyl)naphthalene: To a solution of 8-bromo-1-naphthaldehyde (2.50 g, 1.0 equiv.) in DCM (30 mL) was added a solution of DAST (6.86 g, 4.0 equiv.) in DCM (10 mL) slowly at −40° C. The reaction was stirred at 25° C. for 12 hours. The mixture was neutralized with saturated aqueous ice-cold $NaHCO_3$ solution (300 mL) and layers were separated. The aqueous phase was extracted with ethyl acetate (3×100 mL). The combined organic layers were dried over anhydrous sodium sulfate, concentrated and purified by silica gel chromatography [petroleum ether/ethyl acetate 1:0 to 100:1] to afford the title compound (1.40 g, 51% yield) as a white solid; $^1$H NMR (400 MHz, chloroform-d) δ=8.56-8.56 (m, 1H), 8.12 (d, J=7.2 Hz, 1H), 8.00-7.92 (m, 2H), 7.91-7.86 (m, 1H), 7.61-7.56 (m, 1H), 7.33 (t, J=7.6 Hz, 1H).

Step C. 2-(8-(difluoromethyl)naphthalen-1-yl)-4,4,5,5-tetramethyl-1,3,2-dioxaborolane: A mixture of 1-bromo-8-(difluoromethyl)naphthalene (1.50 g, 1.0 equiv.), 4,4,5,5-tetramethyl-2-(4,4,5,5-tetramethyl-1,3,2-dioxaborolan-2-yl)-1,3,2-dioxaborolane (2.22 g, 1.5 equiv.), KOAc (1.72 g, 3.0 equiv.) and Pd(dppf)Cl$_2$ (427 mg, 0.1 equiv.) in dioxane (30 mL) was degassed and stirred at 90° C. for 2 hours under $N_2$ atmosphere. The mixture was diluted with water (4.0 mL) and extracted with ethyl acetate (3×5.0 mL). The combined organic layers were dried over anhydrous sodium sulfate, concentrated and purified by silica gel chromatography [petroleum ether/ethyl acetate 1:0 to 50:1] to afford the title compound (750 mg, 42% yield) as a white solid; $^1$H NMR (400 MHz, chloroform-d) δ=8.08-7.77 (m, 5H), 7.54-7.46 (m, 2H), 1.46 (s, 12H).

Step D. 7-(8-(difluoromethyl)naphthalen-1-yl)-8-fluoro-2-((hexahydro-1H-pyrrolizin-7a-yl)methoxy)-4-(2,2,2-trifluoroethoxy)pyrido[4,3-d]pyrimidine: A mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (200 mg, 1.0 equiv.), 2-(8-(difluoromethyl)naphthalen-1- yl)-4,4,5,5-tetramethyl-1,3,2-dioxaborolane (159 mg, 1.1 equiv.), CataCXium A Pd G3 (34.6 mg, 0.1 equiv.) and K₃PO₄ (1.5 M in water, 951 µL, 3.0 equiv.) in methoxycyclopentane (4.0 mL) was degassed and stirred at 90° C. for 3 hours under N₂ atmosphere. The mixture was diluted with water (3.0 mL) and extracted with ethyl acetate (3×3.0 mL). The combined organic layers were dried over anhydrous sodium sulfate, concentrated and purified by reversed phase flash chromatography [C18, water (0.1% formic acid)/ACN] to afford the title compound (70 mg, 26% yield) as a yellow solid; ¹H NMR (400 MHz, chloroform-d) δ=9.26 (s, 1H), 8.13-8.05 (m, 2H), 7.95 (d, J=7.2 Hz, 1H), 7.66-7.54 (m, 2H), 7.58-7.54 (m, 1H), 6.58-6.25 (m, 1H), 5.13-5.05 (m, 2H), 4.36 (s, 2H), 3.19-3.09 (m, 2H), 2.68 (td, J=6.8, 10.0 Hz, 2H), 2.11-2.06 (m, 1H), 2.05-2.00 (m, 1H), 1.90 (q, J=6.4 Hz, 4H), 1.74-1.69 (m, 2H).

Step E. 1-(1-(7-(8-(difluoromethyl)naphthalen-1-yl)-8-fluoro-2-((hexahydro-1H-pyrrolizin-7a-yl)methoxy)pyrido[4,3-d]pyrimidin-4-yl)piperidin-3-yl)methanesulfonamide: To a solution of 7-(8-(difluoromethyl)naphthalen-1-yl)-8-fluoro-2-((hexahydro-1H-pyrrolizin-7a-yl)methoxy)-4-(2,2,2-trifluoroethoxy)pyrido[4,3-d]pyrimidine (30 mg, 1.0 equiv.) and piperidin-3-ylmethanesulfonamide (14.3 mg, 1.50 equiv.) in DMF (0.5 mL) were added DIEA (20.7 mg, 3.0 equiv.) and 4 Å molecular sieves (10 mg). The mixture was stirred at 40° C. for 12 hours. The mixture was filtered and purified by prep-HPLC [column: Waters Xbridge 150× 25 mm×5 µm; mobile phase: water (10 mM NH₄HCO₃)-ACN, B %: 40%-70%, 10 min] and re-purified by prep-HPLC [column: Unisil 3-100 C18 Ultra 150×50 mm×3 µm; mobile phase: water (0.225% formic acid)-ACN, B %: 15%-45%, 10 min] and lyophilized to afford the title compound (11.7 mg, 34% yield) as a white solid; ¹H NMR (400 MHz, methanol-d₄) δ 9.17 (s, 1H), 8.24-8.15 (m, 2H), 7.94 (d, J=7.2 Hz, 1H), 7.68 (q, J=8.0 Hz, 2H), 7.63-7.57 (m, 1H), 6.59-6.27 (m, 1H), 5.14 (br d, J=12.0 Hz, 1H), 4.71-4.65 (m, 1H), 4.64-4.54 (m, 2H), 3.76-3.67 (m, 1H), 3.61-3.50 (m, 2H), 3.25-3.10 (m, 4H), 2.61-2.47 (m, 1H), 2.33 (td, J=6.4, 12.8 Hz, 2H), 2.21-2.11 (m, 4H), 2.11-1.88 (m, 5H), 1.85-1.71 (m, 1H), 1.68-1.56 (m, 1H); LCMS (ESI, M+1): m/z=641.4.

Example 464

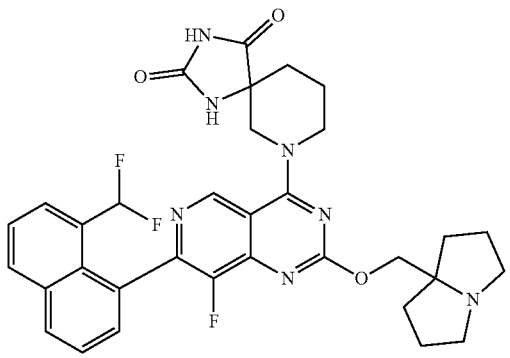 [SMILES: O=C1NC(=O)C2(CCCN(c3nc(OCC45CCCN4CCC5)nc4c(F)c(-c5cccc6cccc(C(F)F)c56)ncc34)C2)N1]

7-(7-(8-(difluoromethyl)naphthalen-1-yl)-8-fluoro-2-((hexahydro-1H-pyrrolizin-7a-yl)methoxy)pyrido[4,3-d]pyrimidin-4-yl)-1,3,7-triazaspiro[4.5]decane-2,4-dione The title compound was synthesized according to the procedure described for example 463. ¹H NMR (400 MHz, methanol-d₄) δ=9.13 (s, 1H), 8.23-8.14 (m, 2H), 7.95 (d, J=7.2 Hz, 1H), 7.73-7.65 (m, 2H), 7.63-7.58 (m, 1H), 6.60-6.26 (m, 1H), 4.69-4.65 (m, 1H), 4.54-4.45 (m, 1H), 4.38-4.26 (m, 2H), 3.84-3.70 (m, 2H), 3.21-3.11 (m, 2H), 2.81-2.72 (m, 2H), 2.30-2.20 (m, 1H), 2.14-2.02 (m, 4H), 1.99-1.87 (m, 5H), 1.84-1.74 (m, 2H); LCMS (ESI, M+1): m/z=632.4.

Example 465

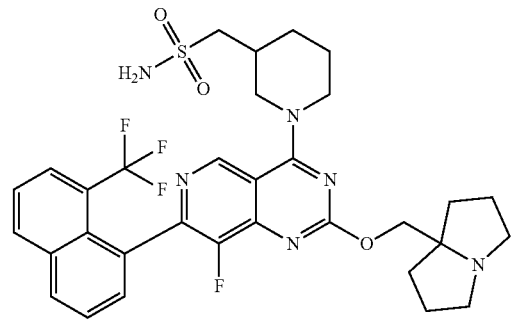 [SMILES: NS(=O)(=O)CC1CCCN(c2nc(OCC34CCCN3CCC4)nc3c(F)c(-c4cccc5cccc(C(F)(F)F)c45)ncc23)C1]

1-(1-(8-fluoro-2-((hexahydro-1H-pyrrolizin-7a-yl)methoxy)-7-(8-(trifluoromethyl)naphthalen-1-yl)pyrido[4,3-d]pyrimidin-4-yl)piperidin-3-yl)methanesulfonamide

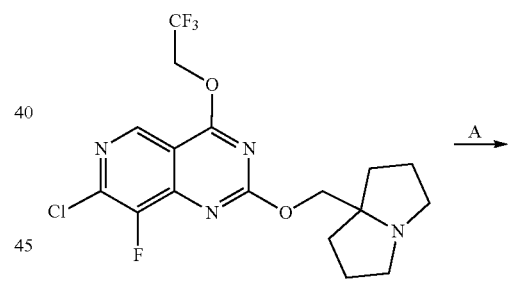

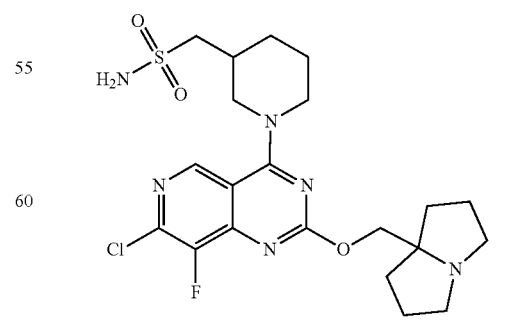

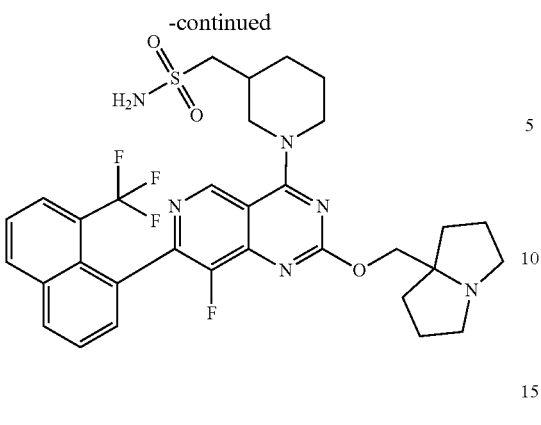

Step A. 1-(1-(7-chloro-8-fluoro-2-((hexahydro-1H-pyrrolizin-7a-yl)methoxy)pyrido[4,3-d]pyrimidin-4-yl)piperidin-3-yl)methanesulfonamide: To a mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (200 mg, 1.0 equiv.), piperidin-3-ylmethanesulfonamide (102 mg, 1.2 equiv.), 4 Å molecular sieves (10.0 mg) in DMF (2 mL) was added DIEA (184 mg, 248 μL, 3.0 equiv.). The reaction was stirred at 40° C. for 4 hours. After reaction completion, the mixture was filtered to give a solution. The crude product was purified by reversed-phase flash chromatography (water (0.1% formic acid)-ACN) to afford the title compound (135 mg, 57% yield) as a yellow solid; LCMS [ESI, M+1]: m/z=499.2.

Step B. 1-(1-(8-fluoro-2-((hexahydro-1H-pyrrolizin-7a-yl)methoxy)-7-(8-(trifluoromethyl)naphthalen-1-yl)pyrido[4,3-d]pyrimidin-4-yl)piperidin-3-yl)methanesulfonamide: To a mixture of (1-(1-(7-chloro-8-fluoro-2-((hexahydro-1H-pyrrolizin-7a-yl)methoxy)pyrido[4,3-d]pyrimidin-4-yl)piperidin-3-yl)methanesulfonamide (135 mg, 1.0 equiv.), 4,4,5,5-tetramethyl-2-(8-(trifluoromethyl)naphthalen-1-yl)-1,3,2-dioxaborolane (113 mg, 1.3 equiv.), $K_3PO_4$ (1.5 M, 541 μL, 3.0 equiv.) in methoxycyclopentane (1 mL) was added CataCXium A Pd G3 (19.7 mg, 0.1 equiv.) under $N_2$. The reaction was stirred at 90° C. for 2 hours. After completion, the reaction mixture was quenched by addition of water (1 mL) and extracted with ethyl acetate (6 mL). The organic layer was dried over anhydrous $Na_2SO_4$, filtered and concentrated under reduced pressure to give a residue. The crude product was purified by reversed-phase flash chromatography (water (0.1% formic acid)-ACN) and prep-HPLC (column: Waters Xbridge 150×25 mm×5 μm; mobile phase: water (10 mM $NH_4HCO_3$)-ACN, B %: 36%-66%, 10 min) and lyophilized to afford the title compound (3.53 mg, 2% yield) as a white solid; $^1$H NMR (400 MHz, methanol-$d_4$): δ=9.06 (d, J=2.4 Hz, 1H), 8.30 (d, J=8.0 Hz, 1H), 8.20 (d, J=8.4 Hz, 1H), 8.05 (d, J=7.2 Hz, 1H), 7.78-7.72 (m, 11H), 7.71-7.63 (m, 2H), 4.98 (br s, 1H), 4.60-4.48 (m, 1H), 4.40-4.27 (m, 2H), 3.69-3.54 (m, 11H), 3.40-3.34 (m, 1H), 3.26-3.07 (m, 4H), 2.79-2.67 (m, 2H), 2.53 (br dd, J=4.0, 7.2 Hz, 1H), 2.11 (qd, J=5.6, 12.0 Hz, 3H), 1.98-1.88 (m, 5H), 1.98-1.71 (m, 3H), 1.68-1.57 (m, 1H); LCMS [ESI, M+1]: m/z=659.5.

Example 466

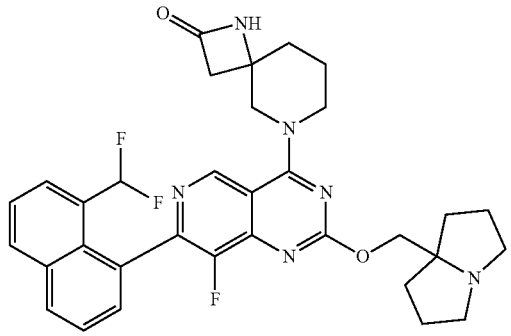 [SMILES: O=C1CC2(CCCN(c3nc(OCC45CCCN4CCC5)nc4c(F)c(-c5cccc6cccc(C(F)F)c56)ncc34)C2)N1]

6-(7-(8-(difluoromethyl)naphthalen-1-yl)-8-fluoro-2-((hexahydro-1H-pyrrolizin-7a-yl)methoxy)pyrido[4,3-d]pyrimidin-4-yl)-1,6-diazaspiro[3.5]nonan-2-one The title compound was synthesized according to the procedure described for example 463. H NMR (400 MHz, methanol-$d_4$) δ=9.14 (s, 1H), 8.25-8.13 (m, 2H), 7.95 (d, J=7.2 Hz, 1H), 7.72-7.65 (m, 2H), 7.62-7.62 (m, 1H), 6.59-6.26 (m, 1H), 4.53-4.39 (m, 3H), 4.37-4.27 (m, 11H), 4.07-3.98 (m, 1H), 3.91-3.78 (m, 1H), 3.42-3.34 (m, 2H), 3.05-2.95 (m, 2H), 2.94-2.74 (m, 2H), 2.24-2.15 (m, 2H), 2.15-2.07 (m, 2H), 2.06-1.96 (m, 6H), 1.96-1.87 (m, 2H); LCMS (ESI, M+1): m/z=603.4.

Example 467

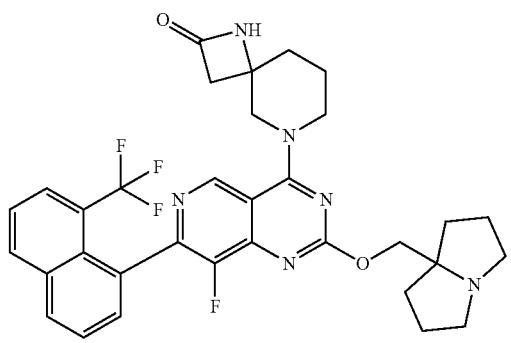 [SMILES: O=C1CC2(CCCN(c3nc(OCC45CCCN4CCC5)nc4c(F)c(-c5cccc6cccc(C(F)(F)F)c56)ncc34)C2)N1]

6-(8-fluoro-2-((hexahydro-1H-pyrrolizin-7a-yl)methoxy)-7-(8-(trifluoromethyl)naphthalen-1-yl)pyrido[4,3-d]pyrimidin-4-yl)-1,6-diazaspiro[3.5]nonan-2-one The title compound was synthesized according to the procedure described for example 465. $^1$H NMR (400 MHz, methanol-$d_4$): δ=9.06 (d, J=3.6 Hz, 1H), 8.31 (d, J=8.0 Hz, 1H), 8.21 (dd, J=1.2, 8.4 Hz, 1H), 8.06 (d, J=7.6 Hz, 1H), 7.80-7.60 (m, 3H), 4.43-4.20 (m, 4H), 4.00 (dd, J=5.6, 13.2 Hz, 1H), 3.88-3.71 (m, 1H), 3.17-3.07 (m, 2H), 2.94-2.84 (m, 1H), 2.80-2.70 (m, 3H), 2.08 (ddd, J=6.0, 13.2, 19.2 Hz, 4H), 2.01-1.87 (m, 6H), 1.82-1.73 (m, 3H); LCMS [ESI, M+1]: m/z=621.4.

Example 468

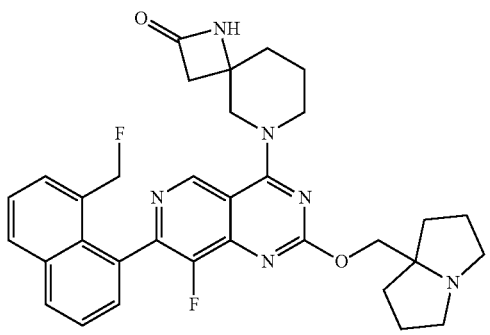 [SMILES: O=C1CC2(CCCN(c3nc(OCC45CCCN4CCC5)nc4c(F)c(-c5cccc6cccc(CF)c56)ncc34)C2)N1]

6-(8-fluoro-7-(8-(fluoromethyl)naphthalen-1-yl)-2-((hexahydro-1H-pyrrolizin-7a-yl)methoxy)pyrido[4,3-d]pyrimidin-4-yl)-1,6-diazaspiro[3.5]nonan-2-one The title compound was synthesized according to the procedure described for example 460. $^1$H NMR (400 MHz, methanol-$d_4$): δ=9.14 (s, 1H), 8.51 (s, 1H), 8.16-8.04 (m, 2H), 7.69-7.51 (m, 4H), 5.15-4.98 (m, 2H), 4.70-4.57 (m, 2H), 4.42 (br d, J=13.2 Hz, 1H), 4.37-4.27 (m, 11H), 4.00 (d, J=13.2 Hz, 1H), 3.90-3.80 (m, 11H), 3.69-3.58 (m, 2H), 3.26-3.17 (m, 2H), 2.95-2.88 (m, 1H), 2.81-2.73 (m, 1H), 2.35-2.25 (m, 2H), 2.24-2.01 (m, 8H), 2.00-1.92 (m, 2H); LCMS [ESI, M+1]: m/z=585.3.

Example 469

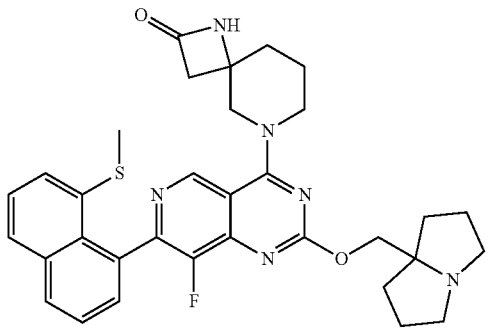 [SMILES: CSc1cccc2cccc(-c3ncc4c(N5CCCC6(CC(=O)N6)C5)nc(OCC56CCCN5CCC6)nc4c3F)c12]

6-(8-fluoro-2-((hexahydro-1H-pyrrolizin-7a-yl)methoxy)-7-(8-(methylthio)naphthalen-1-yl)pyrido[4,3-d]pyrimidin-4-yl)-1,6-diazaspiro[3.5]nonan-2-one The title compound was synthesized according to the procedure described for example 436. $^1$H NMR (400 MHz, METHANOL-$d_4$) δ=9.08 (d, J=4.8 Hz, 1H), 8.06 (dd, J=1.2, 8.0 Hz, 1H), 7.86-7.784 (m, 1H), 7.68-7.58 (m, 1H), 7.55-7.49 (m, 3H), 4.58-4.48 (m, 2H), 4.45-4.18 (m, 2H), 4.07-4.01 (m, 1H), 3.96-3.73 (m, 1H), 3.54-3.41 (m, 2H), 3.13-3.01 (m, 2H), 2.93-2.71 (m, 2H), 2.25 (s, 3H), 2.24-2.19 (m, 1H), 2.17-2.02 (m, 6H), 2.00-1.96 (m, 4H) LCMS (ESI, M+1): m/z=599.3.

Example 470

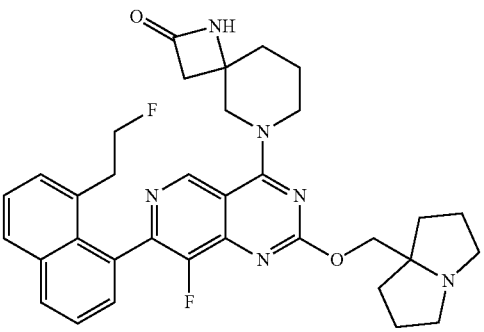 [SMILES: O=C1CC2(CCCN(c3nc(OCC45CCCN4CCC5)nc4c(F)c(-c5cccc6cccc(CCF)c56)ncc34)C2)N1]

6-(8-fluoro-7-(8-(2-fluoroethyl)naphthalen-1-yl)-2-((hexahydro-1H-pyrrolizin-7a-yl)methoxy)pyrido[4,3-d]pyrimidin-4-yl)-1,6-diazaspiro[3.5]nonan-2-one The title compound was synthesized according to the procedure described for example 434; $^1$H NMR (400 MHz, methanol-$d_4$) δ=9.15 (d, J=2.0 Hz, 1H), 8.09 (dd, J=1.2, 8.0 Hz, 1H), 7.95 (d, J=7.2 Hz, 1H), 7.66-7.41 (m, 4H), 4.70-4.60 (m, 2H), 4.47-4.19 (m, 4H), 4.10-3.79 (m, 2H), 3.72-3.61 (m, 2H), 3.30-3.20 (m, 2H), 2.94-2.84 (m, 1H), 2.83-2.65 (m, 3H), 2.37-2.27 (m, 2H), 2.26-2.14 (m, 4H), 2.13-1.93 (m, 6H); LCMS (ESI, M+1): m/z=599.3.

Example 471

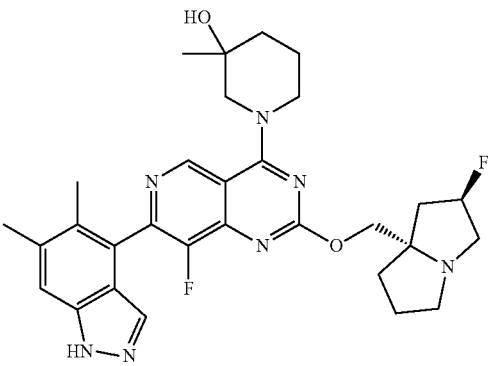 [SMILES: Cc1cc2[nH]ncc2c(-c2ncc3c(N4CCCC(C)(O)C4)nc(OC[C@@]45CCCN4C[C@H](F)C5)nc3c2F)c1C]

1-(7-(5,6-dimethyl-1H-indazol-4-yl)-8-fluoro-2-(((2R,7aS)-2-fluorohexahydro-1H-pyrrolizin-7a-yl)methoxy)pyrido[4,3-d]pyrimidin-4-yl)-3-ylmethylpiperidin-3-ol

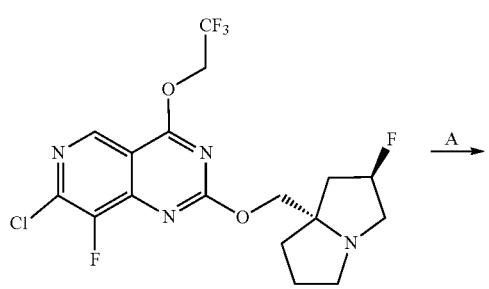

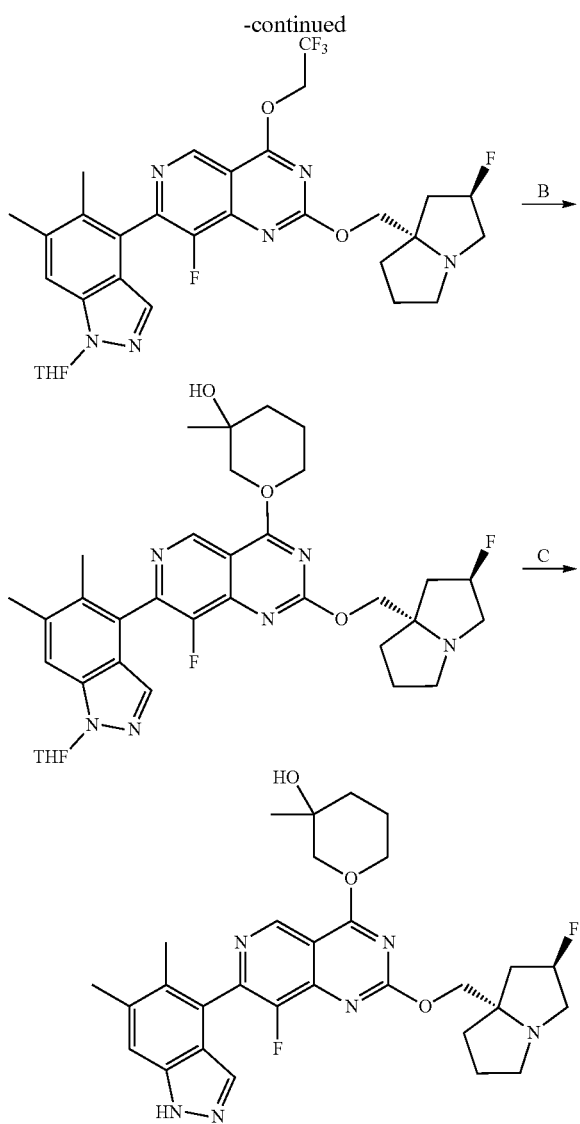

Step A. 7-(5,6-dimethyl-1-(tetrahydro-2H-pyran-2-yl)-1H-indazol-4-yl)-8-fluoro-2-(((2R,7aS)-2-fluorohexahydro-1H-pyrrolizin-7a-yl)methoxy)-4-(2,2,2-trifluorethoxy)pyrido[4,3-d]pyrimidine: A mixture of 7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (200 mg, 1.0 equiv.), 5,6-dimethyl-1-(tetrahydro-2H-pyran-2-yl)-4-(4,4,5,5-tetramethyl-1,3,2-dioxaborolan-2-yl)-1H-indazole (406 mg, 2.5 equiv.), cataCXium A Pd G3 (33.2 mg, 0.1 equiv.) and K$_3$PO$_4$ (1.5 M, 912 µL, 3.0 equiv.) in THF (4.0 mL) was degassed and stirred at 60° C. for 2 hours under N$_2$ atmosphere. The mixture was diluted with water (5.0 mL) and extracted with ethyl acetate (3×5.0 mL). The combined organic layers were dried over anhydrous sodium sulfate, concentrated and purified by reversed phase flash chromatography [C18, water (0.1% formic acid)/ACN] to afford title compound (176 mg, 60% yield) as a yellow solid; $^1$H NMR (400 MHz, chloroform-d) δ=9.35 (d, J=4.4 Hz, 1H), 7.63-7.57 (m, 1H), 7.54 (d, J=16.9 Hz, 11H), 5.78-5.68 (m, 11H), 5.46-5.23 (m, 11H), 5.15-5.01 (m, 2H), 4.54-4.34 (m, 2H), 4.10-3.98 (m, 1H), 3.82-3.72 (m, 11H), 3.54-3.22 ((m, 3H), 3.11-2.99 (m, 1H), 2.64-2.53 (m, 1H), 2.51 (s, 3H), 2.40-2.26 (m, 2H), 2.20 (s, 3H), 2.17-2.13 (m, 1H), 2.11-2.07 (m, 1H), 2.04-1.99 (m, 2H), 1.85-1.60 (m, 5H); LCMS (ESI, M+1): m/z=633.4.

Step B. 1-(7-(5,6-dimethyl-1-(tetrahydro-2H-pyran-2-yl)-1H-indazol-4-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a solution of 7-(5,6-dimethyl-1-(tetrahydro-2H-pyran-2-yl)-1H-indazol-4-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (200 mg, 1.0 equiv.) in DMF (2.0 mL) was added 3-methylpiperidin-3-ol (95.9 mg, 2.0 equiv., HCl), DIEA (204 mg, 5.0 equiv.) and 4 Å molecular sieves (50 mg). The reaction was stirred at 40° C. for 12 hours. The mixture was filtered and purified by reversed phase flash chromatography [C18, water (0.1% formic acid)/ACN] to afford title compound (173 mg, 84% yield) as a yellow solid; $^1$H NMR (400 MHz, chloroform-d) δ=9.28-9.19 (m, 1H), 7.69-7.62 (m, 1H), 7.51 (br d, J=10.4 Hz, 1H), 5.77-5.68 (m, 1H), 5.39-5.15 (m, 1H), 4.52-4.37 (m, 2H), 4.35-4.18 (m, 2H), 4.09-3.96 (m, 1H), 3.83-3.69 (m, 1H), 3.54-3.37 (m, 1H), 3.36-3.22 (m, 3H), 3.20-3.10 ((m, 11H), 3.02-2.92 (m, 1H), 2.63-2.52 (m, 1H), 2.50 (s, 3H), 2.30-2.24 (m, 1H), 2.22 (s, 3H), 2.20-2.10 (m, 3H), 2.08 (br s, 1H), 1.99-1.84 (m, 5H), 1.78-1.62 (m, 5H), 1.35 (s, 3H); LCMS (ESI, M+1): m/z=648.6.

Step C. 1-(7-(5,6-dimethyl-1H-indazol-4-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3_-9: To a solution of 1-(7-(5,6-dimethyl-1-(tetrahydro-2H-pyran-2-yl)-1H-indazol-4-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (50 mg, 1.0 equiv.) in ACN (0.15 mL) was added HCl.dioxane (4 M, 289 µL, 15 equiv.). The reaction was stirred at 0° C. for 1 hour. The mixture was concentrated and purified by prep-HPLC [column: Waters Xbridge 150×25 mm×5 µm; mobile phase: water (10 mM NH$_4$HCO$_3$), B: ACN, B %: 34%-64%, 9 min] and lyophilized to afford the title compound (27.2 mg, 62% yield) as a white solid; $^1$H NMR (400 MHz, methanol-d$_4$) δ 9.28 (dd, J=1.0, 7.2 Hz, 11H), 7.62 (d, J=2.2 Hz, 1H), 7.50 (s, 11H), 5.40-5.19 (m, 11H), 4.68-4.51 (m, 2H), 4.37-4.23 (m, 3H), 3.69-3.61 (m, 11H), 3.51-3.37 (m, 1H), 3.24 (br s, 11H), 3.19 (br s, 11H), 3.07-2.96 (m, 11H), 2.51 (s, 3H), 2.41-2.26 (m, 1H), 2.26-2.19 (m, 4H), 2.19-2.10 (m, 2H), 2.05-1.95 (m, 2H), 1.94-1.83 (m, 2H), 1.82-1.72 (m, 2H), 1.29 (d, J=1.2 Hz, 3H); LCMS (ESI, M+1): m/z=564.4.

Example 472

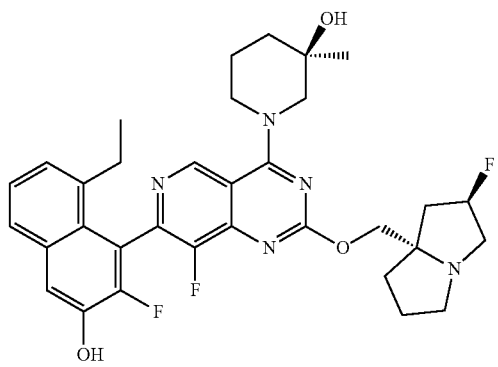 [SMILES: CCc1cccc2cc(O)c(F)c(-c3ncc4c(N5CCC[C@@](C)(O)C5)nc(OC[C@@]56CCCN5C[C@H](F)C6)nc4c3F)c12]

653

(3R)-1-(7-(8-ethyl-2-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol

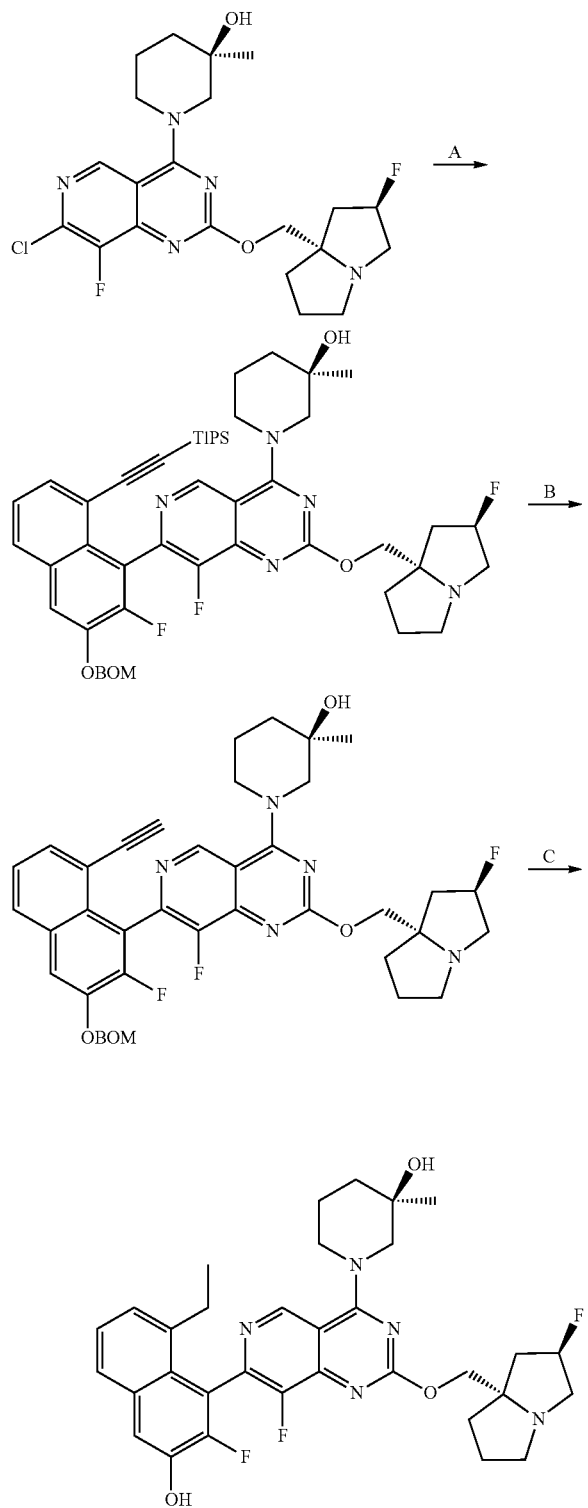

654

Step A. (3R)-1-(7-(3-((benzyloxy)methoxy)-2-fluoro-8-((triisopropylsilyl)ethynyl)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a mixture of (R)-1-(7-chloro-8-fluoro-2-(((2R,7aS)-2-fluorohexahydro-11H-pyrrolizin-7a-yl)methoxy)pyrido[4,3-d]pyrimidin-4-yl)-3-methylpiperidin-3-ol (2.00 g, 1.0 equiv.), ((6-((benzyloxy)methoxy)-7-fluoro-8-(4,4,5,5-tetramethyl-1,3,2-dioxaborolan-2-yl)naphthalen-1-yl)ethynyl)triisopropylsilane (3.89 g, 1.5 equiv.), $K_3PO_4$ (1.5 M in water, 8.81 mL, 3.0 equiv.) in methoxycyclopentane (30 mL) was added CataCXium A Pd G3 (321 mg, 0.1 equiv.) under $N_2$. The mixture was stirred at 90° C. for 8 hours. The reaction mixture was diluted with water (10 mL) and extracted with ethyl acetate (2×15 mL). The combined organic phase was washed with brine (20 mL), dried over anhydrous sodium sulfate, concentrated and purified by reversed phase flash chromatography [C18, water (0.1% formic acid)/ACN] to afford the title compound (1.20 g, 31% yield) as a brown oil; LCMS (ESI, M+1): m/z=880.5.

Step B. (3R)-1-(7-(3-((benzyloxy)methoxy)-8-ethynyl-2-fluoronaphthalen-1-yl)-8-fluoro-2-(((2R,7aS)-2-fluorohexahydro-1H-pyrrolizin-7a-yl)methoxyl)pyrido[4,3-d]pyrimidin-4-yl)-3-methylpiperidin-3-ol: To the solution of (3R)-1-(7-(3-((benzyloxy)methoxy)-2-fluoro-8-((triisopropylsilyl)ethynyl)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (1.10 g, 1.0 equiv.) in DMF (5 mL) was added CsF (1.90 g, 10 equiv.). The mixture was stirred at 25° C. for 1 hour. The mixture was filtered and purified by reversed phase flash chromatography [C18, water (0.1% formic acid)/ACN] to afford the title compound (820 mg, 89% yield) as a yellow oil; LCMS (ESI, M+1): m/z=724.4.

Step C. (3R)-1-(7-(8-ethyl-2-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: To a solution of (3R)-1-(7-(3-((benzyloxy)methoxy)-8-ethynyl-2-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (200 mg, 1.0 equiv.) in MeOH (3 mL) was added Pd/C (40.0 mg, 10% purity) under $N_2$ atmosphere. The mixture was degassed, purged with $H_2$ and stirred at 25° C. for 12 hours under $H_2$ (15 psi) atmosphere. The mixture was filtered, concentrated and purified by prep-HPLC [column: Phenomenex luna C18 150×25 mm×10 μm; mobile phase: water (0.25% formic acid)-ACN; B %: 14%-44%, 10 minutes] to afford the title compound (37.8 mg, 21% yield, 0.5FORMIC ACID) as a yellow solid; $^1$H NMR (400 MHz, METHANOL-$d_4$) δ=9.28 (d, J=3.2 Hz, 1H), 7.64 (d, J=7.6 Hz, 1H), 7.46 (d, J=9.6 Hz, 1H), 7.35 (t, J=7.6 Hz, 1H), 7.20 (d, J=7.2 Hz, 1H), 5.56-5.33 (m, 1H), 4.64-4.40 (m, 3H), 4.37-4.26 (m, 1H), 3.75-3.38 (m, 5H), 3.28-3.18 (m, 1H), 2.61-2.33 (m, 2H), 2.33-2.23 (m, 2H), 2.23-2.10 (m, 4H), 2.09-1.97 (m, 1H), 1.91-1.71 (m, 3H), 1.29 (d, J=9.2 Hz, 3H), 0.89 (td, J=7.5, 9.7 Hz, 3H); LCMS (ESI, M+1): m/z=608.4.

655
Example 473
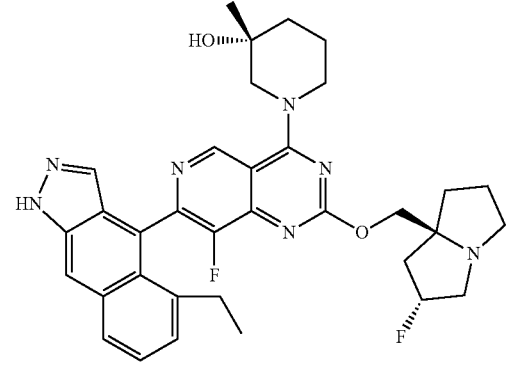 [SMILES: CCc1cccc2cc3[nH]ncc3c(-c3ncc4c(N5CCC[C@@](C)(O)C5)nc(OC[C@@]56CCCN5C[C@H](F)C6)nc4c3F)c12]
(3R)-1-(7-(5-ethyl-1H-benzo[f]indazol-4-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol
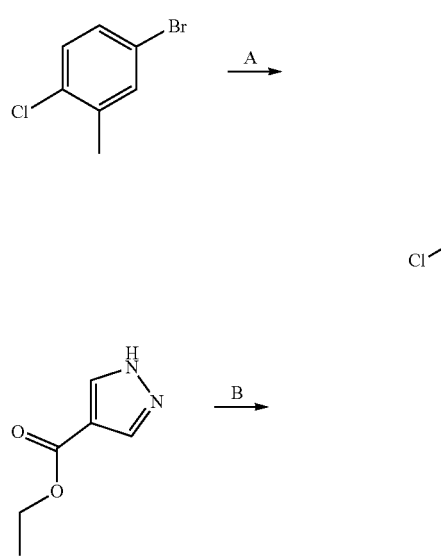
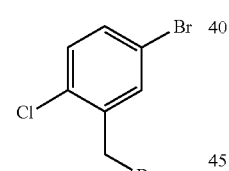
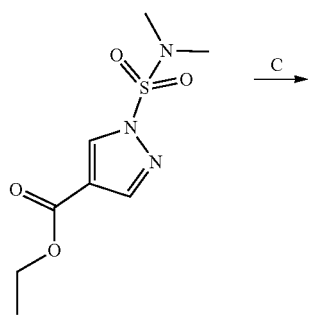
656
-continued
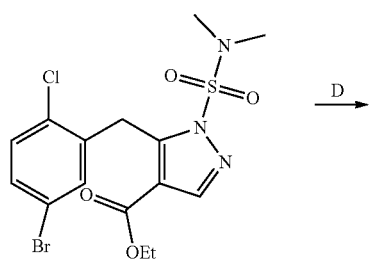
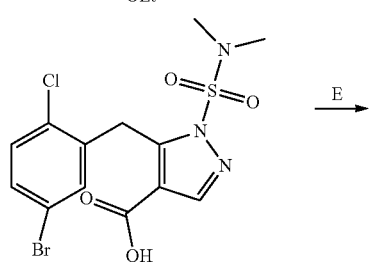
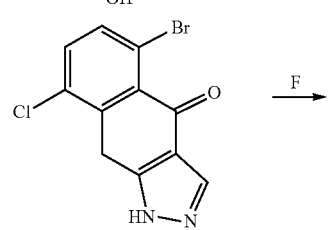
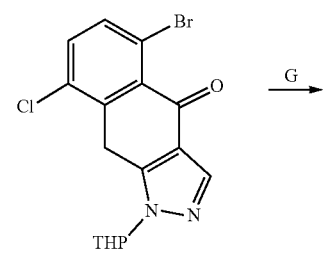
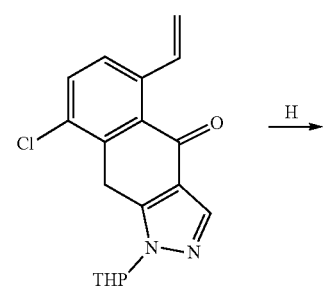
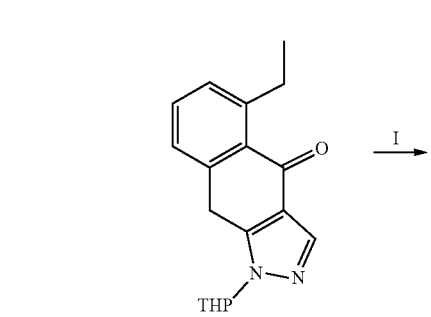

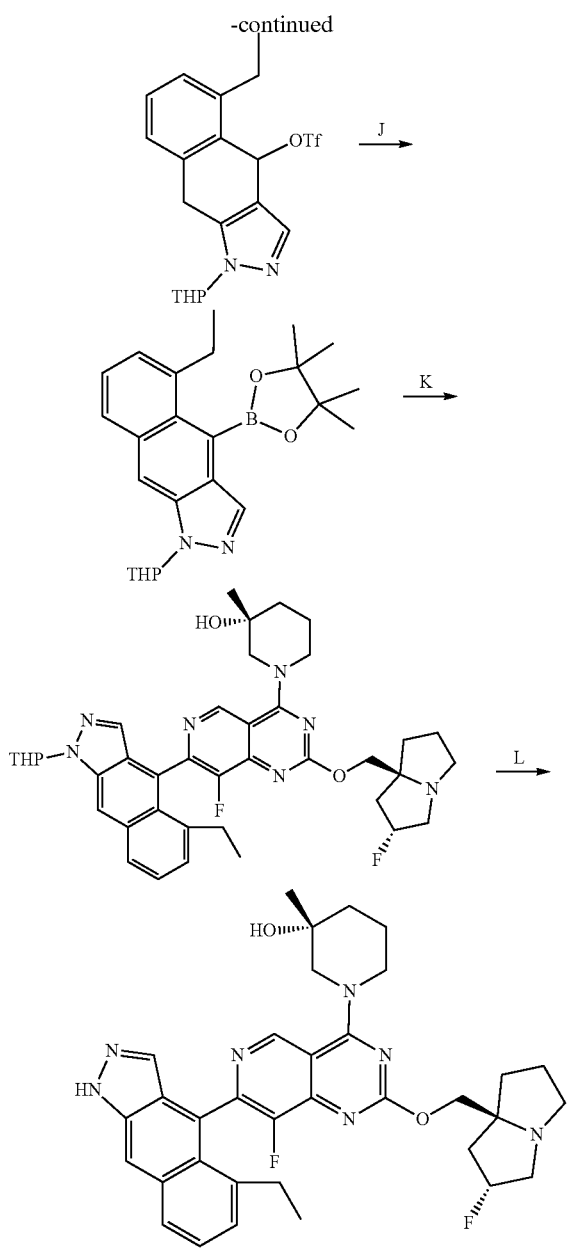

Step A. 4-bromo-2-(bromomethyl)-1-chlorobenzene: A mixture of 4-bromo-1-chloro-2-methylbenzene (50 g, 1.0 equiv.), NBS (47.6 g, 1.1 equiv.), AIBN (799 mg, 0.02 equiv.) in MeCN (600 mL) was stirred at 90° C. for 12 hours. The mixture was concentrated in vacuum and the residue was purified by column chromatography (Silica gel, ethyl acetate/petroleum ether 10:1) to afford the title compound (60 g, 87% yield) as a white solid $^1$H NMR (400 MHz, CDCl$_3$-d) δ 7.61 (d, J=2.4 Hz, 1H), 7.40 (dd, J=2.4, 8.4 Hz, 1H), 7.30-7.26 (in, 1H), 4.54 (s, 2H).

Step B. ethyl 1-(N,N-dimethylsulfamoyl-1H-pyrazole-4-carboxylate: To a mixture of ethyl 1H-pyrazole-4-carboxylate (10 g, 1.0 equiv.) and DABCO (8.81 g, 1.1 equiv.) in MeCN (100 mL) was added N,N-dimethylsulfamoyl chloride (11.3 g, 8.41 mL, 1.1 equiv.). The mixture was stirred at 20° C. for 1 hour before being concentrated in vacuum and the residue was purified by column chromatography (Silica gel, petroleum ether/ethyl acetate 3:1) to afford the title compound (15 g, 85% yield) as a white solid. LCMS (ESI, M+1): m/z=248.0.

Step C. ethyl 5-(5-bromo-2-chlorobenzyl-1-(N,N-dimethylsulfamoyl-1H-pyrazole-4-carboxylate: To a solution of ethyl 1-(N,N-dimethylsulfamoyl)-1H-pyrazole-4-carboxylate (6 g, 1.0 equiv.) in THF (60 mL) was added LDA (2 M, 14.6 mL, 1.2 equiv.) and HMPA (5.22 g, 5.12 mL, 1.2 equiv.) at −78° C. After stirring at −78° C. for 1 hour, 4-bromo-2-(bromomethyl)-1-chlorobenzene (8.28 g, 1.2 equiv.) was added into the mixture. The mixture was stirred at −78° C. for 2 hours and at 20° C. for 1 hour before being diluted with ethyl acetate (100 mL), washed with water (100 mL) and brine (100 mL), dried over Na$_2$SO$_4$ and concentrated in vacuum. The residue was purified by column chromatography (Silica gel, petroleum ether/ethyl acetate 3:1). The desired fractions were collected and concentrated in vacuum to give a residue and the residue was triturated with methanol (30 mL), dried in vacuum to afford the title compound (3 g, 27% yield) as a white solid. LCMS (ESI, M+1): m/z=452.1.

Step D. 5-(5-bromo-2-chlorobenzyl)-1-(N,N-dimethylsulfamoyl)-1H-pyrazole-4-carboxylic acid: A mixture of ethyl 5-(5-bromo-2-chlorobenzyl)-1-(N,N-dimethylsulfamoyl)-1H-pyrazole-4-carboxylate (20 g, 1.0 equiv.) and NaOH (44.4 g, 25 equiv.) in dioxane (120 mL) and water (120 mL) was stirred at 90° C. for 2 hours. The mixture was extracted with ethyl acetate (300 mL), washed with brine (200 mL), dried over Na$_2$SO$_4$ and concentrated in vacuum to afford the title compound (20.5 g, crude) as a white solid and used into next step without further purification.

Step E. 5-bromo-8-chloro-1H-benzo[f]indazol-4(9H)-one: A mixture of 5-(5-bromo-2-chlorobenzyl)-1-(N,N-dimethylsulfamoyl)-1H-pyrazole-4-carboxylic acid (22 g, 1.0 equiv.) in CF$_3$SO$_3$H (220 mL) was stirred at 90° C. for 3 hours. The mixture was poured into ice water (500 mL) and filtered. The filter cake was diluted with ethyl acetate (500 mL) and filtered, the filtrate was washed with saturated sodium bicarbonate (400 mL), brine (400 mL), dried over Na$_2$SO$_4$ and concentrated in vacuum to afford the title compound (7.5 g, 48% yield) that was used in the next step without further purification as a yellow solid. LCMS (ESI, M+1): m/z=298.8.

Step F. 5-bromo-8-chloro-1-(tetrahydro-2H-pyran-2-yl)-1H-benzo[f]indazol-4(9H)-one: To a mixture of 5-bromo-8-chloro-1H-benzo[f]indazol-4(9H)-one (6.5 g, 1.0 equiv.) and TsOH (376 mg, 0.1 equiv.) in THF (60 mL) was added DHP (5.51 g, 5.99 mL, 3.0 equiv.) at 15° C. The mixture was stirred at 15° C. for 15 mins before being concentrated in vacuum. The residue was purified by reversed phase flash chromatography [water (0.1% formic acid)/acetonitrile] to afford the title compound (3.7 g, 40% yield) as a yellow oil. LCMS (ESI, M−83): m/z=298.8.

Step G. 8-chloro-1-(tetrahydro-2H-pyran-2-yl)-5-vinyl-1H-benzo[f]indazol-4(9H)-one: A mixture of 5-bromo-8-chloro-1-(tetrahydro-2H-pyran-2-yl)-1H-benzo[f]indazol-4(9H)-one (550 mg, 1.0 equiv.), potassium trifluoro(vinyl)boranuide (579 mg, 3 equiv.), Pd(dppf)Cl2(105 mg, 0.1 equiv.) and Na$_2$CO$_3$ (458 mg, 3.0 equiv.) in dioxane (5 mL) and water (1.5 mL) was stirred at 90° C. for 3 hours. The mixture was concentrated in vacuum and the residue was purified by reversed phase flash chromatography [water (0.1% formic acid)/acetonitrile] to afford the title compound (220 mg, 46% yield) as a yellow solid. LCMS (ESI, M+1): m/z=328.9.

Step H. 5-ethyl-1-(tetrahydro-2H-pyran-2-yl)-1H-benzo[f]indazol-4(9H)-one: A mixture of 8-chloro-1-(tetrahydro- 2H-pyran-2-yl)-5-vinyl-1H-benzo[f]indazol-4(9H)-one (300 mg, 1.0 equiv.), Pd/C (10 mg, 10%, 1 equiv.) and NaHCO₃ (76.6 mg, 1.0 equiv.) in MeOH (10 mL) was stirred at 20° C. for 1 hours under H₂ atmosphere (15 psi). The mixture was filtered and concentrated in vacuum and the residue was purified by reversed phase flash chromatography [water (0.1% formic acid)/acetonitrile] to afford the tide compound (110 mg, 41% yield) as a yellow solid. LCMS (ESI, M+1): m/z=297.2.

Step I. 5-ethyl-1-(tetrahydro-2H-pyran-2-yl)-1H-benzo[f] indazol-4-yl) trifluoromethanesulfonate: To a solution of 5-ethyl-1-(tetrahydro-2H-pyran-2-yl)-1H-benzo[f]indazol-4 (9H)-one (50 mg, 1.0 equiv.) and DIEA (87.2 mg, 4.0 equiv.) in DCM (1.0 mL) was added Tf₂O (95.2 mg, 2.0 equiv.) at −40° C. The mixture was stirred at −40° C. for 15 mins. After completion, the residue was purified by column chromatography (Silica gel, petroleum ether/ethyl acetate 5:1) to afford the title compound (45 mg, 51% yield) as a yellow solid. LCMS (ESI, M+1): m/z=429.1.

Step J. 5-ethyl-1-(tetrahydro-2H-pyran-2-yl)-4-(4,4,5,5-tetramethyl-1,3,2-dioxaborolan-2-yl)-1H-benzo[f]indazole: A mixture of 5-ethyl-1-(tetrahydro-2H-pyran-2-yl)-1H-benzo[f]indazol-4-yl trifluoromethanesulfonate (30 mg, 1.0 equiv.), 4,4,5,5-tetramethyl-1,3,2-dioxaborolane (35.9 mg, 40.6 μL, 4.0 equiv.), TEA (28.3 mg, 4.0 equiv.) and Pd(dppf)Cl₂ (5.12 mg, 0.1 equiv.) in MeCN (1 mL) was stirred at 80° C. for 5 hours under N₂ atm. The mixture was concentrated in vacuum and the residue was purified by column chromatography (Silica gel, petroleum ether/ethyl acetate 5:1) to afford the title compound (24 mg, 71% yield) as a yellow oil. LCMS (ESI, M+1): m/z=407.2.

Step K. (3R)-1-(7-(5-ethyl-)-(tetrahydro-2H-pyran-2-yl)-1H-benzo[f]indazol-4-yl)-8-fluoro-2-(((2R,7aS)-2-fluoro-hexahydro-1H-pyrrolizin-7a-yl methoxy)pyrido[4,3-d]pyrimidin-4-yl)-3-methylpiperidin-3-ol: A mixture of 5-ethyl-1-(tetrahydro-2H-pyran-2-yl)-4-(4,4,5,5-tetramethyl-1,3,2-dioxaborolan-2-yl)-1H-benzo[f]indazole (15 mg, 1.0 equiv.), (R)-1-(7-chloro-8-fluoro-2-(((2R,7aS)-2-fluoro-hexahydro-1H-pyrrolizin-7a-yl)methoxy)pyrido[4,3-d]pyrimidin-4-yl)-3-methylpiperidin-3-ol (33.5 mg, 2.0 equiv.), CataCXium A Pd G3 (2.69 mg, 0.1 equiv.) and K₃PO₄ (1.5 M in water, 3.0 equiv.) in THF (1.0 mL) was stirred at 60° C. for 12 hours under N₂. The mixture was concentrated in vacuum to give a residue and the residue was purified by reversed phase flash chromatography [water (0.1% formic acid)/acetonitrile] to afford the title compound (18 mg, 50% yield) as a yellow oil. LCMS (ESI, M+1): m/z=698.4.

Step L. (3R)-1-(7-(5-ethyl-1H-benzo[f]indazol-4-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol: A mixture of (3R)-1-(7-(5-ethyl-1-(tetrahydro-2H-pyran-2-yl)-1H-benzo[f]indazol-4-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (16 mg, 1.0 equiv.) in TFA (1.23 g, 471 equiv.) and DCM (0.5 mL) was stirred at 15° C. for 0.5 hours. After completion, the mixture was concentrated in vacuum and the residue was purified by reversed phase flash chromatography [water (0.1% formic acid)/acetonitrile] followed by prep-HPLC (column: Phenomenex Synergi C18 150×25 mm×10 μm; mobile phase: water (0.225% formic acid)-ACN, B %: 16%-36%, 10 min) to afford the title compound (2.51 mg, 17% yield) as a yellow solid. ¹H NMR (400 MHz, METHANOL-d₄) δ=9.34 (d, J=10.4 Hz, 1H), 8.22 (s, 1H), 7.97 (d, J=8.4 Hz, 1H), 7.77 (d, J=18.4 Hz, 1H), 7.43 (dd, J=6.8, 8.4 Hz, 1H), 5.49-5.31 (m, 1H), 4.61 (br s, 1H), 4.48-4.33 (m, 3H), 3.75-3.60 (m, 1H), 3.55-3.37 (m, 4H), 3.19-3.09 (m, 1H), 2.63-2.30 (m, 4H), 2.29-1.95 (m, 5H), 1.94-1.76 (m, 3H), 1.33 (d, J=10.0 Hz, 3H), 1.00 (q, J=7.6 Hz, 3H). LCMS (ESI, M+1): m/z=614.4.

Example 474

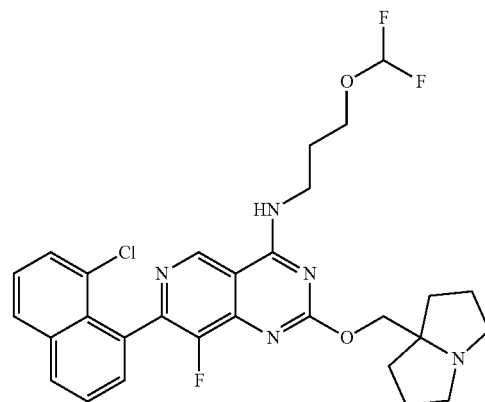

7-(8-chloronaphthalen-1-yl)-N-(3-(difluoromethoxy) propyl)-8-fluoro-2-((tetrahydro-1H-pyrrolizin-7a (5H)-yl)methoxy)pyrido[4,3-d]pyrimidin-4-amine The title compound was synthesized according to the procedure described for example 101. LCMS (ESI, M+1): m/z=572.2

Example 475

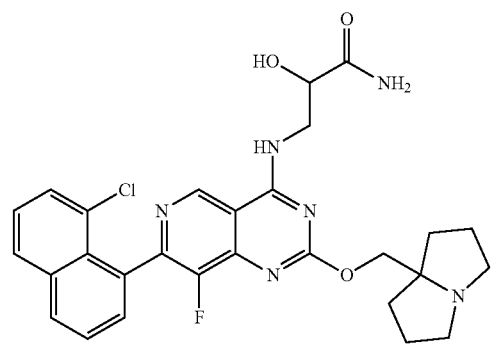 [SMILES: NC(=O)C(O)CNc1nc(OCC23CCCN2CCC3)nc2c(F)c(-c3cccc4cccc(Cl)c34)ncc12]

3-((7-(8-chloronaphthalen-1-yl)-8-fluoro-2-((tetrahydro-1H-pyrrolizin-7a(5H)-yl)methoxy)pyrido[4,3-d]pyrimidin-4-yl)amino)-2-hydroxypropanamide The title compound was synthesized according to the procedure described for example 101. LCMS (ESI, M+1): m/z=551.1

Example 476

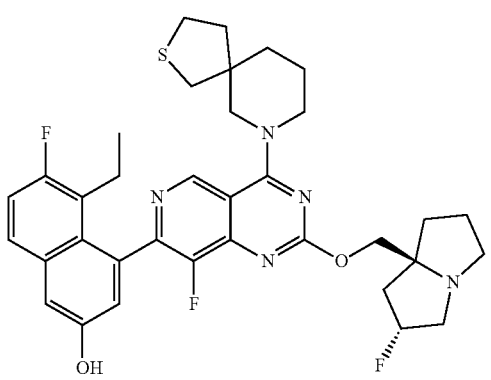 [SMILES: CCc1c(F)ccc2cc(O)cc(-c3ncc4c(N5CCCC6(CCSC6)C5)nc(OC[C@@]56CCCN5C[C@H](F)C6)nc4c3F)c12]

5-ethyl-6-fluoro-4-(8-fluoro-2-(((2R,7aS)-2-fluoro-tetrahydro-1H-pyrrolizin-7a(5H)-yl)methoxy)-4-(2-thia-7-azaspiro[4.5]decan-7-yl)pyrido[4,3-d]pyrimidin-7-yl)naphthalen-2-ol The title compound was synthesized according to the procedure described for example 135. ¹H NMR (400 MHz, Acetic) δ=9.50 (s, 1H), 8.16-8.09 (m, 1H), 7.71 (dd, J=6.0, 8.8 Hz, 1H), 7.42 (d, J=2.4 Hz, 1H), 7.29 (t, J=9.6 Hz, 1H), 7.22 (t, J=2.8 Hz, 1H), 5.69-5.49 (m, 1H), 5.02-4.73 (m, 2H), 4.72-4.52 (m, 1H), 4.51-4.26 (m, 1H), 4.21-4.09 (m, 2H), 4.07-3.63 (m, 3H), 3.49-3.36 (m, 1H), 3.07-2.74 (m, 4H), 2.72-2.46 (m, 4H), 2.39-2.25 (m, 4H), 2.08 (br s, 1H), 2.02-1.78 (m, 5H), 0.86 (t, J=7.2 Hz, 3H); LCMS (ESI, M+1): m/z=650.2.

Example 477

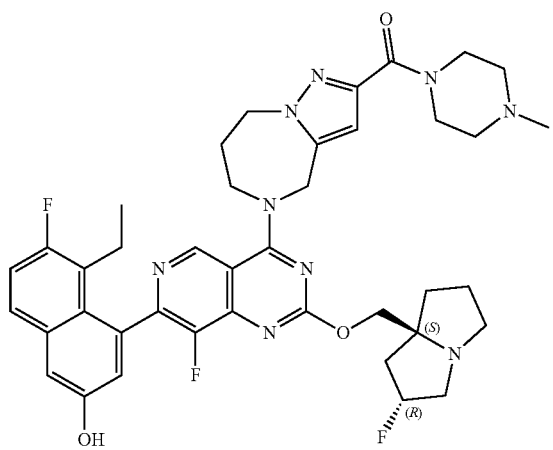

(5-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-5,6,7,8-tetrahydro-4H-pyrazolo[1,5-a][1,4]diazepin-2-yl)(4-methylpiperazin-1-yl)methanone The title compound was synthesized according to the procedure described for example 330. ¹H NMR (400 MHz, METHANOL-d₄) δ=9.23 (s, 1H), 7.69 (dd, J=6.0, 9.0 Hz, 1H), 7.32 (d, J=2.4 Hz, 1H), 7.26 (t, J=9.6 Hz, 1H), 7.04 (d, J=2.4 Hz, 1H), 6.87 (s, J H), 5.67-5.51 (m, 1H), 5.41-5.20 (m, 3H), 5.01-4.90 (m, 2H), 4.82 (br s, 2H), 4.75-4.36 (m, 7H), 4.11-3.80 (m, 3H), 3.46 (td, J=5.6, 10.7 Hz, 3H), 2.95 (s, 3H), 2.81-2.03 (m, 11H), 0.78 (br t, J=7.2 Hz, 3H), LCMS (ESI, M+1): m/z=756.5.

Example 478

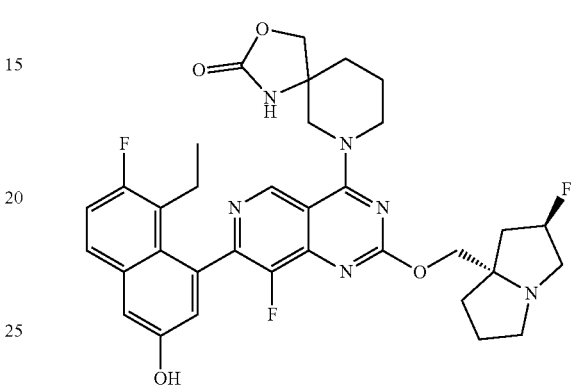

7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-oxa-1,7-diazaspiro[4.5]decan-2-one The title compound was synthesized according to the procedure described for example 330. ¹H NMR (400 MHz, METHANOL-d₄) δ=9.10 (s, 1H), 7.71-7.65 (m, 1H), 7.31 (d, J=2.6 Hz, 1H), 7.25 (t, J=9.4 Hz, 1H), 7.05 (d, J=2.6 Hz, 1H), 5.45-5.26 (m, 1H), 4.44-4.28 (m, 4H), 4.16 (d, J=9.0 Hz, 2H), 4.00-3.82 (m, 2H), 3.51-3.38 (m, 1H), 3.14-3.05 (m, 1H), 2.62-2.11 (m, 6H), 2.09-1.96 (m, 6H), 1.94-1.79 (m, 2H), 0.86-0.73 (m, 3H); LCMS (ESI, M+1): m/z=649.2.

Example 479

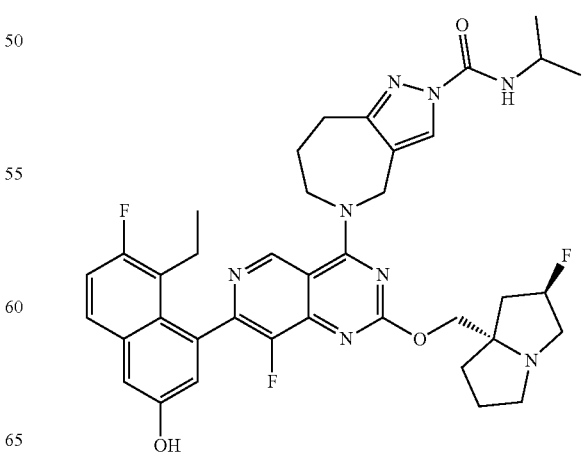

5-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-N-isopropyl-5,6,7,8-tetrahydropyrazolo[4,3-c]azepine-2(4H)-carboxamide The title compound was synthesized according to the procedure described for example 330. $^1$H NMR (400 MHz, DMSO-d$_6$) δ=10.16-9.72 (m, 1H), 9.15 (s, 1H), 8.25 (s, 1H), 8.22 (s, 1H), 8.05 (d, J=8.6 Hz, 11H), 7.76 (dd, J=6.0, 9.1 Hz, 1H), 7.40-7.29 (m, 2H), 7.01 (d, J=2.4 Hz, 1H), 5.38-5.18 (m, 1H), 5.11-4.97 (m, 2H), 4.31 (br s, 2H), 4.17-4.05 (m, 2H), 4.00-3.89 (m, 1H), 3.12-3.05 (m, 2H), 3.01 (br s, 1H), 2.99-2.92 (m, 2H), 2.86-2.79 (m, 1H), 2.41-2.35 (m, 1H), 2.21-1.98 (m, 6H), 1.88-1.72 (m, 3H), 1.17 (d, J=6.8 Hz, 6H), 0.70 (t, J=7.2 Hz, 3H), LCMS (ESI, M+1): m/z=715.5.

Example 480

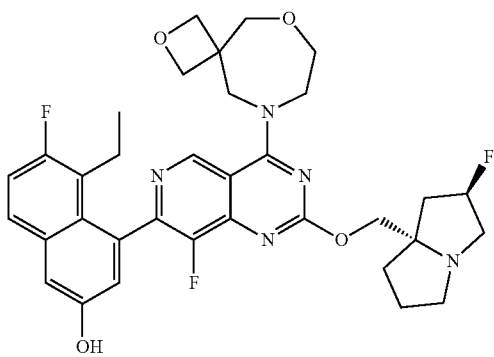 [SMILES: CCc1c(F)ccc2cc(O)cc(-c3ncc4c(N5CCOCC6(COC6)C5)nc(OC[C@@]56CCCN5C[C@H](F)C6)nc4c3F)c12]

5-ethyl-6-fluoro-4-(8-fluoro-2-(((2R,7aS)-2-fluorohexahydro-1H-pyrrolizin-7a-yl)methoxy)-4-(2,6-dioxa-9-azaspiro[3.6]decan-9-yl)pyrido[4,3-d]pyrimidin-7-yl)naphthalen-2-ol The title compound was synthesized according to the procedure described for example 330. $^1$H NMR (400 MHz, DMSO-d$_6$) δ=9.93 (s, 1H), 9.22 (s, 11H), 7.83-7.70 (m, 1H), 7.42-7.28 (m, 2H), 7.01 (d, J=2.4 Hz, 1H), 5.28 (d, J=64.0 Hz 1H), 4.62-4.48 (m, 3H), 4.36 (t, J=6.8 Hz 3H), 4.18-4.12 (m, 11H), 4.07 (d, J=1.2 Hz 11H), 4.02-3.92 (m, 4H), 3.89 (d, J=4.4 Hz 211), 3.09 (d, J=10.0 Hz, 2H), 3.01 (s, 11H), 2.86-2.79 (m, 11H), 2.41-2.34 (m, 11H), 2.21-2.08 (m, 2H), 2.02 (d, J=10.4 Hz, 2H), 1.90-1.71 (m, 3H), 0.73 (t, J=7.2 Hz, 3H); LCMS [M+1]: m/z=636.2.

Example 481

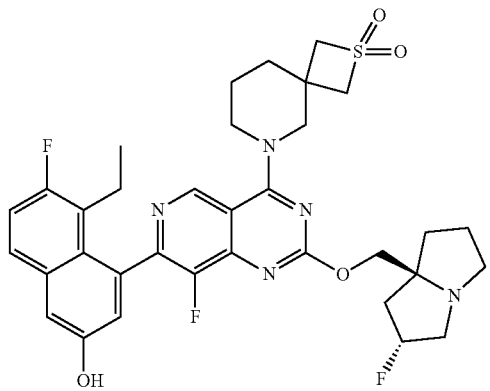 [SMILES: CCc1c(F)ccc2cc(O)cc(-c3ncc4c(N5CCCC6(C5)CS(=O)(=O)C6)nc(OC[C@@]56CCCN5C[C@H](F)C6)nc4c3F)c12]

6-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2-thia-6-azaspiro[3.5]nonane 2,2-dioxide The title compound was synthesized according to the procedure described for example 135. $^1$H NMR (400 MHz, METHANOL-d$_4$) δ=9.12 (s, 1H), 7.68 (dd, J=6.0, 9.2 Hz, 1H), 7.31 (d, J=2.4 Hz, 1H), 7.25 (t, J=9.6 Hz, 1H), 7.04 (d, J=2.4 Hz, 1H), 5.5-5.32 (m, 1H), 4.52 (s, 2H), 4.46-4.30 (m, 2H), 4.22-4.06 (m, 4H), 4.05-3.97 (m, 2H), 3.70-3.55 (m, 1H), 3.55-3.42 (m, 2H), 3.26-3.16 (m, 1H), 2.61-2.42 (m, 2H), 2.40-2.26 (m, 2H), 2.25-2.10 (m, 3H), 2.10-2.02 (m, 3H), 1.82 (br s, 2H), 0.80 (dt, J=1.2, 7.2 Hz, 3H); LCMS (ESI, M+1): m/z=668.4.

Example 482

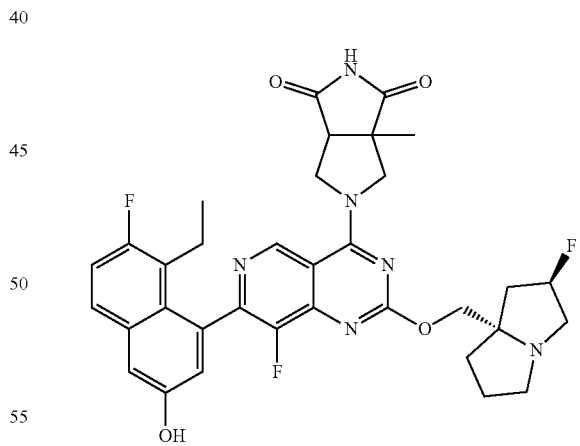

5-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3a-methyltetrahydropyrrolo[3,4-c]pyrrole-1,3(2H,3aH)-dione The title compound was synthesized according to the procedure described for example 330. $^1$H NMR (400 MHz, DMSO-d$_6$) δ=11.85-10.93 (m, 1H), 9.26 (s, 1H), 8.18 (s, 1H), 7.77 (dd, J=6.0, 9.2 Hz, 1H), 7.42-7.29 (m, 2H), 7.02 (d, J=2.4 Hz, 1H), 5.41-5.17 (m, 1H), 4.55-4.41 (m, 2H), 4.40-4.30 (m, 1H), 4.20-4.12 (m, 1H), 4.10-4.04 (m, 1H), 3.95 (d, J=12.0 Hz, 1H), 3.44 (s, 1H), 3.10 (d, J=11.2 Hz, 2H), 3.02 (s, 1H), 2.87-2.81 (m, 1H), 2.36-2.31 (m, 1H), 2.17-1.97 (m, 4H), 1.89-1.74 (m, 3H), 1.50 (s, 3H), 0.80-0.66 (m, 3H); LCMS [M+1]+: m/z=647.2.

Example 483

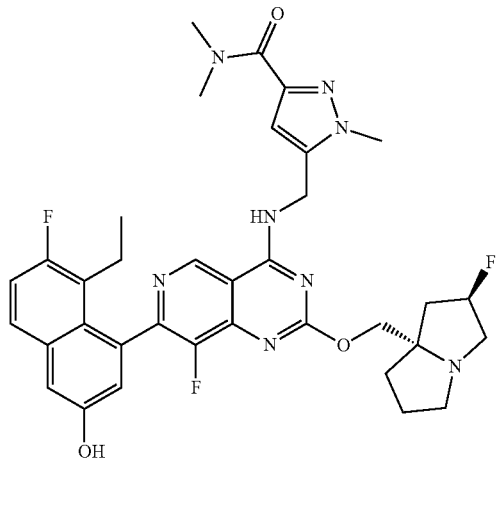 [SMILES: CCc1c(F)ccc2cc(O)cc(-c3ncc4c(NCc5cc(C(=O)N(C)C)nn5C)nc(OC[C@@]56CCCN5C[C@H](F)C6)nc4c3F)c12]

5-(((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)methyl)-N,N,1-trimethyl-1H-pyrazole-3-carboxamide

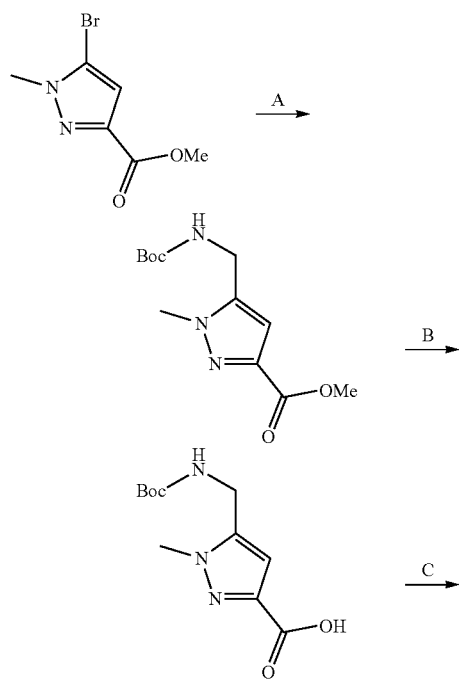

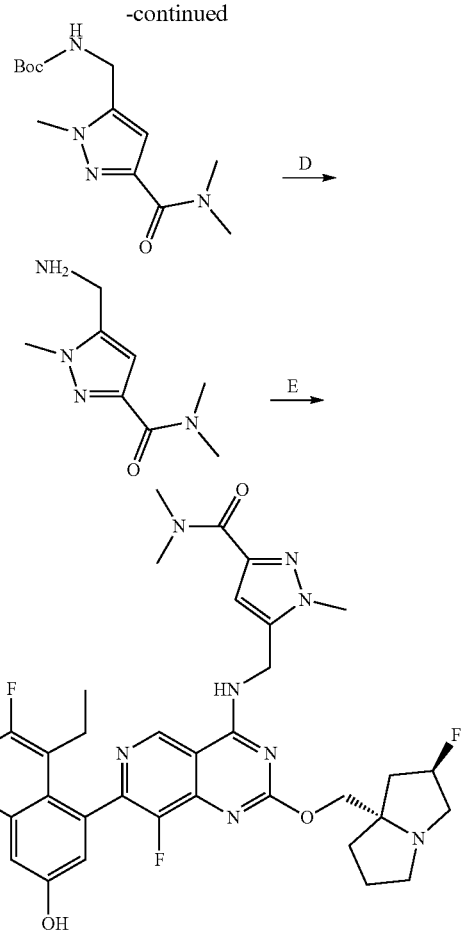

Step A. methyl 5-[(tert-butoxycarbonylamino)methyl]-1-methyl-pyrazole-3-carboxylate: A mixture of methyl 5-bromo-1-methyl-pyrazole-3-carboxylate (0.95 g, 1.0 equiv.), potassium (((tert-butoxycarbonyl)amino)methyl)trifluoroborate (1.2 g, 1.2 equiv.), Pd(PPh₃)₂Cl2 (152 mg, 0.05 equiv.), RuPhos (405 mg, 0.2 equiv.) and Na₂CO₃ (1.4 g, 3.0 equiv.) in dioxane (20 mL) and H₂O (2 mL) was degassed and stirred at 120° C. for 12 hours. The residue was diluted with H₂O (30 mL) and extracted with EtOAc (3×30 mL). The combined organic layers were washed with brine (3×30 mL), dried over Na₂SO₄, filtered and concentrated to give a residue, which was purified by flash silica gel chromatography (Ethyl acetate in Petroleum ether 42~46%) to afford the title compound (0.82 g, 70% yield) as a yellow gum; ¹H NMR (400 MHz, CDCl₃) δ=6.71 (s, 1H), 4.82 (s, 1H), 4.37 (d, J=5.6 Hz, 2H), 3.92 (m, 6H), 1.46 (s, 9H).

Step B. 5-[(tert-butoxycarbonylamino)methyl)-1-methyl]-pyrazole-3-carboxylic acid: To a solution of methyl 5-[(tert-butoxycarbonylamino)methyl]-1-methyl-pyrazole-3-carboxylate (700 mg, 1.0 equiv.) in THF (10 mL) and H₂O (10 mL) was added LiOH·H₂O (218 mg, 2.0 equiv.). The reaction was stirred at 25° C. for 2 hours. The pH of the mixture was adjusted to 2~3 with 1 N HCl. The resulting mixture was diluted with H₂O (150 mL) and extracted with DCM (3×150 mL), dried over Na₂SO₄, filtered and concentrated under reduced pressure to afford the title compound (560 mg, 2.19 mmol, 84% yield) as a yellow gum. ¹H NMR (400 MHz, CDCl₃) δ=6.76 (s, 1H), 4.89 (br s, 1H), 4.39 (d, J=4.4 Hz, 2H), 3.95 (s, 3H), 1.46 (s, 9H)

Step C. tert-butyl N-[[5-(dimethylcarbamoyl)-2-methyl-pyrazol-3yl]methyl]carbamate: To a solution of 5-[(tert-butoxycarbonylamino)methyl]-1-methyl-pyrazole-3-carboxylic acid (550 mg, 1 equiv.) and dimethylamine (351 mg, 2.0 equiv, HCl) in DMF (10 mL) was added HATU (1.64 g, 2.0 equiv.) and DIEA (1.39 g, 5.0 equiv.). The reaction was stirred at 25° C. for 2 hours. The reaction mixture was diluted with water (30 mL) and extracted with ethyl acetate (3×30 mL). The combined organic layers were washed with brine (30 mL), dried over Na$_2$SO$_4$, filtered and concentrated to give a residue. The residue was purified by flash silica gel chromatography (Ethyl acetate in Petroleum ether 72~80%) to afford the title compound (600 mg, 96% yield, 97% purity) as a white solid. $^1$H NMR (400 MHz, CDCl$_3$) δ=6.54 (s, 1H), 4.96 (s, 1H), 4.36 (d, J=5.6 Hz, 2H), 3.87 (s, 3H), 3.32 (s, 3H), 3.09 (s, 3H), 1.45 (s, 9H)

Step D. 5-(aminomethyl)-N,N,1-trimethyl-pyrazole-3-carboxamide: To a solution of tert-butyl N-[[5-(dimethyl-carbamoyl)-2-methyl-pyrazol-3-yl]methyl]carbamate (300 mg, 1.0 equiv.) in DCM (3 mL) was added HCl.dioxane (4 M, 0.1 equiv.). The reaction was stirred at 25° C. for 12 hours. The reaction mixture was concentrated under reduced pressure to afford the title compound (228 mg, 98% yield, HCl) as a white solid.

Step E. 5-(((7-(8-ethyl-7-fluoro-3-hydroxynaphthalen-1-yl)-8-fluoro-2-(((2R,7aS)-2-fluorotetrahydro-1H-pyr-rolizin-7a(5H)-yl)methoxy)pyrido[4,3-d]pyrimidin-4-yl)amino)methyl)-N,N,1-trimethyl-1H-pyrazole-3-carboxamide: To a solution of 5-(aminomethyl)-N,N,1-trimethyl-pyrazole-3-carboxamide (129 mg, 5.0 equiv, HCl) in DMSO (1.5 mL) were added K$_2$CO$_3$ (49.0 mg, 3.0 equiv.) and 4 Å molecular sieves (10 mg). The reaction was stirred at 25° C. for 0.5 hour before 5-ethyl-6-fluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (70 mg, 1 equiv.) was added and the resulting mixture was stirred at 40° C. for 2 hours. The mixture was concentrated and the residue was purified by prep-HPLC (column: Phenomenex luna C18 150×25 mm×10 um; mobile phase: [water(0.1% formic acid)-ACN]; B %: 13%-43%, 9 min) to afford the title compound (12.3 mg, 13% yield, 93.1% purity, formic acid salt) as a white solid; $^1$H NMR (400 MHz, DMSO-d$_4$) δ=9.49 (br t, J=5.2 Hz, 1H), 9.34 (s, 1H), 8.18 (s, 1H), 7.76 (dd, J=6.0, 9.2 Hz, 1H), 7.40-7.28 (m, 2H), 7.00 (d, J=2.4 Hz, 1H), 6.59 (s, 1H), 5.42-5.15 (m, 1H), 4.93-4.75 (m, 2H), 4.19-4.05 (m, 2H), 3.98 (s, 3H), 3.28 (s, 31H), 3.09 (d, J=10.4 Hz, 2H), 3.01 (s, 1H), 2.95 (s, 3H), 2.87-2.78 (m, 1H), 2.38-2.28 (m, 11H), 2.18-1.95 (m, 4H), 1.88-1.72 (m, 3H), 0.71 (t, J=7.2 Hz, 3H). LCMS [M+1]$^+$: m/z=675.3

Example 484

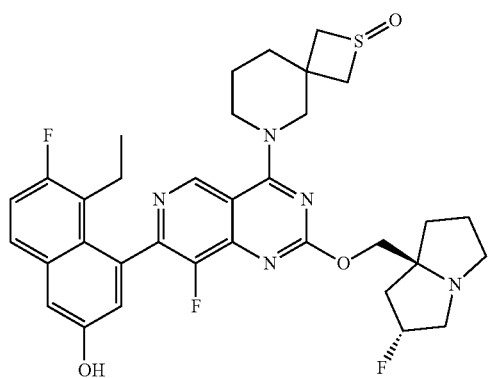 [SMILES: CCc1c(F)ccc2cc(O)cc(-c3ncc4c(N5CCCC6(C5)CS(=O)C6)nc(OC[C@@]56CCCN5C[C@H](F)C6)nc4c3F)c12]

6-(7-(8-ethyl-7-fluoro-3-hydroxynaphthalen-1-yl)-8-fluoro-2-(((2R,7aS)-2-fluorohexahydro-1H-pyr-rolizin-7a-yl)methoxy)pyrido[4,3-d]pyrimidin-4-yl)-2-thia-6-azaspiro[3.5]nonane 2-oxide

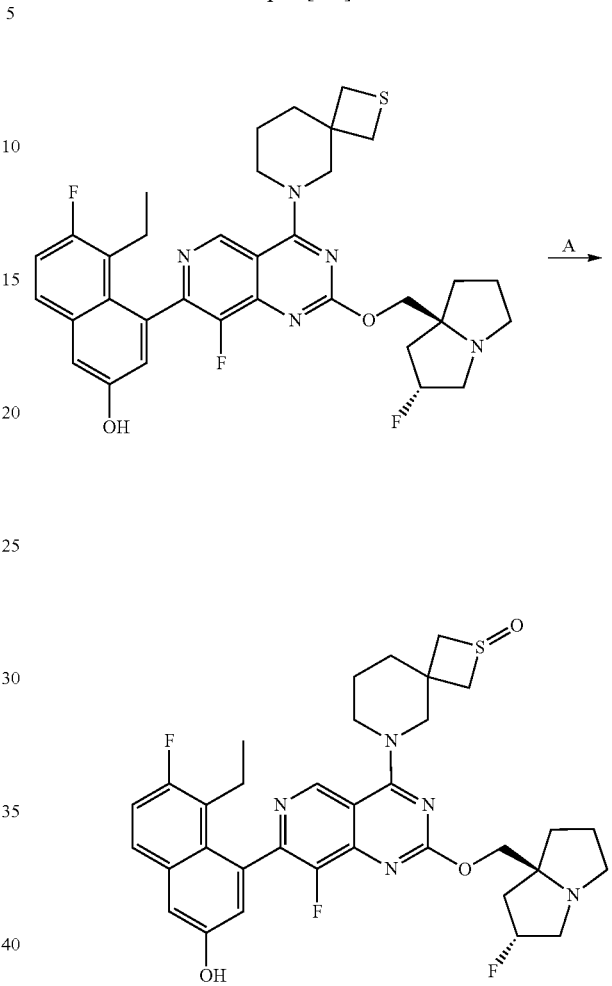

Step A. 6-(7-(8-ethyl-7-fluoro-3-hydroxynaphthalen-1-yl)-8-fluoro-2-(((2R,7aS)-2-fluorohexahydro-1H-pyr-rolizin-7a-yl)methoxy)pyrido[4,3-d]pyrimidin-4-yl)-2-thia-6-azaspiro[3.5]nonane 2-oxide: To a solution of NaIO$_4$ (7.07 mg, 1.05 equiv.) in H$_2$O (0.5 mL) was added 5-ethyl-6-fluoro-4-(8-fluoro-2-(((2R,7aS)-2-fluorohexahydro-1H-pyr-rolizin-7a-yl)methoxy)-4-(2-thia-6-azaspiro[3.5]nonan-6-yl)pyrido[4,3-d]pyrimidin-7-yl)naphthalen-2-ol (20.0 mg, 1.0 equiv.) at 0° C. Then MeOH (0.4 mL) and dioxane (0.3 mL) was added to the mixture. The reaction mixture was stirred at 0° C. for 12 hours. The residue was filtered, washed with MeOH (1 mL), and the filtrate was purified by prep-HPLC [column: Waters Xbridge 150×25 mm×5 μm; mobile phase: water (10 mM NH$_4$HCO$_3$)-ACN; B %: 32%-62%, 8 min] and lyophilized to afford the title compound (4.36 mg, 21% yield) as a white solid; $^1$H NMR (400 MHz, METHA-NOL-d$_4$) δ=9.06 (s, 1H), 7.68 (dd, J=6.0, 9.2 Hz, 1H), 7.30 (d, J=2.4 Hz, 1H), 7.25 (t, J=9.6 Hz, 1H), 7.06 (d, J=2.4 Hz, 1H), 5.42-5.17 (m, 1H), 4.43-4.19 (m, 4H), 4.08-3.96 (m, 2H), 3.73-3.62 (m, 2H), 3.27-3.12 (m, 5H), 3.06-2.97 (m, 1H), 2.55-2.43 (m, 1H), 2.41-2.20 (m, 2H), 2.20-2.12 (m, 2H), 2.04-1.83 (m, 7H), 0.80 (t, J=7.2 Hz, 3H); LCMS (ESI, M+1): m/z=652.4.

Example 485

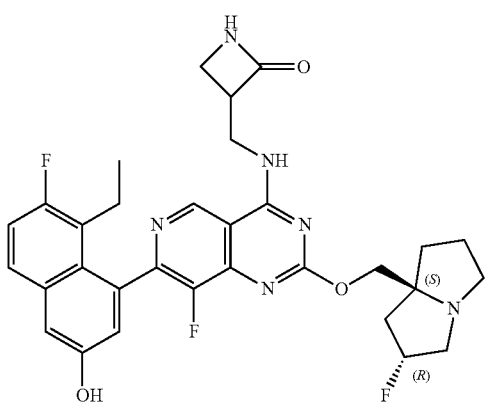

3-(((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)methyl)azetidin-2-one

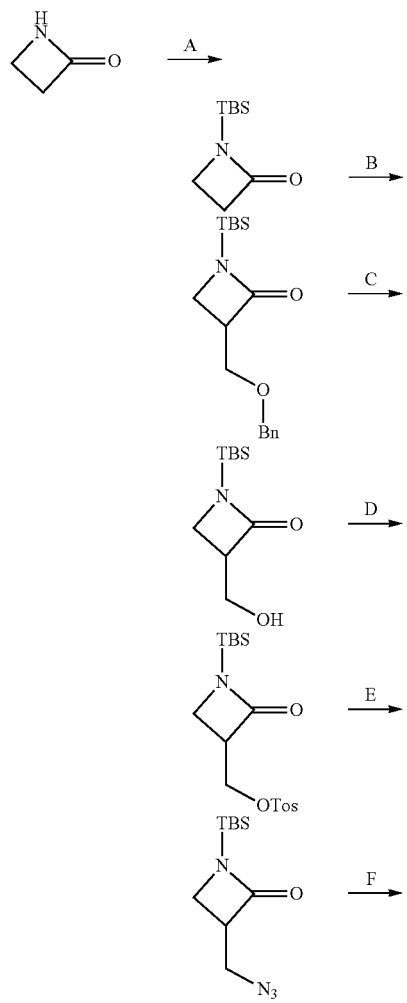

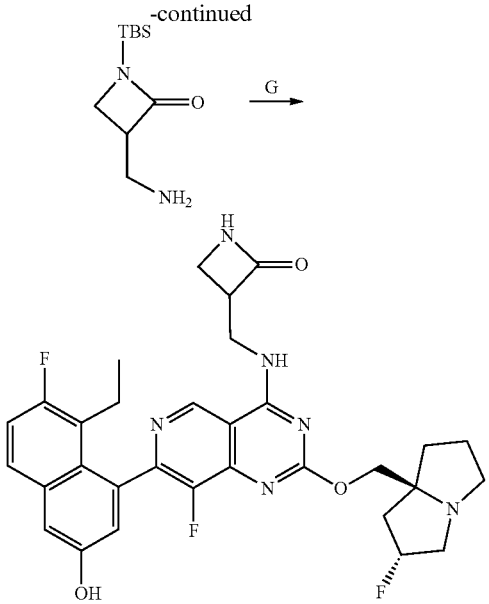

Step A. 1-[tert-butyl(dimethyl)silyl]azetidin-2-one: azetidin-2-one (2.00 g, 1.0 equiv.) and tert-butylchlorodimethylsilane (4.88 g, 1.1 equiv.) were dissolved in dichloromethane (25 mL) at 20° C. under nitrogen atmosphere. A solution of diisopropylethylamine (5.46 g, 1.5 equiv.) in dichloromethane (15 mL) was added dropwise. The resulting mixture was stirred at 25° C. for 20 hours. The mixture was concentrated. The residue was diluted with petroleum ether/ethyl acetate (1:1, 100 mL) and the mixture was filtered. The filtrate was concentrated. The residue was purified by flash silica gel chromatography (ethyl acetate/petroleum ether 1:4) to afford the title compound (4.90 g, 94% yield) as a colorless oil; $^1$H NMR (400 MHz, CDCl$_3$) δ=3.21-3.17 (m, 2H), 3.09-3.04 (m, 2H), 0.95 (d, J=0.8 Hz, 9H), 0.23 (d, J=1.2 Hz, 6H); LCMS (ESI, M+1): m/z=186.2.

Step B. 3-(benzyloxymethyl)-1-[tert-butyl(dimethyl)silyl]azetidin-2-one: To a solution of ((chloromethoxy)methyl)benzene (1.86 g, 1.1 equiv.) in tetrahydrofuran (40 mL) was added lithium diisopropylamide (2.0 M in THF, 1.2 equiv.) at −70° C. under nitrogen atmosphere. After stirring at −70° C. for 0.5 hour, a solution of 1-[tert-butyl(dimethyl)silyl]azetidin-2-one (2.00 g, 1.0 equiv.) in tetrahydrofuran (8 mL) was added to above mixture at −70° C. The resulting mixture was stirred at −70° C. for 1 hour and then warmed up to 25° C. and stirred at 25° C. for 16 hours. The mixture was quenched with saturated ammonium chloride solution (150 mL) at 0° C. under nitrogen atmosphere and extracted with ethyl acetate (3×100 mL). The combined organic layers were washed with brine, dried over anhydrous sodium sulfate, filtered and concentrated in vacuum. The residue was purified by flash silica gel chromatography (petroleum ether/ethyl acetate 0 to 100%) to afford the title compound (1.8 g, 39% yield) as a colorless oil; LCMS (ESI, M+1): m/z=306.2.

Step C. 1-[tert-butyl(dimethyl)silyl]-3-(hydroxymethyl)azetidin-2-one: To a solution of 3-(benzyloxymethyl)-1-[tert-butyl(dimethyl)silyl]azetidin-2-one (2.06 g, 1.0 equiv.) in methanol (40 mL) was added palladium/carbon (2.00 g, 10% purity, wet) under nitrogen atmosphere. The suspension was degassed under vacuum and purged with hydrogen The mixture was stirred under hydrogen atmosphere (15.0 psi) at 40° C. for 16 hours. The reaction mixture was filtered. The filter cake was washed with methanol (2×20 mL). The combined filtrate was concentrated in vacuum to afford the title compound (1.20 g, 66% yield) as a yellow oil; LCMS (ESI, M+1): m/z=216.1.

Step D. [1-[tert-butyl(dimethyl)silyl]-2-oxo-azetidin-3-yl]methyl 4-methylbenzenesulfonate: To a solution of 1-[tert-butyl(dimethyl)silyl]-3-(hydroxymethyl)azetidin-2-one (0.20 g, 1.0 equiv.) in dichloromethane (2 mL) was added 4-methylbenzenesulfonyl chloride (195 mg, 1.1 equiv.) and triethylamine (188 mg, 2.0 equiv.) at 0° C. The mixture was stirred at 25° C. for 16 hours. The mixture was poured into water (10 mL) and extracted with dichloromethane (3×10 mL). The combined organic phase was washed with brine (2×10 mL), dried over anhydrous sodium sulfate, filtered and concentrated in vacuum. Then the crude was purified by flash silica gel chromatography (petroleum ether/ethyl acetate 0 to 100%) to afford the title compound (130 mg, 37% yield) as a colorless oil; $^1$H NMR (400 MHz, DMSO-$d_6$) δ=7.78 (m, 2H), 7.50 (m, 2H), 4.23 (m, 2H), 3.67-3.59 (m, 1H), 3.26 (m, 1H), 2.93 (m, 1H), 2.43 (s, 3H), 0.87 (s, 9H), 0.17 (s, 3H), 0.13 (s, 3H); LCMS (ESI, M+1): m/z=370.2.

Step E. 3-(azidomethyl)-1-(tert-butyldimethylsilyl)azetidin-2-one: To a solution of [1-[tert-butyl(dimethyl)silyl]-2-oxo-azetidin-3-yl]methyl 4-methylbenzenesulfonate (130 mg, 1.0 equiv.) in dimethylformamide (2 mL) was added sodium azide (68.6 mg, 3.0 equiv. The mixture was stirred at 60° C. for 16 hours. The mixture was poured into water (10 mL) and extracted with ethyl acetate (3×10 mL). The combined organic layers were washed with brine (3×10 mL), dried over anhydrous sodium sulfate, filtered and concentrated to afford the title compound (80 mg, crude) as a colorless liquid; LCMS (ESI, M+1): m/z=240.1.

Step F. 3-(aminomethyl)-1-[tert-butyl(dimethyl)silyl]azetidin-2-one: To a solution of 3-(azidomethyl)-1-[tert-butyl(dimethyl)silyl]azetidin-2-one (80.0 mg, 1.0 equiv.) in methanol (1 mL) was added palladium/carbon (40.0 mg, 10% purity, wet) under nitrogen atmosphere. The suspension was degassed under vacuum and purged with hydrogen. The mixture was stirred under hydrogen atmosphere (15.0 psi) at 25° C. for 16 hours. The reaction mixture was filtered. The filter cake was washed with methanol (2×5 mL). The filtrate was concentrated in vacuum to afford the title compound (60 mg, crude in 1 mL N,N-dimethylform amide) as a white liquid; LCMS (ESI, M+1): m/z=215.1.

Step G. 3-(((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d$_1$pyrimidin-4-yl)amino)methyl)azetidin-2-one: To a solution of 5-ethyl-6-fluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (30.0 mg, 1.0 equiv.) and 3-(aminomethyl)-1-[tert-butyl(dimethyl)silyl]azetidin-2-one (21.7 mg, 2.0 equiv.) in N,N-dimethylformamide (0.5 mL) was added diisopropylethylamine (19.6 mg, 3.0 equiv.) and 4 Å molecular sieves (30 mg) at 25° C. The mixture was stirred at 40° C. for 2 hours. The reaction mixture was filtered and the filtrate was purified by prep-HPLC [column: Waters Xbridge 150×25 mm×5 μm; mobile phase: water (10 mM ammonium bicarbonate)/acetonitrile. B %: 34%-64%, 8 min] to afford the title compound (2.33 mg, 7.7% yield) as a white solid; $^1$H NMR (400 MHz, DMSO-$d_6$) δ=9.95 (s, 1H), 9.32 (s, 1H), 9.20 (m, 1H), 7.92 (s, 1H), 7.77 (dd, J=6.0, 9.2 Hz, 1H), 7.40-7.31 (m, 2H), 7.00 (d, J=2.4 Hz, 1H), 5.46-5.24 (m, 1H), 4.25-4.10 (m, 2H), 4.03-3.94 (m, 1H), 3.78 (m, 1H), 3.60 (m, 1H), 3.14 (m, 2H), 2.94-2.75 (m, 2H), 2.44-2.23 (m, 2H), 2.22-2.04 (m, 4H), 1.91-1.77 (m, 3H), 1.24 (br s, 1H), 0.72 (t, J=7.2 Hz, 3H); LCMS (ESI, M+1): m/z=593.4.

Example 486

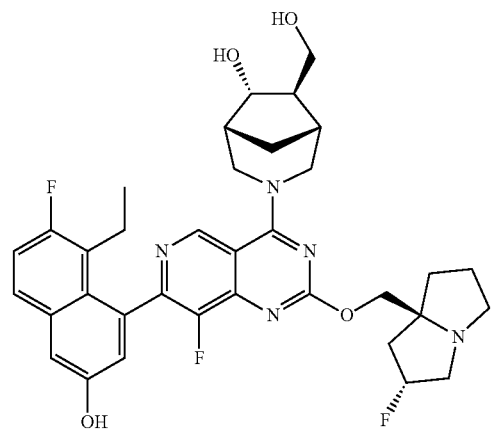 [SMILES: CCc1c(F)ccc2cc(O)cc(-c3ncc4c(N5C[C@H]6C[C@@H](C5)[C@H](CO)[C@H]6O)nc(OC[C@@]56CCCN5C[C@H](F)C6)nc4c3F)c12]

(1 R,5R,6S,7R)-3-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-7-(hydroxymethyl)-3-azabicyclo[3.2.1]octan-6-ol

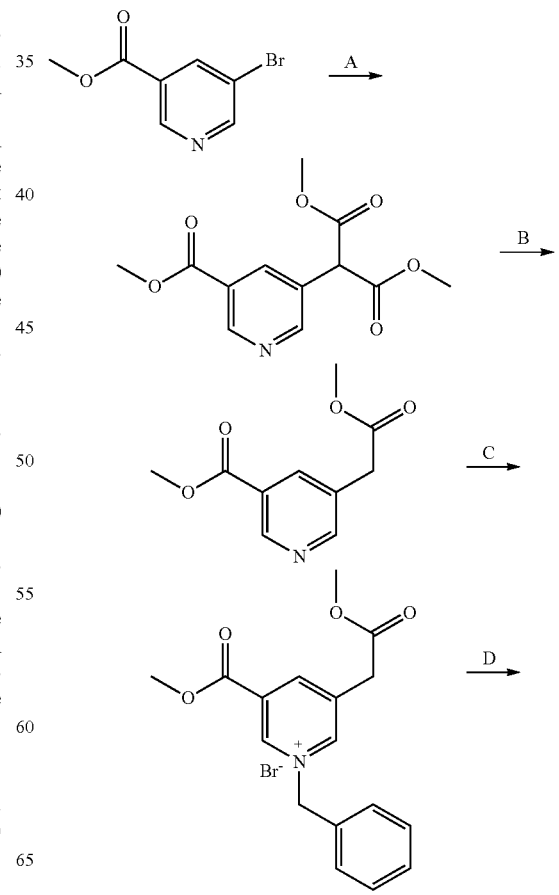

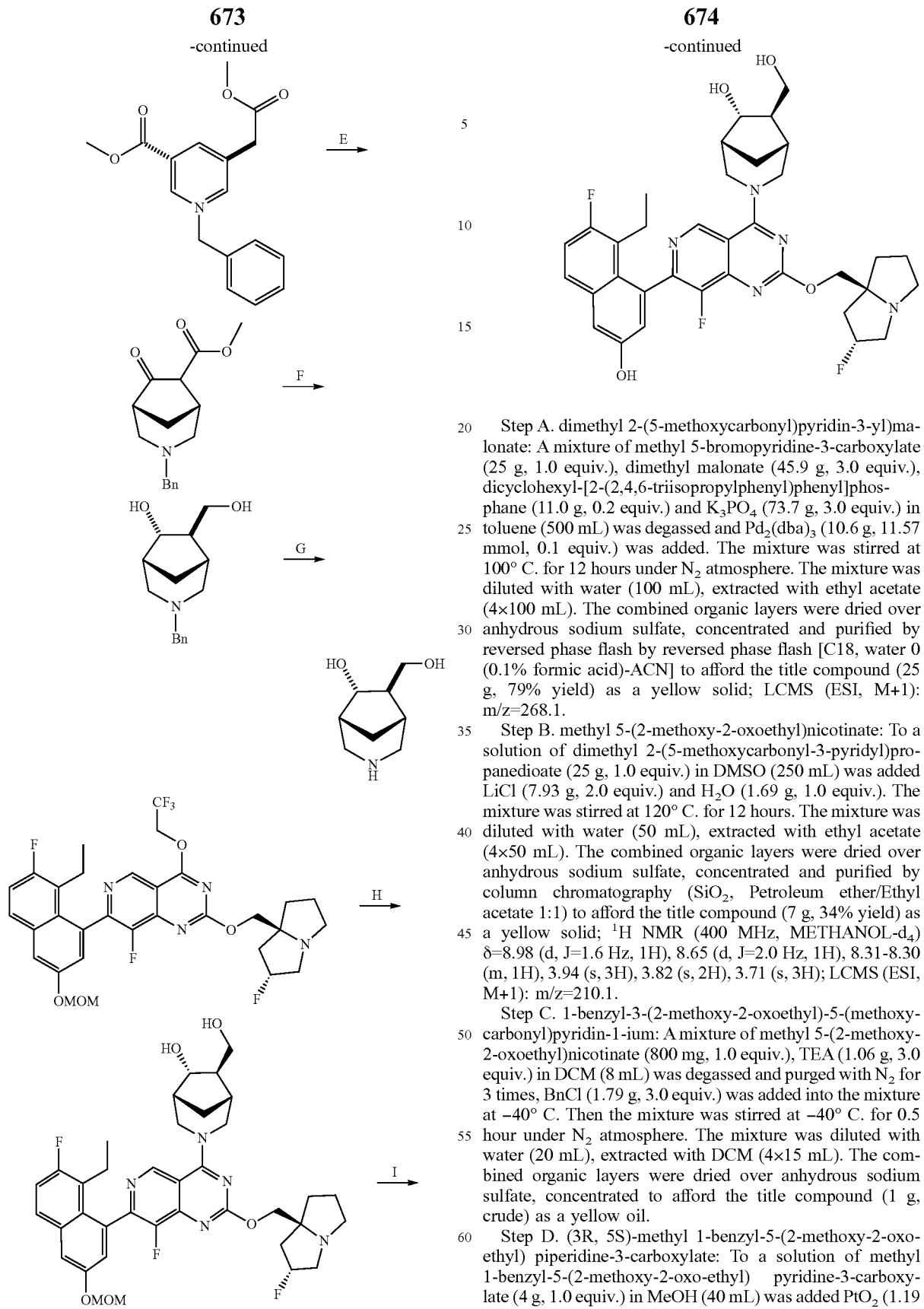

Step A. dimethyl 2-(5-methoxycarbonyl)pyridin-3-yl)malonate: A mixture of methyl 5-bromopyridine-3-carboxylate (25 g, 1.0 equiv.), dimethyl malonate (45.9 g, 3.0 equiv.), dicyclohexyl-[2-(2,4,6-triisopropylphenyl)phenyl]phosphane (11.0 g, 0.2 equiv.) and $K_3PO_4$ (73.7 g, 3.0 equiv.) in toluene (500 mL) was degassed and $Pd_2(dba)_3$ (10.6 g, 11.57 mmol, 0.1 equiv.) was added. The mixture was stirred at 100° C. for 12 hours under $N_2$ atmosphere. The mixture was diluted with water (100 mL), extracted with ethyl acetate (4×100 mL). The combined organic layers were dried over anhydrous sodium sulfate, concentrated and purified by reversed phase flash by reversed phase flash [C18, water 0 (0.1% formic acid)-ACN] to afford the title compound (25 g, 79% yield) as a yellow solid; LCMS (ESI, M+1): m/z=268.1.

Step B. methyl 5-(2-methoxy-2-oxoethyl)nicotinate: To a solution of dimethyl 2-(5-methoxycarbonyl-3-pyridyl)propanedioate (25 g, 1.0 equiv.) in DMSO (250 mL) was added LiCl (7.93 g, 2.0 equiv.) and $H_2O$ (1.69 g, 1.0 equiv.). The mixture was stirred at 120° C. for 12 hours. The mixture was diluted with water (50 mL), extracted with ethyl acetate (4×50 mL). The combined organic layers were dried over anhydrous sodium sulfate, concentrated and purified by column chromatography ($SiO_2$, Petroleum ether/Ethyl acetate 1:1) to afford the title compound (7 g, 34% yield) as a yellow solid; $^1$H NMR (400 MHz, METHANOL-$d_4$) δ=8.98 (d, J=1.6 Hz, 1H), 8.65 (d, J=2.0 Hz, 1H), 8.31-8.30 (m, 1H), 3.94 (s, 3H), 3.82 (s, 2H), 3.71 (s, 3H); LCMS (ESI, M+1): m/z=210.1.

Step C. 1-benzyl-3-(2-methoxy-2-oxoethyl)-5-(methoxycarbonyl)pyridin-1-ium: A mixture of methyl 5-(2-methoxy-2-oxoethyl)nicotinate (800 mg, 1.0 equiv.), TEA (1.06 g, 3.0 equiv.) in DCM (8 mL) was degassed and purged with $N_2$ for 3 times, BnCl (1.79 g, 3.0 equiv.) was added into the mixture at −40° C. Then the mixture was stirred at −40° C. for 0.5 hour under $N_2$ atmosphere. The mixture was diluted with water (20 mL), extracted with DCM (4×15 mL). The combined organic layers were dried over anhydrous sodium sulfate, concentrated to afford the title compound (1 g, crude) as a yellow oil.

Step D. (3R, 5S)-methyl 1-benzyl-5-(2-methoxy-2-oxoethyl) piperidine-3-carboxylate: To a solution of methyl 1-benzyl-5-(2-methoxy-2-oxo-ethyl) pyridine-3-carboxylate (4 g, 1.0 equiv.) in MeOH (40 mL) was added $PtO_2$ (1.19 g, 0.4 equiv.) under $N_2$ atmosphere. The suspension was degassed and purged with $H_2$. The mixture was stirred under $H_2$ (50 Psi) at 40° C. for 12 hours. The reaction mixture was filtered and purified by prep-HPLC [column: Kromasil Eternity XT 250×80 mm×10 μm; mobile phase: water (0.1% ammonia hydroxide)-ACN; B %: 45° %6-75%, 20 min) and lyophilized to afford the title compound (1.2 g, 22% yield) as a yellow oil; $^1$H NMR (400 MHz, METHANOL-d$_4$) δ=7.33-7.23 (m, 5H), 3.65-3.60 (m, 6H), 3.60-3.49 (m, 2H), 3.12-3.04 (m, 1H), 2.93-2.91 (m, 11H), 2.69-2.59 (m, 1H), 2.08-2.07 (m, 2H), 2.05-2.04 (m, 2H), 1.95-1.63 (m, 1H), 1.68-1.63 (m, 1H), 1.14-1.01 (m, 1H); LCMS (ESI, M+1): m/z=306.0.

Step E. methyl 3-benzyl-7-oxo-3-azabicyclo [3.2.1] octane-6-carboxylate: To a solution of (3R, 5S)-methyl 1-benzyl-5-(2-methoxy-2-oxo-ethyl) piperidine-3-carboxylate (1.0 g, 1.0 equiv.) in THF (90 mL) was added t-BuOK (1.0 M, 9.82 mL, 3.0 equiv.). The mixture was stirred at 25° C. for 12 hours. The mixture was diluted with water (50 mL), extracted with ethyl acetate (4×30 mL). The combined organic layers were dried over anhydrous sodium sulfate, concentrated and purified by column chromatography (SiO$_2$, Petroleum ether/Ethyl acetate 15:1 to 10:1) to afford the title compound (350 mg, 24% yield) as a yellow oil; LCMS (ESI, M+1): m/z=274.0.

Step F. (6S,7R)-3-benzyl-7-(hydroxymethyl-3-azabicyclo [3.2.1] octan-6-ol: To a solution of methyl 3-benzyl-7-oxo-3-azabicyclo [3,2,1]octane-6-carboxylate (350 mg, 1.0 equiv.) in THF (1 mL) was added LiAlH$_4$ (146 mg, 3.0 equiv.). The mixture was stirred at 0° C. for 2 hours. The mixture was diluted with water (20 mL), extracted with ethyl acetate (4×20 mL). The combined organic layers were dried over anhydrous sodium sulfate, concentrated and purified by prep-HPLC [column: Waters Xbridge 150×25 mm×5 μm; mobile phase: water (0.1% ammonia hydroxide)-ACN; B %: 23%-53%, 9 min] to afford the title compound (200 mg, 63% yield) as a yellow oil; LCMS (ESI, M+1): m/z=248.0.

Step G. (6S,7R)-7-(hydroxymethyl)-3-azabicyclo[3.2.1] octan-6-ol: To a solution of 3-benzyl-7-(hydroxymethyl)-3-azabicyclo[3,2,1]octan-6-ol (200 mg, 1.0 equiv.) in MeOH (3 mL) was added Pd/C (50 mg, 1.0 equiv.) under N$_2$atmosphere. The suspension was degassed and purged with H$_2$ The mixture was stirred under H$_2$ (15 psi) at 25° C. for 12 hours before being filtered and concentrated to afford the title compound (100 mg, 79% yield) as a white oil.

Step H. (1R,5R,6S,7R)-3-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-7-(hydroxymethyl)-3-azabicyclo[3.2.1] octan-6-ol: To a solution of 7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (100 mg, 1.0 equiv.) and (1R,5R,6S,7R)-7-(hydroxymethyl)-3-azabicyclo [3,2,1]octan-6-ol (44.4 mg, 1.8 equiv.) in DMF (0.5 mL) was added DIEA (60.9 mg, 3.0 equiv.) and 4 Å molecular sieves (20 mg). The mixture was stirred at 40° C. for 12 hours. The reaction mixture was filtered and purified by prep-HPLC [column: Phenomenex luna C18 150×25 mm×10 μm; mobile phase: water (0.1% formic acid), /ACN; B %: 15%-45%, 2 min] to afford the title compound (50 mg, 46% yield) as white solid.

Step I (1R,5R,6S,7R)-3-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-7-(hydroxymethyl)-3-azabicyclo[3.2.1]octan-6-ol: To a solution of (1R,5R,6S,7R)-3-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-7-(hydroxymethyl)-3-azabicyclo[3,2,1] octan-6-ol (50 mg, 1.0 equiv.) in MeOH (2 mL) was added HCl-MeOH (4 M, 2 mL, 111 equiv.). The mixture was stirred at 0° C. for 1 hour. The residue was filtered and the filtrate was purified by prep-HPLC [column: Waters Xbridge 150×25 mm×5 μm; mobile phase: water (0.1% ammonia hydroxide)/ACN; B %: 28%-58%, 9 min] and lyophilized to afford the title compound (37.8 mg, 80% yield) as a yellow solid; $^1$H NMR (400 MHz, METHANOL-d$_4$) δ=9.31-9.18 (m, 1H), 7.68-7.65 (m, 1H), 7.29-7.26 (m, 1H), 7.24-7.22 (m, 1H), 7.07-7.04 (m, 1H), 5.40-5.21 (m, 1H), 5.07-4.95 (m, 1H), 4.83-4.75 (m, 1H), 4.39-4.15 (m, 2H), 3.90-3.68 (m, 2H), 3.68-3.58 (m, 1H), 3.57-3.41 (m, 2H), 3.29-3.11 (m, 3H), 3.19-2.99 (m, 1H), 2.51-2.30 (m, 1H), 2.38-2.07 (m, 6H), 2.05-1.74 (m, 6H), 0.86-0.72 (m, 3H); LCMS (ESI, M+1): m/z=650.4.

Example 487

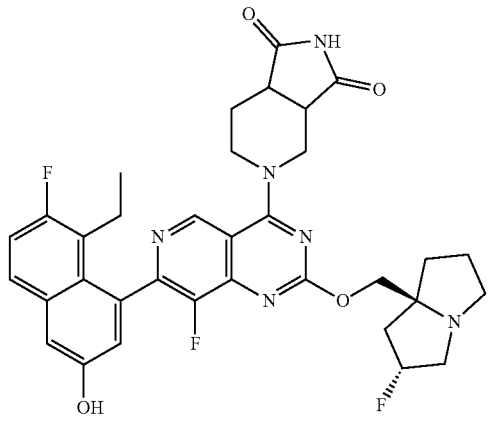 [SMILES: CCc1c(F)ccc2cc(O)cc(-c3ncc4c(N5CCC6C(=O)NC(=O)C6C5)nc(OC[C@@]56CCCN5C[C@H](F)C6)nc4c3F)c12]

5-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl) hexahydro-1H-pyrrolo[3,4-c]pyridine-1,3(2H)-dione The title compound was synthesized according to the procedure described for example 330. $^1$H NMR (400 MHz, METHANOL-d$_4$) δ=9.22 (s, 1H), 8.57 (s, 1H), 7.69 (dd, J=5.6, 9.2 Hz, 1H), 7.32 (d, J=2.8 Hz, 1H), 7.26 (t, J=9.6 Hz, 1H), 7.08 (t, J=2.8 Hz, 1H), 5.43-5.21 (m, 1H), 4.75 (br dd, J=3.6, 13.6 Hz, 1H), 4.41-4.24 (m, 2H), 4.20-4.04 (m, 2H), 4.04-3.92 (m, 1H), 3.36 (br d, J=3.6 Hz, 1H), 3.32-3.23 (m, 3H), 3.15 (br d, J=1.6 Hz, 1H), 3.05-2.99 (m, 1H), 2.52-2.39 (m, 2H), 2.38-2.33 (m, 1H), 2.33-2.25 (m, 1H), 2.24-2.10 (m, 3H), 2.04-1.91 (m, 3H), 1.28-1.20 (m, 1H), 0.81 (q, J=7.6 Hz, 3H); LCMS (ESI, M+1): m/z=647.

Example 488

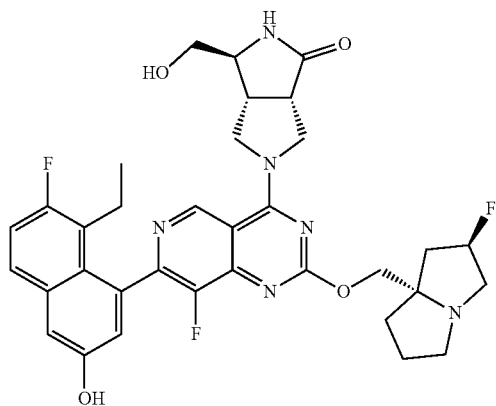 [SMILES: CCc1c(F)ccc2cc(O)cc(-c3ncc4c(N5C[C@@H]6[C@@H](CO)NC(=O)[C@@H]6C5)nc(OC[C@@]56CCCN5C[C@H](F)C6)nc4c3F)c12]

(3R,3aR,6aS)-5-(7-(8-ethyl-7-fluoro-3-hydroxynaph-thalen-1-yl)-8-fluoro-2-(((2R,7aS)-2-fluorotetra-hydro-1H-pyrrolizin-7a(5H)-yl)methoxy)pyrido[4,3-d]pyrimidin-4-yl)-3-(hydroxymethyl)hexahydropyrrolo[3,4-c]pyrrol-1(2H)-one

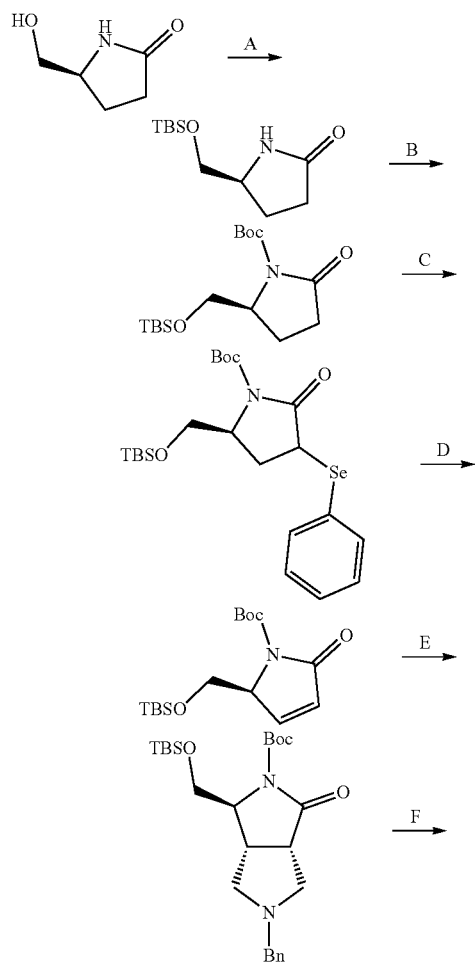

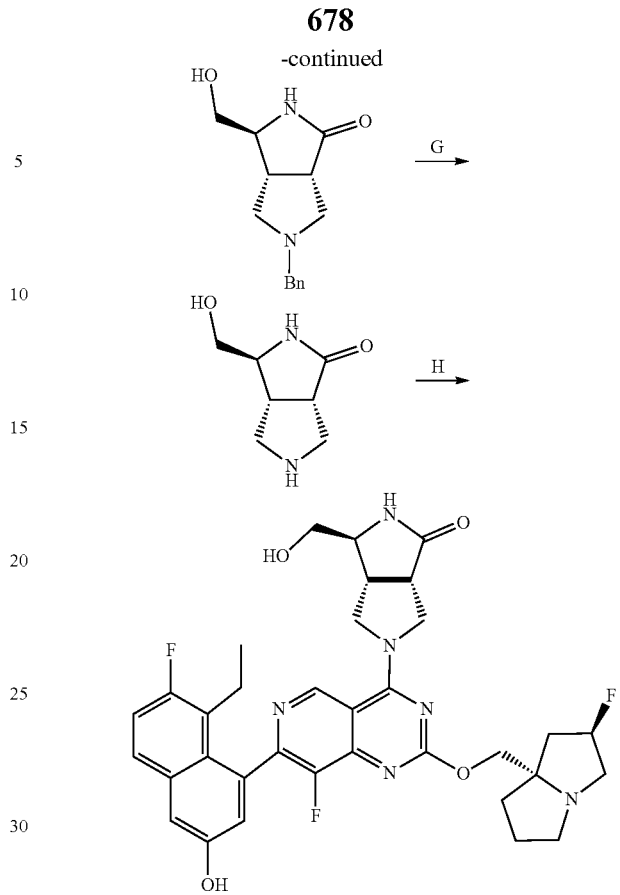

Step A. (S)-5-(((tert-butyldimethylsilyl)oxy)methyl)pyrrolidin-2-one: To a solution of (5S)-5-(hydroxymethyl)pyrrolidin-2-one (10.0 g, 1.0 equiv.) and imidazole (8.80 g, 1.5 equiv.) in dichloromethane (100 mL) was added tert-butyldimethylsilyl chloride (15.7 g, 1.2 equiv.) portion wise at 0-5° C. The resulting mixture was allowed to warm up to 25-30° C. and stirred for 12 hours. The mixture was diluted with water (150 mL) and the layers were separated. The aqueous phase was extracted with dichloromethane (2×50 mL). The combined organic layers were washed with brine, dried over sodium sulfate, filtered, and concentrated in vacuum. The residue was purified by flash silica gel chromatography [Ethyl acetate/Petroleum ether 50 to 100%] to afford the title compound (17.5 g, 83% yield) as a colorless liquid; $^1$H NMR (400 MHz, CDCl$_3$-d$_4$) δ=5.98 (br s, 1H), 3.81-3.71 (m, 1H), 3.62 (dd, J=4.0, 10.0 Hz, 1H), 3.44 (dd, J=7.6, 10.0 Hz, 1H), 2.40-2.30 (m, 2H), 2.22-2.11 (m, 1H), 1.81-1.69 (m, 1H), 0.88 (s, 9H), 0.06 (s, 6H); LCMS (ESI, M+1): m/z=230.2.

Step B. tert-butyl (S)-2-(((tert-butyldimethylsilyl)oxy)methyl)-5-oxopyrrolidine-1-carboxylate: To a solution of (5S)-5-[[tert-butyl(dimethyl)silyl]oxymethyl]pyrrolidin-2-one (2.0 g, 1.0 equiv.) in dichloromethane (20 mL) was added tert-butyldicarbonate (2.8 g, 1.5 equiv.), triethylamine (1.7 g, 2.0 equiv.) and 4-dimethylaminopyridine (106 mg, 0.1 equiv.). The resulting mixture was stirred at 25° C. for 12 hours. The mixture was concentrated in vacuum. The residue was purified by flash silica gel chromatography [Ethyl acetate/Petroleum ether 1:4] to afford the title compound (2.25 g, 78% yield) as a colorless oil; $^1$H NMR (400 MHz, CDCl$_3$-d) δ=4.22-4.13 (m, 1H), 3.92 (dd, J=4.0, 10.4 Hz, 1H), 3.69 (dd, J=2.0, 10.4 Hz, 1H), 2.78-2.64 (m, 1H), 2.38 (ddd, J=2.0, 9.6, 17.6 Hz, 1H), 2.16-1.96 (m, 2H), 1.54 (s, 9H), 0.88 (s, 9H), 0.04 (d, J=5.2 Hz, 6H); LCMS (ESI, M−99): m/z=230.2.

Step C. tert-butyl (5S)-5-(((tert-butyldimethylsilyl)oxy methyl)-2-oxo-3-(phenylselanyl)pyrrolidine-1-carboxylate: To a solution of tert-butyl (2S)-2-[[tert-butyl(dimethyl)silyl] oxymethyl]-5-oxo-pyrrolidine-1-carboxylate (1.0 g, 1.0 equiv.) in tetrahydrofuran (25 mL) was added lithium hexamethyldisilazide (1 M, 3.3 mL, 1.1 equiv.) dropwise at −60° C. under nitrogen atmosphere. The solution was stirred at −60° C. for 0.5 hour before a solution of phenyl selenohypochlorite (1.0 g, 1.75 equiv.) in tetrahydrofuran (5.0 mL) was added at −60° C. The resulting mixture was stirred at −60 for additional 1 hour and then warmed to 25° C. and stirred at 25° C. for 12 hours. The mixture was quenched with saturated ammonium chloride (40 mL) at 0-5° C. under nitrogen, and allowed to warm to 25° C. and stirred for 0.5 hour. The mixture was extracted with ethyl acetate (3×25 mL). The combined organic layers were washed with brine, dried over sodium sulfate, filtered and concentrated in vacuum. The residue was purified by flash silica gel chromatography [Ethyl acetate/Petroleum ether 10 to 15%] to afford the title compound (740 mg, 50% yield) as a yellow oil; LCMS (ESI, M−99): m/z=386.2.

Step D. tert-butyl (S)-2-(((tert-butyldimethylsilyl)oxy) methyl)-5-oxo-2,5-dihydro-1H-pyrrole-1-carboxylate: To a solution of tert-butyl (5S)-5-[[tert-butyl(dimethyl)silyl] oxymethyl]-2-oxo-3-phenylselanyl-pyrrolidine-1-carboxylate (740 mg, 1.0 equiv.) in dichloromethane (10.0 mL) was added pyridine (362 mg, 3.0 equiv.) at −70° C., followed by slow addition of hydrogen peroxide (606 mg, 30% in water, 3.5 equiv.). The resulting mixture was allowed to warm up to 25° C. and stirred at 25° C. for 12 hours. The mixture was diluted with water (20 mL) and extracted with dichloromethane (2×10 mL). The combined organic layers were washed with saturated sodium sulfite and brine, dried over sodium sulfate, filtered and concentrated in vacuum. The residue was purified by flash silica gel chromatography [Ethyl acetate/Petroleum ether 10 to 15%] to afford the title compound (230 mg, 34% yield) as a colorless oil; LCMS (ESI, M−99): m/z=228.1.

Step E. tert-butyl (1S,3aS,6aR)-5-benzyl-1-(((tert-butyldimethylsilyl)oxy)methyl)-3-oxohexahydropyrrolo[3,4-c]pyrrole-2(1H)-carboxylate: To a solution of tert-butyl (2S)-2-[[tert-butyl(dimethyl)silyl]oxymethyl]-5-oxo-2H-pyrrole-1-carboxylate (180 mg, 1.0 equiv.) and N-(methoxymethyl)-1-phenyl-N-(trimethylsilylmethyl) methanamine (391 mg, 3.0 equiv.) in dichloromethane (5.0 mL) was added TFA (25 mg, 0.4 equiv.) at 0° C. After addition, the resulting mixture was stirred at 25° C. for 12 hours. The mixture was concentrated in vacuum. The residue was purified by prep-HPLC [column: Phenomenex Luna C18 75×30 mm×3 μm; mobile phase: water (0.1% HCl)—CH₃CN, B %: 39%-59%, 6 min] to afford the title compound (102 mg, 37% yield) as a yellow solid; LCMS (ESI, M+1): m/z=461.4.

Step F. (3S,3aR,6aS)-5-benzyl-3-(hydroxymethyl)hexahydropyrrolo[3,4-c]pyrrol-1(2H)-one: To a solution of tert-butyl (3aS,6S,6aR)-2-benzyl-6-[[tert-butyl(dimethyl)silyl] oxymethyl]-4-oxo-3,3a,6,6a-tetrahydro-1H-pyrrolo[3,4-c] pyrrole-5-carboxylate (102 mg, 1 equiv.) in methanol (1.0 mL) was added HCl-MeOH (1.0 mL, 4M). The resulting mixture was stirred at 25° C. for 2 hours. The mixture was concentrated in vacuum to afford the title compound (65 mg, crude, HCl) as a white solid. LCMS (ESI, M+1): m/z=247.1.

Step G. (3S,3aR,6aS)-5-benzyl-3-(hydroxymethyl)hexahydropyrrolo[3,4-c]pyrrol-1(2H)-one: To a flask charged with Pd/C (20 mg, 10% purity) was added a solution of (1S,3aS,6aR)-5-benzyl-1-(hydroxymethyl)-1,2,3a,4,6,6a-hexahydropyrrolo[3,4-c]pyrrol-3-one (65 mg, 1.0 equiv, hydrochloride) in methanol (2.0 mL). The mixture was degassed and stirred at 70° C. under H₂ (50 psi) for 24 hours. The mixture was filtered and the filtrate was concentrated. The residue was diluted with acetonitrile/water (v/v, 1/2) and lyophilized directly to give the title compound (45 mg, crude, hydrochloride) as a white gum; LCMS (ESI, M+1): m/z=157.2.

Step H. (3R,3aR,6aS)-5-(7-(8-ethyl-7-fluoro-3-hydroxynaphthalen-1-yl)-8-fluoro-2-(((2R,7aS)-2-fluorotetrahydro-1H-pyrrolizin-7a(5H)y-yl)methoxy)pyrido[4,3-d]pyrimidin-4-yl)-3-(hydroxymethyl)hexahydropyrrolo[3,4-c] pyrrol-1(2H)-one: To a solution of (3aS,6S,6aR)-6-(hydroxymethyl)-2,3,3a,5,6,6a-hexahydro-1H-pyrrolo[3,4-c]pyrrol-4-one (32.5 mg, 2.5 equiv, hydrochloride) and 5-ethyl-6-fluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (40 mg, 1.0 equiv.) in N,N-Dimethylformamide (3.0 mL) was added N,N-Diisopropylethylamine (34.9 mg, 4.0 equiv.) and 4 Å molecular sieves (80 mg). The resulting mixture was stirred at 40° C. for 12 hours. The filtrate was purified by prep-HPLC [column: Phenomenex Luna C18 75×30 mm×3 μm; mobile phase: water (0.1% HCl)—CH₃CN; B %: 19%-39%, 6 min] to afford the title compound (13.8 mg, 29% yield, hydrochloride) as yellow solid; ¹H NMR (400 MHz, MeOD-d₄) δ=9.48 (br s, 1H), 7.73 (br dd, J=5.6, 8.8 Hz, 1H), 7.40 (s, 1H), 7.31 (br t, J=9.2 Hz, 1H), 7.17 (br s, 1H), 5.73-5.47 (m, 1H), 4.55 (br s, 6H), 4.30-3.81 (m, 4H), 3.70 (br s, 3H), 3.48 (br s, 2H), 2.88-2.11 (m, 8H), 0.86 (br s, 3H); LCMS (ESI, M+1): m/z=649.4.

Example 489

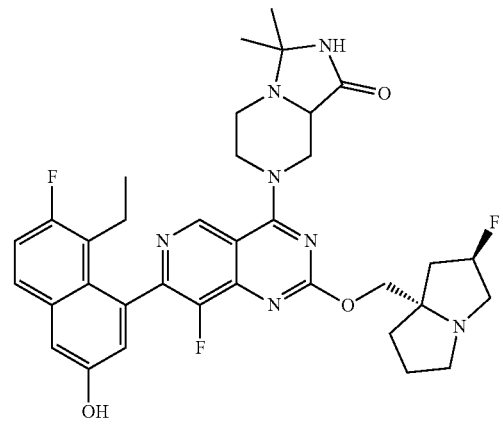 [SMILES: CCc1c(F)ccc2cc(O)cc(-c3ncc4c(N5CCN6C(C5)C(=O)NC6(C)C)nc(OC[C@@]56CCCN5C[C@H](F)C6)nc4c3F)c12]

7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,3-dimethylhexahydroimidazo[1,5-a]pyrazin-1(5H)-one

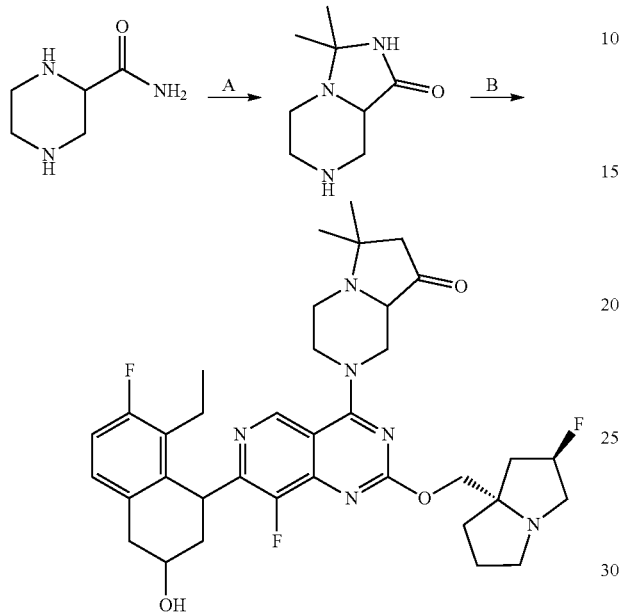

Step A. 3,3-dimethylhexahydroimidazo[1,5-a]pyrazin-1(5H)-one: To a solution of piperazine-2-carboxamide (300 mg, 1.0 equiv.) in acetone (3.0 mL) was added 2-methoxyethanol (265 mg, 1.50 equiv.). The mixture was stirred at 40° C. for 2 hours. After completion, the reaction mixture was cooled to 25° C., filtered and the filtrate was concentrated under reduced pressure to afford the title compound (170 mg, 43% yield) as a white solid; LCMS (ESI, M+1): m/z=170.1.

Step B. 7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3,3-dimethylhexahydroimidazo[1,5-a]pyrazin-1(5H)-one: To a solution of 5-ethyl-6-fluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (60.0 mg, 1.0 equiv.) and 3,3-dimethyl-2,5,6,7,8,8a-hexahydroimidazo[1,5-a]pyrazin-1-one (85.7 mg, 5.0 equiv.) in DMF (0.50 mL) was added 4 Å molecular sieves (10 mg) and diisopropylethylamine (39.3 mg, 3.0 equiv.). The mixture was stirred at 60° C. for 12 hours. The reaction mixture was cooled to 25° C., filtered and the filtrate was partitioned between ethyl acetate (10 mL) and water (10 ml). The organic phase was separated, washed with saturated brine (2×5 mL), dried over sodium sulfate, filtered and concentrated under reduced pressure to give a residue. The residue was purified by prep-HPLC (column: Phenomenex Luna C18 150×25 mm×10 μm; mobile phase: A: water (0.1% formic acid)-ACN]; B %: 14%-44%, 10 min) to afford the title compound (2.88 mg, 4.23% yield) as an off-white solid; $^1$H NMR (400 MHz, CD3OD) δ=9.16 (s, 1H), 7.72-7.65 (m, 1H), 7.32 (d, J=2.8 Hz, 1H), 7.26 (t, J=9.6 Hz, 1H), 7.06 (d, J=2.4 Hz, 1H), 5.53-5.36 (m, 1H), 4.58 (br s, 3H), 4.55-4.44 (m, 2H), 3.70-3.64 (m, 1H), 3.58-3.50 (m, 2H), 3.46 (br s, 2H), 3.17 (br d, J=11.2 Hz, 1H), 2.85-2.76 (m, 1H), 2.59-1.99 (m, 9H), 1.46 (s, 3H), 1.31 (s, 3H), 0.83-0.76 (m, 3H); LCMS (ESI, M+1): m/z=662.4.

Example 490

(3R,6R)-1-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)azepane-3,6-diol

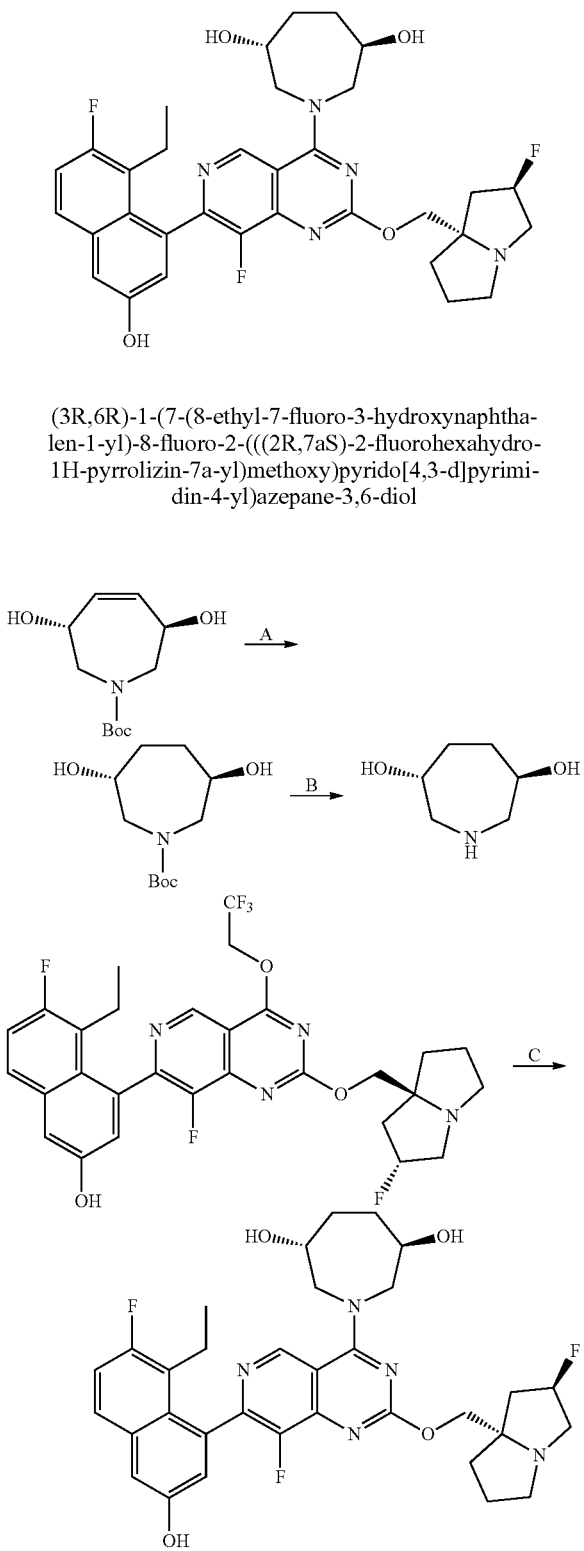

683

Step A. (3R,6R)-tert-butyl 3,6-dihydroxazepine-1-carboxylate: To a solution of tert-butyl 3,6-dihydroxy-2,3,6,7-tetrahydroazepine-1-carboxylate (500 mg, 2.18 mmol, 1.0 equiv.) in MeOH (8 mL) was added Pd/C (100 mg, 10% purity) under Ar. The suspension was degassed and purged with $H_2$. The mixture was stirred under $H_2$ (50 psi) at 30° C. for 16 hours. The mixture was filtered and the filtrate was concentrated under vacuum to afford the title compound (500 mg, crude) as a yellow oil; $^1$H NMR (400 MHz, METHANOL-$d_4$) δ=3.84 (br s, 2H), 3.63 (br dd, J=4.8, 14.4 Hz, 1H), 3.53 (br dd, J=4.8, 14.2 Hz, 1H), 3.35 (s, 1H), 3.14 (br dd, J=7.6, 14.0 Hz, 1H), 2.02-1.89 (m, 2H), 1.74-1.59 (m, 1H), 1.47 (s, 9H), 1.45-1.38 (m, 1H).

Step B. (3R,6R)-azepane-3,6-diol: To a solution of tert-butyl 3,6-dihydroxazepine-1-carboxylate (500 mg, 2.16 mmol, 1.0 equiv.) in MeCN (3 mL) was added HCl·dioxane (4 M, 6 mL) at 0° C. The reaction mixture was stirred at 0° C. for 1 hour. The mixture was concentrated in vacuum to afford the title compound (283 mg, crude, HCl) as a yellow oil.

Step C. (3R,6R)-1-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)azepane-3,6-diol: A suspension of azepane-3,6-diol (111 mg, 660 μmol, 3.9 equiv, HCl), DIEA (109 mg, 844 μmol, 5.0 equiv.) and 4 Å molecular sieves (10 mg) in DMF (0.5 mL) was stirred at 25° C. for 30 minutes. Then 5-ethyl-6-fluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (100 mg, 169 μmol, 1.0 equiv.) was added into the mixture and the mixture was stirred at 40° C. for 72 hours. The reaction mixture was diluted with ethyl acetate (5 mL) and water (10 mL). The mixture was extracted with ethyl acetate (5 mL) and the combined organic phase was washed with brine (5 mL), dried over anhydrous sodium sulfate, filtered and concentrated to give a residue. The residue was purified by column chromatography (SiO$_2$, petroleum ether/ethyl acetate 3:1 then Dichloromethane: Methanol 5:1). Then the mixture was re-purified by prep-HPLC [column: Waters Xbridge 150×25 mm×5 μm; mobile phase: water (10 mM NH$_4$HCO$_3$)-ACN, B %: 34%-54%, 8 min] to afford the title compound (5.8 mg, 5.47% yield) as a white solid; $^1$H NMR (400 MHz, METHANOL-$d_4$) δ=9.57-9.43 (m, 1H), 7.67 (dd, J=5.6, 9.2 Hz, 1H), 7.30 (d, J=2.8 Hz, 1H), 7.25 (t, J=9.6 Hz, 1H), 7.05 (s, 1H), 5.41-5.20 (m, 1H), 4.38-4.19 (m, 6H), 3.94-3.83 (m, 2H), 3.29-3.16 (m, 3H), 3.07-2.97 (m, 1H), 2.56-2.42 (m, 1H), 2.40-2.06 (m, 6H), 2.05-1.86 (m, 3H), 1.70-1.58 (m, 2H), 0.84-0.76 (m, 3H); 1.53-1.31 (m, 1H); LCMS (ESI, M+1): m/z=624.4.

Example 491

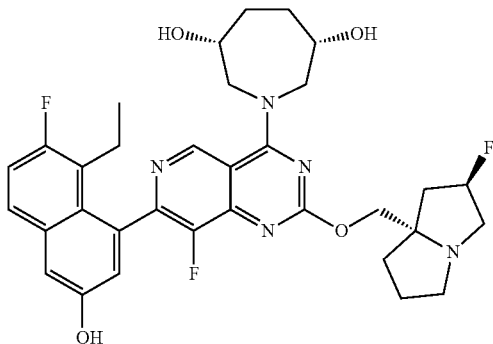 [SMILES: CCc1c(F)ccc2cc(O)cc(-c3ncc4c(N5C[C@H](O)CC[C@H](O)C5)nc(OC[C@@]56CCCN5C[C@H](F)C6)nc4c3F)c12]

684

(3R,6S)-1-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)azepane-3,6-diol

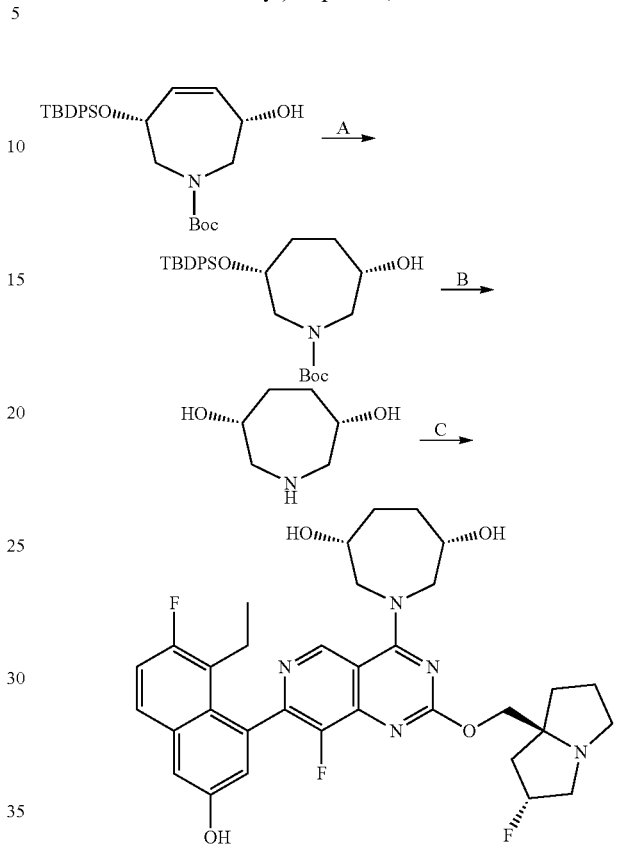

Step A. (3R,6S)-tert-butyl 3-((tert-butyldiphenylsilyl)oxy)-6-hydroxyazepane-1-carboxylate: To a mixture of Pd/C (20 mg, 10% purity) in MeOH (5 mL) was added (3R,6S)-tert-butyl 3-((tert-butyldiphenylsilyl)oxy)-6-hydroxy-2,3,6,7-tetrahydro-1H-azepine-1-carboxylate (0.20 g, 1.0 equiv.). The mixture was degassed and purged with $H_2$ before being stirred at 25° C. for 16 hours (50 Psi). The mixture was filtered and concentrated to afford the tittle compound (165 mg, 82% yield) as a white solid. LCMS (ESI, M+1): m/z=470.2.

Step B. (3R,6S)-azepane-3,6-diol: To a solution of (3R,6S)-tert-butyl 3-((tert-butyldiphenylsilyl)oxy)-6-hydroxyazepane-1-carboxylate (160 mg, 1.0 equiv.) in ACN (2 mL) was added HCl-dioxane (4 M, 2.0 mL) at 0° C. The solution was stirred at 0° C. for 0.5 hour. The mixture was filtered and triturated with ethyl acetate (2 mL) at 25° C. for 0.5 hour to afford the title compound (40 mg, 70% yield) as a white solid.

Step C. (3R,6S)-1-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)azepane-3,6-diol: To a solution of 5-ethyl-6-fluoro-4-(8-fluoro-2-(((2R,7aS)-2-fluorohexahydro-1H-pyrrolizin-7a-yl)methoxy)-4-(2,2,2-trifluoroethoxy)pyrido[4,3-d]pyrimidin-7-yl)naphthalen-2-ol (150 mg, 1.0 equiv.) and (3R,6S)-azepane-3,6-diol (39.8 mg, 1.2 equiv.) in DMF (0.3 mL) were added DIEA (98.1 mg, 132 μL, 3.0 equiv.) and 4 Å molecular sieves (20 mg). The mixture was stirred at 60° C. for 12 hours. The mixture was filtered and purified by reversed phase flash chromatography [C18, water (0.1% formic acid)-ACN] to afford the title compound (15.8 mg, 10% yield) as a white solid. ¹H NMR (400 MHz, METHANOL-d₄) δ=9.37 (s, 1H), 7.67 (dd, J=5.6, 8.8 Hz, 1H), 7.30 (d, J=2.8 Hz, 1H), 7.25 (t, J=9.2 Hz, 1H), 7.06 (d, J=2.4 Hz, 1H), 5.30 (d, J=54.4 Hz, 1H), 4.56-4.40 (m, 2H), 4.37-4.13 (m, 4H), 3.92-3.83 (m, 2H), 3.29-3.16 (m, 3H), 3.05-2.88 (m, 1H), 2.56-2.42 (m, 1H), 2.39-2.10 (m, 4H), 2.07-1.88 (m, 5H), 1.86-1.74 (m, 2H), 0.80 (t, J=7.2 Hz, 3H); LCMS (ESI, M+1): m/z=624.1.

Example 492

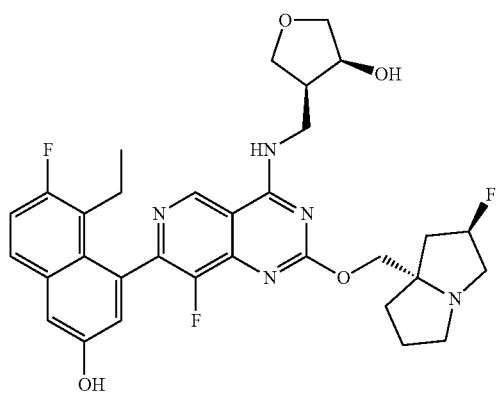 [SMILES: CCc1c(F)ccc2cc(O)cc(-c3ncc4c(NC[C@H]5COC[C@H]5O)nc(OC[C@@]56CCCN5C[C@H](F)C6)nc4c3F)c12]

(3S,4S)-4-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)tetrahydrofuran-3-ol Example 493

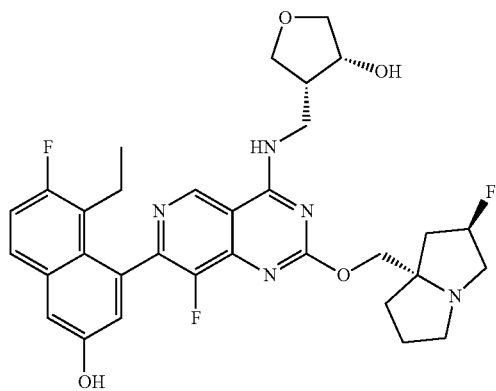 [SMILES: CCc1c(F)ccc2cc(O)cc(-c3ncc4c(NC[C@@H]5COC[C@@H]5O)nc(OC[C@@]56CCCN5C[C@H](F)C6)nc4c3F)c12]

(3R,4R)-4-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)tetrahydrofuran-3-ol

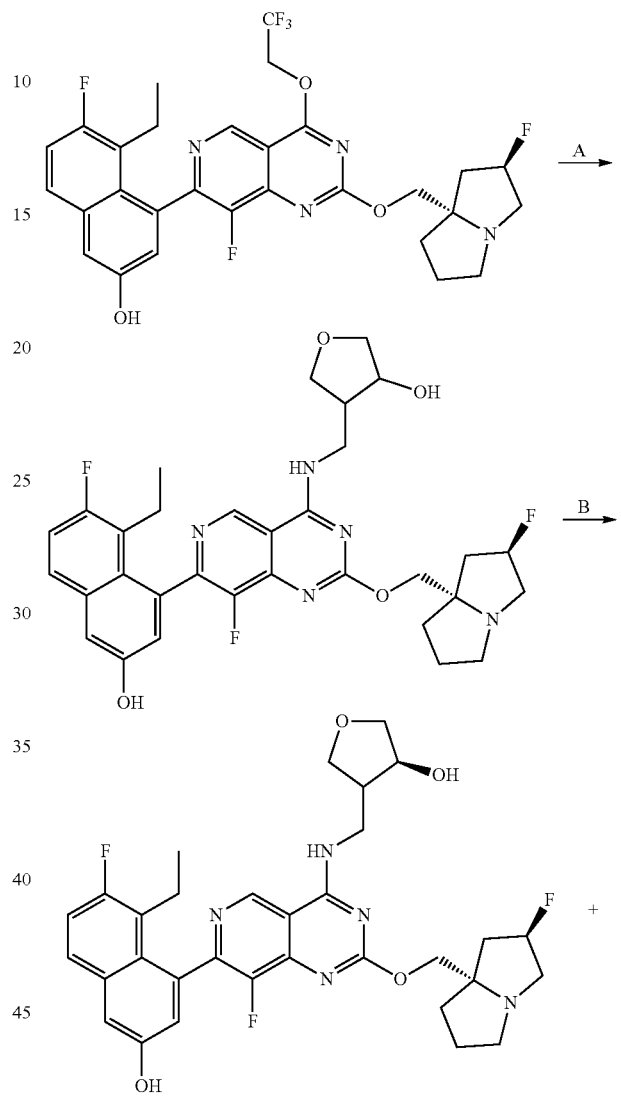

Example 492

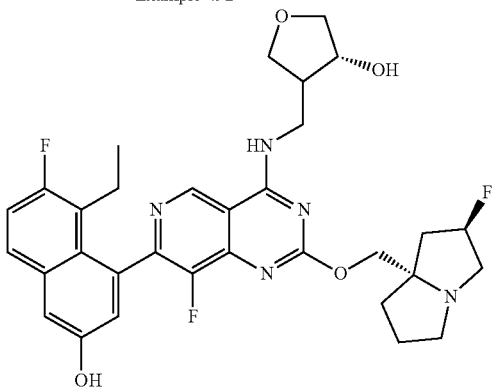

Example 493

Step A. 4-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)tetrahydrofuran-3-ol: To a solution of 5-ethyl-6-fluoro-4-(8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidin-7-yl)naphthalen-2-ol (200 mg, 337 μmol, 1 equiv.) in DMF (4 mL) was added 4 Å molecular sieves (50 mg), cis-4-(aminomethyl)tetrahydrofuran-3-ol (79.1 mg, 2.0 equiv.) and DIPEA (175 mg, 1.35 mmol, 4.0 equiv.). The mixture was stirred at 40° C. for 2 hours and concentrated. The residue was purified by prep-HPLC (column: Phenomenex luna C18 150×25 mm×10 μm; mobile phase: A: water (0.1% formic acid),-ACN; B %: 12/0-42%, 9 min) to afford the title compound (120 mg, 51% yield) as a white solid; LCMS(ESI, M+1): m/z=610.2.

Step B. (3S,4S)-4-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)tetrahydrofuran-3-ol: The mixture of 4-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)tetrahydrofuran-3-ol (120 mg, 196.84 μmol, 1.0 equiv.) was separated by chiral SFC (column: DAICEL CHIRALCEL OJ (250 mm×30 mm, 10 μm); mobile phase: A: [0.1% NH$_3$·H$_2$O, B: IPA; B %: 25%-25%, 10.6; 159 min) to afford Example 492, second eluting peak (33.4 mg, 24% yield, HCOOH) as a yellow solid; $^1$H NMR (400 MHz, DMSO-d$_6$) δ=9.94 (s, 1H), 9.31 (s, 1H), 8.98-8.94 (m, 1H), 7.78-7.74 (m, 1H), 7.37-7.32 (m, 2H), 6.99 (s, 1H), 5.35-5.16 (m, 2H), 4.31 (s, 1H), 4.16 (d, J=10.4 Hz, 1H), 4.07 (d, J=10.4 Hz, 1H), 3.91-3.74 (m, 3H), 3.64-3.54 (m, 3H), 3.14-3.08 (m, 2H), 3.02 (s, 1H), 2.85-2.79 (m, 1H), 2.59-2.54 (m, 1H), 2.37-2.32 (m, 1H), 2.19-2.06 (m, 3H), 2.04-1.91 (m, 2H), 1.85-1.77 (m, 3H), 1.74 (s, 1H), 0.71 (t, J=7.6 Hz, 3H); LCMS (ESI, M+1): m/z=610.2, and Example 493, first eluting peak (35.7 mg, 26% yield, HCOOH) as a yellow solid; $^1$H NMR (400 MHz, DMSO-d$_6$) δ=9.96 (s, 1H), 9.31 (s, 1H), 8.96 (d, J=4.4 Hz, 1H), 8.16 (s, 1H), 7.76 (t, J=6.8 Hz, 1H), 7.36-7.32 (m, 2H), 6.99 (s, 1H), 5.34-5.16 (m, 2H), 4.31 (s, 1H), 4.15 (d, J=10.4 Hz, 1H), 4.07 (d, J=10.4 Hz, 1H), 3.91-3.83 (m, 2H), 3.80-3.74 (m, 1H), 3.64-3.55 (m, 4H), 3.14-3.02 (m, 1H), 2.83-2.82 (m, 2H), 2.33 (s, 1H), 2.19-1.94 (m, 4H), 1.90-1.77 (m, 3H), 0.71 (t, J=7.6 Hz, 3H); LCMS (ESI, M+1): m/z=610.2.

Example 494

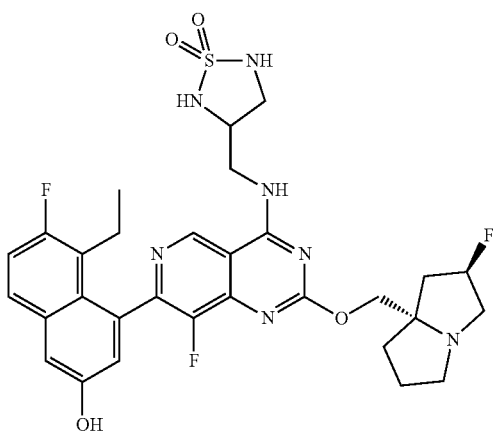 [SMILES: CCc1c(F)ccc2cc(O)cc(-c3ncc4c(NCC5CNS(=O)(=O)N5)nc(OC[C@@]56CCCN5C[C@H](F)C6)nc4c3F)c12]

3-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)-1,2,5-thiadiazolidine 1,1-dioxide

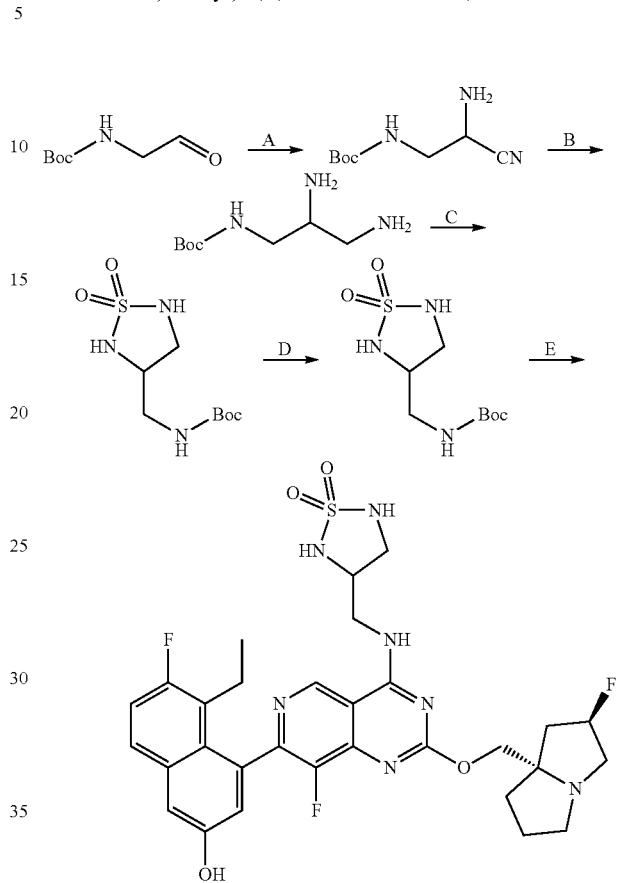

Step A. tert-butyl (2-amino-2-cyanoethyl)carbamatet: To a solution of tert-butyl (2-oxoethyl)carbamate (1.00 g, 1.0 equiv.) in methanol (10 mL) were added Ti(i-PrO)$_4$ (1.79 g, 1.0 equiv.) and NH$_3$ in methanol (7.00 M, 2.0 equiv.). TMSCN (1.25 g, 2.0 equiv.) was added dropwise to the mixture at 0° C. The mixture was stirred at 25° C. for 16 hours. The mixture was diluted with water (50 mL) and filtered. The filtrate was extracted with ethyl acetate (3×100 mL). The combined organic layers were dried over Na$_2$SO$_4$ and concentrated to afford the title compound (1.14 g, 83% yield) as a yellow oil; $^1$H NMR (400 MHz, dimethylsulfoxide-d$_4$) δ=7.14 (br t, J=5.6 Hz, 1H), 3.75 (br s, 1H), 3.21-3.06 (m, 2H), 2.36 (br s, 2H), 1.38 (s, 9H).

Step B. tert-butyl (2,3-diaminopropyl)carbamate: A mixture of tert-butyl (2-amino-2-cyanoethyl)carbamatet (500 mg, 1.0 equiv.) and Raney Ni (694 mg, 3.0 equiv.) in MeOH (5 mL) and NH$_3$ in methanol (7.00 M, 1 mL) was degassed and purged with H$_2$ for 3 times. The mixture was stirred at 25° C. for 16 hours under H$_2$ atmosphere (15 psi). The reaction mixture was filtered and the filtrate was concentrated to afford the title compound (500 mg, crude) as a yellow oil; $^1$H NMR (400 MHz, dimethylsulfoxide-d$_6$) δ=6.71 (br s, 1H), 2.94-2.84 (m, 1H), 2.82-2.73 (m, 1H), 2.57 (br s, 1H), 2.45 (br d, J=6.2 Hz, 1H), 2.35-2.23 (m, 1H), 1.37 (s, 9H).

Step C. tert-butyl ((1,1-dioxido-1,2,5-thiadiazolidin-3-yl)methyl)carbamate: To a solution of tert-butyl (2,3-diaminopropyl)carbamate (400 mg, 1.0 equiv.) in pyridine (4 mL)

was added dropwise sulfamide (203 mg, 1.0 equiv.) at 25° C. The resulting mixture was stirred at 115° C. for 20 hours. The reaction mixture was filtered and the filtrate was concentrated. The residue was purified by prep-TLC (dichloromethane/methanol 10:1) to afford the title compound (100 mg, 16% yield over two steps) as a yellow oil; $^1$H NMR (400 MHz, dimethylsulfoxide-d$_4$) δ=6.96-6.85 (m, 3H), 3.65-3.55 (m, 1H), 3.33-3.30 (m, 1H), 3.09-2.97 (m, 3H), 1.38 (s, 9H).

Step D. 3-(aminomethyl)-1,2,5-thiadiazolidine 1,1-dioxide: To a solution of tert-butyl (((1,1-dioxido-1,2,5-thiadiazolidin-3-yl)methyl)carbamate (41.0 mg, 1.0 equiv.) in DCM (0.50 mL) was added HCl-dioxane (4 M, 12.6 equiv.) at 0° C. The mixture was stirred at 25° C. for 1 hour. The reaction mixture was concentrated in vacuum to afford the title compound (30.0 mg, 98% yield, HCl) as a brown solid.

Step E. 3-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)methyl)-1,2,5-thiadiazolidine 1,1-dioxide: To a mixture of 3-(aminomethyl)-1,2,5-thiadiazolidine 1,1-dioxide (30.0 mg, 1.0 equiv, HCl), 5-ethyl-6-fluoro-4-(8-fluoro-2-(((2R,7aS)-2-fluorotetrahydro-1H-pyrrolizin-7a-yl)methoxy)-4-(2,2,2-trifluoroethoxy)pyrido[4,3-d]pyrimidin-7-yl)naphthalen-2-ol (47.4 mg, 1.0 equiv.) in DMF (0.5 mL) were added DIEA (31.0 mg, 3.0 equiv.) and 4 Å molecular sieves (10 mg). The mixture was stirred at 60° C. for 24 hours. The mixture was filtered and purified by prep-HPLC [column: Waters xbridge 150×25 mm×10 μm; mobile phase: water (10 mM NH$_4$HCO$_3$), B: ACN, B %: 29%-59%, 8 min] to afford the title compound (10.4 mg, 19% yield) as a white solid; $^1$H NMR (400 MHz, dimethylsulfoxide-d$_4$) δ=9.94 (s, 1H), 9.33 (s, 1H), 9.13 (br d, J=2.4 Hz, 1H), 7.77 (dd, J=6.4, 9.2 Hz, 1H), 7.39-7.28 (m, 2H), 7.26-7.16 (m, 1H), 7.05 (br t, J=7.6 Hz, 1H), 6.99 (d, J=2.4 Hz, 1H), 5.48-5.18 (m, 1H), 4.31-3.97 (m, 3H), 3.76-3.59 (m, 2H), 3.57-3.45 (m, 1H), 3.22 (br dd, J=5.2, 11.2 Hz, 5H), 2.97-2.84 (m, 1H), 2.27-2.17 (m, 1H), 2.16-2.00 (m, 3H), 1.97-1.72 (m, 3H), 0.71 (br t, J=7.2 Hz, 3H); LCMS (ESI, M+1): m/z=644.0.

Example 495

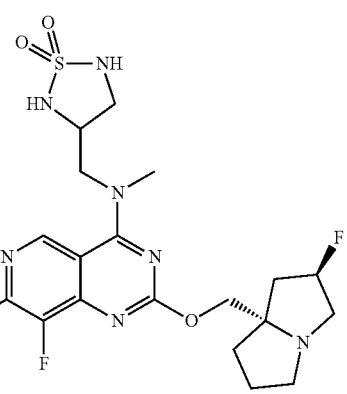

3-(((7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)methyl)amino)methyl)-1,2,5-thiadiazolidine 1,1-dioxide The title compound was synthesized according to the procedure described for example 494 using tert-butyl methyl (2-oxoethyl)carbamate instead of tert-butyl (2-oxoethyl)carbamate in step A. $^1$H NMR (400 MHz, dimethylsulfoxide-d$_4$) δ=9.95-9.87 (m, 1H), 9.35-9.24 (m, 1H), 7.81-7.70 (m, 1H), 7.40-7.27 (m, 2H), 7.25-7.15 (m, 1H), 7.08-7.02 (m, 1H), 7.02-6.98 (m, 1H), 5.42-5.17 (m, 1H), 4.30-3.99 (m, 4H), 3.98-3.82 (m, 1H), 3.67-3.58 (m, 3H), 3.57-3.45 (m, 1H), 3.23-2.96 (m, 5H), 2.94-2.77 (m, 1H), 2.19-2.02 (m, 4H), 1.91-1.75 (m, 3H), 0.78-0.70 (m, 3H); LCMS (ESI, M+1): m/z=658.2.

Example 496

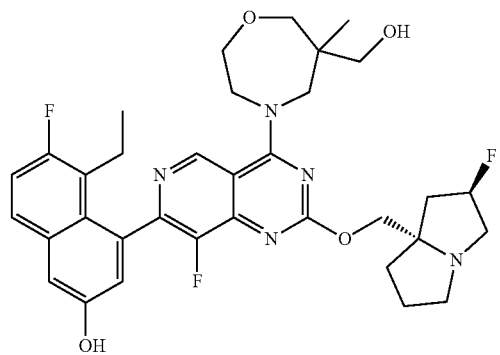 [SMILES: CCc1c(F)ccc2cc(O)cc(-c3ncc4c(N5CCOCC(C)(CO)C5)nc(OC[C@@]56CCCN5C[C@H](F)C6)nc4c3F)c12]

5-ethyl-6-fluoro-4-(8-fluoro-2-(((2R,7aS)-2-fluorotetrahydro-1H-pyrrolizin-7a(5H)-yl)methoxy)-4-(6-(hydroxymethyl)-6-methyl-1,4-oxazepan-4-yl)pyrido[4,3-d]pyrimidin-7-yl)naphthalen-2-ol The title compound was synthesized according to the procedure described for example 330. $^1$H NMR (400 MHz, METHANOL-d$_4$) δ=9.19 (d, J=5.3 Hz, 1H), 7.67 (dd, J=6.0, 8.8 Hz, 1H), 7.30 (d, J=2.8 Hz, 1H), 7.24 (t, J=9.2 Hz, 1H), 7.06 (s, 1H), 5.43-5.25 (m, 1H), 4.49-4.23 (m, 4H), 4.22-3.98 (m, 4H), 3.77-3.65 (m, 1H), 3.59-3.45 (m, 2H), 3.44-3.34 (m, 2H), 3.29-3.19 (m, 1H), 3.11-3.02 (m, 1H), 2.58-2.34 (m, 2H), 2.34-2.09 (m, 4H), 2.08-1.98 (m, 2H), 1.97-1.87 (m, 1H), 0.98 (br d, J=12.4 Hz, 3H), 0.84-0.74 (m, 3H); LCMS (ESI, M+1): m/z=638.2

Example 497

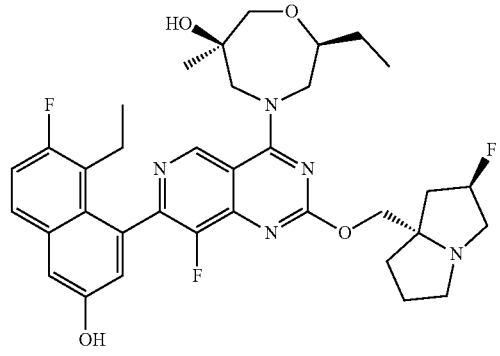 [SMILES: CCc1c(F)ccc2cc(O)cc(-c3ncc4c(N5C[C@H](CC)OC[C@](C)(O)C5)nc(OC[C@@]56CCCN5C[C@H](F)C6)nc4c3F)c12]

(2R,6R)-4-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2-(hydroxymethyl)-6-methyl-1,4-oxazepan-6-ol The title compound was synthesized according to the procedure described for example 330. ¹H NMR (400 MHz, CDCl₃) δ=9.67 (d, J=5.6 Hz, 1H), 7.69-7.66 (m, 1H), 7.30 (t, J=2.4 Hz, 1H), 7.25 (t, J=9.6 Hz, 1H), 7.08-7.01 (m, 1H), 5.49-5.35 (m, 1H), 4.54 (d, J=11.2 Hz, 1H), 4.44 (d, J=11.2 Hz, 1H), 4.40-4.35 (m, 1H), 4.32 (d, J=14.8 Hz, 1H), 4.18-4.02 (m, 3H), 3.86-3.82 (m, 1H), 3.74-3.64 (m, 3H), 3.55-3.49 (m, 2H), 3.25-3.18 (m, 1H), 2.56-2.11 (m, 8H), 2.06-2.00 (m, 1H), 1.25 (d, J=4.0 Hz, 3H), 0.84-0.75 (m, 3H); LCMS (ESI, M+1): m/z=654.4.

Example 498

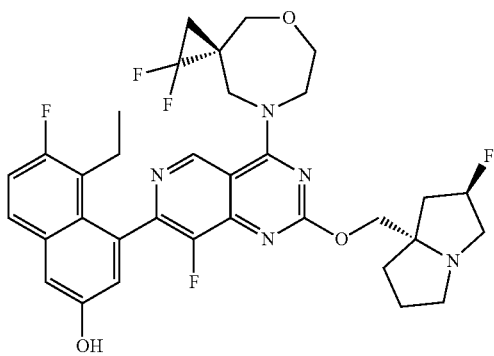 [SMILES: CCc1c(F)ccc2cc(O)cc(-c3ncc4c(N5CCOC[C@@]6(C5)CC6(F)F)nc(OC[C@@]56CCCN5C[C@H](F)C6)nc4c3F)c12]

4-(4-((S)-1,1-difluoro-5-oxa-8-azaspiro[2.6]nonan-8-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 330. ¹H NMR (400 MHz, DMSO-d₆) δ=9.95 (s, 1H), 9.15 (d, J=6.4 Hz, 1H), 8.22 (s, 1H), 7.77 (m, 1H), 7.40-7.26 (m, 2H), 7.05-6.93 (m, 1H), 5.41-5.17 (m, 1H), 4.40-4.28 (m, 2H), 4.26-4.18 (m, 1H), 4.18-4.10 (m, 1H), 4.10-4.02 (m, 2H), 4.02-3.91 (m, 2H), 3.86-3.73 (m, 2H), 3.15-3.03 (m, 2H), 3.01 (s, 1H), 2.88-2.77 (m, 1H), 2.40-2.34 (m, 1H), 2.21-2.09 (m, 2H), 2.05 (m, 1H), 1.99 (m, 1H), 1.90-1.68 (m, 5H), 0.73 (m, 3H); LCMS (ESI, M+1): m/z=656.1.

Example 499

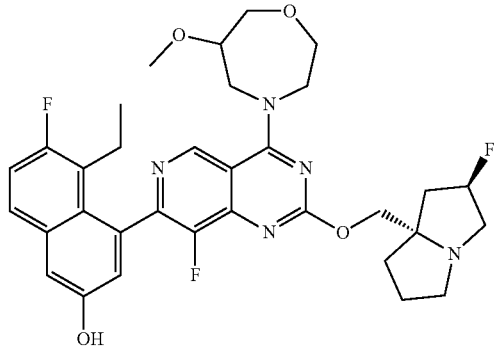 [SMILES: CCc1c(F)ccc2cc(O)cc(-c3ncc4c(N5CCOCC(OC)C5)nc(OC[C@@]56CCCN5C[C@H](F)C6)nc4c3F)c12]

5-ethyl-6-fluoro-4-(8-fluoro-2-(((2R,7aS)-2-fluorotetrahydro-1H-pyrrolizin-7a(5H)-yl)methoxy)-4-(6-methoxy-1,4-oxazepan-4-yl)pyrido[4,3-d]pyrimidin-7-yl)naphthalen-2-ol The tide compound was synthesized according to the procedure described for example 330. ¹H NMR (400 MHz, DMSO-d₆) δ=10.04-9.84 (m, 1H), 9.23 (d, J=2.4 Hz, 1H), 8.15 (s, 1H), 7.77 (dd, J=6.0, 9.2 Hz, 1H), 7.42-7.25 (m, 2H), 7.02 (dd, J=2.0, 5.6 Hz, 1H), 5.40-5.16 (m, 1H), 4.50-4.32 (m, 1H), 4.24-3.98 (m, 6H), 3.97-3.88 (m, 1H), 3.87-3.76 (m, 2H), 3.76-3.64 (m, 1H), 3.38 (d, J=2.0 Hz, 3H), 3.14-3.05 (m, 2H), 3.02 (s, 1H), 2.87-2.78 (m, 1H), 2.21-1.93 (m, 5H), 1.90-1.75 (m, 3H), 0.73 (d, J=3.2 Hz, 3H); LCMS (ESI, M+1): m/z=624.2.

Example 500

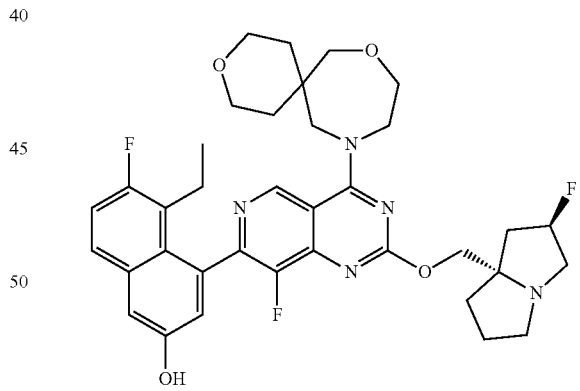

5-ethyl-6-fluoro-4-(8-fluoro-2-(((2R,7aS)-2-fluorohexahydro-1H-pyrrolizin-7a-yl)methoxy)-4-(3,8-dioxa-11-azaspiro[5.6]dodecan-11-yl)pyrido[4,3-d]pyrimidin-7-yl)naphthalen-2-ol The title compound was synthesized according to the procedure described for example 330. ¹H NMR (400 MHz, DMSO-d₆) δ=9.94 (s, 1H), 9.19 (s, 1H), 8.15 (s, 1H), 7.76 (m, 1H), 7.48-7.18 (m, 2H), 7.03 (d, J=2.4 Hz, 1H), 5.29 (d, J=54.0 1H), 4.55 (d, J=14.0 Hz, 1H), 4.26-4.12 (m, 2H), 4.11-4.02 (m, 4H), 3.68-3.47 (m, 6H), 3.18-3.00 (m, 3H), 2.86-2.80 (m, 1H), 2.54 (s, 1H), 2.41-2.34 (m, 1H), 2.20-1.94 (m, 4H), 1.89-1.89 (m, 3H), 1.54-1.27 (m, 4H), 0.72 (t, J=7.38 Hz, 3H); LCMS (ESI, M+1): m/z=664.3.

Example 501

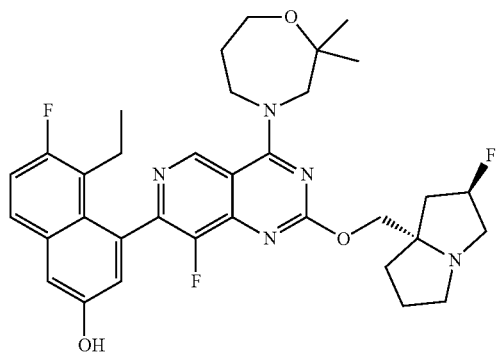 [SMILES: CCc1c(F)ccc2cc(O)cc(-c3ncc4c(N5CCCOC(C)(C)C5)nc(OC[C@@]56CCCN5C[C@H](F)C6)nc4c3F)c12]

4-(4-(2,2-dimethyl-1,4-oxazepan-4-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 330. $^1$H NMR (400 MHz, DMSO-d$_6$) δ=10.05-9.87 (m, 1H), 9.10 (s, 1H), 8.24 (s, 1H), 7.76 (dd, J=5.2, 8.4 Hz, 1H), 7.39-7.29 (m, 2H), 7.03 (d, J=2.0 Hz, 1H), 5.21 (s, 1H), 4.45-4.31 (m, 1H), 4.19-4.00 (m, 4H), 4.00-3.92 (m, 1H), 3.88-3.77 (m, 2H), 3.08 (d, J=6.8 Hz, 2H), 3.00 (s, 1H), 2.86-2.79 (m, 1H), 2.67 (s, 1H), 2.33 (s, 2H), 2.17-1.96 (m, 7H), 1.89-1.75 (m, 3H), 1.21-1.08 (m, 6H), 0.73 (t, J=7.2 Hz, 3H); LCMS (ESI, M+1): m/z=622.2.

Example 502

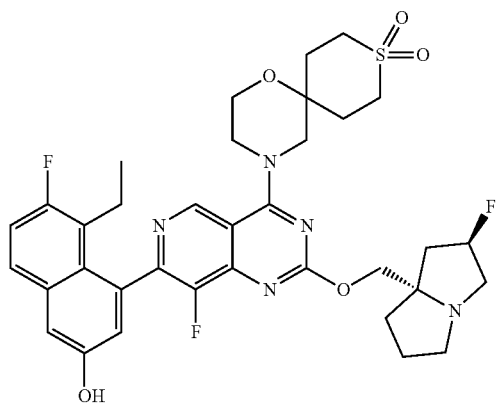 [SMILES: CCc1c(F)ccc2cc(O)cc(-c3ncc4c(N5CCOC6(CCS(=O)(=O)CC6)C5)nc(OC[C@@]56CCCN5C[C@H](F)C6)nc4c3F)c12]

4-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-1-oxa-9-thia-4-azaspiro[5.5]undecane 9,9-dioxide The title compound was synthesized according to the procedure described for example 330. $^1$H NMR (400 MHz, DMSO-d$_6$) δ=9.16 (s, 1H), 8.18 (s, 1H), 7.79-7.76 (m, 1H), 7.37 (d, J=9.6 Hz, 1H), 7.34 (d, J=2.4 Hz, 1H), 7.02 (d, J=2.4 Hz, 1H), 5.36-5.22 (m, 1H), 4.18-4.15 (m, 1H), 4.10-4.07 (m, 1H), 4.02-4.00 (m, 2H), 3.96-3.90 (m, 4H), 3.17-3.14 (m, 2H), 3.11 (s, 1H), 3.07 (t, J=3.2 Hz, 1H), 3.02 (s, 1H), 2.86-2.81 (m, 1H), 2.54 (s, 1H), 2.53-2.52 (m, 1H), 2.37-2.33 (m, 3H), 2.15-2.01 (m, 6H), 1.87-1.77 (m, 3H), 0.73 (t, J=7.2 Hz, 3H); LCMS (ESI, M+1): m/z=698.3.

Example 503

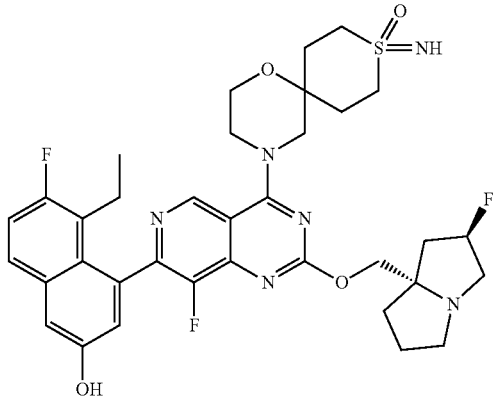 [SMILES: CCc1c(F)ccc2cc(O)cc(-c3ncc4c(N5CCOC6(CCS(=N)(=O)CC6)C5)nc(OC[C@@]56CCCN5C[C@H](F)C6)nc4c3F)c12]

4-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-9-imino-1-oxa-9-thia-4-azaspiro[5.5]undecane 9-oxide The title compound was synthesized according to the procedure described for example 330. $^1$H NMR (400 MHz, DMSO-d$_6$) δ=10.08-9.84 (s, 1H), 9.22-9.06 (s, 1H), 7.79-7.75 (m, 1H), 7.40-7.30 (m, 2H), 7.01 (d, J=2.4 Hz, 1H), 5.28 (d, J=64.0 Hz, 1H), 4.21-4.12 (m, 1H), 4.10-4.05 (m, 1H), 4.04-3.95 (m, 2H), 3.95-3.84 (m, 4H), 3.53 (s, 1H), 3.11-3.00 (m, 5H), 2.95 (d, J=12.8 Hz, 2H), 2.86-2.78 (m, 1H), 2.26 (d, J=12.4 Hz, 2H), 2.18-2.10 (m, 2H), 2.10-1.94 (m, 5H), 1.87-1.74 (m, 3H), 0.72 (t, J=7.2 Hz, 3H); LCMS (ESI, M+1): m/z=697.7.

Example 504

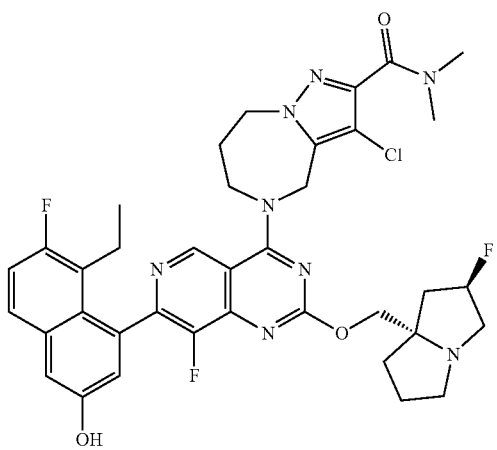 [SMILES: CCc1c(F)ccc2cc(O)cc(-c3ncc4c(N5CCCn6nc(C(=O)N(C)C)c(Cl)c6C5)nc(OC[C@@]56CCCN5C[C@H](F)C6)nc4c3F)c12]

3-chloro-5-(7-(8-ethyl-7-fluoro-3-hydroxynaphtha-len-1-yl)-8-fluoro-2-(((2R,7aS)-2-fluorohexahydro-1H-pyrrolizin-7a-yl)methoxy)pyrido[4,3-d]pyrimi-din-4-yl)-N,N-dimethyl-5,6,7,8-tetrahydro-4H-pyrazolo[1,5-a][1,4]diazepine-2-carboxamide

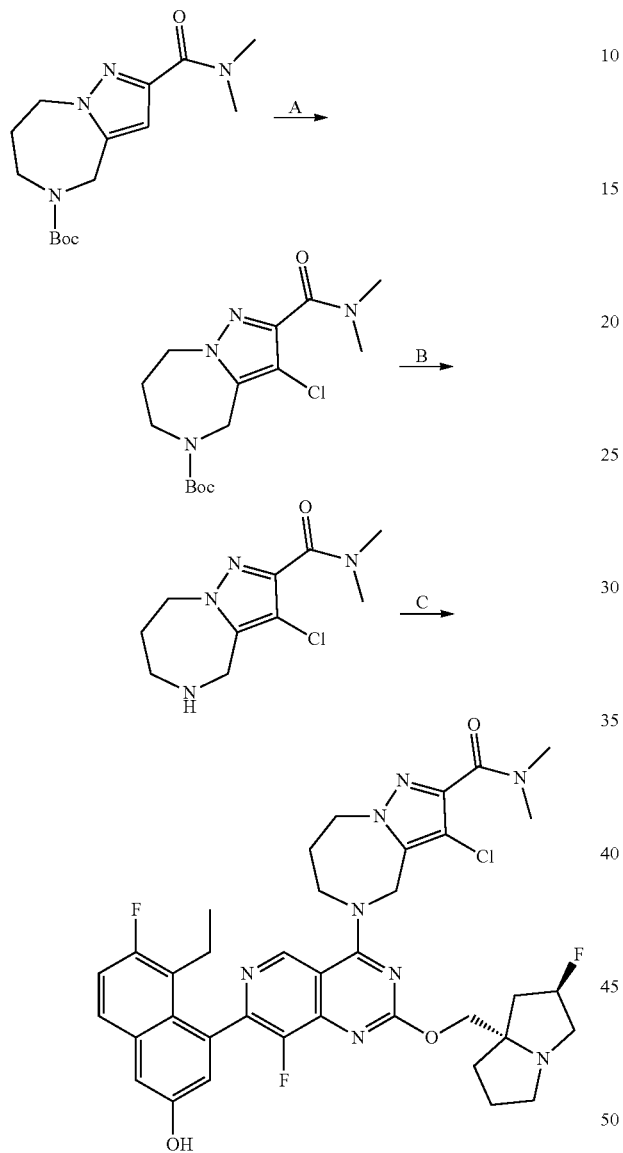

Step A. tert-butyl 3-chloro-2-(dimethylcarbamoyl-4,6,7,8-tetrahydropyrazolo[1,5-a][1,4]diazepine-5-carboxylate: To a solution of tert-butyl 2-(dimethylcarbamoyl)-4,6,7,8-tetrahydropyrazolo[1,5-a][1,4]diazepine-5-carboxylate (1.2 g, 1.0 equiv.) in DMF (12 mL) was added NCS (779 mg, 1.5 equiv.) at 0° C. The mixture was stirred at 55° C. for 1 hour. The mixture was diluted with H$_2$O (30 mL) and extracted with ethyl acetate (3×10 mL). The combined organic layers were washed with brine (3×10 mL), dried over anhydrous Na$_2$SO$_4$, concentrated and purified by column chromatography [SiO$_2$, petroleum ether/ethyl acetate 10:1 to 1:1] to afford the title compound (740 mg, 51% yield) as a light yellow oil; $^1$H NMR (400 MHz, CDCl$_3$) δ=4.50 (s, 2H), 4.45-4.35 (m, 2H), 3.75 (s, 2H), 3.10 (s, 6H), 1.97 (s, 2H), 1.44 (s, 9H); LCMS (ESI, M+1): m/z=343.4.

Step B. 3-chloro-N,N-dimethyl-5,6,7,8-tetrahydro-4H-pyrazolo[1,5-a][1,4]diazepine-2-carboxamide: A mixture of tert-butyl 3-chloro-2-(dimethylcarbamoyl)-4,6,7,8-tetrahydropyrazolo[1,5-a][1,4]diazepine-5-carboxylate (100 mg, 292 μmol, 1.0 equiv.) in HCl-dioxane (1.0 mL) was stirred at 25° C. for 1 hour. The mixture concentrated to afford the title compound (45 mg, 50% yield, HCl) as a white solid, LCMS (ESI, M+1): m/z=243.0.

Step C: 3-chloro-547-(8-ethyl-7-fluoro-3-hydroxynaph-thalen-1-yl)-8-fluoro-2-(((2R,7aS)-2-fluorohexahydro-1H-pyrrolizin-7a-yl)methoxy)pyrido[4,3-d]pyrimidin-4-yl)-N,N-dimethyl-5,6,7,8-tetrahydro-4H-pyrazolo[1,5-a][1,4]diazepine-2-carboxamide: A mixture of 3-chloro-N,N-dimethyl-5,6,7,8-tetrahydro-4H-pyrazolo[1,5-a][1,4]diazepine-2-carboxamide (45 mg, 3.5 equiv, HCl), 4 Å molecular sieve (100 mg) and DIEA (16.4 mg, 3.0 equiv.) in DMF (0.05 mL) was stirred at 25° C. for 30 minutes. 5-ethyl-6-fluoro-4-(8-fluoro-2-(((2R,7aS)-2-fluorohexahydro-1H-pyrrolizin-7a-yl)methoxy)-4-(2,2,2-trifluoroethoxy)pyrido[4,3-d]pyrimidin-7-yl)naphthalen-2-ol (25 mg, 1.0 equiv.) was added and the mixture was stirred at 40° C. for 36 hours. The mixture was filtered and the filtrate was purified by prep-HPLC [column: Phenomenex luna C18 150×25 mm×10 μm; mobile phase: A: water (0.1% formic acid)-ACN; B %: 15%-45%, 9 minutes] to afford the title compound (8.52 mg, 24% yield, formic acid salt) as a white solid; $^1$H NMR (400 MHz, DMSO-d$_6$) δ=9.93 (s, 1H), 9.16 (s, 1H), 8.13 (s, 1H), 7.77 (dd, J=9.2 Hz, 6.0 Hz, 1H), 7.39-7.30 (m, 2H), 7.00 (d, J=2.4 Hz, 1H), 5.45-5.35 (m, 1H), 5.31-5.09 (m, 3H), 4.47 (d, J=6.8 Hz, 2H), 4.40-4.30 (m, 2H), 4.25-4.06 (m, 2H), 3.21-3.04 (m, 3H), 2.99 (d, J=15.2 Hz, 6H), 2.96-2.72 (m, 2H), 2.42-2.37 (m, 2H), 2.17-1.77 (m, 8H), 0.72 (t, J=7.6 Hz, 3H); LCMS (ESI, M+1): m/z=735.2.

Example 505

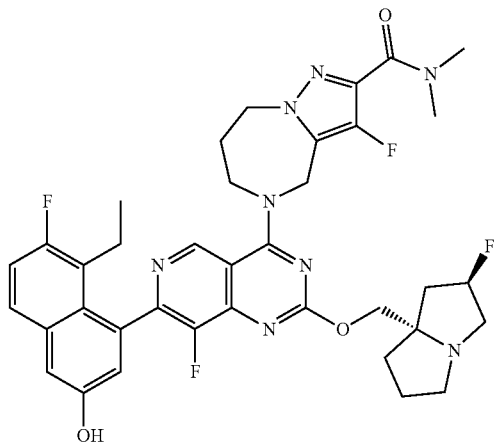 [SMILES: CCc1c(F)ccc2cc(O)cc(-c3ncc4c(N5CCCn6nc(C(=O)N(C)C)c(F)c6C5)nc(OC[C@@]56CCCN5C[C@H](F)C6)nc4c3F)c12]

5-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-fluoro-N,N-dimethyl-5,6,7,8-tetrahydro-4H-pyrazolo[1,5-a][1,4]diazepine-2-carboxamide

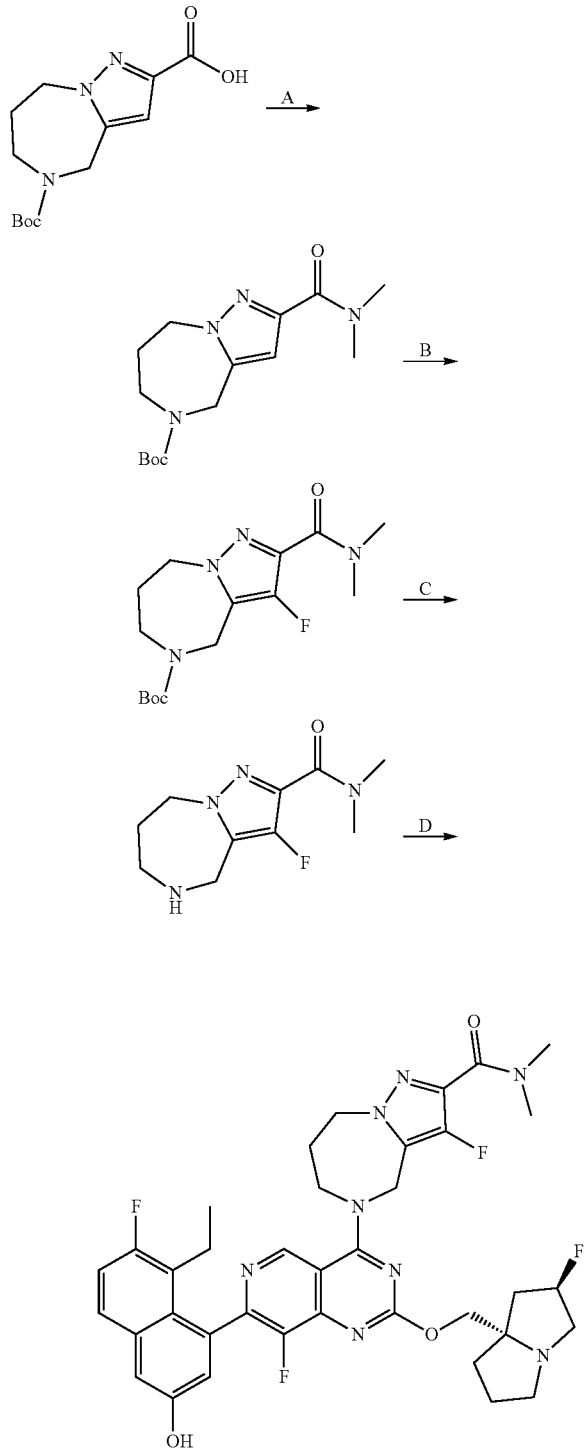

Step A. tert-butyl 2-(dimethylcarbamoyl)-4,6,7,8-tetrahydropyrazolo[1,5-a][1,4]diazepine-5-carboxylate: To a solution of 5-tert-butoxycarbonyl-4,6,7,8-tetrahydropyrazolo[1,5-a][1,4]diazepine-2-carboxylic acid (1.0 g, 1.0 equiv.) in Me$_2$NH (2 M in THF, 8.89 mL, 5.0 equiv.) was added DIEA (689 mg, 1.5 equiv.) and HATU (2.03 g, 1.5 equiv.). The mixture was stirred at 25° C. for 12 hours. The mixture was diluted with H$_2$O (4 mL) and filtered. The filtrate was extracted with ethyl acetate (3×5 mL). The combined organic layer was washed with brine (5 mL), dried over anhydrous sodium sulfate, concentrated and purified by reversed phase flash [water (0.1% formic acid)/acetonitrile] to afford the title compound (981 mg, 89% yield) as a yellow oil; $^1$H NMR (400 MHz, CDCl$_3$) δ=6.67-6.39 (m, 1H), 4.61-4.31 (m, 4H), 3.80-3.60 (m, 2H), 3.45-3.20 (m, 3H), 3.18-2.93 (m, 3H), 1.99-1.88 (m, 2H), 1.41 (s, 9H); LCMS (ESI, M+1): m/z=308.9.

Step B. tert-butyl 2-(dimethylcarbamoyl)-3-fluoro-4,6,7,8-tetrahydropyrazolo[1,5-a][1,4]diazepine-5-carboxylate: To a solution of tert-butyl 2-(dimethylcarbamoyl)-4,6,7,8-tetrahydropyrazolo[1,5-a][1,4]diazepine-5-carboxylate (760 mg, 1.0 equiv.) in ACN (10 mL) was added 1-chloromethyl-4-fluoro-1,4-diazoniabicyclo[2.2.2]octane bis(tetrafluoroborate) (4.37 g, 5.0 equiv.). The mixture was stirred at 25° C. for 16 hours. The mixture was concentrated and purified by prep-HPLC [column: Phenomenex luna C18 200×40 mm×10 μm; mobile phase: A: water (0.1% formic acid)-MeCN; B %: 25%-55%, 10 minutes] to afford the title compound (107 mg, 13% yield) as a yellow oil; LCMS (ESI, M+1): m/z=326.9.

Step C. 3-fluoro-N,N-dimethyl-5,6,7,8-tetrahydro-4H-pyrazolo[1,5-a][1,4]diazepine-2-carboxamide: To a solution of tert-butyl 2-(dimethylcarbamoyl)-3-fluoro-4,6,7,8-tetrahydropyrazolo[1,5-a][1,4]diazepine-5-carboxylate (56 mg, 1.0 equiv.) in DCM (0.25 mL) and TFA (0.25 mL) was stirred at 25° C. for 1 hour. The mixture was concentrated to afford the title compound (91 mg, crude, TFA) as a yellow oil; LCMS (ESI, M+1): 226.9.

Step D: 5-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-fluoro-N,N-dimethyl-5,6,7,8-tetrahydro-4H-pyrazolo[1,5-a][1,4]diazepine-2-carboxamide: A mixture of 5-ethyl-6-fluoro-4-(8-fluoro-2-(((2R,7aS)-2-fluorohexahydro-1H-pyrrolizin-7a-yl)methoxy)-4-(2,2,2-trifluoroethoxy)pyrido[4,3-d]pyrimidin-7-yl)naphthalen-2-ol (31.7 mg, 1.0 equiv.), 3-fluoro-N,N-dimethyl-5,6,7,8-tetrahydro-4H-pyrazolo[1,5-a][1,4]diazepine-2-carboxamide (91 mg, crude), 4 Å molecular sieve (10 mg) and K$_2$CO$_3$ (37.0 mg, 5.0 equiv.) in DMSO (0.5 mL) was stirred at 40° C. for 2 hours under N$_2$ atmosphere. The mixture was filtered and the filtrate was purified by prep-HPLC [column: Phenomenex luna C18 100×30 mm×5 μm; mobile phase: A: water (0.1% formic acid)-MeCN; B %: 10%-40%, 10 minutes] to afford the title compound (8.89 mg, 20% yield, formic acid salt) as a white solid; $^1$H NMR (400 MHz, DMSO-d$_6$) δ=9.94 (s, 1H), 9.18 (s, 1H), 8.15-8.12 (m, 1H), 7.77 (m, 1H), 7.40-7.29 (m, 2H), 7.00 (d, J=2.4 Hz, 1H), 5.47-5.26 (m, 1H), 5.26-5.19 (m, 1H), 5.18-5.09 (m, 1H), 4.46 (d, J=6.0 Hz, 4H), 4.29-3.95 (m, 2H), 3.14-3.09 (m, 3H), 2.98-2.91 (m, 3H), 2.42-2.28 (m, 4H), 2.27-1.53 (m, 9H), 0.71 (t, J=7.2 Hz, 3H); LCMS (ESI, M+1): 719.1.

Example 506

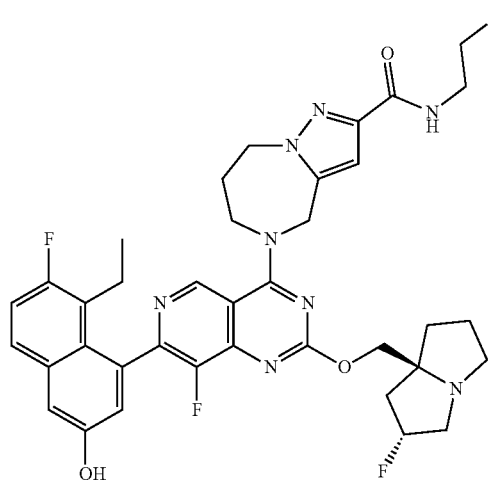

5-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-N-(2-hydroxyethyl)-5,6,7,8-tetrahydro-4H-pyrazolo[1,5-a][1,4]diazepine-2-carboxamide

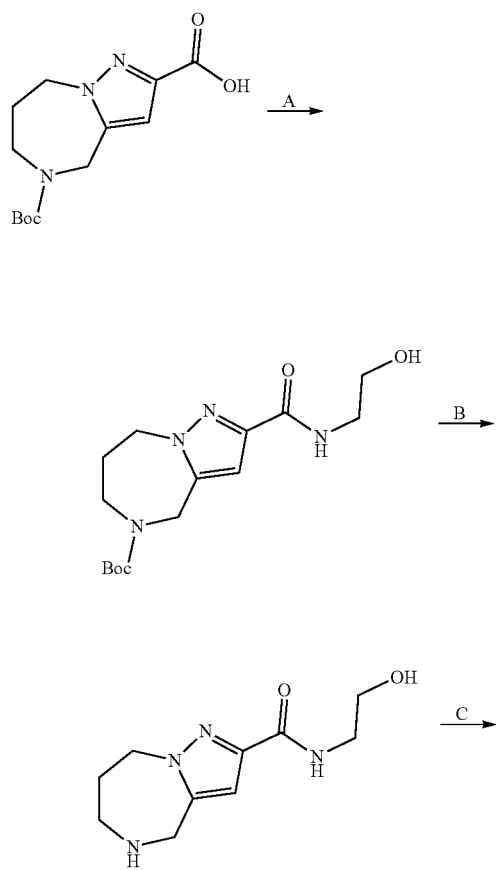

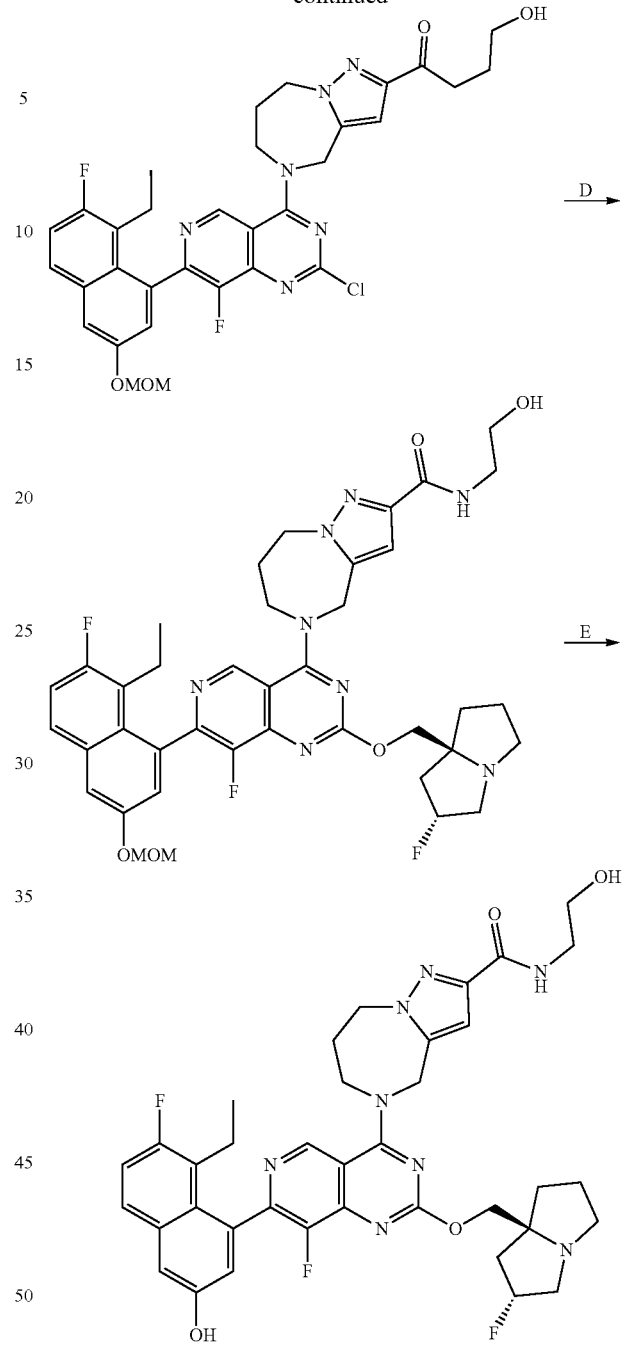

Step A. tert-butyl 2-((2-hydroxyethyl)carbamoyl)-7,8-dihydro-4H-pyrazolo[1,5-a][1,4]diazepine-5(6H)-carboxylate: To a solution of 5-tert-butoxycarbonyl-4,6,7,8-tetrahydropyrazolo[1,5-a][1,4]diazepine-2-carboxylic acid (200 mg, 1.0 equiv.) and TEA (108 mg, 1.5 equiv.) in DMF (2 mL) was added HATU (405 mg, 1.5 equiv.) and 2-aminoethanol (174 mg, 4.0 equiv.). The reaction was stirred at 20° C. for 0.5 hour. The reaction mixture was filtered and concentrated under reduced pressure to give a residue. The residue was purified by prep-TLC (SiO$_2$, Petroleum ether/Ethyl acetate 1:1) to afford the title compound (160 mg, 69% yield) as a colorless oil; LCMS (ESI, M+1): m/z=325.1

Step B. N-(2-hydroxyethyl)-5,6,7,8-tetrahydro-4H-pyrazolo[1,5-a][1,4]diazepine-2-carboxamide: A solution of tert-butyl 2-(2-hydroxyethylcarbamoyl)-4,6,7,8-tetrahydropyrazolo[1,5-a][1,4]diazepine-5-carboxylate (160 mg, 1.0 equiv.) in HCl.dioxane (2 M, 2 mL, 8.1 equiv.) was stirred at 20° C. for 0.5 hour. The reaction mixture filtered, concentrated under reduced pressure to give a residue. The residue was purified by prep-H PLC (column: Waters Xbridge 150×25 mm×5 μm; mobile phase: A: water (10 mM NH$_4$HCO$_3$)-ACN]; B %: 1%-10%, 8 minutes) to afford the title compound (70.0 mg, 63% yield) as a white solid; LCMS (ESI, M+1): m/z=225.2.

Step C. 5-(2-chloro-7-(8-ethyl-7-fluoro-3-(methoxymethoxy)naphthalen-1-yl-8-fluoropyrido[4,3-d]pyrimidin-4-yl)-N-(2-hydroxyethyl)-5,6,7,8-tetrahydro-4H-pyrazolo[1,5-a][1,4]diazepine-2-carboxamide: To a solution of N-(2-hydroxyethyl)-5,6,7,8-tetrahydro-4H-pyrazolo[1,5-a][1,4]diazepine-2-carboxamide (70.0 mg, 1.0 equiv.) in DMF (1 mL) were added 2,4-dichloro-7-[8-ethyl-7-fluoro-3-(methoxymethoxy)-1-naphthyl]-8-fluoro-pyrido[4,3-d]pyrimidine (141 mg, 1.0 equiv.) and DIEA (121 mg, 3.0 equiv.), and then the mixture was stirred at −40° C. for 10 minutes. The reaction mixture was filtered and concentrated under reduced pressure to give a residue. The crude product was purified by reversed phase flash chromatography (C18, water (0.1% formic acid)-ACN) to afford the title compound (60.0 mg, 30% yield) as a white solid; LCMS (ESI, M+1): m/z=638.3.

Step D. 5-(7-(8-ethyl-7-fluoro-3-(methoxymethoxy)naphthalen-1-yl)-8-fluoro-2-(((2R,7aS-2-fluorotetrahydro-1H-pyrrolizin-7a(5H)-yl)methoxy)pyrido[4,3-d]pyrimidin-4-yl)-N-(2-hydroxyethyl)-5,6,7,8-tetrahydro-4H-pyrazolo[1,5-a][1,4]diazepine-2-carboxamide: To a solution of 5-[2-chloro-7-[8-ethyl-7-fluoro-3-(methoxymethoxy)-1-naphthyl]-8-fluoro-pyrido[4,3-d]pyrimidin-4-yl]-N-(2-hydroxyethyl)-4,6,7,8-tetrahydropyrazolo[1,5-a][1,4]diazepine-2-carboxamide (30.0 mg, 1.0 equiv.) in THF (1.0 mL) were added ((2R,7aS)-2-fluorohexahydro-1H-pyrrolizin-7a-yl)methanol (11.0 mg, 1.5 equiv.), DIEA (18.0 mg, 3.0 equiv.) and 4 Å molecular sieves (10 mg). The mixture was stirred at 50° C. for 3 hours. The reaction mixture was concentrated under reduced pressure to afford the title compound as a colorless oil. LCMS (ESI, M+1): m/z=761.5.

Step E. 5-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-N-(2-hydroxyethyl)-5,6,7,8-tetrahydro-4H-pyrazolo[1,5-a][1,4]diazepine-2-carboxamide: To a solution of 5-(7-(8-ethyl-7-fluoro-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-N-(2-hydroxyethyl)-5,6,7,8-tetrahydro-4H-pyrazolo[1,5-a][1,4]diazepine-2-carboxamide (25.0 mg, 1.0 equiv.) in MeOH (1 mL) was added HCl-MeOH (4 mol/L, 1.0 mL, 122 equiv.). The mixture was stirred at 0° C. for 0.5 hour. The reaction mixture was filtered and concentrated under reduced pressure to give a residue. The residue was purified by prep-HPLC (column: Waters Xbridge 150×25 mm×5 μm; mobile phase: water (10 mM NH$_4$HCO$_3$)-ACN]; B %: 35%-55%, 8 minutes) to afford the title compound (16.0 mg, 68% yield) as a white solid; $^1$H NMR (400 MHz, METHANOL-d$_4$) δ=9.19 (d, J=2.8 Hz, 1H), 7.81-7.57 (m, 1H), 7.36-7.21 (m, 2H), 7.05 (d, J=2.4 Hz, 1H), 6.84 (s, 1H), 5.43-5.15 (m, 3H), 4.68-4.16 (m, 9H), 3.67 (t, J=5.6 Hz, 2H), 3.49-3.44 (m, 2H), 3.14-3.04 (m, 1H), 2.53-2.32 (m, 4H), 2.33-2.15 (m, 3H), 2.12-1.91 (m, 3H), 0.78 (br t, J=6.8 Hz, 3H); LCMS (ESI, M+1): m/z=717.5.

Example 507

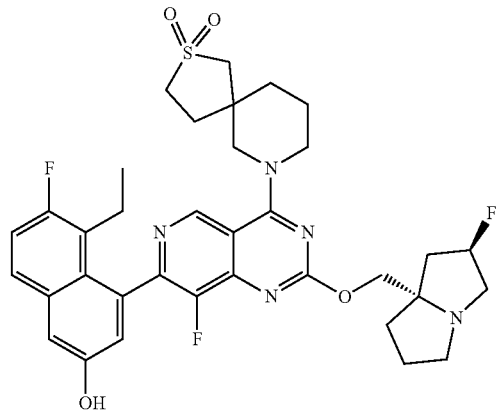 [SMILES: CCc1c(F)ccc2cc(O)cc(-c3ncc4c(N5CCCC6(CCS(=O)(=O)C6)C5)nc(OC[C@@]56CCCN5C[C@H](F)C6)nc4c3F)c12]

7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2-thia-7-azaspiro[4.5]decane 2,2-dioxide The title compound was synthesized according to the procedure described for example 330. $^1$H NMR (400 MHz, Methanol-d$_4$) δ 9.08 (s, 1H), 7.66 (dd, J=5.6, 9.0 Hz, 1H), 7.28 (d, J=2.8 Hz, 1H), 7.23 (t, J=9.6 Hz, 1H), 7.04 (d, J=2.4 Hz, 1H), 5.42-5.18 (m, 1H), 4.49-4.31 (m, 2H), 4.30-4.14 (m, 2H), 4.06-3.83 (m, 2H), 3.44-3.33 (m, 1H), 3.29-3.12 (m, 5H), 3.08-2.96 (m, 2H), 2.58-2.42 (m, 1H), 0.85-0.73 (m, 3H); LCMS [ESI, M+1]: m/z=682.4.

Example 508

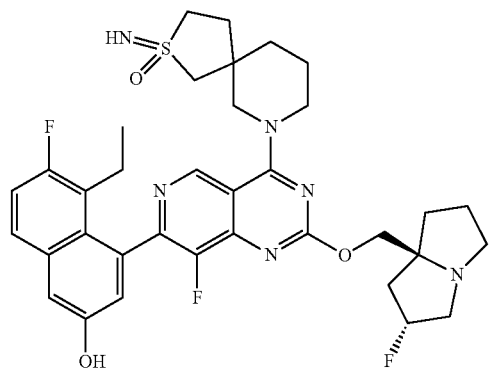 [SMILES: CCc1c(F)ccc2cc(O)cc(-c3ncc4c(N5CCCC6(CCS(=N)(=O)C6)C5)nc(OC[C@@]56CCCN5C[C@H](F)C6)nc4c3F)c12]

7-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-2-imino-2-thia-7-azaspiro[4.5]decane 2-oxide The title compound was synthesized according to the procedure described for example 330. $^1$H NMR (400 MHz, METHANOL-d$_4$) δ=9.16-9.04 (m, 11H), 7.74-7.63 (m, 1H), 7.37-7.20 (m, 2H), 7.12-6.99 (m, 1H), 5.40-5.38 (m, 1H), 5.28-5.25 (m, 1H), 4.52-4.14 (m, 4H), 4.09-3.88 (m, 2H), 3.34 (br s, 4H), 3.26-2.98 (m, 4H), 2.49 (br s, 6H), 2.12-1.84 (m, 8H), 0.85-0.74 (m, 3H); LCMS[ESI, M+1]: m/z=681.3.

Example 509

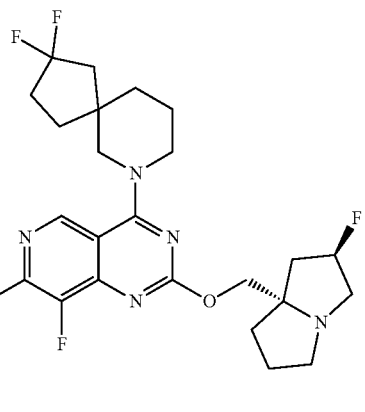

4-(4-(2,2-difluoro-7-azaspiro[4.5]decan-7-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol The title compound was synthesized according to the procedure described for example 330. ¹H NMR (400 MHz, METHANOL-d4) δ=9.10 (s, 1H), 8.58-8.46 (m, 1H), 7.70 (dd, J=6.0, 8.8 Hz, 11H), 7.33 (d, J=2.4 Hz, 11H), 7.27 (t, J=9.6 Hz, 11H), 7.08 (s, 11H), 5.53-5.31 (m, 1H), 4.53-4.36 (m, 2H), 4.33-4.17 (m, 1H), 4.16-3.95 (m, 2H), 3.95-3.79 (m, 1H), 3.63-3.39 (m, 3H), 3.27-3.12 (m, 1H), 2.57-2.34 (m, 3H), 2.28-2.09 (m, 7H), 2.05-1.94 (m, 2H), 1.93-1.66 (m, 6H), 0.87-0.77 (m, 3H); ¹⁹F NMR (377 MHz, METHANOL-d₄) δ=-76.89 (br s, 1F), -88.50-94.55 (m, 1F), -121.07 (br d, J=5.7 Hz, 1F), -137.84-141.32 (m, 1F), -173.71 (br s, 1F); LCMS (ESI, M+1): m/z=668.5.

Example 510

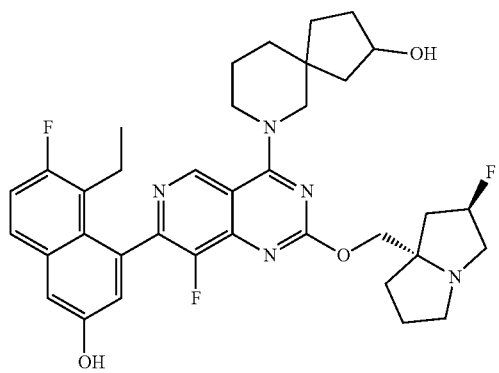 [SMILES: CCc1c(F)ccc2cc(O)cc(-c3ncc4c(N5CCCC6(CCC(O)C6)C5)nc(OC[C@@]56CCCN5C[C@H](F)C6)nc4c3F)c12]

7-(7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-7-azaspiro[4.5]decan-2-ol The title compound was synthesized according to the procedure described for example 330. ¹H NMR (400 MHz, DMSO-d₆) δ=0.69-0.47 (m, 3H) 1.15 (s, 1H) 1.30-1.64 (m, 7H) 1.71-1.86 (m, 6H) 2.00-2.15 (m, 4H) 2.78-2.86 (m, 1H) 3.01 (s, 1H) 3.08 (d, J=11.6 Hz, 2H) 3.76 (m, 2H) 3.93 (s, 1H) 4.03-4.19 (m, 4H) 4.42-4.56 (m, 1H) 5.17-5.38 (m, 1H) 7.03 (s, 1H) 7.28-7.40 (m, 2H) 7.76 (s, 1H) 8.23 (s, 1H) 9.12 (s, 1H) 9.93 (s, 1H); LCMS [M+1]⁺: m/z=648.3.

Example 511

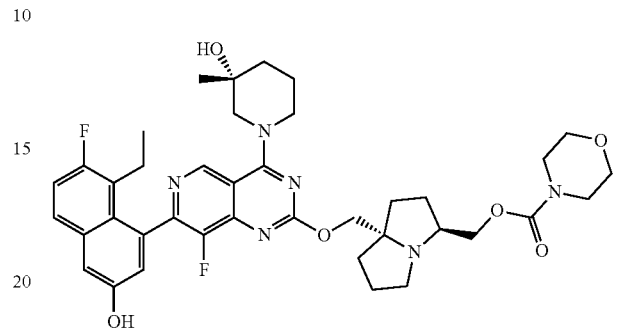

((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl morpholine-4-carboxylate The title compound was synthesized according to the procedure described for example 313. ¹H NMR (400 MHz, METHANOL-d₄) δ=9.21 (d, J=3.6 Hz, 1H), 7.67 (dd, J=5.6, 9.2 Hz, 1H), 7.30 (d, J=2.4 Hz, 1H), 7.25 (t, J=9.2 Hz, 1H), 7.07 (t, J=3.2 Hz, 1H), 4.71-4.41 (m, 2H), 4.34-4.19 (m, 3H), 4.16-4.06 (m, 1H), 4.06-3.92 (m, 1H), 3.68-3.57 (m, 5H), 3.49-3.42 (m, 4H), 3.10-2.97 (m, 2H), 2.91-2.70 (m, 1H), 2.55-2.40 (m, 1H), 2.25-2.09 (m, 3H), 2.07-1.99 (m, 1H), 1.98-1.88 (m, 3H), 1.87-1.72 (m, 5H), 1.72-1.62 (m, 1H), 1.29 (d, J=10.4 Hz, 3H), 0.88-0.74 (m, 3H); LCMS (ESI, M+1): m/z=733.4.

Example 512

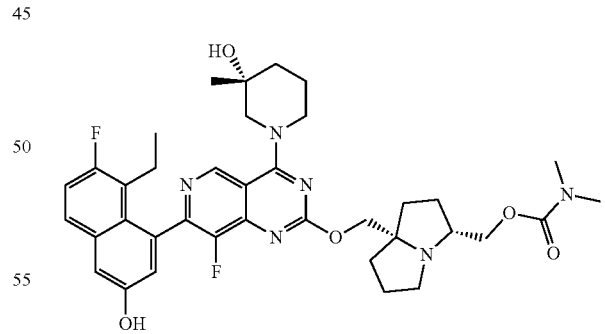

((3R,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl dimethylcarbamate The title compound was synthesized according to the procedure described for example 362. ¹H NMR (400 MHz, METHANOL-d₄) δ=9.21 (d, J=4.0 Hz, 1H), 7.70-7.66 (m, 1H), 7.31-7.23 (m, 2H), 7.07-7.06 (m, 1H), 4.59-4.49 (m, 2H), 4.39-4.19 (m, 3H), 4.18-3.92 (m, 2H), 3.71-3.55 (m, 1H), 3.52-3.40 (m, 1H), 3.22-3.02 (m, 2H), 2.93-2.88 (m, 6H), 2.53-2.39 (m, 1H), 2.30-2.10 (m, 3H), 2.09-2.02 (m, 1H), 2.00-1.89 (m, 3H), 1.88-1.63 (m, 6H), 1.30-1.28 (m, 3H), 0.84-0.78 (m, 3H); LCMS (ESI, M+1): m/z=691.4.

Example 513

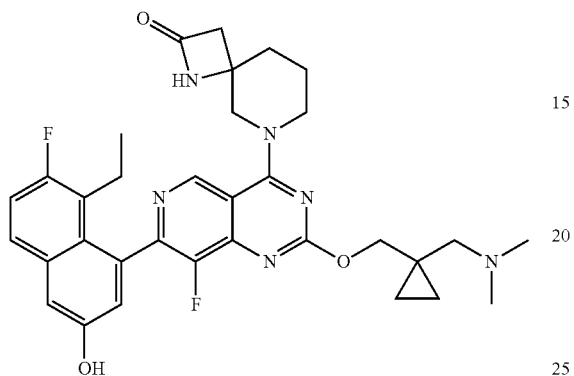

6-(2-((1-((dimethylamino)methyl)cyclopropyl)methoxy)-7-(8-ethyl-7-fluoro-3-hydroxynaphthalen-1-yl)-8-fluoropyrido[4,3-d]pyrimidin-4-yl)-1,6-diazaspiro[3.5]nonan-2-one The title compound was synthesized according to the procedure described for example 364. ¹H NMR (400 MHz, Methanol-d₄) δ 9.07 (s, 1H), 7.67 (dd, J=5.6, 9.2 Hz, 1H), 7.29 (d, J=2.4 Hz, 1H), 7.24 (t, J=9.6 Hz, 1H), 7.04 (t, J=2.8 Hz, 1H), 4.42-4.21 (m, 4H), 3.96 (dd, J=13.2, 18.4 Hz, 1H), 3.84-3.64 (m, 1H), 2.88 (dd, J=6.0, 14.8 Hz, 1H), 2.78-2.68 (m, 1H), 2.50-2.36 (m, 3H), 2.29 (s, 6H), 2.21-2.04 (m, 2H), 2.04-1.86 (m, 3H), 0.79 (dt, J=2.8, 7.2 Hz, 3H), 0.75-0.71 (m, 2H), 0.56-0.50 (m, 2H); LCMS [ESI, M+1]: m/z=603.4.

Example 514

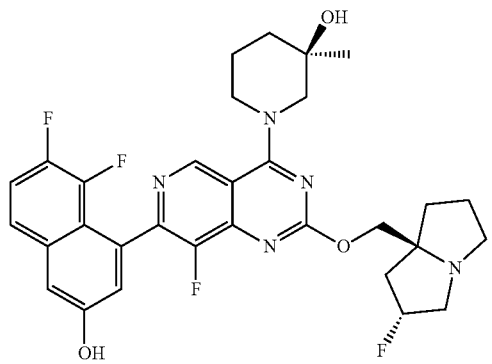 [SMILES: C[C@@]1(O)CCCN(c2nc(OC[C@@]34CCCN3C[C@H](F)C4)nc3c(F)c(-c4cc(O)cc5ccc(F)c(F)c45)ncc23)C1]

(R)-1-(7-(7,8-difluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol The title compound was synthesized according to the procedure described for example 133. ¹H NMR (400 MHz, METHANOL-d₄) δ=9.20 (d, J=7.2 Hz, 1H), 7.64-7.56 (m, 1H), 7.44-7.35 (m, 1H), 7.32 (t, J=2.0 Hz, 1H), 7.24 (dd, J=2.0, 7.6 Hz, 1H), 5.30 (d, J=54.4 Hz, 1H), 4.53 (br d, J=12.4 Hz, 1H), 4.37-4.21 (m, 3H), 3.63 (dd, J=2.4, 13.2 Hz, 1H), 3.45 (br t, J=12.0 Hz, 1H), 3.30-3.12 (m, 3H), 3.04-2.96 (m, 1H), 2.40-2.09 (m, 4H), 2.05-1.71 (m, 6H), 1.29 (d, J=5.2 Hz, 3H); LCMS (ESI, M+1): m/z=598.2.

Example 515

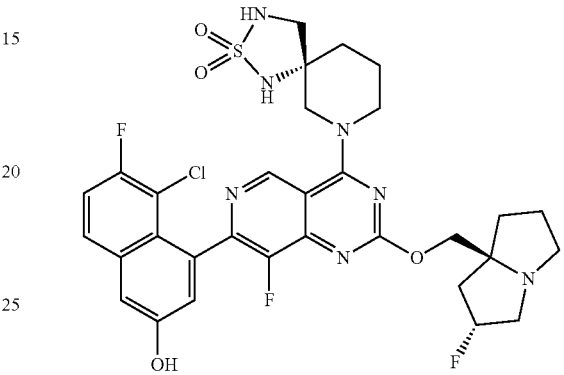

(R)-7-(7-(8-chloro-7-fluoro-3-hydroxynaphthalen-1-yl)-8-fluoro-2-(((2R,7aS)-2-fluorotetrahydro-1H-pyrrolizin-7a(5B)-yl)methoxy)pyrido[4,3-d]pyrimidin-4-yl)-2-thia-1,3,7-triazaspiro[4.5]decane2,2-dioxide

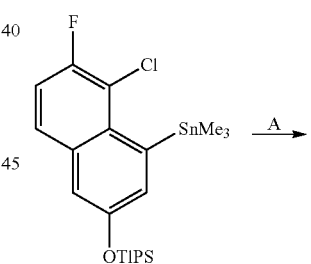

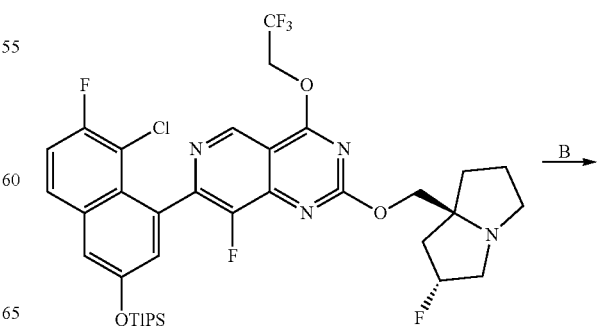

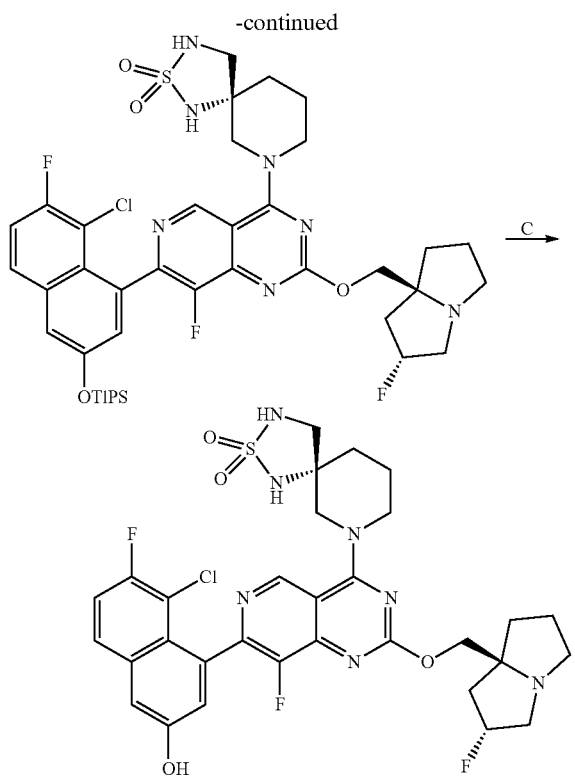

Step A. 7-(8-chloro-7-fluoro-3-((triisopropylsilyl)oxy)naphthalen-1-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine: A mixture of 7-chloro-8-fluoro-2-(((2R,7aS)-2-fluorohexahydro-1H-pyrrolizin-7a-yl)methoxy)-4-(2,2,2-trifluoroethoxy)pyrido[4,3-d]pyrimidine (800 mg, 1.0 equiv.), ((5-chloro-6-fluoro-4-(trimethylstannyl)naphthalen-2-yl)oxy)triisopropylsilane (1.40 g, 1.49 equiv.), Pd(dppf)Cl$_2$ (133 mg, 0.1 equiv.), BINAP (227 mg, 0.2 equiv.) and CuI (104 mg, 0.3 equiv.) in toluene (30 mL) was degassed and stirred at 90° C. for 6 hours under N$_2$ atmosphere. The mixture was filtered and the filtrate was concentrated under reduced pressure to give a residue. The residue was purified by column chromatography by prep-TLC (SiO$_2$, Petroleum ether/Ethyl acetate 1:1) to give the title compound (230 mg, 14% yield) as a yellow oil. LCMS (ESI, M+1): m/z=754.9.

Step B. (R)-7-(7-(8-chloro-7-fluoro-3-((triisopropylsilyl)oxy)naphthalen-1-yl)-8-fluoro-2-(((2R,7aS)-2-fluorotetrahydro-1H-pyrrolizin-7a(5H)-yl)methoxypyrido[4,3-d]pyrimidin-4-yl)-2-thia-1,3,7-triazaspiro[4.5]decane 2,2-dioxide: To a solution of 7-(8-chloro-7-fluoro-3-((triisopropylsilyl)oxy)naphthalen-1-yl)-8-fluoro-2-(((2R,7aS)-2-fluorotetrahydro-1H-pyrrolizin-7a(5H)-yl)methoxy)-4-(2,2,2-trifluoroethoxy)pyrido[4,3-d]pyrimidine (230 mg, 1.0 equiv.), (R)-2-thia-1,3,7-triazaspiro[4.5]decane 2,2-dioxide (87.3 mg, 1.5 equiv.) in DMF (2 mL) was added DIEA (196 mg, 5.0 equiv.) and 4 Å molecular sieves (300 mg). The mixture was stirred at 60° C. for 12 hours. The mixture was poured into water (20 mL) and extracted with EtOAc (2×30 mL). The combined organic layer was washed with brine (50 mL), dried over Na$_2$SO$_4$, filtered and the filtrate was concentrated to afford the title compound (262 mg, crude) as a yellow oil.

Step C. (R)-7-(7-(8-chloro-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2-thia-1,3,7-triazaspiro[4.5]decane 2,2-dioxide: To a solution of (R)-7-(7-(8-chloro-7-fluoro-3-((triisopropylsilyl)oxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2-thia-1,3,7-triazaspiro[4.5]decane 2,2-dioxide (260 mg, 1.0 equiv.) in DMF (2.0 mL) was added CsF (46.6 mg, 1.0 equiv.). The mixture was stirred at 25° C. for 0.5 hour. The mixture was poured into water (30 mL) and extracted with EtOAc (2×30 mL). The combined organic layers were washed with brine (50 mL), dried over Na$_2$SO$_4$, then the mixture was filtered and the filtrate was concentrated. The residue was purified by prep-HPLC (column: Phenomenex C18 75×30 mm×3 µm; mobile phase: water (0.1% formic acid)-ACN; B %: 20%-30%, 7 min) to afford the title compound (108 mg, 50.4% yield) as a white solid; $^1$H NMR (400 MHz, methanol-d$_4$) δ=9.11 (d, J=1.8 Hz, 1H), 8.48 (s, 1H), 7.81 (ddd, J=3.4, 5.5, 9.0 Hz, 1H), 7.46-7.34 (m, 2H), 7.21 (t, J=2.8 Hz, 1H), 5.59-5.34 (m, 1H), 4.76-4.37 (m, 5H), 3.86-3.54 (m, 5H), 3.42 (dd, J=2.4, 11.9 Hz, 1H), 3.22 (dd, J=3.2, 11.9 Hz, 1H), 2.65-2.37 (m, 2H), 2.37-2.29 (m, 1H), 2.27-2.15 (m, 2H), 2.13-1.99 (m, 3H), 1.98-1.93 (m, 1H), 1.92-1.83 (m, 1H); LCMS (ESI, M+1): m/z=690.2.

Example 516

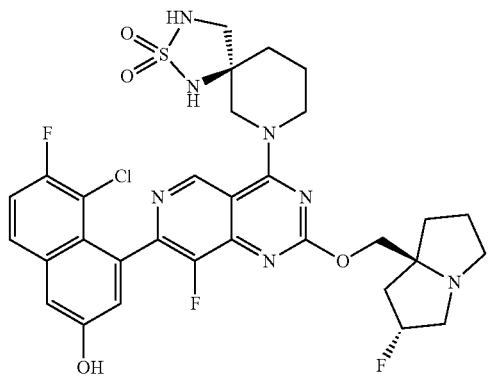 [SMILES: O=S1(=O)NC[C@@]2(CCCN(c3nc(OC[C@@]45CCCN4C[C@H](F)C5)nc4c(F)c(-c5cc(O)cc6ccc(F)c(Cl)c56)ncc34)C2)N1]

(S)-7-(7-(8-chloro-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2-thia-1,3,7-triazaspiro [4.5]decane2,2-dioxide The title compound was synthesized according to the procedure described for example 515. $^1$H NMR (400 MHz, methanol-d$_4$) δ=9.12 (d, J=3.3 Hz, 1H), 8.47 (s, 1H), 7.81 (ddd, J=3.5, 5.5, 9.1 Hz, 1H), 7.47-7.34 (m, 2H), 7.21 (dd, J=2.5, 4.2 Hz, 1H), 5.60-5.37 (m, 1H), 4.77-4.32 (m, 5H), 3.89-3.53 (m, 5H), 3.41 (dd, J=3.1, 12.0 Hz, 1H), 3.22 (dd, J=3.4, 11.9 Hz, 1H), 2.65-2.40 (m, 2H), 2.38-2.29 (m, 1H), 2.27-2.16 (m, 2H), 2.13-2.00 (m, 3H), 1.96 (br d, J=11.0 Hz, 1H), 1.92-1.83 (m, 1H); LCMS (ESI, M+1): m/z=690.2.

Example 517

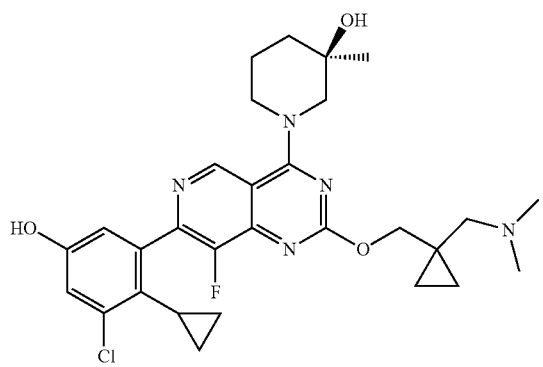 [SMILES: CN(C)CC1(COc2nc(N3CCC[C@@](C)(O)C3)c3cnc(-c4cc(O)cc(Cl)c4C4CC4)c(F)c3n2)CC1]

(R)-1-(7-(3-chloro-2-cyclopropyl-5-hydroxyphenyl)-2-((1-((dimethylamino)methyl)cyclopropyl)methoxy)-8-fluoropyrido[4,3-d]pyrimidin-4-yl)-3-methylpiperidin-3-ol

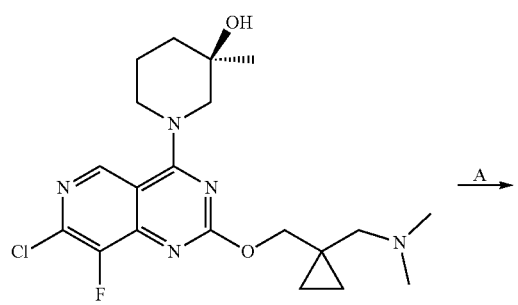
A →
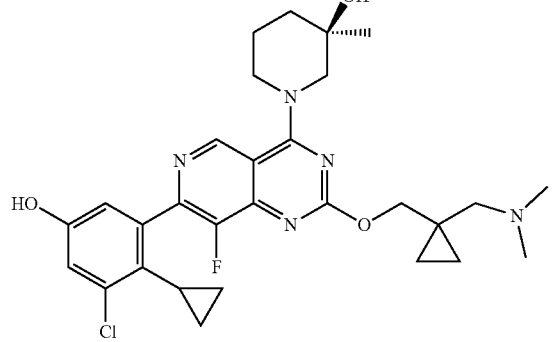

Step A. (R)-1-(7-(3-chloro-2-cyclopropyl-5-hydroxyphenyl)-2-((1-((dimethylamino)methyl)cyclopropyl)methoxy)-8-fluoropyrido[4,3-d]pyrimidin-4-yl)-3-methylpiperidin-3-ol: A mixture of (R)-1-(7-chloro-2-((1-((dimethylamino)methyl)cyclopropyl)methoxy)-8-fluoropyrido[4,3-d]pyrimidin-4-yl)-3-methylpiperidin-3-ol (100 mg, 1.0 equiv.), 3-chloro-4-cyclopropyl-5-(4,4,5,5-tetramethyl-1,3,2-dioxaborolan-2-yl)phenol (104 mg, 1.5 equiv.), cataCXium® A Pd G3 (34.4 mg, 0.2 equiv.), Cs$_2$CO$_3$ (1.0 M, 3.0 equiv.) in methoxycyclopentane (1.0 mL) was degassed and stirred at 80° C. for 3 hours under N$_2$ atmosphere. The mixture was diluted with water (5 mL), extracted with ethyl acetate (3×5 mL), the combined organic layers were dried over Na$_2$SO$_4$ and concentrated. The crude product was purified by prep-HPLC [column: Phenomenex luna C18 150×25 mm×10 μm; mobile phase: water (0.1% formic acid)-ACN; B %: 13%-43%, 10 min] and lyophilized to afford the title compound (53.4 mg, 39% yield) as a yellow solid; $^1$H NMR (400 MHz, METHANOL-d$_4$) δ=9.24 (s, 1H), 6.97 (d, J=2.8 Hz, 1H), 6.79 (d, J=2.8 Hz, 1H), 4.61-4.52 (m, 1H), 4.42 (s, 2H), 4.31-4.26 (m, 1H), 3.60 (d, J=13.2 Hz, 1H), 3.49-3.37 (m, 1H), 3.14-2.99 (m, 2H), 2.79 (s, 6H), 2.22-2.08 (m, 1H), 1.91-1.72 (m, 4H), 1.29 (s, 3H), 0.94-0.88 (m, 2H), 0.79-0.76 (m, 2H), 0.67-0.61 (m, 2H), 0.10-0.07 (m, 2H); LCMS (ESI, M+1): m/z=556.2.

Example 518

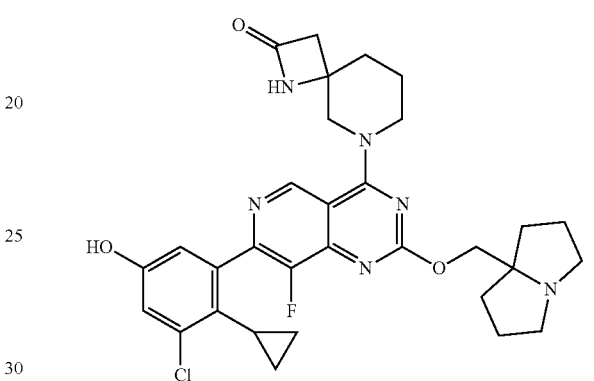

6-(7-(3-chloro-2-cyclopropyl-5-hydroxyphenyl)-8-fluoro-2-(((tetrahydro-1H-pyrrolizin-7a(5H)-yl)methoxy)pyrido[4,3-d]pyrimidin-4-yl)-1,6-diazaspiro[3.5]nonan-2-one

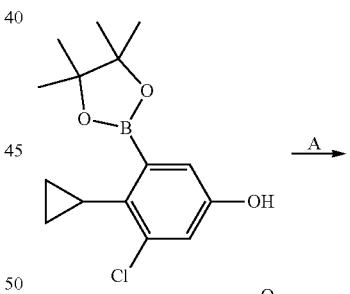
A →
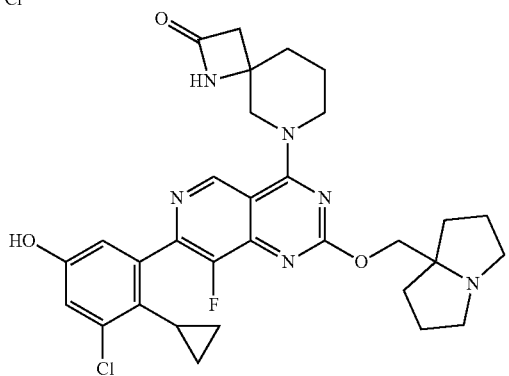

Step A. 6-(7-(3-chloro-2-cyclopropyl-5-hydroxyphenyl)-8-fluoro-2-(((tetrahydro-1H-pyrrolizin-7a(5H)-yl)methoxy)

pyrido[4,3-d]pyrimidin-4-yl)-1,6-diazaspiro[3.5]nonan-2-one: To a solution of 6-(7-chloro-8-fluoro-2-((tetrahydro-1H-pyrrolizin-7a(5H)-yl)methoxy)pyrido[4,3-d]pyrimidin-4-yl)-1,6-diazaspiro[3.5]nonan-2-one (50.0 mg, 1.0 equiv.) in CPME (1 mL) was added CataCXium A Pd G3 (15.8 mg, 0.2 equiv.), 3-chloro-4-cyclopropyl-5-(4,4,5,5-tetramethyl-1,3,2-dioxaborolan-2-yl)phenol (47.9 mg, 1.5 equiv.) and Cs$_2$CO$_3$ (1.5 M, 3.0 equiv.). The mixture was stirred at 100° C. for 2 hours under nitrogen atmosphere. The reaction mixture was poured into saturated aqueous NH$_4$Cl (5 mL) and extracted with EtOAc (3×2 mL). The combined organic layers were washed with brine (5 mL), dried over anhydrous sodium sulfate, filtered and concentrated. The residue was diluted with MeOH (1 mL). The residue was purified by prep-HPLC [column: Phenomenex Luna C18 150×25 mm×10 μm; mobile phase: water (0.1% formic acid)-ACN. B %: 12%-42%, 10 min] to afford the title compound (11.8 mg, 17% yield, formic acid salt) as a yellow solid; $^1$H NMR (400 MHz, METHANOL-d$_4$) δ=9.13 (s, 1H), 8.51 (br s, 1H), 6.98 (d, J=2.4 Hz, 1H), 6.82-6.79 (m, 1H), 4.69-4.58 (m, 2H), 4.44-4.28 (m, 2H), 4.01 (br dd, J=2.9, 13.0 Hz, 1H), 3.88-3.81 (m, 1H), 3.73-3.60 (m, 2H), 3.26 (td, J=6.0, 11.6 Hz, 2H), 2.94-2.87 (m, 1H), 2.81-2.74 (m, 1H), 2.36-2.28 (m, 2H), 2.25-2.15 (m, 4H), 2.08 (td, J=6.5, 12.6 Hz, 4H), 1.97 (br s, 2H), 1.89-1.81 (m, 1H), 0.67-0.47 (m, 2H), 0.13-0.02 (m, 2H); LCMS (ESI, M+1): m/z=593.3.

Example 519

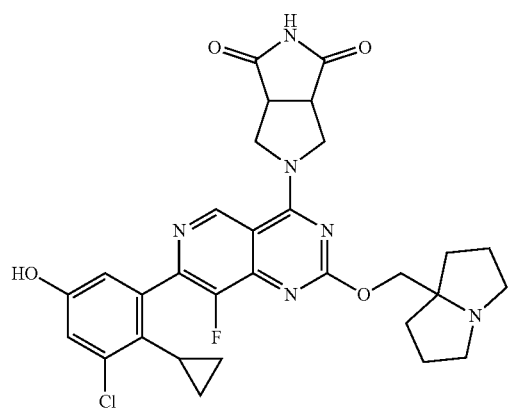 [SMILES: O=C1NC(=O)C2CN(c3nc(OCC45CCCN4CCC5)nc4c(F)c(-c5cc(O)cc(Cl)c5C5CC5)ncc34)CC12]

5-(7-(3-chloro-2-cyclopropyl-5-hydroxyphenyl)-8-fluoro-2-((tetrahydro-1H-pyrrolizin-7a(5H)-yl)methoxy)pyrido[4,3-d]pyrimidin-4-yl)tetrahydropyrrolo[3,4-c]pyrrole-1,3(2H,3aH)-dione

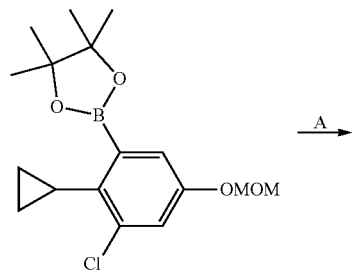

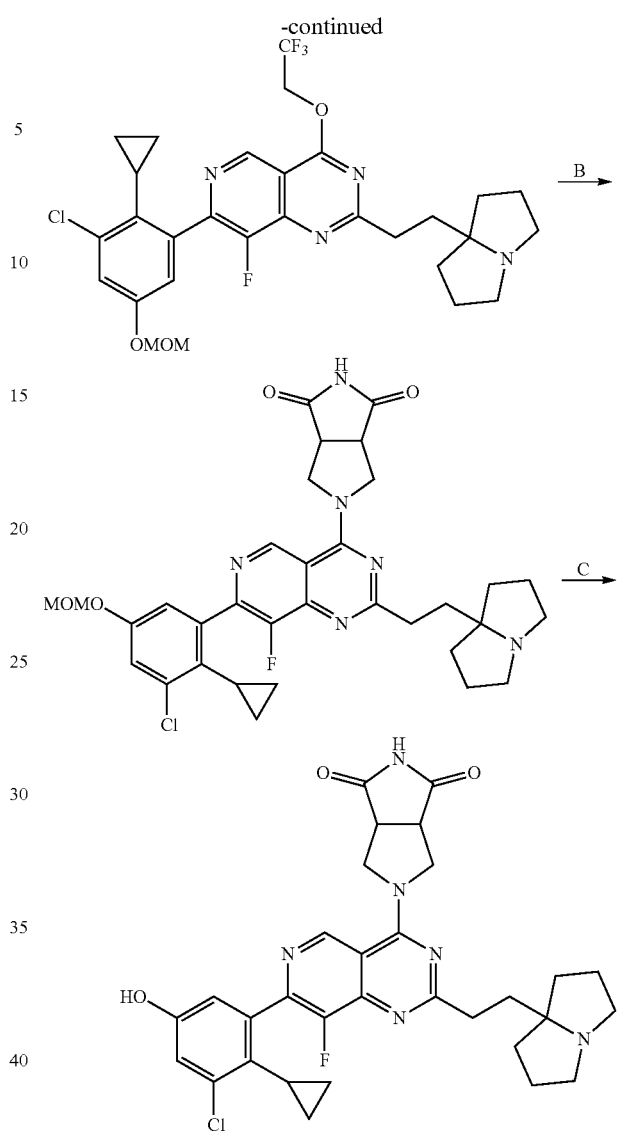

Step A. 7-(3-chloro-2-cyclopropyl-5-(methoxymethoxy)phenyl)-8-fluoro-2-((tetrahydro-1H-pyrrolizin-7a(5H)-yl)methoxy)-4-(2,2,2-trifluoroethoxy)pyrido[4,3-d]pyrimidine: To a solution of 7-chloro-8-fluoro-2-((tetrahydro-1H-pyrrolizin-7a(5H)-yl)methoxy)-4-(2,2,2-trifluoroethoxy)pyrido[4,3-d]pyrimidine (600 mg, 1.0 equiv.) in THF (12 mL) was added 2-[3-chloro-2-cyclopropyl-5-(methoxymethoxy)phenyl]-4,4,5,5-tetramethyl-1,3,2-dioxaborolane (579 mg, 1.2 equiv.), K$_3$PO$_4$ (1.5 M, 3.0 equiv.) and CataCXium A Pd G3 (104 mg, 0.1 equiv.). The mixture was stirred at 60° C. for 3 hours under nitrogen atmosphere. The mixture was diluted with water (200 mL) and extracted with EtOAc (2×50 mL). The combined organic layers were washed with brine (100 mL), dried over anhydrous sodium sulfate, filtered and concentrated. The residue was purified by column chromatography [SiO$_2$, petroleum ether/ethyl acetate 10:1 to 0:1] to afford the title compound (400 mg, 41% yield) as a light yellow solid; LCMS (ESI, M+1): m/z=597.3.

Step B. 5-(7-(3-chloro-2-cyclopropyl-5-(methoxymethoxy)phenyl)-8-fluoro-2-((tetrahydro-1H-pyrrolizin-7a(5H)-yl)methoxy)pyrido[4,3-d]pyrimidin-4-yl)tetrahydropyrrolo[3,4-c]pyrrole-1,3(2H,3aH)-dione: To a solution of 7-(3-chloro-2-cyclopropyl-5-(methoxymethoxy) phenyl)-8-fluoro-2-((tetrahydro-1H-pyrrolizin-7a(5H)-yl) methoxy)-4-(2,2,2-trifluoroethoxy)pyrido[4,3-d]pyrimidine (50.0 mg, 1.0 equiv.) and 2,3,3a,6a-tetrahydro-1H-pyrrolo [3,4-c]pyrrole-4,6-dione (14.1 mg, 1.2 equiv.) in DMF (0.25 mL) and ACN (0.25 mL) was added $K_3PO_4$ (53.3 mg, 3.0 equiv.). The mixture was stirred at 40° C. for 16 hours. The mixture was diluted with water (20 mL) and extracted with EtOAc (2×10 mL). The organic layer was washed with brine (20 mL), dried over anhydrous sodium sulfate, filtered and concentrated to afford the title compound (50.0 mg, crude) as a light yellow oil; LCMS (ESI, M+1): m/z=637.4.

Step C. 5-(7-(3-chloro-2-cyclopropyl-5-hydroxyphenyl)-8-fluoro-2-((tetrahydro-1H-pyrrolizin-7a(5H)-yl)methoxy) pyrido[4,3-d]pyrimidin-4-yl)tetrahydropyrrolo[3,4-c]pyrrole-1,3(2H,3aH)-dione: To a solution of 5-(7-(3-chloro-2-cyclopropyl-5-(methoxymethoxy)phenyl)-8-fluoro-2-((tetrahydro-1H-pyrrolizin-7a(5H)-yl)methoxy)pyrido[4,3-d]pyrimidin-4-yl)tetrahydropyrrolo[3,4-c]pyrrole-1,3(2H, 3aH)-dione (50.0 mg, 1.0 equiv.) in ACN (1.0 mL) was added HCl-dioxane (4 M, 102 equiv.). The mixture was stirred at 20° C. for 1 hour. The mixture was concentrated. The residue was purified by prep-HPLC [column: Phenomenex Synergi C18 150×25 mm×10 μm; mobile phase: water (0.1% formic acid)-ACN. B %: 8/0-38%, 10 min] to afford the title compound (19.5 mg, 36% yield, FORMIC ACID) as a white solid; $^1$H NMR (400 MHz, METHANOL-$d_4$) δ=9.29 (s, 1H), 8.53 (s, 1H), 6.98 (d, J=2.5 Hz, 1H), 6.81 (d, J=2.5 Hz, 1H), 4.64 (br d, J=13.9 Hz, 2H), 4.60 (s, 2H), 4.41-4.29 (m, 2H), 3.82-3.73 (m, 2H), 3.65-3.55 (m, 2H), 3.26-3.14 (m, 2H), 2.35-2.24 (m, 2H), 2.15 (tt, J=6.6, 13.3 Hz, 4H), 2.09-1.99 (m, 2H), 1.90-1.79 (m, 1H), 0.69-0.53 (m, 2H), 0.06 (br s, 2H); LCMS (ESI, M+1): m/z=593.2.

Example 520

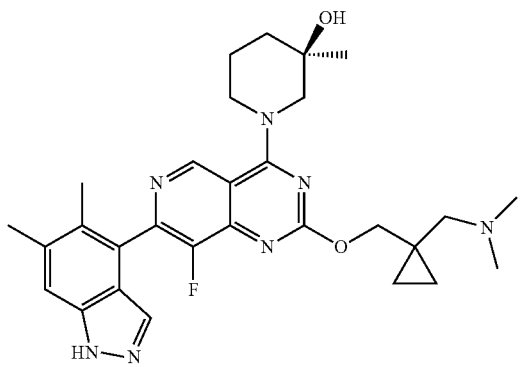

(3R)-1-(7-(5,6-dimethyl-1H-indazol-4-yl)-2-((1-((dimethylamino)methyl)cyclopropyl)methoxy)-8-fluoropyrido[4,3-d]pyrimidin-4-yl)-3-methylpiperidin-3-ol

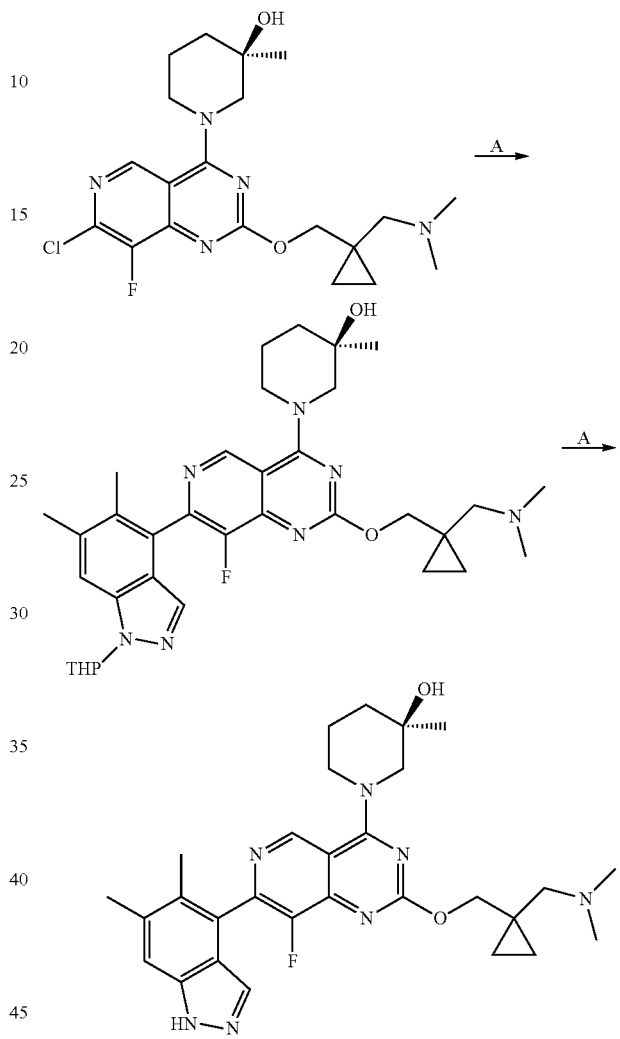

Step A. (3R)-1-(7-(5,6-dimethyl-1-(tetrahydro-2H-pyran-2-yl)-1H-indazol-4-yl)-2-((1-((dimethylamino)methyl)cyclopropyl)methoxy)-8-fluoropyrido[4,3-d]pyrimidin-4-yl)-3-methylpiperidin-3-ol: A mixture of (3R)-1-[7-chloro-2-[[1-[(dimethylamino)methyl]cyclopropyl]methoxy]-8-fluoro-pyrido[4,3-d]pyrimidin-4-yl]-3-methyl-piperidin-3-ol (120 mg, 1.0 equiv.), 5,6-dimethyl-1-tetrahydropyran-2-yl)-4-(4,4,5,5-tetramethyl-1,3,2-dioxaborolan-2-yl)indazole (111 mg, 1.10 equiv.), $K_3PO_4$ (1.5 M in water, 0.5 mL, 2.70 equiv.), and CataCXium A Pd G3 (20.6 mg, 0.1 equiv.) in methoxycyclopentane (2 mL) was degassed and stirred at 90° C. for 4 hours under $N_2$ atmosphere. The reaction mixture was diluted with ethyl acetate (5 mL) and water (10 mL) and the aqueous phase was extracted with ethyl acetate (5 mL). The combined organic phase was washed with brine (10 mL), dried over anhydrous sodium sulfate, filtered and concentrated to give a residue. The residue was purified by reversed phase flash [water (0.1% formic acid)-ACN] to afford the title compound (135 mg, 74% yield) as a white solid; LCMS (ESI, M+1): m/z=618.5.

Step B. (3R)-1-(7-(5,6-dimethyl-1H-indazol-4-yl)-2-((1-((dimethylamino)methy)cyclopropyl)methoxy)-8-fluoro-pyrido[4,3-d]pyrimidin-4-yl)-3-methylpiperidin-3-ol: To a solution of (3R)-1-[2-[[1-[(dimethylamino)methyl]cyclopropyl]methoxy]-7-(5,6-dimethyl-1-tetrahydropyran-2-yl-indazol-4-yl)-8-fluoro-pyrido[4,3-d]pyrimidin-4-yl]-3-methyl-piperidin-3-ol (120 mg, 194 µmol, 1.0 equiv.) in DCM (2.0 mL) was added TFA (3.08 g, 139 equiv.). The reaction mixture was stirred at 20° C. for 1 hour. The mixture was poured into saturated NaHCO$_3$ solution (60 mL) and the pH was adjusted to 8. The mixture was extracted with ethyl acetate (2×20 mL), the organic layer was washed with saturated brine (20 mL). The combined organic layers were dried over anhydrous sodium sulfate and concentrated under vacuum to give a residue. The residue was purified by prep-HPLC [column: Unisil 3-100 C18 Ultra 150×50 mm×3 µm; mobile phase: water (0.1% formic acid)-ACN, B %: 3%-33% over 10 min] to afford the title compound (45.8 mg, 44% yield) as a white solid. $^1$H NMR (400 MHz, METHANOL-d$_4$) δ=9.30 (d, J=10.4 Hz, 1H), 8.53 (s, 1H), 7.62 (d, J=2.4 Hz, 1H), 7.51 (s, 1H), 4.67-4.53 (m, 1H), 4.49-4.39 (m, 2H), 4.32 (br d, J=1.2 Hz, 1H), 3.62 (dd, J=4.4, 13.2 Hz, 1H), 3.49-3.34 (m, 1H), 3.17-3.02 (m, 2H), 2.82 (s, 6H), 2.51 (s, 3H), 2.23 (d, J=3.2 Hz, 3H), 2.20-2.08 (m, 1H), 1.91-1.72 (m, 3H), 1.29 (d, J=2.4 Hz, 3H), 0.96-0.88 (m, 2H), 0.83-0.75 (m, 2H); LCMS (ESI, M+1): m/z=534.4.

Example 521

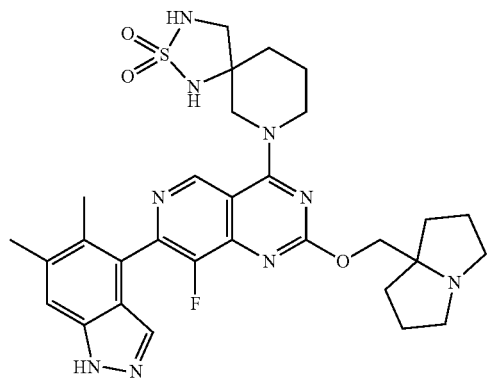 [SMILES: Cc1cc2[nH]ncc2c(-c2ncc3c(N4CCCC5(CNS(=O)(=O)N5)C4)nc(OCC45CCCN4CCC5)nc3c2F)c1C]

7-(7-(5,6-dimethyl-1H-indazol-4-yl)-8-fluoro-2-((hexahydro-1H-pyrrolizin-7a-yl)methoxy)pyrido[4,3-d]pyrimidin-4-yl)-2-thia-1,3,7-triazaspiro[4.5]decane 2,2-dioxide

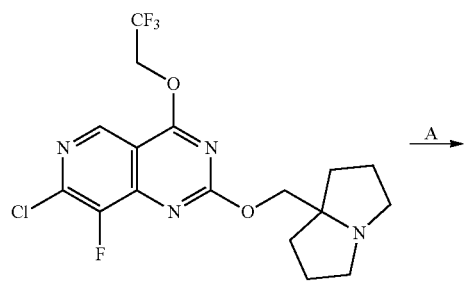

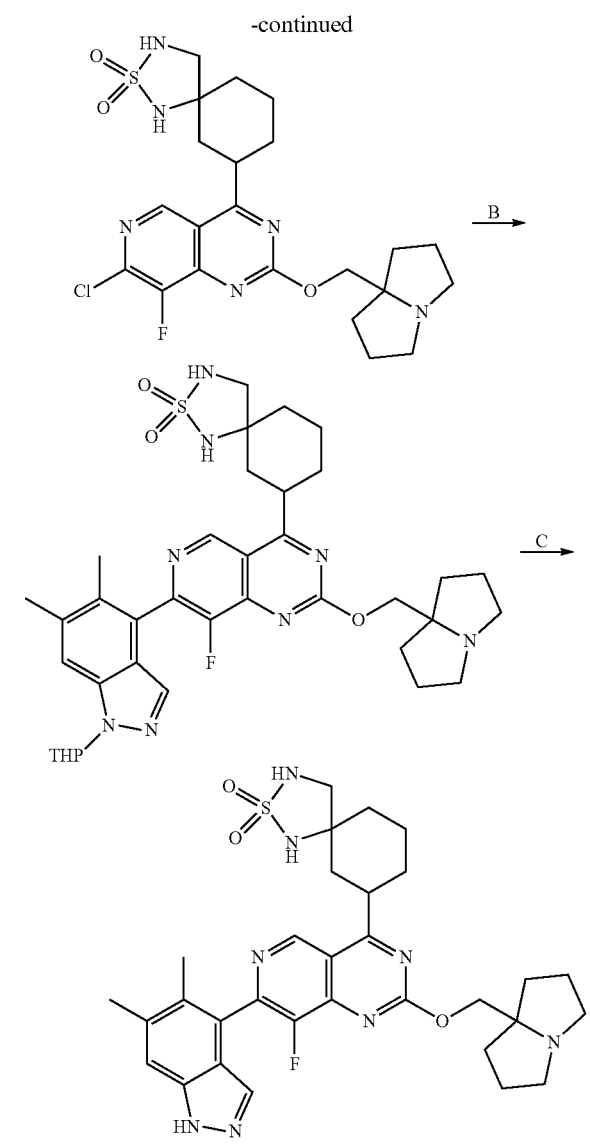

Step A. 7-(7-chloro-8-fluoro-2-((hexahydro-1H-pyrrolizin-7a-yl)methoxyl)pyrido[4,3-d]pyrimidin-4-yl)-2-thia-1,3,7-triazaspiro[4.5]decane 2,2-dioxide: A mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (0.4 g, 1 equiv.), 2-thia-1,3,7-triazaspiro[4.5]decane 2,2-dioxide (200 mg, 1.1 equiv.), DIPEA (246 mg, 2 equiv.) and 4 Å molecular sieves (50 mg) in DMF (2.5 mL) was stirred at 40° C. for 13 hours under N$_2$ atmosphere. The mixture was filtered and purified by reversed phase flash chromatography [C18, water (0.1% formic acid)-ACN] to afford the title compound (0.3 g, 59% yield) as a yellow solid; LCMS (ESI, M+1): m/z=512.2.

Step B. 7-(7-(5,6-dimethyl-14tetrahydro-2H-pyran-2-yl)-1H-indazol-4-yl)-8-fluoro-2-((hexahydro-1H-pyrrolizin-7a-yl)methoxy)pyrido[4,3-d]pyrimidin-4-yl)-2-thia-1,3,7-triazaspiro[4.5]decane 2,2-dioxide: To a mixture of 7-(7-chloro-8-fluoro-2-((hexahydro-1H-pyrrolizin-7a-yl)methoxy)pyrido[4,3-d]pyrimidin-4-yl)-2-thia-1,3,7-triazaspiro[4.5]decane 2,2-dioxide (140 mg, 1.0 equiv.), 5,6-dimethyl-1-(tetrahydro-2H-pyran-2-yl)-4-(4,4,5,5-tetramethyl-1,3,2-dioxaborolan-2-yl)-1H-indazole (100 mg, 1.0 equiv.) and $K_3PO_4$ (1.5 M, 547 μL, 3.0 equiv.) in methoxycyclopentane (2.5 mL) was added CataCXium A Pd G3 (20 mg, 0.1 equiv.) and the mixture was degassed and stirred at 90° C. for 2 hours under $N_2$ atmosphere. The mixture was diluted with $H_2O$ (1 mL) and extracted with ethyl acetate (4×2 mL). The combined organic layers were dried over anhydrous $Na_2SO_4$, concentrated and purified by reversed phase flash [C18, water (0.1% formic acid)-ACN] to afford the title compound (74 mg, 36% yield) as a light yellow solid; LCMS (ESI, M+1): m/z=706.4.

Step C. 7-(7-(5,6-dimethyl-1H-indazol-4-yl)-8-fluoro-2-((hexahydro-1H-pyrrolizin-7a-yl)methoxy)pyrido[4,3-d]pyrimidin-4-yl)-2-thia-1,3,7-triazaspiro[4.5]decane 2,2-dioxide: To a solution of 7-(7-(5,6-dimethyl-1-(tetrahydro-2H-pyran-2-yl)-1H-indazol-4-yl)-8-fluoro-2-((hexahydro-1H-pyrrolizin-7a-yl)methoxy)pyrido[4,3-d]pyrimidin-4-yl)-2-thia-1,3,7-triazaspiro[4.5]decane 2,2-dioxide (85 mg, 1.0 equiv.) in DCM (1.0 mL) was added TFA (1.2 mL) dropwise at 0° C. The mixture was stirred at 0° C. for 0.75 hour. The mixture was poured into DCM (10 mL) and saturated $NaHCO_3$ aqueous (20 mL) at 0° C. The pH of the mixture was adjusted to 9 with solid $Na_2CO_3$ while maintaining the temperature below 10° C. The mixture was extracted with DCM (4×5 mL). The combined organic layers were dried over anhydrous $Na_2SO_4$ and concentrated. The residue was purified by prep-HPLC [column: Phenomenex Luna C18 150×25 mm×10 μm; mobile phase: water (0.1% formic acid)-ACN; B %: 7/.-37%, 10 minutes] to afford the tittle compound (66.6 mg, 83% yield, 0.6 formic acid salt) as a white solid; $^1$H NMR (400 MHz, METHANOL-$d_4$) δ=9.21 (s, 1H), 7.63 (br d, J=17.2 Hz, 1H), 7.52 (br s, 1H), 4.75 (br d, J=12.0 Hz, 2H), 4.64-4.54 (m, 2H), 3.82-3.67 (m, 4H), 3.45-3.36 (m, 1H), 3.27-3.22 (m, 3H), 2.51 (s, 3H), 2.33 (dt, J=7.2, 12.0 Hz, 2H), 2.27-2.13 (m, 7H), 2.10-1.87 (m, 6H); LCMS (ESI, M+1): m/z=622.4.

Example 522

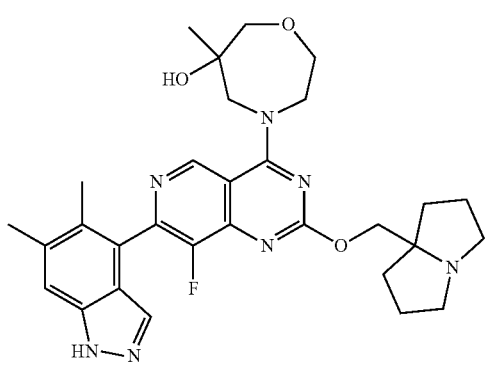 [SMILES: Cc1cc2[nH]ncc2c(-c2ncc3c(N4CCOCC(C)(O)C4)nc(OCC45CCCN4CCC5)nc3c2F)c1C]

4-(7-(5,6-dimethyl-1H-indazol-4-yl)-8-fluoro-2-((hexahydro-1H-pyrrolizin-7a-yl)methoxy)pyrido[4,3-d]pyrimidin-4-yl)-6-methyl-1,4-oxazepan-6-ol 26. The title compound was synthesized according to the procedure described for example 521. $^1$H NMR (400 MHz, METHANOL-$d_4$) δ=9.67 (br d, J=6.8 Hz, 11H), 7.60 (d, J=7.2 Hz, 1H), 7.52 (s, 1H), 4.67-4.51 (m, 4H), 4.27-4.15 (m, 11H), 4.09-3.85 (m, 3H), 3.78-3.66 (m, 4H), 3.30-3.26 (m, 2H), 2.51 (s, 3H), 2.38-2.27 (m, 2H), 2.26-2.09 (m, 9H), 1.29 (s, 3H); LCMS (ESI, M+1): m/z=562.4.

Example 523

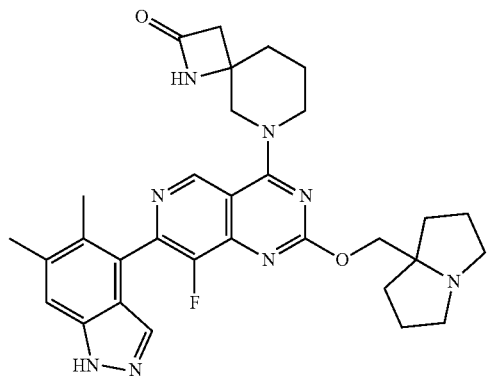 [SMILES: Cc1cc2[nH]ncc2c(-c2ncc3c(N4CCCC5(CC(=O)N5)C4)nc(OCC45CCCN4CCC5)nc3c2F)c1C]

6-(7-(5,6-dimethyl-1H-indazol-4-yl)-8-fluoro-2-((hexahydro-1H-pyrrolizin-7a-yl)methoxy)pyrido[4,3-d]pyrimidin-4-yl)-1,6-diazaspiro[3.5]nonan-2-one The title compound was synthesized according to the procedure described for example 521. $^1$H NMR (400 MHz, METHANOL-$d_4$) δ=9.21 (s, 1H), 7.60 (s, 1H), 7.52 (3, 1H), 4.69-4.58 (m, 2H), 4.41-4.39 (m, 1H), 4.38-4.29 (m, 1H), 4.03-3.93 (m, 1H), 3.92-3.79 (m, 11H), 3.72-3.61 (m, 2H), 3.27-3.21 (m, 2H), 2.95-2.90 (m, 1H), 2.81-2.73 (m, 1H), 2.51 (s, 3H), 2.35-2.27 (m, 2H), 2.25-2.20 (m, 4H), 2.20-2.11 (m, 4H), 2.11-2.02 (m, 3H), 2.07-1.95 (m, 2H); LCMS (ESI, M+1): m/z=571.4.

Example A: KRas Binding Assay

This Example illustrates that exemplary compounds of the present invention bind to KRas and are capable of displacing a labeled tracer ligand occupying the KRas binding site. $KRas^{WT}$, $KRaS^{G12A}$, $KRaS^{G12C}$, $KRaS^{G12D}$, $KRaS^{G12R}$, $KRaS^{G12S}$, $KRaS^{G12V}$, $KRaS^{G13D}$, or $KRaS^{Q61H}$ was used in the assay.

The ability of a compound to bind to KRas was measured using a TR-FRET displacement assay. Biotinylated KRas (corresponding to amino acids 1-169, produced at Accelegan Inc.) was incubated with custom made Cy5 labelled tracer, terbium streptavidin (Cisbio Inc.) and compound (1% DMSO final) in buffer (50 mM HEPES, pH 7.5, 5 mM $MgCl_2$, 0.005% Tween-20 and 1 mM DTT). After a 60-minute incubation at room temperature, the reaction was measured using a BMG LABTECH CLARIO star Plus via TR-FRET. 100 percent of control (POC) is determined by using a DMSO control and 0 POC is determined using a concentration of control compound that completely inhibits binding of the tracer to KRas. The POC values were fit to a 4-parameter $IC_{50}$ equation and the $IC_{50}$ value reported.

TABLE 2

Binding to KRas (IC$_{50}$ nM) by Exemplary Compounds of Formula (I)

| Ex. No. | G12D | G12V | G12R | G12A | G12S | G12C | WT | G13D | Q61H |
|---|---|---|---|---|---|---|---|---|---|
| 1 | 330 | 565 | 866 | | | | | | |
| 2 | 632 | 1006 | 2179 | | | | | | |
| 3 | 8181 | 11740 | 20400 | | | | 23 | | |
| 4 | 43 | 21 | 31 | | | | | | |
| 5 | ≤2 | ≤2 | ≤2 | ≤2 | ≤2 | ≤2 | ≤2 | ≤2 | ≤2 |
| 6 | 29 | 19 | 14 | 16 | 20 | 18 | 22 | 21 | 23 |
| 7 | ≤2 | ≤2 | ≤2 | ≤2 | ≤2 | ≤2 | 3 | 3 | 3 |
| 8 | 2242 | 2626 | 5406 | | | | | | |
| 9 | 456 | 333 | 354 | | | | | | |
| 10 | ≤2 | ≤2 | 3 | | | | | | |
| 11 | 15510 | 20810 | 40130 | | | | | | |
| 12 | 3 | 3 | 4 | | | | | | |
| 13 | ≤2 | ≤2 | ≤2 | ≤2 | ≤2 | ≤2 | ≤2 | ≤2 | ≤2 |
| 14 | 29 | 52 | 109 | 58 | 58 | 51 | 51 | 61 | 80 |
| 15 | 24 | 42 | 81 | 38 | 42 | 37 | 41 | 42 | 52 |
| 16 | 26 | 39 | 60 | 29 | 31 | 29 | 32 | 33 | 40 |
| 17 | 746 | 1488 | 2227 | 961 | 921 | 1188 | 956 | 925 | 1861 |
| 18 | 23950 | 4446 | 6776 | 7540 | 4981 | 8795 | 6809 | 9372 | 13160 |
| 19 | ≥100000 | 64510 | 84320 | | | | | | |
| 20 | 2395 | 3398 | 7389 | 2779 | 2982 | 3178 | 2967 | | |
| 21 | 14850 | 9727 | 10720 | 12570 | 18800 | 12710 | 11430 | 12570 | 19430 |
| 22 | 9970 | 12130 | 14880 | | | 62060 | | | |
| 23 | 5275 | 4301 | 6176 | | | 4737 | | | |
| 24 | ≤2 | ≤2 | ≤2 | ≤2 | ≤2 | ≤2 | ≤2 | | |
| 25 | 433 | 633 | 1312 | | | 679 | | | |
| 26 | 845 | 1261 | 2317 | | | | | | |
| 27 | ≤2 | ≤2 | ≤2 | ≤2 | ≤2 | ≤2 | ≤2 | ≤2 | ≤2 |
| 28 | 3 | ≤2 | 3 | ≤2 | ≤2 | ≤2 | 3 | 3 | 3 |
| 29 | 20540 | 1965 | 4382 | 6198 | 3114 | 4319 | 5842 | 8190 | 13860 |
| 30 | 209 | 800 | 1271 | 1758 | 1452 | 1287 | 1743 | 1999 | 2900 |
| 31 | .14040 | 13200 | 12810 | | | | | | |
| 32 | 98600 | ≥100000 | 86270 | | | | | | |
| 33 | 6373 | 6612 | 10050 | | | | | | |
| 34 | 11090 | 14960 | ≥100000 | 48730 | 53460 | 34950 | 28140 | | |
| 35 | 12110 | 2522 | 1611 | | | | | 1659 | 4013 |
| 36 | 9 | 20 | 24 | | | | | | |
| 37 | 41 | 57 | 93 | 52 | 63 | 56 | 68 | 88 | 88 |
| 38 | ≤2 | ≤2 | ≤2 | | | | | | |
| 39 | 12520 | 25480 | 19750 | | | | | | |
| 40 | 54950 | 66350 | 76920 | | | | | | |
| 41 | 6477 | 3407 | 6391 | | | | | | |
| 42 | 1861 | 1614 | 3088 | | | | | | |
| 43 | 3782 | 1301 | 2270 | | | | | | |
| 44 | 3229 | 2987 | 6238 | | | | | | |
| 45 | 89 | 189 | 362 | | | | | | |
| 46 | 14070 | 24030 | 22490 | | | | | 8793 | 18460 |
| 47 | 63390 | 70100 | ≥100000 | | | | | | |
| 48 | 18360 | 20350 | 24070 | | | | | 16010 | 19890 |
| 49 | 69970 | 27940 | 18940 | | | | | | |
| 50 | 39000 | 22590 | 22670 | | | | | | |
| 51 | 21 | 35 | 69 | 36 | 38 | 35 | 32 | 36 | 50 |
| 52 | 235 | 25 | 39 | | | | | | |
| 53 | 66380 | 49380 | 90250 | | | | | | |
| 54 | 162 | 321 | 528 | | | | | | |
| 55 | 139 | 212 | 410 | | | 295 | | | |
| 56 | 2614 | 3757 | 8341 | | | | | | |
| 57 | ≤2 | ≤2 | ≤2 | | | | | 3 | ≤2 |
| 58 | 6 | ≤2 | ≤2 | | | | | | |
| 59 | ≤2 | ≤2 | ≤2 | | | | | | |
| 60 | ≤2 | ≤2 | ≤2 | | | | | | |
| 61 | ≤2 | ≤2 | ≤2 | | | | | | |
| 62 | 3 | ≤2 | ≤2 | | | | | 3 | ≤2 |
| 63 | 3 | ≤2 | 4 | | | | | 5 | 3 |
| 64 | 568 | 1356 | 2551 | 1303 | 1149 | 1059 | 997 | 1359 | 1547 |
| 65 | 14090 | 14990 | 45130 | | | 21030 | | | |
| 66 | 26920 | 44540 | 67780 | | | | | | |
| 67 | 10370 | 11520 | 16100 | | | 14240 | | | |
| 68 | 11610 | 16950 | 27560 | | | | | | |
| 69 | 2089 | 2733 | 4168 | | | | | | |
| 70 | 14070 | 397 | 215 | 403 | 418 | 224 | 2857 | 11660 | 10840 |
| 71 | 3 | ≤2 | 6 | | | | | | |
| 72 | 14050 | 10770 | 14020 | | | | | | |
| 73 | 5 | ≤2 | ≤2 | | | | | | |
| 74 | ≤2 | ≤2 | 3 | | | | | | |
| 75 | 63100 | 2393 | 977 | | | 1835 | | | |
| 76 | 15490 | 3148 | 8872 | | | | | | |

TABLE 2-continued

Binding to KRas (IC$_{50}$ nM) by Exemplary Compounds of Formula (I)

| Ex. No. | G12D | G12V | G12R | G12A | G12S | G12C | WT | G13D | Q61H |
|---|---|---|---|---|---|---|---|---|---|
| 77 | 12820 | 1350 | 2205 | 1065 | 1172 | 1640 | 1410 | 1208 | 1907 |
| 78 | 677 | 1532 | 1759 | 2198 | 1242 | 1263 | 2676 | 3797 | 3297 |
| 79 | 15460 | 539 | 650 | | | | | | |
| 80 | 29790 | 1595 | 1475 | 1576 | 2566 | 1253 | 6843 | 6313 | 10670 |
| 81 | 3564 | 802 | 1039 | 759 | 531 | 891 | 864 | 860 | 1168 |
| 82 | ≤2 | ≤2 | ≤2 | | | | | | |
| 83 | 392 | 498 | 992 | 735 | 703 | 509 | 1195 | 1885 | 1992 |
| 84 | 12740 | 1864 | 2499 | 1647 | 2073 | 863 | 4288 | 5071 | 5864 |
| 85 | 44020 | 3704 | 2118 | 2845 | 4641 | 2153 | 4518 | 4656 | 10870 |
| 86 | 6901 | 3098 | 8490 | 2245 | 2391 | 3078 | 2408 | 3001 | 4775 |
| 87 | 3363 | 3657 | 11910 | 7119 | 10850 | 5938 | 6086 | 5257 | 9503 |
| 88 | 30710 | 2177 | 4367 | 1821 | 4239 | 2509 | 7175 | 9308 | 14660 |
| 89 | 2283 | 1021 | 2600 | 1252 | 1548 | 1061 | 1399 | 1811 | 3272 |
| 90 | 40220 | 3466 | 4190 | 5138 | 6483 | 4182 | 7236 | 8214 | 19550 |
| 91 | ≥100000 | 12660 | 2197 | 12700 | 17910 | 11350 | 14140 | 36630 | 31360 |
| 92 | 20760 | 1718 | 1976 | 6549 | 6867 | 3411 | 8804 | 8557 | 17330 |
| 93 | 83570 | 2935 | 3386 | 7842 | 10190 | 4053 | 14880 | 20410 | 21820 |
| 94 | 4510 | 146 | 115 | 240 | 368 | 183 | 1395 | 1246 | 1846 |
| 95 | 54980 | 4991 | 3061 | 4996 | 4122 | 3619 | 3994 | 7183 | 10350 |
| 96 | 62940 | 1944 | 3191 | 2497 | 3229 | 1947 | 5709 | 10730 | 22110 |
| 97 | 175 | 189 | 348 | 227 | 272 | 192 | 333 | 297 | 412 |
| 98 | 1889 | 3009 | 6415 | 2908 | 4014 | 2841 | 3356 | 3207 | 4765 |
| 99 | ≥100000 | 3967 | 16650 | 13590 | 21750 | 8334 | 32380 | 59770 | 98550 |
| 100 | 11810 | 17290 | ≥100000 | 50370 | 28810 | 39930 | 40320 | 49290 | 42010 |
| 101 | 15310 | 966 | 615 | 994 | 1343 | 679 | 3032 | 4233 | 2578 |
| 102 | 2289 | 365 | 479 | 634 | 191 | 399 | 1168 | 769 | 1178 |
| 103 | 15520 | 1834 | 1503 | 2086 | 2452 | 1891 | 3946 | 4212 | 4944 |
| 104 | 7613 | 2868 | 2819 | 1742 | 2018 | 2300 | 2333 | 3638 | 3208 |
| 105 | 9051 | 2806 | 5925 | 6703 | 5754 | 3511 | 8005 | 13840 | 13810 |
| 106 | 3631 | 612 | 1507 | 722 | 369 | 1125 | 2098 | 2335 | 2340 |
| 107 | 10750 | 3414 | 4619 | 6518 | 6848 | 3519 | 8525 | 8792 | 8776 |
| 108 | 19720 | 8102 | 4192 | | | | | | |
| 109 | 10160 | 7426 | 4113 | 4275 | 7389 | 4250 | 3991 | 4340 | 4944 |
| 110 | 26900 | 3974 | 2482 | 9285 | 4365 | 5222 | 8814 | 9330 | 10080 |
| 111 | 2716 | 2012 | 3717 | 2416 | 2696 | 1742 | 2324 | 3624 | 3445 |
| 112 | 37540 | 25940 | 28120 | 25320 | 30990 | 27470 | 36620 | 13260 | 20740 |
| 113 | 14250 | 12000 | 16010 | 9476 | 10570 | 7110 | 8467 | 12060 | 12230 |
| 114 | 4380 | 2856 | 3747 | 2645 | 2806 | 2475 | 2705 | 29890 | 43270 |
| 115 | 30890 | 5804 | 4636 | 10530 | 10860 | 6558 | 11600 | 21170 | 22290 |
| 116 | 3309 | 4089 | 6267 | 2743 | 3593 | 4411 | 3449 | 2698 | 5199 |
| 117 | 31970 | 11110 | 10080 | 9152 | 11010 | 6570 | 9856 | 5679 | 8239 |
| 118 | 16100 | 7531 | 11350 | 8142 | 6237 | 7451 | 8554 | 8813 | 13960 |
| 119 | 31940 | 18040 | 15560 | 14400 | 14580 | 11600 | 15680 | 17210 | 27610 |
| 120 | ≥100000 | ≥100000 | ≥100000 | 33300 | 85290 | 19770 | 34070 | ≥100000 | ≥100000 |
| 121 | 42820 | 6637 | 12320 | 15460 | 18580 | 9100 | 12990 | 17330 | 25370 |
| 122 | ≥100000 | 6909 | 12450 | 14410 | 21750 | 3471 | 25970 | 86370 | 88200 |
| 123 | 4436 | 3192 | 7503 | 3181 | 2760 | 2341 | 3499 | 3484 | 4979 |
| 124 | 12620 | 1507 | 2190 | 2068 | 3869 | 1483 | 7022 | 7821 | 7135 |
| 125 | 60420 | 3923 | 4394 | 5517 | 7425 | 4250 | 13310 | 29060 | 39020 |
| 126 | 67250 | ≥100000 | 18430 | 13800 | 3967 | 9288 | 5967 | 7293 | 7502 |
| 127 | 25080 | 1698 | 2578 | 2681 | 1715 | 2192 | 4220 | 8699 | 11080 |
| 128 | 48980 | 8793 | 4142 | 11460 | 7803 | 9569 | 12810 | 13400 | 18430 |
| 129 | 2255 | 2795 | 4434 | 2687 | 2795 | 2531 | 3113 | 2496 | 4359 |
| 130 | 8361 | 10850 | 18260 | 10510 | 14240 | 9076 | 11430 | 25770 | 21930 |
| 131 | 14640 | 8300 | 2793 | 4463 | 9294 | 3453 | 8212 | 6561 | 7694 |
| 132 | 9 | 5 | 6 | | | | | | |
| 133 | ≤2 | ≤2 | ≤2 | | | | | | |
| 134 | 17 | ≤2 | ≤2 | | | | | | |
| 135 | 31 | 3 | 3 | | | | | | |
| 136 | 3 | ≤2 | ≤2 | | | | | | |
| 137 | ≤2 | ≤2 | 3 | | | | | | |
| 138 | 12 | 5 | 5 | | | | | | |
| 139 | 8 | ≤2 | ≤2 | | | | | | |
| 140 | ≤2 | ≤2 | ≤2 | | | | | | |
| 141 | ≤2 | ≤2 | ≤2 | | | | | | |
| 142 | 14 | ≤2 | ≤2 | | | | | | |
| 143 | 4 | ≤2 | ≤2 | | | | | | |
| 144 | 43 | 48 | 96 | 71 | 65 | 77 | 74 | 60 | 82 |
| 145 | 9 | 6 | 3 | | | | | | |
| 146 | ≤2 | ≤2 | 3 | | | | | | |
| 147 | 4 | 3 | 3 | | | | | | |
| 148 | 3 | ≤2 | ≤2 | | | | | | |
| 149 | 4 | ≤2 | 3 | | | | | | |
| 150 | ≤2 | ≤2 | ≤2 | | | | | | |
| 151 | 12 | 8 | 9 | | | | | | |
| 152 | 175 | 8 | 10 | | | | | | |

TABLE 2-continued

Binding to KRas (IC$_{50}$ nM) by Exemplary Compounds of Formula (I)

| Ex. No. | G12D | G12V | G12R | G12A | G12S | G12C | WT | G13D | Q61H |
|---|---|---|---|---|---|---|---|---|---|
| 153 | 6 | 5 | 10 | 7 | 7 | 7 | 6 | 8 | 7 |
| 154 | 33 | 28 | 66 | 42 | 43 | 43 | 54 | 34 | 53 |
| 155 | 118 | 4 | 3 | | | | | | |
| 156 | ≤2 | ≤2 | ≤2 | | | | | | |
| 157 | 12 | ≤2 | ≤2 | | | | | | |
| 158 | 152 | 78 | 81 | 85 | 69 | 41 | 103 | 83 | 102 |
| 159 | 39 | 3 | 5 | | | | | | |
| 160 | 15 | ≤2 | ≤2 | | | | | | |
| 161 | 68 | 7 | 9 | 1.2 | 15 | 7 | 20 | 16 | 17 |
| 162 | 31 | ≤2 | 3 | | | | | | |
| 163 | 95 | 14 | 17 | | | | | | |
| 164 | 28 | 3 | 3 | | | | | | |
| 165 | 51 | 7 | 13 | 17 | 17 | 12 | 13 | 13 | 14 |
| 166 | 7 | ≤2 | ≤2 | | | | | | |
| 167 | 16 | ≤2 | ≤2 | | | | | | |
| 168 | 5 | ≤2 | ≤2 | | | | | | |
| 169 | 4 | ≤2 | ≤2 | | | | | | |
| 170 | ≤2 | ≤2 | ≤2 | | | | | | |
| 171 | 89 | 3 | 9 | | | | | | |
| 172 | 9 | ≤2 | ≤2 | | | | | | |
| 173 | 6 | 4 | 6 | | | | | | |
| 174 | 89 | 4 | 13 | | | | | | |
| 175 | 38 | ≤2 | ≤2 | | | | | | |
| 176 | 108 | 20 | 30 | | | | | | |
| 177 | 3 | ≤2 | ≤2 | | | | | | |
| 178 | 18 | 7 | 14 | | | | | | |
| 179 | 12 | 4 | 3 | | | | | | |
| 180 | 4 | ≤2 | 4 | | | | | | |
| 181 | 29 | 17 | 10 | | | | | | |
| 182 | 9 | ≤2 | ≤2 | | | | | | |
| 183 | 4 | 4 | 5 | | | | | | |
| 184 | ≤2 | ≤2 | 3 | | | | | | |
| 185 | 11 | 9 | 9 | | | | | | |
| 186 | 21 | 9 | 10 | | | | | | |
| 187 | 12 | 5 | 6 | | | | | | |
| 188 | 48 | 19 | 23 | | | | | | |
| 189 | 32 | 18 | 18 | | | | | | |
| 190 | 3 | ≤2 | ≤2 | | | | | | |
| 191 | 9 | 4 | 4 | | | | | | |
| 192 | ≤2 | ≤2 | ≤2 | | | | | | |
| 193 | ≤2 | ≤2 | ≤2 | | | | | | |
| 194 | ≤2 | ≤2 | ≤2 | | | | | | |
| 195 | 16600 | 4909 | 1714 | | | | | | |
| 196 | ≤2 | ≤2 | ≤2 | | | | | | |
| 197 | ≤2 | ≤2 | ≤2 | | | | | | |
| 198 | 86 | 9 | 8 | | | | | | |
| 199 | 3 | ≤2 | ≤2 | | | | | | |
| 200 | ≤2 | ≤2 | ≤2 | | | | | | |
| 201 | ≤2 | ≤2 | ≤2 | | | | | | |
| 202 | ≤2 | ≤2 | ≤2 | | | ≤2 | | | |
| 203 | ≤2 | ≤2 | ≤2 | | | | | | |
| 204 | 1287 | 43 | 21 | 38 | 51 | 20 | 233 | 317 | 283 |
| 205 | 307 | 8 | 7 | 13 | 16 | 10 | 80 | 69 | 95 |
| 206 | ≤2 | ≤2 | ≤2 | | | | | | |
| 207 | 17270 | 6166 | 13080 | 18100 | 46210 | 11750 | 26720 | 30390 | 46370 |
| 208 | 17450 | 824 | 494 | 1297 | 2263 | 677 | 4011 | 6246 | 7154 |
| 209 | 63350 | 2345 | 1615 | 3699 | 10080 | 2517 | 4957 | 13260 | 12720 |
| 210 | ≥100000 | 2940 | 37770 | 66550 | ≥100000 | 43260 | ≥100000 | ≥100000 | ≥100000 |
| 211 | ≥100000 | 14680 | 8034 | 12240 | 18720 | 10400 | 16940 | 20220 | 29830 |
| 212 | 15590 | 1349 | 880 | 2831 | 6449 | 3124 | 8356 | 10070 | 17370 |
| 213 | ≥100000 | 5573 | 4252 | 6194 | 7252 | 4198 | 16840 | 20540 | 17690 |
| 214 | ≥100000 | 12550 | 16350 | 28800 | 34560 | 9588 | 60030 | 95150 | 81100 |
| 215 | ≥100000 | 17000 | 8948 | 26070 | 23480 | 17750 | 33970 | 47000 | 57470 |
| 216 | ≥100000 | 17890 | 2571 | 13750 | 41050 | 6302 | 30890 | 59030 | 83190 |
| 217 | 64450 | 5159 | 7568 | 8986 | 11330 | 9878 | 13980 | 11610 | 19530 |
| 218 | 65930 | 2844 | 6534 | 14830 | 23180 | 6879 | 28910 | ≥100000 | 84810 |
| 219 | 65290 | 8833 | 4777 | 16210 | 13130 | 5652 | 15020 | 18130 | 20180 |
| 220 | 10820 | 6067 | 8672 | 6749 | 6309 | 8246 | 5570 | 6699 | 7473 |
| 221 | 586 | 556 | 191 | 271 | 313 | 498 | 284 | 308 | 231 |
| 222 | ≥100000 | 18230 | 31250 | 17790 | 26890 | 8984 | 35880 | 70090 | 52900 |
| 223 | 21110 | 930 | 665 | 1357 | 1801 | 1189 | 5601 | 6870 | 8654 |
| 224 | 64760 | 8476 | 4018 | 8455 | 7111 | 11710 | 6285 | 4834 | 9675 |
| 225 | 21660 | 6241 | 9389 | 14900 | 9898 | 8121 | 16590 | 23510 | 26140 |
| 226 | 6070 | 14070 | 51930 | | | | | | |
| 227 | 1242 | 2430 | 3056 | | | 2718 | 3386 | | |
| 228 | 147 | 148 | 224 | 1212 | 202 | 1019 | 2698 | 465 | 822 |

TABLE 2-continued

Binding to KRas (IC$_{50}$ nM) by Exemplary Compounds of Formula (I)

| Ex. No. | G12D | G12V | G12R | G12A | G12S | G12C | WT | G13D | Q61H |
|---|---|---|---|---|---|---|---|---|---|
| 229 | 85340 | 3121 | 2117 | | | 4724 | 36850 | | |
| 230 | 38750 | 7987 | 9849 | 11260 | 19660 | 10640 | 28440 | 35510 | 23350 |
| 231 | 97900 | 24560 | 8681 | 52100 | 31620 | 29610 | 49370 | 61490 | 62320 |
| 232 | 11920 | 7781 | 9993 | 17340 | 19370 | 13600 | 19190 | 17970 | 25900 |
| 233 | 6699 | 4635 | 5563 | 2647 | 7451 | 6154 | 4303 | 7383 | 5348 |
| 234 | 2022 | 1603 | 1846 | 2302 | 1764 | 1622 | 2640 | 1979 | 2587 |
| 235 | 2660 | 1700 | 2870 | 2152 | 2011 | 1650 | 2653 | 2714 | 3356 |
| 236 | 2331 | 623 | 3352 | 3395 | 897 | 2043 | 3497 | 2462 | 4439 |
| 237 | 9560 | 7612 | 9743 | 5337 | 8916 | 7594 | 4362 | 8292 | 6382 |
| 238 | ≥100000 | 19350 | 9182 | | | | | | |
| 239 | 8653 | 4934 | 4812 | 1978 | 2212 | 1608 | 1830 | 1640 | 2673 |
| 240 | 1138 | 1550 | 777 | 586 | 492 | 597 | 478 | 350 | 498 |
| 241 | 17150 | 13610 | 8624 | | | | | | |
| 242 | 8032 | 7632 | 12950 | 8192 | 6226 | 6956 | 11010 | 7859 | 13620 |
| 243 | 25360 | 2187 | 1056 | 1049 | 1808 | 1146 | 3320 | 2963 | 3585 |
| 244 | 18210 | 3574 | 3095 | 1848 | 3061 | 2823 | 5138 | 4856 | 5077 |
| 245 | 2991 | 11710 | 9831 | | | | | | |
| 246 | 6414 | 22140 | 11260 | | | | | | |
| 247 | 429 | 1827 | 2555 | 2108 | 2152 | 2682 | 1585 | 1182 | 2058 |
| 248 | 6807 | 9778 | 10530 | | | | | | |
| 249 | 7856 | 1287 | 424 | 981 | 742 | 979 | 1061 | 1280 | 808 |
| 250 | 7315 | 3408 | 3992 | 3927 | 3799 | 6839 | 3579 | 3513 | 5313 |
| 251 | 6831 | 3870 | 14580 | 6125 | 5753 | 6401 | 3841 | 3784 | 6246 |
| 252 | 11 | 17 | 27 | 5 | 8 | 17 | 7 | 6 | 9 |
| 253 | 67330 | 4353 | 4082 | 3032 | 3589 | 2408 | 6002 | 14090 | 7718 |
| 254 | 2839 | 10830 | 7908 | | | | | | |
| 255 | 6227 | 11010 | 15130 | | | | | | |
| 256 | 2416 | 4536 | 8144 | 4627 | 5308 | 4048 | 4031 | 3796 | 6017 |
| 257 | 2432 | 3793 | 6914 | 5493 | 5219 | 4004 | 4026 | 3957 | 6028 |
| 258 | 320 | 858 | 1183 | 2066 | 1014 | 1381 | 3249 | 4383 | 4614 |
| 259 | 158 | 380 | 769 | 1521 | 649 | 825 | 2208 | 3299 | 3181 |
| 260 | 61 | 204 | 455 | 294 | 419 | 591 | 864 | 1173 | 1062 |
| 261 | 1606 | 3984 | 2606 | 5743 | 2317 | 2392 | 7099 | 9609 | 10650 |
| 262 | 960 | 1790 | 1663 | | | | 1534 | | |

| Ex. No. | G12D | G12V | G12R | G12A | G12S | G12C | WT | G13D | Q61H |
|---|---|---|---|---|---|---|---|---|---|
| 263 | 1981 | 4033 | 3038 | 4936 | 3554 | 4408 | 9086 | 10960 | 12120 |
| 264 | 8160 | 13570 | 9856 | | | | | | |
| 265 | 5309 | 2735 | 1923 | 3019 | 2505 | 3311 | 2458 | 2384 | 3188 |
| 266 | 6061 | 5255 | 13860 | | | | | | |
| 267 | 4369 | 1712 | 1719 | 2496 | 2074 | 2253 | 1565 | 1367 | 2430 |
| 268 | 11350 | 6442 | 8884 | | | | | | |
| 269 | 1909 | 1000 | 1056 | 1052 | 725 | 608 | 1063 | 1494 | 1826 |
| 270 | 2627 | 2095 | 7593 | | | 2834 | 4194 | | |
| 271 | 2429 | 2444 | 7693 | | | | 3001 | | |
| 272 | 194 | 130 | 120 | 138 | 132 | 141 | 116 | 134 | 144 |
| 273 | 5150 | 2309 | 5202 | | | | 3068 | | |
| 274 | 375 | 867 | 2762 | | | | 14700 | | |
| 275 | 1656 | 9053 | 7165 | | | | 24340 | | |
| 276 | 212 | 303 | 1215 | | | | 3219 | | |
| 277 | 765 | 1801 | 4911 | | | | 5287 | | |
| 278 | 801 | 1985 | 1860 | | | | 3673 | | |
| 279 | 34330 | 3388 | 3624 | | | | | | |
| 280 | ≥100000 | ≥100000 | ≥100000 | ≥100000 | ≥100000 | 9859 | ≥100000 | ≥100000 | ≥100000 |
| 281 | 213 | 170 | 81 | 59 | 67 | 75 | 61 | 125 | 51 |
| 282 | 30 | 15 | 18 | 16 | 15 | 16 | 15 | 18 | 17 |
| 283 | 97 | 90 | 129 | 97 | 91 | 77 | 113 | 157 | 142 |
| 284 | 38 | 41 | 58 | 46 | 45 | 44 | 46 | 54 | 50 |
| 285 | 976 | 864 | 350 | 367 | 359 | 426 | 323 | 447 | 293 |
| 286 | 313 | 521 | 674 | 370 | 407 | 410 | 608 | 498 | 555 |
| 287 | 8169 | 225 | 225 | 648 | 590 | 321 | 838 | 423 | 1158 |
| 288 | 53 | 67 | 78 | 95 | 82 | 68 | 89 | 71 | 113 |
| 289 | 5610 | 807 | 754 | 607 | 520 | 407 | 818 | 960 | 1071 |
| 290 | 582 | 171 | 176 | 183 | 147 | 207 | 276 | 236 | 290 |
| 291 | 140 | 277 | 439 | 229 | 192 | 161 | 269 | 209 | 218 |
| 292 | 21 | 61 | 180 | 97 | 26 | 88 | 68 | 55 | 77 |
| 293 | 10 | 4 | 5 | 5 | 6 | 6 | 6 | 7 | 5 |
| 294 | 9 | 9 | 15 | 13 | 12 | 13 | 14 | 16 | 14 |
| 295 | 2454 | 948 | 593 | 1801 | 2385 | 1896 | 2851 | 2873 | 3259 |
| 296 | 4 | ≤2 | ≤2 | | | | | | |
| 297 | 54 | ≤2 | 9 | | | | | | |

-continued

| Ex. No. | G12D | G12V | G12R | G12A | G12S | G12C | WT | G13D | Q61H |
|---|---|---|---|---|---|---|---|---|---|
| 298 | 1516 | 133 | 99 | | | | | | |
| 299 | 3 | ≤2 | ≤2 | | | | | | |
| 300 | ≤2 | ≤2 | ≤2 | | | | | | |
| 301 | ≤2 | ≤2 | ≤2 | | | | | | |
| 302 | ≤2 | ≤2 | ≤2 | | | | | | |
| 303 | ≤2 | ≤2 | ≤2 | | | | | | |
| 304 | ≤2 | ≤2 | ≤2 | | | | | | |
| 305 | 25 | 6 | 14 | | | | | | |
| 306 | 7 | 4 | 4 | | | | | | |
| 307 | ≤2 | ≤2 | ≤2 | | | | | | |
| 308 | 6 | 4 | 10 | | | | | | |
| 309 | 4 | ≤2 | 3 | | | | | | |
| 310 | 8 | ≤2 | ≤2 | | | | | | |
| 311 | ≤2 | ≤2 | ≤2 | | | | | | |
| 312 | 388 | 254 | 203 | 156 | 172 | 212 | 202 | 242 | 280 |
| 313 | ≤2 | ≤2 | ≤2 | ≤2 | ≤2 | ≤2 | ≤2 | ≤2 | ≤2 |
| 314 | ≤2 | ≤2 | ≤2 | ≤2 | ≤2 | ≤2 | ≤2 | ≤2 | ≤2 |
| 315 | ≤2 | ≤2 | ≤2 | ≤2 | ≤2 | ≤2 | ≤2 | 3 | ≤2 |
| 316 | ≤2 | ≤2 | ≤2 | ≤2 | ≤2 | ≤2 | ≤2 | ≤2 | ≤2 |
| 317 | ≤2 | ≤2 | ≤2 | ≤2 | ≤2 | ≤2 | ≤2 | ≤2 | ≤2 |
| 318 | ≤2 | ≤2 | ≤2 | ≤2 | ≤2 | ≤2 | ≤2 | ≤2 | ≤2 |
| 319 | ≤2 | ≤2 | ≤2 | ≤2 | ≤2 | ≤2 | ≤2 | ≤2 | ≤2 |
| 320 | 3 | ≤2 | 3 | ≤2 | ≤2 | ≤2 | ≤2 | ≤2 | ≤2 |
| 321 | ≤2 | ≤2 | ≤2 | ≤2 | ≤2 | ≤2 | ≤2 | ≤2 | ≤2 |
| 322 | ≤2 | ≤2 | ≤2 | | | ≤2 | ≤2 | | |
| 323 | ≤2 | ≤2 | ≤2 | ≤2 | ≤2 | ≤2 | ≤2 | ≤2 | ≤2 |
| 324 | ≤2 | ≤2 | ≤2 | ≤2 | ≤2 | ≤2 | ≤2 | ≤2 | ≤2 |
| 325 | ≤2 | ≤2 | ≤2 | ≤2 | ≤2 | ≤2 | ≤2 | ≤2 | ≤2 |
| 326 | ≤2 | ≤2 | ≤2 | ≤2 | ≤2 | ≤2 | ≤2 | ≤2 | ≤2 |
| 327 | ≤2 | ≤2 | ≤2 | | | | | | |
| 328 | 9 | 6 | 18 | | | 9 | 9 | | |
| 329 | 6602 | 1784 | 3379 | | | 2618 | 1029 | | |
| 330 | ≤2 | ≤2 | ≤2 | | | ≤2 | ≤2 | | |
| 331 | ≤2 | ≤2 | ≤2 | | | | | | |
| 332 | ≤2 | ≤2 | 3 | | | | | | |
| 333 | ≤2 | ≤2 | 5 | | | | | | |
| 334 | 1480 | 699 | 738 | | | | | | |
| 335 | 7827 | ≥100000 | 84490 | | | | | | |
| 336 | ≤2 | ≤2 | ≤2 | | | | | | |
| 337 | 3 | 3 | 5 | | | | | | |
| 338 | ≤2 | 3 | 4 | | | | | | |
| 339 | ≤2 | ≤2 | ≤2 | | | | | | |
| 340 | ≤2 | ≤2 | ≤2 | | | | | | |
| 341 | ≤2 | 3 | ≤2 | | | | | | |
| 342 | 3 | ≤2 | ≤2 | | | | | | |
| 343 | ≤2 | ≤2 | ≤2 | | | | | | |
| 344 | 138 | 83 | 94 | | | | | | |
| 345 | 5 | 3 | 4 | | | | | | |
| 346 | ≤2 | ≤2 | ≤2 | | | | | | |
| 347 | 3 | 3 | 3 | | | | | | |
| 348 | 6 | 3 | ≤2 | | | | | | |
| 349 | 20 | 4 | 7 | | | | | | |
| 350 | 30 | 8 | 8 | | | | | | |
| 351 | 13 | 15 | 11 | | | | | | |
| 352 | ≤2 | ≤2 | ≤2 | | | | | | |
| 353 | ≤2 | ≤2 | ≤2 | | | | | | |
| 354 | ≤2 | ≤2 | ≤2 | | | | | | |
| 355 | ≤2 | ≤2 | ≤2 | | | | | | |
| 356 | ≤2 | ≤2 | ≤2 | | | | | | |
| 357 | ≤2 | ≤2 | ≤2 | | | | | | |
| 358 | ≤2 | ≤2 | ≤2 | | | | | | |
| 359 | ≤2 | ≤2 | ≤2 | | | | | | |
| 360 | 5 | ≤2 | ≤2 | | | | | | |
| 361 | ≤2 | ≤2 | ≤2 | | | | | | |
| 362 | 3 | 3 | 4 | | | | | | |
| 363 | 201 | 57 | 10 | | | | | | |
| 364 | ≤2 | ≤2 | ≤2 | | | | | | |
| 365 | ≤2 | ≤2 | ≤2 | | | | | | |
| 366 | 3 | 3 | 9 | | | | | | |
| 367 | ≤2 | ≤2 | ≤2 | | | | | | |
| 368 | 4 | 24 | 11 | | | | | | |
| 369 | 5 | 3 | 4 | | | | | | |
| 370 | 11 | ≤2 | 5 | | | | | | |
| 371 | 7 | ≤2 | 5 | | | | | | |
| 372 | 56 | 5 | 13 | | | | | | |
| 373 | 5 | ≤2 | ≤2 | | | | | | |
| 374 | ≤2 | 9 | 15 | | | | | | |

-continued

| Ex. No. | G12D | G12V | G12R | G12A | G12S | G12C | WT | G13D | Q61H |
|---|---|---|---|---|---|---|---|---|---|
| 375 | 44 | 8 | 9 | | | | | | |
| 376 | 16 | 3 | 4 | | | | | | |
| 377 | ≤2 | 3 | 12 | | | | | | |
| 378 | 104 | 14 | 25 | | | | | | |
| 379 | 111 | 14 | 34 | | | | 21 | 26 | |
| 380 | 275 | 51 | 71 | | | | 54 | 18 | |
| 381 | 23 | 11 | 21 | | | | 16 | 5 | |
| 382 | 9 | ≤2 | 3 | | | | | | |
| 383 | 13 | 3 | 8 | | | | | | |
| 384 | 38 | 12 | 32 | | | | | | |
| 385 | ≤2 | ≤2 | ≤2 | | | | | | |
| 386 | 7 | 5 | 6 | | | | | | |
| 387 | 124 | 130 | 125 | 128 | 113 | 96 | 106 | 130 | 153 |
| 388 | ≤2 | ≤2 | ≤2 | ≤2 | ≤2 | ≤2 | ≤2 | ≤2 | ≤2 |
| 389 | ≤2 | ≤2 | 3 | ≤2 | ≤2 | ≤2 | ≤2 | ≤2 | ≤2 |
| 390 | ≤2 | ≤2 | ≤2 | | | | | | |
| 391 | ≤2 | ≤2 | ≤2 | | | | | | |
| 392 | ≤2 | 3 | 3 | | | | | | |
| 393 | ≤2 | ≤2 | ≤2 | | | | | | |
| 394 | ≤2 | ≤2 | ≤2 | | | | | | |
| 395 | ≤2 | ≤2 | ≤2 | | | | | | |
| 396 | ≤2 | 3 | 3 | | | | | | |
| 397 | ≤2 | ≤2 | ≤2 | | | | | | |
| 398 | ≤2 | ≤2 | ≤2 | | | | | | |
| 399 | ≤2 | ≤2 | ≤2 | | | | | | |
| 400 | ≤2 | ≤2 | ≤2 | | | | | | |
| 401 | ≤2 | ≤2 | ≤2 | | | | | | |
| 402 | ≤2 | ≤2 | ≤2 | | | | | | |
| 403 | 6 | ≤2 | ≤2 | | | | | | |
| 404 | ≤2 | ≤2 | ≤2 | | | | | | |
| 405 | ≤2 | ≤2 | ≤2 | | | | | | |
| 406 | 4 | 5 | 11 | | | | | | |
| 407 | ≤2 | ≤2 | ≤2 | | | | | | |
| 408 | ≤2 | ≤2 | ≤2 | | | | | | |
| 409 | ≤2 | ≤2 | ≤2 | | | | | | |
| 410 | ≤2 | ≤2 | ≤2 | | | | | | |
| 411 | ≤2 | ≤2 | ≤2 | | | | | | |
| 412 | ≤2 | ≤2 | ≤2 | | | | | | |
| 413 | ≤2 | ≤2 | 3 | | | | | | |
| 414 | ≤2 | ≤2 | 4 | | | | | | |
| 415 | ≤2 | 40 | 3 | | | | | | |
| 416 | ≤2 | ≤2 | ≤2 | | | | | | |
| 417 | ≤2 | ≤2 | ≤2 | | | ≤2 | ≤2 | | |
| 418 | ≤2 | ≤2 | 3 | | | | | | |
| 419 | 3 | 3 | 8 | | | | | | |
| 420 | 3 | ≤2 | 4 | | | | | | |
| 421 | 3 | ≤2 | ≤2 | | | | | | |
| 422 | 7 | ≤2 | 5 | | | | | | |
| 423 | ≤2 | ≤2 | ≤2 | | | | | | |
| 424 | 3 | 4 | 8 | | | | | | |
| 425 | ≤2 | ≤2 | ≤2 | | | | | | |
| 426 | ≤2 | ≤2 | ≤2 | | | | | | |
| 427 | ≤2 | ≤2 | ≤2 | | | | | | |
| 428 | ≤2 | ≤2 | ≤2 | | | | | | |
| 429 | 2456 | 4438 | 8253 | | | | | | |
| 430 | 6452 | 4764 | 8774 | 6824 | 7717 | 7825 | 8049 | 5493 | 8858 |
| 431 | 9624 | 15880 | 34430 | 19620 | 19670 | 17850 | 19720 | 13300 | 22220 |
| 432 | 1139 | 1930 | 3036 | 2267 | 2405 | 2413 | 2476 | 1675 | 2808 |
| 433 | 8780 | 10030 | 15370 | | | | | | |
| 434 | 2203 | 3209 | 4510 | 5619 | 3523 | 3480 | 5130 | 6601 | 9266 |
| 435 | 3886 | 5440 | 6857 | 4911 | 5636 | 4839 | 4452 | 2062 | 6096 |
| 436 | 798 | 652 | 331 | 204 | 217 | 271 | 193 | 212 | 173 |
| 437 | 1432 | 2681 | 2764 | 1359 | 904 | 1401 | 715 | 754 | 897 |
| 438 | 238 | 239 | 99 | 109 | 106 | 130 | 95 | 117 | 87 |
| 439 | 7966 | 5785 | 2833 | 2145 | 2258 | 2528 | 2035 | 2435 | 1905 |
| 440 | 510 | 844 | 1722 | 758 | 690 | 550 | 714 | 767 | 940 |
| 441 | 3 | ≤2 | ≤2 | | | | | | |
| 442 | ≤2 | ≤2 | ≤2 | | | | | | |
| 443 | 53010 | 4206 | 6379 | 8474 | 6309 | 8200 | 18790 | 22220 | 32610 |
| 444 | 5 | ≤2 | ≤2 | | | | | | |
| 445 | 4 | ≤2 | ≤2 | | | | | | |
| 446 | 4 | ≤2 | 4 | | | | | | |
| 447 | 1100 | 744 | 964 | 665 | 587 | 608 | 557 | 578 | 752 |
| 448 | 87 | 54 | 61 | 59 | 49 | 53 | 53 | 62 | 60 |
| 449 | 8394 | 3659 | 4382 | 5620 | 4163 | 3604 | 4072 | 5528 | 6403 |
| 450 | 250 | 238 | 344 | 356 | 276 | 235 | 335 | 481 | 388 |
| 451 | 2577 | 2856 | 4173 | 3123 | 2061 | 1902 | 2271 | 1994 | 3814 |

-continued

| Ex. No. | G12D | G12V | G12R | G12A | G12S | G12C | WT | G13D | Q61H |
|---|---|---|---|---|---|---|---|---|---|
| 452 | 4 | ≤2 | ≤2 | | | | | | |
| 453 | 274 | 569 | 1119 | 559 | 459 | 484 | 467 | 503 | 679 |
| 454 | 105 | 191 | 421 | 176 | 167 | 157 | 163 | 200 | 213 |
| 455 | 6352 | 5153 | 4506 | 5987 | 8171 | 8469 | 11720 | 13070 | 11620 |
| 456 | 48800 | 10680 | 6371 | | | | | | |
| 457 | 31 | 6 | 10 | | | | | | |
| 458 | 15 | 39 | 172 | 97 | 28 | 75 | 53 | 46 | 67 |
| 459 | 537 | 766 | 1006 | 815 | 821 | 822 | 688 | 586 | 793 |
| 460 | 2322 | 1469 | 548 | 760 | 759 | 916 | 693 | 763 | 664 |
| 461 | ≤2 | ≤2 | ≤2 | | | | | | |
| 462 | 880 | 350 | 418 | 321 | 311 | 430 | 493 | 393 | 567 |
| 463 | 6494 | 3064 | 1362 | 1549 | 1401 | 2145 | 2402 | 1908 | 1685 |
| 464 | 986 | 469 | 513 | 507 | 355 | 459 | 661 | 506 | 717 |
| 465 | 15640 | 6097 | 10060 | | | | | | |
| 466 | 2323 | 1656 | 2255 | 3312 | 2135 | 2313 | 2684 | 3579 | 3508 |
| 467 | 915 | 651 | 1015 | 968 | 1136 | 1110 | 1477 | 1800 | 1648 |
| 468 | 2876 | 2311 | 2902 | 2807 | 2482 | 2406 | 3018 | 4191 | 5109 |
| 469 | 127 | 105 | 149 | 180 | 146 | 135 | 196 | 256 | 231 |
| 470 | 406 | 355 | 503 | 347 | 341 | 348 | 475 | 565 | 663 |
| 471 | 309 | 427 | 1072 | 332 | 391 | 459 | 362 | 319 | 451 |
| 472 | 6 | 16 | 18 | | | | | | |
| 473 | 11 | 8 | 14 | 8 | 9 | 9 | 10 | 11 | 11 |
| 474 | 8598 | 1751 | 3628 | 2953 | 3452 | 2386 | 6166 | 5974 | 6350 |
| 475 | 8546 | 1455 | 2621 | 3676 | 2748 | 2749 | 4600 | 7516 | 8141 |
| 476 | ≤2 | ≤2 | 4 | | | | | | |
| 477 | ≤2 | ≤2 | ≤2 | | | | | | |
| 478 | ≤2 | ≤2 | 5 | | | | | | |
| 479 | 5 | 4 | 12 | | | | | | |
| 480 | 38 | 7 | 6 | | | | | | |
| 481 | 4 | 4 | 7 | | | | | | |
| 482 | ≤2 | ≤2 | 3 | | | | | | |
| 483 | ≤2 | ≤2 | ≤2 | | | | | | |
| 484 | 23 | 28 | 48 | | | | | | |
| 485 | 9 | ≤2 | 3 | | | | | | |
| 486 | 336 | 170 | 186 | | | | | | |
| 487 | 14 | 5 | 6 | | | | | | |
| 488 | 22 | 27 | 51 | | | | | | |
| 489 | 221 | 151 | 310 | | | | | | |
| 490 | ≤2 | ≤2 | 3 | | | | | | |
| 491 | 4 | 4 | 6 | | | | | | |
| 492 | 84 | 15 | 14 | | | | | | |
| 493 | 130 | 11 | 9 | | | | | | |
| 494 | 3 | ≤2 | ≤2 | | | | | | |
| 495 | 8 | ≤2 | 7 | | | | | | |
| 496 | 24 | 11 | 6 | | | | | | |
| 497 | 13 | 3 | ≤2 | | | | | | |
| 498 | 5 | 3 | 3 | | | | | | |
| 499 | 27 | 8 | 6 | | | | | | |
| 500 | 235 | 104 | 103 | | | | | | |
| 501 | 606 | 169 | 176 | | | | | | |
| 502 | 638 | 457 | 607 | | | | | | |
| 503 | 305 | 82 | 124 | | | | | | |
| 504 | ≤2 | ≤2 | ≤2 | | | | | | |
| 505 | ≤2 | ≤2 | ≤2 | | | | | | |
| 506 | ≤2 | ≤2 | ≤2 | | | | | | |
| 507 | ≤2 | ≤2 | 4 | | | | | | |
| 508 | 5 | 12 | 14 | | | | | | |
| 509 | 6 | 6 | 12 | | | | | | |
| 510 | 10 | 8 | 9 | | | | | | |
| 511 | ≤2 | ≤2 | ≤2 | | | | | | |
| 512 | 5 | 5 | 8 | | | | | | |
| 513 | ≤2 | ≤2 | 3 | | | | | | |
| 514 | ≤2 | ≤2 | ≤2 | | | | | | |
| 515 | ≤2 | ≤2 | ≤2 | | | | | | |
| 516 | | | | | | | | | |
| 517 | ≤2 | 3 | 6 | | | | | | |
| 518 | ≤2 | ≤2 | ≤2 | | | | | | |
| 519 | ≤2 | ≤2 | ≤2 | | | | | | |
| 520 | 692 | 614 | 1749 | | | | | | |
| 521 | 4 | ≤2 | 3 | | | | | | |
| 522 | 292 | 390 | 759 | | | | | | |
| 523 | 166 | 129 | 217 | | | | | | |

Example B: Inhibition of KRas Phosphorylation of ERK by Exemplary Compounds of Formula (I)

This Example illustrates that exemplary compounds of the present invention inhibit the phosphorylation of ERK downstream of KRas WT, G12C, G12D, G12R, G12S, G12V, G13D, Q61H.

AsPC-1 (G12D, ATCC CRL-1682), A549 (G12S, ATCC CCL-185), HCT116 (G13D, ATCC CCL-247) cells were grown in DMEM medium supplemented with 10% fetal bovine serum and Penicillin/Streptomycin. NCI-H358 (G12C, ATCC CRL-5807), NCI-H460 (Q61H, ATCC HTB-117), NCI-H727 (G12V, ATCC CRL-5815), MKN1 (WT-dep, JCRB JCRB0252), PSN-1 (G12R, ATCC CRM-CRL-3211) cells were grown in RPMI medium supplemented with 10% fetal bovine serum, 10 mM HEPES, 10 mM Sodium Pyruvate, and Penicillin/Streptomycin. Cells were plated in black well clear bottom tissue culture treated 96 well plates (Corning, 3904) at a density of 20,000 cells/well and allowed to attach for 12-14 hours. Diluted compounds were then added in a final concentration of 0.5% DMSO. After 3 hours, 50 μL of 4.0% formaldehyde was added and the plates incubated at room temperature for 20 minutes. The plates were then dumped and permeabilized with 150 μL of ice cold 100% methanol for 10 minutes. Non-specific antibody binding to the plates was blocked using 100 μL Odyssey blocking buffer (LI-COR Biosciences, 927-60010) for 1 hour at room temperature.

The amount of phospho-ERK was determined using an antibody specific for the phosphorylated form of ERK and compared to the amount of GAPDH. Primary antibodies used for the detection were added as follows: Phospho-ERK (Cell Signaling CS-9101) diluted 1:500 and GAPDH (Millipore MAB374) diluted 1:5000 in Odyssey blocking buffer+0.05% Tween 20. The plates were incubated overnight at 4° C. The plates were washed 3× with 150 uL PBS+0.1% Tween 20.

Secondary antibodies used to visualize primary antibodies were added as follows: Goat Anti-Rabbit-800 (LI-COR, 926-32211) and Goat Anti-Mouse-680 (LI-COR, 926-68070) diluted 1:800 both in Odyssey blocking buffer+0.05% TweeN$_2$O, and were incubated for 1 hour at room temperature. The plates were washed 3× with 150 uL PBS+0.1% Tween 20. Plates were imaged dry on a Li-COR Odyssey CLX plate reader.

The phospho-ERK (Thr202/Tyr204) signal was normalized to the GAPDH signal for each well and percent of DMSO control values were calculated. IC50 values were generated using a 4-parameter fit of the dose response curve.

TABLE 3

Inhibition (IC$_{50}$, nM) of KRas-mediated Phosphorylation of ERK, Exemplary Compounds of Formula (I)

| Ex. No. | AsPC-1 | H727 | MKN1 | PSN1 | A549 | H460 | HCT116 | H358 |
|---|---|---|---|---|---|---|---|---|
| 4 | 519 | | | | | | | |
| 5 | 9 | 29 | 3 | 681 | 11 | 12 | 23 | 6 |
| 7 | 802 | 530 | 32 | 3592 | 1094 | 416 | 627 | 199 |
| 10 | 297 | | | | | | | |
| 12 | 497 | | | | | | | |
| 13 | 18 | 44 | 10 | 773 | 140 | 13 | 42 | 11 |
| 14 | 847 | 4585 | 1383 | ≥10000 | ≥10000 | ≥10000 | 1594 | 725 |
| 15 | 731 | ≥10000 | 1255 | ≥10000 | 3635 | ≥10000 | 5157 | 495 |
| 16 | 654 | ≥10000 | 802 | ≥10000 | 1758 | 113 | 2176 | 1179 |
| 24 | 1684 | 4725 | 406 | 3687 | ≥10000 | 2825 | 1368 | 454 |
| 27 | 45 | 232 | 20 | 2924 | 300 | 33 | 88 | 22 |
| 28 | 78 | 308 | 24 | ≥10000 | 523 | 54 | 153 | 60 |
| 36 | 1544 | 3387 | 1181 | ≥10000 | 2151 | 557 | 1610 | 1127 |
| 37 | 2213 | ≥10000 | 1674 | ≥10000 | 8947 | ≥10000 | 4358 | 1719 |
| 38 | 966 | 1187 | 143 | 7617 | 3274 | 573 | 814 | 324 |
| 51 | 586 | 7226 | 873 | ≥10000 | 2638 | ≥10000 | 3719 | 715 |
| 57 | 82 | 115 | 22 | 4143 | 668 | 119 | 1075 | 50 |
| 58 | 24 | 242 | 23 | 1312 | 455 | 111 | 1457 | 24 |
| 59 | 577 | 769 | 107 | ≥10000 | 3562 | 296 | 1272 | 176 |
| 60 | 3892 | 1265 | 230 | ≥10000 | 5533 | 1031 | 3600 | 389 |
| 61 | 306 | 1109 | 46 | ≥10000 | 699 | 550 | 518 | 162 |
| 62. | 591 | 178 | 7 | ≥10000 | 87 | 154 | 410 | 24 |
| 63 | 15 | 56 | 5 | 1043 | 139 | 38 | 44 | 27 |
| 71 | 4734 | 2237 | 140 | ≥10000 | ≥10000 | 2170 | 1947 | 361 |
| 73 | 3494 | 756 | 23 | ≥10000 | 191 | 176 | 128 | 98 |
| 74 | 72 | 355 | 8 | ≥10000 | 63 | 55 | 662 | 10 |
| 82 | 18 | 65 | 10 | 1741 | 25 | 180 | 216 | 3 |
| 132 | 104 | ≥10000 | 27 | ≥10000 | 206 | ≥10000 | 206 | 131 |
| 133 | 156 | 612 | 171 | ≥10000 | 55 | 49 | 650 | 41 |
| 134 | ≥10000 | ≥10000 | 178 | ≥10000 | 1489 | 666 | ≥10000 | 48 |
| 135 | 2061 | ≥10000 | 53 | ≥10000 | 2458 | 647 | 3272 | 37 |
| 136 | 351 | 181 | 7 | ≥10000 | 19 | 75 | 631 | 4 |
| 137 | ≥10000 | ≥10000 | ≥10000 | ≥10000 | ≥10000 | ≥10000 | ≥10000 | 2035 |
| 138 | ≥10000 | ≥10000 | ≥10000 | ≥10000 | ≥10000 | ≥10000 | ≥10000 | ≥10000 |
| 139 | ≥10000 | ≥10000 | 307 | ≥10000 | ≥10000 | 7514 | ≥10000 | 115 |
| 140 | 27 | 28 | 2 | 1 | 9 | 17 | 11 | |
| 141 | 210 | ≥10000 | 282 | ≥10000 | 875 | 1108 | ≥10000 | 88 |
| 142 | 2866 | ≥10000 | 45 | ≥10000 | ≥10000 | 212 | 6959 | 78 |
| 143 | ≥10000 | ≥10000 | 300 | ≥10000 | ≥10000 | ≥10000 | ≥10000 | 527 |
| 145 | ≥10000 | ≥10000 | 258 | ≥10000 | ≥10000 | 847 | ≥10000 | 379 |
| 146 | 22 | ≥10000 | 22 | 2526 | 1057 | 204 | 1003 | 15 |
| 147 | ≥10000 | ≥10000 | 65 | ≥10000 | 1951 | 383 | ≥10000 | 79 |
| 148 | 105 | 260 | 76 | 3785 | 550 | 68 | ≥10000 | 15 |

TABLE 3-continued

Inhibition (IC$_{50}$, nM) of KRas-mediated Phosphorylation of ERK, Exemplary Compounds of Formula (I)

| Ex. No. | AsPC-1 | H727 | MKN1 | PSN1 | A549 | H460 | HCT116 | H358 |
|---|---|---|---|---|---|---|---|---|
| 149 | 9 | 206 | 16 | 1758 | 83 | 71 | 292 | 10 |
| 150 | 435 | 626 | 13 | ≥10000 | 45 | 362 | 996 | 4 |
| 152 | ≥10000 | ≥10000 | 6290 | ≥10000 | ≥10000 | ≥10000 | ≥10000 | ≥10000 |
| 153 | 233 | 500 | | | | 306 | | |
| 154 | | ≥10000 | | ≥10000 | 8447 | | 1455 | 840 |
| 155 | 1724 | 2666 | 196 | ≥10000 | ≥10000 | 399 | ≥10000 | 329 |
| 156 | 335 | 189 | 14 | ≥10000 | 33 | 141 | 323 | 10 |
| 157 | 751 | 4725 | 31 | ≥10000 | 448 | 585 | 893 | 31 |
| 159 | ≥10000 | 1997 | 133 | ≥10000 | 4070 | 1508 | 2112 | 139 |
| 160 | 5520 | 727 | 146 | ≥10000 | 974 | 471 | 1597 | 149 |
| 162 | 4526 | 4166 | | | | 6769 | | |
| 164 | ≥10000 | ≥10000 | 207 | ≥10000 | ≥10000 | 6825 | ≥10000 | 602 |
| 165 | ≥10000 | ≥10000 | 412 | ≥10000 | ≥10000 | 2923 | ≥10000 | 701 |
| 166 | | ≥10000 | | ≥10000 | ≥10000 | | ≥10000 | 328 |
| 167 | 6763 | 1252 | | | | 623 | | |
| 168 | | 1805 | | ≥10000 | ≥10000 | | 821 | 156 |
| 169 | 2892 | 1807 | | | | 931 | | |
| 170 | | 3395 | | ≥10000 | ≥10000 | | 2353 | 470 |
| 171 | | ≥10000 | | ≥10000 | ≥10000 | | ≥10000 | ≥10000 |
| 172 | 481 | 192 | | | | 79 | | |
| 173 | 180 | 304 | | | | 145 | | |
| 174 | | ≥10000 | | ≥10000 | 4952 | | ≥10000 | 1288 |
| 175 | 1725 | 756 | | | | 675 | | |
| 176 | ≥10000 | 3954 | 701 | ≥10000 | ≥10000 | 3511 | ≥10000 | 1254 |
| 177 | | ≥10000 | | ≥10000 | 764 | | 1699 | 54 |
| 178 | 606 | 2110 | | | | 728 | | |
| 179 | 785 | 675 | | | | 274 | | |
| 180 | 205 | 623 | | | | 113 | | |
| 181 | 1543 | 1613 | | | | 584 | | |
| 182 | 547 | 355 | | | | 157 | | |
| 183 | 399 | 720 | | | | 137 | | |
| 184 | 66 | 201 | | | | 30 | | |
| 185 | 306 | 481 | | | | 424 | | |
| 186 | 1593 | 1062 | | | | 592 | | |
| 187 | 470 | 550 | | | | 133 | | |
| 188 | 2067 | 2136 | | | | 478 | | |
| 189 | 1241 | 1426 | | | | 377 | | |
| 190 | 189 | 272 | | | | 62 | | |
| 191 | 665 | 714 | | | | 230 | | |
| 192 | 90 | 191 | | | | 51 | | |
| 193 | 94 | 133 | 4 | | 12 | 44 | 63 | 41 |
| 194 | 92 | 89 | 7 | | | 65 | | |
| 196 | 361 | 452 | | | | 48 | | |
| 197 | 144 | 841 | 11 | | | 293 | | |
| 198 | 2686 | 1754 | | | | 803 | | |
| 199 | 1318 | 798 | | | | 314 | | |
| 200 | 47 | 67 | 3 | | 3 | 22 | 21 | 13 |
| 201 | 91 | 110 | 2 | | | 100 | | |
| 202 | 60 | 159 | 3 | | | 74 | | |
| 203 | 8014 | 1266 | | | | 758 | | |
| 206 | 6961 | 3330 | | | | 3384 | | |
| 296 | 2195 | 2085 | | | | 619 | | |
| 297 | 3430 | 450 | | | | 660 | | |
| 298 | ≥10000 | ≥10000 | 2712 | ≥10000 | ≥10000 | ≥10000 | ≥10000 | 5008 |
| 299 | | 126 | | ≥10000 | 108 | | 333 | 29 |
| 300 | 251 | 372 | 37 | | | 71 | | |
| 301 | 216 | 520 | 15 | | | 416 | | |
| 302 | 152 | 360 | 5 | | | 193 | | |
| 303 | 3288 | 3687 | | | | 4115 | | |
| 304 | 1369 | 2576 | | | | 804 | | |
| 305 | ≥10000 | ≥10000 | | | | ≥10000 | | |
| 306 | 405 | 461 | | | | 306 | | |
| 307 | 117 | 215 | | | | 11 | | |
| 308 | 489 | 627 | | | | 372 | | |
| 309 | 176 | 272 | | | | 59 | | |
| 310 | ≥10000 | 3372 | | | | 3793 | | |
| 311 | 738 | 2603 | | | | 501 | | |
| 386 | 1185 | 1024 | | | | 299 | | |
| 388 | | 16 | | | | 16 | | |
| 441 | 119 | 139 | | | | 70 | | |
| 442 | 134 | 234 | | | | 124 | | |
| 444 | 2438 | 1736 | | | | 656 | | |
| 445 | 1615 | 2934 | | | | 1189 | | |
| 446 | 3669 | 2500 | | | | 2194 | | |
| 452 | 182 | 793 | | | | 154 | | |

TABLE 3-continued

Inhibition (IC$_{50}$, nM) of KRas-mediated Phosphorylation of ERK, Exemplary Compounds of Formula (I)

| Ex. No. | AsPC-1 | H727 | MKN1 | PSN1 | A549 | H460 | HCT116 | H358 |
|---|---|---|---|---|---|---|---|---|
| 457 | | 3954 | | | | 9409 | | |
| 459 | 9936 | ≥10000 | | | | ≥10000 | | |
| 473 | | 320 | | | | 325 | | |

Example C

Inhibition of KRas Phosphorylation of ERK (HTRF) by Exemplary Compounds of Formula (I)
Cisbio HTRF Advanced pERK Assay Catalog #64AERPEH
Cells: MKN1, PSN1
Procedure:
  Day 1: Seed 6,000 cells/well ~25 µl/well in 384-well white solid bottom plate; RPM1_10% FBS. Incubate overnight at 37° C./5% CO$_2$.
  Day 2: Echo transfer 25 nl of 10 mM compound 10 point dilution at 1:3 (Cf=10 uM) and incubate for 3 hour at 37° C./5% CO$_2$.
  Add 8.5 µl/well of 4× Lysis Buffer/25× Blocking reagent (do not dump media) and incubate for 30 min at room temperature on shaker.
  Add conjugate mixture of 4.25 ul/well 1×-pERK-D2 and 1×-pERK-K diluted in Detection Buffer for a total of 8.5 µl/well.
  Incubate for 4 hours at room temperature covered.
  Read HTRF using ClarioStar
Cells: ASPC1, H727, A549, H460, HCT116, H358
Culture/Assay media: RPMI-1640+10% h FBS
Procedure:
Cell seeding
1. To harvest cells from flask using 0.05% Trypsin/EDTA solution. Add 10 mL of media to stop trypsinizing. Pipette the cells into a conical bottom 50 mL centrifuge tube and centrifuge 5 min×1000 rpm.
2. Re-suspend the cell pellet in media, take a cell count, and then adjust the cell density using fresh media.
3. Seed 6,000 cells into cell culture plate with 50 µL media. The
4. Incubate cell plate overnight in a 37° C., 5% CO$_2$ incubator.

Compound titrations
1. Use Tecan to complete the compound addition. Compounds start from 10 uM top, 3-fold dilution, and 10 doses. The final DMSO concentration is 0.8%. Dispensed 0.2 uM Trametinib as Min control.
2. Incubate cell plate for 3 hrs in the incubator.
Detection with cisbio pERK HTRF kit
1. Dilute 1 volume of 4× lysis buffer with 3 volumes of deionized water. Then, add 100× the blocking reagent. Keep lysis buffer on the ice.
2. At the end of the compound treatment, flick-off the media.
3. Add 35 µL of lysis buffer per well using a Multidrop Combi. Then place on a plate agitator shaking at 300 rpm at 4° C. for 40 mins.
4. Make up the HTRF antibody buffer. For each assay plate, mix 50 µL of d2-conjugate antibody with 950 µL of detection buffer. Similarly, mix 50 µL of Cryptate antibody with 950 µL of detection buffer. Then mix the two diluted antibodies together.
5. Dispense 3.4 µL the antibody buffer to wells of an empty assay plate. Seal the plate and centrifuge plate 30 sec×1000 rpm.
6. At the end of the 4° C. lysis, centrifuge the lysate plates 3 mins×1500 rpm.
7. Use the Bravo to transfer 13.6 µL of lysate from cell culture plate to assay plate.
Then incubate assay plate for 2 hrs at room temperature.
8. At the end of incubation, read plate on the Envision after centrifuging plate 30 sec× 1000 rpm.

Table 4

Inhibition (HTRF IC$_{50}$ nM) of KRas-mediated Phosphorylation of ERK by Exemplary Compounds of Formula (I)

| Ex. No. | AsPC-1 | H727 | MKN1 | PSN1 | A549 | H460 | HCT116 | H358 |
|---|---|---|---|---|---|---|---|---|
| 4 | | 943 | 113 | ≥10000 | | | | |
| 5 | 2 | 6 | 1 | 364 | 2 | 5 | 10 | 2 |
| 10 | | | 13 | 3341 | | | | |
| 12 | | | 26 | ≥10000 | | | | |
| 13 | 4 | 13 | 5 | 1090 | 43 | 27 | 33 | |
| 16 | | | 275 | ≥10000 | | | | |
| 25 | ≥10000 | ≥10000 | | | | | | |
| 26 | ≥10000 | ≥10000 | | | | | | |
| 28 | 20 | 159 | 21 | 7246 | 156 | 101 | 155 | |
| 57 | 32 | 55 | | | 175 | 119 | 2011 | |
| 58 | 75 | 45 | | | | 69 | 179 | |
| 61 | 126 | 250 | | | | 336 | 1644 | |
| 63 | 4 | 28 | | | 19 | 21 | 63 | |
| 71 | 2103 | 1924 | | | | | | |
| 74 | 65 | 84 | | | | 151 | 336 | |
| 82 | 15 | 16 | 6 | 2325 | 15 | 22 | 106 | 10 |
| 132 | 623 | 912 | | | | | | |
| 133 | 144 | 246 | | | | | 360 | |

-continued

Inhibition (HTRF IC$_{50}$ nM) of KRas-mediated Phosphorylation of ERK by Exemplary Compounds of Formula (I)

| Ex. No. | AsPC-1 | H727 | MKN1 | PSN1 | A549 | H460 | HCT116 | H358 |
|---|---|---|---|---|---|---|---|---|
| 136 | 318 | 52 | | | | 83 | 243 | |
| 140 | 7 | 4 | 1 | 922 | 2 | 4 | 7 | |
| 141 | 641 | 2134 | | | | | | |
| 146 | 92 | 400 | | | | 327 | 607 | |
| 148 | 59 | 110 | | | | 132 | 2209 | |
| 149 | 25 | 111 | | | 290 | 180 | 276 | |
| 150 | 66 | 12 | | | | 167 | 115 | |
| 156 | 125 | 72 | | | | 143 | 349 | |
| 162 | | | 187 | ≥10000 | | | | |
| 167 | | | 3 | ≥10000 | | | | |
| 169 | | | 100 | ≥10000 | | | | |
| 172 | 96 | 26 | 41 | ≥10000 | | 32 | 170 | 6 |
| 173 | 56 | 263 | 42 | 5542 | | 176 | 454 | 95 |
| 175 | | | 39 | ≥10000 | | | | |
| 178 | | | 49 | ≥10000 | | | | |
| 179 | | | 10 | 6955 | | | | |
| 180 | | | 10 | 6905 | | | | |
| 181 | | | 139 | 6701 | | | | |
| 182 | | | 5 | 6896 | | | | |
| 183 | | | 2 | 4234 | | | | |
| 184 | 7 | 90 | 7 | 1228 | 44 | 39 | 91 | 15 |
| 185 | | | 17 | 4837 | | | | |
| 186 | | | 108 | ≥10000 | | | | |
| 187 | | | 38 | ≥10000 | | | | |
| 188 | | | 77 | ≥10000 | | | | |
| 189 | | | 29 | 5543 | | | | |
| 190 | | | 11 | 4990 | | | | |
| 191 | | | 15 | 5847 | | | | |
| 192 | | | 4 | 7340 | | | | |
| 193 | 8 | 36 | 7 | 3789 | 44 | 42 | 82 | |
| 194 | 20 | 34 | 3 | 1346 | 63 | 55 | 686 | 4 |
| 196 | 97 | 167 | 39 | 314 | | 33 | 114 | 31 |
| 197 | 57 | 348 | 23 | ≥10000 | | 183 | 620 | 112 |
| 198 | | | 183 | ≥10000 | | | | |
| 199 | | | 7 | ≥10000 | | | | |
| 200 | 3 | 6 | 2 | 1010 | 5 | 5 | 11 | |
| 201 | 23 | 42 | 15 | 2388 | 223 | 118 | 187 | 12 |
| 202 | 7 | 33 | 5 | 2493 | 9 | 28 | 47 | 4 |
| 203 | | | 35 | 3711 | | | | |
| 206 | | | 34 | ≥10000 | | | | |
| 296 | | | 53 | ≥10000 | | | | |
| 297 | | | 154 | ≥10000 | | | | |
| 300 | 38 | 89 | 7 | 1378 | | | | 14 |
| 301 | 54 | 199 | 14 | 3928 | | 216 | 456 | 46 |
| 302 | 31 | 82 | 3 | 2533 | 65 | 120 | 179 | 26 |
| 303 | | | 358 | ≥10000 | | | | |
| 304 | | | 29 | ≥10000 | | | | |
| 306 | | | 57 | 6803 | | | | |
| 307 | 58 | 85 | 5 | 106 | | 12 | 33 | 15 |
| 308 | 155 | 278 | 40 | ≥10000 | | | 284 | |
| 309 | 54 | 37 | 2 | 8328 | 113 | 57 | 26 | 26 |
| 311 | | | 15 | ≥10000 | | | | |
| 313 | 13 | 28 | 7 | 2120 | 38 | 38 | 42 | 4 |
| 314 | 9 | 21 | 3 | 407 | 19 | 14 | 21 | 2 |
| 315 | 20 | 20 | 5 | 1959 | 28 | 34 | 24 | 5 |
| 316 | 8 | 32 | 1 | 2040 | 51 | 69 | 30 | 9 |
| 317 | 40 | 46 | 20 | 3931 | 197 | 287 | 98 | 985 |
| 318 | 133 | 69 | 13 | 877 | | 65 | 60 | |
| 319 | 433 | 808 | 120 | ≥10000 | | | 6358 | |
| 320 | 115 | 82 | 10 | 5182 | | 100 | 65 | |
| 321 | 16 | 30 | 3 | 7757 | 99 | 71 | 39 | 7 |
| 322 | 484 | 255 | 32 | 9090 | | | 300 | |
| 323 | 8 | 8 | 2 | 600 | 19 | 11 | 22 | 2 |
| 324 | 35 | 22 | 3 | 1442 | 95 | 99 | 61 | 14 |
| 325 | 49 | 45 | 17 | 5152 | | 61 | 56 | 164 |
| 326 | 10 | 26 | 8 | ≥10000 | 138 | 253 | 274 | 18 |
| 327 | 23 | 98 | 14 | 6687 | 238 | 206 | 381 | 10 |
| 328 | 1719 | | 271 | ≥10000 | | | 1278 | |
| 329 | ≥20000 | | ≥10000 | ≥10000 | | | ≥20000 | |
| 330 | 29 | 61 | 8 | 305 | 84 | 52 | 57 | 11 |
| 331 | 4 | 35 | 1 | | 6 | 16 | 27 | 3 |
| 332 | 6 | 31 | 2 | 710 | 13 | 22 | 48 | 3 |
| 333 | 603 | 2108 | 425 | ≥10000 | | | 9189 | |
| 336 | 32 | 129 | 4 | 4120 | 75 | 162 | 208 | 59 |

-continued

Inhibition (HTRF IC$_{50}$ nM) of KRas-mediated Phosphorylation of ERK by Exemplary Compounds of Formula (I)

| Ex. No. | AsPC-1 | H727 | MKN1 | PSN1 | A549 | H460 | HCT116 | H358 |
|---|---|---|---|---|---|---|---|---|
| 337 | 514 | 395 | 49 | 1843 | | | 438 | |
| 338 | 695 | 377 | 24 | 2878 | | | 487 | |
| 339 | 48 | 72 | 12 | ≥10000 | 557 | 991 | 826 | 95 |
| 340 | 39 | 149 | 26 | ≥10000 | 353 | 373 | 999 | 55 |
| 341 | 472 | 1036 | 86 | ≥10000 | | | 1320 | |
| 342 | 23 | 46 | 4 | 2245 | 167 | 203 | 470 | 62 |
| 343 | 60 | 24 | 4 | 5928 | 91 | 128 | 128 | 7 |
| 344 | 3407 | 4815 | 796 | ≥10000 | | | | |
| 345 | 83 | 138 | 13 | 8785 | | 82 | 296 | 20 |
| 346 | 99 | 113 | 11 | 7392 | | 166 | 133 | 57 |
| 347 | 118 | 73 | 98 | 4458 | | 127 | 195 | |
| 348 | 275 | 273 | 7 | ≥10000 | | | 245 | |
| 349 | 475 | 1856 | 149 | ≥10000 | | | 2251 | |
| 350 | 241 | 334 | 209 | ≥10000 | | | 797 | |
| 351 | 228 | 551 | 48 | 7176 | 185 | 182 | 346 | |
| 352 | 948 | 1267 | 46 | ≥10000 | | | | |
| 353 | 7 | 34 | 24 | 4807 | 80 | 149 | 396 | 19 |
| 354 | 14 | 48 | 14 | ≥10000 | 65 | 304 | 623 | 17 |
| 355 | 8 | 30 | 17 | 6773 | 140 | 270 | 471 | 16 |
| 356 | 16 | 63 | 40 | 9301 | 232 | 458 | 767 | 20 |
| 357 | 13 | 63 | 71 | 7478 | 576 | 805 | 1354 | 27 |
| 358 | 12 | 15 | 4 | 9767 | 44 | 131 | 167 | 3 |
| 359 | 345 | 782 | 60 | 4095 | | | 576 | |
| 360 | 49 | 62 | 2 | 9186 | | 54 | 140 | 19 |
| 361 | 8 | 49 | 3 | 6817 | 122 | 85 | 231 | 17 |
| 362 | 73 | 313 | 37 | 5130 | 629 | 404 | 763 | 113 |
| 363 | ≥10000 | ≥10000 | ≥10000 | ≥10000 | | | | |
| 364 | 121 | 578 | 26 | ≥10000 | 219 | 117 | 645 | |
| 365 | 17 | 24 | 10 | 2856 | 11 | 17 | 77 | 6 |
| 366 | 60 | 185 | 11 | 5531 | | 108 | 321 | 61 |
| 367 | 505 | 244 | 58 | ≥10000 | | | 375 | |
| 368 | 4683 | 617 | 191 | ≥10000 | | | | |
| 369 | 1341 | 471 | 294 | ≥10000 | | | | |
| 370 | 2985 | 516 | 330 | ≥10000 | | | | |
| 371 | ≥20000 | | 387 | ≥10000 | | | 9341 | |
| 372 | | | 660 | ≥10000 | | | | |
| 373 | 4066 | | 103 | ≥10000 | | | 3841 | |
| 374 | 9382 | | | | | | ≥10000 | |
| 376 | ≥10000 | | | | | | 6491 | |
| 377 | ≥10000 | 7783 | 2298 | ≥10000 | | | | |
| 378 | ≥10000 | | | | | | ≥10000 | |
| 379 | ≥20000 | | ≥10000 | ≥10000 | | | ≥20000 | |
| 380 | ≥20000 | | 1103 | ≥10000 | | | 3215 | |
| 381 | ≥20000 | | 282 | ≥10000 | | | 741 | |
| 382 | ≥10000 | 5899 | 781 | ≥10000 | | | | |
| 383 | ≥10000 | | | | | | ≥10000 | |
| 384 | ≥10000 | ≥10000 | | | | | | |
| 385 | ≥10000 | 4648 | 421 | ≥10000 | | | | |
| 386 | | | 44 | 2877 | | | | |
| 388 | 14 | 5 | 8 | 409 | 18 | 21 | 9 | 1 |
| 389 | 268 | 970 | 95 | ≥10000 | | | 1090 | |
| 390 | 195 | 16 | 8 | 748 | 114 | 175 | 190 | |
| 391 | 61 | 74 | 12 | 3987 | | 143 | 563 | 22 |
| 392 | 1184 | 1371 | 336 | 6019 | | | 2250 | |
| 393 | 68 | 24 | 8 | 449 | 133 | 110 | 68 | 20 |
| 394 | 158 | 368 | 46 | ≥10000 | 567 | 1072 | 1715 | |
| 395 | 477 | 1377 | 299 | ≥10000 | | | | |
| 396 | 3075 | 7481 | 525 | ≥10000 | | | | |
| 397 | 903 | 1000 | | | | | 1460 | |
| 398 | 25 | 26 | 7 | 6694 | 102 | 387 | 348 | 10 |
| 399 | 3 | 16 | 1 | 357 | 14 | 18 | 23 | 4 |
| 400 | 27 | 87 | 7 | 3538 | 62 | 41 | 113 | 9 |
| 401 | 162 | 253 | 82 | 9961 | | | 1146 | |
| 402 | 12 | 14 | 3 | 514 | 34 | 51 | 46 | 4 |
| 403 | 426 | 79 | 20 | 3815 | 96 | 182 | 487 | |
| 404 | 136 | 822 | 55 | ≥10000 | | | 1375 | |
| 405 | 238 | 114 | 45 | 6734 | 247 | 155 | 2214 | |
| 406 | 880 | 748 | 306 | ≥10000 | | | | |
| 407 | 27 | 15 | 15 | 1333 | 27 | 26 | 41 | 3 |
| 408 | 721 | 570 | 351 | ≥10000 | | | | |
| 409 | 398 | 593 | 94 | ≥10000 | | | 1176 | |
| 410 | 365 | 603 | 157 | 3146 | | | 602 | |
| 411 | 63 | 83 | 40 | 146 | | 48 | 92 | 9 |
| 412 | 19 | 51 | 34 | 5981 | 242 | 413 | 586 | 11 |

-continued

Inhibition (HTRF IC$_{50}$ nM) of KRas-mediated Phosphorylation of ERK by Exemplary Compounds of Formula (I)

| Ex. No. | AsPC-1 | H727 | MKN1 | PSN1 | A549 | H460 | HCT116 | H358 |
|---|---|---|---|---|---|---|---|---|
| 413 | 479 | 408 | 33 | 2530 | | | 484 | |
| 414 | 1334 | 269 | 32 | 3475 | | | 514 | |
| 415 | 548 | 903 | 46 | ≥10000 | | | 2557 | |
| 416 | 141 | 83 | 3 | 1305 | | 283 | 2194 | |
| 417 | 182 | 57 | 20 | 110 | | 63 | 79 | |
| 418 | 25 | 32 | 3 | 596 | 74 | 52 | 60 | 11 |
| 419 | 71 | 154 | 14 | 3481 | | 182 | 319 | 58 |
| 420 | 859 | 366 | 56 | ≥10000 | | | 1313 | |
| 421 | 61 | 26 | 4 | 1498 | 39 | 73 | 70 | 16 |
| 422 | 430 | 112 | 26 | 1813 | | 303 | 539 | |
| 423 | 556 | 2218 | 110 | ≥10000 | | | | |
| 424 | 817 | 1300 | 95 | 2815 | | | | |
| 425 | 42 | 37 | 5 | 921 | 54 | 99 | 73 | 12 |
| 426 | 652 | 1220 | 264 | ≥10000 | | | | |
| 427 | 32 | 59 | 84 | 7684 | 379 | 878 | 916 | 52 |
| 428 | 339 | 425 | 28 | 3280 | 183 | | 896 | |
| 441 | | | 6 | 2884 | | | | |
| 442 | | | 9 | 2847 | | | | |
| 444 | 1690 | 1161 | 37 | ≥10000 | 734 | 1559 | 1761 | |
| 445 | | | 8199 | ≥10000 | | | | |
| 446 | | | 786 | ≥10000 | | | | |
| 452 | 204 | 165 | 41 | 4084 | 224 | 639 | 1512 | |
| 461 | 1148 | 239 | 18 | 3759 | | | 172 | |
| 472 | 89 | 406 | 80 | 9295 | | 414 | 1072 | 231 |
| 476 | 36 | 148 | 14 | 3592 | | 99 | 275 | 35 |
| 477 | 61 | 456 | 67 | ≥10000 | 865 | 1571 | 2835 | 180 |
| 478 | 192 | 871 | 80 | ≥10000 | 1247 | 713 | 5434 | |
| 479 | 203 | 115 | 328 | ≥10000 | | 987 | | |
| 480 | 240 | 100 | 6 | ≥10000 | 215 | 47 | 111 | |
| 481 | 387 | 643 | 49 | 5411 | | 827 | 3150 | |
| 482 | 546 | 128 | 26 | ≥10000 | 390 | 124 | | |
| 483 | 890 | 339 | 83 | ≥10000 | | 1589 | | |
| 484 | 4859 | 3034 | 1059 | ≥10000 | | | | |
| 485 | 6623 | 1221 | | | | | | |
| 486 | ≥10000 | ≥10000 | | | | | | |
| 487 | ≥10000 | 4993 | | | | | | |
| 488 | ≥10000 | | ≥10000 | ≥10000 | | | | |
| 490 | 395 | 205 | 41 | ≥10000 | 298 | 305 | 368 | |
| 491 | 1705 | 1532 | 182 | ≥10000 | | | | |
| 492 | 3519 | | 254 | ≥10000 | | | | |
| 493 | ≥10000 | | 622 | ≥10000 | | | | |
| 494 | 354 | 795 | 135 | ≥10000 | | 982 | 2169 | |
| 495 | 1350 | 1821 | | | | | | |
| 496 | 95 | 407 | 68 | 8288 | 261 | 245 | 525 | 117 |
| 497 | 987 | 503 | 43 | ≥10000 | | | | |
| 498 | 47 | 64 | 13 | ≥10000 | 48 | 66 | 168 | 21 |
| 499 | 109 | 100 | 13 | ≥10000 | 145 | 162 | 474 | |
| 500 | 1103 | 1898 | 239 | ≥10000 | | | | |
| 501 | 2064 | 3234 | 225 | ≥10000 | | | | |
| 502 | 2102 | 6458 | 1938 | ≥10000 | | | | |
| 503 | ≥10000 | ≥10000 | ≥10000 | ≥10000 | | | | |
| 504 | 4 | 6 | 8 | 4834 | 11 | 53 | 81 | 2 |
| 505 | 14 | 50 | 31 | ≥10000 | | 327 | | 16 |
| 506 | 302 | 2221 | 703 | ≥10000 | | 8909 | ≥10000 | |
| 507 | 25 | 262 | 7 | 1952 | 345 | 179 | 341 | 40 |
| 508 | 1552 | 2191 | | | | | | |
| 509 | 144 | 338 | 89 | 6139 | 211 | 206 | 314 | |
| 510 | 186 | 388 | 73 | 5103 | 515 | 397 | 954 | |
| 511 | 8 | 25 | 2 | 1041 | 23 | 27 | 45 | 6 |
| 512 | 55 | 80 | 14 | 2827 | 68 | 130 | 291 | 53 |
| 513 | 1313 | 869 | 221 | ≥10000 | | | | |
| 514 | 15 | 19 | 5 | 859 | 20 | 60 | 30 | 11 |
| 515 | 35 | 19 | | | 36 | 19 | 24 | 7 |
| 516 | 9316 | 5686 | | | | | | |
| 517 | 203 | 321 | 42 | ≥10000 | | | | |
| 518 | ≥10000 | 9212 | | | | | | |
| 519 | ≥10000 | ≥10000 | | | | | | |
| 520 | ≥10000 | ≥10000 | | | | | | |
| 521 | ≥10000 | ≥10000 | | | | | | |
| 522 | ≥10000 | ≥10000 | | | | | | |
| 523 | ≥10000 | ≥10000 | | | | | | |

Example D: Anti-Proliferative Activity of Pan-KRas Inhibitors Against Mutations that Confer Resistance to Adagrasib To test the anti-proliferative activity of a prototype pan KRas inhibitor against mutations that confer resistance to adagrasib, mouse 3T3 fibroblasts were transduced with retroviruses that expressed various engineered human KRas mutant constructs. Cells were selected with puromycin to select for cells that were successfully transduced by the retrovirus and plated in ultra-low attachment plates where cells grew as 3 dimensional cultures. Cells were treated with a serial dilution of MRTX849 or Example 5 and 50% inhibitory concentration (IC50) values were calculated (Table 5). Example 5 demonstrated activity against numerous codon 12 mutations including the G12W mutation predicted to result from a single nucleotide substitution from the cysteine 12 codon.

TABLE 5

IC50 Values of the KRas G12C Inhibitor MRTX849 and the Pan KRas Inhibitor Example 5 in a 5-day Viability Assay in 3T3 Cells Engineered to Express MRTX849 Resistance Mutations

|      | MRTX849 (nM) | Example 5 (nM) |
|------|--------------|----------------|
| G12A | >3000        | 32             |
| G12C | 16.62        | 28.1           |
| G12D | >3000        | 20.25          |
| G12R | >3000        | 1742           |
| G12V | >3000        | 94             |
| G12W | >3000        | 50             |
| G13D | >3000        | 610            |
| Q61H | >3000        | 58             |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound of Formula (I):

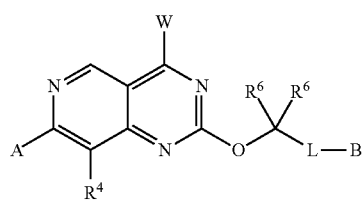

Formula (I)

or a pharmaceutically acceptable salt thereof, wherein:

W is:

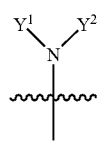

A is naphthyl optionally substituted with 1-4 $R^1$;

B is:

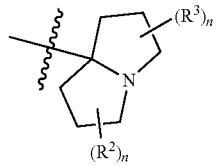

$Y^1$ and $Y^2$ join to form:

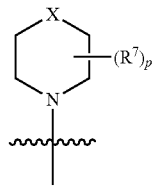

where X is selected from: a bond, —S—, —O—, —N< bound to a fused ring, —CH$_2$—, —CH$_2$—N—, —CH$_2$—N—CH$_2$—, —CH$_2$—CH$_2$—CH$_2$—, —CH$_2$—CH$_2$—, —O—CH$_2$— and —S—CH$_2$—;

each $R^1$ is independently halogen, cyano, hydroxy, C$_1$-C$_4$ alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxyC1-C3 alkyl, —CH$_2$C(=O)N(R$^5$)$_2$, —C3-C4 alkynyl(NR$^5$)$_2$, —N(R$^5$)$_2$, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl;

each $R^2$ is independently hydrogen, hydroxy, halogen, C1-C3 alkyl, C1-C3 cyanoalkyl, C1-C3 hydroxyalkyl, HC(=O)—, -L-OC(O)N(R$^5$)$_2$, —CO$_2$R$^5$, or —CO$_2$N(R$^5$)$_2$;

each $R^3$ is independently hydrogen, hydroxy, halogen, C1-C3 alkyl, C1-C3 cyanoalkyl, C1-C3 hydroxyalkyl, HC(=O)—, -L-OC(O)N(R$^5$)$_2$, —CO$_2$R$^5$, or —CO$_2$N(R$^5$)$_2$;

each $R^4$ is independently hydrogen, halogen or C1-C3 alkyl;

each $R^5$ is independently hydrogen or C1-C3 alkyl;

each $R^6$ is independently hydrogen, hydroxy, C1-C4 hydroxyalkyl or heteroaryl, or two $R^6$ join to form C3-C6 cycloalkyl or heterocycle;

each $R^7$ is independently hydrogen, C1-C3 alkyl, hydroxy, halogen, C1-C3 haloalkyl, -L-NH$_2$, —NH(C1-C3 alkyl), —N(C1-C3 alkyl)$_2$, oxo (=O), —O—(C1-C3 alkyl), —(C1-C3 alkyl)-OH, —C(O)OH, —C(O)O(C1-C3 alkyl), —C(O)N(R$^{10}$)$_2$, —CN, aryl, —(CH$_2$)S(O)$_2$N(R$^{10}$)$_2$, or heteroaryl optionally independently substituted with 1-2 substituents independently selected from C1-C3 alkyl, —CN and C(O)NH$_2$, two $R^7$ on the same atom optionally join to form a spirocyclic ring selected from C3-C6 cycloalkyl and heterocycle, where said spirocyclic ring is optionally substituted with 1-4 substituents independently selected from oxo (=O), halogen, hydroxy, C1-C3 alkyl and —O—(C1-C3 alkyl), two $R^7$ on adjacent atoms optionally join to form a bond or a fused ring selected from C3-C6 cycloalkyl optionally substituted with 1-4 R⁸, heteroaryl optionally substituted with 1-4 R⁸, aryl optionally substituted with 1-4 R⁸, and heterocycle optionally substituted with 1-4 R⁸, and two R⁷ on non-adjacent atoms optionally join to form a 1-2 carbon bridge;

each R⁸ is independently C1-C3 alkyl, hydroxy, halogen, oxo (=O), —O—(C1-C3 alkyl), —(C1-C3 alkyl)-OH, —C(O)OH, —C(O)O(C1-C3 alkyl), —C(O)N(R10)₂, or —CN;

each R¹⁰ is hydrogen

L is a bond each n is 0-3; and p is 1-8.

2. The compound or salt of claim 1, wherein:
X is selected from: —CH₂—, —CH₂—CH₂— and —O—CH₂.

3. The compound or salt of claim 2, wherein each R¹ is independently selected from halogen, hydroxy, C1-C3 alkoxy and C1-C4 alkyl.

4. The compound or salt of claim 2, wherein each R², if present, is selected from hydrogen and halogen, and wherein each R³, if present, is selected from hydrogen and halogen.

5. The compound or salt of claim 2, wherein each R⁷ is independently selected from hydrogen, C1-C3alkyl, hydroxy, C1-C3 alkoxy, and wherein two R⁷ on non-adjacent atoms optionally join to form a 1-2 carbon bridge.

6. The compound or salt of claim 2, wherein each R⁶ is independently hydrogen or hydroxy.

7. The compound or salt of claim 1, wherein at least one R¹ is C1-C4 alkyl.

8. The compound or salt of claim 1, wherein at least one R¹ is halogen.

9. The compound or salt of claim 8, wherein said halogen is a fluorine.

10. The compound or salt of claim 1, wherein at least one R¹ is hydroxy.

11. The compound or salt of claim 1, wherein at least one R² is halogen.

12. The compound or salt of claim 11, wherein said halogen is a fluorine.

13. The compound or salt of claim 1, wherein at least one R³ is C1-C4 alkyl.

14. The compound or salt of claim 1, wherein at least one R³ is halogen.

15. The compound or salt of claim 14, wherein said halogen is fluorine.

16. The compound or salt of claim 1, wherein R⁴ is halogen.

17. The compound or salt of claim 16, wherein said halogen is fluorine.

18. The compound or salt of claim 1, wherein at least one R⁵ is C1-C4 alkyl.

19. The compound or salt of claim 1, wherein at least one R⁵ is hydrogen.

20. The compound or salt of claim 1, wherein one or both R⁶ are hydrogen.

21. The compound or salt of claim 1, wherein Y¹ and Y² join to form piperidine, azepane, azocane, thiazepine, diazepane, oxazepane, pyrrolidine, piperazine bound to a fused ring via nitrogen or thiomorpholine.

22. The compound or salt of claim 1, wherein two R⁷ on the same atom join to form a spirocyclic ring selected from C3-C6 cycloalkyl and heterocycle, where said spirocyclic ring is optionally substituted with one or more substituents selected from oxo (=O), halogen, hydroxy, C1-C3 alkyl and —O—(C1-C3 alkyl).

23. The compound or salt of claim 1, wherein two R⁷ on adjacent atoms join to form a bond or a fused ring selected from C3-C6 cycloalkyl optionally substituted with 1-4 R⁸ heteroaryl optionally substituted with 1-4 R⁸; aryl optionally substituted with 1-4 R⁸, and heterocycle optionally substituted with 1-4 R⁸.

24. The compound or salt of claim 1, wherein two R⁷ on nonadjacent atoms join to form a 1-2 carbon bridge.

25. A compound selected from:

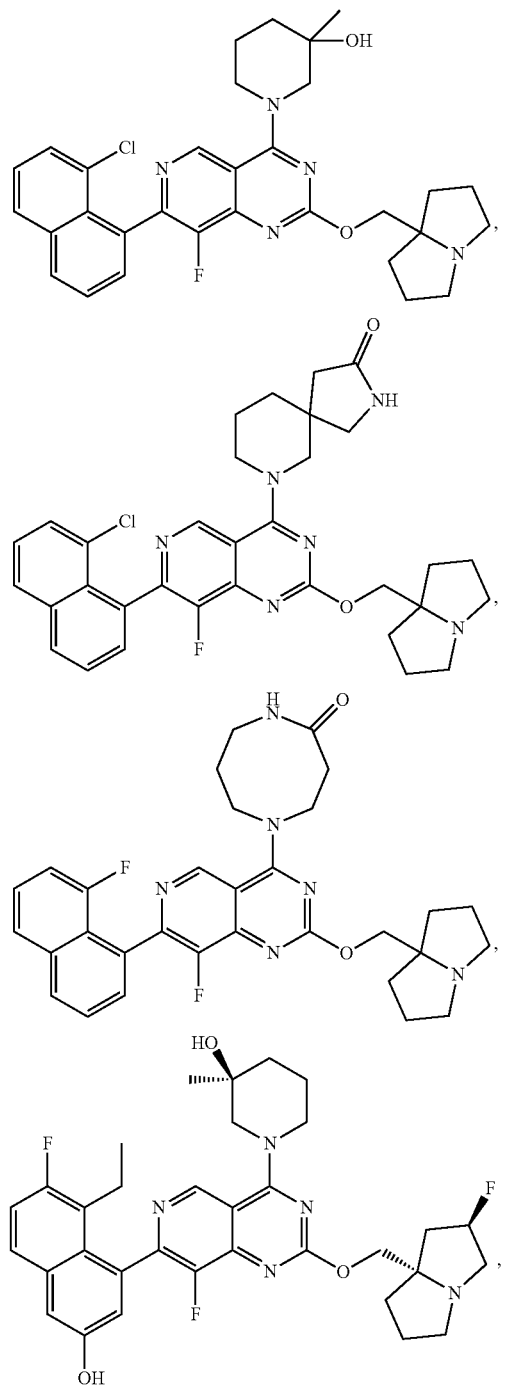

749
-continued
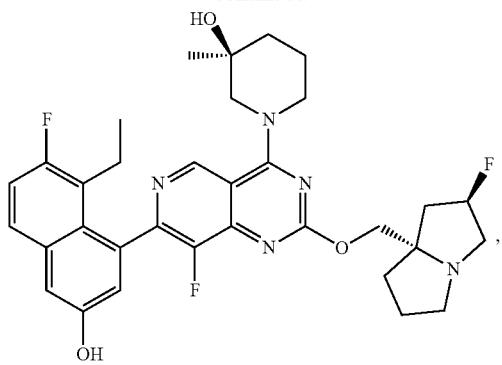
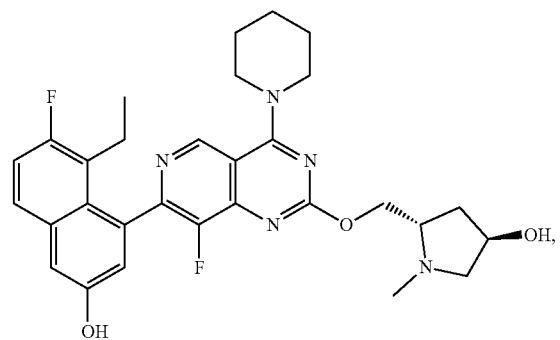
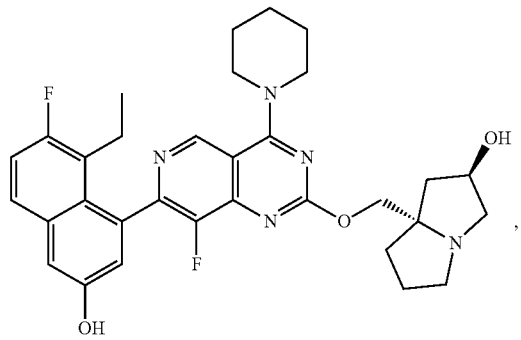
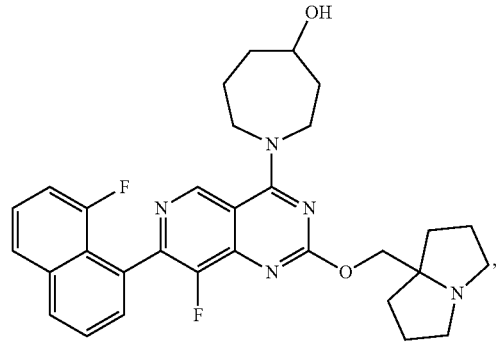
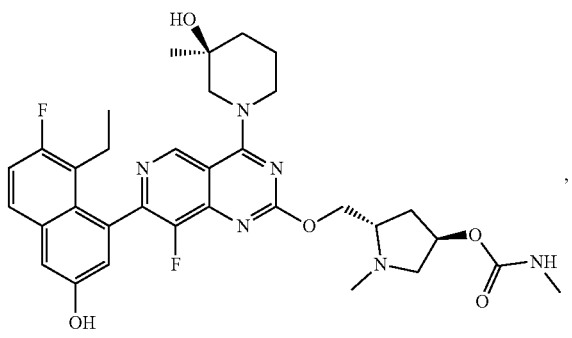
750
-continued
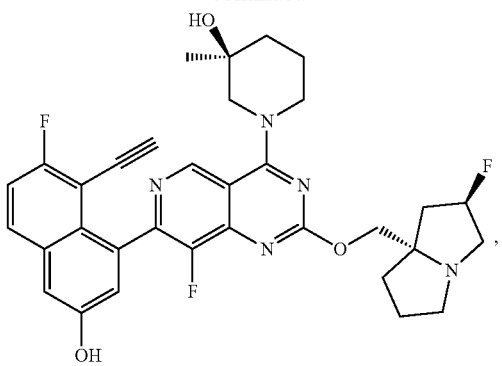
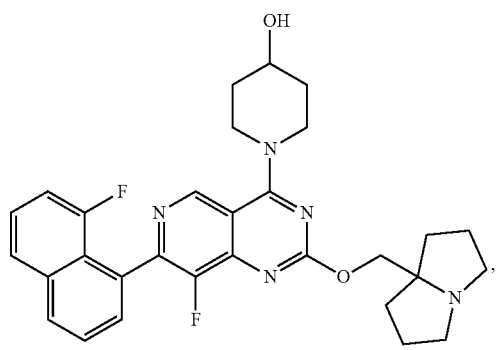
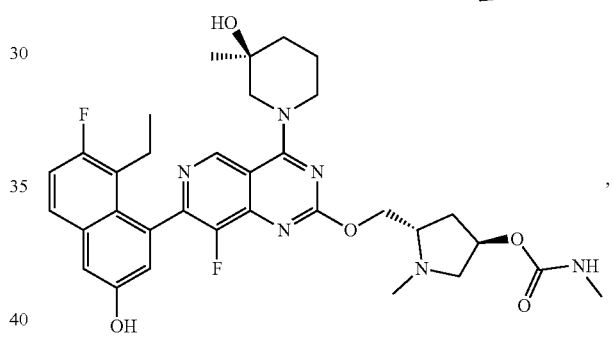
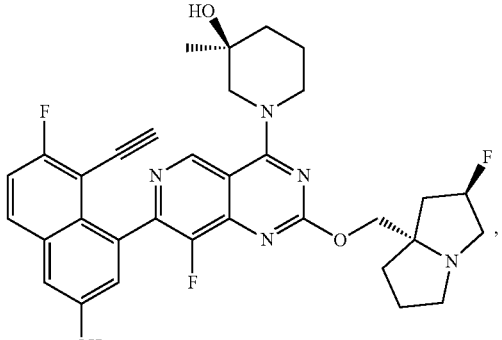
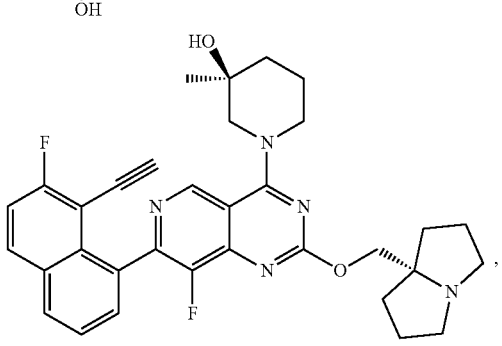

751
-continued
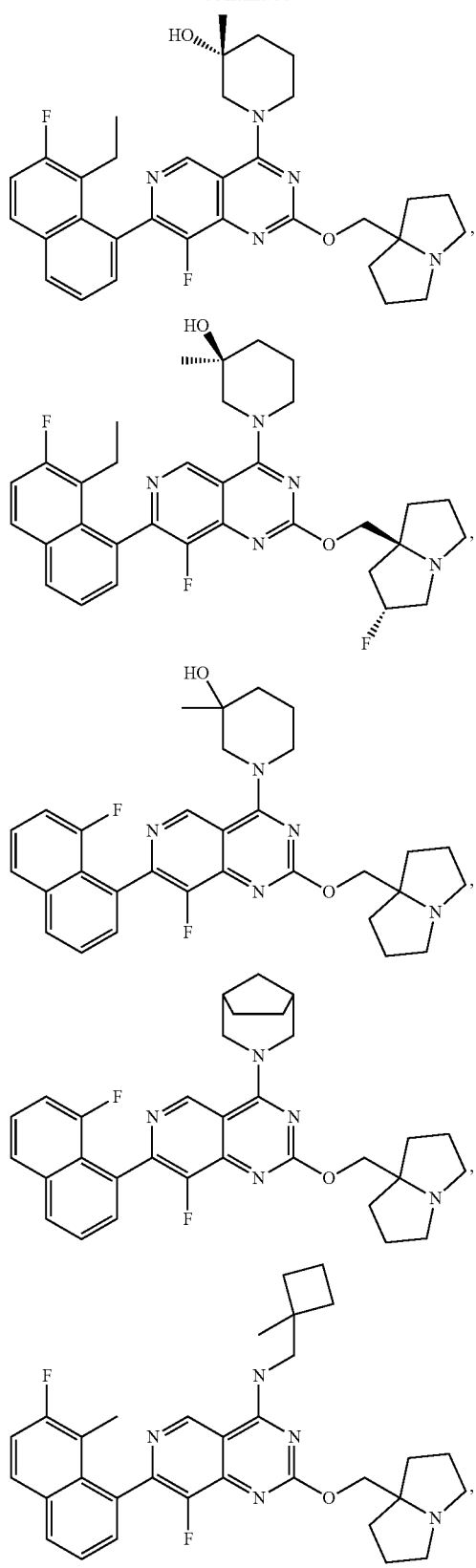
752
-continued
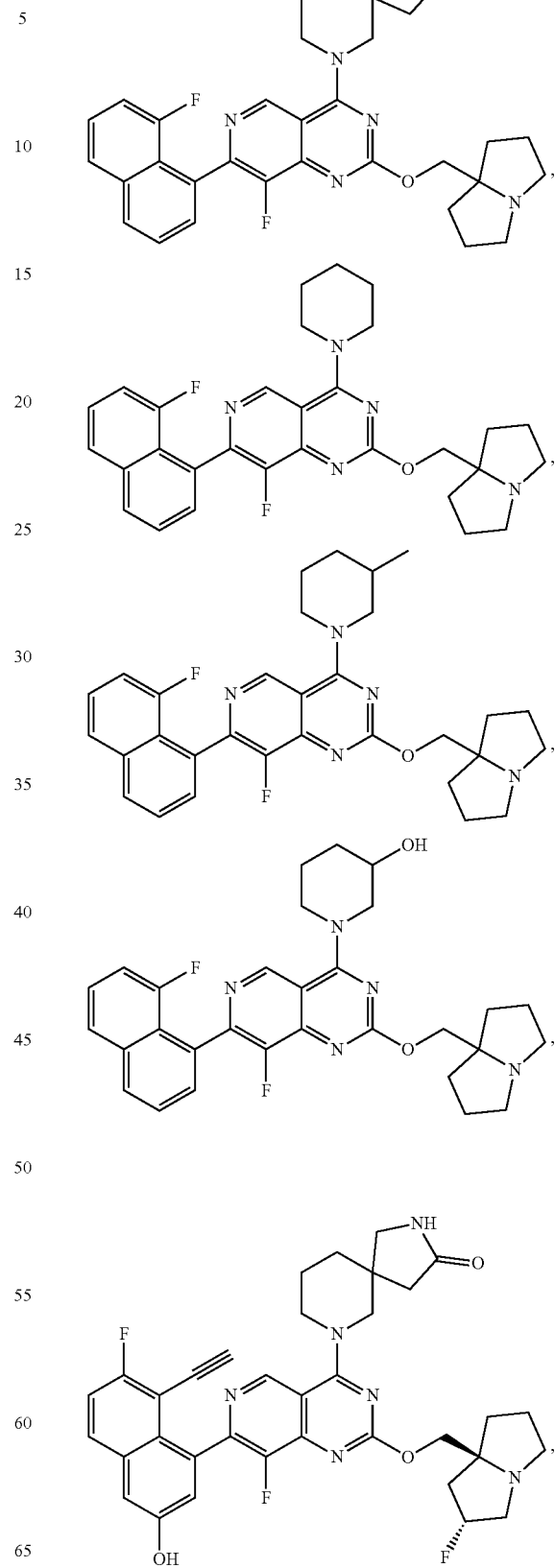

753
-continued
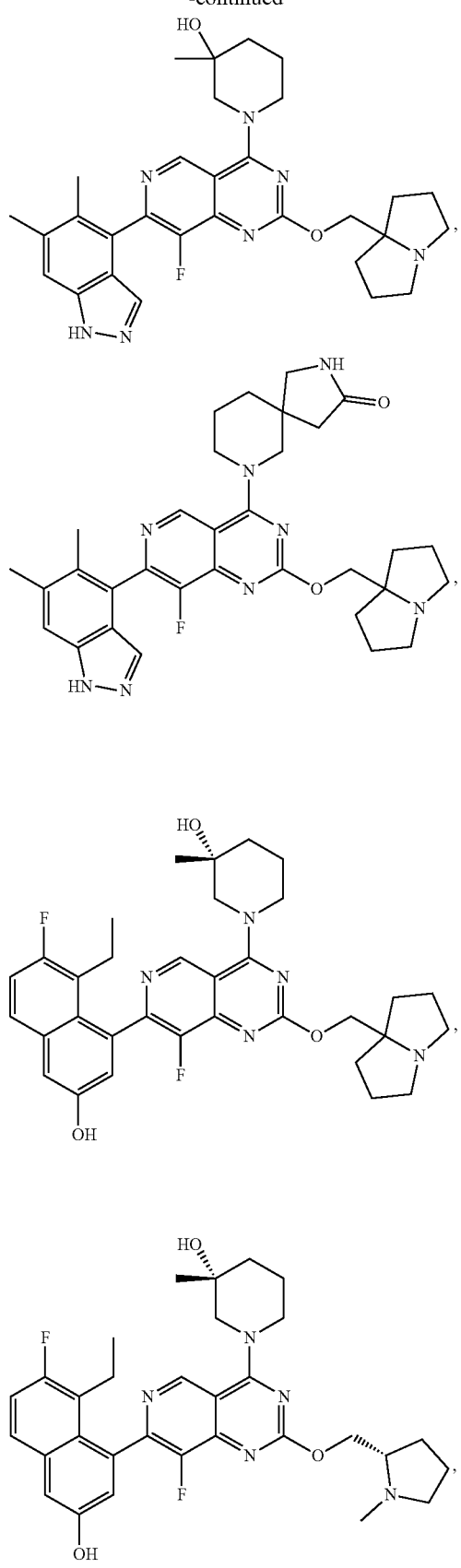
754
-continued
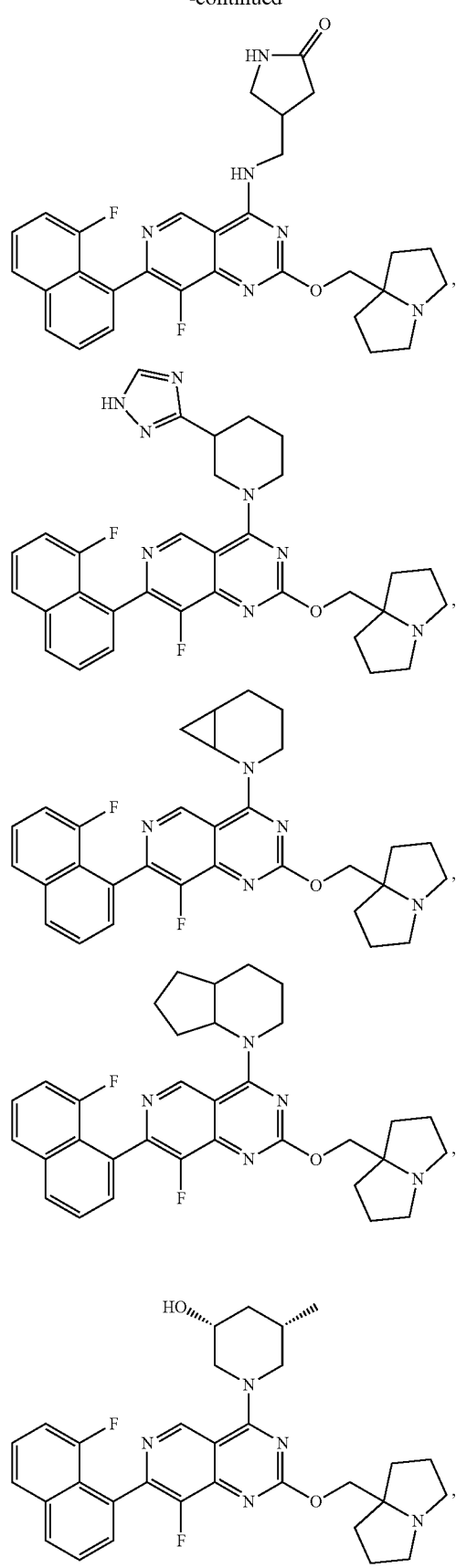

755
-continued
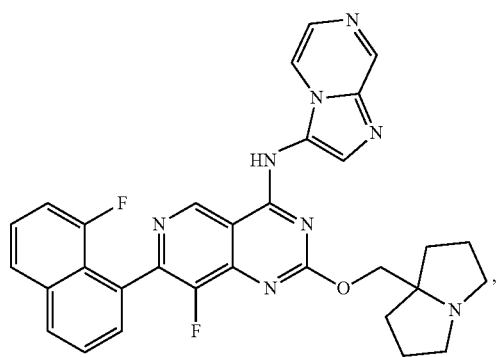
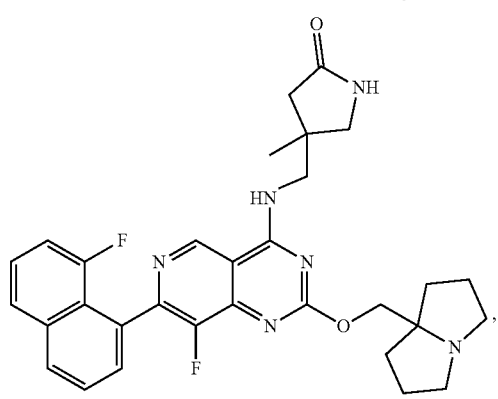
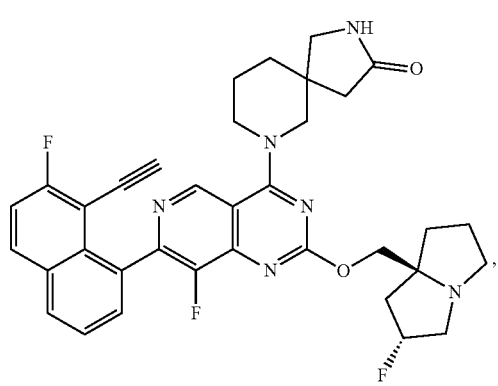
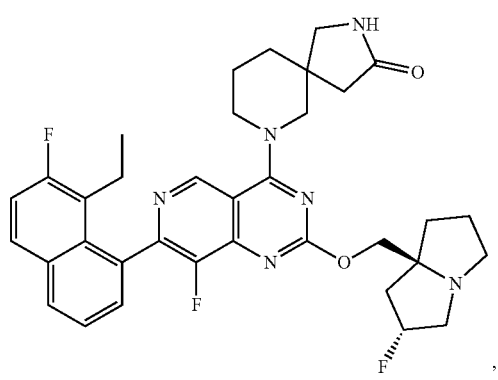
756
-continued
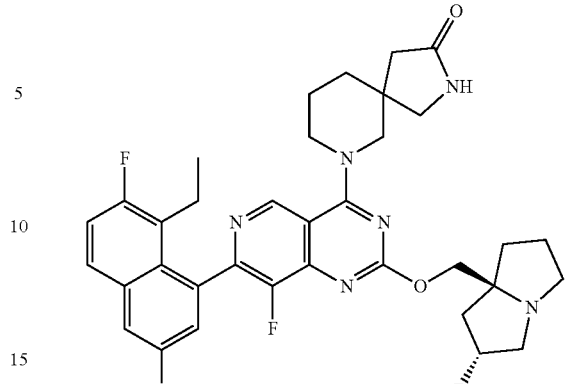
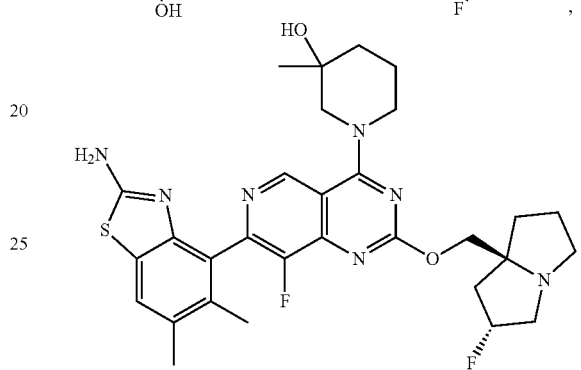
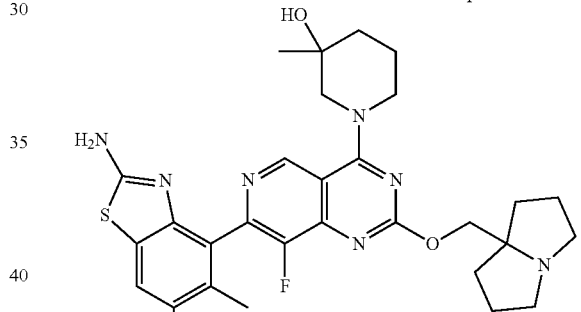
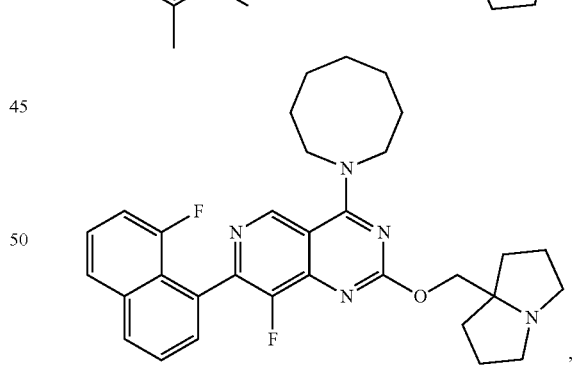
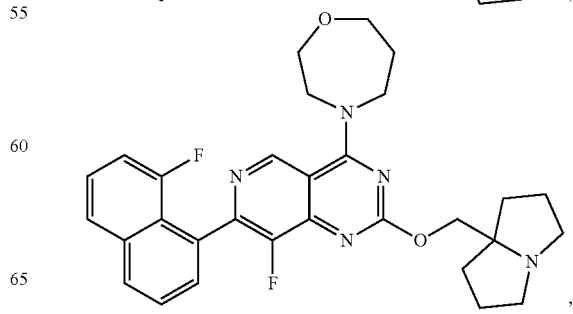

757
-continued
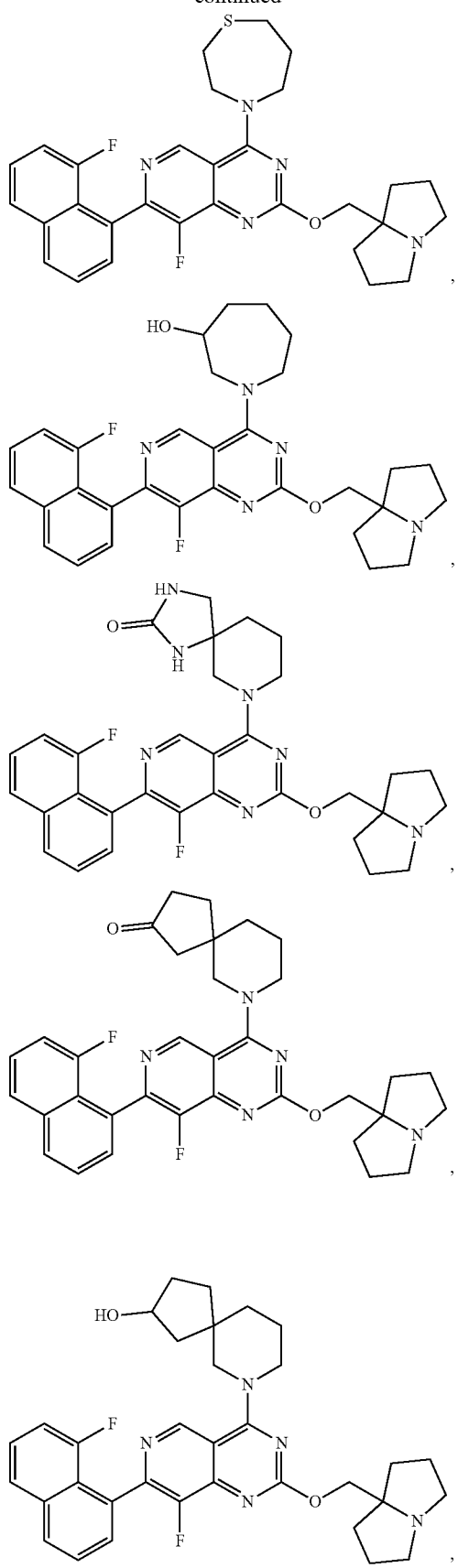
758
-continued
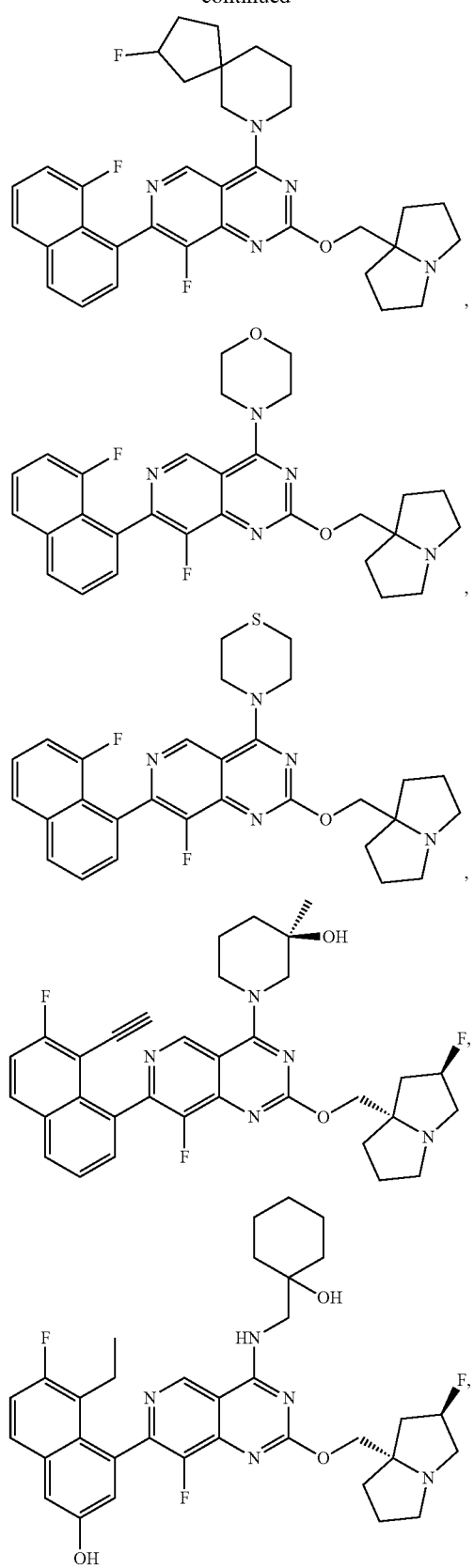

759
-continued
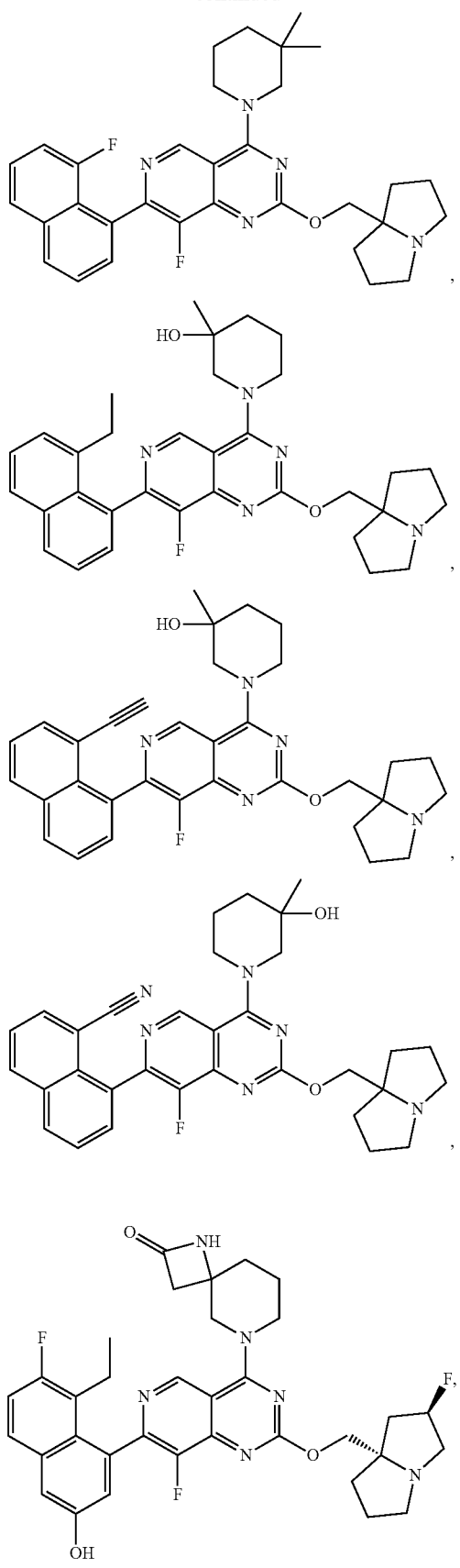
760
-continued
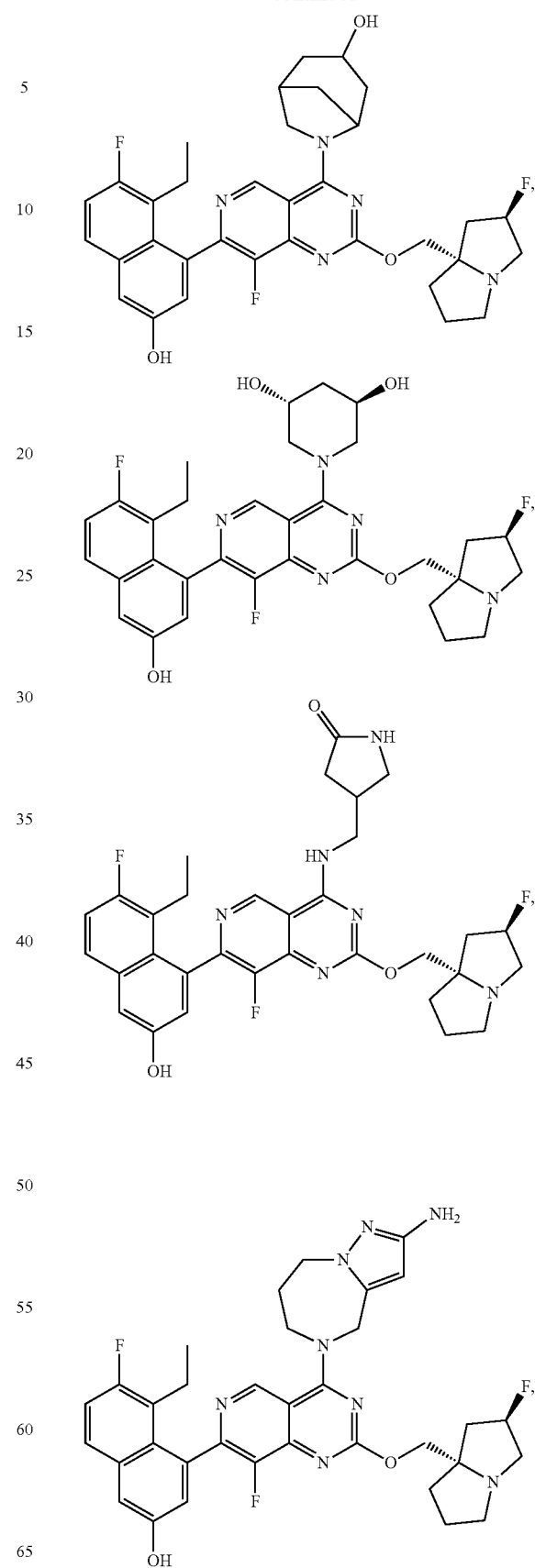

761
-continued
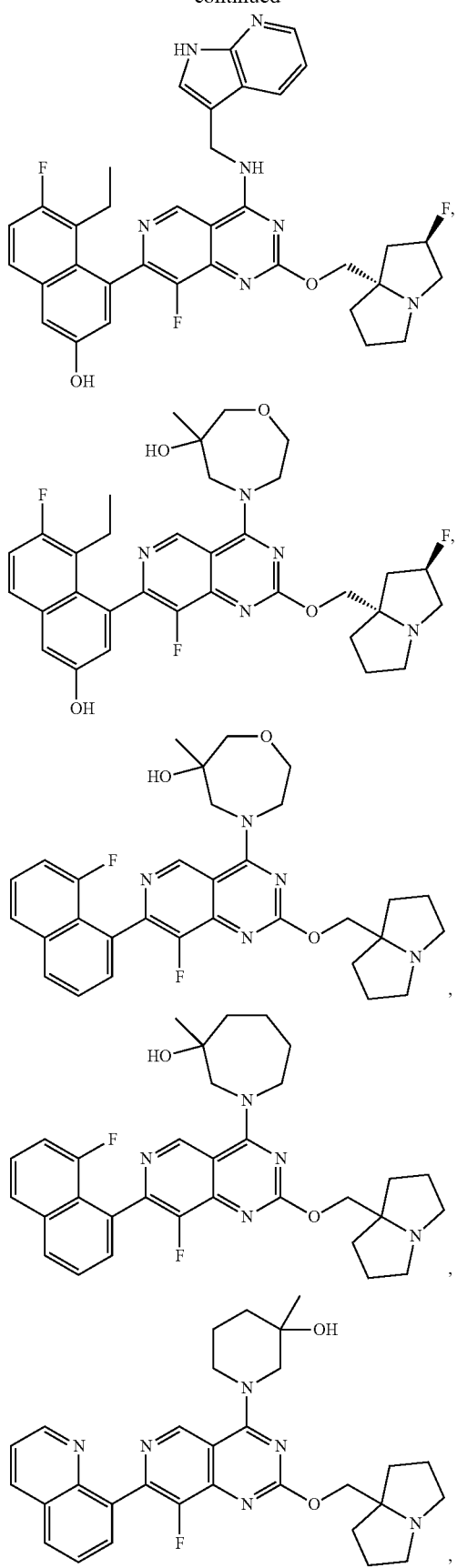
762
-continued
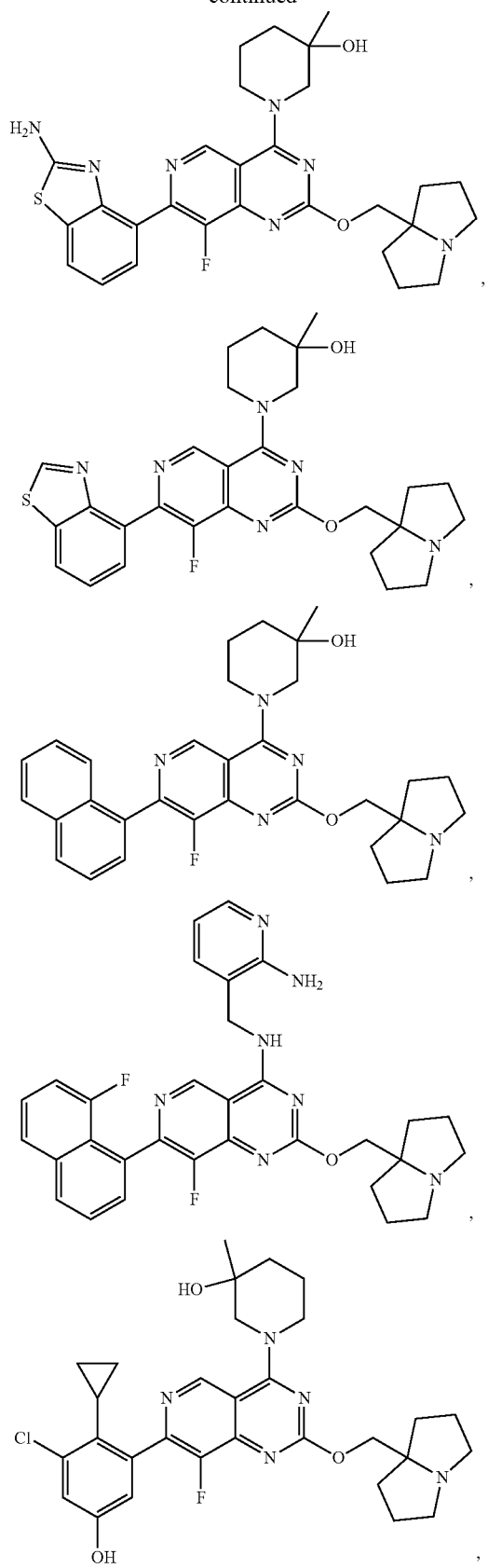

763 -continued
764 -continued
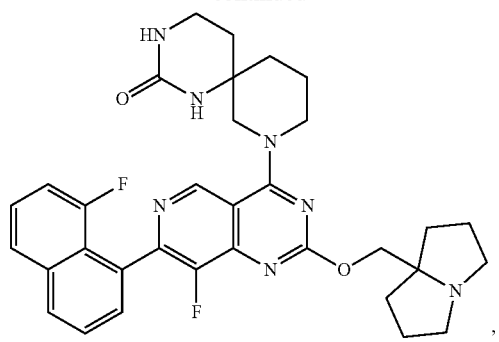
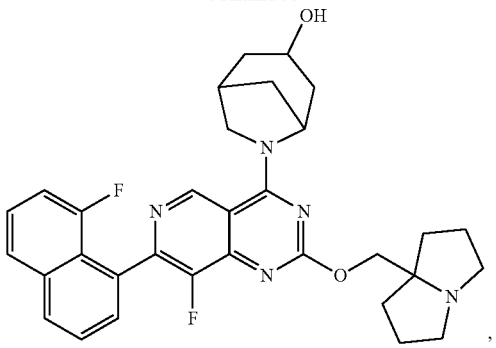

765
-continued
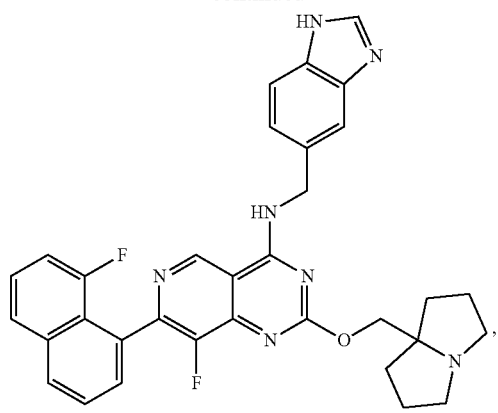
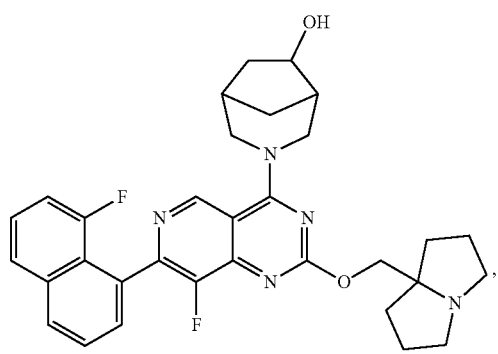
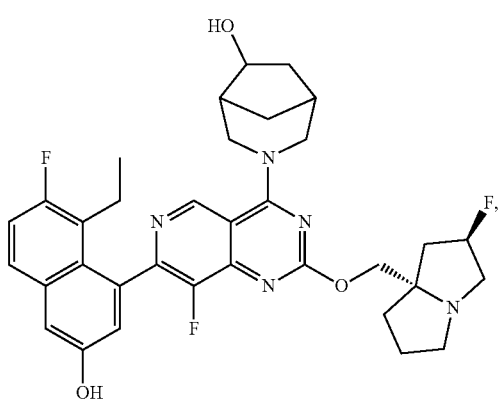
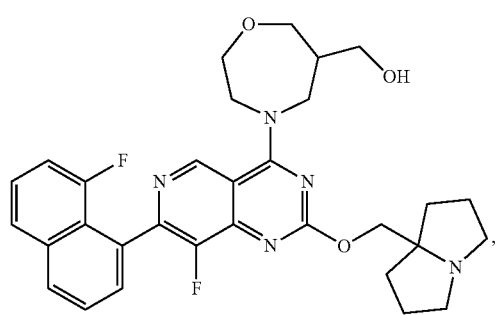
766
-continued
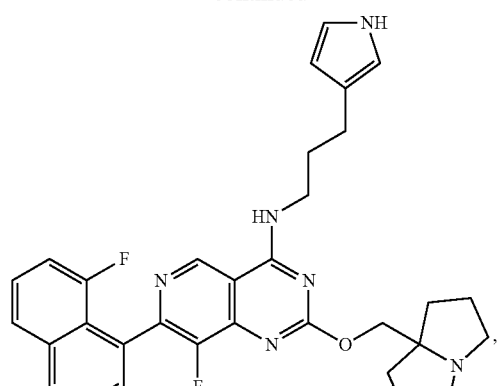
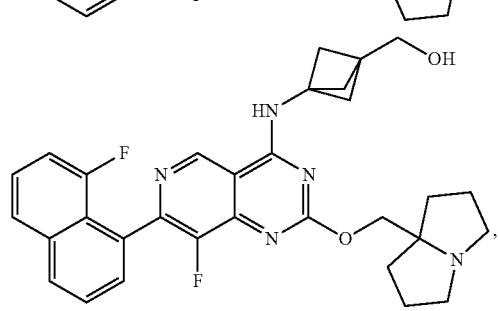
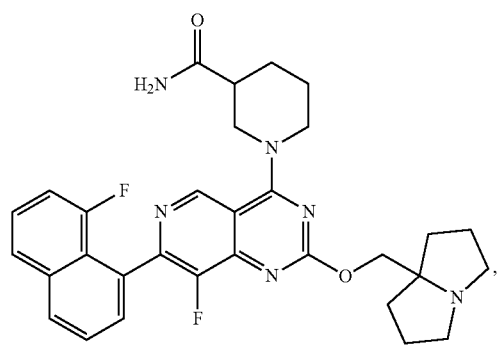
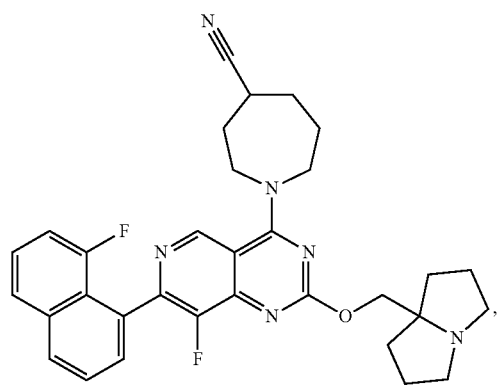

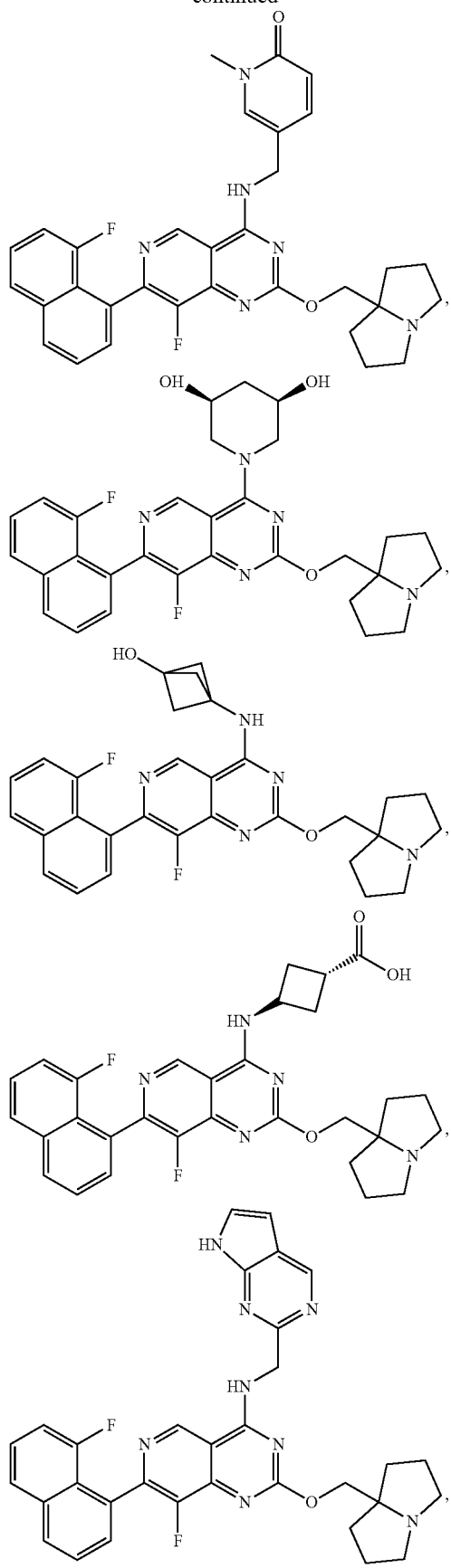
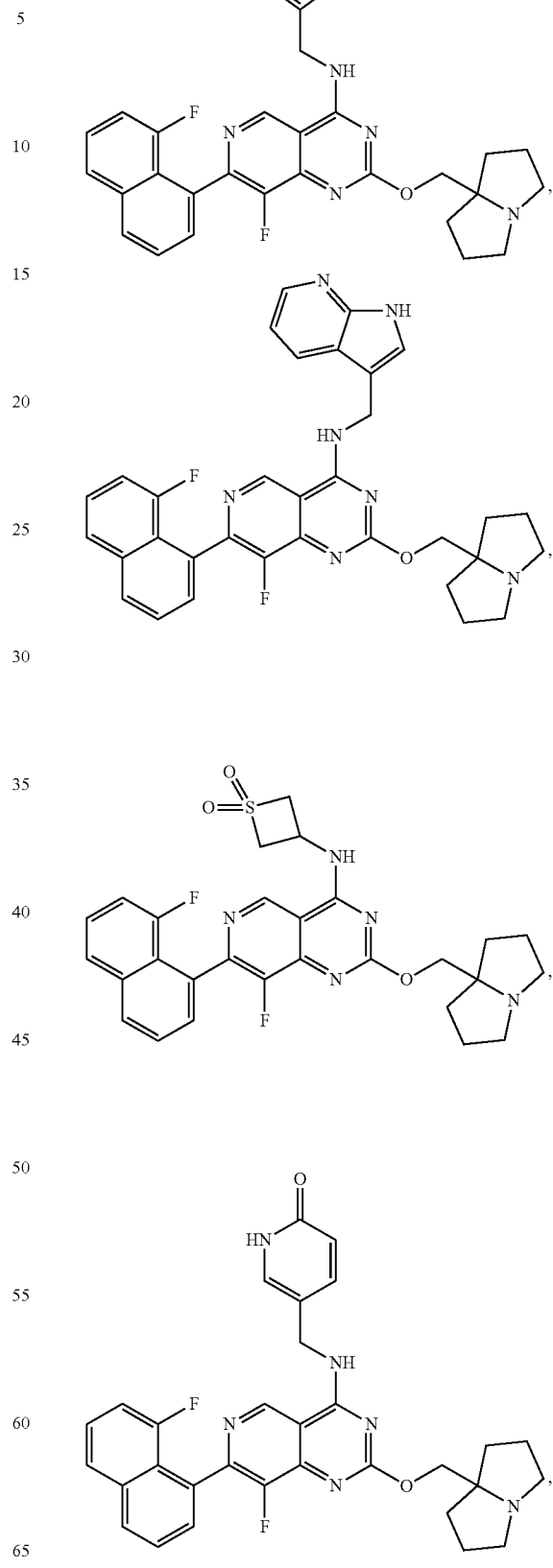

769
-continued
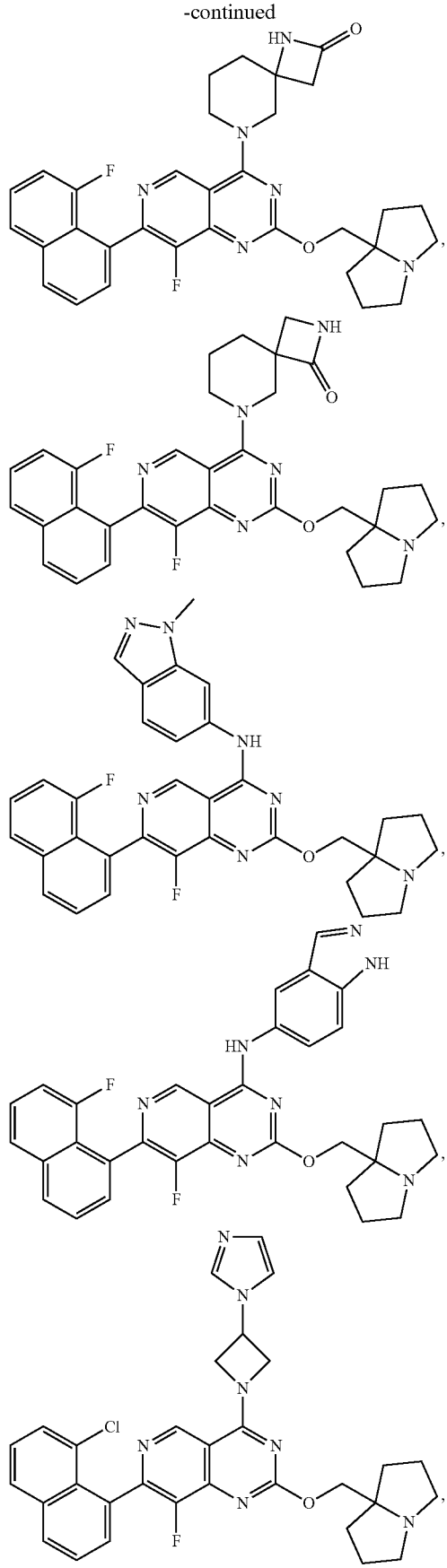
770
-continued
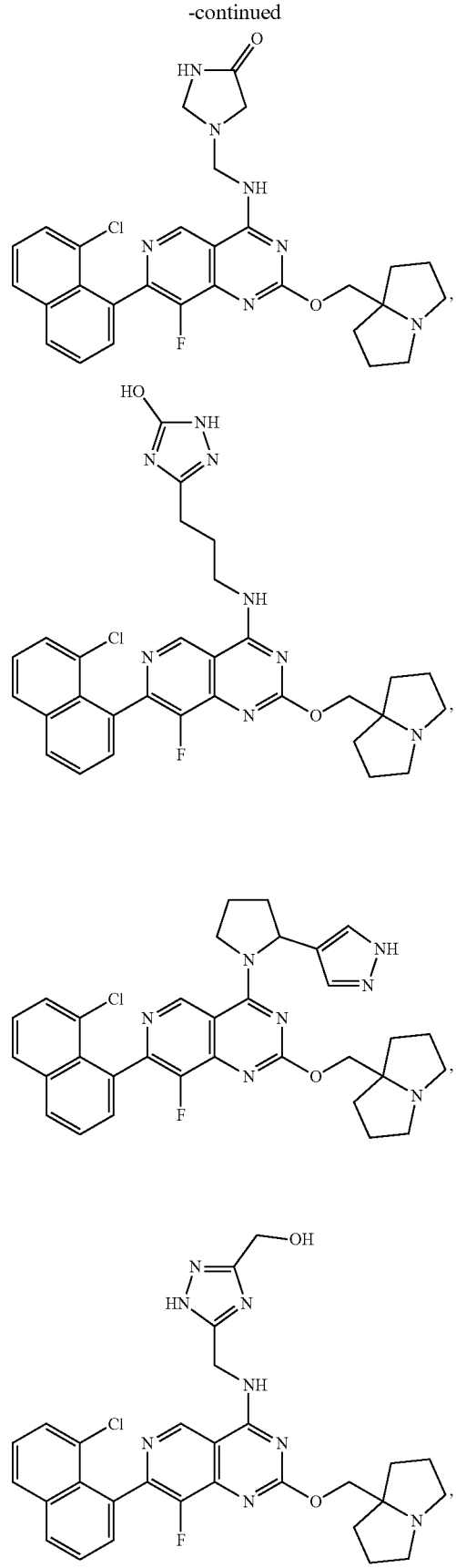

771
-continued
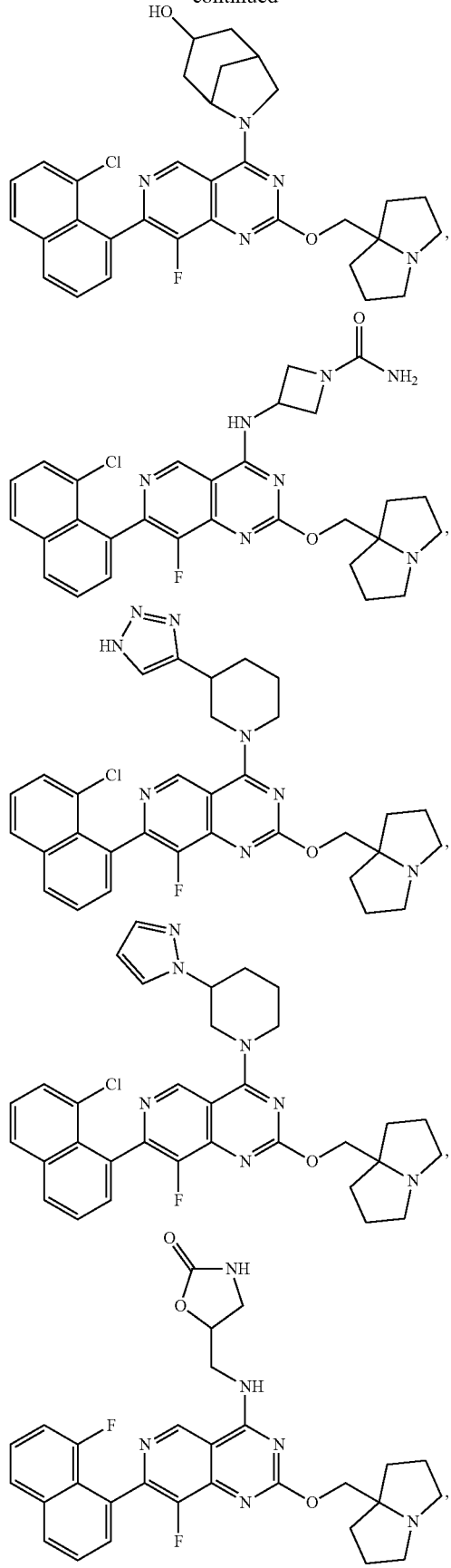
772
-continued
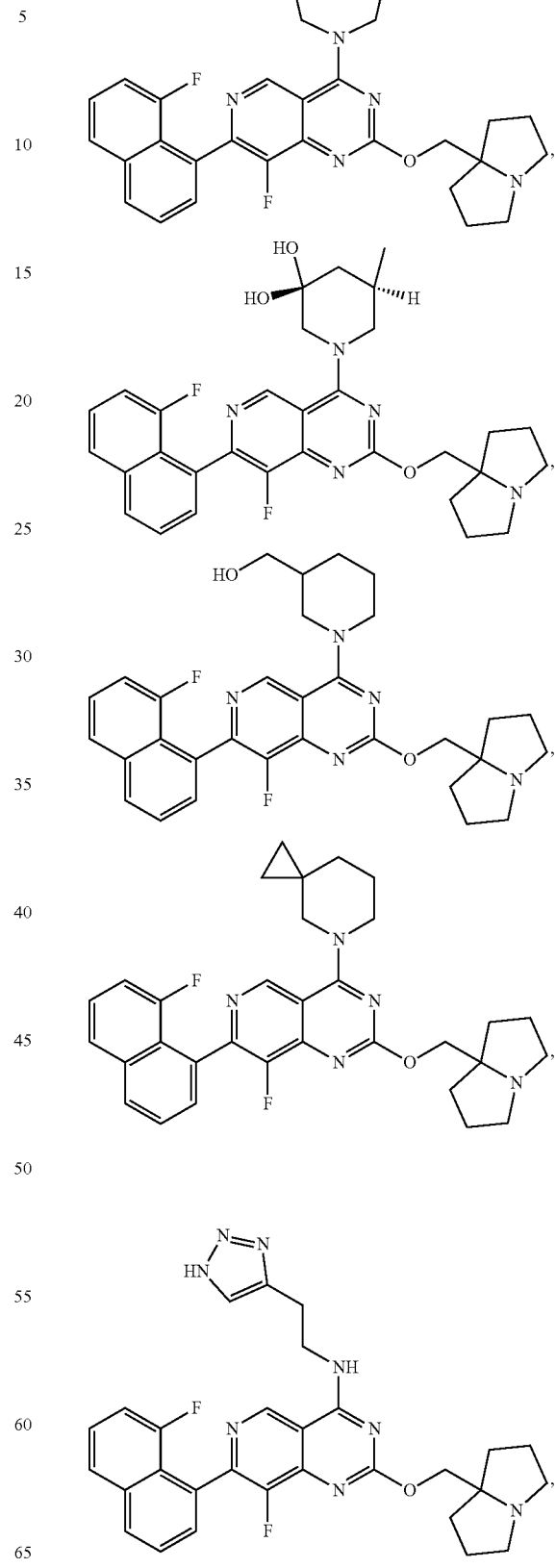

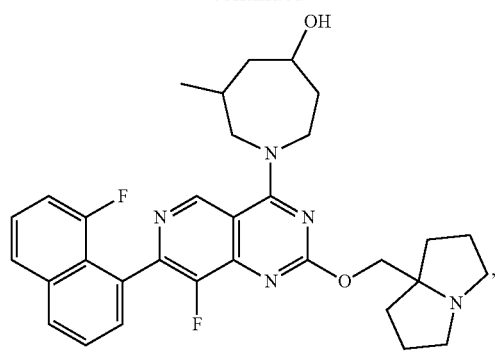
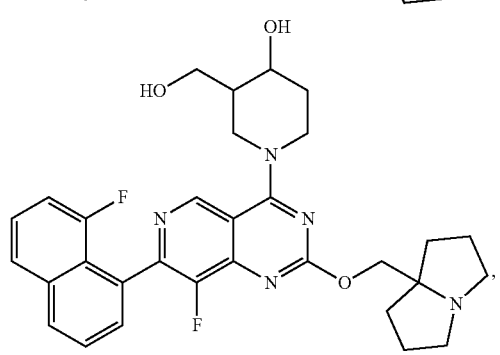
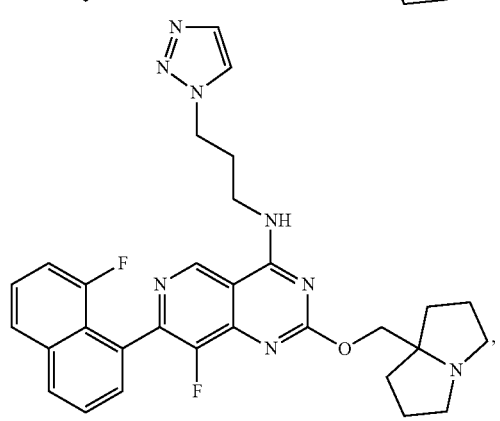
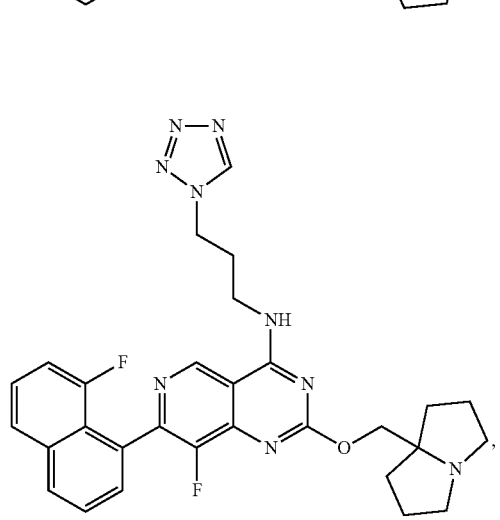
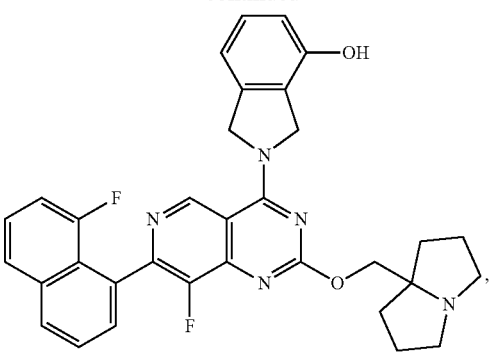
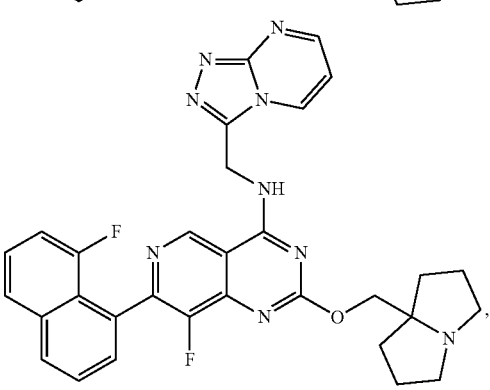
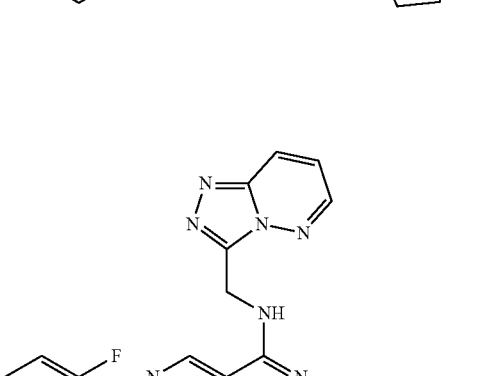
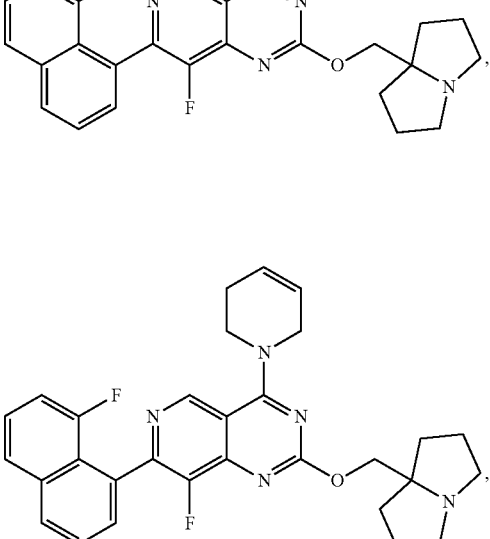

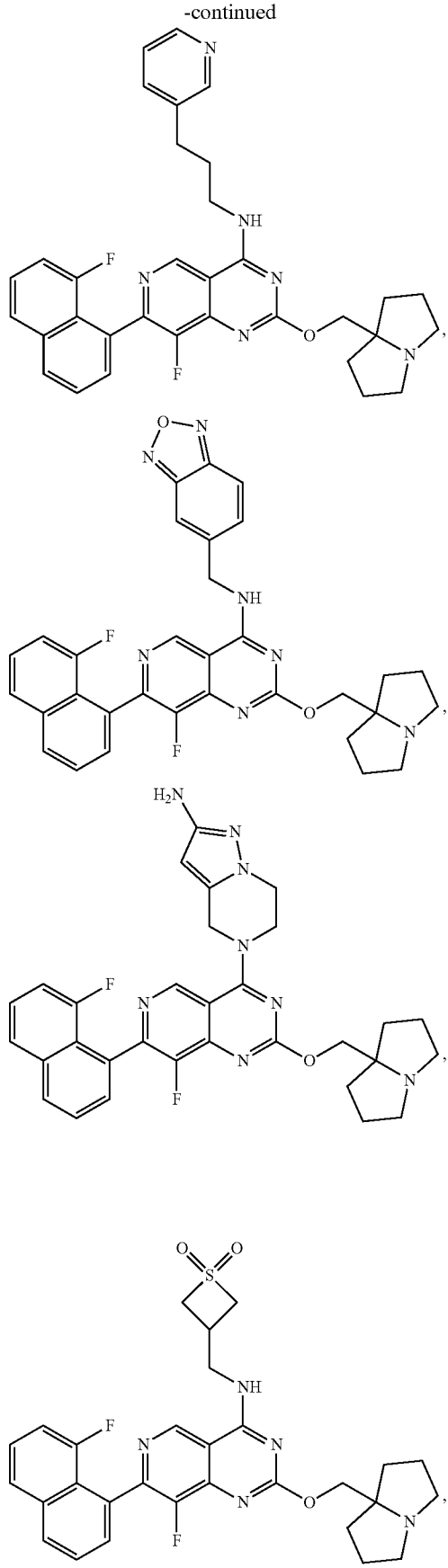
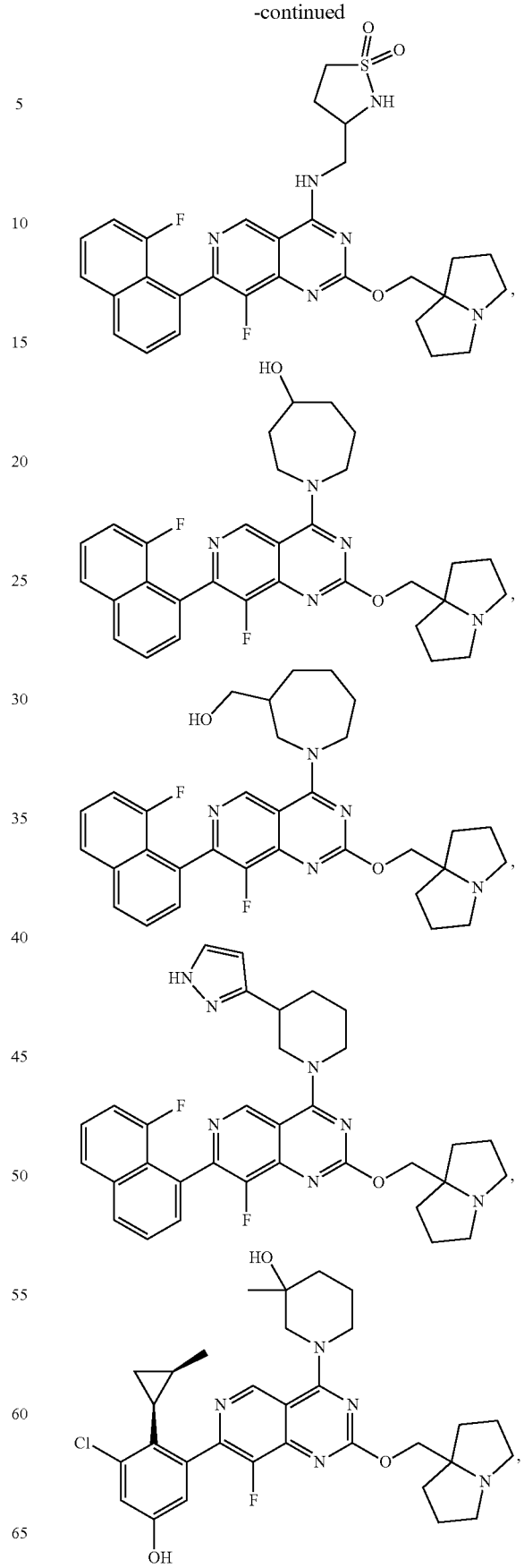

777
-continued
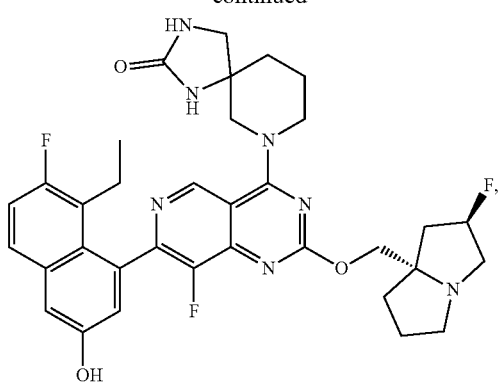
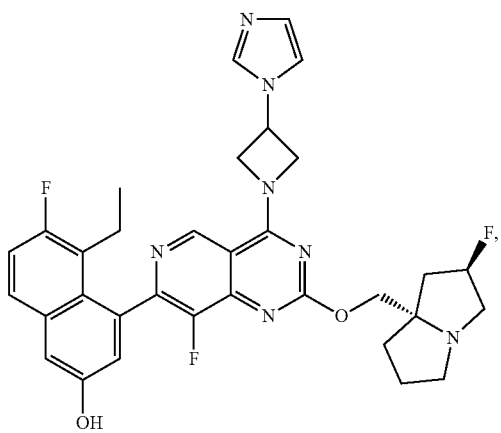
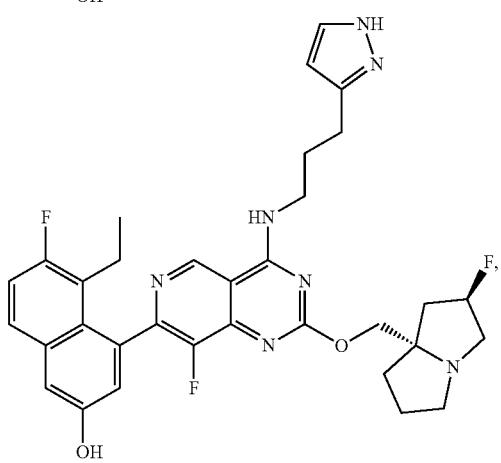
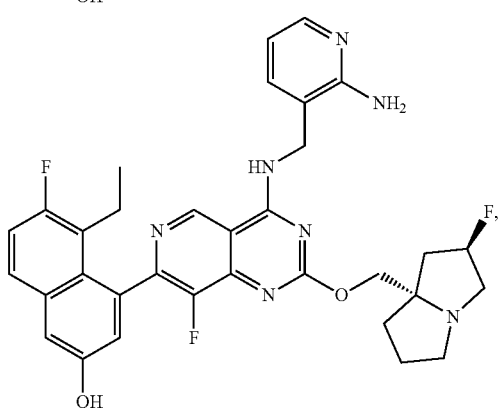
778
-continued
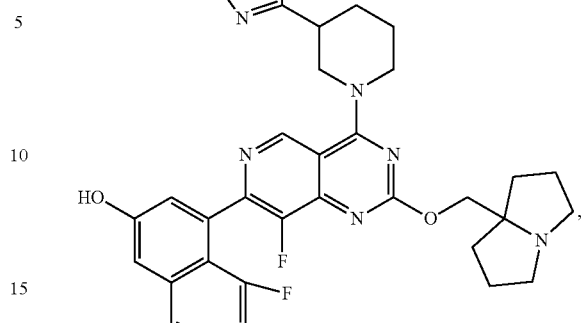
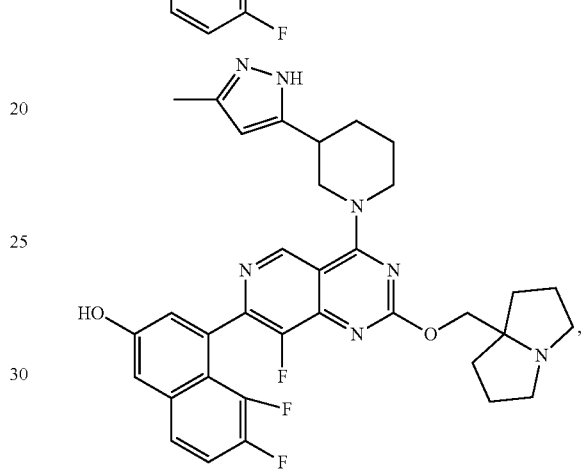
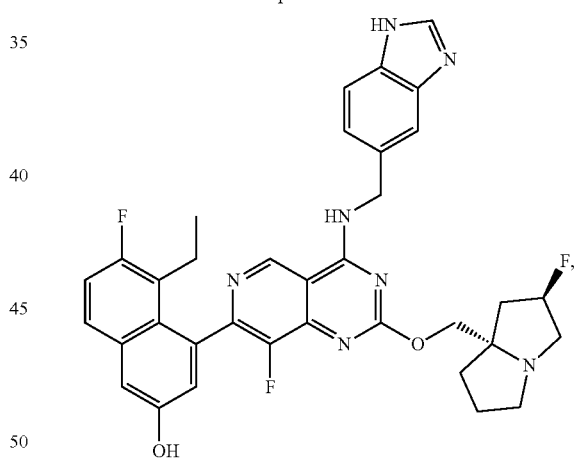
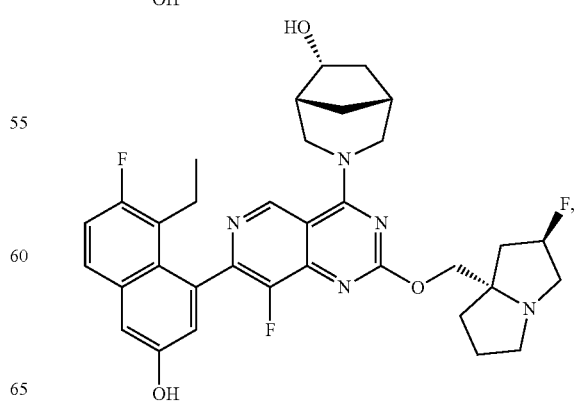

779
-continued
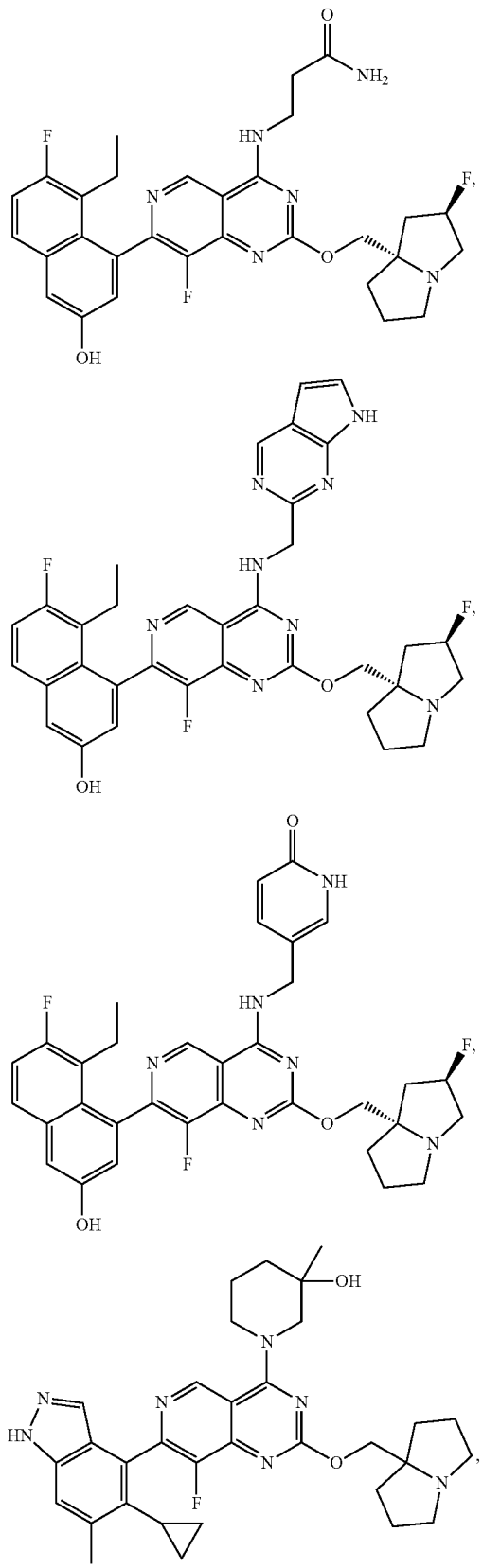
780
-continued
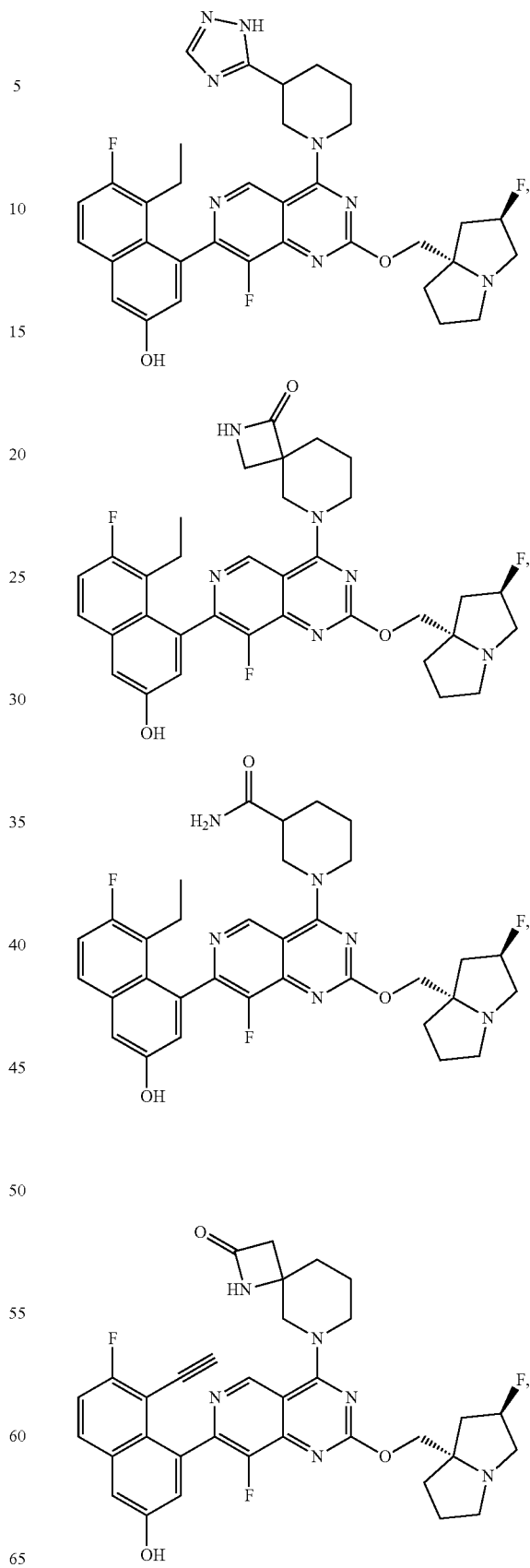

781
-continued
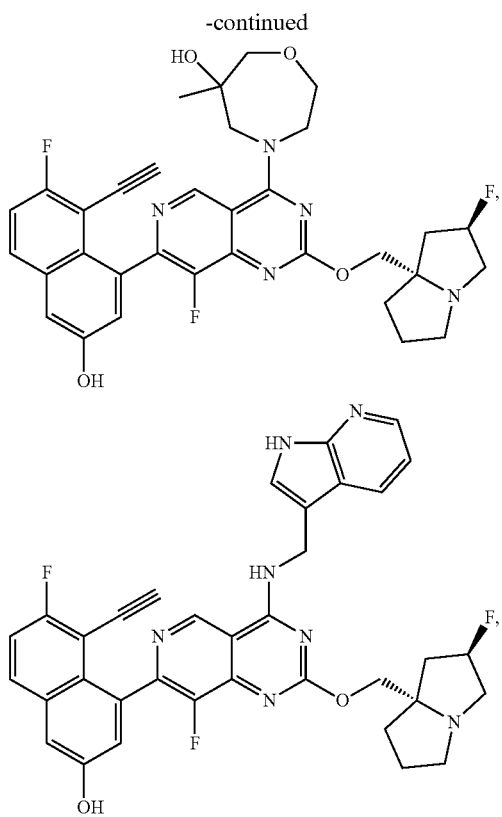
782
-continued
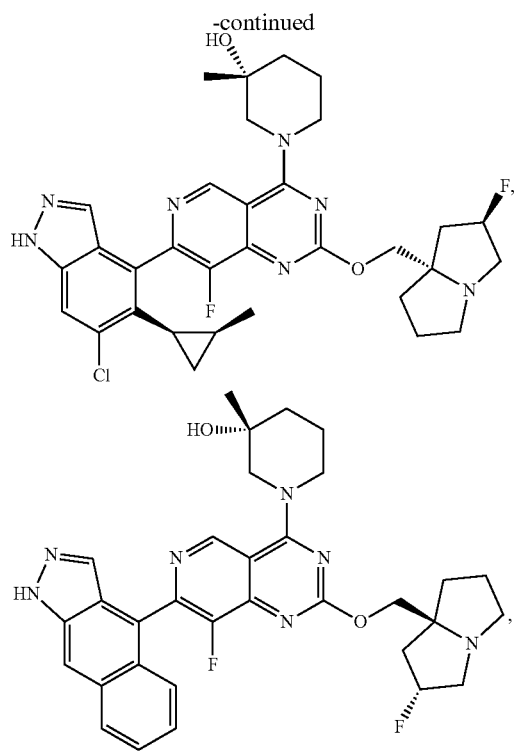
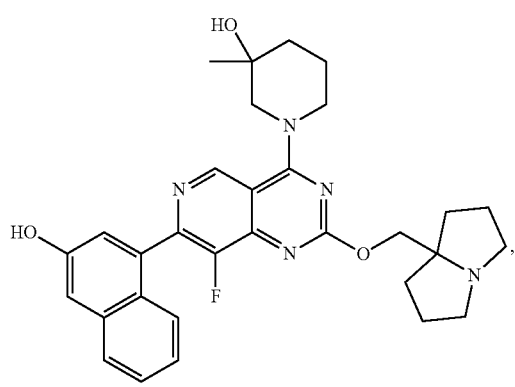
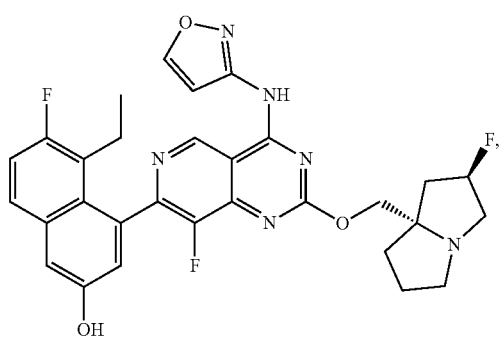

783
-continued
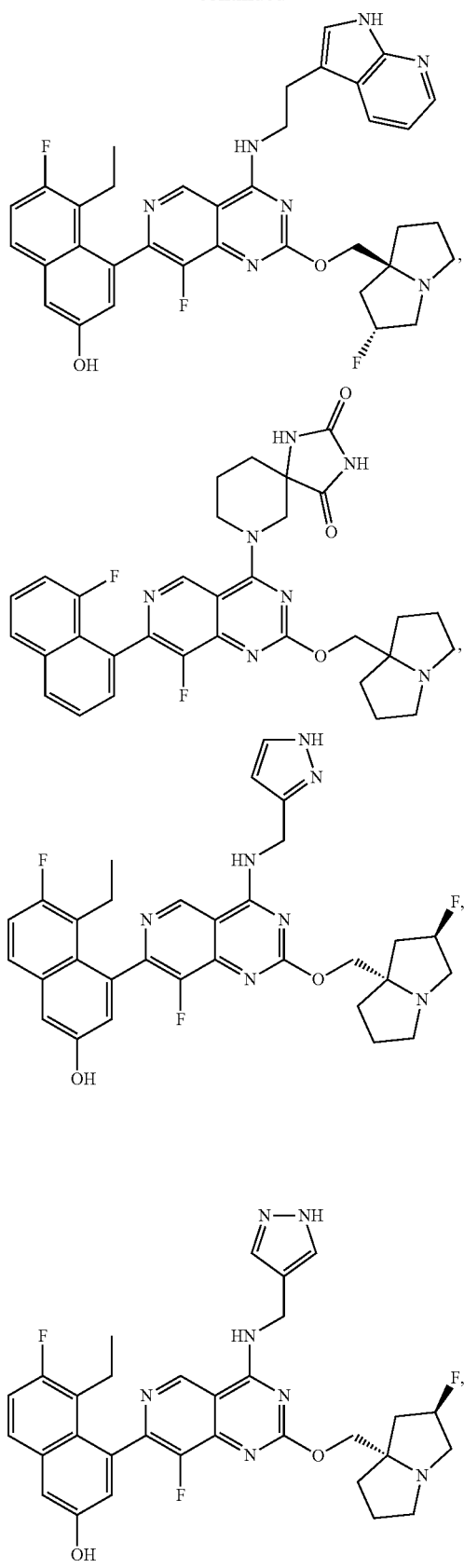
784
-continued
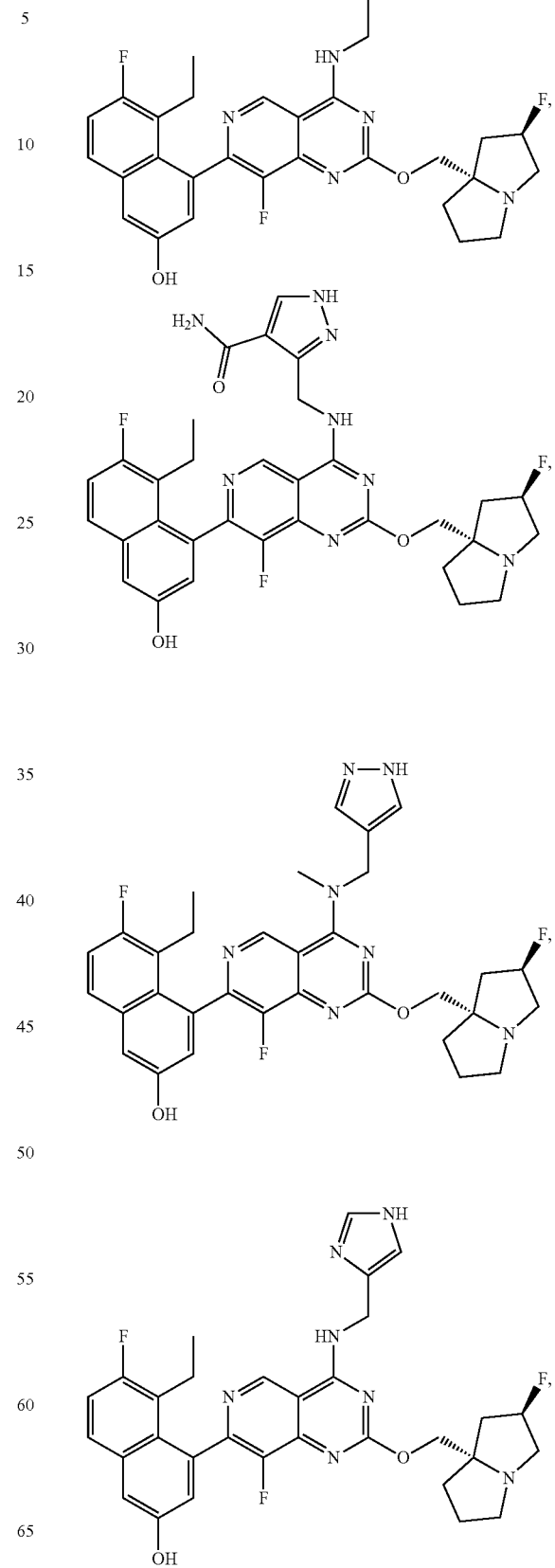

785
-continued
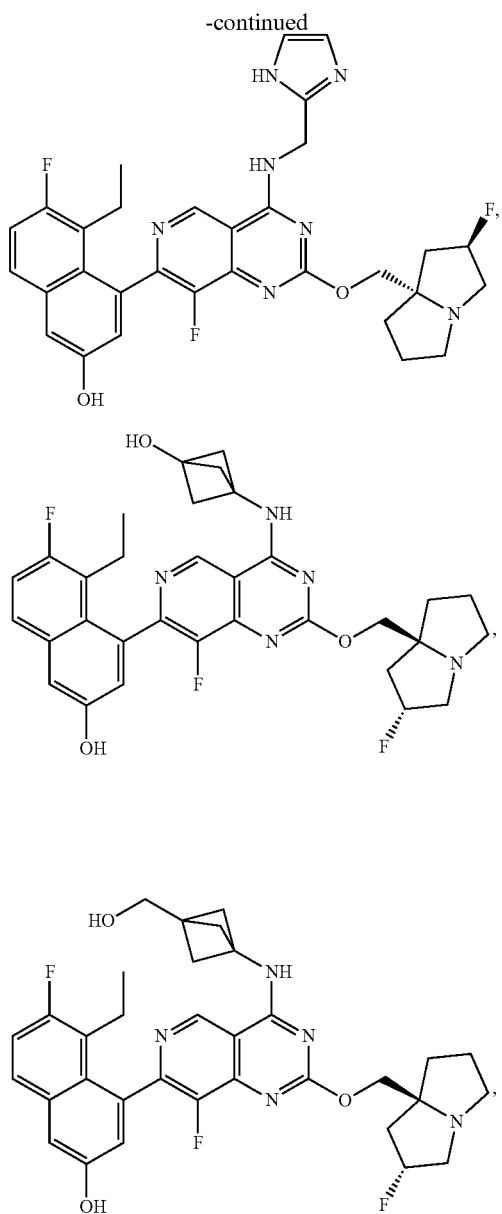
786
-continued
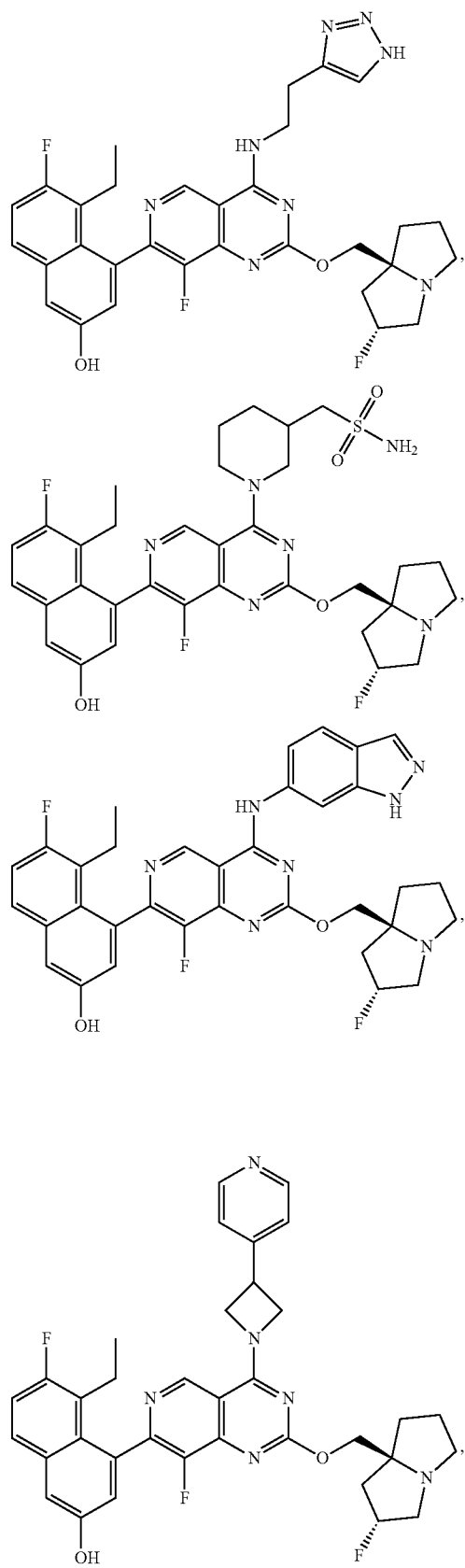

787
-continued
788
-continued
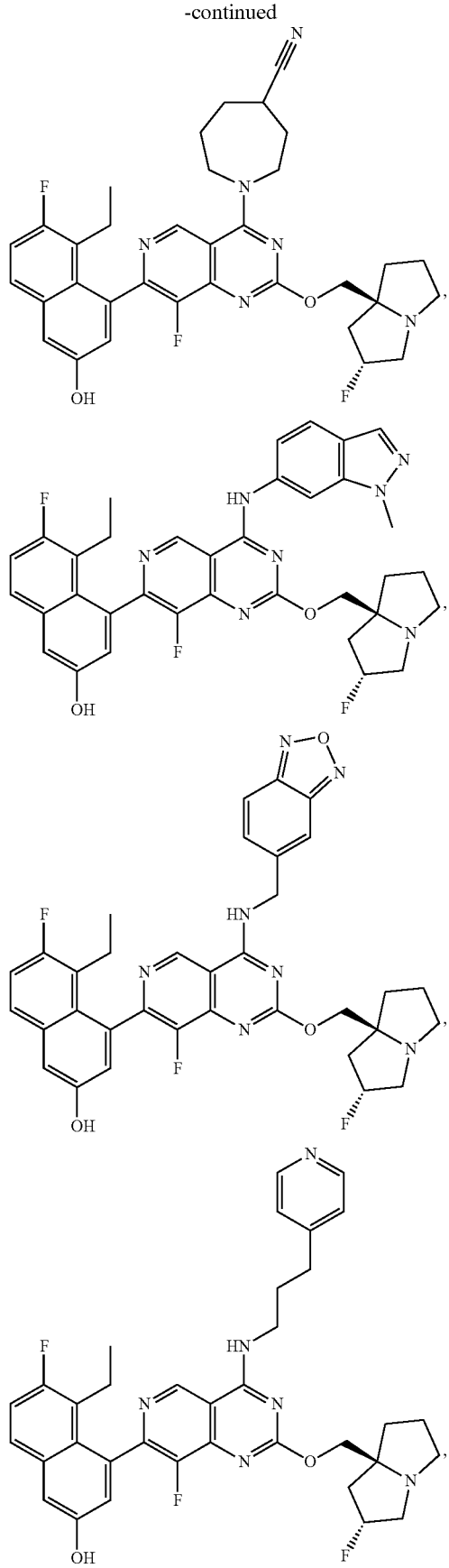
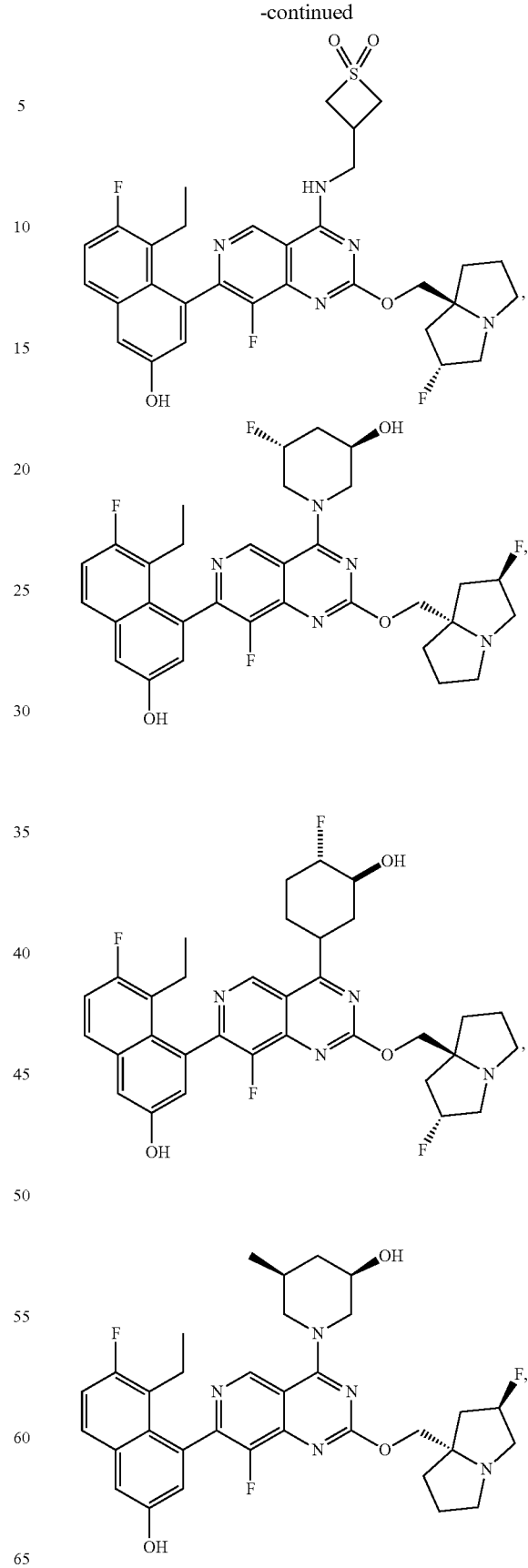

789
-continued
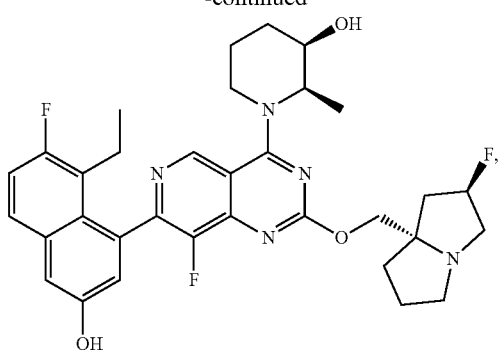
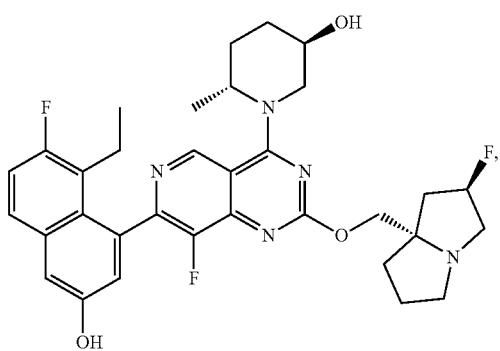
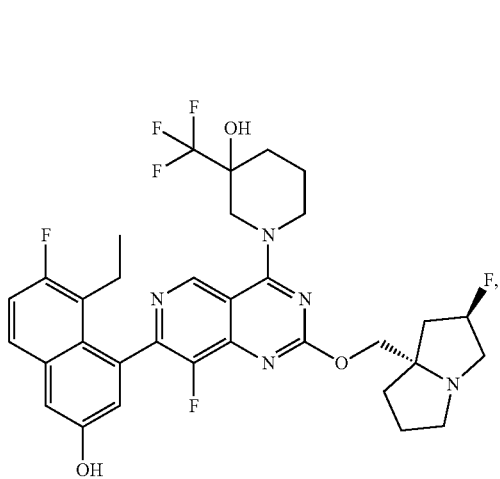
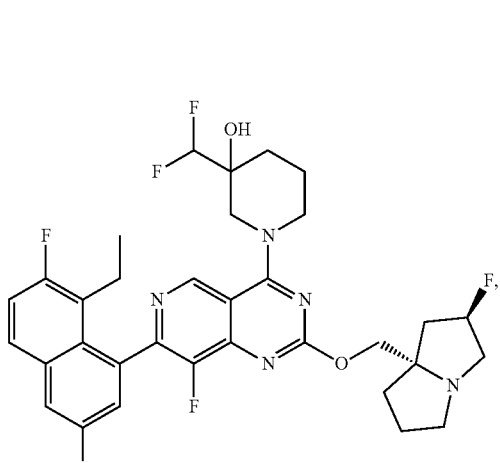
790
-continued
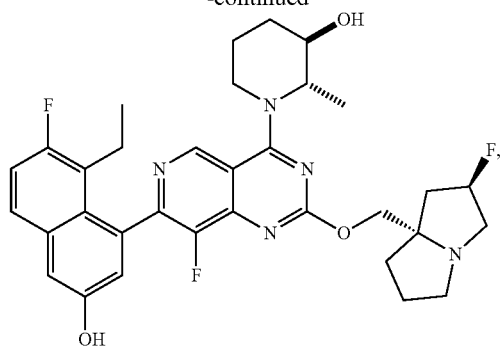
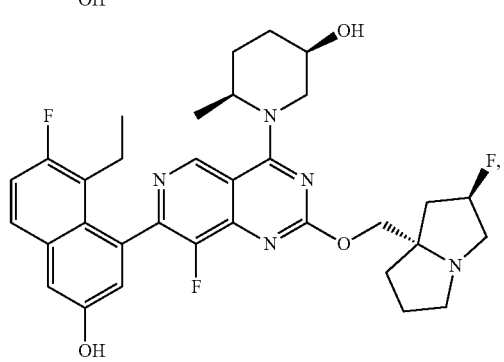
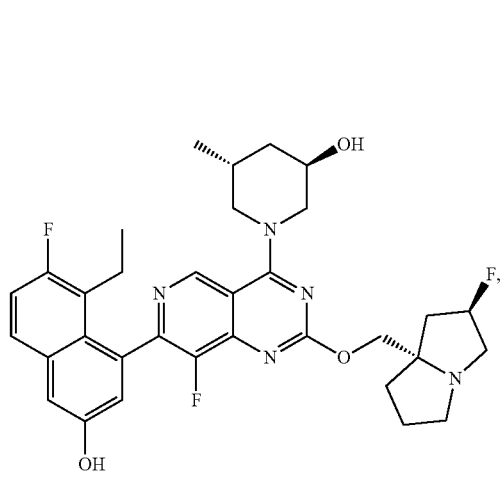
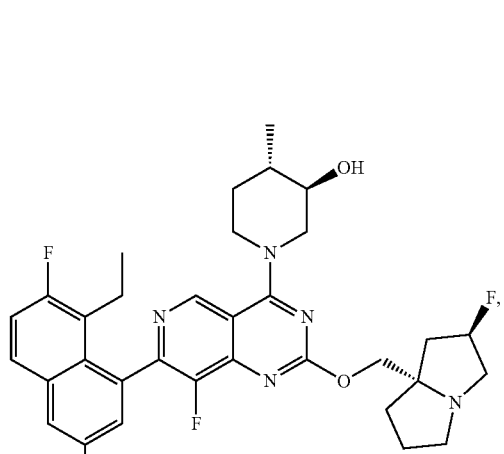

791
-continued
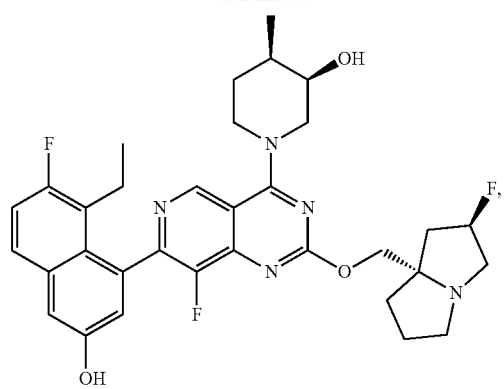
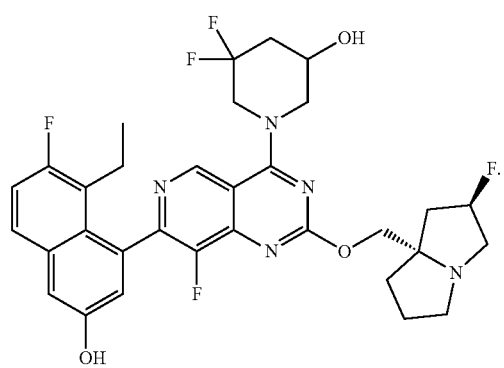
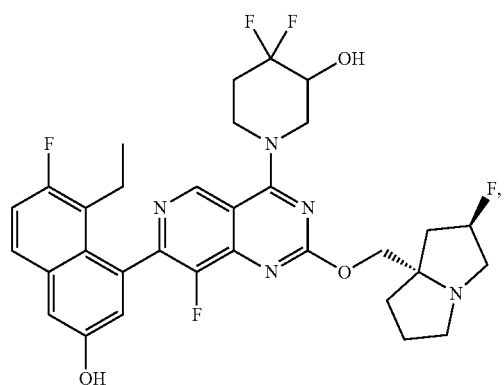
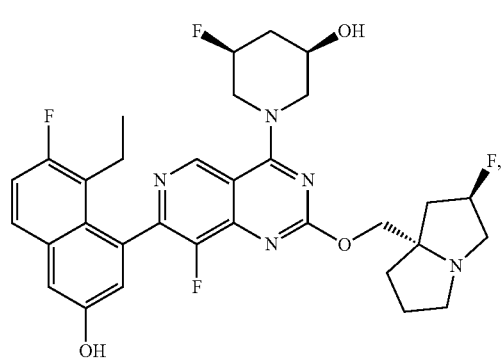
792
-continued
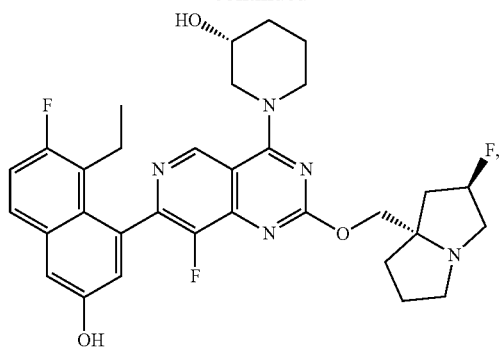
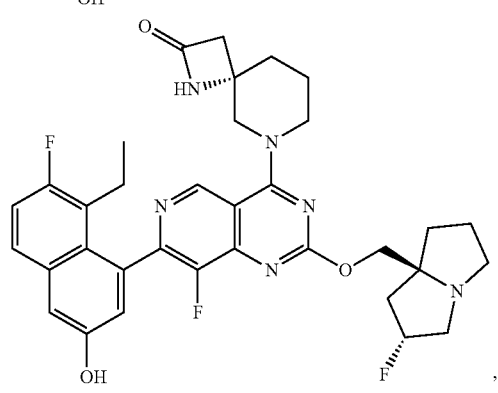
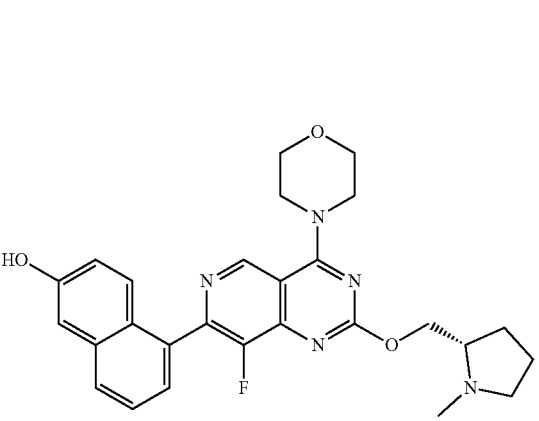
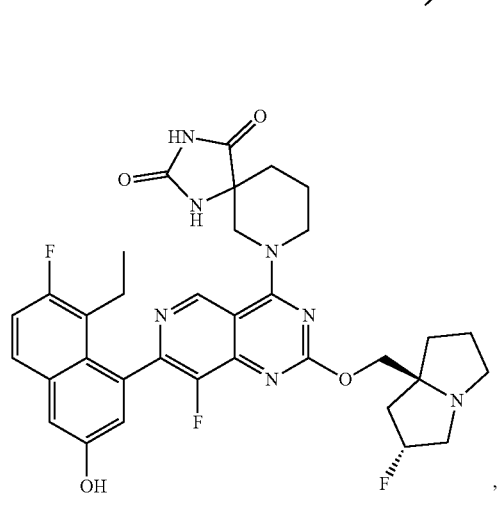

793
-continued
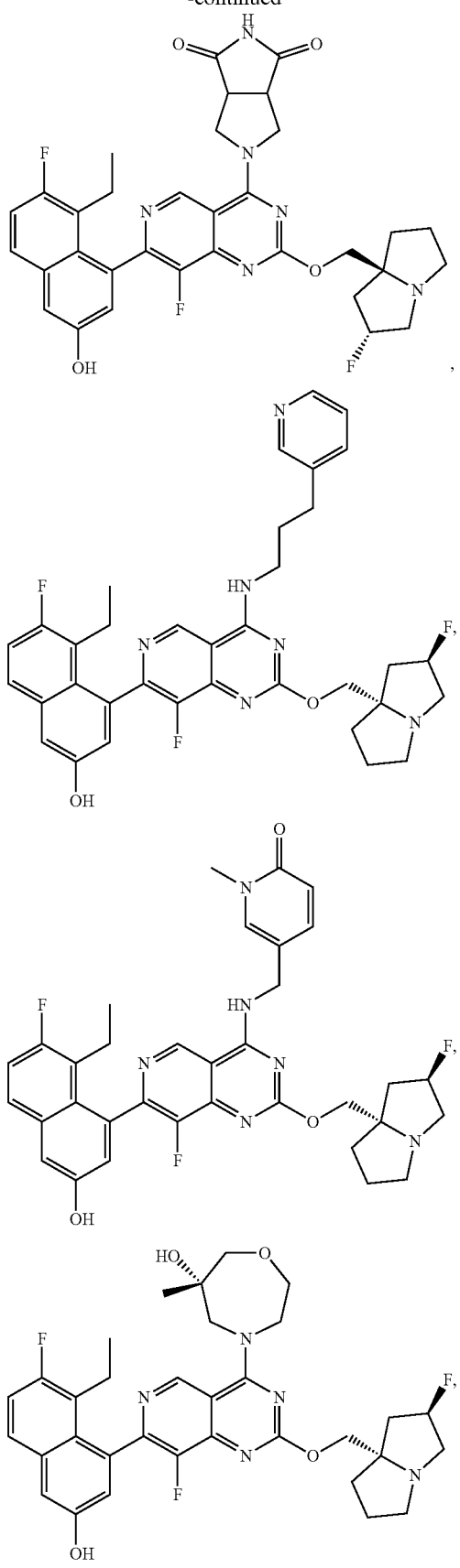
794
-continued
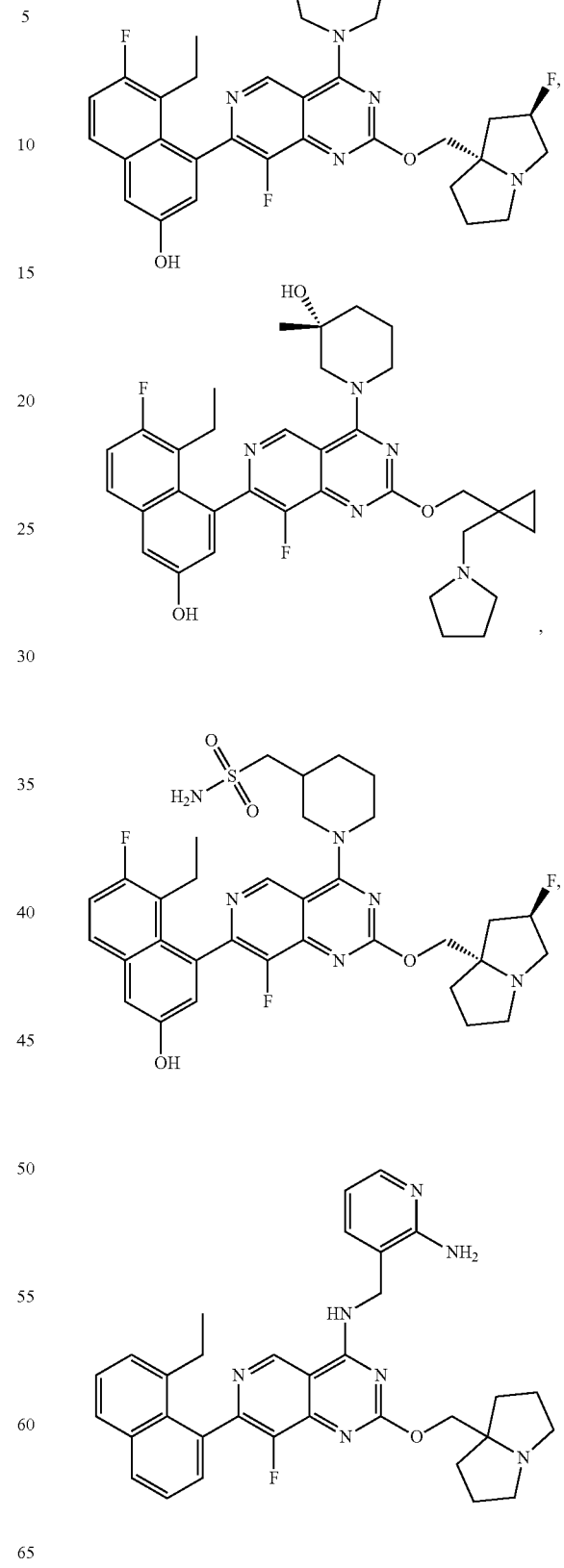

795
-continued
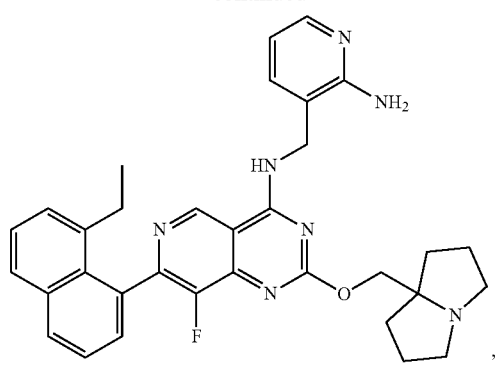
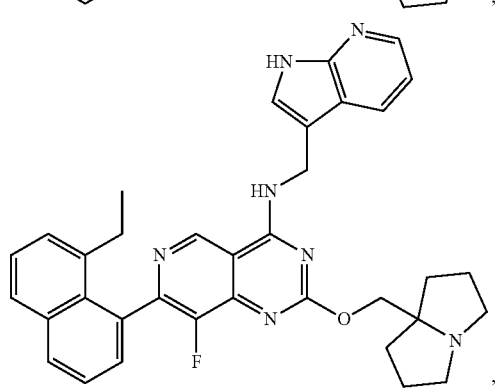
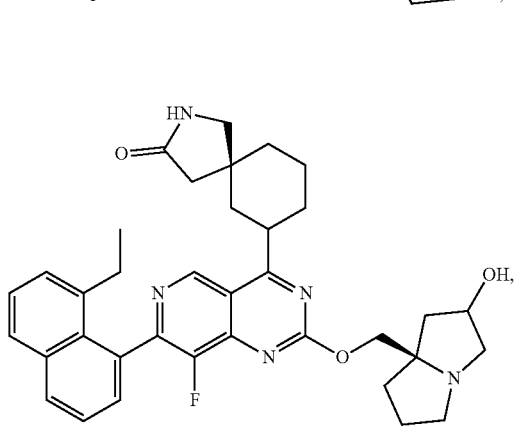
796
-continued
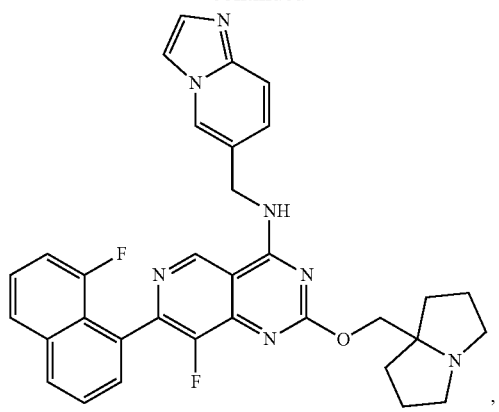
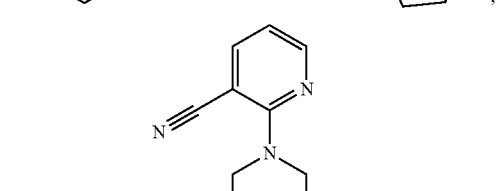
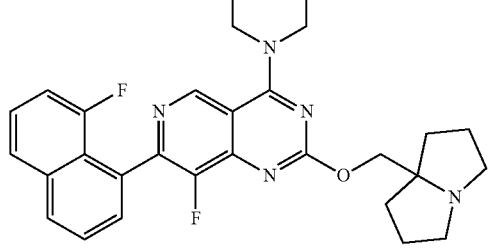
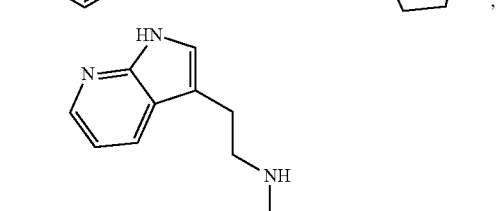
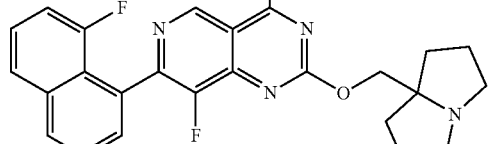
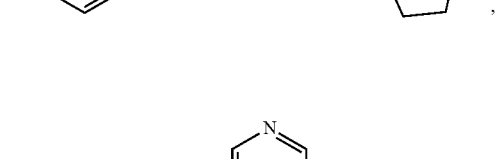
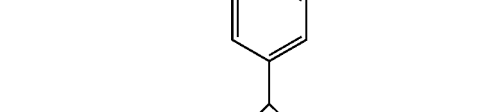

797
-continued
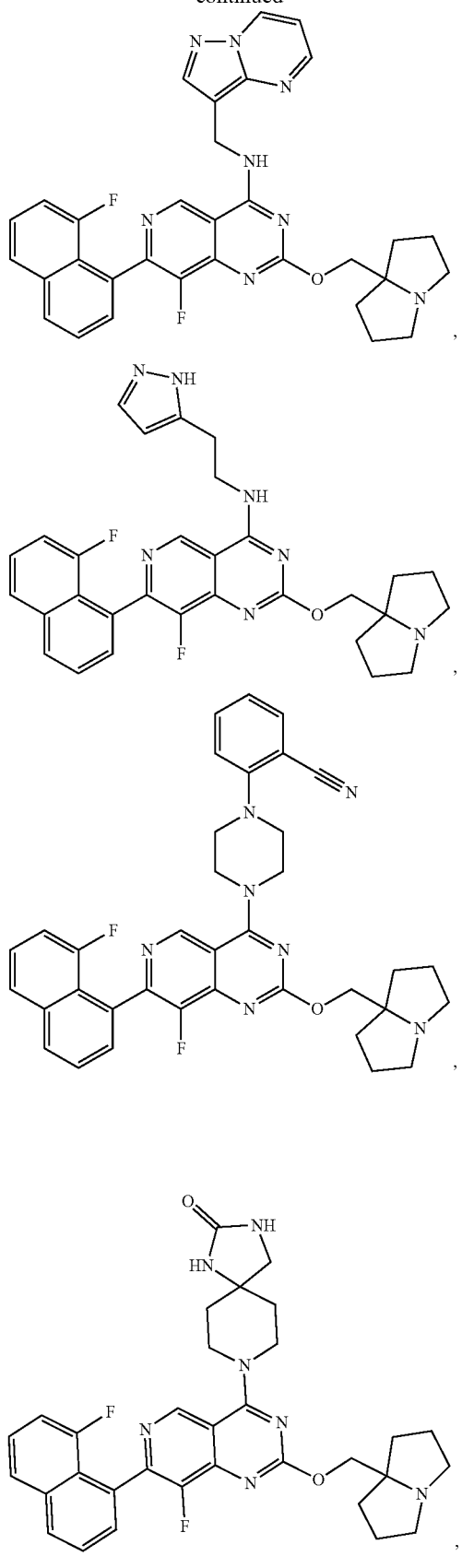
798
-continued
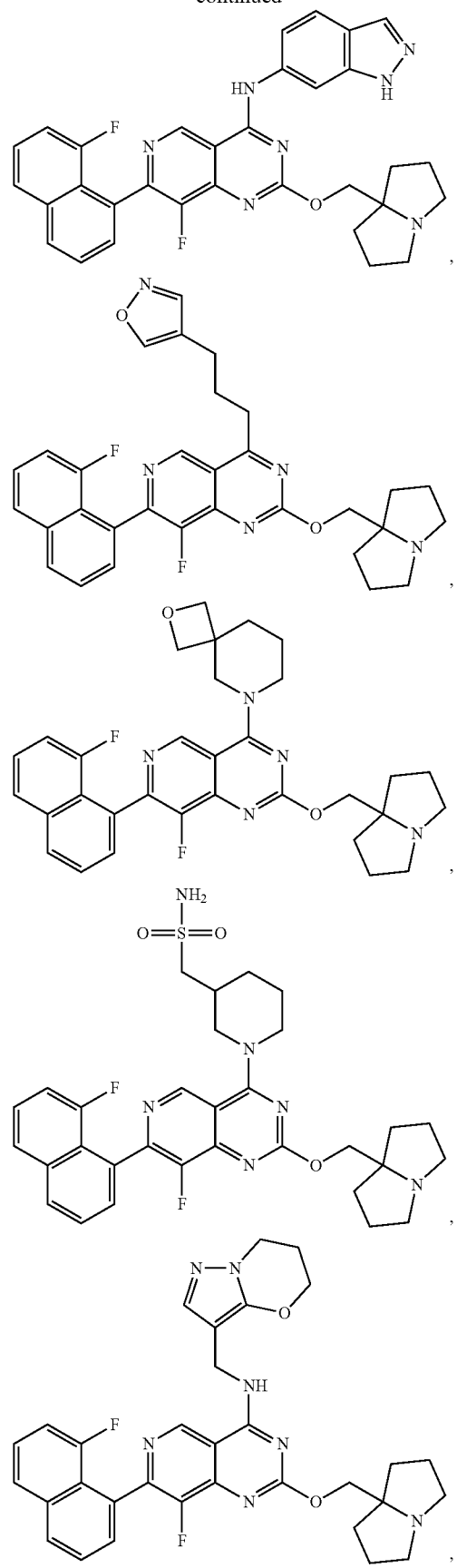

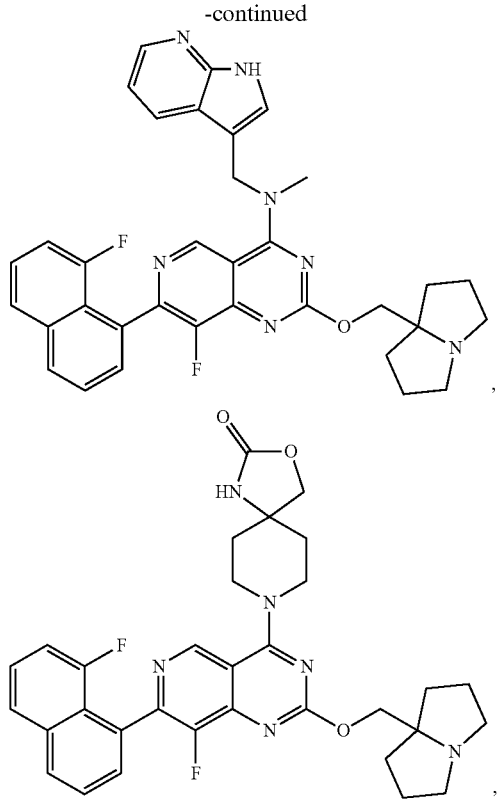
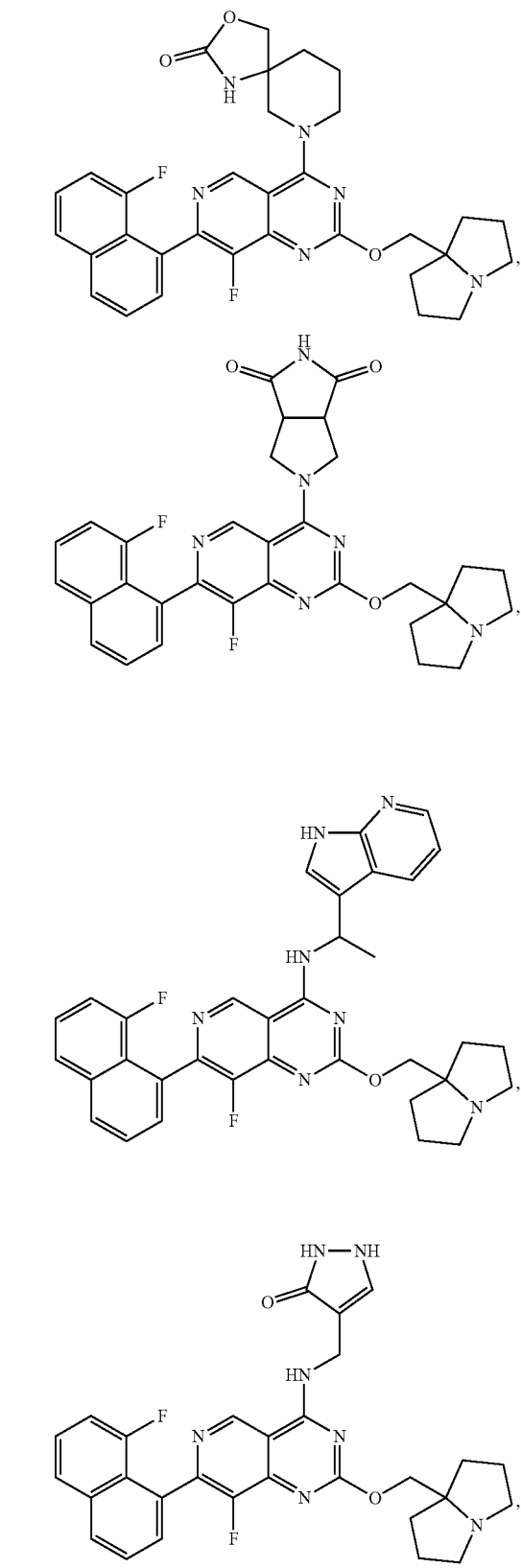

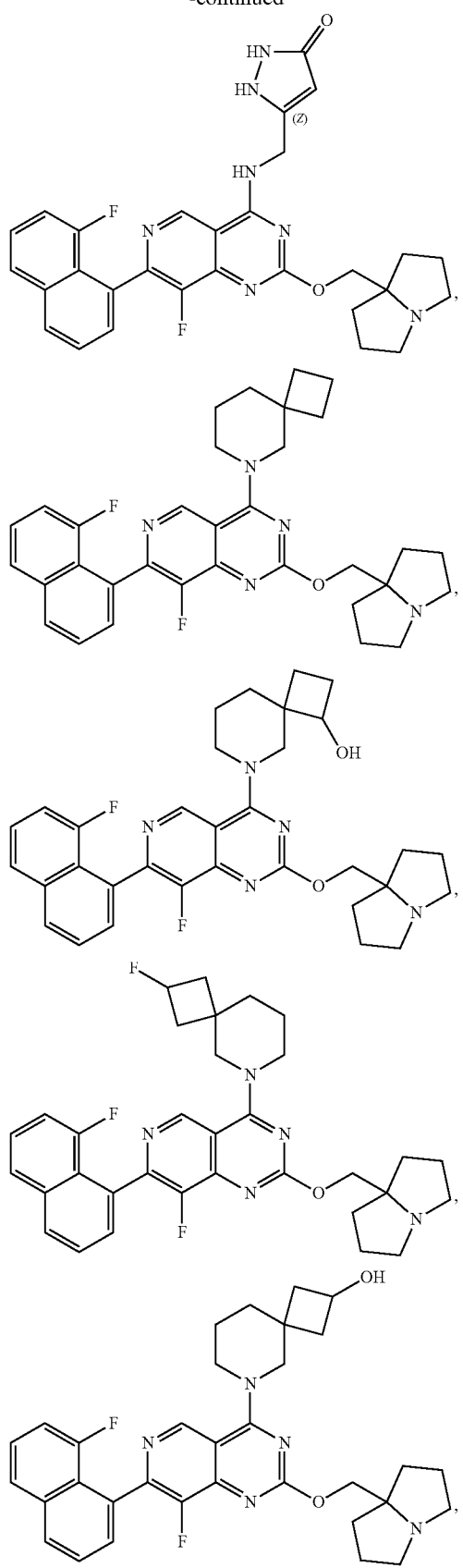
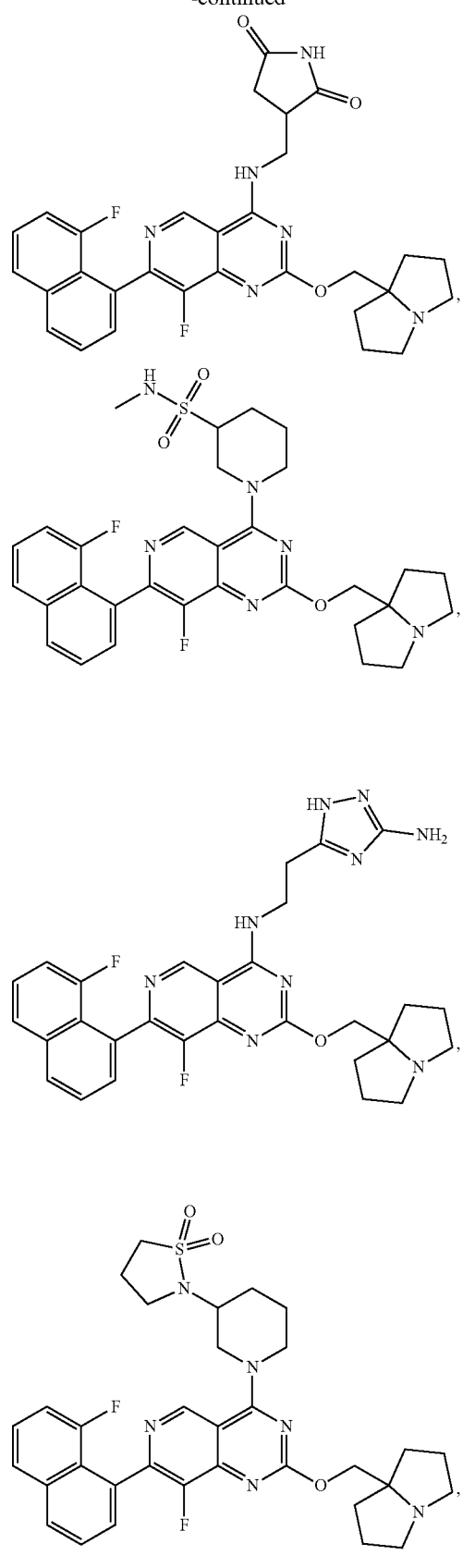

803
-continued
804
-continued
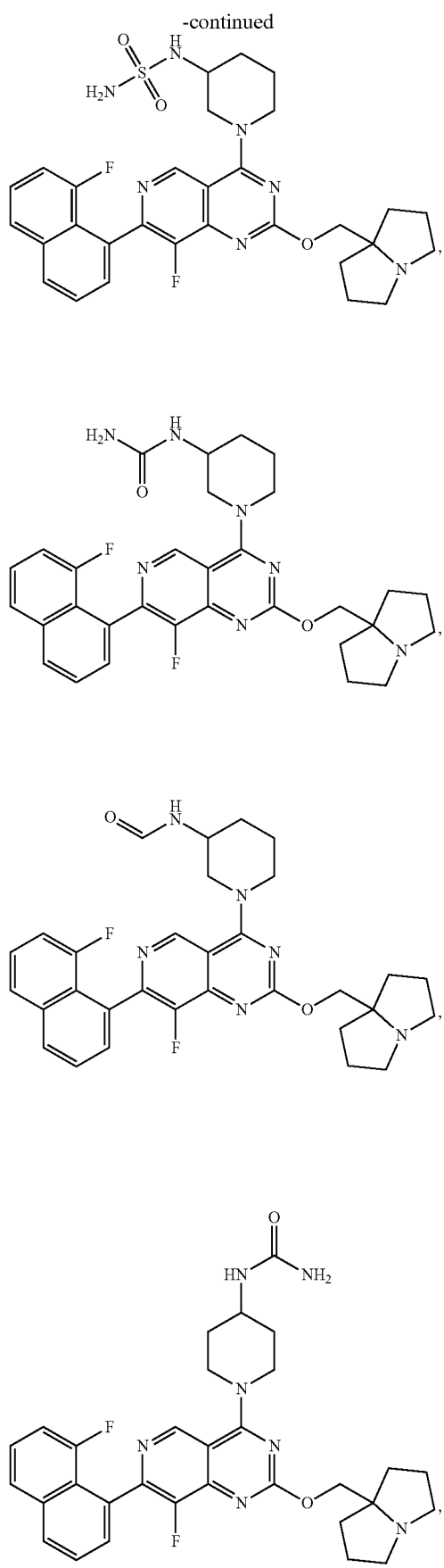
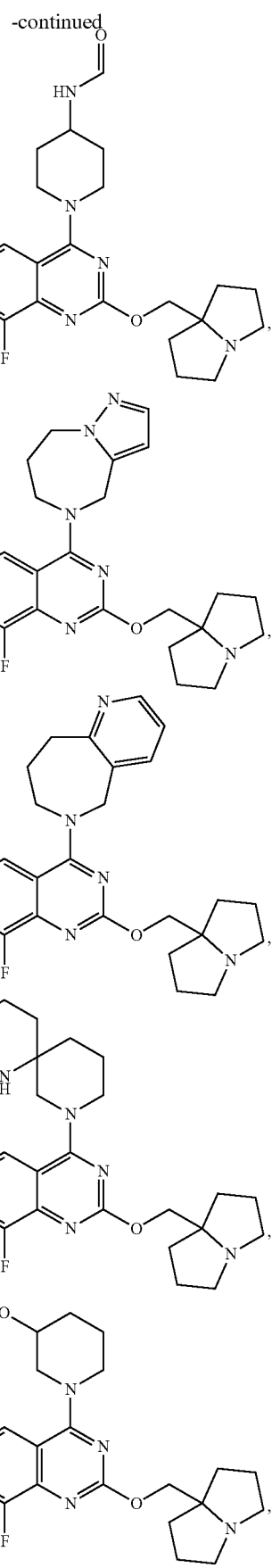

805
-continued
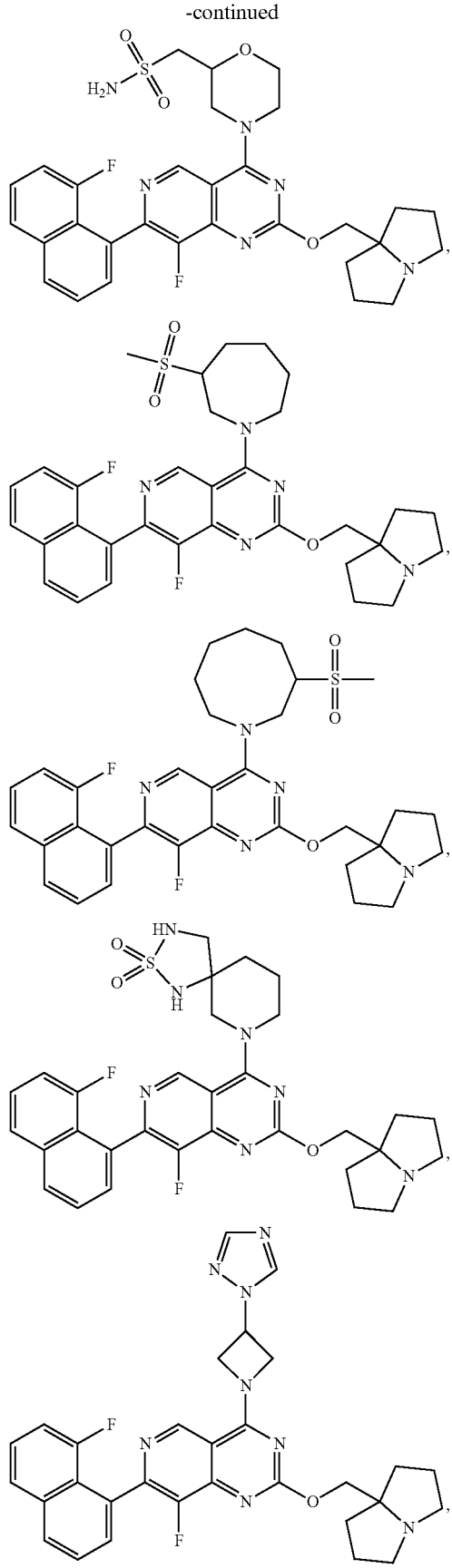
806
-continued
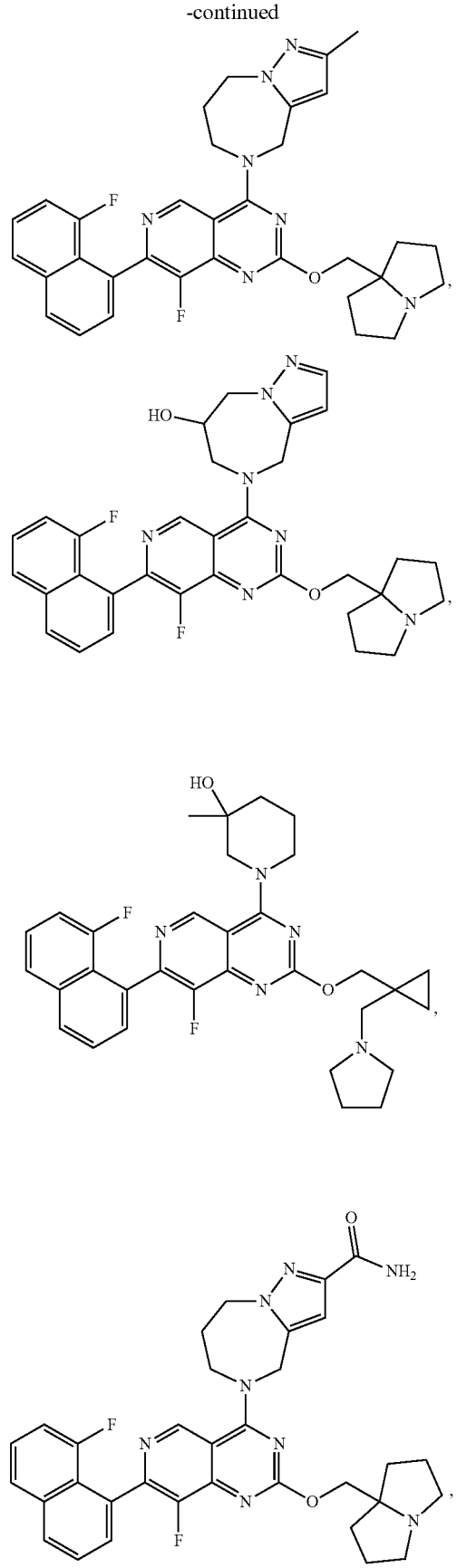

807
-continued
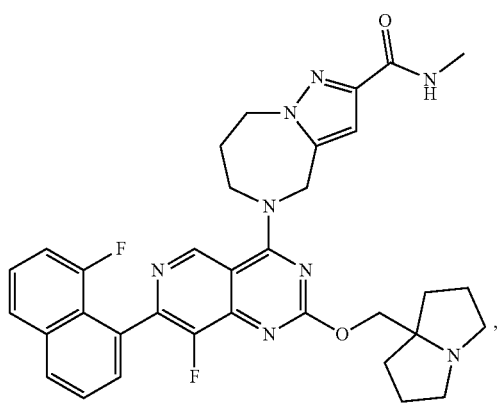
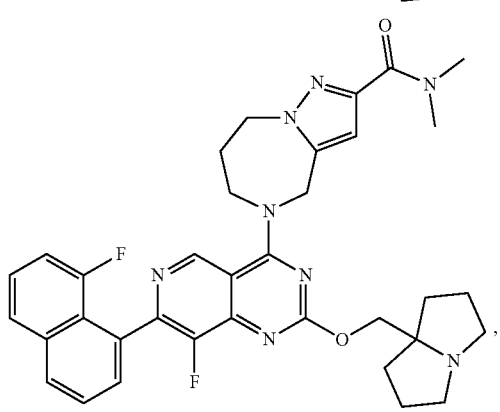
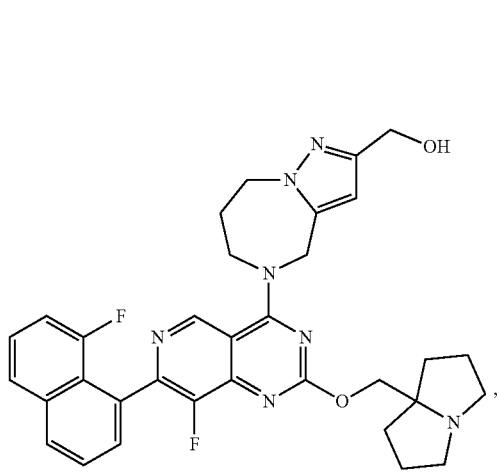
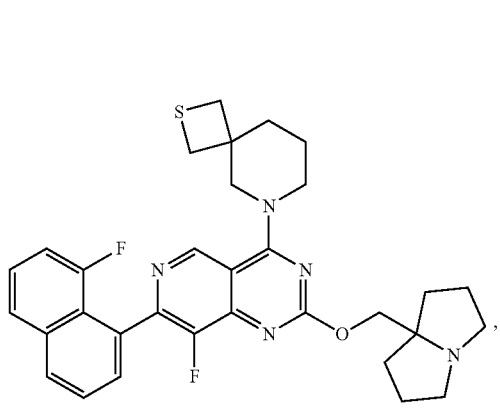
808
-continued
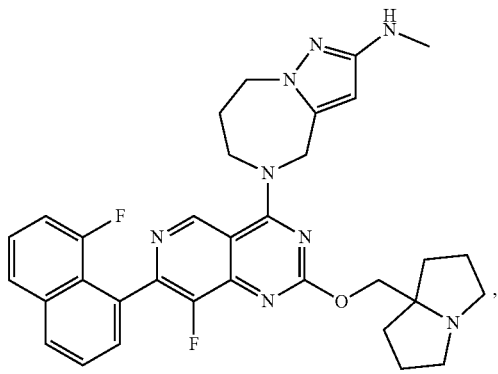
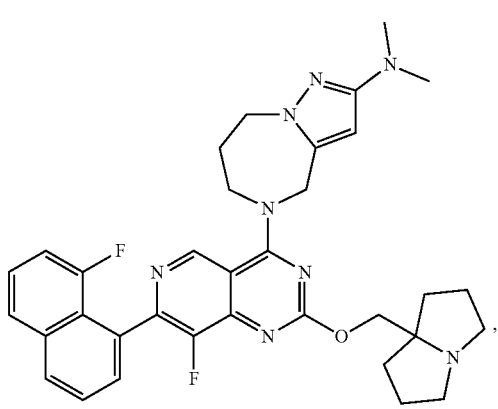
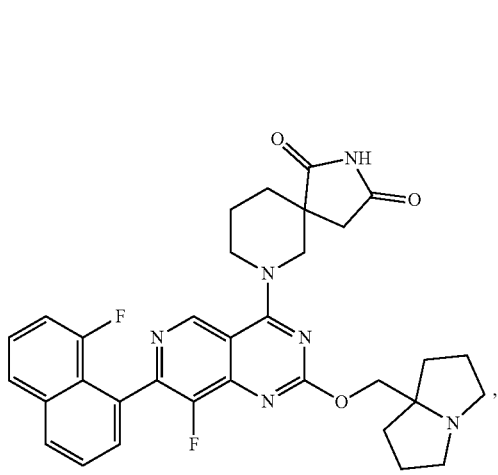
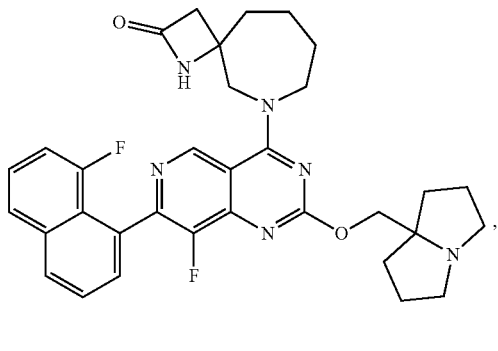

809
-continued
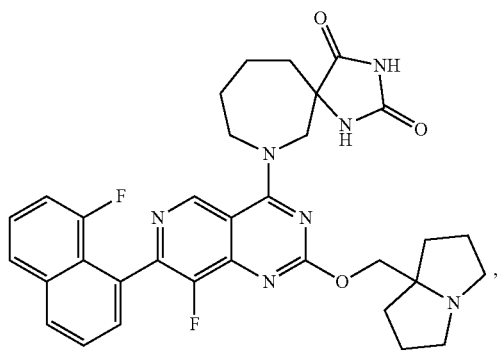
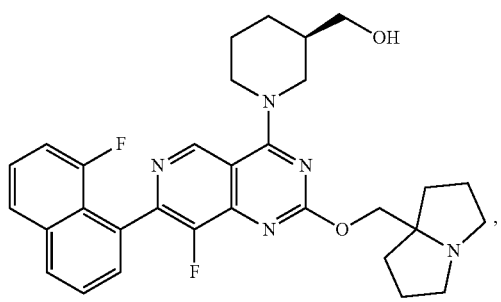
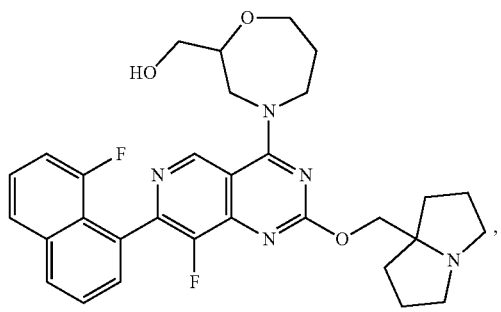
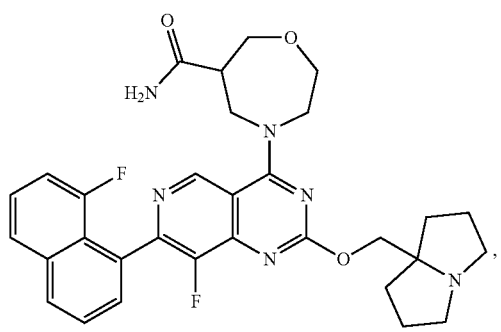
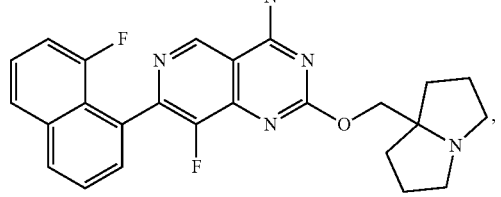
810
-continued
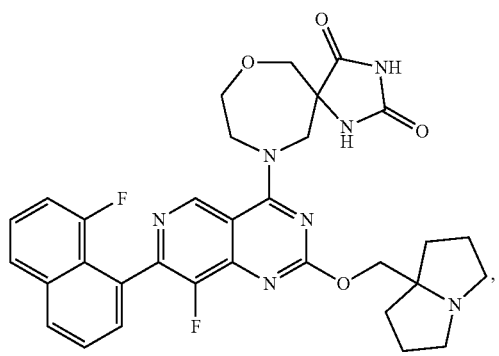
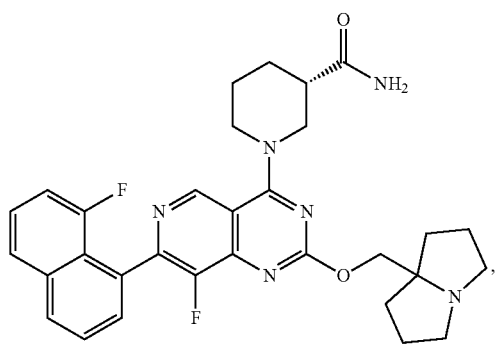
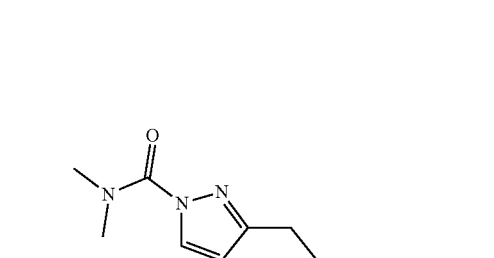
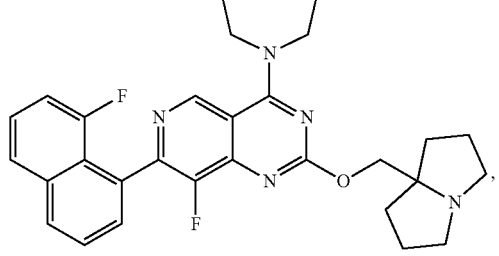
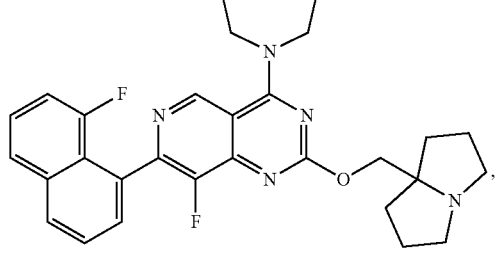

811
-continued
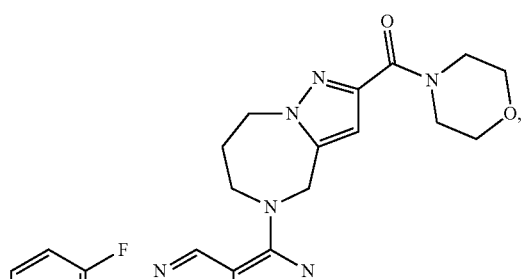
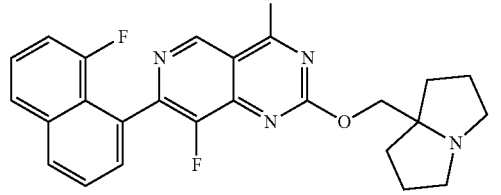
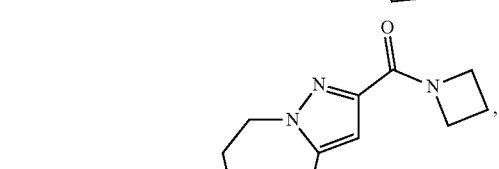
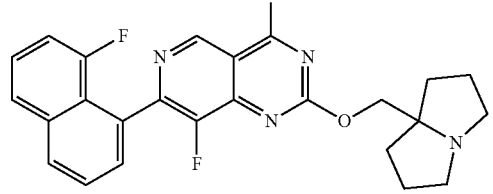
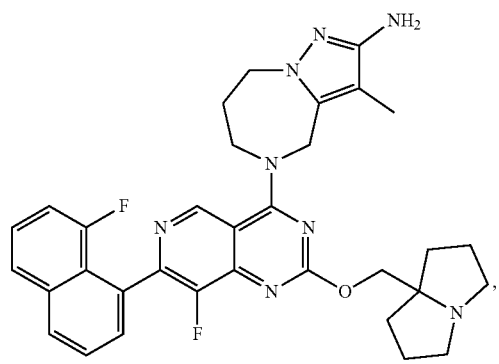
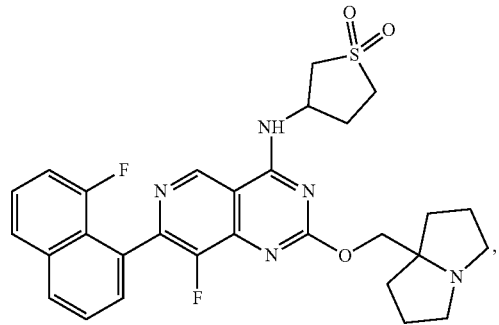
812
-continued
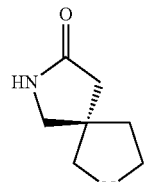
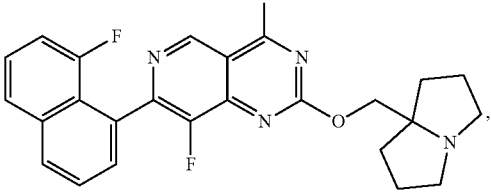
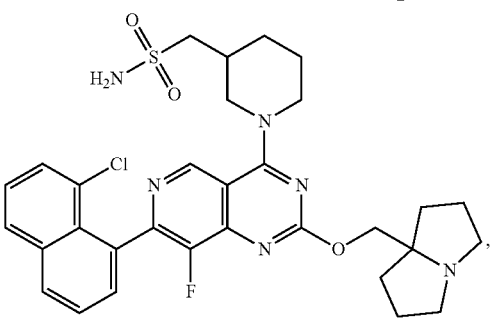
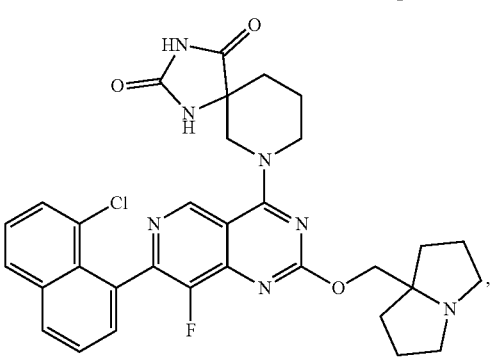
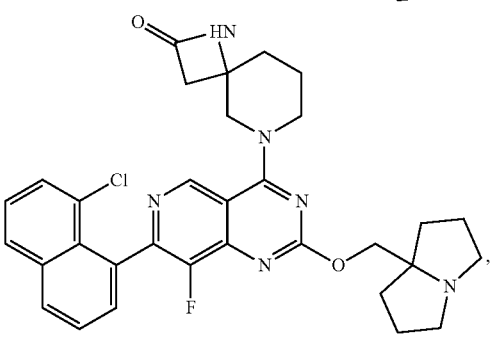
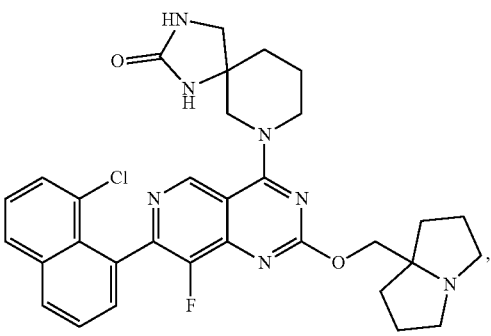

813
-continued
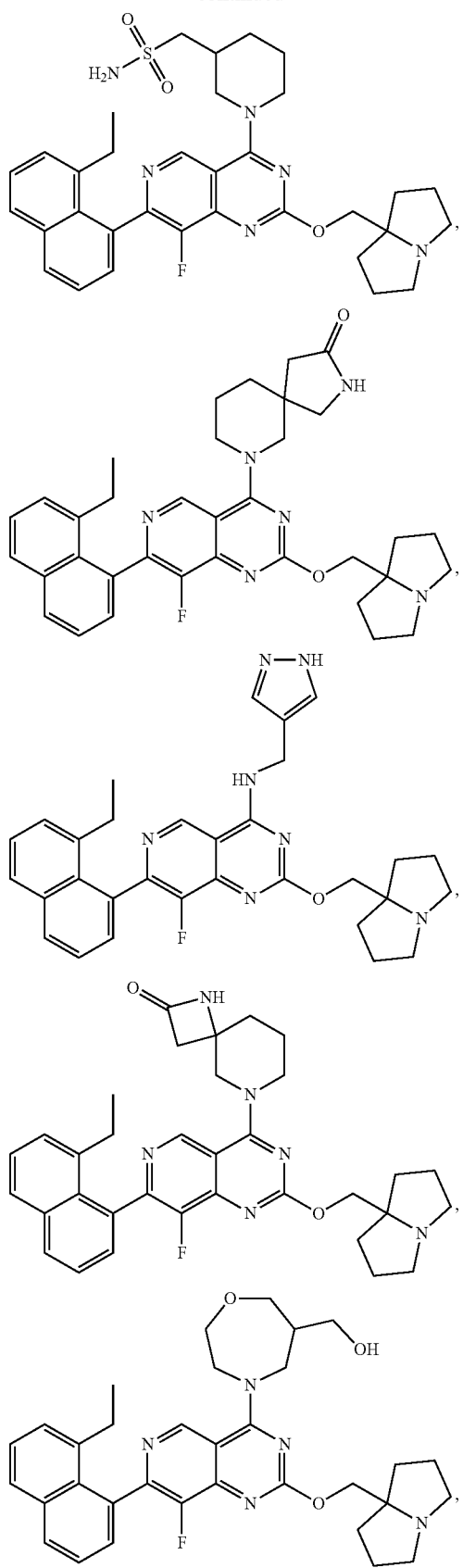
814
-continued
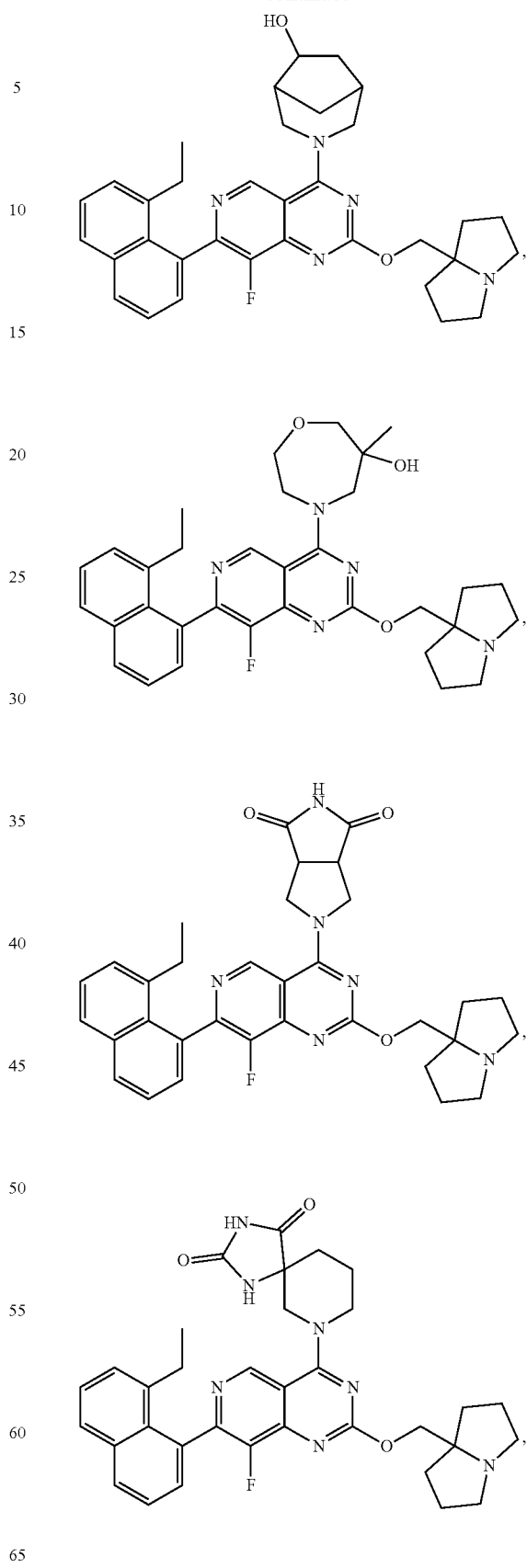

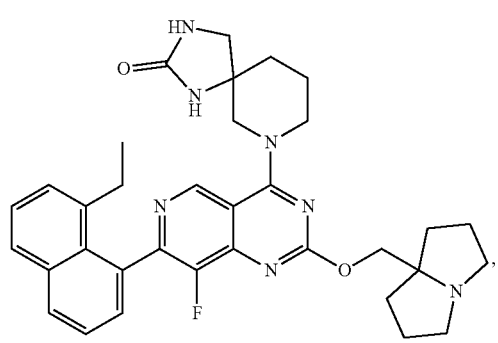
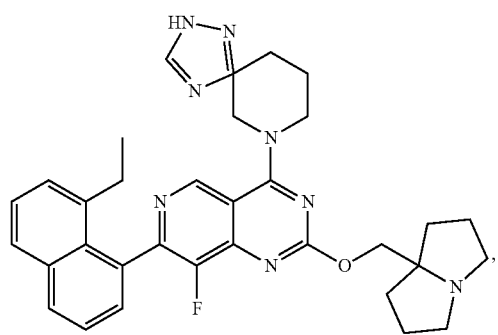
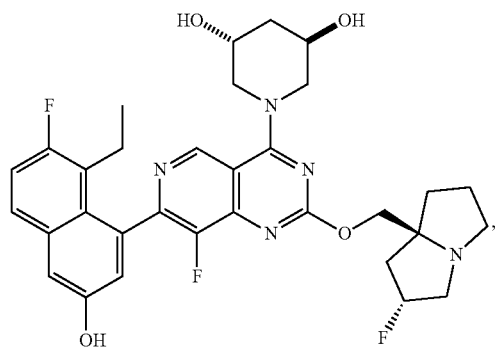
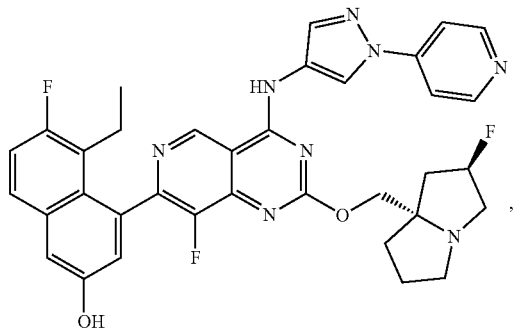
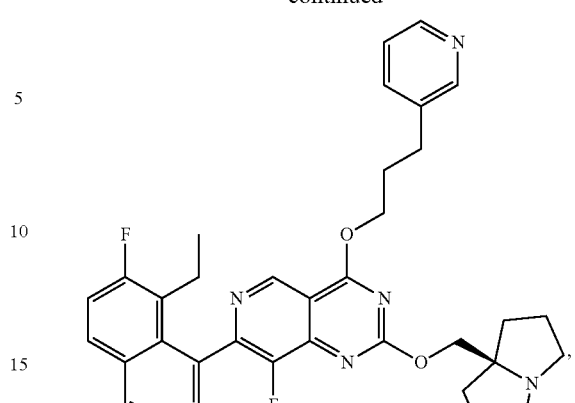
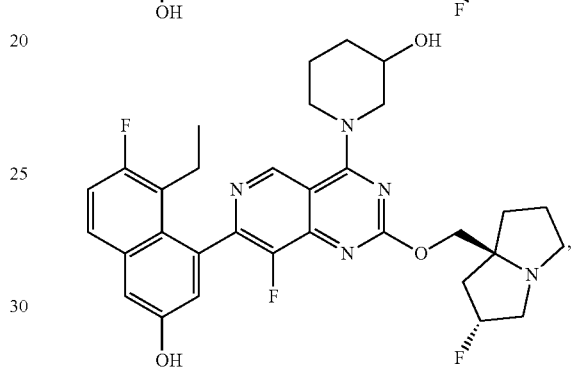

817
-continued
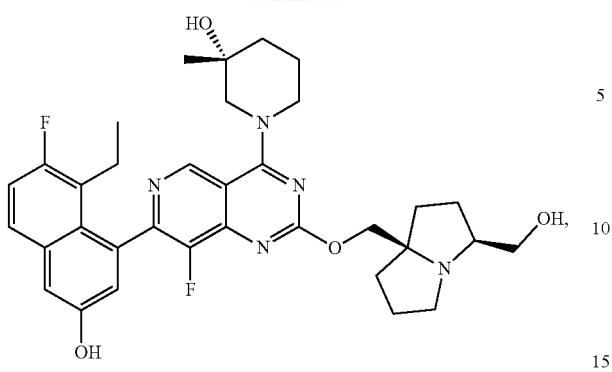
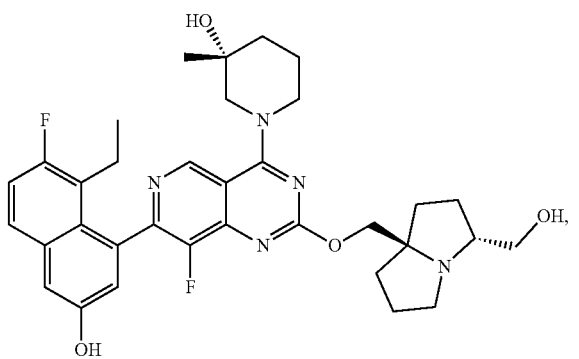
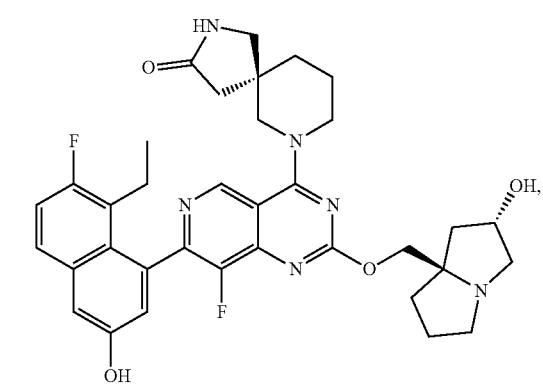
818
-continued
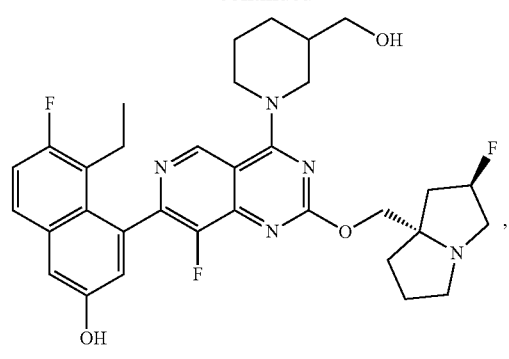
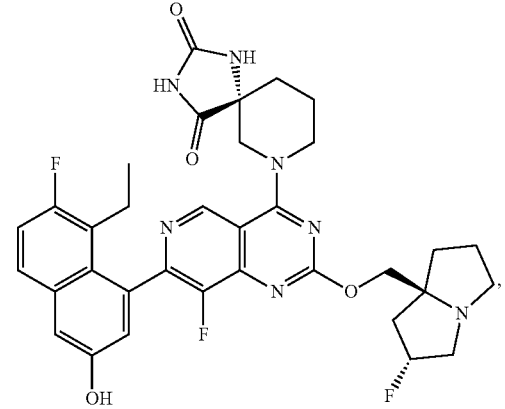
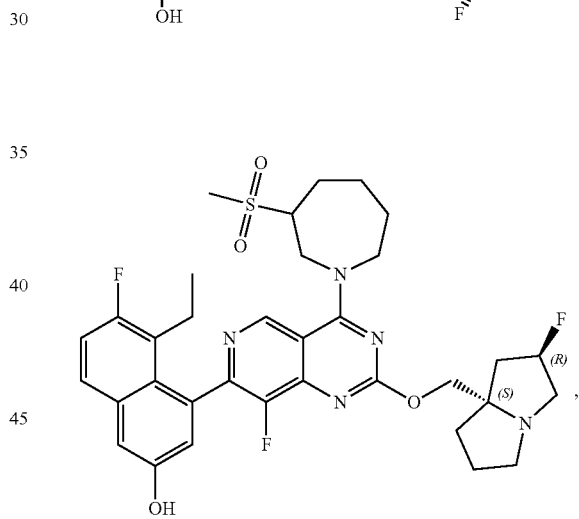
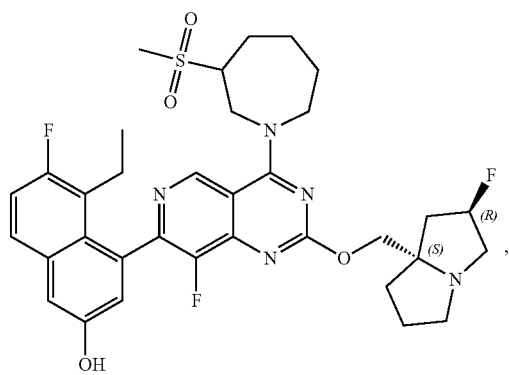
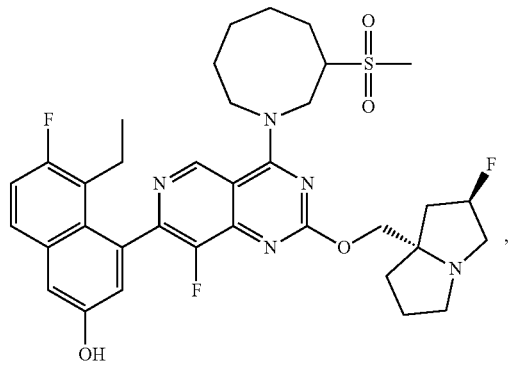

819
-continued
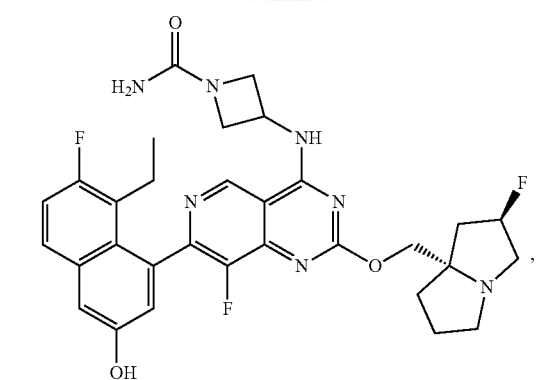
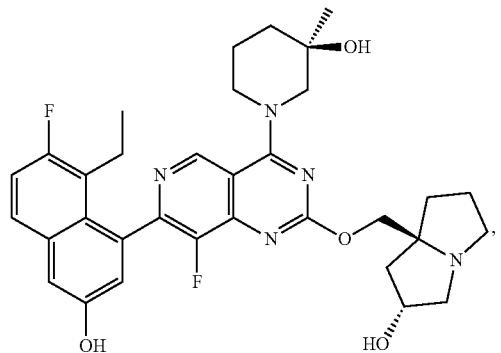
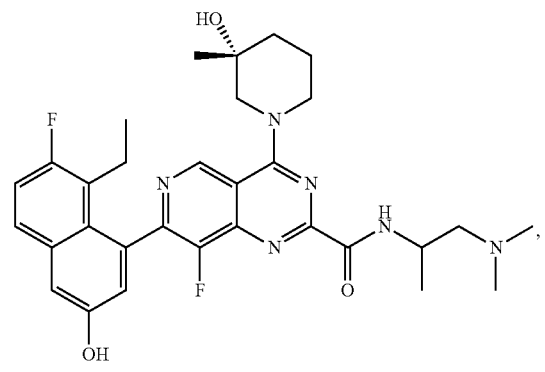
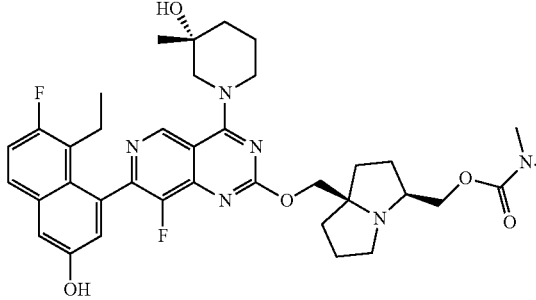
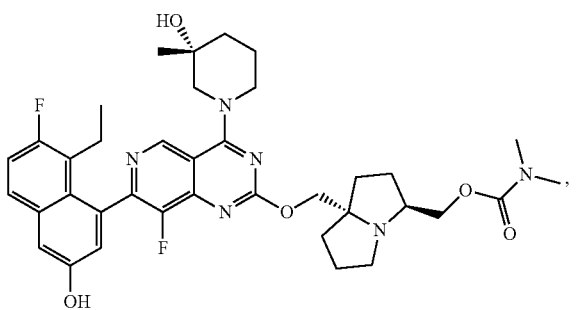
820
-continued
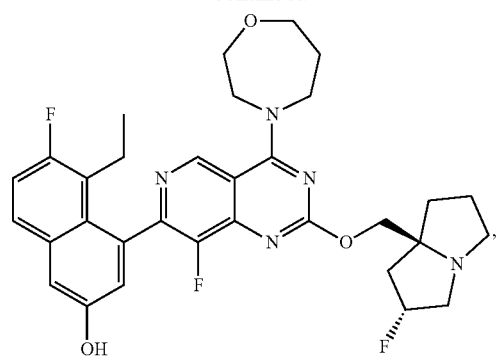
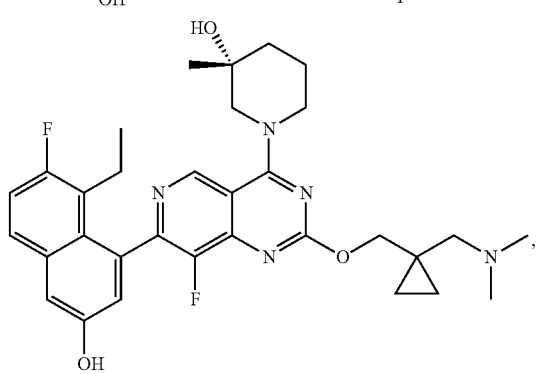
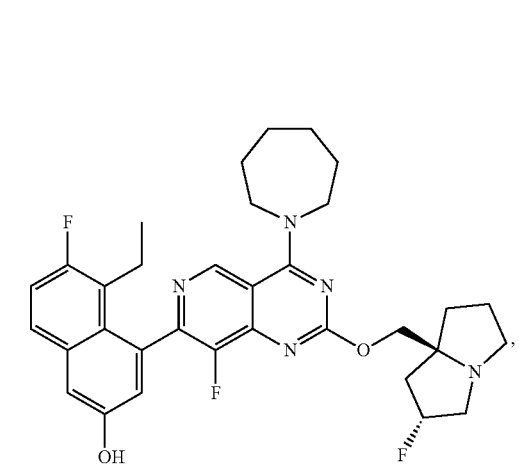
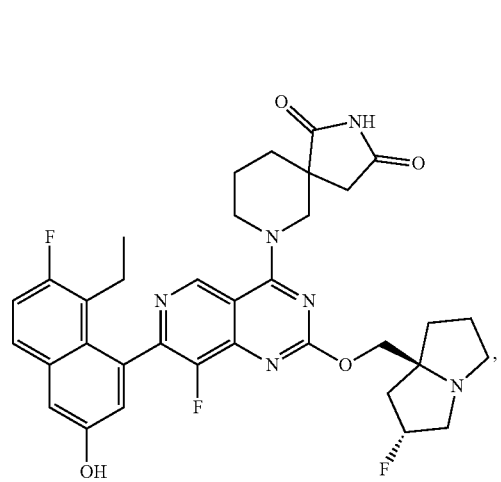

821
-continued
822
-continued
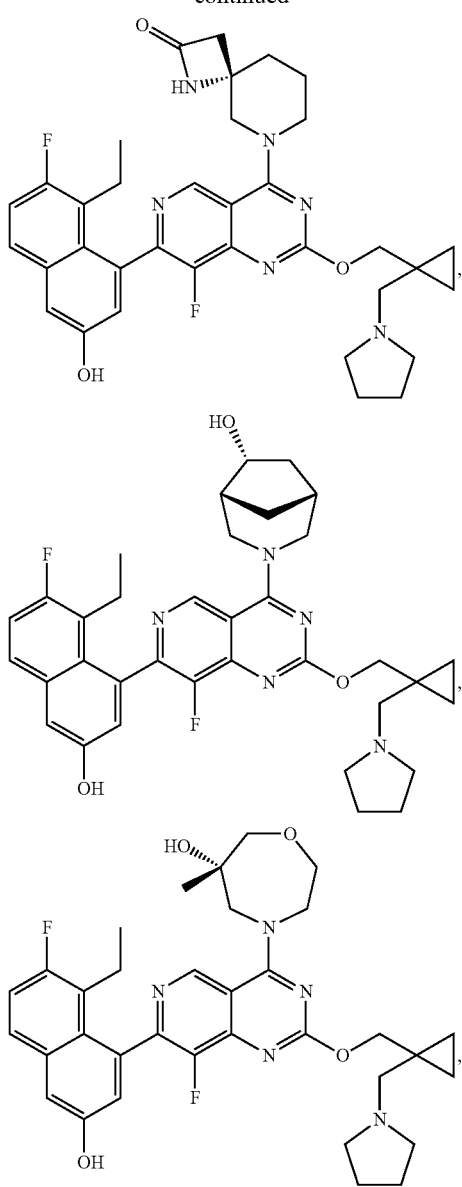
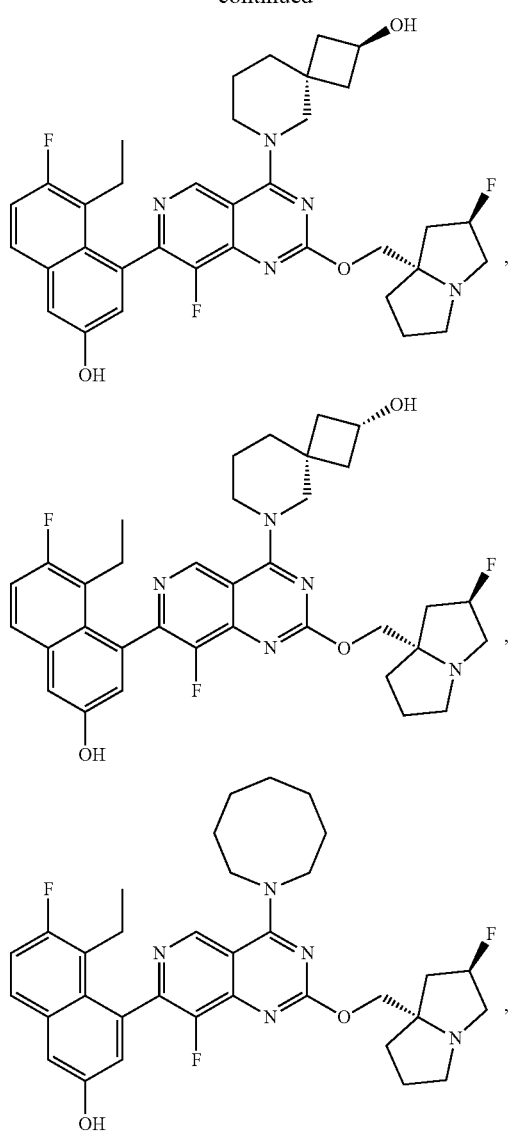
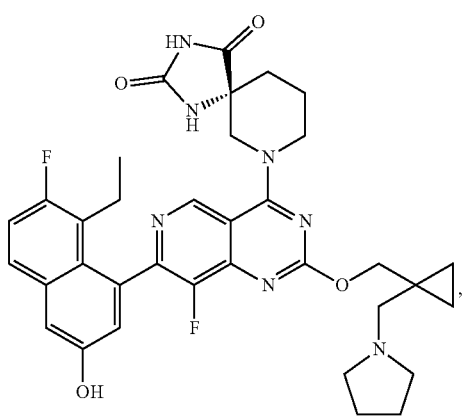

823
-continued
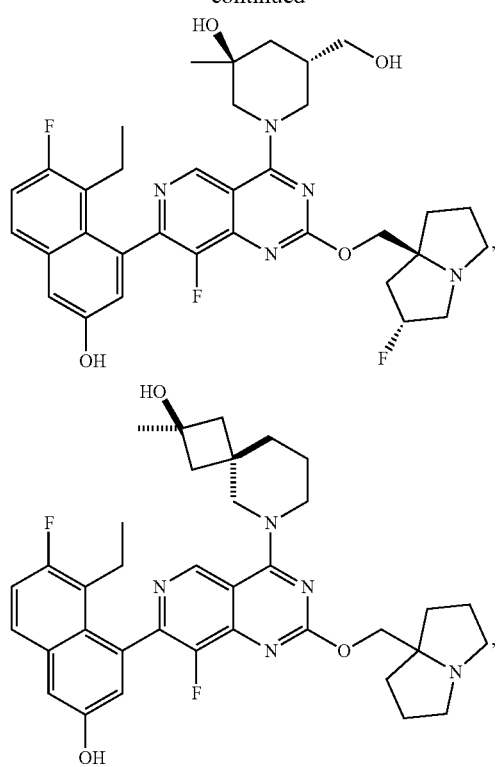
824
-continued
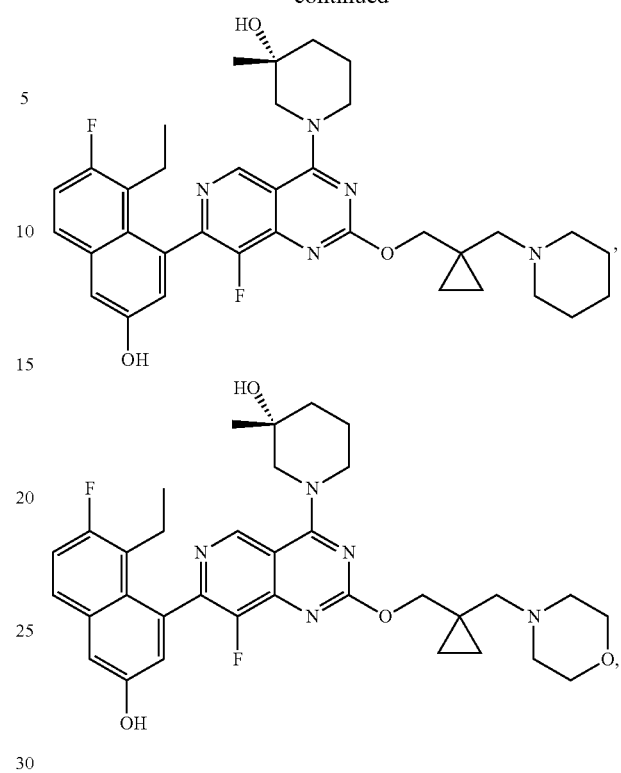

825
-continued
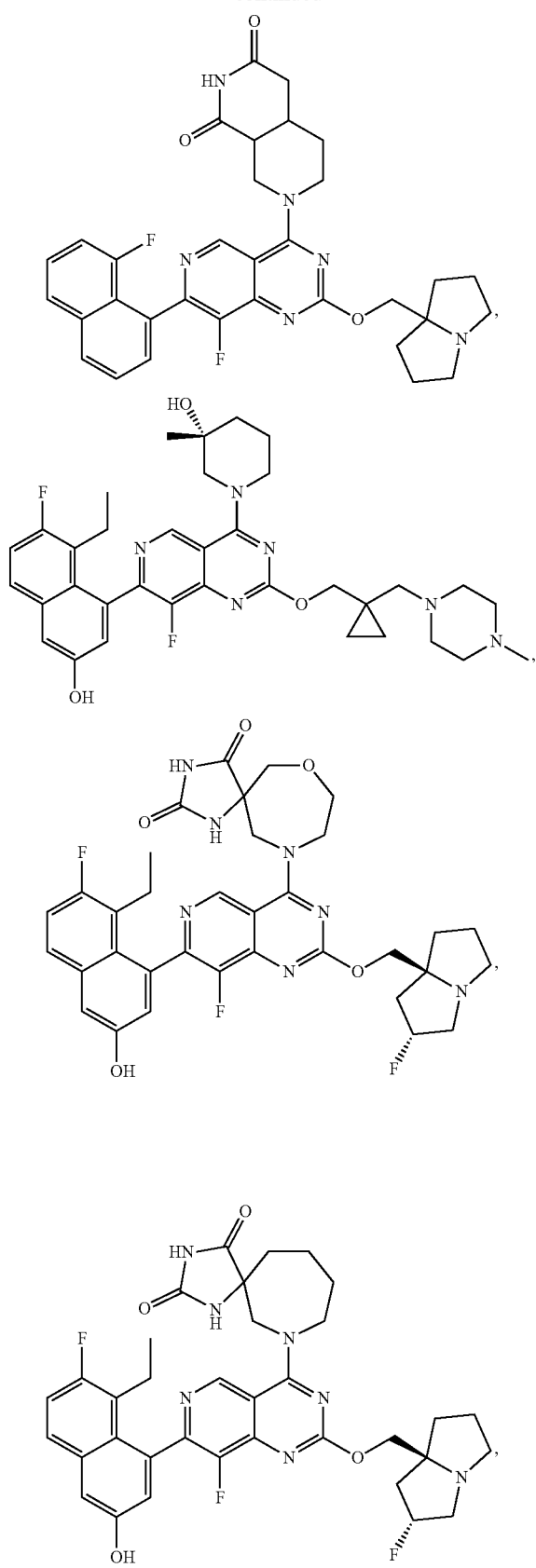
826
-continued
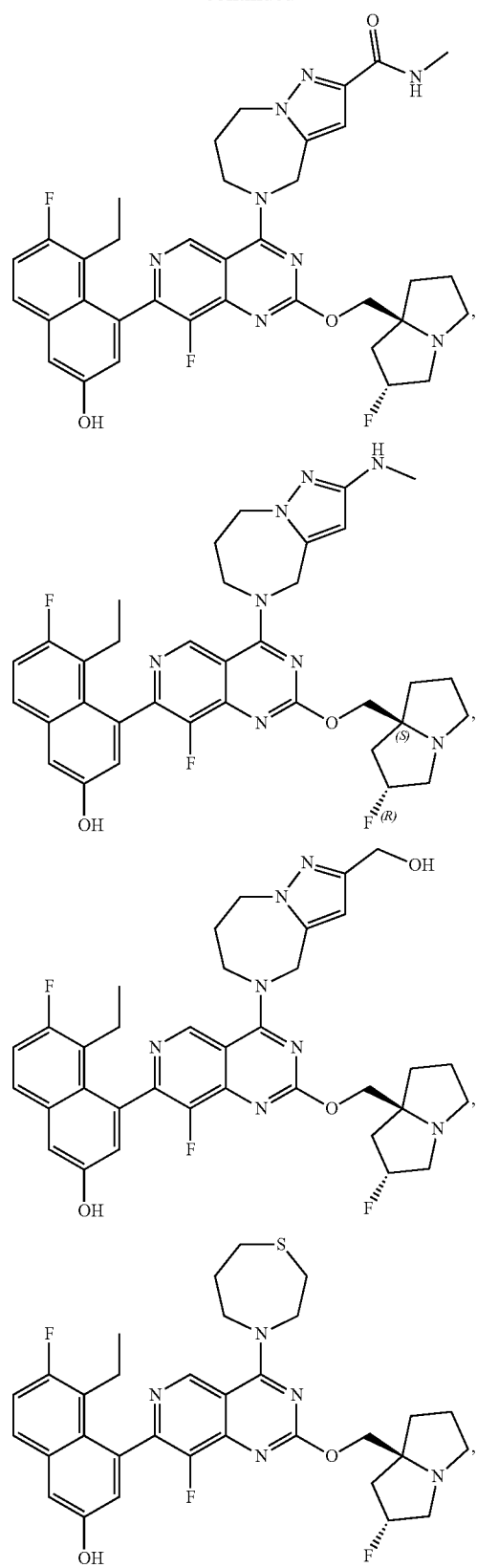

827
-continued
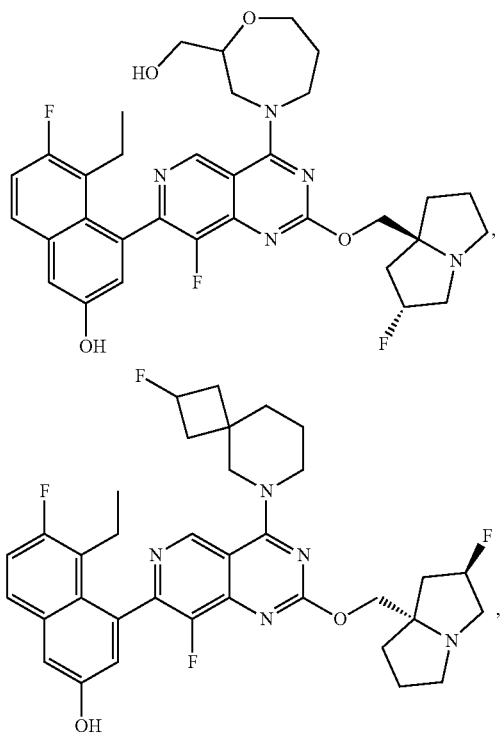
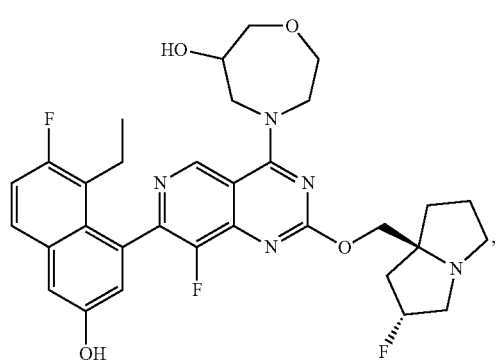
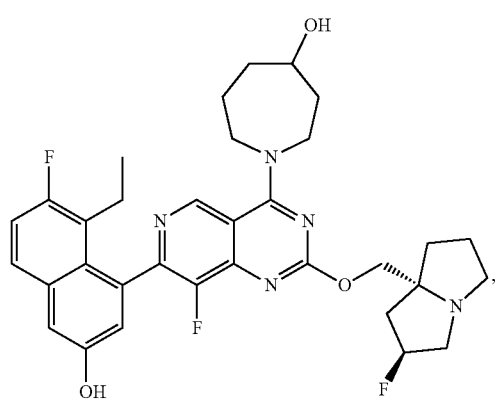
828
-continued
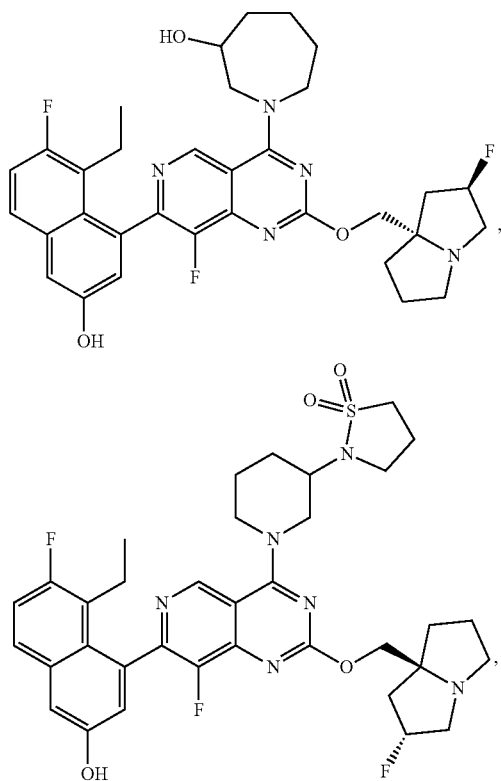
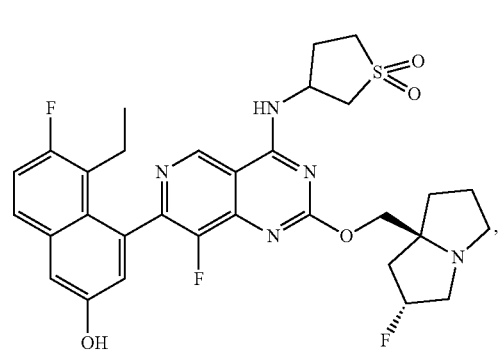
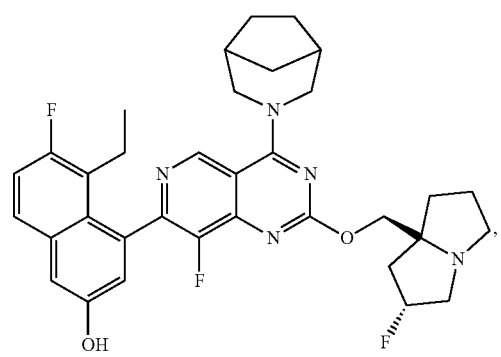

829
-continued
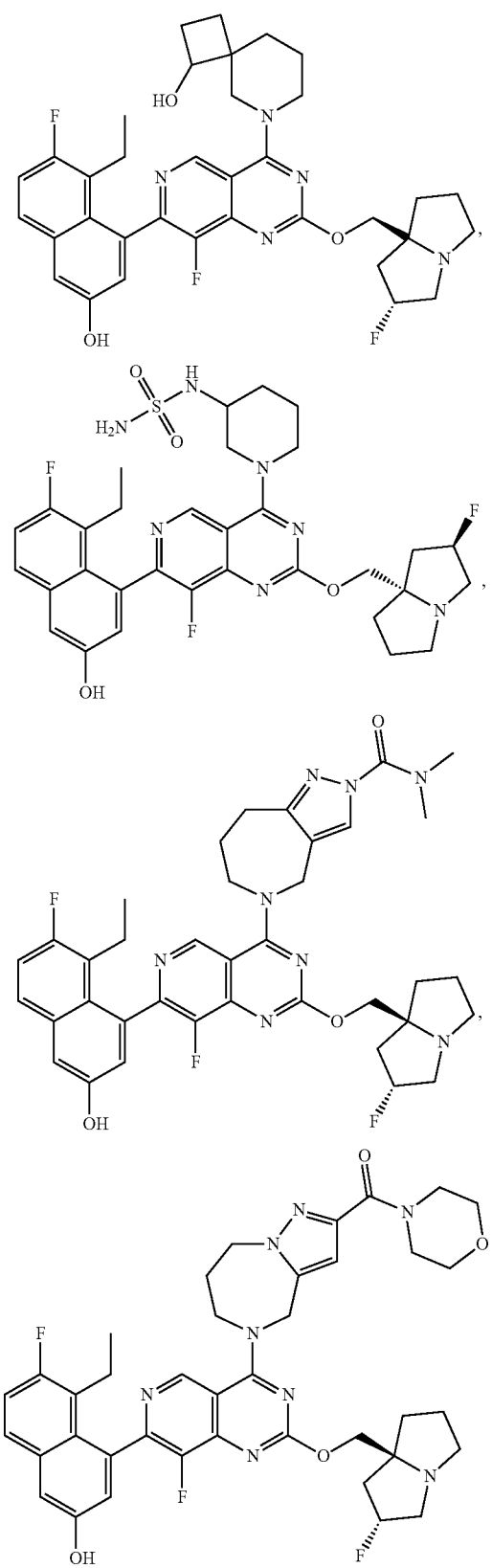
830
-continued
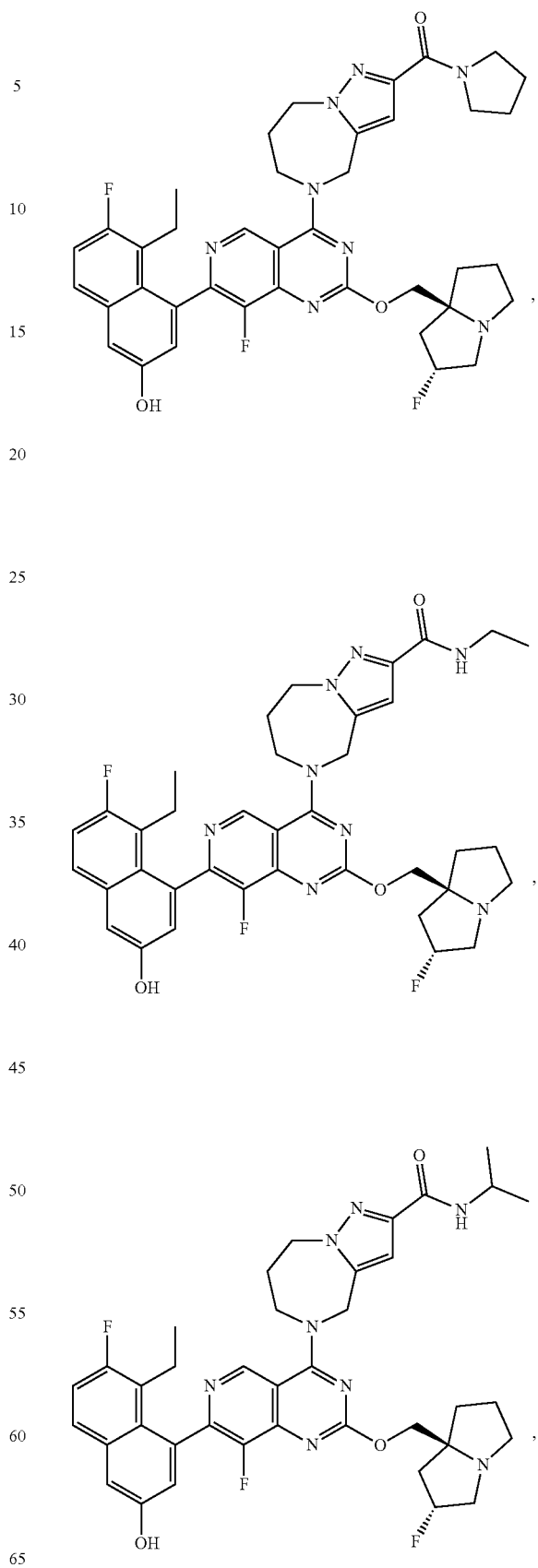

831
-continued
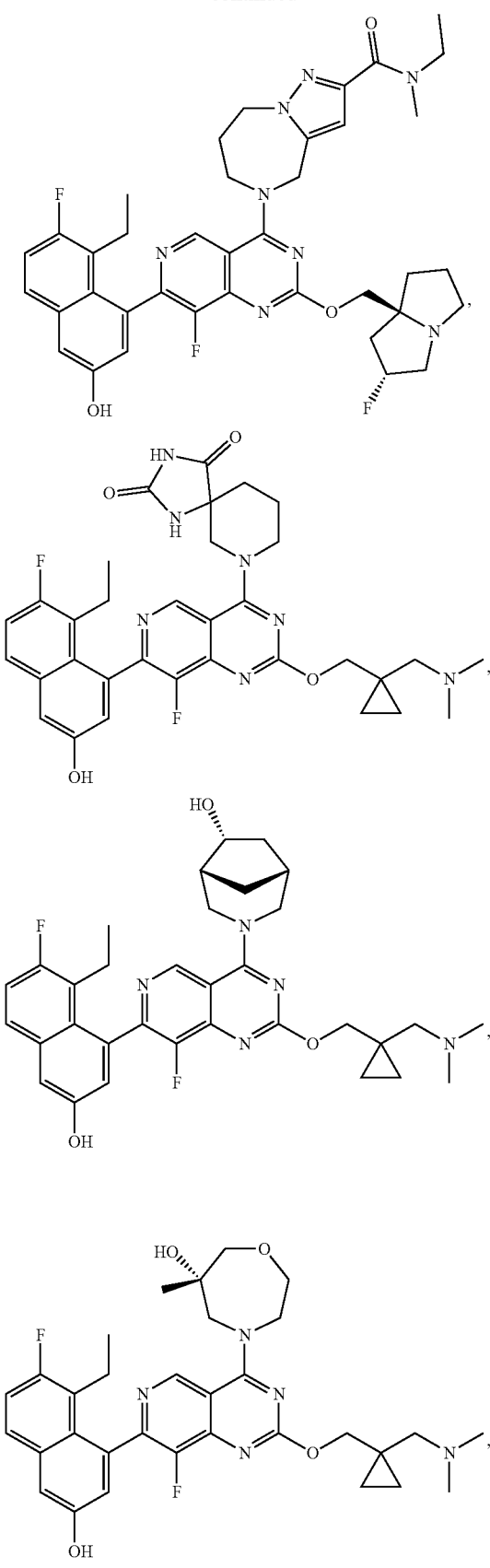
832
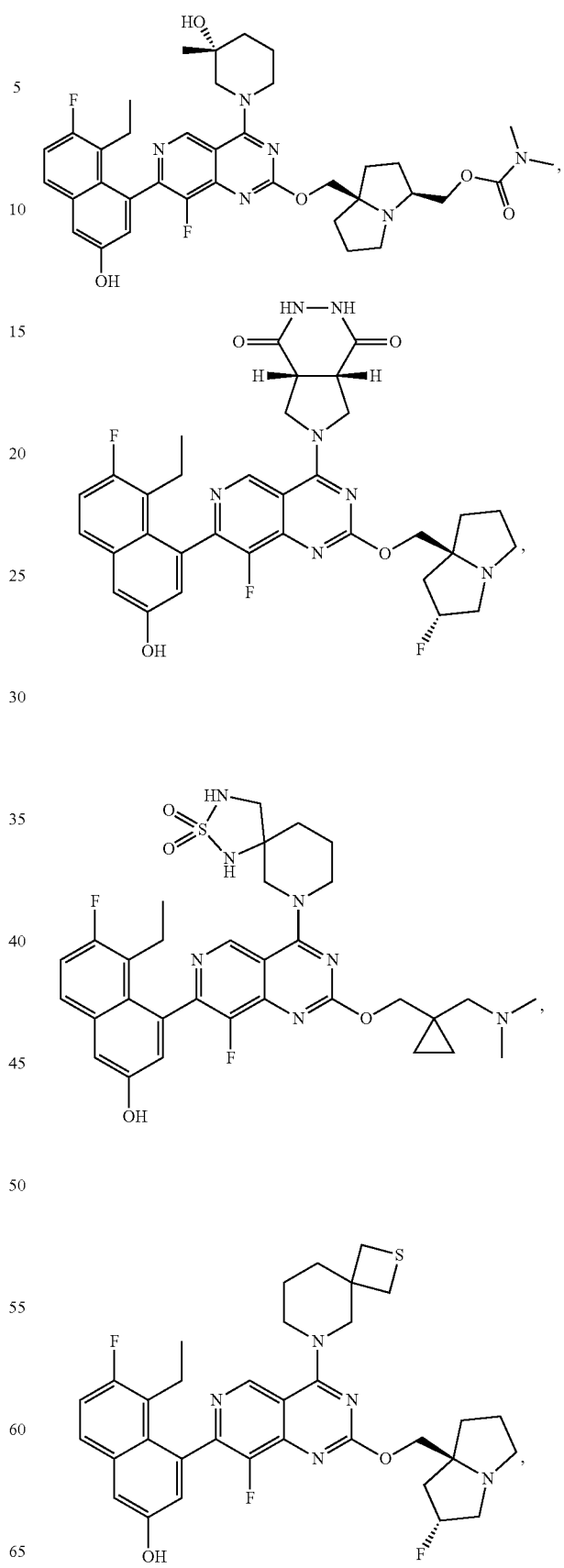

833
-continued
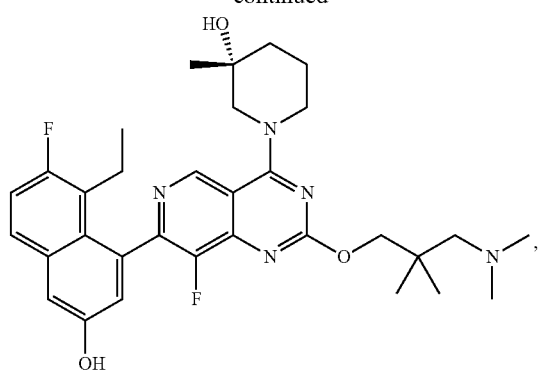
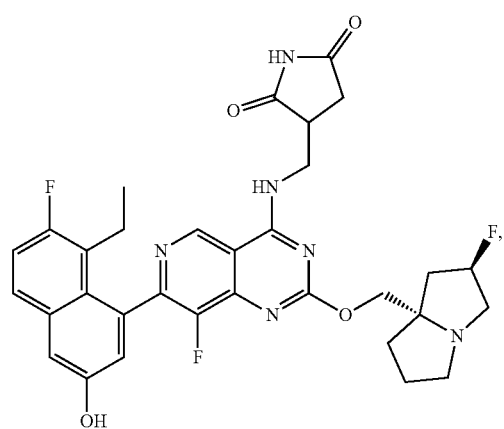
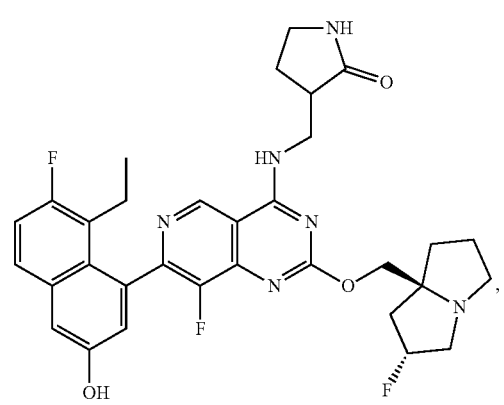
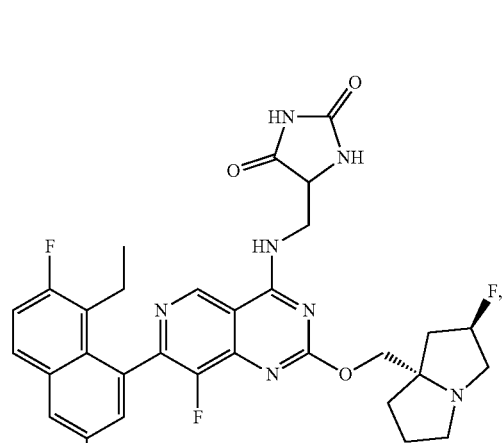
834
-continued
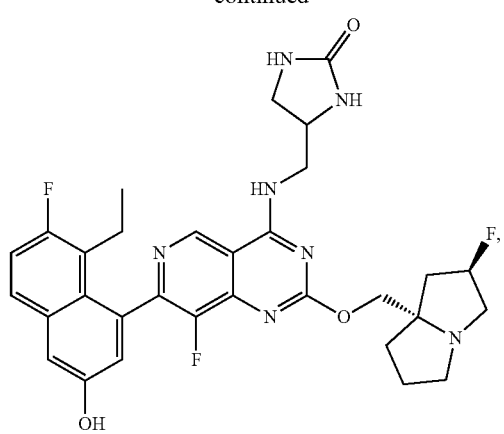
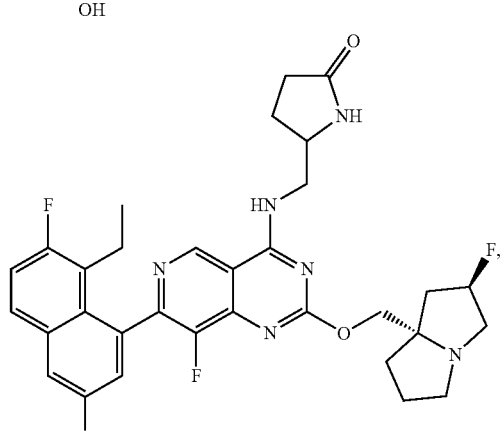
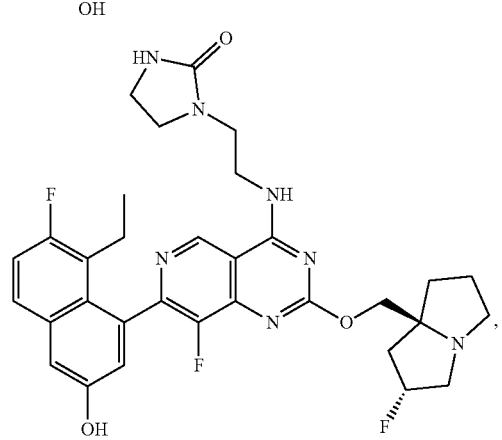
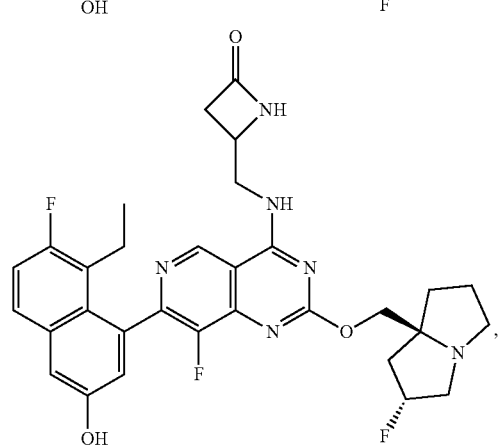

835
-continued
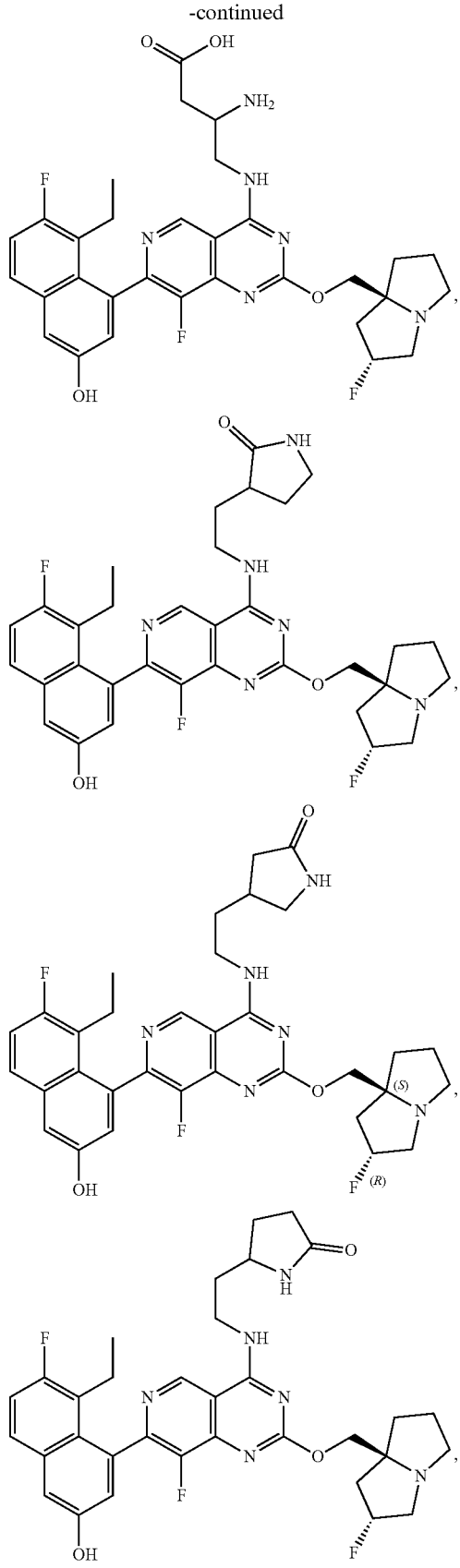
836
-continued
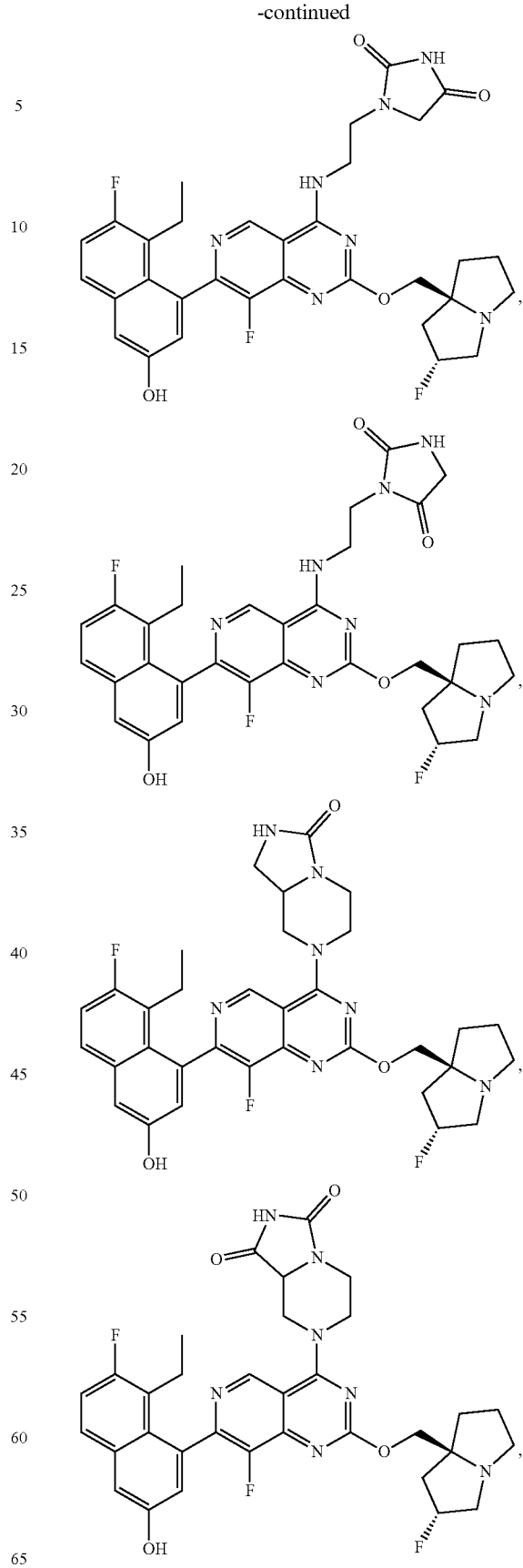

837
-continued
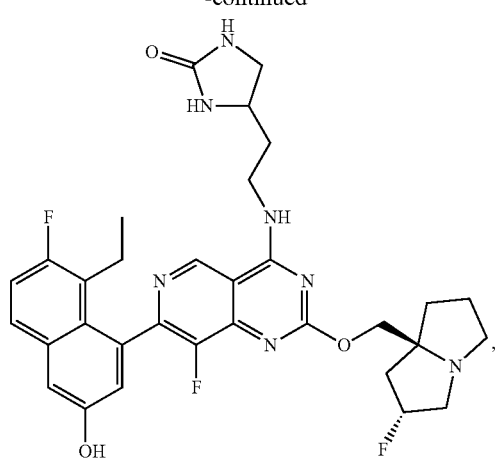
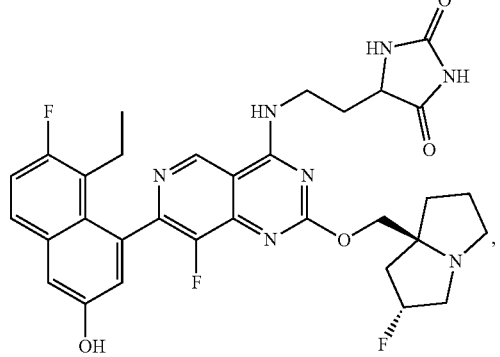
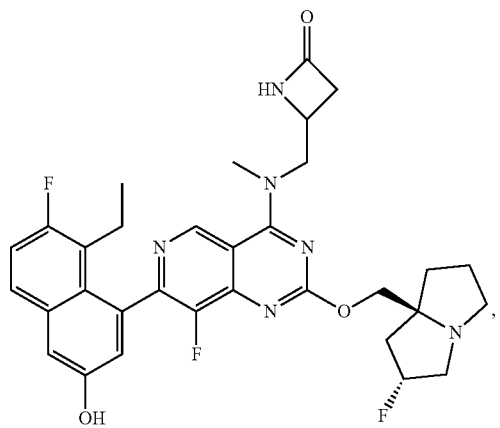
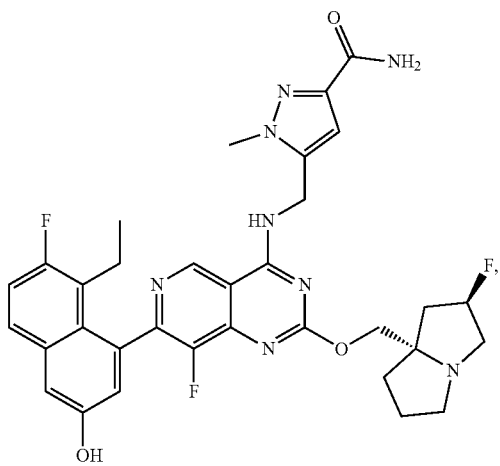
838
-continued
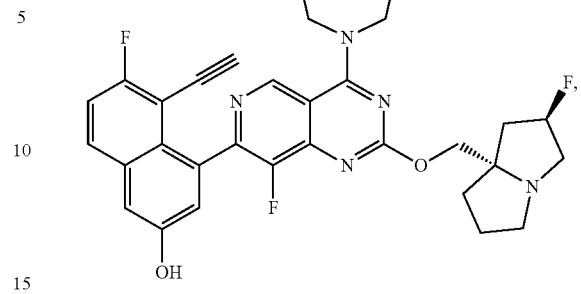
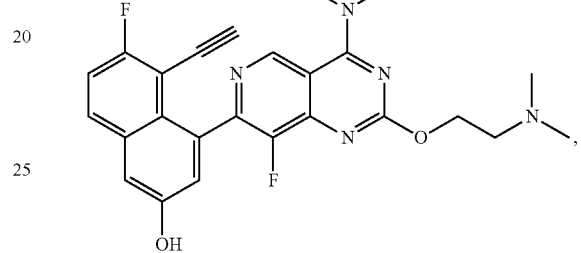
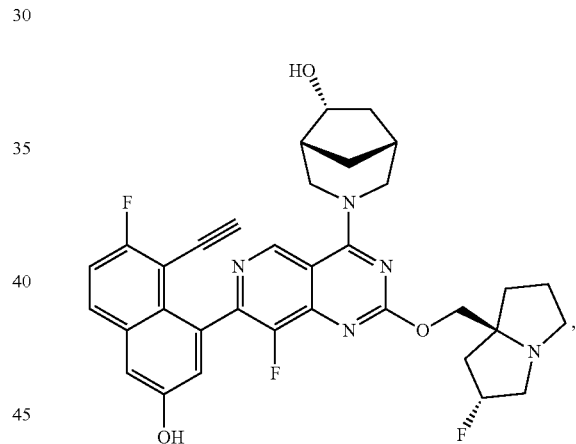
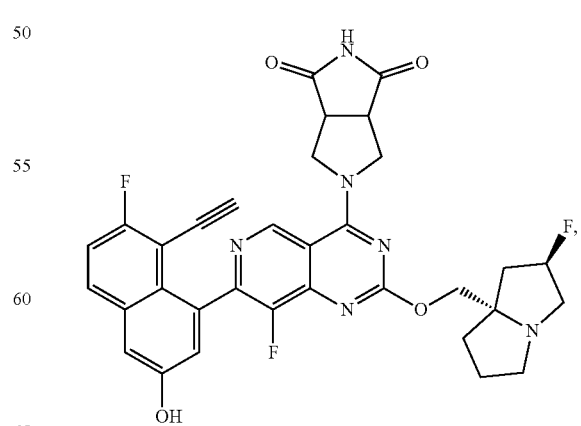

839
-continued
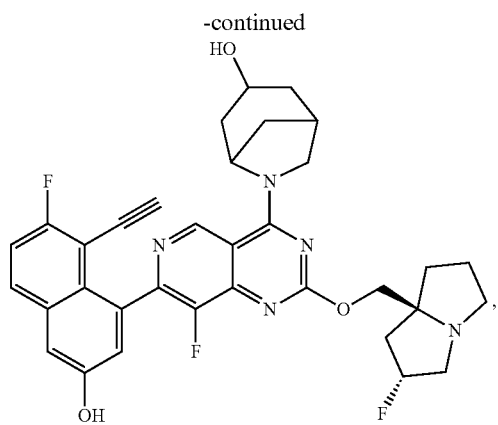
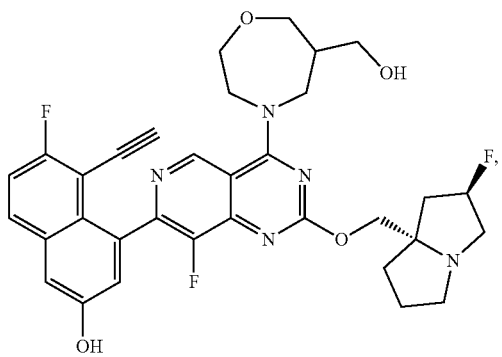
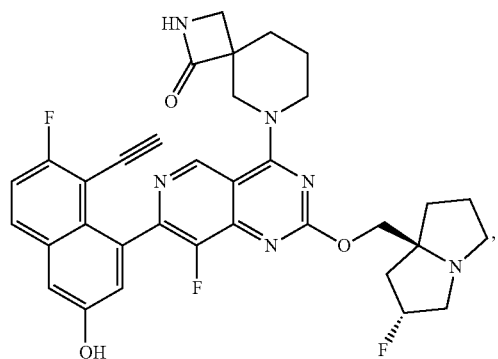
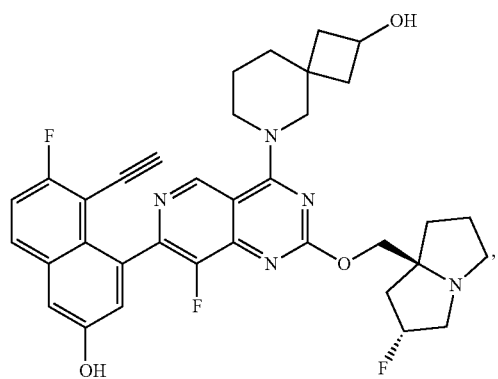
840
-continued
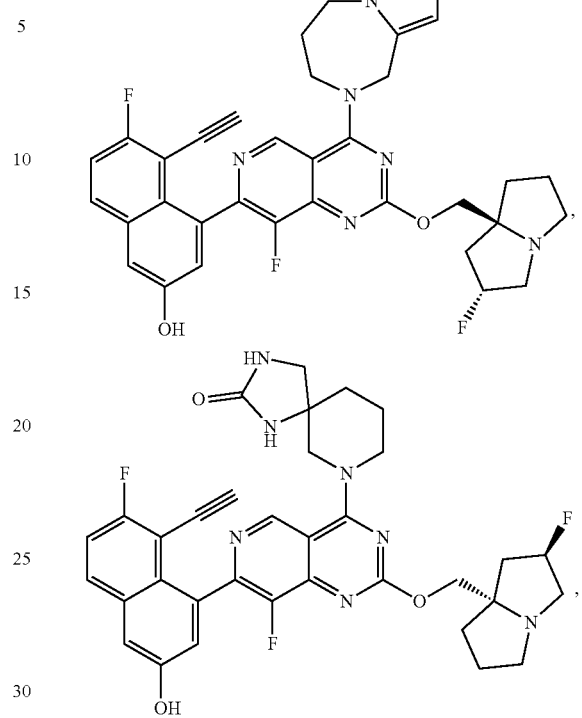
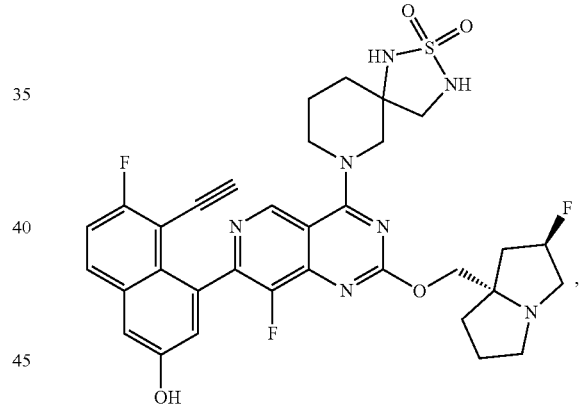
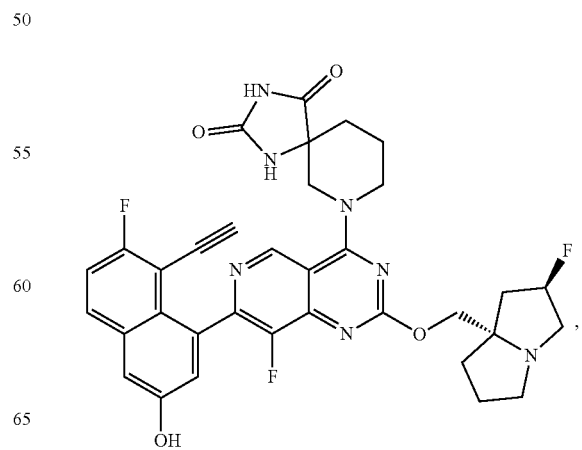

841
-continued
842
-continued
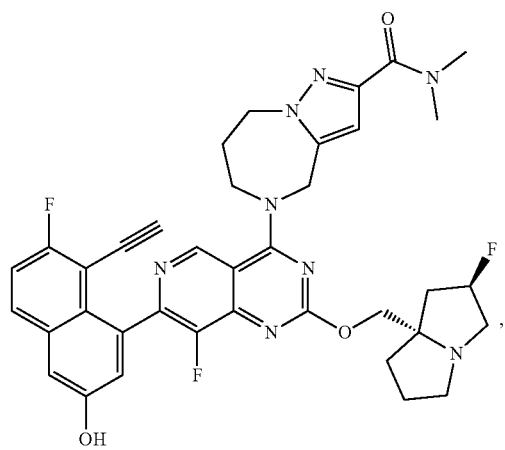
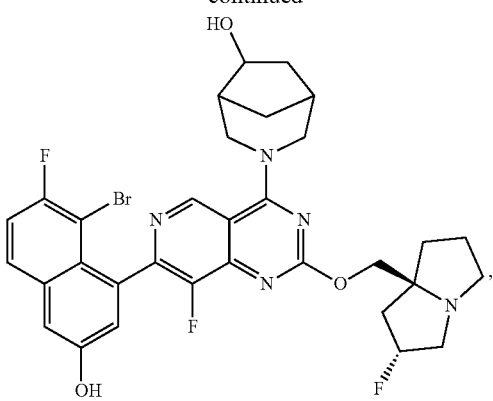
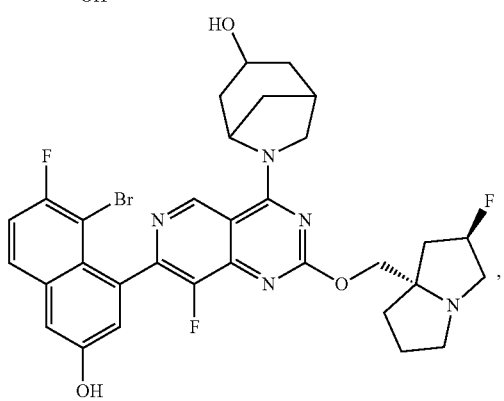
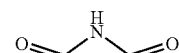
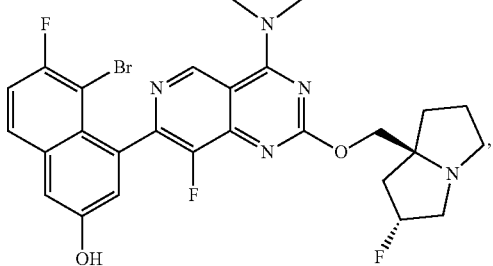
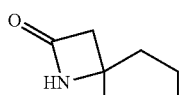
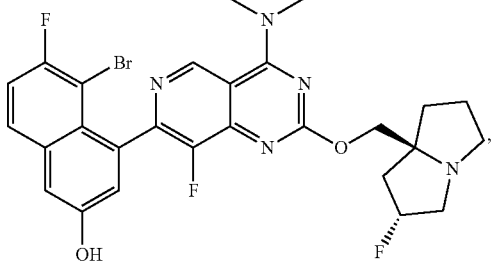

843
-continued
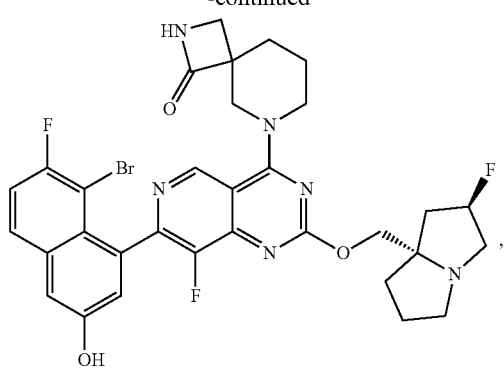
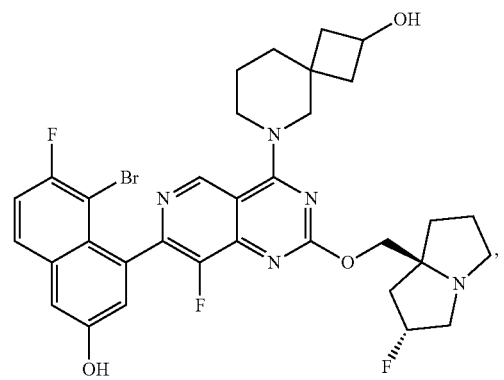
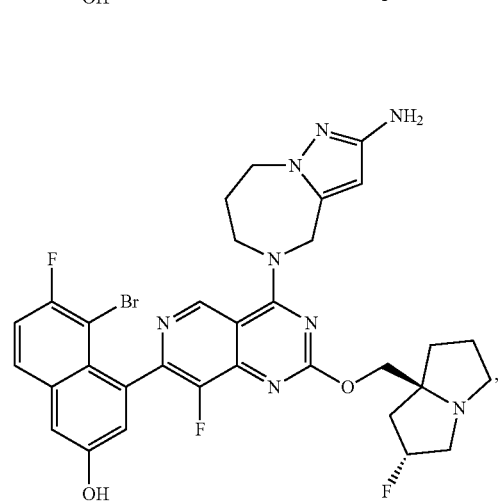
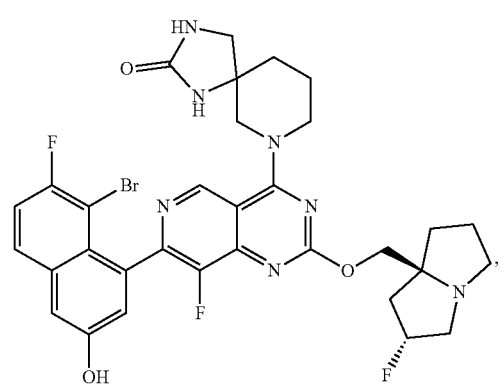
844
-continued
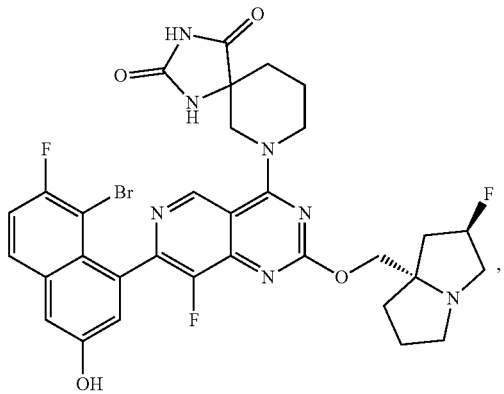
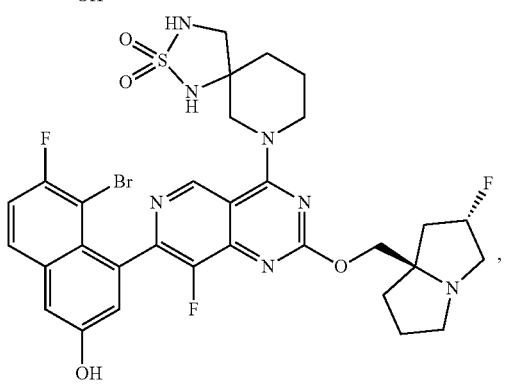
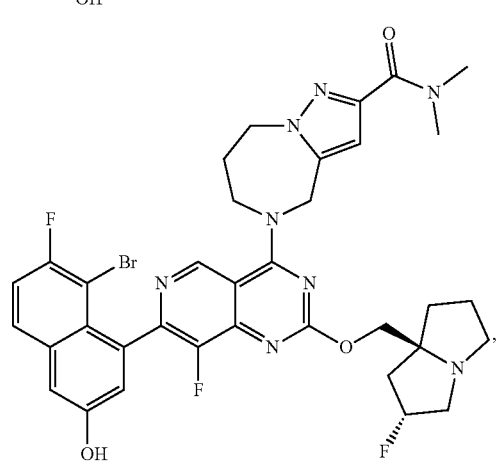
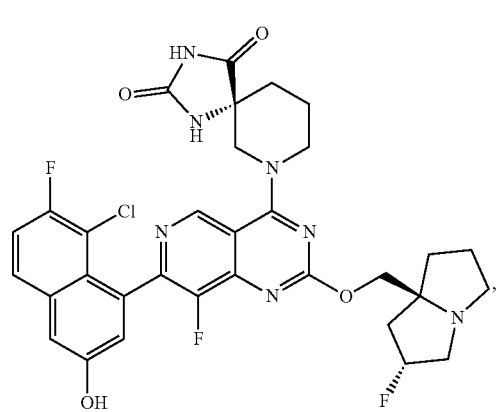

| 845 -continued | 846 -continued |
|---|---|
| 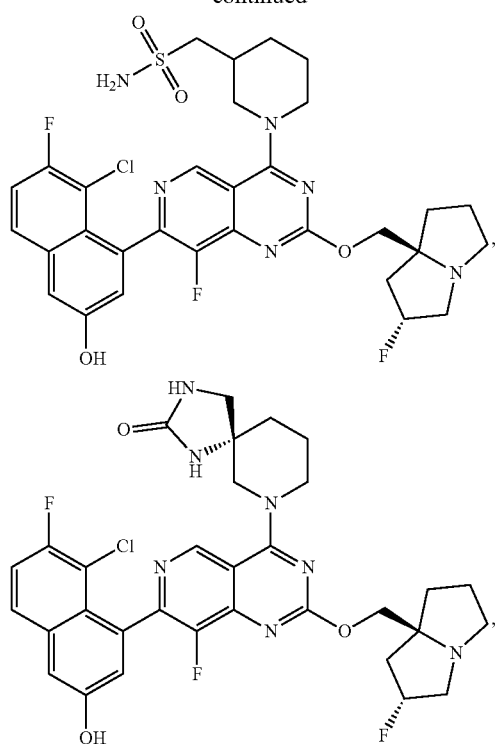 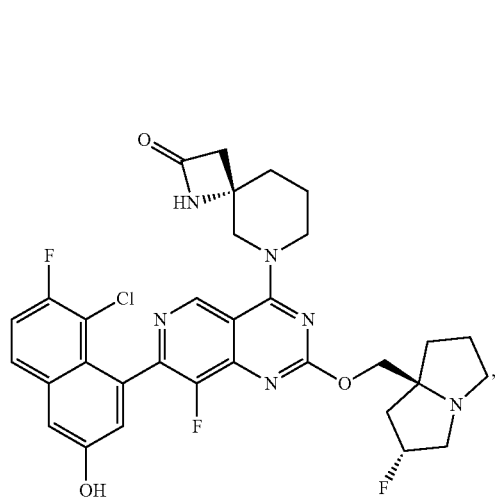 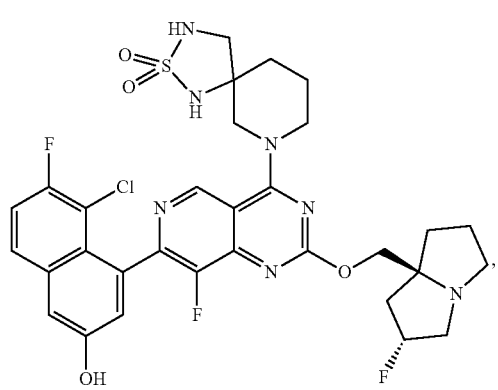 | 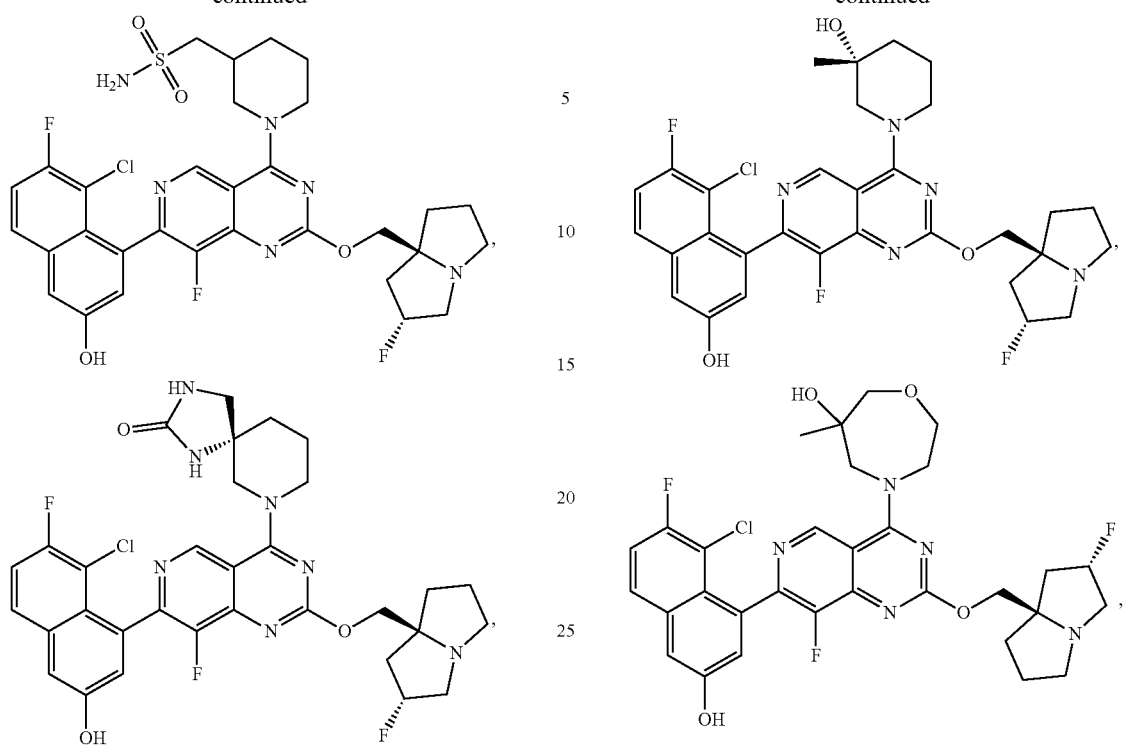 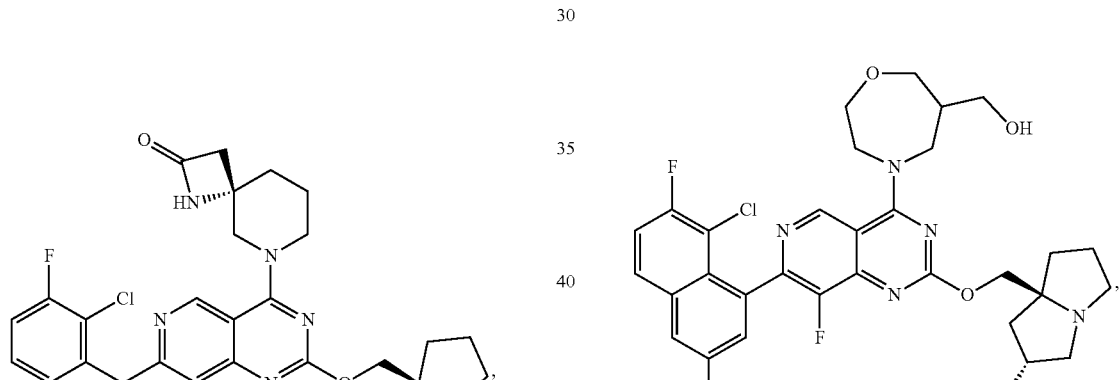 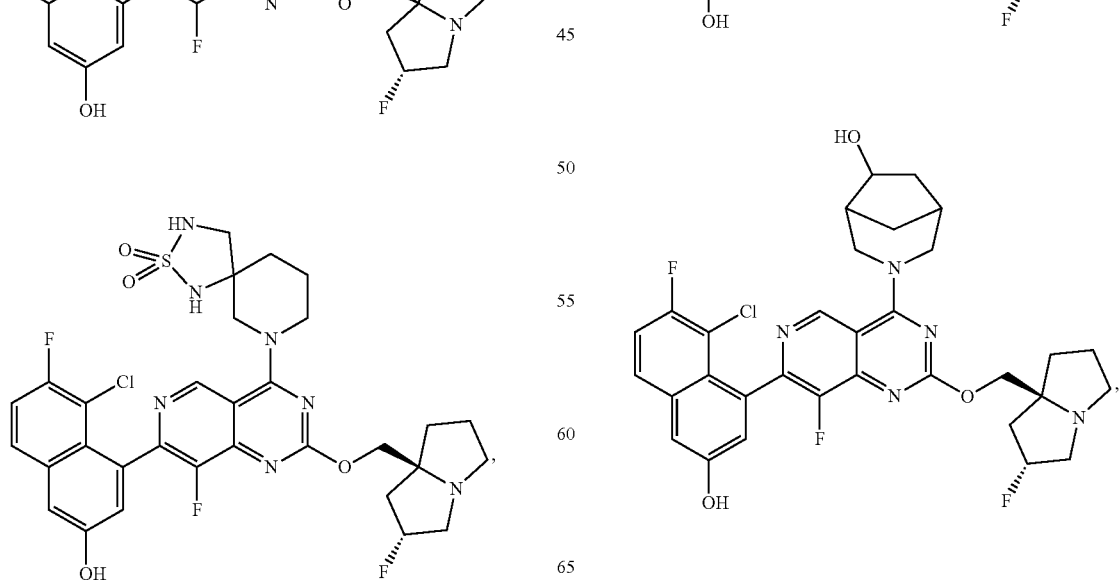 |

847
-continued
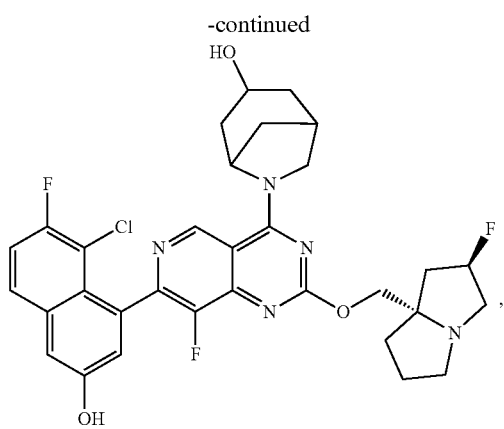
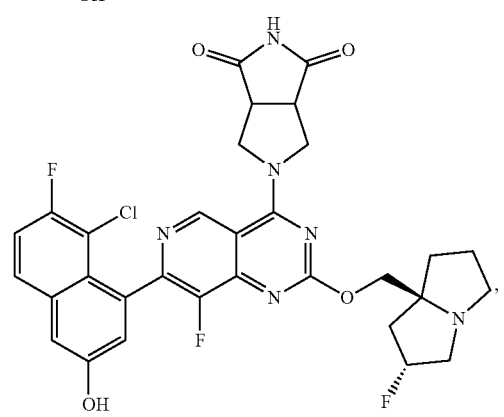
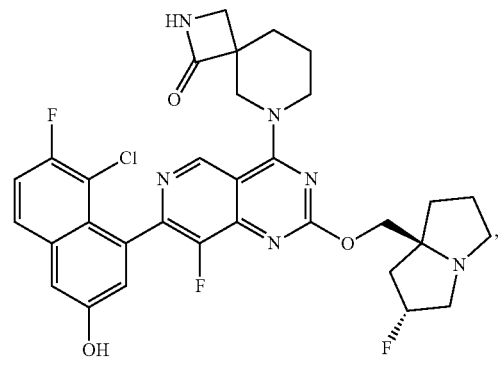
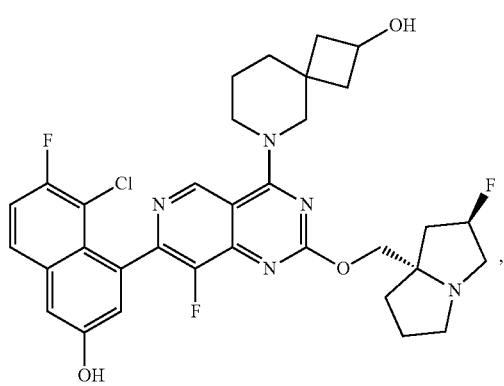
848
-continued
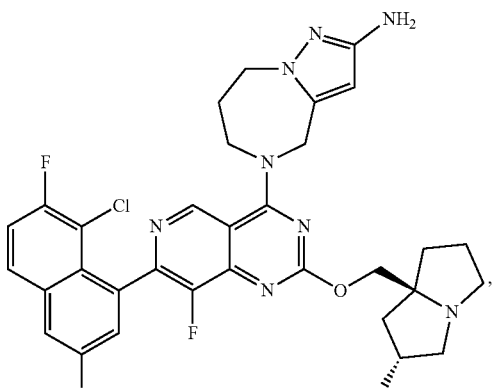
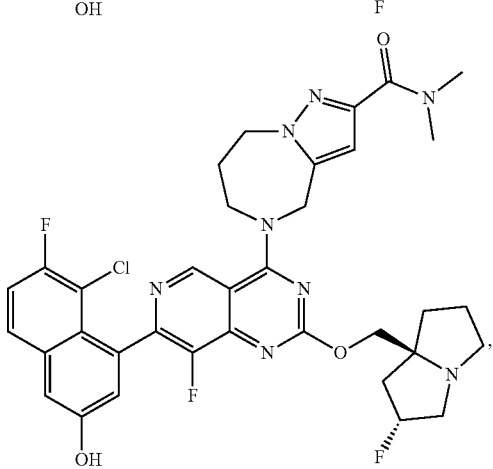
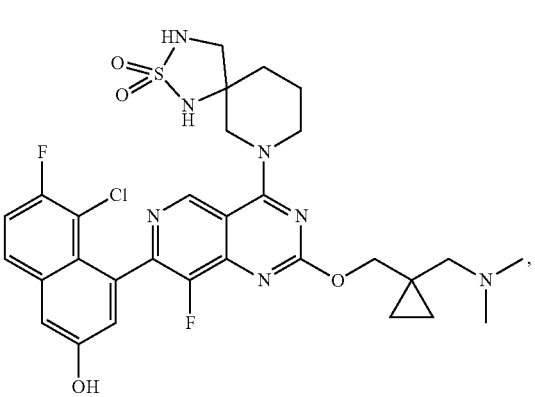
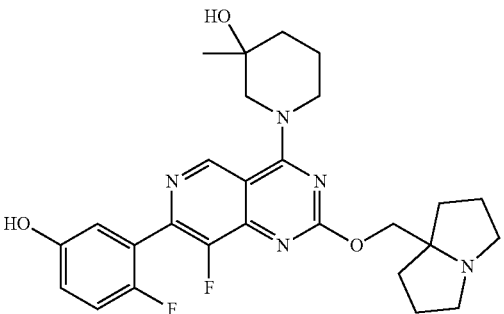

849
-continued
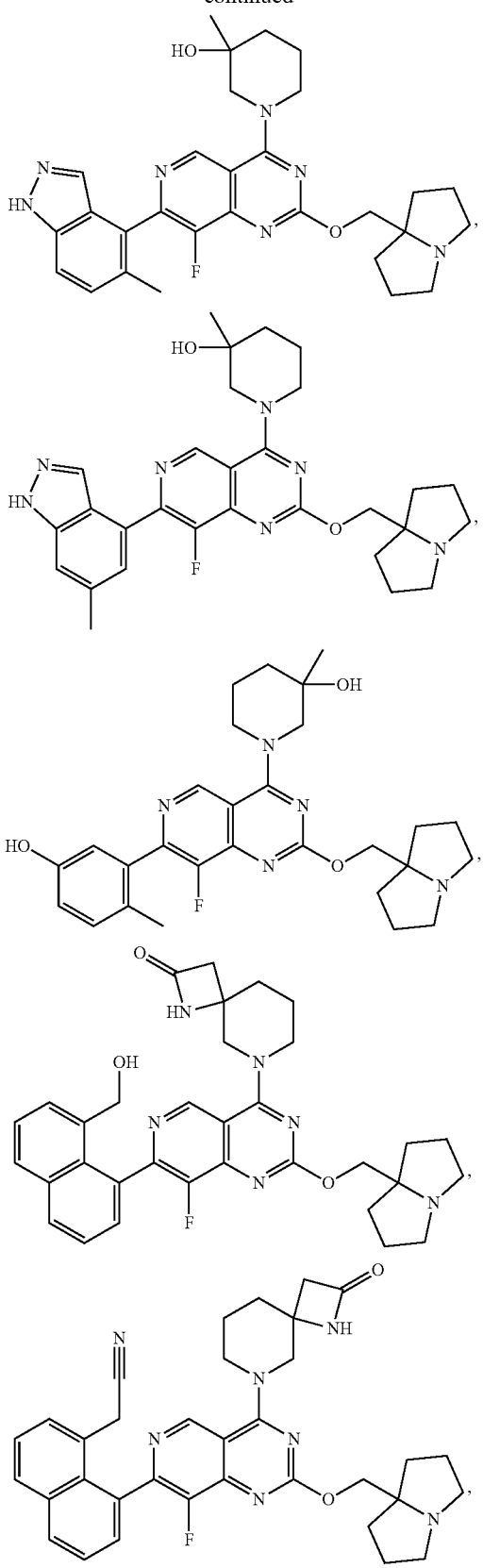
850
-continued
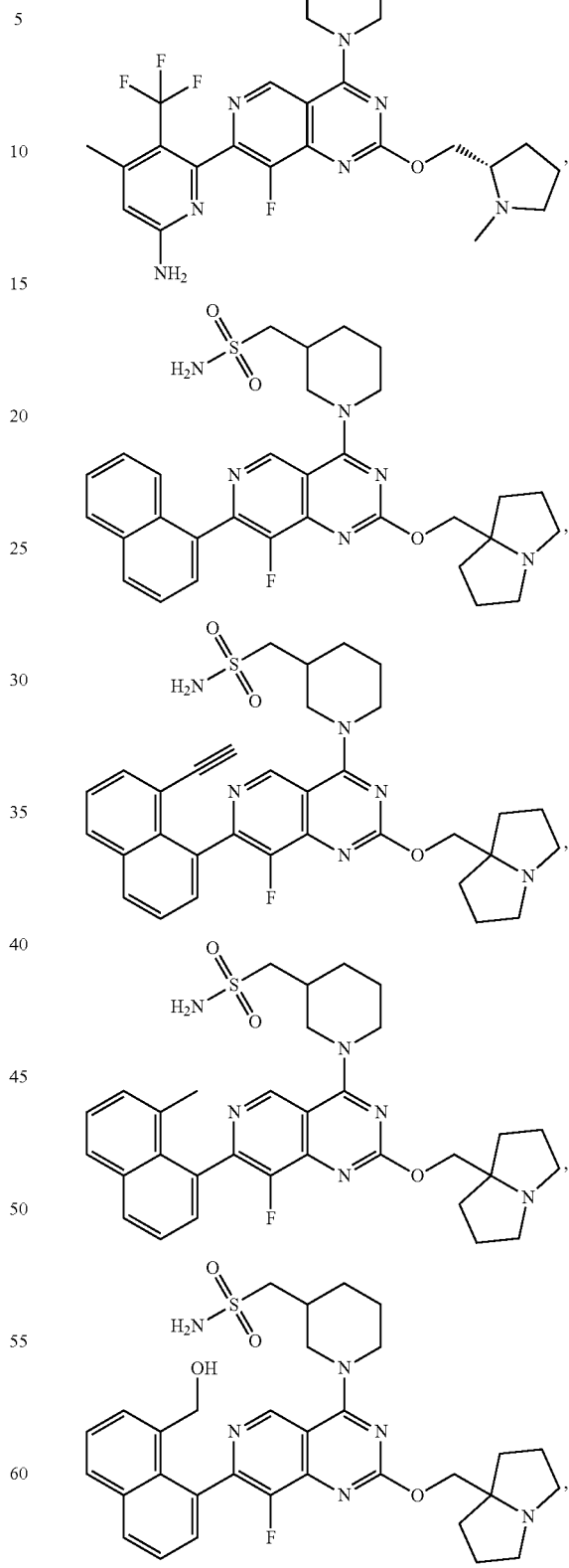

-continued
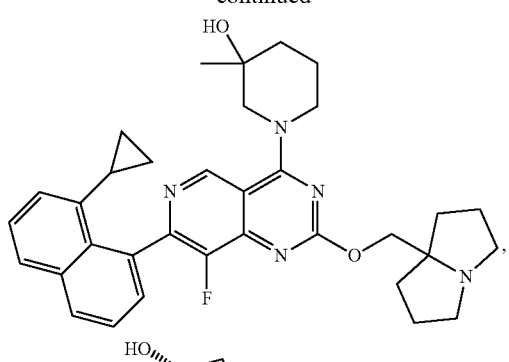
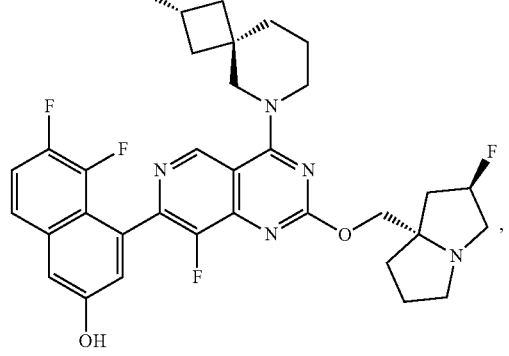
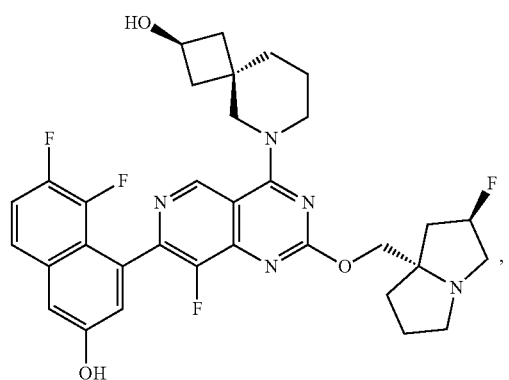
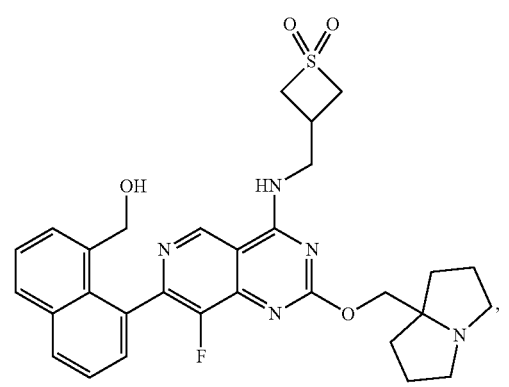
-continued
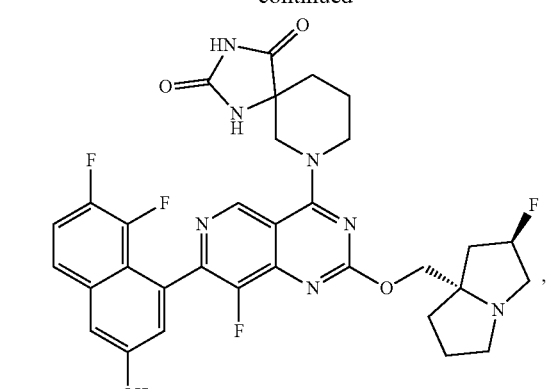
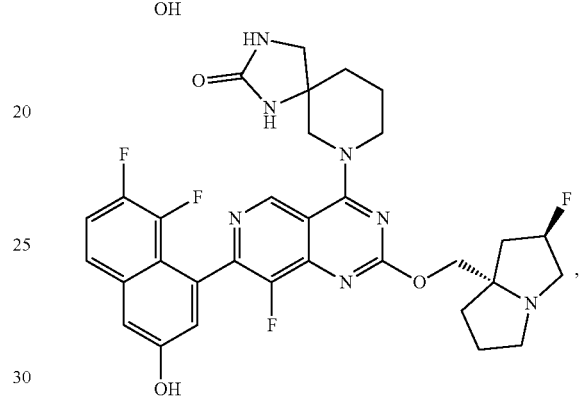
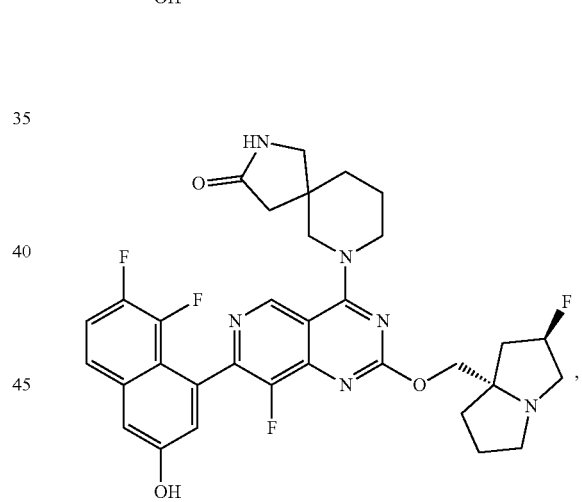
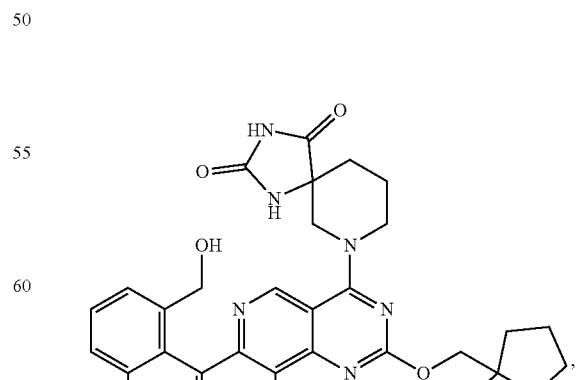

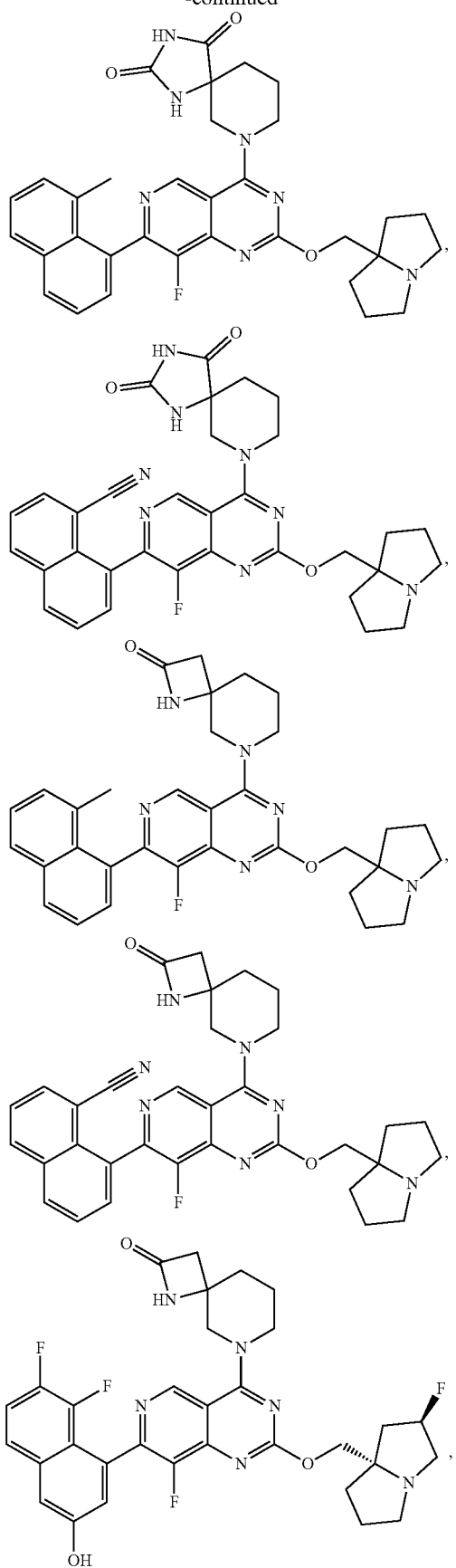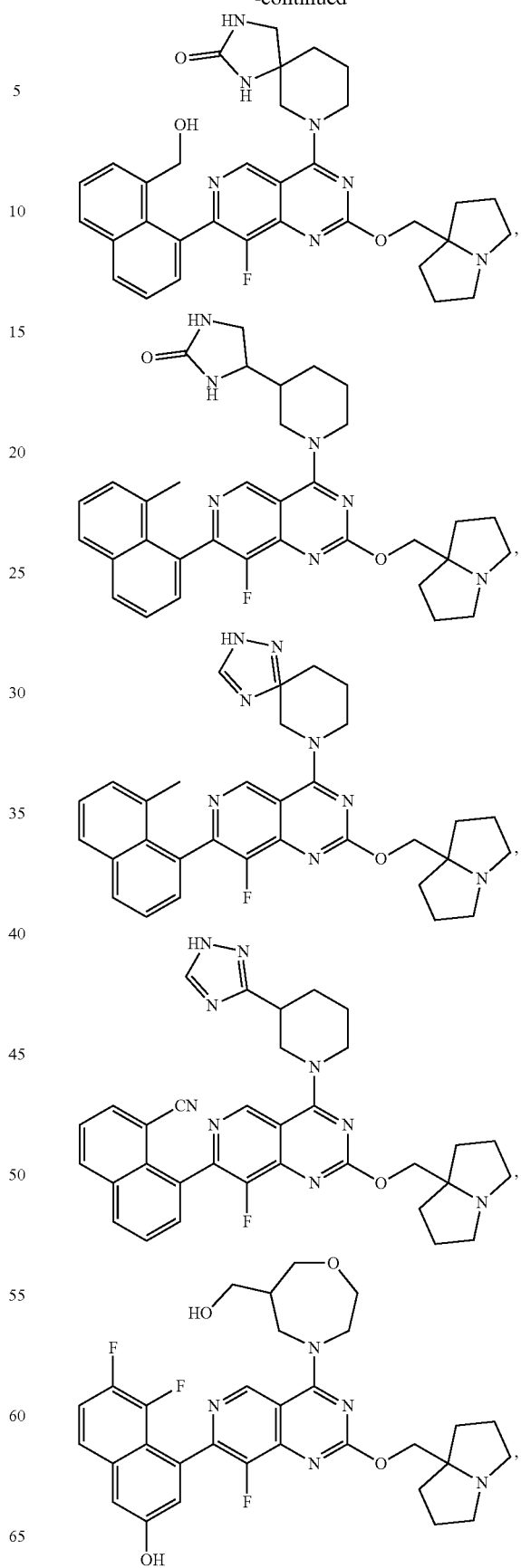

855
-continued
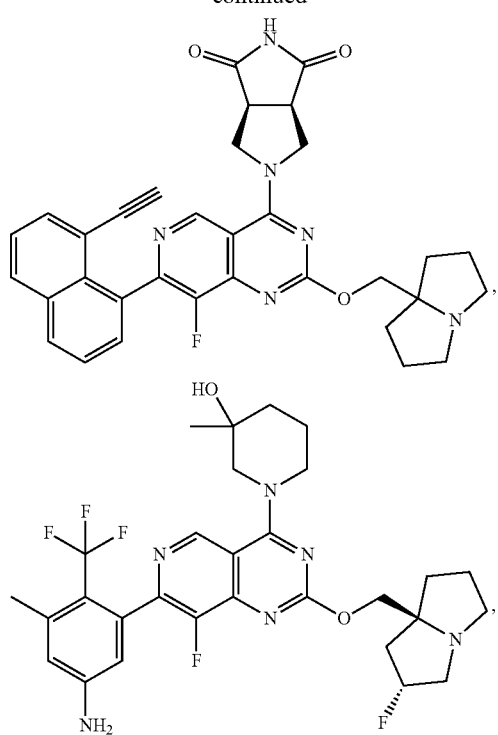
856
-continued
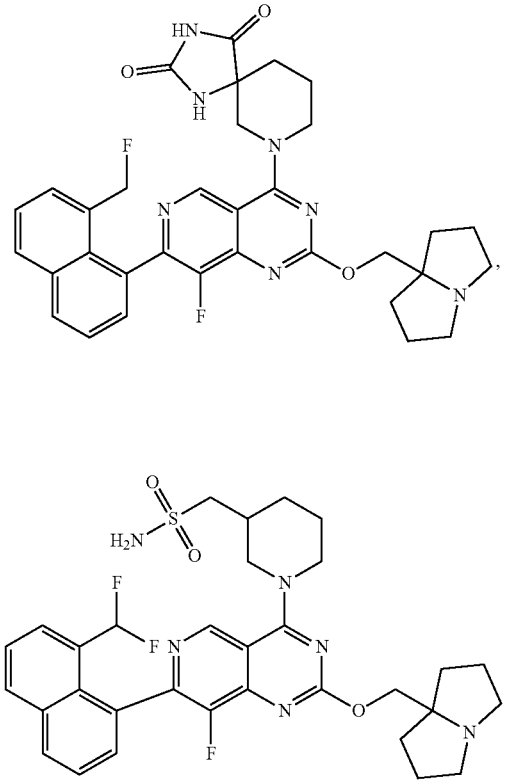
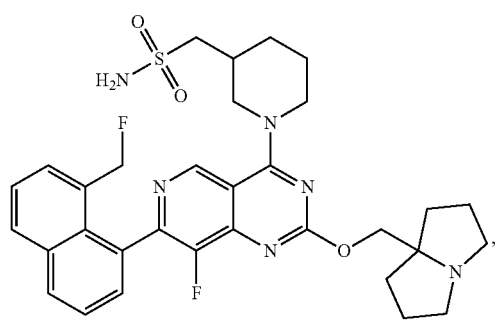
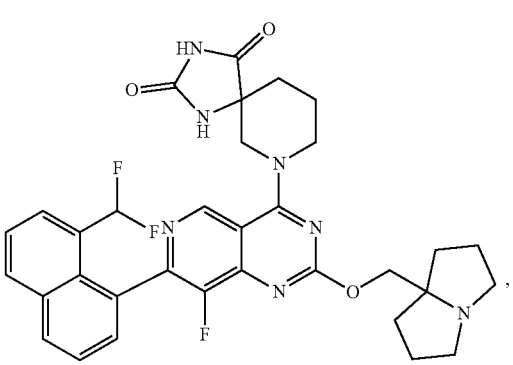
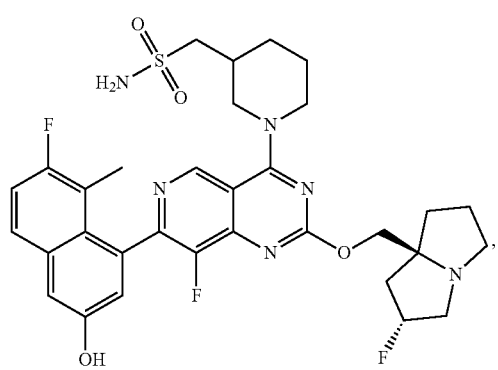
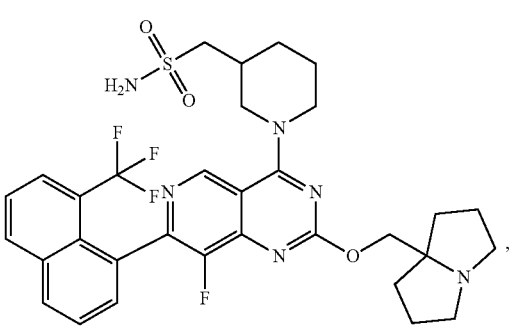

857
-continued
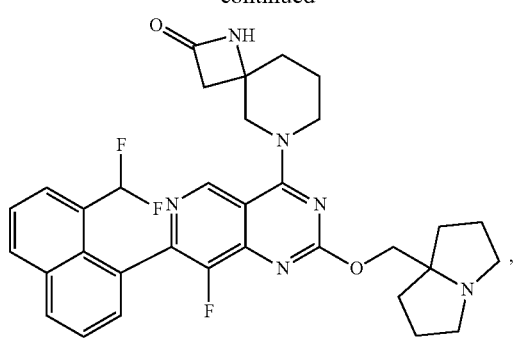
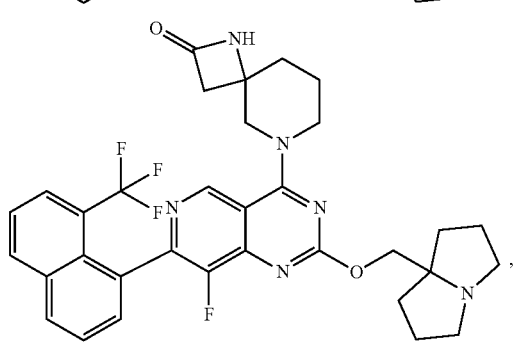
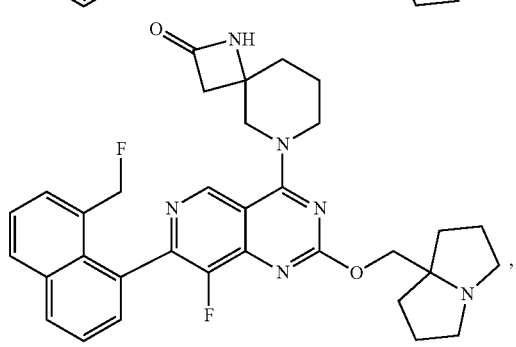
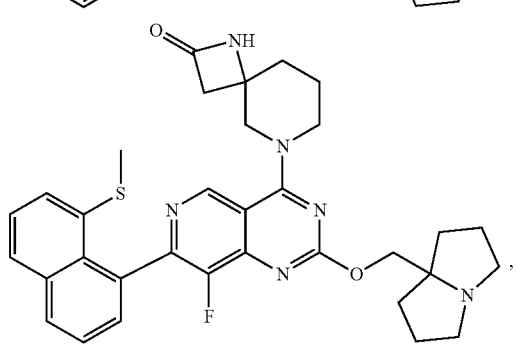
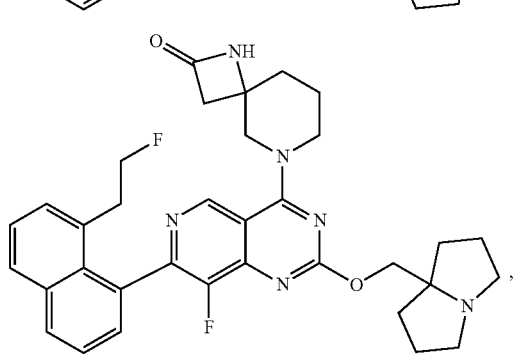
858
-continued
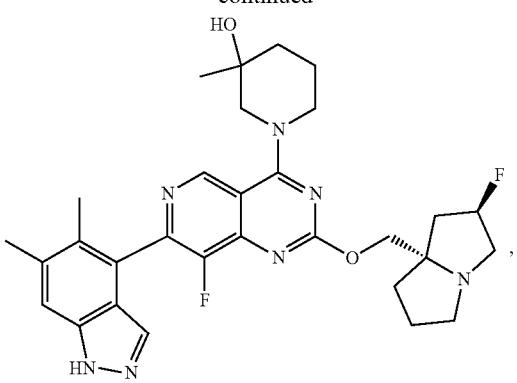
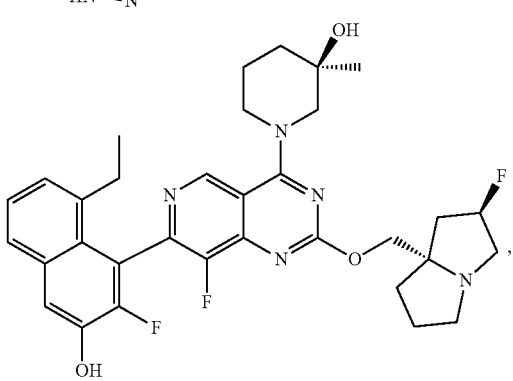
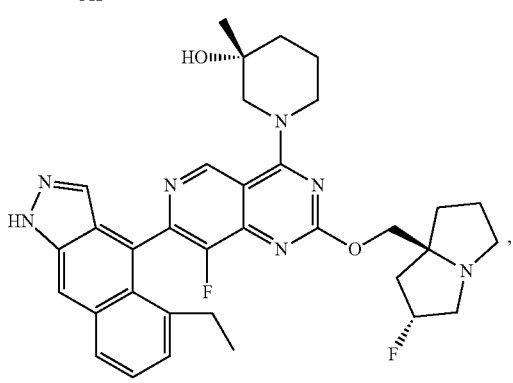
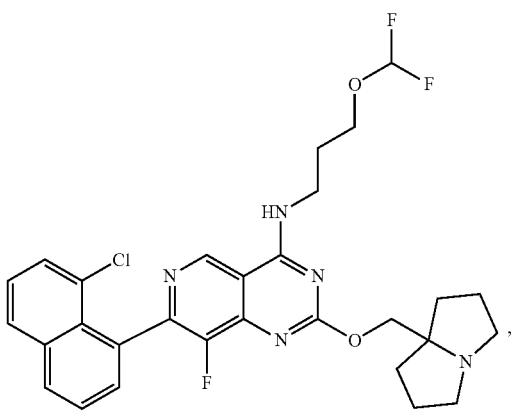

859
-continued
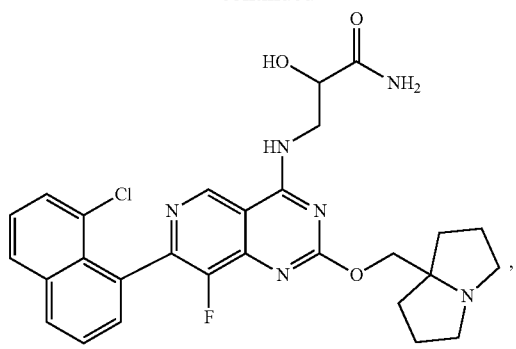
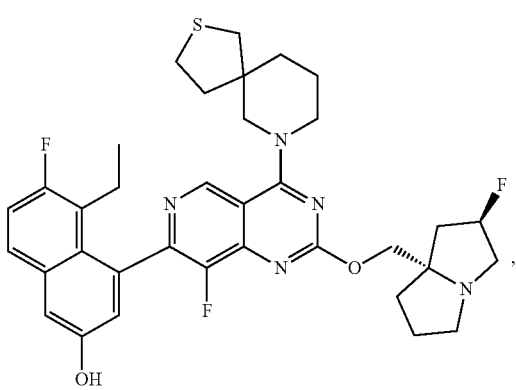
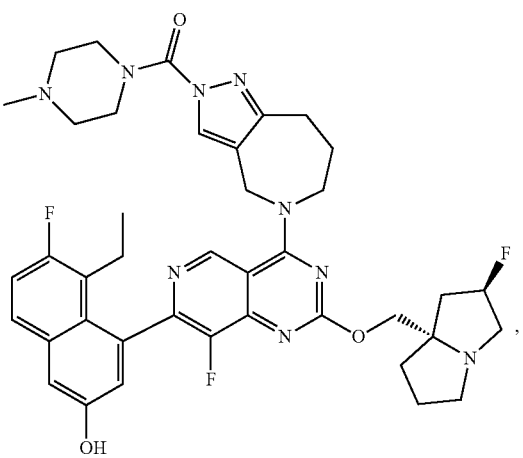
860
-continued
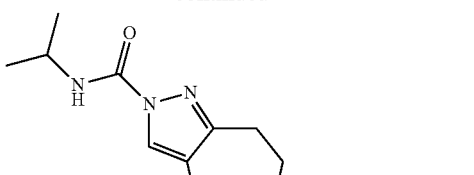
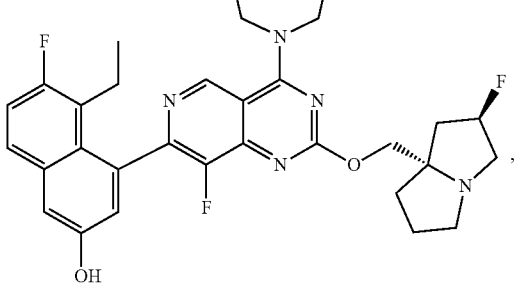
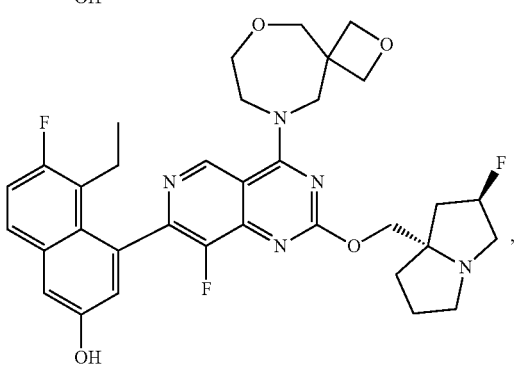
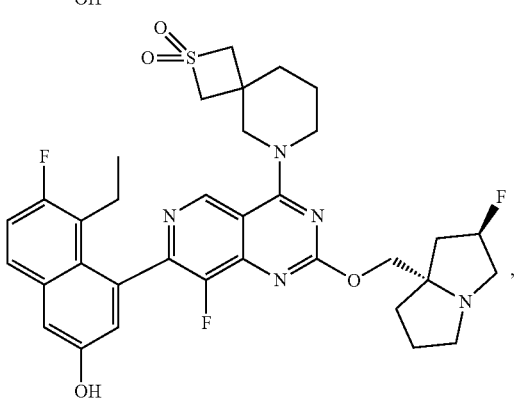

-continued
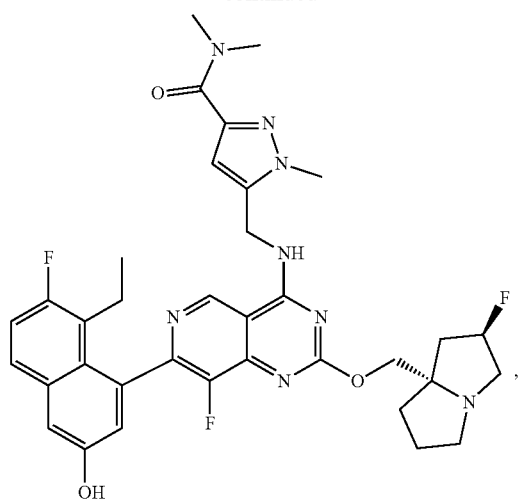
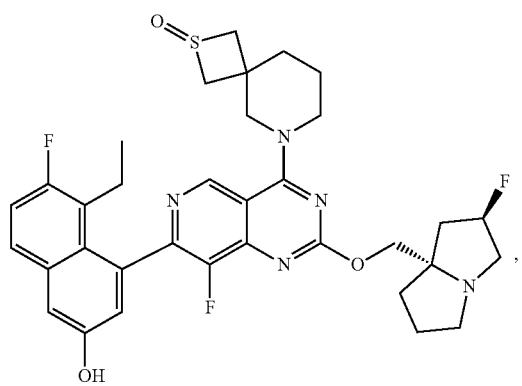
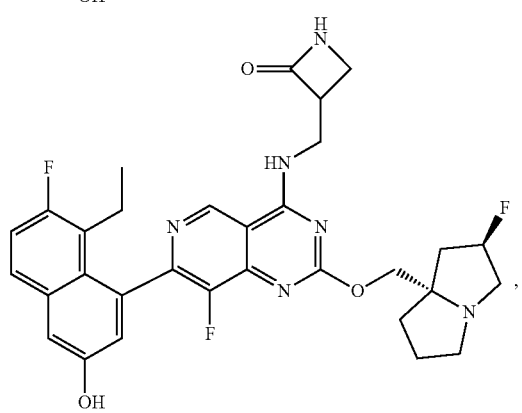
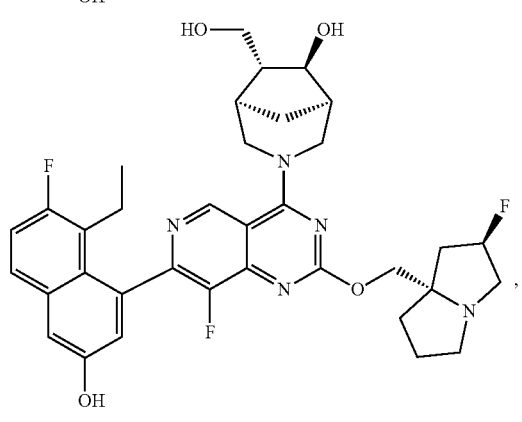
-continued
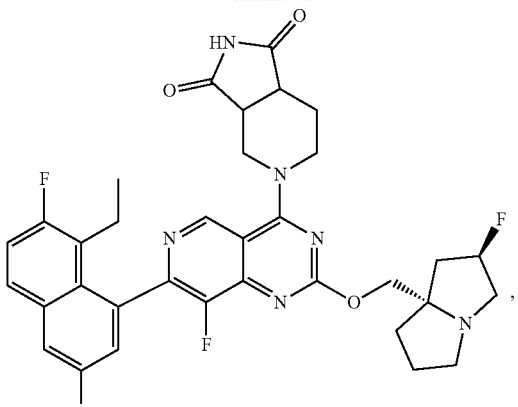
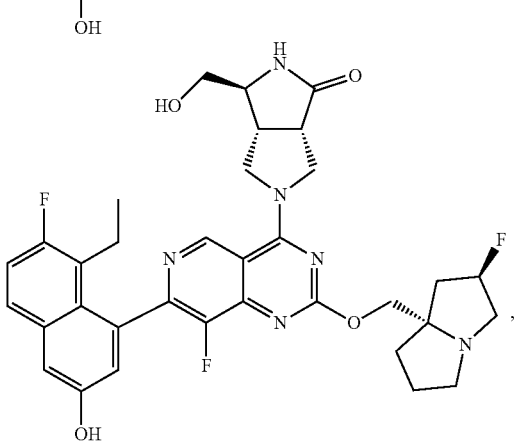
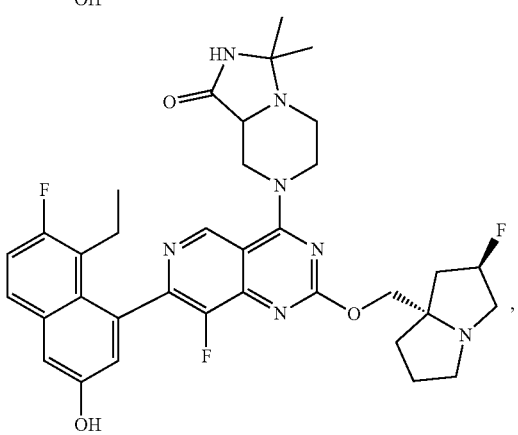
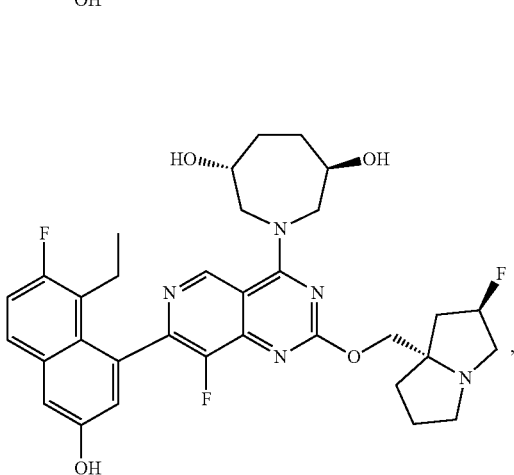

863
-continued
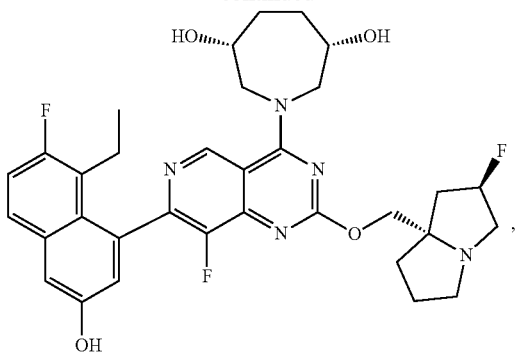
864
-continued
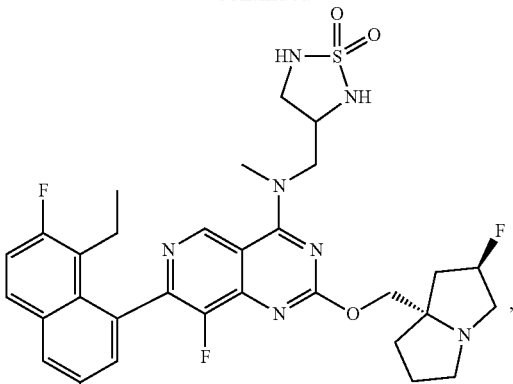
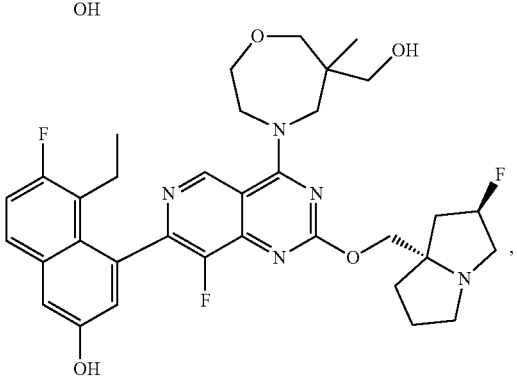
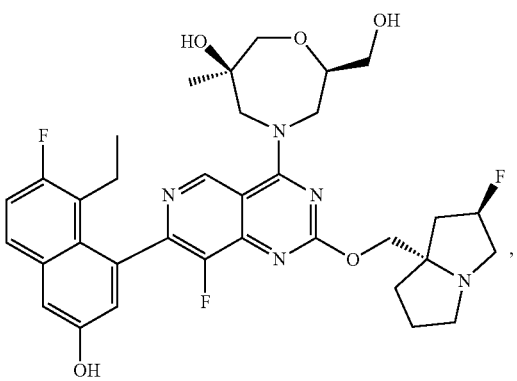
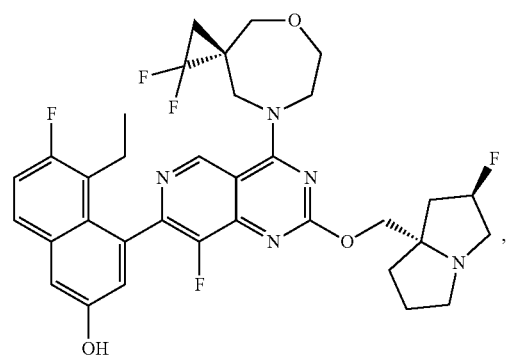

865
-continued
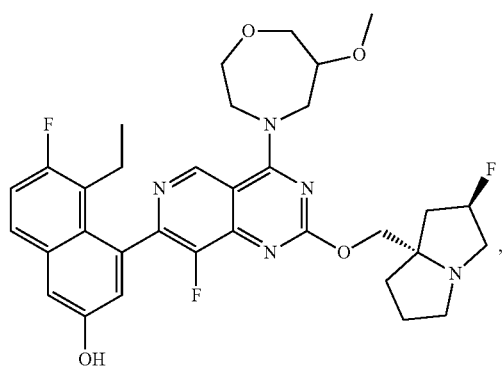
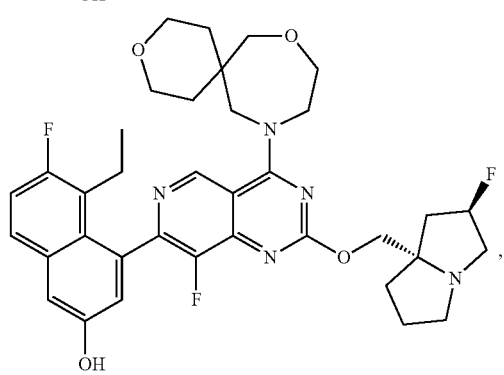
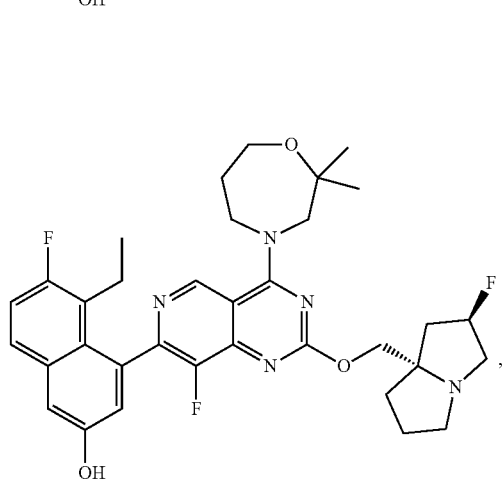
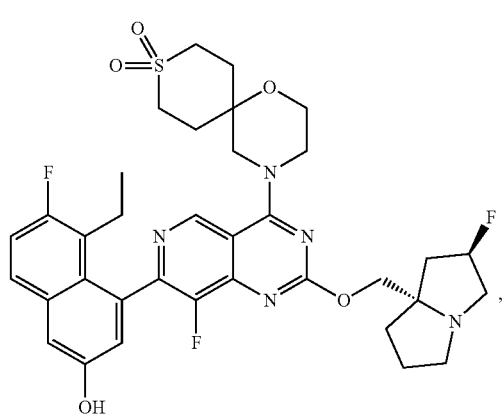
866
-continued
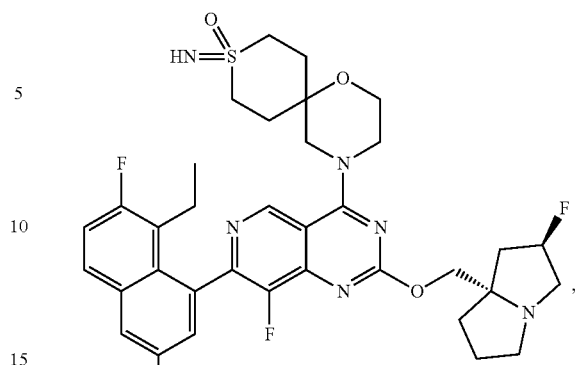
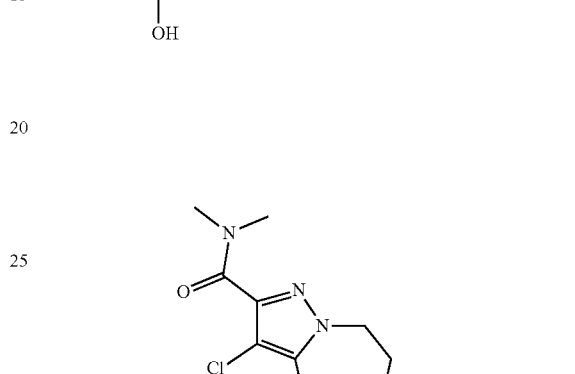
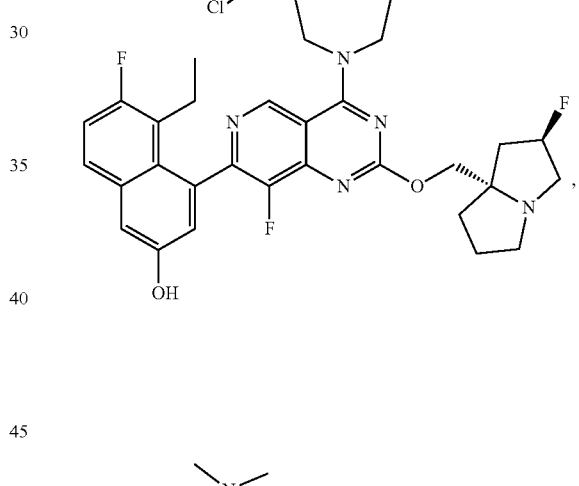
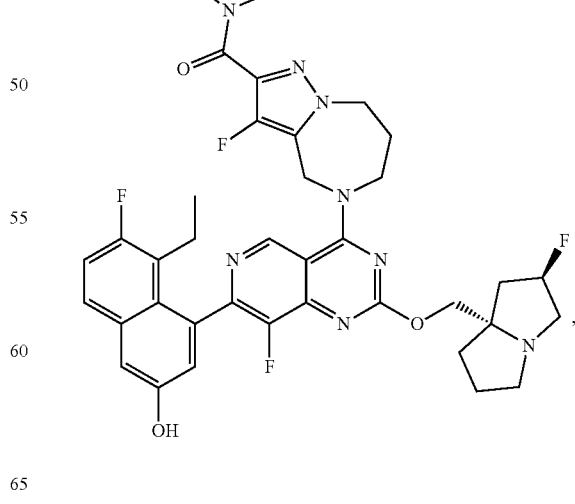

867
-continued
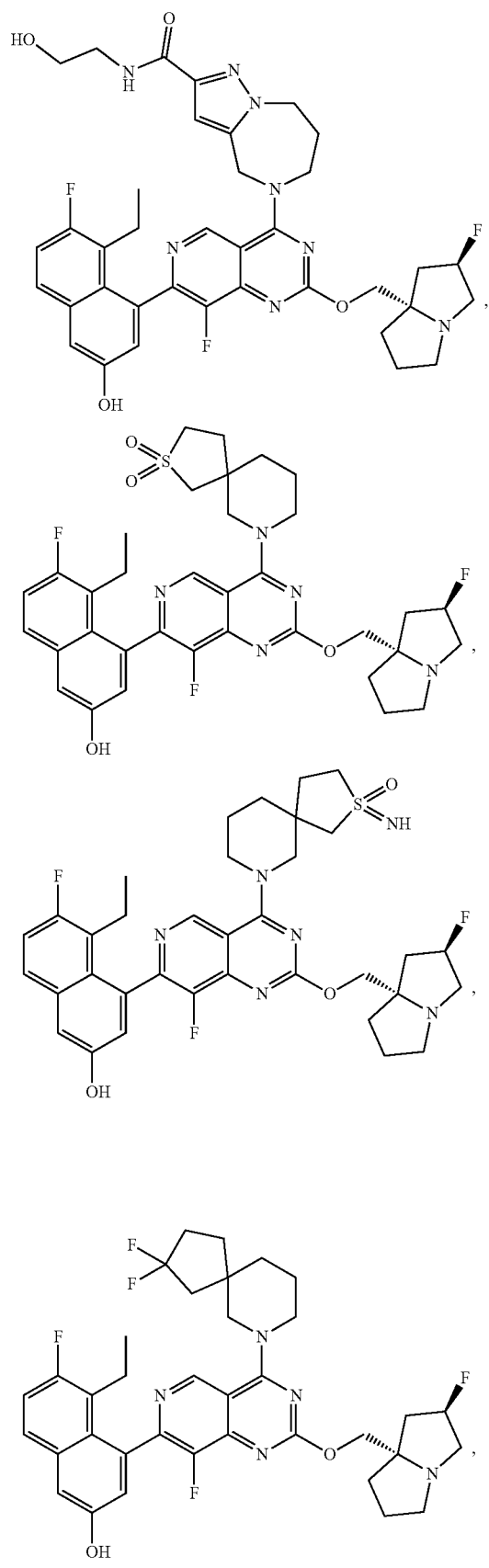
868
-continued
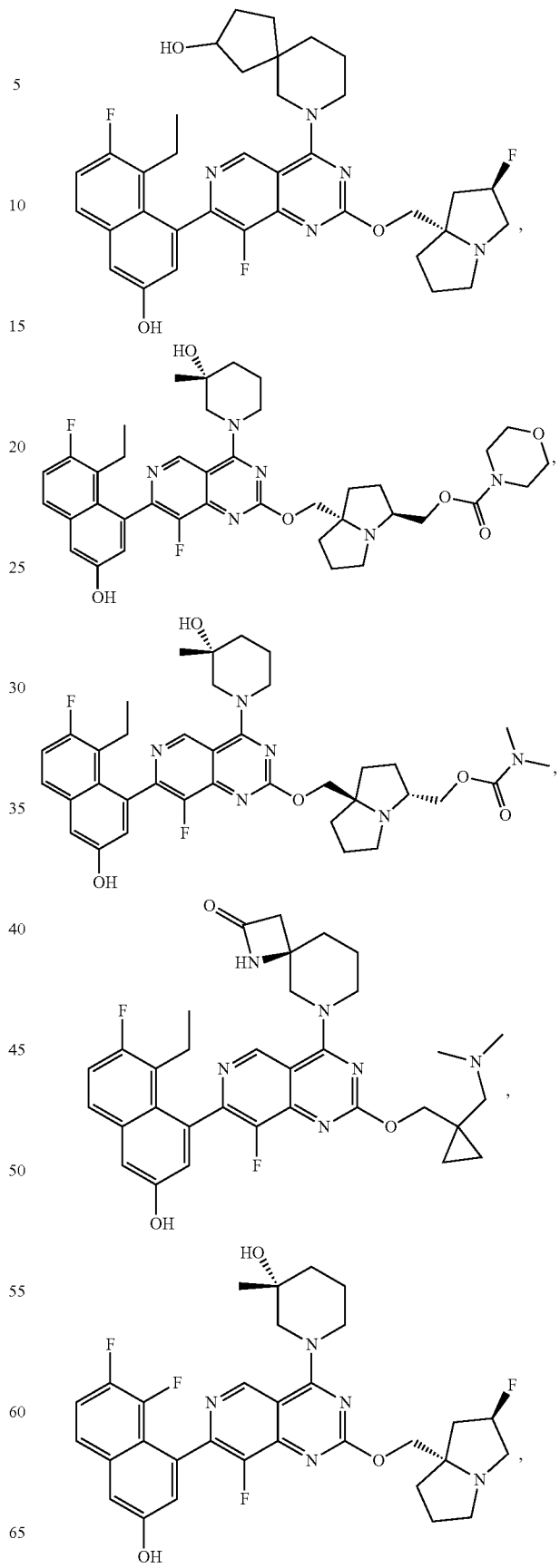

869
-continued
870
-continued
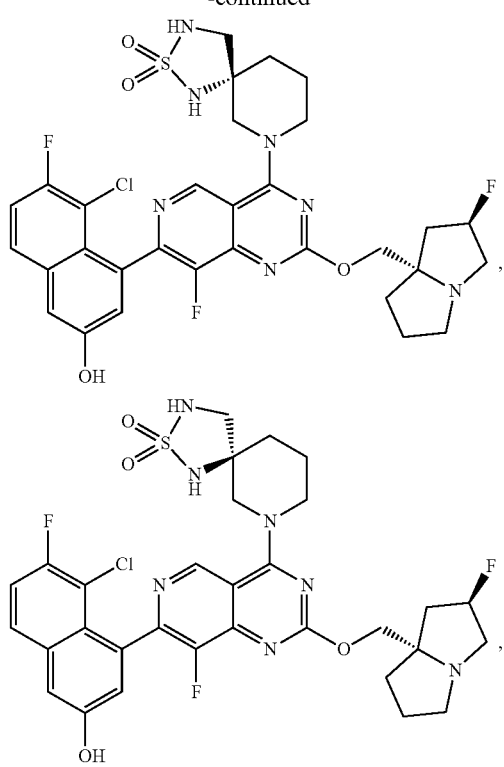
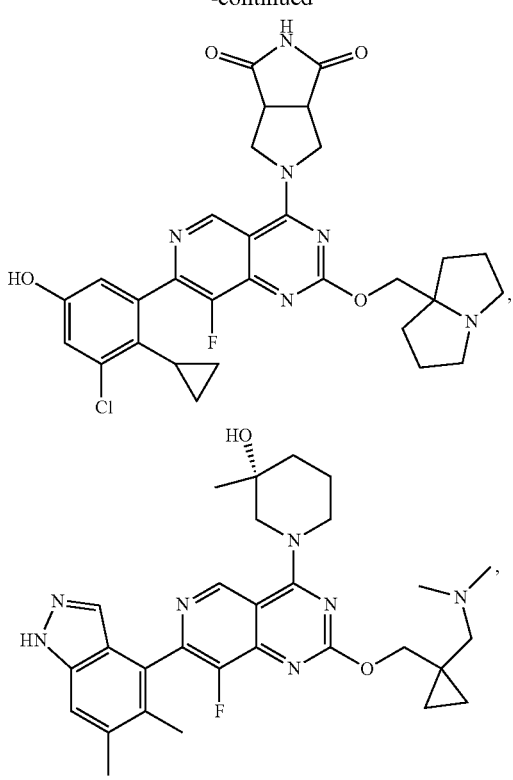
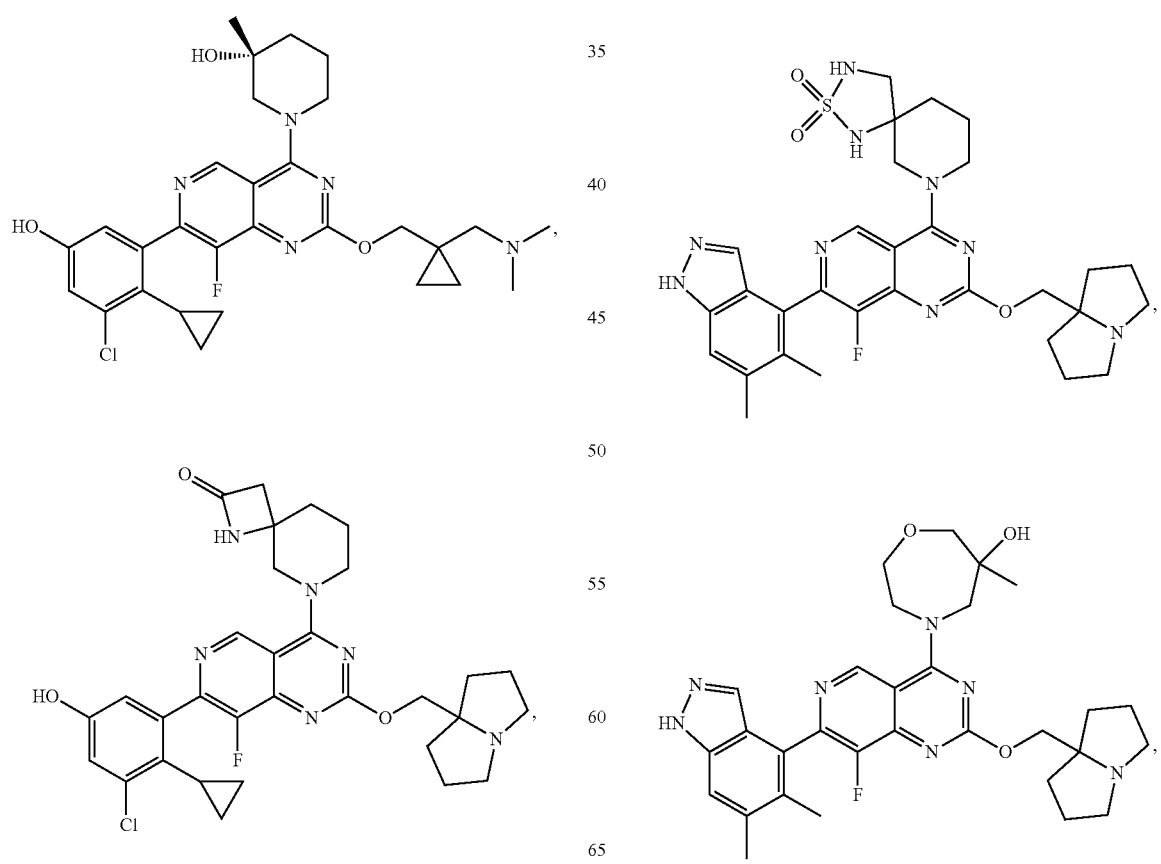

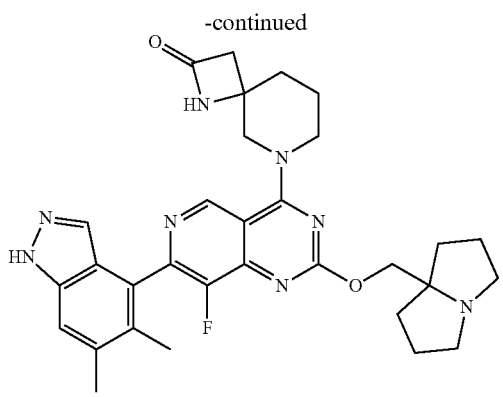

and pharmaceutically acceptable salts thereof.

26. A pharmaceutical composition, comprising a therapeutically effective amount of a compound of claim 1 or a pharmaceutically acceptable salt thereof, and a pharmaceutically acceptable excipient.

27. A method for inhibiting wild type KRas, KRas G12A, KRas G12C, KRas G12D, KRas G12R, KRas G12S, KRas G12V, KRas G13D or KRas Q61H activity in a cell, comprising contacting a cell in which inhibition of KRas activity is desired with an effective amount of a compound of according to claim 1 or a pharmaceutically acceptable salt thereof, or the pharmaceutical composition of claim 26.

28. A method for treating cancer comprising administering to a patient having cancer a therapeutically effective amount of a compound according to claim 1 or a pharmaceutically acceptable salt thereof, or the pharmaceutical composition of claim 26.

29. The method of claim 28, wherein the therapeutically effective amount of the compound is between about 0.01 to 100 mg/kg per day.

30. The method of claim 29, wherein the therapeutically effective amount of the compound is between about 0.1 to 50 mg/kg per day.

31. The method of claim 28, wherein the cancer is selected from the group consisting of Cardiac: sarcoma, myxoma, rhabdomyoma, fibroma, lipoma and teratoma; Lung: bronchogenic carcinoma, alveolar carcinoma, bronchial adenoma, sarcoma, lymphoma, chondromatous hamartoma, mesothelioma; Gastrointestinal: esophagus, stomach, pancreas, small bowel, large bowel; Genitourinary tract: kidney, bladder and urethra, prostate, testis; Liver: hepatoma, cholangiocarcinoma, hepatoblastoma, angiosarcoma, hepatocellular adenoma, hemangioma, Biliary tract: gall bladder carcinoma, ampullary carcinoma, cholangiocarcinoma; Bone: osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors; Nervous system: skull, meninges, brain; Gynecological: uterus, vulva, vagina; Hematologic: blood, Hodgkin's disease, non-Hodgkin's lymphoma; Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma neuroblastoma.

32. The method of claim 28, wherein the cancer is a KRas G12A-associated cancer.

33. The method of claim 28, wherein the cancer is a KRas G12C-associated cancer.

34. The method of claim 28, wherein the cancer is a KRas G12D-associated cancer.

35. The method of claim 28, wherein the cancer is a KRas G12R-associated cancer.

36. The method of claim 28, wherein the cancer is a KRas G12S-associated cancer.

37. The method of claim 28, wherein the cancer is a KRas G12V-associated cancer.

38. The method of claim 28, wherein the cancer is a KRas G13D-associated cancer.

39. The method of claim 28, wherein the cancer is a KRas Q61H-associated cancer.

40. The method of claim 28, wherein the cancer is a KRas G12A-associated cancer.

41. The method of claim 28, wherein the cancer is associated with at least one of wild type KRas, KRas G12A, KRas G12C, KRas G12D, KRas G12R, KRas G12S, KRas G12V, KRas G13D or KRas Q61H.

42. The method of claim 28, wherein the cancer is non-small cell lung cancer, small cell lung cancer, colorectal cancer, rectal cancer or pancreatic cancer.

43. A method for treating cancer in a patient in need thereof, the method comprising (a) determining that the cancer is associated with wild type KRas or a KRas G12A, KRas G12C, KRas G12D, KRas G12R, KRas G12S, KRas G12V, KRas G13D or KRas Q61H mutation; and (b) administering to the patient a therapeutically effective amount of a compound according to claim 1 or a pharmaceutically acceptable salt thereof, or the pharmaceutical composition of claim 26.

44. The method of claim 28, wherein the administering is done via a route selected from the group consisting of parenteral, intraperitoneal, intradermal, intracardiac, intraventricular, intracranial, intracerebrospinal, intrasynovial, intrathecal administration, intramuscular injection, intravitreous injection, intravenous injection, intra-arterial injection, oral, buccal, sublingual, transdermal, topical, intratracheal, intrarectal, subcutaneous, and topical administration.

45. The method of claim 44, wherein the administration route is oral.

46. The method of claim 44, wherein the administration is intravenous injection.

47. The method of claim 44, wherein the administration route is intramuscular injection.

48. The method of claim 44, wherein the administration route utilizes a delivery device.

49. The method of claim 44, wherein administration is done in a hospital setting.

* * * * *